US012490741B2

(12) United States Patent
Heemstra et al.

(10) Patent No.: US 12,490,741 B2
(45) Date of Patent: *Dec. 9, 2025

(54) MOLECULES HAVING PESTICIDAL UTILITY, AND INTERMEDIATES, COMPOSITIONS, AND PROCESSES, RELATED THERETO

(71) Applicant: CORTEVA AGRISCIENCE LLC, Indianapolis, IN (US)

(72) Inventors: Ronald J. Heemstra, Fishers, IN (US); Ronald Ross, Jr., Mt. Dora, FL (US); Kyle A. Dekorver, Grandville, MI (US); Kaitlyn Gray, Indianapolis, IN (US); Daniel I. Knueppel, Zionsville, IN (US); Peter Vednor, Novi, MI (US); Timothy P. Martin, Noblesville, IN (US); Joseph D Eckelbarger, Carmel, IN (US); John F. Daeuble, Sr., Carmel, IN (US); Ricky Hunter, Westfield, IN (US); David A. Demeter, Fishers, IN (US); Tony K. Trullinger, Westfield, IN (US); Erich W. Baum, South Hamilton, MA (US); Zoltan L. Benko, Indianapolis, IN (US); Nakyen Choy, Carmel, IN (US); Gary D. Crouse, Noblesville, IN (US); Fangzheng Li, Carmel, IN (US); Jeffrey Nissen, Indianapolis, IN (US); Monica B. Olson, Indianapolis, IN (US); Michelle Riener, Waltham, MA (US); Thomas C. Sparks, Greenfield, IN (US); Frank J. Wessels, Indianapolis, IN (US); Maurice C. Yap, Zionsville, IN (US)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/986,968

(22) Filed: Dec. 19, 2024

(65) Prior Publication Data

US 2025/0134105 A1 May 1, 2025

Related U.S. Application Data

(60) Continuation of application No. 18/802,256, filed on Aug. 13, 2024, now abandoned, which is a (Continued)

(51) Int. Cl.
*A01N 53/00* (2006.01)
*A01N 37/22* (2006.01)
(Continued)

(52) U.S. Cl.
CPC ............ *A01N 53/00* (2013.01); *A01N 37/22* (2013.01); *A01N 37/34* (2013.01); *A01N 41/10* (2013.01);
(Continued)

(58) Field of Classification Search
CPC ........ A01N 37/22; A01N 37/34; A01N 41/10; A01N 43/40; A01N 43/60; A01N 43/653;
(Continued)

(56) References Cited

U.S. PATENT DOCUMENTS 7,754,717 B2 7/2010 DiMauro et al.
8,067,599 B2 11/2011 Honold et al.
(Continued)

FOREIGN PATENT DOCUMENTS

EP 0604019 B1 5/1996
EP 0816330 B1 12/2000
(Continued)

OTHER PUBLICATIONS

Bastin R.J., et al., "Salt Selection and Optimisation Procedures for Pharmaceutical New Chemical Entities," Organic Process Research & Development, 2000, vol. 4, No. 5, pp. 427-435.
Chemical Encyclopedic Dictionary, Editor-in-chief IL Knunyants, Moskov, Soviet Encyclopedia, 1983, vol. 792, pp. 559-560.
Extended European Search Report for European Application No. 19174918.3, mailed Oct. 31, 2019, 07 Pages.
Extended European Search Report for European Application No. 19174959.7, mailed Oct. 31, 2019, 07 Pages.
Extended European Search Report for European Application No. 19175296.3, mailed Oct. 31, 2019, 09 Pages.
(Continued)

*Primary Examiner* — Yong L Chu

(57) ABSTRACT

This disclosure relates to the field of molecules having pesticidal utility against pests in Phyla Arthropoda, Mollusca, and Nematoda, processes to produce such molecules, intermediates used in such processes, pesticidal compositions containing such molecules, and processes of using such pesticidal compositions against such pests. These pesticidal compositions may be used, for example, as acaricides, insecticides, miticides, molluscicides, and nematicides. This document discloses molecules having the following formula ("Formula One").

Formula One

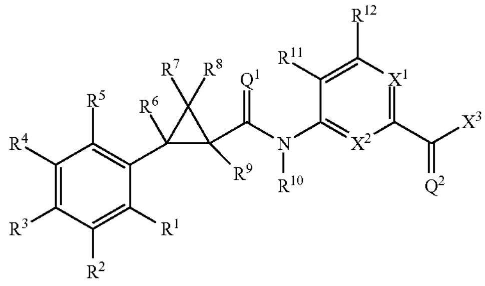

10 Claims, No Drawings

Related U.S. Application Data continuation of application No. 18/166,601, filed on Feb. 9, 2023, which is a continuation of application No. 16/794,955, filed on Feb. 19, 2020, now Pat. No. 11,632,957, which is a continuation of application No. 16/203,690, filed on Nov. 29, 2018, now abandoned, which is a continuation of application No. 15/679,415, filed on Aug. 17, 2017, now Pat. No. 10,219,516, which is a division of application No. 15/092,650, filed on Apr. 7, 2016, now Pat. No. 9,781,935.

(60) Provisional application No. 62/148,809, filed on Apr. 17, 2015, provisional application No. 62/148,814, filed on Apr. 17, 2015, provisional application No. 62/148,837, filed on Apr. 17, 2015, provisional application No. 62/148,830, filed on Apr. 17, 2015, provisional application No. 62/148,818, filed on Apr. 17, 2015, provisional application No. 62/148,824, filed on Apr. 17, 2015.

(51) Int. Cl.

| | |
|---|---|
| ***A01N 37/34*** | (2006.01) |
| ***A01N 41/10*** | (2006.01) |
| ***A01N 43/40*** | (2006.01) |
| ***A01N 43/60*** | (2006.01) |
| ***A01N 43/653*** | (2006.01) |
| ***A01N 43/707*** | (2006.01) |
| ***A01N 43/82*** | (2006.01) |
| ***A01N 43/90*** | (2006.01) |
| ***C07C 233/63*** | (2006.01) |
| ***C07C 233/65*** | (2006.01) |
| ***C07C 237/22*** | (2006.01) |
| ***C07C 237/42*** | (2006.01) |
| ***C07C 255/29*** | (2006.01) |
| ***C07C 255/46*** | (2006.01) |
| ***C07C 255/57*** | (2006.01) |
| ***C07C 255/60*** | (2006.01) |
| ***C07C 259/10*** | (2006.01) |
| ***C07C 271/28*** | (2006.01) |
| ***C07C 271/66*** | (2006.01) |
| ***C07C 311/08*** | (2006.01) |
| ***C07C 311/46*** | (2006.01) |
| ***C07C 317/14*** | (2006.01) |
| ***C07C 317/28*** | (2006.01) |
| ***C07C 317/40*** | (2006.01) |
| ***C07C 317/50*** | (2006.01) |
| ***C07C 323/41*** | (2006.01) |
| ***C07C 323/42*** | (2006.01) |
| ***C07C 323/59*** | (2006.01) |
| ***C07C 331/12*** | (2006.01) |
| ***C07C 381/10*** | (2006.01) |
| ***C07D 205/04*** | (2006.01) |
| ***C07D 207/10*** | (2006.01) |
| ***C07D 207/273*** | (2006.01) |
| ***C07D 207/452*** | (2006.01) |
| ***C07D 209/49*** | (2006.01) |
| ***C07D 213/56*** | (2006.01) |
| ***C07D 213/75*** | (2006.01) |
| ***C07D 213/81*** | (2006.01) |
| ***C07D 213/84*** | (2006.01) |
| ***C07D 213/89*** | (2006.01) |
| ***C07D 215/227*** | (2006.01) |
| ***C07D 215/38*** | (2006.01) |
| ***C07D 231/12*** | (2006.01) |
| ***C07D 231/56*** | (2006.01) |
| ***C07D 233/36*** | (2006.01) |
| ***C07D 233/80*** | (2006.01) |
| ***C07D 235/30*** | (2006.01) |
| ***C07D 241/20*** | (2006.01) |
| ***C07D 249/08*** | (2006.01) |
| ***C07D 253/07*** | (2006.01) |
| ***C07D 261/12*** | (2006.01) |
| ***C07D 263/26*** | (2006.01) |
| ***C07D 277/30*** | (2006.01) |
| ***C07D 277/36*** | (2006.01) |
| ***C07D 285/06*** | (2006.01) |
| ***C07D 295/32*** | (2006.01) |
| ***C07D 305/08*** | (2006.01) |
| ***C07D 307/33*** | (2006.01) |
| ***C07D 307/52*** | (2006.01) |
| ***C07D 309/14*** | (2006.01) |
| ***C07D 331/04*** | (2006.01) |
| ***C07D 333/36*** | (2006.01) |
| ***C07D 333/48*** | (2006.01) |
| ***C07D 333/60*** | (2006.01) |
| ***C07D 487/04*** | (2006.01) |

(52) U.S. Cl.

CPC ............ *A01N 43/40* (2013.01); *A01N 43/60* (2013.01); *A01N 43/653* (2013.01); *A01N 43/707* (2013.01); *A01N 43/82* (2013.01); *A01N 43/90* (2013.01); *C07C 233/63* (2013.01); *C07C 233/65* (2013.01); *C07C 237/22* (2013.01); *C07C 237/42* (2013.01); *C07C 255/29* (2013.01); *C07C 255/46* (2013.01); *C07C 255/57* (2013.01); *C07C 255/60* (2013.01); *C07C 259/10* (2013.01); *C07C 271/28* (2013.01); *C07C 271/66* (2013.01); *C07C 311/08* (2013.01); *C07C 311/46* (2013.01); *C07C 317/14* (2013.01); *C07C 317/28* (2013.01); *C07C 317/40* (2013.01); *C07C 317/50* (2013.01); *C07C 323/41* (2013.01); *C07C 323/42* (2013.01); *C07C 323/59* (2013.01); *C07C 331/12* (2013.01); *C07C 381/10* (2013.01); *C07D 205/04* (2013.01); *C07D 207/10* (2013.01); *C07D 207/273* (2013.01); *C07D 207/452* (2013.01); *C07D 209/49* (2013.01); *C07D 213/56* (2013.01); *C07D 213/75* (2013.01); *C07D 213/81* (2013.01); *C07D 213/84* (2013.01); *C07D 213/89* (2013.01); *C07D 215/227* (2013.01); *C07D 215/38* (2013.01); *C07D 231/12* (2013.01); *C07D 231/56* (2013.01); *C07D 233/36* (2013.01); *C07D 233/80* (2013.01); *C07D 235/30* (2013.01); *C07D 241/20* (2013.01); *C07D 249/08* (2013.01); *C07D 253/07* (2013.01); *C07D 261/12* (2013.01); *C07D 263/26* (2013.01); *C07D 277/30* (2013.01); *C07D 277/36* (2013.01); *C07D 285/06* (2013.01); *C07D 295/32* (2013.01); *C07D 305/08* (2013.01); *C07D 307/33* (2013.01); *C07D 307/52* (2013.01); *C07D 309/14* (2013.01); *C07D 331/04* (2013.01); *C07D 333/36* (2013.01); *C07D 333/48* (2013.01); *C07D 333/60* (2013.01); *C07D 487/04* (2013.01); *C07C 2601/02* (2017.05); *C07C 2601/04* (2017.05); *C07C 2601/08* (2017.05); *C07C 2601/14* (2017.05)

(58) Field of Classification Search

CPC ...... A01N 43/707; A01N 43/82; A01N 43/90; C07C 233/63; C07C 233/65; C07C 237/22; C07C 237/42; C07C 255/29; C07C 255/46; C07C 255/57; C07C 255/60; C07C 259/10; C07C 271/28; C07C 271/66; C07C 311/08; C07C 311/46; C07C 317/14; C07C 317/28; C07C 317/40; C07C 317/50; C07C 323/41; C07C 323/42; C07C 323/59; C07C 331/12; C07C 381/10; C07D 205/04; C07D 207/10; C07D 207/273; C07D 207/452; C07D 209/49; C07D 213/56; C07D 213/75; C07D 213/81; C07D 213/84; C07D 213/89; C07D 215/277; C07D 215/38; C07D 233/36; C07D 233/80; C07D 235/30; C07D 241/20; C07D 249/08; C07D 253/07; C07D 261/12; C07D 263/26; C07D 277/30; C07D 277/36; C07D 285/06

See application file for complete search history.

(56) References Cited

U.S. PATENT DOCUMENTS

| | | | |
|---|---|---|---|
| 8,247,597 B2 | 8/2012 | Fair et al. | |
| 8,492,404 B2 * | 7/2013 | Martin .................... | A61P 17/06 546/162 |
| 8,756,068 B2 | 6/2014 | Kikuiri et al. | |
| 9,215,870 B2 | 12/2015 | Lo et al. | |
| 9,781,935 B2 * | 10/2017 | Heemstra ............. | C07D 277/36 |
| 9,795,139 B2 | 10/2017 | Eckelbarger et al. | |
| 9,795,140 B2 | 10/2017 | Martin et al. | |
| 10,219,516 B2 * | 3/2019 | Heemstra .............. | C07C 311/08 |
| 10,239,817 B2 | 3/2019 | Choy et al. | |
| 10,258,045 B2 | 4/2019 | Heemstra et al. | |
| 10,993,440 B2 | 5/2021 | Heemstra et al. | |
| 11,632,957 B2 | 4/2023 | Heemstra et al. | |
| 2002/0068838 A1 | 6/2002 | Demassey et al. | |
| 2003/0225302 A1 | 12/2003 | Demassey et al. | |
| 2007/0072862 A1 | 3/2007 | DiMauro et al. | |
| 2009/0306189 A1 | 12/2009 | Raemaekers et al. | |
| 2009/0326065 A1 | 12/2009 | Matsumoto et al. | |
| 2010/0234373 A1 | 9/2010 | DiMauro et al. | |
| 2014/0171308 A1 | 6/2014 | Lo et al. | |
| 2016/0302417 A1 | 10/2016 | Eckelbarger et al. | |
| 2017/0339961 A1 | 11/2017 | Heemstra et al. | |
| 2018/0000087 A1 | 1/2018 | Eckelbarger et al. | |
| 2018/0007911 A1 | 1/2018 | Martin et al. | |
| 2018/0098541 A1 | 4/2018 | Heemstra et al. | |
| 2018/0099919 A1 | 4/2018 | Choy et al. | |
| 2019/0090488 A1 | 3/2019 | Heemstra et al. | |
| 2019/0150452 A1 | 5/2019 | Heemstra et al. | |
| 2019/0166847 A1 | 6/2019 | Heemstra et al. | |
| 2021/0015098 A1 | 1/2021 | Martin et al. | |
| 2023/0180761 A1 | 6/2023 | Heemstra et al. | |

FOREIGN PATENT DOCUMENTS

| | | | |
|---|---|---|---|
| EP | 2319830 | A1 | 5/2011 |
| EP | 3283459 | B1 | 5/2019 |
| EP | 3578543 | A1 | 12/2019 |
| JP | H1171336 | A | 3/1999 |
| WO | 9008126 | A1 | 7/1990 |
| WO | 9310100 | A1 | 5/1993 |
| WO | 2005019240 | A2 | 3/2005 |
| WO | 2008107091 | A1 | 9/2008 |
| WO | 2010127928 | A1 | 11/2010 |
| WO | 2010144959 | A1 | 12/2010 |
| WO | 2011002951 | A1 | 1/2011 |
| WO | 2014120355 | A1 | 8/2014 |
| WO | 2016168056 | A1 | 10/2016 |
| WO | 2016168058 | A1 | 10/2016 |
| WO | 2016168059 | A1 | 10/2016 |
| WO | 2017165256 | A1 | 9/2017 |
| WO | 2018071320 | A1 | 4/2018 |
| WO | 2018071327 | A1 | 4/2018 |
| WO | 2018224455 | A1 | 12/2018 |
| WO | 2019121143 | A1 | 6/2019 |
| WO | 2019185413 | A1 | 10/2019 |
| WO | 2019194982 | A1 | 10/2019 |

OTHER PUBLICATIONS

Gall D.L., et al., "Stereochemical Features of Glutathione-Dependent Enzymes in the *Sphingobium* sp. Strain SYK-6 Beta-Aryl Etherase Pathway," The Journal of Biological Chemistry, Mar. 21, 2014, vol. 289, No. 12, pp. 8656-8667.

Govorushko S.M., "Mammals and Birds as Agricultural Pests: Global Situation," Agricultural Biology, 2014, vol. 6, pp. 15-25.

International Preliminary Report on Patentability for International Application No. PCT/US2016/026409, mailed Oct. 26, 2017, 07 Pages.

International Preliminary Report on Patentability for International Application No. PCT/US2016/026413, mailed Oct. 26, 2017, 7 Pages.

International Preliminary Report on Patentability for International Application No. PCT/US2016/026417, mailed Oct. 26, 2017, 08 Pages.

International Search Report and Written Opinion for International Application No. PCT/US2016/026409, mailed Jun. 23, 2016, 09 Pages.

International Search Report and Written Opinion for International Application No. PCT/US2016/026413, mailed Jun. 17, 2016, 8 Pages.

International Search Report and Written Opinion for International Application No. PCT/US2016/026417, mailed Jun. 17, 2016, 10 Pages.

International Search Report and Written Opinion for International Application No. PCT/US2017/055699, mailed Jan. 3, 2018, 8 Pages.

International Search Report and Written Opinion for International Application No. PCT/US2017/055738, mailed Jan. 4, 2018, 10 Pages.

Izvestiya Akademii Nauk SSSR, Seriya Khimicheskaya, 1975, pp. 2577-2579, vol. 11, ISSN 0004274310.

Izvestiya Akademii Nauk SSSR, Seriya Khimicheskaya, 1979, vol. 10, pp. 2381-2383, ISSN 0004274312.

Kovalenko V.N., et al., "The Resolution of Trans-2,2-Dichloro-3-Methylcyclopropanecarboxylic Acid via Crystallization of its Salts With (+)- and (-)-α-Phenylethylamine, and the Transformation of the Resulting Enantiomers into R)- and (S)-Dimethyl 2-Methylsuccinates," Tetrahedron: Asymmetry, Elsevier Science Publishers, Amsterdam, NL, Jan. 17, 2011, vol. 22, No. 1, pp. 26-30.

Kryshtal G.V., et al., "Recoverable Phase-Transfer Catalysts with Fluorinated Anions: Generation and Reactions of Dichlorocarbene and CCI3 Anion in the Heterogeneous System KOH(s)/CHCI3/nBu4NPF6," European Journal of Organic Chemistry, 2008, vol. 10, pp. 1777-1782.

Russian Journal of Organic Chemistry, 2013, vol. 4911, pp. 1580-1593, ISSN 0004274313.

Shchekina E.G., "Helminthiasis: a Modern View of the Problem," Provisional, 2007, No. 12, 8 pages, found on the Internet: https://provisor.com.ua/archive/2007/N12/gelmintoza.php, entire document.

Sheshenev A.E., et al., "Generation and Stereoselective Transformations of 3-Phenylcyclopropene," Tetrahedron, Elsevier Science Publishers, Amsterdam, NL, Sep. 30, 2009, vol. 65, No. 48, pp. 10036-10046, DOI:10.1016/j.tet.2009.09.098, ISSN 0040-4020, XP026707925.

Sheshenev A.E., et al., "Stereo-and Regiocontrol in Ene-dimerisation and Trimerisation of 1-Trimethylsilyl-3-Phenylcyclopropene," Tetrahedron, Elsevier Science Publishers, Amsterdam, NL, Dec. 19, 2009, vol. 65, No. 51, pp. 10552-10564.

(56) References Cited

OTHER PUBLICATIONS

Shvetsov S.V., et al., "Modern Computational Methods of Evaluation of Herbicidal and Pesticidal Activity of Organic Compounds," Bashkir Chemical Journal, 2013, vol. 20(2), pp. 134-136.

Tetrahedron Letters, 2002, vol. 43, pp. 2699-2703, ISSN 0004562943.

Tyukavkina N.A., et al., Bioorganic Chemistry, 3rd edition, revised and updated, M.: Drofa, Moscow, 2004, vol. 539, pp. 47-85.

University of Groningen, Sel. Org. React. Database(SORD)1993, 1993, pp. 13-35, ISSN 0004274307.

Yasukochi H., et al., "Practical, General, and Systematic Method for Optical Resolution of Gem-Dihalo—and Monohalocyclopropanecarboxylic Acids Utilizing Chiral 1, 1'-Binaphtholmonemethyl Ethers: Application to the Synthesis of Three Chiral Pesticides," Organic & Biomolecular Chemistry, Royal Society of Chemistry, United Kingdom, 2008, vol. 6, No. 3, pp. 540 to 547.

Zhurnal Organicheskoi Khimii, 1983, vol. 192, pp. 263-265, ISSN 0004562946.

* cited by examiner

MOLECULES HAVING PESTICIDAL UTILITY, AND INTERMEDIATES, COMPOSITIONS, AND PROCESSES, RELATED THERETO

CROSS-REFERENCES TO RELATED APPLICATIONS

This application is a continuation of and claims the benefit of U.S. application Ser. No. 18/802,256, which is a continuation of and claims the benefit of U.S. application Ser. No. 18/166,601, which is a continuation of and claims the benefit of U.S. application Ser. No. 16/794,955, now U.S. Pat. No. 11,632,957, which is a continuation of and claims the benefit of U.S. application Ser. No. 16/203,690, which is a continuation of and claims the benefit of U.S. application Ser. No. 15/679,415, now U.S. Pat. No. 10,219,516, which is a divisional of and claims the benefit of U.S. application Ser. No. 15/092,650, now U.S. Pat. No. 9,781,935, which claims the benefit of, and priority from, U.S. provisional application Ser. Nos. 62/148,830; 62/148,837; 62/148,809; 62/148,814; 62/148,818; and 62/148,824; all of which were filed on Apr. 17, 2015. The entire contents of all of the above-identified applications are hereby incorporated by reference into this application.

FIELD OF THIS DISCLOSURE

This disclosure relates to the field of molecules having pesticidal utility against pests in Phyla Arthropoda, Mollusca, and Nematoda, processes to produce such molecules, intermediates used in such processes, pesticidal compositions containing such molecules, and processes of using such pesticidal compositions against such pests. These pesticidal compositions may be used, for example, as acaricides, insecticides, miticides, molluscicides, and nematicides.

BACKGROUND OF THIS DISCLOSURE

"Many of the most dangerous human diseases are transmitted by insect vectors" (Rivero et al.). "Historically, malaria, dengue, yellow fever, plague, filariasis, louse-borne typhus, trypanomiasis, leishmaniasis, and other vector borne diseases were responsible for more human disease and death in the $17^{th}$ through the early $20^{th}$ centuries than all other causes combined" (Gubler). Vector-borne diseases are responsible for about 17% of the global parasitic and infectious diseases. Malaria alone causes over 800,000 deaths a year, 85% of which occur in children under five years of age. Each year there are about 50 to about 100 million cases of dengue fever. A further 250,000 to 500,000 cases of dengue hemorrhagic fever occur each year (Matthews). Vector control plays a critical role in the prevention and control of infectious diseases. However, insecticide resistance, including resistance to multiple insecticides, has arisen in all insect species that are major vectors of human diseases (Rivero et al.). Recently, more than 550 arthropod species have developed resistance to at least one pesticide (Whalon et al.). Furthermore, the cases of insect resistance continue to exceed by far the number of cases of herbicide and fungicide resistance (Sparks et al.).

Each year insects, plant pathogens, and weeds, destroy more than 40% of all food production. This loss occurs despite the application of pesticides and the use of a wide array of non-chemical controls, such as, crop rotations, and biological controls. If just some of this food could be saved, it could be used to feed the more than three billion people in the world who are malnourished (Pimental).

Plant parasitic nematodes are among the most widespread pests, and are frequently one of the most insidious and costly. It has been estimated that losses attributable to nematodes are from about 9% in developed countries to about 15% in undeveloped countries. However, in the United States of America a survey of 35 States on various crops indicated nematode-derived losses of up to 25% (Nicol et al.).

It is noted that gastropods (slugs and snails) are pests of less economic importance than other arthropods or nematodes, but in certain places, they may reduce yields substantially, severely affecting the quality of harvested products, as well as, transmitting human, animal, and plant diseases. While only a few dozen species of gastropods are serious regional pests, a handful of species are important pests on a worldwide scale. In particular, gastropods affect a wide variety of agricultural and horticultural crops, such as, arable, pastoral, and fiber crops; vegetables; bush and tree fruits; herbs; and ornamentals (Speiser).

Termites cause damage to all types of private and public structures, as well as to agricultural and forestry resources. In 2005, it was estimated that termites cause over US$50 billion in damage worldwide each year (Korb).

Consequently, for many reasons, including those mentioned above, there is an on-going need for the costly (estimated to be about US$256 million per pesticide in 2010), time-consuming (on average about 10 years per pesticide), and difficult, development of new pesticides (CropLife America).

CERTAIN REFERENCES CITED IN THIS DISCLOSURE

CropLife America, The Cost of New Agrochemical Product Discovery, Development & Registration, and Research & Development predictions for the Future, 2010.

Drewes, M., Tietjen, K., Sparks, T. C., High-Throughput Screening in Agrochemical Research, *Modern Methods in Crop Protection Research*, Part I, *Methods for the Design and Optimization of New Active Ingredients*, Edited by Jeschke, P., Kramer, W., Schirmer, U., and Matthias W., p. 1-20, 2012.

Gubler, D., Resurgent Vector-Borne Diseases as a Global Health Problem, Emerging Infectious Diseases, Vol. 4, No. 3, p. 442-450, 1998.

Korb, J., Termites, Current Biology, Vol. 17, No. 23, 2007.

Matthews, G., Integrated Vector Management: Controlling Vectors of Malaria and Other Insect Vector Borne Diseases, Ch. 1, p. 1, 2011.

Nicol, J., Turner S., Coyne, L., den Nijs, L., Hocksland, L., Tahna-Maafi, Z., Current Nematode Threats to World Agriculture, *Genomic and Molecular Genetics of Plant—Nematode Interactions*, p. 21-43, 2011.

Pimental, D., Pest Control in World Agriculture, *Agricultural Sciences*—Vol. II, 2009.

Rivero, A., Vezilier, J., Weill, M., Read, A., Gandon, S., Insect Control of Vector-Borne Diseases: When is Insect Resistance a Problem?*Public Library of Science Pathogens*, Vol. 6, No. 8, p. 1-9, 2010.

Sparks T. C., Nauen R., IRAC: Mode of action classification and insecticide resistance management, *Pesticide Biochemistry and Physiology* (2014) available online 4 Dec. 2014.

Speiser, B., Molluscicides, *Encyclopedia of Pest Management*, Ch. 219, p. 506-508, 2002.

Whalon, M., Mota-Sanchez, D., Hollingworth, R., Analysis of Global Pesticide Resistance in Arthropods, *Global Pesticide Resistance in Arthropods*, Ch. 1, p. 5-33, 2008.

Definitions Used in this Disclosure

The examples given in these definitions are generally non-exhaustive and must not be construed as limiting this disclosure. It is understood that a substituent should comply with chemical bonding rules and steric compatibility constraints in relation to the particular molecule to which it is attached. These definitions are only to be used for the purposes of this disclosure.

The phrase "active ingredient" means a material having activity useful in controlling pests, and/or that is useful in helping other materials have better activity in controlling pests, examples of such materials include, but are not limited to, acaricides, algicides, antifeedants, avicides, bactericides, bird repellents, chemosterilants, fungicides, herbicide safeners, herbicides, insect attractants, insect repellents, insecticides, mammal repellents, mating disrupters, molluscicides, nematicides, plant activators, plant growth regulators, rodenticides, synergists, and virucides (see alanwood.net). Specific examples of such materials include, but are not limited to, the materials listed in active ingredient group alpha.

The phrase "active ingredient group alpha" (hereafter "AIGA") means collectively the following materials:

(1) (3-ethoxypropyl)mercury bromide, 1,2-dibromoethane, 1,2-dichloroethane, 1,2-dichloropropane, 1,3-dichloropropene, 1-MCP, 1-methylcyclopropene, 1-naphthol, 2-(octylthio)ethanol, 2,3,3-TPA, 2,3,5-triiodobenzoic acid, 2,3,6-TBA, 2,4,5-T, 2,4,5-TB, 2,4,5-TP, 2,4-D, 2,4-DB, 2,4-DEB, 2,4-DEP, 2,4-DES, 2,4-DP, 2,4-MCPA, 2,4-MCPB, 2iP, 2-methoxyethylmercury chloride, 2-phenylphenol, 3,4-DA, 3,4-DB, 3,4-DP, 3,6-dichloropicolinic acid, 4-aminopyridine, 4-CPA, 4-CPB, 4-CPP, 4-hydroxyphenethyl alcohol, 8-hydroxyquinoline sulfate, 8-phenylmercurioxyquinoline, abamectin, abamectin-aminomethyl, abscisic acid, ACC, acephate, acequinocyl, acetamiprid, acethion, acetochlor, acetofenate, acetophos, acetoprole, acibenzolar, acifluorfen, aclonifen, ACN, acrep, acrinathrin, acrolein, acrylonitrile, acypetacs, afidopyropen, afoxolaner, alachlor, alanap, alanycarb, albendazole, aldicarb, aldicarb sulfone, aldimorph, aldoxycarb, aldrin, allethrin, allicin, allidochlor, allosamidin, alloxydim, allyl alcohol, allyxycarb, alorac, a/pha-cypermethrin, alpha-endosulfan, alphamethrin, altretamine, aluminium phosphide, aluminum phosphide, ametoctradin, ametridione, ametryn, ametryne, amibuzin, amicarbazone, amicarthiazol, amidithion, amidoflumet, amidosulfuron, aminocarb, aminocyclopyrachlor, aminopyralid, aminotriazole, amiprofos-methyl, amiprophos, amiprophos-methyl, amisulbrom, amiton, amitraz, amitrole, ammonium sulfamate, amobam, amorphous silica gel, amorphous silicon dioxide, ampropylfos, AMS, anabasine, ancymidol, anilazine, anilofos, anisuron, anthraquinone, antu, apholate, aramite, arprocarb, arsenous oxide, asomate, aspirin, asulam, athidathion, atraton, atrazine, aureofungin, avermectin B1, AVG, aviglycine, azaconazole, azadirachtin, azafenidin, azamethiphos, azidithion, azimsulfuron, azinphosethyl, azinphos-ethyl, azinphosmethyl, azinphos-methyl, aziprotryn, aziprotryne, azithiram, azobenzene, azocyclotin, azothoate, azoxystrobin, bachmedesh, barban, barbanate, barium hexafluorosilicate, barium polysulfide, barium silicofluoride, barthrin, basic copper carbonate, basic copper chloride, basic copper sulfate, BCPC, beflubutamid, benalaxyl, benalaxyl-M, benazolin, bencarbazone, benclothiaz, bendaqingbingzhi, bendiocarb, bendioxide, benefin, benfluralin, benfuracarb, benfuresate, benmihuangcaoan, benodanil, benomyl, benoxacor, benoxafos, benquinox, bensulfuron, bensulide, bensultap, bentaluron, bentazon, bentazone, benthiavalicarb, benthiazole, benthiocarb, bentranil, benzadox, benzalkonium chloride, benzamacril, benzamizole, benzamorf, benzene hexachloride, benzfendizone, benzimine, benzipram, benzobicyclon, benzoepin, benzofenap, benzofluor, benzohydroxamic acid, benzomate, benzophosphate, benzothiadiazole, benzovindiflupyr, benzoximate, benzoylprop, benzthiazuron, benzuocaotong, benzyl benzoate, benzyladenine, berberine, beta-cyfluthrin, beta-cypermethrin, bethoxazin, BHC, bialaphos, bicyclopyrone, bifenazate, bifenox, bifenthrin, bifujunzhi, bilanafos, binapacryl, bingqingxiao, bioallethrin, bioethanomethrin, biopermethrin, bioresmethrin, biphenyl, bisazir, bismerthiazol, bismerthiazol-copper, bisphenylmercury methylenedi(x-naphthalene-y-sulphonate), bispyribac, bistrifluron, bisultap, bitertanol, bithionol, bixafen, blasticidin-S, borax, Bordeaux mixture, boric acid, boscalid, BPPS, brassinolide, brassinolide-ethyl, brevicomin, brodifacoum, brofenprox, brofenvalerate, broflanilide, brofluthrinate, bromacil, bromadiolone, bromchlophos, bromethalin, bromethrin, bromfenvinfos, bromoacetamide, bromobonil, bromobutide, bromociclen, bromocyclen, bromo-DDT, bromofenoxim, bromofos, bromomethane, bromophos, bromophos-ethyl, bromopropylate, bromothalonil, bromoxynil, brompyrazon, bromuconazole, bronopol, BRP, BTH, bucarpolate, bufencarb, buminafos, bupirimate, buprofezin, Burgundy mixture, busulfan, busulphan, butacarb, butachlor, butafenacil, butam, butamifos, butane-fipronil, butathiofos, butenachlor, butene-fipronil, butethrin, buthidazole, buthiobate, buthiuron, butifos, butocarboxim, butonate, butopyronoxyl, butoxycarboxim, butralin, butrizol, butroxydim, buturon, butylamine, butylate, butylchlorophos, butylene-fipronil, cacodylic acid, cadusafos, cafenstrole, calciferol, calcium arsenate, calcium chlorate, calcium cyanamide, calcium cyanide, calcium polysulfide, calvinphos, cambendichlor, camphechlor, camphor, captafol, captan, carbam, carbamorph, carbanolate, carbaril, carbaryl, carbasulam, carbathion, carbendazim, carbendazol, carbetamide, carbofenotion, carbofuran, carbon disulfide, carbon tetrachloride, carbonyl sulfide, carbophenothion, carbophos, carbosulfan, carboxazole, carboxide, carboxin, carfentrazone, carpropamid, cartap, carvacrol, carvone, CAVP, CDAA, CDEA, CDEC, cellocidin, CEPC, ceralure, cerenox, cevadilla, Cheshunt mixture, chinalphos, chinalphos-methyl, chinomethionat, chinomethionate, chiralaxyl, chitosan, chlobenthiazone, chlomethoxyfen, chloralose, chloramben, chloramine phosphorus, chloramphenicol, chloraniformethan, chloranil, chloranocryl, chlorantraniliprole, chlorazifop, chlorazine, chlorbenside, chlorbenzuron, chlorbicyclen, chlorbromuron, chlorbufam, chlordane, chlordecone, chlordimeform, chlorempenthrin, chloretazate, chlorethephon, chlorethoxyfos, chloreturon, chlorfenac, chlorfenapyr, chlorfenazole, chlorfenethol, chlorfenidim, chlorfenprop, chlorfenson, chlorfensulphide, chlorfenvinphos, chlorfenvinphos-methyl, chlorfluazuron, chlorflurazole, chlorflurecol, chlorfluren, chlorflurenol, chloridazon, chlorimuron, chlorinate, chlor-IPC, chlormephos, chlormequat, chlormesulone, chlormethoxynil, chlornidine, chlornitrofen, chloroacetic acid, chlorobenzilate, chlorodinitronaphthalenes, chlorofénizon, chloroform, chloromebuform, chloromethiuron, chloroneb, chlorophacinone, chlorophos, chloropicrin, chloropon, chloropropylate, chlorothalonil, chlorotoluron, chloroxifenidim, chloroxuron, chloroxynil, chlorphonium, chlorphoxim, chlorprazophos, chlorprocarb, chlorpropham, chlorpyrifos, chlorpyrifos-methyl, chlorquinox, chlorsulfuron, chlorthal, chlorthiamid, chlorthiophos, chlortoluron, chlozolinate, chltosan, cholecalciferol, choline chloride, chromafenozide, cicloheximide, cimectacarb, cimetacarb, cinerin I, cinerin II, cinerins, cinidon-ethyl, cinmethylin, cinosulfuron, cintofen, ciobutide, cisanilide, cismethrin, clacyfos, clefoxydim, clenpirin, clenpyrin, clethodim, climbazole, cliodinate, clodinafop, cloethocarb, clofencet, clofenotane, clofentezine, clofenvinfos, clofibric acid, clofop, clomazone, clomeprop, clonitralid, cloprop, cloproxydim, clopyralid, cloquintocet, cloransulam, closantel, clothianidin, clotrimazole, cloxyfonac, cloxylacon, clozylacon, CMA, CMMP, CMP, CMU, codlelure, colecalciferol, colophonate, copper 8-quinolinolate, copper acetate, copper acetoarsenite, copper arsenate, copper carbonate, basic, copper hydroxide, copper naphthenate, copper oleate, copper oxychloride, copper silicate, copper sulfate, copper sulfate, basic, copper zinc chromate, coumachlor, coumafène, coumafos, coumafuryl, coumaphos, coumatetralyl, coumethoxystrobin, coumithoate, coumoxystrobin, CPMC, CPMF, CPPC, credazine, cresol, cresylic acid, crimidine, crotamiton, crotoxyfos, crotoxyphos, crufomate, cryolite, cue-lure, cufraneb, cumyleron, cumyluron, cuprobam, cuprous oxide, curcumenol, CVMP, cyanamide, cyanatryn, cyanazine, cyanofenphos, cyanogen, cyanophos, cyanthoate, cyantraniliprole, cyanuric acid, cyazofamid, cybutryne, cyclafuramid, cyclanilide, cyclaniliprole, cyclethrin, cycloate, cycloheximide, cycloprate, cycloprothrin, cyclopyrimorate, cyclosulfamuron, cycloxydim, cycluron, cyenopyrafen, cyflufenamid, cyflumetofen, cyfluthrin, cyhalofop, cyhalothrin, cyhexatin, cymiazole, cymoxanil, cyometrinil, cypendazole, cypermethrin, cyperquat, cyphenothrin, cyprazine, cyprazole, cyproconazole, cyprodinil, cyprofuram, cypromid, cyprosulfamide, cyromazine, cythioate, cytrex, daimuron, dalapon, daminozide, dayoutong, dazomet, DBCP, d-camphor, DCB, DCIP, DCPA, DCPTA, DCU, DDD, DDPP, DDT, DDVP, debacarb, decafentin, decamethrin, decarbofuran, deet, dehydroacetic acid, deiquat, delachlor, delnav, deltamethrin, demephion, demephion-O, demephion-S, demeton, demeton-methyl, demeton-O, demeton-O-methyl, demeton-S, demeton-S-methyl, demeton-S-methyl sulphone, demeton-S-methylsulphon, DEP, depalléthrine, derris, desmedipham, desmetryn, desmetryne, d-fanshiluquebingjuzhi, diafenthiuron, dialifor, dialifos, diallate, diamidafos, dianat, diatomaceous earth, diatomite, diazinon, dibrom, dibutyl phthalate, dibutyl succinate, dicamba, dicapthon, dichlobenil, dichlofenthion, dichlofluanid, dichlone, dichloralurea, dichlorbenzuron, dichlorfenidim, dichlorflurecol, dichlorflurenol, dichlormate, dichlormid, dichloromethane, dichloromezotiaz, dichlorophen, dichlorprop, dichlorprop-P, dichlorvos, dichlozolin, dichlozoline, diclobutrazol, diclocymet, diclofop, diclomezine, dicloran, diclosulam, dicofol, dicophane, dicoumarol, dicresyl, dicrotophos, dicryl, dicumarol, dicyclanil, dicyclonon, dieldrin, dienochlor, diethamquat, diethatyl, diethion, diéthion, diethofencarb, dietholate, diéthon, diethyl pyrocarbonate, diethyltoluamide, difenacoum, difenoconazole, difenopenten, difenoxuron, difenzoquat, difethialone, diflovidazin, diflubenzuron, diflufenican, diflufenicanil, diflufenzopyr, diflumetorim, dikegulac, dilor, dimatif, dimefluthrin, dimefox, dimefuron, dimehypo, dimepiperate, dimetachlone, dimetan, dimethacarb, dimethachlone, dimethachlor, dimethametryn, dimethenamid, dimethenamid-P, dimethipin, dimethirimol, dimethoate, dimethomorph, dimethrin, dimethyl carbate, dimethyl disulfide, dimethyl phthalate, dimethylvinphos, dimetilan, dimexano, dimidazon, dimoxystrobin, dimpylate, dimuron, dinex, dingjunezuo, diniconazole, diniconazole-M, dinitramine, dinitrophenols, dinobuton, dinocap, dinocap-4, dinocap-6, dinocton, dinofenate, dinopenton, dinoprop, dinosam, dinoseb, dinosulfon, dinotefuran, dinoterb, dinoterbon, diofenolan, dioxabenzofos, dioxacarb, dioxathion, dioxation, diphacin, diphacinone, diphenadione, diphenamid, diphenamide, diphenyl sulfone, diphenylamine, diphenylsulphide, diprogulic acid, dipropalin, dipropetryn, dipterex, dipymetitrone, dipyrithione, diquat, disodium tetraborate, disosultap, disparlure, disugran, disul, disulfiram, disulfoton, ditalimfos, dithianon, dithicrofos, dithioether, dithiométon, dithiopyr, diuron, dixanthogen, d-limonene, DMDS, DMPA, DNOC, dodemorph, dodicin, dodine, dofenapyn, doguadine, dominicalure, doramectin, DPC, drazoxolon, DSMA, d-trans-allethrin, d-trans-resmethrin, dufulin, dymron, EBEP, EBP, ebufos, ecdysterone, echlomezol, EDB, EDC, EDDP, edifenphos, eglinazine, emamectin, EMPC, empenthrin, enadenine, endosulfan, endothal, endothall, endothion, endrin, enestroburin, enilconazole, enoxastrobin, ephirsulfonate, EPN, epocholeone, epofenonane, epoxiconazole, eprinomectin, epronaz, EPTC, erbon, ergocalciferol, erlujixiancaoan, esdépalléthrine, esfenvalerate, ESP, esprocarb, etacelasil, etaconazole, etaphos, etem, ethaboxam, ethachlor, ethalfluralin, ethametsulfuron, ethaprochlor, ethephon, ethidimuron, ethiofencarb, ethiolate, ethion, ethiozin, ethiprole, ethirimol, ethoate-methyl, ethobenzanid, ethofumesate, ethohexadiol, ethoprop, ethoprophos, ethoxyfen, ethoxyquin, ethoxysulfuron, ethychlozate, ethyl formate, ethyl pyrophosphate, ethylan, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, ETM, etnipromid, etobenzanid, etofenprox, etoxazole, etridiazole, etrimfos, étrimphos, eugenol, EXD, famoxadone, famphur, fenac, fenamidone, fenaminosulf, fenaminstrobin, fenamiphos, fenapanil, fenarimol, fenasulam, fenazaflor, fenazaquin, fenbuconazole, fenbutatin oxide, fenchlorazole, fenchlorphos, fenclofos, fenclorim, fenethacarb, fenfluthrin, fenfuram, fenhexamid, fenidin, fenitropan, fenitrothion, fénizon, fenjuntong, fenobucarb, fenolovo, fenoprop, fenothiocarb, fenoxacrim, fenoxanil, fenoxaprop, fenoxaprop-P, fenoxasulfone, fenoxycarb, fenpiclonil, fenpirithrin, fenpropathrin, fenpropidin, fenpropimorph, fenpyrazamine, fenpyroximate, fenquinotrione, fenridazon, fenson, fensulfothion, fenteracol, fenthiaprop, fenthion, fenthion-ethyl, fentiaprop, fentin, fentrazamide, fentrifanil, fenuron, fenuron-TCA, fenvalerate, ferbam, ferimzone, ferric phosphate, ferrous sulfate, fipronil, flamprop, flamprop-M, flazasulfuron, flocoumafen, flometoquin, flonicamid, florasulam, fluacrypyrim, fluazifop, fluazifop-P, fluazinam, fluazolate, fluazuron, flubendiamide, flubenzimine, flubrocythrinate, flucarbazone, flucetosulfuron, fluchloralin, flucofuron, flucycloxuron, flucythrinate, fludioxonil, fluénéthyl, fluenetil, fluensulfone, flufenacet, flufenerim, flufenican, flufenoxuron, flufenoxystrobin, flufenprox, flufenpyr, flufenzine, flufiprole, fluhexafon, flumethrin, flumetover, flumetralin, flumetsulam, flumezin, flumiclorac, flumioxazin, flumipropyn, flumorph, fluometuron, fluopicolide, fluopyram, fluorbenside, fluoridamid, fluoroacetamide, fluoroacetic acid, fluorochloridone, fluorodifen, fluoroglycofen, fluoroimide, fluoromide, fluoromidine, fluoronitrofen, fluoroxypyr, fluothiuron, fluotrimazole, fluoxastrobin, flupoxam, flupropacil, flupropadine, flupropanate, flupyradifurone, flupyrsulfuron, fluquinconazole, fluralaner, flurazole, flurecol, flurenol, fluridone, flurochloridone, fluromidine, fluroxypyr, flurprimidol, flursulamid, flurtamone, flusilazole, flusulfamide, flutenzine, fluthiacet, fluthiamide, flutianil, flutolanil, flutriafol, fluvalinate, fluxapyroxad, fluxofenim, folpel, folpet, fomesafen, fonofos, foramsulfuron, forchlorfenuron, formaldehyde, formetanate, formothion, formparanate, fosamine, fosetyl, fosmethilan, fospirate, fosthiazate, fosthietan, frontalin, fthalide, fuberidazole, fucaojing, fucaomi, fujunmanzhi, fulumi, fumarin, funaihecaoling, fuphenthiourea, furalane, furalaxyl, furamethrin, furametpyr, furan tebufenozide, furathiocarb, furcarbanil, furconazole, furconazole-cis, furethrin, furfural, furilazole, furmecyclox, furophanate, furyloxyfen, gamma-BHC, gamma-cyhalothrin, gamma-HCH, genit, gibberellic acid, gibberellin A3, gibberellins, gliftor, glitor, glucochloralose, glufosinate, glufosinate-P, glyodin, glyoxime, glyphosate, glyphosine, gossyplure, grandlure, griseofulvin, guanoctine, guazatine, halacrinate, halauxifen, halfenprox, halofenozide, halosafen, halosulfuron, haloxydine, haloxyfop, haloxyfop-P, haloxyfop-R, HCA, HCB, HCH, hemel, hempa, HEOD, heptachlor, heptafluthrin, heptenophos, heptopargil, herbimycin, herbimycin A, heterophos, hexachlor, hexachloran, hexachloroacetone, hexachlorobenzene, hexachlorobutadiene, hexachlorophene, hexaconazole, hexaflumuron, hexafluoramin, hexaflurate, hexalure, hexamide, hexazinone, hexylthiofos, hexythiazox, HHDN, holosulf, homobrassinolide, huancaiwo, huanchongjing, huangcaoling, huanjunzuo, hydramethylnon, hydrargaphen, hydrated lime, hydrogen cyanamide, hydrogen cyanide, hydroprene, hydroxyisoxazole, hymexazol, hyquincarb, IAA, IBA, IBP, icaridin, imazalil, imazamethabenz, imazamox, imazapic, imazapyr, imazaquin, imazethapyr, imazosulfuron, imibenconazole, imicyafos, imidacloprid, imidaclothiz, iminoctadine, imiprothrin, inabenfide, indanofan, indaziflam, indoxacarb, inezin, infusorial earth, iodobonil, iodocarb, iodofenphos, iodomethane, iodosulfuron, iofensulfuron, ioxynil, ipazine, IPC, ipconazole, ipfencarbazone, iprobenfos, iprodione, iprovalicarb, iprymidam, ipsdienol, ipsenol, IPSP, IPX, isamidofos, isazofos, isobenzan, isocarbamid, isocarbamide, isocarbophos, isocil, isodrin, isofenphos, isofenphos-methyl, isofetamid, isolan, isomethiozin, isonoruron, isopamphos, isopolinate, isoprocarb, isoprocil, isopropalin, isopropazol, isoprothiolane, isoproturon, isopyrazam, isopyrimol, isothioate, isotianil, isouron, isovaledione, isoxaben, isoxachlortole, isoxadifen, isoxaflutole, isoxapyrifop, isoxathion, isuron, ivermectin, ixoxaben, izopamfos, izopamphos, japonilure, japothrins, jasmolin I, jasmolin II, jasmonic acid, jiahuangchongzong, jiajizengxiaolin, jiaxiangjunzhi, jiecaowan, jiecaoxi, jinganmycin A, jodfenphos, juvenile hormone I, juvenile hormone II, juvenile hormone III, kadethrin, kappa-bifenthrin, kappa-tefluthrin, karbutilate, karetazan, kasugamycin, kejunlin, kelevan, ketospiradox, kieselguhr, kinetin, kinoprene, kiralaxyl, kresoxim-methyl, kuicaoxi, lactofen, lambda-cyhalothrin, latilure, lead arsenate, lenacil, lepimectin, leptophos, lianbenjingzhi, lime sulfur, lindane, lineatin, linuron, lirimfos, litlure, looplure, lufenuron, lüxiancaolin, lvdingjunzhi, lvfumijvzhi, lvxiancaolin, lythidathion, M-74, M-81, MAA, magnesium phosphide, malathion, maldison, maleic hydrazide, malonoben, maltodextrin, MAMA, mancopper, mancozeb, mandestrobin, mandipropamid, maneb, matrine, mazidox, MCC, MCP, MCPA, MCPA-thioethyl, MCPB, MCPP, mebenil, mecarbam, mecarbinzid, mecarphon, mecoprop, mecoprop-P, medimeform, medinoterb, medlure, mefenacet, mefenoxam, mefenpyr, mefluidide, megatomoic acid, melissyl alcohol, melitoxin, MEMC, menazon, MEP, mepanipyrim, meperfluthrin, mephenate, mephosfolan, mepiquat, mepronil, meptyldinocap, mercaptodimethur, mercaptophos, mercaptophos thiol, mercaptothion, mercuric chloride, mercuric oxide, mercurous chloride, merphos, merphos oxide, mesoprazine, mesosulfuron, mesotrione, mesulfen, mesulfenfos, mesulphen, metacresol, metaflumizone, metalaxyl, metalaxyl-M, metaldehyde, metam, metamifop, metamitron, metaphos, metaxon, metazachlor, metazosulfuron, metazoxolon, metconazole, metepa, metflurazon, methabenzthiazuron, methacrifos, methalpropalin, metham, methamidophos, methasulfocarb, methazole, methfuroxam, methibenzuron, methidathion, methiobencarb, methiocarb, methiopyrisulfuron, methiotepa, methiozolin, methiuron, methocrotophos, métholcarb, methometon, methomyl, methoprene, methoprotryn, methoprotryne, methoquin-butyl, methothrin, methoxychlor, methoxyfenozide, methoxyphenone, methyl apholate, methyl bromide, methyl eugenol, methyl iodide, methyl isothiocyanate, methyl parathion, methylacetophos, methylchloroform, methyldithiocarbamic acid, methyldymron, methylene chloride, methyl-isofenphos, methylmercaptophos, methylmercaptophos oxide, methylmercaptophos thiol, methylmercury benzoate, methylmercury dicyandiamide, methylmercury pentachlorophenoxide, methylneodecanamide, methylnitrophos, methyltriazothion, metiozolin, metiram, metiram-zinc, metobenzuron, metobromuron, metofluthrin, metolachlor, metolcarb, metometuron, metominostrobin, metosulam, metoxadiazone, metoxuron, metrafenone, metriam, metribuzin, metrifonate, metriphonate, metsulfovax, metsulfuron, mevinphos, mexacarbate, miechuwei, mieshuan, miewenjuzhi, milbemectin, milbemycin oxime, milneb, mima2nan, mipafox, MIPC, mirex, MNAF, moguchun, molinate, molosultap, momfluorothrin, monalide, monisuron, monoamitraz, monochloroacetic acid, monocrotophos, monolinuron, monomehypo, monosulfiram, monosulfuron, monosultap, monuron, monuron-TCA, morfamquat, moroxydine, morphothion, morzid, moxidectin, MPMC, MSMA, MTMC, muscalure, myclobutanil, myclozolin, myricyl alcohol, N-(ethylmercury)-p-toluenesulphonanilide, NAA, NAAm, nabam, naftalofos, naled, naphthalene, naphthaleneacetamide, naphthalic anhydride, naphthalophos, naphthoxyacetic acids, naphthylacetic acids, naphthylindane-1,3-diones, naphthyloxyacetic acids, naproanilide, napropamide, napropamide-M, naptalam, natamycin, NBPOS, neburea, neburon, nendrin, neonicotine, nichlorfos, niclofen, niclosamide, nicobifen, nicosulfuron, nicotine, nicotine sulfate, nifluridide, nikkomycins, NIP, nipyraclofen, nipyralofen, nitenpyram, nithiazine, nitralin, nitrapyrin, nitrilacarb, nitrofen, nitrofluorfen, nitrostyrene, nitrothal-isopropyl, nobormide, nonanol, norbormide, norea, norflurazon, nornicotine, noruron, novaluron, noviflumuron, NPA, nuarimol, nuranone, OCH, octachlorodipropyl ether, octhilinone, o-dichlorobenzene, ofurace, omethoate, o-phenylphenol, orbencarb, orfralure, orthobencarb, ortho-dichlorobenzene, orthosulfamuron, oryctalure, orysastrobin, oryzalin, osthol, osthole, ostramone, ovatron, ovex, oxabetrinil, oxadiargyl, oxadiazon, oxadixyl, oxamate, oxamyl, oxapyrazon, oxapyrazone, oxasulfuron, oxathiapiprolin, oxaziclomefone, oxine-copper, oxine-Cu, oxolinic acid, oxpoconazole, oxycarboxin, oxydemeton-methyl, oxydeprofos, oxydisulfoton, oxyenadenine, oxyfluorfen, oxymatrine, oxytetracycline, oxythioquinox, PAC, paclobutrazol, paichongding, palléthrine, PAP, para-dichlorobenzene, parafluron, paraquat, parathion, parathion-methyl, parinol, Paris green, PCNB, PCP, PCP—Na, p-dichlorobenzene, PDJ, pebulate, pédinex, pefurazoate, pelargonic acid, penconazole, pencycuron, pendimethalin, penfenate, penflufen, penfluron, penoxalin, penoxsulam, pentachlorophenol, pentachlorophenyl laurate, pentanochlor, penthiopyrad, pentmethrin, pentoxazone, perchlordecone, perfluidone, permethrin, pethoxamid, PHC, phenamacril, phenamacril-ethyl, phénaminosulf, phenazine oxide, phénétacarbe, phenisopham, phenkapton, phenmedipham, phenmedipham-ethyl, phenobenzuron, phenothiol, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosametine, phosazetim, phosazetin, phoscyclotin, phosdiphen, phosethyl, phosfolan, phosfolan-methyl, phosglycin, phosmet, phosnichlor, phosphamide, phosphamidon, phosphine, phosphinothricin, phosphocarb, phosphorus, phostin, phoxim, phoxim-methyl, phthalide, phthalophos, phthalthrin, picarbutrazox, picaridin, picloram, picolinafen, picoxystrobin, pimaricin, pindone, pinoxaden, piperalin, piperazine, piperonyl butoxide, piperonyl cyclonene, piperophos, piproctanly, piproctanyl, piprotal, pirimetaphos, pirimicarb, piriminil, pirimioxyphos, pirimiphos-ethyl, pirimiphos-methyl, pival, pivaldione, plifenate, PMA, PMP, polybutenes, polycarbamate, polychlorcamphene, polyethoxyquinoline, polyoxin D, polyoxins, polyoxorim, polythialan, potassium arsenite, potassium azide, potassium cyanate, potassium ethylxanthate, potassium naphthenate, potassium polysulfide, potassium thiocyanate, pp'-DDT, prallethrin, precocene I, precocene II, precocene III, pretilachlor, primidophos, primisulfuron, probenazole, prochloraz, proclonol, procyazine, procymidone, prodiamine, profenofos, profluazol, profluralin, profluthrin, profoxydim, profurite-aminium, proglinazine, prohexadione, prohydrojasmon, promacyl, promecarb, prometon, prometryn, prometryne, promurit, pronamide, propachlor, propafos, propamidine, propamocarb, propanil, propaphos, propaquizafop, propargite, proparthrin, propazine, propetamphos, propham, propiconazole, propidine, propineb, propisochlor, propoxur, propoxycarbazone, propyl isome, propyrisulfuron, propyzamide, proquinazid, prosuler, prosulfalin, prosulfocarb, prosulfuron, prothidathion, prothiocarb, prothioconazole, prothiofos, prothoate, protrifenbute, proxan, prymidophos, prynachlor, psoralen, psoralene, pydanon, pyflubumide, pymetrozine, pyracarbolid, pyraclofos, pyraclonil, pyraclostrobin, pyraflufen, pyrafluprole, pyramat, pyrametostrobin, pyraoxystrobin, pyrasulfotole, pyraziflumid, pyrazolate, pyrazolynate, pyrazon, pyrazophos, pyrazosulfuron, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridaphenthione, pyridate, pyridinitril, pyrifenox, pyrifluquinazon, pyriftalid, pyrimetaphos, pyrimethanil, pyrimicarbe, pyrimidifen, pyriminobac, pyriminostrobin, pyrimiphos-éthyl, pyrimiphos-methyl, pyrimisulfan, pyrimitate, pyrinuron, pyriofenone, pyriprole, pyripropanol, pyriproxyfen, pyrisoxazole, pyrithiobac, pyrolan, pyroquilon, pyroxasulfone, pyroxsulam, pyroxychlor, pyroxyfur, qincaosuan, qingkuling, quassia, quinacetol, quinalphos, quinalphos-methyl, quinazamid, quinclorac, quinconazole, quinmerac, quinoclamine, quinomethionate, quinonamid, quinothion, quinoxyfen, quintiofos, quintozene, quizalofop, quizalofop-P, quwenzhi, quyingding, rabenzazole, rafoxanide, R-diniconazole, rebemide, reglone, renriduron, rescalure, resmethrin, rhodethanil, rhodojaponin-III, ribavirin, rimsulfuron, rizazole, R-metalaxyl, rodéthanil, ronnel, rotenone, ryania, sabadilla, saflufenacil, saijunmao, saisentong, salicylanilide, salifluofen, sanguinarine, santonin, S-bioallethrin, schradan, scilliroside, sebuthylazine, secbumeton, sedaxane, selamectin, semiamitraz, sesamex, sesamolin, sesone, sethoxydim, sevin, shuangjiaancaolin, shuangjianancaolin, S-hydroprene, siduron, sifumijvzhi, siglure, silafluofen, silatrane, silica aerogel, silica gel, silthiofam, silthiopham, silthiophan, silvex, simazine, simeconazole, simeton, simetryn, simetryne, sintofen, S-kinoprene, slaked lime, SMA, S-methoprene, S-metolachlor, sodium arsenite, sodium azide, sodium chlorate, sodium cyanide, sodium fluoride, sodium fluoroacetate, sodium hexafluorosilicate, sodium naphthenate, sodium o-phenylphenoxide, sodium orthophenylphenoxide, sodium pentachlorophenate, sodium pentachlorophenoxide, sodium polysulfide, sodium silicofluoride, sodium tetrathiocarbonate, sodium thiocyanate, solan, sophamide, spinetoram, spinosad, spirodiclofen, spiromesifen, spirotetramat, spiroxamine, stirofos, streptomycin, strychnine, sulcatol, sulcofuron, sulcotrione, sulfallate, sulfentrazone, sulfiram, sulfluramid, sulfodiazole, sulfometuron, sulfosate, sulfosulfuron, sulfotep, sulfotepp, sulfoxaflor, sulfoxide, sulfoxime, sulfur, sulfuric acid, sulfuryl fluoride, sulglycapin, sulphosate, sulprofos, sultropen, swep, tau-fluvalinate, tavron, tazimcarb, TBTO, TBZ, TCA, TCBA, TCMTB, TCNB, TDE, tebuconazole, tebufenozide, tebufenpyrad, tebufloquin, tebupirimfos, tebutam, tebuthiuron, tecloftalam, tecnazene, tecoram, tedion, teflubenzuron, tefluthrin, tefuryltrione, tembotrione, temefos, temephos, tepa, TEPP, tepraloxydim, teproloxydim, terallethrin, terbacil, terbucarb, terbuchlor, terbufos, terbumeton, terbuthylazine, terbutol, terbutryn, terbutryne, terraclor, terramicin, terramycin, tetcyclacis, tetrachloroethane, tetrachlorvinphos, tetraconazole, tetradifon, tetradisul, tetrafluron, tetramethrin, tetramethylfluthrin, tetramine, tetranactin, tetraniliprole, tetrapion, tetrasul, thallium sulfate, thallous sulfate, thenylchlor, theta-cypermethrin, thiabendazole, thiacloprid, thiadiazine, thiadifluor, thiamethoxam, thiameturon, thiapronil, thiazafluron, thiazfluron, thiazone, thiazopyr, thicrofos, thicyofen, thidiazimin, thidiazuron, thiencarbazone, thifensulfuron, thifluzamide, thimerosal, thimet, thiobencarb, thiocarboxime, thiochlorfenphim, thiochlorphenphime, thiocyanatodinitrobenzenes, thiocyclam, thiodan, thiodiazole-copper, thiodicarb, thiofanocarb, thiofanox, thiofluoximate, thiohempa, thiomersal, thiometon, thionazin, thiophanate, thiophanate-ethyl, thiophanate-methyl, thiophos, thioquinox, thiosemicarbazide, thiosultap, thiotepa, thioxamyl, thiram, thiuram, thuringiensin, tiabendazole, tiadinil, tiafenacil, tiaojiean, TIBA, tifatol, tiocarbazil, tioclorim, tioxazafen, tioxymid, tirpate, TMTD, tolclofos-methyl, tolfenpyrad, tolprocarb, tolpyralate, tolyfluanid, tolylfluanid, tolylmercury acetate, tomarin, topramezone, toxaphene, TPN, tralkoxydim, tralocythrin, tralomethrin, tralopyril, transfluthrin, transpermethrin, tretamine, triacontanol, triadimefon, triadimenol, triafamone, triallate, tri-allate, triamiphos, triapenthenol, triarathene, triarimol, triasulfuron, triazamate, triazbutil, triaziflam, triazophos, triazothion, triazoxide, tribasic copper chloride, tribasic copper sulfate, tribenuron, tribufos, tributyltin oxide, tricamba, trichlamide, trichlopyr, trichlorfon, trichlormetaphos-3, trichloronat, trichloronate, trichlorotrinitrobenzenes, trichlorphon, triclopyr, triclopyricarb, tricresol, tricyclazole, tricyclohexyltin hydroxide, tridemorph, tridiphane, trietazine, trifenmorph, trifenofos, trifloxystrobin, trifloxysulfuron, trifludimoxazin, triflumezopyrim, triflumizole, triflumuron, trifluralin, triflusulfuron, trifop, trifopsime, triforine, trihydroxytriazine, trimedlure, trimethacarb, trimeturon, trinexapac, triphenyltin, triprene, tripropindan, triptolide, tritac, trithialan, triticonazole, tritosulfuron, trunc-call, tuoyelin, uniconazole, uniconazole-P, urbacide, uredepa, valerate, validamycin, validamycin A, valifenalate, valone, vamidothion, vangard, vaniliprole, vernolate, vinclozolin, vitamin D3, warfarin, xiaochongliulin, xinjunan, xiwojunan, xiwojunzhi, XMC, xylachlor, xylenols, xylylcarb, xymiazole, yishijing, zarilamid, zeatin, zengxiaoan, zengxiaolin, zeta-cypermethrin, zinc naphthenate, zinc phosphide, zinc thiazole, zinc thiozole, zinc trichlorophenate, zinc trichlorophenoxide, zineb, ziram, zolaprofos, zoocoumarin, zoxamide, zuoanjunzhi, zuocaoan, zuojunzhi, zuomihuanglong, α-chlorohydrin, α-ecdysone, α-multistriatin, α-naphthaleneacetic acids, and β-ecdysone;

(2) the following molecules (a) N-(3-chloro-1-(pyridin-3-yl)-1H-pyrazol-4-yl)-N-ethyl-3-((3,3,3-trifluoropropyl)thio)propanamide (hereafter "AI-1")

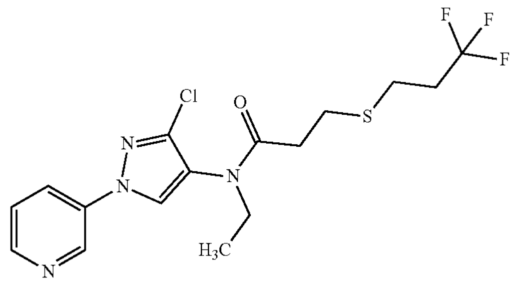 [SMILES: CCN(C(=O)CCSCCC(F)(F)F)c1cn(-c2cccnc2)nc1Cl]

(b) (3S,6S,7R,8R)-8-benzyl-3-(3-((isobutyryloxy)methoxy)-4-methoxypicolinamido)-6-methyl-4,9-dioxo-1,5-dioxonan-7-yl isobutyrate (hereafter "AI-2")

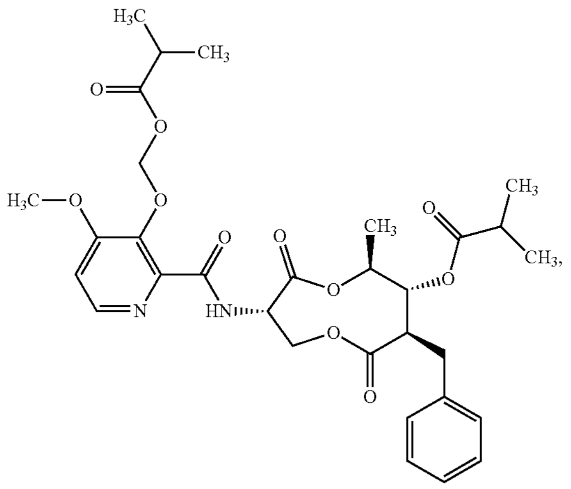 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

(3) a molecule known as Lotilaner that has the following structure

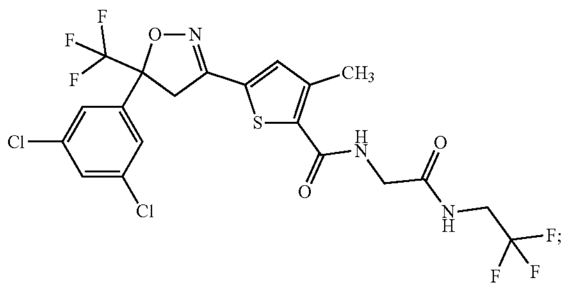 [SMILES: Cc1cc(C2=NOC(c3cc(Cl)cc(Cl)c3)(C(F)(F)F)C2)sc1C(=O)NCC(=O)NCC(F)(F)F]

and (4) the following molecules in Table A

TABLE A

| Structure of M#- active ingredients | |
|---|---|
| M# | Structure |
| M1 | 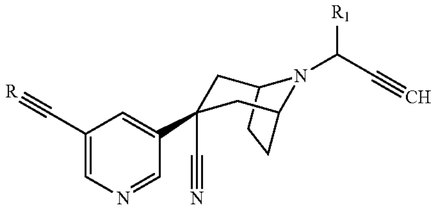 R = CH, N $R_1$ = H, Me |
| M2 | 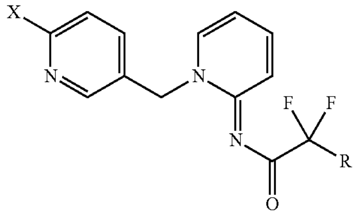 X = F, Cl R = H, F |
| M3 | 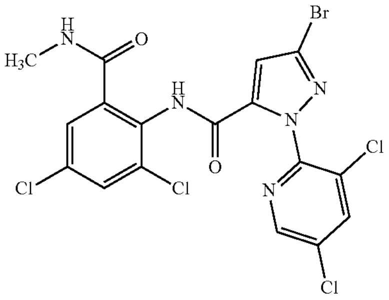 [SMILES: CNC(=O)c1cc(Cl)cc(Cl)c1NC(=O)c1cc(Br)nn1-c1ncc(Cl)cc1Cl] |
| M4 | 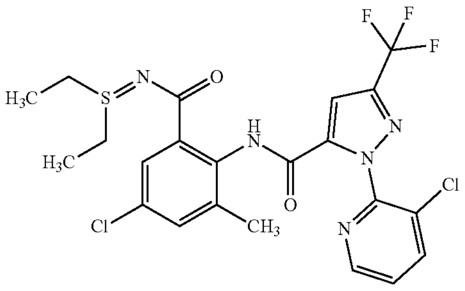 [SMILES: CCS(CC)=NC(=O)c1cc(Cl)cc(C)c1NC(=O)c1cc(C(F)(F)F)nn1-c1ncccc1Cl] |
| M5 | 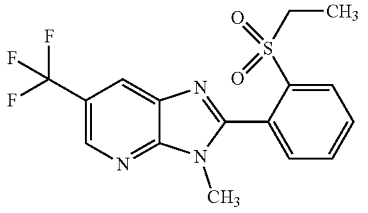 [SMILES: CCS(=O)(=O)c1ccccc1-c1nc2cc(C(F)(F)F)cnc2n1C] |

TABLE A-continued

| Structure of M#- active ingredients | |
|---|---|
| M# | Structure |
| M6 | 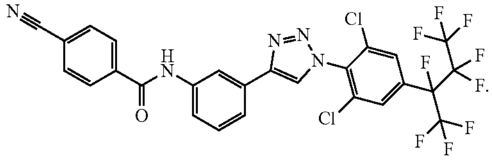 [SMILES: N#Cc1ccc(C(=O)Nc2cccc(-c3cn(-c4c(Cl)cc(C(F)(C(F)(F)F)C(F)(F)C(F)(F)F)cc4Cl)nn3)c2)cc1] |

As used in this disclosure, each of the above is an active ingredient. For more information consult the "Compendium of Pesticide Common Names" located at Alanwood.net and various editions, including the on-line edition, of "The Pesticide Manual" located at bcpcdata.com.

A particularly preferred selection of active ingredients are 1,3 dichloropropene, chlorpyrifos, hexaflumuron, methoxyfenozide, noviflumuron, spinetoram, spinosad, and sulfoxaflor (hereafter "AIGA-2").

Additionally, another particularly preferred selection of active ingredients are acequinocyl, acetamiprid, acetoprole, avermectin, azinphos-methyl, bifenazate, bifenthrin, carbaryl, carbofuran, chlorfenapyr, chlorfluazuron, chromafenozide, clothianidin, cyfluthrin, cypermethrin, deltamethrin, diafenthiuron, emamectin benzoate, endosulfan, esfenvalerate, ethiprole, etoxazole, fipronil, flonicamid, fluacrypyrim, gamma-cyhalothrin, halofenozide, indoxacarb, lambda-cyhalothrin, lufenuron, malathion, methomyl, novaluron, permethrin, pyridalyl, pyrimidifen, spirodiclofen, tebufenozide, thiacloprid, thiamethoxam, thiodicarb, tolfenpyrad, and zeta-cypermethrin (hereafter "AIGA-3").

The term "alkenyl" means an acyclic, unsaturated (at least one carbon-carbon double bond), branched or unbranched, substituent consisting of carbon and hydrogen, for example, vinyl, allyl, butenyl, pentenyl, and hexenyl.

The term "alkenyloxy" means an alkenyl further consisting of a carbon-oxygen single bond, for example, allyloxy, butenyloxy, pentenyloxy, hexenyloxy.

The term "alkoxy" means an alkyl further consisting of a carbon-oxygen single bond, for example, methoxy, ethoxy, propoxy, isopropoxy, butoxy, isobutoxy, and tertbutoxy.

The term "alkyl" means an acyclic, saturated, branched or unbranched, substituent consisting of carbon and hydrogen, for example, methyl, ethyl, propyl, isopropyl, butyl, and tertbutyl.

The term "alkynyl" means an acyclic, unsaturated (at least one carbon-carbon triple bond), branched or unbranched, substituent consisting of carbon and hydrogen, for example, ethynyl, propargyl, butynyl, and pentynyl.

The term "alkynyloxy" means an alkynyl further consisting of a carbon-oxygen single bond, for example, pentynyloxy, hexynyloxy, heptynyloxy, and octynyloxy.

The term "aryl" means a cyclic, aromatic substituent consisting of hydrogen and carbon, for example, phenyl, naphthyl, and biphenyl.

The term "biopesticide" means a microbial biological pest control agent that, in general, is applied in a similar manner to chemical pesticides. Commonly they are bacterial, but there are also examples of fungal control agents, including *Trichoderma* spp. and *Ampelomyces quisqualis*. One well-known biopesticide example is *Bacillus* species, a bacterial disease of Lepidoptera, Coleoptera, and Diptera. Biopesticides include products based on entomopathogenic fungi (e.g. *Metarhizium anisopliae*), entomopathogenic nematodes (e.g. *Steinernema feltiae*), and entomopathogenic viruses (e.g. *Cydia pomonella* granulovirus). Other examples of entomopathogenic organisms include, but are not limited to, baculoviruses, protozoa, and Microsporidia. For the avoidance of doubt, biopesticides are active ingredients.

The term "cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

The term "cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

The term "cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

The term "cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

The term "halo" means fluoro, chloro, bromo, and iodo.

The term "haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

The term "haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

The term "heterocyclyl" means a cyclic substituent that may be aromatic, fully saturated, or partially or fully unsaturated, where the cyclic structure contains at least one carbon and at least one heteroatom, where said heteroatom is nitrogen, sulfur, or oxygen. Examples are:

(1) aromatic heterocyclyl substituents aromatic heterocyclyl substituents include, but are not limited to, benzofuranyl, benzoimidazolyl, benzoisothiazolyl, benzoisoxazolyl, benzothienyl, benzothiazolyl, benzothiophenyl, benzoxazolyl, cinnolinyl, furanyl, imidazolyl, imidazolylpyridinyl, indazolyl, indolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyrazolopyridinyl, pyridazinyl, pyridyl, pyrimidinyl, pyrrolyl, pyrrolopyridinyl, quinazolinyl, quinolinyl, quinoxalinyl, tetrazolyl, thiadiazolyl, thiazolinyl, thiazolyl, thienyl, triazinyl, [1,2,4]triazolo[1,5-c]pyrimidinyl, and triazolyl;

(2) fully saturated heterocyclyl substituents include, but are not limited to, piperazinyl, piperidinyl, morpholinyl, pyrrolidinyl, tetrahydrofuranyl, tetrahydropyranyl, tetrahydrothiophenyl, tetrahydrothiophenyl-oxide, and tetrahydrothiophenyl-dioxide;

(3) partially or fully unsaturated heterocyclyl substituents include, but are not limited to, 2,3-dihydro-1H-imidazolonyl, 4,5-dihydro-isoxazolyl, 4,5-dihydro-oxazolyl, 2,3-dihydrophthalazinyl, 2,3-dihydrophthalazine-1,4-dionyl, 4,5-dihydro-1H-pyrazolyl, 2,3-dihydro-[1,3,4]-oxadiazolyl, 2,5-dioxoimidazolidinyl, 2,4-dioxo-1,3-diazaspiro[4.4]nonanylisoxazolidinonyl, indolinyl, imidazolidinonyl, isoxazolidinonyl, oxazolidinonyl, pyrimidine-2,4(1H,3H)-dionyl, pyrrolidinonyl, 1,2,3,4-tetrahydro-pyrimidinyl, 1,2,3,4-tetrahydro-quinolinyl, and thioxothiazolidinonyl; and (4) Additional examples of heterocyclyls include the following:

thietanyl

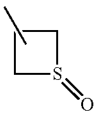
thietanyl-oxide and

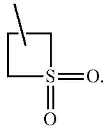
.

thietanyl-dioxide

The term "locus" means a habitat, breeding ground, plant, seed, soil, material, or environment, in which a pest is growing, may grow, or may traverse. For example, a locus may be: where crops, trees, fruits, cereals, fodder species, vines, turf, and/or ornamental plants, are growing; where domesticated animals are residing; the interior or exterior surfaces of buildings (such as places where grains are stored); the materials of construction used in buildings (such as impregnated wood); and the soil around buildings.

The phrase "MoA Material" means an active ingredient having a mode of action ("MoA") as indicated in IRAC MoA Classification v. 7.3, located at irac-online.org., which describes the following groups.

(1) Acetylcholinesterase (AChE) inhibitors, includes the following active ingredients alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC, xylylcarb, acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion.

(2) GABA-gated chloride channel antagonists, includes the following active ingredients chlordane, endosulfan, ethiprole, and fipronil.

(3) Sodium channel modulators, includes the following active ingredients acrinathrin, allethrin, d-cis-trans allethrin, d-trans allethrin, bifenthrin, bioallethrin, bioallethrin S-cyclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomers], deltamethrin, empenthrin [(EZ)-(1R)-isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomers], tralomethrin, and transfluthrin, and methoxychlor.

(4) Nicotinic acetylcholine receptor (nAChR) agonists, includes the following active ingredients
 (4A) acetamiprid, clothianidin, dinotefuran, imidacloprid, nitenpyram, thiacloprid, thiamethoxam,
 (4B) nicotine,
 (4C) sulfoxaflor,
 (4D) flupyradifurone,
 (4E) triflumezopyrim and dicloromezotiaz.

(5) Nicotinic acetylcholine receptor (nAChR) allosteric activators, includes the following active ingredients spinetoram and spinosad.

(6) Chloride channel activators, includes the following active ingredients abamectin, emamectin benzoate, lepimectin, and milbemectin.

(7) Juvenile hormone mimics, includes the following active ingredients hydroprene, kinoprene, methoprene, fenoxycarb, and pyriproxyfen.

(8) Miscellaneous nonspecific (multi-site) inhibitors, includes the following active ingredients methyl bromide, chloropicrin, sulfuryl fluoride, borax, and tartar emetic.

(9) Modulators of Chordotonal Organs, includes the following active ingredients pymetrozine and flonicamid.

(10) Mite growth inhibitors, includes the following active ingredients clofentezine, hexythiazox, diflovidazin, and etoxazole.

(11) Microbial disruptors of insect midgut membranes, includes the following active ingredients *Bacillus thuringiensis* subsp. *Israelensis, Bacillus thuringiensis* subsp. *aizawai, Bacillus thuringiensis* subsp. Kurstaki, *Bacillus thuringiensis* subsp. *tenebrionenis*, Bt crop proteins (Cry1Ab, Cry1Ac, Cry1Fa, Cry1A.105, Cry2Ab, Vip3A, mCry3A, Cry3Ab, Cry3Bb, Cry34Ab1/Cry35Ab1), and *Bacillus sphaericus.*

(12) Inhibitors of mitochondrial ATP synthase, includes the following active ingredients tetradifon, propargite, azocyclotin, cyhexatin, fenbutatin oxide, and diafenthiuron.

(13) Uncouplers of oxidative phosphorylation via disruption of the proton gradient, includes the following active ingredients chlorfenapyr, DNOC, and sulfluramid.

(14) Nicotinic acetylcholine receptor (nAChR) channel blockers, includes the following active ingredients bensultap, cartap hydrochloride, thiocyclam, and thiosultap-sodium.

(15) Inhibitors of chitin biosynthesis, type 0, includes the following active ingredients bistrifluron, chlorfluazuron, diflubenzuron, flucycloxuron, flufenoxuron, hexaflumuron, lufenuron, novaluron, noviflumuron, teflubenzuron, and triflumuron.

(16) Inhibitors of chitin biosynthesis, type 1, includes the following active ingredient buprofezin.

(17) Moulting disruptor, Dipteran, includes the following active ingredient cyromazine.

(18) Ecdysone receptor agonists, includes the following active ingredients chromafenozide, halofenozide, methoxyfenozide, and tebufenozide.

(19) Octopamine receptor agonists, includes the following active ingredient amitraz.

(20) Mitochondrial complex III electron transport inhibitors, includes the following active ingredients hydramethylnon, acequinocyl, and fluacrypyrim.

(21) Mitochondrial complex I electron transport inhibitors, includes the following active ingredients fenazaquin, fenpyroximate, pyrimidifen, pyridaben, tebufenpyrad, tolfenpyrad, and rotenone.

(22) Voltage-dependent sodium channel blockers, includes the following active ingredients indoxacarb and metaflumizone.

(23) Inhibitors of acetyl CoA carboxylase, includes the following active ingredients spirodiclofen, spiromesifen, and spirotetramat.

(24) Mitochondrial complex IV electron transport inhibitors, includes the following active ingredients, aluminium phosphide, calcium phosphide, phosphine, zinc phosphide, and cyanide.

(25) Mitochondrial complex II electron transport inhibitors, includes the following active ingredients cyenopyrafen and cyflumetofen. and

(28) Ryanodine receptor modulators, includes the following active ingredients chlorantraniliprole, cyantraniliprole, and flubendiamide.

Groups 26 and 27 are unassigned in this version of the classification scheme. Additionally, there is a Group UN that contains active ingredients of unknown or uncertain mode of action. This group includes the following active ingredients, azadirachtin, benzoximate, bifenazate, bromopropylate, chinomethionat, cryolite, dicofol, pyridalyl, and pyrifluquinazon.

The term "pest" means an organism that is detrimental to humans, or human concerns (such as, crops, food, livestock, etc.), where said organism is from Phyla Arthropoda, Mollusca, or Nematoda. Particular examples are ants, aphids, bed bugs, beetles, bristletails, caterpillars, cockroaches, crickets, earwigs, fleas, flies, grasshoppers, grubs, hornets, killer bees, leafhoppers, lice, locusts, maggots, mites, moths, nematodes, planthoppers, psyllids, sawflies, scales, silverfish, slugs, snails, spiders, springtails, stink bugs, symphylans, termites, *thrips*, ticks, wasps, whiteflies, and wireworms.

Additional examples are pests in (1) Subphyla Chelicerata, Myriapoda, and Hexapoda.

(2) Classes of Arachnida, Symphyla, and Insecta.

(3) Order Anoplura. A non-exhaustive list of particular genera includes, but is not limited to, *Haematopinus* spp., *Hoplopleura* spp., *Linognathus* spp., *Pediculus* spp., *Polyplax* spp., *Solenopotes* spp., and *Neohaematopinis* spp. A non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis.*

(4) Order Coleoptera. A non-exhaustive list of particular genera includes, but is not limited to, *Acanthoscelides* spp., *Agriotes* spp., *Anthonomus* spp., *Apion* spp., *Apogonia* spp., *Araecerus* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Dinoderus* spp., *Gnathocerus* spp., *Hemicoelus* spp., *Heterobostruchus* spp., *Hypera* spp., *Ips* spp., *Lyctus* spp., *Megascelis* spp., *Meligethes* spp., *Mezium* spp., *Niptus* spp., *Otiorhynchus* spp., *Pantomorus* spp., *Phyllophaga* spp., *Phyllotreta* spp., *Ptinus* spp., *Rhizotrogus* spp., *Rhynchites* spp., *Rhynchophorus* spp., *Scolytus* spp., *Sphenophorus* spp., *Sitophilus* spp.,

*Tenebrio* spp., and *Tribolium* spp. A non-exhaustive list of particular species includes, but is not limited to, *Acanthoscelides obtectus, Agrilus planipennis, Ahasverus advena, Alphitobius diaperinus, Anoplophora glabripennis, Anthonomus grandis, Anthrenus verbasci, Anthrenus falvipes, Ataenius spretulus, Atomaria linearis, Attagenus unicolor, Bothynoderes punctiventris, Bruchus pisorum, Callosobruchus maculatus, Carpophilus hemipterus, Cassida vittata, Cathartus quadricollis, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Euvrilletta peltata, Faustinus cubae, Hylobius pales, Hylotrupes bajulus, Hypera postica, Hypothenemus hampei, Lasioderma serricorne, Leptinotarsa decemlineata, Limonius canus, Liogenys fuscus, Liogenys suturalis, Lissorhoptrus oryzophilus, Lophocateres pusillus, Lyctus planicollis, Maecolaspis joliveti, Melanotus communis, Meligethes aeneus, Melolontha melolontha, Necrobia rufipes, Oberea brevis, Oberea linearis, Oryctes rhinoceros, Oryzaephilus mercator, Oryzaephilus surinamensis, Oulema melanopus, Oulema oryzae, Phyllophaga cuyabana, Polycaon stoutti, Popillia japonica, Prostephanus truncatus, Rhyzopertha dominica, Sitona lineatus, Sitophilus granarius, Sitophilus oryzae, Sitophilus zeamais, Stegobium paniceum, Tenebroides mauritanicus, Tribolium castaneum, Tribolium confusum, Trogoderma granarium, Trogoderma variabile, Xestobium rufovillosum*, and *Zabrus tenebrioides.*

(5) Order Dermaptera. A non-exhaustive list of particular species includes, but is not limited to, *Forficula auricularia.*

(6) Order *Blattaria*. A non-exhaustive list of particular species includes, but is not limited to, *Blattella germanica, Blattella asahinai, Blatta orientalis, Blatta lateralis, Parcoblatta pennsylvanica, Periplaneta americana, Periplaneta australasiae, Periplaneta brunnea, Periplaneta fuliginosa, Pycnoscelus surinamensis*, and *Supella longipalpa.*

(7) Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Culicoides* spp., *Dasineura* spp., *Delia* spp., *Drosophila* spp., *Fannia* spp., *Hylemya* spp., *Liriomyza* spp., *Musca* spp., *Phorbia* spp., *Pollenia* spp., *Psychoda* spp., *Simulium* spp., *Tabanus* spp., and *Tipula* spp. A non-exhaustive list of particular species includes, but is not limited to, *Agromyza frontella, Anastrepha suspensa, Anastrepha ludens, Anastrepha obliqua, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Piophila casei, Psila rosae, Rhagoletis cerasi, Rhagoletis pomonella, Rhagoletis mendax, Sitodiplosis mosellana*, and *Stomoxys calcitrans.*

(8) Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Euschistus* spp., *Lepidosaphes* spp., *Lagynotomus* spp., *Lygus* spp., *Macrosiphum* spp., *Nephotettix* spp., *Nezara* spp., *Nilaparvata* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp., and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bactericera cockerelli, Bagrada hilaris, Bemisia argentifolii, Bemisia tabaci, Blissus leucopterus, Boisea trivittata, Brachycorynella asparagi, Brevennia rehi, Brevicoryne brassicae, Cacopsylla pyri, Cacopsylla pyricola, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus conspersus, Euschistus heros, Euschistus servus, Halyomorpha halys, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Megacopta cribraria, Metopolophium dirhodum, Mictis longicornis, Myzus persicae, Nephotettix cincticeps, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis*, and *Zulia entrerriana.*

(9) Order Hymenoptera. A non-exhaustive list of particular genera includes, but is not limited to, *Acromyrmex* spp., *Atta* spp., *Camponotus* spp., *Diprion* spp., *Dolichovespula* spp., *Formica* spp., *Monomorium* spp., *Neodiprion* spp., *Paratrechina* spp., *Pheidole* spp., *Pogonomyrmex* spp., *Polistes* spp., *Solenopsis* spp., *Technomyrmex*, spp., *Tetramorium* spp., *Vespula* spp., *Vespa* spp., and *Xylocopa* spp. A non-exhaustive list of particular species includes, but is not limited to, *Athalia rosae, Atta texana, Caliroa cerasi, Cimbex americana, Iridomyrmex humilis, Linepithema humile, Mellifera Scutellata, Monomorium minimum, Monomorium pharaonis, Neodiprion sertifer, Solenopsis invicta, Solenopsis geminata, Solenopsis molesta, Solenopsis richtery, Solenopsis xyloni, Tapinoma sessile*, and *Wasmannia auropunctata.*

(10) Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes acinaciformis, Coptotermes curvignathus, Coptotermes frenchi, Coptotermes formosanus, Coptotermes gestroi, Cryptotermes brevis, Heterotermes aureus, Heterotermes tenuis, Incisitermes minor, Incisitermes snyderi, Microtermes obesi, Nasutitermes corniger, Odontotermes formosanus, Odontotermes obesus, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis*, and *Reticulitermes virginicus.*

(11) Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Nemapogon* spp., *Peridroma* spp., *Phyllonorycter* spp., *Pseudaletia* spp., *Plutella* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Corcyra cephalonica, Cossus cossus, Cydia caryana, Cydia funebrana, Cydia molesta, Cydia nigricana, Cydia pomonella, Darna diducta, Diaphania nitidalis, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Estigmene acrea, Eupoecilia ambiguella, Euxoa auxiliaris, Galleria mellonella, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Manduca sexta, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Phyllonorycter blancardella, Pieris rapae, Plathypena scabra, Platynota idaeusalis, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tinea pellionella, Tineola bisselliella, Trichoplusia ni, Tuta absoluta, Zeuzera coffeae*, and *Zeuzea pyrina.*

(12) Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae*, and *Trichodectes canis.*

(13) Order Orthoptera. A non-exhaustive list of particular genera includes, but is not limited to, *Melanoplus* spp. and *Pterophylla* spp. A non-exhaustive list of particular species includes, but is not limited to, *Acheta domesticus, Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria*, and *Scudderia furcata.*

(14) Order Psocoptera. A non-exhaustive list of particular species includes, but is not limited to, Liposcelis decolor, Liposcelis *entomophila, Lachesilla quercus*, and *Trogium pulsatorium.*

(15) Order Siphonaptera. A non-exhaustive list of particular species includes, but is not limited to, *Ceratophyllus gallinae, Ceratophyllus niger, Ctenocephalides canis, Ctenocephalides felis*, and *Pulex irritans.*

(16) Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular species includes, but is not limited to, *Frankliniella bispinosa, Frankliniella fusca, Frankliniella occidentalis, Frankliniella schultzei, Frankliniella tritici, Frankliniella williamsi, Heliothrips haemorrhoidalis, Rhipiphorothrips cruentatus, Scirtothrips citri, Scirtothrips dorsalis, Taeniothrips rhopalantennalis, Thrips hawaiiensis, Thrips nigropilosus, Thrips orientalis, Thrips palmi*, and *Thrips tabaci.*

(17) Order Thysanura. A non-exhaustive list of particular genera includes, but is not limited to, *Lepisma* spp. and *Thermobia* spp.

(18) Order Acarina. A non-exhaustive list of particular genera includes, but is not limited to, *Acarus* spp., *Aculops* spp., *Argus* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Liponyssoides sanguineus, Notoedres cati, Oligonychus coffeae, Oligonychus ilicis, Ornithonyssus bacoti, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae, Tyrophagus longior*, and *Varroa destructor.*

(19) Order Araneae. A non-exhaustive list of particular genera includes, but is not limited to, *Loxosceles* spp., *Latrodectus* spp., and *Atrax* spp. A non-exhaustive list of particular species includes, but is not limited to, *Loxosceles reclusa, Latrodectus mactans*, and *Atrax robustus.*

(20) Class Symphyla. A non-exhaustive list of particular species includes, but is not limited to, *Scutigerella immaculata.*

(21) Subclass Collembola. A non-exhaustive list of particular species includes, but is not limited to, *Bourletiella hortensis, Onychiurus armatus, Onychiurus fimetarius*, and *Sminthurus viridis.*

(22) Phylum Nematoda. A non-exhaustive list of particular genera includes, but is not limited to, *Aphelenchoides* spp., *Belonolaimus* spp., *Criconemella* spp., *Ditylenchus* spp., *Globodera* spp., *Heterodera* spp., *Hirschmanniella* spp., *Hoplolaimus* spp., *Meloidogyne* spp., *Pratylenchus* spp., and *Radopholus* spp. A non-exhaustive list of particular species includes, but is not limited to, *Diroflaria immitis, Globodera pallida, Heterodera glycines, Heterodera zeae, Meloidogyne incognita, Meloidogyne javanica, Onchocerca volvulus, Pratylenchus penetrans, Radopholus similis*, and *Rotylenchulus reniformis.*

(23) Phylum Mollusca. A non-exhaustive list of particular species includes, but is not limited to, *Anon vulgaris, Cornu aspersum, Deroceras reticulatum, Limax flavus, Milax gagates*, and *Pomacea canaliculata.*

A particularly preferred pest group to control is sap-feeding pests. Sap-feeding pests, in general, have piercing and/or sucking mouthparts and feed on the sap and inner plant tissues of plants. Examples of sap-feeding pests of particular concern to agriculture include, but are not limited to, aphids, leafhoppers, moths, scales, *thrips*, psyllids, mealybugs, stinkbugs, and whiteflies. Specific examples of Orders that have sap-feeding pests of concern in agriculture include but are not limited to, Anoplura and Hemiptera. Specific examples of Hemiptera that are of concern in agriculture include, but are not limited to, *Aulacaspis* spp., *Aphrophora* spp., *Aphis* spp., *Bemisia* spp., *Coccus* spp., *Euschistus* spp., *Lygus* spp., *Macrosiphum* spp., *Nezara* spp., and *Rhopalosiphum* spp.

Another particularly preferred pest group to control is chewing pests. Chewing pests, in general, have mouthparts that allow them to chew on the plant tissue including roots, stems, leaves, buds, and reproductive tissues (including, but not limited to flowers, fruit, and seeds). Examples of chewing pests of particular concern to agricultural include, but are not limited to, caterpillars, beetles, grasshoppers, and locusts. Specific examples of Orders that have chewing pests of concern in agriculture include but are not limited to, Coleoptera and Lepidoptera. Specific examples of Coleoptera that are of concern in agriculture include, but are not limited to, *Anthonomus* spp., *Cerotoma* spp., *Chaetocnema* spp., *Colaspis* spp., *Cyclocephala* spp., *Diabrotica* spp., *Hypera* spp., *Phyllophaga* spp., *Phyllotreta* spp., *Sphenophorus* spp., *Sitophilus* spp.

The phrase "pesticidally effective amount" means the amount of a pesticide needed to achieve an observable effect on a pest, for example, the effects of necrosis, death, retardation, prevention, removal, destruction, or otherwise diminishing the occurrence and/or activity of a pest in a locus. This effect may come about when pest populations are repulsed from a locus, pests are incapacitated in, or around, a locus, and/or pests are exterminated in, or around, a locus. Of course, a combination of these effects can occur. Generally, pest populations, activity, or both are desirably reduced more than fifty percent, preferably more than 90 percent, and most preferably more than 99 percent. In general, a pesticidally effective amount, for agricultural purposes, is from about 0.0001 grams per hectare to about 5000 grams per hectare, preferably from about 0.0001 grams per hectare to about 500 grams per hectare, and it is even more preferably from about 0.0001 grams per hectare to about 50 grams per hectare.

DETAILED DESCRIPTION OF THIS DISCLOSURE

This document discloses molecules of Formula One

Formula One

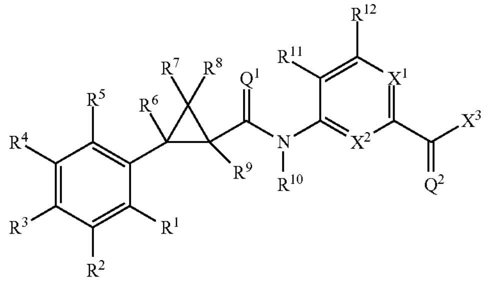

wherein:

(A) $R^1$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

(B) $R^2$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

(C) $R^3$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

(D) $R^4$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

(E) $R^5$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

(F) $R^6$ is selected from the group consisting of H and $(C_1-C_6)$alkyl;

(G) $R^7$ is selected from the group consisting of H, F, Cl, Br, and I;

(H) $R^8$ is selected from the group consisting of F, Cl, Br, and I;

(I) $R^9$ is selected from the group consisting of H and $(C_1-C_6)$alkyl;

(J) $Q^1$ is selected from the group consisting of O and S;

(K) $Q^2$ is selected from the group consisting of O and S;

(L) $R^{10}$ is selected from the group consisting of H, $(C_1-C_6)$alkyl, $(C_2-C_6)$alkenyl, $(C_1-C_6)$haloalkyl, $(C_1-C_6)$alkyl$(C_1-C_6)$alkoxy, $C(=O)(C_1-C_6)$alkyl, and $(C_1-C_6)$alkoxy$C(=O)(C_1-C_6)$alkyl;

(M) $R^{11}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

(N) $R^{12}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

(O) $X^1$ is selected from the group consisting of (1) N, (2) NO, and (3) $CR^{13}$, wherein $R^{13}$ is selected from the group consisting of H, F, Cl, Br, I, CN, $NH_2$, $NO_2$, CHO, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and triazolyl;

(P) $X^2$ is selected from the group consisting of (1) N, (2) NO, and (3) $CR^{14}$, wherein $R^{14}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

(Q) $X^3$ is selected from the group consisting of $N(R^{15})$(substituted or unsubstituted phenyl), $N(R^{15})$(substituted or unsubstituted heterocyclyl), and substituted or unsubstituted heterocyclyl, (a) wherein said $R^{15}$ is selected from the group consisting of H, $(C_1-C_6)$alkyl, $(C_2-C_6)$alkenyl, $(C_2-C_6)$alkynyl, $(C_1-C_6)$haloalkyl, $(C_1-C_6)$alkyl$(C_1-C_6)$alkoxy, $C(=O)(C_1-C_6)$alkyl, and $(C_1-C_6)$alkoxy$C(=O)(C_1-C_6)$alkyl, (b) wherein said substituted phenyl and substituted heterocyclyl has one or more substituents selected from the group consisting of F, Cl, Br, I, H, CN, CHO, NHOH, NO, $NO_2$, OH, $(C_1-C_6)$alkoxy, $(C_1-C_6)$alkyl, $(C_1-C_6)$alkylphenyl, $(C_1-C_6)$alkyl-$S(O)_2NH_2$, $(C_1-C_6)$haloalkoxy, $(C_1-C_6)$haloalkyl, $(C_1-C_6)$haloalkyl-$S(O)_2NH_2$, $(C_2-C_6)$alkenyl, $(C_2-C_6)$alkynyl, $(C_2-C_6)$haloalkenyl, $(C_3-C_6)$cycloalkenyl, $(C_3-C_6)$cycloalkyl, $(C_3-C_6)$halocycloalkenyl, $(C_3-C_6)$halocycloalkyl, $(C_1-C_6)$alkyl$((C_1-C_6)$alkyl$)(=NO(C_1-C_6)$alkyl$)$, $C(=NO(C_1-C_6)$alkyl$)(C_1-C_6)$alkyl, $C(O)(C_1-C_6)$alkyl, $C(O)NH(C_1-C_6)$alkyl, C(O)NHphenyl, $C(O)O(C_1-C_6)$alkyl, $CH(=NO(C_1-C_6)$alkyl$)$, imidazolyl, $N((C_1-C_6)$alkyl$)(C(O)(C_1-C_6)$alkyl$)$, $N((C_1-C_6)$alkyl$)(C(O)(C_1-C_6)$alkyl-$O(C_1-C_6)$alkyl$)$, $N((C_1-C_6)$alkyl$)(C(O)(C_1-C_6)$haloalkyl$)$, $N((C_1-C_6)$alkyl$)(C(O)O(C_1-C_6)$alkyl$)$, $N((C_1-C_6)$alkyl$)_2$, $N(C(O)O(C_1-C_6)$alkyl$)_2$, N=CH— phenyl, $NH((C_1-C_6)$alkyl$C(O)(C_1-C_6)$alkyl$)$, $NH(C(O)(C_1-C_6)$alkyl$)$, $NH(C(O)(C_2-C_6)$alkenyl$)$, $NH(C(O)(C_3-C_6)$cycloalkyl$)$, $NH(C_1-C_6)$alkyl, $NH(C_1-C_6)$alkenyl, $NH(C_1-C_6)$alkynyl, $NH(C_1-C_6)$alkylphenyl, $NH(S(O)_2(C_1-C_6)$alkyl$)$, $NH_2$, $NHC(O)(C_1-C_6)$alkyl, $NHC(O)(C_1-C_6)$alkylphenyl, $NHC(O)(C_1-C_6)$alkylphenyl, $NHC(O)(C_1-C_6)$haloalkyl, $NHC(O)(C_2-C_6)$alkenyl, NH—$C(O)O(C_1-C_6)$alkyl, oxazolyl, phenyl, pyrazolyl, pyridinyl, $S(=NCN)((C_1-C_6)$alkyl$)$, $S(C_1-C_6)$alkyl, $S(C_1-C_6)$haloalkyl, $S(O)(=NCN)((C_1-C_6)$alkyl$)$, $S(O)(C_1-C_6)$alkyl, $S(O)(C_1-C_6)$haloalkyl, $S(O)_2(C_1-C_6)$alkyl, $S(O)_2(C_1-C_6)$haloalkyl, SCN, thiazolyl, thienyl, and triazolyl, wherein each alkoxy, alkyl, haloalkoxy, haloalkyl, alkenyl, alkynyl, haloalkenyl, cycloalkenyl, cycloalkyl, halocycloalkenyl, halocycloalkyl, imidazolyl, phenyl, pyrazolyl, pyridinyl, thiazolyl, thienyl, and triazolyl, may be optionally substituted with one or more substituents selected from the group consisting of F, Cl, Br, I, CN, OH, $NH(C_1-C_6)$alkyl, $NH(C_3-C_6)$cycloalkyl$CH_2O(C_1-C_6)$alkyl, $NH(C_3-C_6)$cycloalkyl$CH_2O(C_1-C_6)$haloalkyl, $NHCH_2(C_3-C_6)$cycloalkyl, $NH_2$, $NO_2$, oxo, $(C_1-C_6)$alkyl, $(C_1-C_6)$alkyl, $(C_1-C_6)$alkoxy, and $C(O)O$—$(C_1-C_6)$alkyl; and N-oxides, agriculturally acceptable acid addition salts, salt derivatives, solvates, ester derivatives, crystal polymorphs, isotopes, resolved stereoisomers, and tautomers, of the molecules of Formula One.

The molecules of Formula One may exist in different geometric or optical isomeric or different tautomeric forms. One or more centers of chirality may be present in which case molecules of Formula One may be present as pure enantiomers, mixtures of enantiomers, pure diastereomers or mixtures of diastereomers. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. There may be double bonds present in the molecule, in which case compounds of Formula One may exist as single geometric isomers (cis or trans, E or Z) or mixtures of geometric isomers (cis and trans, E and Z). Centers of tautomerisation may be present. This disclosure covers all such isomers, tautomers, and mixtures thereof, in all proportions.

In another embodiment the molecules of Formula One, the carboxamido, and the phenyl, which are bonded to the cyclopropane, are in the R,R configuration. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $R^1$ is selected from the group consisting of H, F, or Cl. This embodiment may be used in combination with the other embodiments of $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $R^2$ is selected from the group consisting of H, F, Cl, Br, $CH_3$, and $CF_3$. This embodiment may be used in combination with the other embodiments of $R^1$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $R^3$ is selected from the group consisting of H, F, Cl, Br, $CH_3$, $CF_3$, and $OCF_3$. This embodiment may be used in combination with the other embodiments of $R^1$, $R^2$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $R^4$ is selected from the group consisting of H, F, Cl, Br, $CH_3$, and $CF_3$. This embodiment may be used in combination with the other embodiments of $R^1$, $R^2$, $R^3$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $R^5$ is selected from the group consisting of H and $C_1$. This embodiment may be used in combination with the other embodiments of $R^1$, $R^2$, $R^3$, $R^4$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $R^6$ is H. This embodiment may be used in combination with the other embodiments of $R^1$, $R^2$, $R^3$, $R^4$, $R^5$, $R^7$, $R^8$, $R^9$, $R^{10}$, $R^{11}$, $R^{12}$, $Q^1$, $Q^2$, $X^1$, $X^2$, and $X^3$.

In another embodiment $R^7$ is selected from the group consisting of Cl and Br. This embodiment may be used in combination with the other embodiments of $R^1$, $R^2$, $R^3$, $R^4$, $R^5$, $R^6$, $R^8$, $R^9$, $R^{10}$, $R^{11}$, $R^{12}$, $Q^1$, $Q^2$, $X^1$, $X^2$, and $X^3$.

In another embodiment $R^8$ is selected from the group consisting of Cl and Br. This embodiment may be used in combination with the other embodiments of $R^1$, $R^2$, $R^3$, $R^4$, $R^5$, $R^6$, $R^7$, $R^9$, $R^{10}$, $R^{11}$, $R^{12}$, $Q^1$, $Q^2$, $X^1$, $X^2$, and $X^3$.

In another embodiment $R^9$ is H. This embodiment may be used in combination with the other embodiments of $R^1$, $R^2$, $R^3$, $R^4$, $R^5$, $R^6$, $R^7$, $R^8$, $R^{10}$, $R^{11}$, $R^{12}$, $Q^1$, $Q^2$, $X^1$, $X^2$, and $X^3$.

In another embodiment $R^{10}$ is H or $CH_3$. This embodiment may be used in combination with the other embodiments of $R^1$, $R^2$, $R^3$, $R^4$, $R^5$, $R^6$, $R^7$, $R^8$, $R^9$, $R^{11}$, $R^{12}$, $Q^1$, $Q^2$, $X^1$, $X^2$, and $X^3$.

In another embodiment $R^{11}$ is selected from the group consisting of H, F, Cl, and $CH_3$. This embodiment may be used in combination with the other embodiments of $R^1$, $R^2$, $R^3$, $R^4$, $R^5$, $R^6$, $R^7$, $R^8$, $R^9$, $R^{10}$, $R^{12}$, $Q^1$, $Q^2$, $X^1$, $X^2$, and $X^3$.

In another embodiment $R^{12}$ is selected from the group consisting of H and Cl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $Q^1$, $Q^2$, $X^1$, $X^2$, and $X^3$.

In another embodiment $Q^1$ is O. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^2$, $X^1$, $X^2$, and $X^3$.

In another embodiment $Q^2$ is selected from the group consisting of O and S. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $X^1$, $X^2$, and $X^3$.

In another embodiment $X^1$ is selected from the group consisting of N, NO, and $CR^{13}$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^2$, and $X^3$.

In another embodiment $R^{13}$ is selected from the group consisting of H, F, Cl, Br, I, CN, $CH_3$, $CF_3$, $OCH_3$, $OCF_3$, $SCH_3$, $S(O)CH_3$, $S(O)_2CH_3$, and triazolyl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^2$, and $X^3$.

In another embodiment $X^2$ is selected from the group consisting of N and $CR^{14}$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, and $X^3$.

In another embodiment $R^{14}$ is selected from the group consisting of H, F, Cl, and $OCH_3$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, and $X^3$.

In another embodiment $X^3$ is selected from the group consisting of (1)

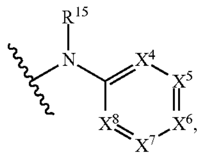

(2)

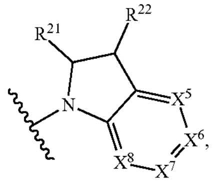

(3)

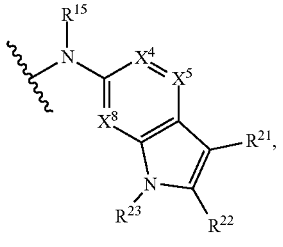

(4)

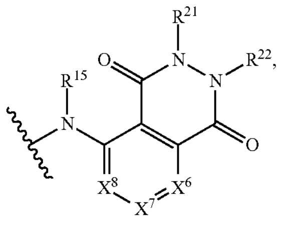

-continued (5)

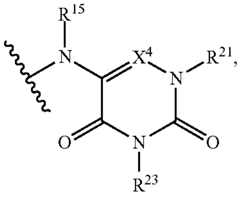

(6)

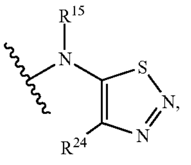

(7)

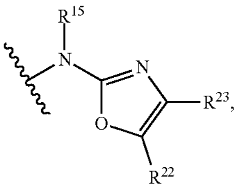

(8)

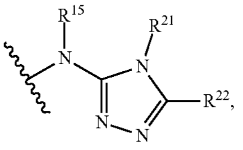

(9)

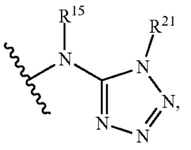

(10)

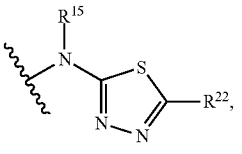

(11)

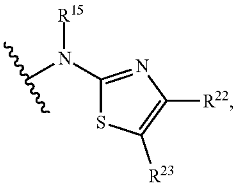

(12)

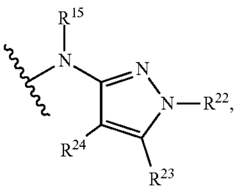

-continued (13)

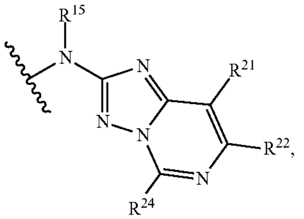

and (14)

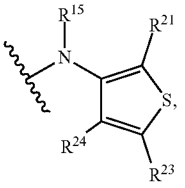

wherein:

(a) $R^{15}$ is selected from the group consisting of H, $(C_1\text{-}C_6)$alkyl, $(C_2\text{-}C_6)$alkenyl, $(C_2\text{-}C_6)$alkynyl, $(C_1\text{-}C_6)$haloalkyl, $(C_1\text{-}C_6)$alkyl$(C_1\text{-}C_6)$alkoxy, C(═O)$(C_1\text{-}C_6)$alkyl, and $(C_1\text{-}C_6)$alkoxyC(═O)$(C_1\text{-}C_6)$alkyl;

(b) $X^4$ is selected from the group consisting of (i) N, (ii) NO, and (iii) $CR^{16}$, wherein $R^{16}$ is selected from the group consisting of H, F, Cl, Br, I, CN, $NH_2$, $NO_2$, CHO, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $CO(C_1\text{-}C_6)$alkyl, CH(═NO$(C_1\text{-}C_6)$alkyl), C(═NO$(C_1\text{-}C_6)$alkyl)$(C_1\text{-}C_6)$alkyl, $(C_1\text{-}C_6)$alkyl-$S(O)_2NH_2$, and $(C_1\text{-}C_6)$haloalkyl-$S(O)_2NH_2$, wherein each alkyl, cycloalkyl, alkenyl, cycloalkenyl, alkynyl, alkoxy, haloalkyl, halocycloalkyl, haloalkenyl, halocycloalkenyl, and haloalkoxy, may be optionally substituted with one or more substituents selected from the group consisting of F, Cl, Br, I, CN, OH, $NH_2$, $NO_2$, oxo, $(C_1\text{-}C_6)$alkyl, $(C_1\text{-}C_6)$alkoxy, and C(O)O—$(C_1\text{-}C_6)$alkyl;

(c) $X^5$ is selected from the group consisting of (i) N, (ii) NO, and (iii) $CR^{17}$, wherein $R^{17}$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $C(O)O(C_1\text{-}C_6)$alkyl, $(C_1\text{-}C_6)$alkyl-$S(O)_2NH_2$, and $(C_1\text{-}C_6)$haloalkyl-$S(O)_2NH_2$;

(d) $X^6$ is selected from the group consisting of (i) N, (ii) NO, and (iii) and $CR^{18}$, wherein $R^{18}$ is selected from the group consisting of H, F, Cl, Br, I, CN, $NO_2$, OH, $NH_2$, SCN, CHO, $(C_1-C_6)$alkyl, $(C_2-C_6)$alkenyl, $(C_2-C_6)$alkynyl, $(C_1-C_6)$haloalkyl, $(C_1-C_6)$alkoxy, $(C_1-C_6)$haloalkoxy, $NH(C_1-C_6)$alkyl, $N((C_1-C_6)alkyl)_2$, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $CO(C_1-C_6)$alkyl, CONH$(C_1-C_6)$alkyl, NHCO$(C_1-C_6)$alkyl, $N(C_1-C_6)$alkyl-CO$(C_1-C_6)$alkyl, NHCO$(C_2-C_6)$alkenyl, NHCO$(C_3-C_6)$cycloalkyl, NHCO$(C_1-C_6)$haloalkyl, $N(C_1-C_6)$alkyl-CO$(C_1-C_6)$haloalkyl, NHCO$(C_1-C_6)$alkylphenyl, NH—C(O)O$(C_1-C_6)$alkyl, $N(C_1-C_6)$alkyl-C(O)O$(C_1-C_6)$alkyl, CH(=NO$(C_1-C_6)$alkyl), C(=NO$(C_1-C_6)$alkyl)$(C_1-C_6)$alkyl, phenyl, pyrazolyl, imidazolyl, and triazolyl, wherein each alkyl, alkenyl, alkynyl, haloalkyl, alkoxy, haloalkoxy, halocycloalkyl, cycloalkyl, phenyl, imidazolyl, and triazolyl, may be optionally substituted with one or more substituents selected from the group consisting of F, Cl, Br, I, CN, OH, $NH_2$, $NO_2$, oxo, $(C_1-C_6)$alkyl, $(C_1-C_6)$alkoxy, and C(O)O—$(C_1-C_6)$alkyl;

(e) $X^7$ is selected from the group consisting of (i) N, (ii) NO, and (iii) $CR^{19}$, wherein $R^{19}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, C(O)O$(C_1-C_6)$alkyl, $(C_1-C_6)$alkyl-$S(O)_2NH_2$, and $(C_1-C_6)$haloalkyl-$S(O)_2NH_2$;

(f) $X^8$ is selected from the group consisting of (i) N, (ii) NO, and (iii) $CR^{20}$, wherein $R^{20}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, C(O)O$(C_1-C_6)$alkyl, $(C_1-C_6)$alkyl-$S(O)_2NH_2$, and $(C_1-C_6)$haloalkyl-$S(O)_2NH_2$;

(g) $R^{21}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, phenyl, pyridinyl, and thienyl, wherein each alkyl, alkenyl, alkynyl, haloalkyl, alkoxy, haloalkoxy, phenyl, imidazolyl, and triazolyl, may be optionally substituted with one or more substituents selected from the group consisting of F, Cl, Br, I, CN, OH, $NH_2$, $NO_2$, oxo, $(C_1-C_6)$alkyl, $(C_1-C_6)$alkoxy, and C(O)O—$(C_1-C_6)$alkyl.

(h) $R^{22}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, phenyl, pyridinyl, and thienyl, wherein each alkyl, alkenyl, alkynyl, haloalkyl, alkoxy, haloalkoxy, phenyl, imidazolyl, and triazolyl, may be optionally substituted with one or more substituents selected from the group consisting of F, Cl, Br, I, CN, OH, $NH_2$, $NO_2$, oxo, $(C_1-C_6)$alkyl, $(C_1-C_6)$alkoxy, and C(O)O—$(C_1-C_6)$alkyl.

(i) $R^{23}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, phenyl, pyridinyl, and thienyl, wherein each alkyl, alkenyl, alkynyl, haloalkyl, alkoxy, haloalkoxy, phenyl, imidazolyl, and triazolyl, may be optionally substituted with one or more substituents selected from the group consisting of F, Cl, Br, I, CN, OH, $NH_2$, $NO_2$, oxo, $(C_1-C_6)$alkyl, $(C_1-C_6)$alkoxy, and C(O)O—$(C_1-C_6)$alkyl.

(j) $R^{24}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, phenyl, pyridinyl, and thienyl, wherein each alkyl, alkenyl, alkynyl, haloalkyl, alkoxy, haloalkoxy, phenyl, imidazolyl, and triazolyl, may be optionally substituted with one or more substituents selected from the group consisting of F, Cl, Br, I, CN, OH, $NH_2$, $NO_2$, oxo, $(C_1-C_6)$alkyl, $(C_1-C_6)$alkoxy, and C(O)O—$(C_1-C_6)$alkyl.

This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, and $X^2$.

In another embodiment $X^3$ is selected from the group consisting of (1)

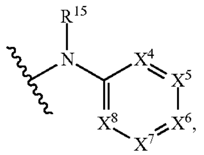

-continued (2)

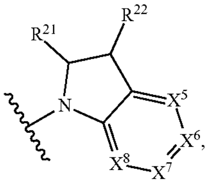

(6)

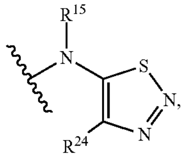

and (7)

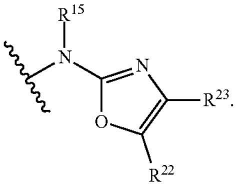

This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, and $X^2$.

In another embodiment $X^3$ said substituted or unsubstituted heterocyclyl is selected from the group consisting of indolyl, oxazolyl, pyrazinyl, pyrazolyl, pyridazinyl, pyridyl, pyrimidinyl, tetrazolyl, thiadiazolyl, thiazolyl, thienyl, triazinyl, [1,2,4]triazolo[1,5-c]pyrimidinyl, triazolyl, 2,3-dihydrophthalazine-1,4-dionyl, indolinyl, and pyrimidine-2,4(1H,3H)-dionyl, wherein substituents are selected from the group consisting of F, Cl, Br, I, H, CN, $NH_2$, $NO_2$, ($C_1$-$C_6$)alkoxy, ($C_1$-$C_6$)alkyl, ($C_1$-$C_6$)haloalkoxy, ($C_1$-$C_6$)haloalkyl, ($C_2$-$C_6$)haloalkenyl, ($C_3$-$C_6$)halocycloalkenyl, and ($C_3$-$C_6$)halocycloalkyl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, and $X^2$.

In another embodiment $X^3$ said substituted or unsubstituted heterocyclyl is selected from the group consisting of indolinyl, oxazolyl, pyridyl, and thiadiazolyl, wherein substituents are selected from the group consisting of F, Cl, Br, I, H, CN, $NO_2$, $NH_2$, ($C_1$-$C_6$)alkoxy, ($C_1$-$C_6$)alkyl, ($C_1$-$C_6$)haloalkoxy, ($C_1$-$C_6$)haloalkyl, ($C_2$-$C_6$)haloalkenyl, ($C_3$-$C_6$)halocycloalkenyl, and ($C_3$-$C_6$)halocycloalkyl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, and $X^2$.

In another embodiment $X^3$ is $N(R^{15})$(substituted or unsubstituted phenyl), (a) wherein said $R^{15}$ is selected from the group consisting of H, and ($C_1$-$C_6$)alkyl, (b) wherein said substituted phenyl has one or more substituents selected from the group consisting of F, Cl, Br, I, CN, $NO_2$, $NH_2$, ($C_1$-$C_6$)alkoxy, ($C_1$-$C_6$)alkyl, ($C_1$-$C_6$)haloalkoxy, ($C_1$-$C_6$)haloalkyl, ($C_2$-$C_6$)haloalkenyl, ($C_3$-$C_6$)cycloalkenyl, ($C_3$-$C_6$)cycloalkyl, ($C_3$-$C_6$)halocycloalkenyl, and ($C_3$-$C_6$)halocycloalkyl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, and $X^2$.

In another embodiment $R^{15}$ is selected from the group consisting of H, $CH_3$, $CH_2CH_3$, $CH_2CH_2CH_3$, $CH_2CH{=}CH_2$, $CH_2{-}C{\equiv}CH$, and $CH_2CF_3$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $X^4$ is selected from the group consisting of N and $CR^{16}$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $R^{16}$ is selected from the group consisting of H, F, Cl, CN, $NH_2$, $CH_3$, $CH_2CH_3$, and $CH_2(CH_3)_2$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $X^5$ is selected from the group consisting of N, NO, and $CR^{17}$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $R^{17}$ is selected from the group consisting of H, F, Cl, and CN, $NH_2$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $X^6$ is selected from the group consisting of N, NO, and $CR^{18}$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $R^{18}$ is selected from the group consisting of H, F, Cl, CN, $NO_2$, $NH_2$, $CH_3$, $CF_3$, $OCH_3$, $OCHCF_2$, $OCF_3$, $SCH_3$, $S(O)CH_3$, $S(O)_2CH_3$, $C(O)NHCH_3$, and $NHC(O)CH_3$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $X^7$ is $CR^{19}$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $R^{19}$ is selected from the group consisting of H, F, and $NH_2$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $X^8$ is $CR^{20}$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $R^{20}$ is selected from the group consisting of H, F, Cl, and $CH_3$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^{11}$, $Q^2$, $X^1$, $X^2$, and $X^3$.

In another embodiment $R^{21}$ is H. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $R^{22}$ is H. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $R^{23}$ is H. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment $R^{24}$ is H. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $Q^1$, $Q^2$, $X^1$, $X^2$, and $X^3$.

In another embodiment:

(A) $R^1$, $R^2$, $R^3$, $R^4$, $R^5$, $R^{11}$, and $R^{12}$ are each independently selected from the group consisting of H, F, Cl, Br, $(C_1\text{-}C_6)$alkyl, $(C_1\text{-}C_6)$haloalkyl, and $(C_1\text{-}C_6)$haloalkoxy;

(B) $R^6$ and $R^9$ are H;

(C) $R^7$ is selected from the group consisting of Cl and Br;

(D) $R^8$ is selected from the group consisting of Cl and Br;

(E) $Q^1$ and $Q^2$ are each independently selected from the group consisting of O and S;

(F) $R^{10}$ is H;

(G) $X^1$ is selected from the group consisting of (1) N, (2) NO, and (3) $CR^{13}$, wherein $R^{13}$ is selected from the group consisting of H, F, Cl, Br, I, CN, $(C_1\text{-}C_6)$alkyl, $(C_1\text{-}C_6)$alkoxy, $(C_1\text{-}C_6)$haloalkyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, and triazolyl;

(H) $X^2$ is selected from the group consisting of (1) N and (2) $CR^{14}$, wherein $R^{14}$ is selected from the group consisting of H, F, Cl, and $(C_1\text{-}C_6)$alkoxy;

(I) $X^3$ is selected from the group consisting of (1)

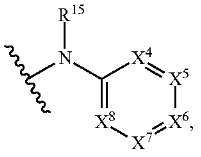

(2)

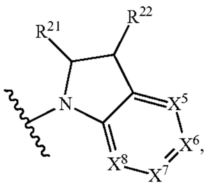

(6)

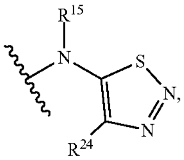

and (7)

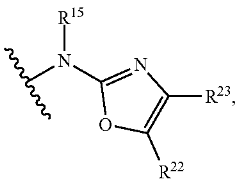

wherein:

(a) $R^{15}$ is selected from the group consisting of H, $(C_1\text{-}C_6)$alkyl, $(C_2\text{-}C_6)$alkenyl, and $(C_1\text{-}C_6)$haloalkyl;

(b) $X^4$ is selected from the group consisting of (i) N, and (ii) $CR^{16}$, wherein $R^{16}$ is selected from the group consisting of H, F, Cl, CN, $NH_2$, and $(C_1\text{-}C_6)$alkyl;

(c) $X^5$ is selected from the group consisting of (i) N, (ii) NO, and (iii) $CR^{17}$, wherein $R^{17}$ is selected from the group consisting of H, F, Cl, $NH_2$, and CN;

(d) $X^6$ is selected from the group consisting of (i) N, (ii) NO, and (iii) and $CR^{18}$, wherein $R^{18}$ is selected from the group consisting of H, F, Cl, CN, $NO_2$, $NH_2$, $(C_1\text{-}C_6)$alkyl, $(C_1\text{-}C_6)$haloalkyl, $(C_1\text{-}C_6)$alkoxy, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $CONH(C_1\text{-}C_6)$alkyl, and $NHCO(C_1\text{-}C_6)$alkyl;

(e) $X^7$ is $CR^{19}$, wherein $R^{19}$ is selected from the group consisting of H, $NH_2$, and F;

(f) $X^8$ is $CR^{20}$, wherein $R^{20}$ is selected from the group consisting of H, F, Cl, $NH_2$, and $(C_1\text{-}C_6)$alkyl; and (g) $R^{21}$, $R^{22}$, $R^{23}$, and $R^{24}$ are H.

In another embodiment:

(A) $R^1$ is H;

(B) $R^2$ is selected from the group consisting of H, Cl, Br, $(C_1\text{-}C_6)$alkyl, and $(C_1\text{-}C_6)$haloalkyl;

(C) $R^3$ is selected from the group consisting of H, F, Cl, Br, $(C_1\text{-}C_6)$alkyl, $(C_1\text{-}C_6)$haloalkyl, and $(C_1\text{-}C_6)$haloalkoxy;

(D) $R^4$ is selected from the group consisting of H, Cl, Br, $(C_1\text{-}C_6)$alkyl, and $(C_1\text{-}C_6)$haloalkyl;

(E) $R^5$ is selected from the group consisting of H and $C_1$;

(F) $R^6$ is H;

(G) $R^7$ is selected from the group consisting of Cl and Br;

(H) $R^8$ is selected from the group consisting of Cl and Br;

(I) $R^9$ is H;

(J) $Q^1$ is O;

(K) $Q^2$ is selected from the group consisting of O and S;

(L) $R^{10}$ is H;

(M) $R^{11}$ is selected from the group consisting of H, F, Cl, and $(C_1\text{-}C_6)$alkyl;

(N) $R^{12}$ is selected from the group consisting of H and $C_1$;

(O) $X^1$ is selected from the group consisting of (1) N, (2) NO, and (3) $CR^{13}$, wherein $R^{13}$ is selected from the group consisting of H, F, Cl, Br, I, CN, $(C_1\text{-}C_6)$alkyl, $(C_1\text{-}C_6)$alkoxy, $(C_1\text{-}C_6)$haloalkyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, and triazolyl;

(P) $X^2$ is selected from the group consisting of (1) N and (2) $CR^{14}$, wherein $R^{14}$ is selected from the group consisting of H, F, Cl, and $(C_1\text{-}C_6)$alkoxy; and (Q) $X^3$ is selected from the group consisting of (4)

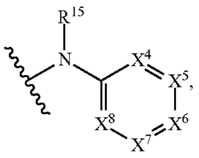

-continued (5)

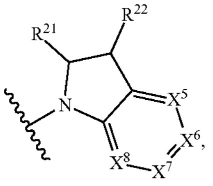

(6)

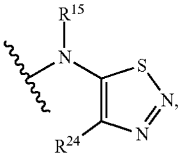

and (7)

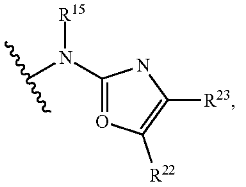

wherein:

(a) $R^{15}$ is selected from the group consisting of H, $(C_1-C_6)$alkyl, $(C_2-C_6)$alkenyl, and $(C_1-C_6)$haloalkyl;

(b) $X^4$ is selected from the group consisting of
 (i) N, and
 (ii) $CR^{16}$,
 wherein $R^{16}$ is selected from the group consisting of H, F, CI, CN, $NH_2$, and $(C_1-C_6)$alkyl;

(c) $X^5$ is selected from the group consisting of
 (i) N,
 (ii) NO, and
 (iii) $CR^{17}$,
 wherein $R^{17}$ is selected from the group consisting of H, F, Cl, $NH_2$, and CN;

(d) $X^6$ is selected from the group consisting of
 (i) N,
 (ii) NO, and
 (iii) and $CR^{18}$,
 wherein $R^{18}$ is selected from the group consisting of H, F, Cl, CN, $NO_2$, $NH_2$, $(C_1-C_6)$alkyl, $(C_1-C_6)$ haloalkyl, $(C_1-C_6)$alkoxy, $(C_1-C_6)$haloalkoxy, $S(C_1-C_6)$alkyl, $S(O)(C_1-C_6)$alkyl, $S(O)_2(C_1-C_6)$ alkyl, $CONH(C_1-C_6)$alkyl, and $NHCO(C_1-C_6)$alkyl;

(e) $X^7$ is $CR^{19}$,
 wherein $R^{19}$ is selected from the group consisting of H, $NH_2$, and F;

(f) $X^8$ is $CR^{20}$,
 wherein $R^{20}$ is selected from the group consisting of H, F, Cl, $NH_2$, and $(C_1-C_6)$alkyl; and (g) $R^{21}$, $R^{22}$, $R^{23}$, and $R^{24}$ are H.

In another embodiment:

(A) $R^1$ is selected from the group consisting of H, F, or $C_1$;

(B) $R^2$ is selected from the group consisting of H, F, Cl, Br, $(C_1-C_6)$alkyl, and $(C_1-C_6)$haloalkyl;

(C) $R^3$ is selected from the group consisting of H, F, Cl, Br, $(C_1-C_6)$alkyl, $(C_1-C_6)$haloalkyl, and $(C_1-C_6)$haloalkoxy;

(D) $R^4$ is selected from the group consisting of H, F, Cl, Br, $(C_1-C_6)$alkyl, and $(C_1-C_6)$haloalkyl;

(E) $R^5$ is selected from the group consisting of H, F, and $C_1$;

(F) $R^6$ is H;

(G) $R^7$ is selected from the group consisting of Cl and Br;

(H) $R^8$ is selected from the group consisting of Cl and Br;

(I) $R^9$ is H;

(J) $Q^1$ is O;

(K) $Q^2$ is selected from the group consisting of O and S;

(L) $R^{10}$ is H;

(M) $R^{11}$ is selected from the group consisting of H, F, Cl, and $(C_1-C_6)$alkyl;

(N) $R^{12}$ is selected from the group consisting of H and $C_1$;

(O) $X^1$ is $CR^{13}$,
 wherein $R^{13}$ is selected from the group consisting of H, F, Cl, Br, I, CN, $(C_1-C_6)$alkyl, $(C_1-C_6)$alkoxy, $(C_1-C_6)$haloalkyl, and $(C_1-C_6)$haloalkoxy; (P) $X^2$ is $CR^{14}$,
 wherein $R^{14}$ is selected from the group consisting of H, F, Cl, and $(C_1-C_6)$alkyl, $(C_1-C_6)$alkoxy, $(C_1-C_6)$haloalkyl, and $(C_1-C_6)$haloalkoxy; and (Q) $X^3$ is

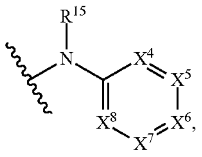

wherein:
 $R^{15}$ is selected from the group consisting of H, $(C_1-C_6)$alkyl, $(C_2-C_6)$alkenyl, and $(C_1-C_6)$haloalkyl;
 $X^4$ is $CR^{16}$ wherein $R^{16}$ is selected from the group consisting of H, F, Cl, $NH_2$, CN, $NO_2$, $(C_1-C_6)$alkyl, $(C_1-C_6)$haloalkyl, $(C_1-C_6)$alkoxy, and $(C_1-C_6)$haloalkoxy;
 $X^5$ is $CR^{17}$ wherein $R^{17}$ is selected from the group consisting of H, F, Cl, $NH_2$, CN, $NO_2$, $(C_1-C_6)$alkyl, $(C_1-C_6)$haloalkyl, $(C_1-C_6)$alkoxy, and $(C_1-C_6)$haloalkoxy;
 $X^6$ is $CR^{18}$ wherein $R^{18}$ is selected from the group consisting of H, F, Cl, $NH_2$, CN, $NO_2$, $(C_1-C_6)$alkyl, $(C_1-C_6)$haloalkyl, $(C_1-C_6)$alkoxy, and $(C_1-C_6)$haloalkoxy;
 $X^7$ is $CR^{19}$ wherein $R^{19}$ is selected from the group consisting of H, F, Cl, $NH_2$, CN, $NO_2$, $(C_1-C_6)$alkyl, $(C_1-C_6)$haloalkyl, $(C_1-C_6)$alkoxy, and $(C_1-C_6)$haloalkoxy;
 $X^8$ is $CR^{20}$ wherein $R^{20}$ is selected from the group consisting of H, F, Cl, CN, $NH_2$, $NO_2$, $(C_1-C_6)$alkyl, $(C_1-C_6)$haloalkyl, $(C_1-C_6)$alkoxy, and $(C_1-C_6)$haloalkoxy.

Preparation of Cyclopropyl Carboxylic Acids

Stilbenes 1-1, wherein $R^1$, $R^2$, $R^3$, $R^4$, $R^5$, $R^6$, and $R^9$ are as previously disclosed, may be treated with a base such as sodium hydroxide in the presence of a carbene source such as chloroform or bromoform and a phase transfer catalyst such as N-benzyl-N,N-diethylethanaminium chloride in a polar protic solvent such as water at temperatures from about 0° C. to about 40° C. to provide diaryl cyclopropanes 1-2, wherein $R^1$, $R^2$, $R^3$, $R^4$, $R^5$, $R^6$, $R^7$, $R^8$, and $R^9$ are as previously disclosed (Scheme 1, step a). Treatment of diaryl cyclopropanes 1-2 with a transition metal such as ruthenium (III) chloride in the presence of a stoichiometric oxidant such as sodium periodate in a solvent mixture preferably water, ethyl acetate, and acetonitrile at temperatures from about 0° C. to about 40° C. may provide cyclopropyl carboxylic acids 1-3, wherein $R^1$, $R^2$, $R^3$, $R^4$, $R^5$, $R^6$, $R^7$, $R^8$, and $R^9$ are as previously disclosed (Scheme 1, step b).

Scheme 1

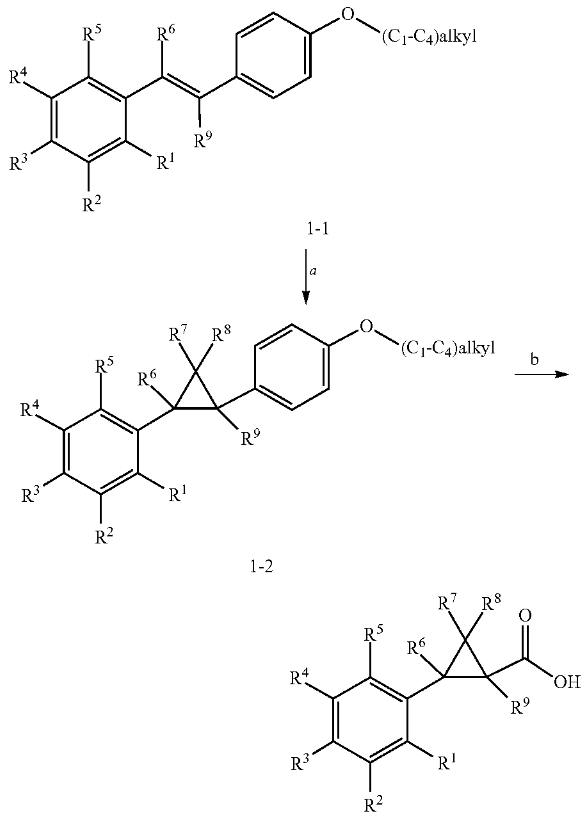

1-1

1-2

1-3

Thiophene carbonyl 1.4-1, wherein $R^9$ is as previously disclosed, may be treated with alkoxy benzyl phosphonate 2-2, wherein $R^1$, $R^2$, $R^4$, $R^5$ are as previously disclosed, in the presence of a base such as sodium methoxide in a polar aprotic solvent such as N,N-dimethylformamide at temperatures from about −10° C. to about 80° C. to provide stilbene 1.4-2, wherein $R^1$, $R^2$, $R^4$, $R^5$, $R^6$, and $R^9$ are as previously disclosed (Scheme 1.4, step a). Stilbene 1.4-2, wherein $R^1$, $R^2$, $R^4$, $R^5$, $R^6$, and $R^9$ are as previously disclosed, may be treated with a base such as sodium hydroxide in the presence of a carbene source such as chloroform or bromoform and a phase transfer catalyst such as N-benzyl-N,N-diethylethanaminium chloride in a polar protic solvent such as water at temperatures from about 0° C. to about 40° C. to provide thiophene cyclopropane 1.4-3, wherein $R^1$, $R^2$, $R^4$, $R^5$, $R^6$, $R^7$, $R^8$, and $R^9$ are as previously disclosed (Scheme 1.4, step b). Treatment of thiophene cyclopropane 1.4-3 with a transition metal such as ruthenium(III) chloride in the presence of a stoichiometric oxidant such as sodium periodate in a solvent mixture preferably water, ethyl acetate, and acetonitrile at temperatures from about 0° C. to about 40° C. may provide cyclopropyl carboxylic acid 1-3, wherein $R^3$ is a $(C_1\text{-}C_4)$alkoxy group and $R^1$, $R^2$, $R^4$, $R^5$, $R^6$, $R^7$, $R^8$, and $R^9$ are as previously disclosed (Scheme 1.4, step c).

Scheme 1.4

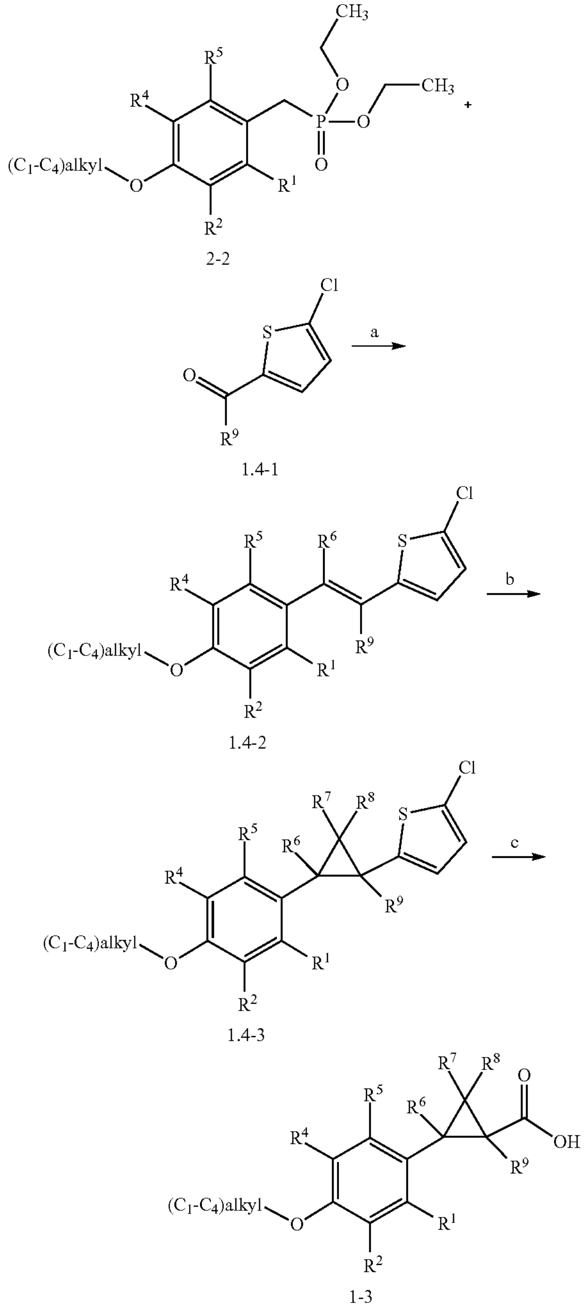

2-2

1.4-1

1.4-2

1.4-3

1-3

Phenyl carbonyls 1.7-1, wherein $R^1$, $R^2$, $R^3$, $R^4$, $R^5$, and $R^6$ are as previously disclosed, may be treated with alkoxy phosphonate 1.7-2 in the presence of a base such as sodium hydride in a polar aprotic solvent such as tetrahydrofuran at temperatures from about −10° C. to about 40° C. to provide stilbenes 1.7-3, wherein $R^1$, $R^2$, $R^3$, $R^4$, $R^5$, $R^6$, and $R^9$ are as previously disclosed (Scheme 1.7, step a). Stilbenes 1.7-3, wherein $R^1$, $R^2$, $R^3$, $R^4$, $R^5$, $R^6$, and $R^9$ are as previously disclosed, may be treated with a reducing agent such as diisobutylaluminum hydride (DIBAL) in a polar aprotic solvent such as toluene at temperatures from about −80° C. to about 0° C. to provide alcohols 1.7-4, wherein $R^1$, $R^2$, $R^3$, $R^4$, $R^5$, $R^6$, and $R^9$ are as previously disclosed (Scheme 1.7, step b). Alcohols 1.7-4, wherein $R^1$, $R^2$, $R^3$, $R^4$, $R^5$, $R^6$, and $R^9$ are as previously disclosed, may be protected by treatment with 3,4-dihydro-2H-pyran in the presence of an acid catalyst such as p-toluenesulfonic acid in a polar aprotic solvent such as diethyl ether at temperatures from about 0° C. to about 40° C. to give protected stilbenes 1.7-5, wherein $R^1$, $R^2$, $R^3$, $R^4$, $R^5$, $R^6$, and $R^9$ are as previously disclosed (Scheme 1.7, step c). Protected stilbenes 1.7-5, wherein $R^1$, $R^2$, $R^3$, $R^4$, $R^5$, $R^6$, and $R^9$ are as previously disclosed, may be treated with a base such as sodium hydroxide in the presence of a carbene source such as chloroform or bromoform and a phase transfer catalyst such as N-benzyl-N,N-diethylethanaminium chloride in a polar protic solvent such as water at temperatures from about 0° C. to about 40° C. to provide cyclopropanes 1.7-7, wherein $R^1$, $R^2$, $R^3$, $R^4$, $R^5$, $R^6$, $R^7$, $R^8$, and $R^9$ are as previously disclosed (Scheme 1.7, step d). Cyclopropanes 1.7-6, wherein $R^1$, $R^2$, $R^3$, $R^4$, $R^5$, $R^6$, $R^7$, $R^8$, and $R^9$ are as previously disclosed, may be treated with an acid such as p-toluenesulfonic acid in a polar protic solvent such as methanol at temperatures from about 0° C. to about 40° C. to provide alcohols 1.7-7, wherein $R^1$, $R^2$, $R^3$, $R^4$, $R^5$, $R^6$, $R^7$, $R^8$, and $R^9$ are as previously disclosed (Scheme 1.7, step e). Treatment of alcohols 1.7-7, wherein $R^1$, $R^2$, $R^3$, $R^4$, $R^5$, $R^6$, $R^7$, $R^8$, and $R^9$ are as previously disclosed, with an oxidant such as Jones reagent in a polar aprotic solvent such as acetone at temperatures from about −10° C. to about 40° C. to provide cyclopropyl carboxylic acids 1-3, wherein $R^1$, $R^2$, $R^3$, $R^4$, $R^5$, $R^6$, $R^7$, $R^8$, and $R^9$ are as previously disclosed (Scheme 1.7, step f).

Scheme 1.7

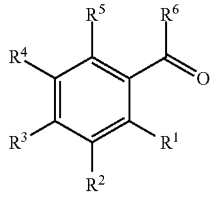

1.7-1

+

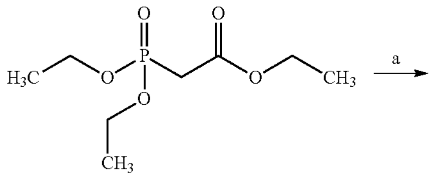

1.7-2

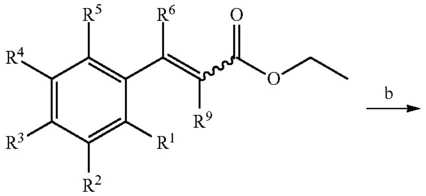

1.7-3

-continued

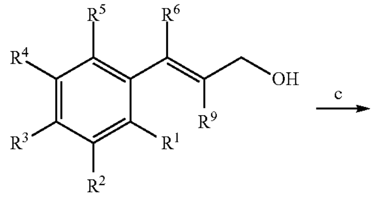

1.7-4

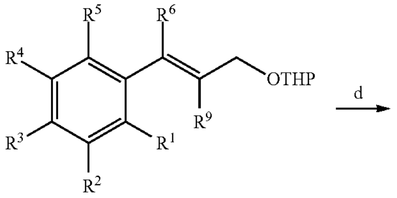

1.7-5

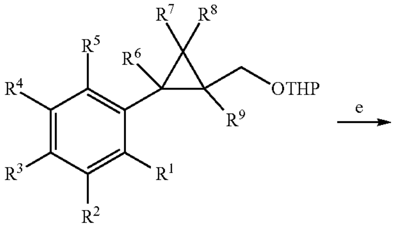

1.7-6

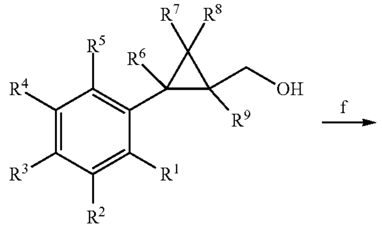

1.7-7

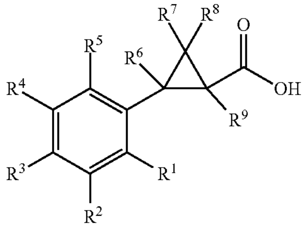

1-3

Preparation of Stilbenes

Stilbenes 1-1 may be prepared by several different methods as outlined in Scheme 2. Phenyl carbonyls 2-1, wherein $R^1$, $R^2$, $R^3$, $R^4$, $R^5$, and $R^6$ are as previously disclosed, may be treated with alkoxy benzyl phosphonates 2-2 in the presence of a base such as sodium methoxide in a polar aprotic solvent such as N,N-dimethylformamide at temperatures from about −10° C. to about 30° C. and subsequently heated to 40° C. to about 80° C. to provide stilbenes 1-1 (Scheme 2, step a).

Scheme 2

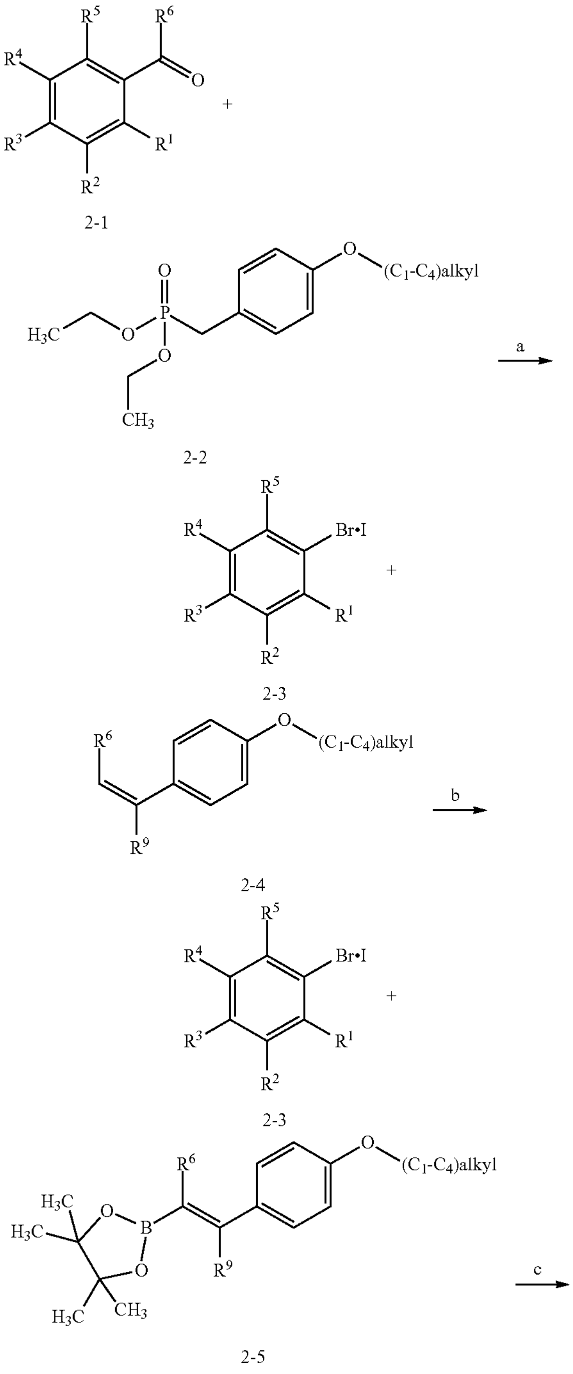

2-1, 2-2, 2-3, 2-4, 2-3, 2-5, 1-1

Aryl halides 2-3, wherein $R^1$, $R^2$, $R^3$, $R^4$, and $R^5$ are as previously disclosed, may be treated with vinylbenzenes 2-4, wherein $R^6$ and $R^9$ are as previously disclosed, in the presence of a transition metal catalyst such as palladium(II) acetate and a bisphosphine ligand such as 1,1'-bis(diphenylphosphino)ferrocene in a basic solvent such as triethylamine at temperatures from about 60° C. to about 100° C. to provide stilbenes 1-1 (Scheme 2, step b). Alternatively, Aryl halides 2-3 may be treated with vinylboronates 2-5, wherein $R^6$ and $R^9$ are as previously disclosed, in the presence of a transition metal catalyst such as tetrakis(triphenylphosphine)palladium(0) and a base such as potassium carbonate in a solvent mixture such as 1,2-dimethoxyethane and water at temperatures from about 60° C. to about 100° C. to provide stilbenes 1-1 (Scheme 2, step c).

In yet another embodiment, stilbenes 1-1 may also be prepared by the Wittig olefination method (Chalal, M.; Vervandier-Fasseur, D.; Meunier, P.; Cattey, H.; Hierso, J.-C. *Tetrahedron* 2012, 68, 3899-3907) as outlined in Scheme 2.5. Phenyl carbonyls 2-1, wherein $R^1$, $R^2$, $R^3$, $R^4$, and $R^5$ are as previously disclosed and $R^6$ is H, may be treated with alkoxy benzyl triphenylphosphonium chlorides 2.5-2 in the presence of a base such as n-butyl lithium in a polar aprotic solvent such as tetrahydrofuran at temperatures from about −78° C. to ambient temperature to provide stilbenes 1-1 (Scheme 2.5, step a).

Scheme 2.5

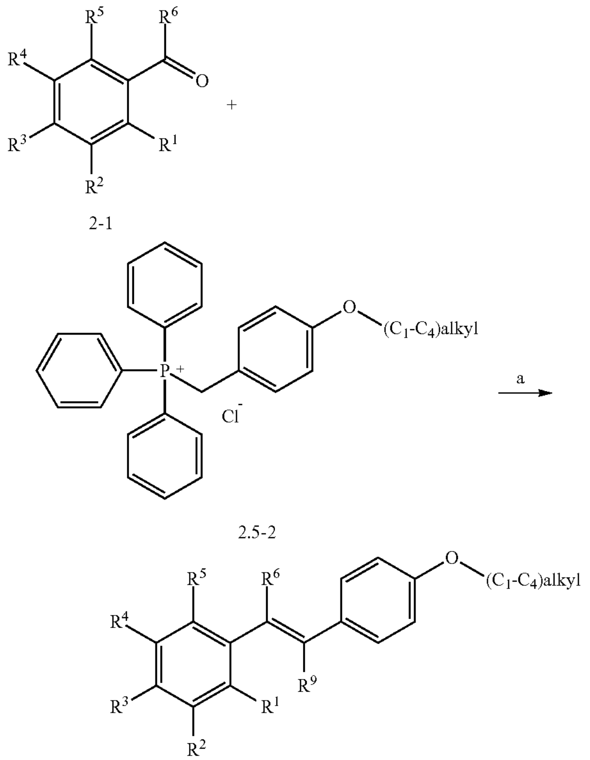

2-1, 2.5-2, 1-1

Preparation of Cyclopropyl Amides

Cyclopropyl amides 3-3, wherein $R^1$, $R^2$, $R^3$, $R^4$, $R^5$, $R^6$, $R^7$, $R^8$, $R^9$, $R^{10}$, $R^{11}$, $R^{12}$, $X^1$, $X^2$, and $Q^2$ are as previously disclosed, and $X^3$ is as previously disclosed and OH, may be prepared by treatment with amines or amine salts 3-2, wherein $R^{10}$, $R^{11}$, $R^{12}$, $X^1$, $X^2$, $Q^2$, and $X^3$ are as previously disclosed, and activated carboxylic acids 3-1, wherein A is an activating group, and $R^1$, $R^2$, $R^3$, $R^4$, $R^5$, $R^6$, $R^7$, $R^8$, and $R^9$ are as previously disclosed, with a base, such as triethylamine, diisopropylethylamine, 4-methylmorpholine, 4-dimethylaminopyridine, or pyridine in an anhydrous aprotic solvent such as dichloromethane, tetrahydrofuran, 1,2-dichloroethane, dimethylformamide, or any combination thereof, at temperatures between about 0° C. and about 120° C. (Scheme 3, step a).

Activated carboxylic acids 3-1 may be an acid halide, such as an acid chloride, an acid bromide, or an acid fluoride; a carboxylic ester, such as a para-nitrophenyl ester, a pentafluorophenyl ester, an ethyl (hydroxyiminio)cyanoacetate ester, a methyl ester, an ethyl ester, a benzyl ester, an N-hydroxysuccinimidyl ester, a hydroxybenzotriazol-1-yl ester, or a hydroxypyridyltriazol-1-yl ester; an O-acylisourea; an acid anhydride; or a thioester. Acid chlorides may be prepared from the corresponding carboxylic acids by treatment with a dehydrating chlorinating reagent, such as oxalyl chloride or thionyl chloride. Activated carboxylic esters 3-1 may be prepared from carboxylic acids in situ with a uronium salt, such as 1-[bis(dimethylamino)methylene]-1H-1,2,3-triazolo[4,5-b]pyridinium 3-oxid hexafluorophosphate (HATU), 0-(benzotriazol-1-yl)-N,N,N',N'-tetramethyluronium hexafluorophosphate (HBTU), or (1-cyano-2-ethoxy-2-oxoethylidenaminooxy)dimethylamino-morpholino-carbenium hexafluorophosphate (COMU). Activated carboxylic esters 3-1 may also be prepared from carboxylic acids in situ with a phosphonium salt such as benzotriazol-1-yl-oxytripyrrolidinophosphonium hexafluorophosphate (PyBop). Activated carboxylic esters 3-1 may also be prepared from carboxylic acids in situ with a coupling reagent such as 1-(3-dimethylamino propyl)-3-ethylcarbodiimide, propylphosphonic anhydride, or dicyclohexylcarbodiimide with or without the presence of a triazole such as hydroxybenzotriazole·monohydrate (HOBt) or 1-hydroxy-7-azabenzotriazole (HOAt). O-Acylisoureas may be prepared with a dehydrating carbodimide such as 1-(3-dimethylamino propyl)-3-ethylcarbodiimide or dicyclohexylcarbodiimide. Activated carboxylic esters 3-1 may also be prepared from carboxylic acids in situ with a coupling reagent such as 2-chloro-1,3-dimethylimidazolidinium hexafluorophosphate (CIP) in the presence of a triazole such as 1-hydroxy-7-azabenzotriazole (HOAt).

Cyclopropyl amides 3-3 containing a sulfide may be oxidized to the corresponding sulfoxide or sulfone by treatment with about one equivalent of meta-chloroperoxybenzoic acid (sulfoxide) in a polar aprotic solvent such as dichloromethane or about two equivalents of meta-chloroperoxybenzoic acid (sulfone) at temperatures between about 0° C. to about 40° C. Alternatively, cyclopropyl amides 3-3 containing a sulfide may be oxidized to the corresponding sulfoxide or sulfone by treatment with one equivalent of sodium perborate in a protic solvent such as acetic acid (sulfoxide) or two equivalents of sodium perborate (sulfone). The oxidation may be performed at temperatures between about 40° C. to about 100° C. using about 1.5 equivalents of sodium perborate to provide chromatographically separable mixtures of sulfoxide and sulfone cyclopropyl amides 3-3. Alternatively, cyclopropyl amides 3-3 containing a sulfide may be oxidized to the corresponding sulfilimine by treating with about one equivalent of an amine such as cyanamide, about one equivalent of a base such as potassium tert-butoxide, and between one and two equivalents of an oxidant such as N-bromosuccinimide in a polar protic solvent such as methanol at temperatures between about 0° C. to about 40° C. The sulfilimine may be further oxidized to the corresponding sulfoximine by treatment with about one equivalent of meta-chloroperoxybenzoic acid and about two equivalents of potassium carbonate in a mixture of solvents such as 2:1:1 ethanol:dichloromethane:water at temperatures between about 0° C. to about 40° C.

Cyclopropyl amides 3-3, wherein $X^1$, $X^2$, $X^4$, $X^5$, $X^6$, $X^7$, or, $X^8$ is N may be oxidized to the corresponding N-oxide by treatment with about one equivalent of meta-chloroperoxybenzoic acid in a polar aprotic solvent such as dichloromethane at temperatures between about 0° C. to about 40° C.

Cyclopropyl amides 3-3, wherein $R^3$ is $NO_2$ may be reduced to the corresponding $NH_2$ by treatment with an acid source, such as ammonium chloride, and iron in a polar protic solvent, such as methanol, water, or any combination thereof, at temperatures from about 20° C. to about 60° C.

Amines or amine salts 3-2, wherein $Q^2$ is O may be treated directly with a source of sulfur, such as phosphorus pentasulfide or 2,4-bis(4-methoxyphenyl)-1,3,2,4-dithiadiphosphetane 2,4-disulfide (Lawesson's reagent) with or without additives such as 1,1,1,3,3,3-hexamethyldisoloxane, in an aprotic solvent chosen from tetrahydrofuran, dichloromethane, chloroform, toluene, or pyridine, at temperatures from about 40° C. to about 120° C. to provide amines or amine salts 3-2, wherein $Q^2$ is S.

Scheme 3

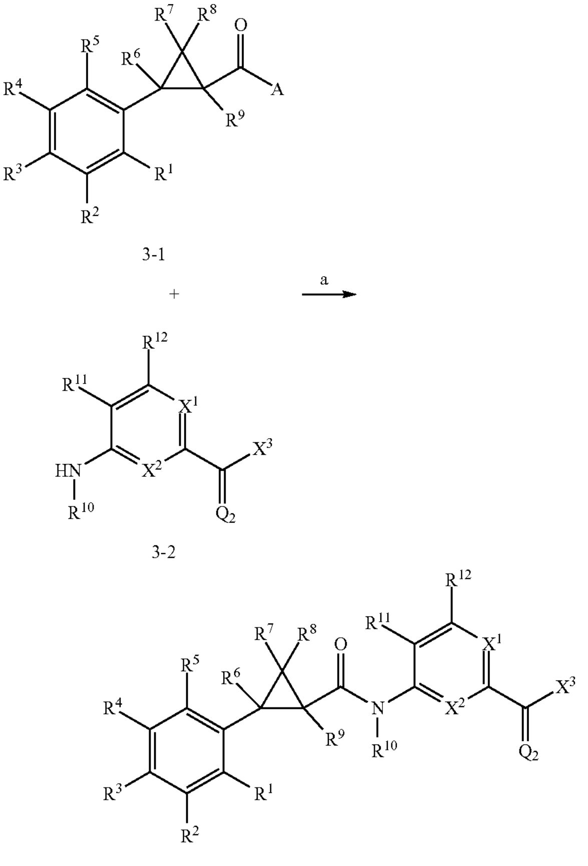

3-1
+
3-2
3-3

Cyclopropyl amides 4-3, wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, and $X^3$ are as previously disclosed, may be prepared by treatment with amines or amine salts 4-2, wherein $X^3$ is as previously disclosed, and activated carboxylic acids 4-1, wherein A is an activating group, and $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, and $X^2$ are as previously disclosed, with a base, such as triethylamine, diisopropylethylamine, 4-methylmorpholine, 4-dimethylaminopyridine, or pyridine in an anhydrous aprotic solvent such as dichloromethane, tetrahydrofuran, 1,2-dichloroethane, dimethylformamide, or any combination thereof, at temperatures between about 0° C. and about 120° C. (Scheme 4, step a).

Activated carboxylic acids 4-1 may be an acid halide, such as an acid chloride, an acid bromide, or an acid fluoride; a carboxylic ester, such as a p-nitrophenyl ester, a pentafluorophenyl ester, an ethyl (hydroxyimino)cyanoacetate ester, a methyl ester, an ethyl ester, a benzyl ester, an N-hydroxysuccinimidyl ester, a hydroxybenzotriazol-1-yl ester, or a hydroxypyridyltriazol-1-yl ester; an O-acylisourea; an acid anhydride; or a thioester. Acid chlorides may be prepared from the corresponding carboxylic acids by treatment with a dehydrating chlorinating reagent, such as oxalyl chloride or thionyl chloride. Activated carboxylic esters 4-1 may be prepared from carboxylic acids in situ with a uronium salt, such as 1-[bis(dimethylamino)methylene]-1H-1,2,3-triazolo[4,5-b]pyridinium 3-oxid hexafluorophosphate (HATU), 0-(benzotriazol-1-yl)-N,N,N',N'-tetramethyluronium hexafluorophosphate (HBTU), or (1-cyano-2-ethoxy-2-oxoethylidenaminooxy)dimethylamino-morpholino-carbenium hexafluorophosphate (COMU). Activated carboxylic esters 4-1 may also be prepared from carboxylic acids in situ with a phosphonium salt such as benzotriazol-1-yl-oxytripyrrolidinophosphonium hexafluorophosphate (PyBop). Activated carboxylic esters 4-1 may also be prepared from carboxylic acids in situ with a coupling reagent such as 1-(3-dimethylamino propyl)-3-ethylcarbodiimide, propylphosphonic anhydride, or dicyclohexylcarbodiimide with or without the presence of a triazole such as hydroxybenzotriazole·monohydrate (HOBt) or 1-hydroxy-7-azabenzotriazole (HOAt). O-Acylisoureas may be prepared with a dehydrating carbodimide such as 1-(3-dimethylamino propyl)-3-ethylcarbodiimide or dicyclohexylcarbodiimide. Activated carboxylic esters 4-1 may also be prepared from carboxylic acids in situ with a coupling reagent such as 2-chloro-1,3-dimethylimidazolidinium hexafluorophosphate (CIP) in the presence of a triazole such as 1-hydroxy-7-azabenzotriazole (HOAt).

Scheme 4

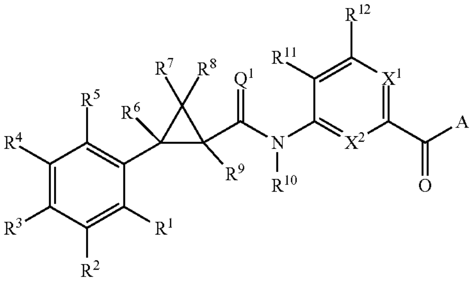

4-1

+

HX$^3$ 4-2 a

-continued

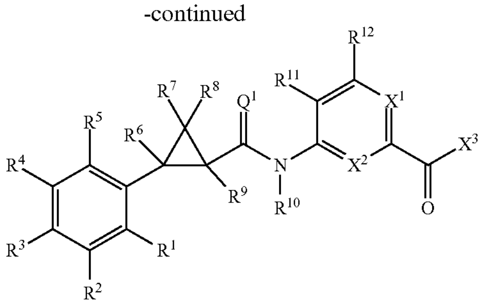

4-3

Cyclopropyl amides 5-2, wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, $Q^2$, $R^{15}$, $X^4$, $X^5$, $X^6$, $X^7$, and $X^8$ are as previously disclosed, may be prepared by treatment of amines 5-1, wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, $Q^2$, $R^{15}$, $X^4$, $X^5$, $X^6$, $X^7$, and $X^8$ are as previously disclosed, with a methylating agent such as methylboronic acid and a copper catalyst such as diacetoxycopper in the presence of an aprotic amine base like pyridine in a solvent such as 1,4-dioxane at a temperature of about 110° C. (Scheme 5, step a).

Cyclopropyl amides 5-4, wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, $Q^2$, $R^{15}$, $X^4$, $X^5$, $X^6$, $X^7$, and $X^8$ are as previously disclosed, and L is $(C_1-C_6)$alkyl, $(C_2-C_6)$alkenyl, $(C_3-C_6)$cycloalkyl, $(C_1-C_6)$haloalkyl, $(C_1-C_6)$alkylphenyl, and $(C_1-C_6)$alkoxy, wherein each alkyl, alkenyl, cycloalkyl, haloalkyl, and phenyl, may be optionally substituted with one or more substituents selected from F, Cl, Br, I, CN, OH, $NH_2$, $NO_2$, oxo, $(C_1-C_6)$alkyl, $(C_1-C_6)$alkoxy, and $C(O)O(C_1-C_6)$alkyl, may be prepared by treatment of amines 5-1, wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, $Q^2$, $R^{15}$, $X^4$, $X^5$, $X^6$, $X^7$, and $X^8$ are as previously disclosed, or amines 5-2, wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, $Q^2$, $R^{15}$, $X^4$, $X^5$, $X^6$, $X^7$, and $X^8$ are as previously disclosed, and activated carboxylic acids 5-3, wherein A is an activating group, and L is as previously disclosed, with a base, such as triethylamine, diisopropylethylamine, 4-methylmorpholine, 4-dimethylaminopyridine, or pyridine, in an anhydrous aprotic solvent such as dichloromethane, tetrahydrofuran, 1,2-dichloroethane, N,N-dimethylformamide, or any combination thereof, at temperatures between about 0° C. and about 120° C. (Scheme 5, steps b and c).

Activated carboxylic acids 5-3 may be an acid halide, such as an acid chloride, an acid bromide, or an acid fluoride; a carboxylic ester, such as a p-nitrophenyl ester, a pentafluorophenyl ester, an ethyl (hydroxyiminio)cyanoacetate ester, a methyl ester, an ethyl ester, a benzyl ester, an N-hydroxysuccinimidyl ester, a hydroxybenzotriazol-1-yl ester, or a hydroxypyridyltriazol-1-yl ester; an O-acylisourea; an acid anhydride; or a thioester. Acid chlorides may be prepared from the corresponding carboxylic acids by treatment with a dehydrating chlorinating reagent, such as oxalyl chloride or thionyl chloride. Activated carboxylic esters 5-3 may be prepared from carboxylic acids in situ with a uronium salt, such as 1-[bis(dimethylamino)methylene]-1H-1,2,3-triazolo[4,5-b]pyridinium 3-oxid hexafluorophosphate (HATU), 0-(benzotriazol-1-yl)-N,N,N',N'-tetramethyluronium hexafluorophosphate (HBTU), or (1-cyano-2-ethoxy-2-oxoethylidenaminooxy)dimethylamino-morpholino-carbenium hexafluorophosphate (COMU). Activated carboxylic esters 5-3 may also be prepared from carboxylic acids in situ with a phosphonium salt such as benzotriazol-1-yl-oxytripyrrolidinophosphonium hexafluorophosphate (PyBop). Activated carboxylic esters 5-3 may also be prepared from carboxylic acids in situ with a coupling reagent, such as 1-(3-dimethylamino propyl)-3-ethylcarbodiimide or dicyclohexylcarbodiimide, in the presence of a triazole such as hydroxybenzotriazole·monohydrate (HOBt) or 1-hydroxy-7-azabenzotriazole (HOAt). O-Acylisoureas may be prepared with a dehydrating carbodimide such as 1-(3-dimethylaminopropyl)-3-ethylcarbodiimide or dicyclohexylcarbodiimide. Activated carboxylic esters 5-3 may also be prepared from carboxylic acids in situ with a coupling reagent such as 2-chloro-1,3-dimethylimidazolidinium hexafluorophosphate (CIP) in the presence of a triazolol such as 1-hydroxy-7-azabenzotriazole (HOAt). Activated carboxylic esters 5-3 may also be prepared from carboxylic acids in situ with a coupling reagent such as 2,4,6-tripropyl-1,3,5,2,4,6-trioxatriphosphinane 2,4,6-trioxide (T3P®) in the presence of a base such as pyridine.

Scheme 5

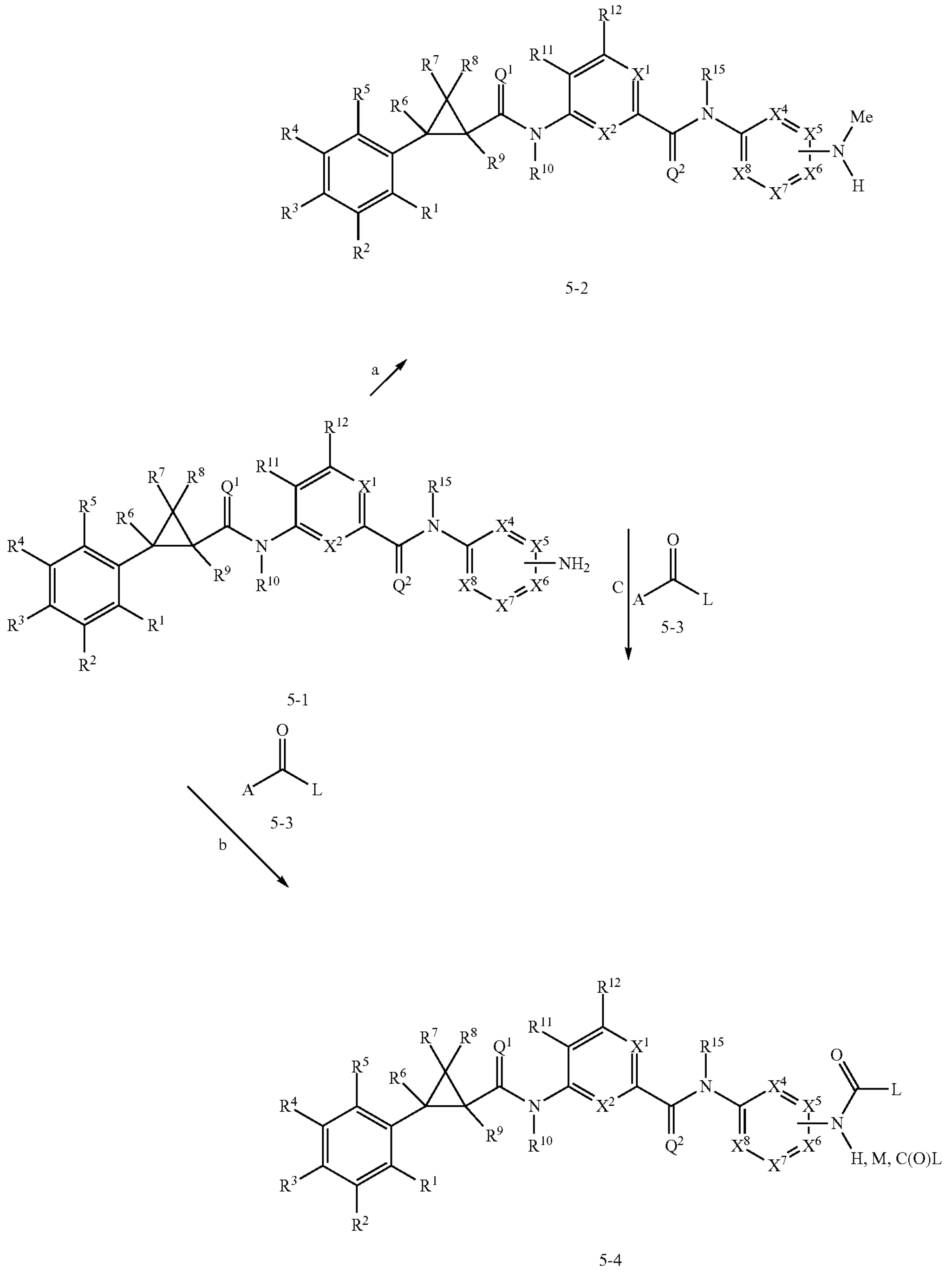

Cyclopropyl amides 6-3, wherein $R^1$, $R^2$, $R^3$, $R^4$, $R^5$, $R^6$, $R^7$, $R^8$, $R^9$, $R^{10}$, $R^{11}$, $R^{12}$, $X^1$, $X^2$, $Q^2$, $R^{15}$, $X^5$, $X^6$, $X^7$, and $X^8$ are as previously disclosed, may be prepared by treatment of aldehydes or ketones 6-1 wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, $Q^2$, $R^{15}$, $X^5$, $X^6$, $X^7$, and $X^8$ are as previously disclosed, and hydroxylamines 6-2, wherein each alkyl may be optionally substituted with one or more substituents selected from F, Cl, Br, I, CN, OH, $NH_2$, $NO_2$, oxo, $(C_1-C_6)$alkyl, $(C_1-C_6)$alkoxy, and C(O)O$(C_1-C_6)$alkyl, with or without an acid, such as acetic acid, in a polar aprotic solvent such as ethanol, at temperatures between about 0° C. and about 80° C. (Scheme 6, step a).

Scheme 6

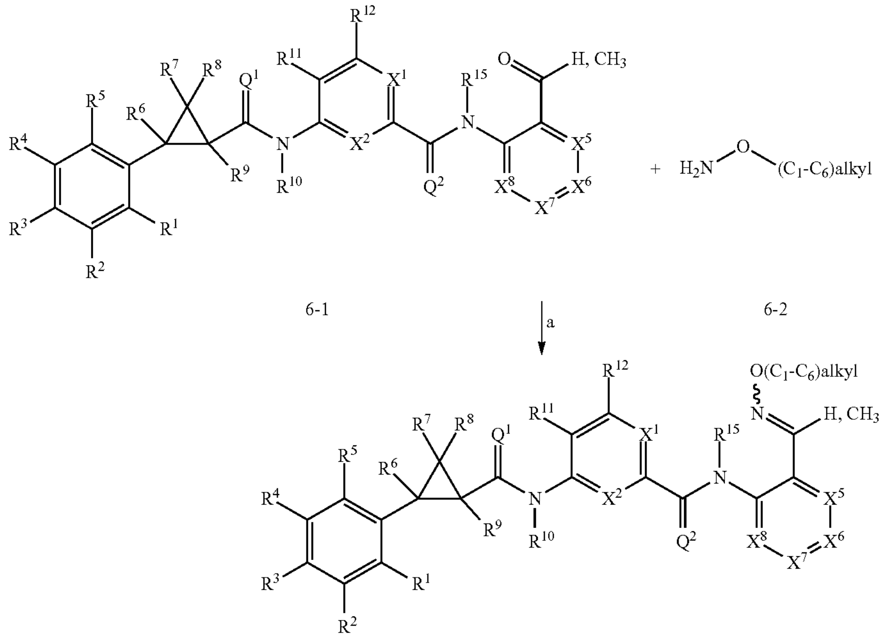

6-1 6-2

6-3

Cyclopropyl amides 7-3, wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, $Q^2$, $R^{15}$, $X^4$, $X^5$, $X^7$, and $X^8$ are as previously disclosed, may be prepared by treatment of aldehydes or ketones 7-1 wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, $Q^2$, $R^{15}$, $X^4$, $X^5$, $X^7$, and $X^8$ are as previously disclosed, and hydroxylamines 7-2, wherein each alkyl may be optionally substituted with one or more substituents selected from F, Cl, Br, I, CN, OH, $NH_2$, $NO_2$, oxo, $(C_1-C_6)$alkyl, $(C_1-C_6)$alkoxy, and C(O)O$(C_1-C_6)$alkyl, with or without an acid, such as acetic acid, in a polar aprotic solvent such as ethanol, at temperatures between about 0° C. and about 80° C. (Scheme 7, step a).

Scheme 7

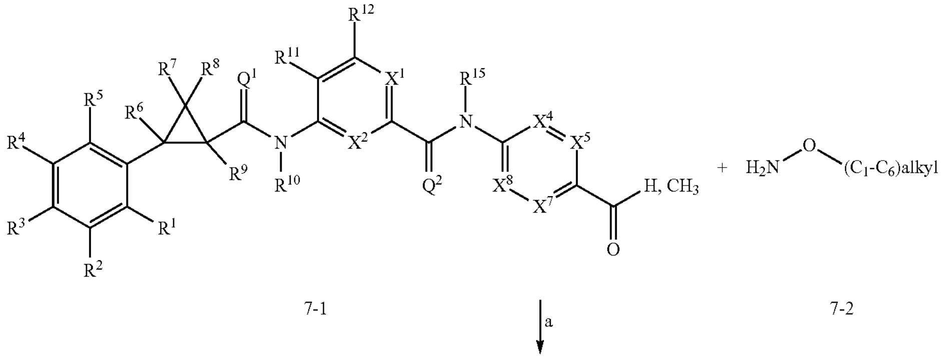

7-1 7-2

-continued

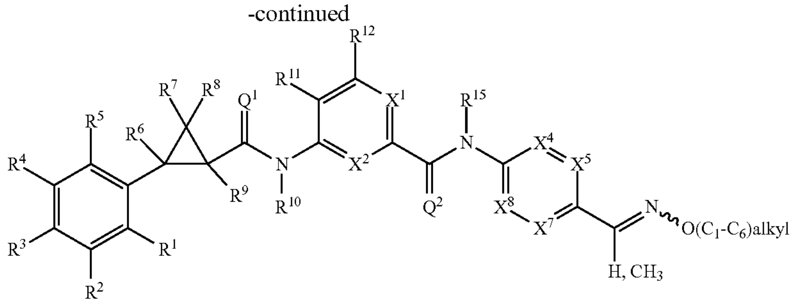

7-3

Cyclopropyl amides 8-3, wherein $R^1$, $R^2$, $R^4$, $R^5$, $R^6$, $R^7$, $R^8$, $R^9$, $Q^1$, $R^{10}$, $R^{11}$, $R^{12}$, $X^1$, $X^2$, $X^3$, and $Q^2$ are as previously disclosed, may be prepared by treatment of aryl bromide 8-1, wherein $R^1$, $R^2$, $R^4$, $R^5$, $R^6$, $R^7$, $R^8$, $R^9$, $Q^1$, $R^{10}$, $R^{11}$, $R^{12}$, $X^1$, $X^2$, $X^3$, and $Q^2$ are as previously disclosed, and ($C_1$-$C_6$)alkenyl or ($C_1$-$C_6$)alkynyl stannane 8-2, wherein each alkenyl or alkynyl group may be optionally substituted with one or more substituents selected from F and $SiMe_3$, with a palladium source, such as bis(triphenylphosphine)palladium(II) dichloride in an aprotic solvent such as 1,4-dioxane, at temperatures between about 20° C. and about 120° C. (Scheme 8, step a).

Cyclopropyl amides 8-3, wherein ($C_1$-$C_6$)alkynyl is trimethylsilyl alkyne may be treated with a source of fluoride, such as potassium fluoride, in a polar solvent, such as dichloromethane, methanol, or a combination thereof, at temperatures from about 0° C. to about 50° C. to provide cyclopropyl amide 8-3, wherein ($C_1$-$C_6$)alkynyl is CCH.

Scheme 8

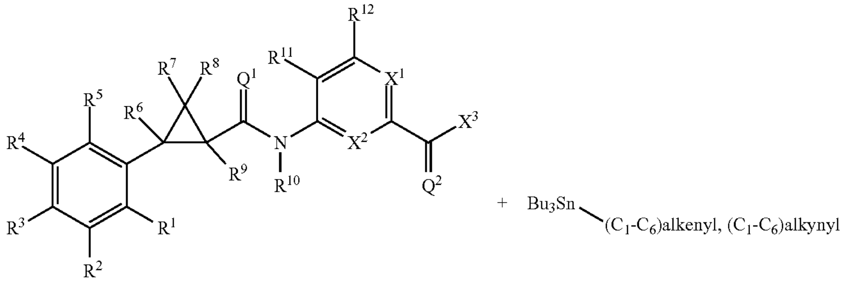

8-1

8-2

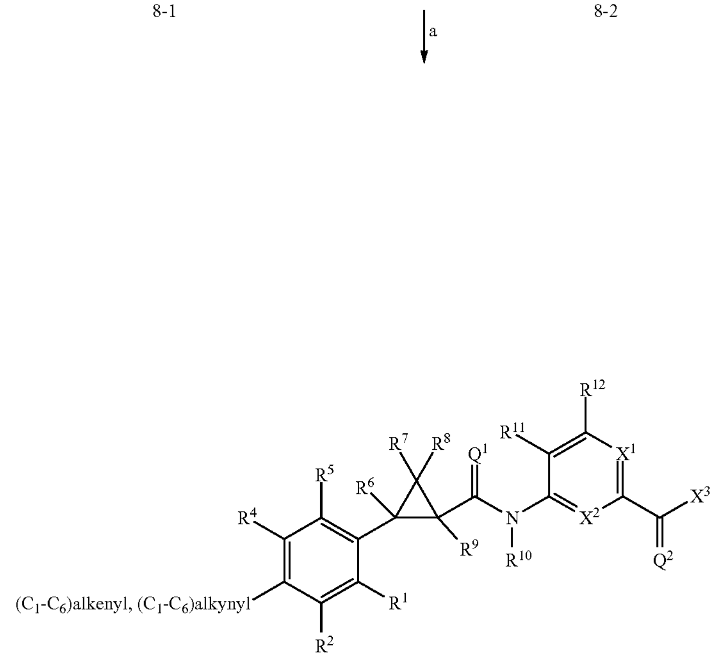

8-3

Cyclopropyl amides 9-3, wherein $R^1$, $R^2$, $R^3$, $R^5$, $R^6$, $R^7$, $R^8$, $R^9$, $Q^1$, $R^{10}$, $R^{11}$, $R^{12}$, $X^1$, $X^2$, $X^3$, and $Q^2$ are as previously disclosed, may be prepared by treatment of aryl bromide 9-1, wherein $R^1$, $R^2$, $R^3$, $R^5$, $R^6$, $R^7$, $R^8$, $R^9$, $Q^1$, $R^{10}$, $R^{11}$, $R^{12}$, $X^1$, $X^2$, $X^3$, and $Q^2$ are as previously disclosed, and $(C_1\text{-}C_6)$alkenyl or $(C_1\text{-}C_6)$alkynyl stannane 9-2, wherein each alkenyl or alkynyl group may be optionally substituted with one or more substituents selected from F and $SiMe_3$, with a palladium source, such as bis(triphenylphosphine)palladium(II) dichloride in an aprotic solvent such as 1,4-dioxane, at temperatures between about 20° C. and about 120° C. (Scheme 9, step a).

Cyclopropyl amides 9-3, wherein $(C_1\text{-}C_6)$alkynyl is trimethylsilyl alkyne may be treated with a source of fluoride, such as potassium fluoride, in a polar solvent, such as dichloromethane, methanol, or a combination thereof, at temperatures from about 0° C. to about 50° C. to provide cyclopropyl amide 9-3, wherein $(C_1\text{-}C_6)$alkynyl is CCH.

Scheme 9

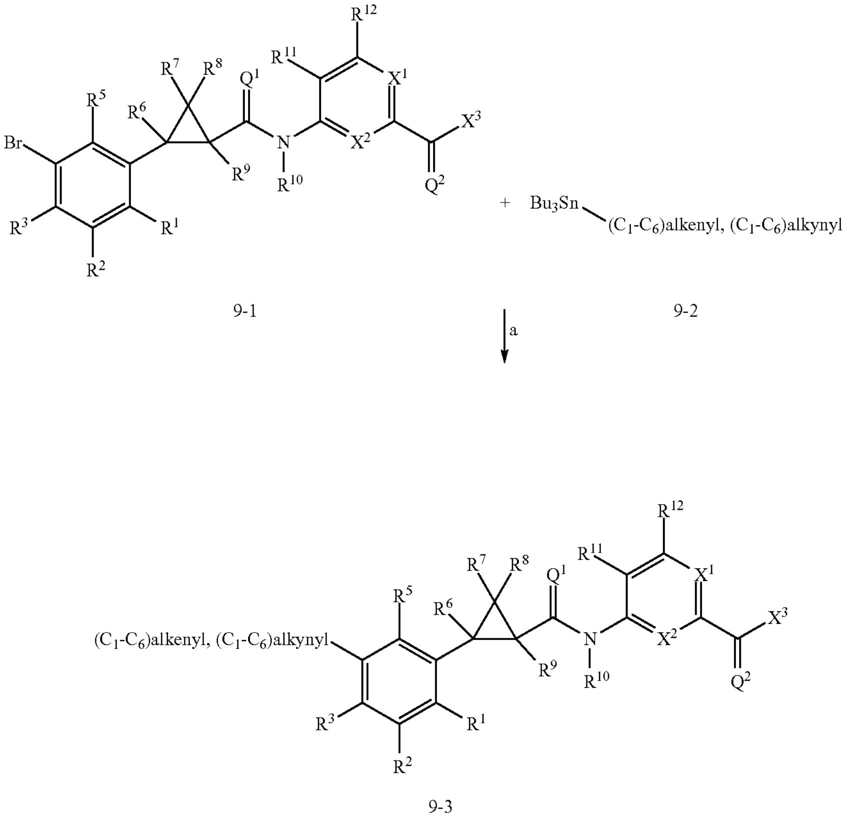

9-1

9-2

9-3

Cyclopropyl amides 10-3, wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, $X^4$, $X^5$, $X^6$, $X^7$, and $X^8$ are as previously disclosed, may be prepared by treatment of primary amides 10-1, wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, and $X^2$ are as previously disclosed, and aryl bromides 10-2, wherein $X^4$, $X^5$, $X^6$, $X^7$, and $X^8$ are as previously disclosed, with a palladium catalyst such as tris(dibenzylideneacetone)dipalladium(0), a phosphine ligand such as 4,5-Bis(diphenylphosphino)-9,9-dimethylxanthene, and an inorganic base such as cesium carbonate, in an aprotic solvent such as 1,4-dioxane, at temperatures between about 60° C. and about 80° C. (Scheme 10, step a).

Scheme 10

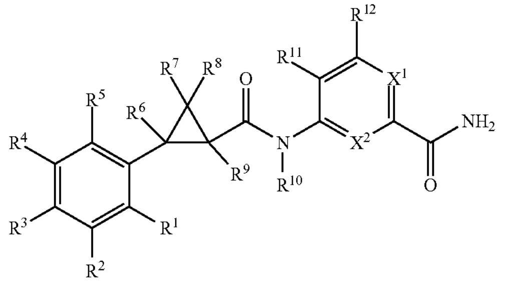

10-1

+

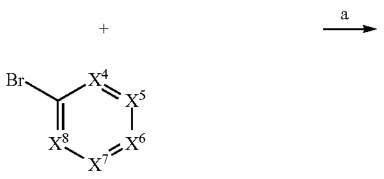

10-2

-continued

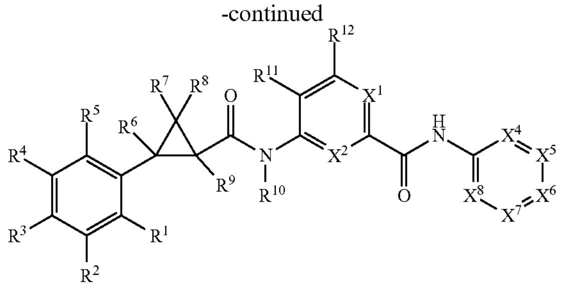

10-3

Cyclopropyl amides 11-3, wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, $X^4$, $X^5$, $X^6$, $X^7$, and $X^8$ are as previously disclosed, may be prepared by treatment of 11-1, wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, $X^4$, $X^5$, $X^6$, $X^7$, and $X^8$ are as previously disclosed, with a metal such as palladium on carbon in the presence of a reducing agent such as hydrogen gas in a solvent such as ethyl acetate or with a metal such as iron in the presence of a reducing agent such as ammonium chloride in a solvent mixture such as methanol and water at a temperature of about 25° C. to about 60° C. (Scheme 11, step a). Alternatively, cyclopropyl amides 11-3, wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, $X^4$, $X^5$, $X^6$, $X^7$, and $X^8$ are as previously disclosed, may be prepared by treatment of 11-2 wherein $R^3$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, $X^4$, $X^5$, $X^6$, $X^7$, and $X^8$ are as previously disclosed, with an anhydrous acid solution such as hydrochloric acid in 1,4-dioxane and dichloromethane at a temperature of about 25° C. (Scheme 11, step b).

Scheme 11

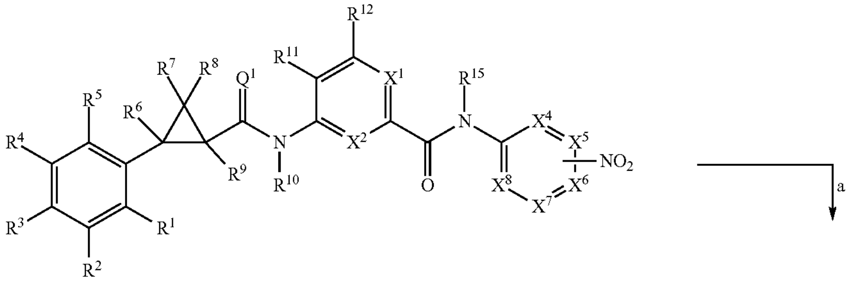

11-1

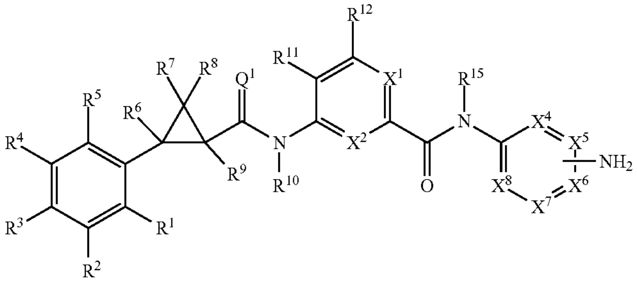

11-3

-continued

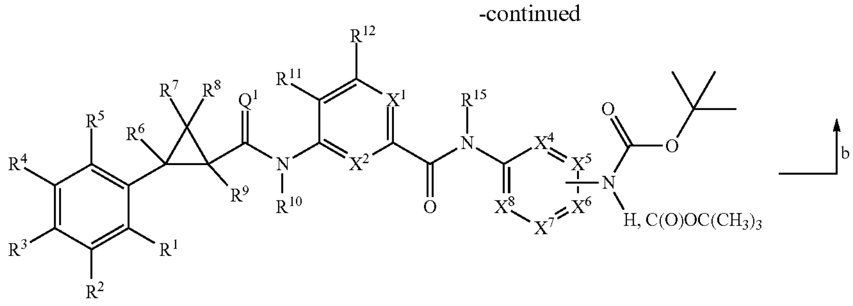

11-2

Cyclopropyl amides 12-3, wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^1$, $X^2$, $Q^2$, $R^{15}$, $X^4$, $X^5$, $X^6$, $X^7$, and $X^8$ are as previously disclosed and $L^2$ is a $(C_1-C_6)$ alkenyl or $(C_1-C_6)$alkynyl group, wherein each alkenyl or alkynyl group may be optionally substituted with one or more substituents selected from F, Cl, and $(C_1-C_6)$alkyl, may be prepared by treatment of aryl halides 12-1, wherein $R^1$, $R^2$, $R^3$, $R^4$, $R^5$, $R^6$, $R^7$, $R^8$, $R^9$, $Q^1$, $R^{10}$, $R^{11}$, $R^{12}$, $X^3$, $X^2$, $Q^2$, $R^{15}$, $X^4$, $X^5$, $X^6$, $X^7$, and $X^8$ are as previously disclosed, with a stannane such as 12-2, wherein $L^2$ is as previously disclosed, in the presence of a metal catalyst such as bis(triphenylphosphine)palladium(II) dichloride in an aprotic solvent like 1,4-dioxane at a temperature of about 90° C. (Scheme 12, step a).

Scheme 12

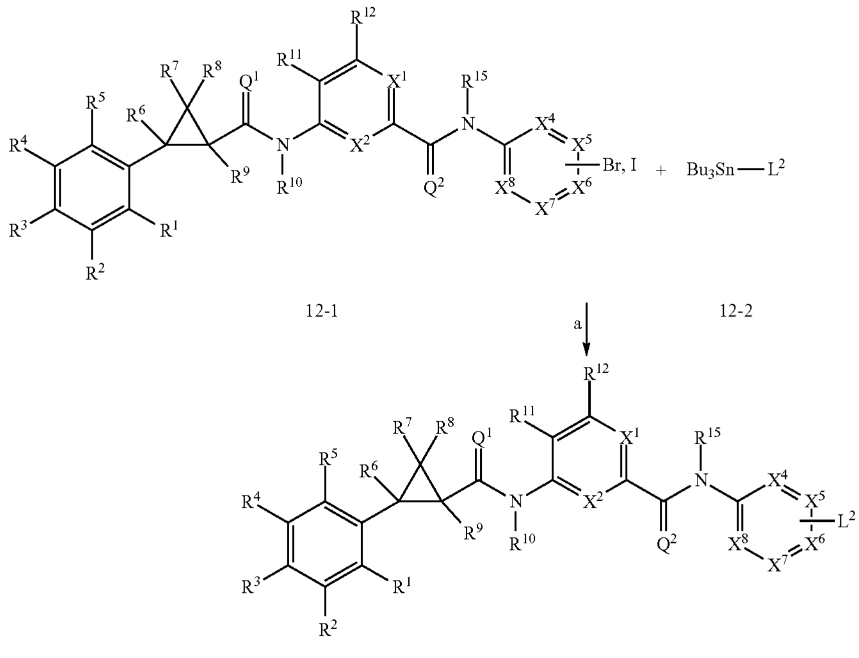

12-1 12-2

12-3

In some embodiments, 1-3 may be prepared from the α,β-unsaturated aldehyde 13-1, wherein $R^1$, $R^2$, $R^3$, $R^4$, $R^5$, $R^6$, and $R^9$ are as previously. It will be understood by one skilled in the art that compound 13-1 may be synthesized via Aldol condensation (see Yoshikawa, M.; Kamei, T. PCT Int. Appl. 2010123006, 2010) of an appropriately substituted, commercially available aldehyde and acetaldehyde. Treatment of 13-1 with a $(C_1-C_6)$alkyl orthoformate, in the presence of an acid whose pH is 0-5 such as hydrobromic acid, N-bromosuccinimide, hydrochloric acid, N-chlorosuccinimide, and pyridinium p-toluenesulfonate (PPTS), in a $(C_1-C_6)$alkanol solvent, at a temperature from 0° C. to ambient and under ambient pressure provides the acetal 13-2, wherein $R^1$, $R^2$, $R^3$, $R^4$, $R^5$, $R^6$, and $R^9$ are as previously disclosed and $R^a$ is a $(C_1-C_6)$alkyl or $R^a$ and $R^a$ taken together can form a cyclic acetal (Scheme 13, step a). The acetal 13-2 may be converted to the cyclopropyl acetal 13-3, wherein $R^1$, $R^2$, $R^3$, $R^4$, $R^5$, $R^6$, $R^7$, $R^8$, $R^9$, and $R^a$ are as previously disclosed, by treatment with a carbene source such as a haloform, for example, bromoform or chloroform, in the presence of an inorganic base, such as sodium or potassium hydroxide or sodium or potassium carbonate, and a phase-transfer catalyst such as benzyl triethylammonium chloride, (−)—N-dodecyl-N-methylephedrinium bromide, tetramethylammonium bromide, tetrapropylammonium bromide, tetrabutylammonium tetrafluoroborate, tetramethylammonium chloride or tetrabutylammonium hexafluorophosphate at a temperature from about ambient temperature up to below the boiling point of the haloform (Scheme 13, step b). Caution: Step B is an exothermic reaction and careful control of the exotherm should be exercised when conducting this reaction. The cyclopropyl acetal 13-3 may be transformed into the aldehyde 13-4, wherein $R^1$, $R^2$, $R^3$, $R^4$, $R^5$, $R^6$, $R^7$, $R^8$, and $R^9$ are as previously disclosed, in a polar solvent selected from the group consisting of acetone, acetonitrile, methanol, ethanol, nitromethane, N,N-dimethylformamide, dimethyl sulfoxide, ethyl acetate, tetrahydrofuran and 1,4-dioxane, in the presence of an aqueous mineral acid selected from the group consisting of nitric acid, hydrochloric acid, hydrobromic acid, and sulfuric acid (Scheme 5, step c) at ambient temperature. The cyclopropyl acid 1-3, wherein $R^1$, $R^2$, $R^3$, $R^4$, $R^5$, $R^6$, $R^7$, $R^8$, and $R^9$ are as previously disclosed, may be obtained by oxidation of the aldehyde 13-4 with oxidants such sodium permanganate or potassium permanganate, or under Pinnick oxidation conditions in a polar aprotic solvent selected from the group consisting of acetone, acetonitrile, N,N-dimethylformamide, dimethyl sulfoxide, ethyl acetate, tetrahydrofuran and 1,4-dioxane at a temperature from about 0° C. to about ambient temperature (Scheme 13, step d). Standard safety precautions should be exercised because an exotherm may occur when conducting this reaction.

Scheme 13

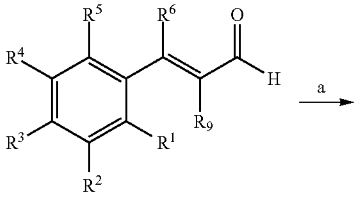

13-1

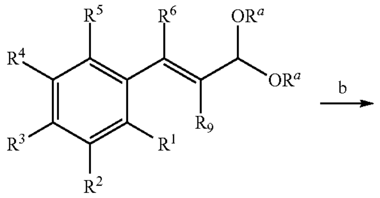

13-2

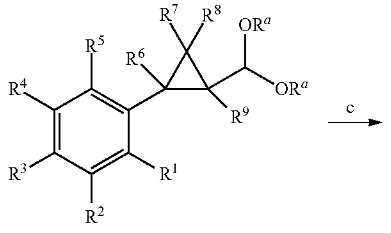

13-3

-continued

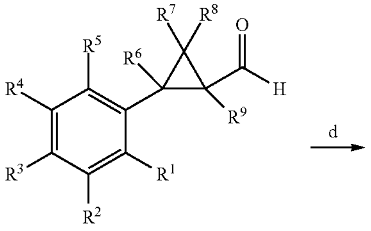

13-4

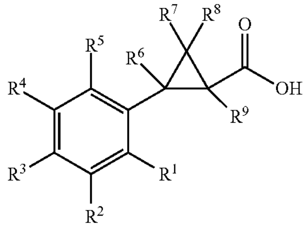

1-3

It will be understood by those skilled in the art that, in some embodiments, the cyclopropyl acid 1-3, wherein $R^1$, $R^2$, $R^3$, $R^4$, $R^5$, $R^6$, $R^7$, $R^8$, and Rare as previously disclosed, may be resolved into its (R,R) and (S,S) enantiomers via a method such as that in Kovalenko V. N., Kulinkovich O. G. *Tetrahedron: Asymmetry* 2011, 22, 26 (Scheme 14, step a).

Scheme 14

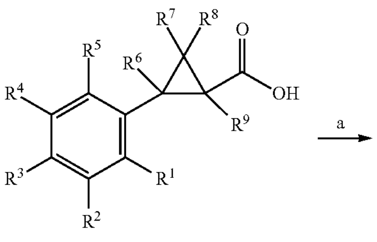

1-3

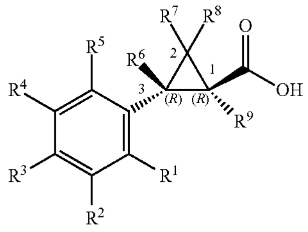

(R,R)

+

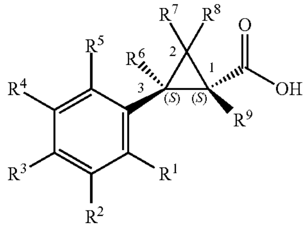

(S,S)

EXAMPLES

These examples are for illustration purposes and are not to be construed as limiting this disclosure to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw, or ACD Name Pro. If such programs are unable to name a molecule, such molecule is named using conventional naming rules. $^1H$ NMR spectral data are in ppm (δ) and were recorded at 300, 400, 500, or 600 MHz; $^{13}C$ NMR spectral data are in ppm (δ) and were recorded at 75, 100, or 150 MHz, and $^{19}F$ NMR spectral data are in ppm (δ) and were recorded at 376 MHz, unless otherwise stated.

Example 1: Preparation of trans-2,2-dichloro-3-(3,5-dichlorophenyl)cyclopropanecarboxylic acid (C1)

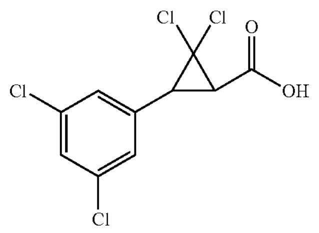 [SMILES: O=C(O)C1C(c2cc(Cl)cc(Cl)c2)C1(Cl)Cl]

Ruthenium(III) chloride (0.080 g, 0.39 mmol) was added to a stirred mixture of trans-1,3-dichloro-5-(-2,2-dichloro-3-(4-methoxyphenyl)cyclopropyl)benzene (C22) (2.8 g, 7.7 mmol) and sodium periodate (33 g, 160 mmol) in water:ethyl acetate:acetonitrile (8:1:1, 155 mL) at 23° C. The resulting biphasic brown mixture was vigorously stirred at 23° C. for 5 hours. The reaction mixture was diluted with water (1000 mL) and extracted with dichloromethane (4×200 mL). The combined organic layers were dried over magnesium sulfate, filtered, and concentrated. The residue was diluted with a sodium hydroxide solution (1 M, 100 mL) and washed with diethyl ether (4×50 mL). The aqueous layer was adjusted to pH 2, using concentrated hydrochloric acid, and extracted with dichloromethane (3×50 mL). The combined organic layers were dried over magnesium sulfate, filtered, and concentrated to afford the title product as a light brown powder (0.78 g, 34%): mp 117-120° C.; $^1H$ NMR (400 MHz, DMSO-$d_6$) δ 13.38 (br s, 1H), 7.52-7.65 (m, 3H), 3.57 (d, J=8.5 Hz, 1H), 3.50 (d, J=8.5 Hz, 1H); IR (thin film) 3083 (s), 3011 (s), 1731 (s), 1590 (w), 1566 (s), 1448 (w), 1431 (m), 1416 (m) $cm^{-1}$.

The following compounds were prepared in like manner to the procedure outlined in Example 1:

trans-2,2-Dichloro-3-(3,4,5-trichlorophenyl)cyclopropanecarboxylic acid (C2)

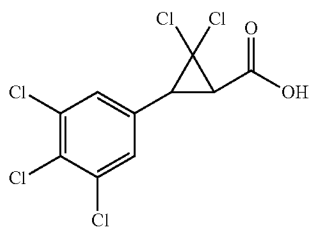 [SMILES: O=C(O)C1C(c2cc(Cl)c(Cl)c(Cl)c2)C1(Cl)Cl]

Isolated as a yellow powder (1.5 g, 39%): $^1H$ NMR (400 MHz, $CDCl_3$) δ 7.31 (d, J=0.7 Hz, 2H), 3.40 (d, J=8.2 Hz, 1H), 2.86 (d, J=8.3 Hz, 1H); $^{13}C$ NMR (101 MHz, $CDCl_3$) δ 171.05, 134.55, 132.44, 131.75, 128.89, 61.18, 39.26, 37.14; ESIMS m/z 333 ($[M-H]^-$).

trans-2,2-Dichloro-3-(3,4-dichlorophenyl)cyclopropanecarboxylic acid (C3)

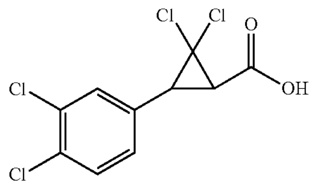 [SMILES: O=C(O)C1C(c2ccc(Cl)c(Cl)c2)C1(Cl)Cl]

Isolated as a pale yellow solid (3.2 g, 51%): $^1H$ NMR (400 MHz, $CDCl_3$) δ 7.47 (d, J=8.3 Hz, 1H), 7.37 (d, J=1.6 Hz, 1H), 7.12 (ddd, J=8.3, 2.1, 0.6 Hz, 1H), 3.43 (d, J=8.3 Hz, 1H), 2.86 (d, J=8.3 Hz, 1H); $^{13}C$ NMR (101 MHz, $CDCl_3$) δ 171.52, 132.91, 132.76, 132.29, 130.66, 130.62, 128.02, 61.48, 39.65, 37.13; ESIMS m/z 298 ($[M-H]^-$).

Example 2: Preparation of trans-2,2-dichloro-3-(4-(trifluoromethyl)phenyl)cyclopropanecarboxylic acid (C4)

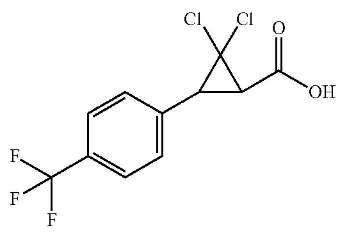 [SMILES: O=C(O)C1C(c2ccc(C(F)(F)F)cc2)C1(Cl)Cl]

To a stirred mixture of trans-1-(2,2-dichloro-3-(4-(trifluoromethyl)phenyl)cyclopropyl)-4-methoxybenzene (C25) (3.50 g, 9.60 mmol) and sodium periodate (30.8 g, 144 mmol) in water:ethyl acetate:acetonitrile (8:1:1, 200 mL) was added ruthenium(III) chloride (0.100 g, 0.400 mmol) at 23° C. The resulting mixture was vigorously stirred at 23° C. for about 5 hours. The reaction mixture was diluted with dichloromethane and washed with water. The combined organic layers were dried over sodium sulfate, filtered, and concentrated. Purification by flash column chromatography provided the title compound as an off-white solid (0.630 g, 38%): mp 100-102° C.; $^{1}$H NMR (400 MHz, DMSO-$d_6$) δ 13.43 (brs, 1H), 7.77-7.73 (m, 2H), 7.67-7.64 (m, 2H), 3.55 (d, J=8.8 Hz, 1H), 3.44 (d, J=8.8 Hz, 1H); ESIMS m/z 347 ([M−H]$^-$).

The following compounds were prepared in like manner to the procedure outlined in Example 2:

trans-2,2-Dichloro-3-(3-(trifluoromethyl)phenyl) cyclopropane carboxylic acid (C5)

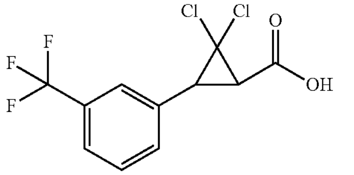 [SMILES: O=C(O)C1C(c2cccc(C(F)(F)F)c2)C1(Cl)Cl]

Isolated as an off-white solid (0.81 g, 33%): mp 86-88° C.; $^{1}$H NMR (400 MHz, DMSO-$d_6$) δ 13.37 (brs, 1H), 7.83 (s, 1H), 7.76-7.69 (m, 2H), 7.65-7.59 (m, 1H), 3.59-3.51 (m, 2H); ESIMS m/z 297 ([M−H]$^-$).

trans-2,2-Dichloro-3-(3-chloro-4-(trifluoromethoxy) phenyl)cyclopropanecarboxylic acid (C6)

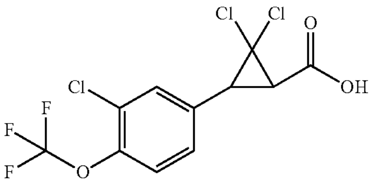 [SMILES: O=C(O)C1C(c2ccc(OC(F)(F)F)c(Cl)c2)C1(Cl)Cl]

Isolated as an off-white solid (0.3 g, 19%): mp 134-136° C.; $^{1}$H NMR (400 MHz, DMSO-$d_6$) δ 13.45 (brs, 1H), 7.82 (d, J=1.6 Hz, 1H), 7.60-7.53 (m, 2H), 3.53-3.47 (m, 2H); ESIMS m/z 347 ([M−H]$^-$).

trans-2,2-Dichloro-3-(2,4,5-trichlorophenyl)cyclopropanecarboxylic acid (C7)

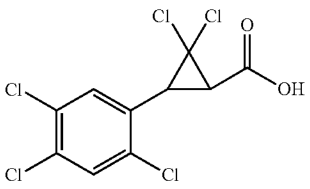 [SMILES: O=C(O)C1C(c2cc(Cl)c(Cl)cc2Cl)C1(Cl)Cl]

Isolated as an off-white solid (0.267 g, 18%): mp 189-192° C.; $^{1}$H NMR (400 MHz, DMSO-$d_6$) δ 13.44 (brs, 1H), 8.01 (s, 1H), 7.82 (s, 1H), 3.52 (d, J=8.2 Hz, 1H), 3.29 (d, J=8.2 Hz, 1H); ESIMS m/z 333 ([M−H]$^-$).

trans-3-(3,5-bis(trifluoromethyl)phenyl)-2,2-dichlorocyclopropanecarboxylic acid (C8)

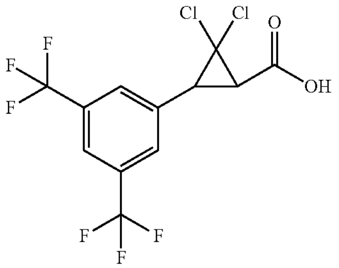 [SMILES: O=C(O)C1C(c2cc(C(F)(F)F)cc(C(F)(F)F)c2)C1(Cl)Cl]

Isolated as an off-white solid (0.5 g, 31%): mp 112-114° C.; $^{1}$H NMR (400 MHz, DMSO-$d_6$) δ 13.43 (brs, 1H), 8.22 (s, 2H), 8.08 (s, 1H), 3.80-3.71 (m, 2H); ESIMS m/z 365 ([M−H]$^-$).

trans-2,2-dichloro-3-(3,5-dibromophenyl)cyclopropanecarboxylic acid (C9)

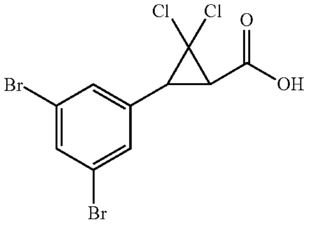

Isolated as an off-white solid (0.5 g, 24%): mp 157-159° C.; $^{1}$H NMR (400 MHz, DMSO-$d_6$) δ 13.36 (brs, 1H), 7.81 (d, J=1.5 Hz, 2H), 7.72 (d, J=1.5 Hz, 2H), 3.57-3.53 (m, 1H), 3.51-3.47 (m, 1H); ESIMS m/z 387 ([M−H]$^-$).

trans-2,2-Dichloro-3-(3-chloro-5-(trifluoromethyl) phenyl)cyclopropanecarboxylic acid (C10)

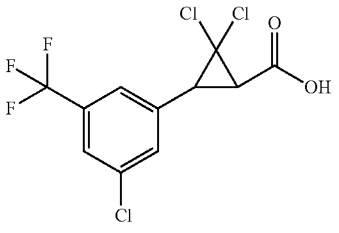 [SMILES: O=C(O)C1C(c2cc(Cl)cc(C(F)(F)F)c2)C1(Cl)Cl]

Isolated as an off-white solid (0.73 g, 28%): mp 113-115° C.; $^{1}$H NMR (400 MHz, DMSO-$d_6$) δ 13.39 (brs, 1H), 7.91 (s, 1H), 7.86 (s, 1H), 7.84 (s, 1H), 3.69-3.60 (m, 2H); ESIMS m/z 333 ([M−H]$^-$).

trans-2,2-Dichloro-3-(3,5-dichloro-4-fluorophenyl) cyclopropanecarboxylic acid (C11)

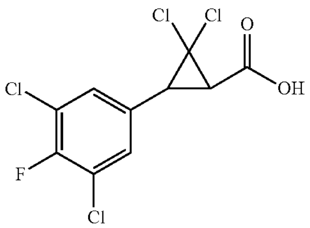 [SMILES: O=C(O)C1C(c2cc(Cl)c(F)c(Cl)c2)C1(Cl)Cl]

Isolated as an off-white solid (0.539 g, 34%): $^1$H NMR (400 MHz, DMSO-$d_6$): δ 13.37 (brs, 1H), 7.71 (d, J=6.4 Hz, 2H), 3.42 (s, 2H); ESIMS m/z 317 ([M−H]$^-$).

trans-3-(4-Bromo-3,5-dichlorophenyl)-2,2-dichloro-cyclopropanecarboxylic acid (C12)

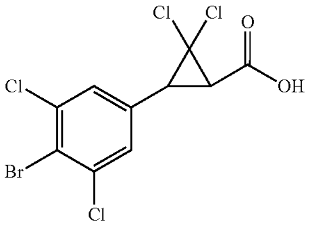 [SMILES: O=C(O)C1C(c2cc(Cl)c(Br)c(Cl)c2)C1(Cl)Cl]

Isolated as an off-white solid (0.100 g, 10%): $^1$H NMR (400 MHz, DMSO-$d_6$) δ 13.37 (brs, 1H), 7.76 (s, 3H), 3.57 (d, J=8.8 Hz, 1H), 3.48 (d, J=8.8 Hz, 1H); ESIMS m/z 377 ([M−H]$^-$).

trans-3-(3-Bromo-5-chlorophenyl)-2,2-dichlorocy-clopropanecarboxylic acid (C13)

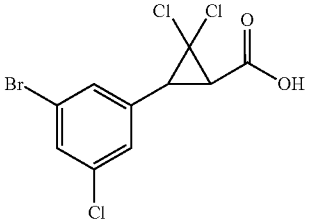

Isolated as an off-white solid (0.4 g, 25%): mp 161-163° C.; $^1$H NMR (400 MHz, DMSO-$d_6$) δ 13.38 (br s, 1H), 7.70 (d, J=5.3 Hz, 2H), 7.66-7.52 (m, 1H), 3.59-3.43 (m, 2H); ESIMS m/z 341 ([M−H]$^-$).

trans-2,2-Dichloro-3-(3-chloro-5-fluorophenyl)cy-clopropanecarboxylic acid (C14)

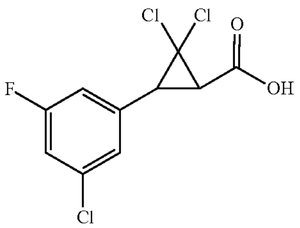

Isolated as an off-white solid (0.700 g, 25%): mp 138-140° C.; $^1$H NMR (400 MHz, DMSO-$d_6$) δ 13.38 (brs, 1H), 7.46 (s, 1H), 7.42 (td, J=2.0, 8.7 Hz, 1H), 7.37 (d, J=9.8 Hz, 1H), 3.52 (q, J=8.5 Hz, 2H); ESIMS m/z 281 ([M−H]$^-$).

trans-2,2-Dichloro-3-(4-chloro-3-fluorophenyl)cy-clopropanecarboxylic acid (C15)

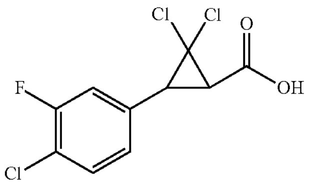

Isolated as an off-white solid (0.500 g, 20%): mp 140-142° C.; $^1$H NMR (400 MHz, DMSO-$d_6$) δ 13.40 (brs, 1H), 7.59 (m, 1H), 7.55 (d, J=8.4 Hz, 1H), 7.33 (dd, J=2.0, 8.4 Hz, 1H), 3.55-3.38 (m, 2H); ESIMS m/z 281 ([M−H]$^-$).

trans-2,2-Dichloro-3-(3-chloro-4-fluorophenyl)cy-clopropanecarboxylic acid (C16)

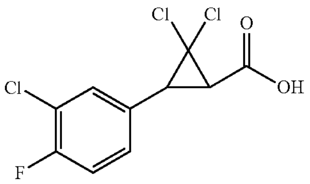

Isolated as an off-white solid (1.0 g, 53%): mp 121-123° C.; $^1$H NMR (400 MHz, DMSO-$d_6$) δ 13.35 (brs, 1H), 7.71 (dd, J=2.0, 7.2 Hz, 1H), 7.53-7.35 (m, 2H), 3.50-3.41 (m, 2H); ESIMS m/z 281 ([M−H]$^-$).

trans-2,2-Dichloro-3-(3-chloro-5-methylphenyl)cyclopropanecarboxylic acid (C17)

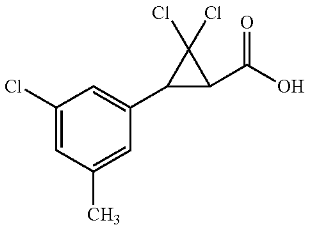 [SMILES: Cc1cc(Cl)cc(C2C(C(=O)O)C2(Cl)Cl)c1]

Isolated as an off-white solid (1.0 g, 42%): mp 124-126° C.; $^1$H NMR (400 MHz, DMSO-$d_6$) δ 13.33 (brs, 1H), 7.30 (s, 1H), 7.23 (s, 1H), 7.21 (s, 1H), 3.38 (s, 2H), 2.31 (s, 3H); ESIMS m/z 277 ([M−H]$^-$).

trans-2,2-Dichloro-3-(3,5-dichloro-4-methylphenyl) cyclopropanecarboxylic acid (C18)

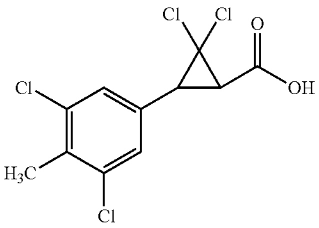 [SMILES: Cc1c(Cl)cc(C2C(C(=O)O)C2(Cl)Cl)cc1Cl]

Isolated as an off-white solid (0.8 g, 40%): mp 181-183° C.; $^1$H NMR (400 MHz, DMSO-$d_6$) δ 13.40 (s, 1H), 7.56 (s, 2H), 3.53-3.50 (m, 1H), 3.46-3.43 (m, 1H), 2.40 (s, 3H); ESIMS m/z 311 ([M−H]$^-$).

trans-2,2-Dichloro-3-(3,4-dichloro-5-methylphenyl) cyclopropanecarboxylic acid (C19)

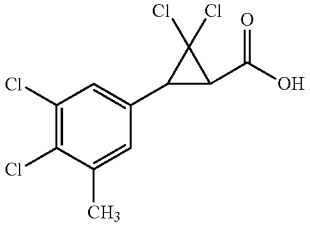 [SMILES: Cc1cc(C2C(C(=O)O)C2(Cl)Cl)cc(Cl)c1Cl]

Isolated as an off-white solid (0.73 g, 45%): mp 157-159° C.; $^1$H NMR (400 MHz, DMSO-$d_6$) δ 13.40 (s, 1H), 7.59 (d, J=2.0 Hz, 1H), 7.44 (d, J=1.6 Hz, 1H), 3.43 (q, J=8.5 Hz, 2H), 2.39 (s, 3H); ESIMS m/z 311 ([M−H]$^-$).

trans-2,2-Dichloro-3-(4-(perfluoroethyl)phenyl)cyclopropanecarboxylic acid

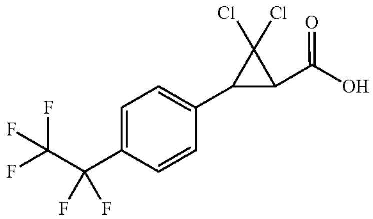 [SMILES: O=C(O)C1C(c2ccc(C(F)(F)C(F)(F)F)cc2)C1(Cl)Cl]

Isolated as an off-white solid (0.020 g, 10%): mp 116-118° C.; $^1$H NMR (300 MHz, $CDCl_3$) δ 7.63 (d, J=8.1 Hz, 2H), 7.42 (d, J=8.1 Hz, 2H), 3.53 (d, J=8.4 Hz, 1H), 2.94 (d, J=8.4 Hz, 1H); ESIMS m/z 347 ([M−H]$^-$).

trans-2,2-dichloro-3-(4-ethoxyphenyl)cyclopropanecarboxylic acid (C21)

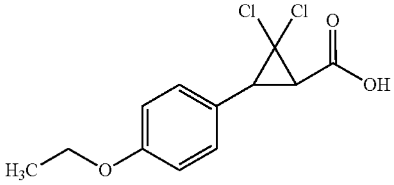 [SMILES: CCOc1ccc(C2C(C(=O)O)C2(Cl)Cl)cc1]

Isolated as an off-white solid (0.025 g, 5%): mp 129-130° C.; $^1$H NMR (400 MHz, $CDCl_3$) δ 7.16 (d, J=8.4 Hz, 2H), 6.88 (d, J=8.31 Hz, 2H), 4.03 (q, J=6.8 Hz, 2H), 3.41 (d, J=8.0 Hz, 1H), 2.81 (d, J=8.0 Hz, 1H), 1.41 (t, J=6.8 Hz, 3H); ESIMS m/z 273 ([M−H]$^-$).

Example 3: Preparation of trans-1,3-dichloro-5-(2,2-dichloro-3-(4-methoxyphenyl)cyclopropyl)benzene (C22)

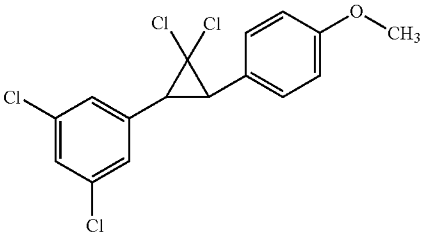 [SMILES: COc1ccc(C2C(c3cc(Cl)cc(Cl)c3)C2(Cl)Cl)cc1]

Aqueous sodium hydroxide (50%, 6.8 mL, 130 mmol) was added to a stirred solution of (E)-1,3-dichloro-5-(4-methoxystyryl)benzene (C43) (2.4 g, 8.6 mmol) and N-benzyl-N,N-diethylethanaminium chloride (0.20 g, 0.86 mmol) in chloroform (14 mL, 170 mmol) at 23° C. The resulting biphasic, dark brown mixture was vigorously stirred at 23° C. for 24 hours. The reaction mixture was diluted with water (200 mL) and extracted with dichloromethane (2×100 mL). The combined organic layers were dried over magnesium sulfate, filtered, and concentrated to afford the title product as a brown oil (2.8 g, 90%): $^1$H NMR (400 MHz, $CDCl_3$) δ 7.34 (t, J=1.8 Hz, 1H), 7.21-7.30 (m, 4H), 6.93 (m, 2H), 3.83

(s, 3H), 3.14 (d, J=8.5 Hz, 1H), 3.08 (d, J=8.5 Hz, 1H); IR (thin film) 3075 (w), 2934 (w), 2836 (w), 1724 (w), 1640 (w), 1609 (m), 1584 (m), 1568 (s), 1513 (s) $cm^{-1}$.

The following compounds were prepared in like manner to the procedure outlined in Example 3:

trans-1,2,3-Trichloro-5-(2,2-dichloro-3-(4-methoxy-phenyl)cyclopropyl)benzene (C23)

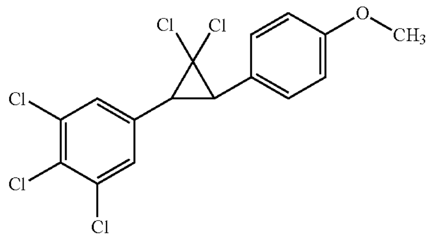 [SMILES: COc1ccc(C2C(c3cc(Cl)c(Cl)c(Cl)c3)C2(Cl)Cl)cc1]

Isolated as a dark foam (4.7 g, 100%): $^1H$ NMR (400 MHz, $CDCl_3$) δ 7.40 (d, J=0.6 Hz, 2H), 7.29-7.22 (m, 2H), 6.96-6.89 (m, 2H), 3.83 (s, 3H), 3.12 (d, J=8.8 Hz, 1H), 3.06 (d, J=8.7 Hz, 1H); $^{13}C$ NMR (101 MHz, $CDCl_3$) δ 159.46, 135.08, 134.23, 130.91, 129.85, 129.16, 125.42, 114.02, 64.67, 55.32, 39.62, 38.48. trans-1,2-Dichloro-4-(2,2-dichloro-3-(4-methoxyphenyl)cyclopropyl)benzene (C24)

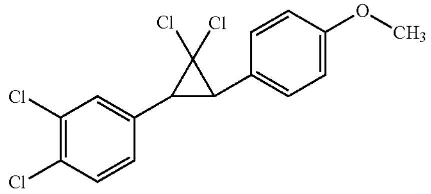 [SMILES: COc1ccc(C2C(c3ccc(Cl)c(Cl)c3)C2(Cl)Cl)cc1]

Isolated as an orange-red oil (7.6 g, 99%): $^1H$ NMR (400 MHz, $CDCl_3$) δ 7.47 (d, J=4.9 Hz, 1H), 7.45 (bs, 1H), 7.30-7.23 (m, 2H), 7.21 (dd, J=8.2, 1.9 Hz, 1H), 6.96-6.90 (m, 2H), 3.83 (s, 3H), 3.11 (app. q, J=8.8 Hz, 2H); $^{13}C$ NMR (101 MHz, $CDCl_3$) δ 159.39, 134.90, 132.62, 131.99, 130.90, 130.40, 129.90, 128.33, 125.81, 113.98, 64.94, 55.33, 39.52, 38.75.

Example 4: Preparation of trans-1-(2,2-dichloro-3-(4-(trifluoromethyl)phenyl)cyclopropyl)-4-methoxy-benzene (C25)

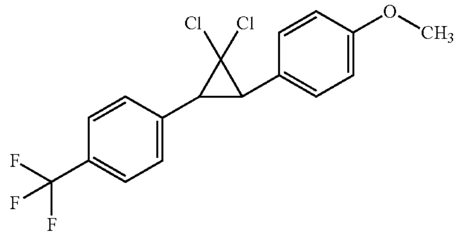 [SMILES: COc1ccc(C2C(c3ccc(C(F)(F)F)cc3)C2(Cl)Cl)cc1]

To a stirred solution of (E)-1-methoxy-4-(4-(trifluoromethyl)styryl)benzene (C46) (4.00 g, 14.0 mmol) and N-benzyl-N,N-diethylethanaminium chloride (0.320 g, 14.0 mmol) in chloroform (23.1 g, 288 mmol), was added aqueous sodium hydroxide (50%, 8.64 g, 216 mmol) in water (17 mL) at 23° C., and the resulting mixture was vigorously stirred at 23° C. for 16 hours. The reaction mixture was diluted with water and extracted with dichloromethane. The combined organic layers were dried over sodium sulfate, filtered, and concentrated. Purification by flash column chromatography provided the title compound as an off-white solid (3.70 g, 68%): $^1H$ NMR (300 MHz, $CDCl_3$) δ 7.65 (d, J=8.4 Hz, 2H), 7.49 (d, J=8.4 Hz, 2H), 7.29 (d, J=8.4 Hz, 2H), 6.94 (d, J=8.4 Hz, 2H), 3.83 (s, 3H), 3.19 (s, 2H); ESIMS m/z 361 ($[M+H]^+$).

The following compounds were prepared in like manner to the procedure outlined in Example 4:

trans-1-(2,2-Dichloro-3-(4-methoxyphenyl)cyclopropyl)-3-(trifluoromethyl)benzene (C26)

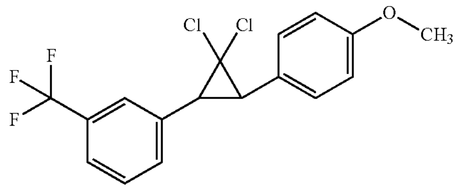 [SMILES: COc1ccc(C2C(c3cccc(C(F)(F)F)c3)C2(Cl)Cl)cc1]

Isolated as a brown liquid (3.5 g, 67%): $^1H$ NMR (300 MHz, $CDCl_3$) δ 7.62-7.50 (m, 4H), 7.29 (d, J=9.0 Hz, 2H), 6.94 (d, J=9.0 Hz, 2H), 7.35-7.25 (m, 3H), 7.97-6.88 (m, 1H), 3.83 (s, 3H), 3.19 (m, 2H); ESIMS m/z 361 ($[M+H]^+$).

trans-2-Chloro-4-(2,2-dichloro-3-(4-methoxyphenyl)cyclopropyl)-1-(trifluoromethoxy)benzene (C27)

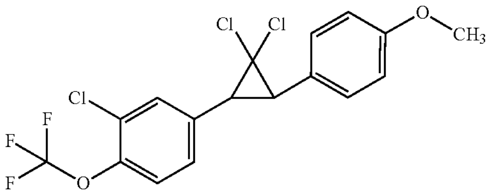 [SMILES: COc1ccc(C2C(c3ccc(OC(F)(F)F)c(Cl)c3)C2(Cl)Cl)cc1]

Isolated as an off-white solid (2.5 g, 65%): $^1H$ NMR (400 MHz, $CDCl_3$) δ 7.57 (d, J=2.0 Hz, 1H), 7.44 (d, J=8.8 Hz, 1H), 7.35-7.25 (m, 3H), 7.97-6.88 (m, 1H), 3.84 (s, 3H), 3.15-3.05 (m, 2H); ESIMS m/z 411 ($[M+H]^+$).

trans-1,2,4-Trichloro-5-(2,2-dichloro-3-(4-methoxy-phenyl)cyclopropyl)benzene (C28)

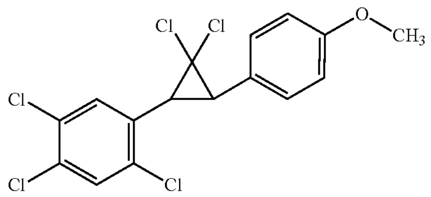 [SMILES: COc1ccc(C2C(c3cc(Cl)c(Cl)cc3Cl)C2(Cl)Cl)cc1]

Isolated as a brown liquid (2.0 g, 58%): EIMS m/z 394 ($[M]^+$).

trans-1-(2,2-Dichloro-3-(4-methoxyphenyl)cyclopropyl)-3,5-bis(trifluoromethyl)benzene (C29)

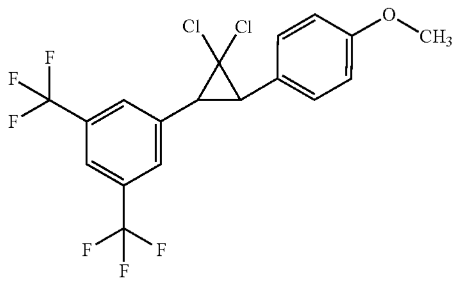 [SMILES: COc1ccc(C2C(c3cc(C(F)(F)F)cc(C(F)(F)F)c3)C2(Cl)Cl)cc1]

Isolated as a brown liquid (3.0 g, 61%): EIMS m/z 428 ($[M]^+$).

trans-1,3-Dibromo-5-(2,2-dichloro-3-(4-methoxyphenyl)cyclopropyl)benzene (C30)

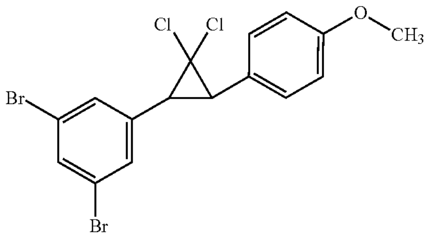

Isolated as a brown liquid (3.0 g, 57%): $^1$H NMR (300 MHz, $CDCl_3$) δ 7.64 (s, 1H), 7.45 (s, 2H), 7.25 (d, J=9.0 Hz, 2H), 6.92 (d, J=9.0 Hz, 1H), 3.83 (s, 3H), 3.15-3.05 (m, 2H); ESIMS m/z 453 ($[M+H]^+$).

trans-1-Chloro-3-(2,2-dichloro-3-(4-methoxyphenyl) cyclopropyl)-5-(trifluoromethyl)benzene (C31)

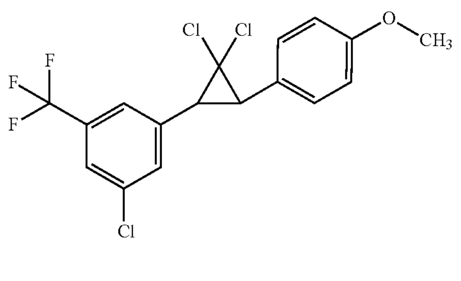 [SMILES: COc1ccc(C2C(c3cc(Cl)cc(C(F)(F)F)c3)C2(Cl)Cl)cc1]

Isolated as a brown solid (4.0 g, 74%): $^1$H NMR (300 MHz, $CDCl_3$) δ 7.64 (s, 1H), 7.45 (s, 1H), 7.42 (s, 1H), 7.26 (d, J=9.0 Hz, 2H), 6.93 (d, J=9.0 Hz, 1H), 3.83 (s, 3H), 3.15-3.05 (m, 2H); ESIMS m/z 395 ($[M+H]^+$).

trans-1,3-Dichloro-5-(2,2-dichloro-3-(4-methoxyphenyl)cyclopropyl)-2-fluorobenzene (C32)

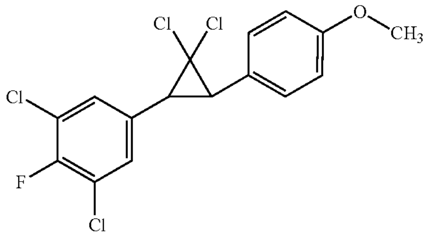 [SMILES: COc1ccc(C2C(c3cc(Cl)c(F)c(Cl)c3)C2(Cl)Cl)cc1]

Isolated as a brown solid (1.6 g, 54%): $^1$H NMR (300 MHz, $CDCl_3$) δ 7.32 (d, J=6.0 Hz, 2H), 7.30 (d, J=9.0 Hz, 1H), 6.93 (d, J=9.0 Hz, 1H), 3.83 (s, 3H), 3.12-3.05 (m, 2H); ESIMS m/z 297 ($[M+H]^+$).

trans-2-Bromo-1,3-dichloro-5-(2,2-dichloro-3-(4-methoxyphenyl)cyclopropyl)benzene (C33)

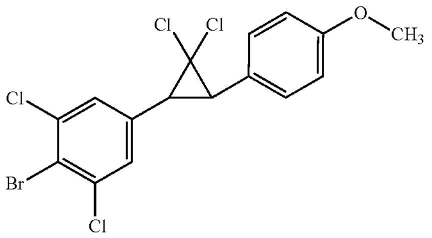

Isolated as an off-white solid (1.5 g, 44%): $^1$H NMR (300 MHz, $CDCl_3$) δ 7.36 (d, J=9.0 Hz, 2H), 7.20 (s, 2H), 6.93 (d, J=9.0 Hz, 2H), 3.83 (s, 3H), 3.15-3.05 (m, 2H); ESIMS m/z 439 ($[M+H]^+$).

trans-1-Bromo-3-chloro-5-(2,2-dichloro-3-(4-methoxyphenyl)cyclopropyl)benzene (C34)

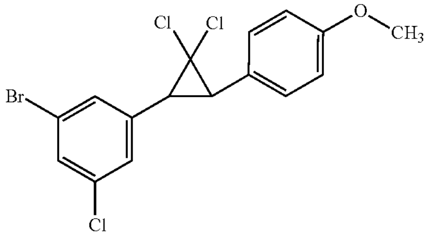

Isolated as an off-white solid (2.5 g, 50%): $^1$H NMR (400 MHz, $CDCl_3$) δ 7.49 (s, 1H), 7.30 (s, 1H), 7.28-7.24 (m, 3H), 6.92 (d, J=8.0 Hz, 2H), 3.92 (s, 3H), 3.01 (q, J=8.8 Hz, 2H); ESIMS m/z 405 ($[M+H]^+$).

trans-1-Chloro-3-(2,2-dichloro-3-(4-methoxyphenyl) cyclopropyl)-5-fluorobenzene (C35)

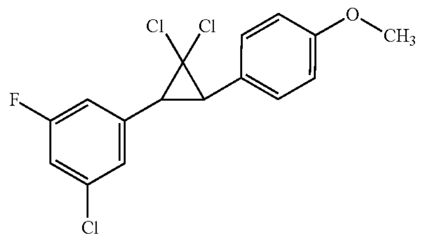 [SMILES: COc1ccc(C2C(c3cc(F)cc(Cl)c3)C2(Cl)Cl)cc1]

Isolated as a brown liquid (3.5 g, 67%): ESIMS m/z 345 ([M+H]$^+$).

trans-1-Chloro-4-(2,2-dichloro-3-(4-methoxyphenyl) cyclopropyl)-2-fluorobenzene (C36)

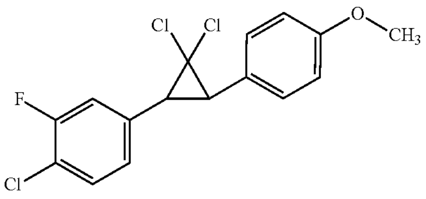 [SMILES: COc1ccc(C2C(c3ccc(Cl)c(F)c3)C2(Cl)Cl)cc1]

Isolated as an off-white solid (2.5 g, 65%): ESIMS m/z 345 ([M+H]$^+$).

trans-2-Chloro-4-(2,2-dichloro-3-(4-methoxyphenyl) cyclopropyl)-1-fluorobenzene (C37)

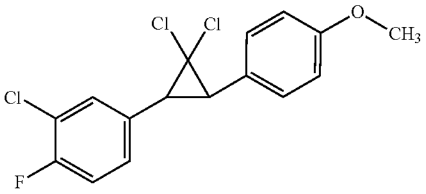 [SMILES: COc1ccc(C2C(c3ccc(F)c(Cl)c3)C2(Cl)Cl)cc1]

Isolated as a brown liquid (2.0 g, 58%): ESIMS m/z 345 ([M+H]$^+$).

trans-1-Chloro-3-(2,2-dichloro-3-(4-methoxyphenyl) cyclopropyl)-5-methylbenzene (C38)

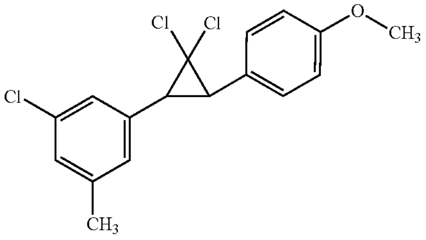 [SMILES: COc1ccc(C2C(c3cc(C)cc(Cl)c3)C2(Cl)Cl)cc1]

Isolated as an off-white solid (3.0 g, 47%): $^1$H NMR (400 MHz, $CDCl_3$) δ 7.27 (d, J=8.8 Hz, 2H), 7.14 (s, 2H), 7.06 (s, 1H), 6.92 (d, J=8.8 Hz, 2H), 3.82 (s, 3H), 3.10 (q, J=8.8 Hz, 2H), 2.36 (s, 3H); ESIMS m/z 341 ([M+H]$^+$).

trans-1,3-Dichloro-5-(2,2-dichloro-3-(4-methoxy-phenyl)cyclopropyl)-2-methylbenzene (C39)

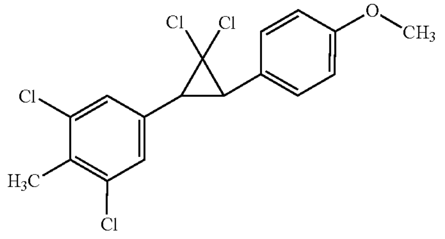

Isolated as a brown liquid (2.5 g, 80%): $^1$H NMR (400 MHz, $CDCl_3$) δ 7.25 (d, J=8.0 Hz, 2H), 7.17 (d, J=8.8 Hz, 1H), 6.92 (d, J=8.0 Hz, 2H), 6.88 (d, J=8.8 Hz, 1H), 3.82 (s, 3H), 3.12-3.03 (m, 2H), 2.47 (s, 3H); ESIMS m/z 375 ([M+H]$^+$).

trans-1,2-Dichloro-5-(2,2-dichloro-3-(4-methoxy-phenyl)cyclopropyl)-3-methylbenzene (C40)

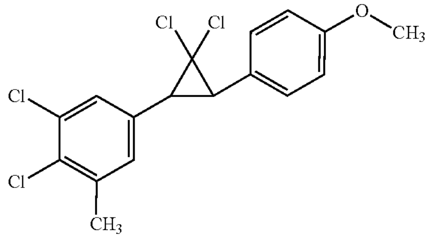 [SMILES: COc1ccc(C2C(c3cc(C)c(Cl)c(Cl)c3)C2(Cl)Cl)cc1]

Isolated as a Brown liquid (4.0 g, 90%): ESIMS m/z 375 ([M+H]$^+$).

trans-1-(2,2-Dichloro-3-(4-(perfluoroethyl)phenyl) cyclopropyl)-4-methoxybenzene (C41)

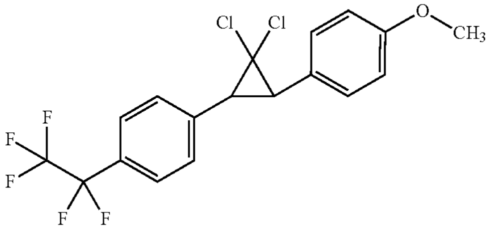 [SMILES: COc1ccc(C2C(c3ccc(C(F)(F)C(F)(F)F)cc3)C2(Cl)Cl)cc1]

Isolated as an off-white solid (0.5 g, 46%): $^1$H NMR (400 MHz, $CDCl_3$) δ 7.60-7.50 (m, 4H), 7.47 (d, J=8.0 Hz, 2H), 6.92 (d, J=8.0 Hz, 2H), 3.82 (s, 3H), 3.20 (s, 2H); ESIMS m/z 411 ([M+H]$^+$).

trans-4,4'-(3,3-Dichlorocyclopropane-1,2-diyl)bis (ethoxybenzene) (C42)

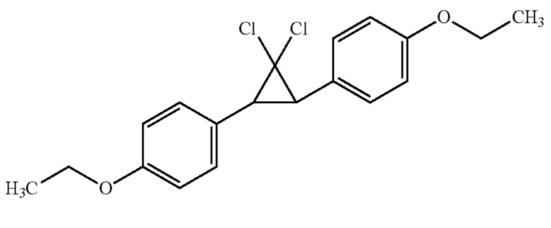 [SMILES: CCOc1ccc(C2C(c3ccc(OCC)cc3)C2(Cl)Cl)cc1]

Isolated as an off-white solid (1.5 g, 45%): $^1$H NMR (400 MHz, $CDCl_3$) δ 7.27 (d, J=8.0 Hz, 4H), 6.90 (d, J=8.0 Hz, 4H), 4.04 (q, J=6.8 Hz, 4H), 3.09 (s, 2H), 1.42 (t, J=6.8 Hz, 6H); ESIMS m/z 351 ($[M+H]^+$).

Example 5: Preparation of (E)-1,3-dichloro-5-(4-methoxystyryl)benzene (C43)

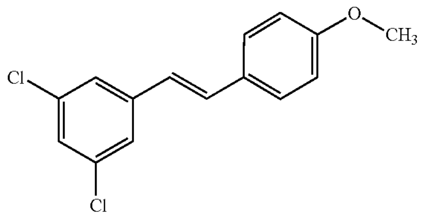 [SMILES: COc1ccc(/C=C/c2cc(Cl)cc(Cl)c2)cc1]

Sodium methoxide powder (98%, 0.63 g, 11 mmol) was added to a stirred solution of 3,5-dichlorobenzaldehyde (2.0 g, 11 mmol) and diethyl 4-methoxybenzylphosphonate (2.0 mL, 11 mmol) in dry N,N-dimethylformamide (38 mL) at 23° C. The resulting heterogeneous dark blue mixture was heated to 80° C., resulting in a dark brown mixture, and stirred for 24 hours. The cooled reaction mixture was diluted with water (500 mL) and extracted with diethyl ether (3×100 mL). The combined organic layers were diluted with hexane (150 mL) and washed with water (300 mL). The organic layer was dried over magnesium sulfate, filtered, and concentrated to afford the title product as a light brown oil (2.4 g, 75%): $^1$H NMR (400 MHz, $CDCl_3$) δ 7.44 (m, 2H), 7.34 (d, J=2 Hz, 2H), 7.20 (t, J=2 Hz, 1H), 7.06 (d, J=16.5 Hz, 1H), 6.91 (m, 2H), 6.82 (d, J=16.5 Hz, 1H), 3.84 (s, 3H); IR (thin film) 2934 (w), 2835 (w), 1724 (w), 1637 (w), 1605 (m), 1581 (m), 1558 (m), 1511 (s) $cm^{-1}$.

The following compounds were prepared in like manner to the procedure outlined in Example 5:

(E)-1,2,3-Trichloro-5-(4-methoxystyryl)benzene (C44)

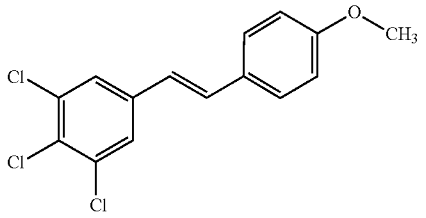 [SMILES: COc1ccc(/C=C/c2cc(Cl)c(Cl)c(Cl)c2)cc1]

Isolated as an off-white solid (3.7 g, 31%): $^1$H NMR (400 MHz, $CDCl_3$) δ 7.49-7.46 (m, 2H), 7.47-7.39 (m, 2H), 7.04 (d, J=16.3 Hz, 1H), 6.93-6.89 (m, 2H), 6.78 (d, J=16.3 Hz, 1H), 3.84 (s, 3H); $^{13}$C NMR (101 MHz, $CDCl_3$) δ 159.46, 135.08, 134.23, 130.91, 129.85, 129.16, 125.42, 114.02, 64.67, 55.32, 39.62, 38.48; EIMS m/z 313 ($[M]^+$).

(E)-1,2-Dichloro-4-(4-methoxystyryl)benzene (C45)

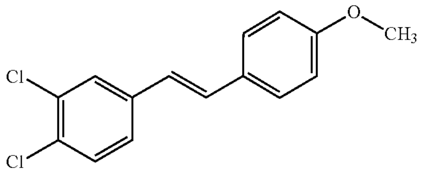 [SMILES: COc1ccc(/C=C/c2ccc(Cl)c(Cl)c2)cc1]

Isolated as an off-white solid (6.0 g, 53%): mp 91-94° C.; $^1$H NMR (400 MHz, $CDCl_3$) δ 7.56 (d, J=2.0 Hz, 1H), 7.46-7.42 (m, 2H), 7.39 (d, J=8.4 Hz, 1H), 7.29 (dd, J=8.4, 2.1 Hz, 1H), 7.04 (d, J=16.2 Hz, 1H), 6.93-6.88 (m, 2H), 6.85 (d, J=16.3 Hz, 1H), 3.84 (s, 3H); $^{13}$C NMR (101 MHz, $CDCl_3$) δ 159.75, 137.86, 132.72, 130.58, 130.49, 130.12, 129.33, 127.96, 127.77, 125.37, 123.98, 114.24, 55.35; EIMS m/z 279 ($[M]^+$).

Example 6: Preparation of (E)-1-methoxy-4-(4-(trifluoromethyl)styryl)benzene (C46)

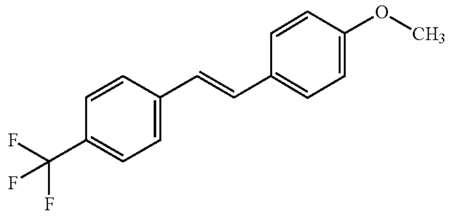 [SMILES: COc1ccc(/C=C/c2ccc(C(F)(F)F)cc2)cc1]

To a stirred solution of diethyl 4-methoxybenzyl phosphonate (8.89 g, 34.0 mmol) in N,N-dimethylformamide (30 mL) was added sodium methoxide powder (1.86 g, 34.0 mmol). The reaction mixture was stirred at room temperature for 1 hour. The reaction mixture was cooled to 0° C. and 4-(trifluoromethyl)benzaldehyde (5.00 g, 28.0 mmol) in N,N-dimethylformamide (30 mL) was added dropwise. The reaction mixture was stirred at 60° C. for 2 hours. The reaction mixture was poured in ice cold water, filtered, and dried to afford the title compound as an off-white solid (3.60 g, 80%): 1H NMR (300 MHz, $CDCl_3$) δ 7.61-7.52 (m, 4H), 7.47 (d, J=9.0 Hz, 2H), 7.14 (d, J=16.5 Hz, 1H), 6.97 (d, J=16.5 Hz, 1H), 6.91 (d, J=9.0 Hz, 2H), 3.84 (s, 3H); ESIMS m/z 279 ($[M+H]^+$).

The following compounds were prepared in like manner to the procedure outlined in Example 6:

(E)-1-(4-Methoxystyryl)-3-(trifluoromethyl)benzene (C47)

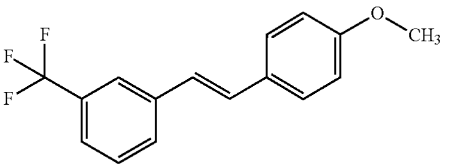 [SMILES: COc1ccc(/C=C/c2cccc(C(F)(F)F)c2)cc1]

Isolated as an off-white solid (4.0 g, 85%): $^1$H NMR (400 MHz, $CDCl_3$) δ 7.72 (s, 1H), 7.64 (d, J=6.8 Hz, 1H), 7.50-7.44 (m, 4H), 7.12 (d, J=16.0 Hz, 1H), 6.98 (d, J=16.0 Hz, 1H), 6.91 (d, J=8.8 Hz, 2H), 3.84 (s, 3H); ESIMS m/z 279 ([M+H]$^+$).

(E)-2-Chloro-4-(4-methoxystyryl)-1-(trifluoromethoxy)benzene (C48)

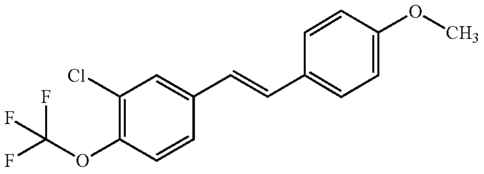 [SMILES: COc1ccc(/C=C/c2ccc(OC(F)(F)F)c(Cl)c2)cc1]

Isolated: ESIMS m/z 329 ([M+H]$^+$).

(E)-1-(4-Methoxystyryl)-3,5-bis(trifluoromethyl) benzene (C49)

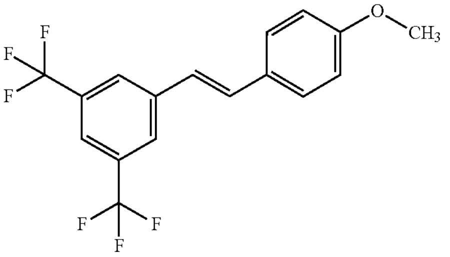 [SMILES: COc1ccc(/C=C/c2cc(C(F)(F)F)cc(C(F)(F)F)c2)cc1]

Isolated as an off-white solid (4.0 g, 56%): $^1$H NMR (300 MHz, $CDCl_3$) δ 7.88 (s, 2H), 7.70 (s, 1H), 7.49 (d, J=8.4 Hz, 2H), 7.19 (d, J=16.5 Hz, 1H), 6.99 (d, J=16.5 Hz, 1H), 6.92 (d, J=8.4 Hz, 2H), 3.84 (m, 3H); ESIMS m/z 347 ([M+H]$^+$).

(E)-1,3-Dibromo-5-(4-methoxystyryl)benzene (C50)

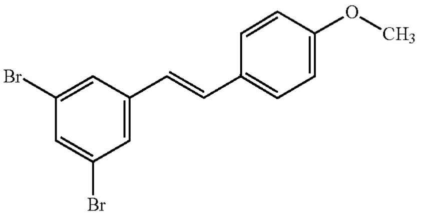 [SMILES: COc1ccc(/C=C/c2cc(Br)cc(Br)c2)cc1]

Isolated as an off-white solid (2.2 g, 54%): $^1$H NMR (300 MHz, $CDCl_3$) δ 7.53 (s, 1H), 7.50 (s, 2H), 7.43 (d, J=9.0 Hz, 2H), 7.05 (d, J=16.2 Hz, 1H), 6.90 (d, J=9.0 Hz, 2H), 6.79 (d, J=16.2 Hz, 1H), 3.80 (s, 3H); ESIMS m/z 367 ([M+H]$^+$).

(E)-1-Chloro-3-(4-methoxystyryl)-5-(trifluoromethyl)benzene (C51)

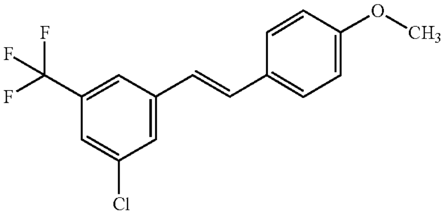 [SMILES: COc1ccc(/C=C/c2cc(Cl)cc(C(F)(F)F)c2)cc1]

Isolated as an off-white solid (4.3 g, 58%): $^1$H NMR (300 MHz, $CDCl_3$) δ 7.62 (s, 1H), 7.58 (s, 1H), 7.48-7.42 (m, 3H), 7.12 (d, J=16.2 Hz, 1H), 6.95-6.85 (m, 3H), 3.84 (s, 3H); ESIMS m/z 313 ([M+H]$^+$).

(E)-2-Bromo-1,3-dichloro-5-(4-methoxystyryl)benzene (C52)

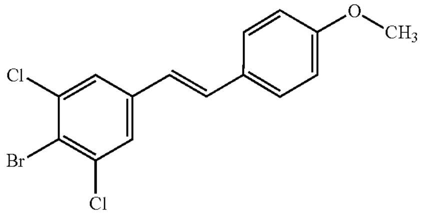 [SMILES: COc1ccc(/C=C/c2cc(Cl)c(Br)c(Cl)c2)cc1]

Isolated as an off-white solid (2.8 g, 40%): $^1$H NMR (300 MHz, $CDCl_3$) δ 7.46 (s, 2H), 7.43 (d, J=9.0 Hz, 2H), 7.07 (d, J=13.5 Hz, 1H), 6.90 (d, J=9.0 Hz, 1H), 6.73 (d, J=13.5 Hz, 1H), 3.84 (s, 3H); ESIMS m/z 358 ([M+H]$^+$).

(E)-1-Bromo-3-chloro-5-(4-methoxystyryl)benzene (C53)

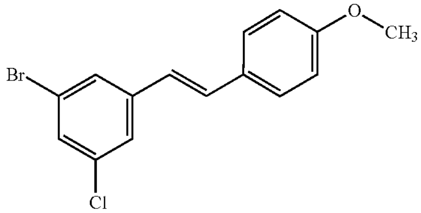 [SMILES: COc1ccc(/C=C/c2cc(Cl)cc(Br)c2)cc1]

Isolated as an off-white solid (4.0 g, 63%): $^1$H NMR (300 MHz, $CDCl_3$) δ 7.49 (s, 1H), 7.43 (d, J=8.4 Hz, 2H), 7.38 (s, 1H), 7.35 (s, 1H), 7.05 (d, J=16.5 Hz, 1H), 6.91 (d, J=8.4 Hz, 2H), 6.80 (d, J=16.5 Hz, 1H), 3.82 (s, 3H); ESIMS m/z 323 ([M+H]$^+$).

(E)-1-Chloro-3-fluoro-5-(4-methoxystyryl)benzene (C54)

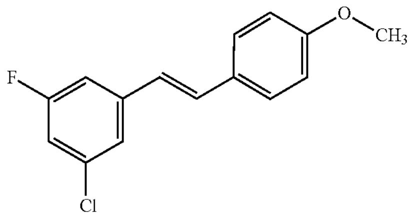 [SMILES: COc1ccc(/C=C/c2cc(F)cc(Cl)c2)cc1]

Isolated as an off-white solid (5.0 g, 60%): $^1$H NMR (400 MHz, $CDCl_3$) δ 7.45 (d, J=8.4 Hz, 2H), 7.10-7.0 (m, 3H), 6.96-6.80 (m, 4H), 3.80 (s, 3H); ESIMS m/z 263 ([M+H]$^+$).

(E)-1-Chloro-2-fluoro-4-(4-methoxystyryl)benzene (C55)

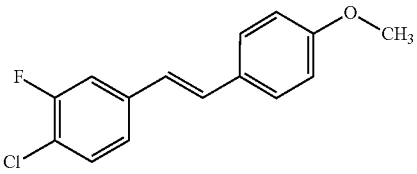 [SMILES: COc1ccc(/C=C/c2ccc(Cl)c(F)c2)cc1]

Isolated as an off-white solid (7.0 g, 84%): $^1$H NMR (400 MHz, $CDCl_3$) δ 7.44 (d, J=8.0 Hz, 2H), 7.35-7.31 (m, 1H), 7.28-7.24 (m, 1H), 7.17 (dd, J=1.6, 8.0 Hz, 1H), 7.03 (d, J=16.0 Hz, 1H), 6.90 (d, J=8.0 Hz, 1H), 7.49 (d, J=8.0 Hz, 1H), 6.86 (d, J=16.0 Hz, 1H), 3.82 (s, 3H); ESIMS m/z 263 ([M+H]$^+$).

(E)-2-Chloro-1-fluoro-4-(4-methoxystyryl)benzene (C56)

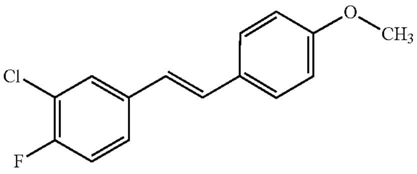 [SMILES: COc1ccc(/C=C/c2ccc(F)c(Cl)c2)cc1]

Isolated as an off-white solid (6.0 g, 72%): ESIMS m/z 263 ([M+H]$^+$).

(E)-1-Chloro-3-(4-methoxystyryl)-5-methylbenzene (C57)

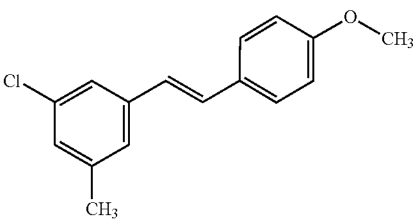

Isolated as an off-white solid (5.0 g, 60%): $^1$H NMR (300 MHz, $CDCl_3$) δ 7.44 (d, J=8.4 Hz, 2H), 7.28 (s, 1H), 7.15 (s, 1H), 7.05-7.00 (m, 2H), 6.91-6.83 (m, 3H), 3.83 (s, 3H), 2.24 (s, 3H); ESIMS m/z 259 ([M+H]$^+$).

(E)-1-Methoxy-4-(4-(perfluoroethyl)styryl)benzene (C58)

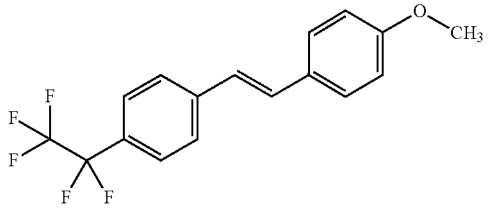 [SMILES: COc1ccc(/C=C/c2ccc(C(F)(F)C(F)(F)F)cc2)cc1]

Isolated as an off-white solid (0.5 g, 42%): $^1$H NMR (400 MHz, $CDCl_3$) δ 7.60-7.50 (m, 4H), 7.47 (d, J=8.8 Hz, 2H), 7.15 (d, J=16.8 Hz, 1H), 6.98 (d, J=16.8 Hz, 1H), 6.92 (d, J=8.8 Hz, 2H), 3.82 (s, 3H); ESIMS m/z 329 ([M+H]$^+$).

(E)-1,2-bis(4-ethoxyphenyl)ethene (C59)

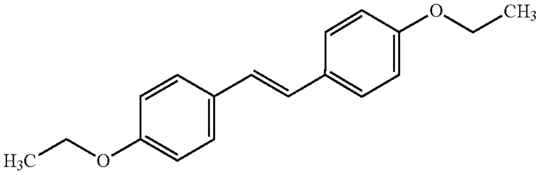 [SMILES: CCOc1ccc(/C=C/c2ccc(OCC)cc2)cc1]

Isolated as an off-white solid (1.7 g, 34%): $^1$H NMR (300 MHz, $CDCl_3$) δ 7.40 (d, J=9.0 Hz, 4H), 6.91 (s, 2H), 6.87 (d, J=9.0 Hz, 4H), 4.05 (q, J=6.9 Hz, 4H), 1.42 (t, J=6.9 Hz, 6H); ESIMS m/z 269 ([M+H]$^+$).

Example 7: Preparation of (E)-1,3-dichloro-2-fluoro-5-(4-methoxystyryl)benzene (C60)

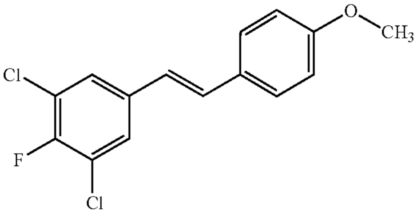 [SMILES: COc1ccc(/C=C/c2cc(Cl)c(F)c(Cl)c2)cc1]

A stirred mixture of 5-bromo-1,3-dichloro-2-fluorobenzene (2.00 g, 8.20 mmol), 1-methoxy-4-vinylbenzene (1.32 g, 9.80 mmol), and triethylamine (20 mL) under argon was degassed for 5 minutes. Palladium(II) acetate (0.0368 g, 0.164 mmol) and 1,1'-bis(diphenylphosphino)ferrocene (0.181 g, 0.328 mmol) were added and the reaction was heated to 90° C. for 16 hours. The reaction mixture was poured into water and extracted with ethyl acetate. The combined organic layers were dried over sodium sulfate, filtered, and concentrated. Purification by flash column chromatography provided the title compound as an off-white solid (1.60 g, 67%): $^{1}$H NMR (300 MHz, $CDCl_3$) δ 7.41 (d, J=8.8 Hz, 2H), 7.31 (s, 1H), 7.37 (s, 1H), 6.96 (d, J=16.0 Hz, 1H), 6.89 (d, J=8.8 Hz, 2H), 6.76 (d, J=16.0 Hz, 1H), 3.84 (s, 3H); ESIMS m/z 297 ($[M+H]^+$).

The following compounds were prepared in like manner to the procedure outlined in Example 7:

(E)-1,3-Dichloro-5-(4-methoxystyryl)-2-methylbenzene (C61)

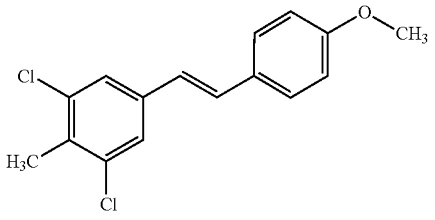

Isolated as an off-white solid (2.5 g, 67%): $^{1}$H NMR (300 MHz, $CDCl_3$) δ 7.43 (d, J=8.7 Hz, 2H), 7.38 (s, 2H), 7.02 (d, J=16.5 Hz, 1H), 6.90 (d, J=8.7 Hz, 2H), 6.79 (d, J=16.5 Hz, 1H), 3.82 (s, 3H), 2.42 (s, 3H); ESIMS m/z 293 ($[M+H]^+$).

(E)-1,2-Dichloro-5-(4-methoxystyryl)-3-methylbenzene (C62)

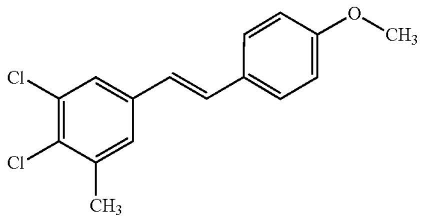 [SMILES: COc1ccc(/C=C/c2cc(C)c(Cl)c(Cl)c2)cc1]

Isolated as an off-white solid (3.0 g, 55%): $^{1}$H NMR (300 MHz, $CDCl_3$) δ 7.50-7.40 (m, 3H), 7.24 (s, 1H), 7.02 (d, J=15.9 Hz, 1H), 6.90 (d, J=9.0 Hz, 2H), 6.81 (d, J=15.9 Hz, 1H), 3.83 (s, 3H), 2.42 (s, 3H); ESIMS m/z 293 ($[M+H]^+$).

Example 8: Preparation of (E)-1,2,4-trichloro-5-(4-methoxystyryl)benzene (C63)

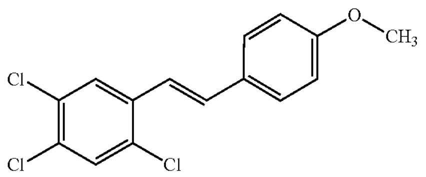 [SMILES: COc1ccc(/C=C/c2cc(Cl)c(Cl)cc2Cl)cc1]

To a sealed tube were added 1-bromo-2,4,5-trichlorobenzene (3.0 g, 12 mmol), 1,2-dimethoxyethane:water (10:1, 30 mL), (E)-2-(4-methoxystyryl)-4,4,5,5-tetramethyl-1,3,2-dioxaborolane (C64) (3.7 g, 14 mmol), and potassium carbonate (3.2 g, 24 mmol). The reaction mixture was degassed for 10 minutes with argon, followed by addition of tetrakis (triphenylphosphine)palladium(0) (0.55 g, 0.48 mmol). The reaction mixture was degassed for 10 minutes then heated at 90° C. for 16 hours. The reaction mixture was poured in to water and extracted with ethyl acetate. The combined organic layers were dried over sodium sulfate, filtered, and concentrated. Purification by flash column chromatography provided the title compound as an off-white solid (3.0 g, 80%): $^{1}$H NMR (400 MHz, $CDCl_3$) δ 7.73 (s, 1H), 7.50-7.45 (m, 3H), 7.20 (d, J=16.0 Hz, 1H), 7.02 (d, J=16 Hz, 1H), 6.92 (d, J=8.0 Hz, 2H), 3.84 (m, 3H); ESIMS m/z 313 ($[M+H]^+$).

Example 9: Preparation of (E)-2-(4-methoxystyryl)-4,4,5,5-tetramethyl-1,3,2-dioxaborolane (C64)

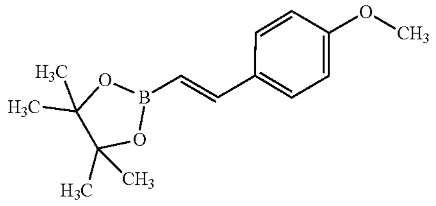

To a 50 mL round-bottomed flask were added 1-ethynyl-4-methoxybenzene (4.0 g, 30 mmol), 4,4,5,5-tetramethyl-1,3,2-dioxaborolane (3.3 g, 36 mmol), zirconocene hydrochloride (1.2 g, 4.0 mmol), and triethylamine (2.8 mL, 15 mmol) at 0° C. The reaction mixture was then stirred at 65° C. for 16 hours. The reaction mixture was poured in water and extracted with ethyl acetate. The combined organic layers were dried over sodium sulfate, filtered, and concentrated. Purification by flash column chromatography provided the title compound as an off-white semi solid (3.0 g, 38%): 1H NMR (400 MHz, $CDCl_3$) δ 7.43 (d, J=8.8 Hz, 2H), 7.35 (d, J=18.0 Hz, 1H), 6.86 (d, J=8.8 Hz, 2H), 6.01 (d, J=18.0 Hz, 1H), 3.81 (s, 3H), 1.30 (s, 12H).

Example 10: Preparation of 3,4,5-trichlorobenzaldehyde (C65)

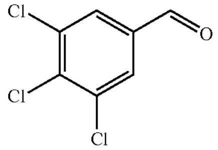 [SMILES: O=Cc1cc(Cl)c(Cl)c(Cl)c1]

In an oven dried, nitrogen flushed, 500 mL round-bottomed flask equipped with a pressure equalizing addition funnel, 5-bromo-1,2,3-trichlorobenzene (10.0 g, 38.4 mmol) was dissolved in tetrahydrofuran (100 mL), and the resulting solution was cooled in an ice bath under nitrogen. isoPropyl magnesium chloride (2 M solution tetrahydrofuran, 21.1 mL, 42.3 mmol) was added dropwise with good stirring over 15 minutes via the addition funnel. After 0.5 hours, N,N-dimethylformamide (3.72 mL, 48.0 mmol) was added to the dark solution with stirring. After an additional 0.5 hours, hydrochloric acid (1 N, 100 mL) was added with stirring. The layers were separated, and the organic layer was washed with brine. The combined aqueous layers were extracted with ether, and the combined organics were dried over sodium sulfate, filtered, and concentrated to afford the title compound as a white solid (10:1 mixture of title compound to 1,2,3-trichlorobenzene, 7.96 g, 99%): $^{1}$H NMR ($CDCl_3$) δ 9.91 (s, 1H), 7.88 (s, 2H); EIMS m/z 209 ([M]$^+$).

Example 11: Preparation of 1-bromo-4-(perfluoroethyl)benzene (C66)

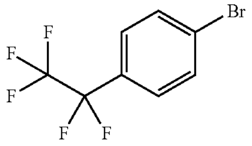 [SMILES: FC(F)(F)C(F)(F)c1ccc(Br)cc1]

To a stirred solution of 1-(4-bromophenyl)-2,2,2-trifluoroethanone (5.00 g, 19.7 mmol) in dichloromethane under argon were added 4-tert-butyl-2,6-dimethylphenylsulfur trifluoride (2.90 g, 11.8 mmol) and hydrogen fluoride pyridine complex (0.190 g, 9.80 mmol) at 0° C. The reaction mixture was allowed to warm to room temperature and stirred for 16 hours. The reaction mixture was poured into water and extracted with ethyl acetate. The combined organic extracts were dried over sodium sulfate, filtered, and concentrated. Purification by flash column chromatograph provided the title compound as colorless liquid (1.00 g, 20%): $^{1}$H NMR (300 MHz, $CDCl_3$) δ 7.65 (d, J=9.0 Hz, 2H), 7.47 (d, J=9.0 Hz, 2H); EIMS m/z 274 ([M]$^+$).

Example 12: Preparation of trans-2-chloro-5-(2,2-dichloro-3-(3,5-dichlorophenyl)cyclopropanecarboxamido)benzoic acid (C67)

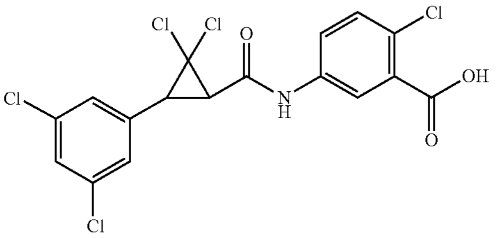

To a solution of trans-2,2-dichloro-3-(3,5-dichlorophenyl) cyclopropanecarboxylic acid (C1) (0.300 g, 1.00 mmol) in dichloromethane (5.00 mL) stirred at 0° C., were added N,N-dimethylformamide (1 drop) followed by oxalyl chloride (0.131 mL, 1.50 mmol) over 2 minutes. The ice batch was removed and the reaction allowed to warm to room temperature over 90 minutes. The reaction was then concentrated to yield a yellow-orange semi-solid. The semi-solid was dissolved in dichloromethane (3.5 mL), and the solution was added slowly to a cooled solution of 5-amino-2-chlorobenzoic acid (0.206 g, 1.20 mmol) and triethylamine (0.209 mL, 1.50 mmol) in dichloromethane (7 mL). The ice bath was removed and the reaction was allowed to warm to room temperature over 90 minutes. The reaction was diluted with dichloromethane (10 mL) and washed with hydrochloric acid (0.1 N). The resulting slurry was filtered and the solid washed with water. The precipitated solid was dried in a vacuum oven at 40° C. to provide the title compound as a light brown solid (0.421 g, 93%): mp 234-236° C.; 1H NMR (400 MHz, DMSO-$d_6$) δ 13.47 (s, 1H), 10.90 (s, 1H), 8.16 (d, J=2.3 Hz, 1H), 7.78 (dd, J=8.7, 2.4 Hz, 1H), 7.59 (m, 4H), 3.56 (dd, J=49.8, 8.5 Hz, 2H), 1.09 (m, 1H); $^{13}$C NMR (101 MHz, DMSO-$d_6$) δ 166.26, 165.77, 162.61, 137.57, 137.27, 134.04, 132.18, 131.44, 131.22, 127.88, 127.66, 126.40, 125.92, 122.88, 121.17, 102.37, 62.11, 38.41, 36.83; ESIMS m/z 454 ([M+H]$^+$).

Example 13: Preparation of trans-2-chloro-5-(2,2-dichloro-3-(3,5-dichlorophenyl)cyclopropane-1-carboxamido)-N-(4-fluorophenyl)benzamide (F1)

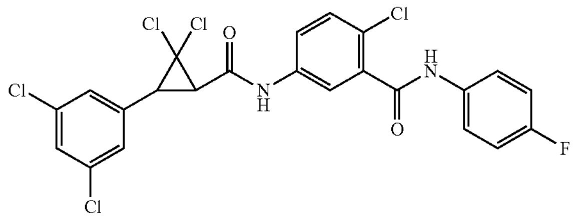

5-Amino-2-chloro-N-(4-fluorophenyl)benzamide (C69) (0.174 g, 0.656 mmol) and 4-dimethylaminopyridine (0.087 g, 0.711 mmol) were sequentially added to a stirred mixture of trans-2,2-dichloro-3-(3,5-dichlorophenyl)cyclopropanecarboxylic acid (C1) (0.164 g, 0.547 mmol) and 1-ethyl-3-(3-dimethylaminopropyl)carbodiimide hydrochloride (0.157 g, 0.820 mmol) in 1,2-dichloroethane (5.5 mL) at room temperature. The reaction was stirred at room temperature for 20 hours. The reaction was diluted with dichloromethane, washed with saturated aqueous sodium bicarbonate (2×), and washed with hydrochloric acid (1 N) (2×). The organic phase was dried over magnesium sulfate, filtered, and concentrated. Purification by flash column chromatography using 0-100% ethyl acetate/hexanes as eluent provided the title compound as a white foam (0.138 g, 46%).

The following compounds were prepared in like manner to the procedure outlined in Example 13:

trans-3-(2,2-Dichloro-3-(3,5-dichlorophenyl)cyclopropane-1-carboxamido)-N-(4-fluorophenyl)benzamide (F2)

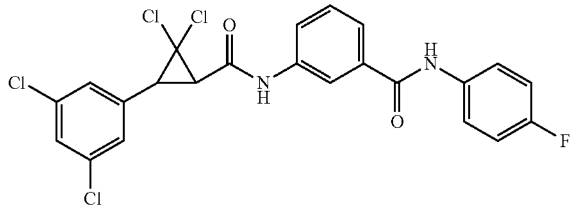 [SMILES: O=C(Nc1ccc(F)cc1)c1cccc(NC(=O)C2C(c3cc(Cl)cc(Cl)c3)C2(Cl)Cl)c1]

Isolated as a brown solid (0.106 g, 79%).

trans-5-(2,2-Dichloro-3-(3,5-dichlorophenyl)cyclopropane-1-carboxamido)-N-(4-fluorophenyl)-2-(trifluoromethyl)benzamide (F3)

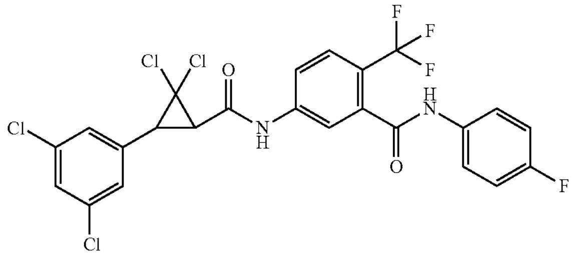 [SMILES: O=C(Nc1ccc(F)cc1)c1cc(NC(=O)C2C(c3cc(Cl)cc(Cl)c3)C2(Cl)Cl)ccc1C(F)(F)F]

Isolated as a yellow solid (0.074 g, 34%).

trans-5-(2,2-Dichloro-3-(3,5-dichlorophenyl)cyclopropane-1-carboxamido)-N-(4-fluorophenyl)-2-iodobenzamide (F4)

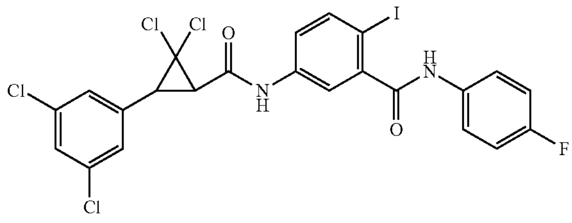 [SMILES: O=C(Nc1ccc(F)cc1)c1cc(NC(=O)C2C(c3cc(Cl)cc(Cl)c3)C2(Cl)Cl)ccc1I]

Isolated as a brown solid (0.078 g, 50%).

trans-2-Chloro-N-(4-cyanophenyl)-5-(2,2-dichloro-3-(3,5-dichlorophenyl)cyclopropane-1-carboxamido)benzamide (F5)

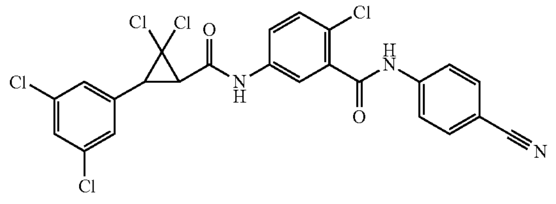 [SMILES: N#Cc1ccc(NC(=O)c2cc(NC(=O)C3C(c4cc(Cl)cc(Cl)c4)C3(Cl)Cl)ccc2Cl)cc1]

Isolated as a yellow solid (0.081 g, 39%).

trans-2-Chloro-5-(2,2-dichloro-3-(3,5-dichlorophenyl)cyclopropane-1-carboxamido)-N-(4-(trifluoromethyl)phenyl)benzamide (F6)

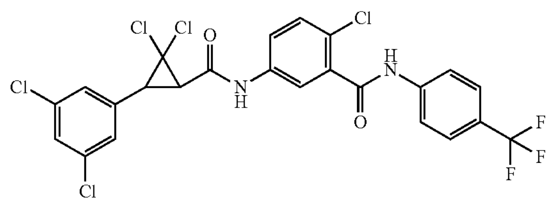 [SMILES: O=C(Nc1ccc(C(F)(F)F)cc1)c1cc(NC(=O)C2C(c3cc(Cl)cc(Cl)c3)C2(Cl)Cl)ccc1Cl]

Isolated as a yellow solid (0.082 g, 49%).

trans-2-Chloro-N-(4-chlorophenyl)-5-(2,2-dichloro-3-(3,5-dichlorophenyl)cyclopropane-1-carboxamido)benzamide (F7)

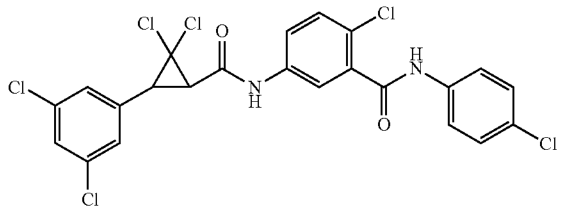 [SMILES: O=C(Nc1ccc(Cl)cc1)c1cc(NC(=O)C2C(c3cc(Cl)cc(Cl)c3)C2(Cl)Cl)ccc1Cl]

Isolated as a yellow solid (0.083 g, 47%).

trans-2-Chloro-N-(2-chloro-4-fluorophenyl)-5-(2,2-dichloro-3-(3,5-dichlorophenyl)cyclopropane-1-carboxamido)benzamide (F8)

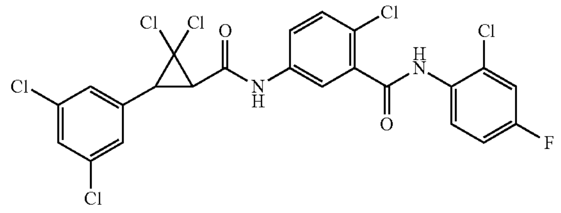

Isolated as a yellow solid (0.075 g, 42%).

trans-2-Chloro-5-(2,2-dichloro-3-(3,5-dichlorophenyl)cyclopropane-1-carboxamido)-N-(o-tolyl)benzamide (F9)

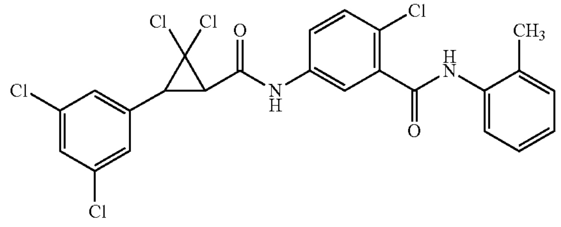

Isolated as a brown solid (0.104 g, 54%).

trans-5-(2,2-Dichloro-3-(3,5-dichlorophenyl)cyclopropane-1-carboxamido)-N-(4-fluorophenyl)-2-methylbenzamide (F10)

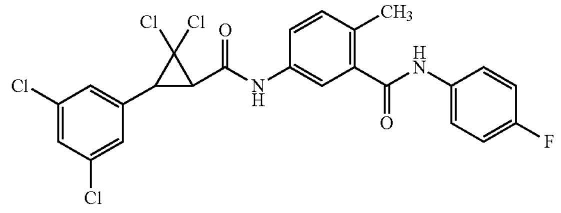

Isolated as a white solid (0.095 g, 50%).

trans-2-Bromo-5-(2,2-dichloro-3-(3,5-dichlorophenyl)cyclopropane-1-carboxamido)-N-(4-fluorophenyl)benzamide (F11)

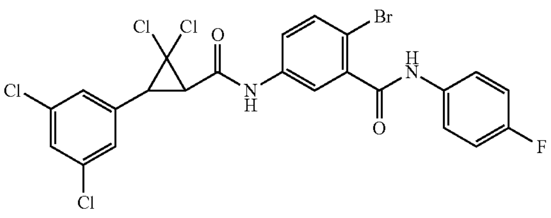

Isolated as a red solid (0.085 g, 51%).

trans-5-(2,2-Dichloro-3-(3,5-dichlorophenyl)cyclopropane-1-carboxamido)-N-(4-fluorophenyl)-2-(1H-1,2,4-triazol-1-yl)benzamide (F12)

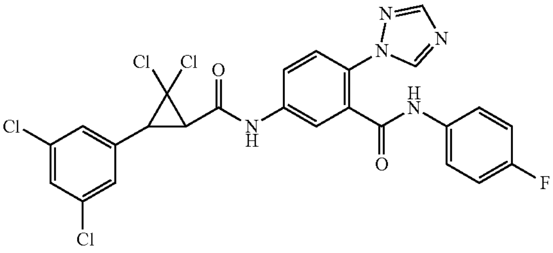 [SMILES: O=C(Nc1ccc(F)cc1)c1cc(NC(=O)C2C(c3cc(Cl)cc(Cl)c3)C2(Cl)Cl)ccc1-n1cncn1]

Isolated as a brown solid (0.103 g, 60%).

trans-2-Chloro-5-(2,2-dichloro-3-(3,4,5-trichlorophenyl)cyclopropane-1-carboxamido)-N-(4-fluorophenyl)benzamide (F13)

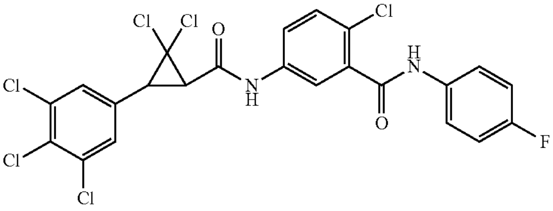

Isolated as a white powder (0.090 g, 79%).

trans-2-Chloro-5-(2,2-dichloro-3-(3,4-dichlorophenyl)cyclopropane-1-carboxamido)-N-(4-fluorophenyl)benzamide (F14)

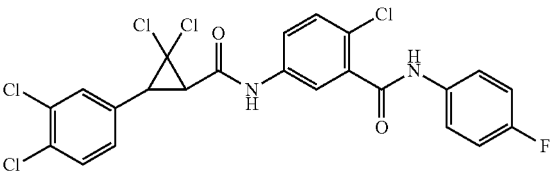

Isolated as an off-white powder (0.155 g, 77%).

trans-3-(2,2-Dichloro-3-(3,5-dichlorophenyl)cyclopropane-1-carboxamido)-2-fluoro-N-(4-fluorophenyl)benzamide (F15)

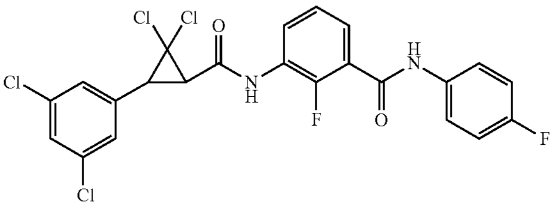

Isolated as a yellow oil (0.025 g, 18%).

trans-2-Chloro-5-(2,2-Dichloro-3-(3,5-dichlorophenyl)cyclopropane-1-carboxamido)-N-phenylbenzamide (F16)

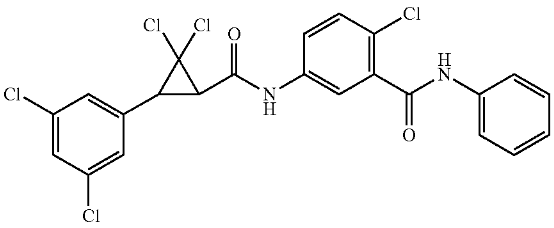

Isolated as a white solid (0.092 g, 66%).

trans-2-Chloro-5-(2,2-dichloro-3-(3,5-dichlorophenyl)cyclopropane-1-carboxamido)-N-(2-fluorophenyl)benzamide (F17)

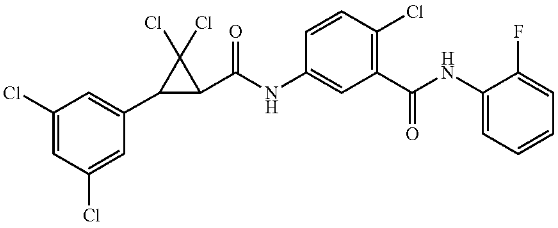

Isolated as a white solid (0.030 g, 21%).

trans-2-Chloro-5-(2,2-dichloro-3-(3,5-dichlorophenyl)cyclopropane-1-carboxamido)-N-(2,4-difluorophenyl)benzamide (F18)

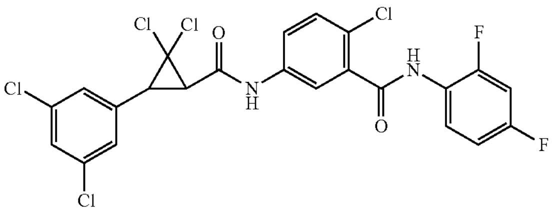

Isolated as a white solid (0.108 g, 72%).

trans-2-Chloro-5-(2,2-dichloro-3-(3,5-dichlorophenyl)cyclopropane-1-carboxamido)-N-(4-fluorophenyl)-N-methylbenzamide (F19)

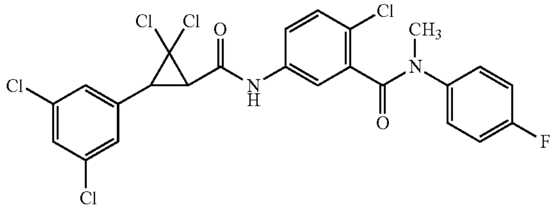 [SMILES: CN(C(=O)c1cc(NC(=O)C2C(c3cc(Cl)cc(Cl)c3)C2(Cl)Cl)ccc1Cl)c1ccc(F)cc1]

Isolated as a white solid (0.137 g, 92%).

trans-2-Chloro-5-(2,2-dichloro-3-(3,5-dichlorophenyl)cyclopropane-1-carboxamido)-N-(3-fluorophenyl)benzamide (F20)

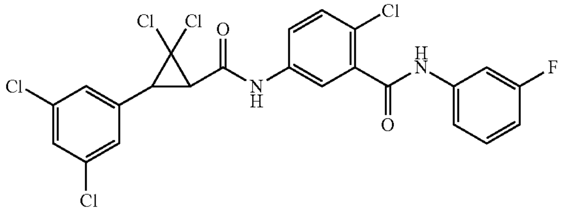 [SMILES: O=C(Nc1cccc(F)c1)c1cc(NC(=O)C2C(c3cc(Cl)cc(Cl)c3)C2(Cl)Cl)ccc1Cl]

Isolated as a pink solid (0.115 g, 79%).

trans-2-Chloro-N-(3-cyanophenyl)-5-(2,2-dichloro-3-(3,5-dichlorophenyl)cyclopropane-1-carboxamido) benzamide (F21)

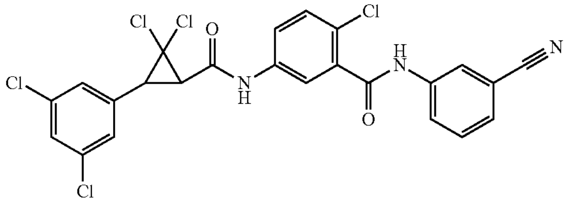 [SMILES: N#Cc1cccc(NC(=O)c2cc(NC(=O)C3C(c4cc(Cl)cc(Cl)c4)C3(Cl)Cl)ccc2Cl)c1]

Isolated as a white solid (0.113 g, 76%).

trans-2-Chloro-5-(2,2-dichloro-3-(3,5-dichlorophenyl)cyclopropane-1-carboxamido)-N-(2,3-difluorophenyl)benzamide (F22)

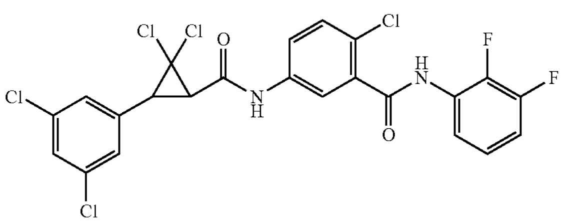 [SMILES: O=C(Nc1cccc(F)c1F)c1cc(NC(=O)C2C(c3cc(Cl)cc(Cl)c3)C2(Cl)Cl)ccc1Cl]

Isolated as a white solid (0.120 g, 79%).

trans-2-Chloro-5-(2,2-dichloro-3-(3,5-dichlorophenyl)cyclopropane-1-carboxamido)-N-(3,4-difluorophenyl)benzamide (F23)

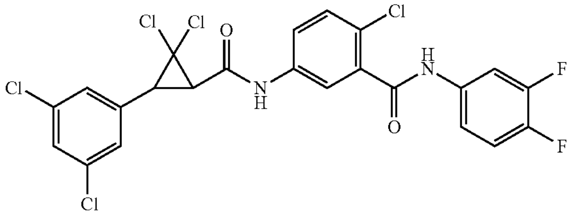 [SMILES: O=C(Nc1ccc(F)c(F)c1)c1cc(NC(=O)C2C(c3cc(Cl)cc(Cl)c3)C2(Cl)Cl)ccc1Cl]

Isolated as a white solid (0.121 g, 80%).

trans-2-Chloro-5-(2,2-dichloro-3-(3,5-dichlorophenyl)cyclopropane-1-carboxamido)-N-(2,4,6-trifluorophenyl)benzamide (F24)

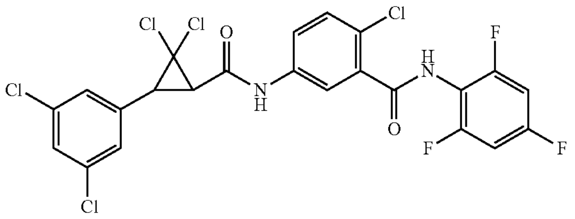 [SMILES: O=C(Nc1c(F)cc(F)cc1F)c1cc(NC(=O)C2C(c3cc(Cl)cc(Cl)c3)C2(Cl)Cl)ccc1Cl]

Isolated as a light pink solid (0.109 g, 70%).

trans-2-Chloro-5-(2,2-dichloro-3-(3,5-dichlorophenyl)cyclopropane-1-carboxamido)-N-(2,6-difluorophenyl)benzamide (F25)

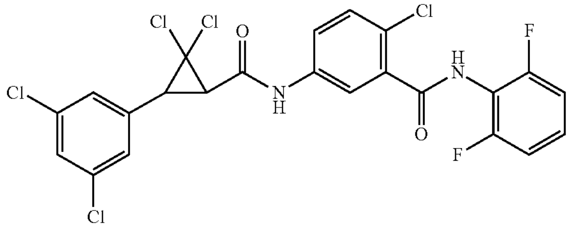 [SMILES: O=C(Nc1c(F)cccc1F)c1cc(NC(=O)C2C(c3cc(Cl)cc(Cl)c3)C2(Cl)Cl)ccc1Cl]

Isolated as a light pink solid (0.092 g, 61%).

trans-2-Chloro-5-(2,2-dichloro-3-(3,5-dichlorophenyl)cyclopropane-1-carboxamido)-N-(pyridin-4-yl)benzamide (F26)

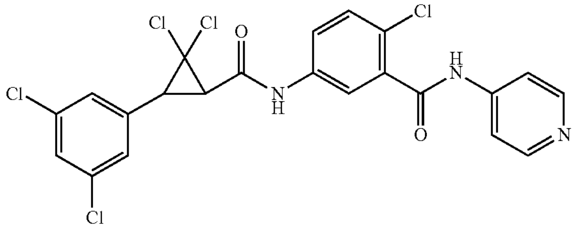 [SMILES: O=C(Nc1ccncc1)c1cc(NC(=O)C2C(c3cc(Cl)cc(Cl)c3)C2(Cl)Cl)ccc1Cl]

Isolated as a white solid (0.112 g, 64%).

trans-2-Chloro-5-(2,2-dichloro-3-(3,5-dichlorophenyl)cyclopropane-1-carboxamido)-N-(pyridin-3-yl)benzamide (F27)

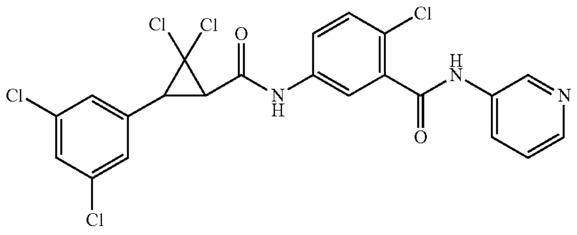 [SMILES: O=C(Nc1cccnc1)c1cc(NC(=O)C2C(c3cc(Cl)cc(Cl)c3)C2(Cl)Cl)ccc1Cl]

Isolated as a white solid (0.138 g, 78%).

trans-5-(2,2-Dichloro-3-(3,4-dichlorophenyl)cyclopropane-1-carboxamido)-2-fluoro-N-(4-fluorophenyl)benzamide (F28)

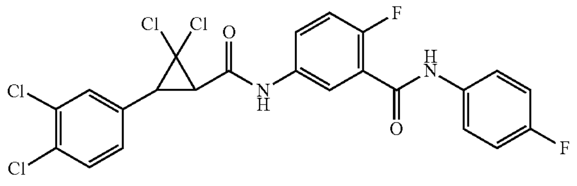 [SMILES: O=C(Nc1ccc(F)cc1)c1cc(NC(=O)C2C(c3ccc(Cl)c(Cl)c3)C2(Cl)Cl)ccc1F]

Isolated as a white solid (0.130 g, 92%).

trans-5-(2,2-Dichloro-3-(3,4,5-trichlorophenyl)cyclopropane-1-carboxamido)-2-fluoro-N-(4-fluorophenyl)benzamide (F29)

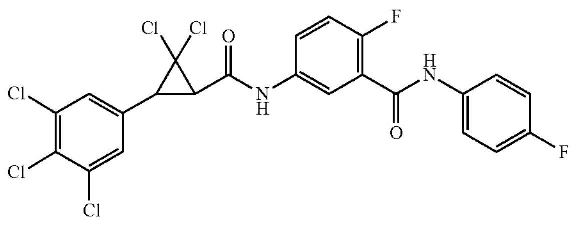 [SMILES: O=C(Nc1ccc(F)cc1)c1cc(NC(=O)C2C(c3cc(Cl)c(Cl)c(Cl)c3)C2(Cl)Cl)ccc1F]

Isolated as a white solid (0.121 g, 90%).

trans-3-(2,2-Dichloro-3-(3,5-dichlorophenyl)cyclopropane-1-carboxamido)-N-(4-fluorophenyl)-2-methoxybenzamide (F30)

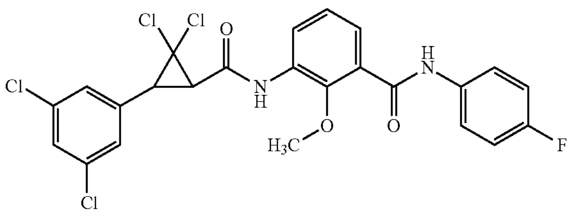 [SMILES: COc1c(NC(=O)C2C(c3cc(Cl)cc(Cl)c3)C2(Cl)Cl)cccc1C(=O)Nc1ccc(F)cc1]

Isolated as a yellow solid (0.069 g, 47%).

trans-2-Chloro-N-(2-chloropyridin-3-yl)-5-(2,2-dichloro-3-(3,5-dichlorophenyl)cyclopropane-1-carboxamido)benzamide (F31)

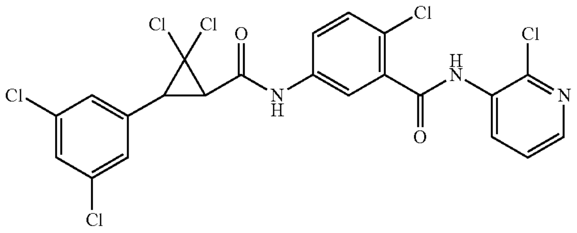

Isolated as a white solid (0.126 g, 67%).

trans-2-Chloro-N-(6-chloropyridin-3-yl)-5-(2,2-dichloro-3-(3,5-dichlorophenyl)cyclopropane-1-carboxamido)benzamide (F32)

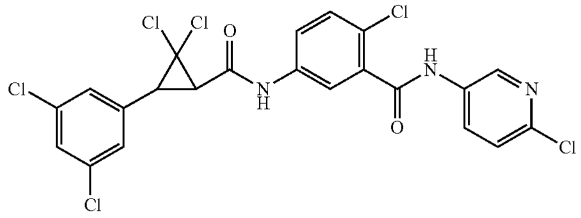 [SMILES: O=C(Nc1ccc(Cl)nc1)c1cc(NC(=O)C2C(c3cc(Cl)cc(Cl)c3)C2(Cl)Cl)ccc1Cl]

Isolated as a white solid (0.131 g, 70%).

trans-2-Chloro-N-(6-cyanopyridin-3-yl)-5-(2,2-dichloro-3-(3,5-dichlorophenyl)cyclopropane-1-carboxamido)benzamide (F33)

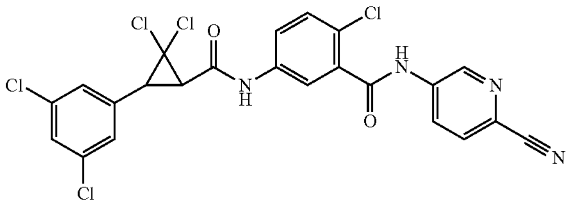 [SMILES: N#Cc1ccc(NC(=O)c2cc(NC(=O)C3C(c4cc(Cl)cc(Cl)c4)C3(Cl)Cl)ccc2Cl)cn1]

Isolated as a white solid (0.094 g, 51%).

trans-2-Chloro-5-(2,2-dichloro-3-(3,5-dichlorophenyl)cyclopropane-1-carboxamido)-N-(3-fluorophenyl)-N-methylbenzamide (F34)

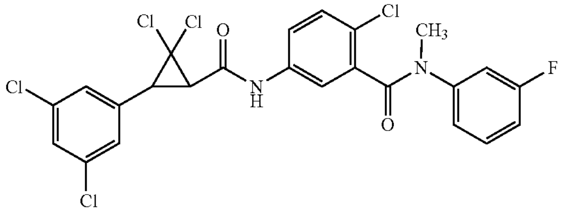

Isolated as a white solid (0.119 g, 80%).

trans-2-Chloro-5-(2,2-dichloro-3-(3,5-dichlorophenyl)cyclopropane-1-carboxamido)-N-(2-fluorophenyl)-N-methylbenzamide (F35)

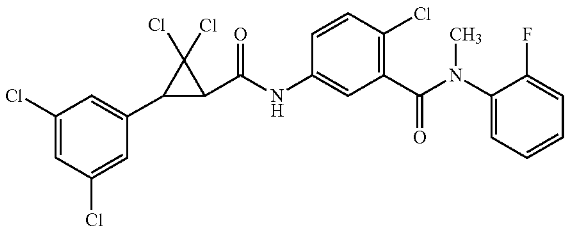 [SMILES: CN(C(=O)c1cc(NC(=O)C2C(c3cc(Cl)cc(Cl)c3)C2(Cl)Cl)ccc1Cl)c1ccccc1F]

Isolated as a white solid (0.123 g, 82%).

trans-2-Chloro-N-(4-cyano-2-methylphenyl)-5-(2,2-dichloro-3-(3,5-dichlorophenyl)cyclopropane-1-carboxamido)benzamide (F36)

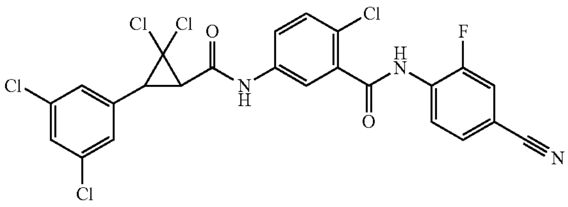

Isolated as a white solid (0.103 g, 68%).

trans-2-Chloro-5-(2,2-dichloro-3-(3,5-dichlorophenyl)cyclopropane-1-carboxamido)-N-(4-fluoro-2-methylphenyl)benzamide (F37)

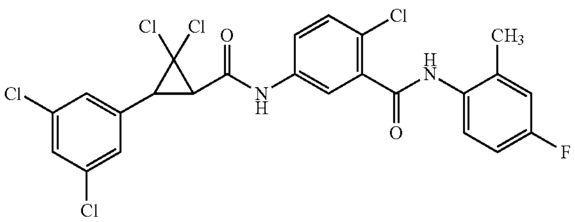 [SMILES: Cc1cc(F)ccc1NC(=O)c1cc(NC(=O)C2C(c3cc(Cl)cc(Cl)c3)C2(Cl)Cl)ccc1Cl]

Isolated as a white solid (0.112 g, 75%).

trans-2-Chloro-N-(2-chlorophenyl)-5-(2,2-dichloro-3-(3,5-dichlorophenyl)cyclopropane-1-carboxamido) benzamide (F38)

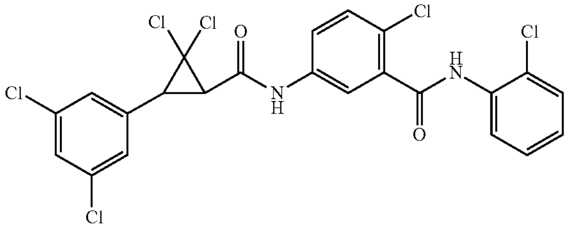 [SMILES: O=C(Nc1ccccc1Cl)c1cc(NC(=O)C2C(c3cc(Cl)cc(Cl)c3)C2(Cl)Cl)ccc1Cl]

Isolated as a white foam (0.101 g, 77%).

trans-2-Chloro-5-(2,2-dichloro-3-(3,4-dichlorophenyl)cyclopropane-1-carboxamido)-N-(2,4-difluorophenyl)benzamide (F39)

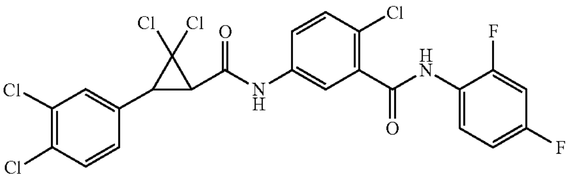 [SMILES: O=C(Nc1ccc(F)cc1F)c1cc(NC(=O)C2C(c3ccc(Cl)c(Cl)c3)C2(Cl)Cl)ccc1Cl]

Isolated as a white foam (0.096 g, 68%).

trans-2-Chloro-5-(2,2-dichloro-3-(3,4,5-trichlorophenyl)cyclopropane-1-carboxamido)-N-(2,4-difluorophenyl)benzamide (F40)

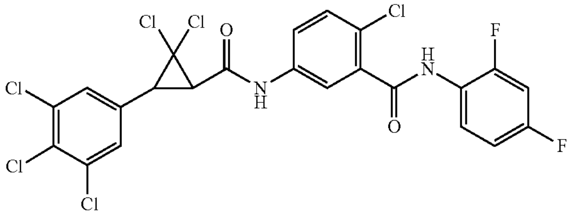 [SMILES: O=C(Nc1ccc(F)cc1F)c1cc(NC(=O)C2C(c3cc(Cl)c(Cl)c(Cl)c3)C2(Cl)Cl)ccc1Cl]

Isolated as a white solid (0.104 g, 77%).

trans-2-Chloro-5-(2,2-dichloro-3-(3,5-dichlorophenyl)cyclopropane-1-carboxamido)-N-(2-isopropylphenyl)benzamide (F41)

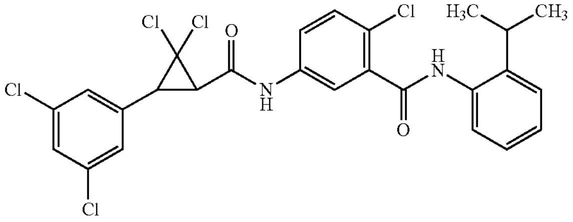 [SMILES: CC(C)c1ccccc1NC(=O)c1cc(NC(=O)C2C(c3cc(Cl)cc(Cl)c3)C2(Cl)Cl)ccc1Cl]

Isolated as a white solid (0.104 g, 78%).

trans-2-Chloro-5-(2,2-dichloro-3-(3,5-dichlorophenyl)cyclopropane-1-carboxamido)-N-(2-ethyl-6-methylphenyl)benzamide (F42)

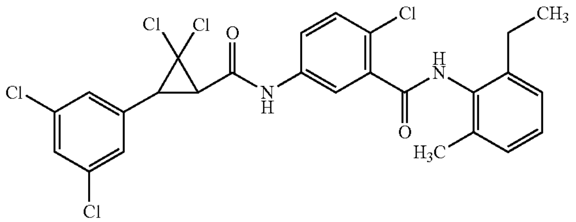 [SMILES: CCc1cccc(C)c1NC(=O)c1cc(NC(=O)C2C(c3cc(Cl)cc(Cl)c3)C2(Cl)Cl)ccc1Cl]

Isolated as a white solid (0.103 g, 77%).

trans-2-Chloro-N-(3-chlorophenyl)-5-(2,2-dichloro-3-(3,5-dichlorophenyl)cyclopropane-1-carboxamido) benzamide (F43)

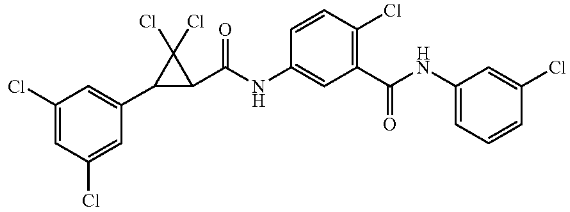 [SMILES: O=C(Nc1cccc(Cl)c1)c1cc(NC(=O)C2C(c3cc(Cl)cc(Cl)c3)C2(Cl)Cl)ccc1Cl]

Isolated as a white solid (0.029 g, 22%).

trans-2-Chloro-5-(2,2-dichloro-3-(3,5-dichlorophenyl)cyclopropane-1-carboxamido)-N-(2,4-difluorophenyl)-N-methylbenzamide (F44)

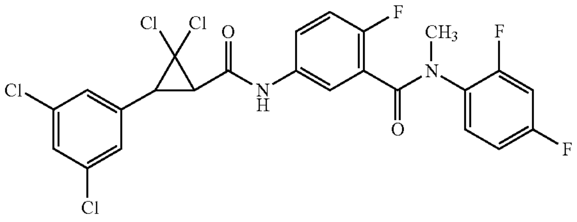 [SMILES: CN(C(=O)c1cc(NC(=O)C2C(c3cc(Cl)cc(Cl)c3)C2(Cl)Cl)ccc1F)c1ccc(F)cc1F]

Isolated as a white foam (0.082 g, 57%).

trans-5-(2,2-Dichloro-3-(3,5-dichlorophenyl)cyclopropane-1-carboxamido)-2-fluoro-N-(4-fluorophenyl)-N-methylbenzamide (F45)

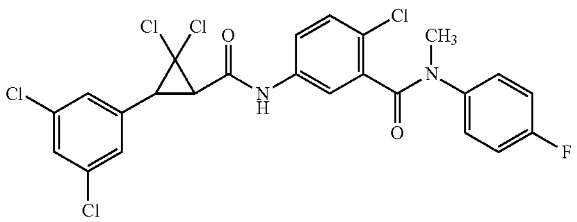 [SMILES: CN(C(=O)c1cc(NC(=O)C2C(c3cc(Cl)cc(Cl)c3)C2(Cl)Cl)ccc1Cl)c1ccc(F)cc1]

Isolated as a white solid (0.077 g, 57%).

trans-5-(2,2-Dichloro-3-(3,5-dichlorophenyl)cyclopropane-1-carboxamido)-2-fluoro-N-(3-fluorophenyl)-N-methylbenzamide (F46)

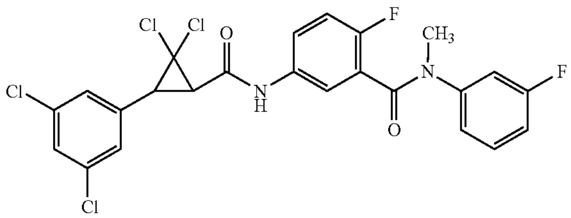

Isolated as a white solid (0.096 g, 70%).

trans-3-(2,2-Dichloro-3-(3,5-dichlorophenyl)cyclopropane-1-carboxamido)-2-fluoro-N-(4-fluorophenyl)-N-methylbenzamide (F47)

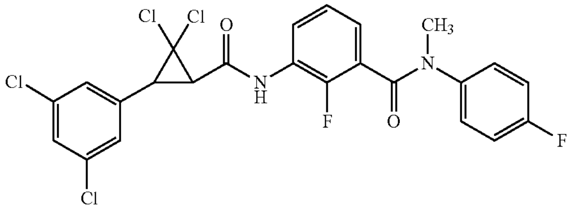 [SMILES: CN(C(=O)c1cccc(NC(=O)C2C(c3cc(Cl)cc(Cl)c3)C2(Cl)Cl)c1F)c1ccc(F)cc1]

Isolated as a yellow glass (0.106 g, 78%).

trans-2-Chloro-5-(2,2-dichloro-3-(3,5-dichlorophenyl)cyclopropane-1-carboxamido)-4-fluoro-N-(4-fluorophenyl)benzamide (F48)

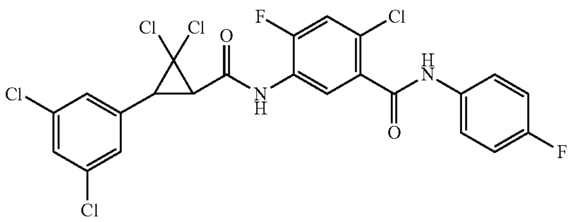 [SMILES: O=C(Nc1ccc(F)cc1)c1cc(NC(=O)C2C(c3cc(Cl)cc(Cl)c3)C2(Cl)Cl)c(F)cc1Cl]

Isolated as a yellow foam (0.083 g, 59%).

trans-5-(2,2-Dichloro-3-(3,5-dichlorophenyl)cyclopropane-1-carboxamido)-2,4-difluoro-N-(4-fluorophenyl)benzamide (F49)

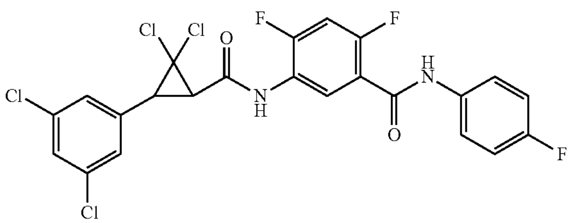 [SMILES: O=C(Nc1ccc(F)cc1)c1cc(NC(=O)C2C(c3cc(Cl)cc(Cl)c3)C2(Cl)Cl)c(F)cc1F]

Isolated as a white solid (0.061 g, 45%).

trans-2-Chloro-5-(2,2-dichloro-3-(3,4,5-trichlorophenyl)cyclopropane-1-carboxamido)-N-(3-fluorophenyl)benzamide (F50)

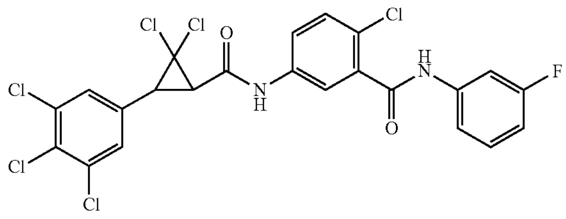 [SMILES: O=C(Nc1cccc(F)c1)c1cc(NC(=O)C2C(c3cc(Cl)c(Cl)c(Cl)c3)C2(Cl)Cl)ccc1Cl]

Isolated as a white solid (0.108 g, 83%).

trans-2-Chloro-5-(2,2-dichloro-3-(3,4-dichlorophenyl)cyclopropane-1-carboxamido)-N-(3-fluorophenyl)benzamide (F51)

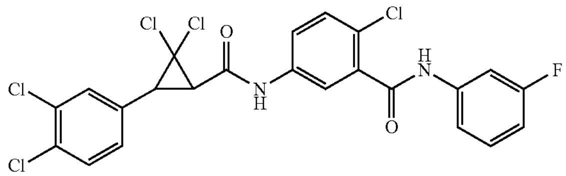 [SMILES: O=C(Nc1cccc(F)c1)c1cc(NC(=O)C2C(c3ccc(Cl)c(Cl)c3)C2(Cl)Cl)ccc1Cl]

Isolated as a white solid (0.104 g, 76%).

trans-2-Chloro-5-(2,2-dichloro-3-(3,4,5-trichlorophenyl)cyclopropane-1-carboxamido)-N-(4-fluorophenyl)-N-methylbenzamide (F52)

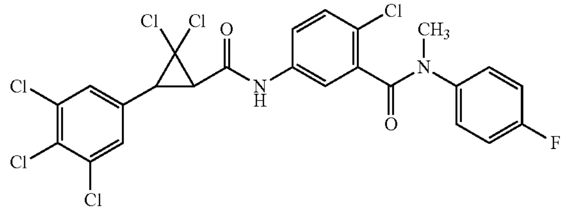

Isolated as a white solid (0.113 g, 85%).

trans-2-Chloro-5-(2,2-dichloro-3-(3,4-dichlorophenyl)cyclopropane-1-carboxamido)-N-(4-fluorophenyl)-N-methylbenzamide (F53)

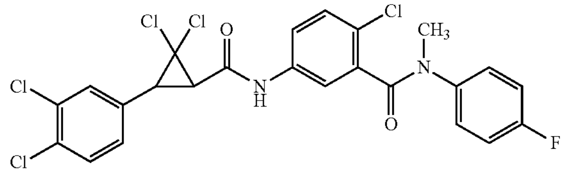 [SMILES: CN(C(=O)c1cc(NC(=O)C2C(c3ccc(Cl)c(Cl)c3)C2(Cl)Cl)ccc1Cl)c1ccc(F)cc1]

Isolated as a white solid (0.094 g, 67%).

trans-2-Chloro-N-(4-cyano-2-methylphenyl)-5-(2,2-dichloro-3-(3,4,5-trichlorophenyl)cyclopropane-1-carboxamido)benzamide (F54)

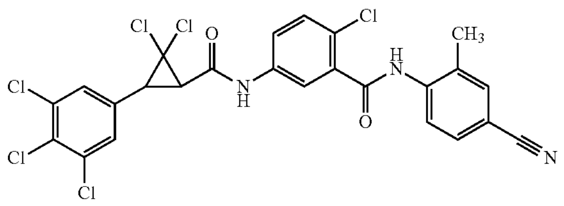 [SMILES: Cc1cc(C#N)ccc1NC(=O)c1cc(NC(=O)C2C(c3cc(Cl)c(Cl)c(Cl)c3)C2(Cl)Cl)ccc1Cl]

Isolated as a white solid (0.085 g, 63%).

trans-2-Chloro-N-(4-cyano-2-methylphenyl)-5-(2,2-dichloro-3-(3,4-dichlorophenyl)cyclopropane-1-carboxamido)benzamide (F55)

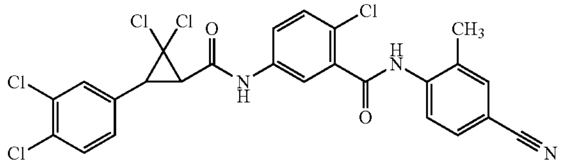

Isolated as a white solid (0.088 g, 62%).

trans-2-Chloro-5-(2,2-dichloro-3-(3-(trifluoromethyl)phenyl)cyclopropane-1-carboxamido)-N-(4-fluorophenyl)benzamide (F56)

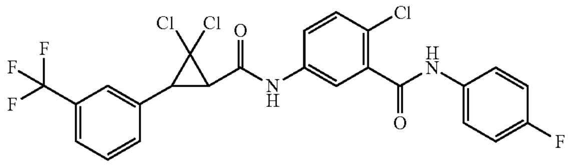

Isolated as a white solid (0.120 g, 78%).

trans-2-Chloro-5-(2,2-dichloro-3-(3-(trifluoromethyl)phenyl)cyclopropane-1-carboxamido)-N-(4-fluorophenyl)-N-methylbenzamide (F57)

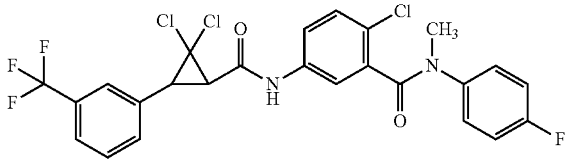 [SMILES: CN(C(=O)c1cc(NC(=O)C2C(c3cccc(C(F)(F)F)c3)C2(Cl)Cl)ccc1Cl)c1ccc(F)cc1]

Isolated as a white solid (0.102 g, 61%).

trans-2-Chloro-5-(2,2-dichloro-3-(3-(trifluoromethyl)phenyl)cyclopropane-1-carboxamido)-N-(2,6-difluorophenyl)benzamide (F58)

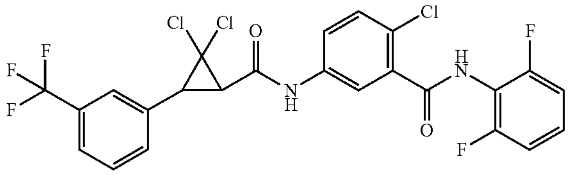 [SMILES: O=C(Nc1c(F)cccc1F)c1cc(NC(=O)C2C(c3cccc(C(F)(F)F)c3)C2(Cl)Cl)ccc1Cl]

Isolated as a white solid (0.066 g, 42%).

trans-5-(2,2-Dichloro-3-(3,4-dichlorophenyl)cyclopropane-1-carboxamido)-2-fluoro-N-(4-fluorophenyl)-N-methylbenzamide (F59)

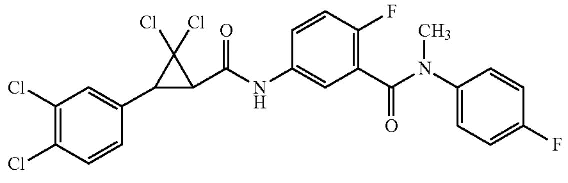 [SMILES: CN(C(=O)c1cc(NC(=O)C2C(c3ccc(Cl)c(Cl)c3)C2(Cl)Cl)ccc1F)c1ccc(F)cc1]

Isolated as a white solid (0.117 g, 86%).

trans-5-(2,2-dichloro-3-(3,4,5-trichlorophenyl)cyclopropane-1-carboxamido)-2-fluoro-N-(4-fluorophenyl)-N-methylbenzamide (F60)

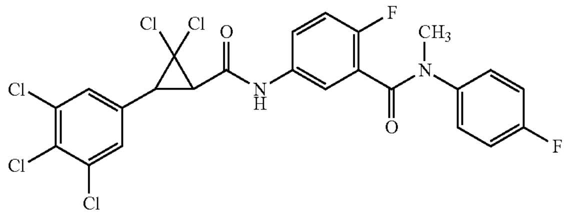 [SMILES: CN(C(=O)c1cc(NC(=O)C2C(c3cc(Cl)c(Cl)c(Cl)c3)C2(Cl)Cl)ccc1F)c1ccc(F)cc1]

Isolated as a white solid (0.027 g, 21%).

trans-5-(2,2-Dichloro-3-(3,5-dichlorophenyl)cyclopropane-1-carboxamido)-N-(2,4-difluorophenyl)-2-fluorobenzamide (F61)

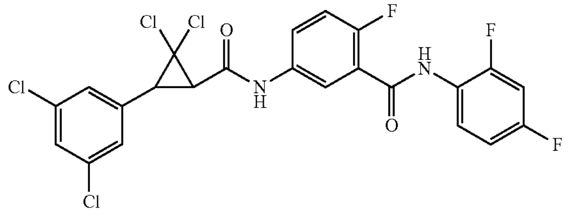 [SMILES: O=C(Nc1ccc(F)cc1F)c1cc(NC(=O)C2C(c3cc(Cl)cc(Cl)c3)C2(Cl)Cl)ccc1F]

Isolated as a white solid (0.120 g, 73%).

trans-5-(2,2-Dichloro-3-(3,4-dichlorophenyl)cyclopropane-1-carboxamido)-N-(2,4-difluorophenyl)-2-fluorobenzamide (F62)

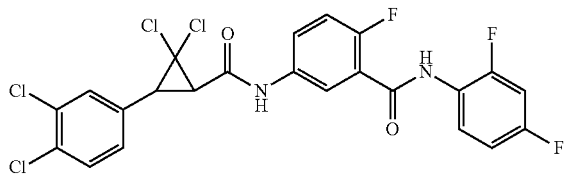 [SMILES: O=C(Nc1ccc(F)cc1F)c1cc(NC(=O)C2C(c3ccc(Cl)c(Cl)c3)C2(Cl)Cl)ccc1F]

Isolated as a white solid (0.102 g, 62%).

trans-5-(2,2-Dichloro-3-(3,5-dichlorophenyl)cyclopropane-1-carboxamido)-N-(2,4-difluorophenyl)-2-fluoro-N-methylbenzamide (F63)

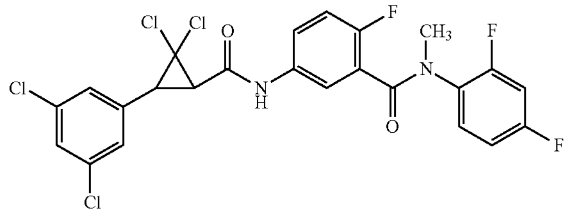 [SMILES: CN(C(=O)c1cc(NC(=O)C2C(c3cc(Cl)cc(Cl)c3)C2(Cl)Cl)ccc1F)c1ccc(F)cc1F]

Isolated as a white solid (0.123 g, 73%).

trans-5-(2,2-Dichloro-3-(3,4-dichlorophenyl)cyclopropane-1-carboxamido)-N-(2,4-difluorophenyl)-2-fluoro-N-methylbenzamide (F64)

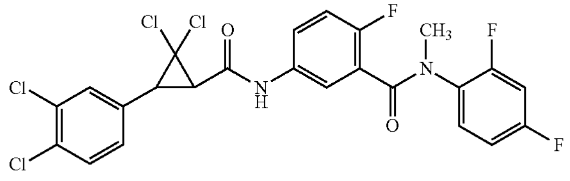 [SMILES: CN(C(=O)c1cc(NC(=O)C2C(c3ccc(Cl)c(Cl)c3)C2(Cl)Cl)ccc1F)c1ccc(F)cc1F]

Isolated as a white foam (0.110 g, 65%).

trans-5-(2,2-Dichloro-3-(3,4,5-trichlorophenyl)cyclopropane-1-carboxamido)-N-(2,4-difluorophenyl)-2-fluoro-N-methylbenzamide (F65)

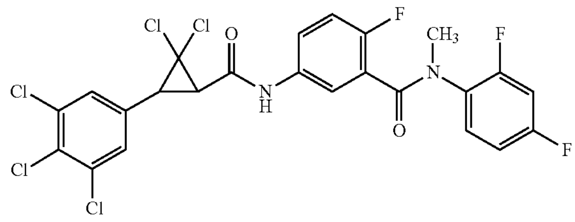 [SMILES: CN(C(=O)c1cc(NC(=O)C2C(c3cc(Cl)c(Cl)c(Cl)c3)C2(Cl)Cl)ccc1F)c1ccc(F)cc1F]

Isolated as a white solid (0.098 g, 55%).

trans-5-(2,2-Dichloro-3-(3,5-dichlorophenyl)cyclopropane-1-carboxamido)-2-fluoro-N-methyl-N-phenylbenzamide (F66)

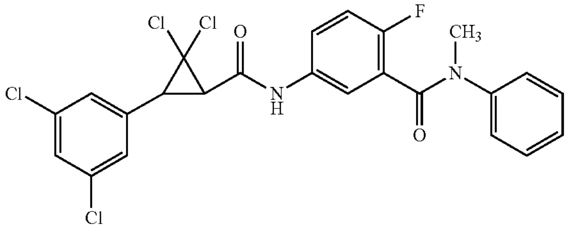 [SMILES: CN(C(=O)c1cc(NC(=O)C2C(c3cc(Cl)cc(Cl)c3)C2(Cl)Cl)ccc1F)c1ccccc1]

Isolated as a white foam (0.123 g, 78%).

trans-5-(2,2-Dichloro-3-(3,4-dichlorophenyl)cyclopropane-1-carboxamido)-2-fluoro-N-methyl-N-phenylbenzamide (F67)

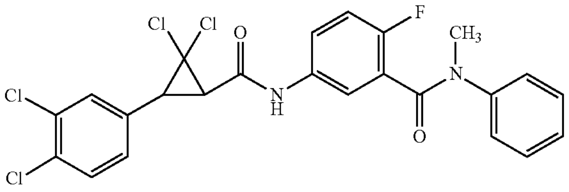 [SMILES: CN(C(=O)c1cc(NC(=O)C2C(c3ccc(Cl)c(Cl)c3)C2(Cl)Cl)ccc1F)c1ccccc1]

Isolated as a white foam (0.124 g, 79%).

trans-5-(2,2-Dichloro-3-(3,4,5-trichlorophenyl)cyclopropane-1-carboxamido)-2-fluoro-N-methyl-N-phenylbenzamide (F68)

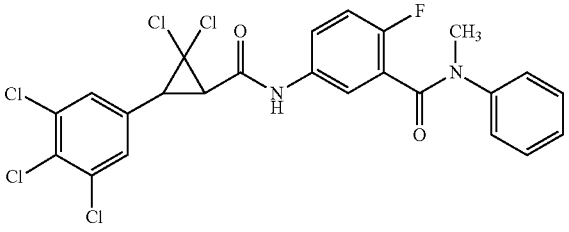 [SMILES: CN(C(=O)c1cc(NC(=O)C2C(c3cc(Cl)c(Cl)c(Cl)c3)C2(Cl)Cl)ccc1F)c1ccccc1]

Isolated as a white solid (0.122 g, 72%).

trans-3-(2,2-Dichloro-3-(3,5-dichlorophenyl)cyclopropane-1-carboxamido)-2-fluoro-N-methyl-N-phenylbenzamide (F69)

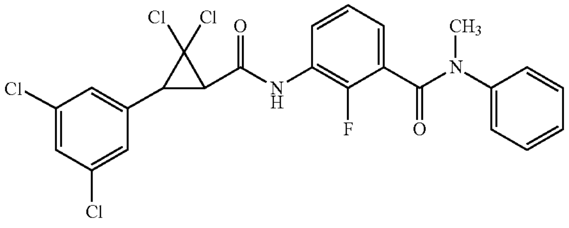 [SMILES: CN(C(=O)c1cccc(NC(=O)C2C(c3cc(Cl)cc(Cl)c3)C2(Cl)Cl)c1F)c1ccccc1]

Isolated as a yellow foam (0.101 g, 64%).

trans-3-(2,2-Dichloro-3-(3,4-dichlorophenyl)cyclopropane-1-carboxamido)-2-fluoro-N-methyl-N-phenylbenzamide (F70)

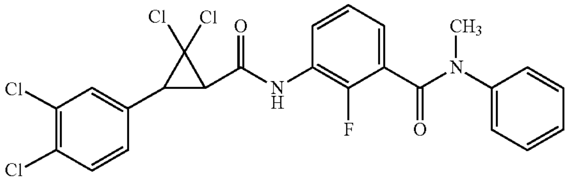 [SMILES: CN(C(=O)c1cccc(NC(=O)C2C(c3ccc(Cl)c(Cl)c3)C2(Cl)Cl)c1F)c1ccccc1]

Isolated as a light yellow foam (0.107 g, 68%).

trans-3-(2,2-Dichloro-3-(3,4,5-trichlorophenyl)cyclopropane-1-carboxamido)-2-fluoro-N-methyl-N-phenylbenzamide (F71)

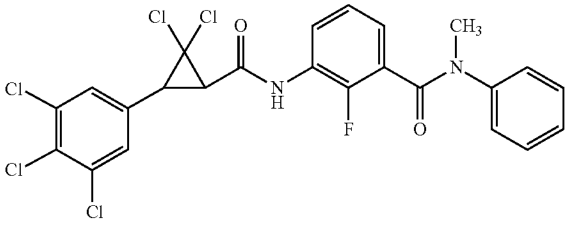 [SMILES: CN(C(=O)c1cccc(NC(=O)C2C(c3cc(Cl)c(Cl)c(Cl)c3)C2(Cl)Cl)c1F)c1ccccc1]

Isolated as a light yellow foam (0.114 g, 68%).

trans-5-(3-(4-Bromo-3,5-dichlorophenyl)-2,2-dichlorocyclopropane-1-carboxamido)-2-chloro-N-(4-fluorophenyl)benzamide (F72)

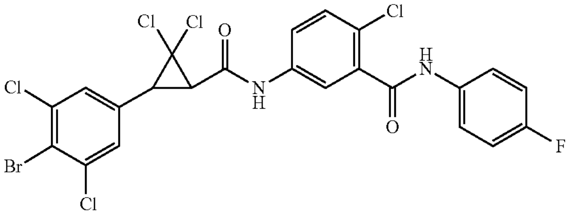 [SMILES: O=C(Nc1ccc(F)cc1)c1cc(NC(=O)C2C(c3cc(Cl)c(Br)c(Cl)c3)C2(Cl)Cl)ccc1Cl]

Isolated as a white solid (0.030 g, 22%).

trans-2-Chloro-5-(2,2-dichloro-3-(2,4,5-trichlorophenyl)cyclopropane-1-carboxamido)-N-(4-fluorophenyl)benzamide (F73)

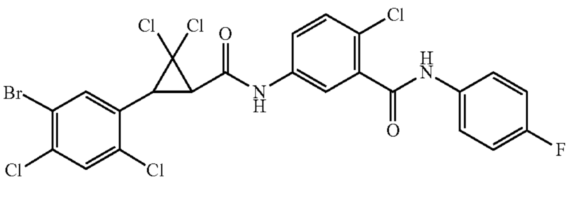 [SMILES: O=C(Nc1ccc(F)cc1)c1cc(NC(=O)C2C(c3cc(Br)c(Cl)cc3Cl)C2(Cl)Cl)ccc1Cl]

Isolated as a white solid (0.047 g, 32%).

trans-2-Chloro-5-(2,2-dichloro-3-(2,4,5-trichlorophenyl)cyclopropane-1-carboxamido)-N-(4-fluorophenyl)-N-methylbenzamide (F74)

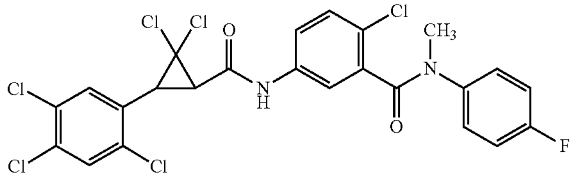 [SMILES: CN(C(=O)c1cc(NC(=O)C2C(c3cc(Cl)c(Cl)cc3Cl)C2(Cl)Cl)ccc1Cl)c1ccc(F)cc1]

Isolated as a white solid (0.109 g, 73%).

trans-5-(2,2-Dichloro-3-(3,4,5-trichlorophenyl)cyclopropane-1-carboxamido)-N-(2,4-difluorophenyl)-2-fluorobenzamide (F75)

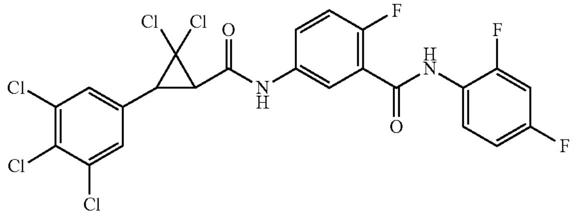 [SMILES: O=C(Nc1ccc(F)cc1F)c1cc(NC(=O)C2C(c3cc(Cl)c(Cl)c(Cl)c3)C2(Cl)Cl)ccc1F]

Isolated as a white solid (0.098 g, 56%).

trans-2-Chloro-5-(2,2-dichloro-3-(3,5-dichlorophenyl)cyclopropane-1-carboxamido)-N-(5-fluoropyridin-2-yl)benzamide (F76)

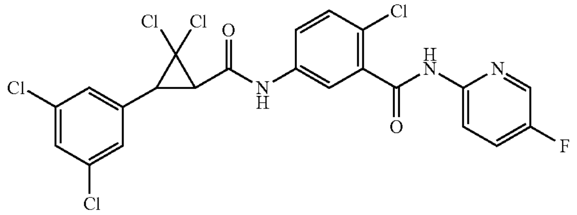 [SMILES: O=C(Nc1ccc(F)cn1)c1cc(NC(=O)C2C(c3cc(Cl)cc(Cl)c3)C2(Cl)Cl)ccc1Cl]

Isolate as a white solid (0.029 g, 23%).

trans-5-(2-Chloro-5-(2,2-dichloro-3-(3,5-dichlorophenyl)cyclopropane-1-carboxamido)benzamido)-N-methylpicolinamide (F77)

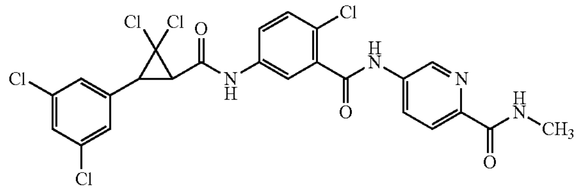 [SMILES: CNC(=O)c1ccc(NC(=O)c2cc(NC(=O)C3C(c4cc(Cl)cc(Cl)c4)C3(Cl)Cl)ccc2Cl)cn1]

Isolated as a white solid (0.039 g, 25%).

trans-2-Chloro-5-(2,2-dichloro-3-(3,5-dichlorophenyl)cyclopropane-1-carboxamido)-N-(pyridin-2-yl)benzamide (F78)

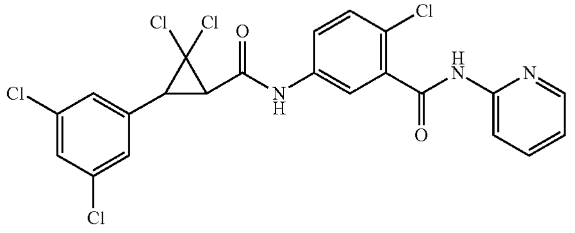 [SMILES: O=C(Nc1ccccn1)c1cc(NC(=O)C2C(c3cc(Cl)cc(Cl)c3)C2(Cl)Cl)ccc1Cl]

Isolated as a white solid (0.071 g, 51%).

trans-2-Chloro-5-(2,2-dichloro-3-(3-chloro-4-(trifluoromethoxy)phenyl)cyclopropane-1-carboxamido)-N-(4-fluorophenyl)benzamide (F79)

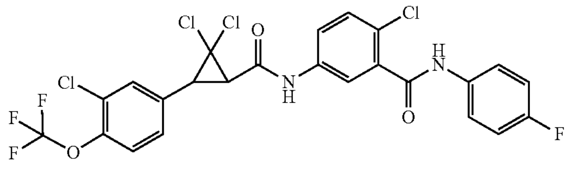 [SMILES: O=C(Nc1ccc(F)cc1)c1cc(NC(=O)C2C(c3ccc(OC(F)(F)F)c(Cl)c3)C2(Cl)Cl)ccc1Cl]

Isolated as a white solid (0.082 g, 57%).

trans-2-Chloro-5-(2,2-dichloro-3-(3-chloro-4-(trifluoromethoxy)phenyl)cyclopropane-1-carboxamido)-N-(4-fluorophenyl)-N-methylbenzamide (F80)

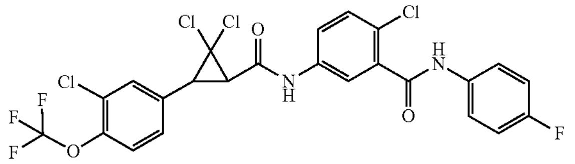 [SMILES: O=C(Nc1ccc(F)cc1)c1cc(NC(=O)C2C(c3ccc(OC(F)(F)F)c(Cl)c3)C2(Cl)Cl)ccc1Cl]

Isolated as a white solid (0.111 g, 75%).

trans-2-Chloro-5-(2,2-dichloro-3-(4-(trifluoromethyl)phenyl)cyclopropane-1-carboxamido)-N-(4-fluorophenyl)benzamide (F81)

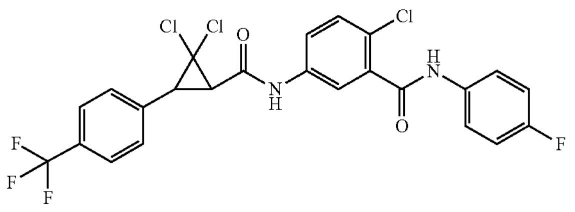 [SMILES: O=C(Nc1ccc(F)cc1)c1cc(NC(=O)C2C(c3ccc(C(F)(F)F)cc3)C2(Cl)Cl)ccc1Cl]

Isolated as a white solid (0.123 g, 80%).

trans-2-Chloro-5-(2,2-dichloro-3-(4-(trifluoromethyl)phenyl)cyclopropane-1-carboxamido)-N-(4-fluorophenyl)-N-methylbenzamide (F82)

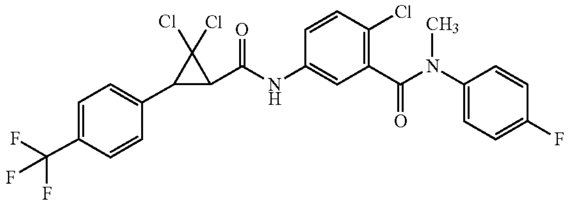 [SMILES: CN(C(=O)c1cc(NC(=O)C2C(c3ccc(C(F)(F)F)cc3)C2(Cl)Cl)ccc1Cl)c1ccc(F)cc1]

Isolated as a white solid (0.130 g, 82%).

trans-2-Chloro-5-(2,2-dichloro-3-(4-(trifluoromethyl)phenyl)cyclopropane-1-carboxamido)-N-(2,6-difluorophenyl)benzamide (F83)

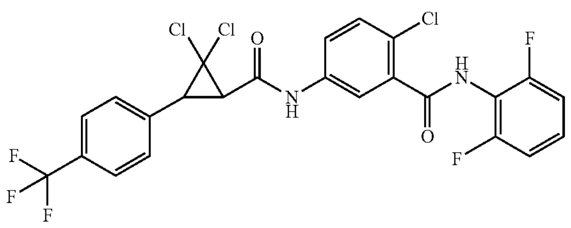 [SMILES: O=C(Nc1c(F)cccc1F)c1cc(NC(=O)C2C(c3ccc(C(F)(F)F)cc3)C2(Cl)Cl)ccc1Cl]

Isolated as a white solid (0.082 g, 52%).

trans-5-(3-(3,5-Bis(trifluoromethyl)phenyl)-2,2-dichlorocyclopropane-1-carboxamido)-2-chloro-N-(4-fluorophenyl)benzamide (F84)

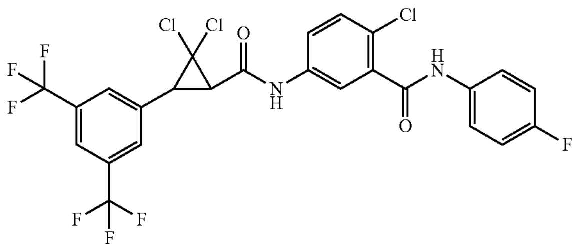 [SMILES: O=C(Nc1ccc(F)cc1)c1cc(NC(=O)C2C(c3cc(C(F)(F)F)cc(C(F)(F)F)c3)C2(Cl)Cl)ccc1Cl]

Isolated as a white solid (0.042 g, 30%).

trans-5-(3-(3,5-Bis(trifluoromethyl)phenyl)-2,2-dichlorocyclopropane-1-carboxamido)-2-chloro-N-(4-fluorophenyl)-N-methylbenzamide (F85)

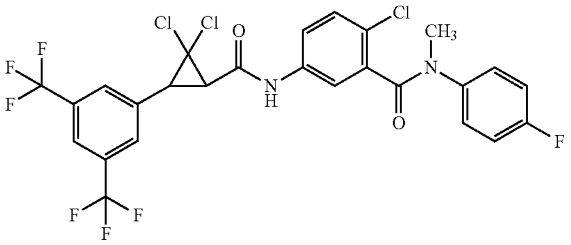 [SMILES: CN(C(=O)c1cc(NC(=O)C2C(c3cc(C(F)(F)F)cc(C(F)(F)F)c3)C2(Cl)Cl)ccc1Cl)c1ccc(F)cc1]

Isolated as a white solid (0.092 g, 64%).

trans-5-(3-(3,5-Bis(trifluoromethyl)phenyl)-2,2-dichlorocyclopropane-1-carboxamido)-2-chloro-N-(2,6-difluorophenyl)benzamide (F86)

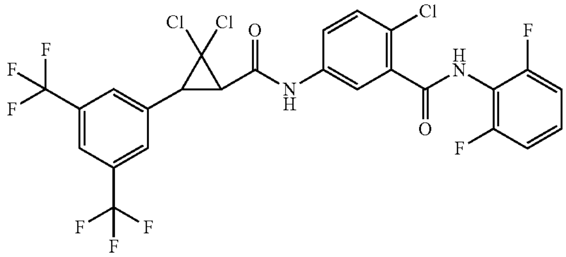 [SMILES: O=C(Nc1c(F)cccc1F)c1cc(NC(=O)C2C(c3cc(C(F)(F)F)cc(C(F)(F)F)c3)C2(Cl)Cl)ccc1Cl]

Isolated as a white solid (0.038 g, 26%).

trans-2-Chloro-5-(2,2-dichloro-3-(3-chloro-5-(trifluoromethyl)phenyl)cyclopropane-1-carboxamido)-N-(4-fluorophenyl)benzamide (F87)

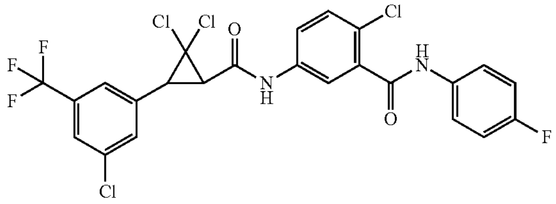 [SMILES: O=C(Nc1ccc(F)cc1)c1cc(NC(=O)C2C(c3cc(Cl)cc(C(F)(F)F)c3)C2(Cl)Cl)ccc1Cl]

Isolated as a white solid (0.055 g, 38%).

trans-2-Chloro-5-(2,2-dichloro-3-(3-chloro-5-(trifluoromethyl)phenyl)cyclopropane-1-carboxamido)-N-(4-fluorophenyl)-N-methylbenzamide (F88)

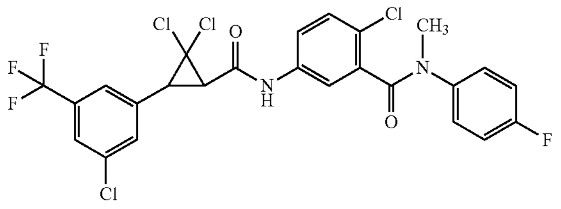 [SMILES: CN(C(=O)c1cc(NC(=O)C2C(c3cc(Cl)cc(C(F)(F)F)c3)C2(Cl)Cl)ccc1Cl)c1ccc(F)cc1]

Isolated as a white solid (0.095 g, 63%).

trans-2-Chloro-5-(2,2-dichloro-3-(3-chloro-5-(trifluoromethyl)phenyl)cyclopropane-1-carboxamido)-N-(2,6-difluorophenyl)benzamide (F89)

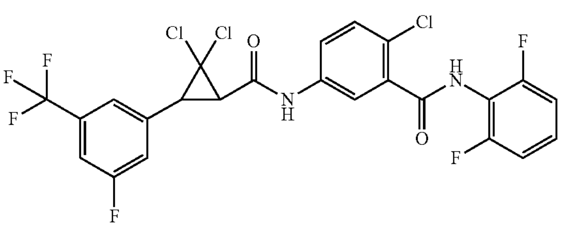 [SMILES: O=C(Nc1c(F)cccc1F)c1cc(NC(=O)C2C(c3cc(F)cc(C(F)(F)F)c3)C2(Cl)Cl)ccc1Cl]

Isolated as a white solid (0.032 g, 21%).

trans-2-Chloro-5-(2,2-dichloro-3-(3,5-dibromophenyl)cyclopropane-1-carboxamido)-N-(4-fluorophenyl)benzamide (F90)

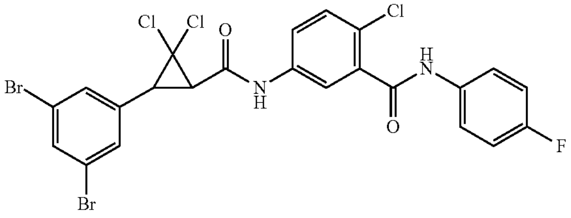

Isolated as a white solid (0.023 g, 16%).

trans-2-Chloro-5-(2,2-dichloro-3-(3,5-dibromophenyl)cyclopropane-1-carboxamido)-N-(4-fluorophenyl)-N-methylbenzamide (F91)

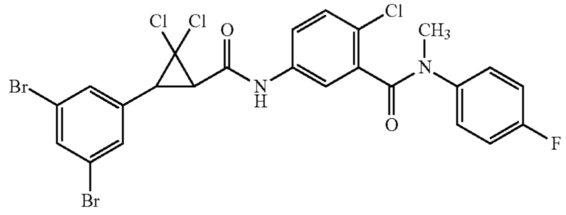

Isolated as a white solid (0.066 g, 47%).

trans-2-Chloro-5-(2,2-dichloro-3-(3,5-dibromophenyl)cyclopropane-1-carboxamido)-N-(2,6-difluorophenyl)benzamide (F92)

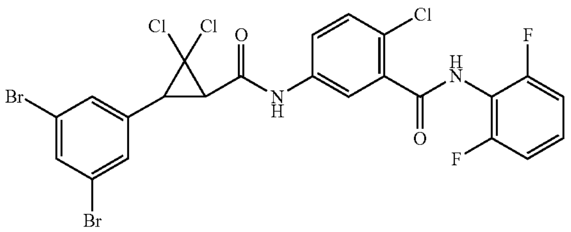

Isolated as a white solid (0.020 g, 14%).

trans-N-(4-Cyano-2-fluorophenyl)-5-(2,2-dichloro-3-(3,5-dichlorophenyl)cyclopropane-1-carboxamido)-2-fluorobenzamide (F93)

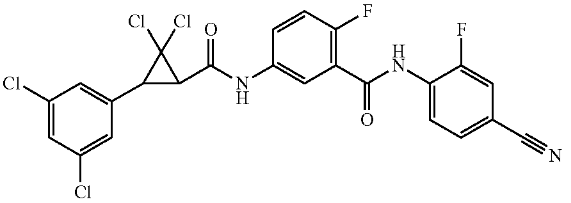

Isolated as a white solid (0.108 g, 78%).

trans-N-(4-Cyano-2-fluorophenyl)-5-(2,2-dichloro-3-(3,4-dichlorophenyl)cyclopropane-1-carboxamido)-2-fluorobenzamide (F94)

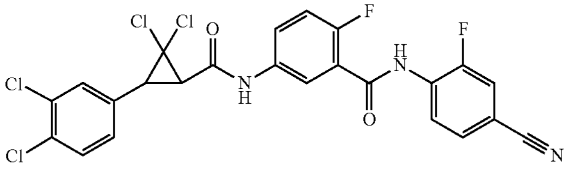 [SMILES: N#Cc1ccc(NC(=O)c2cc(NC(=O)C3C(c4ccc(Cl)c(Cl)c4)C3(Cl)Cl)ccc2F)c(F)c1]

Isolated as a white solid (0.122 g, 88%).

trans-N-(4-Cyano-2-fluorophenyl)-5-(2,2-dichloro-3-(3,4,5-trichlorophenyl)cyclopropane-1-carboxamido)-2-fluorobenzamide (F95)

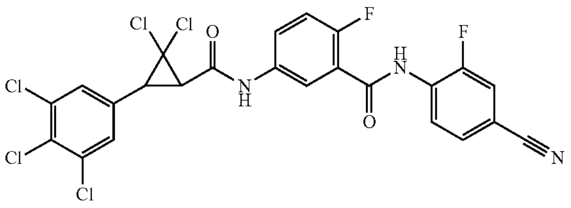 [SMILES: N#Cc1ccc(NC(=O)c2cc(NC(=O)C3C(c4cc(Cl)c(Cl)c(Cl)c4)C3(Cl)Cl)ccc2F)c(F)c1]

Isolated as a white solid (0.013 g, 10%).

trans-2-Chloro-5-(2,2-dichloro-3-(3,5-dichloro-4-fluorophenyl)cyclopropane-1-carboxamido)-N-(4-fluorophenyl)benzamide (F96)

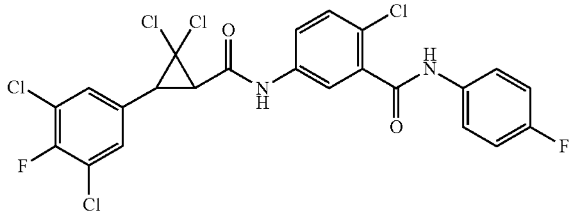 [SMILES: O=C(Nc1ccc(F)cc1)c1cc(NC(=O)C2C(c3cc(Cl)c(F)c(Cl)c3)C2(Cl)Cl)ccc1Cl]

Isolated as a white solid (0.017 g, 11%).

trans-2-Chloro-5-(2,2-dichloro-3-(3,5-dichloro-4-fluorophenyl)cyclopropane-1-carboxamido)-N-(4-fluorophenyl)-N-methylbenzamide (F97)

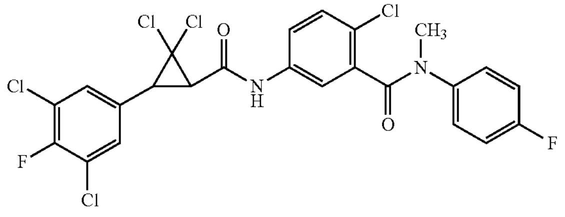 [SMILES: CN(C(=O)c1cc(NC(=O)C2C(c3cc(Cl)c(F)c(Cl)c3)C2(Cl)Cl)ccc1Cl)c1ccc(F)cc1]

Isolated as a white solid (0.063 g, 41%).

trans-2-Chloro-5-(2,2-dichloro-3-(3,5-dichloro-4-fluorophenyl)cyclopropane-1-carboxamido)-N-(2,6-difluorophenyl)benzamide (F98)

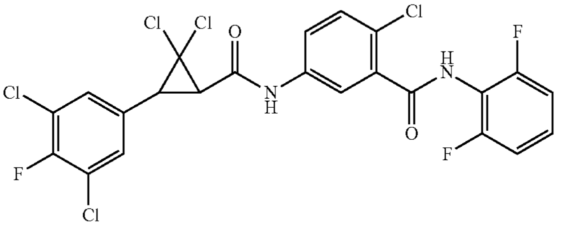 [SMILES: O=C(Nc1c(F)cccc1F)c1cc(NC(=O)C2C(c3cc(Cl)c(F)c(Cl)c3)C2(Cl)Cl)ccc1Cl]

Isolated as a white solid (0.025 g, 16%).

trans-2-Chloro-5-(2,2-dichloro-3-(3,5-dichlorophenyl)cyclopropane-1-carboxamido)-N-ethyl-N-(4-fluorophenyl)benzamide (F99)

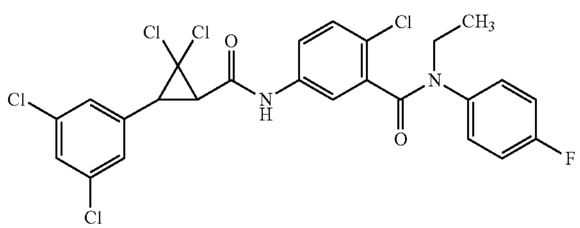 [SMILES: CCN(C(=O)c1cc(NC(=O)C2C(c3cc(Cl)cc(Cl)c3)C2(Cl)Cl)ccc1Cl)c1ccc(F)cc1]

Isolated as a white solid (0.087 g, 60%).

trans-2-Chloro-5-(2,2-dichloro-3-(3,5-dichlorophenyl)cyclopropane-1-carboxamido)-N-(4-fluorophenyl)-N-(2,2,2-trifluoroethyl)benzamide (F100)

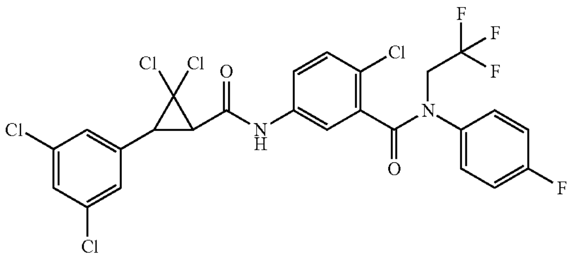 [SMILES: O=C(Nc1ccc(Cl)c(C(=O)N(CC(F)(F)F)c2ccc(F)cc2)c1)C1C(c2cc(Cl)cc(Cl)c2)C1(Cl)Cl]

Isolated as a white solid (0.095 g, 60%).

trans-2-Chloro-5-(2,2-dichloro-3-(3,5-dichlorophenyl)cyclopropane-1-carboxamido)-N-(4-fluorophenyl)-N-propylbenzamide (F101)

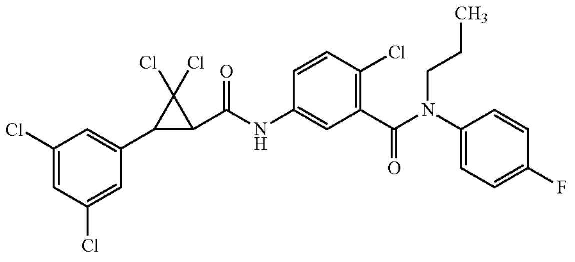 [SMILES: CCCN(C(=O)c1cc(NC(=O)C2C(c3cc(Cl)cc(Cl)c3)C2(Cl)Cl)ccc1Cl)c1ccc(F)cc1]

Isolated as a yellow foam (0.090 g, 61%).

trans-N-Allyl-2-chloro-5-(2,2-dichloro-3-(3,5-dichlorophenyl)cyclopropane-1-carboxamido)-N-(4-fluorophenyl)benzamide (F102)

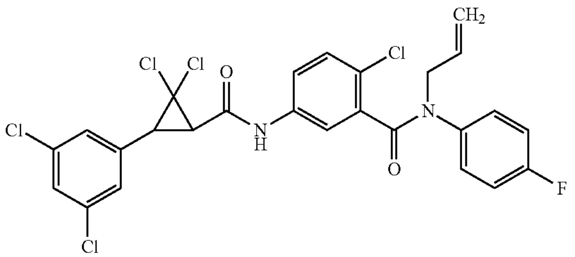 [SMILES: C=CCN(C(=O)c1cc(NC(=O)C2C(c3cc(Cl)cc(Cl)c3)C2(Cl)Cl)ccc1Cl)c1ccc(F)cc1]

Isolated as an orange foam (0.047 g, 32%).

trans-2-chloro-N-(4-cyano-2-fluorophenyl)-5-(2,2-dichloro-3-(3,4-dichlorophenyl)cyclopropane-1-carboxamido)benzamide (F103)

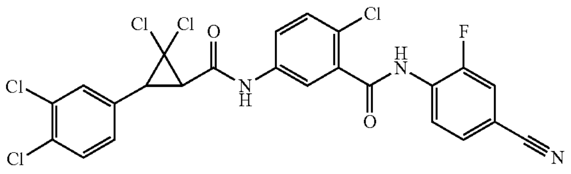

Isolated as a colorless oil (0.032 g, 22%).

trans-2-Chloro-N-(4-cyano-2-fluorophenyl)-5-(2,2-dichloro-3-(3,4,5-trichlorophenyl)cyclopropane-1-carboxamido)benzamide (F104)

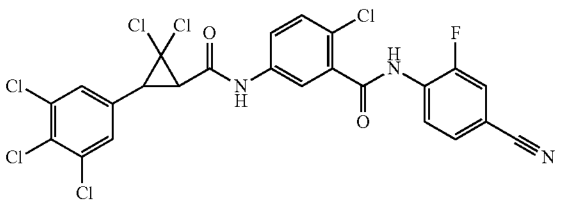

Isolated as a white foam (0.016 g, 11%).

trans-N-(4-Cyano-2-fluorophenyl)-5-(2,2-dichloro-3-(3,4,5-trichlorophenyl)cyclopropane-1-carboxamido)-2-fluoro-N-methylbenzamide (F105)

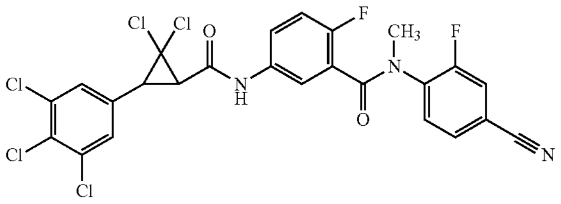 [SMILES: CN(C(=O)c1cc(NC(=O)C2C(c3cc(Cl)c(Cl)c(Cl)c3)C2(Cl)Cl)ccc1F)c1ccc(C#N)cc1F]

Isolated as a white foam (0.020 g, 20%).

trans-2-Chloro-N-(4-cyano-2-fluorophenyl)-5-(2,2-dichloro-3-(3,5-dichlorophenyl)cyclopropane-1-carboxamido)-N-methylbenzamide (F106)

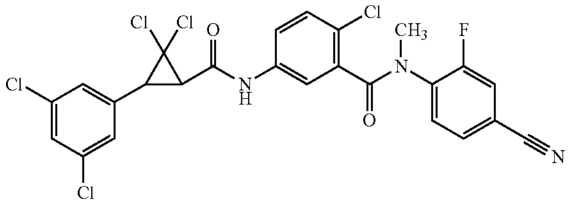 [SMILES: CN(C(=O)c1cc(NC(=O)C2C(c3cc(Cl)cc(Cl)c3)C2(Cl)Cl)ccc1Cl)c1ccc(C#N)cc1F]

Isolated as a colorless oil (0.041 g, 28%).

trans-2-Chloro-N-(4-cyano-2-fluorophenyl)-5-(2,2-dichloro-3-(3,4-dichlorophenyl)cyclopropane-1-carboxamido)-N-methylbenzamide (F107)

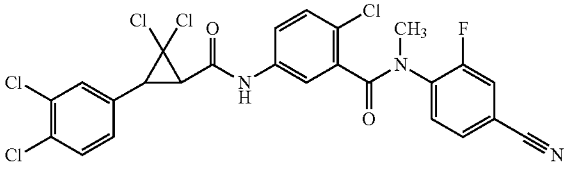 [SMILES: CN(C(=O)c1cc(NC(=O)C2C(c3ccc(Cl)c(Cl)c3)C2(Cl)Cl)ccc1Cl)c1ccc(C#N)cc1F]

Isolated as a white foam (0.034 g, 23%).

trans-2-Chloro-N-(4-cyano-2-fluorophenyl)-5-(2,2-dichloro-3-(3,4,5-trichlorophenyl)cyclopropane-1-carboxamido)-N-methylbenzamide (F108)

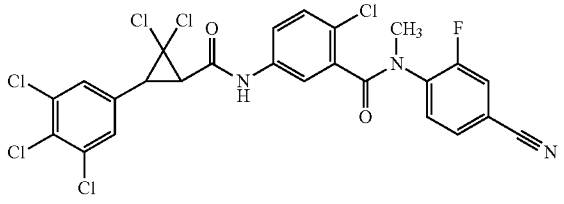

Isolated as a colorless oil (0.039 g, 25%).

trans-2-Chloro-5-(2,2-dichloro-3-phenylcyclopropane-1-carboxamido)-N-(4-fluorophenyl)benzamide (F109)

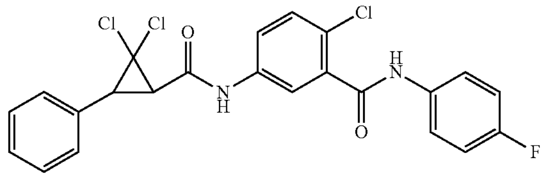 [SMILES: O=C(Nc1ccc(F)cc1)c1cc(NC(=O)C2C(c3ccccc3)C2(Cl)Cl)ccc1Cl]

Isolated as a yellow film (0.011 g, 6%).

trans-2-Chloro-5-(2,2-dichloro-3-phenylcyclopropane-1-carboxamido)-N-(4-fluorophenyl)-N-methylbenzamide (F110)

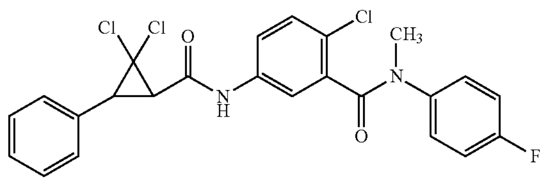 [SMILES: CN(C(=O)c1cc(NC(=O)C2C(c3ccccc3)C2(Cl)Cl)ccc1Cl)c1ccc(F)cc1]

Isolated as a yellow solid (0.044 g, 25%).

trans-2-Chloro-5-(2,2-dichloro-3-phenylcyclopropane-1-carboxamido)-N-(2,6-difluorophenyl)benzamide (F111)

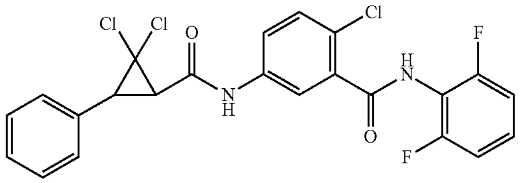 [SMILES: O=C(Nc1c(F)cccc1F)c1cc(NC(=O)C2C(c3ccccc3)C2(Cl)Cl)ccc1Cl]

Isolated as a yellow film (0.011 g, 6%).

trans-2,2-Dichloro-N-(4-chloro-3-((4-fluorophenyl)(methyl)carbamothioyl)phenyl)-3-(3,5-dichlorophenyl)cyclopropane-1-carboxamide (F112)

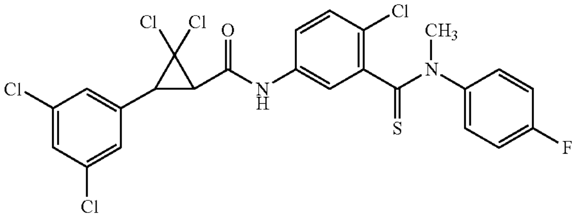

Isolated as a yellow solid (0.024 g, 25%).

trans-2,2-Dichloro-N-(4-chloro-3-((4-fluorophenyl)carbamothioyl)phenyl)-3-(3,5-dichlorophenyl)cyclopropane-1-carboxamide (F113)

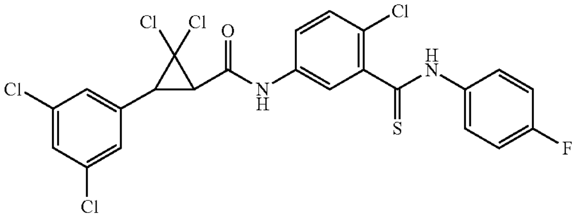

Isolated as a yellow solid (0.027 g, 13%).

trans-N-(4-Cyano-2-fluorophenyl)-5-(2,2-dichloro-3-(3,5-dichlorophenyl)cyclopropane-1-carboxamido)-2-fluoro-N-methylbenzamide (F114)

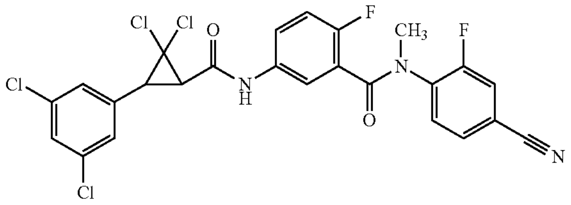 [SMILES: CN(C(=O)c1cc(NC(=O)C2C(c3cc(Cl)cc(Cl)c3)C2(Cl)Cl)ccc1F)c1ccc(C#N)cc1F]

Isolated as a colorless glass (0.004 g, 4%).

trans-5-(2,2-Dichloro-3-(3,5-dichlorophenyl)cyclopropane-1-carboxamido)-N-(4-fluorophenyl)-2-(methylthio)benzamide (F115)

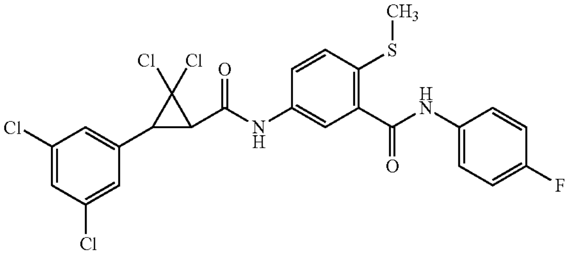

Isolated as a white solid (0.173 g, 28%).

trans-2-Chloro-5-(2,2-dichloro-3-(3-chloro-5-methylphenyl)cyclopropane-1-carboxamido)-N-(4-fluorophenyl)benzamide (F116)

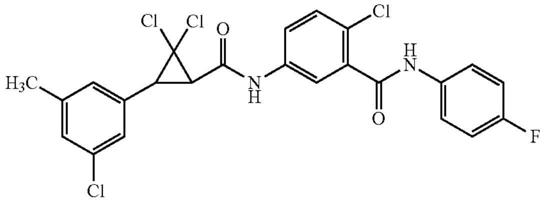 [SMILES: Cc1cc(Cl)cc(C2C(C(=O)Nc3ccc(Cl)c(C(=O)Nc4ccc(F)cc4)c3)C2(Cl)Cl)c1]

Isolated as a white solid (0.083 g, 59%).

trans-2-Chloro-5-(2,2-dichloro-3-(3-chloro-5-methylphenyl)cyclopropane-1-carboxamido)-N-(4-fluorophenyl)-N-methylbenzamide (F117)

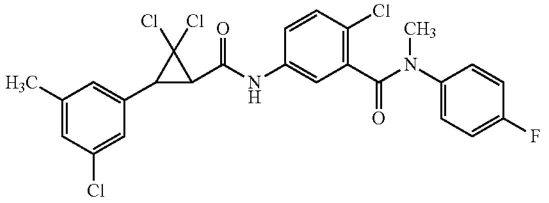 [SMILES: Cc1cc(Cl)cc(C2C(C(=O)Nc3ccc(Cl)c(C(=O)N(C)c4ccc(F)cc4)c3)C2(Cl)Cl)c1]

Isolated as a white foam (0.100 g, 69%).

trans-2-Chloro-5-(2,2-dichloro-3-(3-chloro-5-methylphenyl)cyclopropane-1-carboxamido)-N-(2,6-difluorophenyl)benzamide (F118)

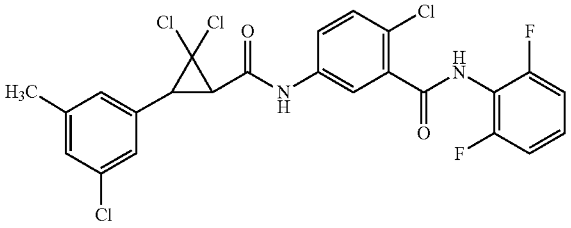 [SMILES: Cc1cc(Cl)cc(C2C(C(=O)Nc3ccc(Cl)c(C(=O)Nc4c(F)cccc4F)c3)C2(Cl)Cl)c1]

Isolated as a white foam (0.066 g, 45%).

trans-2-Chloro-5-(2,2-dichloro-3-(3,5-dichloro-4-methylphenyl)cyclopropane-1-carboxamido)-N-(4-fluorophenyl)benzamide (F119)

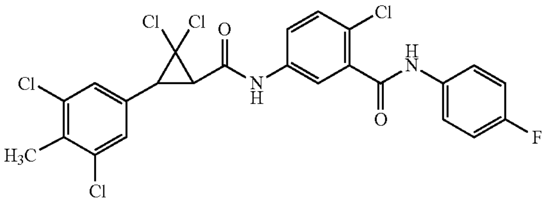 [SMILES: Cc1c(Cl)cc(C2C(C(=O)Nc3ccc(Cl)c(C(=O)Nc4ccc(F)cc4)c3)C2(Cl)Cl)cc1Cl]

Isolated as a white foam (0.028 g, 21%).

trans-2-Chloro-5-(2,2-dichloro-3-(3,5-dichloro-4-methylphenyl)cyclopropane-1-carboxamido)-N-(4-fluorophenyl)-N-methylbenzamide (F120)

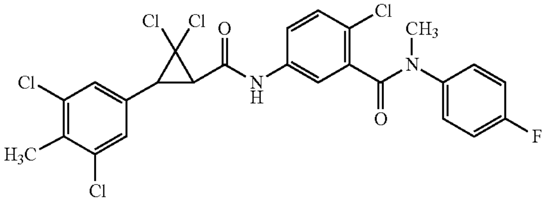 [SMILES: Cc1c(Cl)cc(C2C(C(=O)Nc3ccc(Cl)c(C(=O)N(C)c4ccc(F)cc4)c3)C2(Cl)Cl)cc1Cl]

Isolated as a white solid (0.077 g, 56%).

trans-2-Chloro-5-(2,2-dichloro-3-(3,5-dichloro-4-methylphenyl)cyclopropane-1-carboxamido)-N-(2,6-difluorophenyl)benzamide (F121)

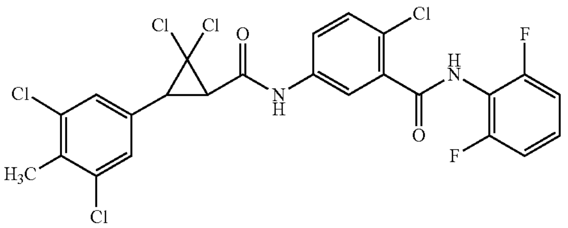 [SMILES: Cc1c(Cl)cc(C2C(C(=O)Nc3ccc(Cl)c(C(=O)Nc4c(F)cccc4F)c3)C2(Cl)Cl)cc1Cl]

Isolated as a white foam (0.025 g, 18%).

trans-2-Chloro-5-(2,2-dibromo-3-(3,5-dichlorophenyl)cyclopropane-1-carboxamido)-N-(4-fluorophenyl)benzamide (F122)

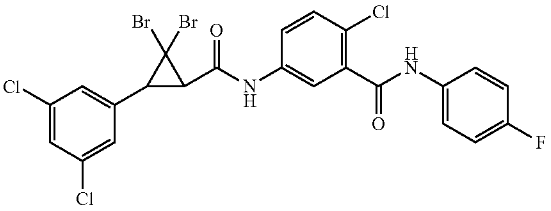

Isolated as an off-white solid (0.075 g, 45%).

trans-2-Chloro-5-(2,2-dichloro-3-(3,4-dichloro-5-methylphenyl)cyclopropane-1-carboxamido)-N-(4-fluorophenyl)benzamide (F123)

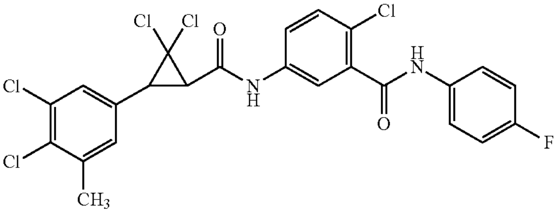 [SMILES: Cc1cc(C2C(C(=O)Nc3ccc(Cl)c(C(=O)Nc4ccc(F)cc4)c3)C2(Cl)Cl)cc(Cl)c1Cl]

Isolated as a white foam (0.102 g, 76%).

trans-2-Chloro-5-(2,2-dichloro-3-(3,4-dichloro-5-methylphenyl)cyclopropane-1-carboxamido)-N-(4-fluorophenyl)-N-methylbenzamide (F124)

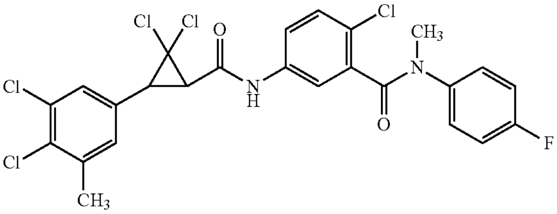

Isolated as a white foam (0.071 g, 52%).

trans-2-Chloro-5-(2,2-dichloro-3-(3,4-dichloro-5-methylphenyl)cyclopropane-1-carboxamido)-N-(2,6-difluorophenyl)benzamide (F125)

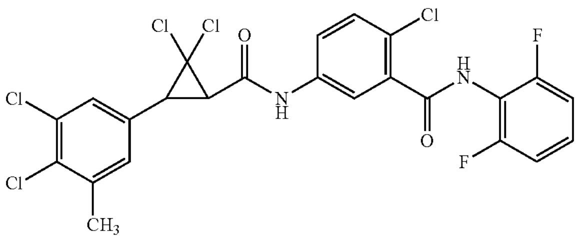 [SMILES: Cc1cc(C2C(C(=O)Nc3ccc(Cl)c(C(=O)Nc4c(F)cccc4F)c3)C2(Cl)Cl)cc(Cl)c1Cl]

Isolated as a white foam (0.094 g, 68%).

Example 14: Preparation of trans-4-(2,2-dichloro-3-(3,5-dichlorophenyl)cyclopropane-1-carboxamido)-N-(4-fluorophenyl)picolinamide (F126)

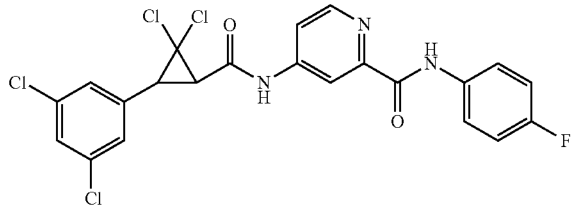

To a solution of trans-2,2-dichloro-3-(3,5-dichlorophenyl) cyclopropanecarboxylic acid (C1) (0.100 g, 0.333 mmol) in dichloromethane (3.33 mL) at 0° C. was added N,N-dimethylformamide (1 drop) and oxalyl chloride (0.0440 mL, 0.500 mmol) dropwise. The cold bath was removed and the reaction was stirred at room temperature for 1 hour. The reaction was again cooled to 0° C., and N-methylmorpholine (0.110 mL, 1.000 mmol) followed by 4-amino-N-(4-fluorophenyl)picolinamide (C81) (0.154 g, 0.667 mmol) were added. The reaction was stirred at room temperature for 1 hour. The reaction was diluted with dichloromethane, washed with saturated aqueous sodium bicarbonate (2×), and washed with hydrochloric acid (1 N) (2×). The organic phase was dried over magnesium sulfate, filtered, and concentrated. Purification by flash column chromatography using 0-100% ethyl acetate/hexanes as eluent provided the title compound as a glassy clear solid (0.0800 g, 44%).

The following compounds were prepared in like manner to the procedure outlined in Example 14:

trans-2-Chloro-3-(2,2-dichloro-3-(3,5-dichlorophenyl)cyclopropane-1-carboxamido)-N-(4-fluorophenyl)benzamide (F127)

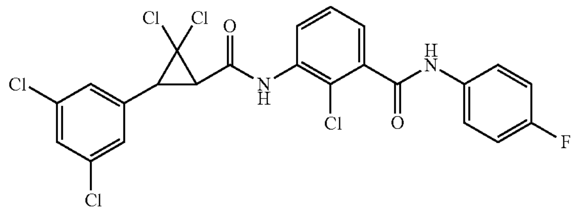

Isolated as a white solid (0.102 g, 67%).

trans-5-(2,2-Dichloro-3-(3,5-dichlorophenyl)cyclopropane-1-carboxamido)-N-(4-fluorophenyl)-2-methoxybenzamide (F128)

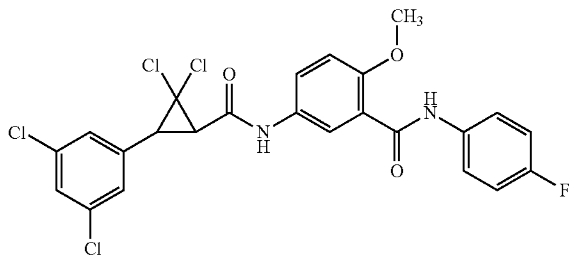

Isolated as a white solid (0.040 g, 26%).

trans-5-(2,2-Dichloro-3-(3,5-dichlorophenyl)cyclopropane-1-carboxamido)-2-fluoro-N-(4-fluorophenyl)benzamide (F129)

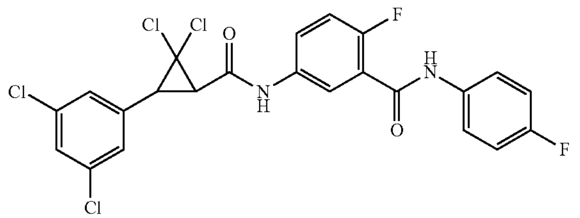

Isolated as a white solid (0.081 g, 58%).

trans-4-Chloro-3-(2,2-dichloro-3-(3,5-dichlorophenyl)cyclopropane-1-carboxamido)-N-(4-fluorophenyl)benzamide (F130)

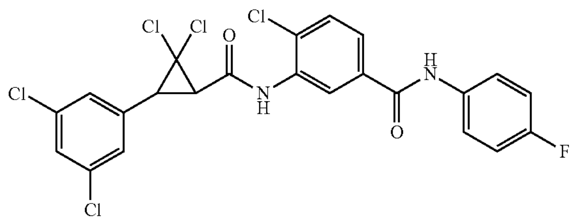

Isolated as an off-white solid (0.099 g, 65%).

trans-3-Chloro-6-(2,2-dichloro-3-(3,5-dichlorophenyl)cyclopropane-1-carboxamido)-N-(4-fluorophenyl)picolinamide (F131)

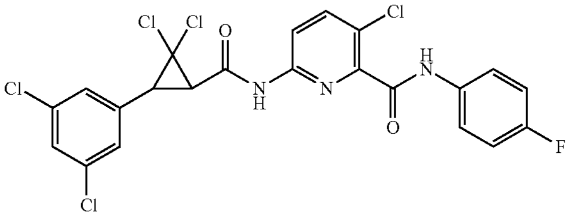 [SMILES: O=C(Nc1ccc(F)cc1)c1cc(NC(=O)C2C(c3cc(Cl)cc(Cl)c3)C2(Cl)Cl)ccc1F]

Isolated as a faint yellow solid (0.116 g, 75%).

trans-2-Cyano-5-(2,2-dichloro-3-(3,5-dichlorophenyl)cyclopropane-1-carboxamido)-N-(4-fluorophenyl)benzamide (F132)

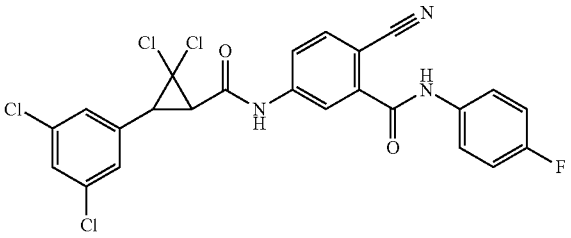 [SMILES: N#Cc1ccc(NC(=O)C2C(c3cc(Cl)cc(Cl)c3)C2(Cl)Cl)cc1C(=O)Nc1ccc(F)cc1]

Isolated as a yellow film (0.043 g, 38%).

trans-6-(2,2-Dichloro-3-(3,5-dichlorophenyl)cyclopropane-1-carboxamido)-N-(4-fluorophenyl)picolinamide (F133)

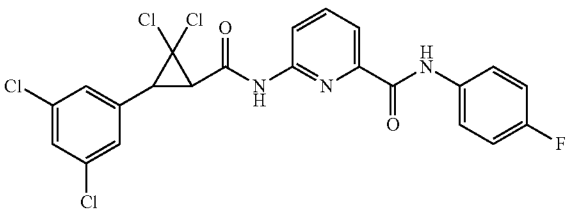 [SMILES: O=C(Nc1ccc(F)cc1)c1cccc(NC(=O)C2C(c3cc(Cl)cc(Cl)c3)C2(Cl)Cl)n1]

Isolated as a clear glassy solid (0.033 g, 40%).

trans-3-(2,2-Dichloro-3-(3,5-dichlorophenyl)cyclopropane-1-carboxamido)-N-(4-fluorophenyl)-4-methylbenzamide (F134)

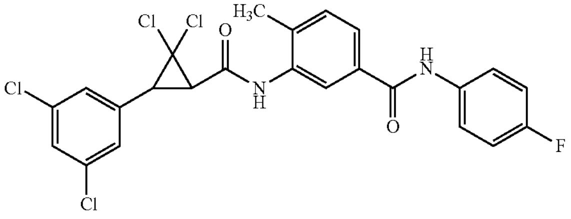 [SMILES: Cc1ccc(C(=O)Nc2ccc(F)cc2)cc1NC(=O)C1C(c2cc(Cl)cc(Cl)c2)C1(Cl)Cl]

Isolated as an off-white solid (0.039 g, 35%).

trans-5-(2,2-Dichloro-3-(3,5-dichlorophenyl)cyclopropane-1-carboxamido)-N-(4-fluorophenyl)-2-(trifluoromethoxy)benzamide (F135)

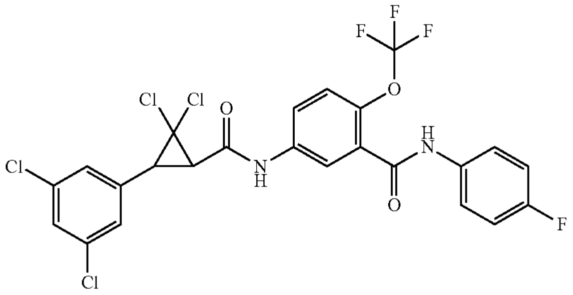 [SMILES: O=C(Nc1ccc(F)cc1)c1cc(NC(=O)C2C(c3cc(Cl)cc(Cl)c3)C2(Cl)Cl)ccc1OC(F)(F)F]

Isolated as a white solid (0.108 g, 65%).

trans-3-Chloro-5-(2,2-dichloro-3-(3,5-dichlorophenyl)cyclopropane-1-carboxamido)-N-(4-fluorophenyl)benzamide (F136)

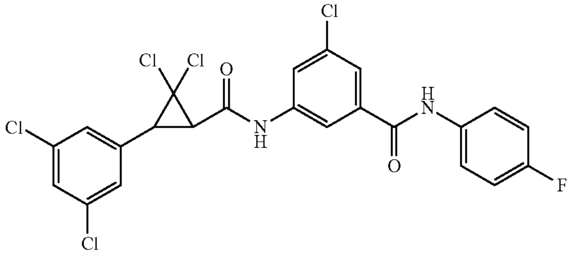 [SMILES: O=C(Nc1ccc(F)cc1)c1cc(Cl)cc(NC(=O)C2C(c3cc(Cl)cc(Cl)c3)C2(Cl)Cl)c1]

Isolated as a clear glassy solid (0.078 g, 51%).

Example 15: Preparation of trans-2-chloro-5-(2,2-dichloro-3-(3,5-dichlorophenyl)cyclopropane-1-carboxamido)-N-(4-nitrophenyl)benzamide (F137)

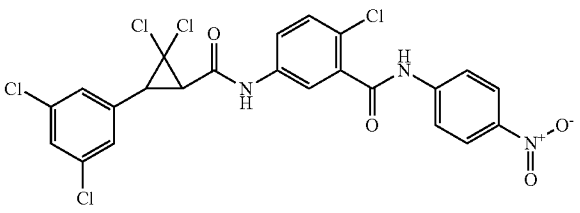 [SMILES: O=C(Nc1ccc([N+](=O)[O-])cc1)c1cc(NC(=O)C2C(c3cc(Cl)cc(Cl)c3)C2(Cl)Cl)ccc1Cl]

To a solution of 4-nitroaniline (0.0270 g, 0.198 mmol) in dichloromethane (2 mL) was added in sequence 1-ethyl-3-(3-dimethylaminopropyl)carbodiimide hydrochloride (0.0480 g, 0.248 mmol), 4-dimethylaminopyridine (0.0240 g, 0.198 mmol), and trans-2-chloro-5-(2,2-dichloro-3-(3,5-dichlorophenyl)cyclopropanecarboxamido)benzoic acid (C67) (0.0750 g, 0.165 mmol). The reaction was stirred at room temperature for 16 hours. The reaction was loaded onto Celite®, and purification by flash column chromatography using 0-25% ethyl acetate/hexanes as eluent provided the title compound as a yellow solid (0.0131 g, 14%).

The following compounds were prepared in like manner to the procedure outlined in Example 15:

trans-2-Chloro-5-(2,2-dichloro-3-(3,5-dichlorophenyl)cyclopropane-1-carboxamido)-N-(1,2,3-thiadiazol-5-yl)benzamide (F138)

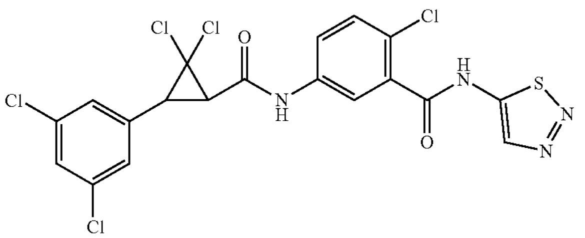 [SMILES: O=C(Nc1cnns1)c1cc(NC(=O)C2C(c3cc(Cl)cc(Cl)c3)C2(Cl)Cl)ccc1Cl]

Isolated as a white solid (0.024 g, 27%).

Example 16: Preparation of trans-3-(2-chloro-5-(2,2-dichloro-3-(3,5-dichlorophenyl)cyclopropane-1-carboxamido)benzamido)pyridine 1-oxide (F139)

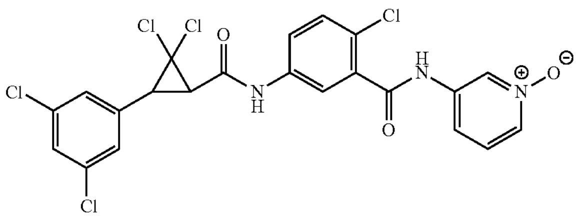 [SMILES: O=C(Nc1ccc[n+]([O-])c1)c1cc(NC(=O)C2C(c3cc(Cl)cc(Cl)c3)C2(Cl)Cl)ccc1Cl]

To a solution of trans-2-chloro-5-(2,2-dichloro-3-(3,5-dichlorophenyl)cyclopropane-1-carboxamido)-N-(pyridin-3-yl)benzamide (F27) (0.0930 g, 0.176 mmol) in dichloromethane (4 mL) was added meta-chloroperoxybenzoic acid (0.0404 g, 0.176 mmol). The reaction was stirred at room temperature for 14 hours. Celite® was added to the reaction and the solvent was concentrated. Purification by flash column chromatography using 0-10% methanol/dichloromethane as eluent provided the title compound as a white solid (0.0813 g, 85%).

The following compounds were prepared in like manner to the procedure outlined in Example 16:

trans-4-(2-Chloro-5-(2,2-dichloro-3-(3,5-dichlorophenyl)cyclopropane-1-carboxamido)benzamido) pyridine 1-oxide (F140)

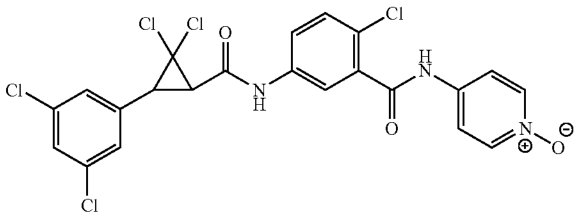 [SMILES: O=C(Nc1cc[n+]([O-])cc1)c1cc(NC(=O)C2C(c3cc(Cl)cc(Cl)c3)C2(Cl)Cl)ccc1Cl]

Isolated as a white solid (0.035 g, 34%).

trans-4-(2,2-Dichloro-3-(3,5-dichlorophenyl)cyclopropane-1-carboxamido)-2-((4-fluorophenyl)carbamoyl)pyridine 1-oxide (F141)

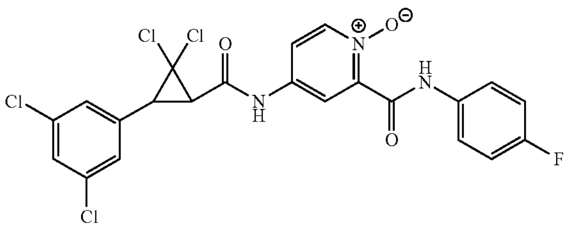 [SMILES: O=C(Nc1ccc(F)cc1)c1cc(NC(=O)C2C(c3cc(Cl)cc(Cl)c3)C2(Cl)Cl)cc[n+]1[O-]]

Isolated as a faint yellow solid (0.038 g, 58%).

Example 17: Preparation of trans-2-chloro-5-(2,2-dichloro-3-(3,5-dichlorophenyl)cyclopropane-1-carboxamido)-N-(6-fluoropyridin-3-yl)benzamide (F142)

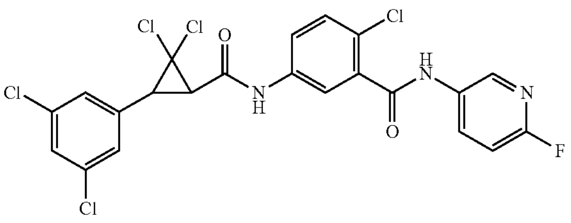 [SMILES: O=C(Nc1ccc(F)nc1)c1cc(NC(=O)C2C(c3cc(Cl)cc(Cl)c3)C2(Cl)Cl)ccc1Cl]

6-Fluoropyridin-3-amine (0.0290 g, 0.254 mmol) was dissolved in dichloromethane (2 mL). The solution was cooled in an ice bath. Triethylamine (0.0440 mL, 0.318 mmol) was added. trans-2-Chloro-5-(2,2-dichloro-3-(3,5-dichlorophenyl)cyclopropane-1-carboxamido)benzoyl chloride (C68) (0.100 g, 0.212 mmol) was dissolved in dichloromethane (2 mL), and the solution was added to the reaction mixture. The ice bath was removed and the reaction allowed to stir overnight at room temperature. The reaction was loaded onto Celite® and purified by flash column chromatography using 0-40% ethyl acetate/hexanes as eluent to afford the title compound as a white solid (0.0339 g, 29%).

The following compounds were prepared in like manner to the procedure outlined in Example 17:

trans-2-Chloro-5-(2,2-dichloro-3-(3,5-dichlorophenyl)cyclopropane-1-carboxamido)-N-(4-(methylsulfonyl)phenyl)benzamide (F143)

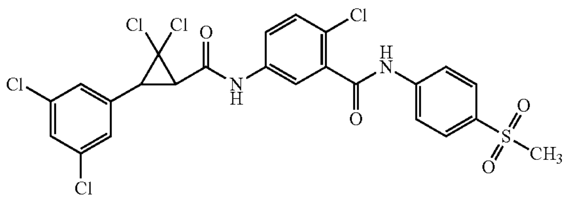 [SMILES: CS(=O)(=O)c1ccc(NC(=O)c2cc(NC(=O)C3C(c4cc(Cl)cc(Cl)c4)C3(Cl)Cl)ccc2Cl)cc1]

Isolated as a white solid (0.040 g, 30%).

trans-2-Chloro-N-(4-cyano-2-fluorophenyl)-5-(2,2-dichloro-3-(3,5-dichlorophenyl)cyclopropane-1-carboxamido)benzamide (F144)

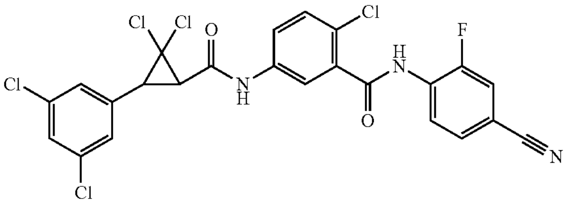 [SMILES: N#Cc1ccc(NC(=O)c2cc(NC(=O)C3C(c4cc(Cl)cc(Cl)c4)C3(Cl)Cl)ccc2Cl)c(F)c1]

Isolated as a white solid (0.028 g, 23%).

trans-2-Chloro-5-(2,2-dichloro-3-(3,5-dichlorophenyl)cyclopropane-1-carboxamido)-N-(oxazol-2-yl) benzamide (F145)

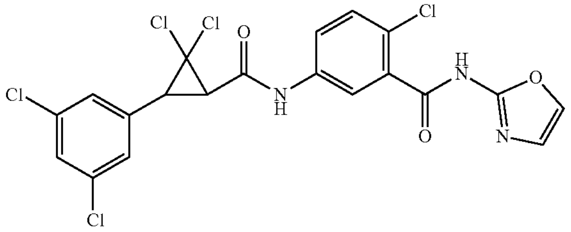 [SMILES: O=C(Nc1ncco1)c1cc(NC(=O)C2C(c3cc(Cl)cc(Cl)c3)C2(Cl)Cl)ccc1Cl]

Isolated as a light brown solid (0.021 g, 19%).

Example 18: Preparation of trans-2-chloro-5-(2,2-dichloro-3-(3,5-dichlorophenyl)cyclopropane-1-carboxamido)-N-(4-methoxyphenyl)benzamide (F146)

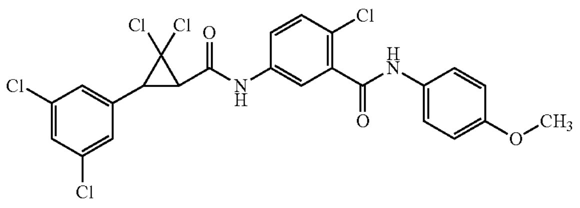 [SMILES: COc1ccc(NC(=O)c2cc(NC(=O)C3C(c4cc(Cl)cc(Cl)c4)C3(Cl)Cl)ccc2Cl)cc1]

To a solution of trans-2-chloro-5-(2,2-dichloro-3-(3,5-dichlorophenyl)cyclopropanecarboxamido)benzoic acid (C67) (0.100 g, 0.212 mmol) in dichloromethane (0.1 mL) was added N,N-dimethylformamide (one drop), and the reaction cooled in an ice bath. Oxalyl chloride (0.0438 mL, 0.254 mmol) was charged slowly over about 5 minutes. The reaction was removed the ice bath and allowed to warm to room temperature over 90 minutes. The reaction was then concentrated. The residue was re-dissolved in dichloromethane (0.1 mL). This solution was added to a cooled (ice bath) separate solution of 4-methoxyaniline (0.0310 g, 0.254 mmol) and triethylamine (0.0440 mL, 0.318 mmol) in dichloromethane (0.5 mL). The reaction was removed the ice bath and stirred at room temperature for 14 hours. The reaction was adsorbed directly onto Celite® and purified by flash column chromatography using ethyl acetate/hexanes as eluent followed by trituration with dichloromethane/hexanes to provide the title compound as a white solid (0.0666 g, 56%).

The following compounds were prepared in like manner to the procedure outlined in Example 18:

trans-2-Chloro-5-(2,2-dichloro-3-(3,5-dichlorophenyl)cyclopropane-1-carboxamido)-N-(4-(trifluoromethoxy)phenyl)benzamide (F147)

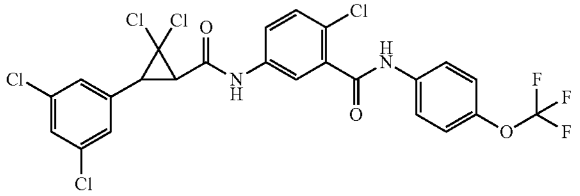 [SMILES: O=C(Nc1ccc(OC(F)(F)F)cc1)c1cc(NC(=O)C2C(c3cc(Cl)cc(Cl)c3)C2(Cl)Cl)ccc1Cl]

Isolated as a yellow solid (0.078 g, 60%).

trans-2-Chloro-5-(2,2-dichloro-3-(3,5-dichlorophenyl)cyclopropane-1-carboxamido)-N-(4-(difluoromethoxy)phenyl)benzamide (F148)

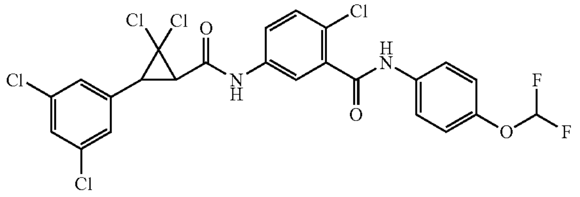 [SMILES: O=C(Nc1ccc(OC(F)F)cc1)c1cc(NC(=O)C2C(c3cc(Cl)cc(Cl)c3)C2(Cl)Cl)ccc1Cl]

Isolated as a light brown solid (0.089 g, 70%).

trans-2-Chloro-5-(2,2-dichloro-3-(3,5-dichlorophenyl)cyclopropane-1-carboxamido)-N-(4-(methylthio) phenyl)benzamide (F149)

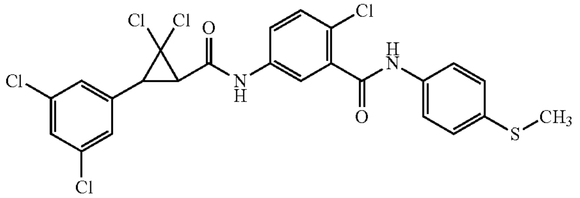 [SMILES: CSc1ccc(NC(=O)c2cc(NC(=O)C3C(c4cc(Cl)cc(Cl)c4)C3(Cl)Cl)ccc2Cl)cc1]

Isolated as a light brown solid (0.068 g, 56%).

trans-2-Chloro-5-(2,2-dichloro-3-(3,5-dichlorophenyl)cyclopropane-1-carboxamido)-N-(2-fluoro-4-methoxyphenyl)benzamide (F150)

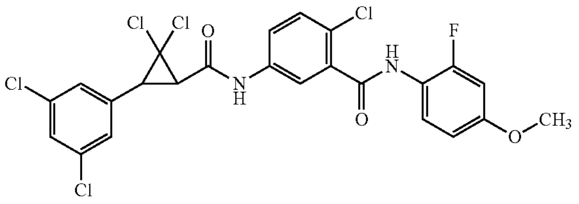 [SMILES: COc1ccc(NC(=O)c2cc(NC(=O)C3C(c4cc(Cl)cc(Cl)c4)C3(Cl)Cl)ccc2Cl)c(F)c1]

Isolated as a beige solid (0.060 g, 49%).

trans-2-Chloro-5-(2,2-dichloro-3-(3,5-dichlorophenyl)cyclopropane-1-carboxamido)-N-(2-fluoro-4-methylphenyl)benzamide (F151)

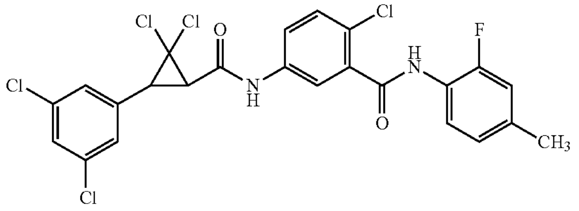

Isolated as a white solid (0.057 g, 48%).

trans-2-Chloro-5-(2,2-dichloro-3-(3,5-dichlorophenyl)cyclopropane-1-carboxamido)-N-(4-(methylcarbamoyl)phenyl)benzamide (F152)

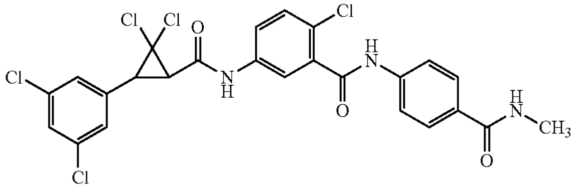 [SMILES: CNC(=O)c1ccc(NC(=O)c2cc(NC(=O)C3C(c4cc(Cl)cc(Cl)c4)C3(Cl)Cl)ccc2Cl)cc1]

Isolated as a white solid (0.062 g, 50%).

trans-N-(4-Acetamidophenyl)-2-chloro-5-(2,2-dichloro-3-(3,5-dichlorophenyl)cyclopropane-1-carboxamido)benzamide (F153)

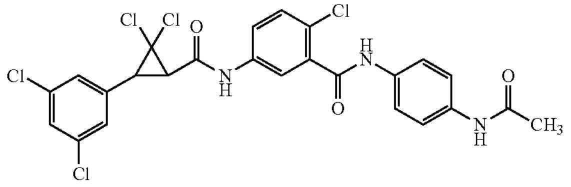 [SMILES: CC(=O)Nc1ccc(NC(=O)c2cc(NC(=O)C3C(c4cc(Cl)cc(Cl)c4)C3(Cl)Cl)ccc2Cl)cc1]

Isolated as a white solid (0.096 g, 77%).

trans-2-Chloro-5-(2,2-dichloro-3-(3,5-dichlorophenyl)cyclopropane-1-carboxamido)-N-(3,5-difluorophenyl)benzamide (F154)

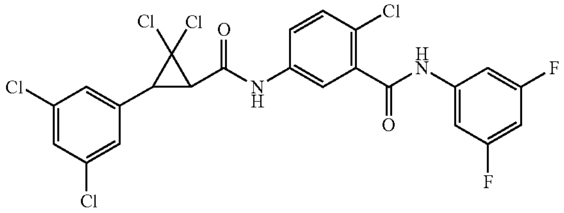 [SMILES: O=C(Nc1cc(F)cc(F)c1)c1cc(NC(=O)C2C(c3cc(Cl)cc(Cl)c3)C2(Cl)Cl)ccc1Cl]

Isolated as a white solid (0.044 g, 37%).

trans-2,2-Dichloro-N-(4-chloro-3-(5-fluoroindoline-1-carbonyl)phenyl)-3-(3,5-dichlorophenyl)cyclopropane-1-carboxamide (F155)

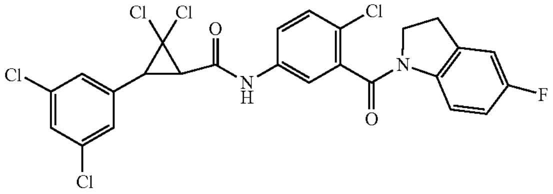 [SMILES: O=C(Nc1ccc(Cl)c(C(=O)N2CCc3cc(F)ccc32)c1)C1C(c2cc(Cl)cc(Cl)c2)C1(Cl)Cl]

Isolated as a white foam (0.052 g, 41%).

trans-2-Chloro-5-(2,2-dichloro-3-(3,5-dichlorophenyl)cyclopropane-1-carboxamido)-N-(2-fluoropyridin-3-yl)benzamide (F156)

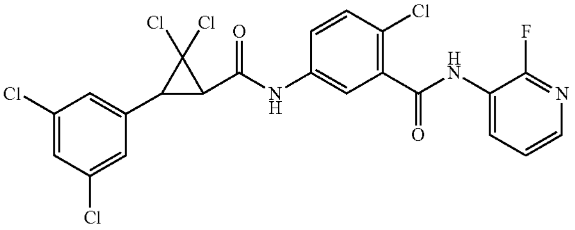 [SMILES: O=C(Nc1cccnc1F)c1cc(NC(=O)C2C(c3cc(Cl)cc(Cl)c3)C2(Cl)Cl)ccc1Cl]

Isolated as a white solid (0.058 g, 48%).

Example 19: Preparation of trans-5-(2,2-dichloro-3-(3,5-dichlorophenyl)cyclopropane-1-carboxamido)-N-(4-fluorophenyl)-2-(methylsulfonyl)benzamide (F157)

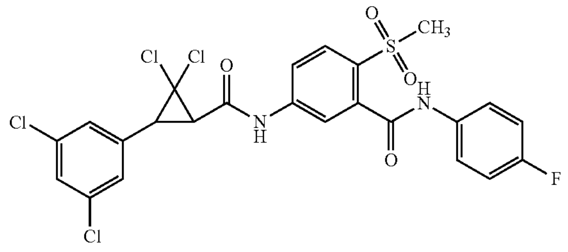 [SMILES: CS(=O)(=O)c1ccc(NC(=O)C2C(c3cc(Cl)cc(Cl)c3)C2(Cl)Cl)cc1C(=O)Nc1ccc(F)cc1]

To a solution of trans-5-(2,2-dichloro-3-(3,5-dichlorophenyl)cyclopropane-1-carboxamido)-N-(4-fluorophenyl)-2-(methylthio)benzamide (F115) (0.049 g, 0.088 mmol) in dichloromethane (0.878 mL) was added meta-chloroperoxybenzoic acid (0.049 g, 0.22 mmol). The reaction was stirred at room temperature for 3 hours. Saturated aqueous sodium bicarbonate was added, and the mixture was extracted with ethyl acetate. The combined organic phases were washed with brine, dried over magnesium sulfate, filtered, and concentrated. Purification by flash column chromatography using 0-15% methanol/dichloromethane as eluent provided the title compound as a white solid (0.042 g, 73%).

Example 20: Preparation of trans-5-(2,2-dichloro-3-(3,5-dichlorophenyl)cyclopropane-1-carboxamido)-N-(4-fluorophenyl)-2-(methylsulfinyl)benzamide (F158)

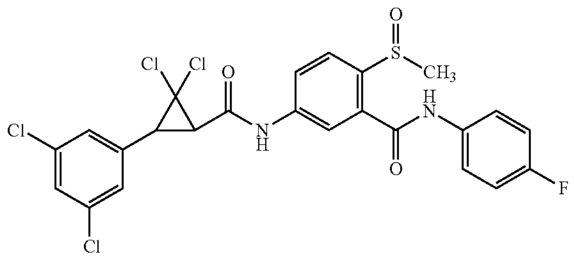 [SMILES: CS(=O)c1ccc(NC(=O)C2C(c3cc(Cl)cc(Cl)c3)C2(Cl)Cl)cc1C(=O)Nc1ccc(F)cc1]

To a solution of trans-5-(2,2-dichloro-3-(3,5-dichlorophenyl)cyclopropane-1-carboxamido)-N-(4-fluorophenyl)-2-(methylthio)benzamide (F115) (0.051 g, 0.091 mmol) in dichloromethane (0.9 mL) was added meta-chloroperoxybenzoic acid (0.021 g, 0.096 mmol). The reaction was stirred at room temperature for 1 hour. Saturated aqueous sodium bicarbonate was added, and the mixture was extracted with ethyl acetate. The combined organic phases were washed with brine, dried over magnesium sulfate, filtered, and concentrated. Purification by flash column chromatography using 0-15% methanol/dichloromethane as eluent provided the title compound as a white solid (0.036 g, 65%).

The following compounds were prepared in like manner to the procedure outlined in Example 20:

trans-2-Chloro-5-(2,2-dichloro-3-(3,5-dichlorophenyl)cyclopropane-1-carboxamido)-N-(4-(methylsulfinyl)phenyl)benzamide (F159)

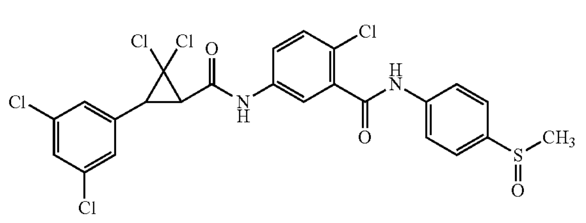 [SMILES: CS(=O)c1ccc(NC(=O)c2cc(NC(=O)C3C(c4cc(Cl)cc(Cl)c4)C3(Cl)Cl)ccc2Cl)cc1]

Isolated as a white solid (0.013 g, 24%).

Example 21: Preparation of trans-2-chloro-5-(2,2-dichloro-3-(3,5-dichlorophenyl)cyclopropane-1-carboxamido)benzoyl chloride (C68)

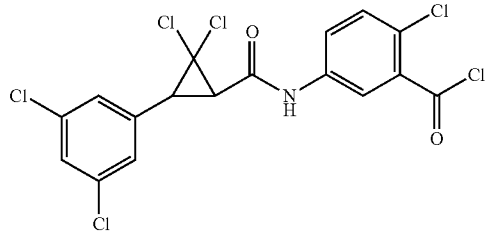 [SMILES: O=C(Cl)c1cc(NC(=O)C2C(c3cc(Cl)cc(Cl)c3)C2(Cl)Cl)ccc1Cl]

To a solution of trans-2-chloro-5-(2,2-dichloro-3-(3,5-dichlorophenyl)cyclopropanecarboxamido)benzoic acid (C67) (0.200 g, 0.441 mmol) in dichloromethane (2.2 mL) stirred at 0° C. was added N,N-dimethylformamide (1 drop) followed by oxalyl chloride (0.0579 mL, 0.661 mmol) over 2 minutes. The ice batch was removed, and the reaction allowed to warm to room temperature over 90 minutes. The reaction was then concentrated to provide the title compound as a cream colored foam which was used without further purification or characterization (0.211 g, quant).

Example 22: Preparation of 5-amino-2-chloro-N-(4-fluorophenyl)benzamide (C69) and 3-amino-N-(4-fluorophenyl)benzamide (C70)

C69

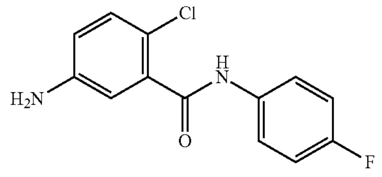 [SMILES: Nc1ccc(Cl)c(C(=O)Nc2ccc(F)cc2)c1]

C70

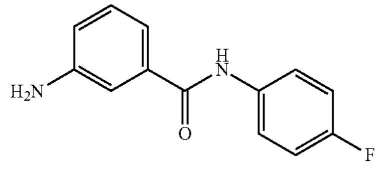

Palladium on alumina (5%, 0.0065 g, 0.061 mmol) was added to a deoxygenated solution of 2-chloro-N-(4-fluorophenyl)-5-nitrobenzamide (C143) (0.18 g, 0.61 mmol) in ethyl acetate (6 mL) at room temperature. The mixture was purged with nitrogen, and the reaction was stirred under a balloon of hydrogen at room temperature for 3 hours. Palladium on carbon (10%, 0.0070 g) was added, and the reaction was stirred under a balloon of hydrogen overnight. The reaction was diluted with dichloromethane, and the reaction was washed with hydrochloric acid (1 N). The aqueous layer was neutralized with saturated aqueous sodium bicarbonate and extracted with dichloromethane to provide (C69) as a yellow oil (0.028 g, 16%): $^1H$ NMR (400 MHz, $CDCl_3$) δ 8.09 (s, 1H), 7.65-7.51 (m, 2H), 7.17 (d, J=8.6 Hz, 1H), 7.08-7.00 (m, 3H), 6.68 (dd, J=8.6, 2.9 Hz, 1H), 3.85 (s, 2H); IR (thin film) 3349, 1654 $cm^{-1}$; ESIMS m/z 265 ($[M+H]^+$). The organic layer was concentrated to a give a yellow solid, which was suspended in degassed methanol (6 mL). Palladium on carbon (10%, 0.010 g) was added, and the reaction was stirred under a balloon of hydrogen overnight. The reaction was diluted with ethyl acetate and extracted with hydrochloric acid (1 N). The aqueous layer was basified with saturated aqueous sodium bicarbonate, extracted with dichloromethane, and concentrated to provide (C70) as a yellow solid (0.060 g, 38%): $^1H$ NMR (400 MHz, $CDCl_3$) δ 7.85 (s, 1H), 7.58 (dd, J=9.0, 4.8 Hz, 2H), 7.25-7.20 (m, 1H), 7.20-7.15 (m, 1H), 7.04 (t, J=8.7 Hz, 2H), 6.83 (ddd, J=7.9, 2.4, 0.9 Hz, 1H), 3.83 (s, 2H); IR (thin film) 3328, 1648 $cm^{-1}$; ESIMS m/z 231 ($[M+H]^+$).

Example 23: Preparation of 5-amino-2-chloro-N-(4-fluorophenyl)benzamide (C69)

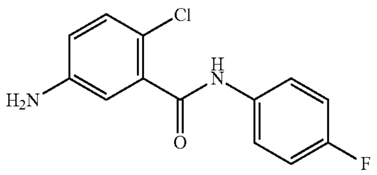

To a solution of 2-chloro-N-(4-fluorophenyl)-5-nitrobenzamide (C143) (3.57 g, 12.1 mmol) in methanol (81 mL) and water (40.4 mL) was added iron powder (3.38 g, 60.6 mmol) and ammonium chloride (1.94 g, 36.3 mmol). The reaction was heated at 60° C. for 2 hours. The reaction was filtered through Celite®. The filtrate was diluted with ethyl acetate and washed with brine. The organic phase was extracted with hydrochloric acid (1 N). The combined aqueous phases were neutralized with saturated aqueous sodium bicarbonate and extracted with dichloromethane. The combined organic phases were dried over magnesium sulfate, filtered, and concentrated to provide the title compound as a white solid (1.75 g, 54%).

The following compounds were prepared in like manner to the procedure outlined in Example 23:

5-Amino-N-(4-fluorophenyl)-2-(trifluoromethyl) benzamide (C71)

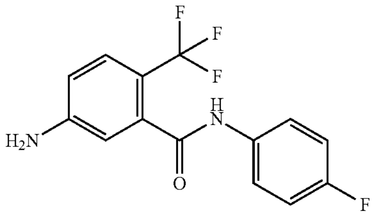 [SMILES: Nc1ccc(C(F)(F)F)c(C(=O)Nc2ccc(F)cc2)c1]

Isolated as a brown solid (0.182 g, 63%): $^1H$ NMR (400 MHz, DMSO-$d_6$) δ 10.47 (s, 1H), 7.79-7.62 (m, 2H), 7.41 (d, J=8.3 Hz, 1H), 7.18 (t, J=8.9 Hz, 2H), 6.77-6.62 (m, 2H), 6.06 (s, 2H); EIMS m/z 298 ($[M]^+$).

5-Amino-N-(4-fluorophenyl)-2-iodobenzamide (C72)

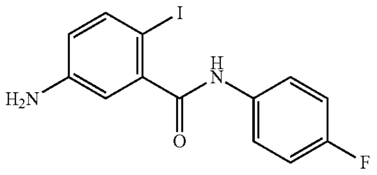 [SMILES: Nc1ccc(I)c(C(=O)Nc2ccc(F)cc2)c1]

Isolated as a brown solid (0.205 g, 84%): $^1H$ NMR (400 MHz, DMSO-$d_6$) δ 10.34 (s, 1H), 7.78-7.66 (m, 2H), 7.45 (d, J=8.5 Hz, 1H), 7.24-7.10 (m, 2H), 6.67 (d, J=2.7 Hz, 1H), 6.45 (dd, J=8.5, 2.7 Hz, 1H), 5.50 (s, 2H); IR (thin film) 3247, 1650 $cm^{-1}$; ESIMS m/z 357 ($[M+H]^+$).

5-Amino-2-chloro-N-(4-cyanophenyl)benzamide (C73)

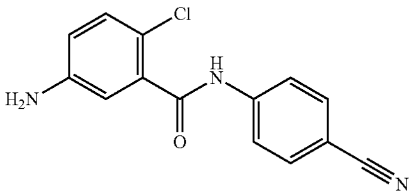 [SMILES: N#Cc1ccc(NC(=O)c2cc(N)ccc2Cl)cc1]

Isolated as a yellow solid (0.119 g, 52%): $^1H$ NMR (400 MHz, DMSO-$d_6$) δ 10.83 (s, 1H), 7.90 (d, J=8.7 Hz, 2H), 7.81 (d, J=8.8 Hz, 2H), 7.15 (d, J=8.6 Hz, 1H), 6.71 (d, J=2.7 Hz, 1H), 6.67 (dd, J=8.6, 2.7 Hz, 1H), 5.51 (s, 2H); IR (thin film) 3365, 3100, 2223, 1670 $cm^{-1}$; ESIMS m/z 273 ($[M+H]^+$).

5-Amino-2-chloro-N-(4-(trifluoromethyl)phenyl) benzamide (C74)

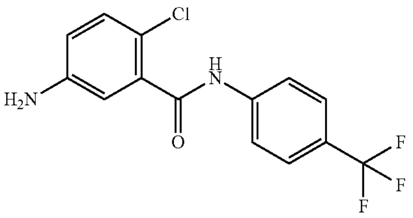 [SMILES: Nc1ccc(Cl)c(C(=O)Nc2ccc(C(F)(F)F)cc2)c1]

Isolated as a yellow solid (0.253 g, 79%): $^1$H NMR (400 MHz, DMSO-$d_6$) δ 10.76 (s, 1H), 7.93 (d, J=8.5 Hz, 2H), 7.72 (d, J=8.6 Hz, 2H), 7.15 (d, J=8.6 Hz, 1H), 6.72 (d, J=2.7 Hz, 1H), 6.67 (dd, J=8.6, 2.7 Hz, 1H), 5.51 (s, 2H); IR (thin film) 3230, 3039, 1666 $cm^{-1}$; ESIMS m/z 316 ($[M+H]^+$).

5-Amino-2-chloro-N-(4-chlorophenyl)benzamide (C75)

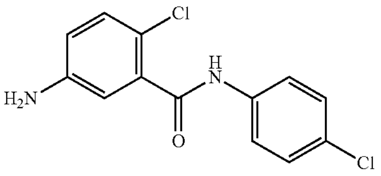

Isolated as a yellow solid (0.290 g, 90%): $^1$H NMR (400 MHz, DMSO-$d_6$) δ 10.51 (s, 1H), 7.80-7.68 (m, 2H), 7.44-7.32 (m, 2H), 7.13 (d, J=8.6 Hz, 1H), 6.69 (d, J=2.7 Hz, 1H), 6.65 (dd, J=8.6, 2.8 Hz, 1H), 5.48 (s, 2H); IR (thin film) 3375, 3212, 1660 $cm^{-1}$; ESIMS m/z 282 ($[M+H]^+$).

5-Amino-2-chloro-N-(2-chloro-4-fluorophenyl)benzamide (C76)

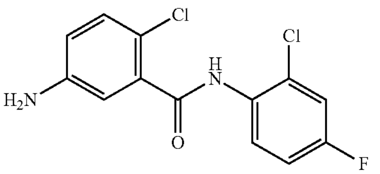

Isolated as a white solid (0.092 g, 68%): IR (thin film) 3377, 3157, 1659 $cm^{-1}$; ESIMS m/z 300 ($[M+H]^+$).

5-Amino-2-chloro-N-(4-chlorophenyl)benzamide (C77)

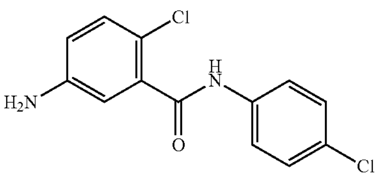

Isolated as a red solid (0.185 g, 84%): $^1$H NMR (400 MHz, DMSO-$d_6$) δ 9.82 (s, 1H), 7.35 (d, J=7.5 Hz, 1H), 7.26-7.10 (m, 4H), 6.75 (d, J=2.7 Hz, 1H), 6.63 (dd, J=8.6, 2.7 Hz, 1H), 5.46 (s, 2H), 2.27 (s, 3H); IR (thin film) 3351, 3228, 1654 $cm^{-1}$; ESIMS m/z 262 ($[M+H]^+$).

5-Amino-N-(4-fluorophenyl)-2-methylbenzamide (C78)

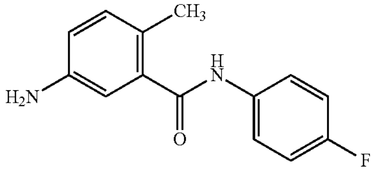

Isolated as a brown solid (0.390 g, 83%): $^1$H NMR (400 MHz, DMSO-$d_6$) δ 10.23 (s, 1H), 7.82-7.68 (m, 2H), 7.23-7.08 (m, 2H), 6.92 (d, J=8.2 Hz, 1H), 6.65 (d, J=2.4 Hz, 1H), 6.58 (dd, J=8.1, 2.4 Hz, 1H), 5.07 (s, 2H), 2.18 (s, 3H); IR (thin film) 3422, 3339, 3256, 1649 $cm^{-1}$; ESIMS m/z 245 ($[M+H]^+$).

5-Amino-2-bromo-N-(4-fluorophenyl)benzamide (C79)

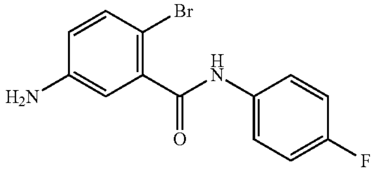

Isolated as a brown solid (0.308 g, 87%): $^1$H NMR (400 MHz, DMSO-$d_6$) δ 10.40 (s, 1H), 7.76-7.66 (m, 2H), 7.26 (d, J=8.6 Hz, 1H), 7.21-7.11 (m, 2H), 6.68 (d, J=2.7 Hz, 1H), 6.58 (dd, J=8.6, 2.8 Hz, 1H), 5.50 (s, 2H); IR (thin film) 3382, 3236, 1645 $cm^{-1}$; ESIMS m/z 310 ($[M+H]^+$).

5-Amino-N-(4-fluorophenyl)-2-(1H-1,2,4-triazol-1-yl)benzamide (C80)

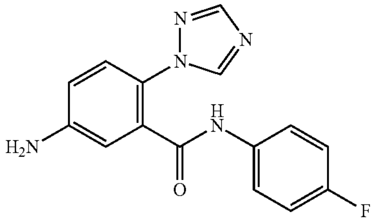 [SMILES: Nc1ccc(-n2cncn2)c(C(=O)Nc2ccc(F)cc2)c1]

Isolated as a beige solid (0.182 g, 54%): $^1$H NMR (400 MHz, DMSO-$d_6$) δ 10.32 (s, 1H), 8.63 (s, 1H), 7.99 (s, 1H), 7.59-7.51 (m, 2H), 7.24 (d, J=8.5 Hz, 1H), 7.15-7.08 (m, 2H), 6.81 (d, J=2.5 Hz, 1H), 6.74 (dd, J=8.5, 2.5 Hz, 1H), 5.75 (s, 2H); IR (thin film) 3344, 3227, 3051, 1659 $cm^{-1}$; ESIMS m/z 298 ($[M+H]^+$).

4-Amino-N-(4-fluorophenyl)picolinamide (C81)

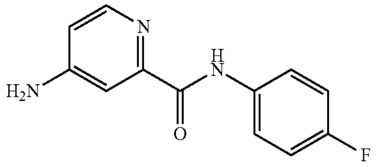

Isolated as a brown solid (0.321 g, 57%): $^1$H NMR (400 MHz, DMSO-$d_6$) δ 10.53 (s, 1H), 8.11 (d, J=5.5 Hz, 1H), 7.91 (dd, J=9.0, 5.0 Hz, 2H), 7.32 (d, J=2.1 Hz, 1H), 7.18 (t, J=8.9 Hz, 2H), 6.66 (dd, J=5.5, 2.2 Hz, 1H), 6.44 (s, 2H); IR (thin film) 3484, 3359, 3321, 3234, 1642 cm$^{-1}$; ESIMS m/z 232 ([M+H]$^+$).

3-Amino-2-chloro-N-(4-fluorophenyl)benzamide (C82)

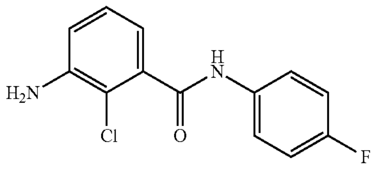

Isolated as a yellow solid (0.332 g, 65%): $^1$H NMR (400 MHz, DMSO-$d_6$) δ 10.42 (s, 1H), 7.81-7.65 (m, 2H), 7.25-7.13 (m, 2H), 7.10 (t, J=7.7 Hz, 1H), 6.88 (dd, J=8.1, 1.3 Hz, 1H), 6.67 (dd, J=7.3, 1.3 Hz, 1H), 5.57 (s, 2H); IR (thin film) 3372, 3237, 3011, 1655 cm$^{-1}$; ESIMS m/z 265 ([M+H]$^+$).

5-Amino-N-(4-fluorophenyl)-2-methoxybenzamide (C83)

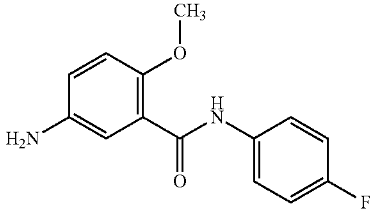 [SMILES: COc1ccc(N)cc1C(=O)Nc1ccc(F)cc1]

Isolated as a light brown solid (0.356 g, 61%): $^1$H NMR (400 MHz, DMSO-$d_6$) δ 10.12 (s, 1H), 7.80-7.69 (m, 2H), 7.21-7.11 (m, 2H), 6.96 (d, J=2.9 Hz, 1H), 6.90 (d, J=8.8 Hz, 1H), 6.71 (dd, J=8.7, 2.9 Hz, 1H), 4.89 (s, 2H), 3.79 (s, 3H); IR (thin film) 3338, 1662 cm$^{-1}$; ESIMS m/z 261 ([M+H]$^+$).

5-Amino-2-chloro-N-phenylbenzamide (C84)

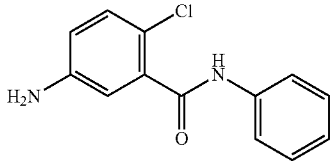 [SMILES: Nc1ccc(Cl)c(C(=O)Nc2ccccc2)c1]

Isolated as a white foam (1.28 g, 96%): $^1$H NMR (400 MHz, $CDCl_3$) δ 7.97 (s, 1H), 7.68-7.60 (m, 2H), 7.43-7.34 (m, 2H), 7.22-7.13 (m, 2H), 7.10 (d, J=2.9 Hz, 1H), 6.71 (dd, J=8.5, 2.9 Hz, 1H), 3.83 (s, 2H); $^{13}$C NMR (101 MHz, $CDCl_3$) δ 164.43, 145.71, 137.61, 135.33, 131.12, 129.12, 124.77, 120.12, 118.92, 118.22, 116.55; ESIMS m/z 247 ([M+H]$^+$).

5-Amino-2-chloro-N-(2-fluorophenyl)benzamide (C85)

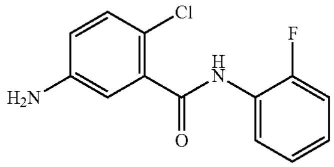 [SMILES: Nc1ccc(Cl)c(C(=O)Nc2ccccc2F)c1]

Isolated as a white solid (1.24 g, quant): $^1$H NMR (400 MHz, $CDCl_3$) δ 8.48 (td, J=8.1, 1.6 Hz, 1H), 8.34 (s, 1H), 7.23-7.08 (m, 5H), 6.72 (dd, J=8.5, 2.9 Hz, 1H), 3.85 (s, 2H), 3.48 (s, 1H); $^{19}$F NMR (376 MHz, $CDCl_3$) δ −130.65; ESIMS m/z 265 ([M+H]$^+$).

5-Amino-2-chloro-N-(2,4-difluorophenyl)benzamide (C86)

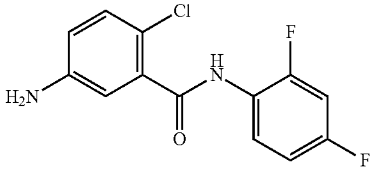

Isolated as a purple solid (0.37 g, 28%): $^1$H NMR (400 MHz, $CDCl_3$) δ 8.42 (tdd, J=9.7, 6.0, 3.6 Hz, 1H), 8.25 (s, 1H), 7.21 (d, J=8.5 Hz, 1H), 7.13 (d, J=2.9 Hz, 1H), 6.97-6.88 (m, 2H), 6.73 (dd, J=8.5, 2.9 Hz, 1H), 3.84 (s, 2H); $^{19}$F NMR (376 MHz, $CDCl_3$) δ −114.57 (d, J=4.6 Hz), −125.78 (d, J=4.6 Hz); ESIMS m/z 283 ([M+H]$^+$).

5-Amino-2-chloro-N-(4-fluorophenyl)-N-methylbenzamide (C87)

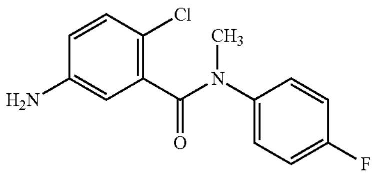

Isolated as a white solid (0.81 g, 60%): $^{1}$H NMR (400 MHz, $CDCl_3$) δ 7.17-7.07 (m, 2H), 6.96-6.83 (m, 3H), 6.49-6.40 (m, 2H), 3.60 (s, 2H), 3.45 (s, 3H); $^{19}$F NMR (376 MHz, $CDCl_3$) δ −114.12; ESIMS m/z 279 ($[M+H]^+$).

5-Amino-2-chloro-N-(3-fluorophenyl)benzamide (C88)

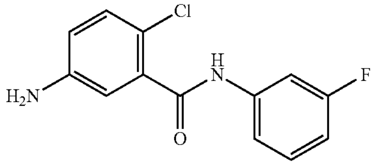 [SMILES: Nc1ccc(Cl)c(C(=O)Nc2cccc(F)c2)c1]

Isolated as a white solid (1.18 g, 95%): $^{1}$H NMR (400 MHz, $CDCl_3$) δ 8.05 (s, 1H), 7.63 (dt, J=10.9, 2.2 Hz, 1H), 7.31 (td, J=8.1, 6.2 Hz, 1H), 7.26-7.22 (m, 1H), 7.20 (d, J=8.5 Hz, 1H), 7.09 (d, J=3.0 Hz, 1H), 6.86 (tdd, J=8.3, 2.5, 1.1 Hz, 1H), 6.71 (dd, J=8.6, 2.9 Hz, 1H), 3.84 (s, 2H); $^{19}$F NMR (376 MHz, $CDCl_3$) δ −111.22; ESIMS m/z 265 ($[M+H]^+$).

5-Amino-2-chloro-N-(3-cyanophenyl)benzamide (C89)

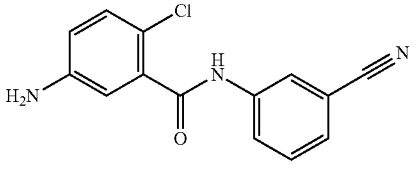 [SMILES: N#Cc1cccc(NC(=O)c2cc(N)ccc2Cl)c1]

Isolated as a white solid (0.89 g, 70%): $^{1}$H NMR (400 MHz, DMSO-$d_6$) δ 10.75 (s, 1H), 8.23-8.14 (m, 1H), 7.95 (td, J=4.7, 2.2 Hz, 1H), 7.66-7.50 (m, 2H), 7.15 (d, J=8.6 Hz, 1H), 6.76-6.60 (m, 2H), 5.52 (s, 2H); $^{13}$C NMR (101 MHz, DMSO-$d_6$) δ 165.98, 147.85, 139.77, 136.41, 130.29, 129.99, 127.17, 123.96, 121.98, 118.63, 116.18, 115.03, 113.32, 111.60; ESIMS m/z 272 ($[M+H]^+$).

5-Amino-2-chloro-N-(2,3-difluorophenyl)benzamide (C90)

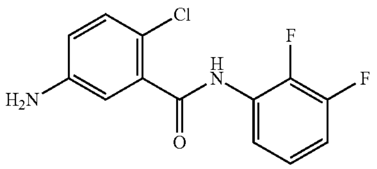 [SMILES: Nc1ccc(Cl)c(C(=O)Nc2cccc(F)c2F)c1]

Isolated as a white solid (1.11 g, 99%): $^{1}$H NMR (400 MHz, $CDCl_3$) δ 8.38 (s, 1H), 8.29-8.20 (m, 1H), 7.22 (d, J=8.6 Hz, 1H), 7.17-7.06 (m, 2H), 6.95 (dddd, J=9.9, 8.6, 7.6, 1.5 Hz, 1H), 6.73 (dd, J=8.6, 2.9 Hz, 1H), 3.85 (s, 2H); $^{19}$F NMR (376 MHz, $CDCl_3$) δ −137.88 (d, J=20.5 Hz), −154.65 (d, J=20.4 Hz); ESIMS m/z 283 ($[M+H]^+$).

5-Amino-2-chloro-N-(3,4-difluorophenyl)benzamide (C91)

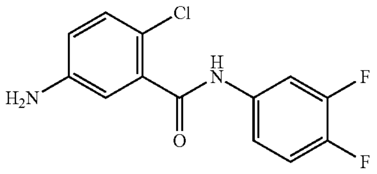

Isolated as a grey solid (1.26 g, 93%): $^{1}$H NMR (400 MHz, $CDCl_3$) δ 8.03 (s, 1H), 7.76 (ddd, J=12.1, 7.2, 2.3 Hz, 1H), 7.23-7.08 (m, 4H), 6.72 (dd, J=8.6, 2.9 Hz, 1H), 3.85 (s, 2H); $^{19}$F NMR (376 MHz, $CDCl_3$) δ −135.39 (d, J=21.6 Hz), −141.93 (d, J=21.7 Hz); ESIMS m/z 283 ($[M+H]^+$).

5-Amino-2-chloro-N-(2,4,6-trifluorophenyl)benzamide (C92)

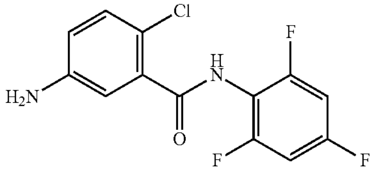

Isolated as a light brown solid (1.20 g, 73%): $^{1}$H NMR (400 MHz, DMSO-$d_6$) δ 10.08 (s, 1H), 7.38-7.27 (m, 2H), 7.14 (d, J=8.6 Hz, 1H), 6.74 (d, J=2.7 Hz, 1H), 6.65 (dd, J=8.6, 2.8 Hz, 1H), 5.52 (s, 2H); $^{19}$F NMR (376 MHz, DMSO-$d_6$) δ −109.56 (t, J=5.5 Hz), −114.48 (d, J=5.5 Hz); ESIMS m/z 301 ($[M+H]^+$).

5-Amino-2-chloro-N-(2,6-difluorophenyl)benzamide (C93)

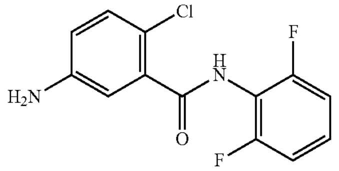 [SMILES: Nc1ccc(Cl)c(C(=O)Nc2c(F)cccc2F)c1]

Isolated as a light brown solid (0.93 g, 98%): $^1$H NMR (400 MHz, DMSO-$d_6$) δ 10.09 (s, 1H), 7.40 (tt, J=8.4, 6.3 Hz, 1H), 7.26-7.10 (m, 3H), 6.75 (d, J=2.7 Hz, 1H), 6.65 (dd, J=8.6, 2.8 Hz, 1H), 5.51 (s, 2H); $^{19}$F NMR (376 MHz, DMSO-$d_6$) δ −117.62; ESIMS m/z 283 ([M+H]$^+$).

3-Amino-4-chloro-N-(4-fluorophenyl)benzamide (C94)

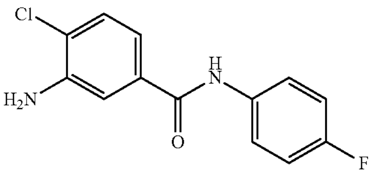

Isolated as a white solid (0.147 g, 23%): $^1$H NMR (400 MHz, DMSO-$d_6$) δ 10.21 (s, 1H), 7.83-7.69 (m, 2H), 7.39-7.27 (m, 2H), 7.23-7.14 (m, 2H), 7.10 (dd, J=8.3, 2.1 Hz, 1H), 5.61 (s, 2H); IR (thin film) 3472, 3379, 1659 cm$^{-1}$; ESIMS m/z 265 ([M+H]$^+$).

5-Amino-2-chloro-N-(pyridin-4-yl)benzamide (C95)

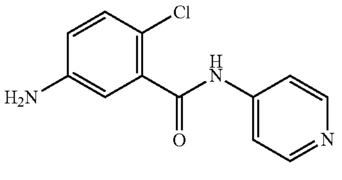 [SMILES: Nc1ccc(Cl)c(C(=O)Nc2ccncc2)c1]

Isolated as a yellow solid (0.385 g, 89%): $^1$H NMR (400 MHz, $CD_3OD$) δ 8.44 (dt, J=5.0, 1.3 Hz, 2H), 7.78-7.71 (m, 2H), 7.17 (dd, J=8.6, 1.2 Hz, 1H), 6.83 (dd, J=2.8, 1.1 Hz, 1H), 6.77 (ddd, J=8.6, 2.8, 1.1 Hz, 1H); $^{13}$C NMR (101 MHz, $CDCl_3$) δ 171.98, 153.55, 153.30, 151.33, 150.57, 140.02, 134.02, 121.26, 117.90; ESIMS m/z 248 ([M+H]$^+$).

5-Amino-2-chloro-N-(pyridin-3-yl)benzamide (C96)

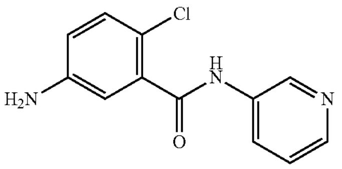 [SMILES: Nc1ccc(Cl)c(C(=O)Nc2cccnc2)c1]

Isolated as a yellow solid (0.341 g, 80%): $^1$H NMR (400 MHz, $CD_3OD$) δ 8.82 (d, J=2.5 Hz, 1H), 8.31 (dt, J=4.9, 1.2 Hz, 1H), 8.23 (ddt, J=8.4, 2.6, 1.2 Hz, 1H), 7.45 (dd, J=8.4, 4.9 Hz, 1H), 7.17 (dd, J=8.6, 1.0 Hz, 1H), 6.85 (dd, J=2.7, 1.0 Hz, 1H), 6.77 (ddd, J=8.7, 2.8, 1.0 Hz, 1H); $^{13}$C NMR (126 MHz, $CD_3OD$) δ 167.78, 147.36, 144.18, 140.67, 136.19, 135.99, 130.06, 127.82, 123.97, 117.41, 117.22, 114.04; ESIMS m/z 248 ([M+H]$^+$).

3-Amino-N-(4-fluorophenyl)-2-methoxybenzamide (C97)

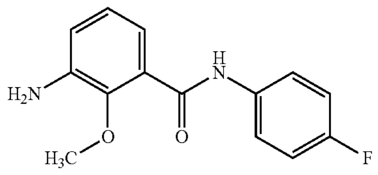 [SMILES: COc1c(N)cccc1C(=O)Nc1ccc(F)cc1]

Isolated as a yellow oil (0.541 g, quant): $^1$H NMR (400 MHz, $CDCl_3$) δ 9.61 (s, 1H), 7.69-7.61 (m, 2H), 7.50 (dd, J=7.8, 1.6 Hz, 1H), 7.13-7.02 (m, 3H), 6.92 (dd, J=7.8, 1.6 Hz, 1H), 3.93 (s, 2H), 3.87 (s, 3H); $^{19}$F NMR (376 MHz, $CDCl_3$) δ −118.16; ESIMS m/z 261 ([M+H]$^+$).

5-Amino-2-chloro-N-(2-chloropyridin-3-yl)benzamide (C98)

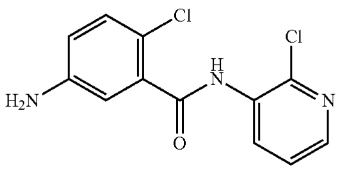 [SMILES: Nc1ccc(Cl)c(C(=O)Nc2cccnc2Cl)c1]

Isolated as a yellow solid (0.269 g, 83%): $^1$H NMR (400 MHz, DMSO-$d_6$) δ 10.25 (s, 1H), 8.30 (dd, J=4.7, 1.8 Hz, 1H), 8.09 (d, J=8.1 Hz, 1H), 7.49 (dd, J=7.9, 4.7 Hz, 1H), 7.14 (d, J=8.6 Hz, 1H), 6.79 (d, J=2.8 Hz, 1H), 6.66 (dd, J=8.6, 2.7 Hz, 1H), 5.51 (s, 2H); $^{13}$C NMR (101 MHz, DMSO-$d_6$) δ 165.98, 147.76, 146.42, 145.29, 135.89, 135.82, 131.61, 129.99, 123.44, 116.25, 115.23, 113.61; ESIMS m/z 282 ([M+H]$^+$).

5-Amino-2-chloro-N-(6-chloropyridin-3-yl)benzamide (C99)

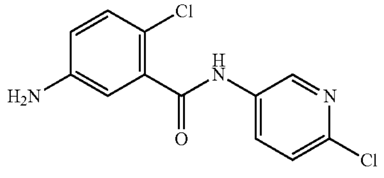 [SMILES: Nc1ccc(Cl)c(C(=O)Nc2ccc(Cl)nc2)c1]

Isolated as a yellow solid (0.560 g, 69%): $^1$H NMR (400 MHz, DMSO-$d_6$) δ 10.77 (s, 1H), 8.72 (d, J=2.7 Hz, 1H), 8.19 (dd, J=8.7, 2.7 Hz, 1H), 7.52 (d, J=8.7 Hz, 1H), 7.16 (d, J=8.6 Hz, 1H), 6.73 (d, J=2.7 Hz, 1H), 6.68 (dd, J=8.6, 2.8 Hz, 1H), 5.52 (s, 2H); $^{13}$C NMR (101 MHz, DMSO-$d_6$) δ

165.95, 147.84, 143.95, 140.56, 136.17, 135.28, 130.02, 129.94, 124.27, 116.25, 115.04, 113.36; ESIMS m/z 282 ($[M+H]^+$).

5-Amino-2-chloro-N-(6-cyanopyridin-3-yl)benzamide (C100)

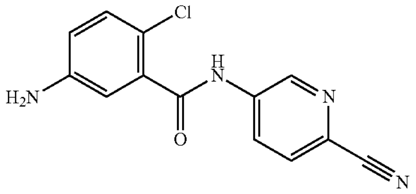 [SMILES: N#Cc1ccc(NC(=O)c2cc(N)ccc2Cl)cn1]

Isolated as a yellow solid (0.292 g, 45%): $^1$H NMR (400 MHz, DMSO-$d_6$) δ 11.10 (s, 1H), 8.98 (d, J=2.5 Hz, 1H), 8.38 (dd, J=8.6, 2.6 Hz, 1H), 8.03 (d, J=8.7 Hz, 1H), 7.17 (d, J=8.6 Hz, 1H), 6.74 (d, J=2.7 Hz, 1H), 6.69 (dd, J=8.6, 2.8 Hz, 1H), 5.54 (d, J=9.0 Hz, 2H); $^{13}$C NMR (101 MHz, DMSO-$d_6$) δ 166.45, 147.89, 142.08, 138.85, 135.78, 130.11, 129.70, 126.37, 126.12, 117.64, 116.48, 114.98, 113.33; ESIMS m/z 273 ($[M+H]^+$).

5-Amino-2-chloro-N-(3-fluorophenyl)-N-methylbenzamide (C101)

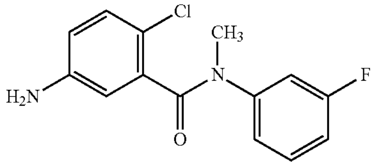

Isolated as a yellow oil (0.446 g, 99%): $^1$H NMR (400 MHz, $CDCl_3$) δ 7.16 (d, J=7.9 Hz, 2H), 7.03-6.77 (m, 4H), 6.47 (s, 2H), 3.61 (s, 2H), 3.47 (s, 3H); $^{19}$F NMR (376 MHz, $CDCl_3$) δ −111.45; ESIMS m/z 279 ($[M+H]^+$).

5-Amino-2-chloro-N-(2-fluorophenyl)-N-methylbenzamide (C102)

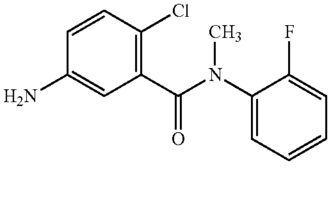 [SMILES: CN(C(=O)c1cc(N)ccc1Cl)c1ccccc1F]

Isolated as a red-orange oil (0.542 g, quant): $^1$H NMR (400 MHz, $CDCl_3$) δ 7.26-7.13 (m, 2H), 7.04-6.94 (m, 2H), 6.91 (d, J=8.6 Hz, 1H), 6.52 (dd, J=2.8, 1.4 Hz, 1H), 6.41 (dd, J=8.6, 2.8 Hz, 1H), 3.59 (s, 2H), 3.42 (d, J=0.6 Hz, 3H); $^{19}$F NMR (376 MHz, $CDCl_3$) δ −120.54; ESIMS m/z 279 ($[M+H]^+$).

5-Amino-2-chloro-N-(4-cyano-2-methylphenyl)benzamide (C103)

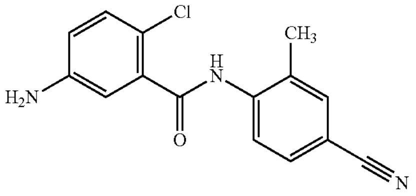 [SMILES: Cc1cc(C#N)ccc1NC(=O)c1cc(N)ccc1Cl]

Isolated as a white solid (0.390 g, 86%): $^1$H NMR (400 MHz, $CDCl_3$) δ 8.43 (d, J=8.6 Hz, 1H), 8.23 (s, 1H), 7.57 (dd, J=8.5, 2.0 Hz, 1H), 7.50 (d, J=1.9 Hz, 1H), 7.22 (d, J=8.6 Hz, 1H), 7.19 (d, J=2.9 Hz, 1H), 6.75 (dd, J=8.6, 2.9 Hz, 1H), 3.88 (s, 2H), 2.38 (s, 3H); $^{13}$C NMR (101 MHz, $CDCl_3$) δ 145.97, 140.12, 134.26, 134.01, 131.35, 131.27, 128.18, 121.64, 118.89, 118.76, 118.44, 117.09, 107.72, 17.93; ESIMS m/z 286 ($[M+H]^+$).

5-Amino-2-chloro-N-(4-fluoro-2-methylphenyl)benzamide (C104)

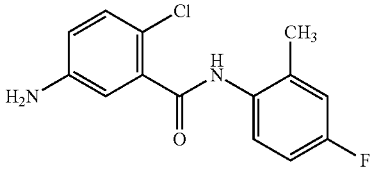

Isolated as a red solid (0.430 g, 95%): $^1$H NMR (400 MHz, DMSO-$d_6$) δ 9.84 (s, 1H), 7.34 (dd, J=8.8, 5.7 Hz, 1H), 7.12 (dd, J=9.0, 2.4 Hz, 2H), 7.04 (td, J=8.6, 3.0 Hz, 1H), 6.74 (d, J=2.7 Hz, 1H), 6.63 (dd, J=8.6, 2.8 Hz, 1H), 5.46 (s, 2H), 2.27 (s, 3H); $^{19}$F NMR (376 MHz, DMSO-$d_6$) δ −117.12; ESIMS m/z 279 ($[M+H]^+$).

6-Amino-N-(4-fluorophenyl)picolinamide (C105)

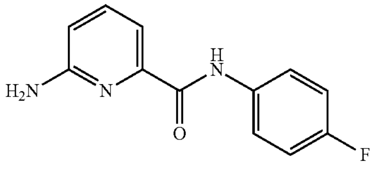

Isolated as a green film (0.072 g, 15%): $^1$H NMR (400 MHz, $CDCl_3$) δ 9.82 (s, 1H), 7.70 (dd, J=7.2, 4.8 Hz, 2H), 7.67-7.52 (m, 2H), 7.05 (t, J=8.3 Hz, 2H), 6.67 (d, J=7.6 Hz, 1H), 4.63 (s, 2H); IR (thin film) 3333, 1671, 1608 $cm^{-1}$; ESIMS m/z 232 ($[M+H]^+$).

3-Amino-N-(4-fluorophenyl)-4-methylbenzamide (C106)

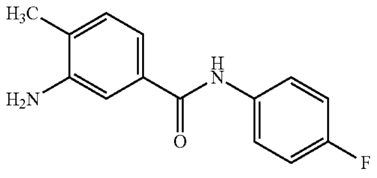 [SMILES: Cc1ccc(C(=O)Nc2ccc(F)cc2)cc1N]

Isolated as a faint yellow solid (0.102 g, 15%): $^{1}$H NMR (400 MHz, DMSO-$d_6$) δ 10.05 (s, 1H), 7.82-7.71 (m, 2H), 7.20-7.11 (m, 3H), 7.09-7.01 (m, 2H), 5.07 (s, 2H), 2.11 (s, 3H); IR (thin film) 3366, 2924, 1655 $cm^{-1}$; ESIMS m/z 245 ($[M+H]^+$).

5-Amino-N-(4-fluorophenyl)-2-(trifluoromethoxy) benzamide (C107)

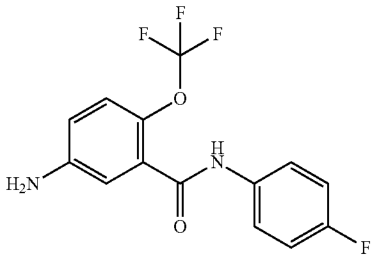 [SMILES: Nc1ccc(OC(F)(F)F)c(C(=O)Nc2ccc(F)cc2)c1]

Isolated as a white solid (0.448 g, 81%): mp 115-117 OC; $^{1}$H NMR (400 MHz, DMSO-$d_6$) δ 10.39 (s, 1H), 7.76-7.64 (m, 2H), 7.23-7.15 (m, 2H), 7.10 (d, J=8.9 Hz, 1H), 6.76 (d, J=2.8 Hz, 1H), 6.70 (dd, J=8.8, 2.8 Hz, 1H), 5.57 (s, 2H); ESIMS m/z 315 ($[M+H]^+$).

3-Amino-5-chloro-N-(4-fluorophenyl)benzamide (C108)

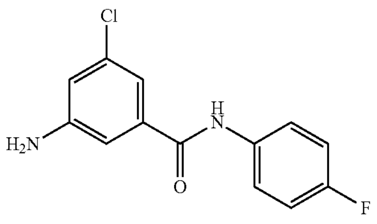 [SMILES: Nc1cc(Cl)cc(C(=O)Nc2ccc(F)cc2)c1]

Isolated as a light brown solid (0.497 g, 81%): mp 133-136° C.; $^{1}$H NMR (400 MHz, DMSO-$d_6$) δ 10.23 (d, J=8.3 Hz, 1H), 7.82-7.68 (m, 2H), 7.25-7.12 (m, 2H), 7.10-7.00 (m, 2H), 6.76 (t, J=2.0 Hz, 1H), 5.69 (s, 2H); ESIMS m/z 265 ($[M]^+$).

5-Amino-2-chloro-N-(2-chlorophenyl)benzamide (C109)

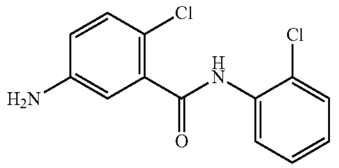 [SMILES: Nc1ccc(Cl)c(C(=O)Nc2ccccc2Cl)c1]

Isolated as a red oil (0.391 g, 69%): $^{1}$H NMR (400 MHz, $CDCl_3$) δ 8.60-8.53 (m, 2H), 7.41 (dd, J=8.0, 1.5 Hz, 1H), 7.33 (td, J=8.0, 1.6 Hz, 1H), 7.22 (d, J=8.5 Hz, 1H), 7.13 (dd, J=6.1, 2.2 Hz, 1H), 7.09 (td, J=7.8, 1.6 Hz, 1H), 6.73 (dd, J=8.6, 2.9 Hz, 1H), 3.85 (s, 2H); $^{13}$C NMR (101 MHz, $CDCl_3$) δ 145.70, 134.98, 131.82, 131.30, 129.17, 127.77, 126.29, 125.00, 122.04, 121.82, 118.45, 116.57; ESIMS m/z 281 ($[M+H]^+$).

5-Amino-2-chloro-N-(2-isopropylphenyl)benzamide (C110)

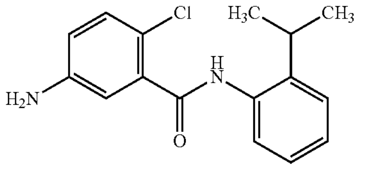 [SMILES: CC(C)c1ccccc1NC(=O)c1cc(N)ccc1Cl]

Isolated as a red oil (0.461 g, 81%): $^{1}$H NMR (400 MHz, $CDCl_3$) δ 7.92 (s, 1H), 7.85 (dd, J=7.5, 1.9 Hz, 1H), 7.34 (dd, J=7.2, 2.2 Hz, 1H), 7.29-7.18 (m, 3H), 7.17 (d, J=2.9 Hz, 1H), 6.71 (dd, J=8.6, 2.9 Hz, 1H), 3.84 (s, 2H), 3.16 (hept, J=6.9 Hz, 1H), 1.27 (d, J=6.8 Hz, 6H); $^{13}$C NMR (101 MHz, $CDCl_3$) δ 162.79, 145.76, 140.95, 133.86, 131.14, 126.46, 126.40, 125.71, 124.85, 118.20, 116.87, 28.04, 23.22; ESIMS m/z 289 ($[M+H]^+$).

5-Amino-2-chloro-N-(2-ethyl-6-methylphenyl)benzamide (C111)

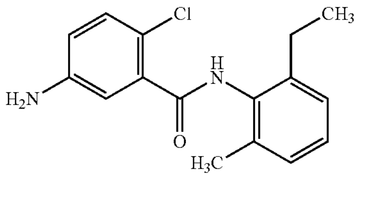 [SMILES: CCc1cccc(C)c1NC(=O)c1cc(N)ccc1Cl]

Isolated as a red oil (0.512 g, 74%): $^{1}$H NMR (400 MHz, $CDCl_3$) δ 7.57 (s, 1H), 7.25-7.10 (m, 5H), 6.71 (dd, J=8.6, 2.9 Hz, 1H), 3.83 (s, 2H), 2.70 (q, J=7.6 Hz, 2H), 2.34 (s, 3H), 1.22 (t, J=7.6 Hz, 3H); $^{13}$C NMR (101 MHz, $CDCl_3$) δ 161.01, 145.71, 144.07, 141.41, 136.23, 135.17, 131.13, 128.40, 127.96, 126.51, 118.95, 118.13, 116.80, 25.18, 18.86, 14.74; ESIMS m/z 289 ($[M+H]^+$).

5-Amino-2-chloro-N-(3-chlorophenyl)benzamide (C112)

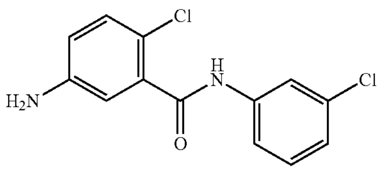 [SMILES: Nc1ccc(Cl)c(C(=O)Nc2cccc(Cl)c2)c1]

Isolated as an orange solid (0.470 g, 62%): $^1$H NMR (400 MHz, $CDCl_3$) δ 8.02 (d, J=8.1 Hz, 1H), 7.76 (dt, J=3.8, 2.1 Hz, 1H), 7.53-7.43 (m, 1H), 7.34-7.28 (m, 1H), 7.19 (d, J=8.5 Hz, 1H), 7.14 (ddd, J=8.0, 2.0, 1.0 Hz, 1H), 7.07 (d, J=2.9 Hz, 1H), 6.71 (dd, J=8.6, 2.9 Hz, 1H), 3.84 (s, 2H); ESIMS m/z 281 ([M+H]$^+$).

5-Amino-2-chloro-N-(2,4-difluorophenyl)-N-methylbenzamide (C113)

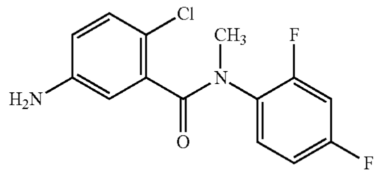 [SMILES: CN(C(=O)c1cc(N)ccc1Cl)c1ccc(F)cc1F]

Isolated as a yellow foam (0.495 g, 91%): $^1$H NMR (300 MHz, $CDCl_3$) δ 6.93 (d, J=8.6 Hz, 1H), 6.82-6.64 (m, 3H), 6.52 (d, J=2.6 Hz, 1H), 6.44 (dd, J=8.6, 2.8 Hz, 1H), 3.62 (s, 2H), 3.39 (s, 3H); IR (thin film) 3355, 1645, 1510 cm$^{-1}$; ESIMS m/z 297 ([M+H]$^+$).

5-Amino-2-chloro-4-fluoro-N-(4-fluorophenyl)benzamide (C114)

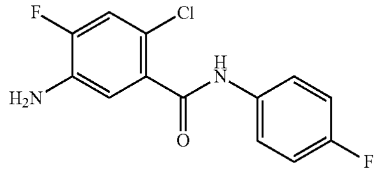 [SMILES: Nc1cc(C(=O)Nc2ccc(F)cc2)c(Cl)cc1F]

Isolated as a yellow foam (0.442 g, 95%): $^1$H NMR (300 MHz, DMSO-$d_6$) δ 10.44 (s, 1H), 7.87-7.63 (m, 2H), 7.28 (d, J=11.2 Hz, 1H), 7.24-7.12 (m, 2H), 6.92 (d, J=9.4 Hz, 1H), 5.56 (s, 2H); ESIMS m/z 283 ([M+H]$^+$).

5-Amino-2-chloro-N-(5-fluoropyridin-2-yl)benzamide (C115)

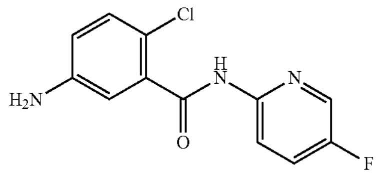

Isolated as a yellow solid (0.073 g, 90%): $^1$H NMR (400 MHz, DMSO-$d_6$) δ 10.96 (s, 1H), 8.35 (d, J=3.1 Hz, 1H), 8.26-8.15 (m, 1H), 7.79 (td, J=8.7, 3.0 Hz, 1H), 7.18 (d, J=8.8 Hz, 1H), 6.89-6.73 (m, 2H), 5.44 (s, 2H); $^{19}$F NMR (376 MHz, DMSO-$d_6$) δ −132.77; ESIMS m/z 266 ([M+H]$^+$).

5-(5-Amino-2-chlorobenzamido)-N-methylpicolinamide (C116)

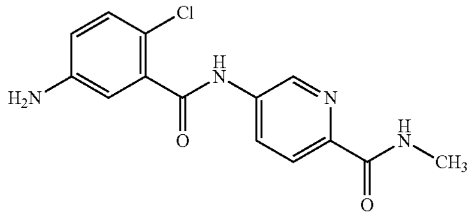 [SMILES: CNC(=O)c1ccc(NC(=O)c2cc(N)ccc2Cl)cn1]

Isolated as a yellow foam (0.187 g, quant): $^1$H NMR (400 MHz, DMSO-$d_6$) δ 10.86 (s, 1H), 8.92 (dd, J=5.0, 2.4 Hz, 1H), 8.66 (d, J=5.0 Hz, 1H), 8.30 (dt, J=8.6, 2.3 Hz, 1H), 8.03 (dd, J=8.6, 2.5 Hz, 1H), 7.16 (d, J=8.6 Hz, 1H), 6.74 (d, J=2.7 Hz, 1H), 6.68 (dd, J=8.6, 2.7 Hz, 1H), 5.52 (s, 2H), 2.81 (d, J=4.8 Hz, 3H); ESIMS m/z 305 ([M+H]$^+$).

5-Amino-2-chloro-N-(pyridin-2-yl)benzamide (C117)

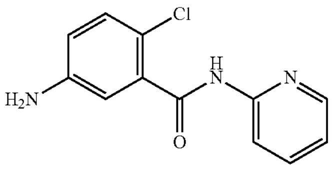 [SMILES: Nc1ccc(Cl)c(C(=O)Nc2ccccn2)c1]

Isolated as a yellow foam (0.152 g, 49%): $^1$H NMR (400 MHz, DMSO-$d_6$) δ 11.25 (s, 1H), 8.74 (d, J=2.7 Hz, 1H), 8.46 (d, J=2.8 Hz, 1H), 8.41-8.35 (m, 1H), 8.32 (dd, J=8.9, 2.8 Hz, 1H), 8.25 (dd, J=8.8, 2.7 Hz, 1H), 8.20 (d, J=8.4 Hz, 1H), 7.92-7.78 (m, 3H), 7.21 (ddd, J=7.4, 4.9, 1.0 Hz, 1H); EIMS m/z 248 ([M+H]$^+$).

N-Allyl-5-amino-2-chloro-N-(4-fluorophenyl)benzamide (C118)

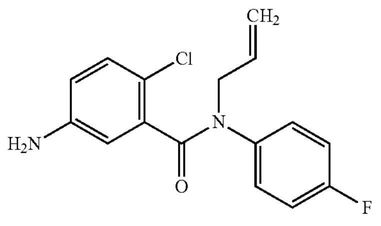

Isolated as an orange solid (0.269 g, 60%): ESIMS m/z 305 ([M+H]$^+$).

Example 24: Preparation of 5-amino-2-fluoro-N-(4-fluorophenyl)benzamide (C119)

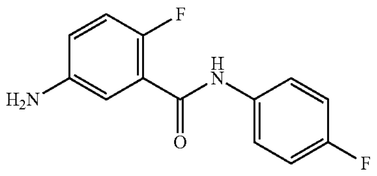

To a solution of 2-fluoro-N-(4-fluorophenyl)-5-nitrobenzamide (C183) (1.06 g, 3.81 mmol) in ethyl acetate (15 mL) under a nitrogen blanket was added palladium on carbon (0.120 g, 0.0560 mmol). The reaction flask was placed on a Parr shaker at room temperature under hydrogen (45 psi) for 16 hours. The reaction was filtered through Celite®, washed with ethyl acetate, and concentrated to provide the title product as a white solid (0.955 g, quant) $^1$H NMR (400 MHz, $CDCl_3$) δ 8.46 (d, J=17.1 Hz, 1H), 7.65-7.58 (m, 2H), 7.42 (dd, J=6.5, 3.1 Hz, 1H), 7.11-7.03 (m, 2H), 6.98 (dd, J=11.8, 8.8 Hz, 1H), 6.78 (ddd, J=8.7, 4.1, 3.1 Hz, 1H), 3.74 (s, 2H); $^{19}$F NMR (376 MHz, $CDCl_3$) δ −117.55, −126.58; EIMS m/z 249 ([M+H]$^+$).

The following compounds were prepared in like manner to the procedure outlined in Example 24:

3-Amino-2-fluoro-N-(4-fluorophenyl)benzamide (C120)

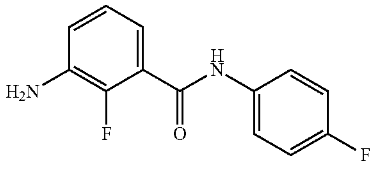 [SMILES: Nc1cccc(C(=O)Nc2ccc(F)cc2)c1F]

Isolated as a white solid (1.05 g, 96%): $^1$H NMR (400 MHz, $CDCl_3$) δ 8.28 (d, J=13.9 Hz, 1H), 7.66-7.57 (m, 2H), 7.43 (ddd, J=7.8, 7.0, 1.7 Hz, 1H), 7.12-7.03 (m, 3H), 6.95 (ddd, J=8.7, 7.9, 1.7 Hz, 1H), 3.87 (s, 2H); $^{19}$F NMR (376 MHz, $CDCl_3$) δ −117.54, −136.71; EIMS m/z 249 ([M+H]$^+$).

5-Amino-2-fluoro-N-(4-fluorophenyl)-N-methylbenzamide (C121)

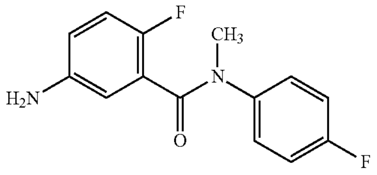 [SMILES: CN(C(=O)c1cc(N)ccc1F)c1ccc(F)cc1]

Isolated as a white foam (0.618 g, 98%): $^1$H NMR (300 MHz, $CDCl_3$) δ 7.12-7.01 (m, 2H), 6.96-6.83 (m, 2H), 6.67-6.44 (m, 3H), 3.54 (br s, 2H), 3.44 (s, 3H); IR (thin film) 3351, 2922, 1638, 1509 cm$^{-1}$; ESIMS m/z 263 ([M+H]$^+$).

5-Amino-2-fluoro-N-(3-fluorophenyl)-N-methylbenzamide (C122)

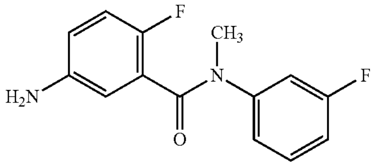 [SMILES: CN(C(=O)c1cc(N)ccc1F)c1cccc(F)c1]

Isolated as a white foam (0.595 g, quant): EIMS m/z 263 ([M+H]$^+$).

3-Amino-2-fluoro-N-(4-fluorophenyl)-N-methylbenzamide (C123)

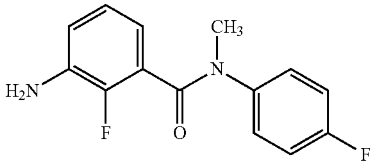 [SMILES: CN(C(=O)c1cccc(N)c1F)c1ccc(F)cc1]

Isolated as a green solid (0.595 g, quant): $^1$H NMR (300 MHz, $CDCl_3$) δ 7.05 (s, 2H), 6.89 (t, J=8.3 Hz, 2H), 6.77 (t, J=7.7 Hz, 1H), 6.59 (dt, J=13.9, 7.6 Hz, 2H), 3.62 (s, 2H), 3.45 (s, 3H); EIMS m/z 263 ([M+H]$^+$).

5-Amino-2,4-difluoro-N-(4-fluorophenyl)benzamide (C124)

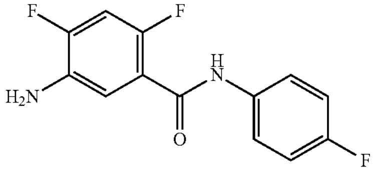 [SMILES: Nc1cc(C(=O)Nc2ccc(F)cc2)c(F)cc1F]

Isolated as a white foam (0.436 g, 87%): $^1$H NMR (300 MHz, $CDCl_3$) δ 8.37 (d, J=16.6 Hz, 1H), 7.66-7.53 (m, 3H), 7.11-7.02 (m, 2H), 6.89 (dd, J=11.6, 10.2 Hz, 1H), 3.79 (s, 2H); EIMS m/z 267 ([M+H]$^+$).

5-Amino-N-(2,4-difluorophenyl)-2-fluorobenzamide (C125)

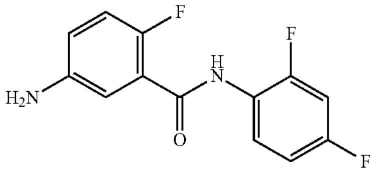 [SMILES: Nc1ccc(F)c(C(=O)Nc2ccc(F)cc2F)c1]

Isolated as a white solid (0.90 g, quant): $^1$H NMR (400 MHz, $CDCl_3$) δ 8.71 (d, J=17.8 Hz, 1H), 8.43 (td, J=9.1, 6.0 Hz, 1H), 7.42 (dd, J=6.4, 3.1 Hz, 1H), 6.99 (dd, J=11.7, 8.7

Hz, 1H), 6.96-6.86 (m, 2H), 6.80 (ddd, J=8.7, 4.1, 3.1 Hz, 1H), 3.82 (s, 2H); $^{19}$F NMR (376 MHz, $CDCl_3$) δ −114.82 (d, J=4.6 Hz), −125.88 (d, J=4.6 Hz), −126.34 (d, J=1.4 Hz); EIMS m/z 267 ([M+H]$^+$).

5-Amino-N-(2,4-difluorophenyl)-2-fluoro-N-methylbenzamide (C126)

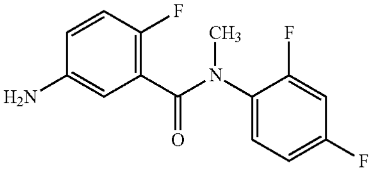 [SMILES: CN(C(=O)c1cc(N)ccc1F)c1ccc(F)cc1F]

Isolated as a brown oil (0.54 g, 57%): $^1$H NMR (400 MHz, DMSO-$d_6$) δ 7.40-7.21 (m, 2H), 7.00 (t, J=8.6 Hz, 1H), 6.63 (t, J=9.1 Hz, 1H), 6.50-6.37 (m, 2H), 5.01 (s, 2H), 3.25 (s, 3H); $^{19}$F NMR (376 MHz, DMSO-$d_6$) δ −109.77 (d, J=7.6 Hz), −116.51 (t, J=7.1 Hz), −131.34 (d, J=6.2 Hz); EIMS m/z 281 ([M+H]$^+$).

5-Amino-2-fluoro-N-methyl-N-phenylbenzamide (C127)

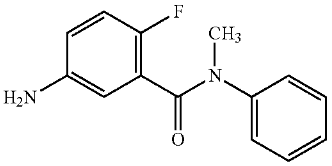 [SMILES: CN(C(=O)c1cc(N)ccc1F)c1ccccc1]

Isolated as a white solid (0.92 g, 71%): $^1$H NMR (400 MHz, DMSO-$d_6$) δ 7.40-7.05 (m, 5H), 6.63 (s, 1H), 6.43 (s, 2H), 4.97 (s, 2H), 3.32 (s, 3H); $^{19}$F NMR (376 MHz, DMSO-$d_6$) δ −131.23; EIMS m/z 245 ([M+H]$^+$).

3-Amino-2-fluoro-N-methyl-N-phenylbenzamide (C128)

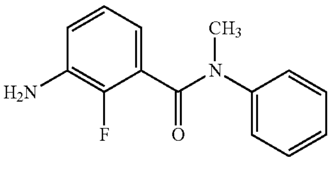 [SMILES: CN(C(=O)c1cccc(N)c1F)c1ccccc1]

Isolated as a white solid (1.07 g, 87%): $^1$H NMR (400 MHz, DMSO-$d_6$) δ 7.41-7.00 (m, 5H), 6.64 (d, J=39.8 Hz, 2H), 6.35 (s, 1H), 5.07 (s, 2H), 3.32 (s, 3H); $^{19}$F NMR (376 MHz, DMSO-$d_6$) δ −137.79; EIMS m/z 245 ([M+H]$^+$).

5-Amino-N-(4-cyano-2-fluorophenyl)-2-fluorobenzamide (C129)

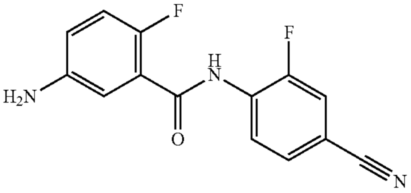 [SMILES: N#Cc1ccc(NC(=O)c2cc(N)ccc2F)c(F)c1]

Isolated as a yellow solid (0.447 g, 95%): $^1$H NMR (400 MHz, DMSO-$d_6$) δ 10.32-10.14 (m, 1H), 8.17 (t, J=8.1 Hz, 1H), 7.95 (dd, J=10.8, 1.8 Hz, 1H), 7.72 (dt, J=8.4, 1.2 Hz, 1H), 7.01 (dd, J=10.5, 8.8 Hz, 1H), 6.89 (dd, J=6.0, 2.9 Hz, 1H), 6.73 (ddd, J=8.8, 4.2, 2.9 Hz, 1H), 5.25 (s, 2H); $^{19}$F NMR (376 MHz, DMSO-$d_6$) δ −120.96, −130.61; EIMS m/z 274 ([M+H]$^+$).

5-Amino-2-chloro-N-ethyl-N-(4-fluorophenyl)benzamide (C130)

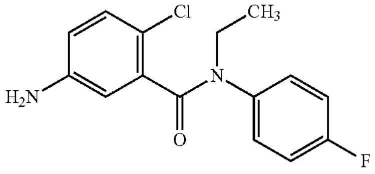 [SMILES: CCN(C(=O)c1cc(N)ccc1Cl)c1ccc(F)cc1]

Isolated as a white solid (0.201 g, 98%): EIMS m/z 293 ([M+H]$^+$).

5-Amino-2-chloro-N-(4-fluorophenyl)-N-(2,2,2-trifluoroethyl)benzamide (C131)

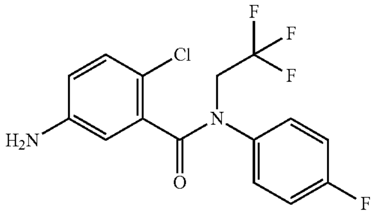 [SMILES: Nc1ccc(Cl)c(C(=O)N(CC(F)(F)F)c2ccc(F)cc2)c1]

Isolated as a white solid (0.125 g, 97%): EIMS m/z 347 ([M+H]$^+$).

5-Amino-2-chloro-N-(4-fluorophenyl)-N-propylbenzamide (C132)

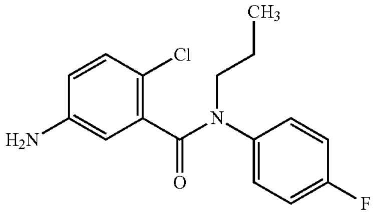 [SMILES: CCCN(C(=O)c1cc(N)ccc1Cl)c1ccc(F)cc1]

Isolated as a white solid (0.267 g, 99%): EIMS m/z 307 ([M+H]$^+$).

5-Amino-N-(4-cyano-2-fluorophenyl)-2-fluoro-N-methylbenzamide (C133)

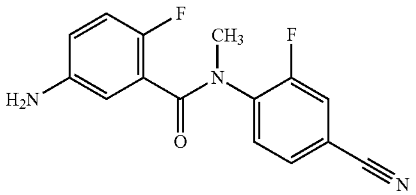

Isolated as an orange solid (0.120 g, 22%): $^1$H NMR (400 MHz, $CDCl_3$) δ 7.45-7.17 (m, 4H), 6.70 (dd, J=5.4, 2.8 Hz, 1H), 6.68-6.52 (m, 1H), 3.63 (s, 2H), 3.40 (s, 3H); $^{19}$F NMR (376 MHz, $CDCl_3$) δ −116.04, −126.81; EIMS m/z 288 ([M+H]$^+$).

5-Amino-2-chloro-N-(4-cyano-2-fluorophenyl)-N-methylbenzamide (C134)

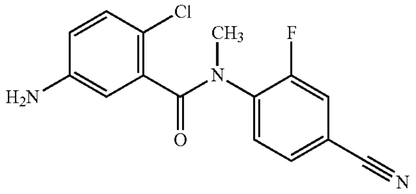

Isolated as a red-orange solid (0.248 g, 33%): EIMS m/z 304 ([M+H]$^+$).

Example 25: Preparation of 6-Amino-3-chloro-N-(4-fluorophenyl)picolinamide (C135)

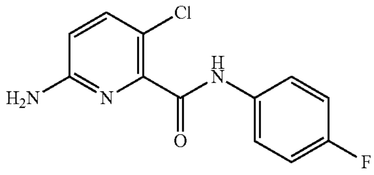 [SMILES: Nc1ccc(Cl)c(C(=O)Nc2ccc(F)cc2)n1]

Step 1. 6-[bis(tert-butoxycarbonyl)amino]-3-chloro-pyridine-2-carboxylic acid (C136) and 6-(tert-butoxycarbonylamino)-3-chloro-pyridine-2-carboxylic acid (C137):

C136

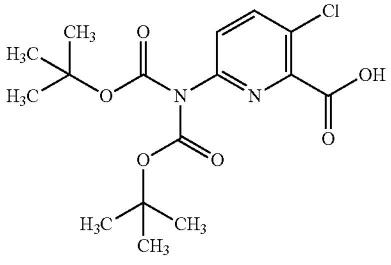

-continued

C137

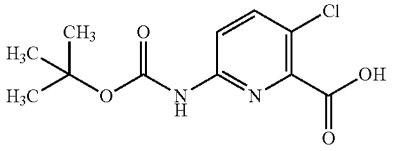

To a solution of methyl 6-[bis(tert-butoxycarbonyl)amino]-3-chloro-pyridine-2-carboxylate (C211) (0.500 g, 1.29 mmol) in tetrahydrofuram (6.5 mL) and water (1.4 mL) was added lithium hydroxide (0.0930 g, 3.88 mmol). After 3 hours, the reaction was acidified with hydrochloric acid (0.5 N), and the reaction mixture was extracted with ethyl acetate. The combined organic phases were washed with water, dried over magnesium sulfate, and concentrated to provide a 3:1 mixture of (C136) and (C137) (0.308 g).

Step 2. tert-butyl N-tert-butoxycarbonyl-N-[5-chloro-6-[(4-fluorophenyl)carbamoyl]-2-pyridyl]carbamate (C138) and tert-butyl N-[5-chloro-6-[(4-fluorophenyl)carbamoyl]-2-pyridyl]carbamate (C139)

C138

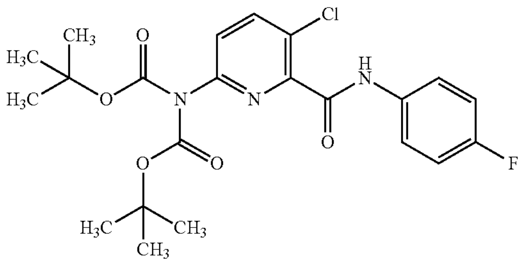

C139

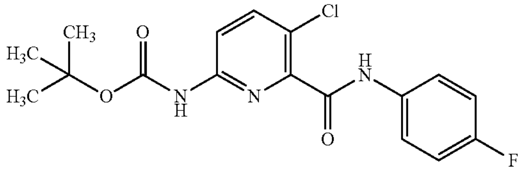

6-[Bis(tert-butoxycarbonyl)amino]-3-chloro-pyridine-2-carboxylic acid (C136) and 6-(tert-butoxycarbonylamino)-3-chloro-pyridine-2-carboxylic acid (C137) (0.308 g) was dissolved in 1,2-dichloroethane (3.5 mL) and 4-dimethylaminopyridine (0.165 g, 1.35 mmol), 4-fluoroaniline (0.118 mL, 1.24 mmol), and 1-ethyl-3-(3-dimethylaminopropyl) carbodiimide hydrochloride (0.298 g, 1.56 mmol) were added at room temperature. The reaction was stirred at room temperature overnight. The reaction mixture was diluted with dichloromethane and washed with saturated aqueous sodium bicarbonate followed by hydrochloric acid (1 N) to provide a 3:1 mixture of (C138) and (C139) (0.537 g).

Step 3. 6-amino-3-chloro-N-(4-fluorophenyl)picolinamide (C135): The mixture of (C138) and (C139) (0.537 g) were dissolved in dichloromethane (2.4 mL), and trifluoroacetic acid (2.4 mL) was added. After 30 minutes, the reaction was poured into a separatory funnel and carefully quenched with saturated aqueous sodium bicarbonate. The mixture was extracted with dichloromethane. The combined organic phases were dried over magnesium sulfate, and concentrated to provide the title compound as a white solid (0.223 g, 0.797 mmol): $^1H$ NMR (400 MHz, DMSO-$d_6$) δ 10.49 (s, 1H), 7.79-7.66 (m, 2H), 7.54 (d, J=8.8 Hz, 1H), 7.24-7.14 (m, 2H), 6.58 (d, J=8.8 Hz, 1H), 6.44 (s, 2H); IR (thin film) 3476, 3339, 1685 $cm^{-1}$; EIMS m/z 266 ($[M]^+$).

Example 26: Preparation of 5-amino-2-chloro-N-(4-fluorophenyl)-N-methylbenzothioamide (C140)

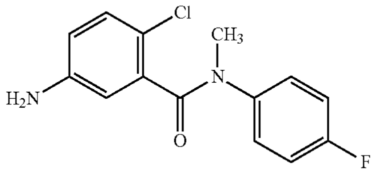

To a solution of 5-amino-2-chloro-N-(4-fluorophenyl) benzamide (C69) (0.300 g, 1.13 mmol) in tetrahydrofuran (4 mL) was added 1,1,1,3,3,3-hexamethyldisiloxane (1.21 mL, 5.67 mmol) followed by phosphorus pentasulfide (0.529 g, 2.38 mmol) in one portion. The reaction was warmed to 60° C. for 3 hours, cooled to room temperature, and filtered over a pad of Celite®. The filtrates were partitioned between ethyl acetate and water. Brine was added until a phase cut was achieved. The phases were separated, and the organic layer adsorbed onto several scoops of Celite®. Purification by flash column chromatography provided the title compound as a yellow solid (0.108 g, 34%): ESIMS m/z 295 ($[M+H]^+$).

The following compounds were prepared in like manner to the procedure outlined in Example 26:

5-Amino-2-chloro-N-(4-fluorophenyl)benzothioamide (C141)

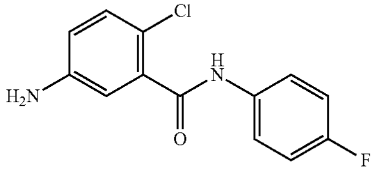

Isolated as a yellow solid (0.108 g, 34%): ESIMS m/z 281 ($[M+H]^+$).

Example 27: Preparation of 5-amino-2-cyano-N-(4-fluorophenyl)benzamide (C142)

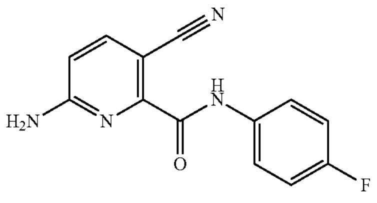

To a solution of 5-amino-2-bromo-N-(4-fluorophenyl) benzamide (C79) (0.460 g, 1.49 mmol) in N,N-dimethylformamide (4.25 mL) was added copper(I) cyanide (0.666 g, 7.44 mmol). The reaction was degassed under vacuum, backfilled with nitrogen, capped in a 25-mL vial, and heated at 160° C. for 20 minutes in a Biotage Initiator® microwave reactor with external IR-sensor temperature monitoring from the side of the vessel. The reaction was diluted with ethyl acetate while stirring vigorously and filtered through Celite® washing with ethyl acetate. The filtrate was washed with brine. The organic phase was dried over magnesium sulfate, filtered, and concentrated to provide the title compound as a yellow solid (0.106 g, 24%): $^1H$ NMR (400 MHz, DMSO-$d_6$) δ 9.53 (s, 1H), 7.85 (d, J=8.0 Hz, 1H), 7.48-7.42 (m, 2H), 7.37-7.29 (m, 2H), 6.94 (s, 1H), 6.89 (d, J=9.0 Hz, 1H), 6.21 (s, 2H); ESIMS m/z 256 ($[M+H]^+$).

Example 28: Preparation of 2-chloro-N-(4-fluorophenyl)-5-nitrobenzamide (C143)

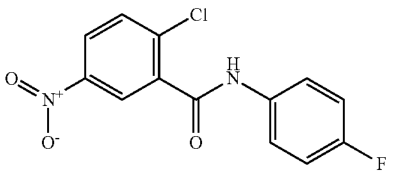

2-Chloro-5-nitrobenzoic acid (0.250 g, 1.24 mmol) and 4-dimethylaminopyridine (0.197 g, 1.61 mmol) were sequentially added to a stirred mixture of 4-fluoroaniline (0.141 ml, 1.49 mmol) and 1-ethyl-3-(3-dimethylaminopropyl)carbodiimide hydrochloride (0.357 g, 1.86 mmol) in 1,2-dichloroethane (12.4 mL) at room temperature. The reaction was stirred at room temperature for 20 hours. The reaction mixture was diluted with dichloromethane and washed with saturated aqueous sodium bicarbonate followed by hydrochloric acid (1 N) to provide the title compound as a light brown solid (0.188 g, 49%): $^1H$ NMR (400 MHz, $CDCl_3$) δ 8.59 (d, J=2.7 Hz, 1H), 8.26 (dd, J=8.8, 2.8 Hz, 1H), 7.90 (s, 1H), 7.66 (d, J=8.8 Hz, 1H), 7.64-7.57 (m, 2H), 7.15-7.05 (m, 2H); $^{19}F$ NMR (376 MHz, $CDCl_3$) δ −116.03; ESIMS m/z 295 ($[M+H]^+$).

The following compounds were prepared in like manner to the procedure outlined in Example 28:

N-(4-Fluorophenyl)-5-nitro-2-(trifluoromethyl)benzamide (C144)

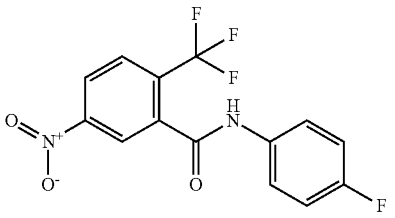 [SMILES: O=C(Nc1ccc(F)cc1)c1cc([N+](=O)[O-])ccc1C(F)(F)F]

Isolated as a light brown solid (0.299 g, 41%): $^1H$ NMR (400 MHz, $CDCl_3$) δ 8.52 (d, J=2.1 Hz, 1H), 8.44 (dd, J=8.7, 1.4 Hz, 1H), 7.99 (d, J=8.6 Hz, 1H), 7.61-7.52 (m, 2H), 7.47 (s, 1H), 7.15-7.06 (m, 2H); EIMS m/z 328 ($[M]^+$).

N-(4-Fluorophenyl)-2-iodo-5-nitrobenzamide (C145)

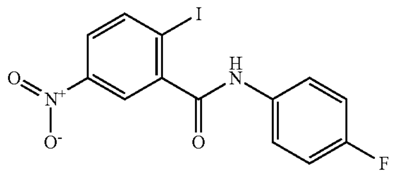

Isolated as a brown solid (0.258 g, 37%): $^{1}$H NMR (400 MHz, DMSO-$d_6$) δ 10.68 (s, 1H), 8.29 (d, J=2.7 Hz, 1H), 8.26 (d, J=8.6 Hz, 1H), 8.03 (dd, J=8.6, 2.7 Hz, 1H), 7.77-7.67 (m, 2H), 7.30-7.19 (m, 2H); IR (thin film) 3219, 3069, 1651 $cm^{-1}$; ESIMS m/z 387 ($[M+H]^+$).

2-Chloro-N-(4-cyanophenyl)-5-nitrobenzamide (C146)

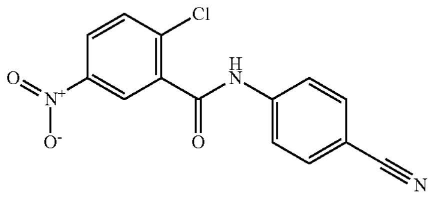

Isolated as a yellow solid (0.252 g, 30%): $^{1}$H NMR (400 MHz, DMSO-$d_6$) δ 11.15 (s, 1H), 8.55 (d, J=2.7 Hz, 1H), 8.37 (dd, J=8.8, 2.8 Hz, 1H), 7.98-7.80 (m, 5H); IR (thin film) 3275, 3100, 2222, 1667 $cm^{-1}$; ESIMS m/z 303 ($[M+H]^+$).

2-Chloro-5-nitro-N-(4-(trifluoromethyl)phenyl)benzamide (C147)

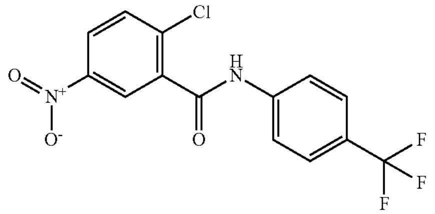 [SMILES: O=C(Nc1ccc(C(F)(F)F)cc1)c1cc([N+](=O)[O-])ccc1Cl]

Isolated as a yellow solid (0.316 g, 35%): $^{1}$H NMR (400 MHz, $CDCl_3$) δ 8.63 (d, J=2.7 Hz, 1H), 8.30 (dd, J=8.8, 2.7 Hz, 1H), 8.00 (s, 1H), 7.79 (d, J=8.5 Hz, 2H), 7.72-7.63 (m, 3H); IR (thin film) 3255, 3078, 1663 $cm^{-1}$; ESIMS m/z 346 ($[M+H]^+$).

2-Chloro-N-(4-chlorophenyl)-5-nitrobenzamide (C148)

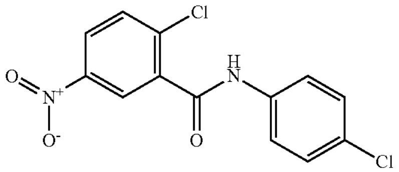 [SMILES: O=C(Nc1ccc(Cl)cc1)c1cc([N+](=O)[O-])ccc1Cl]

Isolated as a yellow solid (0.339 g, 42%): $^{1}$H NMR (400 MHz, $CDCl_3$) δ 8.62 (d, J=2.7 Hz, 1H), 8.28 (dd, J=8.8, 2.7 Hz, 1H), 7.84 (s, 1H), 7.67 (d, J=8.8 Hz, 1H), 7.60 (d, J=8.8 Hz, 2H), 7.38 (d, J=8.8 Hz, 2H); IR (thin film) 3246, 3105, 1657 $cm^{-1}$; ESIMS m/z 312 ($[M+H]^+$).

2-Chloro-N-(2-chloro-4-fluorophenyl)-5-nitrobenzamide (C149)

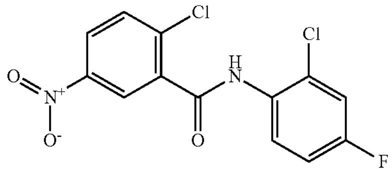

Isolated as a yellow solid (0.135 g, 13%): $^{1}$H NMR (400 MHz, $CDCl_3$) δ 8.70 (d, J=2.7 Hz, 1H), 8.49 (dd, J=9.2, 5.6 Hz, 1H), 8.37 (s, 1H), 8.31 (dd, J=8.8, 2.7 Hz, 1H), 7.70 (d, J=8.8 Hz, 1H), 7.22 (dd, J=7.9, 2.9 Hz, 1H), 7.11 (ddd, J=9.2, 7.9, 2.9 Hz, 1H); IR (thin film) 3237, 3104, 1660 $cm^{-1}$; ESIMS m/z 330 ($[M+H]^+$).

2-Chloro-5-nitro-N-(o-tolyl)benzamide (C150)

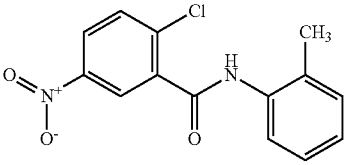

Isolated as a light red solid (0.221 g, 28%): $^{1}$H NMR (400 MHz, $CDCl_3$) δ 8.68 (d, J=2.7 Hz, 1H), 8.28 (dd, J=8.8, 2.7 Hz, 1H), 7.94 (d, J=8.0 Hz, 1H), 7.74 (s, 1H), 7.68 (d, J=8.8 Hz, 1H), 7.33-7.26 (m, 2H), 7.18 (t, J=7.0 Hz, 1H), 2.36 (s, 3H); IR (thin film) 3239, 3103, 1656 $cm^{-1}$; ESIMS m/z 290 ($[M-H]^-$).

N-(4-Fluorophenyl)-2-methyl-5-nitrobenzamide (C151)

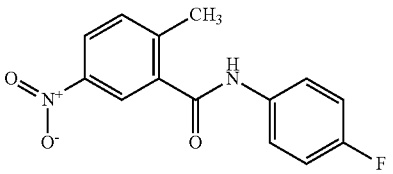

Isolated as a light brown solid (0.504 g, 63%): $^{1}$H NMR (400 MHz, $CDCl_3$) δ 8.36 (s, 1H), 8.23 (d, J=8.4 Hz, 1H), 7.67-7.56 (m, 2H), 7.53 (s, 1H), 7.47 (d, J=8.5 Hz, 1H), 7.10 (t, J=8.2 Hz, 2H), 2.62 (s, 3H); IR (thin film) 3264, 3074, 1648 $cm^{-1}$; ESIMS m/z 275 ($[M+H]^+$).

2-Bromo-N-(4-fluorophenyl)-5-nitrobenzamide (C152)

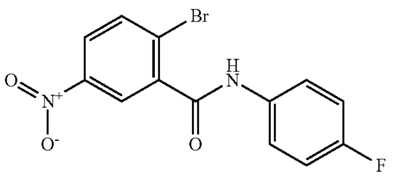

Isolated as a light brown solid (0.370 g, 51%): $^{1}$H NMR (400 MHz, $CDCl_3$) δ 8.48 (d, J=2.6 Hz, 1H), 8.17 (dd, J=8.8, 2.7 Hz, 1H), 7.86 (d, J=8.8 Hz, 1H), 7.66 (s, 1H), 7.64-7.56 (m, 2H), 7.15-7.06 (m, 2H); IR (thin film) 3241, 3097, 1657 $cm^{-1}$; ESIMS m/z 340 ($[M+H]^+$).

N-(4-Fluorophenyl)-5-nitro-2-(1H-1,2,4-triazol-1-yl) benzamide (C153)

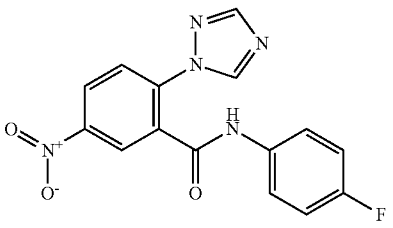 [SMILES: O=C(Nc1ccc(F)cc1)c1cc([N+](=O)[O-])ccc1-n1cncn1]

Isolated as a brown solid (0.367 g, 47%): $^{1}$H NMR (400 MHz, $CDCl_3$) δ 8.69 (d, J=2.5 Hz, 1H), 8.59 (s, 1H), 8.49 (dd, J=8.7, 2.6 Hz, 1H), 8.19 (s, 1H), 7.90 (s, 1H), 7.79 (d, J=8.8 Hz, 1H), 7.50-7.42 (m, 2H), 7.10-7.03 (m, 2H); IR (thin film) 3135, 3013, 1673 $cm^{-1}$; ESIMS m/z 328 ($[M+H]^+$).

N-(4-Fluorophenyl)-4-nitropicolinamide (C154)

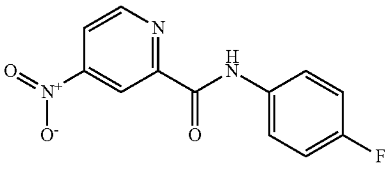 [SMILES: O=C(Nc1ccc(F)cc1)c1cc([N+](=O)[O-])ccn1]

Isolated as a yellow solid (0.602 g, 74%): $^{1}$H NMR (400 MHz, $CDCl_3$) δ 9.84 (s, 1H), 8.99 (dd, J=2.2, 0.6 Hz, 1H), 8.94 (dd, J=5.3, 0.6 Hz, 1H), 8.24 (dd, J=5.3, 2.2 Hz, 1H), 7.80-7.70 (m, 2H), 7.16-7.07 (m, 2H); IR (thin film) 3309, 3076, 1680 $cm^{-1}$; ESIMS m/z 262 ($[M+H]^+$).

2-Chloro-N-(4-fluorophenyl)-3-nitrobenzamide (C155)

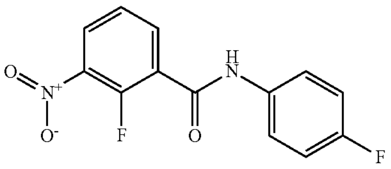

Isolated as a yellow solid (0.544 g, 71%): $^{1}$H NMR (400 MHz, $CDCl_3$) δ 7.87 (ddd, J=12.8, 7.9, 1.6 Hz, 2H), 7.65 (s, 1H), 7.62-7.57 (m, 2H), 7.54 (t, J=7.9 Hz, 1H), 7.14-7.06 (m, 2H); IR (thin film) 3263, 3079, 1654 $cm^{-1}$; ESIMS m/z 296 ($[M+H]^+$).

N-(4-Fluorophenyl)-2-methoxy-5-nitrobenzamide (C156)

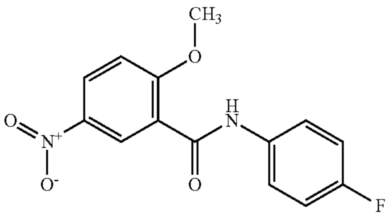 [SMILES: COc1ccc([N+](=O)[O-])cc1C(=O)Nc1ccc(F)cc1]

Isolated as a light brown solid (0.624 g, 81%): $^{1}$H NMR (400 MHz, $CDCl_3$) δ 9.46 (s, 1H), 9.15 (d, J=2.9 Hz, 1H), 8.38 (dd, J=9.1, 3.0 Hz, 1H), 7.66-7.58 (m, 2H), 7.16 (d, J=9.1 Hz, 1H), 7.11-7.04 (m, 2H), 4.20 (s, 3H); IR (thin film) 3350, 2082, 1658 $cm^{-1}$; ESIMS m/z 291 ($[M+H]^+$).

2-Chloro-5-nitro-N-phenylbenzamide (C157)

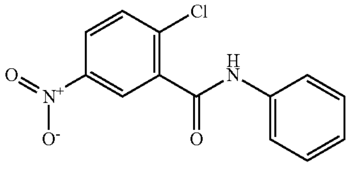 [SMILES: O=C(Nc1ccccc1)c1cc([N+](=O)[O-])ccc1Cl]

Isolated as a white solid (1.51 g, 73%): $^1$H NMR (400 MHz, $CDCl_3$) δ 8.61 (d, J=2.7 Hz, 1H), 8.26 (dd, J=8.8, 2.7 Hz, 1H), 7.85 (s, 1H), 7.70-7.59 (m, 3H), 7.46-7.36 (m, 2H), 7.25-7.18 (m, 1H); $^{13}$C NMR (101 MHz, $CDCl_3$) δ 162.10, 137.49, 136.87, 136.54, 131.63, 129.30, 126.00, 125.55, 125.37, 120.33, 99.98; ESIMS m/z 277 ([M+H]$^+$).

2-Chloro-N-(2-fluorophenyl)-5-nitrobenzamide
(C158)

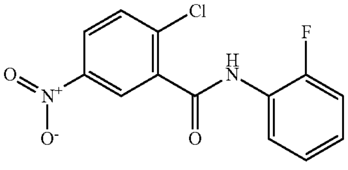 [SMILES: O=C(Nc1ccccc1F)c1cc([N+](=O)[O-])ccc1Cl]

Isolated as a white solid (1.38 g, 63%): $^1$H NMR (400 MHz, $CDCl_3$) δ 8.68 (d, J=2.7 Hz, 1H), 8.50-8.40 (m, 1H), 8.29 (dd, J=8.8, 2.8 Hz, 1H), 8.19 (s, 1H), 7.68 (d, J=8.8 Hz, 1H), 7.26-7.20 (m, 1H), 7.20-7.12 (m, 2H); $^{19}$F NMR (376 MHz, $CDCl_3$) δ −130.45; ESIMS m/z 295 ([M+H]$^+$).

2-Chloro-N-(2,4-difluorophenyl)-5-nitrobenzamide
(C159)

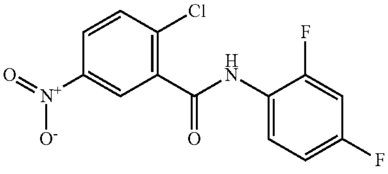

Isolated as a light purple solid (1.48 g, 64%): $^1$H NMR (400 MHz, $CDCl_3$) δ 8.68 (d, J=2.7 Hz, 1H), 8.40 (td, J=9.1, 6.7 Hz, 1H), 8.30 (dd, J=8.8, 2.7 Hz, 1H), 8.09 (s, 1H), 7.69 (d, J=8.8 Hz, 1H), 7.04-6.89 (m, 2H); $^{19}$F NMR (376 MHz, $CDCl_3$) δ −113.04 (d, J=5.0 Hz), −125.45 (d, J=5.1 Hz); ESIMS m/z 313 ([M+H]$^+$). 2-Chloro-N-(4-fluorophenyl)-N-methyl-5-nitrobenzamide (C160)

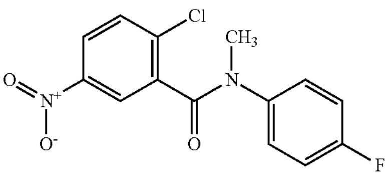 [SMILES: CN(C(=O)c1cc([N+](=O)[O-])ccc1Cl)c1ccc(F)cc1]

Isolated as a green solid (1.80 g, 78%): $^1$H NMR (400 MHz, $CDCl_3$) δ 8.04-7.97 (m, 2H), 7.40 (dd, J=8.5, 0.7 Hz, 1H), 7.19-7.11 (m, 2H), 6.96-6.88 (m, 2H), 3.50 (s, 3H); $^{19}$F NMR (376 MHz, $CDCl_3$) δ −112.30; ESIMS m/z 309 ([M+H]$^+$).

2-Chloro-N-(3-fluorophenyl)-5-nitrobenzamide
(C161)

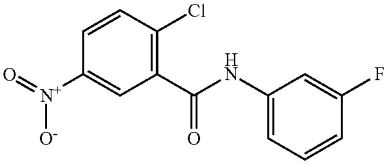 [SMILES: O=C(Nc1cccc(F)c1)c1cc([N+](=O)[O-])ccc1Cl]

Isolated as a white solid (1.38 g, 63%): $^1$H NMR (400 MHz, $CDCl_3$) δ 8.62 (d, J=2.8 Hz, 1H), 8.28 (dd, J=8.8, 2.7 Hz, 1H), 7.90 (s, 1H), 7.67 (d, J=8.8 Hz, 1H), 7.61 (dt, J=10.5, 2.3 Hz, 1H), 7.36 (td, J=8.2, 6.2 Hz, 1H), 7.30-7.27 (m, 1H), 6.93 (tdd, J=8.2, 2.5, 1.0 Hz, 1H); $^{19}$F NMR (376 MHz, $CDCl_3$) δ −110.61; ESIMS m/z 295 ([M+H]$^+$).

2-Chloro-N-(3-cyanophenyl)-5-nitrobenzamide
(C162)

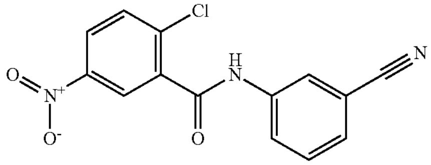 [SMILES: N#Cc1cccc(NC(=O)c2cc([N+](=O)[O-])ccc2Cl)c1]

Isolated as a light solid (1.41 g, 63%): ESIMS m/z 302 ([M+H]$^+$). 2-Chloro-N-(2,3-difluorophenyl)-5-nitrobenzamide (C163)

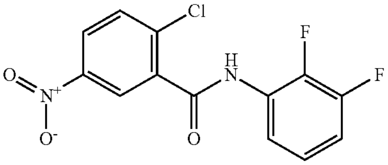 [SMILES: O=C(Nc1cccc(F)c1F)c1cc([N+](=O)[O-])ccc1Cl]

Isolated as a white solid (1.24 g, 53%): $^1$H NMR (400 MHz, $CDCl_3$) δ 8.69 (d, J=2.8 Hz, 1H), 8.31 (dd, J=8.8, 2.7 Hz, 1H), 8.23 (t, J=7.3 Hz, 2H), 7.70 (d, J=8.8 Hz, 1H), 7.22-7.11 (m, 1H), 7.09-6.96 (m, 1H); $^{19}$F NMR (376 MHz, $CDCl_3$) δ −137.23 (d, J=20.2 Hz), −154.19 (d, J=20.3 Hz); ESIMS m/z 313 ([M+H]$^+$).

2-Chloro-N-(3,4-difluorophenyl)-5-nitrobenzamide
(C164)

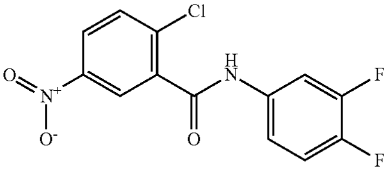 [SMILES: O=C(Nc1ccc(F)c(F)c1)c1cc([N+](=O)[O-])ccc1Cl]

Isolated as a dark colored solid (1.50 g, 65%): $^1$H NMR (400 MHz, DMSO-$d_6$) δ 10.95 (s, 1H), 8.51 (d, J=2.8 Hz, 1H), 8.36 (dd, J=8.8, 2.8 Hz, 1H), 7.91 (d, J=8.9 Hz, 1H), 7.89-7.83 (m, 1H), 7.54-7.37 (m, 2H); $^{19}F$ NMR (376 MHz, DMSO-$d_6$) δ −136.87 (d, J=23.1 Hz), −143.43 (d, J=23.0 Hz); ESIMS m/z 313 ($[M+H]^+$).

2-Chloro-5-nitro-N-(2,4,6-trifluorophenyl)benzamide (C165)

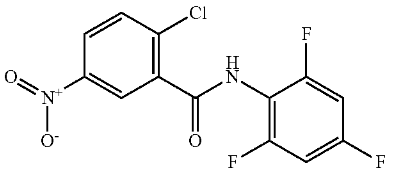 [SMILES: O=C(Nc1c(F)cc(F)cc1F)c1cc([N+](=O)[O-])ccc1Cl]

Isolated as a white solid (1.80 g, 73%): $^1H$ NMR (400 MHz, DMSO-$d_6$) δ 10.59 (s, 1H), 8.43-8.30 (m, 2H), 7.93 (d, J=8.7 Hz, 1H), 7.44-7.30 (m, 2H); $^{19}F$ NMR (376 MHz, DMSO-$d_6$) δ −108.89 (d, J=5.8 Hz), −114.25 (d, J=5.7 Hz); ESIMS m/z 331 ($[M+H]^+$).

2-Chloro-N-(2,6-difluorophenyl)-5-nitrobenzamide (C166)

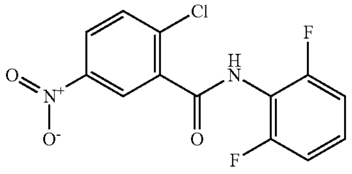 [SMILES: O=C(Nc1c(F)cccc1F)c1cc([N+](=O)[O-])ccc1Cl]

Isolated as a white solid (1.06 g, 46%): $^1H$ NMR (400 MHz, DMSO-$d_6$) δ 10.61 (s, 1H), 8.51-8.21 (m, 2H), 7.93 (d, J=8.7 Hz, 1H), 7.60-7.36 (m, 1H), 7.25 (t, J=8.2 Hz, 2H); $^{19}F$ NMR (376 MHz, DMSO-$d_6$) δ −117.43; ESIMS m/z 313 ($[M+H]^+$).

4-Chloro-N-(4-fluorophenyl)-3-nitrobenzamide (C167)

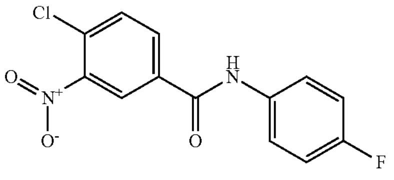 [SMILES: O=C(Nc1ccc(F)cc1)c1ccc(Cl)c([N+](=O)[O-])c1]

Isolated as a yellow solid (0.679 g, 88%): $^1H$ NMR (400 MHz, $CDCl_3$) δ 8.36 (d, J=2.1 Hz, 1H), 8.04 (dd, J=8.4, 2.1 Hz, 1H), 7.95 (s, 1H), 7.69 (d, J=8.4 Hz, 1H), 7.62-7.54 (m, 2H), 7.13-7.04 (m, 2H); IR (thin film) 3342, 3075, 1651 $cm^{-1}$; ESIMS m/z 295 ($[M+H]^+$).

N-(4-Fluorophenyl)-2-methoxy-3-nitrobenzamide (C168)

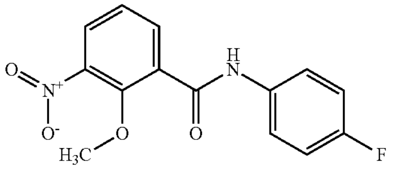

Isolated as a yellow solid (0.600 g, 65%): $^1H$ NMR (400 MHz, DMSO-$d_6$) δ 10.60 (s, 1H), 8.04 (dd, J=8.1, 1.7 Hz, 1H), 7.85 (dd, J=7.7, 1.7 Hz, 1H), 7.78-7.68 (m, 2H), 7.44 (t, J=7.9 Hz, 1H), 7.23 (dt, J=11.5, 8.9 Hz, 2H), 3.88 (s, 3H); $^{13}C$ NMR (101 MHz, DMSO-$d_6$) δ 163.36, 149.49, 143.90, 135.07, 133.51, 133.03, 126.15, 124.42, 121.53 (d, $J_{CF}$=7.8 Hz), 115.43 (d, $J_{CF}$=22.3 Hz), 99.49, 63.30; ESIMS m/z 291 ($[M+H]^+$).

2-Chloro-N-(3-fluorophenyl)-N-methyl-5-nitrobenzamide (C169)

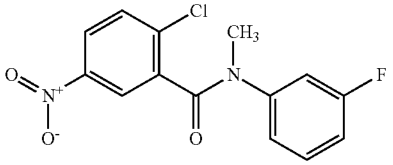 [SMILES: CN(C(=O)c1cc([N+](=O)[O-])ccc1Cl)c1cccc(F)c1]

Isolated as a yellow solid (1.46 g, 64%): $^1H$ NMR (400 MHz, $CDCl_3$) δ 8.02 (d, J=8.3 Hz, 2H), 7.42 (d, J=8.5 Hz, 1H), 7.19 (td, J=8.7, 6.6 Hz, 1H), 6.96-6.86 (m, 3H), 3.52 (s, 3H); $^{19}F$ NMR (376 MHz, $CDCl_3$) δ −110.00; ESIMS m/z 309 ($[M+H]^+$).

2-Chloro-N-(2-fluorophenyl)-N-methyl-5-nitrobenzamide (C170)

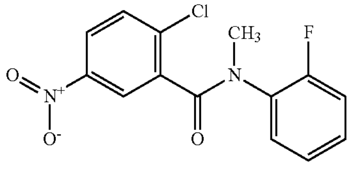 [SMILES: CN(C(=O)c1cc([N+](=O)[O-])ccc1Cl)c1ccccc1F]

Isolated as a light brown solid (0.61 g, 27%): $^1H$ NMR (400 MHz, $CDCl_3$) δ 8.13 (dd, J=2.7, 1.3 Hz, 1H), 7.99 (dd, J=8.8, 2.7 Hz, 1H), 7.38 (d, J=8.8 Hz, 1H), 7.25-7.15 (m, 2H), 7.05-6.97 (m, 2H), 3.48 (d, J=0.5 Hz, 3H).

2-Chloro-N-(4-cyano-2-methylphenyl)-5-nitrobenzamide (C171)

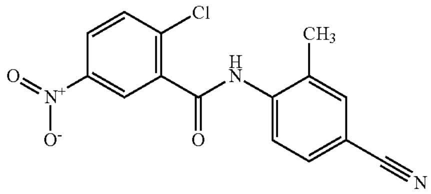

Isolated as a white solid (1.14 g, 49%): $^1H$ NMR (400 MHz, DMSO-$d_6$) δ 10.43 (s, 1H), 8.56 (d, J=2.8 Hz, 1H), 8.35 (dd, J=8.8, 2.8 Hz, 1H), 7.89 (dd, J=14.0, 8.6 Hz, 2H), 7.79 (d, J=1.9 Hz, 1H), 7.77-7.69 (m, 1H), 2.34 (s, 3H); $^{13}C$ NMR (101 MHz, DMSO-$d_6$) δ 163.33, 146.15, 140.02, 137.41, 137.00, 134.26, 133.14, 131.25, 130.22, 125.78, 125.48, 124.03, 118.76, 107.91, 17.62; ESIMS m/z 316 ($[M+H]^+$).

2-Chloro-N-(4-fluoro-2-methylphenyl)-5-nitrobenzamide (C172)

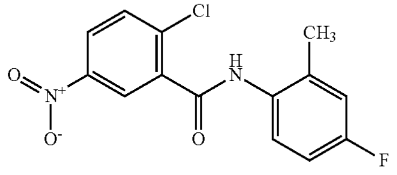

Isolated as a light purple solid (1.45 g, 63%): $^1H$ NMR (400 MHz, DMSO-$d_6$) δ 10.20 (s, 1H), 8.50 (d, J=2.8 Hz, 1H), 8.34 (dd, J=8.8, 2.8 Hz, 1H), 7.90 (d, J=8.9 Hz, 1H), 7.51 (dd, J=8.8, 5.6 Hz, 1H), 7.16 (dd, J=9.8, 3.0 Hz, 1H), 7.09 (td, J=8.6, 3.0 Hz, 1H), 2.30 (s, 3H); $^{19}F$ NMR (376 MHz, $CDCl_3$) δ −116.56; ESIMS m/z 309 ($[M+H]^+$).

N-(4-Fluorophenyl)-6-nitropicolinamide (C173)

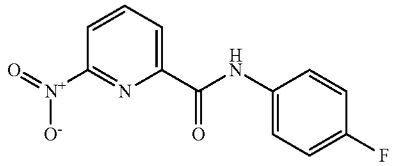

Isolated as a light brown solid (0.511 g, 49%): mp 169-170° C.; $^1H$ NMR (400 MHz, DMSO-$d_6$) δ 10.62 (s, 1H), 8.68-8.29 (m, 3H), 7.92-7.80 (m, 2H), 7.29-7.15 (m, 2H); ESIMS m/z 262 ($[M+H]^+$).

N-(4-Fluorophenyl)-4-methyl-3-nitrobenzamide (C174)

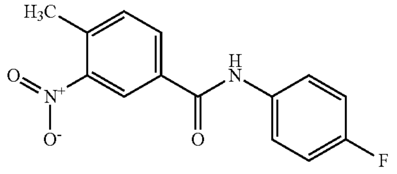 [SMILES: Cc1ccc(C(=O)Nc2ccc(F)cc2)cc1[N+](=O)[O-]]

Isolated as an off-white solid (0.711 g, 89%): mp 136-138° C.; $^1H$ NMR (400 MHz, DMSO-$d_6$) δ 10.52 (s, 1H), 8.57 (d, J=1.8 Hz, 1H), 8.21 (dd, J=8.0, 1.8 Hz, 1H), 7.83-7.74 (m, 2H), 7.69 (d, J=8.1 Hz, 1H), 7.28-7.16 (m, 2H), 2.60 (s, 3H); ESIMS m/z 275 ($[M+H]^+$).

N-(4-fluorophenyl)-5-nitro-2-(trifluoromethoxy)benzamide (C175)

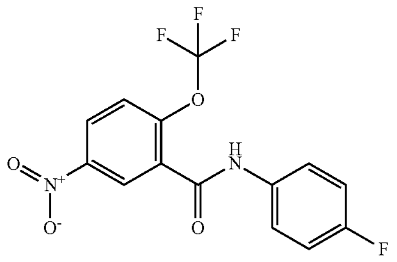 [SMILES: O=C(Nc1ccc(F)cc1)c1cc([N+](=O)[O-])ccc1OC(F)(F)F]

Isolated as a yellow solid (0.544 g, 75%): mp 175-177° C.; $^1H$ NMR (400 MHz, $CDCl_3$) δ 8.97 (d, J=2.9 Hz, 1H), 8.43 (dd, J=9.0, 2.9 Hz, 1H), 8.24 (s, 1H), 7.63-7.57 (m, 2H), 7.57-7.52 (m, 1H), 7.15-7.07 (m, 2H); ESIMS m/z 345 ($[M+H]^+$).

3-Chloro-N-(4-fluorophenyl)-5-nitrobenzamide (C176)

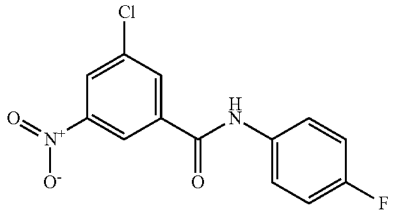 [SMILES: O=C(Nc1ccc(F)cc1)c1cc(Cl)cc([N+](=O)[O-])c1]

Isolated as a yellow solid (0.645 g, 84%): mp 209-210° C.; $^1H$ NMR (400 MHz, DMSO-$d_6$) δ 10.68 (s, 1H), 8.74-8.68 (m, 1H), 8.51 (t, J=2.0 Hz, 1H), 8.47 (t, J=1.7 Hz, 1H), 7.84-7.74 (m, 2H), 7.30-7.17 (m, 2H); ESIMS m/z 295 ($[M-H]^-$).

2-Chloro-N-(2-chlorophenyl)-5-nitrobenzamide (C177)

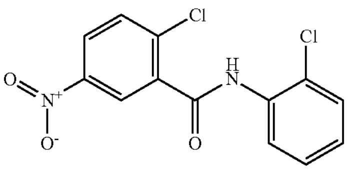 [SMILES: O=C(Nc1ccccc1Cl)c1cc([N+](=O)[O-])ccc1Cl]

Isolated as a yellow solid (1.14 g, 49%): $^1$H NMR (400 MHz, $CDCl_3$) δ 8.69 (d, J=2.7 Hz, 1H), 8.53 (dd, J=8.2, 1.5 Hz, 1H), 8.48 (s, 1H), 8.30 (dd, J=8.8, 2.7 Hz, 1H), 7.69 (d, J=8.8 Hz, 1H), 7.45 (dd, J=8.0, 1.5 Hz, 1H), 7.42-7.32 (m, 1H), 7.20-7.10 (m, 1H); $^{13}$C NMR (101 MHz, $CDCl_3$) δ 161.91, 146.79, 137.41, 136.03, 133.91, 131.81, 129.29, 127.97, 126.28, 125.87, 125.79, 123.41, 122.01; ESIMS m/z 311 ([M+H]$^+$).

2-Chloro-N-(2-isopropylphenyl)-5-nitrobenzamide (C178)

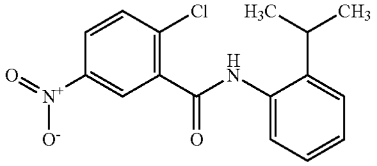 [SMILES: CC(C)c1ccccc1NC(=O)c1cc([N+](=O)[O-])ccc1Cl]

Isolated as a white solid (1.79 g, 75%): $^1$H NMR (400 MHz, DMSO-$d_6$) δ 10.21 (s, 1H), 8.45 (d, J=2.7 Hz, 1H), 8.34 (dd, J=8.8, 2.8 Hz, 1H), 7.89 (d, J=8.8 Hz, 1H), 7.41 (ddd, J=19.3, 7.6, 1.7 Hz, 2H), 7.27 (dtd, J=18.7, 7.3, 1.6 Hz, 2H), 3.34-3.24 (m, 1H), 1.19 (d, J=6.9 Hz, 6H); $^{13}$C NMR (101 MHz, DMSO-$d_6$) δ 163.78, 146.11, 143.95, 138.02, 136.97, 133.74, 131.29, 127.35, 127.05, 125.90, 125.71, 125.50, 123.70, 27.19, 23.25; ESIMS m/z 319 ([M+H]$^+$).

2-Chloro-N-(2-ethyl-6-methylphenyl)-5-nitrobenzamide (C179)

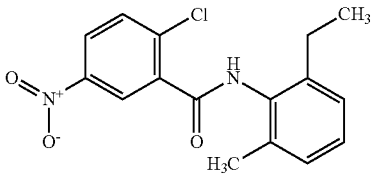 [SMILES: CCc1cccc(C)c1NC(=O)c1cc([N+](=O)[O-])ccc1Cl]

Isolated as a white solid (1.31 g, 55%): $^1$H NMR (400 MHz, DMSO-$d_6$) δ 10.14 (s, 1H), 8.36 (dd, J=8.8, 2.8 Hz, 1H), 8.31 (d, J=2.7 Hz, 1H), 7.92 (d, J=8.8 Hz, 1H), 7.24-7.13 (m, 3H), 2.66 (q, J=7.5 Hz, 2H), 2.30 (s, 3H), 1.17 (t, J=7.5 Hz, 3H); $^{13}$C NMR (101 MHz, DMSO-$d_6$) δ 163.25, 146.11, 141.22, 137.80, 136.96, 135.68, 133.26, 131.56, 127.89, 127.40, 126.30, 125.65, 123.36, 24.41, 18.24, 14.77; ESIMS m/z 319 ([M+H]$^+$).

2-Chloro-N-(3-chlorophenyl)-5-nitrobenzamide (C180)

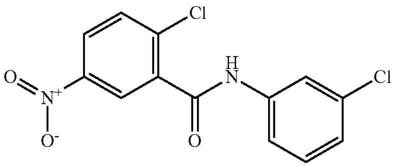 [SMILES: O=C(Nc1cccc(Cl)c1)c1cc([N+](=O)[O-])ccc1Cl]

Isolated as an off-white solid (1.46 g, 63%): $^1$H NMR (400 MHz, DMSO-$d_6$) δ 10.90 (s, 1H), 8.51 (d, J=2.7 Hz, 1H), 8.36 (dd, J=8.8, 2.8 Hz, 1H), 7.99-7.84 (m, 2H), 7.57 (ddd, J=8.2, 2.0, 1.0 Hz, 1H), 7.42 (t, J=8.1 Hz, 1H), 7.22 (ddd, J=8.0, 2.1, 1.0 Hz, 1H); $^{13}$C NMR (101 MHz, DMSO-$d_6$) δ 162.99, 146.13, 139.85, 137.29, 137.02, 133.13, 131.36, 130.60, 125.88, 123.95, 123.93, 119.24, 118.19; ESIMS m/z 311 ([M+H]$^+$).

2-Chloro-N-(2,4-difluorophenyl)-N-methyl-5-nitrobenzamide (C181)

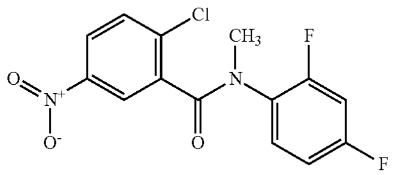

Isolated as a green solid (0.72 g, 36%): $^1$H NMR (300 MHz, $CDCl_3$) δ 8.13 (dd, J=2.7, 1.4 Hz, 1H), 8.03 (dd, J=8.8, 2.7 Hz, 1H), 7.40 (dd, J=8.8, 0.4 Hz, 1H), 7.24 (td, J=8.9, 5.9 Hz, 1H), 6.84-6.71 (m, 2H), 3.45 (d, J=0.5 Hz, 3H); IR (thin film) 3074, 1654, 1527, 1607 $cm^{-1}$; ESIMS m/z 327 ([M+H]$^+$).

2-Chloro-N-(4-cyano-2-fluorophenyl)-5-nitrobenzamide (C182)

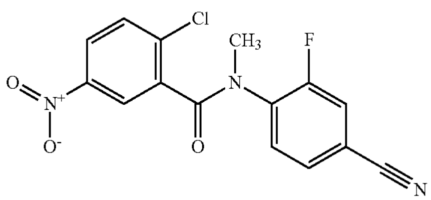 [SMILES: CN(C(=O)c1cc([N+](=O)[O-])ccc1Cl)c1ccc(C#N)cc1F]

Isolated as a tan solid (0.642 g, 41%): $^1$H NMR (400 MHz, DMSO-$d_6$) δ 11.01 (s, 1H), 8.53 (d, J=2.8 Hz, 1H), 8.41-8.24 (m, 2H), 7.98 (dd, J=10.8, 1.9 Hz, 1H), 7.89 (d, J=8.8 Hz, 1H), 7.77 (ddd, J=8.5, 1.9, 0.9 Hz, 1H); $^{19}$F NMR (376 MHz, DMSO-$d_6$) δ −121.17; ESIMS m/z 320 ([M+H]$^+$).

Example 29: Preparation of 2-fluoro-N-(4-fluorophenyl)-5-nitrobenzamide (C183)

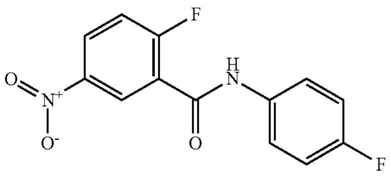

A solution of 2-fluoro-5-nitrobenzoic acid (1.0 g, 5.40 mmol) in thionyl chloride (7.0 mL, 96 mmol) was heated to reflux for 4 hours. The reaction was then concentrated. Dry toluene (1.0 mL) was added to the residue twice and concentrated to remove any residual thionyl chloride. The residue was then dissolved in dry dichloromethane (20 mL). Pyridine (0.87 mL, 11 mmol) was added. The solution was cooled in an ice-bath, and 4-fluoroaniline (0.60 g, 5.4 mmol) dissolved in dichloromethane (5.0 mL) was added over 20 minutes. The reaction was stirred in the ice-bath for 45 minutes. The reaction was washed with hydrochloric acid (1 M) (2×20 mL) followed by saturated aqueous sodium bicarbonate (2×20 mL). The organic layer was poured through a phase separator and concentrated to provide the title compound as a white solid (1.2 g, 71%): $^1$H NMR (400 MHz, $CDCl_3$) δ 9.07 (dd, J=6.6, 3.0 Hz, 1H), 8.42 (ddd, J=9.0, 4.3, 3.0 Hz, 1H), 8.32 (d, J=13.8 Hz, 1H), 7.68-7.59 (m, 2H), 7.40 (dd, J=10.7, 9.0 Hz, 1H), 7.16-7.06 (m, 2H); $^{19}$F NMR (376 MHz, $CDCl_3$) δ −104.29, −116.18; ESIMS m/z 279 ([M+H]$^+$).

The following compounds were prepared in like manner to the procedure outlined in Example 29:

2-Fluoro-N-(4-fluorophenyl)-3-nitrobenzamide (C184)

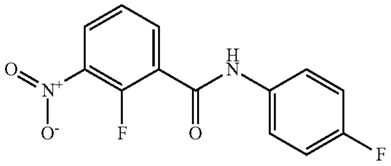

Isolated as a white solid (1.22 g, 81%): $^1$H NMR (400 MHz, $CDCl_3$) δ 8.44 (ddd, J=8.3, 6.6, 1.9 Hz, 1H), 8.27 (s, 1H), 8.22 (ddd, J=8.1, 7.3, 1.9 Hz, 1H), 7.68-7.57 (m, 2H), 7.49 (td, J=8.0, 1.0 Hz, 1H), 7.16-7.05 (m, 2H); $^{19}$F NMR (376 MHz, $CDCl_3$) δ −116.17, −121.77; EIMS m/z 279 ([M]$^+$).

Example 30: Preparation of 2-chloro-5-nitro-N-(pyridin-4-yl)benzamide (C185)

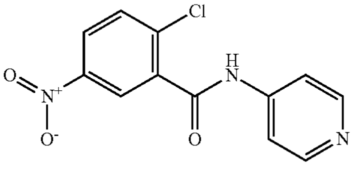 [SMILES: O=C(Nc1ccncc1)c1cc([N+](=O)[O-])ccc1Cl]

To a solution of 2-chloro-5-nitrobenzoic acid (0.500 g, 2.48 mmol) in dichloromethane (8.3 mL) was added oxalyl chloride (0.239 mL, 2.73 mmol) slowly, followed by N,N-dimethylformamide (1 drop). The reaction was stirred at room temperature for 2 hours. To the solution was added triethylamine (0.691 mL, 4.96 mmol) followed by pyridin-4-amine (0.467 g, 4.96 mmol) in dichloromethane (1 mL). The reaction was allowed to stir at room temperature for 16 hours. Purification by flash column chromatography using 0-100% ethyl acetate/hexanes as eluent provided the title compound as a tan solid (0.401 g, 58%): $^1$H NMR (400 MHz, DMSO-$d_6$) δ 11.10 (s, 1H), 8.64-8.45 (m, 3H), 8.37 (dd, J=8.9, 2.8 Hz, 1H), 7.92 (d, J=8.8 Hz, 1H), 7.73-7.61 (m, 2H); $^{13}$C NMR (101 MHz, DMSO-$d_6$) δ 163.67, 150.56, 146.14, 145.04, 136.95, 131.40, 126.06, 124.00, 113.68; ESIMS m/z 278 ([M+H]$^+$).

The following compounds were prepared in like manner to the procedure outlined in Example 30:

2-Chloro-5-nitro-N-(pyridin-3-yl)benzamide (C186)

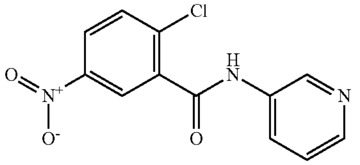 [SMILES: O=C(Nc1cccnc1)c1cc([N+](=O)[O-])ccc1Cl]

Isolated as a white solid (0.480 g, 70%): $^1$H NMR (400 MHz, DMSO-$d_6$) δ 10.95 (s, 1H), 8.85 (dd, J=2.6, 0.7 Hz, 1H), 8.54 (d, J=2.8 Hz, 1H), 8.42-8.31 (m, 2H), 8.15 (ddd, J=8.3, 2.6, 1.5 Hz, 1H), 7.92 (d, J=8.8 Hz, 1H), 7.44 (ddd, J=8.3, 4.7, 0.8 Hz, 1H); $^{13}$C NMR (101 MHz, DMSO-$d_6$) δ 163.19, 146.13, 145.14, 141.29, 137.17, 137.04, 135.17, 131.38, 126.78, 125.92, 123.99, 123.76; ESIMS m/z 278 ([M+H]$^+$).

2-Chloro-N-(2-chloropyridin-3-yl)-5-nitrobenzamide (C187)

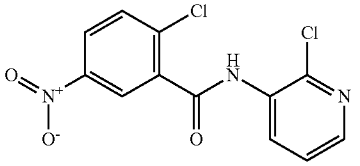 [SMILES: O=C(Nc1cccnc1Cl)c1cc([N+](=O)[O-])ccc1Cl]

Isolated as a white solid (0.364 g, 47%): $^1$H NMR (400 MHz, DMSO-$d_6$) δ 10.67 (s, 1H), 8.53 (d, J=2.8 Hz, 1H), 8.40-8.31 (m, 2H), 8.26 (ddt, J=6.1, 4.5, 2.4 Hz, 1H), 7.91 (d, J=8.9 Hz, 1H), 7.55 (dd, J=7.9, 4.7 Hz, 1H); $^{13}$C NMR (101 MHz, DMSO-$d_6$) δ 146.77, 146.02, 144.78, 137.16, 136.84, 135.87, 131.34, 131.11, 125.95, 124.13, 123.50; ESIMS m/z 312 ([M+H]$^+$).

2-Chloro-N-(6-chloropyridin-3-yl)-5-nitrobenzamide (C188)

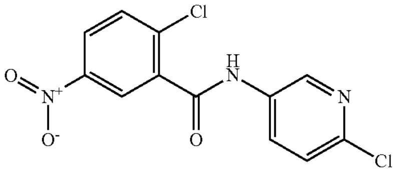 [SMILES: O=C(Nc1ccc(Cl)nc1)c1cc([N+](=O)[O-])ccc1Cl]

Isolated as a white solid (0.639 g, 83%): $^1$H NMR (400 MHz, DMSO-$d_6$) δ 11.10 (s, 1H), 8.71 (d, J=2.7 Hz, 1H), 8.56 (d, J=2.7 Hz, 1H), 8.37 (dd, J=8.8, 2.8 Hz, 1H), 8.19 (dd, J=8.7, 2.8 Hz, 1H), 7.92 (d, J=8.8 Hz, 1H), 7.57 (d, J=8.7 Hz, 1H); $^{13}$C NMR (101 MHz, DMSO-$d_6$) δ 163.20, 146.12, 144.54, 140.93, 137.05, 136.85, 134.79, 131.43, 130.44, 126.08, 124.39, 124.07; ESIMS m/z 312 ([M+H]$^+$).

2-Chloro-N-(6-cyanopyridin-3-yl)-5-nitrobenzamide (C189)

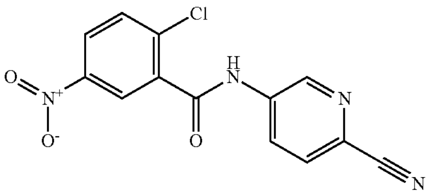 [SMILES: N#Cc1ccc(NC(=O)c2cc([N+](=O)[O-])ccc2Cl)cn1]

Isolated as a white foam (0.433 g, 58%): ESIMS m/z 303 ([M+H]$^+$).

2-Chloro-N-(5-fluoropyridin-2-yl)-5-nitrobenzamide (C190)

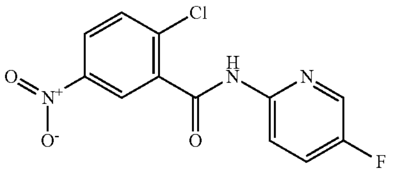

Isolated as a light yellow foam (0.094 g, 21%): $^1$H NMR (300 MHz, Acetone-$d_6$) δ 10.29 (s, 1H), 8.56 (d, J=2.7 Hz, 1H), 8.46-8.34 (m, 2H), 8.27 (d, J=3.0 Hz, 1H), 7.91-7.81 (m, 1H), 7.82-7.70 (m, 1H); IR (thin film) 3112, 1688, 1610, 1576, 1522 cm$^{-1}$; ESIMS m/z 296 ([M+H]$^+$).

5-(2-Chloro-5-nitrobenzamido)-N-methylpicolinamide (C191)

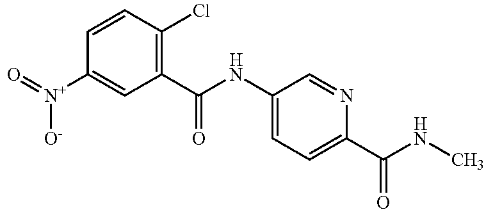 [SMILES: CNC(=O)c1ccc(NC(=O)c2cc([N+](=O)[O-])ccc2Cl)cn1]

Isolated as a light brown foam (0.330 g, 66%): $^1$H NMR (400 MHz, DMSO-$d_6$) δ 11.16 (s, 1H), 8.90 (d, J=2.4 Hz, 1H), 8.66 (q, J=4.8 Hz, 1H), 8.58 (d, J=2.8 Hz, 1H), 8.37 (dd, J=8.9, 2.8 Hz, 1H), 8.30 (dd, J=8.5, 2.4 Hz, 1H), 8.07 (d, J=8.5 Hz, 1H), 7.92 (d, J=8.8 Hz, 1H), 2.82 (d, J=4.8 Hz, 3H); $^{13}$C NMR (101 MHz, DMSO-$d_6$) δ 163.92, 163.34, 146.15, 145.63, 139.52, 137.32, 137.06, 136.89, 131.43, 127.28, 126.07, 124.09, 122.28, 25.90; ESIMS m/z 335 ([M+H]$^+$).

2-Chloro-5-nitro-N-(pyridin-4-yl)benzamide (C192)

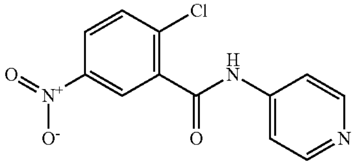 [SMILES: O=C(Nc1ccncc1)c1cc([N+](=O)[O-])ccc1Cl]

Isolated as a tan solid (0.401 g, 58%): $^1$H NMR (400 MHz, DMSO-$d_6$) δ 11.10 (s, 1H), 8.64-8.45 (m, 3H), 8.37 (dd, J=8.9, 2.8 Hz, 1H), 7.92 (d, J=8.8 Hz, 1H), 7.73-7.61 (m, 2H); $^{13}$C NMR (101 MHz, DMSO-$d_6$) δ 163.67, 150.56, 146.14, 145.04, 136.95, 131.40, 126.06, 124.00, 113.68; ESIMS m/z 278 ([M+H]$^+$).

Example 31: Preparation of 2-fluoro-N-(4-fluorophenyl)-N-methyl-5-nitrobenzamide (C193)

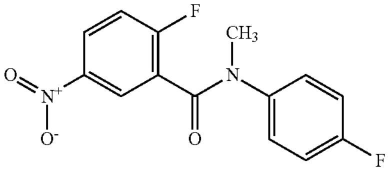 [SMILES: CN(C(=O)c1cc([N+](=O)[O-])ccc1F)c1ccc(F)cc1]

To a solution of 2-fluoro-5-nitrobenzoic acid (0.500 g, 2.70 mmol) in dichloromethane (10 mL) was added oxalyl chloride (0.355 mL, 4.05 mmol) slowly, followed by N,N-dimethylformamide (1 drop). The reaction was stirred at room temperature for 90 minutes. The reaction mixture was concentrated, and the residue was dissolved in dichloromethane (15 mL). To the solution was added pyridine (0.437 mL, 5.40 mmol), and the solution was cooled to 0° C. To the cool solution was added 4-fluoro-N-methylaniline (0.338 g, 2.70 mmol) dissolved in dichloromethane (5 mL) over 20 minutes. After 45 minutes the ice bath was removed, and the reaction was allowed to stir at room temperature for 16 hours. The reaction was diluted with dichloromethane and washed with hydrochloric acid (1 M) (2×20 mL). The organic layer was poured through a phase separator and concentrated to provide the title compound as a white solid (0.804 g, 92%): $^1$H NMR (300 MHz, $CDCl_3$) δ 8.23 (dd, J=5.5, 2.8 Hz, 1H), 8.13 (ddd, J=9.1, 4.4, 2.8 Hz, 1H), 7.14-7.05 (m, 2H), 7.05-6.87 (m, 3H), 3.49 (s, 3H); IR (thin film) 3039, 1647, 1627, 1506 $cm^{-1}$; ESIMS m/z 293 ([M+H]$^+$).

The following compounds were prepared in like manner to the procedure outlined in Example 31:

2-Fluoro-N-(3-fluorophenyl)-N-methyl-5-nitrobenzamide (C194)

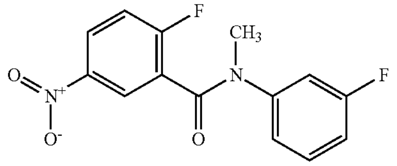 [SMILES: CN(C(=O)c1cc([N+](=O)[O-])ccc1F)c1cccc(F)c1]

Isolated as a white solid (0.740 g, 94%): $^1$H NMR (300 MHz, $CDCl_3$) δ 8.26 (s, 1H), 8.22-8.07 (m, 1H), 7.27-7.13 (m, 1H), 7.03 (t, J=8.6 Hz, 1H), 6.99-6.73 (m, 3H), 3.51 (s, 3H); IR (thin film) 3080, 1659, 1629, 1587 $cm^{-1}$.

2-Fluoro-N-(4-fluorophenyl)-N-methyl-3-nitrobenzamide (C195)

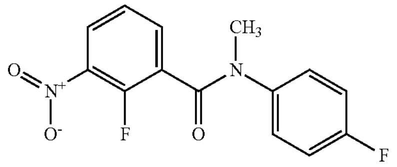 [SMILES: CN(C(=O)c1cccc([N+](=O)[O-])c1F)c1ccc(F)cc1]

Isolated as a yellow solid (0.675 g, 86%): $^1$H NMR (300 MHz, $CDCl_3$) δ 7.93 (ddd, J=8.6, 7.1, 1.8 Hz, 1H), 7.56 (ddd, J=7.4, 5.3, 1.8 Hz, 1H), 7.19 (td, J=8.0, 1.1 Hz, 1H), 7.08 (ddd, J=8.8, 4.7, 1.2 Hz, 2H), 6.99-6.88 (m, 2H), 3.49 (s, 3H); IR (thin film) 3086, 1653, 1614, 1536 $cm^{-1}$; ESIMS m/z 293 ([M+H]$^+$).

2-Chloro-4-fluoro-N-(4-fluorophenyl)-5-nitrobenzamide (C196)

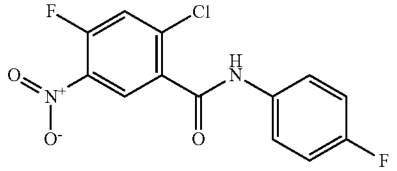 [SMILES: O=C(Nc1ccc(F)cc1)c1cc([N+](=O)[O-])c(F)cc1Cl]

Isolated as a yellow solid (0.532 g, 75%): $^1$H NMR (300 MHz, $CDCl_3$) δ 8.54 (d, J=7.8 Hz, 1H), 7.85 (s, 1H), 7.66-7.54 (m, 2H), 7.48 (d, J=9.9 Hz, 1H), 7.17-7.03 (m, 2H); IR (thin film) 3265, 3072, 1614, 1530 $cm^{-1}$; ESIMS m/z 313 ([M+H]$^+$).

2,4-Difluoro-N-(4-fluorophenyl)-5-nitrobenzamide (C197)

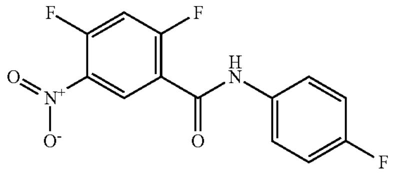 [SMILES: O=C(Nc1ccc(F)cc1)c1cc([N+](=O)[O-])c(F)cc1F]

Isolated as a green solid (0.576 g, 79%): $^1$H NMR (300 MHz, $CDCl_3$) δ 9.00 (t, J=8.2 Hz, 1H), 8.23 (d, J=13.4 Hz, 1H), 7.67-7.53 (m, 2H), 7.21 (dd, J=10.9, 9.7 Hz, 1H), 7.15-7.06 (m, 2H); IR (thin film) 3080, 1687, 1614, 1590 $cm^{-1}$; ESIMS m/z 297 ([M+H]$^+$).

N-(2,4-Difluorophenyl)-2-fluoro-5-nitrobenzamide (C198)

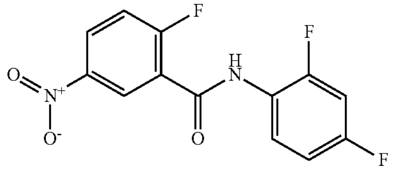 [SMILES: O=C(Nc1ccc(F)cc1F)c1cc([N+](=O)[O-])ccc1F]

Isolated as a grey solid (3.1 g, 97%): $^1$H NMR (400 MHz, $CDCl_3$) δ 9.08 (dd, J=6.6, 3.0 Hz, 1H), 8.56 (d, J=14.5 Hz, 1H), 8.42 (ddt, J=14.1, 8.7, 5.0 Hz, 2H), 7.41 (dd, J=10.6, 9.1 Hz, 1H), 6.95 (tdd, J=11.1, 7.0, 3.2 Hz, 2H); $^{19}$F NMR (376 MHz, $CDCl_3$) δ −104.13, −113.26 (d, J=5.0 Hz), −125.68 (d, J=5.2 Hz); ESIMS m/z 297 ([M+H]$^+$).

2-Fluoro-N-methyl-5-nitro-N-phenylbenzamide (C199)

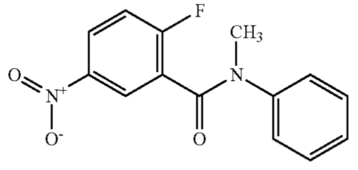 [SMILES: CN(C(=O)c1cc([N+](=O)[O-])ccc1F)c1ccccc1]

Isolated as a brown oil (1.45 g, 98%): $^1$H NMR (400 MHz, $CDCl_3$) δ 8.21 (dd, J=5.6, 2.8 Hz, 1H), 8.15-8.05 (m, 1H), 7.26-7.14 (m, 3H), 7.09 (d, J=7.7 Hz, 2H), 6.98 (t, J=8.6 Hz, 1H), 3.52 (s, 3H); $^{19}$F NMR (376 MHz, $CDCl_3$) δ −102.19; ESIMS m/z 275 ([M+H]$^+$).

2-Fluoro-N-methyl-3-nitro-N-phenylbenzamide (C200)

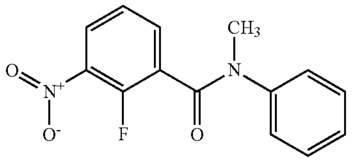 [SMILES: CN(C(=O)c1cccc([N+](=O)[O-])c1F)c1ccccc1]

Isolated as a light brown solid (1.38 g, 93%): $^{1}H$ NMR (400 MHz, $CDCl_3$) δ 7.94-7.85 (m, 1H), 7.55 (ddd, J=7.5, 5.4, 1.8 Hz, 1H), 7.26-7.12 (m, 4H), 7.08 (d, J=7.6 Hz, 2H), 3.51 (s, 3H); $^{19}F$ NMR (376 MHz, $CDCl_3$) δ −118.54; ESIMS m/z 275 ($[M+H]^+$).

N-(4-Cyano-2-fluorophenyl)-2-fluoro-5-nitrobenzamide (C201)

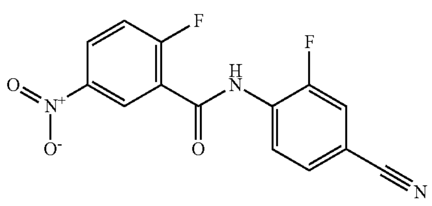 [SMILES: N#Cc1ccc(NC(=O)c2cc([N+](=O)[O-])ccc2F)c(F)c1]

Isolated as a light brown solid (1.1 g, 84%): $^{1}H$ NMR (400 MHz, DMSO-$d_6$) δ 10.89 (s, 1H), 8.59 (dd, J=5.8, 2.9 Hz, 1H), 8.49 (ddd, J=9.1, 4.3, 3.0 Hz, 1H), 8.24 (t, J=8.1 Hz, 1H), 7.99 (dd, J=10.8, 1.8 Hz, 1H), 7.77 (ddd, J=8.4, 1.9, 0.9 Hz, 1H), 7.69 (t, J=9.2 Hz, 1H); $^{19}F$ NMR (376 MHz, DMSO-$d_6$) δ −103.66, −120.88; ESIMS m/z 304 ($[M+H]^+$).

Example 32: Preparation of N-(2,4-difluorophenyl)-2-fluoro-N-methyl-5-nitrobenzamide (C202)

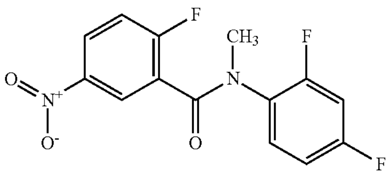 [SMILES: CN(C(=O)c1cc([N+](=O)[O-])ccc1F)c1ccc(F)cc1F]

To a solution of N-(2,4-difluorophenyl)-2-fluoro-5-nitrobenzamide (C198) (1.00 g, 3.38 mmol) in dry N,N-dimethylformamide (15 mL) cooled in an ice bath was added sodium hydride (60% oil immersion, 0.162 g, 4.05 mmol). The slurry was stirred for 30 minutes, and iodomethane (0.422 mL, 6.75 mmol) was added. The reaction was stirred for 2 hours. An additional amount of sodium hydride (0.0400 g) was added. An additional amount of iodomethane (0.100 mL) was added. The reaction was left to stir for 16 hours. The reaction was quenched by the slow addition of water (15 mL) and diluted with ethyl acetate (25 mL). The phases were cut, and the organic layer washed with 1:1 brine/water (3×20 mL). The organic layer was dried over magnesium sulfate, filtered, and concentrated to provide the title compound as a brown oil (1.05 g, quant): $^{1}H$ NMR (400 MHz, $CDCl_3$) δ 8.32-8.24 (m, 1H), 8.15 (ddd, J=9.1, 4.3, 2.8 Hz, 1H), 7.23-7.12 (m, 1H), 7.02 (dd, J=9.1, 8.2 Hz, 1H), 6.85-6.71 (m, 2H), 3.44 (s, 3H); $^{19}F$ NMR (376 MHz, $CDCl_3$) δ −102.79 (d, J=5.6 Hz), −107.11 (d, J=8.2 Hz), −115.48 (dd, J=8.3, 5.6 Hz); ESIMS m/z 311 ($[M+H]^+$).

The following compounds were prepared in like manner to the procedure outlined in Example 32:

2-Chloro-N-ethyl-N-(4-fluorophenyl)-5-nitrobenzamide (C203)

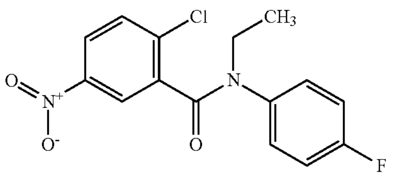 [SMILES: CCN(C(=O)c1cc([N+](=O)[O-])ccc1Cl)c1ccc(F)cc1]

Isolated as a tan solid using iodoethane (0.225 g, quant): $^{1}H$ NMR (400 MHz, $CDCl_3$) δ 8.02-7.94 (m, 2H), 7.42-7.35 (m, 1H), 7.18-7.11 (m, 2H), 6.98-6.86 (m, 2H), 3.97 (q, J=7.2 Hz, 2H), 1.27 (t, J=7.2 Hz, 4H); $^{19}F$ NMR (376 MHz, $CDCl_3$) δ −112.13; ESIMS m/z 323 ($[M+H]^+$).

2-Chloro-N-(4-fluorophenyl)-5-nitro-N-(2,2,2-trifluoroethyl)benzamide (C204)

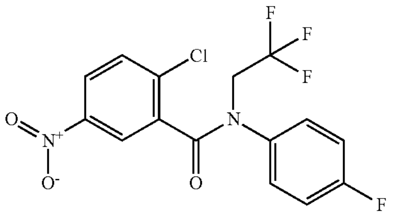 [SMILES: O=C(c1cc([N+](=O)[O-])ccc1Cl)N(CC(F)(F)F)c1ccc(F)cc1]

Isolated as a white solid using 2,2,2-trifluoroethylmethanesulfonate (0.147 g, 58%): $^{1}H$ NMR (400 MHz, $CDCl_3$) δ 8.03 (dd, J=8.7, 2.7 Hz, 1H), 8.00 (d, J=2.5 Hz, 1H), 7.42 (dd, J=8.8, 0.5 Hz, 1H), 7.25-7.19 (m, 2H), 6.99-6.91 (m, 2H), 4.55 (q, J=8.6 Hz, 2H); $^{19}F$ NMR (376 MHz, $CDCl_3$) δ −68.62, −110.49; ESIMS m/z 377 ($[M+H]^+$).

2-Chloro-N-(4-fluorophenyl)-5-nitro-N-propylbenzamide (C205)

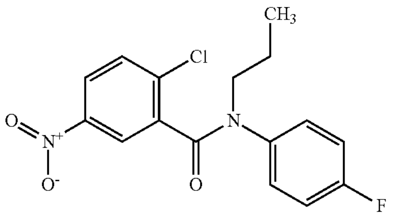 [SMILES: CCCN(C(=O)c1cc([N+](=O)[O-])ccc1Cl)c1ccc(F)cc1]

Isolated as a tan solid using iodopropane (0.296 g, quant): $^{1}H$ NMR (400 MHz, DMSO-$d_6$) δ 8.32 (d, J=2.8 Hz, 1H), 8.05 (dd, J=8.8, 2.8 Hz, 1H), 7.62 (d, J=8.8 Hz, 1H), 7.42-7.34 (m, 2H), 7.15-7.06 (m, 2H), 3.81 (t, J=7.4 Hz, 2H), 1.55 (h, J=7.4 Hz, 2H), 0.93 (t, J=7.4 Hz, 3H); $^{19}F$ NMR (376 MHz, DMSO-$d_6$) δ −113.51; ESIMS m/z 337 ($[M+H]^+$).

N-Allyl-2-chloro-N-(4-fluorophenyl)-5-nitrobenzamide (C206)

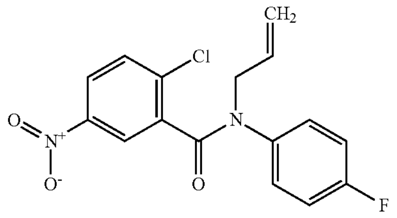 [SMILES: C=CCN(C(=O)c1cc([N+](=O)[O-])ccc1Cl)c1ccc(F)cc1]

Isolated as a white solid using 3-bromoprop-1-ene (0.269 g, 91%): $^1H$ NMR (400 MHz, DMSO-$d_6$) δ 8.40 (d, J=2.8 Hz, 1H), 8.06 (dd, J=8.9, 2.8 Hz, 1H), 7.62 (d, J=8.9 Hz, 1H), 7.43-7.30 (m, 2H), 7.17-7.02 (m, 2H), 5.93 (ddt, J=17.2, 10.2, 6.0 Hz, 1H), 5.31-5.11 (m, 2H), 4.47 (d, J=6.0 Hz, 2H); $^{19}F$ NMR (376 MHz, DMSO-$d_6$) δ −113.49; ESIMS m/z 335 ($[M+H]^+$).

N-(4-Cyano-2-methylphenyl)-2-fluoro-N-methyl-5-nitrobenzamide (C207)

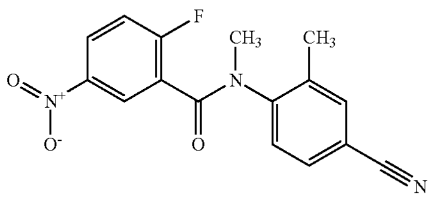 [SMILES: Cc1cc(C#N)ccc1N(C)C(=O)c1cc([N+](=O)[O-])ccc1F]

Isolated as a tan solid (0.595 g, 94%): $^1H$ NMR (400 MHz, DMSO-$d_6$) δ 8.52-8.17 (m, 2H), 7.94 (d, J=10.1 Hz, 1H), 7.84-7.60 (m, 2H), 7.44 (s, 1H), 3.36 (s, 3H); $^{19}F$ NMR (376 MHz, DMSO-$d_6$) δ −104.90, −118.40; ESIMS m/z 318 ($[M+H]^+$).

2-Chloro-N-(4-cyano-2-fluorophenyl)-N-methyl-5-nitrobenzamide (C208)

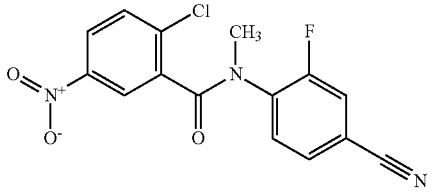 [SMILES: CN(C(=O)c1cc([N+](=O)[O-])ccc1Cl)c1ccc(C#N)cc1F]

Isolated as a white solid (0.826 g, 95%): ESIMS m/z 334 ($[M+H]^+$).

Example 33: Preparation of 5-nitro-2-(1H-1,2,4-triazol-1-yl)benzoic acid (C209)

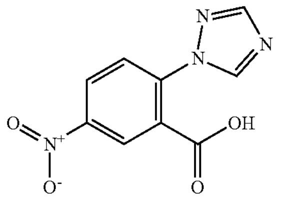 [SMILES: O=C(O)c1cc([N+](=O)[O-])ccc1-n1cncn1]

To a solution of methyl 5-nitro-2-(1H-1,2,4-triazol-1-yl)benzoate (C210) (1.24 g, 5.00 mmol) in tetrahydrofuran (25 mL) and water (5.0 mL) was added lithium hydroxide (0.359 g, 15.0 mmol). The reaction was stirred at room temperature for 2.5 hours. The reaction was acidified with hydrochloric acid (1 N), and the reaction mixture was extracted with ethyl acetate. The combined organic layers were washed with brine, dried over magnesium sulfate, filtered, and concentrated to provide the title compound as a faint yellow solid (1.14 g, 93%): $^1H$ NMR (400 MHz, DMSO-$d_6$) δ 13.83 (s, 1H), 9.11 (s, 1H), 8.63-8.50 (m, 2H), 8.29 (s, 1H), 7.98 (d, J=8.7 Hz, 1H); IR (thin film) 3169, 3097, 1713 $cm^{-1}$; ESIMS m/z 235 ($[M+H]^+$).

Example 34: Preparation of methyl 5-nitro-2-(1H-1,2,4-triazol-1-yl)benzoate (C210)

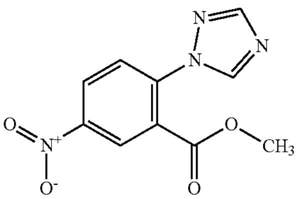 [SMILES: COC(=O)c1cc([N+](=O)[O-])ccc1-n1cncn1]

To a solution of methyl 2-chloro-5-nitrobenzoate (2.00 g, 9.28 mmol) in N,N-dimethylformamide (18.5 mL) was added 1H-1,2,4-triazole (0.673 g, 9.74 mmol). The reaction was stirred at 50° C. for 2 hours, at room temperature overnight, and heated at 80° C. for 2 hours. Water was added, and the mixture was extracted with diethyl ether. The combined organic layers were washed with brine (2×), dried over magnesium sulfate, filtered, and concentrated to provide the title compound as a faint yellow solid (1.25 g, 51%): $^1H$ NMR (400 MHz, DMSO-$d_6$) δ 9.21 (s, 1H), 8.62-8.57 (m, 2H), 8.31 (s, 1H), 8.09-8.03 (m, 1H), 3.75 (s, 3H); ESIMS m/z 249 ($[M+H]^+$).

Example 35: Preparation of methyl 6-[bis(tert-butoxycarbonyl)amino]-3-chloro-pyridine-2-carboxylate (C211)

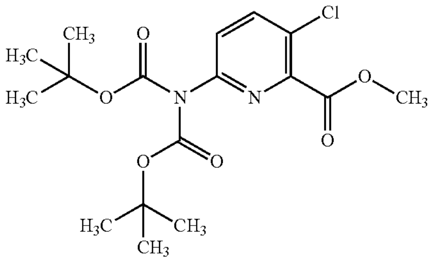 [SMILES: COC(=O)c1nc(N(C(=O)OC(C)(C)C)C(=O)OC(C)(C)C)ccc1Cl]

To a solution of methyl 6-amino-3-chloropicolinate (2.00 g, 10.7 mmol) in tert-butanol (21 mL) and acetone (6.0 mL) was added 4-dimethylaminopyridine (0.0200 g, 0.161 mmol) and di-tert-butyl dicarbonate (8.21 mL, 35.4 mmol). The reaction was stirred at room temperature for 2 days. The reaction was diluted with ethyl acetate, washed with water, dried over magnesium sulfate, filtered, and concentrated.

Purification by flash column chromatography using 0-100% ethyl acetate/hexanes as eluent provided the title compound as a white solid (2.45 g, 56%): $^{1}H$ NMR (400 MHz, $CDCl_3$) δ 7.81 (d, J=8.6 Hz, 1H), 7.40 (d, J=8.6 Hz, 1H), 3.97 (s, 3H), 1.46 (s, 18H); IR (thin film) 2978, 1778, 1742 $cm^{-1}$; EIMS m/z 387 ($[M]^+$).

The following molecules in Table 1 may be prepared according to the procedures disclosed above.

TABLE P1

| Structure and preparation method for prophetic molecules | | |
|---|---|---|
| No. | Structure | Prep* |
| P1 | 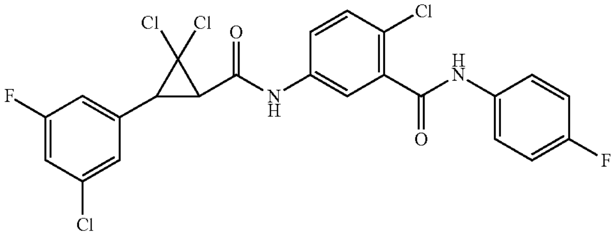 [SMILES: O=C(Nc1ccc(F)cc1)c1cc(NC(=O)C2C(c3cc(F)cc(Cl)c3)C2(Cl)Cl)ccc1Cl] | 13, 14, 15, 18, 18 |
| P2 | 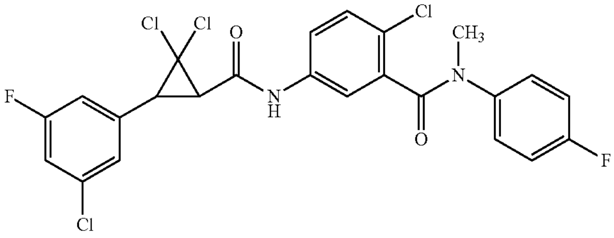 [SMILES: CN(C(=O)c1cc(NC(=O)C2C(c3cc(F)cc(Cl)c3)C2(Cl)Cl)ccc1Cl)c1ccc(F)cc1] | 13, 14, 15, 18, 18 |
| P3 | 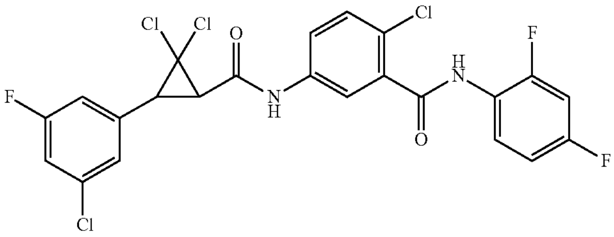 [SMILES: O=C(Nc1ccc(F)cc1F)c1cc(NC(=O)C2C(c3cc(F)cc(Cl)c3)C2(Cl)Cl)ccc1Cl] | 13, 14, 15, 18 |
| P4 | 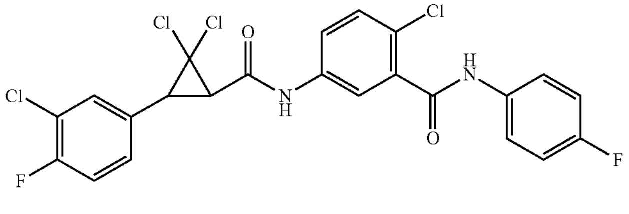 | 13, 14, 15, 18 |

TABLE P1-continued
| Structure and preparation method for prophetic molecules | | |
|---|---|---|
| No. | Structure | Prep* |
| P5 | 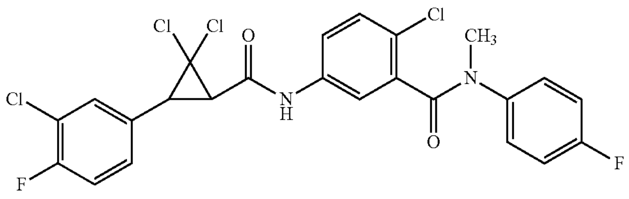 [SMILES: CN(C(=O)c1cc(NC(=O)C2C(c3ccc(F)c(Cl)c3)C2(Cl)Cl)ccc1Cl)c1ccc(F)cc1] | 13, 14, 15, 18 |
| P6 | 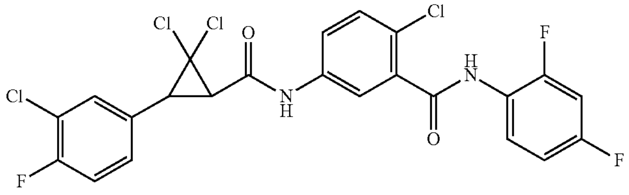 | 13, 14, 15, 18 |
| P7 | 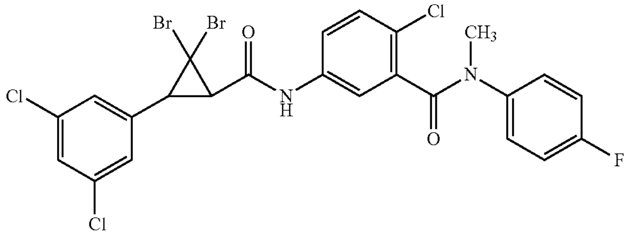 | 13, 14, 15, 18 |
| P8 | 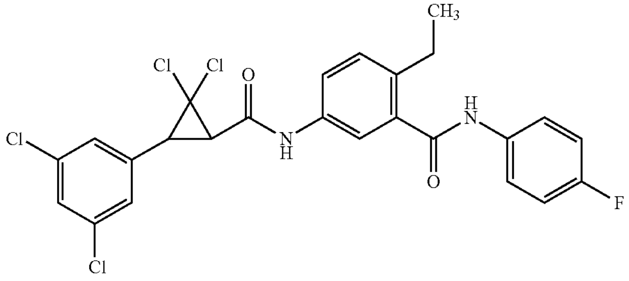 [SMILES: CCc1ccc(NC(=O)C2C(c3cc(Cl)cc(Cl)c3)C2(Cl)Cl)cc1C(=O)Nc1ccc(F)cc1] | 13, 14, 15, 18 |
| P9 | 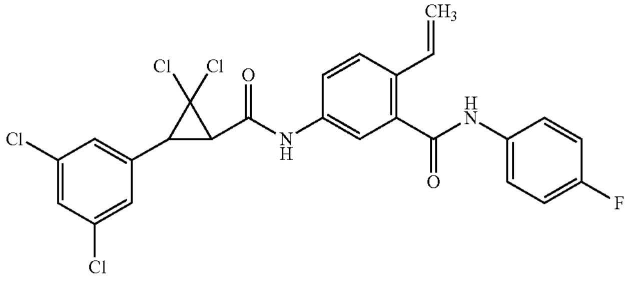 [SMILES: C=Cc1ccc(NC(=O)C2C(c3cc(Cl)cc(Cl)c3)C2(Cl)Cl)cc1C(=O)Nc1ccc(F)cc1] | 13, 14, 15, 18 |
| P10 | 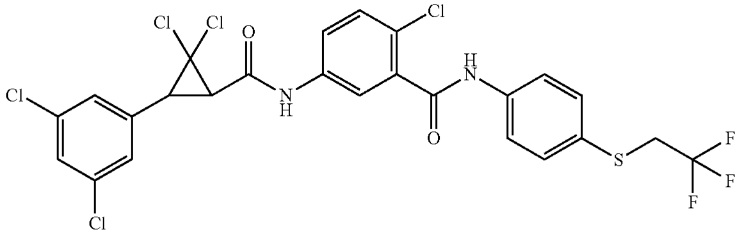 | 13, 14, 15, 18 |

TABLE P1-continued
| Structure and preparation method for prophetic molecules | | |
|---|---|---|
| No. | Structure | Prep* |
| P11 | 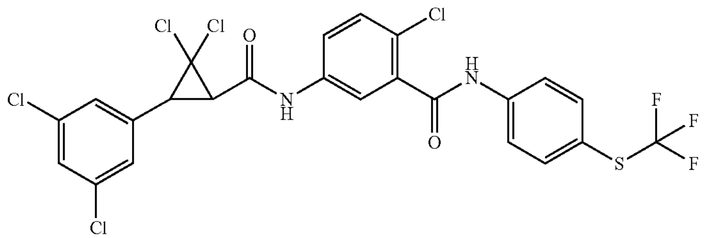 | 13, 14, 15, 18 |
| P12 | 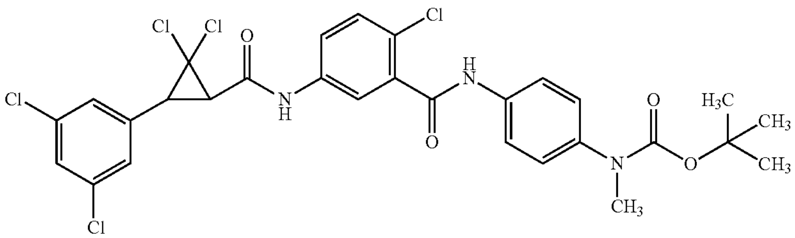 [SMILES: CN(C(=O)OC(C)(C)C)c1ccc(NC(=O)c2cc(NC(=O)C3C(c4cc(Cl)cc(Cl)c4)C3(Cl)Cl)ccc2Cl)cc1] | 13, 14, 15, 18 |
| P13 | 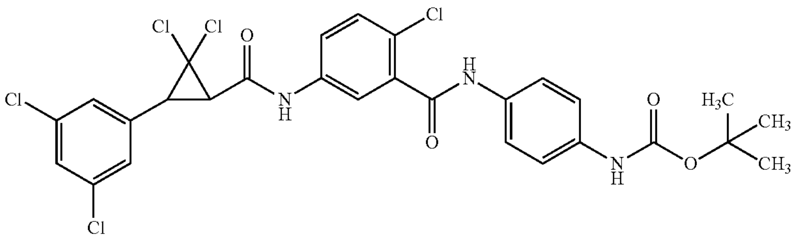 | 13, 14, 15, 18 |
| P14 | 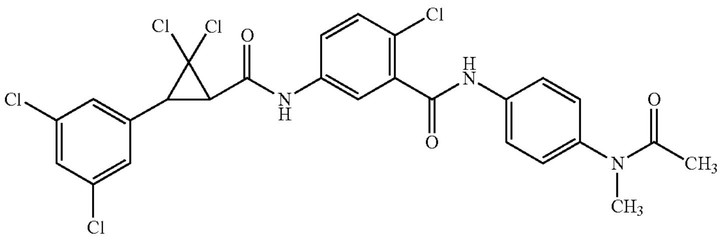 [SMILES: CC(=O)N(C)c1ccc(NC(=O)c2cc(NC(=O)C3C(c4cc(Cl)cc(Cl)c4)C3(Cl)Cl)ccc2Cl)cc1] | 13, 14, 15, 18 |
| P15 | 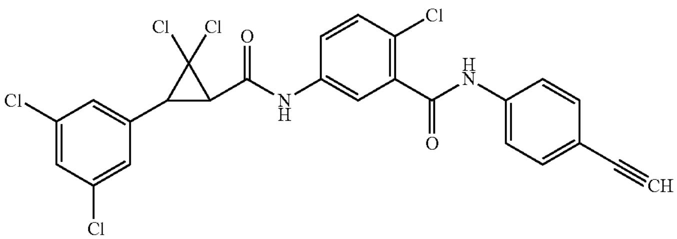 [SMILES: C#Cc1ccc(NC(=O)c2cc(NC(=O)C3C(c4cc(Cl)cc(Cl)c4)C3(Cl)Cl)ccc2Cl)cc1] | 13 ,14, 15, 18 |
| P16 | 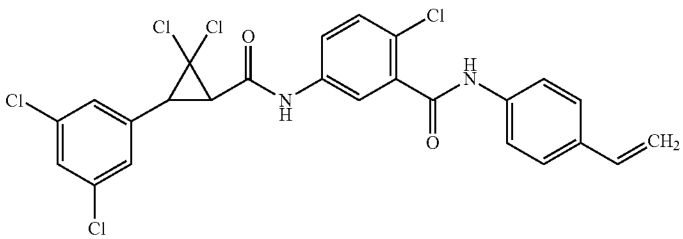 | 13, 14, 15, 18 |

TABLE P1-continued
| Structure and preparation method for prophetic molecules | | |
|---|---|---|
| No. | Structure | Prep* |
| P17 | 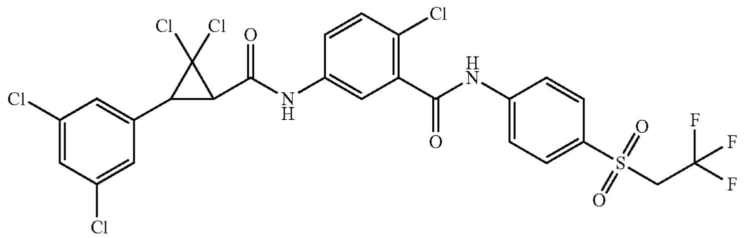 [SMILES: O=C(Nc1ccc(S(=O)(=O)CC(F)(F)F)cc1)c1cc(NC(=O)C2C(c3cc(Cl)cc(Cl)c3)C2(Cl)Cl)ccc1Cl] | 13, 145, 15, 18 |
| P18 | 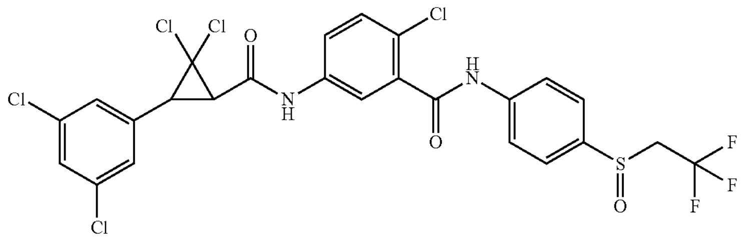 [SMILES: O=C(Nc1ccc(S(=O)CC(F)(F)F)cc1)c1cc(NC(=O)C2C(c3cc(Cl)cc(Cl)c3)C2(Cl)Cl)ccc1Cl] | 13, 14, 15, 18 |
| P19 | 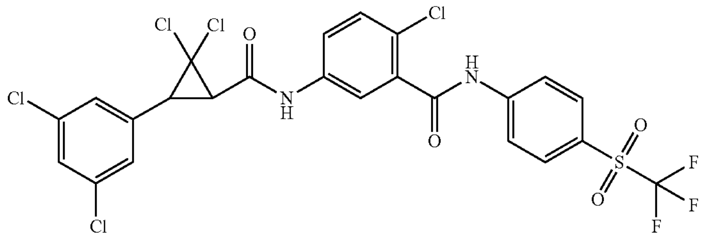 [SMILES: O=C(Nc1ccc(S(=O)(=O)C(F)(F)F)cc1)c1cc(NC(=O)C2C(c3cc(Cl)cc(Cl)c3)C2(Cl)Cl)ccc1Cl] | 13, 14, 15, 18 |
| P20 | 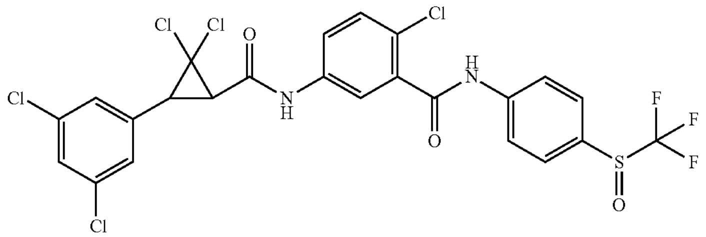 [SMILES: O=C(Nc1ccc(S(=O)C(F)(F)F)cc1)c1cc(NC(=O)C2C(c3cc(Cl)cc(Cl)c3)C2(Cl)Cl)ccc1Cl] | 13, 14, 15, 18 |
| P21 | 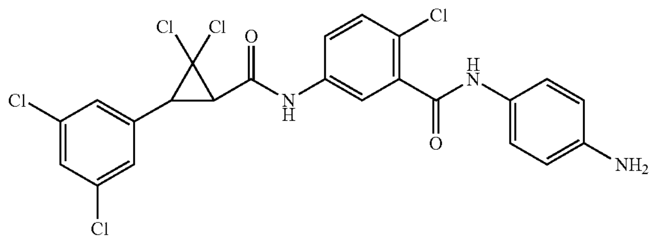 [SMILES: Nc1ccc(NC(=O)c2cc(NC(=O)C3C(c4cc(Cl)cc(Cl)c4)C3(Cl)Cl)ccc2Cl)cc1] | Scheme 5 |
| P22 | 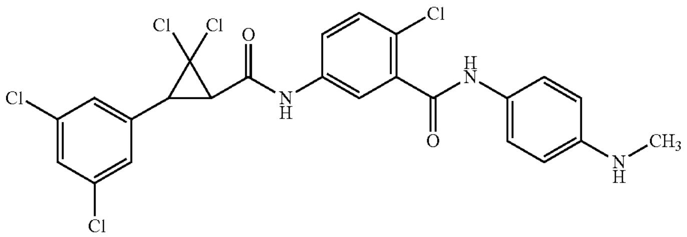 | Scheme 5 |

TABLE P1-continued
| Structure and preparation method for prophetic molecules | | |
|---|---|---|
| No. | Structure | Prep* |
| P23 | 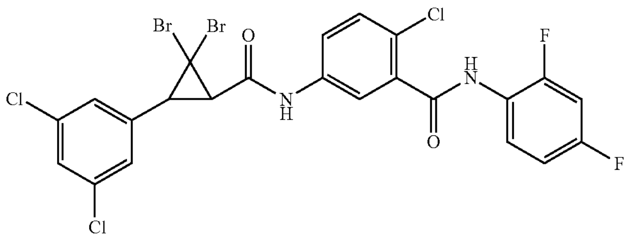 | 13, 14, 15, 18 |
| P24 | 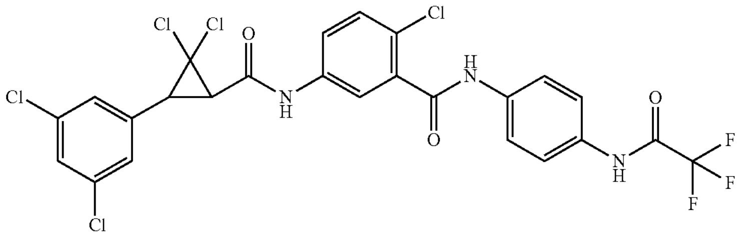 [SMILES: O=C(Nc1ccc(NC(=O)C(F)(F)F)cc1)c1cc(NC(=O)C2C(c3cc(Cl)cc(Cl)c3)C2(Cl)Cl)ccc1Cl] | Scheme 5 |
| P25 | 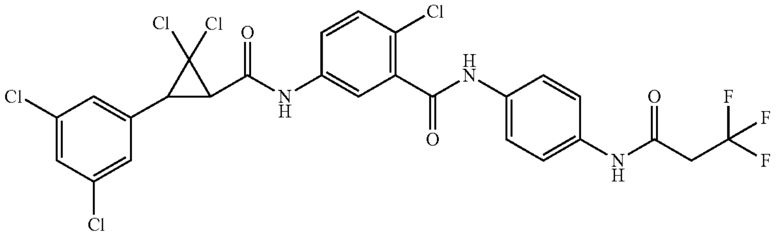 [SMILES: O=C(CC(F)(F)F)Nc1ccc(NC(=O)c2cc(NC(=O)C3C(c4cc(Cl)cc(Cl)c4)C3(Cl)Cl)ccc2Cl)cc1] | Scheme 5 |
| P26 | 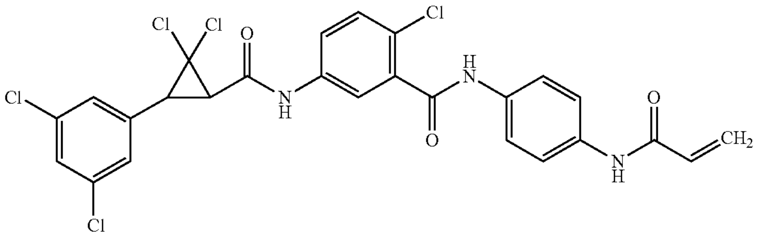 [SMILES: C=CC(=O)Nc1ccc(NC(=O)c2cc(NC(=O)C3C(c4cc(Cl)cc(Cl)c4)C3(Cl)Cl)ccc2Cl)cc1] | Scheme 5 |
| P27 | 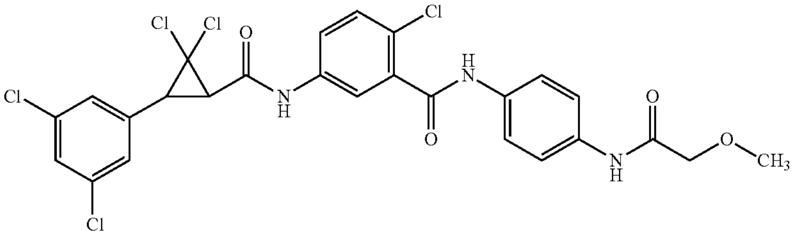 [SMILES: COCC(=O)Nc1ccc(NC(=O)c2cc(NC(=O)C3C(c4cc(Cl)cc(Cl)c4)C3(Cl)Cl)ccc2Cl)cc1] | Scheme 5 |
| P28 | 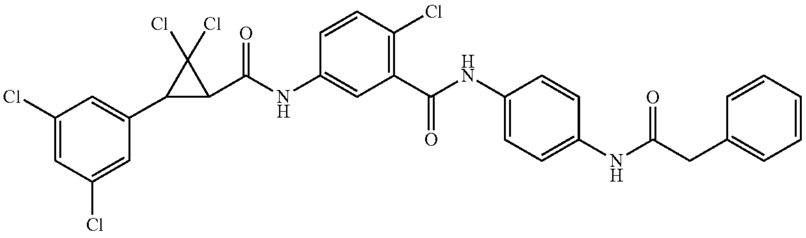 [SMILES: O=C(Cc1ccccc1)Nc1ccc(NC(=O)c2cc(NC(=O)C3C(c4cc(Cl)cc(Cl)c4)C3(Cl)Cl)ccc2Cl)cc1] | Scheme 5 |

TABLE P1-continued
| No. | Structure | Prep* |
|---|---|---|
| P29 | 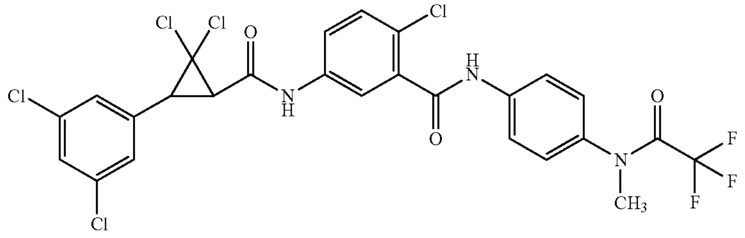 [SMILES: CN(C(=O)C(F)(F)F)c1ccc(NC(=O)c2cc(NC(=O)C3C(c4cc(Cl)cc(Cl)c4)C3(Cl)Cl)ccc2Cl)cc1] | Scheme 5 |
| P30 | 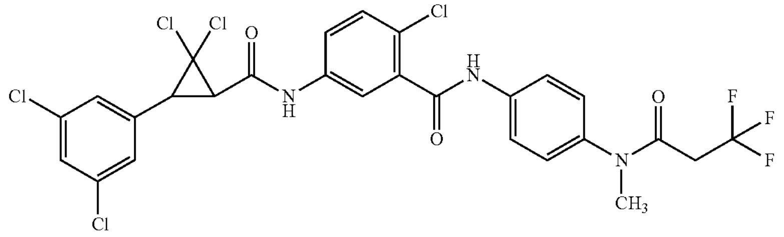 [SMILES: CN(C(=O)CC(F)(F)F)c1ccc(NC(=O)c2cc(NC(=O)C3C(c4cc(Cl)cc(Cl)c4)C3(Cl)Cl)ccc2Cl)cc1] | Scheme 5 |
| P31 | 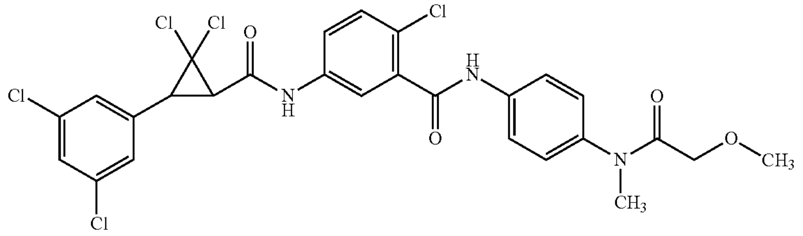 [SMILES: COCC(=O)N(C)c1ccc(NC(=O)c2cc(NC(=O)C3C(c4cc(Cl)cc(Cl)c4)C3(Cl)Cl)ccc2Cl)cc1] | Scheme 5 |
| P32 | 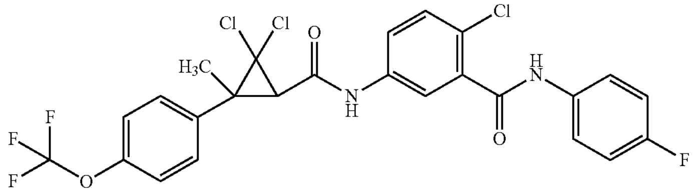 [SMILES: CC1(c2ccc(OC(F)(F)F)cc2)C(C(=O)Nc2ccc(Cl)c(C(=O)Nc3ccc(F)cc3)c2)C1(Cl)Cl] | 13, 14, 15, 18 |
| P33 | 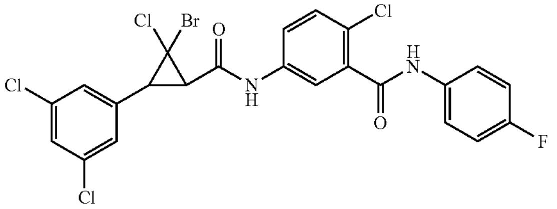 | 13, 14, 15, 18 |
| P34 | 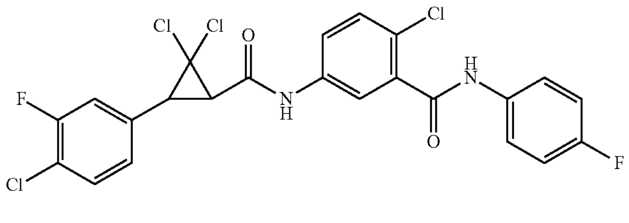 [SMILES: O=C(Nc1ccc(F)cc1)c1cc(NC(=O)C2C(c3ccc(Cl)c(F)c3)C2(Cl)Cl)ccc1Cl] | 13, 14, 15, 18 |
Structure and preparation method for prophetic molecules TABLE P1-continued
Structure and preparation method for prophetic molecules
| No. | Structure | Prep* |
| --- | --- | --- |
| P35 | 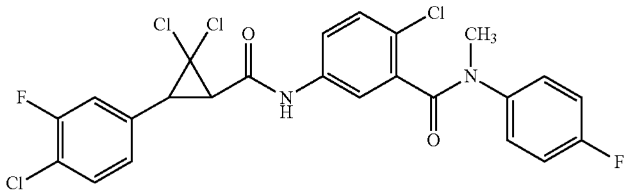 [SMILES: CN(C(=O)c1cc(NC(=O)C2C(c3ccc(Cl)c(F)c3)C2(Cl)Cl)ccc1Cl)c1ccc(F)cc1] | 13, 14, 15, 18 |
| P36 | 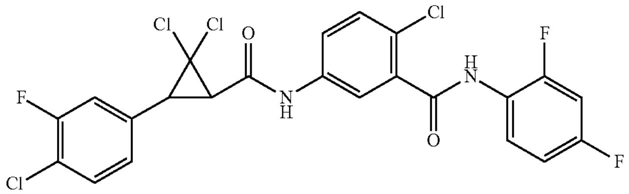 [SMILES: O=C(Nc1ccc(F)cc1F)c1cc(NC(=O)C2C(c3ccc(Cl)c(F)c3)C2(Cl)Cl)ccc1Cl] | 13, 14, 15, 18 |
| P37 | 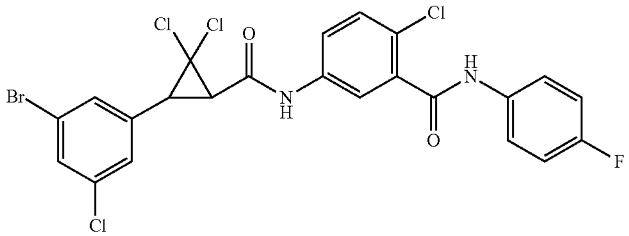 | 13, 14, 15, 18 |
| P38 | 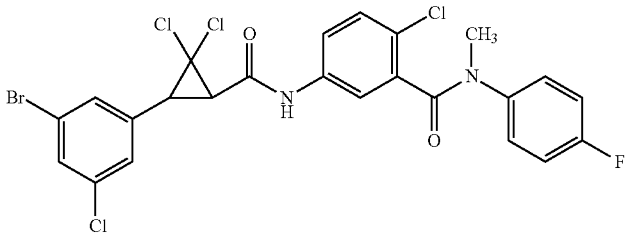 [SMILES: CN(C(=O)c1cc(NC(=O)C2C(c3cc(Cl)cc(Br)c3)C2(Cl)Cl)ccc1Cl)c1ccc(F)cc1] | 13, 14, 15, 18 |
| P39 | 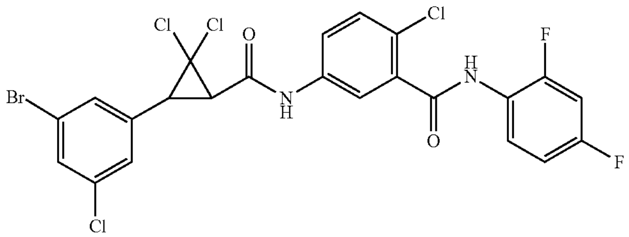 | 13, 14, 15, 18 |
| P40 | 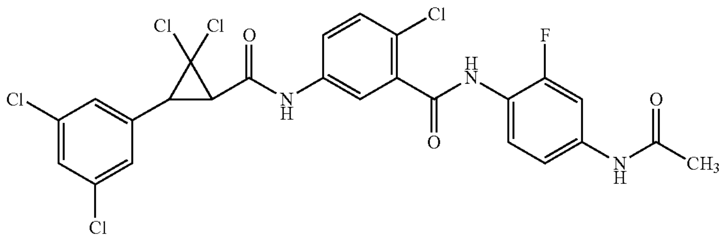 | 13, 14, 15, 18 |

TABLE P1-continued
| Structure and preparation method for prophetic molecules | | |
|---|---|---|
| No. | Structure | Prep* |
| P41 | 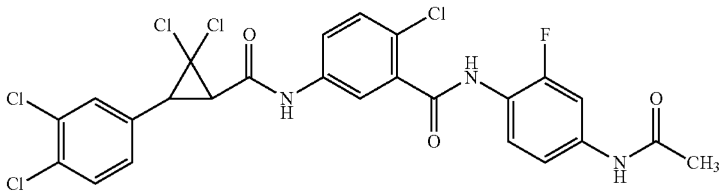 [SMILES: CC(=O)Nc1ccc(NC(=O)c2cc(NC(=O)C3C(c4ccc(Cl)c(Cl)c4)C3(Cl)Cl)ccc2Cl)c(F)c1] | 13, 14, 15, 18 |
| P42 | 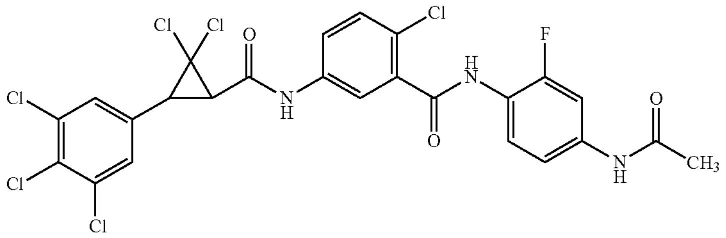 [SMILES: CC(=O)Nc1ccc(NC(=O)c2cc(NC(=O)C3C(c4cc(Cl)c(Cl)c(Cl)c4)C3(Cl)Cl)ccc2Cl)c(F)c1] | 13, 14, 15, 18 |
| P43 | 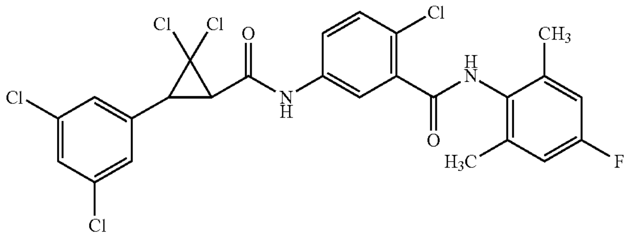 [SMILES: Cc1cc(F)cc(C)c1NC(=O)c1cc(NC(=O)C2C(c3cc(Cl)cc(Cl)c3)C2(Cl)Cl)ccc1Cl] | 13, 14, 15, 18 |
| P44 | 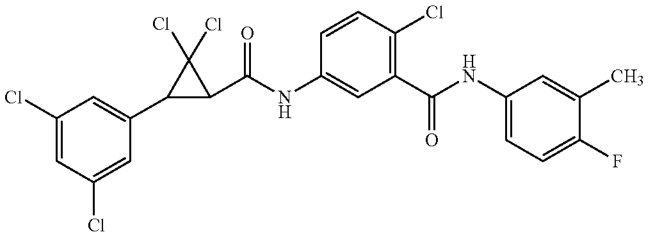 [SMILES: Cc1cc(NC(=O)c2cc(NC(=O)C3C(c4cc(Cl)cc(Cl)c4)C3(Cl)Cl)ccc2Cl)ccc1F] | 13, 14, 15, 18 |
| P45 | 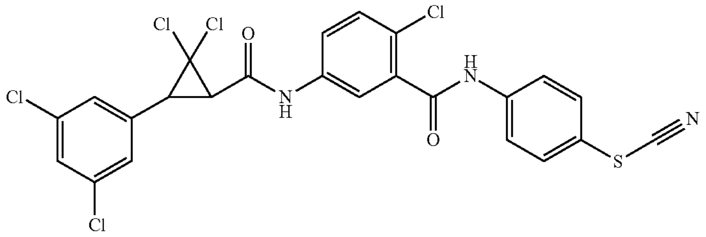 [SMILES: N#CSc1ccc(NC(=O)c2cc(NC(=O)C3C(c4cc(Cl)cc(Cl)c4)C3(Cl)Cl)ccc2Cl)cc1] | 13, 14, 15, 18 |
| P46 | 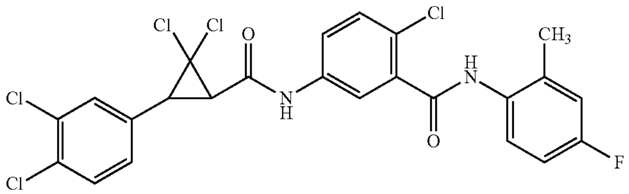 [SMILES: Cc1cc(F)ccc1NC(=O)c1cc(NC(=O)C2C(c3ccc(Cl)c(Cl)c3)C2(Cl)Cl)ccc1Cl] | 13, 14, 15, 18 |

TABLE P1-continued
| Structure and preparation method for prophetic molecules | | |
|---|---|---|
| No. | Structure | Prep* |
| P47 | 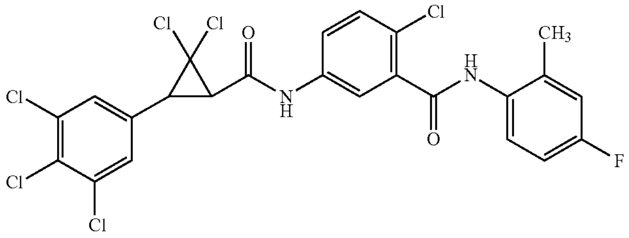 [SMILES: Cc1cc(F)ccc1NC(=O)c1cc(NC(=O)C2C(c3cc(Cl)c(Cl)c(Cl)c3)C2(Cl)Cl)ccc1Cl] | 13, 14, 15, 18 |
| P48 | 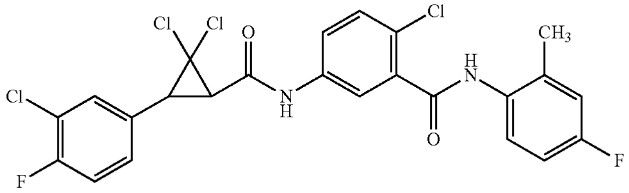 [SMILES: Cc1cc(F)ccc1NC(=O)c1cc(NC(=O)C2C(c3ccc(F)c(Cl)c3)C2(Cl)Cl)ccc1Cl] | 13, 14, 15, 18 |
| P49 | 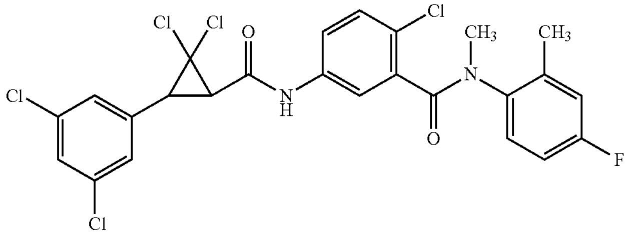 [SMILES: Cc1cc(F)ccc1N(C)C(=O)c1cc(NC(=O)C2C(c3cc(Cl)cc(Cl)c3)C2(Cl)Cl)ccc1Cl] | 13, 14, 15, 18 |
| P50 | 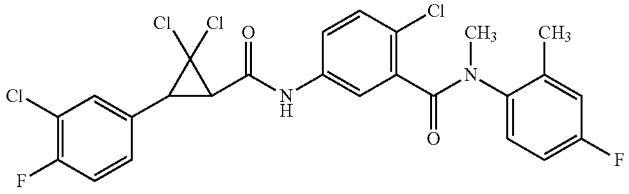 [SMILES: Cc1cc(F)ccc1N(C)C(=O)c1cc(NC(=O)C2C(c3ccc(F)c(Cl)c3)C2(Cl)Cl)ccc1Cl] | 13, 14, 15, 18 |
| P51 | 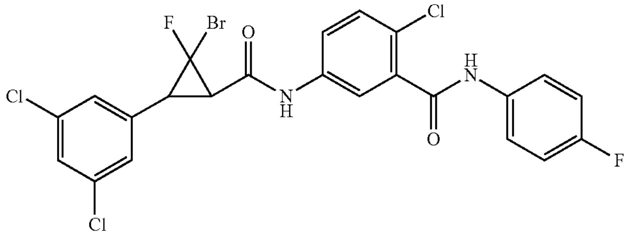 [SMILES: O=C(Nc1ccc(F)cc1)c1cc(NC(=O)C2C(c3cc(Cl)cc(Cl)c3)C2(F)Br)ccc1Cl] | 13, 14, 15, 18 |
| P52 | 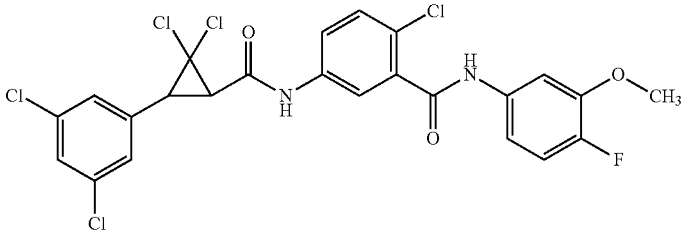 [SMILES: COc1cc(NC(=O)c2cc(NC(=O)C3C(c4cc(Cl)cc(Cl)c4)C3(Cl)Cl)ccc2Cl)ccc1F] | 13, 14, 15, 18 |

TABLE P1-continued
| Structure and preparation method for prophetic molecules | | |
|---|---|---|
| No. | Structure | Prep* |
| P53 | 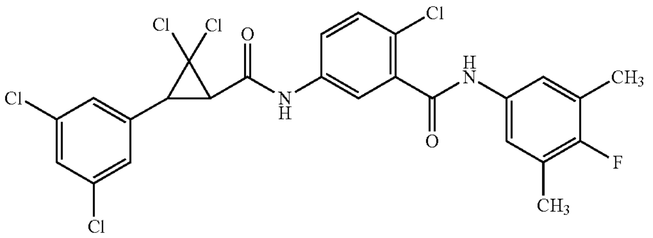 [SMILES: Cc1cc(NC(=O)c2cc(NC(=O)C3C(c4cc(Cl)cc(Cl)c4)C3(Cl)Cl)ccc2Cl)cc(C)c1F] | 13, 14, 15, 18 |
| P54 | 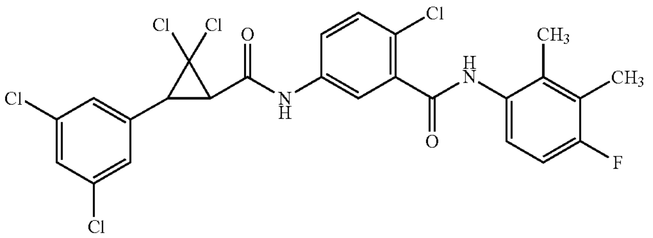 [SMILES: Cc1c(F)ccc(NC(=O)c2cc(NC(=O)C3C(c4cc(Cl)cc(Cl)c4)C3(Cl)Cl)ccc2Cl)c1C] | 13, 14, 15, 18 |
| P55 | 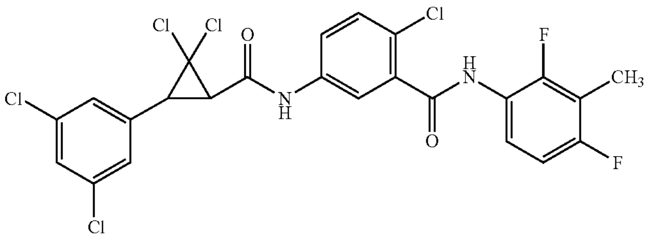 [SMILES: Cc1c(F)ccc(NC(=O)c2cc(NC(=O)C3C(c4cc(Cl)cc(Cl)c4)C3(Cl)Cl)ccc2Cl)c1F] | 13, 14, 15, 18 |
| P56 | 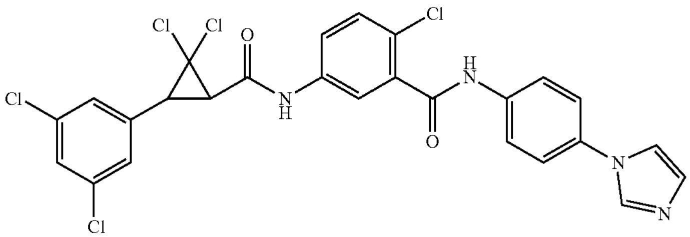 [SMILES: O=C(Nc1ccc(-n2ccnc2)cc1)c1cc(NC(=O)C2C(c3cc(Cl)cc(Cl)c3)C2(Cl)Cl)ccc1Cl] | 13, 14, 15, 18 |
| P57 | 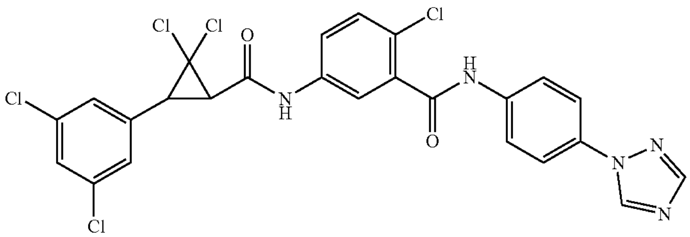 [SMILES: O=C(Nc1ccc(-n2cncn2)cc1)c1cc(NC(=O)C2C(c3cc(Cl)cc(Cl)c3)C2(Cl)Cl)ccc1Cl] | 13, 14, 15, 18 |
| P58 | 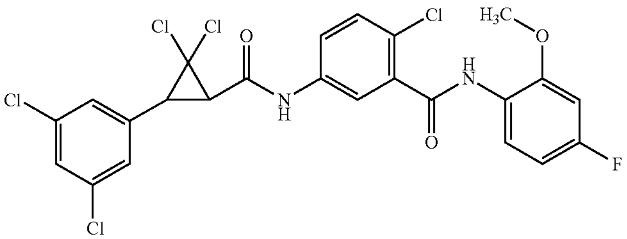 [SMILES: COc1cc(F)ccc1NC(=O)c1cc(NC(=O)C2C(c3cc(Cl)cc(Cl)c3)C2(Cl)Cl)ccc1Cl] | 13, 14, 15, 18 |

TABLE P1-continued
Structure and preparation method for prophetic molecules
| No. | Structure | Prep* |
| --- | --- | --- |
| P59 | 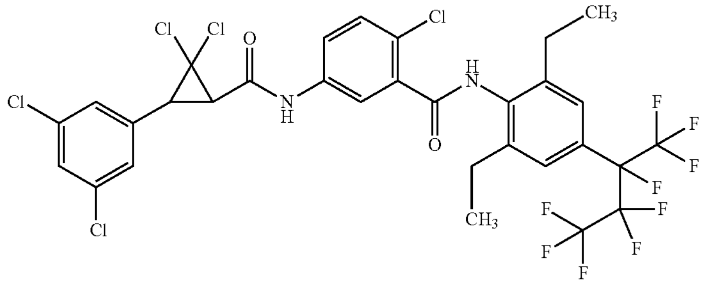 [SMILES: CCc1cc(C(F)(C(F)(F)F)C(F)(F)C(F)(F)F)cc(CC)c1NC(=O)c1cc(NC(=O)C2C(c3cc(Cl)cc(Cl)c3)C2(Cl)Cl)ccc1Cl] | 13, 14, 15, 18 |
| P60 | 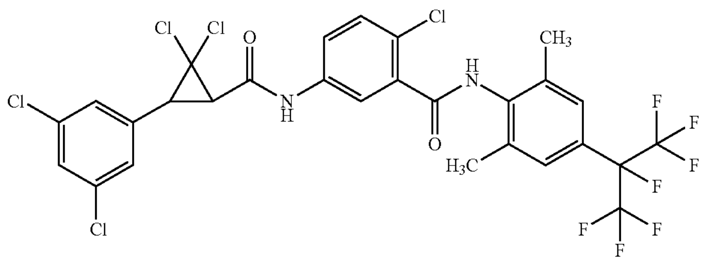 [SMILES: Cc1cc(C(F)(C(F)(F)F)C(F)(F)F)cc(C)c1NC(=O)c1cc(NC(=O)C2C(c3cc(Cl)cc(Cl)c3)C2(Cl)Cl)ccc1Cl] | 13, 14, 15, 18 |
| P61 | 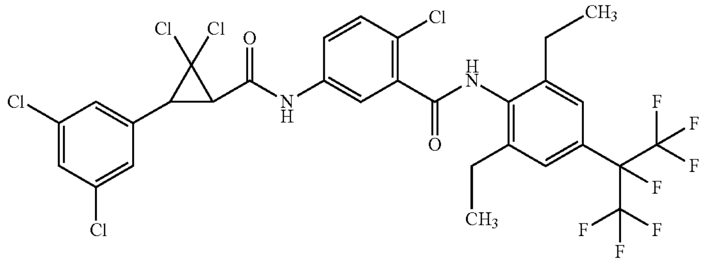 [SMILES: CCc1cc(C(F)(C(F)(F)F)C(F)(F)F)cc(CC)c1NC(=O)c1cc(NC(=O)C2C(c3cc(Cl)cc(Cl)c3)C2(Cl)Cl)ccc1Cl] | 13, 14, 15, 18 |
| P62 | 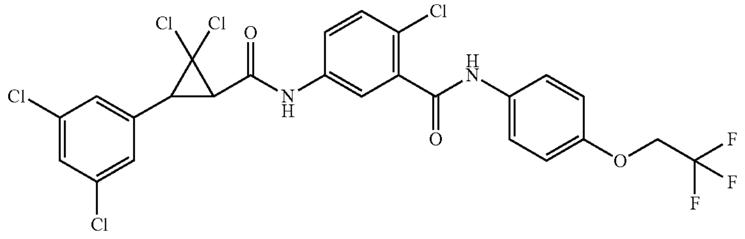 [SMILES: O=C(Nc1ccc(OCC(F)(F)F)cc1)c1cc(NC(=O)C2C(c3cc(Cl)cc(Cl)c3)C2(Cl)Cl)ccc1Cl] | 13, 14, 15, 18 |
| P63 | 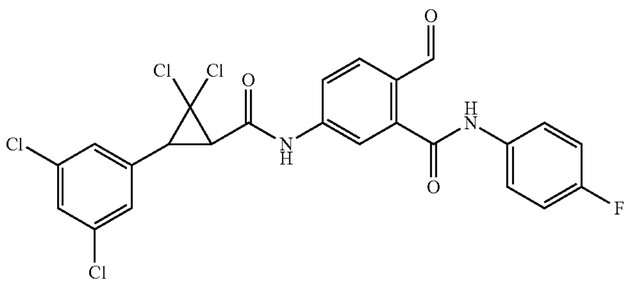 [SMILES: O=Cc1ccc(NC(=O)C2C(c3cc(Cl)cc(Cl)c3)C2(Cl)Cl)cc1C(=O)Nc1ccc(F)cc1] | 13, 14, 15, 18 |

TABLE P1-continued
| Structure and preparation method for prophetic molecules | | |
|---|---|---|
| No. | Structure | Prep* |
| P64 | 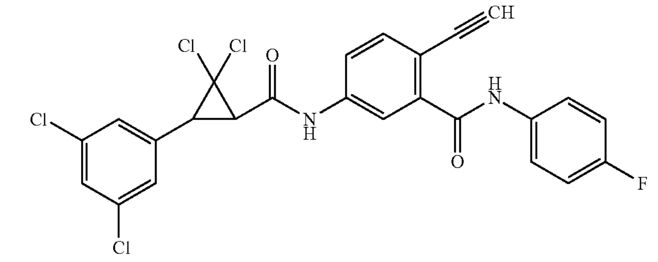 [SMILES: C#Cc1ccc(NC(=O)C2C(c3cc(Cl)cc(Cl)c3)C2(Cl)Cl)cc1C(=O)Nc1ccc(F)cc1] | 13, 14, 15, 18 |
| P65 | 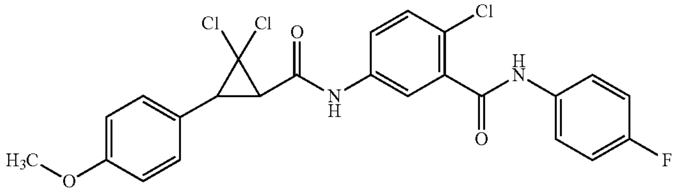 [SMILES: COc1ccc(C2C(C(=O)Nc3ccc(Cl)c(C(=O)Nc4ccc(F)cc4)c3)C2(Cl)Cl)cc1] | 13, 14, 15, 18 |
| P66 | 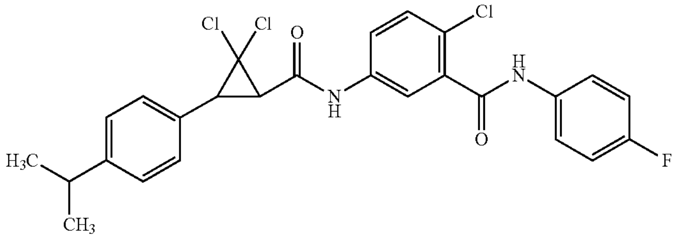 [SMILES: CC(C)c1ccc(C2C(C(=O)Nc3ccc(Cl)c(C(=O)Nc4ccc(F)cc4)c3)C2(Cl)Cl)cc1] | 13, 14, 15, 18 |
| P67 | 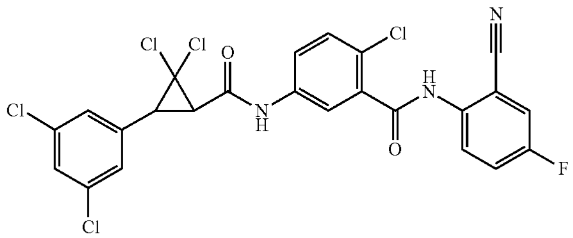 [SMILES: N#Cc1cc(F)ccc1NC(=O)c1cc(NC(=O)C2C(c3cc(Cl)cc(Cl)c3)C2(Cl)Cl)ccc1Cl] | 13, 14, 15, 18 |
| P68 | 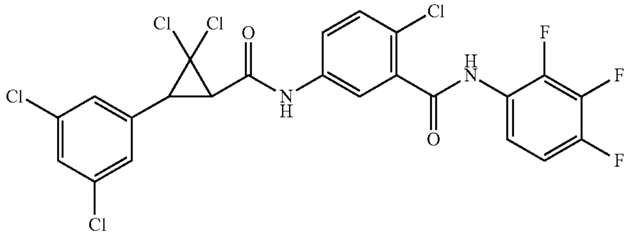 [SMILES: O=C(Nc1ccc(F)c(F)c1F)c1cc(NC(=O)C2C(c3cc(Cl)cc(Cl)c3)C2(Cl)Cl)ccc1Cl] | 13, 14, 15, 18 |
| P69 | 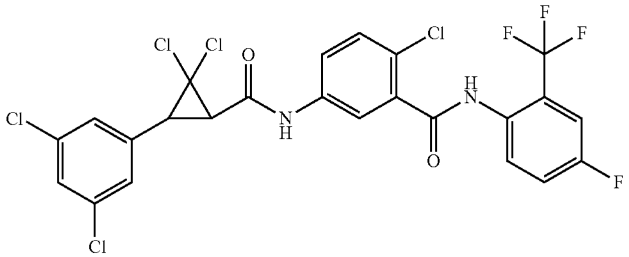 [SMILES: O=C(Nc1ccc(F)cc1C(F)(F)F)c1cc(NC(=O)C2C(c3cc(Cl)cc(Cl)c3)C2(Cl)Cl)ccc1Cl] | 13, 14, 15, 18 |

TABLE P1-continued
Structure and preparation method for prophetic molecules
| No. | Structure | Prep* |
|---|---|---|
| P70 | 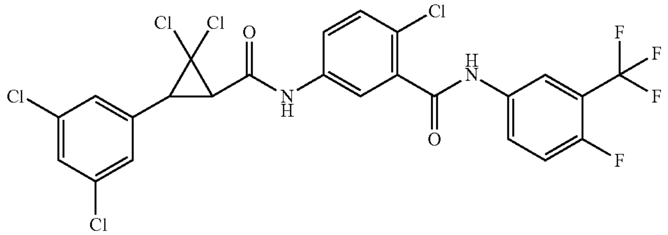 [SMILES: O=C(Nc1ccc(F)c(C(F)(F)F)c1)c1cc(NC(=O)C2C(c3cc(Cl)cc(Cl)c3)C2(Cl)Cl)ccc1Cl] | 13, 14, 15, 18 |
| P71 | 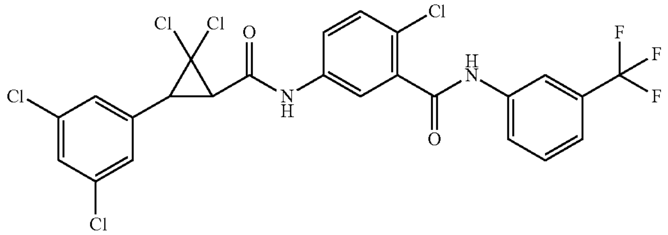 [SMILES: O=C(Nc1cccc(C(F)(F)F)c1)c1cc(NC(=O)C2C(c3cc(Cl)cc(Cl)c3)C2(Cl)Cl)ccc1Cl] | 13, 14, 15, 18 |
| P72 | 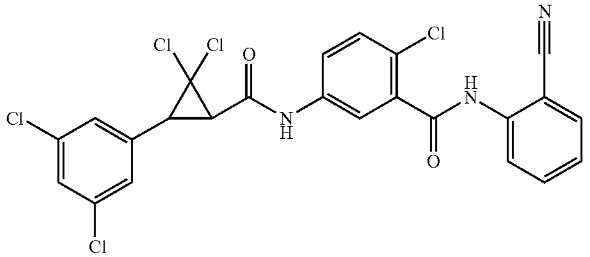 [SMILES: N#Cc1ccccc1NC(=O)c1cc(NC(=O)C2C(c3cc(Cl)cc(Cl)c3)C2(Cl)Cl)ccc1Cl] | 13, 14, 15, 18 |
| P73 | 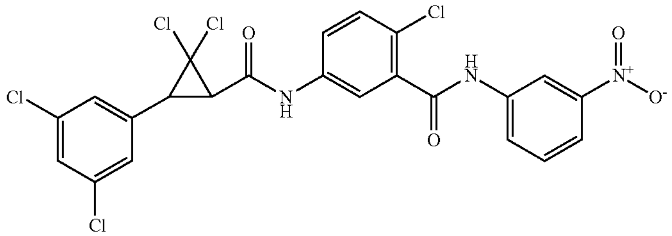 [SMILES: O=C(Nc1cccc([N+](=O)[O-])c1)c1cc(NC(=O)C2C(c3cc(Cl)cc(Cl)c3)C2(Cl)Cl)ccc1Cl] | 13, 14, 15, 18 |
| P74 | 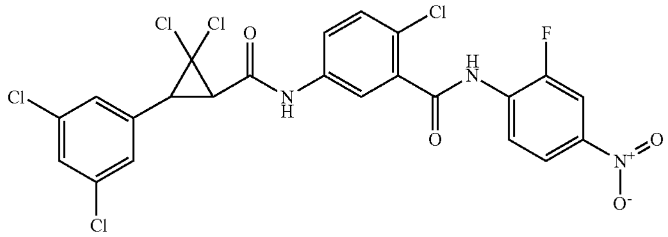 [SMILES: O=C(Nc1ccc([N+](=O)[O-])cc1F)c1cc(NC(=O)C2C(c3cc(Cl)cc(Cl)c3)C2(Cl)Cl)ccc1Cl] | 13, 14, 15, 18 |
| P75 | 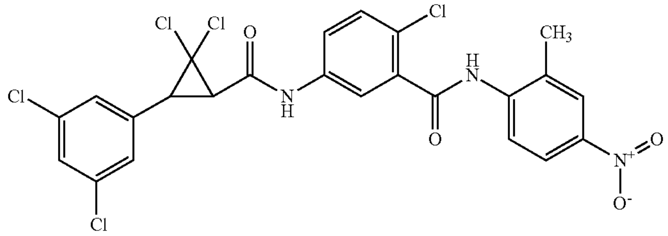 [SMILES: Cc1cc([N+](=O)[O-])ccc1NC(=O)c1cc(NC(=O)C2C(c3cc(Cl)cc(Cl)c3)C2(Cl)Cl)ccc1Cl] | 13, 14, 15, 18 |

TABLE P1-continued
| Structure and preparation method for prophetic molecules | | |
|---|---|---|
| No. | Structure | Prep* |
| P76 | 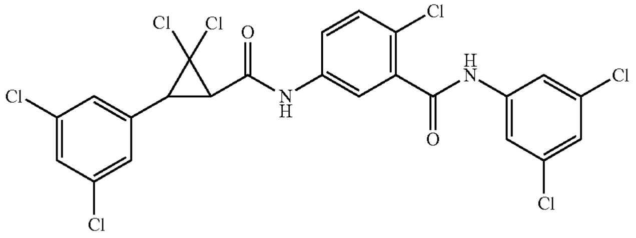 [SMILES: O=C(Nc1cc(Cl)cc(Cl)c1)c1cc(NC(=O)C2C(c3cc(Cl)cc(Cl)c3)C2(Cl)Cl)ccc1Cl] | 13, 14, 15, 18 |
| P77 | 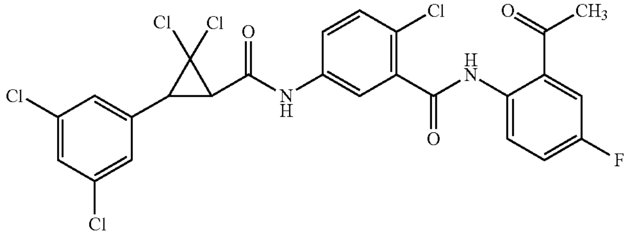 [SMILES: CC(=O)c1cc(F)ccc1NC(=O)c1cc(NC(=O)C2C(c3cc(Cl)cc(Cl)c3)C2(Cl)Cl)ccc1Cl] | 13, 14, 15, 18 |
| P78 | 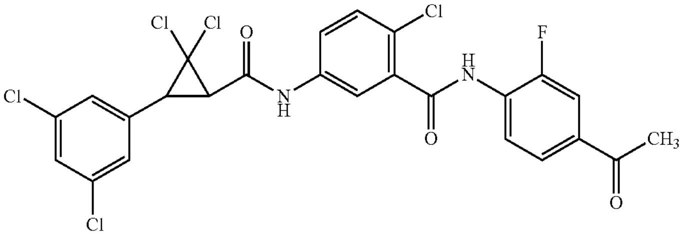 [SMILES: CC(=O)c1ccc(NC(=O)c2cc(NC(=O)C3C(c4cc(Cl)cc(Cl)c4)C3(Cl)Cl)ccc2Cl)c(F)c1] | 13, 14, 15, 18 |
| P79 | 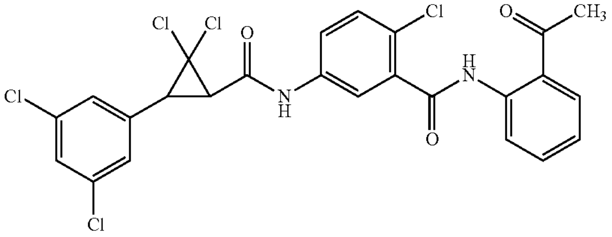 [SMILES: CC(=O)c1ccccc1NC(=O)c1cc(NC(=O)C2C(c3cc(Cl)cc(Cl)c3)C2(Cl)Cl)ccc1Cl] | 13, 14, 15, 18 |
| P80 | 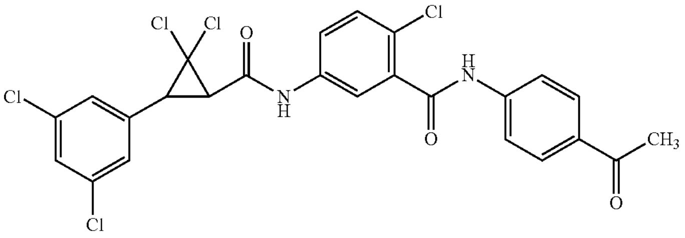 | 13, 14, 15, 18 |
| P81 | 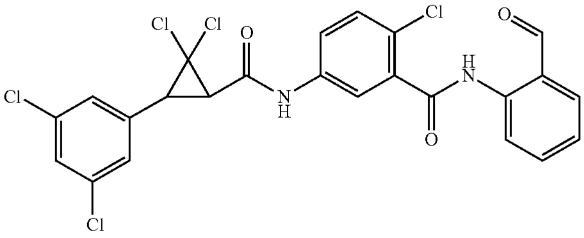 [SMILES: O=Cc1ccccc1NC(=O)c1cc(NC(=O)C2C(c3cc(Cl)cc(Cl)c3)C2(Cl)Cl)ccc1Cl] | 13, 14, 15, 18 |

TABLE P1-continued
| Structure and preparation method for prophetic molecules | | |
|---|---|---|
| No. | Structure | Prep* |
| P82 | 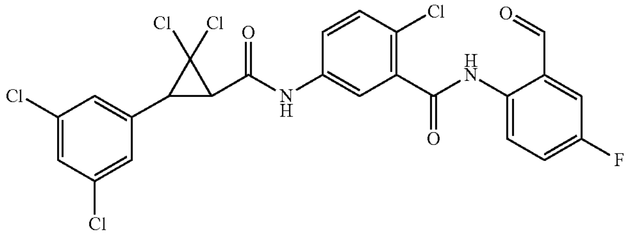 [SMILES: O=Cc1cc(F)ccc1NC(=O)c1cc(NC(=O)C2C(c3cc(Cl)cc(Cl)c3)C2(Cl)Cl)ccc1Cl] | 13, 14, 15, 18 |
| P83 | 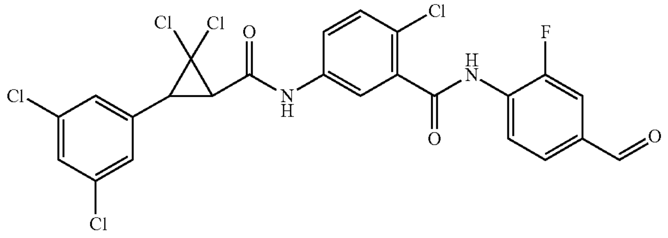 [SMILES: O=Cc1ccc(NC(=O)c2cc(NC(=O)C3C(c4cc(Cl)cc(Cl)c4)C3(Cl)Cl)ccc2Cl)c(F)c1] | 13, 14, 15, 18 |
| P84 | 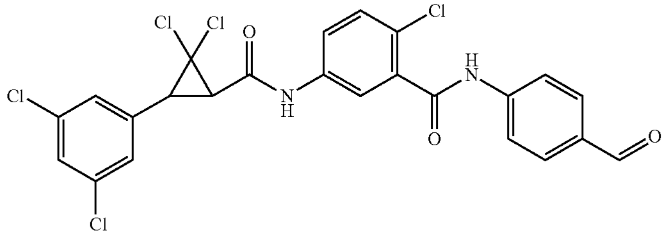 [SMILES: O=Cc1ccc(NC(=O)c2cc(NC(=O)C3C(c4cc(Cl)cc(Cl)c4)C3(Cl)Cl)ccc2Cl)cc1] | 13, 14, 15, 18 |
| P85 | 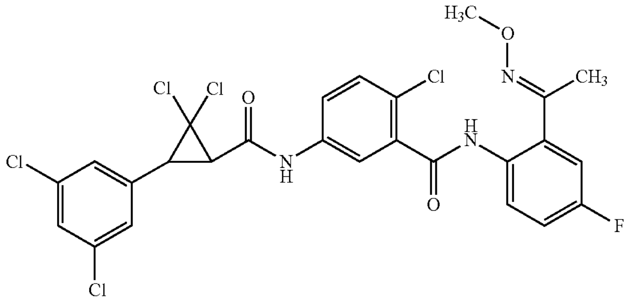 [SMILES: CO/N=C(\C)c1cc(F)ccc1NC(=O)c1cc(NC(=O)C2C(c3cc(Cl)cc(Cl)c3)C2(Cl)Cl)ccc1Cl] | Scheme 6 |
| P86 | 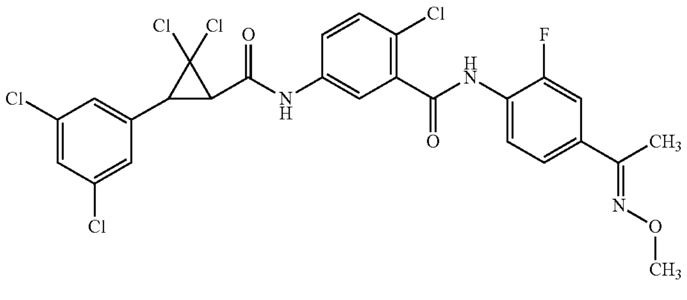 [SMILES: CO/N=C(\C)c1ccc(NC(=O)c2cc(NC(=O)C3C(c4cc(Cl)cc(Cl)c4)C3(Cl)Cl)ccc2Cl)c(F)c1] | Scheme 6 |

TABLE P1-continued
| Structure and preparation method for prophetic molecules | | |
|---|---|---|
| No. | Structure | Prep* |
| P87 | 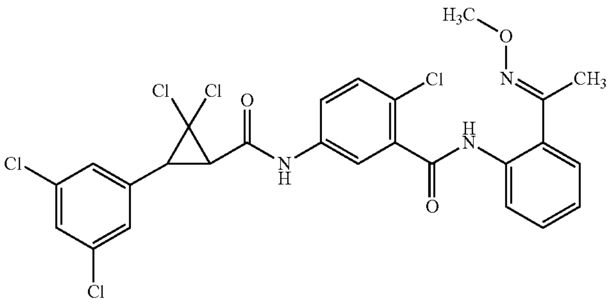 [SMILES: CO/N=C(\C)c1ccccc1NC(=O)c1cc(NC(=O)C2C(c3cc(Cl)cc(Cl)c3)C2(Cl)Cl)ccc1Cl] | Scheme 6 |
| P88 | 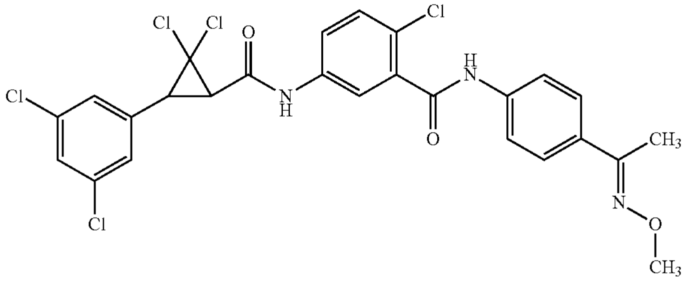 [SMILES: CO/N=C(\C)c1ccc(NC(=O)c2cc(NC(=O)C3C(c4cc(Cl)cc(Cl)c4)C3(Cl)Cl)ccc2Cl)cc1] | Scheme 6 |
| P89 | 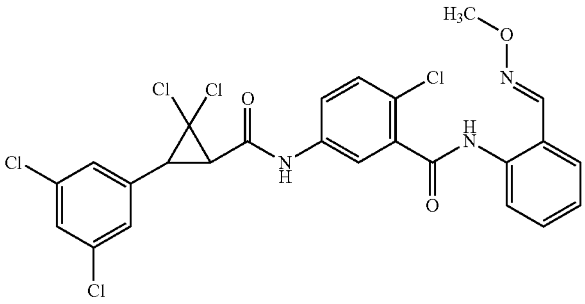 [SMILES: CO/N=C/c1ccccc1NC(=O)c1cc(NC(=O)C2C(c3cc(Cl)cc(Cl)c3)C2(Cl)Cl)ccc1Cl] | Scheme 6 |
| P90 | 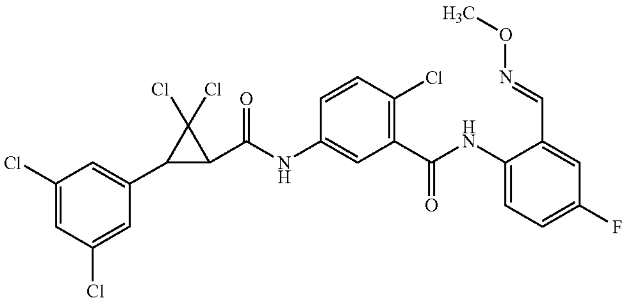 [SMILES: CO/N=C/c1cc(F)ccc1NC(=O)c1cc(NC(=O)C2C(c3cc(Cl)cc(Cl)c3)C2(Cl)Cl)ccc1Cl] | Scheme 6 |
| P91 | 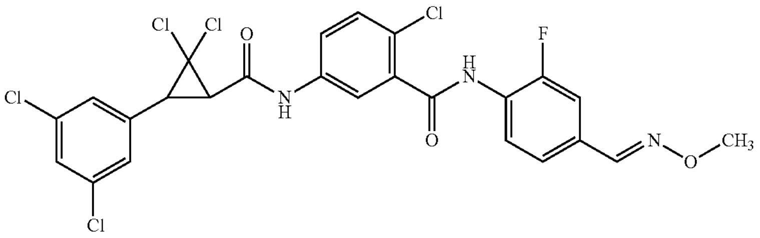 [SMILES: CO/N=C/c1ccc(NC(=O)c2cc(NC(=O)C3C(c4cc(Cl)cc(Cl)c4)C3(Cl)Cl)ccc2Cl)c(F)c1] | Scheme 6 |

TABLE P1-continued
| Structure and preparation method for prophetic molecules | | |
|---|---|---|
| No. | Structure | Prep* |
| P92 | 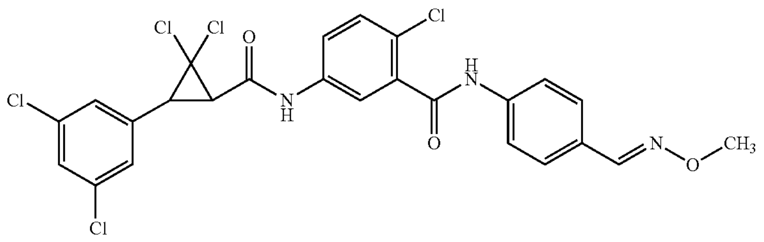 [SMILES: CO/N=C/c1ccc(NC(=O)c2cc(NC(=O)C3C(c4cc(Cl)cc(Cl)c4)C3(Cl)Cl)ccc2Cl)cc1] | Scheme 6 |
| P93 | 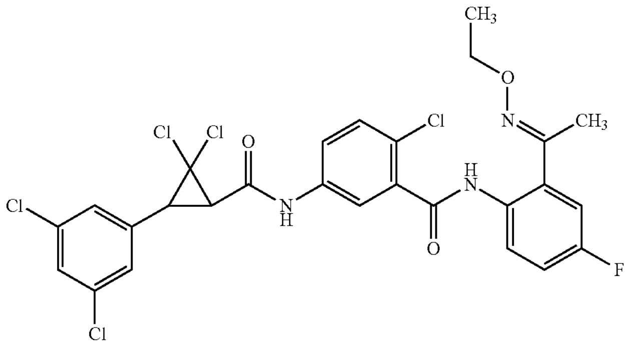 [SMILES: CCO/N=C(\C)c1cc(F)ccc1NC(=O)c1cc(NC(=O)C2C(c3cc(Cl)cc(Cl)c3)C2(Cl)Cl)ccc1Cl] | Scheme 6 |
| P94 | 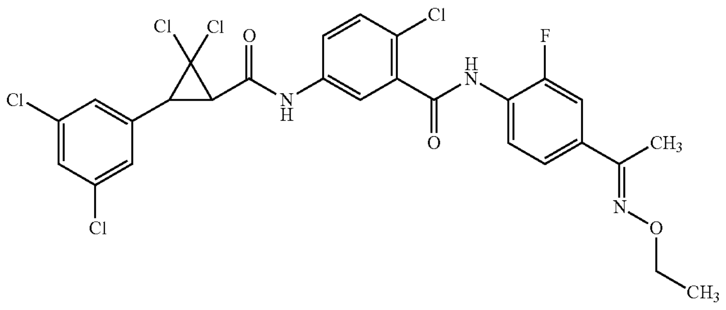 [SMILES: CCO/N=C(\C)c1ccc(NC(=O)c2cc(NC(=O)C3C(c4cc(Cl)cc(Cl)c4)C3(Cl)Cl)ccc2Cl)c(F)c1] | Scheme 6 |
| P95 | 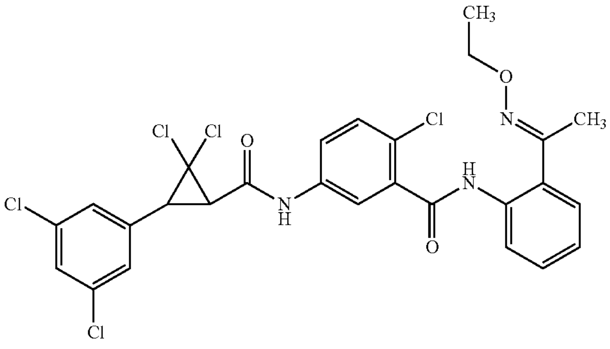 [SMILES: CCO/N=C(\C)c1ccccc1NC(=O)c1cc(NC(=O)C2C(c3cc(Cl)cc(Cl)c3)C2(Cl)Cl)ccc1Cl] | Scheme 6 |
| P96 | 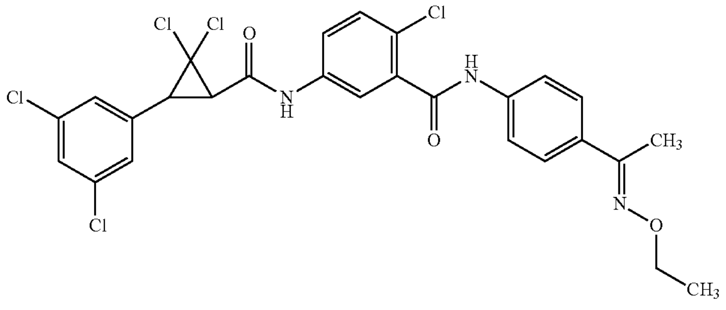 [SMILES: CCO/N=C(\C)c1ccc(NC(=O)c2cc(NC(=O)C3C(c4cc(Cl)cc(Cl)c4)C3(Cl)Cl)ccc2Cl)cc1] | Scheme 6 |

TABLE P1-continued
| Structure and preparation method for prophetic molecules | | |
|---|---|---|
| No. | Structure | Prep* |
| P97 | 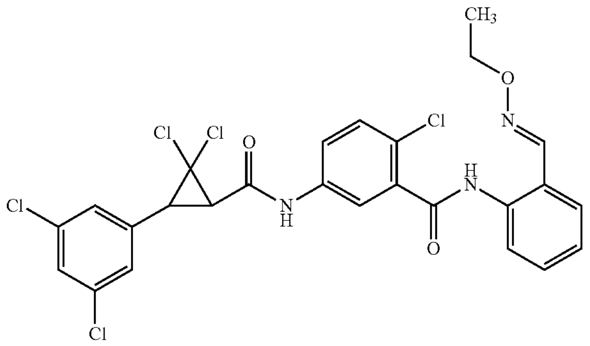 [SMILES: CCO/N=C/c1ccccc1NC(=O)c1cc(NC(=O)C2C(c3cc(Cl)cc(Cl)c3)C2(Cl)Cl)ccc1Cl] | Scheme 6 |
| P98 | 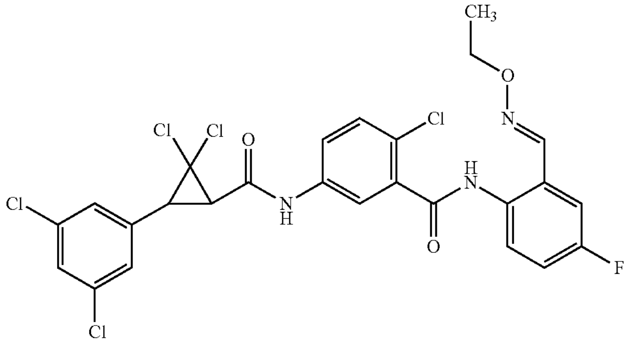 [SMILES: CCO/N=C/c1cc(F)ccc1NC(=O)c1cc(NC(=O)C2C(c3cc(Cl)cc(Cl)c3)C2(Cl)Cl)ccc1Cl] | Scheme 6 |
| P99 | 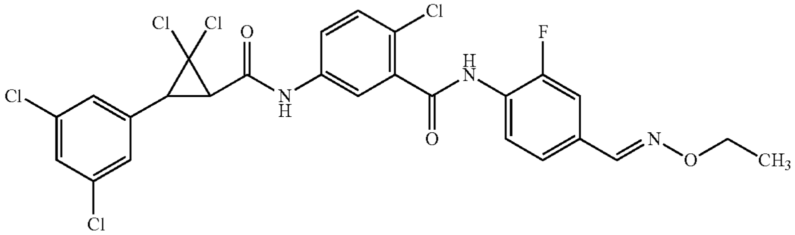 [SMILES: CCO/N=C/c1ccc(NC(=O)c2cc(NC(=O)C3C(c4cc(Cl)cc(Cl)c4)C3(Cl)Cl)ccc2Cl)c(F)c1] | Scheme 6 |
| P100 | 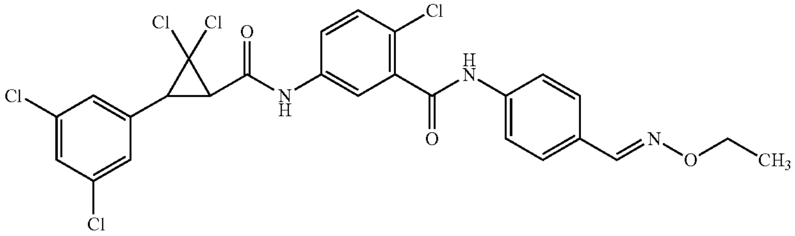 [SMILES: CCO/N=C/c1ccc(NC(=O)c2cc(NC(=O)C3C(c4cc(Cl)cc(Cl)c4)C3(Cl)Cl)ccc2Cl)cc1] | Scheme 6 |
| P101 | 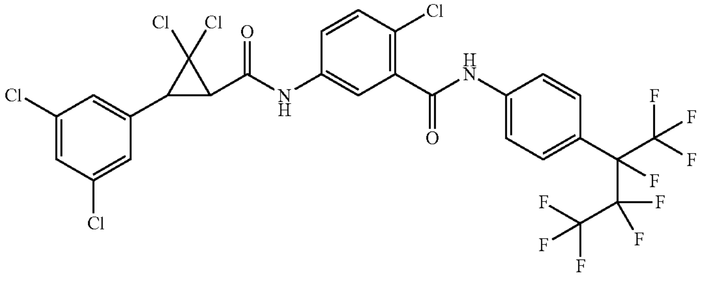 [SMILES: O=C(Nc1ccc(C(F)(C(F)(F)F)C(F)(F)C(F)(F)F)cc1)c1cc(NC(=O)C2C(c3cc(Cl)cc(Cl)c3)C2(Cl)Cl)ccc1Cl] | 13, 14, 15, 18 |

TABLE P1-continued
| Structure and preparation method for prophetic molecules | | |
|---|---|---|
| No. | Structure | Prep* |
| P102 | 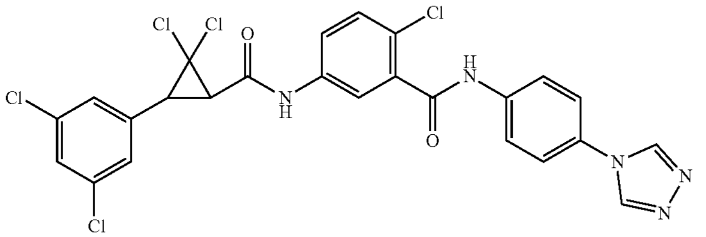 [SMILES: O=C(Nc1ccc(-n2cnnc2)cc1)c1cc(NC(=O)C2C(c3cc(Cl)cc(Cl)c3)C2(Cl)Cl)ccc1Cl] | 13, 14, 15, 18 |
| P103 | 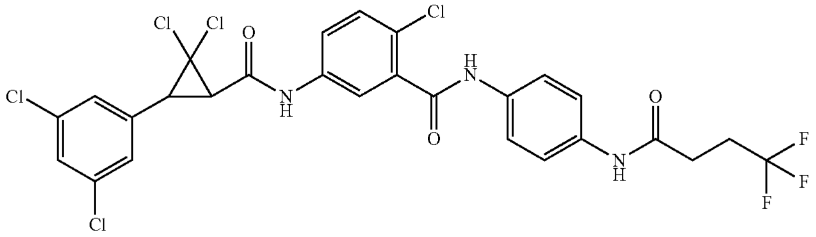 [SMILES: O=C(CCC(F)(F)F)Nc1ccc(NC(=O)c2cc(NC(=O)C3C(c4cc(Cl)cc(Cl)c4)C3(Cl)Cl)ccc2Cl)cc1] | Scheme 5 |
| P104 | 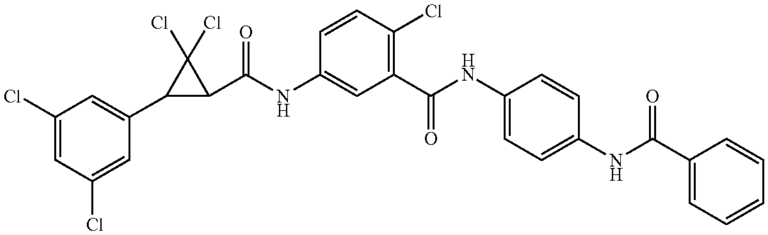 [SMILES: O=C(Nc1ccc(NC(=O)c2cc(NC(=O)C3C(c4cc(Cl)cc(Cl)c4)C3(Cl)Cl)ccc2Cl)cc1)c1ccccc1] | Scheme 5 |
| P105 | 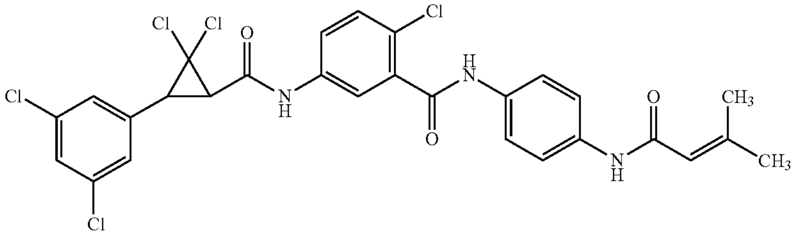 [SMILES: CC(C)=CC(=O)Nc1ccc(NC(=O)c2cc(NC(=O)C3C(c4cc(Cl)cc(Cl)c4)C3(Cl)Cl)ccc2Cl)cc1] | Scheme 5 |
| P106 | 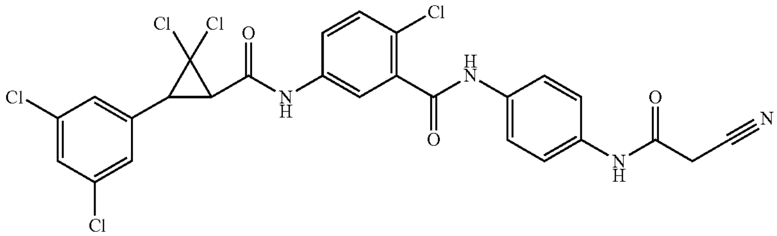 [SMILES: N#CCC(=O)Nc1ccc(NC(=O)c2cc(NC(=O)C3C(c4cc(Cl)cc(Cl)c4)C3(Cl)Cl)ccc2Cl)cc1] | Scheme 5 |
| P107 | 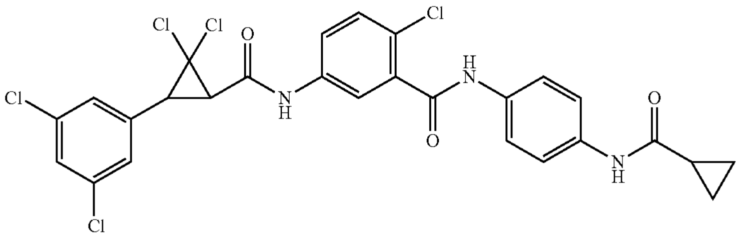 [SMILES: O=C(Nc1ccc(NC(=O)C2CC2)cc1)c1cc(NC(=O)C2C(c3cc(Cl)cc(Cl)c3)C2(Cl)Cl)ccc1Cl] | Scheme 5 |

TABLE P1-continued
| Structure and preparation method for prophetic molecules | | |
|---|---|---|
| No. | Structure | Prep* |
| P108 | 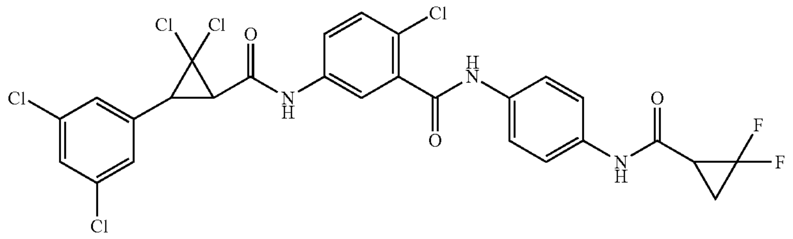 [SMILES: O=C(Nc1ccc(NC(=O)C2CC2(F)F)cc1)c1cc(NC(=O)C2C(c3cc(Cl)cc(Cl)c3)C2(Cl)Cl)ccc1Cl] | Scheme 5 |
| P109 | 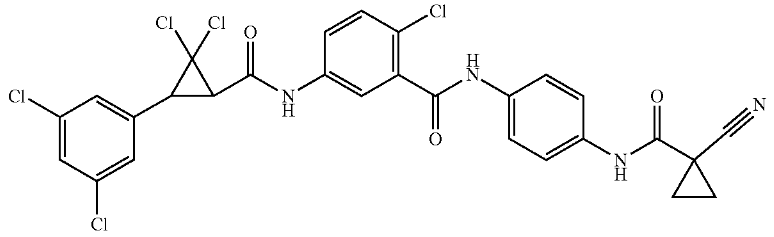 [SMILES: N#CC1(C(=O)Nc2ccc(NC(=O)c3cc(NC(=O)C4C(c5cc(Cl)cc(Cl)c5)C4(Cl)Cl)ccc3Cl)cc2)CC1] | Scheme 5 |
| P110 | 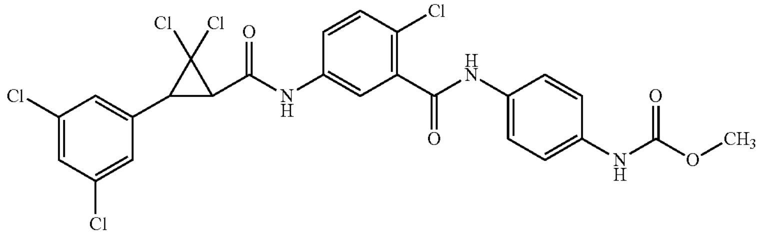 [SMILES: COC(=O)Nc1ccc(NC(=O)c2cc(NC(=O)C3C(c4cc(Cl)cc(Cl)c4)C3(Cl)Cl)ccc2Cl)cc1] | Scheme 5 |
| P111 | 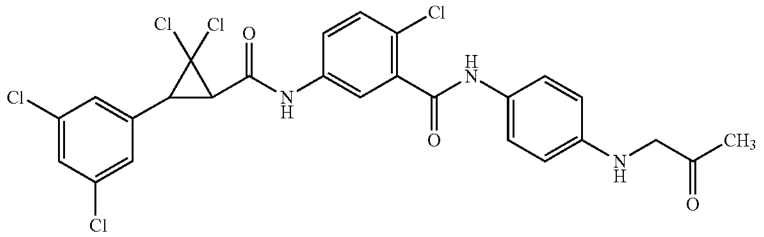 [SMILES: CC(=O)CNc1ccc(NC(=O)c2cc(NC(=O)C3C(c4cc(Cl)cc(Cl)c4)C3(Cl)Cl)ccc2Cl)cc1] | 13, 14, 15, 18 |
| P112 | 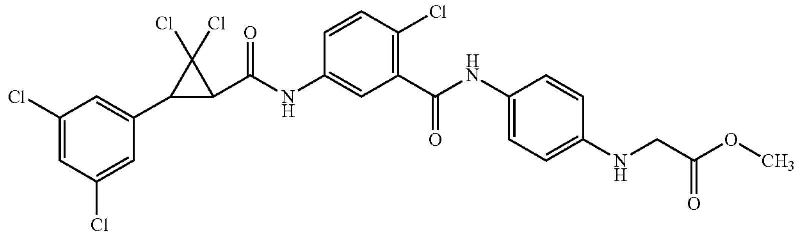 [SMILES: COC(=O)CNc1ccc(NC(=O)c2cc(NC(=O)C3C(c4cc(Cl)cc(Cl)c4)C3(Cl)Cl)ccc2Cl)cc1] | 13, 14, 15, 18 |
| P113 | 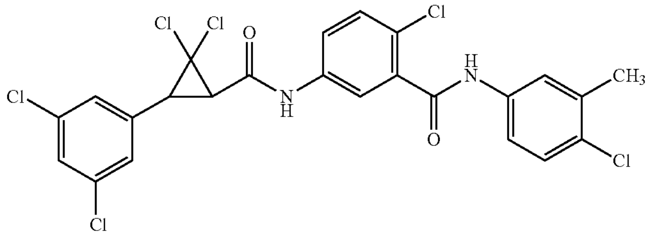 | 13, 14, 15, 18 |

TABLE P1-continued
| Structure and preparation method for prophetic molecules | | |
|---|---|---|
| No. | Structure | Prep* |
| P114 | 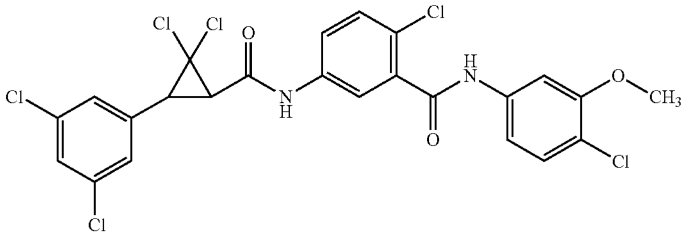 | 13, 14, 15, 18 |
| P115 | 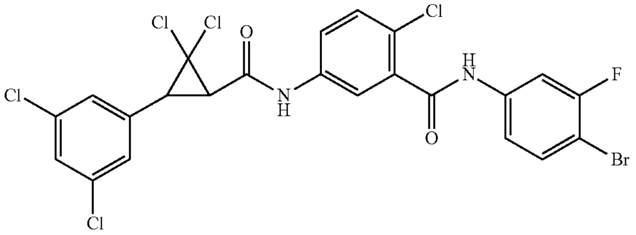 [SMILES: O=C(Nc1ccc(Br)c(F)c1)c1cc(NC(=O)C2C(c3cc(Cl)cc(Cl)c3)C2(Cl)Cl)ccc1Cl] | 13, 14, 15, 18 |
| P116 | 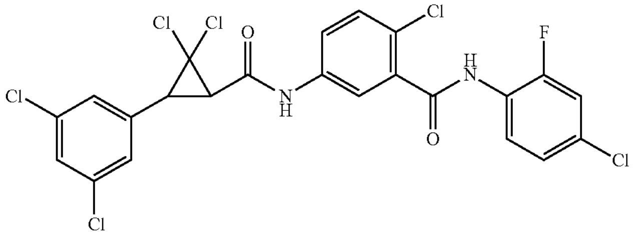 [SMILES: O=C(Nc1ccc(Cl)cc1F)c1cc(NC(=O)C2C(c3cc(Cl)cc(Cl)c3)C2(Cl)Cl)ccc1Cl] | 13, 14, 15, 18 |
| P117 | 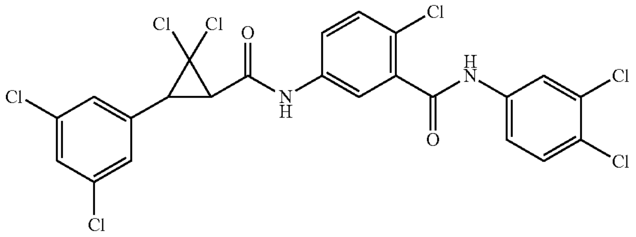 [SMILES: O=C(Nc1ccc(Cl)c(Cl)c1)c1cc(NC(=O)C2C(c3cc(Cl)cc(Cl)c3)C2(Cl)Cl)ccc1Cl] | 13, 14, 15, 18 |
| P118 | 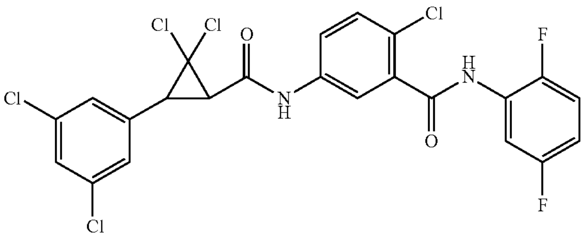 [SMILES: O=C(Nc1cc(F)ccc1F)c1cc(NC(=O)C2C(c3cc(Cl)cc(Cl)c3)C2(Cl)Cl)ccc1Cl] | 13, 14, 15, 18 |
| P119 | 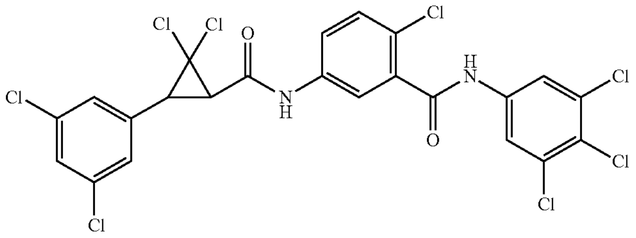 [SMILES: O=C(Nc1cc(Cl)c(Cl)c(Cl)c1)c1cc(NC(=O)C2C(c3cc(Cl)cc(Cl)c3)C2(Cl)Cl)ccc1Cl] | 13, 14, 15, 18 |

TABLE P1-continued
| Structure and preparation method for prophetic molecules | | |
|---|---|---|
| No. | Structure | Prep* |
| P120 | 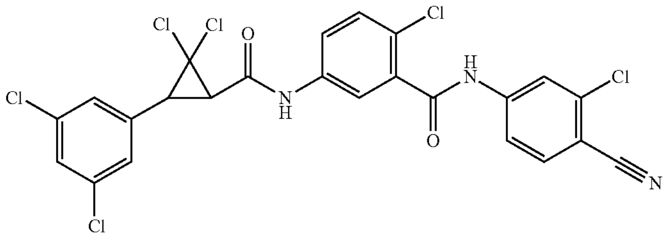 [SMILES: N#Cc1ccc(NC(=O)c2cc(NC(=O)C3C(c4cc(Cl)cc(Cl)c4)C3(Cl)Cl)ccc2Cl)cc1Cl] | 13, 14, 15, 18 |
| P121 | 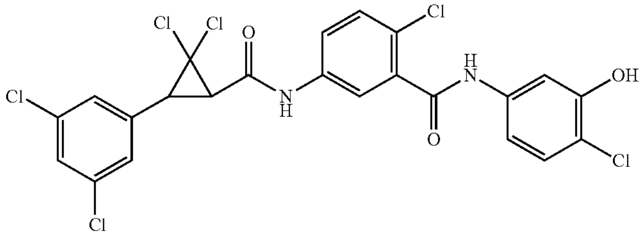 [SMILES: O=C(Nc1ccc(Cl)c(O)c1)c1cc(NC(=O)C2C(c3cc(Cl)cc(Cl)c3)C2(Cl)Cl)ccc1Cl] | 13, 14, 15, 18 |
| P122 | 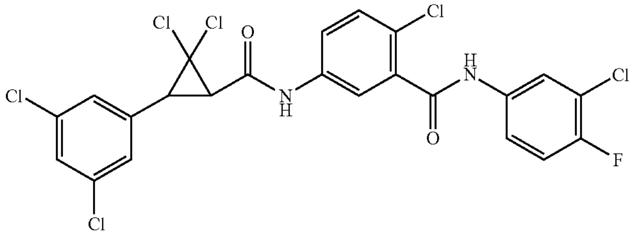 [SMILES: O=C(Nc1ccc(F)c(Cl)c1)c1cc(NC(=O)C2C(c3cc(Cl)cc(Cl)c3)C2(Cl)Cl)ccc1Cl] | 13, 14, 15, 18 |
| P123 | 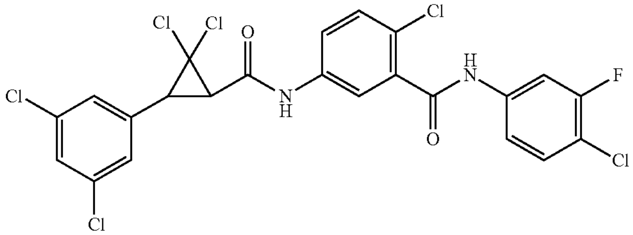 | 13, 14, 15, 18 |
| P124 | 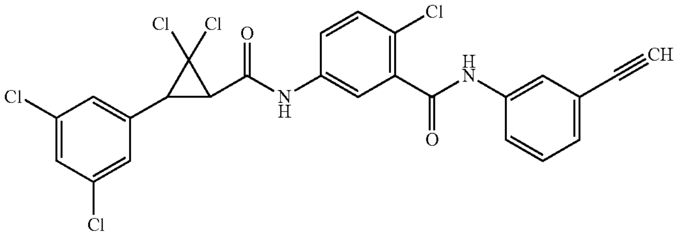 [SMILES: C#Cc1cccc(NC(=O)c2cc(NC(=O)C3C(c4cc(Cl)cc(Cl)c4)C3(Cl)Cl)ccc2Cl)c1] | 13, 14, 15, 18 |
| P125 | 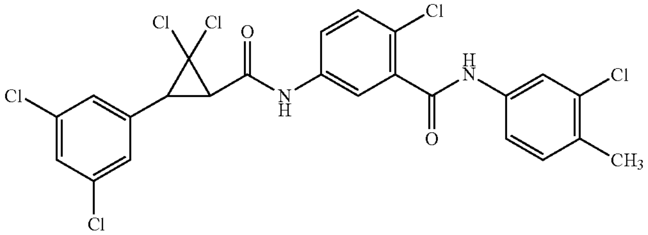 [SMILES: Cc1ccc(NC(=O)c2cc(NC(=O)C3C(c4cc(Cl)cc(Cl)c4)C3(Cl)Cl)ccc2Cl)cc1Cl] | 13, 14, 15, 18 |

TABLE P1-continued
| Structure and preparation method for prophetic molecules | | |
|---|---|---|
| No. | Structure | Prep* |
| P126 | 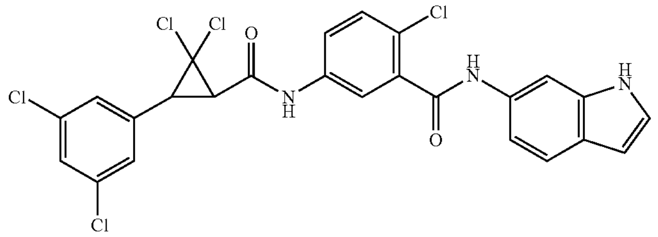 [SMILES: O=C(Nc1ccc2cc[nH]c2c1)c1cc(NC(=O)C2C(c3cc(Cl)cc(Cl)c3)C2(Cl)Cl)ccc1Cl] | 13, 14, 15, 18 |
| P127 | 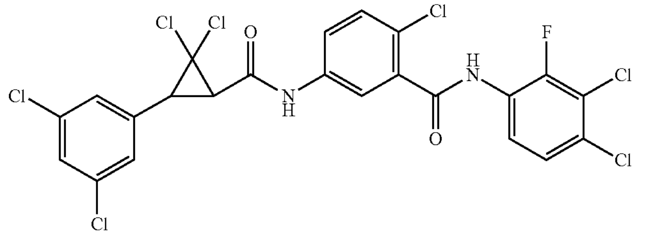 [SMILES: O=C(Nc1ccc(Cl)c(Cl)c1F)c1cc(NC(=O)C2C(c3cc(Cl)cc(Cl)c3)C2(Cl)Cl)ccc1Cl] | 13, 14, 15, 18 |
| P128 | 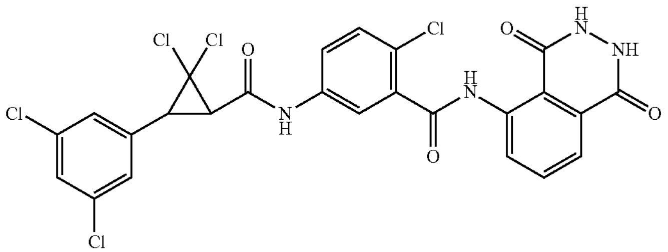 [SMILES: O=C(Nc1cccc2c(=O)[nH][nH]c(=O)c12)c1cc(NC(=O)C2C(c3cc(Cl)cc(Cl)c3)C2(Cl)Cl)ccc1Cl] | 13, 14, 15, 18 |
| P129 | 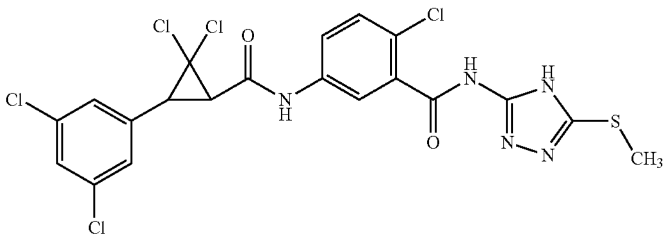 [SMILES: CSc1nnc(NC(=O)c2cc(NC(=O)C3C(c4cc(Cl)cc(Cl)c4)C3(Cl)Cl)ccc2Cl)[nH]1] | 13, 14, 15, 18 |
| P130 | 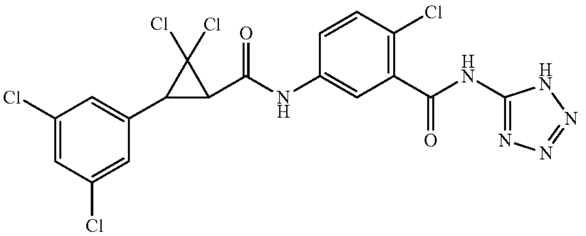 [SMILES: O=C(Nc1nnn[nH]1)c1cc(NC(=O)C2C(c3cc(Cl)cc(Cl)c3)C2(Cl)Cl)ccc1Cl] | 13, 14, 15, 18 |
| P131 | 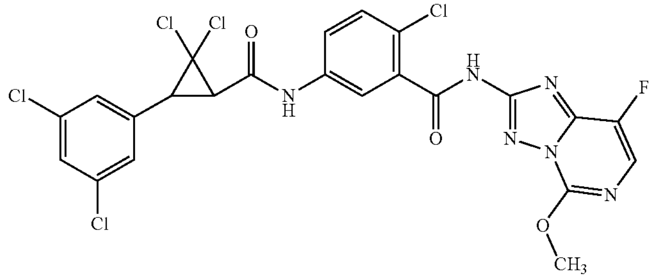 [SMILES: COc1ncc(F)c2nc(NC(=O)c3cc(NC(=O)C4C(c5cc(Cl)cc(Cl)c5)C4(Cl)Cl)ccc3Cl)nn12] | 13, 14, 15, 18 |

TABLE P1-continued
| Structure and preparation method for prophetic molecules | | |
|---|---|---|
| No. | Structure | Prep* |
| P132 | 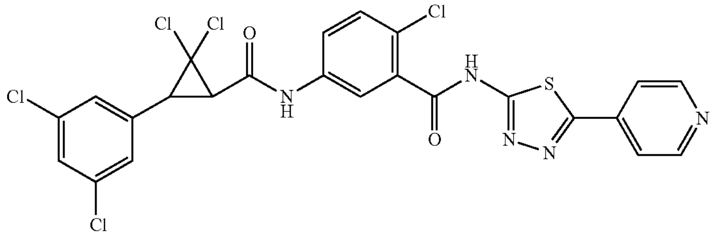 [SMILES: O=C(Nc1nnc(-c2ccncc2)s1)c1cc(NC(=O)C2C(c3cc(Cl)cc(Cl)c3)C2(Cl)Cl)ccc1Cl] | 13, 14, 15, 18 |
| P133 | 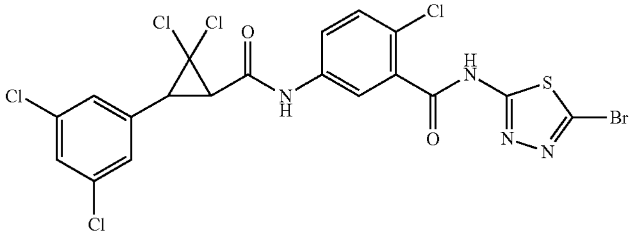 [SMILES: O=C(Nc1nnc(Br)s1)c1cc(NC(=O)C2C(c3cc(Cl)cc(Cl)c3)C2(Cl)Cl)ccc1Cl] | 13, 14, 15, 18 |
| P134 | 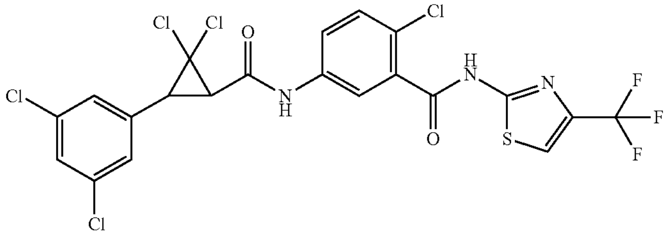 [SMILES: O=C(Nc1nc(C(F)(F)F)cs1)c1cc(NC(=O)C2C(c3cc(Cl)cc(Cl)c3)C2(Cl)Cl)ccc1Cl] | 13, 14, 15, 18 |
| P135 | 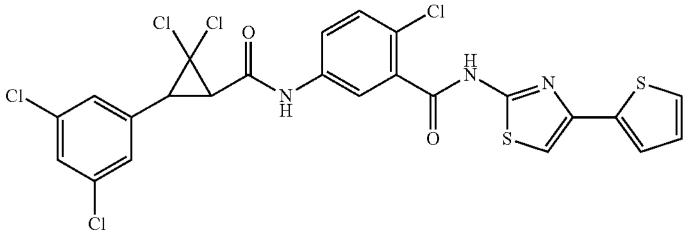 [SMILES: O=C(Nc1nc(-c2cccs2)cs1)c1cc(NC(=O)C2C(c3cc(Cl)cc(Cl)c3)C2(Cl)Cl)ccc1Cl] | 13, 14, 15, 18 |
| P136 | 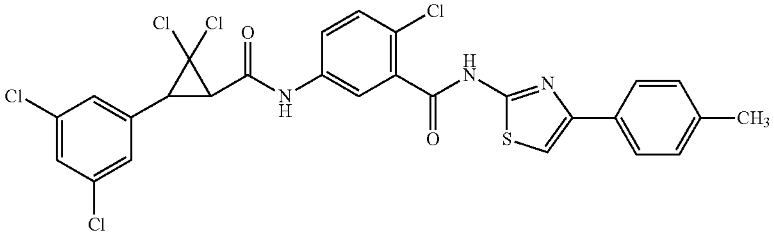 [SMILES: Cc1ccc(-c2csc(NC(=O)c3cc(NC(=O)C4C(c5cc(Cl)cc(Cl)c5)C4(Cl)Cl)ccc3Cl)n2)cc1] | 13, 14, 15, 18 |
| P137 | 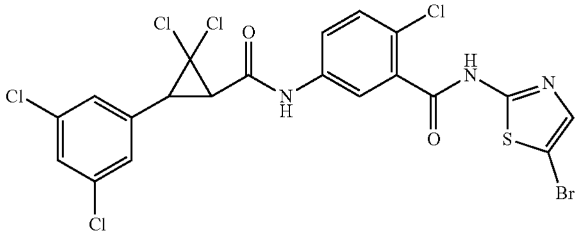 [SMILES: O=C(Nc1ncc(Br)s1)c1cc(NC(=O)C2C(c3cc(Cl)cc(Cl)c3)C2(Cl)Cl)ccc1Cl] | 13, 14, 15, 18 |

TABLE P1-continued
| Structure and preparation method for prophetic molecules | | |
|---|---|---|
| No. | Structure | Prep* |
| P138 | 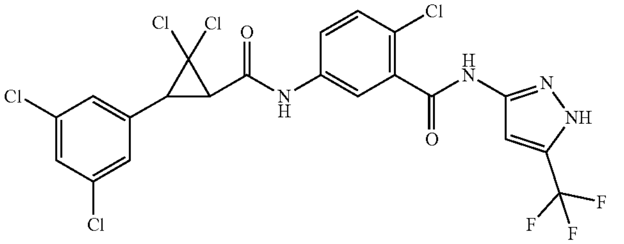 [SMILES: O=C(Nc1cc(C(F)(F)F)[nH]n1)c1cc(NC(=O)C2C(c3cc(Cl)cc(Cl)c3)C2(Cl)Cl)ccc1Cl] | 13, 14, 15, 18 |
| P139 | 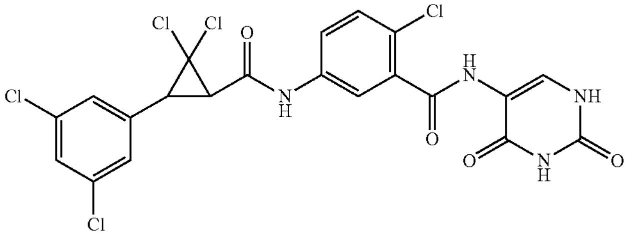 [SMILES: O=C(Nc1c[nH]c(=O)[nH]c1=O)c1cc(NC(=O)C2C(c3cc(Cl)cc(Cl)c3)C2(Cl)Cl)ccc1Cl] | 13, 14, 15, 18 |
| P140 | 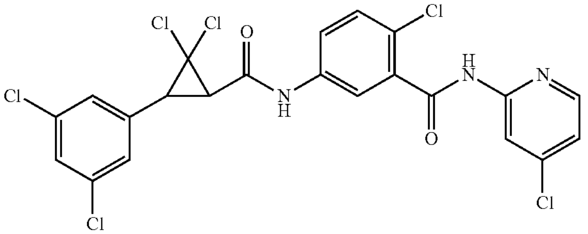 [SMILES: O=C(Nc1cc(Cl)ccn1)c1cc(NC(=O)C2C(c3cc(Cl)cc(Cl)c3)C2(Cl)Cl)ccc1Cl] | 13, 14, 15, 18 |
| P141 | 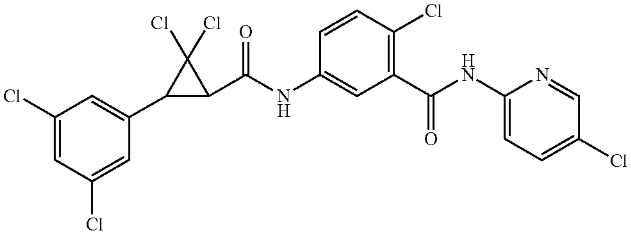 | 13, 14, 15, 18 |
| P142 | 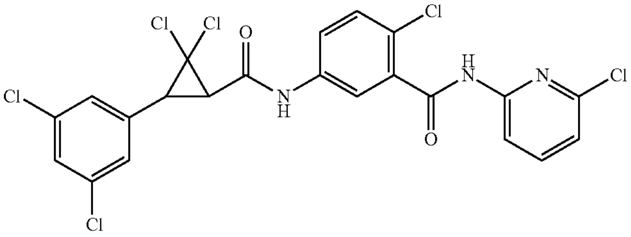 [SMILES: O=C(Nc1cccc(Cl)n1)c1cc(NC(=O)C2C(c3cc(Cl)cc(Cl)c3)C2(Cl)Cl)ccc1Cl] | 13, 14, 15, 18 |
| P143 | 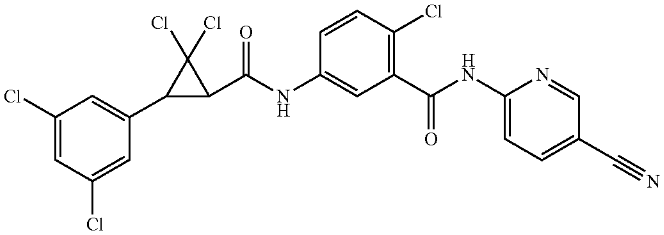 [SMILES: N#Cc1ccc(NC(=O)c2cc(NC(=O)C3C(c4cc(Cl)cc(Cl)c4)C3(Cl)Cl)ccc2Cl)nc1] | 13, 14, 15, 18 |

TABLE P1-continued
Structure and preparation method for prophetic molecules
| No. | Structure | Prep* |
|---|---|---|
| P144 | 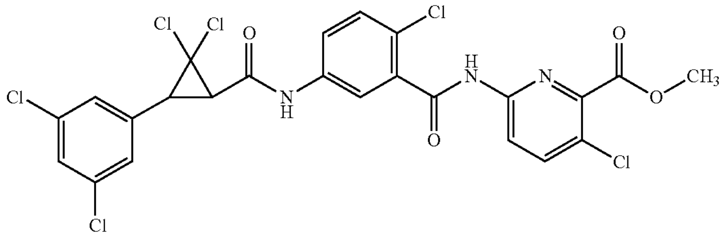 [SMILES: COC(=O)c1nc(NC(=O)c2cc(NC(=O)C3C(c4cc(Cl)cc(Cl)c4)C3(Cl)Cl)ccc2Cl)ccc1Cl] | 13, 14, 15, 18 |
| P145 | 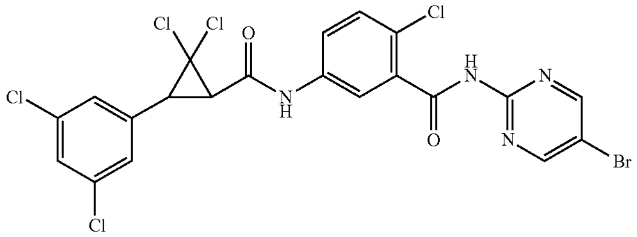 [SMILES: O=C(Nc1ncc(Br)cn1)c1cc(NC(=O)C2C(c3cc(Cl)cc(Cl)c3)C2(Cl)Cl)ccc1Cl] | 13, 14, 15, 18 |
| P146 | 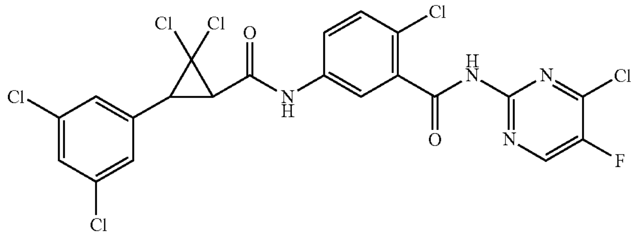 [SMILES: O=C(Nc1ncc(F)c(Cl)n1)c1cc(NC(=O)C2C(c3cc(Cl)cc(Cl)c3)C2(Cl)Cl)ccc1Cl] | 13, 14, 15, 18 |
| P147 | 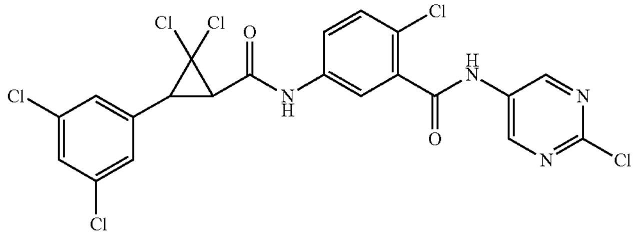 [SMILES: O=C(Nc1cnc(Cl)nc1)c1cc(NC(=O)C2C(c3cc(Cl)cc(Cl)c3)C2(Cl)Cl)ccc1Cl] | 13, 14, 15, 18 |
| P148 | 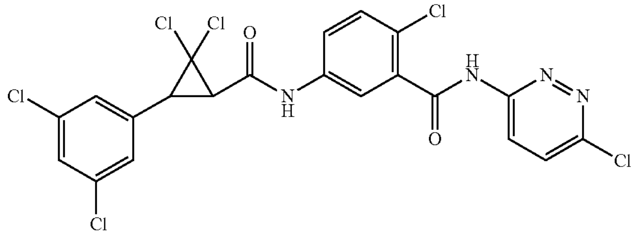 [SMILES: O=C(Nc1ccc(Cl)nn1)c1cc(NC(=O)C2C(c3cc(Cl)cc(Cl)c3)C2(Cl)Cl)ccc1Cl] | 13, 14, 15, 18 |
| P149 | 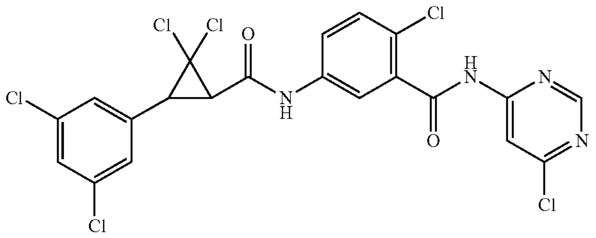 [SMILES: O=C(Nc1cc(Cl)ncn1)c1cc(NC(=O)C2C(c3cc(Cl)cc(Cl)c3)C2(Cl)Cl)ccc1Cl] | 13, 14, 15, 18 |

TABLE P1-continued
Structure and preparation method for prophetic molecules
| No. | Structure | Prep* |
| --- | --- | --- |
| P150 | 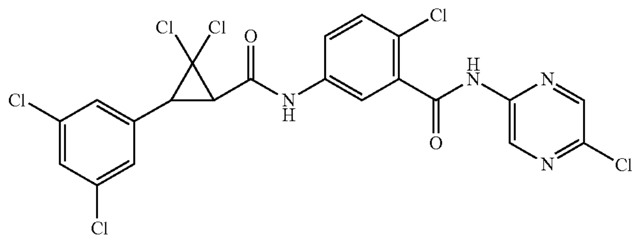 | 13, 14, 15, 18 |
| P151 | 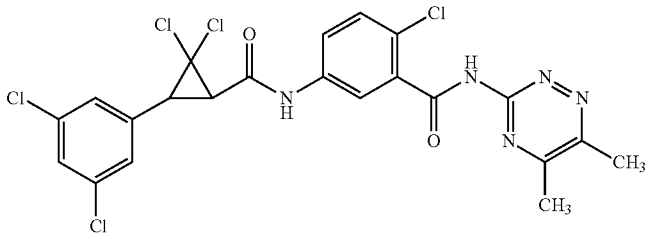 [SMILES: Cc1nnc(NC(=O)c2cc(NC(=O)C3C(c4cc(Cl)cc(Cl)c4)C3(Cl)Cl)ccc2Cl)nc1C] | 13, 14, 15, 18 |
| P152 | 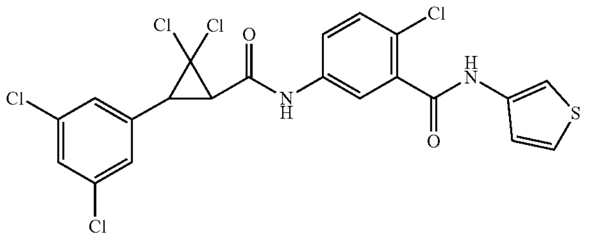 [SMILES: O=C(Nc1ccsc1)c1cc(NC(=O)C2C(c3cc(Cl)cc(Cl)c3)C2(Cl)Cl)ccc1Cl] | 13, 14, 15, 18 |
| P153 | 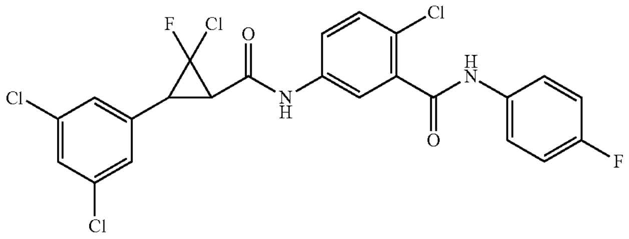 | 13, 14, 15, 18 |
| P154 | 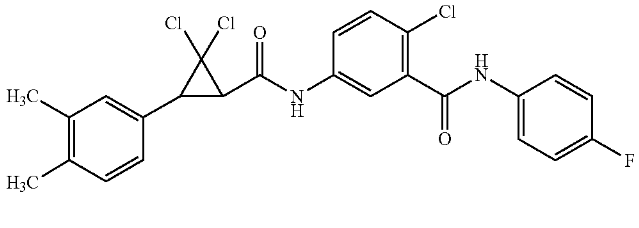 [SMILES: Cc1ccc(C2C(C(=O)Nc3ccc(Cl)c(C(=O)Nc4ccc(F)cc4)c3)C2(Cl)Cl)cc1C] | 13, 14, 15, 18 |
| P155 | 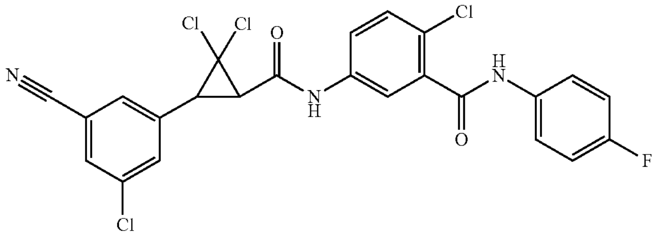 [SMILES: N#Cc1cc(Cl)cc(C2C(C(=O)Nc3ccc(Cl)c(C(=O)Nc4ccc(F)cc4)c3)C2(Cl)Cl)c1] | 13, 14, 15, 18 |

TABLE P1-continued
Structure and preparation method for prophetic molecules
| No. | Structure | Prep* |
| --- | --- | --- |
| P156 | 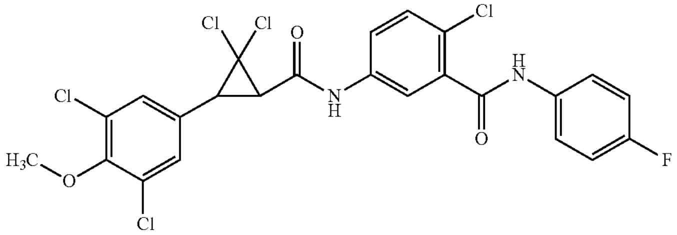 [SMILES: COc1c(Cl)cc(C2C(C(=O)Nc3ccc(Cl)c(C(=O)Nc4ccc(F)cc4)c3)C2(Cl)Cl)cc1Cl] | 13, 14, 15, 18 |
| P157 | 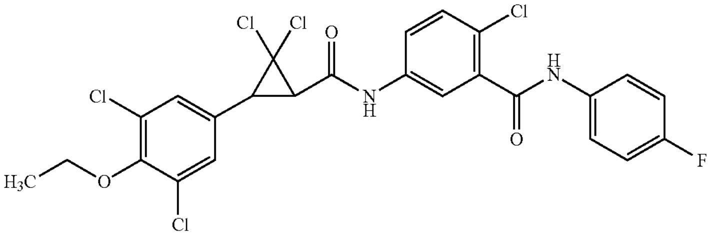 [SMILES: CCOc1c(Cl)cc(C2C(C(=O)Nc3ccc(Cl)c(C(=O)Nc4ccc(F)cc4)c3)C2(Cl)Cl)cc1Cl] | 13, 14, 15, 18 |
| P158 | 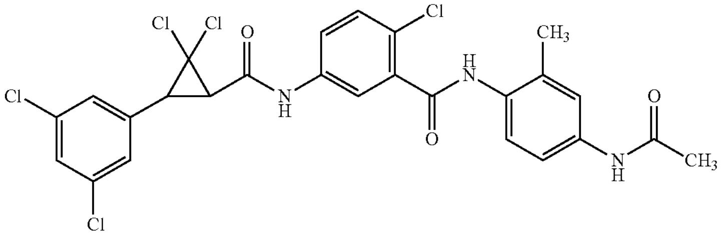 | 13, 14, 15, 18 |
| P159 | 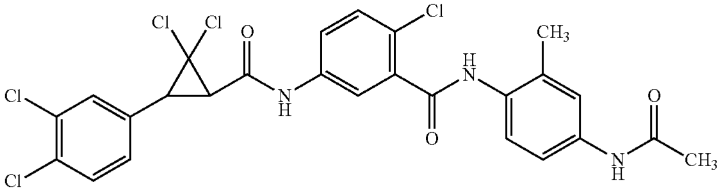 [SMILES: CC(=O)Nc1ccc(NC(=O)c2cc(NC(=O)C3C(c4ccc(Cl)c(Cl)c4)C3(Cl)Cl)ccc2Cl)c(C)c1] | 13, 14, 15, 18 |
| P160 | 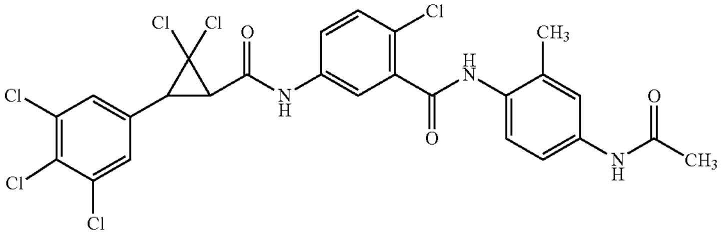 [SMILES: CC(=O)Nc1ccc(NC(=O)c2cc(NC(=O)C3C(c4cc(Cl)c(Cl)c(Cl)c4)C3(Cl)Cl)ccc2Cl)c(C)c1] | 13, 14, 15, 18 |
| P161 | 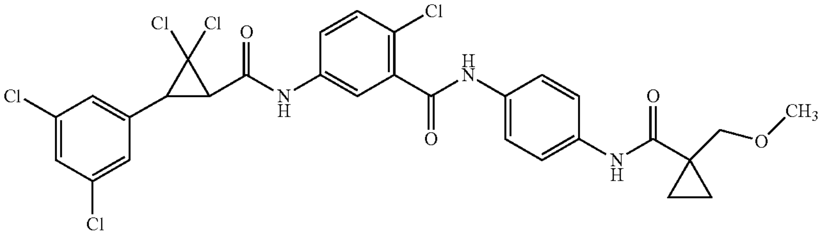 [SMILES: COCC1(C(=O)Nc2ccc(NC(=O)c3cc(NC(=O)C4C(c5cc(Cl)cc(Cl)c5)C4(Cl)Cl)ccc3Cl)cc2)CC1] | Scheme 5 |

TABLE P1-continued

| Structure and preparation method for prophetic molecules | | |
|---|---|---|
| No. | Structure | Prep* |
| P162 | 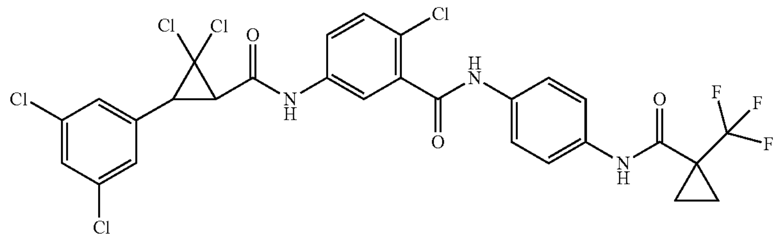 [SMILES: O=C(Nc1ccc(NC(=O)C2(C(F)(F)F)CC2)cc1)c1cc(NC(=O)C2C(c3cc(Cl)cc(Cl)c3)C2(Cl)Cl)ccc1Cl] | Scheme 5 |
| P163 | 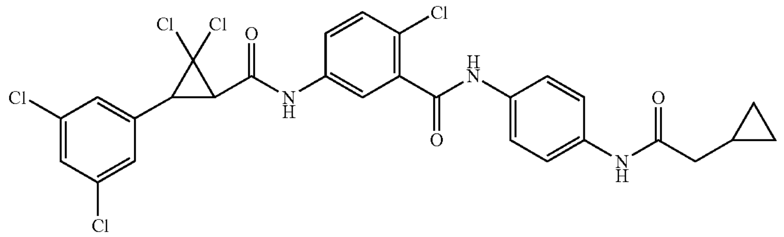 [SMILES: O=C(CC1CC1)Nc1ccc(NC(=O)c2cc(NC(=O)C3C(c4cc(Cl)cc(Cl)c4)C3(Cl)Cl)ccc2Cl)cc1] | Scheme 5 |
| P164 | 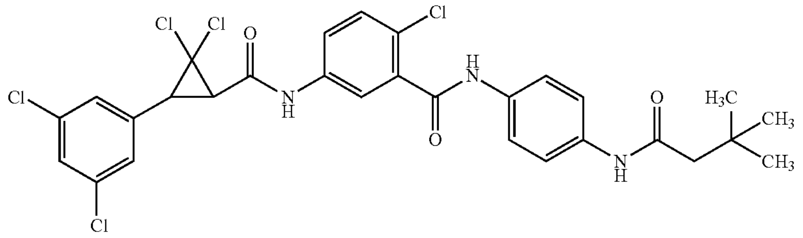 [SMILES: CC(C)(C)CC(=O)Nc1ccc(NC(=O)c2cc(NC(=O)C3C(c4cc(Cl)cc(Cl)c4)C3(Cl)Cl)ccc2Cl)cc1] | Scheme 5 |

Prep* means prepare according to Example or Scheme

The following compounds were prepared in like manner to the procedure outlined in Example 2:

trans-2,2-Dichloro-3-(4-methoxyphenyl) cyclopropane-1-carboxylic acid (C212)

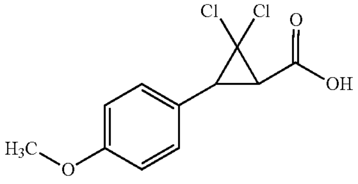 [SMILES: COc1ccc(C2C(C(=O)O)C2(Cl)Cl)cc1]

Isolated as white crystals (0.090 g, 27%): $^1H$ NMR (400 MHZ, $CDCl_3$) δ 11.33 (s, 1H), 7.22-7.15 (m, 2H), 6.94-6.86 (m, 2H), 3.82 (s, 3H), 3.44 (d, J=8.3 Hz, 1H), 2.83 (d, J=8.4 Hz, 1H); $^{13}C$ NMR (101 MHZ, $CDCl_3$) δ 172.23, 159.52, 129.77, 124.17, 114.00, 62.40, 55.31, 40.37, 36.97; ESIMS m/z 260 ($[M-H]^-$).

trans-3-(4-Bromo-3-chlorophenyl)-2,2-dichlorocyclopropane-1-carboxylic acid (C213)

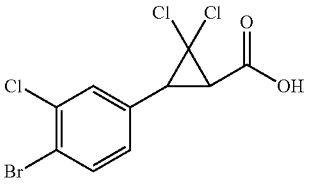

Isolated as a brown solid (0.186 g, 60%): 1H NMR (400 MHZ, $CDCl_3$) δ 7.63 (d, J=8.3 Hz, 1H), 7.40-7.32 (m, 1H), 7.04 (ddd, J=8.3, 2.2, 0.7 Hz, 1H), 3.42 (d, J=8.3 Hz, 1H), 2.86 (d, J=8.3 Hz, 1H); $^{13}C$ NMR (101 MHZ, $CDCl_3$) δ 171.39, 134.91, 133.89, 133.08, 130.54, 128.16, 122.61, 61.39, 39.70, 37.14; ESIMS m/z 342.8 ($[M-H]^-$).

trans-3-(3-Bromo-4-chlorophenyl)-2,2-dichlorocyclopropane-1-carboxylic acid (C214)

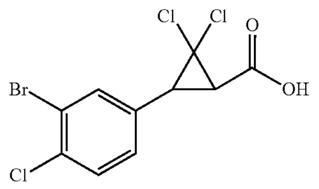

Isolated as a tan solid (0.7577 g, 71%): $^{1}$H NMR (400 MHz, $CDCl_3$) δ 7.53 (d, J=J=2.1 Hz, 1H), 7.47 (d, J=8.3 Hz, 1H), 7.17 (dd, J=8.3, 2.1 Hz, 1H), 3.44 (d, J=8.3 Hz, 1H), 2.86 (d, J=8.3 Hz, 1H); $^{13}$C NMR (101 MHz, $CDCl_3$) δ 171.40, 134.73, 133.87, 132.39, 130.43, 128.70, 122.74, 61.50, 39.53, 37.14; ESIMS m/z 342.7 ([M−H]$^-$).

trans-3-(3-Bromo-5-chlorophenyl)-2,2-dichlorocyclopropane-1-carboxylic acid (C215)

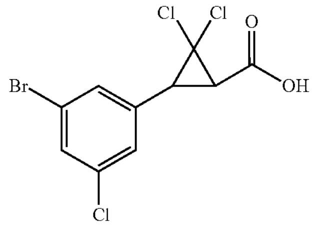

Isolated as a tan solid (0.9102 mg, 40%): $^{1}$H NMR (400 MHz, Acetone-$d_6$) δ 7.67 (d, J=1.6 Hz, 1H), 7.63 (s, 1H), 7.57 (d, J=1.8 Hz, 1H), 3.53 (d, J=8.5 Hz, 1H), 3.38 (d, J=8.5 Hz, 1H); $^{13}$C NMR (101 MHz, Acetone-$d_6$) δ 166.92, 138.16, 135.69, 131.59, 131.55, 129.10, 123.23, 62.52, 39.41, 37.85; ESIMS m/z 342.7 ([M−H]$^-$)].

trans-2, 2-Dichloro-3-(3-chloro-5-(difluoromethyl)phenyl)cyclopropane-1-carboxylic acid (C216)

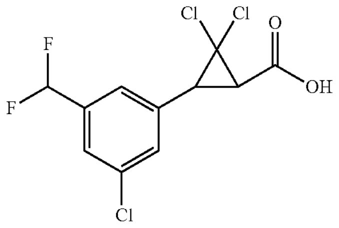

Isolated as an off-white solid (2.6 g, 63%): $^{1}$H NMR (300 MHz, $CDCl_3$) missing COOH signal δ 7.49 (s, 1H), 7.38 (s, 1H), 7.30 (s, 1H), 6.63 (t, J=56.0 Hz, 1H), 3.50 (d, J=8.4 Hz, 1H), 2.91 (d, J=8.0 Hz, 1H); $^{19}$F NMR (282.2 MHz, $CDCl_3$) δ −112.04; ESIMS m/z 313 ([M−H]$^-$).

trans-2,2-Dichloro-3-(4-chloro-3-(difluoromethyl)phenyl)cyclopropane-1-carboxylic acid (C217)

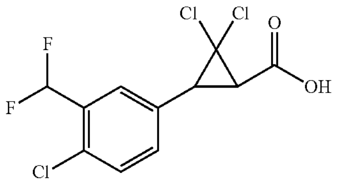 [SMILES: O=C(O)C1C(c2ccc(Cl)c(C(F)F)c2)C1(Cl)Cl]

Isolated as an off-white solid (6.2 g, 69%): $^{1}$H NMR (400 MHz, $CDCl_3$) δ 10.5 (br s, 1H), 7.55 (s, 1H), 7.46 (d, J=8.0 Hz, 1H), 7.34 (d, J=8.4 Hz, 1H), 6.95 (t, J=54.8 Hz, 1H), 3.50 (d, J=8.4 Hz, 1H), 2.91 (d, J=8.4 Hz, 1H); $^{19}$F NMR (376.2 MHz, $CDCl_3$) δ −115.52; ESIMS m/z 313 ([M−H]$^-$).

trans-2,2-Dichloro-3-(3-(difluoromethyl)-5-fluorophenyl)cyclopropane-1-carboxylic acid (C218)

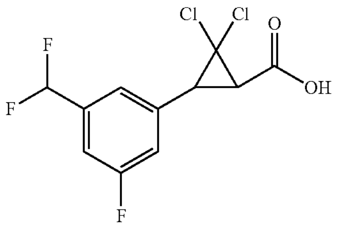 [SMILES: O=C(O)C1C(c2cc(F)cc(C(F)F)c2)C1(Cl)Cl]

Isolated as an off-white solid (5 g, 38%): $^{1}$H NMR (400 MHz, $CDCl_3$) missing COOH signal δ 7.23-7.21 (m, 2H), 7.11 (d, J=8.8 Hz, 1H), 6.64 (t, J=55.6 Hz, 1H), 3.51 (d, J=8.4 Hz, 1H), 2.91 (d, J=8.0 Hz, 1H); $^{19}$F NMR (376.2 MHz, $CDCl_3$) δ −110.37; ESIMS m/z 297.19 ([M−H]$^-$).

trans-2,2-Dichloro-3-(3-(difluoromethyl)-4-fluorophenyl)cyclopropane-1-carboxylic acid (C219)

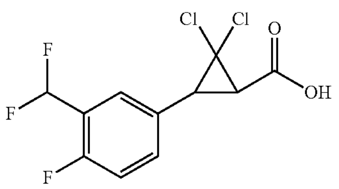 [SMILES: O=C(O)C1C(c2ccc(F)c(C(F)F)c2)C1(Cl)Cl]

Isolated as an off-white solid (6.0 g, 77%): $^{1}$H NMR (400 MHz, $CDCl_3$) missing COOH signal δ 7.49 (d, J=6.0 Hz, 1H), 7.40 (br s, 1H), 7.17 (t, J=9.2 Hz, 1H), 6.90 (t, J=54.8 Hz, 1H), 3.49 (d, J=8.0 Hz, 1H), 2.89 (d, J=8.4 Hz, 1H); $^{19}$F NMR (376.2 MHz, $CDCl_3$) δ −114.47, −119.69; ESIMS m/z 297 ([M−H]$^-$).

trans-2,2-Dichloro-3-(3-chloro-4-(difluoromethyl)phenyl)cyclopropane-1-carboxylic acid (C220)

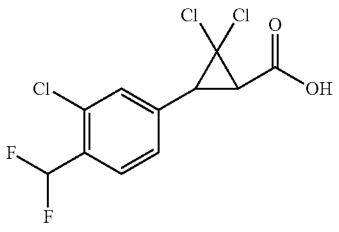

Isolated as an off-white solid (3.5 g, 42%): $^{1}$H NMR (400 MHz, $CDCl_3$) missing COOH signal δ 7.68 (d, J=7.6 Hz, 1H), 7.35 (s, 1H), 7.29 (d, J=8.4 Hz, 1H), 6.94 (t, J=54.8 Hz, 1H), 3.48 (d, J=8.4 Hz, 1H), 2.91 (d, J=8.4 Hz, 1H); $^{19}$F NMR (376.2 MHz, $CDCl_3$) δ −115.46; ESIMS m/z 313 ([M−H]$^-$).

trans-2,2-Dichloro-3-(4-(difluoromethyl)-3-fluorophenyl)cyclopropane-1-carboxylic acid (C221)

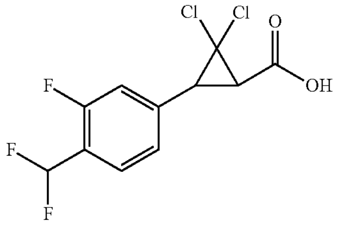 [SMILES: O=C(O)C1C(c2ccc(C(F)F)c(F)c2)C1(Cl)Cl]

Isolated as an off-white solid (4.4 g, 77%): $^{1}$H NMR (400 MHz, $CDCl_3$) δ 7.62 (t, J=7.6 Hz, 1H), 7.18 (d, J=7.6 Hz, 1H), 7.06 (d, J=10.0 Hz, 1H), 6.89 (t, J=54.8 Hz, 1H), 3.50 (d, J=8.4 Hz, 1H), 2.90 (d, J=8.4 Hz, 1H); $^{19}$F NMR (376.2 MHz, $CDCl_3$) δ −114.42, −118.63; ESIMS m/z 297.15 ([M−H]$^-$).

trans-2,2-Dichloro-3-(3-(difluoromethyl)phenyl)cyclopropane-1-carboxylic acid (C222)

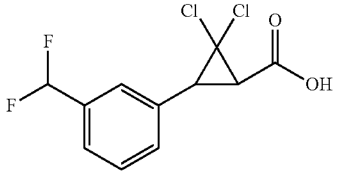

Isolated as an off-white solid (6.2 g, 53%): $^{1}$H NMR (300 MHz, $CDCl_3$) δ 7.49 (br s, 2H), 7.41 (br s, 2H), 6.66 (t, J=56.0 Hz, 1H), 3.53 (d, J=8.4 Hz, 1H), 2.92 (d, J=8.0 Hz, 1H); $^{19}$F NMR (282.2 MHz, $CDCl_3$) δ −111.20; ESIMS m/z 279.20 ([M−H]$^-$).

trans-2, 2-Dichloro-3-(4-(difluoromethyl)phenyl)cyclopropane-1-carboxylic acid (C223)

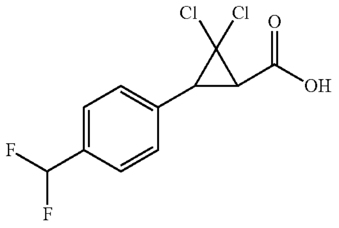

Isolated as an off-white solid (7 g, 61%): $^{1}$H NMR (300 MHz, $CDCl_3$) δ 7.53 (d, J=8.0 Hz, 2H), 7.37 (d, J=8.0 Hz, 2H), 6.66 (t, J=56.4 Hz, 1H), 3.52 (d, J=8.4 Hz, 1H), 2.92 (d, J=8.0 Hz, 1H); $^{19}$F NMR (282.2 MHz, $CDCl_3$) δ −112.20; ESIMS m/z 279.30 ([M−H]$^-$).

trans-3-(4-Bromo-3,5-difluorophenyl)-2,2-dichlorocyclopropane-1-carboxylic acid (C224)

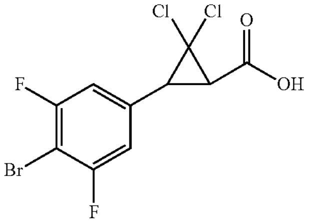

Isolated as a white solid (2.13 g, 72%): mp 178.3-188.6° C.; $^{1}$H NMR (400 MHz, $CDCl_3$) δ 6.90 (d, J=7.1 Hz, 2H), 3.43 (d, J=8.2 Hz, 1H), 2.86 (d, J=8.2 Hz, 1H); $^{19}$F NMR (376 MHz, $CDCl_3$) δ −103.87; ESIMS m/z 344.7 ([M−H]$^-$).

trans-3-(4-Bromo-3-fluoro-5-methoxyphenyl)-2,2-dichlorocyclopropane-1-carboxylic acid (C225)

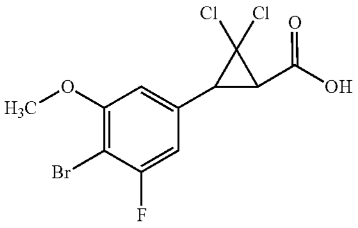

Isolated as an oily solid (0.43 g, 37%): $^{1}$H NMR (400 MHz, $CDCl_3$) δ 6.70-6.64 (m, 1H), 6.61 (d, J=1.6 Hz, 1H), 3.95 (s, 3H), 3.44 (d, J=8.3 Hz, 1H), 2.86 (d, J=8.3 Hz, 1H); $^{19}$F NMR (376 MHz, $CDCl_3$) δ −104.22; ESIMS m/z 356.7 ([M−H]$^-$).

trans-3-(3-Bromo-5-fluoro-4-methoxyphenyl)-2,2-dichlorocyclopropane-1-carboxylic acid (C226)

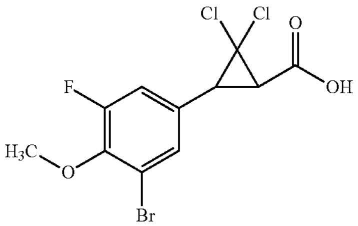 [SMILES: COc1c(F)cc(C2C(C(=O)O)C2(Cl)Cl)cc1Br]

Isolated as a brown oil (0.24 g, 65%): $^{1}H$ NMR (400 MHz, $CDCl_3$) δ 7.24 (d, J=7.9 Hz, 1H), 6.87 (d, J=11.3 Hz, 1H), 3.91 (d, J=3.8 Hz, 3H), 3.44 (d, J=8.3 Hz, 1H), 2.80 (d, J=8.3 Hz, 1H); $^{19}F$ NMR (376 MHz, $CDCl_3$) δ −135.11; ESIMS m/z 356.7 ($[M-H]^-$).

trans-2,2-Dichloro-3-(3,5-difluoro-4-methoxyphenyl)cyclopropane-1-carboxylic acid (C227)

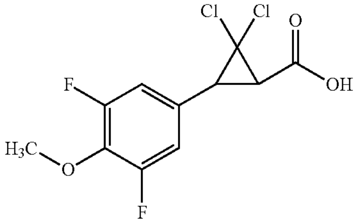 [SMILES: COc1c(F)cc(C2C(C(=O)O)C2(Cl)Cl)cc1F]

Isolated as a tan solid (0.440 g, 53%): $^{1}H$ NMR (400 MHz, $CDCl_3$) δ 10.72 (s, 1H), 6.89-6.77 (m, 2H), 4.02 (t, J=1.2 Hz, 3H), 3.39 (d, J=8.3 Hz, 1H), 2.80 (d, J=8.3 Hz, 1H); $^{19}F$ NMR (376 MHz, $CDCl_3$) δ −127.43, −127.43, −127.44; ESIMS m/z 296 ($[M-H]^-$).

cis/trans-2,2-Dichloro-3-(3,4,5-trifluorophenyl)cyclopropane-1-carboxylic acid (C228)

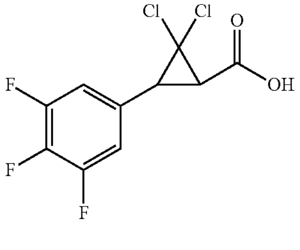 [SMILES: O=C(O)C1C(c2cc(F)c(F)c(F)c2)C1(Cl)Cl]

Isolated as a white solid (0.411 g, 53%): $^{1}H$ NMR (400 MHz, $CDCl_3$) δ 7.72 (s, 1H), 7.06-6.74 (m, 2H), 3.46-3.23 (m, 1H), 3.01-2.74 (m, 1H); $^{19}F$ NMR (376 MHz, $CDCl_3$) δ −132.88, −132.94, −133.81, −133.87, −159.60, −159.65, −159.71, −160.34, −160.39, −160.45; ESIMS m/z 284 ($[M-H]^-$).

The following compounds were prepared in like manner to the procedure outlined in Example 3:

trans-2-Chloro-5-(2,2-dichloro-3-(4-methoxyphenyl)cyclopropyl)thiophene (C229)

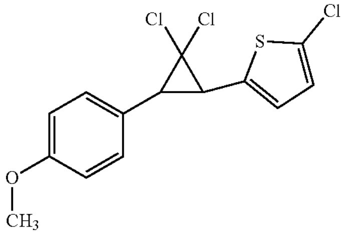 [SMILES: COc1ccc(C2C(c3ccc(Cl)s3)C2(Cl)Cl)cc1]

Isolated as a dark orange oil (0.455 g, 68%): $^{1}H$ NMR (400 MHz, $CDCl_3$) δ 7.25 (d, J=9.5 Hz, 2H), 6.92 (d, J=8.8 Hz, 2H), 6.83 (d, J=3.8 Hz, 1H), 6.80 (d, J=3.5 Hz, 1H), 3.83 (s, 3H), 3.10 (s, 2H); $^{13}C$ NMR (101 MHz, $CDCl_3$) δ 159.40, 136.68, 129.87, 129.36, 126.30, 126.04, 125.59, 113.96, 65.28, 55.32, 41.23, 34.95.

trans-2-((2,2-Dichloro-3-methyl-3-(4-(trifluoromethoxy)phenyl)cyclopropyl)methoxy)tetrahydro-2H-pyran (C230)

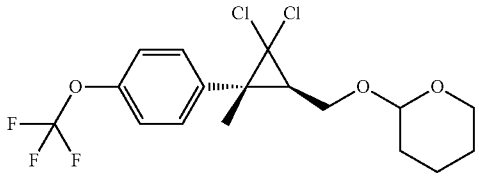 [SMILES: C[C@]1(c2ccc(OC(F)(F)F)cc2)[C@H](COC2CCCCO2)C1(Cl)Cl]

Isolated as a pale yellow liquid (3.3 g, 77%): $^{1}H$ NMR (400 MHz, $CDCl_3$) δ 7.38-7.32 (m, 2H), 7.22-7.16 (d, J=8.4 Hz, 2H), 4.72 (dt, J=17.0, 3.3 Hz, 1H), 4.13 (dd, J=11.2, 6.6 Hz, 0.5H), 4.00-3.82 (m, 2H), 3.63 (dd, J=11.3, 7.4 Hz, 0.5H), 3.60-3.52 (m, 1H), 2.20 (dt, J=11.6, 4.5 Hz, 1H), 1.94-1.82 (m, 1H), 1.82-1.71 (m, 1H), 1.71-1.55 (m, 4H), 1.52 (d, J=5.9 Hz, 3H); $^{19}F$ NMR (376 MHz, $CDCl_3$) δ −57.85; $^{13}C$ NMR (101 MHz, $CDCl_3$) δ 148.26, 141.31, 130.14, 124.32, 121.77, 120.89, 119.21, 116.65, 99.17, 99.08, 67.92, 63.87, 63.77, 62.41, 37.91, 37.83, 36.92, 36.82, 30.74, 25.45, 19.93, 19.88, 19.48, 19.44; ESIMS m/z 441.4 ($M+CH_3CN$); IR (thin film) 1257, 1222, 1208, 1163 $cm^{-1}$.

trans-1-Chloro-3-(2,2-dichloro-3-(4-methoxyphenyl)cyclopropyl)-5-(difluoromethyl)benzene (C231)

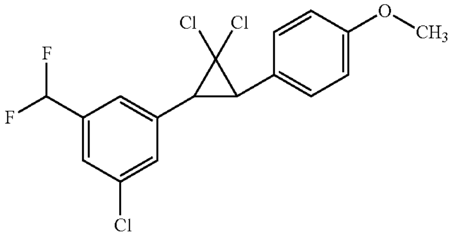 [SMILES: COc1ccc(C2C(c3cc(Cl)cc(C(F)F)c3)C2(Cl)Cl)cc1]

Isolated as a yellow liquid (11.5 g, 69%): $^1$H NMR (300 MHz, $CDCl_3$): δ 7.47 (s, 2H), 7.39 (s, 1H), 7.28 (d, J=8.7 Hz, 2H), 6.93 (d, J=8.7 Hz, 2H), 6.64 (t, J=56.1 Hz, 1H), 3.83 (s, 3H), 3.16 (q, J=8.7 Hz, 2H).

trans-1-Chloro-4-(2, 2-dichloro-3-(4-methoxyphenyl)cyclopropyl)-2-(difluoromethyl) benzene (C232)

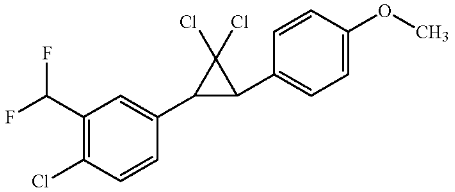 [SMILES: COc1ccc(C2C(c3ccc(Cl)c(C(F)F)c3)C2(Cl)Cl)cc1]

Isolated as a pale yellow solid (10.7 g, 83%): $^1$H NMR (400 MHz, $CDCl_3$) δ 7.65 (s, 1H), 7.46-7.41 (m, 2H), 7.28 (d, J=8.4 Hz, 2H), 7.10-6.83 (m, 3H), 3.83 (s, 3H), 3.18-3.13 (m, 2H).

trans-1-(2, 2-Dichloro-3-(4-methoxyphenyl)cyclopropyl)-3-(difluoromethyl)-5-fluorobenzene (C233)

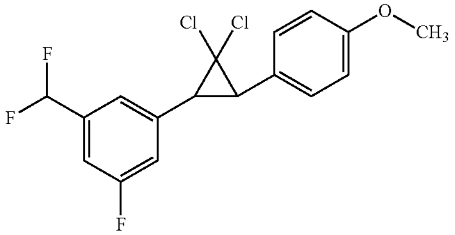 [SMILES: COc1ccc(C2C(c3cc(F)cc(C(F)F)c3)C2(Cl)Cl)cc1]

Isolated as an off-white solid (16.5 g, 64%): $^1$H NMR (400 MHz, $CDCl_3$) δ 7.29 (d, J=8.8 Hz, 2H), 7.20 (d, J=8.8 Hz, 2H), 6.93 (d, J=8.8 Hz, 2H), 6.65 (t, J=56.0 Hz, 2H), 3.83 (s, 3H), 3.16 (s, 2H).

trans-4-(2, 2-Dichloro-3-(4-methoxyphenyl)cyclopropyl)-2-(difluoromethyl)-1-fluorobenzene (C234)

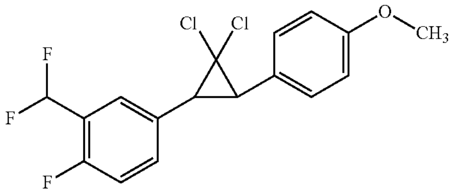

Isolated as an off-white solid (10.0 g, 55%): ESIMS m/z 374 ([M+H]$^+$).

trans-2-Chloro-4-(2,2-dichloro-3-(4-methoxyphenyl)cyclopropyl)-1-(difluoromethyl)benzene (C235)

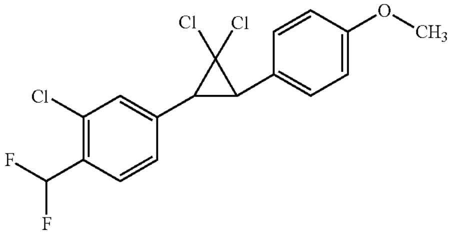 [SMILES: COc1ccc(C2C(c3ccc(C(F)F)c(Cl)c3)C2(Cl)Cl)cc1]

Isolated as an off-white solid (10.0 g, 34%): $^1$H NMR (400 MHz, $CDCl_3$) δ 7.68 (d, J=8.0 Hz, 1H), 7.43 (s, 1H), 7.38 (d, J=8.4 Hz, 1H), 7.28-7.25 (m, 2H), 7.09-6.92 (m, 3H), 3.83 (s, 3H), 3.15 (q, J=12.0 Hz, 2H); ESIMS m/z 376 ([M+H]$^+$).

trans-2-Fluoro-4-(2,2-dichloro-3-(4-methoxyphenyl)cyclopropyl)-1-(difluoromethyl)benzene (C236)

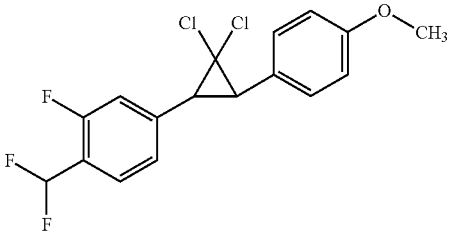 [SMILES: COc1ccc(C2C(c3ccc(C(F)F)c(F)c3)C2(Cl)Cl)cc1]

Isolated as a pale yellow liquid (6.9 g, 58%): $^1$H NMR (400 MHz, $CDCl_3$) δ 7.31 (t, J=7.6 Hz, 1H), 7.27 (d, J=9.2 Hz, 2H), 7.14 (d, J=10.8 Hz, 1H), 7.04-6.76 (m, 4H), 3.83 (s, 3H), 3.16 (t, J=8.8 Hz, 2H); $^{19}$F NMR (376.2 MHz, $CDCl_3$) δ −114.14, −114.32, −119.30.

trans-1-(2,2-Dichloro-3-(4-methoxyphenyl)cyclopropyl)-3-(difluoromethyl)-benzene (C237)

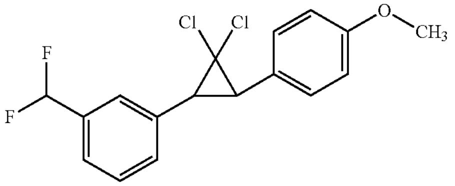 [SMILES: COc1ccc(C2C(c3cccc(C(F)F)c3)C2(Cl)Cl)cc1]

Isolated as a pale yellow solid (6.3 g, 95%): $^1$H NMR (400 MHz, $CDCl_3$) δ 7.50 (br s, 4H), 7.29 (d, J=8.8 Hz, 2H), 6.93 (d, J=8.0 Hz, 2H), 6.67 (t, 1H), 3.83 (s, 3H), 3.19 (s, 2H); $^{19}$F NMR (376.2 MHz, $CDCl_3$) δ −110.87, −111.02.

trans-1-(2, 2-Dichloro-3-(4-(difluoromethyl)phenyl) cyclopropyl)-4-methoxybenzene (C238)

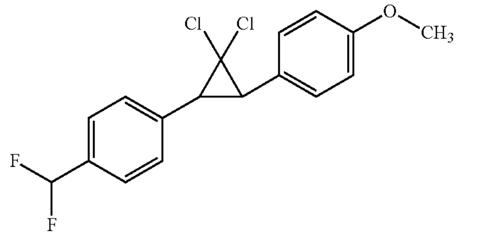 [SMILES: COc1ccc(C2C(c3ccc(C(F)F)cc3)C2(Cl)Cl)cc1]

Isolated as a white solid (14 g, 69%): $^{1}$H NMR (400 MHz, $CDCl_3$) δ 7.54 (d, J=8.0 Hz, 2H), 7.46 (d, J=8.0 Hz, 2H), 7.28 (t, J=8.4 Hz, 2H), 6.93 (d, J=8.0 Hz, 2H), 6.67 (t, J=56.8 Hz, 1H), 3.83 (s, 3H), 3.18 (s, 2H).

The following compounds were prepared in like manner to the procedure outlined in Example 12:

2-Chloro-5-((1R,3R)-2,2-dichloro-3-(3,5-dichlorophenyl)cyclopropane-1-carboxamido)benzoic acid (C239)

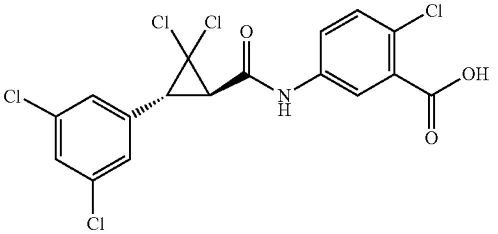

Isolated as a grey solid (3.80 g, 96%): $^{1}$H NMR (300 MHz, DMSO-$d_6$) δ 13.48 (s, 1H), 10.90 (s, 1H), 8.15 (d, J=2.6 Hz, 1H), 7.78 (dd, J=8.8, 2.7 Hz, 1H), 7.63 (t, J=1.9 Hz, 1H), 7.57-7.50 (m, 3H), 3.62 (d, J=8.5 Hz, 1H), 3.49 (d, J=8.5 Hz, 1H); ESIMS m/z 454 ($[M+H]^+$).

2-Chloro-5-((1R,3R)-2,2-dichloro-3-(3,4-dichlorophenyl)cyclopropane-1-carboxamido)benzoic acid (C240)

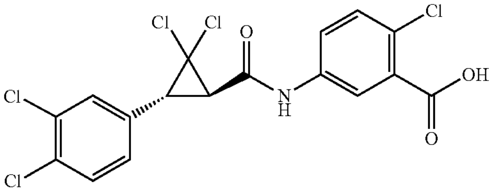

Isolated as a grey solid (3.70 g, 98%): $^{1}$H NMR (300 MHz, DMSO-$d_6$) δ 13.47 (s, 1H), 10.95 (s, 1H), 8.16 (d, J=2.7 Hz, 1H), 7.82-7.73 (m, 2H), 7.69 (d, J=8.3 Hz, 1H), 7.53 (d, J=8.7 Hz, 1H), 7.43 (dd, J=8.5, 2.1 Hz, 1H), 3.60 (d, J=8.5 Hz, 1H), 3.45 (d, J=8.5 Hz, 1H); ESIMS m/z 454 ($[M+H]^+$).

2-Chloro-5-((1R,3R)-2,2-dichloro-3-(3,4,5-trichlorophenyl)cyclopropane-1-carboxamido)benzoic acid (C241)

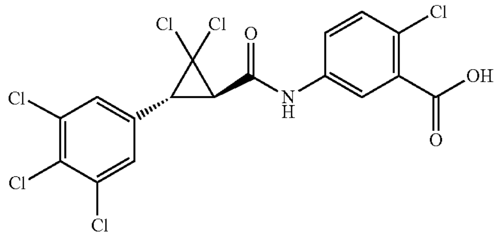 [SMILES: O=C(O)c1cc(NC(=O)[C@H]2[C@H](c3cc(Cl)c(Cl)c(Cl)c3)C2(Cl)Cl)ccc1Cl]

Isolated as a grey solid (3.60 g, 99%): $^{1}$H NMR (400 MHz, DMSO-$d_6$) δ 13.44 (s, 1H), 10.91 (s, 1H), 8.16 (d, J=2.7 Hz, 1H), 7.80-7.76 (m, 3H), 7.54 (d, J=8.7 Hz, 1H), 3.63 (dt, J=8.5, 0.7 Hz, 1H), 3.52 (d, J=8.5 Hz, 1H); ESIMS m/z 488 ($[M+H]^+$).

2-Chloro-5-((1R,3R)-2,2-dichloro-3-(3-chloro-4-fluorophenyl)cyclopropane-1-carboxamido)benzoic acid (C242)

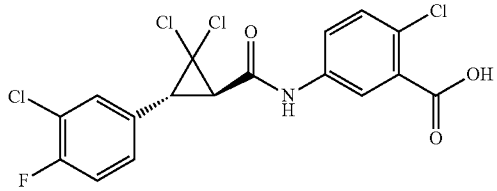

Isolated as a grey solid (3.80 g. 99%): $^{1}$H NMR (400 MHz, DMSO-$d_6$) δ 13.48 (s, 1H), 10.93 (s, 1H), 8.16 (d, J=2.6 Hz, 1H), 7.78 (dd, J=8.8, 2.7 Hz, 1H), 7.71 (dd, J=7.2, 2.0 Hz, 1H), 7.53 (d, J=8.7 Hz, 1H), 7.50-7.42 (m, 2H), 3.58 (d, J=8.4 Hz, 1H), 3.42 (d, J=8.5 Hz, 1H); $^{19}$F NMR (376 MHz, DMSO-$d_6$) δ −117.29; ESIMS m/z 438 ($[M+H]^+$).

trans-2-Chloro-5-(2,2-dichloro-3-(3,5-dichloro-4-methoxyphenyl)cyclo-propane-1-carboxamido)benzoic acid (C243)

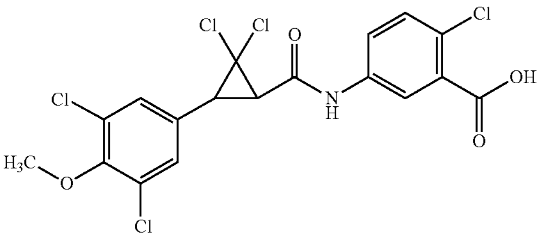 [SMILES: COc1c(Cl)cc(C2C(C(=O)Nc3ccc(Cl)c(C(=O)O)c3)C2(Cl)Cl)cc1Cl]

Isolated as a cream-colored solid (1.565 g, 90%): mp 227-231° C.; $^{1}$H NMR (400 MHz, DMSO-$d_6$) δ 13.48 (s, 1H), 10.89 (s, 1H), 8.16 (d, J=2.4 Hz, 1H), 7.78 (dd, J=8.7, 2.4 Hz, 1H), 7.61 (s, 2H), 7.53 (d, J=8.7 Hz, 1H), 3.84 (s, 3H), 3.57 (d, J=8.4 Hz, 1H), 3.45 (d, J=8.5 Hz, 1H); $^{13}$C NMR (101 MHz, DMSO-$d_6$) δ 166.27, 162.66, 151.18, 137.58, 131.44, 131.42, 131.22, 129.72, 128.18, 125.90, 122.87, 121.16, 62.19, 60.64, 38.51, 36.44; HRMS-ESI (m/z) $[M+]^+$ calcd for $C_{18}H_{12}Cl_5NO_4$, 480.9209; found, 480.9216.

trans-2-Chloro-5-(2,2-dichloro-3-(3-chloro-4-fluorophenyl)cyclopropane-1-carboxamido)benzoic acid (C244)

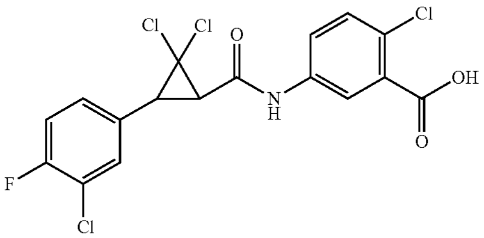 [SMILES: O=C(O)c1cc(NC(=O)C2C(c3ccc(F)c(Cl)c3)C2(Cl)Cl)ccc1Cl]

Isolated as a white solid (6.589 g, 93%): 207-210° C.; $^1H$ NMR (400 MHz, DMSO-$d_6$) δ 13.50 (s, 1H), 10.95 (s, 1H), 8.18 (d, J=2.5 Hz, 1H), 7.80 (dd, J=8.7, 2.5 Hz, 1H), 7.71 (d, J=7.2 Hz, 1H), 7.51 (dd, J=28.2, 8.8 Hz, 3H), 3.59 (d, J=8.4 Hz, 1H), 3.43 (d, J=8.5 Hz, 1H); $^{13}C$ NMR (101 MHz, DMSO-$d_6$) δ 166.22, 162.68, 158.01, 155.55, 137.53, 131.37, 131.17, 131.00, 130.95, 130.91, 129.74, 129.67, 125.86, 122.82, 121.12, 119.49, 119.32, 116.91, 116.70, 62.21, 38.49, 36.58; $^{19}F$ NMR (376 MHz, DMSO-$d_6$) δ −117.26; ESIMS m/z 438 ($[M+H]^+$).

trans-2,3-Dichloro-5-(2,2-dichloro-3-(3,5-dichlorophenyl)cyclopropane-1-carboxamido)benzoic acid (C245)

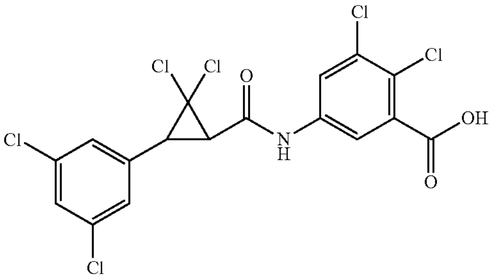 [SMILES: O=C(O)c1cc(NC(=O)C2C(c3cc(Cl)cc(Cl)c3)C2(Cl)Cl)cc(Cl)c1Cl]

Isolated as a tan solid (1.685 g, 79%): mp 231-235° C.; $^1H$ NMR (400 MHz, DMSO-$d_6$) 13.82 (s, 1H), 11.05 (s, 1H), 8.13 (d, J=2.4 Hz, 1H), 7.97 (d, J=2.4 Hz, 1H), 7.63 (s, 1H), 7.56 (s, 2H), 3.63 (d, J=8.5 Hz, 1H), 3.50 (d, J=8.5 Hz, 1H); $^{13}C$ NMR (101 MHz, DMSO-$d_6$) δ 165.84, 162.96, 138.00, 137.09, 134.14, 133.98, 133.01, 127.83, 127.64, 123.41, 122.15, 119.27, 61.94, 38.37, 36.78; HRMS-ESI (m/z) $[M+]^+$ calcd for $C_{17}H_9Cl_6NO_3$, 484.8714; found, 484.8711.

trans-2,4-Dichloro-5-(2,2-dichloro-3-(3,5-dichlorophenyl)cyclopropane-1-carboxamido)benzoic acid (C246)

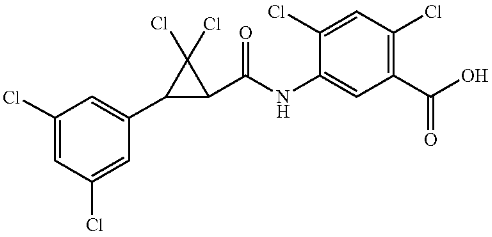 [SMILES: O=C(O)c1cc(NC(=O)C2C(c3cc(Cl)cc(Cl)c3)C2(Cl)Cl)c(Cl)cc1Cl]

Isolated as a light-yellow solid (0.855 g, 42%): mp 263-266° C.; $^1H$ NMR (500 MHz, DMSO-$d_6$) δ 13.67 (s, 1H), 10.37 (s, 1H), 8.37 (s, 1H), 7.85 (s, 1H), 7.63 (s, 1H), 7.53 (d, J=1.6 Hz, 2H), 3.82 (d, J=8.6 Hz, 1H), 3.63 (d, J=8.5 Hz, 1H); $^{13}C$ NMR (126 MHz, DMSO-$d_6$) δ 165.41, 163.35, 137.17, 133.95, 133.66, 131.17, 129.96, 128.80, 128.24, 127.74, 127.60, 126.63, 62.37, 37.24, 37.09; HRMS-ESI (m/z) $[M+]^+$ calcd for $C_{17}H_9Cl_6NO_3$, 484.8714; found, 484.8715.

The following compounds were prepared in like manner to the procedure outlined in Example 13:

trans-2-Chloro-5-(2,2-dibromo-3-(3,5-dichlorophenyl)cyclopropane-1-carboxamido)-N-(2,6-difluorophenyl)benzamide (F162)

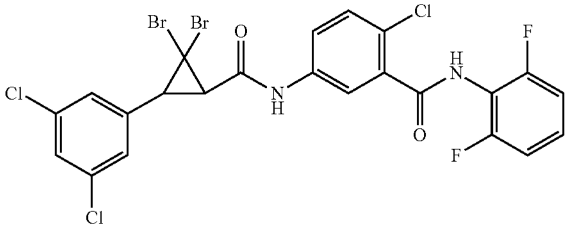 [SMILES: O=C(Nc1c(F)cccc1F)c1cc(NC(=O)C2C(c3cc(Cl)cc(Cl)c3)C2(Br)Br)ccc1Cl]

Isolated as an off-white solid (0.045 g, 38%).

trans-N-(4-(1H-1,2,3-Triazol-1-yl)phenyl)-2-chloro-5-(2,2-dichloro-3-(3,5-dichlorophenyl)cyclopropane-1-carboxamido)benzamide (F217)

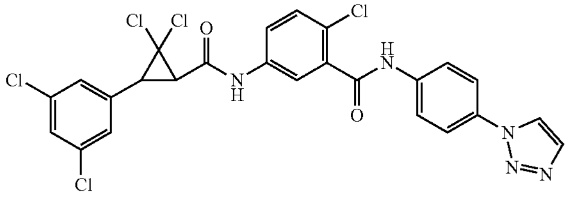 [SMILES: O=C(Nc1ccc(-n2ccnn2)cc1)c1cc(NC(=O)C2C(c3cc(Cl)cc(Cl)c3)C2(Cl)Cl)ccc1Cl]

Isolated as an off-white solid (0.062 g, 44%)

trans-tert-Butyl (4-(3-(2,2-dichloro-3-(3,4,5-trichlorophenyl)cyclopropane-1-carboxamido)benzamido)-3-methylphenyl)carbamate (F262)

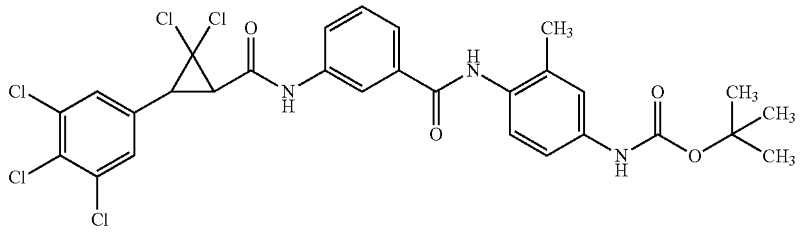 [SMILES: Cc1cc(NC(=O)OC(C)(C)C)ccc1NC(=O)c1cccc(NC(=O)C2C(c3cc(Cl)c(Cl)c(Cl)c3)C2(Cl)Cl)c1]

Isolated as a yellow foam (0.043 g, 27%)

trans-tert-Butyl (4-(3-(2,2-dichloro-3-(3,5-dichlorophenyl)cyclopropane-1-carboxamido)benzamido)-3-methylphenyl)carbamate (F263)

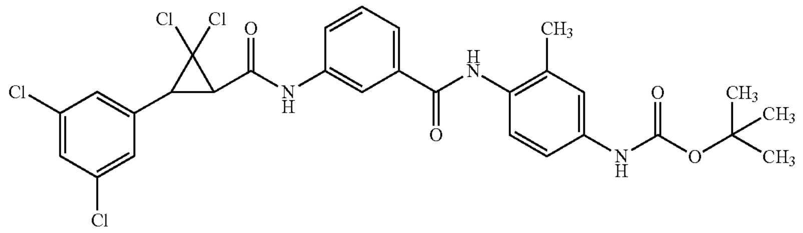 [SMILES: Cc1cc(NC(=O)OC(C)(C)C)ccc1NC(=O)c1cccc(NC(=O)C2C(c3cc(Cl)cc(Cl)c3)C2(Cl)Cl)c1]

Isolated as a light yellow foam (0.043 g, 27.2%).

trans-N-(4-(1H-Pyrazol-1-yl)phenyl)-2-chloro-5-(2,2-dichloro-3-(3,5-dichlorophenyl)cyclopropanecarboxamido)benzamide (F440)

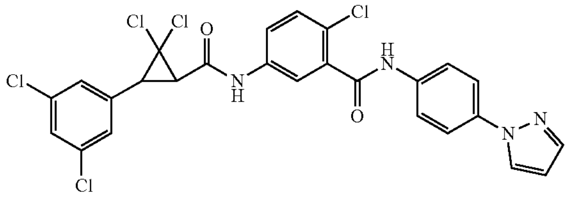 [SMILES: O=C(Nc1ccc(-n2cccn2)cc1)c1cc(NC(=O)C2C(c3cc(Cl)cc(Cl)c3)C2(Cl)Cl)ccc1Cl]

Isolated as a cream solid (0.310 g, 63%).

trans-2-Chloro-5-(2,2-dichloro-3-(3,5-dichlorophenyl)cyclopropane-1-carboxamido)-N-(4-(oxazol-2-yl)phenyl)benzamide (F446)

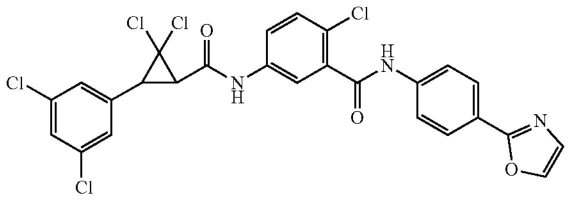

Isolated as an off-white solid (0.203 g, 58.4%).

trans-2-Chloro-5-(2,2-dibromo-3-(3,5-dichlorophenyl)cyclopropane-1-carboxamido)-N-(4-fluorophenyl)-N-methylbenzamide (PF7)

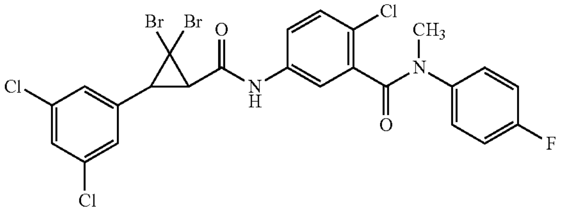

Isolated as a pale yellow glass (0.050 g, 29.6%).

trans-2-Chloro-5-(2,2-dichloro-3-(3,5-dichlorophenyl)cyclopropane-1-carboxamido)-N-(5-(trifluoromethyl)-1H-pyrazol-3-yl)benzamide (PF138)

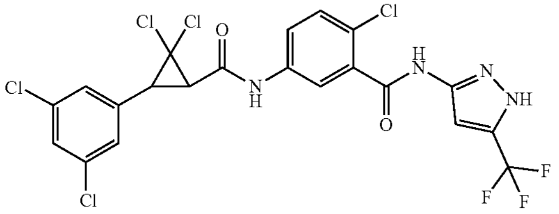 [SMILES: O=C(Nc1cc(C(F)(F)F)[nH]n1)c1cc(NC(=O)C2C(c3cc(Cl)cc(Cl)c3)C2(Cl)Cl)ccc1Cl]

Isolated as an off-white solid (0.092 g, 45.1%).

trans-2-Chloro-5-(2,2-dichloro-3-(3,5-dichlorophenyl)cyclopropane-1-carboxamido)-N-(2,4-dioxo-1,2,3,4-tetrahydropyrimidin-5-yl)benzamide (PF139)

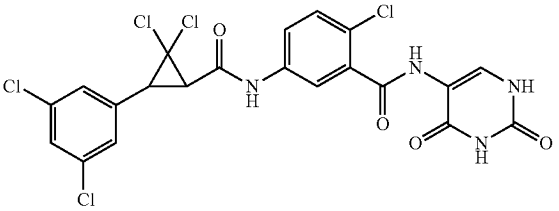 [SMILES: O=C(Nc1c[nH]c(=O)[nH]c1=O)c1cc(NC(=O)C2C(c3cc(Cl)cc(Cl)c3)C2(Cl)Cl)ccc1Cl]

Isolated as a colorless glass (0.008 g, 6.37%).

trans-2-Chloro-N-(4-chloropyridin-2-yl)-5-(2,2-dichloro-3-(3,5-dichlorophenyl)cyclopropane-1-carboxamido)benzamide (PF140)

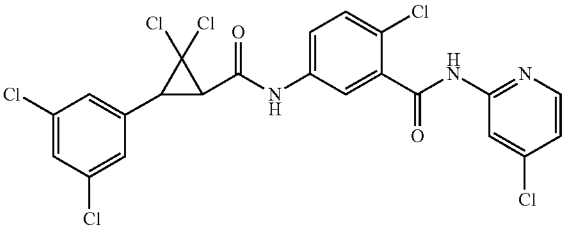 [SMILES: O=C(Nc1cc(Cl)ccn1)c1cc(NC(=O)C2C(c3cc(Cl)cc(Cl)c3)C2(Cl)Cl)ccc1Cl]

Isolated as a colorless glass (0.008 g, 6.37%).

trans-2-Chloro-N-(6-chloropyridazin-3-yl)-5-(2,2-dichloro-3-(3,5-dichlorophenyl)cyclopropane-1-carboxamido)benzamide (PF148)

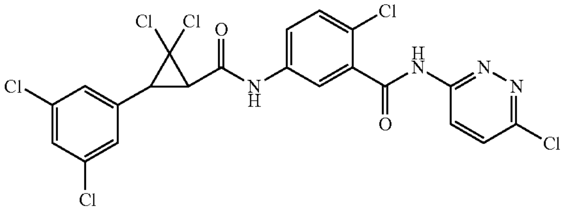 [SMILES: O=C(Nc1ccc(Cl)nn1)c1cc(NC(=O)C2C(c3cc(Cl)cc(Cl)c3)C2(Cl)Cl)ccc1Cl]

Isolated as a dark red glass (0.0177 g, 14%).

trans-2-Chloro-5-(2,2-dichloro-3-(3-chloro-5-fluorophenyl)cyclopropane-1-carboxamido)-N-(4-fluorophenyl)benzamide (PF1)

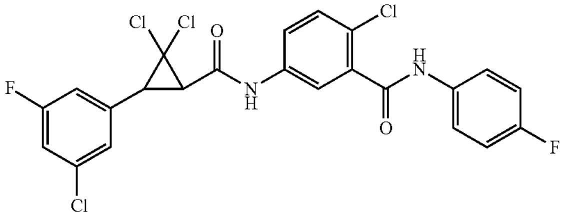 [SMILES: O=C(Nc1ccc(F)cc1)c1cc(NC(=O)C2C(c3cc(F)cc(Cl)c3)C2(Cl)Cl)ccc1Cl]

Isolated as a light yellow oil (0.076 g, 51%).

trans-2-Chloro-5-(2,2-dichloro-3-(3-chloro-5-fluorophenyl)cyclopropane-1-carboxamido)-N-(4-fluorophenyl)-N-methylbenzamide (PF2)

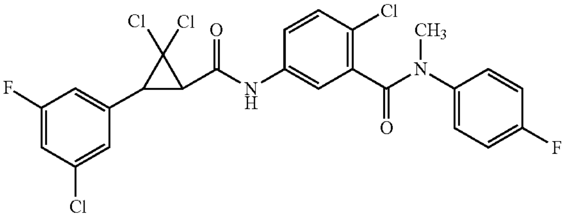 [SMILES: CN(C(=O)c1cc(NC(=O)C2C(c3cc(F)cc(Cl)c3)C2(Cl)Cl)ccc1Cl)c1ccc(F)cc1]

Isolated as a white foam (0.118 g, 77%).

trans-2-Chloro-5-(2,2-dichloro-3-(3-chloro-4-fluorophenyl)cyclopropane-1-carboxamido)-N-(4-fluorophenyl)benzamide (PF4)

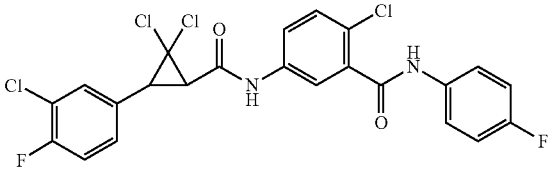

Isolated as a white foam (0.094 g, 67%).

trans-2-Chloro-5-(2,2-dichloro-3-(3-chloro-4-fluorophenyl)cyclopropane-1-carboxamido)-N-(4-fluorophenyl)-N-methylbenzamide (PF5)

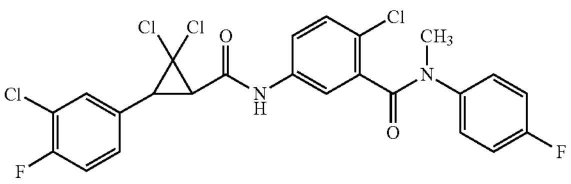 [SMILES: CN(C(=O)c1cc(NC(=O)C2C(c3ccc(F)c(Cl)c3)C2(Cl)Cl)ccc1Cl)c1ccc(F)cc1]

Isolated as a light yellow oil (0.097 g, 63%).

trans-5-(2,2-Dichloro-3-(3,5-dichlorophenyl)cyclopropanecarboxamido)-2-ethyl-N-(4-fluorophenyl)benzamide (PF8)

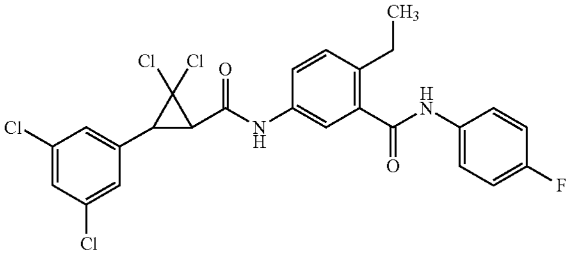 [SMILES: CCc1ccc(NC(=O)C2C(c3cc(Cl)cc(Cl)c3)C2(Cl)Cl)cc1C(=O)Nc1ccc(F)cc1]

Isolated as a clear film (0.103 g, 54.9%).

trans-5-(2,2-Dichloro-3-(3,5-dichlorophenyl)cyclopropanecarboxamido)-N-(4-fluorophenyl)-2-vinylbenzamide (PF9)

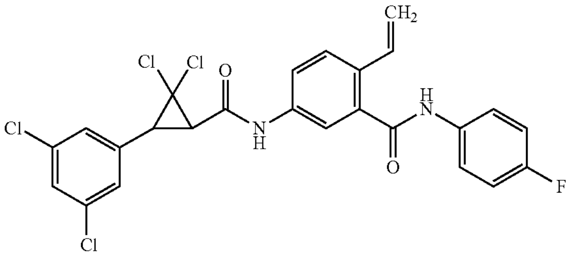 [SMILES: C=Cc1ccc(NC(=O)C2C(c3cc(Cl)cc(Cl)c3)C2(Cl)Cl)cc1C(=O)Nc1ccc(F)cc1]

Isolated as a faint yellow film (0.051 g, 20%).

trans-2-Chloro-5-(2,2-dichloro-3-methyl-3-(4-(trifluoromethoxy)phenyl)cyclopropanecarboxamido)-N-(4-fluorophenyl)benzamide (PF32)

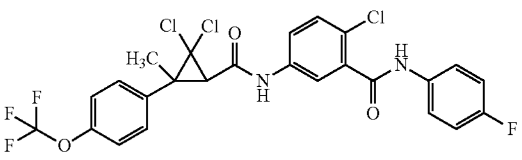 [SMILES: CC1(c2ccc(OC(F)(F)F)cc2)C(C(=O)Nc2ccc(Cl)c(C(=O)Nc3ccc(F)cc3)c2)C1(Cl)Cl]

Isolated as a white solid (0.017 g, 42%).

trans-2-Chloro-5-(2,2-dichloro-3-(4-chloro-3-fluorophenyl)cyclopropane-1-carboxamido)-N-(4-fluorophenyl)benzamide (PF34)

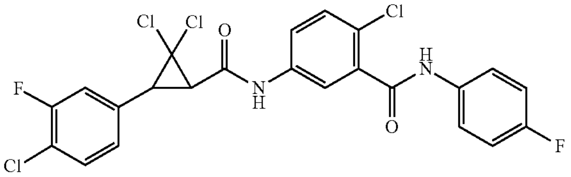 [SMILES: O=C(Nc1ccc(F)cc1)c1cc(NC(=O)C2C(c3ccc(Cl)c(F)c3)C2(Cl)Cl)ccc1Cl]

Isolated as a light yellow oil (0.134 g, 95%).

trans-2-Chloro-5-(2,2-dichloro-3-(4-chloro-3-fluorophenyl)cyclopropane-1-carboxamido)-N-(4-fluorophenyl)-N-methylbenzamide (PF35)

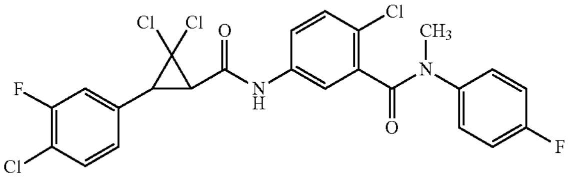 [SMILES: CN(C(=O)c1cc(NC(=O)C2C(c3ccc(Cl)c(F)c3)C2(Cl)Cl)ccc1Cl)c1ccc(F)cc1]

Isolated as a white foam (0.101 g, 70%).

trans-5-(3-(3-Bromo-5-chlorophenyl)-2,2-dichlorocyclopropane-1-carboxamido)-2-chloro-N-(4-fluorophenyl)-N-methylbenzamide (PF38)

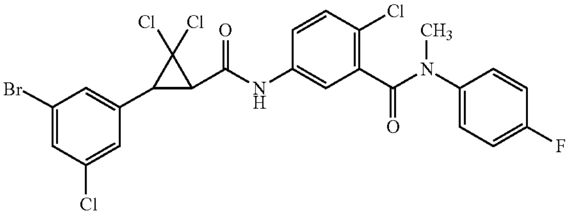 [SMILES: CN(C(=O)c1cc(NC(=O)C2C(c3cc(Cl)cc(Br)c3)C2(Cl)Cl)ccc1Cl)c1ccc(F)cc1]

Isolated as a colorless oil (0.067 g, 64%).

trans-N-(4-Acetamido-2-fluorophenyl)-2-chloro-5-(2,2-dichloro-3-(3,5-dichlorophenyl)cyclopropane-1-carboxamido)benzamide (PF40)

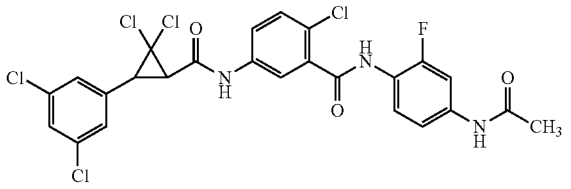 [SMILES: CC(=O)Nc1ccc(NC(=O)c2cc(NC(=O)C3C(c4cc(Cl)cc(Cl)c4)C3(Cl)Cl)ccc2Cl)c(F)c1]

Isolated as a light yellow solid (0.043 g, 31%).

trans-N-(4-Acetamido-2-fluorophenyl)-2-chloro-5-(2,2-dichloro-3-(3,4-dichlorophenyl)cyclopropane-1-carboxamido)benzamide (PF41)

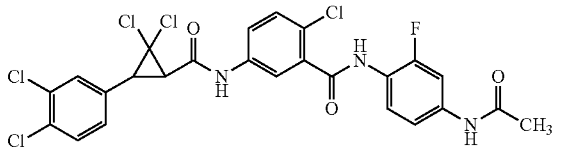 [SMILES: CC(=O)Nc1ccc(NC(=O)c2cc(NC(=O)C3C(c4ccc(Cl)c(Cl)c4)C3(Cl)Cl)ccc2Cl)c(F)c1]

Isolated as a light brown solid (0.078 g, 55%).

trans-N-(4-Acetamido-2-fluorophenyl)-2-chloro-5-(2,2-dichloro-3-(3,4,5-trichlorophenyl)cyclopropane-1-carboxamido)benzamide (PF42)

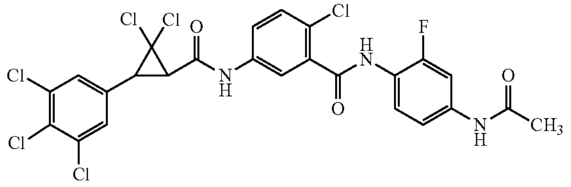 [SMILES: CC(=O)Nc1ccc(NC(=O)c2cc(NC(=O)C3C(c4cc(Cl)c(Cl)c(Cl)c4)C3(Cl)Cl)ccc2Cl)c(F)c1]

Isolated as a white solid (0.085 g, 63%).

trans-2-Chloro-5-(2,2-dichloro-3-(3,4-dichlorophenyl)cyclopropane-1-carboxamido)-N-(4-fluoro-2-methylphenyl)benzamide (PF46)

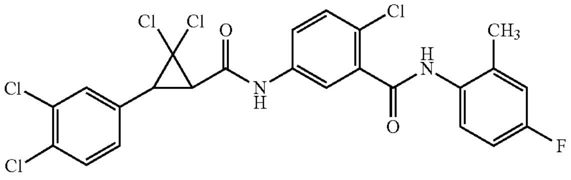 [SMILES: Cc1cc(F)ccc1NC(=O)c1cc(NC(=O)C2C(c3ccc(Cl)c(Cl)c3)C2(Cl)Cl)ccc1Cl]

Isolated as a white solid (0.092 g, 78%).

trans-2-Chloro-5-(2,2-dichloro-3-(3,4,5-trichlorophenyl)cyclopropane-1-carboxamido)-N-(4-fluoro-2-methylphenyl)benzamide (PF47)

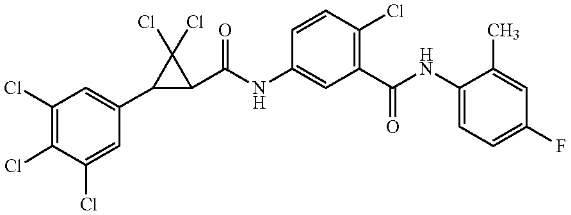 [SMILES: Cc1cc(F)ccc1NC(=O)c1cc(NC(=O)C2C(c3cc(Cl)c(Cl)c(Cl)c3)C2(Cl)Cl)ccc1Cl]

Isolated as a white solid (0.094 g, 75%).

trans-2-Chloro-5-(2,2-dichloro-3-(3-chloro-4-fluorophenyl)cyclopropane-1-carboxamido)-N-(4-fluoro-2-methylphenyl)benzamide (PF48)

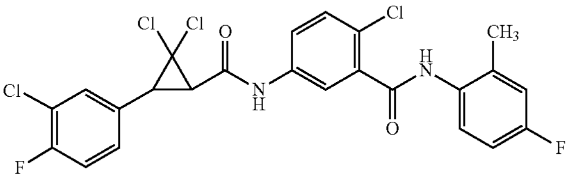

Isolated as a white solid (0.077 g, 68%).

trans-2-Chloro-5-(2,2-dichloro-3-(3,5-dichlorophenyl)cyclopropane-1-carboxamido)-N-(4-fluoro-2-methylphenyl)-N-methylbenzamide (PF49)

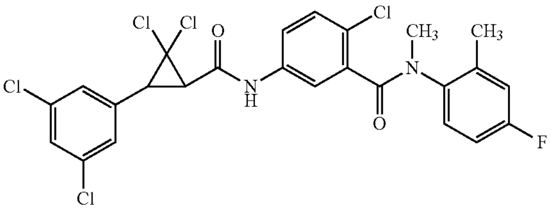

Isolated as a white solid (0.084 g, 69%).

trans-2-Chloro-5-(2,2-dichloro-3-(3-chloro-4-fluorophenyl)cyclopropane-1-carboxamido)-N-(4-fluoro-2-methylphenyl)-N-methylbenzamide (PF50)

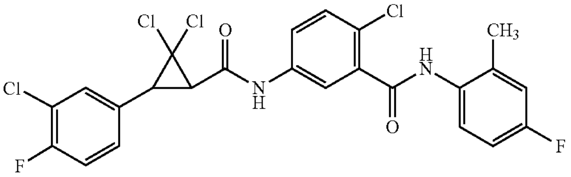

Isolated as a light yellow glass (0.087 g, 73%).

trans-2-Chloro-5-(2,2-dichloro-3-(4-methoxyphenyl)cyclopropane-1-carboxamido)-N-(4-fluorophenyl)benzamide (PF65)

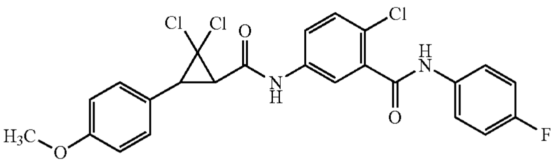 [SMILES: COc1ccc(C2C(C(=O)Nc3ccc(Cl)c(C(=O)Nc4ccc(F)cc4)c3)C2(Cl)Cl)cc1]

Isolated as a white solid (0.052 g, 35.3%).

trans-2-Chloro-5-(2,2-dichloro-3-(4-isopropylphenyl)cyclopropanecarboxamido)-N-(4-fluorophenyl) benzamide (PF66)

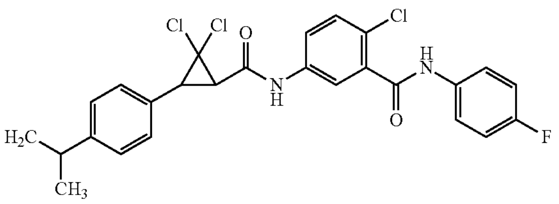 [SMILES: CC(C)c1ccc(C2C(C(=O)Nc3ccc(Cl)c(C(=O)Nc4ccc(F)cc4)c3)C2(Cl)Cl)cc1]

Isolated as a white solid (0.051 g, 31.8%).

trans-2-Chloro-N-(2-cyano-4-fluorophenyl)-5-(2,2-dichloro-3-(3,5-dichlorophenyl)cyclopropane-1-carboxamido)benzamide (PF67)

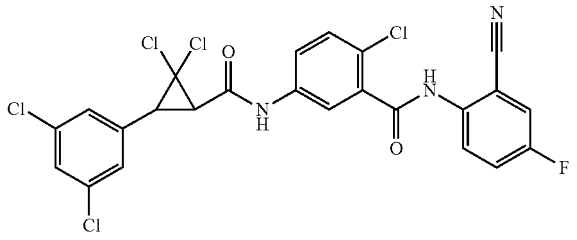 [SMILES: N#Cc1cc(F)ccc1NC(=O)c1cc(NC(=O)C2C(c3cc(Cl)cc(Cl)c3)C2(Cl)Cl)ccc1Cl]

Isolated as a white foam (0.114 g, 85%).

trans-2-Chloro-5-(2,2-dichloro-3-(3,5-dichlorophenyl)cyclopropane-1-carboxamido)-N-(2,3,4-trifluorophenyl)benzamide (PF68)

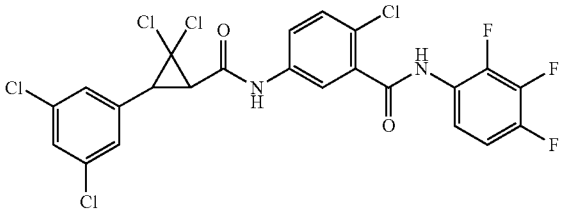 [SMILES: O=C(Nc1ccc(F)c(F)c1F)c1cc(NC(=O)C2C(c3cc(Cl)cc(Cl)c3)C2(Cl)Cl)ccc1Cl]

Isolated as a white solid (0.118 g, 87%).

trans-2-Chloro-N-(2-cyanophenyl)-5-(2,2-dichloro-3-(3,5-dichlorophenyl)cyclopropane-1-carboxamido) benzamide (PF72)

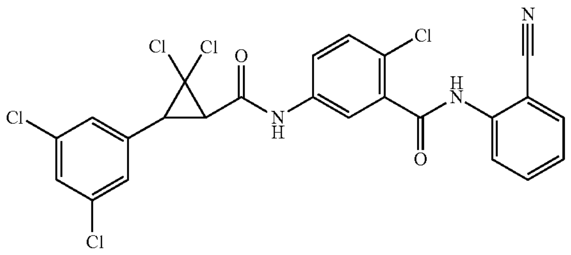 [SMILES: N#Cc1ccccc1NC(=O)c1cc(NC(=O)C2C(c3cc(Cl)cc(Cl)c3)C2(Cl)Cl)ccc1Cl]

Isolated as a white solid (0.104 g, 80%).

trans-2-Chloro-5-(2,2-dichloro-3-(3,5-dichlorophenyl)cyclopropane-1-carboxamido)-N-(4-(trifluoromethyl)thiazol-2-yl)benzamide (PF134)

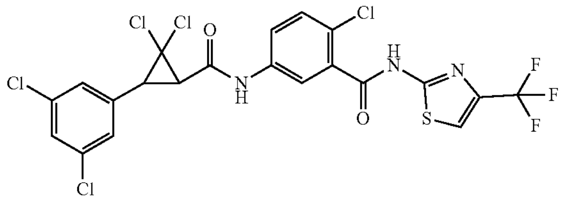 [SMILES: O=C(Nc1nc(C(F)(F)F)cs1)c1cc(NC(=O)C2C(c3cc(Cl)cc(Cl)c3)C2(Cl)Cl)ccc1Cl]

Isolated as a white foam (0.096 g, 48%).

trans-2-Chloro-N-(5-chloropyridin-2-yl)-5-(2,2-dichloro-3-(3,5-dichlorophenyl)cyclopropane-1-carboxamido)benzamide (PF141)

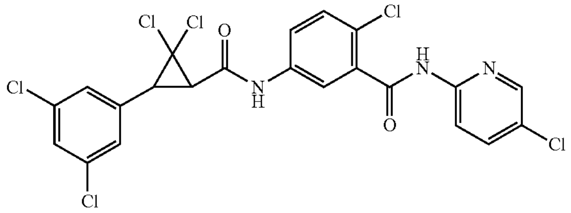 [SMILES: O=C(Nc1ccc(Cl)cn1)c1cc(NC(=O)C2C(c3cc(Cl)cc(Cl)c3)C2(Cl)Cl)ccc1Cl]

Isolated as a yellow foam (0.068 g, 43%).

trans-N-(4-Acetamido-2-methylphenyl)-2-chloro-5-(2,2-dichloro-3-(3,5-dichlorophenyl)cyclopropane-1-carboxamido)benzamide (PF158)

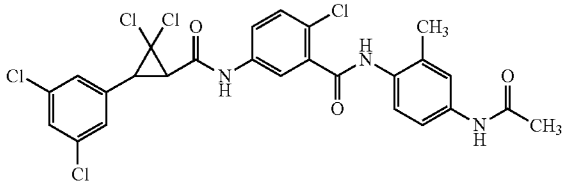 [SMILES: CC(=O)Nc1ccc(NC(=O)c2cc(NC(=O)C3C(c4cc(Cl)cc(Cl)c4)C3(Cl)Cl)ccc2Cl)c(C)c1]

Isolated as a white solid (0.051 g, 37%).

trans-2-Chloro-5-(2,2-dichloro-3-(3-chloro-5-fluorophenyl)cyclopropane-1-carboxamido)-N-(2,6-difluorophenyl)benzamide (F160)

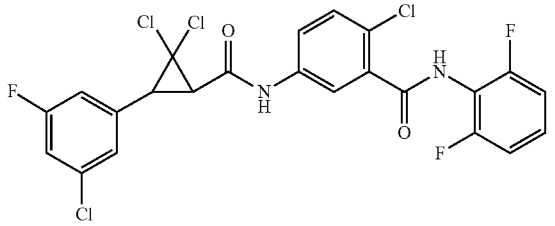 [SMILES: O=C(Nc1c(F)cccc1F)c1cc(NC(=O)C2C(c3cc(F)cc(Cl)c3)C2(Cl)Cl)ccc1Cl]

Isolated as a white foam. (0.064 g, 41%).

trans-2-Chloro-5-(2,2-dichloro-3-(3-chloro-4-fluorophenyl)cyclopropane-1-carboxamido)-N-(2,6-difluorophenyl)benzamide (F161)

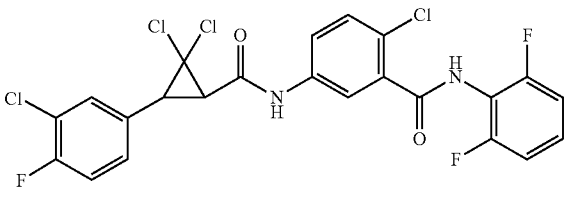 [SMILES: O=C(Nc1c(F)cccc1F)c1cc(NC(=O)C2C(c3ccc(F)c(Cl)c3)C2(Cl)Cl)ccc1Cl]

Isolated as a white foam (0.031 g, 20%).

trans-2-Chloro-5-(2,2-dichloro-3-(4-chloro-3-fluorophenyl)cyclopropane-1-carboxamido)-N-(2,6-difluorophenyl)benzamide (F163)

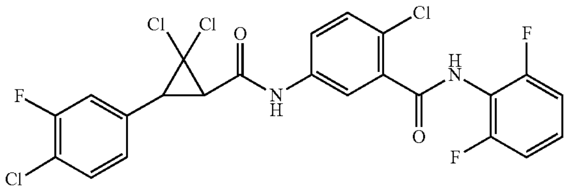 [SMILES: O=C(Nc1c(F)cccc1F)c1cc(NC(=O)C2C(c3ccc(Cl)c(F)c3)C2(Cl)Cl)ccc1Cl]

Isolated as a white foam (0.052 g, 36%).

trans-5-(3-(3-Bromo-5-chlorophenyl)-2,2-dichlorocyclopropane-1-carboxamido)-2-chloro-N-(2,6-difluorophenyl)benzamide (F164)

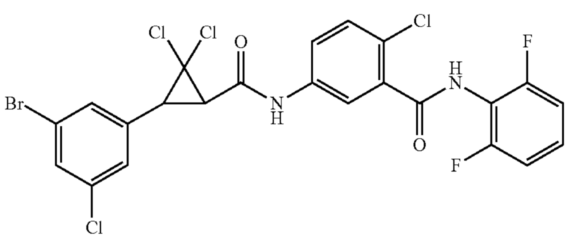

Isolated as a white solid (0.018 g, 17%).

trans-2-Chloro-N-(2-cyano-4-fluorophenyl)-5-(2,2-dichloro-3-(3,4-dichlorophenyl)cyclopropane-1-carboxamido)benzamide (F190)

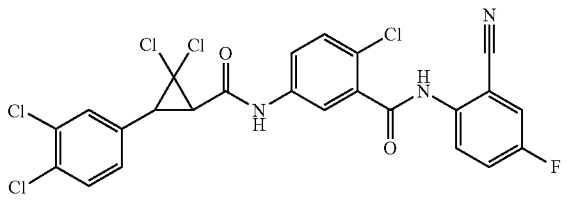 [SMILES: N#Cc1cc(F)ccc1NC(=O)c1cc(NC(=O)C2C(c3ccc(Cl)c(Cl)c3)C2(Cl)Cl)ccc1Cl]

Isolated as an orange foam (0.091 g, 80%).

trans-2-Chloro-N-(2-cyano-4-fluorophenyl)-5-(2,2-dichloro-3-(3,4,5-trichlorophenyl)cyclopropane-1-carboxamido)benzamide (F191)

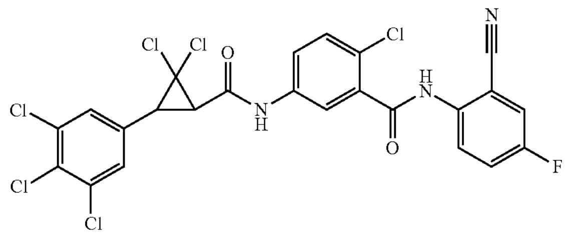 [SMILES: N#Cc1cc(F)ccc1NC(=O)c1cc(NC(=O)C2C(c3cc(Cl)c(Cl)c(Cl)c3)C2(Cl)Cl)ccc1Cl]

Isolated as a white solid (0.088 g, 73%).

trans-2-Chloro-N-(2-cyano-4-fluorophenyl)-5-(2,2-dichloro-3-(3-chloro-4-fluorophenyl)cyclopropane-1-carboxamido)benzamide (F192)

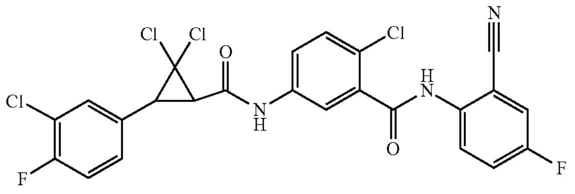 [SMILES: N#Cc1cc(F)ccc1NC(=O)c1cc(NC(=O)C2C(c3ccc(F)c(Cl)c3)C2(Cl)Cl)ccc1Cl]

Isolated as an orange glass (0.076 g, 67%).

trans-2-Chloro-5-(2,2-dichloro-3-(3,5-dichlorophenyl)cyclopropane-1-carboxamido)-N-(4-iodophenyl)benzamide (F193)

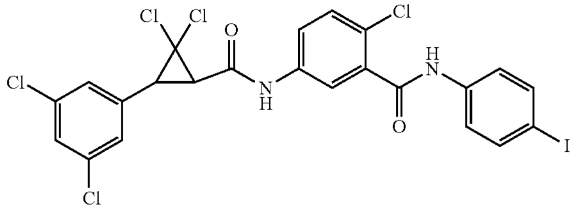 [SMILES: O=C(Nc1ccc(I)cc1)c1cc(NC(=O)C2C(c3cc(Cl)cc(Cl)c3)C2(Cl)Cl)ccc1Cl]

Isolated as a white foam (0.121 g, 79%).

trans-2-Chloro-5-(2,2-dichloro-3-(3,5-dichlorophenyl)cyclopropane-1-carboxamido)-N-(3-iodophenyl)benzamide (F194)

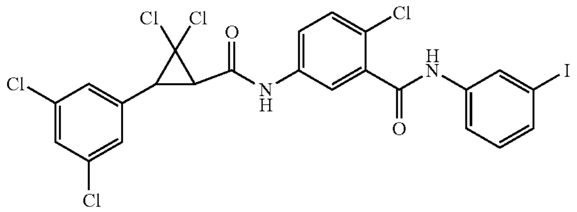 [SMILES: O=C(Nc1cccc(I)c1)c1cc(NC(=O)C2C(c3cc(Cl)cc(Cl)c3)C2(Cl)Cl)ccc1Cl]

Isolated as a light yellow solid (0.118 g, 77%).

trans-2-Chloro-5-(2,2-dichloro-3-(3,5-dichlorophenyl)cyclopropane-1-carboxamido)-N-(2-fluoro-4-iodophenyl)benzamide (F203)

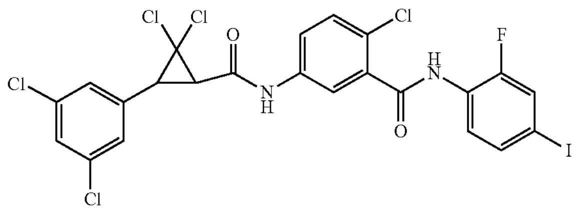 [SMILES: O=C(Nc1ccc(I)cc1F)c1cc(NC(=O)C2C(c3cc(Cl)cc(Cl)c3)C2(Cl)Cl)ccc1Cl]

Isolated as a white solid (0.133 g, 85%).

trans-2-Chloro-5-(2,2-dichloro-3-(3,5-dichlorophenyl)cyclopropane-1-carboxamido)-N-(3-fluoro-4-iodophenyl)benzamide (F204)

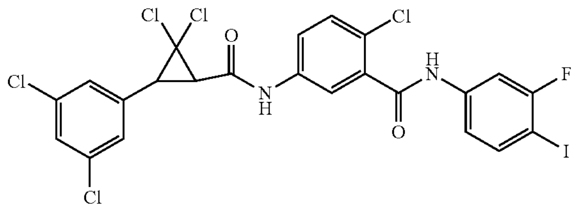 [SMILES: O=C(Nc1ccc(I)c(F)c1)c1cc(NC(=O)C2C(c3cc(Cl)cc(Cl)c3)C2(Cl)Cl)ccc1Cl]

Isolated as a white solid (0.116 g, 74%).

trans-tert-Butyl-(4-(2-chloro-5-(2,2-dichloro-3-(3,4,5-trichlorophenyl)cyclopropane-1-carboxamido)benzamido)-3-methylphenyl)(methyl)carbamate (F218)

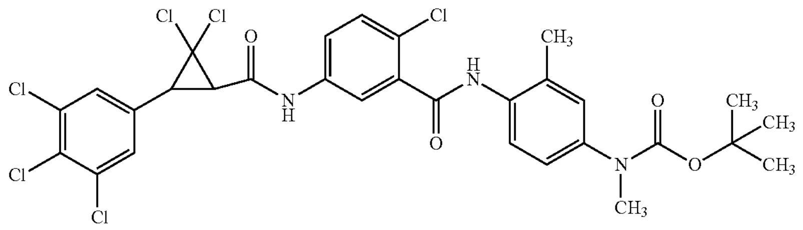 [SMILES: Cc1cc(N(C)C(=O)OC(C)(C)C)ccc1NC(=O)c1cc(NC(=O)C2C(c3cc(Cl)c(Cl)c(Cl)c3)C2(Cl)Cl)ccc1Cl]

Isolated as a white solid (0.104 g, 71%).

trans-tert-Butyl-(4-(2-chloro-5-(2,2-dichloro-3-(3-chloro-4-fluorophenyl)cyclopropane-1-carboxamido)benzamido)-3-methylphenyl)(methyl)carbamate (F219)

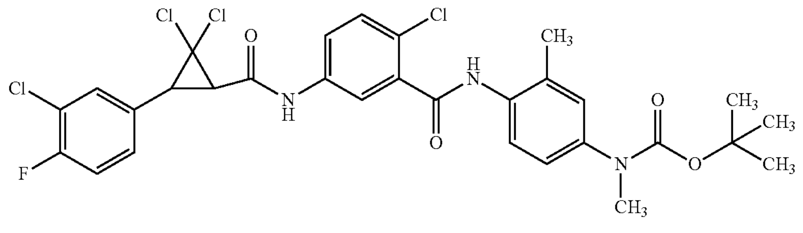 [SMILES: Cc1cc(N(C)C(=O)OC(C)(C)C)ccc1NC(=O)c1cc(NC(=O)C2C(c3ccc(F)c(Cl)c3)C2(Cl)Cl)ccc1Cl]

Isolated as a white solid (0.107 g, 77%).

trans-tert-Butyl-(4-(2-chloro-5-(2,2-dichloro-3-(3,5-dichlorophenyl)cyclopropane-1-carboxamido)-N-methylbenzamido)-3-methylphenyl)(methyl)carbamate (F220)

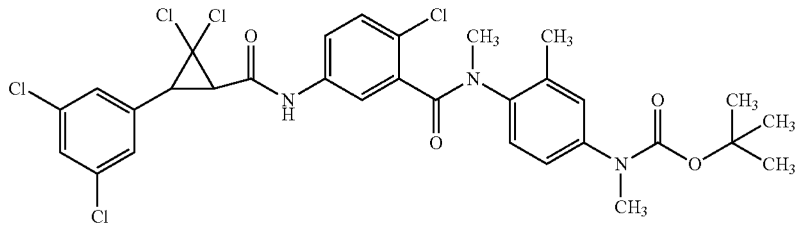 [SMILES: Cc1cc(N(C)C(=O)OC(C)(C)C)ccc1N(C)C(=O)c1cc(NC(=O)C2C(c3cc(Cl)cc(Cl)c3)C2(Cl)Cl)ccc1Cl]

Isolated as a white solid (0.127 g, 82%).

trans-tert-Butyl-(4-(2-chloro-5-((1R,3R)-2,2-dichloro-3-(3,4,5-trichlorophenyl)cyclopropane-1-carboxamido)-N-methylbenzamido)-3-methylphenyl)(methyl)carbamate (F221)

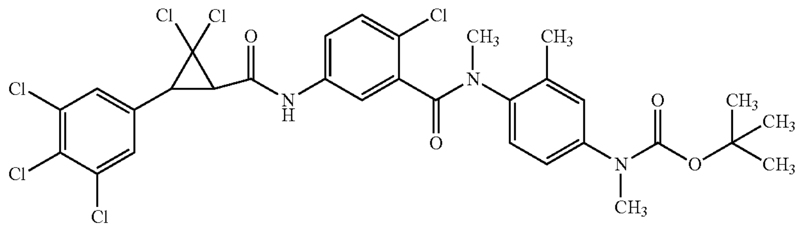 [SMILES: Cc1cc(N(C)C(=O)OC(C)(C)C)ccc1N(C)C(=O)c1cc(NC(=O)C2C(c3cc(Cl)c(Cl)c(Cl)c3)C2(Cl)Cl)ccc1Cl]

Isolated as a white solid (0.101 g, 72%).

trans-2-Chloro-N-(2-cyano-4-fluorophenyl)-5-(2,2-dichloro-3-(3,5-dichlorophenyl)cyclopropane-1-carboxamido)-N-methylbenzamide (F243)

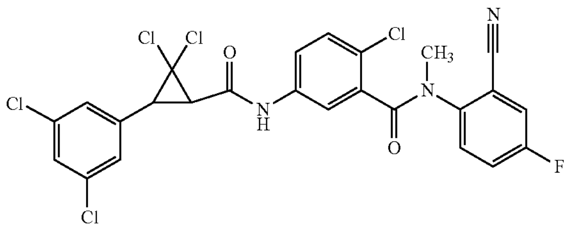 [SMILES: CN(C(=O)c1cc(NC(=O)C2C(c3cc(Cl)cc(Cl)c3)C2(Cl)Cl)ccc1Cl)c1ccc(F)cc1C#N]

Isolated as a white foam (0.084 g, 54%).

trans-2-Chloro-N-(2-cyano-4-fluorophenyl)-5-(2,2-dichloro-3-(3,4,5-trichlorophenyl)cyclopropane-1-carboxamido)-N-methylbenzamide (F244)

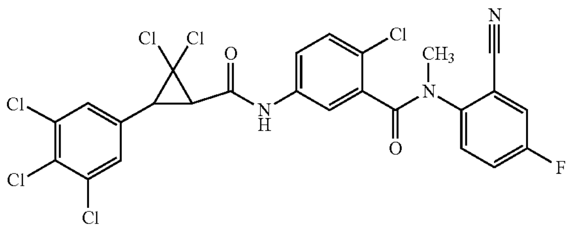 [SMILES: CN(C(=O)c1cc(NC(=O)C2C(c3cc(Cl)c(Cl)c(Cl)c3)C2(Cl)Cl)ccc1Cl)c1ccc(F)cc1C#N]

Isolated as a white foam (0.088 g, 56%).

5-(trans-3-(4-Bromo-3-chlorophenyl)-2,2-dichloro-cyclopropane-1-carboxamido)-2-chloro-N-(4-fluoro-phenyl)benzamide (F270)

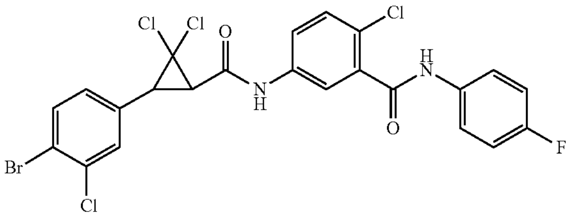

Isolated as an orange solid. (0.1334 g, 67%).

trans-N-(2-Cyano-4-fluorophenyl)-3-(2,2-dichloro-3-(3,5-dichlorophenyl)cyclopropane-1-carboxamido) benzamide (F271)

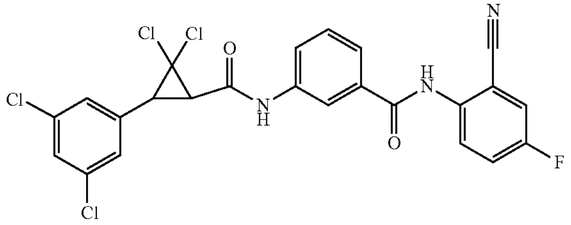 [SMILES: N#Cc1cc(F)ccc1NC(=O)c1cccc(NC(=O)C2C(c3cc(Cl)cc(Cl)c3)C2(Cl)Cl)c1]

Isolated as a white foam (0.112 g, 78%).

trans-3-(2,2-Dichloro-3-(3,5-dichlorophenyl)cyclo-propane-1-carboxamido)-N-(4-fluoro-2-methylphe-nyl)benzamide (F272)

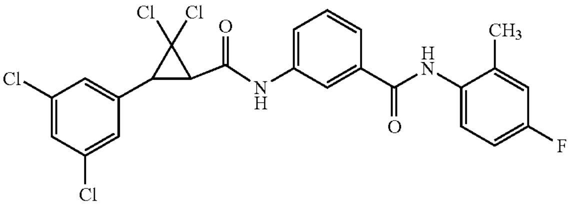 [SMILES: Cc1cc(F)ccc1NC(=O)c1cccc(NC(=O)C2C(c3cc(Cl)cc(Cl)c3)C2(Cl)Cl)c1]

Isolated as a white foam (0.117 g, 84%).

trans-3-(2,2-Dichloro-3-(3,5-dichlorophenyl)cyclo-propane-1-carboxamido)-N-(4-fluorophenyl)-N-methylbenzamide (F273)

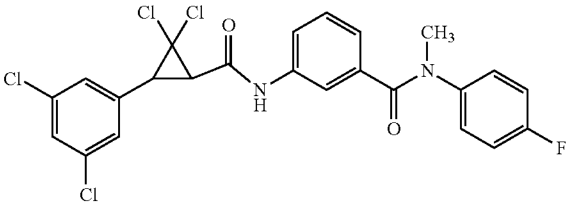 [SMILES: CN(C(=O)c1cccc(NC(=O)C2C(c3cc(Cl)cc(Cl)c3)C2(Cl)Cl)c1)c1ccc(F)cc1]

Isolated as a white foam (0.123 g, 87%).

trans-N-(2-Chloro-4-fluorophenyl)-3-(2,2-dichloro-3-(3,5-dichlorophenyl)cyclopropane-1-carboxamido) benzamide (F274)

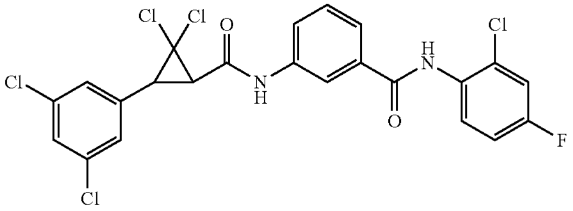 [SMILES: O=C(Nc1ccc(F)cc1Cl)c1cccc(NC(=O)C2C(c3cc(Cl)cc(Cl)c3)C2(Cl)Cl)c1]

Isolated as a white solid (0.076 g, 52%).

5-(trans-3-(4-Bromo-3-chlorophenyl)-2,2-dichloro-cyclopropane-1-carboxamido)-2-chloro-N-(2,4-dif-luorophenyl)benzamide (F306)

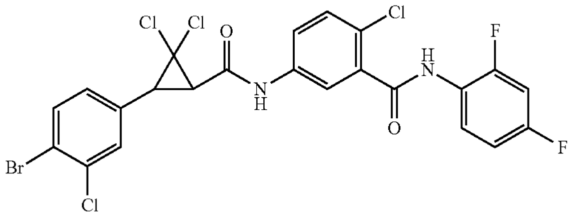 [SMILES: O=C(Nc1ccc(F)cc1F)c1cc(NC(=O)C2C(c3ccc(Br)c(Cl)c3)C2(Cl)Cl)ccc1Cl]

Isolated as an off-white solid (0.2825 g, 61%).

5-(trans-3-(4-Bromo-3-chlorophenyl)-2,2-dichloro-cyclopropane-1-carboxamido)-2-chloro-N-(4-fluoro-phenyl)-N-methylbenzamide (F307)

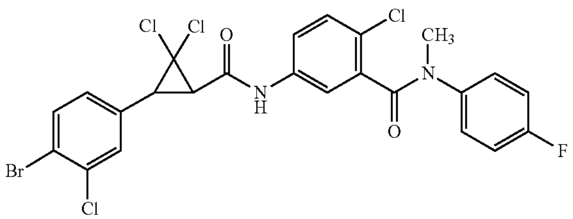 [SMILES: CN(C(=O)c1cc(NC(=O)C2C(c3ccc(Br)c(Cl)c3)C2(Cl)Cl)ccc1Cl)c1ccc(F)cc1]

Isolated as an off-white solid (0.3047 g, 62%).

trans-5-(3-(3,5-bis(Trifluoromethyl)phenyl)-2,2-dichlorocyclopropane-1-carboxamido)-2-chloro-N-(2-cyano-4-fluorophenyl)benzamide (F308)

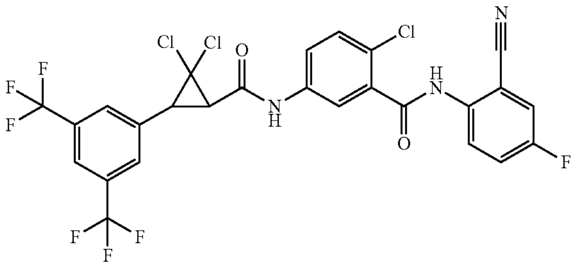 [SMILES: N#Cc1cc(F)ccc1NC(=O)c1cc(NC(=O)C2C(c3cc(C(F)(F)F)cc(C(F)(F)F)c3)C2(Cl)Cl)ccc1Cl]

Isolated as a white solid (0.080 g, 58%).

2-Chloro-5-((1R,3R)-2,2-dichloro-3-(3,5-dichlorophenyl)cyclopropane-1-carboxamido)-N-(3,5-difluoropyridin-2-yl)benzamide (F309)

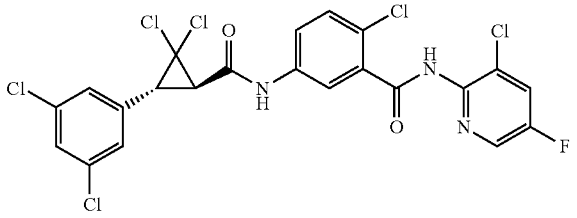

Isolated as a white solid (0.059 g, 39%).

2-Chloro-5-((1R,3R)-2,2-dichloro-3-(3,4-dichlorophenyl)cyclopropane-1-carboxamido)-N-(3,5-difluoropyridin-2-yl)benzamide (F310)

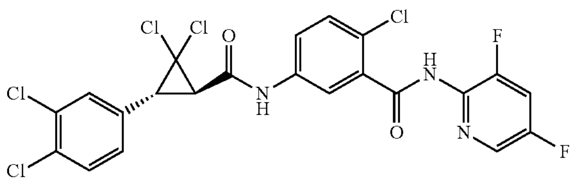

Isolated as a white solid (0.062 g, 41%).

2-Chloro-5-((1R,3R)-2,2-dichloro-3-(3,4,5-trichlorophenyl)cyclopropane-1-carboxamido)-N-(3,5-difluoropyridin-2-yl)benzamide (F311)

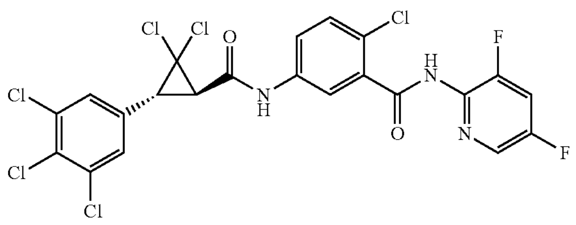

Isolated as a white solid (0.054 g, 37%).

2-Chloro-5-((1R,3R)-2,2-dichloro-3-(3-chloro-4-fluorophenyl)cyclopropane-1-carboxamido)-N-(3,5-difluoropyridin-2-yl)benzamide (F316)

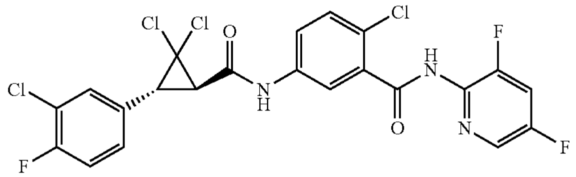

Isolated as a white solid (0.071 g, 46%).

5-(trans-3-(4-Bromo-3-chlorophenyl)-2,2-dichlorocyclopropane-1-carboxamido)-2-chloro-N-(2-cyano-4-fluorophenyl)benzamide (F320)

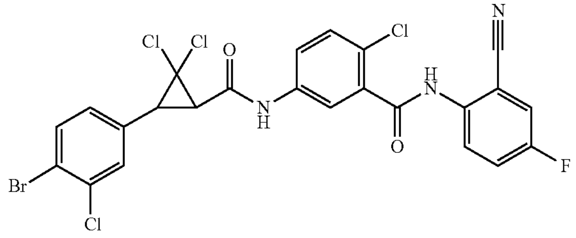 [SMILES: N#Cc1cc(F)ccc1NC(=O)c1cc(NC(=O)C2C(c3ccc(Br)c(Cl)c3)C2(Cl)Cl)ccc1Cl]

Isolated as a white foam (0.1212 g, 42%).

tert-Butyl (4-(5-(trans-3-(4-bromo-3-chlorophenyl)-2,2-dichlorocyclopropane-1-carboxamido)-2-chlorobenzamido)-3-methylphenyl)(methyl)carbamate (F321)

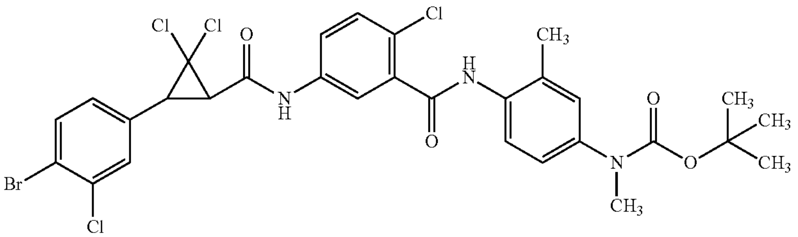 [SMILES: Cc1cc(N(C)C(=O)OC(C)(C)C)ccc1NC(=O)c1cc(NC(=O)C2C(c3ccc(Br)c(Cl)c3)C2(Cl)Cl)ccc1Cl]

Isolated as a white solid (0.2009 g, 61%).

tert-Butyl (4-(5-(trans-3-(4-bromo-3-chlorophenyl)-2,2-dichlorocyclopropane-1-carboxamido)-2-chlorobenzamido)-3-methylphenyl)carbamate (F322)

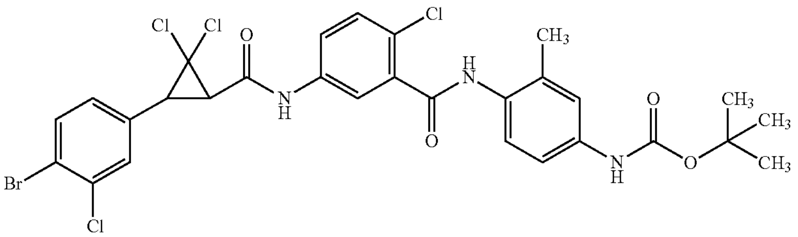 [SMILES: Cc1cc(NC(=O)OC(C)(C)C)ccc1NC(=O)c1cc(NC(=O)C2C(c3ccc(Br)c(Cl)c3)C2(Cl)Cl)ccc1Cl]

Isolated as a white foam (0.0812 g, 25%).

5-(trans-3-(3-Bromo-4-chlorophenyl)-2,2-dichlorocyclopropane-1-carboxamido)-2-chloro-N-(4-fluorophenyl)benzamide (F330)

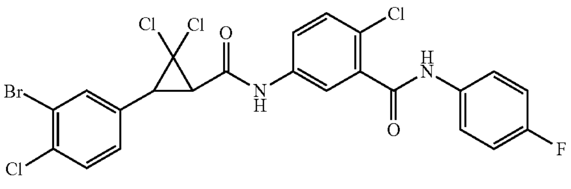 [SMILES: O=C(Nc1ccc(F)cc1)c1cc(NC(=O)C2C(c3ccc(Cl)c(Br)c3)C2(Cl)Cl)ccc1Cl]

Isolated as a pale yellow foam (0.1740 g, 64%).

5-(trans-3-(3-Bromo-4-chlorophenyl)-2,2-dichlorocyclopropane-1-carboxamido)-2-chloro-N-(2,4-difluorophenyl)benzamide (F331)

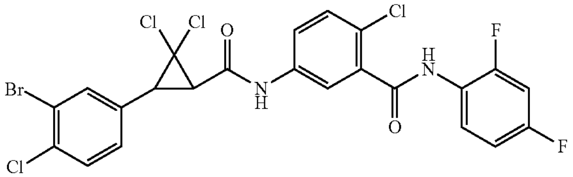

Isolate as a pale yellow foam (0.1959 g, 70%).

5-(trans-3-(3-Bromo-4-chlorophenyl)-2,2-dichlorocyclopropane-1-carboxamido)-2-chloro-N-(2-cyano-4-fluorophenyl)benzamide (F332)

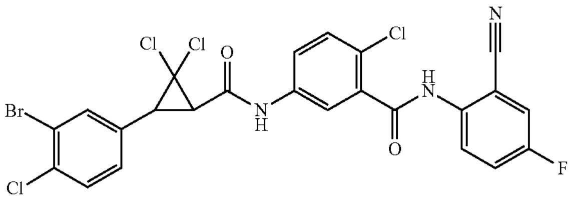 [SMILES: N#Cc1cc(F)ccc1NC(=O)c1cc(NC(=O)C2C(c3ccc(Cl)c(Br)c3)C2(Cl)Cl)ccc1Cl]

Isolated as a pale yellow foam (0.1893 g, 67%).

5-(trans-3-(3-Bromo-5-chlorophenyl)-2,2-dichloro-cyclopropane-1-carboxamido)-2-chloro-N-(2-cyano-4-fluorophenyl)benzamide (F333)

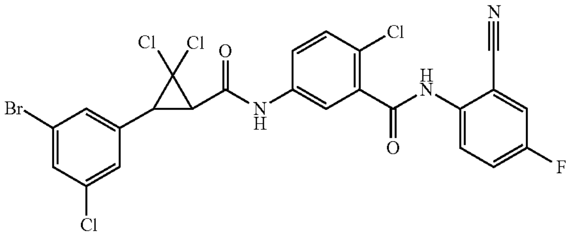

Isolated as a pale yellow foam (0.226 g, 77%).

tert-Butyl (4-(5-(trans-3-(3-bromo-4-chlorophenyl)-2,2-dichlorocyclopropane-1-carboxamido)-2-chlorobenzamido)-3-methylphenyl)carbamate (F334)

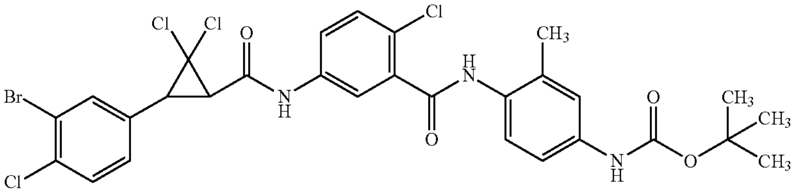 [SMILES: Cc1cc(NC(=O)OC(C)(C)C)ccc1NC(=O)c1cc(NC(=O)C2C(c3ccc(Cl)c(Br)c3)C2(Cl)Cl)ccc1Cl]

Isolated as a pale yellow foam (0.1789 g, 54%).

tert-Butyl (4-(5-(trans-3-(3-bromo-5-chlorophenyl)-2,2-dichlorocyclopropane-1-carboxamido)-2-chlorobenzamido)-3-methylphenyl)carbamate (F335)

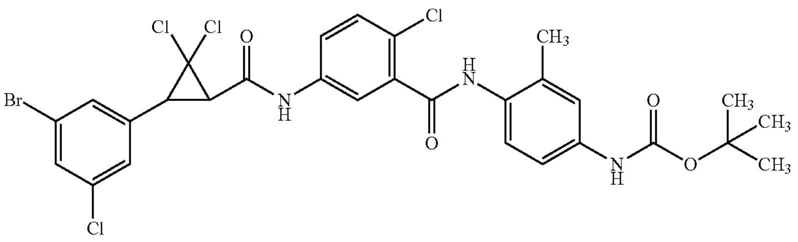 [SMILES: Cc1cc(NC(=O)OC(C)(C)C)ccc1NC(=O)c1cc(NC(=O)C2C(c3cc(Cl)cc(Br)c3)C2(Cl)Cl)ccc1Cl]

Isolated as a pale yellow foam (0.2256 g, 68%).

trans-2-Chloro-N-(2-cyano-4-fluorophenyl)-5-(2,2-dichloro-3-(3-(trifluoromethyl)phenyl)cyclopropane-1-carboxamido)benzamide (F340)

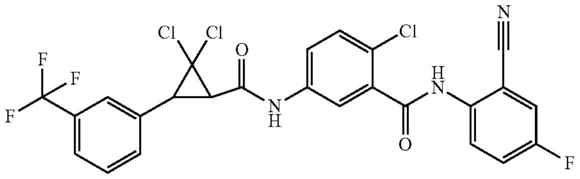 [SMILES: N#Cc1cc(F)ccc1NC(=O)c1cc(NC(=O)C2C(c3cccc(C(F)(F)F)c3)C2(Cl)Cl)ccc1Cl]

Isolated as a white solid (0.106 g, 69%).

trans-2-Chloro-5-(2,2-dichloro-3-(3-chloro-5-cyanophenyl)cyclopropane-1-carboxamido)-N-(3,5-difluoropyridin-2-yl)benzamide (F342)

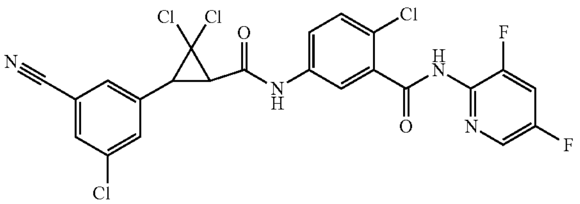 [SMILES: N#Cc1cc(Cl)cc(C2C(C(=O)Nc3ccc(Cl)c(C(=O)Nc4ncc(F)cc4F)c3)C2(Cl)Cl)c1]

Isolated as a light yellow foam (0.061 g, 40%).

trans-2-Chloro-N-(2-cyano-4-fluorophenyl)-5-(2,2-dichloro-3-(3-chloro-5-cyanophenyl)cyclopropane-1-carboxamido)benzamide (F343)

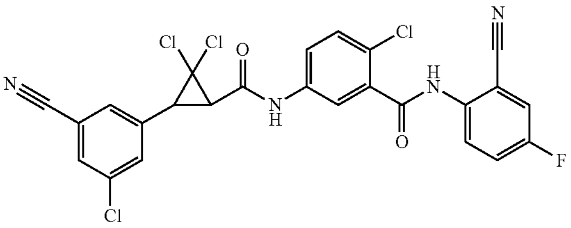 [SMILES: N#Cc1cc(Cl)cc(C2C(C(=O)Nc3ccc(Cl)c(C(=O)Nc4ccc(F)cc4C#N)c3)C2(Cl)Cl)c1]

Isolated as a white solid (0.082 g, 53%).

trans-2-Chloro-5-(2,2-dichloro-3-(3,5-dichlorophenyl)cyclopropane-1-carboxamido)-N-(4-fluorophenyl)-N-(prop-2-yn-1-yl)benzamide (F413)

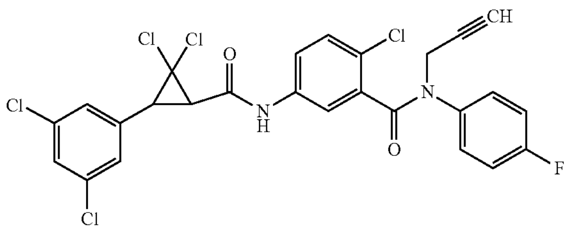 [SMILES: C#CCN(C(=O)c1cc(NC(=O)C2C(c3cc(Cl)cc(Cl)c3)C2(Cl)Cl)ccc1Cl)c1ccc(F)cc1]

Isolated as a white foam (0.117 g, 75%).

2-Chloro-5-((1R,3R)-2,2-dichloro-3-(3-chloro-4-fluorophenyl)cyclopropane-1-carboxamido)-N-(2,4-difluorophenyl)-N-(prop-2-yn-1-yl)benzamide (F414)

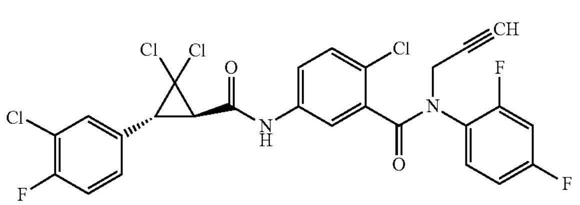 [SMILES: C#CCN(C(=O)c1cc(NC(=O)[C@H]2[C@H](c3ccc(F)c(Cl)c3)C2(Cl)Cl)ccc1Cl)c1ccc(F)cc1F]

Isolated as a light yellow foam (0.131 g, 79%).

trans-2-Chloro-5-(2,2-dichloro-3-(4-nitrophenyl)cyclopropane-1-carboxamido)-N-(4-fluorophenyl)benzamide (F422)

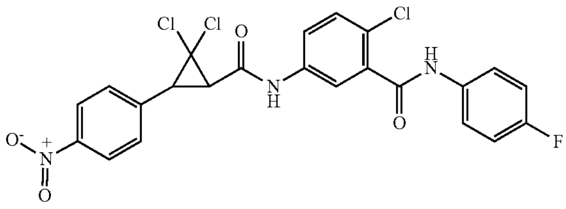

Isolated as a yellow foam (0.1341 g, 54%).

tert-Butyl-N-((tert-butoxy)carbonyl)-N-(3-(2-chloro-5-((1R,3R)-2,2-dichloro-3-(3,5-dichlorophenyl)cyclopropane-1-carboxamido)benzamido)-2,6-difluorophenyl)carbamate (F499)

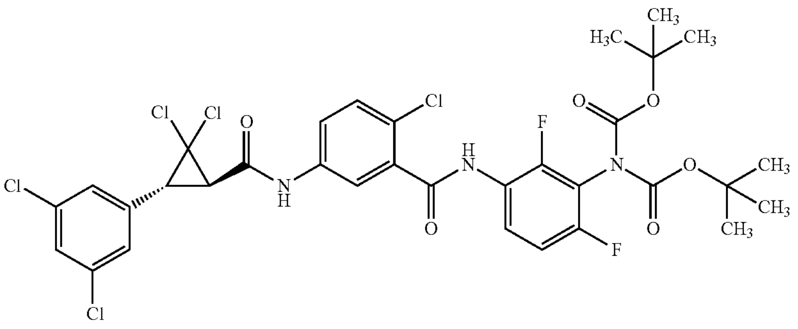 [SMILES: CC(C)(C)OC(=O)N(C(=O)OC(C)(C)C)c1c(F)ccc(NC(=O)c2cc(NC(=O)[C@H]3[C@H](c4cc(Cl)cc(Cl)c4)C3(Cl)Cl)ccc2Cl)c1F]

Isolated as a white solid (0.207 g, 80%).

tert-Butyl-N-((tert-butoxy)carbonyl)-N-(3-(2-chloro-5-((1R,3R)-2,2-dichloro-3-(3,4-dichlorophenyl)cyclopropane-1-carboxamido)benzamido)-2,6-difluorophenyl)carbamate (F500)

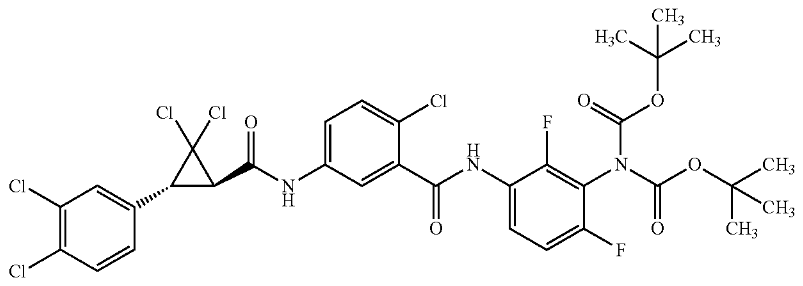 [SMILES: CC(C)(C)OC(=O)N(C(=O)OC(C)(C)C)c1c(F)ccc(NC(=O)c2cc(NC(=O)[C@H]3[C@H](c4ccc(Cl)c(Cl)c4)C3(Cl)Cl)ccc2Cl)c1F]

Isolated as a white solid (0.174 g, 67%).

tert-Butyl-N-((tert-butoxy)carbonyl)-N-(3-(2-chloro-5-((1R,3R)-2,2-dichloro-3-(3,4,5-trichlorophenyl)cyclopropane-1-carboxamido)benzamido)-2,6-difluorophenyl)carbamate (F501)

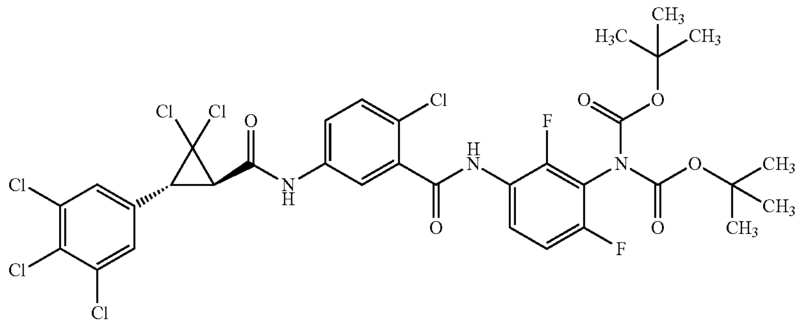 [SMILES: CC(C)(C)OC(=O)N(C(=O)OC(C)(C)C)c1c(F)ccc(NC(=O)c2cc(NC(=O)[C@H]3[C@H](c4cc(Cl)c(Cl)c(Cl)c4)C3(Cl)Cl)ccc2Cl)c1F]

Isolated as a white solid (0.171 g, 64%).

tert-Butyl-N-((tert-butoxy)carbonyl)-N-(3-(2-chloro-5-((1R,3R)-2,2-dichloro-3-(3-chloro-4-fluorophenyl)cyclopropane-1-carboxamido)benzamido)-2,6-difluorophenyl)carbamate (F503)

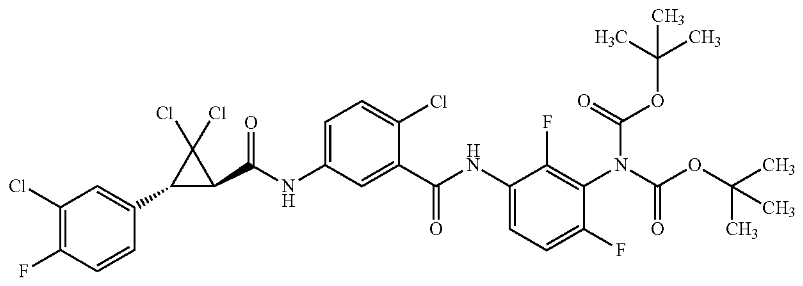 [SMILES: CC(C)(C)OC(=O)N(C(=O)OC(C)(C)C)c1c(F)ccc(NC(=O)c2cc(NC(=O)[C@H]3[C@H](c4ccc(F)c(Cl)c4)C3(Cl)Cl)ccc2Cl)c1F]

Isolated as a white solid (0.161 g, 75%).

tert-Butyl-N-((tert-butoxy)carbonyl)-N-(3-(5-(3-(4-bromo-3-chlorophenyl)-2,2-dichlorocyclopropane-1-carboxamido)-2-chlorobenzamido)-2,6-difluorophenyl)carbamate (F512)

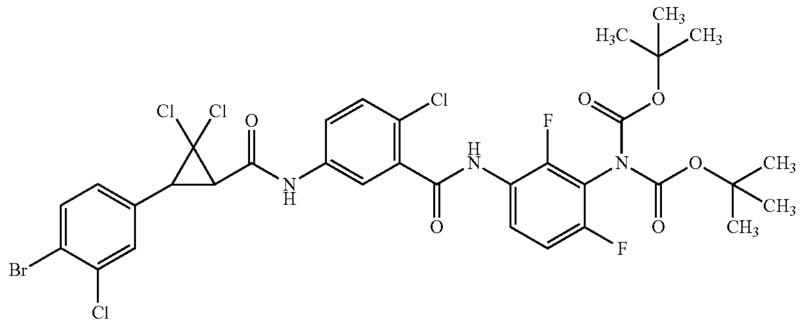 [SMILES: CC(C)(C)OC(=O)N(C(=O)OC(C)(C)C)c1c(F)ccc(NC(=O)c2cc(NC(=O)C3C(c4ccc(Br)c(Cl)c4)C3(Cl)Cl)ccc2Cl)c1F]

Isolated as a white foam (0.2060 g, 55%).

tert-Butyl-N-((tert-butoxy)carbonyl)-N-(3-(5-(3-(3-bromo-4-chlorophenyl)-2,2-dichlorocyclopropane-1-carboxamido)-2-chlorobenzamido)-2,6-difluorophenyl)carbamate (F513)

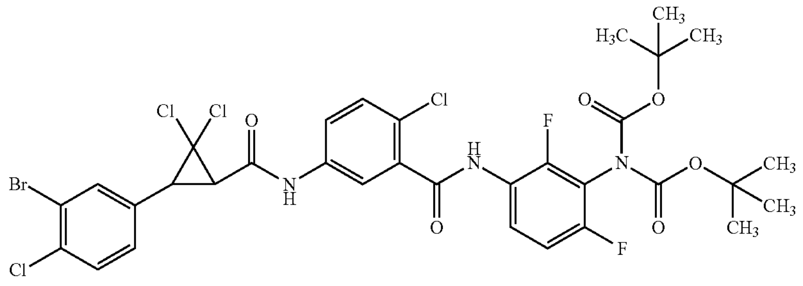 [SMILES: CC(C)(C)OC(=O)N(C(=O)OC(C)(C)C)c1c(F)ccc(NC(=O)c2cc(NC(=O)C3C(c4ccc(Cl)c(Br)c4)C3(Cl)Cl)ccc2Cl)c1F]

Isolated as a pale yellow solid (0.2054 g, 54%).

tert-Butyl-N-((tert-butoxy)carbonyl)-N-(3-(5-(3-(3-bromo-5-chlorophenyl)-2,2-dichlorocyclopropane-1-carboxamido)-2-chlorobenzamido)-2,6-difluorophenyl)carbamate (F514)

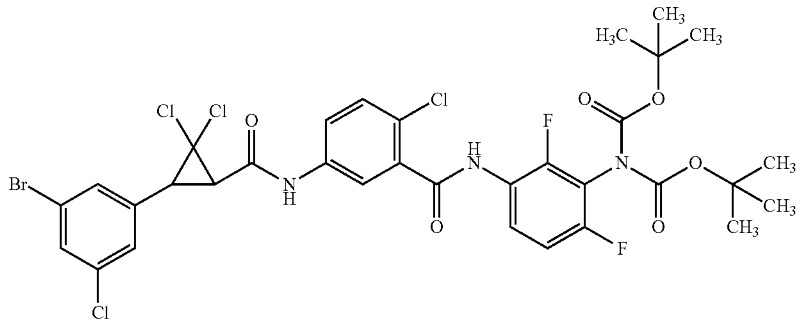

Isolated as a pale yellow foam (0.3134 g, 83%).

trans-tert-Butyl-N-((tert-butoxy)carbonyl)-N-(3-(2-chloro-5-(2,2-dichloro-3-(3-chloro-5-cyanophenyl)cyclopropane-1-carboxamido)benzamido)-2,6-difluorophenyl)carbamate (F515)

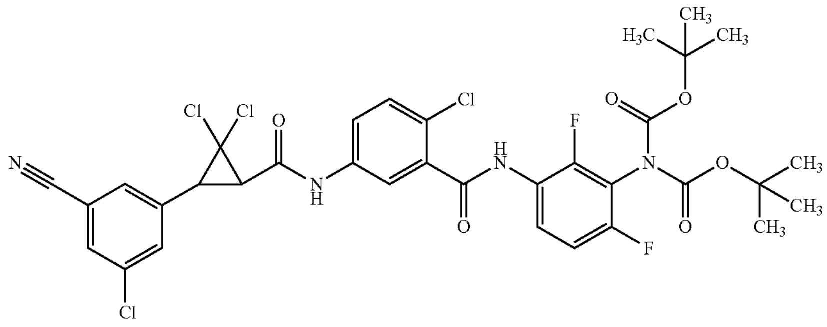 [SMILES: CC(C)(C)OC(=O)N(C(=O)OC(C)(C)C)c1c(F)ccc(NC(=O)c2cc(NC(=O)C3C(c4cc(Cl)cc(C#N)c4)C3(Cl)Cl)ccc2Cl)c1F]

Isolated as a white solid (0.133 g, 63%).

trans-tert-Butyl-N-((tert-butoxy)carbonyl)-N-(3-(2-chloro-5-(2,2-dichloro-3-(3-(trifluoromethyl)phenyl)cyclopropane-1-carboxamido)benzamido)-2,6-difluorophenyl)carbamate (F516)

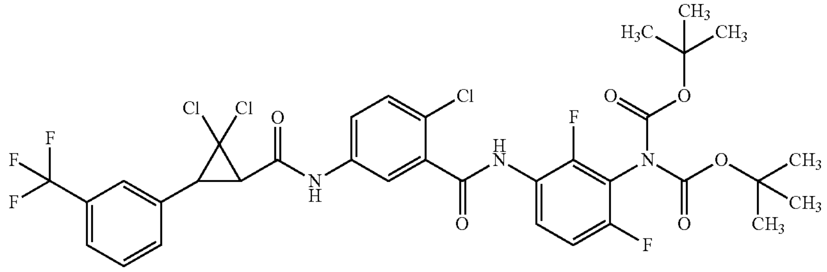 [SMILES: CC(C)(C)OC(=O)N(C(=O)OC(C)(C)C)c1c(F)ccc(NC(=O)c2cc(NC(=O)C3C(c4cccc(C(F)(F)F)c4)C3(Cl)Cl)ccc2Cl)c1F]

Isolated as a white solid (0.187 g, 90%).

5-(trans-3-(3-Bromo-5-chlorophenyl)-2,2-dichlorocyclopropane-1-carboxamido)-2-chloro-N-(4-fluorophenyl)benzamide (PF37)

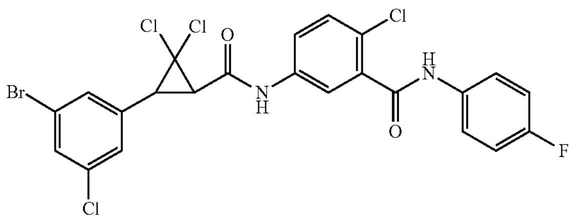

Isolated as a pale yellow foam (0.2287 g, 84%).

5-(trans-3-(3-Bromo-5-chlorophenyl)-2,2-dichlorocyclopropane-1-carboxamido)-2-chloro-N-(2,4-difluorophenyl)benzamide (PF39)

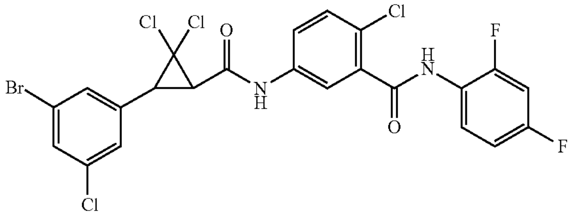

Isolated as a pale yellow foam (0.2352 g, 84%).

trans-tert-Butyl (4-(2-chloro-5-(2,2-dichloro-3-(3,4,5-trichlorophenyl)cyclopropane-1-carboxamido)benzamido)-3-methylphenyl)carbamate (F606)

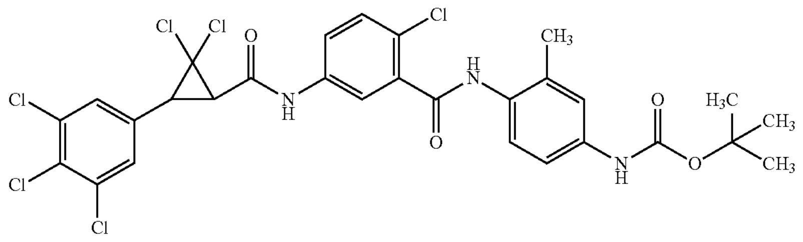 [SMILES: Cc1cc(NC(=O)OC(C)(C)C)ccc1NC(=O)c1cc(NC(=O)C2C(c3cc(Cl)c(Cl)c(Cl)c3)C2(Cl)Cl)ccc1Cl]

Isolated as a white solid (0.068 g, 47%).

trans-tert-Butyl (4-(2-chloro-5-(2,2-dichloro-3-(3-chloro-4-fluorophenyl)cyclopropane-1-carboxamido)benzamido)-3-methylphenyl)carbamate (F607)

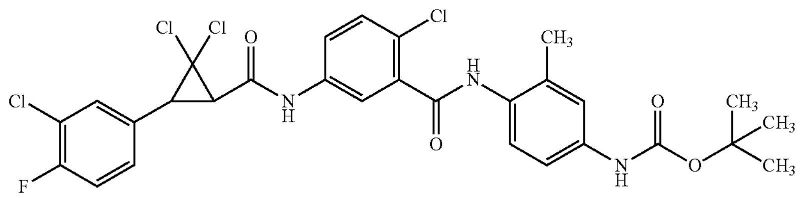

Isolated as a white solid (0.069 g, 51%).

5-(trans-3-(4-bromo-3,5-difluorophenyl)-2,2-dichlorocyclopropane-1-carboxamido)-2-chloro-N-(4-fluorophenyl)benzamide (F538)

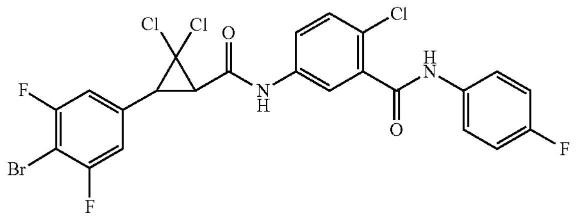

Isolated as a yellow foam (0.1445 g, 40%).

5-(trans-3-(4-Bromo-3-fluoro-5-methoxyphenyl)-2,2-dichlorocyclopropane-1-carboxamido)-2-chloro-N-(4-fluorophenyl)benzamide (F539)

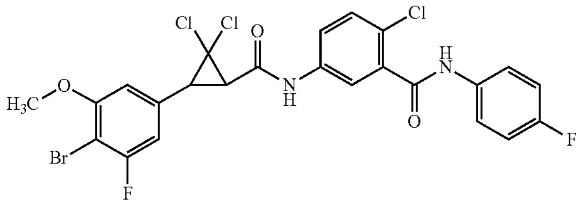 [SMILES: COc1cc(C2C(C(=O)Nc3ccc(Cl)c(C(=O)Nc4ccc(F)cc4)c3)C2(Cl)Cl)cc(F)c1Br]

Isolated as a yellow foam (0.0322 g, 23%).

5-(trans-3-(3-Bromo-5-fluoro-4-methoxyphenyl)-2,2-dichlorocyclopropane-1-carboxamido)-2-chloro-N-(4-fluorophenyl)benzamide (F540)

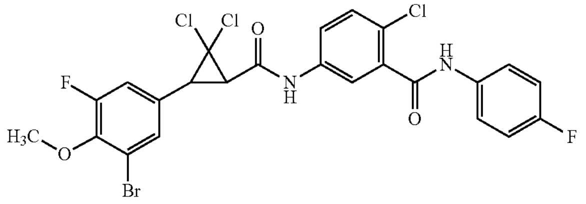 [SMILES: COc1c(F)cc(C2C(C(=O)Nc3ccc(Cl)c(C(=O)Nc4ccc(F)cc4)c3)C2(Cl)Cl)cc1Br]

Isolated as a yellow foam (0.0243 g, 17%).

5-(trans-3-(4-Bromo-3,5-difluorophenyl)-2,2-dichlorocyclopropane-1-carboxamido)-2-chloro-N-(2,4-difluorophenyl)benzamide (F541)

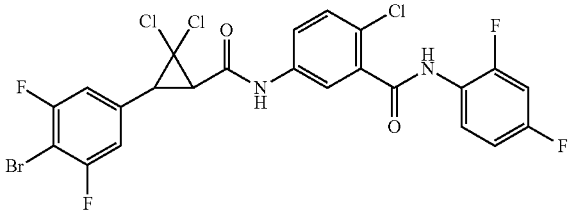

Isolated as a yellow foam (0.1307 g, 88%).

5-(trans-3-(4-Bromo-3-fluoro-5-methoxyphenyl)-2,2-dichlorocyclopropane-1-carboxamido)-2-chloro-N-(2,4-difluorophenyl)benzamide (F542)

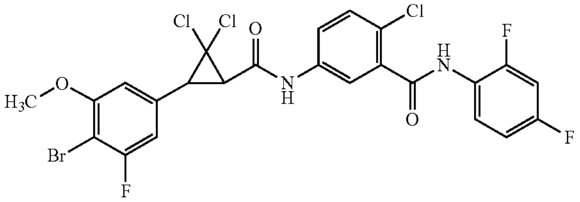 [SMILES: COc1cc(C2C(C(=O)Nc3ccc(Cl)c(C(=O)Nc4ccc(F)cc4F)c3)C2(Cl)Cl)cc(F)c1Br]

Isolated as a yellow foam (0.0712 g, 49%).

5-(trans-3-(3-Bromo-5-fluoro-4-methoxyphenyl)-2,2-dichlorocyclopropane-1-carboxamido)-2-chloro-N-(2,4-difluorophenyl)benzamide (F543)

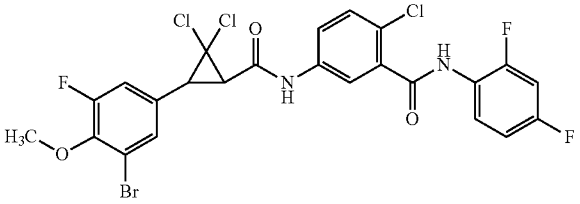 [SMILES: COc1c(F)cc(C2C(C(=O)Nc3ccc(Cl)c(C(=O)Nc4ccc(F)cc4F)c3)C2(Cl)Cl)cc1Br]

Isolated as a yellow foam (0.0273 g, 19%).

5-((1R,3R)-3-(3-Bromo-4-chlorophenyl)-2,2-dichlorocyclopropane-1-carboxamido)-2-chloro-N-(2,4-difluorophenyl)benzamide (F572)

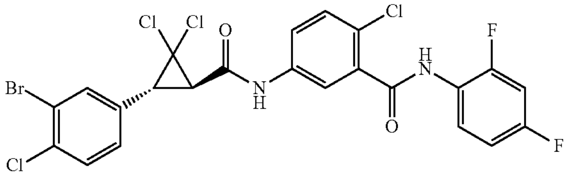 [SMILES: O=C(Nc1ccc(F)cc1F)c1cc(NC(=O)[C@H]2[C@H](c3ccc(Cl)c(Br)c3)C2(Cl)Cl)ccc1Cl]

Isolated as a yellow foam (0.0886 g, 68%).

5-((1S,3S)-3-(3-Bromo-4-chlorophenyl)-2,2-dichlorocyclopropane-1-carboxamido)-2-chloro-N-(2,4-difluorophenyl)benzamide (F573)

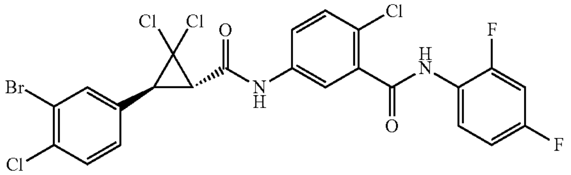 [SMILES: O=C(Nc1ccc(F)cc1F)c1cc(NC(=O)[C@@H]2[C@@H](c3ccc(Cl)c(Br)c3)C2(Cl)Cl)ccc1Cl]

Isolated as a yellow foam (0.0833 g, 64%).

tert-Butyl-N-((tert-butoxy)carbonyl)-N-(3-(5-((1R,3R)-3-(3-bromo-4-chlorophenyl)-2,2-dichlorocyclopropane-1-carboxamido)-2-chlorobenzamido)-2,6-difluorophenyl)carbamate (F616)

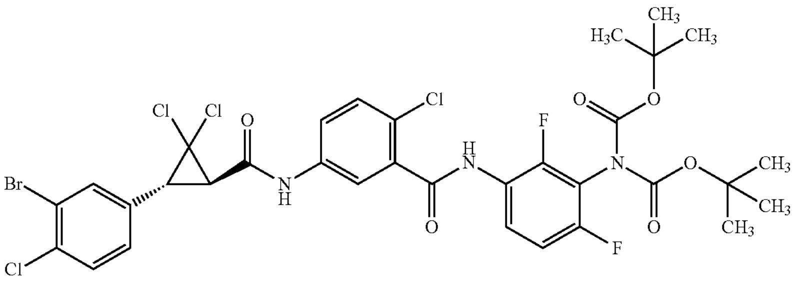 [SMILES: CC(C)(C)OC(=O)N(C(=O)OC(C)(C)C)c1c(F)ccc(NC(=O)c2cc(NC(=O)[C@H]3[C@H](c4ccc(Cl)c(Br)c4)C3(Cl)Cl)ccc2Cl)c1F]

Isolated as a white foam (0.1054 g, 60%).

tert-Butyl-N-((tert-butoxy)carbonyl)-N-(5-(5-((1R, 3R)-3-(3-bromo-4-chlorophenyl)-2,2-dichlorocyclopropane-1-carboxamido)-2-chlorobenzamido)-2,4-difluorophenyl)carbamate (F617)

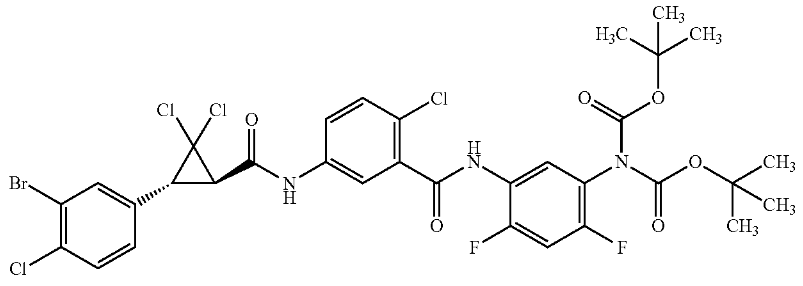

Isolated as a yellow foam (0.0506 g, 29%).

5-(trans)-2-Bromo-2-chloro-3-(3,5-dichlorophenyl) cyclopropane-1-carboxamido)-2-chloro-N-(4-fluorophenyl)benzamide (PF33)

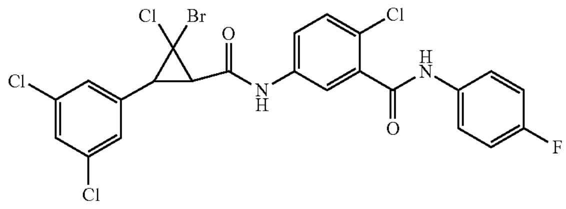 [SMILES: O=C(Nc1ccc(F)cc1)c1cc(NC(=O)C2C(c3cc(Cl)cc(Cl)c3)C2(Cl)Br)ccc1Cl]

Isolated as a white solid (0.069 mg, 48%).

5-(trans)-2-Bromo-3-(3,5-dichlorophenyl)-2-fluorocyclopropane-1-carboxamido)-2-chloro-N-(4-fluorophenyl)benzamide (PF51)

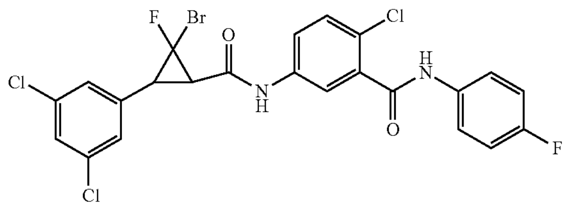 [SMILES: O=C(Nc1ccc(F)cc1)c1cc(NC(=O)C2C(c3cc(Cl)cc(Cl)c3)C2(F)Br)ccc1Cl]

Isolated as a pale yellow solid (0.095 g, 53%).

2-Chloro-5-(trans)-2,2-dichloro-3-(3,5-dichlorophenyl)cyclopropane-1-carboxamido)-N-(3,4,5-trichlorophenyl)benzamide (PF119)

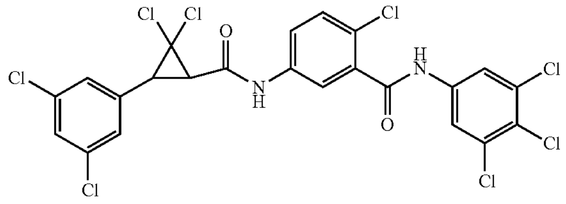 [SMILES: O=C(Nc1cc(Cl)c(Cl)c(Cl)c1)c1cc(NC(=O)C2C(c3cc(Cl)cc(Cl)c3)C2(Cl)Cl)ccc1Cl]

Isolated as a white solid (0.031 g, 22%).

2-Chloro-5-(trans)-2-chloro-3-(3,5-dichlorophenyl)-2-fluorocyclopropane-1-carboxamido)-N-(4-fluorophenyl)benzamide (PF153)

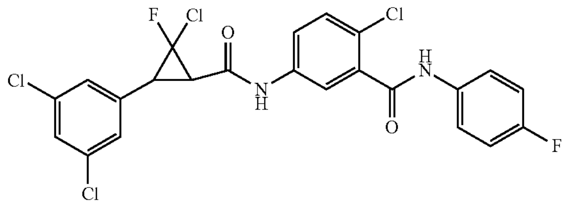 [SMILES: O=C(Nc1ccc(F)cc1)c1cc(NC(=O)C2C(c3cc(Cl)cc(Cl)c3)C2(F)Cl)ccc1Cl]

Isolated as a white foam (0.152 g, 73%).

2-Chloro-5-(trans)-2,2-dichloro-3-(3-chloro-5-cyanophenyl)cyclopropane-1-carboxamido)-N-(4-fluorophenyl)benzamide (PF155)

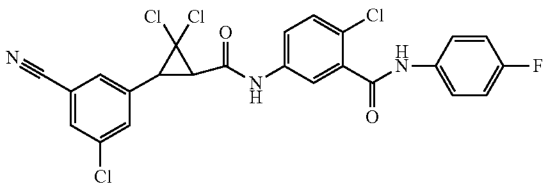 [SMILES: N#Cc1cc(Cl)cc(C2C(C(=O)Nc3ccc(Cl)c(C(=O)Nc4ccc(F)cc4)c3)C2(Cl)Cl)c1]

Isolated as a white solid (0.104 g, 55%).

The following compounds were prepared in like manner to the procedure outlined in Example 14:

trans-2-Chloro-5-(2,2-dichloro-3-(3,5-dichlorophenyl)-N-methylcyclopropane-1-carboxamido)-N-(4-fluorophenyl)benzamide (F183)

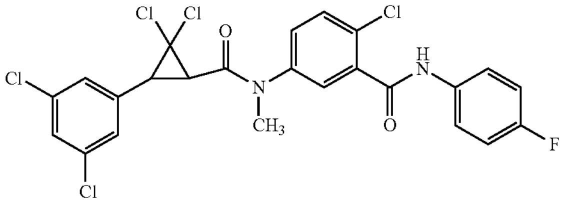 [SMILES: CN(C(=O)C1C(c2cc(Cl)cc(Cl)c2)C1(Cl)Cl)c1ccc(Cl)c(C(=O)Nc2ccc(F)cc2)c1]

Isolated as a brown waxy solid (0.033 g, 23%).

trans-2-Chloro-5-(2,2-dichloro-3-(3,5-dichlorophenyl)cyclopropane-1-carboxamido)-N-(4-fluoro-3-(trifluoromethyl)phenyl)benzamide (PF70)

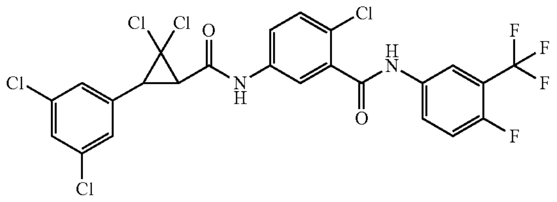 [SMILES: O=C(Nc1ccc(F)c(C(F)(F)F)c1)c1cc(NC(=O)C2C(c3cc(Cl)cc(Cl)c3)C2(Cl)Cl)ccc1Cl]

Isolated as a light brown foam (0.111 g, 29.2%).

trans-2-Chloro-5-(2,2-dichloro-3-(3,5-dichlorophenyl)cyclopropane-1-carboxamido)-N-(3-(trifluoromethyl)phenyl)benzamide (PF71)

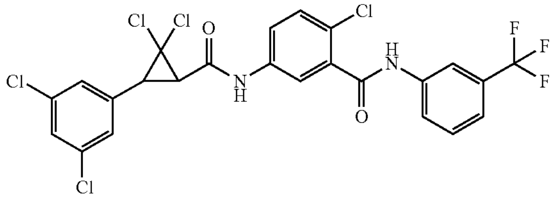 [SMILES: O=C(Nc1cccc(C(F)(F)F)c1)c1cc(NC(=O)C2C(c3cc(Cl)cc(Cl)c3)C2(Cl)Cl)ccc1Cl]

Isolated as a light brown foam (0.147 g, 26.8%)

trans-2-Chloro-N-(4-chloro-3-methylphenyl)-5-(2,2-dichloro-3-(3,5-dichlorophenyl)cyclopropane-1-carboxamido)benzamide (PF113)

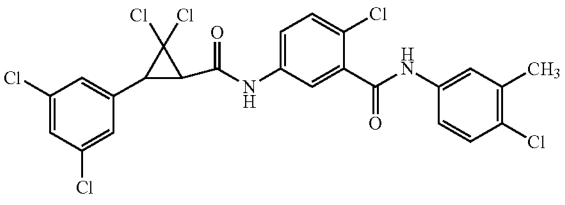 [SMILES: Cc1cc(NC(=O)c2cc(NC(=O)C3C(c4cc(Cl)cc(Cl)c4)C3(Cl)Cl)ccc2Cl)ccc1Cl]

Isolated as a white foam (0.091 g, 70.1%).

2-Chloro-N-(4-chloro-3-methoxyphenyl)-5-(trans)-2,2-dichloro-3-(3,5-dichlorophenyl)cyclopropane-1-carboxamido)benzamide (PF114)

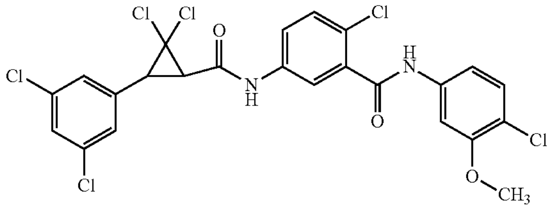 [SMILES: COc1cc(NC(=O)c2cc(NC(=O)C3C(c4cc(Cl)cc(Cl)c4)C3(Cl)Cl)ccc2Cl)ccc1Cl]

Isolated as a white foam (0.095 g, 71.2%).

N-(4-Bromo-3-fluorophenyl)-2-chloro-5-(trans)-2,2-dichloro-3-(3,5-dichlorophenyl)cyclopropane-1-carboxamido)benzamide (PF115)

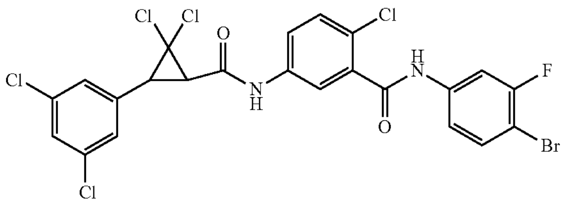 [SMILES: O=C(Nc1ccc(Br)c(F)c1)c1cc(NC(=O)C2C(c3cc(Cl)cc(Cl)c3)C2(Cl)Cl)ccc1Cl]

Isolated as a white foam (0.059 g, 41.9%).

2-Chloro-N-(4-chloro-2-fluorophenyl)-5-(trans)-2,2-dichloro-3-(3,5-dichlorophenyl)cyclopropane-1-carboxamido)benzamide (PF116)

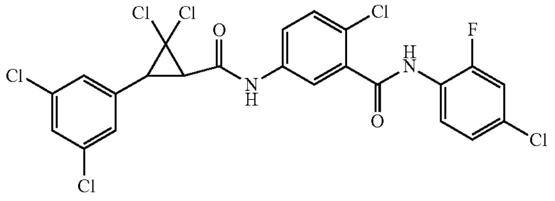 [SMILES: O=C(Nc1ccc(Cl)cc1F)c1cc(NC(=O)C2C(c3cc(Cl)cc(Cl)c3)C2(Cl)Cl)ccc1Cl]

Isolated as a white foam (0.091 g, 69.6%).

2-Chloro-5-(trans)-2,2-dichloro-3-(3,5-dichlorophenyl)cyclopropane-1-carboxamido)-N-(3,4-dichlorophenyl)benzamide (PF117)

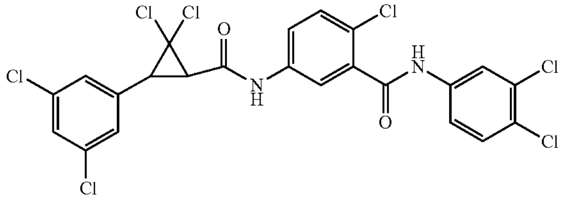 [SMILES: O=C(Nc1ccc(Cl)c(Cl)c1)c1cc(NC(=O)C2C(c3cc(Cl)cc(Cl)c3)C2(Cl)Cl)ccc1Cl]

Isolated as a white foam (0.030 g, 22%).

2-Chloro-5-(trans)-2,2-dichloro-3-(3,5-dichlorophenyl)cyclopropane-1-carboxamido)-N-(2,5-difluorophenyl)benzamide (PF118)

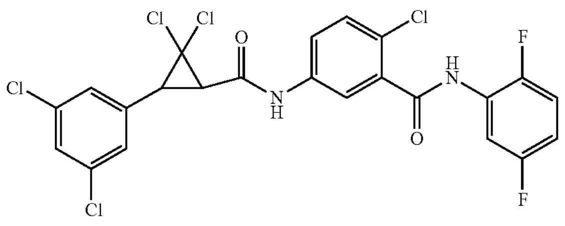 [SMILES: O=C(Nc1cc(F)ccc1F)c1cc(NC(=O)C2C(c3cc(Cl)cc(Cl)c3)C2(Cl)Cl)ccc1Cl]

Isolated as a white foam (0.040 g, 31.5%).

2-Chloro-N-(3-chloro-4-cyanophenyl)-5-(trans)-2,2-dichloro-3-(3,5-dichlorophenyl)cyclopropane-1-carboxamido)benzamide (PF120)

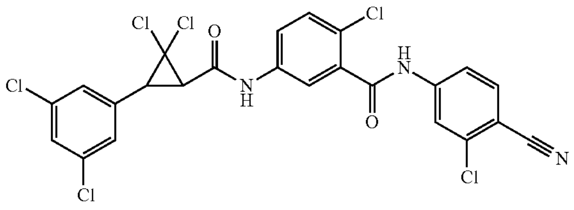 [SMILES: N#Cc1ccc(NC(=O)c2cc(NC(=O)C3C(c4cc(Cl)cc(Cl)c4)C3(Cl)Cl)ccc2Cl)cc1Cl]

Isolated as a white foam (0.020 g, 15%).

2-Chloro-N-(3-chloro-4-fluorophenyl)-5-(trans)-2,2-dichloro-3-(3,5-dichlorophenyl)cyclopropane-1-carboxamido)benzamide (PF122)

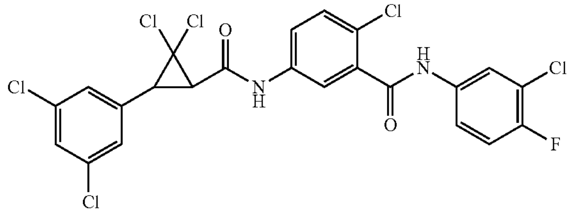 [SMILES: O=C(Nc1ccc(F)c(Cl)c1)c1cc(NC(=O)C2C(c3cc(Cl)cc(Cl)c3)C2(Cl)Cl)ccc1Cl]

Isolated as a gold foam (0.093 g, 71.2%).

2-Chloro-N-(4-chloro-3-fluorophenyl)-5-(trans)-2,2-dichloro-3-(3,5-dichlorophenyl)cyclopropane-1-carboxamido)benzamide (PF123)

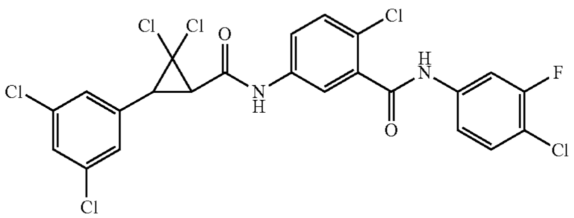 [SMILES: O=C(Nc1ccc(Cl)c(F)c1)c1cc(NC(=O)C2C(c3cc(Cl)cc(Cl)c3)C2(Cl)Cl)ccc1Cl]

Isolated as a white foam (0.084 g, 64.3%).

2-Chloro-5-(trans)-2,2-dichloro-3-(3,5-dichlorophenyl)cyclopropane-1-carboxamido)-N-(3-ethynylphenyl)benzamide (PF124)

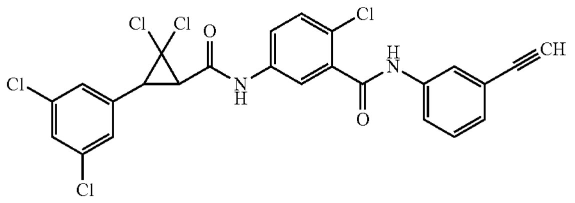 [SMILES: C#Cc1cccc(NC(=O)c2cc(NC(=O)C3C(c4cc(Cl)cc(Cl)c4)C3(Cl)Cl)ccc2Cl)c1]

Isolated as a yellow foam (0.084 g, 56.2%).

2-Chloro-N-(3-chloro-4-methylphenyl)-5-(trans)-2,2-dichloro-3-(3,5-dichlorophenyl)cyclopropane-1-carboxamido)benzamide (PF125)

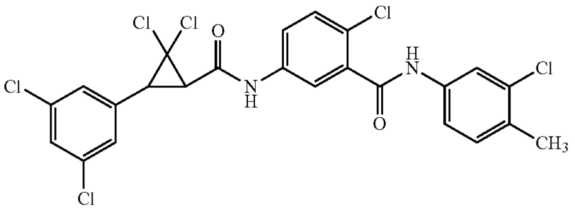 [SMILES: Cc1ccc(NC(=O)c2cc(NC(=O)C3C(c4cc(Cl)cc(Cl)c4)C3(Cl)Cl)ccc2Cl)cc1Cl]

Isolated as a white foam (0.107 g, 68.6%).

2-Chloro-5-(trans)-2,2-dichloro-3-(3,5-dichlorophenyl)cyclopropane-1-carboxamido)-N-(1H-indol-6-yl) benzamide (PF126)

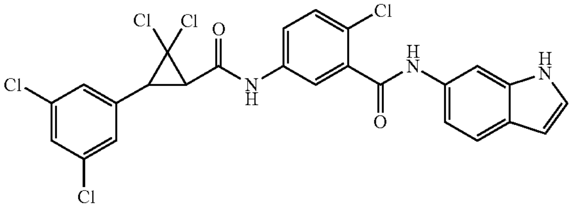

Isolated as a white solid (0.055 g, 35.9%).

2-Chloro-N-(3,4-dichloro-2-fluorophenyl)-5-(trans)-2,2-dichloro-3-(3,5-dichlorophenyl)cyclopropane-1-carboxamido)benzamide (PF127)

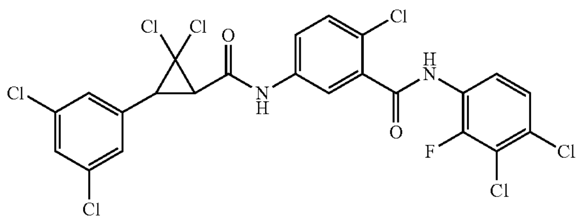 [SMILES: O=C(Nc1ccc(Cl)c(Cl)c1F)c1cc(NC(=O)C2C(c3cc(Cl)cc(Cl)c3)C2(Cl)Cl)ccc1Cl]

Isolated as a white foam (0.016 g, 9.62%).

2-Chloro-5-((1R,3R)-2,2-dichloro-3-(3,5-dichlorophenyl)cyclopropane-1-carboxamido)-N-(4-fluorophenyl)benzamide (F165)

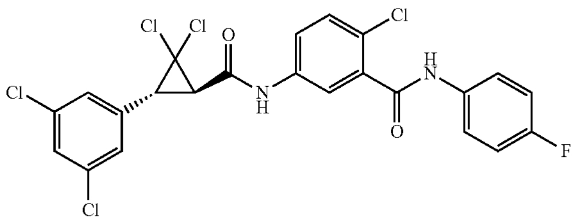 [SMILES: O=C(Nc1ccc(F)cc1)c1cc(NC(=O)[C@H]2[C@H](c3cc(Cl)cc(Cl)c3)C2(Cl)Cl)ccc1Cl]

Isolated as a white foam (0.0242 g, 52.1%).

2-Chloro-5-((1S,3S)-2,2-dichloro-3-(3,5-dichlorophenyl)cyclopropane-1-carboxamido)-N-(4-fluorophenyl)benzamide (F166)

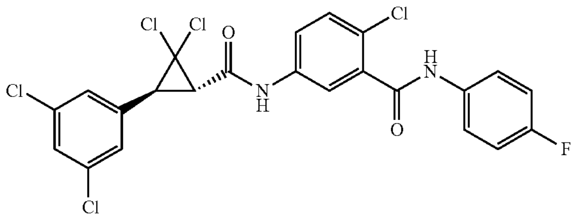 [SMILES: O=C(Nc1ccc(F)cc1)c1cc(NC(=O)[C@@H]2[C@@H](c3cc(Cl)cc(Cl)c3)C2(Cl)Cl)ccc1Cl]

Isolated as a white foam (0.221 g, 48.5%).

2-Chloro-5-((1R,3R)-2,2-dichloro-3-(3,5-dichlorophenyl)cyclopropane-1-carboxamido)-N-(4-fluorophenyl)-N-methylbenzamide (F169)

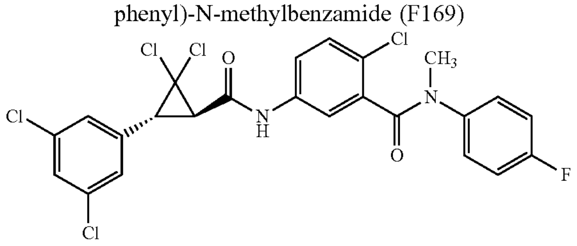

Isolated as a white foam (0.095 g, 52.9%).

2-Chloro-5-((1S,3S)-2,2-dichloro-3-(3,5-dichlorophenyl)cyclopropane-1-carboxamido)-N-(4-fluorophenyl)-N-methylbenzamide (F170)

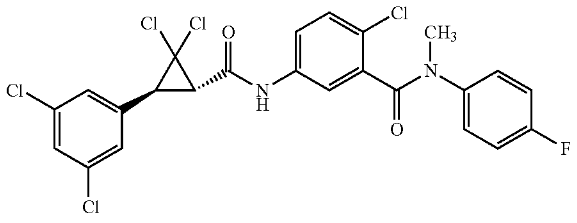 [SMILES: CN(C(=O)c1cc(NC(=O)[C@@H]2[C@@H](c3cc(Cl)cc(Cl)c3)C2(Cl)Cl)ccc1Cl)c1ccc(F)cc1]

Isolated as a white foam (0.103 g, 57.3%).

2-Chloro-5-((1R,3R)-2,2-dichloro-3-(3,5-dichlorophenyl)cyclopropane-1-carboxamido)-N-(2,4-difluorophenyl)benzamide (F185)

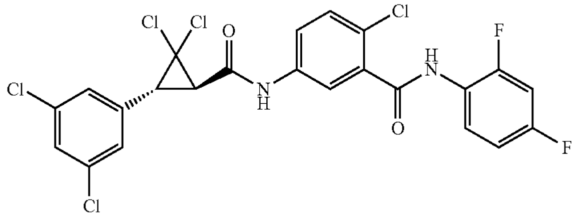

Isolated as a white foam (0.200 g, 52.1%).

3-(trans)-2,2-Dichloro-3-(3,5-dichlorophenyl)cyclopropane-1-carboxamido)-N-(2,4-difluorophenyl) benzamide (F186)

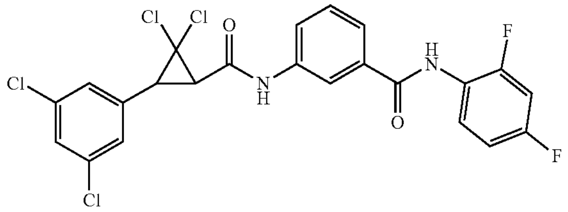 [SMILES: O=C(Nc1ccc(F)cc1F)c1cccc(NC(=O)C2C(c3cc(Cl)cc(Cl)c3)C2(Cl)Cl)c1]

Isolated as a white foam (0.184 g, 68%).

2-Chloro-5-((1S,3S)-2,2-dichloro-3-(3,4-dichlorophenyl)cyclopropane-1-carboxamido)-N-(4-fluorophenyl)benzamide (F208)

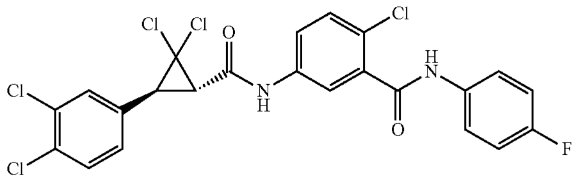

Isolated as a white foam (0.090 g, 34.9%).

2-Chloro-5-((1R,3R)-2,2-dichloro-3-(3,4-dichlorophenyl)cyclopropane-1-carboxamido)-N-(4-fluorophenyl)benzamide (F209)

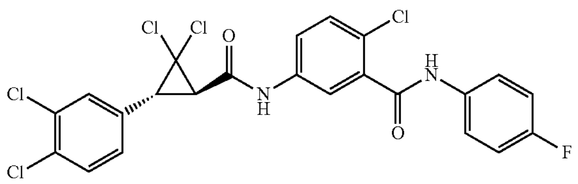 [SMILES: O=C(Nc1ccc(F)cc1)c1cc(NC(=O)[C@H]2[C@H](c3ccc(Cl)c(Cl)c3)C2(Cl)Cl)ccc1Cl]

Isolated as a white foam (0.086 g, 33.4%).

2-Chloro-5-((1S,3S)-2,2-dichloro-3-(3,4-dichlorophenyl)cyclopropane-1-carboxamido)-N-(2,4-difluorophenyl)benzamide (F210)

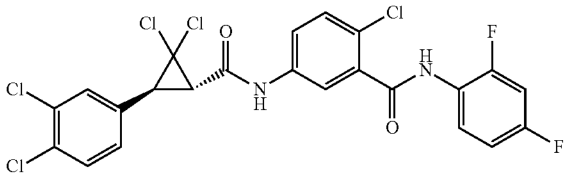

Isolated as a white foam (0.096 g, 36.1%).

2-Chloro-5-((1R,3R)-2,2-dichloro-3-(3,4-dichlorophenyl)cyclopropane-1-carboxamido)-N-(2,4-difluorophenyl)benzamide (F211)

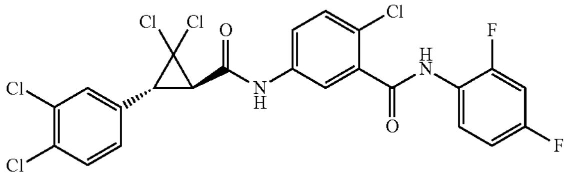 [SMILES: O=C(Nc1ccc(F)cc1F)c1cc(NC(=O)[C@H]2[C@H](c3ccc(Cl)c(Cl)c3)C2(Cl)Cl)ccc1Cl]

Isolated as a white foam (0.076 g, 28.6%).

2-Chloro-5-(trans)-2,2-dichloro-3-(3,5-dichlorophenyl)cyclopropane-1-carboxamido)-N-(2-methylisoindolin-5-yl)benzamide (F498)

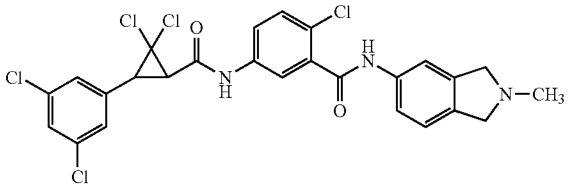 [SMILES: CN1Cc2ccc(NC(=O)c3cc(NC(=O)C4C(c5cc(Cl)cc(Cl)c5)C4(Cl)Cl)ccc3Cl)cc2C1]

Isolated as a tan foam (0.073 g, 53.9%).

2-Chloro-5-(2,2-dichloro-3-cis-(3,5-dichlorophenyl)cyclopropane-1-carboxamido)-N-(4-fluorophenyl)benzamide (F629)

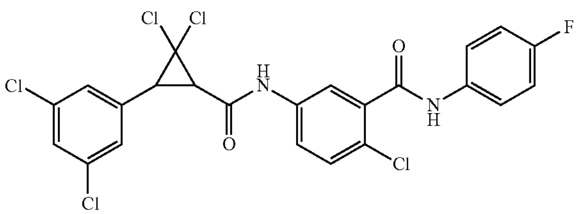 [SMILES: O=C(Nc1ccc(F)cc1)c1cc(NC(=O)C2C(c3cc(Cl)cc(Cl)c3)C2(Cl)Cl)ccc1Cl]

Isolated as an off-white solid (0.027 g, 29%).

The following compounds were prepared in like manner to the procedure outlined in Example 15:

trans-2-Chloro-5-(2,2-dichloro-3-(3,5-dichlorophenyl)cyclopropane-1-carboxamido)-N-(4-fluoro-3-methoxyphenyl)benzamide (PF52)

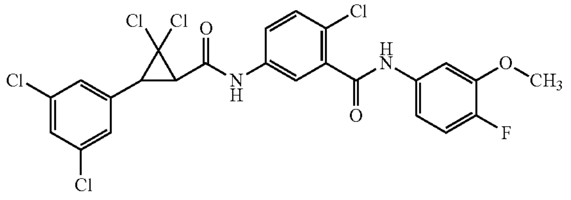 [SMILES: COc1cc(NC(=O)c2cc(NC(=O)C3C(c4cc(Cl)cc(Cl)c4)C3(Cl)Cl)ccc2Cl)ccc1F]

Isolated as a white foam (0.080 g, 78%).

trans-2-Chloro-5-(2,2-dichloro-3-(3,5-dichlorophenyl)cyclopropane-1-carboxamido)-N-(4-fluoro-3,5-dimethylphenyl)benzamide (PF53)

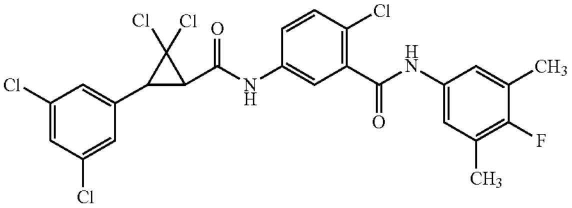 [SMILES: Cc1cc(NC(=O)c2cc(NC(=O)C3C(c4cc(Cl)cc(Cl)c4)C3(Cl)Cl)ccc2Cl)cc(C)c1F]

Isolated as a white solid (0.056 g, 55%).

trans-2-Chloro-5-(2,2-dichloro-3-(3,5-dichlorophenyl)cyclopropane-1-carboxamido)-N-(4-fluoro-2,3-dimethylphenyl)benzamide (PF54)

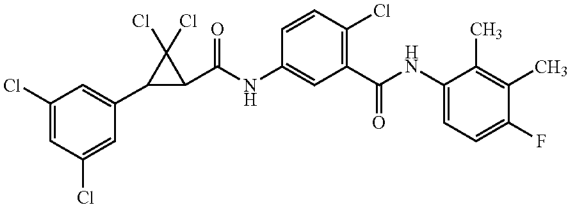 [SMILES: Cc1c(F)ccc(NC(=O)c2cc(NC(=O)C3C(c4cc(Cl)cc(Cl)c4)C3(Cl)Cl)ccc2Cl)c1C]

Isolated as a white solid (0.064 g, 63%).

trans-2-Chloro-5-(2,2-dichloro-3-(3,5-dichlorophenyl)cyclopropane-1-carboxamido)-N-(2,4-difluoro-3-methylphenyl)benzamide (PF55)

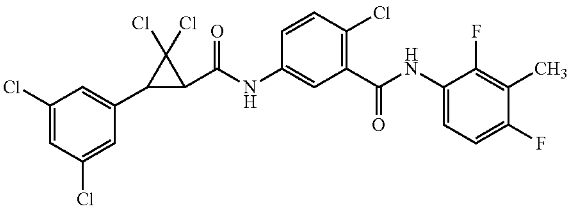 [SMILES: Cc1c(F)ccc(NC(=O)c2cc(NC(=O)C3C(c4cc(Cl)cc(Cl)c4)C3(Cl)Cl)ccc2Cl)c1F]

Isolated as a white solid (0.038 g, 37%).

trans-2-Chloro-5-(2,2-dichloro-3-(3,5-dichlorophenyl)cyclopropane-1-carboxamido)-N-(4-fluoro-2-methoxyphenyl)benzamide (PF58)

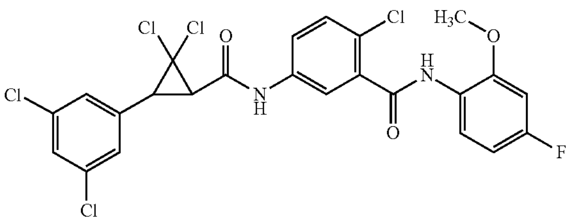 [SMILES: COc1cc(F)ccc1NC(=O)c1cc(NC(=O)C2C(c3cc(Cl)cc(Cl)c3)C2(Cl)Cl)ccc1Cl]

Isolated as a white solid (0.048 g, 47%).

trans-methyl (4-(2-chloro-5-(2,2-dichloro-3-(3,5-dichlorophenyl)cyclopropane-1-carboxamido)benzamido)phenyl)carbamate (PF110)

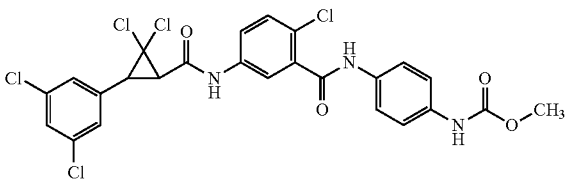 [SMILES: COC(=O)Nc1ccc(NC(=O)c2cc(NC(=O)C3C(c4cc(Cl)cc(Cl)c4)C3(Cl)Cl)ccc2Cl)cc1]

Isolated as a white foam (0.096 g, 72%).

trans-2-Chloro-5-(2,2-dichloro-3-(3,5-dichlorophenyl)cyclopropane-1-carboxamido)-N-(thiophen-3-yl)benzamide (PF152)

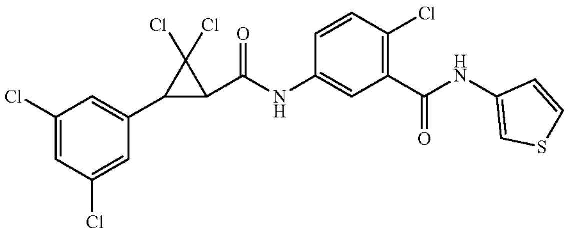 [SMILES: O=C(Nc1ccsc1)c1cc(NC(=O)C2C(c3cc(Cl)cc(Cl)c3)C2(Cl)Cl)ccc1Cl]

Isolated as an off-white glass (0.096 g, 81%).

trans-tert-Butyl-(4-(2-chloro-5-(2,2-dichloro-3-(3,5-dichlorophenyl)cyclopropane-1-carboxamido)benzamido)-3-methylphenyl)carbamate (F197)

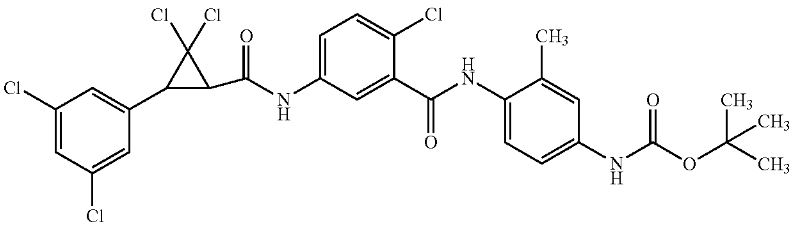 [SMILES: Cc1cc(NC(=O)OC(C)(C)C)ccc1NC(=O)c1cc(NC(=O)C2C(c3cc(Cl)cc(Cl)c3)C2(Cl)Cl)ccc1Cl]

Isolated as a white solid (0.056 g, 55%).

trans-tert-Butyl-(4-(2-chloro-5-(2,2-dichloro-3-(3,5-dichlorophenyl)cyclopropane-1-carboxamido)benzamido)-3-methylphenyl)(methyl)carbamate (F198)

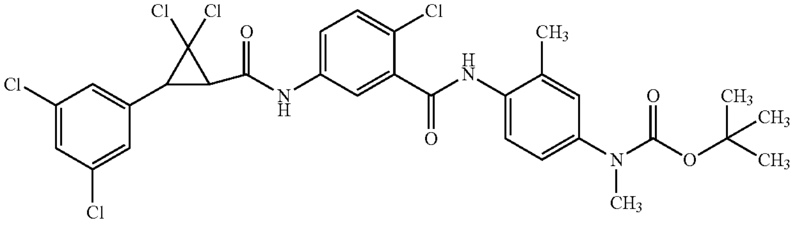 [SMILES: Cc1cc(N(C)C(=O)OC(C)(C)C)ccc1NC(=O)c1cc(NC(=O)C2C(c3cc(Cl)cc(Cl)c3)C2(Cl)Cl)ccc1Cl]

Isolated as a white solid (0.169 g, 44%).

trans-N-(Benzo[b]thiophen-5-yl)-2-chloro-5-(2,2-dichloro-3-(3,5-dichlorophenyl)cyclopropane-1-carboxamido)benzamide (F452)

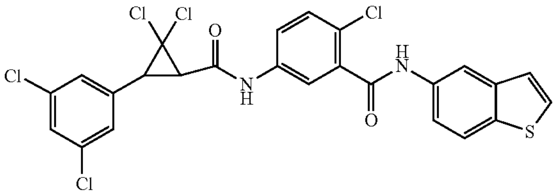 [SMILES: O=C(Nc1ccc2sccc2c1)c1cc(NC(=O)C2C(c3cc(Cl)cc(Cl)c3)C2(Cl)Cl)ccc1Cl]

Isolated as an off-white foam (0.125 g, 81%).

trans-N-(Benzo[d]thiazol-5-yl)-2-chloro-5-(2,2-dichloro-3-(3,5-dichlorophenyl)cyclopropane-1-carboxamido)benzamide (F482)

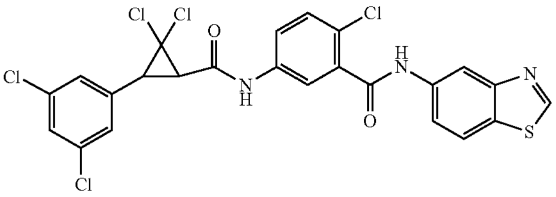 [SMILES: O=C(Nc1ccc2scnc2c1)c1cc(NC(=O)C2C(c3cc(Cl)cc(Cl)c3)C2(Cl)Cl)ccc1Cl]

Isolated as a white powder (0.092 g, 59%).

trans-tert-Butyl (4-(2-chloro-5-(2,2-dichloro-3-(3,5-dichlorophenyl)cyclopropane-1-carboxamido)benzamido)-3-fluorophenyl)(methyl)carbamate (F600)

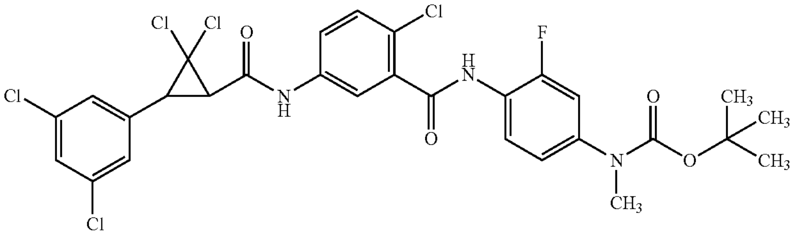 [SMILES: CN(C(=O)OC(C)(C)C)c1ccc(NC(=O)c2cc(NC(=O)C3C(c4cc(Cl)cc(Cl)c4)C3(Cl)Cl)ccc2Cl)c(F)c1]

Isolated as a white solid (0.066 g, 22%).

trans-tert-Butyl-N-((tert-butoxy)carbonyl)-N-(4-(2-chloro-5-(2,2-dichloro-3-(3,5-dichlorophenyl)cyclopropane-1-carboxamido)benzamido)-2-fluorophenyl)carbamate (F601)

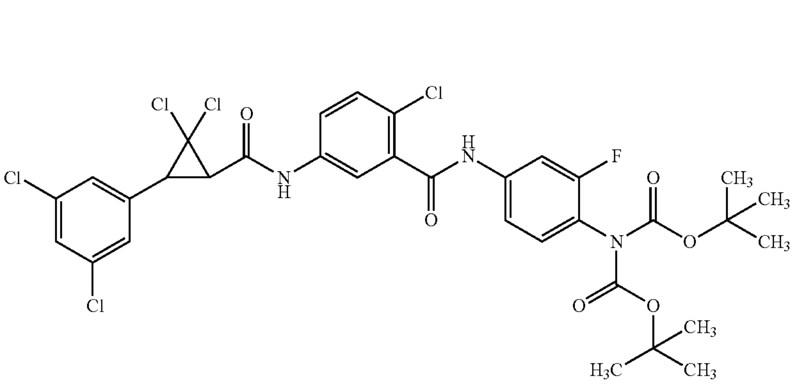 [SMILES: CC(C)(C)OC(=O)N(C(=O)OC(C)(C)C)c1ccc(NC(=O)c2cc(NC(=O)C3C(c4cc(Cl)cc(Cl)c4)C3(Cl)Cl)ccc2Cl)cc1F]

Isolated as a white foam (0.093 g, 55%).

trans-tert-Butyl-N-((tert-butoxy)carbonyl)-N-(4-(2-chloro-5-(2,2-dichloro-3-(3,5-dichlorophenyl)cyclopropane-1-carboxamido)benzamido)-3-fluorophenyl) carbamate (F602)

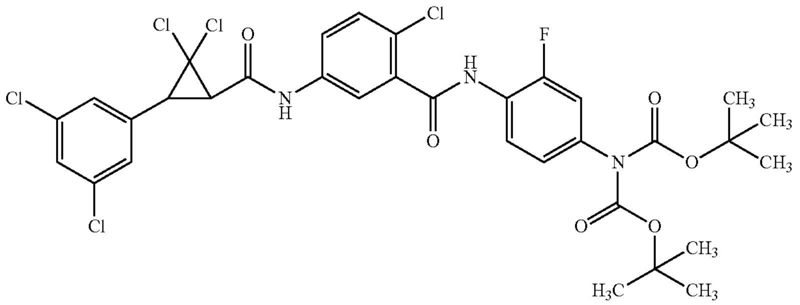 [SMILES: CC(C)(C)OC(=O)N(C(=O)OC(C)(C)C)c1ccc(NC(=O)c2cc(NC(=O)C3C(c4cc(Cl)cc(Cl)c4)C3(Cl)Cl)ccc2Cl)c(F)c1]

Isolated as a white foam (0.029 g, 17%).

trans-tert-Butyl (4-(2-chloro-5-(2,2-dichloro-3-(3,5-dichlorophenyl)cyclopropane-1-carboxamido)benzamido)-2-fluorophenyl)(methyl)carbamate (F603)

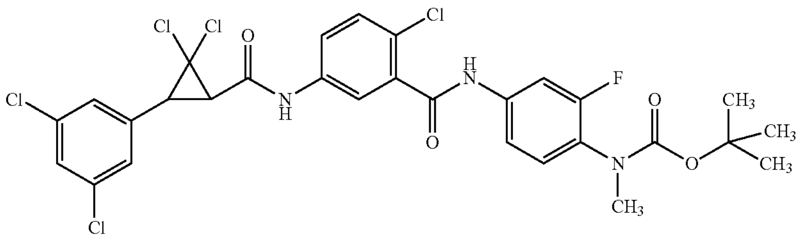 [SMILES: CN(C(=O)OC(C)(C)C)c1ccc(NC(=O)c2cc(NC(=O)C3C(c4cc(Cl)cc(Cl)c4)C3(Cl)Cl)ccc2Cl)cc1F]

Isolated as a white foam (0.090 g, 60.3%)

trans-tert-Butyl (3-(2-chloro-5-(2,2-dichloro-3-(3,5-dichlorophenyl)cyclopropane-1-carboxamido)benzamido)phenyl)carbamate (F604)

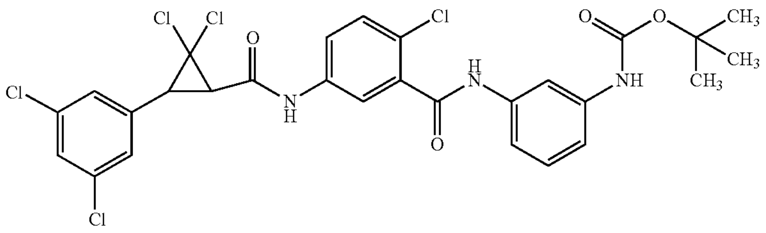 [SMILES: CC(C)(C)OC(=O)Nc1cccc(NC(=O)c2cc(NC(=O)C3C(c4cc(Cl)cc(Cl)c4)C3(Cl)Cl)ccc2Cl)c1]

Isolated as a colorless glass (0.091 g, 68%).

trans-tert-Butyl (3-(2-chloro-5-(2,2-dichloro-3-(3,5-dichlorophenyl)cyclopropane-1-carboxamido)benzamido)phenyl)(methyl) carbamate (F605)

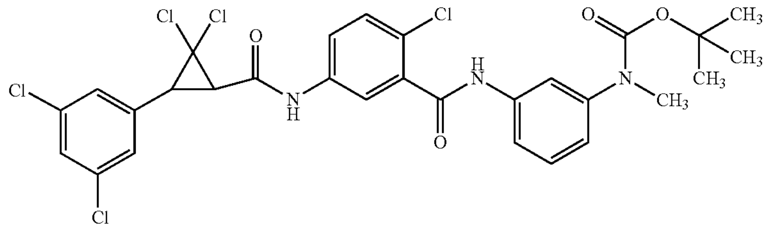 [SMILES: CN(C(=O)OC(C)(C)C)c1cccc(NC(=O)c2cc(NC(=O)C3C(c4cc(Cl)cc(Cl)c4)C3(Cl)Cl)ccc2Cl)c1]

Isolated as a colorless glass (0.074 g, 54%).

trans-tert-Butyl (5-(2-chloro-5-(2,2-dichloro-3-(3,5-dichlorophenyl)cyclopropane-1-carboxamido)benzamido)-2-methoxyphenyl)carbamate (F608)

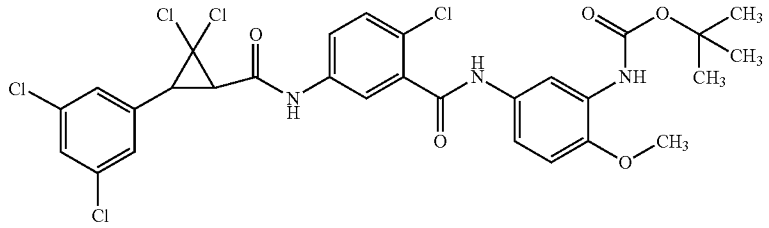 [SMILES: COc1ccc(NC(=O)c2cc(NC(=O)C3C(c4cc(Cl)cc(Cl)c4)C3(Cl)Cl)ccc2Cl)cc1NC(=O)OC(C)(C)C]

Isolated as a pink solid (0.121 g, 87%).

trans-tert-Butyl (5-(2-chloro-5-(2,2-dichloro-3-(3,5-dichlorophenyl)cyclopropane-1-carboxamido)benzamido)-2-methoxyphenyl)(methyl)carbamate (F609)

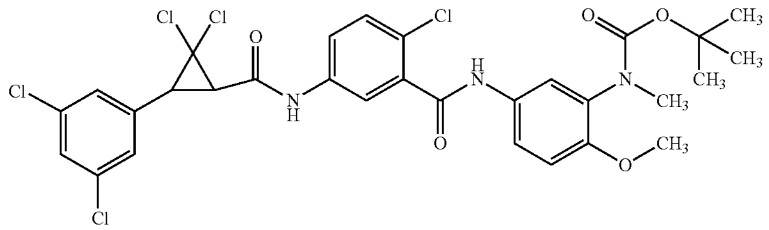 [SMILES: COc1ccc(NC(=O)c2cc(NC(=O)C3C(c4cc(Cl)cc(Cl)c4)C3(Cl)Cl)ccc2Cl)cc1N(C)C(=O)OC(C)(C)C]

Isolated as an orange solid (0.122 g, 86%).

trans-2-Chloro-5-(2,2-dichloro-3-(3,5-dichlorophenyl)cyclopropane-1-carboxamido)-N-(5-(methylthio)-1H-1,2,4-triazol-3-yl)benzamide (F184)

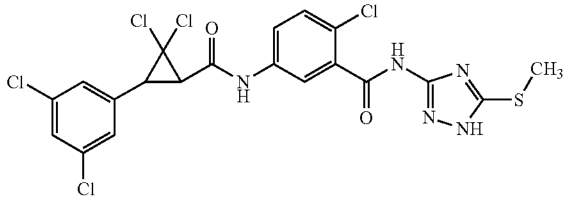 [SMILES: CSc1nc(NC(=O)c2cc(NC(=O)C3C(c4cc(Cl)cc(Cl)c4)C3(Cl)Cl)ccc2Cl)n[nH]1]

Isolated as an off-white solid (0.082 g, 59%)

trans-2-Chloro-5-(2,2-dichloro-3-(3,5-dichlorophenyl)cyclopropane-1-carboxamido)-N-(4-(thiazol-2-yl)phenyl)benzamide (F461)

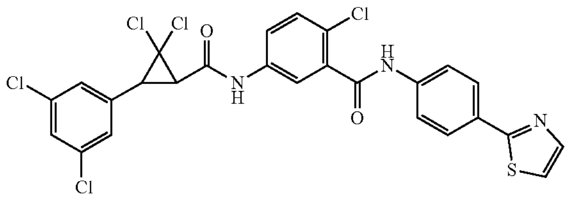 [SMILES: O=C(Nc1ccc(-c2nccs2)cc1)c1cc(NC(=O)C2C(c3cc(Cl)cc(Cl)c3)C2(Cl)Cl)ccc1Cl]

Isolated as an off-white foam (0.085 g, 59.4%).

trans-2-Chloro-5-(2,2-dichloro-3-(3,5-dichlorophenyl)cyclopropane-1-carboxamido)-N-(4-(p-tolyl)thiazol-2-yl)benzamide (PF136)

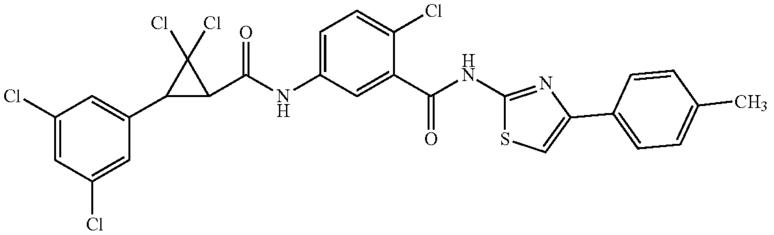 [SMILES: Cc1ccc(-c2csc(NC(=O)c3cc(NC(=O)C4C(c5cc(Cl)cc(Cl)c5)C4(Cl)Cl)ccc3Cl)n2)cc1]

Isolated as an off-white solid (0.087 g, 56.7%).

trans-tert-Butyl (4-(2-chloro-5-(2,2-dichloro-3-(3,5-dichlorophenyl)cyclopropane-1-carboxamido)benzamido)-2-methylphenyl)(methyl)carbamate (F618)

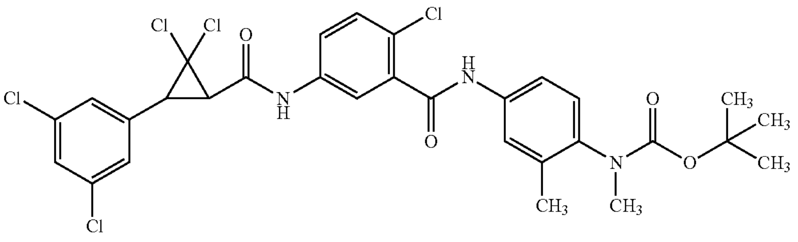 [SMILES: Cc1cc(NC(=O)c2cc(NC(=O)C3C(c4cc(Cl)cc(Cl)c4)C3(Cl)Cl)ccc2Cl)ccc1N(C)C(=O)OC(C)(C)C]

Isolated as an off-white foam (0.041 g, 43%).

trans-tert-Butyl (5-(2-chloro-5-(2,2-dichloro-3-(3,5-dichlorophenyl)cyclopropane-1-carboxamido)benzamido)-2-methylphenyl)(methyl)carbamate (F619)

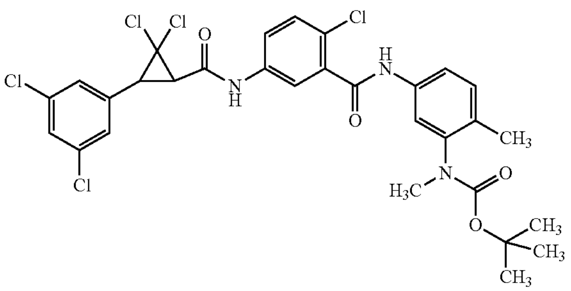 [SMILES: Cc1ccc(NC(=O)c2cc(NC(=O)C3C(c4cc(Cl)cc(Cl)c4)C3(Cl)Cl)ccc2Cl)cc1N(C)C(=O)OC(C)(C)C]

Isolated as an off-white foam (0.064 g, 75%).

trans-tert-Butyl (5-(2-chloro-5-(2,2-dichloro-3-(3,5-dichlorophenyl)cyclopropane-1-carboxamido)benzamido)-2-methylphenyl)carbamate (F620)

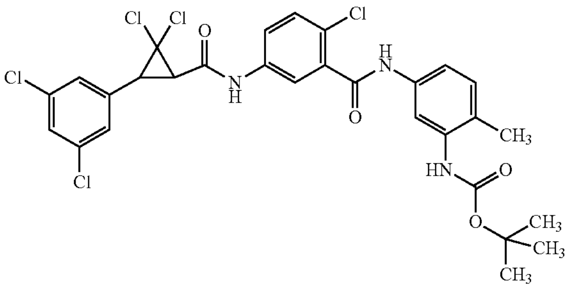 [SMILES: Cc1ccc(NC(=O)c2cc(NC(=O)C3C(c4cc(Cl)cc(Cl)c4)C3(Cl)Cl)ccc2Cl)cc1NC(=O)OC(C)(C)C]

Isolated as an off-white foam (0.104 g, 52%).

5-(trans)-2-Bromo-2-chloro-3-(3,5-dichlorophenyl)cyclopropanecarboxamido)-2-chloro-N-(4-fluorophenyl)-N-methylbenzamide (F167)

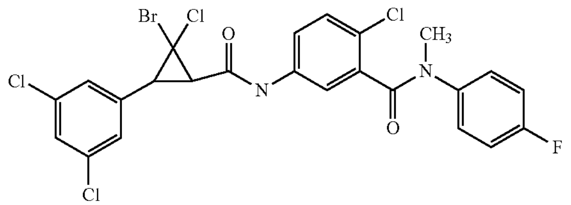 [SMILES: CN(C(=O)c1cc(NC(=O)C2C(c3cc(Cl)cc(Cl)c3)C2(Cl)Br)ccc1Cl)c1ccc(F)cc1]

Isolated as a white foam (0.128 g, 71.4%).

5-(trans)-2-Bromo-2-chloro-3-(3,5-dichlorophenyl)cyclopropane-1-carboxamido)-2-chloro-N-(2,6-difluorophenyl)benzamide (F168)

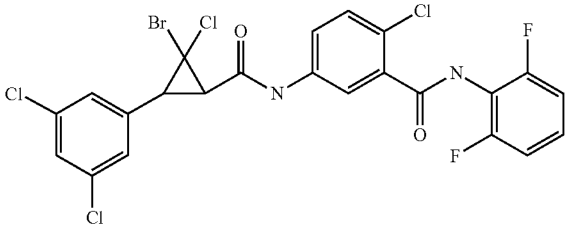 [SMILES: O=C(Nc1c(F)cccc1F)c1cc(NC(=O)C2C(c3cc(Cl)cc(Cl)c3)C2(Cl)Br)ccc1Cl]

Isolated as a white foam (0.096 g, 54.3%).

N-(5-Bromo-1H-indol-6-yl)-2-chloro-5-(trans)-2,2-dichloro-3-(3,5-dichlorophenyl)cyclopropane-1-carboxamido)benzamide (F172)

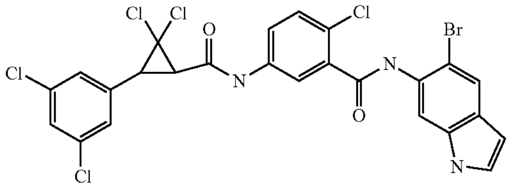 [SMILES: O=C(Nc1cc2[nH]ccc2cc1Br)c1cc(NC(=O)C2C(c3cc(Cl)cc(Cl)c3)C2(Cl)Cl)ccc1Cl]

Isolated as a white foam (0.081 g, 27.8%).

2-Chloro-5-(trans)-2,2-dichloro-3-(3,5-dichlorophenyl)cyclopropane-1-carboxamido)-N-(4-fluoro-1H-indol-6-yl)benzamide (F173)

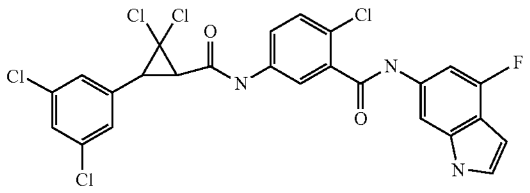 [SMILES: O=C(Nc1cc(F)c2cc[nH]c2c1)c1cc(NC(=O)C2C(c3cc(Cl)cc(Cl)c3)C2(Cl)Cl)ccc1Cl]

Isolated as a gold oil (0.114 g, 41.9%).

2-Chloro-5-(trans)-2,2-dichloro-3-(3,5-dichlorophenyl)cyclopropane-1-carboxamido)-N-(1H-pyrrolo[2,3-b]pyridin-6-yl)benzamide (F178)

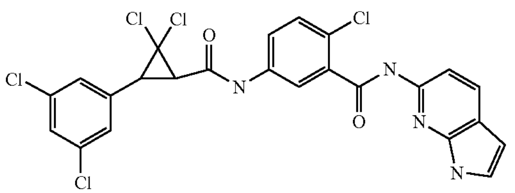 [SMILES: O=C(Nc1ccc2cc[nH]c2n1)c1cc(NC(=O)C2C(c3cc(Cl)cc(Cl)c3)C2(Cl)Cl)ccc1Cl]

Isolated as a white solid (0.121 g, 49.2%).

5-(trans)-2-Bromo-2-chloro-3-(3,5-dichlorophenyl) cyclopropane-1-carboxamido)-2-chloro-N-(2,4-difluorophenyl)benzamide (F187)

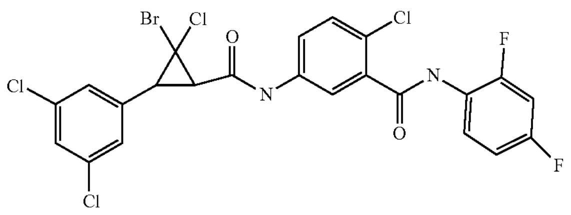 [SMILES: O=C(Nc1ccc(F)cc1F)c1cc(NC(=O)C2C(c3cc(Cl)cc(Cl)c3)C2(Cl)Br)ccc1Cl]

Isolated as a white foam (0.171 g, 63.2%).

2-Chloro-5-(trans)-2,2-dichloro-3-(3-chloro-5-cyanophenyl)cyclopropane-1-carboxamido)-N-(2,4-difluorophenyl)benzamide (F188)

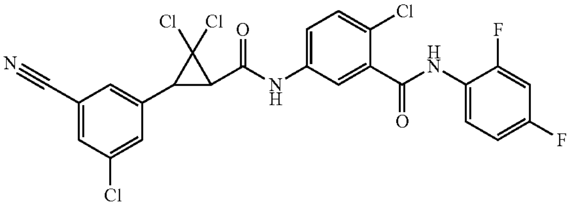 [SMILES: N#Cc1cc(Cl)cc(C2C(C(=O)Nc3ccc(Cl)c(C(=O)Nc4ccc(F)cc4F)c3)C2(Cl)Cl)c1]

Isolated as a white solid (0.105 g, 53.8%).

2-Chloro-5-(trans)-2,2-dichloro-3-(3-chloro-5-cyanophenyl)cyclopropane-1-carboxamido)-N-(4-fluorophenyl)-N-methylbenzamide (F189)

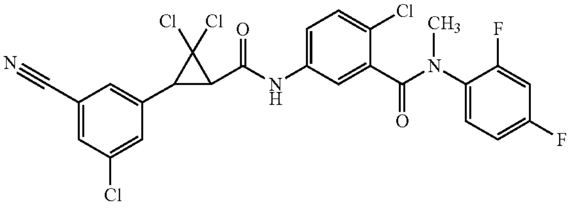 [SMILES: CN(C(=O)c1cc(NC(=O)C2C(c3cc(Cl)cc(C#N)c3)C2(Cl)Cl)ccc1Cl)c1ccc(F)cc1F]

Isolated as a gold foam (0.125 g, 64.6%).

2-Chloro-5-((2S)-2-chloro-3-(3,5-dichlorophenyl) cyclopropane-1-carboxamido)-N-(4-fluorophenyl) benzamide (F212)

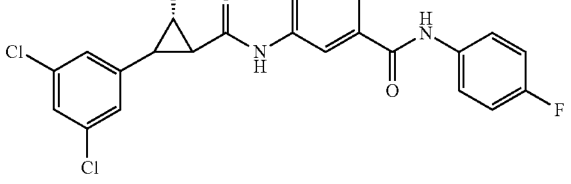

Isolated as a white solid (0.073 g, 27.7%).

2-Chloro-5-((2R)-2-chloro-3-(3,5-dichlorophenyl) cyclopropane-1-carboxamido)-N-(4-fluorophenyl) benzamide (F213)

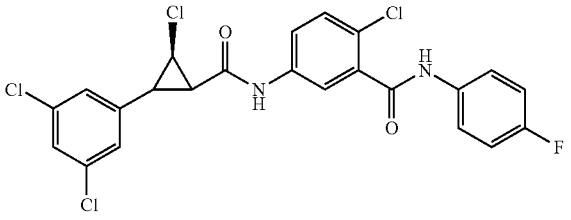 [SMILES: O=C(Nc1ccc(F)cc1)c1cc(NC(=O)C2C(c3cc(Cl)cc(Cl)c3)[C@H]2Cl)ccc1Cl]

Isolated as a white solid (0.078 g, 29.5%).

2-Chloro-5-((2S)-2-chloro-3-(3,5-dichlorophenyl) cyclopropane-1-carboxamido)-N-(2,4-difluorophenyl)benzamide (F214)

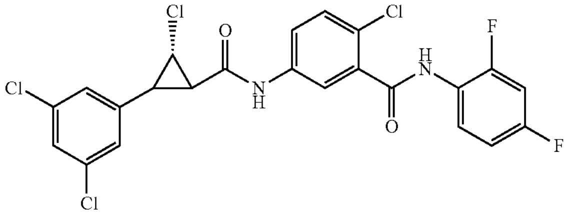 [SMILES: O=C(Nc1ccc(F)cc1F)c1cc(NC(=O)C2C(c3cc(Cl)cc(Cl)c3)[C@@H]2Cl)ccc1Cl]

Isolated as a white solid (0.097 g, 33.9%).

2-Chloro-5-((2R)-2-chloro-3-(3,5-dichlorophenyl) cyclopropane-1-carboxamido)-N-(2,4-difluorophenyl)benzamide (F215)

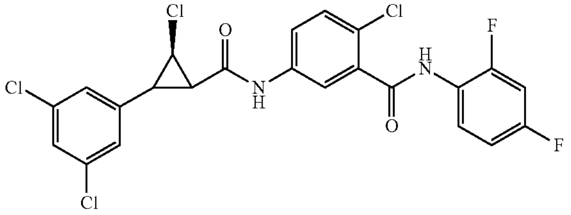 [SMILES: O=C(Nc1ccc(F)cc1F)c1cc(NC(=O)C2C(c3cc(Cl)cc(Cl)c3)[C@H]2Cl)ccc1Cl]

Isolated as a white solid (0.109 g, 38.1%).

N-(Benzo[d]thiazol-6-yl)-2-chloro-5-(trans)-2,2-dichloro-3-(3,5-dichlorophenyl)cyclopropane-1-carboxamido)benzamide (F434)

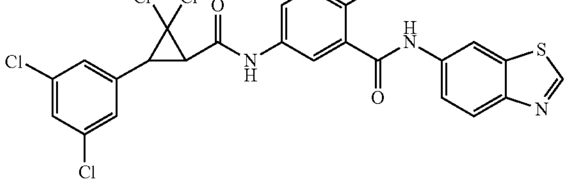

Isolated as a white foam (0.055 g, 41.7%).

2-Chloro-5-(trans)-2,2-dichloro-3-(3,5-dichlorophenyl)cyclopropane-1-carboxamido)-N-(1H-indol-5-yl) benzamide (F435)

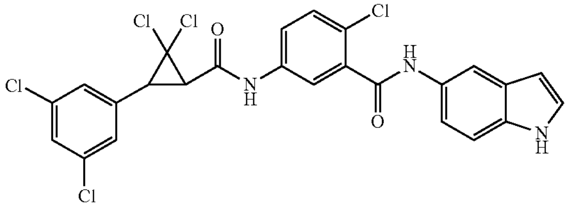 [SMILES: O=C(Nc1ccc2[nH]ccc2c1)c1cc(NC(=O)C2C(c3cc(Cl)cc(Cl)c3)C2(Cl)Cl)ccc1Cl]

Isolated as a tan foam (0.030 g, 11.7%).

2-Chloro-5-(trans)-2,2-dichloro-3-(3,5-dichlorophenyl)cyclopropane-1-carboxamido)-N-(quinolin-7-yl) benzamide (F436)

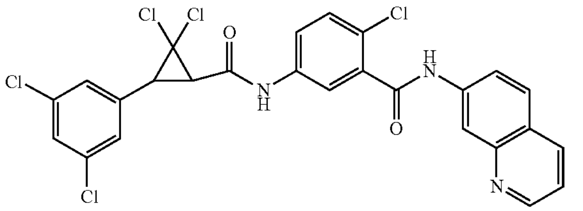 [SMILES: O=C(Nc1ccc2cccnc2c1)c1cc(NC(=O)C2C(c3cc(Cl)cc(Cl)c3)C2(Cl)Cl)ccc1Cl]

Isolated as a tan foam (0.121 g, 46.4%).

2-Chloro-5-(trans)-2,2-dichloro-3-(3,5-dichlorophenyl)cyclopropane-1-carboxamido)-N-(1H-pyrrolo[3, 2-b]pyridin-6-yl)benzamide (F437)

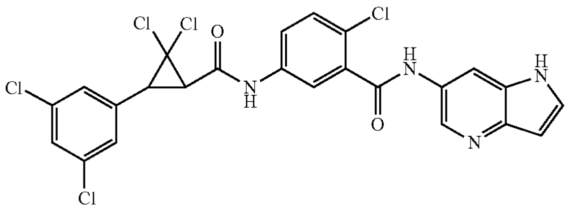 [SMILES: O=C(Nc1cnc2cc[nH]c2c1)c1cc(NC(=O)C2C(c3cc(Cl)cc(Cl)c3)C2(Cl)Cl)ccc1Cl]

Isolated as a tan foam (0.137 g, 53.5%).

2-Chloro-N-(2-chloro-1H-benzo[d]imidazol-6-yl)-5-(trans)-2,2-dichloro-3-(3,5-dichlorophenyl)cyclopropane-1-carboxamido)benzamide (F438)

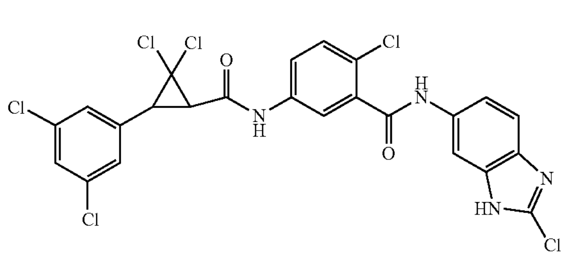 [SMILES: O=C(Nc1ccc2nc(Cl)[nH]c2c1)c1cc(NC(=O)C2C(c3cc(Cl)cc(Cl)c3)C2(Cl)Cl)ccc1Cl]

Isolated as a pale yellow solid (0.101 g, 37.2%).

N-(Benzo[d]thiazol-2-yl)-2-chloro-5-(trans)-2,2-dichloro-3-(3,5-dichlorophenyl)cyclopropane-1-carboxamido)benzamide (F441)

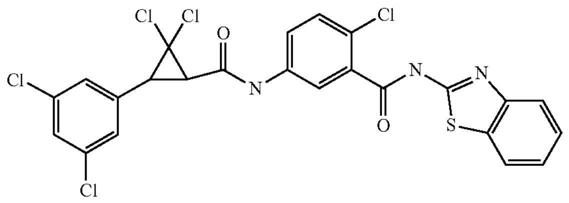 [SMILES: O=C(Nc1nc2ccccc2s1)c1cc(NC(=O)C2C(c3cc(Cl)cc(Cl)c3)C2(Cl)Cl)ccc1Cl]

Isolated as a white solid (0.038 g, 19.22%).

2-Chloro-5-(trans)-2,2-dichloro-3-(3,5-dichlorophenyl)cyclopropane-1-carboxamido)-N-(5-fluorobenzo [d]thiazol-2-yl)benzamide (F442)

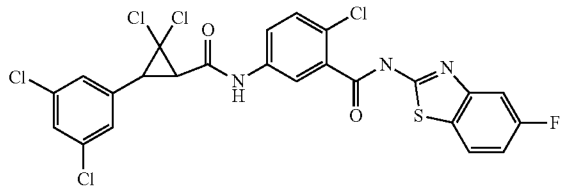 [SMILES: O=C(Nc1nc2cc(F)ccc2s1)c1cc(NC(=O)C2C(c3cc(Cl)cc(Cl)c3)C2(Cl)Cl)ccc1Cl]

Isolated as a white solid (0.109 g, 53.5%).

2-Chloro-N-(4-chlorobenzo[d]thiazol-2-yl)-5-(trans)-2,2-dichloro-3-(3,5-dichlorophenyl)cyclopropane-1-carboxamido)benzamide (F443)

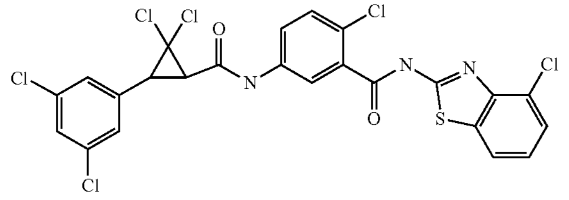 [SMILES: O=C(Nc1nc2c(Cl)cccc2s1)c1cc(NC(=O)C2C(c3cc(Cl)cc(Cl)c3)C2(Cl)Cl)ccc1Cl]

Isolated as a white solid (0.073 g, 34.9%).

2-Chloro-5-(trans)-2,2-dichloro-3-(3,5-dichlorophenyl)cyclopropane-1-carboxamido)-N-(5,6-dichlorobenzo[d]thiazol-2-yl)benzamide (F444)

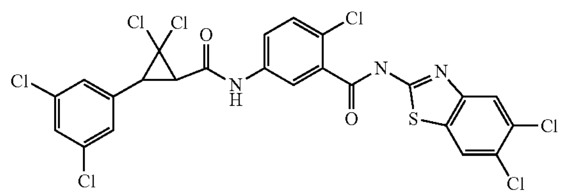 [SMILES: O=C(Nc1nc2cc(Cl)c(Cl)cc2s1)c1cc(NC(=O)C2C(c3cc(Cl)cc(Cl)c3)C2(Cl)Cl)ccc1Cl]

Isolated as a white solid (0.097 g, 43.9%).

2-Chloro-5-(trans)-2,2-dichloro-3-(3,5-dichlorophenyl)cyclopropane-1-carboxamido)-N-(6-fluorobenzo[d]thiazol-2-yl)benzamide (F445)

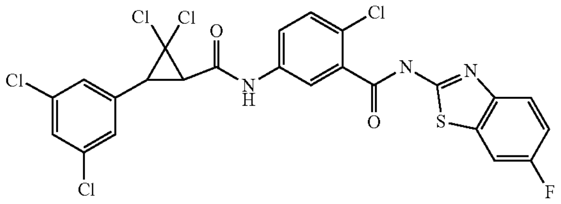 [SMILES: O=C(Nc1nc2ccc(F)cc2s1)c1cc(NC(=O)C2C(c3cc(Cl)cc(Cl)c3)C2(Cl)Cl)ccc1Cl]

Isolated as a white solid (0.122 g, 59.9%).

N-(Benzo[d]oxazol-2-yl)-2-chloro-5-(trans)-2,2-dichloro-3-(3,5-dichlorophenyl)cyclopropane-1-carboxamido)benzamide (F447)

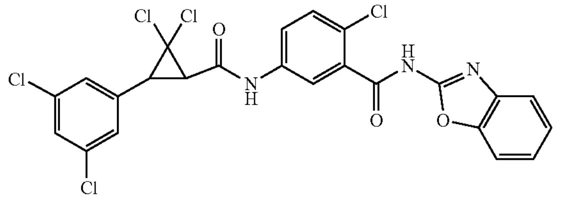 [SMILES: O=C(Nc1nc2ccccc2o1)c1cc(NC(=O)C2C(c3cc(Cl)cc(Cl)c3)C2(Cl)Cl)ccc1Cl]

Isolated as a white solid (0.032 g, 16.6%).

2-Chloro-N-(5-chlorobenzo[d]oxazol-2-yl)-5-(trans)-2,2-dichloro-3-(3,5-dichlorophenyl)cyclopropane-1-carboxamido)benzamide (F448)

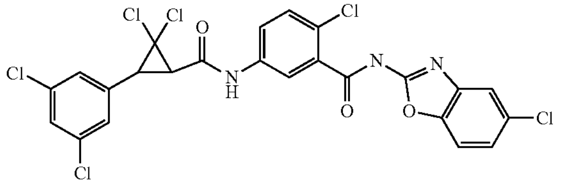 [SMILES: O=C(Nc1nc2cc(Cl)ccc2o1)c1cc(NC(=O)C2C(c3cc(Cl)cc(Cl)c3)C2(Cl)Cl)ccc1Cl]

Isolated as a white solid (0.062 g, 30.4%).

2-Chloro-5-(trans)-2,2-dichloro-3-(3,5-dichlorophenyl)cyclopropane-1-carboxamido)-N-(4-fluoro-1-methyl-1H-indazol-3-yl)benzamide (F449)

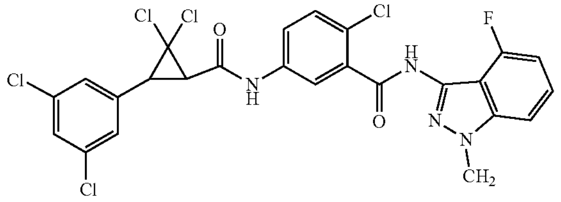 [SMILES: Cn1nc(NC(=O)c2cc(NC(=O)C3C(c4cc(Cl)cc(Cl)c4)C3(Cl)Cl)ccc2Cl)c2c(F)cccc21]

Isolated as a white foam (0.020 g, 9.9%).

N-(Benzo[d]oxazol-6-yl)-2-chloro-5-(trans)-2,2-dichloro-3-(3,5-dichlorophenyl)cyclopropane-1-carboxamido)benzamide (F450)

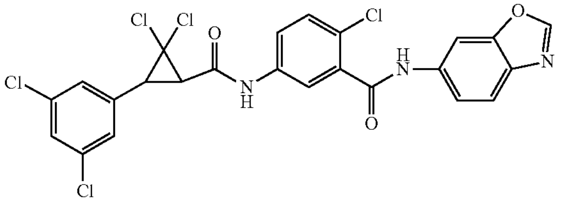 [SMILES: O=C(Nc1ccc2ncoc2c1)c1cc(NC(=O)C2C(c3cc(Cl)cc(Cl)c3)C2(Cl)Cl)ccc1Cl]

Isolated as a tan foam (0.028 g, 14.6%).

2-Chloro-5-(trans)-2,2-dichloro-3-(3,5-dichlorophenyl)cyclopropane-1-carboxamido)-N-(6-fluoro-1H-benzo[d]imidazol-2-yl)benzamide (F451)

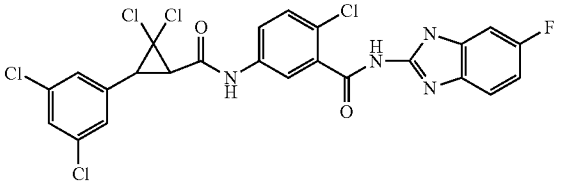 [SMILES: O=C(Nc1nc2ccc(F)cc2[nH]1)c1cc(NC(=O)C2C(c3cc(Cl)cc(Cl)c3)C2(Cl)Cl)ccc1Cl]

Isolated as a tan foam (0.073 g, 36.9%).

2-Chloro-5-(trans)-2,2-dichloro-3-(3,5-dichlorophenyl)cyclopropane-1-carboxamido)-N-(5-fluorobenzo[d]oxazol-6-yl)benzamide (F453)

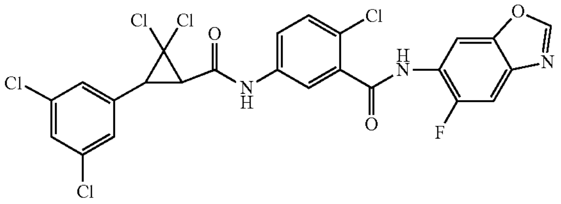 [SMILES: O=C(Nc1cc2ocnc2cc1F)c1cc(NC(=O)C2C(c3cc(Cl)cc(Cl)c3)C2(Cl)Cl)ccc1Cl]

Isolated as a clear colorless oil (0.020 g, 10.1%).

2-Chloro-5-(trans)-2,2-dichloro-3-(3,5-dichlorophenyl)cyclopropane-1-carboxamido)-N-(2-methyl-1H-indol-5-yl)benzamide (F454)

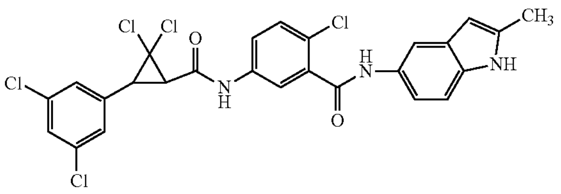 [SMILES: Cc1cc2cc(NC(=O)c3cc(NC(=O)C4C(c5cc(Cl)cc(Cl)c5)C4(Cl)Cl)ccc3Cl)ccc2[nH]1]

Isolated as a yellow foam (0.142 g, 72.3%).

2-Chloro-5-(trans)-2,2-dichloro-3-(3,5-dichlorophenyl)cyclopropane-1-carboxamido)-N-(2-methylbenzo[d]thiazol-5-yl)benzamide (F455)

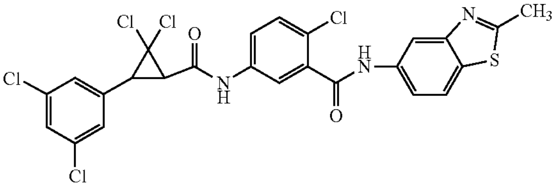 [SMILES: Cc1nc2cc(NC(=O)c3cc(NC(=O)C4C(c5cc(Cl)cc(Cl)c5)C4(Cl)Cl)ccc3Cl)ccc2s1]

Isolated as a white solid (0.063 g, 31.1%).

N-(1H-Benzo[d]imidazol-5-yl)-2-chloro-5-(trans)-2,2-dichloro-3-(3,5-dichlorophenyl)cyclopropane-1-carboxamido)benzamide (F456)

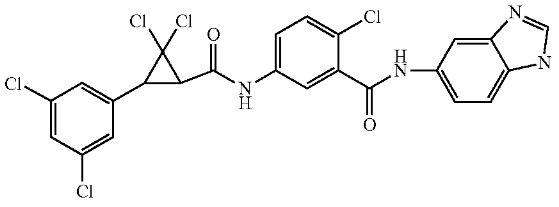 [SMILES: O=C(Nc1ccc2[nH]cnc2c1)c1cc(NC(=O)C2C(c3cc(Cl)cc(Cl)c3)C2(Cl)Cl)ccc1Cl]

Isolated as a white solid (0.037 g, 19.3%).

2-Chloro-5-(trans)-2,2-dichloro-3-(3,5-dichlorophenyl)cyclopropane-1-carboxamido)-N-(1-methyl-1H-indol-5-yl)benzamide (F457)

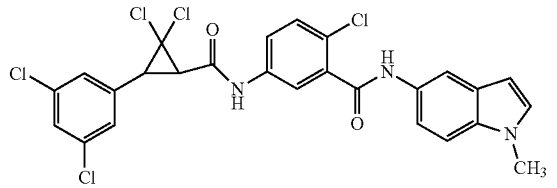 [SMILES: Cn1ccc2cc(NC(=O)c3cc(NC(=O)C4C(c5cc(Cl)cc(Cl)c5)C4(Cl)Cl)ccc3Cl)ccc21]

Isolated as a tan solid (0.133 g, 67.7%).

2-Chloro-5-(trans)-2,2-dichloro-3-(3,5-dichlorophenyl)cyclopropane-1-carboxamido)-N-(imidazo[1,2-a]pyridin-6-yl)benzamide (F475)

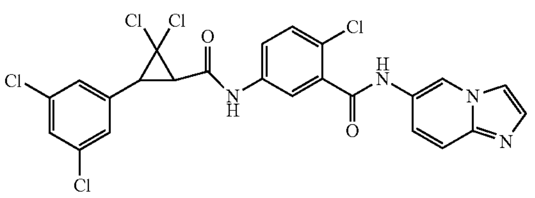 [SMILES: O=C(Nc1ccc2nccn2c1)c1cc(NC(=O)C2C(c3cc(Cl)cc(Cl)c3)C2(Cl)Cl)ccc1Cl]

Isolated as a pale blue solid (0.057 g, 43.2%).

trans-N-(3-(3-Amino-6-cyano-1H-indazole-1-carbonyl)-4-chlorophenyl)-2,2-dichloro-3-(3,5-dichlorophenyl)cyclopropane-1-carboxamide (F493)

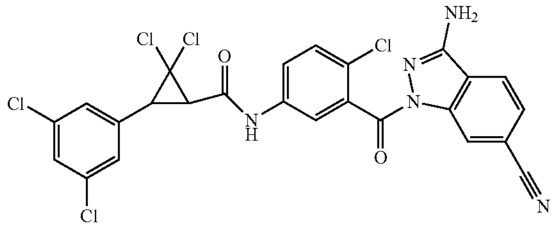 [SMILES: N#Cc1ccc2c(N)nn(C(=O)c3cc(NC(=O)C4C(c5cc(Cl)cc(Cl)c5)C4(Cl)Cl)ccc3Cl)c2c1]

Isolated as a tan solid (0.066 g, 47.9%).

The following compounds were prepared in like manner to the procedure outlined in Example 17:

trans-N-(4-(1H-Imidazol-1-yl)phenyl)-2-chloro-5-(2,2-dichloro-3-(3,5-dichlorophenyl)cyclopropane-1-carboxamido)benzamide (PF56)

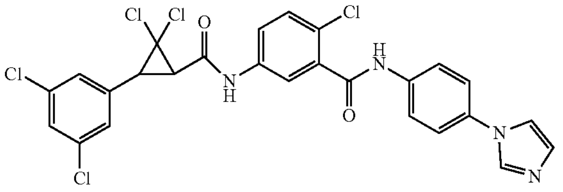 [SMILES: O=C(Nc1ccc(-n2ccnc2)cc1)c1cc(NC(=O)C2C(c3cc(Cl)cc(Cl)c3)C2(Cl)Cl)ccc1Cl]

Isolated as an off-white foam/glass (0.066 g, 49.8%)

trans-N-(4-(1H-1,2,4-Triazol-1-yl)phenyl)-2-chloro-5-(2,2-dichloro-3-(3,5-dichlorophenyl)cyclopropane-1-carboxamido)benzamide (PF57)

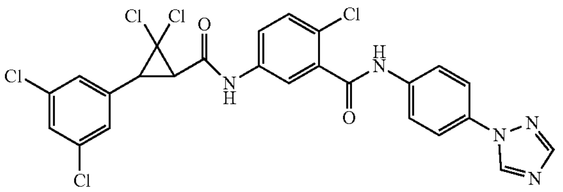 [SMILES: O=C(Nc1ccc(-n2cncn2)cc1)c1cc(NC(=O)C2C(c3cc(Cl)cc(Cl)c3)C2(Cl)Cl)ccc1Cl]

Isolated as a pink foam (0.080 g, 60.2%).

trans-2-Chloro-5-(2,2-dichloro-3-(3,5-dichlorophenyl)cyclopropane-1-carboxamido)-N-(2,6-diethyl-4-(perfluorobutan-2-yl)phenyl)benzamide (PF59)

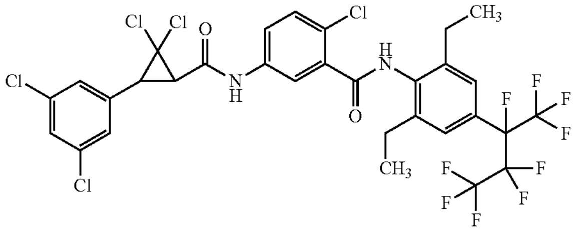 [SMILES: CCc1cc(C(F)(C(F)(F)F)C(F)(F)C(F)(F)F)cc(CC)c1NC(=O)c1cc(NC(=O)C2C(c3cc(Cl)cc(Cl)c3)C2(Cl)Cl)ccc1Cl]

Isolated as an off-white solid (0.030 g, 16.8%)

trans-2-Chloro-5-(2,2-dichloro-3-(3,5-dichlorophenyl)cyclopropane-1-carboxamido)-N-(2,6-dimethyl-4-(perfluoropropan-2-yl)phenyl)benzamide (PF60)

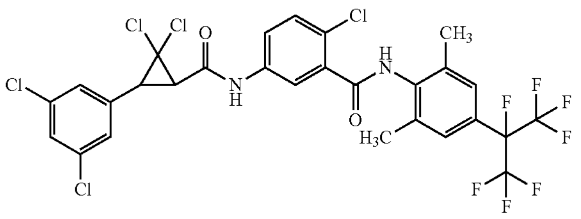 [SMILES: Cc1cc(C(F)(C(F)(F)F)C(F)(F)F)cc(C)c1NC(=O)c1cc(NC(=O)C2C(c3cc(Cl)cc(Cl)c3)C2(Cl)Cl)ccc1Cl]

Isolated as an off-white solid (0.050 g, 29.3%).

trans-2-Chloro-5-(2,2-dichloro-3-(3,5-dichlorophenyl)cyclopropane-1-carboxamido)-N-(2,6-diethyl-4-(perfluoropropan-2-yl)phenyl)benzamide (PF61)

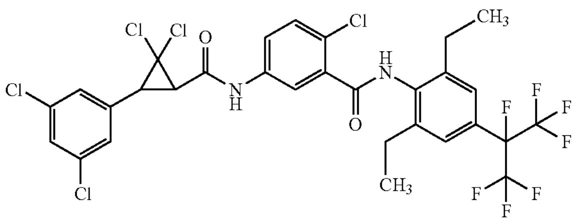 [SMILES: CCc1cc(C(F)(C(F)(F)F)C(F)(F)F)cc(CC)c1NC(=O)c1cc(NC(=O)C2C(c3cc(Cl)cc(Cl)c3)C2(Cl)Cl)ccc1Cl]

Isolated as a light brown foam/glass (0.054 g, 32.2%).

trans-2-Chloro-5-(2,2-dichloro-3-(3,5-dichlorophenyl)cyclopropane-1-carboxamido)-N-(4-(2,2,2-trifluoroethoxy)phenyl)benzamide (PF62)

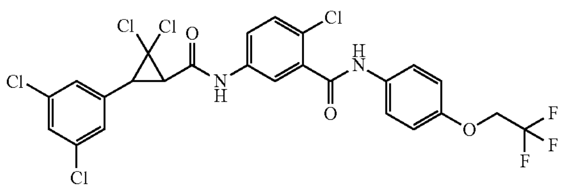 [SMILES: O=C(Nc1ccc(OCC(F)(F)F)cc1)c1cc(NC(=O)C2C(c3cc(Cl)cc(Cl)c3)C2(Cl)Cl)ccc1Cl]

Isolated as a white solid (0.074 g, 50.2%).

trans-2-Chloro-5-(2,2-dichloro-3-(3,5-dichlorophenyl)cyclopropane-1-carboxamido)-N-(3-nitrophenyl) benzamide (PF73)

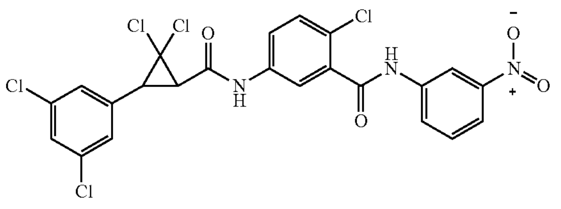 [SMILES: O=C(Nc1cccc([N+](=O)[O-])c1)c1cc(NC(=O)C2C(c3cc(Cl)cc(Cl)c3)C2(Cl)Cl)ccc1Cl]

Isolated as an off-white foam (0.035 g, 27.4%).

trans-2-Chloro-5-(2,2-dichloro-3-(3,5-dichlorophenyl)cyclopropane-1-carboxamido)-N-(2-fluoro-4-nitrophenyl)benzamide (PF74)

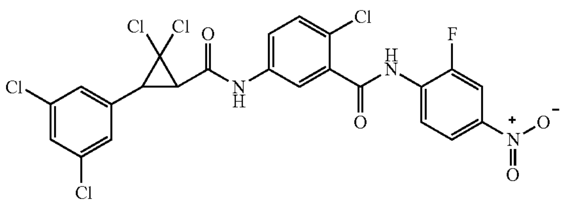 [SMILES: O=C(Nc1ccc([N+](=O)[O-])cc1F)c1cc(NC(=O)C2C(c3cc(Cl)cc(Cl)c3)C2(Cl)Cl)ccc1Cl]

Isolated as a pale yellow glass (0.016 g, 11.5%).

trans-2-Chloro-5-(2,2-dichloro-3-(3,5-dichlorophenyl)cyclopropane-1-carboxamido)-N-(2-methyl-4-nitrophenyl)benzamide (PF75)

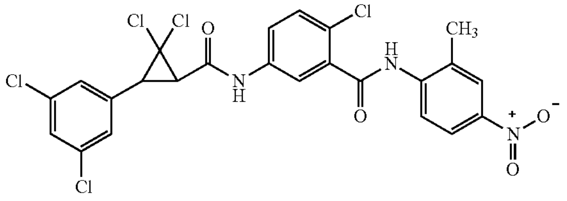 [SMILES: Cc1cc([N+](=O)[O-])ccc1NC(=O)c1cc(NC(=O)C2C(c3cc(Cl)cc(Cl)c3)C2(Cl)Cl)ccc1Cl]

Isolated as a yellow foam (0.028 g, 20.24%).

trans-N-(4-(4H-1,2,4-Triazol-4-yl)phenyl)-2-chloro-5-(2,2-dichloro-3-(3,5-dichlorophenyl)cyclopropane-1-carboxamido)benzamide (PF102)

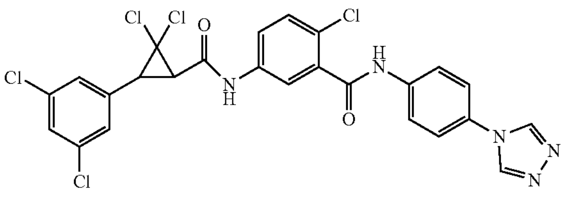 [SMILES: O=C(Nc1ccc(-n2cnnc2)cc1)c1cc(NC(=O)C2C(c3cc(Cl)cc(Cl)c3)C2(Cl)Cl)ccc1Cl]

Isolated as an off-white solid (0.050 g, 35.7%).

trans-2-Chloro-5-(2,2-dichloro-3-(3,5-dichlorophenyl)cyclopropane-1-carboxamido)-N-(1H-tetrazol-5-yl)benzamide (PF130)

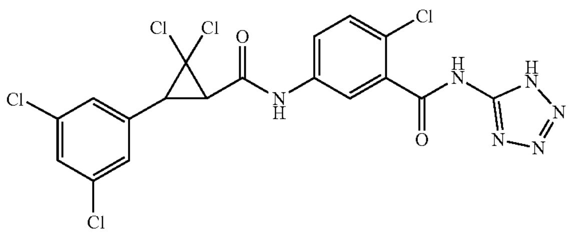 [SMILES: O=C(Nc1nnn[nH]1)c1cc(NC(=O)C2C(c3cc(Cl)cc(Cl)c3)C2(Cl)Cl)ccc1Cl]

Isolated as a white solid (0.027 g, 8.81%).

The following compounds were prepared in like manner to the procedure outlined in Example 18:

trans-2-Chloro-5-(2,2-dichloro-3-(3,5-dichlorophenyl)cyclopropane-1-carboxamido)-N-(4-((2,2,2-trifluoroethyl)thio)phenyl)benzamide (PF10)

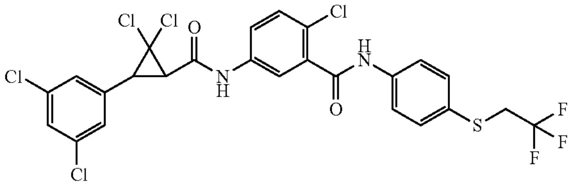 [SMILES: O=C(Nc1ccc(SCC(F)(F)F)cc1)c1cc(NC(=O)C2C(c3cc(Cl)cc(Cl)c3)C2(Cl)Cl)ccc1Cl]

Isolated as a tan solid (0.294 g, 69%).

trans-2-Chloro-5-(2,2-dichloro-3-(3,5-dichlorophenyl)cyclopropane-1-carboxamido)-N-(4-((trifluoromethyl)thio)phenyl)benzamide (PF11)

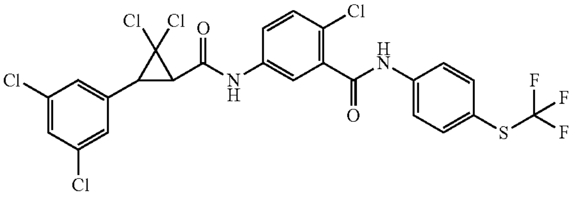 [SMILES: O=C(Nc1ccc(SC(F)(F)F)cc1)c1cc(NC(=O)C2C(c3cc(Cl)cc(Cl)c3)C2(Cl)Cl)ccc1Cl]

Isolated as a tan solid (0.273 g, 66%).

trans-tert-Butyl-(4-(2-chloro-5-(2,2-dichloro-3-(3,5-dichlorophenyl)cyclopropane-1-carboxamido)benzamido)phenyl)(methyl)carbamate (PF12)

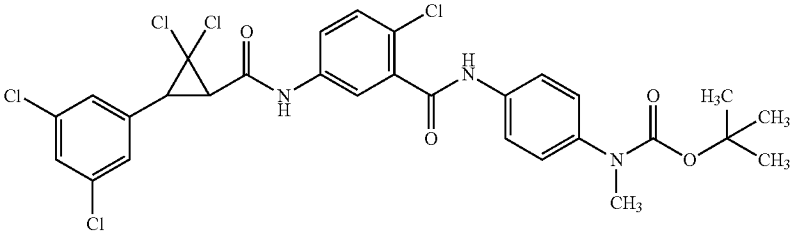 [SMILES: CN(C(=O)OC(C)(C)C)c1ccc(NC(=O)c2cc(NC(=O)C3C(c4cc(Cl)cc(Cl)c4)C3(Cl)Cl)ccc2Cl)cc1]

Isolated as a white solid (0.278 g, 64%).

trans-tert-Butyl-(4-(2-chloro-5-(2,2-dichloro-3-(3,5-dichlorophenyl)cyclopropane-1-carboxamido)benzamido)phenyl)carbamate (PF13)

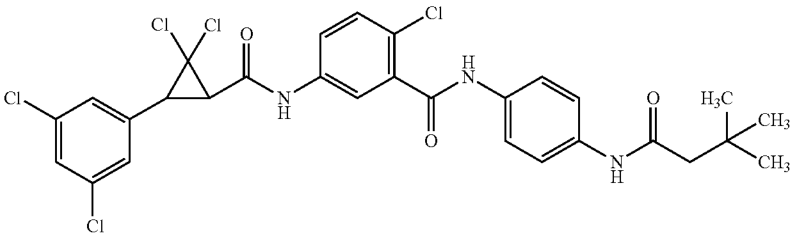 [SMILES: CC(C)(C)CC(=O)Nc1ccc(NC(=O)c2cc(NC(=O)C3C(c4cc(Cl)cc(Cl)c4)C3(Cl)Cl)ccc2Cl)cc1]

Isolated as a white foam (0.273 g, 45%).

trans-2-Chloro-5-(2,2-dichloro-3-(3,5-dichlorophenyl)cyclopropane-1-carboxamido)-N-(4-(N-methylacetamido)phenyl)benzamide (PF14)

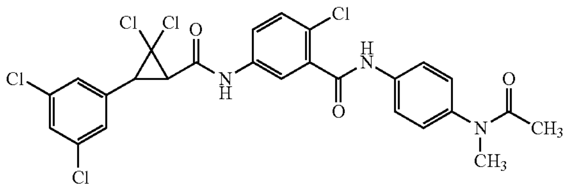 [SMILES: CC(=O)N(C)c1ccc(NC(=O)c2cc(NC(=O)C3C(c4cc(Cl)cc(Cl)c4)C3(Cl)Cl)ccc2Cl)cc1]

Isolated as a white solid (0.098 g, 74%).

trans-2-Chloro-5-(2,2-dichloro-3-(3,5-dichlorophenyl)cyclopropane-1-carboxamido)-N-(4-ethynylphenyl)benzamide (PF15)

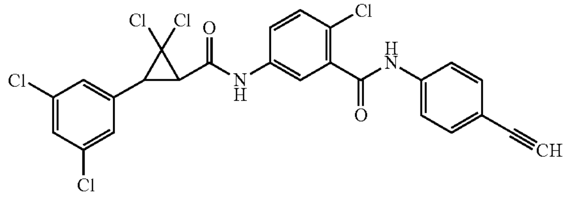 [SMILES: C#Cc1ccc(NC(=O)c2cc(NC(=O)C3C(c4cc(Cl)cc(Cl)c4)C3(Cl)Cl)ccc2Cl)cc1]

Isolated as a tan solid (0.095 g, 78%).

trans-2-Chloro-5-(2,2-dichloro-3-(3,5-dichlorophenyl)cyclopropane-1-carboxamido)-N-(4-vinylphenyl)benzamide (PF16)

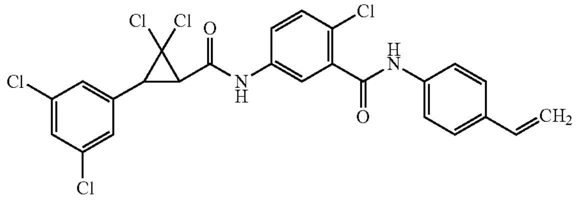 [SMILES: C=Cc1ccc(NC(=O)c2cc(NC(=O)C3C(c4cc(Cl)cc(Cl)c4)C3(Cl)Cl)ccc2Cl)cc1]

Isolated as a tan solid (0.094 g, 77%).

trans-2-Chloro-5-(2,2-dichloro-3-(3,5-dichlorophenyl)cyclopropane-1-carboxamido)-N-(4-fluoro-2,6-dimethylphenyl)benzamide (PF43)

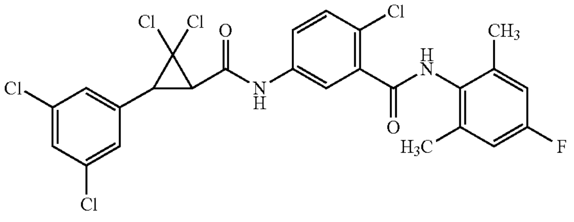 [SMILES: Cc1cc(F)cc(C)c1NC(=O)c1cc(NC(=O)C2C(c3cc(Cl)cc(Cl)c3)C2(Cl)Cl)ccc1Cl]

Isolated as a light brown solid (0.034 g, 28%).

trans-2-Chloro-5-(2,2-dichloro-3-(3,5-dichlorophenyl)cyclopropane-1-carboxamido)-N-(4-fluoro-3-methylphenyl)benzamide (PF44)

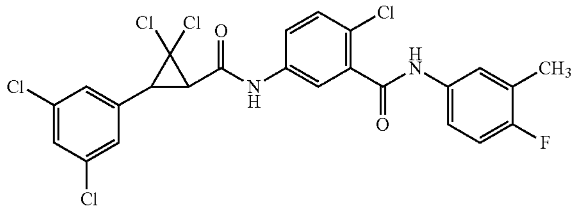 [SMILES: Cc1cc(NC(=O)c2cc(NC(=O)C3C(c4cc(Cl)cc(Cl)c4)C3(Cl)Cl)ccc2Cl)ccc1F]

Isolated as a light brown solid (0.074 g, 62%).

trans-2-Chloro-5-(2,2-dichloro-3-(3,5-dichlorophenyl)cyclopropane-1-carboxamido)-N-(4-thiocyanatophenyl)benzamide (PF45)

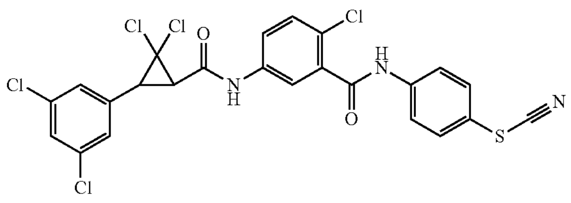 [SMILES: N#CSc1ccc(NC(=O)c2cc(NC(=O)C3C(c4cc(Cl)cc(Cl)c4)C3(Cl)Cl)ccc2Cl)cc1]

Isolated as an orange foam (0.032 g, 26%).

trans-2-Chloro-5-(2,2-dichloro-3-(3,5-dichlorophenyl)cyclopropane-1-carboxamido)-N-(3,5-dichlorophenyl)benzamide (PF76)

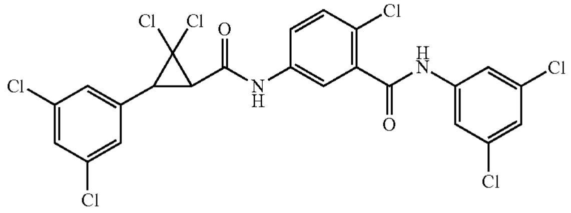 [SMILES: O=C(Nc1cc(Cl)cc(Cl)c1)c1cc(NC(=O)C2C(c3cc(Cl)cc(Cl)c3)C2(Cl)Cl)ccc1Cl]

Isolated as a light brown foam (0.025 g, 20%).

trans-2-Chloro-5-(2,2-dichloro-3-(3,5-dichlorophenyl)cyclopropane-1-carboxamido)-N-(4-(dimethylamino)phenyl)benzamide (F171)

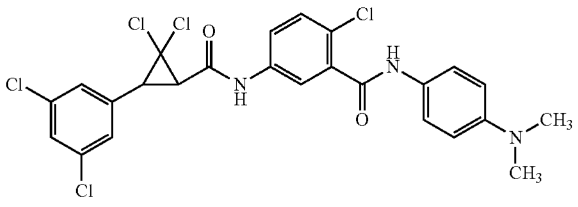 [SMILES: CN(C)c1ccc(NC(=O)c2cc(NC(=O)C3C(c4cc(Cl)cc(Cl)c4)C3(Cl)Cl)ccc2Cl)cc1]

Isolated as a yellow solid (0.045 g, 37%).

The following compounds were prepared in like manner to the procedure outlined in Example 23:

5-Amino-N-(4-fluorophenyl)-2-vinylbenzamide (C247)

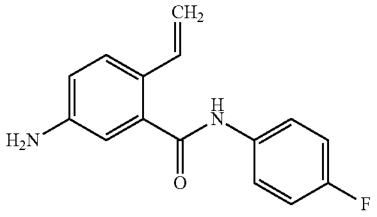

Isolated as a yellow solid (0.053 g, 89%): $^1$H NMR (400 MHz, $CDCl_3$) δ 7.62 (s, 1H), 7.53 (dd, J=8.9, 4.7 Hz, 2H), 7.37 (d, J=8.4 Hz, 1H), 7.02 (t, J=8.6 Hz, 2H), 6.92 (dd, J=17.4, 10.9 Hz, 1H), 6.77 (d, J=2.1 Hz, 1H), 6.70 (dd, J=8.3, 2.2 Hz, 1H), 5.56 (d, J=17.4 Hz, 1H), 5.18 (d, J=11.1 Hz, 1H), 3.86 (s, 2H); IR (thin film) 3279, 1651 $cm^{-1}$; ESIMS m/z 257 ($[M+H]^+$).

5-Amino-2-chloro-N-(2-cyano-4-fluorophenyl)benzamide (C248)

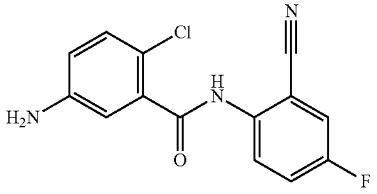

Isolated as a white solid (0.272 g, 100%): $^1$H NMR (400 MHz, DMSO-$d_6$) δ 10.66 (s, 1H), 7.89 (dd, J=8.5, 3.0 Hz, 1H), 7.72-7.50 (m, 2H), 7.15 (d, J=8.6 Hz, 1H), 6.76 (d, J=2.8 Hz, 1H), 6.67 (dd, J=8.6, 2.8 Hz, 1H), 5.53 (s, 2H); $^{19}$F NMR (376 MHz, DMSO-$d_6$) δ −114.72; ESIMS m/z 290 ($[M+H]^+$).

5-Amino-2-chloro-N-(2,4-trifluorophenyl)benzamide (C249)

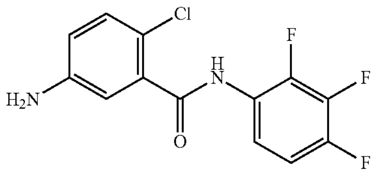

Isolated as a white solid (0.257 g, 94%): $^1$H NMR (400 MHz, DMSO-$d_6$) δ 10.40 (s, 1H), 7.51-7.43 (m, 1H), 7.34 (tdd, J=9.9, 8.1, 2.2 Hz, 1H), 7.14 (d, J=8.6 Hz, 1H), 6.74 (d, J=2.7 Hz, 1H), 6.66 (dd, J=8.6, 2.8 Hz, 1H), 5.50 (s, 2H); $^{19}$F NMR (376 MHz, DMSO-$d_6$) δ −138.77 (dd, J=22.1, 4.5 Hz), −140.67 (dd, J=21.1, 4.5 Hz), −160.53 (t, J=21.6 Hz); ESIMS m/z 301 ($[M+H]^+$).

5-Amino-2-chloro-N-(2-cyanophenyl)benzamide (C250)

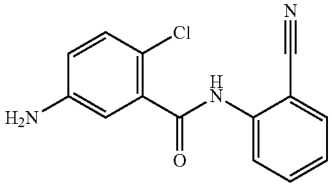

Isolated as a white solid (0.224 g, 83%): $^1$H NMR (400 MHz, DMSO-$d_6$) δ 10.66 (s, 1H), 7.86 (dd, J=7.8, 1.5 Hz, 1H), 7.73 (td, J=7.8, 1.6 Hz, 1H), 7.55 (d, J=8.2 Hz, 1H), 7.42 (td, J=7.6, 1.2 Hz, 1H), 7.15 (d, J=8.6 Hz, 1H), 6.77 (d, J=2.7 Hz, 1H), 6.67 (dd, J=8.6, 2.8 Hz, 1H), 5.53 (s, 2H); IR (thin film) 3361, 2227, 1672, 1520 $cm^{-1}$; ESIMS m/z 272 ($[M+H]^+$).

5-Amino-2-chloro-N-(4-(trifluoromethyl)thiazol-2-yl)benzamide (C251)

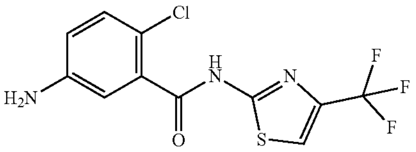

Isolated as a brown solid (0.135 g, 84%): $^1$H NMR (300 MHz, DMSO-$d_6$) δ 13.01 (s, 1H), 8.05 (dd, J=2.7, 1.6 Hz, 1H), 7.16 (d, J=8.6 Hz, 1H), 6.74 (d, J=2.7 Hz, 1H), 6.69 (dd, J=8.6, 2.8 Hz, 1H), 5.54 (s, 2H); IR (thin film) 1663, 1544, 1236 $cm^{-1}$; ESIMS m/z 322 ($[M+H]^+$).

5-Amino-2-chloro-N-(5-chloropyridin-2-yl)benzamide (C252)

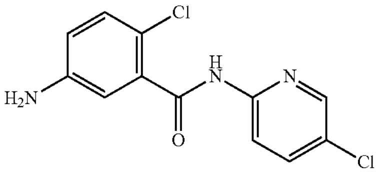

Isolated as a yellow solid (0.083 g, 60%): $^1$H NMR (300 MHz, DMSO-$d_6$) δ 11.13 (s, 1H), 8.34 (dd, J=5.4, 0.6 Hz, 1H), 8.25 (d, J=1.9 Hz, 1H), 7.31 (dd, J=5.4, 1.9 Hz, 1H), 7.11 (d, J=8.6 Hz, 1H), 6.69 (d, J=2.7 Hz, 1H), 6.64 (dd, J=8.6, 2.7 Hz, 1H), 5.47 (s, 2H); IR (thin film) 3359, 3223, 1675, 1565 $cm^{-1}$; ESIMS m/z 282 ($[M+H]^+$).

5-Amino-2-chloro-N-(4-iodophenyl)benzamide (C253)

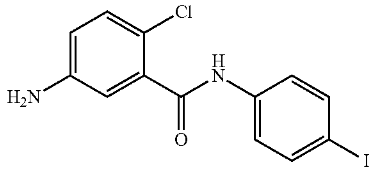

Isolated as a red solid (0.302 g, 99%): $^{1}$H NMR (300 MHz, DMSO-$d_6$) δ 10.48 (s, 1H), 7.73-7.63 (m, 2H), 7.61-7.51 (m, 2H), 7.13 (d, J=8.5 Hz, 1H), 6.71-6.61 (m, 2H), 5.48 (s, 2H); IR (thin film) 3357, 1662, 1597, 1524 $cm^{-1}$; ESIMS m/z 373 ($[M+H]^+$).

5-Amino-2-chloro-N-(3-iodophenyl)benzamide (C254)

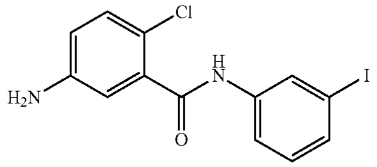

Isolated as a dark brown solid (0.320 g, 100%): $^{1}$H NMR (300 MHz, DMSO-$d_6$) δ 10.48 (s, 1H), 8.22 (t, J=1.9 Hz, 1H), 7.71-7.58 (m, 1H), 7.46 (ddd, J=7.8, 1.7, 0.9 Hz, 1H), 7.18-7.09 (m, 2H), 6.73-6.60 (m, 2H), 5.49 (s, 2H); IR (thin film) 3394, 3158, 1656, 1582, 1530 $cm^{-1}$; ESIMS m/z 373 ($[M+H]^+$).

5-Amino-2-chloro-N-(2-fluoro-4-iodophenyl)benzamide (C255)

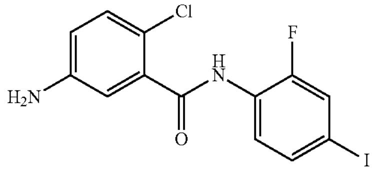

Isolated as a cream-colored solid (0.238 g, 73%): $^{1}$H NMR (400 MHz, DMSO-$d_6$) δ 10.24 (s, 1H), 7.76-7.68 (m, 1H), 7.56 (d, J=6.7 Hz, 2H), 7.12 (d, J=8.6 Hz, 1H), 6.71 (d, J=2.7 Hz, 1H), 6.64 (dd, J=8.6, 2.7 Hz, 1H), 5.47 (s, 2H); $^{19}$F NMR (376 MHz, DMSO-$d_6$) δ −119.45; ESIMS m/z 391 ($[M+H]^+$).

5-Amino-2-chloro-N-(3-fluoro-4-iodophenyl)benzamide (C256)

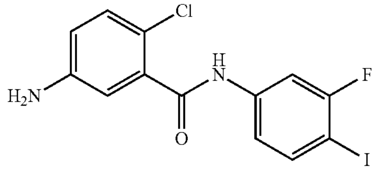 [SMILES: Nc1ccc(Cl)c(C(=O)Nc2ccc(I)c(F)c2)c1]

Isolated as a light brown foam (0.267 g, 93%): $^{1}$H NMR (400 MHz, DMSO-$d_6$) δ 10.68 (s, 1H), 7.82-7.71 (m, 2H), 7.31 (dd, J=8.6, 2.3 Hz, 1H), 7.14 (d, J=8.5 Hz, 1H), 6.70-6.63 (m, 2H), 5.50 (s, 2H); $^{19}$F NMR (376 MHz, DMSO-$d_6$) δ −93.94; ESIMS m/z 391 ($[M+H]^+$).

5-Amino-2-chloro-N-(2-cyano-4-fluorophenyl)-N-methylbenzamide (C257)

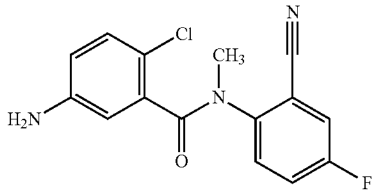 [SMILES: CN(C(=O)c1cc(N)ccc1Cl)c1ccc(F)cc1C#N]

Isolated as a yellow foam (0.200 g, 99%): $^{1}$H NMR (400 MHz, DMSO-$d_6$) δ rotamers 8.01 (dd, J=8.4, 2.9 Hz, 1H), 7.79-7.63 (m, 2H), 7.28 (d, J=8.7 Hz, 0.4H), 7.17 (d, J=8.5 Hz, 0.6H), 6.68-6.61 (m, 1H), 6.41 (dd, J=8.7, 2.7 Hz, 1H), 5.58 (s, 0.8H), 5.37 (s, 1.2H), 3.16 (d, J=1.5 Hz, 3H); $^{19}$F NMR (376 MHz, DMSO-$d_6$) δ rotamers −112.21, −112.23; ESIMS m/z 304 ($[M+H]^+$).

3-Amino-N-(2-cyano-4-fluorophenyl)benzamide (C258)

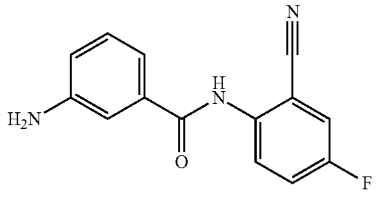 [SMILES: N#Cc1cc(F)ccc1NC(=O)c1cccc(N)c1]

Isolated as a white solid (0.252 g, 91%): $^{1}$H NMR (400 MHz, DMSO-$d_6$) δ 10.40 (s, 1H), 7.88 (dd, J=8.4, 3.0 Hz, 1H), 7.73-7.50 (m, 2H), 7.25-7.04 (m, 3H), 6.79 (ddd, J=7.9, 2.4, 1.1 Hz, 1H), 5.37 (s, 2H); $^{19}$F NMR (376 MHz, DMSO-$d_6$) δ −115.13; ESIMS m/z 256 ($[M+H]^+$).

3-Amino-N-(4-fluoro-2-methylphenyl)benzamide (C259)

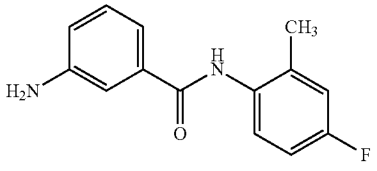 [SMILES: Cc1cc(F)ccc1NC(=O)c1cccc(N)c1]

Isolated as a purple solid (0.297 g, 95%): $^{1}H$ NMR (400 MHz, DMSO-$d_6$) δ 9.66 (s, 1H), 7.31 (dd, J=8.7, 5.6 Hz, 1H), 7.17-7.07 (m, 4H), 7.03 (td, J=8.6, 3.1 Hz, 1H), 6.74 (dd, J=7.6, 2.1 Hz, 1H), 5.30 (s, 2H), 2.21 (s, 3H); $^{19}F$ NMR (376 MHz, DMSO-$d_6$) δ −117.38; ESIMS m/z 245 ([M+H]$^+$).

3-Amino-N-(4-fluorophenyl)-N-methylbenzamide (C260)

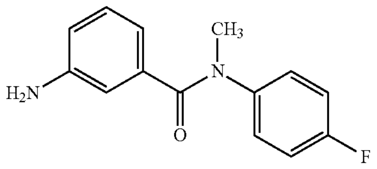 [SMILES: CN(C(=O)c1cccc(N)c1)c1ccc(F)cc1]

Isolated as a green solid (0.267 g, 86%): $^{1}H$ NMR (400 MHz, DMSO-$d_6$) δ 7.24-7.14 (m, 2H), 7.16-7.05 (m, 2H), 6.81 (t, J=7.8 Hz, 1H), 6.54 (t, J=1.9 Hz, 1H), 6.47-6.40 (m, 1H), 6.26 (d, J=7.5 Hz, 1H), 5.10 (s, 2H), 3.30 (s, 3H); $^{19}F$ NMR (376 MHz, DMSO-$d_6$) δ −116.06; ESIMS m/z 245 ([M+H]$^+$).

3-Amino-N-(2-chloro-4-fluorophenyl)benzamide (C261)

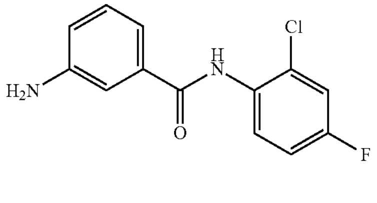 [SMILES: Nc1cccc(C(=O)Nc2ccc(F)cc2Cl)c1]

Isolated as a light brown solid (0.193 g, 65%): $^{1}H$ NMR (400 MHz, DMSO-$d_6$) δ 9.82 (s, 1H), 7.62-7.51 (m, 2H), 7.26 (ddt, J=9.8, 7.3, 2.0 Hz, 1H), 7.18-7.08 (m, 3H), 6.80-6.72 (m, 1H), 5.33 (s, 2H); $^{19}F$ NMR (376 MHz, DMSO-$d_6$) δ −114.44; ESIMS m/z 265 ([M+H]$^+$).

5-Amino-2-chloro-N-(4-fluorophenyl)-N-(prop-2-yn-1-yl)benzamide (C262)

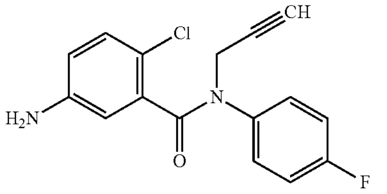 [SMILES: C#CCN(C(=O)c1cc(N)ccc1Cl)c1ccc(F)cc1]

Isolated as a brown solid (0.262 g, 100%): $^{1}H$ NMR (400 MHz, DMSO-$d_6$) δ 7.35-7.23 (m, 2H), 7.13 (t, J=8.6 Hz, 2H), 6.87 (d, J=8.3 Hz, 1H), 6.43-6.34 (m, 2H), 5.26 (s, 2H), 4.61 (d, J=2.3 Hz, 2H), 3.24 (t, J=2.3 Hz, 1H). $^{19}F$ NMR (376 MHz, DMSO-$d_6$) δ −114.03; ESIMS m/z 303 ([M+H]$^+$).

5-Amino-2-chloro-N-(2,4-difluorophenyl)-N-(prop-2-yn-1-yl)benzamide (C263)

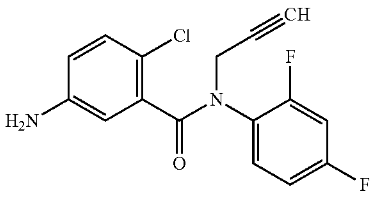 [SMILES: C#CCN(C(=O)c1cc(N)ccc1Cl)c1ccc(F)cc1F]

Isolated as a brown solid (0.249 g, 96%): $^{1}H$ NMR (400 MHz, DMSO-$d_6$) δ rotamers 7.67-7.40 (m, 1H), 7.38-7.13 (m, 1H), 7.11-6.80 (m, 2H), 6.75-6.25 (m, 2H), 5.32 (s, 2H), 4.76-4.35 (m, 2H), 3.24 (s, 1H). $^{19}F$ NMR (376 MHz, DMSO-$d_6$) δ −108.53, −114.00; ESIMS m/z 321 ([M+H]$^+$).

5-Amino-2-chloro-N-(4-(oxazol-2-yl)phenyl)benzamide (C264)

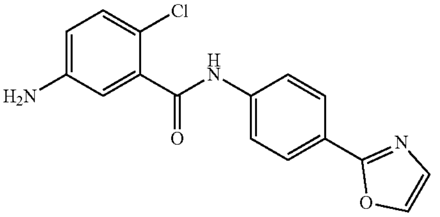

Isolated as a brown solid (0.185 g, 86%): mp 227° C. (dec); $^{1}H$ NMR (400 MHz, DMSO-$d_6$) δ 10.66 (s, 1H), 8.19 (d, J=0.8 Hz, 1H), 8.02-7.92 (m, 2H), 7.93-7.85 (m, 2H), 7.36 (d, J=0.8 Hz, 1H), 7.15 (d, J=8.6 Hz, 1H), 6.72 (d, J=2.7 Hz, 1H), 6.67 (dd, J=8.6, 2.8 Hz, 1H), 5.50 (s, 2H); ESIMS m/z 312 ([M−H]$^-$).

5-Amino-2-chloro-N-(3-fluoro-4-(trifluoromethyl) phenyl)benzamide (C265)

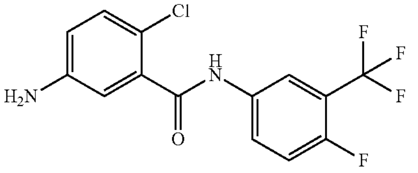

Isolated as a pale brown solid (0.149 g, 49%): $^1$H NMR (400 MHz, Acetone-$d_6$) δ 9.67 (s, 1H), 8.31 (d, J=6.3 Hz, 1H), 8.10 (d, J=8.3 Hz, 1H), 7.43 (t, J=9.6 Hz, 1H), 7.14 (d, J=8.6 Hz, 1H), 6.90-6.85 (m, 1H), 6.77 (d, J=8.8 Hz, 1H), 5.04 (s, 2H); $^{19}$F NMR (376 MHz, Acetone-$d_6$) δ −62.06 (d, J=13.0 Hz), −122.83 (q, J=13.2 Hz); ESIMS m/z 331 ([M−H]$^-$).

5-Amino-2-chloro-N-(3-(trifluoromethyl)phenyl) benzamide (C266)

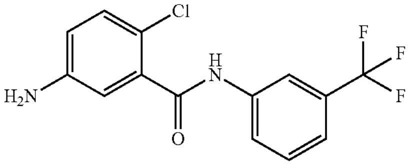

Isolated as an orange gum (0.270 g, 74%): $^1$H NMR (400 MHz, Acetone-$d_6$) δ 9.65 (s, 1H), 8.32 (s, 1H), 8.03 (d, J=8.0 Hz, 1H), 7.61 (t, J=8.0 Hz, 1H), 7.49-7.44 (m, 1H), 7.14 (d, J=8.6 Hz, 1H), 6.88 (d, J=2.8 Hz, 1H), 6.77 (dd, J=8.6, 2.8 Hz, 1H), 5.04 (s, 2H); $^{19}$F NMR (376 MHz, Acetone-$d_6$) δ −63.28; ESIMS m/z 315 ([M−H]$^-$).

5-Amino-2-chloro-N-(5-(trifluoromethyl)-1H-pyrazol-3-yl)benzamide (C267)

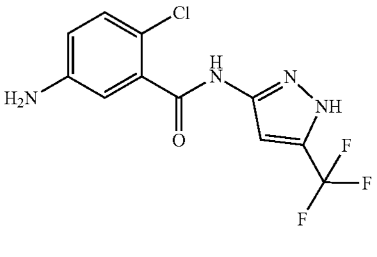

Isolated as a pale yellow/brown solid (0.104 g, 64%): $^1$H NMR (400 MHz, DMSO-$d_6$) δ 13.47 (s, 1H), 11.36 (s, 1H), 7.16 (d, J=8.5 Hz, 1H), 6.72 (d, J=2.7 Hz, 1H), 6.68 (dd, J=8.6, 2.8 Hz, 1H), 6.39 (s, 1H), 5.54 (s, 2H); $^{19}$F NMR (376 MHz, DMSO-$d_6$) δ rotamers −57.81, −60.90, −61.08; ESIMS m/z 303 ([M−H]$^-$).

N-(4-(1H-Pyrazol-1-yl)phenyl)-5-amino-2-chlorobenzamide (C268)

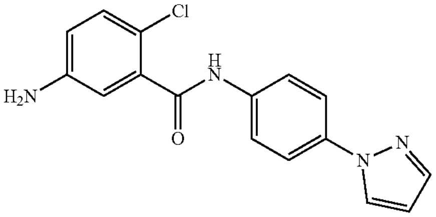

Isolated as a pale yellow/brown solid (0.231 g, 86%): mp 50-81° C.; $^1$H NMR (400 MHz, DMSO-$d_6$) δ 10.52 (d, J=10.7 Hz, 1H), 8.44 (d, J=2.5 Hz, 1H), 7.88-7.76 (m, 4H), 7.72 (d, J=1.8 Hz, 1H), 7.14 (d, J=8.6 Hz, 1H), 6.72 (d, J=2.8 Hz, 1H), 6.66 (dd, J=8.6, 2.7 Hz, 1H), 6.53 (t, J=2.1 Hz, 1H), 5.49 (s, 2H); ESIMS m/z 311 ([M−H]$^-$).

The following compounds were prepared in like manner to the procedure outlined in Example 24:

5-Amino-2-ethyl-N-(4-fluorophenyl)benzamide (C269)

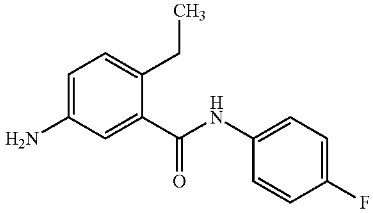

Isolated as a white solid (0.107 g, 75%): mp 129-131° C.; $^1$H NMR (400 MHz, DMSO) δ 10.27 (s, 1H), 7.75 (dd, J=9.1, 5.1 Hz, 2H), 7.20-7.11 (m, 2H), 6.95 (d, J=8.3 Hz, 1H), 6.65-6.54 (m, 2H), 5.09 (s, 2H), 2.54 (dd, J=14.9, 7.4 Hz, 2H), 1.07 (t, J=7.5 Hz, 3H); ESIMS m/z 259 ([M+H]$^+$).

tert-Butyl (4-(3-aminobenzamido)-3-methylphenyl) carbamate (C270)

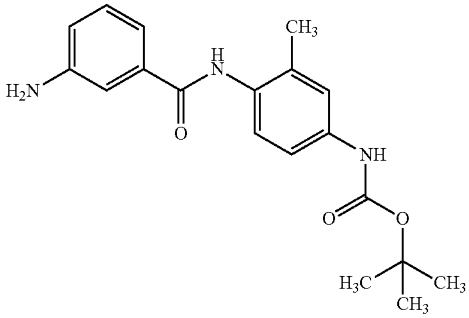 [SMILES: Cc1cc(NC(=O)OC(C)(C)C)ccc1NC(=O)c1cccc(N)c1]

Isolated as a light brown foam (10 g, 91%): mp 143-161° C.; $^1$H NMR (400 MHz, DMSO-$d_6$) δ 9.96 (d, J=2.9 Hz, 1H), 9.32 (s, 1H), 7.95 (d, J=7.3 Hz, 1H), 7.85 (s, 1H), 7.59 (td, J=7.8, 1.9 Hz, 1H), 7.55-7.47 (m, 1H), 7.43-7.37 (m, 1H), 7.27 (dd, J=8.5, 2.4 Hz, 1H), 7.17 (d, J=8.5 Hz, 1H), 2.17 (s, 3H), 1.48 (s, 9H) ($NH_2$ not observed); ESIMS m/z 342 ($[M+H]^+$).

The following compounds were prepared in like manner to the procedure outlined in Example 28:

N-(4-Acetamido-2-fluorophenyl)-2-chloro-5-nitrobenzamide (C271)

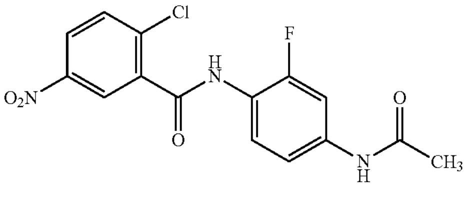 [SMILES: CC(=O)Nc1ccc(NC(=O)c2cc([N+](=O)[O-])ccc2Cl)c(F)c1]

Isolated as a white solid (0.780 g, 83%): $^1$H NMR (400 MHz, DMSO-$d_6$) δ 10.46 (s, 1H), 10.18 (s, 1H), 8.43 (d, J=2.8 Hz, 1H), 8.33 (dd, J=8.8, 2.8 Hz, 1H), 7.88 (d, J=8.8 Hz, 1H), 7.80-7.68 (m, 2H), 7.33-7.23 (m, 1H), 2.06 (s, 3H); $^{19}$F NMR (376 MHz, DMSO-$d_6$) δ −121.16; ESIMS m/z 352 ($[M+H]^+$).

2-Chloro-N-(2-cyano-4-fluorophenyl)-5-nitrobenzamide (C272)

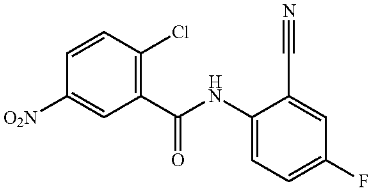 [SMILES: N#Cc1cc(F)ccc1NC(=O)c1cc([N+](=O)[O-])ccc1Cl]

Isolated as a white solid (0.439 g, 55%): $^1$H NMR (400 MHz, DMSO-$d_6$) δ 11.06 (s, 1H), 8.52 (d, J=2.8 Hz, 1H), 8.38 (dd, J=8.8, 2.8 Hz, 1H), 8.02-7.86 (m, 2H), 7.83-7.61 (m, 2H); $^{19}$F NMR (376 MHz, DMSO-$d_6$) δ −113.90; ESIMS m/z 320 ($[M+H]^+$).

2-Chloro-5-nitro-N-(2,3,4-trifluorophenyl)benzamide (C273)

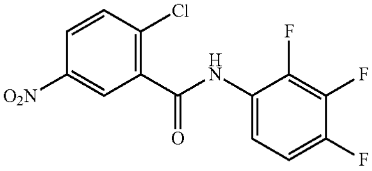 [SMILES: O=C(Nc1ccc(F)c(F)c1F)c1cc([N+](=O)[O-])ccc1Cl]

Isolated as a white solid (0.562 g, 69%): $^1$H NMR (400 MHz, DMSO-$d_6$) δ 10.80 (s, 1H), 8.50 (d, J=2.8 Hz, 1H), 8.36 (dd, J=8.8, 2.8 Hz, 1H), 7.90 (d, J=8.8 Hz, 1H), 7.68 (dtt, J=12.3, 5.4, 2.6 Hz, 1H), 7.40 (tdd, J=10.2, 8.2, 2.3 Hz, 1H); $^{19}$F NMR (376 MHz, DMSO-$d_6$) δ −138.38 (dd, J=22.2, 4.4 Hz), −141.64 (dd, J=21.1, 4.4 Hz), −160.33 (t, J=21.6 Hz); ESIMS m/z 329 ($[M-H]^-$).

2-Chloro-N-(2-cyanophenyl)-5-nitrobenzamide (C274)

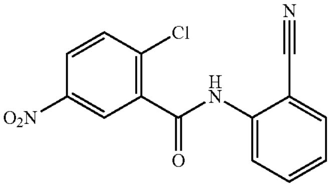

Isolated as a white solid (0.315 g, 42%): $^1$H NMR (400 MHz, DMSO-$d_6$) δ 11.06 (s, 1H), 8.50 (d, J=2.8 Hz, 1H), 8.38 (dd, J=8.8, 2.8 Hz, 1H), 7.99-7.87 (m, 2H), 7.86-7.69 (m, 2H), 7.48 (td, J=7.6, 1.3 Hz, 1H); $^{13}$C NMR (101 MHz, DMSO-$d_6$) δ 163.44, 146.08, 139.08, 137.21, 136.72, 133.95, 133.38, 131.48, 126.81, 126.43, 126.06, 123.98, 116.55, 108.30; ESIMS m/z 302 ($[M+H]^+$).

N-(4-Acetamido-2-methylphenyl)-2-chloro-5-nitrobenzamide (C275)

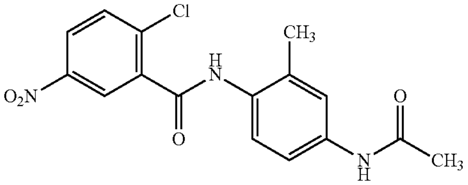

Isolated as a white foam (0.365 g, 53%): $^1$H NMR (400 MHz, DMSO-$d_6$) δ 10.09 (s, 1H), 9.92 (s, 1H), 8.45 (d, J=2.7 Hz, 1H), 8.33 (dd, J=8.8, 2.8 Hz, 1H), 7.89 (d, J=8.8 Hz, 1H), 7.49 (d, J=2.2 Hz, 1H), 7.46-7.36 (m, 2H), 2.26 (s, 3H), 2.04 (s, 3H); IR (thin film) 3245, 1656, 1540, 1352 $cm^{-1}$; ESIMS m/z 346 ($[M-H]^-$).

tert-Butyl (4-chloro-3-((4-fluorophenyl)carbamoyl)phenyl)(methyl)carbamate (C276)

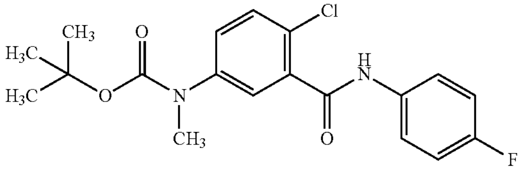 [SMILES: CN(C(=O)OC(C)(C)C)c1ccc(Cl)c(C(=O)Nc2ccc(F)cc2)c1]

Isolated as a white foam (0.371 g, 93%): $^1$H NMR (400 MHz, $CDCl_3$) δ 7.95 (s, 1H), 7.68 (d, J=2.6 Hz, 1H), 7.65-7.58 (m, 2H), 7.40 (d, J=8.7 Hz, 1H), 7.35 (dd, J=8.7, 2.6 Hz, 1H), 7.13-7.03 (m, 2H), 3.28 (s, 3H), 1.48 (s, 9H); $^{19}$F NMR (376 MHz, $CDCl_3$) δ −117.08; ESIMS m/z 377 ($[M-H]^-$).

2-Chloro-N-(4-iodophenyl)-5-nitrobenzamide (C277)

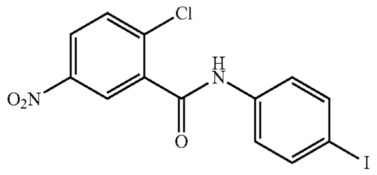 [SMILES: O=C(Nc1ccc(I)cc1)c1cc([N+](=O)[O-])ccc1Cl]

Isolated as a white solid (0.330 g, 55%): $^{1}H$ NMR (400 MHz, DMSO-$d_6$) δ 10.81 (s, 1H), 8.49 (d, J=2.8 Hz, 1H), 8.34 (dd, J=8.8, 2.8 Hz, 1H), 7.90 (d, J=8.8 Hz, 1H), 7.78-7.68 (m, 2H), 7.60-7.48 (m, 2H); IR (thin film) 3234, 1657, 1521 $cm^{-1}$; ESIMS m/z 403 ($[M+H]^+$).

2-Chloro-N-(3-iodophenyl)-5-nitrobenzamide (C278)

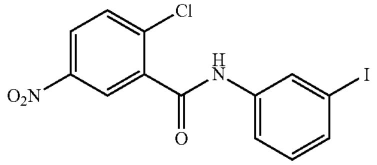 [SMILES: O=C(Nc1cccc(I)c1)c1cc([N+](=O)[O-])ccc1Cl]

Isolated as a white solid (0.340 g, 57%): $^{1}H$ NMR (400 MHz, DMSO-$d_6$) δ 10.81 (s, 1H), 8.50 (d, J=2.7 Hz, 1H), 8.35 (dd, J=8.8, 2.8 Hz, 1H), 8.21 (t, J=1.9 Hz, 1H), 7.90 (d, J=8.8 Hz, 1H), 7.63 (ddd, J=8.1, 2.0, 0.9 Hz, 1H), 7.52 (ddd, J=7.9, 1.7, 0.9 Hz, 1H), 7.19 (t, J=8.0 Hz, 1H); IR (thin film) 3257, 1653, 1521 $cm^{-1}$; ESIMS m/z 403 ($[M+H]^+$).

2-Chloro-N-(2-fluoro-4-iodophenyl)-5-nitrobenzamide (C279)

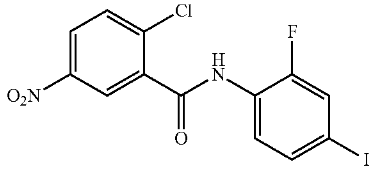 [SMILES: O=C(Nc1ccc(I)cc1F)c1cc([N+](=O)[O-])ccc1Cl]

Isolated as a white solid (0.370 g, 59%): $^{1}H$ NMR (300 MHz, DMSO-$d_6$) δ 10.66 (s, 1H), 8.47 (d, J=2.7 Hz, 1H), 8.34 (dd, J=8.8, 2.8 Hz, 1H), 7.88 (d, J=8.8 Hz, 1H), 7.77 (t, J=8.3 Hz, 2H), 7.62 (d, J=8.4 Hz, 1H); $^{19}F$ NMR (376 MHz, DMSO-$d_6$) δ −120.54; ESIMS m/z 421 ($[M+H]^+$).

2-Chloro-N-(3-fluoro-4-iodophenyl)-5-nitrobenzamide (C280)

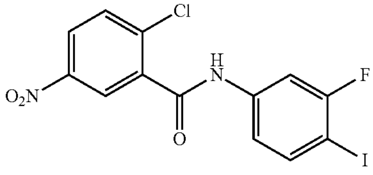

Isolated as a white solid (0.320 g, 51%): $^{1}H$ NMR (300 MHz, DMSO-$d_6$) δ 11.02 (s, 1H), 8.52 (d, J=2.7 Hz, 1H), 8.36 (dd, J=8.8, 2.8 Hz, 1H), 7.91 (d, J=8.8 Hz, 1H), 7.84 (dd, J=8.6, 7.4 Hz, 1H), 7.74 (dd, J=10.5, 2.3 Hz, 1H), 7.29 (dd, J=8.7, 2.3 Hz, 1H); $^{19}F$ NMR (376 MHz, DMSO-$d_6$) δ −93.69; ESIMS m/z 421 ($[M+H]^+$).

tert-Butyl (4-(2-chloro-5-nitrobenzamido)-3-methylphenyl)(methyl)carbamate (C281)

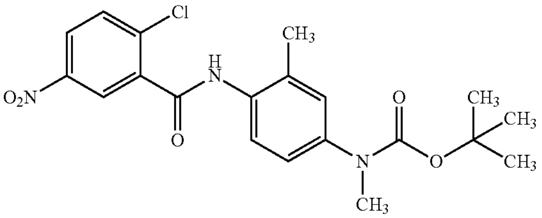 [SMILES: Cc1cc(N(C)C(=O)OC(C)(C)C)ccc1NC(=O)c1cc([N+](=O)[O-])ccc1Cl]

Isolated as a yellow foam (2.27 g, 60%): $^{1}H$ NMR (300 MHz, DMSO-$d_6$) δ 10.16 (s, 1H), 8.49 (d, J=2.7 Hz, 1H), 8.34 (dd, J=8.8, 2.8 Hz, 1H), 7.90 (d, J=8.8 Hz, 1H), 7.46 (d, J=8.4 Hz, 1H), 7.19 (d, J=2.5 Hz, 1H), 7.14 (dd, J=8.4, 2.6 Hz, 1H), 3.18 (s, 3H), 2.28 (s, 3H), 1.41 (s, 9H); ESIMS m/z 418 ($[M-H]^-$).

tert-Butyl (4-(2-chloro-5-nitrobenzamido)-3-methylphenyl)carbamate (C282)

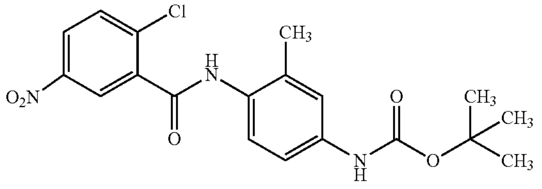 [SMILES: Cc1cc(NC(=O)OC(C)(C)C)ccc1NC(=O)c1cc([N+](=O)[O-])ccc1Cl]

Isolated as a yellow solid (2.19 g, 67%): mp 195-200° C.; $^{1}H$ NMR (300 MHz, DMSO-$d_6$) δ 10.06 (s, 1H), 9.34 (s, 1H), 8.45 (d, J=2.7 Hz, 1H), 8.33 (dd, J=8.8, 2.8 Hz, 1H), 7.88 (d, J=8.8 Hz, 1H), 7.43-7.24 (m, 3H), 2.24 (s, 3H), 1.48 (s, 9H); ESIMS m/z 404 ($[M-H]^-$).

N-(2-Cyano-4-fluorophenyl)-3-nitrobenzamide (C283)

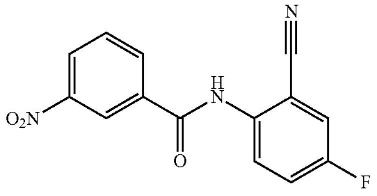 [SMILES: N#Cc1cc(F)ccc1NC(=O)c1cccc([N+](=O)[O-])c1]

Isolated as a white solid (0.316 g, 62%): $^1$H NMR (400 MHz, DMSO-$d_6$) δ 11.02 (s, 1H), 8.84 (t, J=2.0 Hz, 1H), 8.58-8.31 (m, 2H), 8.03-7.82 (m, 2H), 7.76-7.54 (m, 2H); $^{19}$F NMR (376 MHz, DMSO-$d_6$) δ −114.32; ESIMS m/z 286 ($[M+H]^+$).

N-(4-Fluoro-2-methylphenyl)-3-nitrobenzamide (C284)

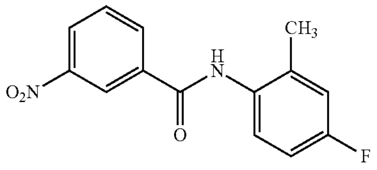 [SMILES: Cc1cc(F)ccc1NC(=O)c1cccc([N+](=O)[O-])c1]

Isolated as a purple solid (0.348 g, 71%): $^1$H NMR (400 MHz, DMSO-$d_6$) δ 10.29 (s, 1H), 8.80 (t, J=2.0 Hz, 1H), 8.52-8.34 (m, 2H), 7.85 (t, J=8.0 Hz, 1H), 7.36 (dd, J=8.7, 5.6 Hz, 1H), 7.18 (dd, J=9.7, 3.0 Hz, 1H), 7.08 (td, J=8.6, 3.0 Hz, 1H), 2.24 (s, 3H); $^{19}$F NMR (376 MHz, DMSO-$d_6$) δ −116.58; ESIMS m/z 275 ($[M+H]^+$).

N-(4-Fluorophenyl)-N-methyl-3-nitrobenzamide (C285)

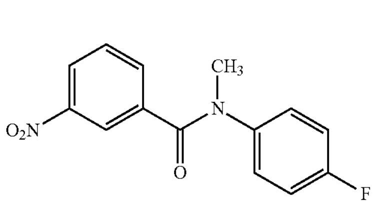 [SMILES: CN(C(=O)c1cccc([N+](=O)[O-])c1)c1ccc(F)cc1]

Isolated as a dark oil (0.335 g, 68%): $^1$H NMR (400 MHz, DMSO-$d_6$) δ 8.14 (d, J=9.3 Hz, 2H), 7.67 (d, J=7.6 Hz, 1H), 7.54 (t, J=7.8 Hz, 1H), 7.35 (dd, J=8.7, 5.0 Hz, 2H), 7.13 (t, J=8.8 Hz, 2H), 3.39 (s, 3H); $^{19}$F NMR (376 MHz, DMSO-$d_6$) δ −114.74; ESIMS m/z 275 ($[M+H]^+$).

N-(2-Chloro-4-fluorophenyl)-3-nitrobenzamide (C286)

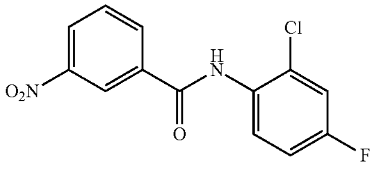 [SMILES: O=C(Nc1ccc(F)cc1Cl)c1cccc([N+](=O)[O-])c1]

Isolated as a tan solid (0.230 g, 44%): $^1$H NMR (400 MHz, DMSO-$d_6$) δ 10.55 (s, 1H), 8.81 (t, J=2.0 Hz, 1H), 8.61-8.26 (m, 2H), 7.86 (t, J=8.0 Hz, 1H), 7.71-7.53 (m, 2H), 7.31 (td, J=8.5, 2.9 Hz, 1H); $^{19}$F NMR (376 MHz, DMSO-$d_6$) δ −113.58; ESIMS m/z 295 ($[M+H]^+$).

tert-Butyl-N-((tert-butoxy)carbonyl)-N-(3-(2-chloro-5-nitrobenzamido)-2,4-difluorophenyl)carbamate (C287)

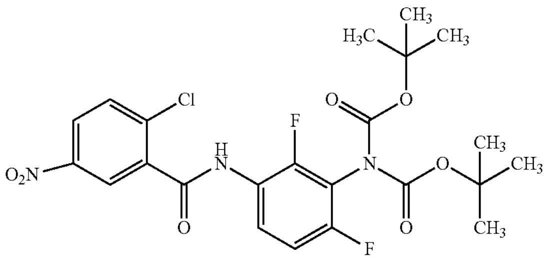 [SMILES: CC(C)(C)OC(=O)N(C(=O)OC(C)(C)C)c1c(F)ccc(NC(=O)c2cc([N+](=O)[O-])ccc2Cl)c1F]

Isolated as a yellow oil (5.2 g, 66%): $^1$H NMR (400 MHz, DMSO-$d_6$) δ 10.69 (s, 1H), 8.51 (d, J=2.7 Hz, 1H), 8.35 (dd, J=8.8, 2.8 Hz, 1H), 7.97-7.79 (m, 2H), 7.30 (td, J=9.3, 1.7 Hz, 1H), 1.41 (s, 18H); $^{19}$F NMR (376 MHz, DMSO-$d_6$) δ −123.43, −127.02 (d, J=2.0 Hz); ESIMS m/z 526 ($[M-H]^-$).

2-Chloro-N-(4-fluoro-2-(trifluoromethyl)phenyl)-5-nitrobenzamide (C288)

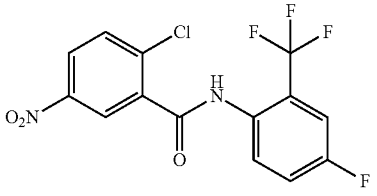 [SMILES: O=C(Nc1ccc(F)cc1C(F)(F)F)c1cc([N+](=O)[O-])ccc1Cl]

Isolated as an orange foam (0.120 g, 10%): $^1$H NMR (400 MHz, Acetone-$d_6$) δ9.57 (s, 1H), 8.49 (d, J=2.8 Hz, 1H), 8.36 (dd, J=8.8, 2.7 Hz, 1H), 7.96 (dd, J=8.8, 5.1 Hz, 1H), 7.85 (d, J=8.8 Hz, 1H), 7.65-7.53 (m, 2H); $^{19}$F NMR (376 MHz, Acetone-$d_6$) δ −61.54, −114.26. ESIMS m/z 360 ($[M-H]^-$).

The following compounds were prepared in like manner to the procedure outlined in Example 30:

2-Chloro-5-nitro-N-(4-(trifluoromethyl)thiazol-2-yl)benzamide (C289)

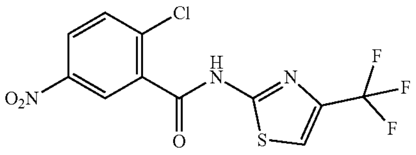 [SMILES: O=C(Nc1nc(C(F)(F)F)cs1)c1cc([N+](=O)[O-])ccc1Cl]

Isolated as a yellow glass (0.181 g, 52%): $^1$H NMR (400 MHz, DMSO-$d_6$) δ 13.41 (s, 1H), 8.63 (d, J=2.8 Hz, 1H), 8.39 (dd, J=8.9, 2.8 Hz, 1H), 8.12 (d, J=1.1 Hz, 1H), 7.92 (d, J=8.9 Hz, 1H); $^{19}$F NMR (376 MHz, DMSO-$d_6$) δ −62.92; ESIMS m/z 352 ([M+H]$^+$).

2-Chloro-N-(5-chloropyridin-2-yl)-5-nitrobenzamide (C290)

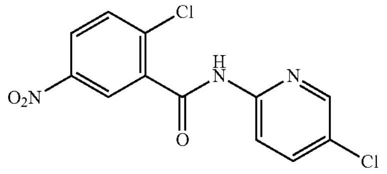 [SMILES: O=C(Nc1ccc(Cl)cn1)c1cc([N+](=O)[O-])ccc1Cl]

Isolated as a white solid (0.110 g, 36%): $^1$H NMR (400 MHz, DMSO-$d_6$) δ 11.55 (s, 1H), 8.50 (d, J=2.7 Hz, 1H), 8.38 (d, J=5.4 Hz, 1H), 8.34 (dd, J=8.8, 2.8 Hz, 1H), 8.28 (t, J=2.6 Hz, 1H), 7.87 (d, J=8.8 Hz, 1H), 7.37 (dd, J=5.4, 1.9 Hz, 1H); IR (thin film) 3103, 1778, 1688, 1566, 1524 cm$^{-1}$; ESIMS m/z 312 ([M+H]$^+$).

The following compounds were prepared in like manner to the procedure outlined in Example 31:

2-Chloro-N-(4-fluoro-3-(trifluoromethyl)phenyl)-5-nitrobenzamide (C291)

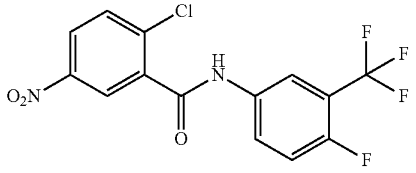 [SMILES: O=C(Nc1ccc(F)c(C(F)(F)F)c1)c1cc([N+](=O)[O-])ccc1Cl]

Isolated as an off-white solid (0.270 g, 55%): mp 192-202° C.; $^1$H NMR (400 MHz, Acetone-$d_6$) δ10.15 (s, 1H), 8.55 (d, J=2.8 Hz, 1H), 8.35 (dd, J=8.8, 2.8 Hz, 1H), 8.26 (dd, J=6.4, 2.7 Hz, 1H), 8.10-8.01 (m, 1H), 7.84 (d, J=8.8 Hz, 1H), 7.44 (t, J=9.6 Hz, 1H); $^{19}$F NMR (376 MHz, Acetone-$d_6$) δ −62.03 (d, J=12.9 Hz), −121.52 (q, J=12.9 Hz).

2-Chloro-5-nitro-N-(3-(trifluoromethyl)phenyl)benzamide (C292)

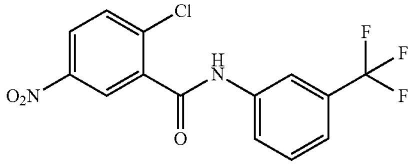 [SMILES: O=C(Nc1cccc(C(F)(F)F)c1)c1cc([N+](=O)[O-])ccc1Cl]

Isolated as a brown solid (0.350 g, 76%): $^1$H NMR (400 MHz, Acetone-$d_6$) δ10.14-10.09 (m, 1H), 8.57 (d, J=2.8 Hz, 1H), 8.35 (dd, J=8.8, 2.8 Hz, 1H), 8.28 (d, J=4.0 Hz, OH), 8.28 (s, 1H), 7.99 (dt, J=8.2, 1.3 Hz, 1H), 7.84 (d, J=8.8 Hz, 1H), 7.63 (t, J=8.0 Hz, 1H), 7.52 (ddt, J=7.8, 1.8, 0.9 Hz, 1H); $^{19}$F NMR (376 MHz, Acetone) δ −63.25; ESIMS m/z 342 ([M−H]$^-$).

N-(4-(1H-Pyrazol-1-yl)phenyl)-2-chloro-5-nitrobenzamide (C293)

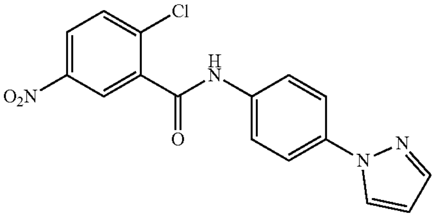 [SMILES: O=C(Nc1ccc(-n2cccn2)cc1)c1cc([N+](=O)[O-])ccc1Cl]

Isolated as a light brown solid (0.270 g, 52%): mp 200-205° C.; $^1$H NMR (400 MHz, DMSO-$d_6$) δ 10.84 (s, 1H), 8.51 (d, J=2.8 Hz, 1H), 8.46 (d, J=2.4 Hz, 1H), 8.35 (dd, J=8.8, 2.8 Hz, 1H), 7.91 (d, J=8.8 Hz, 1H), 7.90-7.78 (m, 4H), 7.74 (d, J=1.7 Hz, 1H), 6.58-6.52 (m, 1H); ESIMS m/z 341 ([M−H]$^-$).

2-Chloro-5-nitro-N-(4-(oxazol-2-yl)phenyl)benzamide (C294)

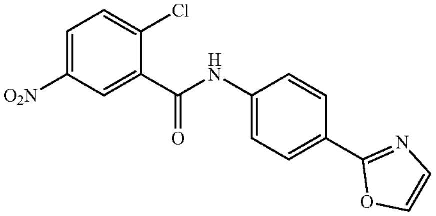 [SMILES: O=C(Nc1ccc(-c2ncco2)cc1)c1cc([N+](=O)[O-])ccc1Cl]

Isolated as a pink foam (0.233 g, 44%): mp 192-194° C.; $^1$H NMR (400 MHz, DMSO-$d_6$) δ 10.99 (s, 1H), 8.53 (d, J=2.8 Hz, 1H), 8.36 (dd, J=8.9, 2.8 Hz, 1H), 8.21 (d, J=0.8 Hz, 1H), 8.06-7.95 (m, 2H), 7.96-7.84 (m, 3H), 7.37 (d, J=0.8 Hz, 1H); ESIMS m/z 342 ([M−H]$^-$).

2-Chloro-5-nitro-N-(5-(trifluoromethyl)-1H-pyrazol-3-yl)benzamide (C295)

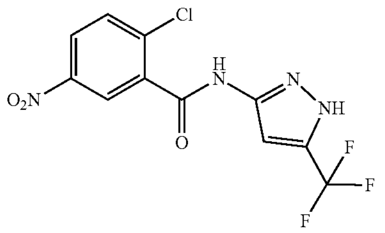 [SMILES: O=C(Nc1cc(C(F)(F)F)[nH]n1)c1cc([N+](=O)[O-])ccc1Cl]

Isolated as an off-white solid (0.170 g, 37%): $^1$H NMR (400 MHz, DMSO-$d_6$) δ13.63 (s, 1H), 11.71 (s, 1H), 8.52 (s, 1H), 8.37 (dd, J=8.8, 2.8 Hz, 1H), 7.91 (d, J=8.9 Hz, 1H), 6.54 (s, 1H); $^{19}$F NMR (376 MHz, DMSO-$d_6$) δ −60.91; ESIMS m/z 332 ([M−H]$^-$).

The following compounds were prepared in like manner to the procedure outlined in Example 32:

2-Chloro-N-(4-fluoro-2-methylphenyl)-N-methyl-5-nitrobenzamide (C296)

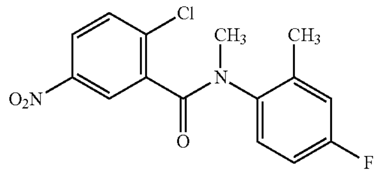 [SMILES: Cc1cc(F)ccc1N(C)C(=O)c1cc([N+](=O)[O-])ccc1Cl]

Isolated as a white solid (0.550 g, 100%): $^1$H NMR (400 MHz, $CDCl_3$) δ 7.99 (dd, J=8.7, 2.7 Hz, 1H), 7.95 (d, J=2.6 Hz, 1H), 7.43 (d, J=8.7 Hz, 1H), 7.16 (dd, J=8.7, 5.3 Hz, 1H), 6.85 (dd, J=9.0, 2.9 Hz, 1H), 6.73 (td, J=8.2, 3.0 Hz, 1H), 3.40 (s, 3H), 2.37 (s, 3H); $^{19}$F NMR (376 MHz, $CDCl_3$) δ −112.14; ESIMS m/z 323 ([M+H]$^+$).

tert-Butyl (4-(2-chloro-N-methyl-5-nitrobenzamido)-3-methylphenyl)(methyl)carbamate (C297)

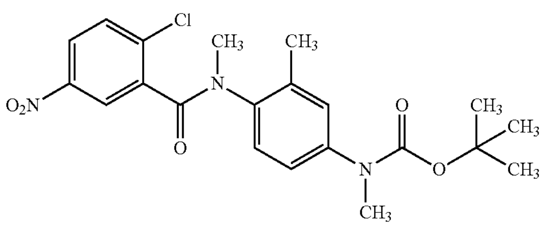 [SMILES: Cc1cc(N(C)C(=O)OC(C)(C)C)ccc1N(C)C(=O)c1cc([N+](=O)[O-])ccc1Cl]

Isolated as a yellow oil (0.240 g, 99%): $^1$H NMR (300 MHz, DMSO-$d_6$) δ rotamers 8.33 (dd, J=8.8, 2.8 Hz, 0.3H), 8.17 (d, J=2.7 Hz, 0.7H), 8.05 (dd, J=8.8, 2.8 Hz, 0.7H), 7.99-7.88 (m, 0.6H), 7.73-7.62 (m, 0.7H), 7.31-7.22 (m, 1H), 7.09 (d, J=2.6 Hz, 1H), 6.95 (dd, J=8.4, 2.6 Hz, 1H), 3.30 (s, 2H), 3.21 (s, 1H), 3.05 (d, J=1.5 Hz, 3H), 2.30 (s, 3H), 1.43 (s, 3H), 1.23 (s, 6H); IR (thin film) 2925, 1697, 1653, 1574 cm$^{-1}$; HRMS-ESI (m/z) [M+H]$^+$ calcd for $C_{21}H_{24}ClN_3O_5$, 434.1477; found, 434.1474.

2-Chloro-N-(2-cyano-4-fluorophenyl)-N-methyl-5-nitrobenzamide (C298)

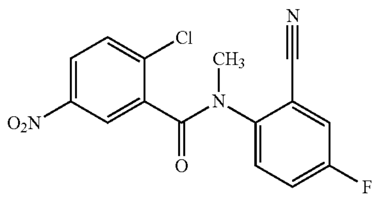 [SMILES: CN(C(=O)c1cc([N+](=O)[O-])ccc1Cl)c1ccc(F)cc1C#N]

Isolated as a yellow solid (0.211 g, 91%): $^1$H NMR (400 MHz, DMSO-$d_6$) δ 8.51-8.46 (m, 1H), 8.38 (d, J=2.8 Hz, 1H), 8.04 (dd, J=8.4, 2.9 Hz, 1H), 7.95 (d, J=8.9 Hz, 1H), 7.92-7.86 (m, 1H), 7.80 (td, J=8.6, 2.9 Hz, 1H), 3.19 (s, 3H); $^{19}$F NMR (376 MHz, DMSO-$d_6$) δ −111.69; ESIMS m/z 334 ([M+H]$^+$).

2-Chloro-N-(4-fluorophenyl)-5-nitro-N-(prop-2-yn-1-yl)benzamide (C299)

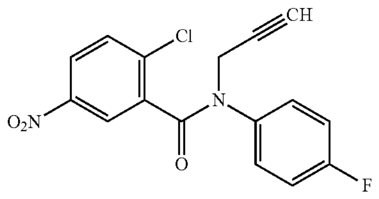

Isolated as a light brown solid (0.296 g, 94%): $^1$H NMR (400 MHz, DMSO-$d_6$) δ 8.37 (d, J=2.8 Hz, 1H), 8.08 (dd, J=8.8, 2.8 Hz, 1H), 7.63 (d, J=8.8 Hz, 1H), 7.49-7.40 (m, 2H), 7.20-7.08 (m, 2H), 4.69 (s, 2H), 3.30 (t, J=2.5 Hz, 1H); $^{19}$F NMR (376 MHz, DMSO-$d_6$) δ −112.89; ESIMS m/z 333 ([M+H]$^+$).

2-Chloro-N-(2,4-difluorophenyl)-5-nitro-N-(prop-2-yn-1-yl)benzamide (C300)

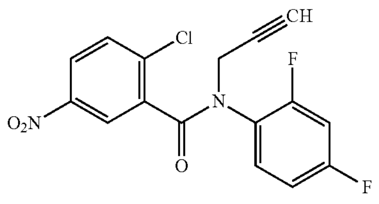

Isolated as a light brown oil (0.293 g, 89%): $^1$H NMR (400 MHz, DMSO-$d_6$) δ 8.21 (d, J=2.6 Hz, 1H), 8.13 (dd, J=8.8, 2.8 Hz, 1H), 7.73-7.65 (m, 2H), 7.29 (ddd, J=10.4, 9.0, 2.8 Hz, 1H), 7.14-7.02 (m, 1H), 4.69 (d, J=2.5 Hz, 2H), 3.30 (t, J=2.5 Hz, 1H); $^{19}$F NMR (376 MHz, DMSO-$d_6$) δ −107.45, −114.08 (d, J=8.4 Hz); ESIMS m/z 351 ([M+H]$^+$).

Example 36: Preparation of trans-2,2-dibromo-3-(3,5-dichlorophenyl)cyclopropane-1-carboxylic acid (C301)

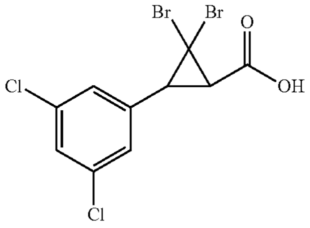 [SMILES: O=C(O)C1C(c2cc(Cl)cc(Cl)c2)C1(Br)Br]

To a solution of trans-2,2-dibromo-3-(3,5-dichlorophenyl)cyclopropane-1-carbaldehyde (C305) (1.67 g, 4.48 mmol) in acetonitrile (15.36 mL) and water (2.5 mL) was added sodium hydrogen sulfite (3.26 g, 31.36 mmol). The resultant solution was cooled to 0° C., sodium chlorite (3.54 g, 17.92 mmol) was added slowly, and the solution was stirred for overnight while slowly warming to room temperature. The mixture was then diluted with aqueous hydrochloric acid solution (1 N) until the pH was equal to or less than 3. The mixture was then repeatedly extracted with ethyl acetate. The combined organic extracts were dried over sodium sulfate, filtered and concentrated under vacuum. Purification of the crude solid by flash column chromatography with 0-100% ethyl acetate/hexanes as eluent provided the title compound as a light brown solid (0.91 g, 52%): $^{1}$H NMR (400 MHz, $CDCl_3$) δ 7.36 (t, J=1.9 Hz, 1H), 7.17 (dd, J=1.9, 0.8 Hz, 2H), 3.39 (d, J=8.2 Hz, 1H), 2.91 (d, J=8.2 Hz, 1H); $^{13}$C NMR (101 MHz, $CDCl^3$) δ 172.15, 136.91, 135.25, 128.64, 127.29, 40.29, 37.32, 26.57; ESIMS m/z 386 ($[M-H]^-$).

Example 37: Preparation of trans-2-chloro-3-(3,5-dichlorophenyl)-cyclopropane-1-carboxylic acid (C302)

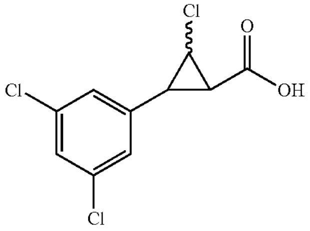 [SMILES: O=C(O)C1C(Cl)C1c1cc(Cl)cc(Cl)c1]

Thionyl chloride (2.55 g, 35.0 mmol) was added dropwise to a stirred solution of trans-2,2-dichloro-3-(3,5-dichlorophenyl)cyclopropanecarboxylic acid (C1) (2.10 g, 7.0 mmol) in anhydrous methanol (20 mL) at room temperature. Upon completion of the addition, the resulting solution was stirred for another 2 hours, then concentrated under vacuum on a rotary evaporator to afford a gold oil. The crude product was diluted with water (100 mL), and the aqueous mixture was extracted with ethyl acetate (3×50 mL). The combined organic extracts were washed with water and brine, dried over anhydrous magnesium sulfate, filtered, and concentrated under reduced pressure on a rotary evaporator to give methyl 2,2-dichloro-3-(3,5-dichlorophenyl)cyclopropane-1-carboxylate (2.168 g, 94%) as a clear colorless oil: $^{1}$H NMR (400 MHz, $CDCl_3$) δ 7.34 (s, 1H), 7.16 (dd, J=1.9, 0.7 Hz, 2H), 3.85 (s, 3H), 3.45-3.37 (m, 1H), 2.84 (d, J=8.3 Hz, 1H).

t-Butylmagnesium chloride (1M in tetrahydrofuran (THF), 8.0 mL, 7.96 mmol) was added dropwise to a stirred solution of methyl 2,2-dichloro-3-(3,5-dichlorophenyl)cyclopropane-1-carboxylate (1.0 g, 3.18 mmol). Hexamethylphosphoramide (0.571 g, 3.18 mmol) and [1,2-bis(diphenylphosphino)ethane]dichlorocobalt(II) (0.084 g, 0.159 mmol) in anhydrous THF (15 mL) at 5° C. Upon completion of the addition, the reaction was warmed to room temperature, stirred for another 30 minutes, and quenched with aqueous hydrochloric acid (1 N, 10 mL). The aqueous mixture was extracted with ethyl ether (3×50 mL). The combined organic extracts were washed with water and brine, dried over anhydrous magnesium sulfate, filtered, and concentrated under reduced pressure on a rotary evaporator. The resulting crude product was purified by silica gel flash chromatography (ethyl acetate/hexanes mobile phase) to give methyl 2-chloro-3-(3,5-dichlorophenyl)cyclopropane-1-carboxylate (0.425 g, 45.3%) as a yellow oil: GC-MS analysis showed a 1:1 mixture of diastereomers.

Powdered lithium hydroxide monohydrate (0.067 g, 1.61 mmol) was added in one portion to a stirred solution of methyl 2-chloro-3-(3,5-dichlorophenyl)cyclopropane-1-carboxylate (0.41 g, 1.47 mmol) in THF (5 mL) and water (1 mL). After stirring for 2 days at room temperature, the resulting pale yellow solution was made acidic (pH 2) with aqueous hydrochloric acid (1 N) and extracted with ethyl acetate (3×50 mL). The combined organic extracts were washed with water and brine, dried over anhydrous magnesium sulfate, filtered, and concentrated under reduced pressure on a rotary evaporator. The resulting crude product was purified by C-18 flash chromatography (acetonitrile/water mobile phase) to give 2-chloro-3-(3,5-dichlorophenyl)cyclopropane-1-carboxylic acid (0.270 g, 65.9%) as a white solid. 400 MHz $^{1}$H NMR spectral analysis showed a 1:1 mixture of diastereomers: $^{1}$H NMR (400 MHz, Acetone-$d_6$) δ 9.11 (s, 1H), 7.43-7.32 (m, 2H), 7.32-7.26 (m, 1H), 4.02-3.76 (m, 1H), 3.19-2.96 (m, 1H), 2.84-2.56 (m, 1H); ESIMS m/z 264 ($[M-H]^-$).

Example 38: Preparation of trans-2,2-dichloro-3-methyl-3-(4-(trifluoromethoxy)phenyl)cyclopropane-1-carboxylic acid (C303)

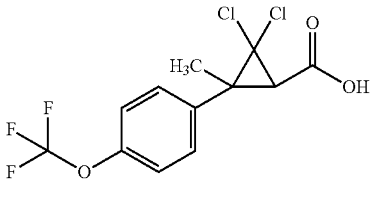 [SMILES: CC1(c2ccc(OC(F)(F)F)cc2)C(C(=O)O)C1(Cl)Cl]

A solution of trans-(2,2-dichloro-3-methyl-3-(4-(trifluoromethoxy)phenyl)cyclopropyl)methanol (C323) (2.4 g, 7.62 mmol) in acetone (20 mL) was added dropwise under rapid stirring to a solution of Jones Reagent (9.7 mL, 4.11 g, 19.04 mmol) in acetone (20 mL) at 2° C. The reaction mixture was allowed to warm slowly to ambient temperature under nitrogen over 14 hours. The mixture was cooled in a freezing salt (salt-ice) bath before adding isopropyl alcohol (20 mL) dropwise over 1 hour. The resultant suspension was warmed to ambient temperature over 3 hours and filtered to remove chromium salts, which were washed thoroughly with acetone (100 mL). The filtrate was concentrated under reduced pressure. The residue was suspended in water (100 mL) and extracted with ethyl acetate (3×70 mL). The combined organic extracts were washed with water (100 mL) and brine (60 mL), dried over magnesium sulfate, and concentrated under reduced pressure. The residue was taken up in ethyl ether (100 mL) and extracted with dilute sodium hydroxide solution (0.2 N, 3×40 mL). The combined aqueous extracts were cooled in an ice bath, acidified to pH 4 using dilute hydrochloric acid and extracted with ethyl acetate (3×50 mL). The combined organic extracts were washed with water (100 mL) and brine (80 mL), dried over magnesium sulfate, and concentrated under reduced pressure. The residue was dried in vacuo at 44° C. for 14 hours to leave a yellow solid (1.93 g, 77%): mp 99-101° C.; $^{1}$H NMR (400 MHz, $CDCl_3$) δ 7.36 (dt, J=9.1, 2.3 Hz, 2H), 7.24 (br d, J=8.8 Hz, 2H), 2.79 (s, 1H), 1.77 (s, 3H); $^{19}$F NMR (376 MHz, $CDCl_3$) δ −57.85; $^{13}$C NMR (101 MHz, $CDCl_3$) δ 171.49, 148.63, 139.63, 129.69, 124.25, 121.69, 121.19, 119.13, 116.57, 66.23, 42.85, 38.91, 20.39; ESIMS m/z 327.99 ([M−H]$^-$); IR (thin film) 1714.9, 1253.3, 1206.0, 1160.3 $cm^{-1}$.

Example 39: Preparation of trans-2,2-dichloro-3-(4-nitrophenyl)cyclopropyl)methanol (C304)

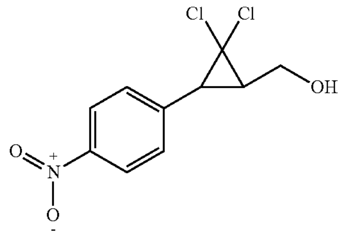

To a stirred solution of (E)-2-((3-(4-nitrophenyl)allyl)oxy)tetrahydro-2H-pyran (C322) (0.5 g, 1.899 mmol) and tetrabutylammonium hexafluorophosphate(V) (0.037 g, 0.095 mmol) in chloroform (6.33 mL) was added powdered sodium hydroxide (1.139 g, 28.5 mmol), and the reaction mixture was vigorously stirred at room temperature for 18 hours. The reaction mixture was diluted with water and dichloromethane, and the layers were separated. The organic layer was concentrated and purified by flash column chromatography giving 2-((trans-2,2-dichloro-3-(4-nitrophenyl)cyclopropyl)methoxy)-tetrahydro-2H-pyran as a mixture of diastereomers. The mixture was dissolved in methanol (10 mL). To the methanol solution was added p-toluenesulfonic acid (0.020 g, 0.107 mmol), and the reaction mixture was stirred at room temperature for 18 hours. The reaction mixture was quenched with saturated sodium bicarbonate and extracted with ethyl acetate (2×). The combined organic layers were dried over sodium sulfate, filtered, and concentrated giving the title compound as a yellow oil (310 mg, 53% over 2 steps): $^{1}$H NMR (400 MHz, $CDCl_3$) δ 8.22 (d, J=8.7 Hz, 2H), 7.52-7.34 (m, 2H), 4.10 (ddd, J=12.4, 7.2, 5.3 Hz, 1H), 3.95 (ddd, J=12.0, 8.0, 5.0 Hz, 1H), 2.78 (d, J=8.3 Hz, 1H), 2.37 (td, J=8.2, 5.4 Hz, 1H); $^{13}$C NMR (101 MHz, $CDCl_3$) δ 147.43, 141.42, 129.77, 123.59, 63.74, 62.25, 38.50, 37.04; IR (thin film) 1598, 1514, 1345, 1046 $cm^{-1}$; HRMS-ESI (m/z) $[M+Na]^+$ calcd for $C_{10}H_9Cl_2NO_3Na$, 283.9852; found, 283.9844.

Example 40: Preparation of trans-2,2-dibromo-3-(3,5-dichlorophenyl)cyclopropane-1-carbaldehyde (C305)

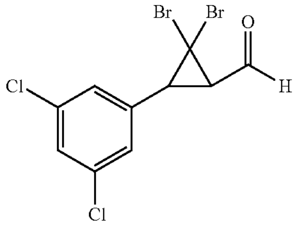 [SMILES: O=CC1C(c2cc(Cl)cc(Cl)c2)C1(Br)Br]

To a solution of (E)-1,3-dichloro-5-(3,3-diethoxyprop-1-en-1-yl)benzene (C449) (500 mg, 1.817 mmol) in bromoform (12.1 mL) were added tetrabutylammonium hexafluorophosphate(V) (70.4 mg, 0.182 mmol) followed by solid sodium hydroxide (Careful! Add slowly! 1454 mg, 36.3 mmol). The mixture was heated to 90° C. while stirring overnight. The mixture was then diluted with dichloromethane and water and extracted with additional dichloromethane. The organic layer was then dried over sodium sulfate and concentrated. Purification by flash column chromatography using 0-100% ethyl acetate/hexanes as eluent provided the resulting elutant, which was then dissolved in acetone (4 mL) and aqueous hydrochloric acid (2 N, 1 mL, 2 mmol). The mixture was stirred overnight. The mixture was diluted with saturated sodium bicarbonate solution until the pH of the solution was greater than 7. The mixture was then extracted with diethyl ether and ethyl acetate, and the combined organic layers were dried over sodium sulfate and concentrated providing the dark brown product (0.03 g, 4%): $^{1}$H NMR (400 MHz, $CDCl_3$) δ 9.48 (d, J=4.0 Hz, 1H), 7.37 (t, J=1.9 Hz, 1H), 7.17 (dd, J=1.9, 0.7 Hz, 2H), 3.60-3.36 (m, 1H), 2.90 (dd, J=7.9, 4.0 Hz, 1H); $^{13}$C NMR (101 MHz, $CDCl_3$) δ 194.74, 136.55, 135.31, 128.76, 127.34, 42.34, 39.84, 26.05; ESIMS m/z 343 ([M−CHO]$^-$).

Example 41: Preparation of 1-bromo-2-chloro-4-(trans-2,2-dichloro-3-(4-methoxyphenyl)cyclopropyl)benzene (C306)

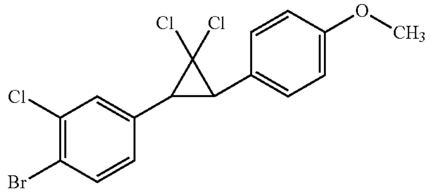

To a stirred solution of (E)-1-bromo-2-chloro-4-(4-methoxystyryl)benzene (C312) (0.38 g, 1.174 mmol) and tetrabutylammonium hexafluorophosphate(V) (0.045 g, 0.117 mmol) in chloroform (5.61 g, 3.77 mL, 47.0 mmol) was added aqueous sodium hydroxide (50%, 2.348 g, 29.4 mmol), and the resulting mixture was stirred vigorously at room temperature for 40 hours. The reaction mixture was diluted with water and was extracted with dichloromethane. The combined organic layers were dried over sodium sulfate, filtered, and concentrated. Purification by flash column chromatography using 0-10% ethyl acetate/hexanes as eluent provided the title compound as a colorless oil (0.362 g, 72%): $^1$H NMR (400 MHz, $CDCl_3$) δ 7.62 (d, J=8.3 Hz, 1H), 7.46 (d, J=2.0 Hz, 1H), 7.29-7.23 (m, 2H), 7.13 (dd, J=8.3, 2.1 Hz, 1H), 6.93 (d, J=8.7 Hz, 2H), 3.83 (s, 3H), 3.12 (d, J=8.7 Hz, 1H), 3.07 (d, J=8.7 Hz, 1H); $^{13}$C NMR (101 MHz, $CDCl_3$) δ 159.43, 135.68, 134.63, 133.68, 130.80, 129.90, 128.49, 125.81, 121.83, 114.01, 64.86, 55.33, 39.54, 38.85; IR (thin film) 3356 (br), 3002, 2835, 1514, 1248 $cm^{-1}$.

The following compounds were prepared in like manner to the procedure outlined in Example 41:

2-bromo-1-chloro-4-(trans-2,2-dichloro-3-(4-methoxyphenyl)cyclopropyl)benzene (C307)

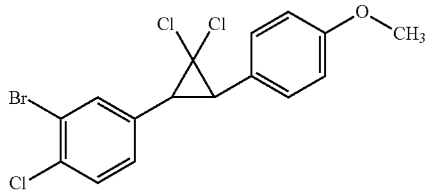

Isolated as a thick yellow oil (1.1321 g, 74.4%): $^1$H NMR (400 MHz, $CDCl_3$) δ 7.62 (d, J=2.1 Hz, 1H), 7.46 (d, J=8.3 Hz, 1H), 7.30-7.20 (m, 3H), 6.93 (d, J=8.7 Hz, 2H), 3.82 (s, 3H), 3.12 (d, J=8.8 Hz, 1H), 3.08 (d, J=8.8 Hz, 1H); $^{13}$C NMR (101 MHz, $CDCl_3$) δ 159.42, 135.02, 134.13, 133.97, 130.24, 129.90, 129.01, 125.82, 122.51, 114.01, 64.98, 55.33, 39.57, 38.66; IR (thin film) 3001, 2932, 2835, 1514, 1248 $cm^{-1}$.

1-Bromo-3-chloro-5-(trans-2,2-dichloro-3-(4-methoxyphenyl)cyclopropyl)benzene (C308)

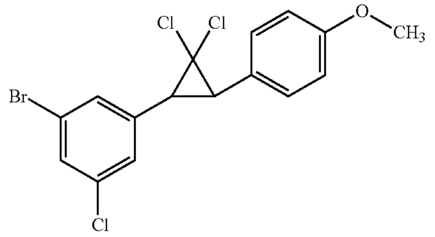

Isolated as a thick yellow oil (2.612 g, 83%): $^1$H NMR (400 MHz, $CDCl_3$) δ 7.49 (t, J=1.8 Hz, 1H), 7.41 (d, J=1.7 Hz, 1H), 7.30 (d, J=1.8 Hz, 1H), 7.28-7.23 (m, 2H), 6.93 (d, J=8.7 Hz, 2H), 3.83 (s, 3H), 3.13 (d, J=8.7 Hz, 1H), 3.08 (d, J=8.8 Hz, 1H); $^{13}$C NMR (101 MHz, $CDCl_3$) δ 159.45, 138.28, 135.18, 130.82, 130.41, 129.88, 128.00, 125.66, 122.72, 114.02, 64.81, 55.32, 39.56, 38.89; IR (thin film) 3000, 2931, 2835, 1588, 1550, 1513 $cm^{-1}$.

2-Bromo-5-(trans-2,2-dichloro-3-(4-methoxyphenyl)cyclopropyl)-1,3-difluorobenzene (C309)

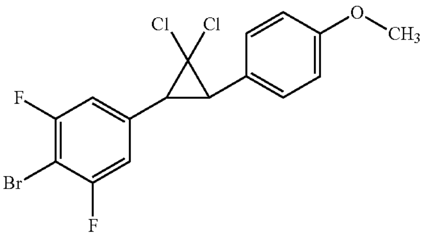 [SMILES: COc1ccc(C2C(c3cc(F)c(Br)c(F)c3)C2(Cl)Cl)cc1]

Isolated as a yellow solid (3.44 g, 79%): mp 104.0-109.3° C.; $^1$H NMR (400 MHz, $CDCl_3$) δ 7.28-7.22 (m, 2H), 7.02-6.96 (m, 2H), 6.96-6.90 (m, 2H), 3.83 (s, 3H), 3.12 (d, J=8.7 Hz, 1H), 3.08 (d, J=8.7 Hz, 1H); $^{13}$C NMR (101 MHz, $CDCl_3$) δ 161.10, 159.49, 129.86, 125.47, 114.04, 112.79, 112.56, 112.53, 64.66, 55.33, 39.77, 39.01; $^{19}$F NMR (376 MHz, $CDCl_3$) δ −104.75.

2-Bromo-5-(trans-2,2-dichloro-3-(4-methoxyphenyl)cyclopropyl)-1-fluoro-3-methoxybenzene (C310)

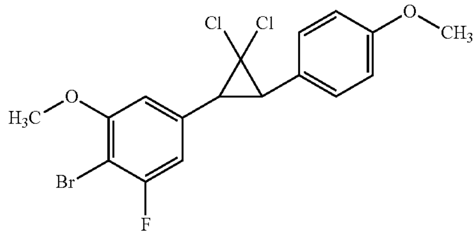

Isolated as a yellow oil (1.18 g, 76%): $^1$H NMR (400 MHz, $CDCl_3$) δ 7.30-7.26 (m, 2H), 6.96-6.91 (m, 2H), 6.80-6.74 (m, 1H), 6.70 (d, J=1.6 Hz, 1H), 3.96 (s, 3H), 3.83 (s, 3H), 3.15-3.07 (m, 2H); $^{13}$C NMR (101 MHz, $CDCl_3$) δ 161.20, 159.43, 136.09, 135.99, 129.91, 125.85, 114.01, 109.29, 109.05, 108.20, 64.91, 56.79, 55.33, 39.59, 39.49; $^{19}$F NMR (376 MHz, $CDCl_3$) δ −104.96.

1-Bromo-5-(trans-2,2-dichloro-3-(4-methoxyphenyl)cyclopropyl)-3-fluoro-2-methoxybenzene (C311)

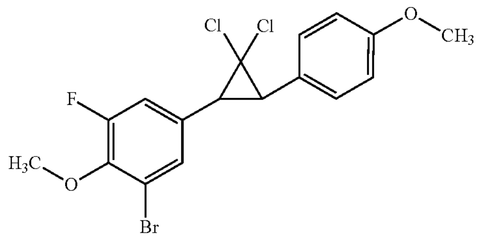

Isolated as a yellow oil (0.37 g, 59%); $^1$H NMR (400 MHz, $CDCl_3$) δ 7.31-7.23 (m, 3H), 6.98 (d, J=11.6 Hz, 1H), 6.96-6.90 (m, 2H), 3.92 (s, 3H), 3.83 (s, 3H), 3.13 (d, J=8.8 Hz, 1H), 3.07 (d, J=8.8 Hz, 1H); $^{13}$C NMR (101 MHz, $CDCl_3$) δ 159.38, 152.57, 147.73, 129.93, 127.93, 125.93, 120.63, 117.66, 117.23, 113.97, 65.40, 56.57, 55.33, 40.10, 39.59; $^{19}$F NMR (376 MHz, $CDCl_3$) δ −135.58.

Example 42: Preparation of (E)-1-bromo-2-chloro-4-(4-methoxystyryl)benzene (C312)

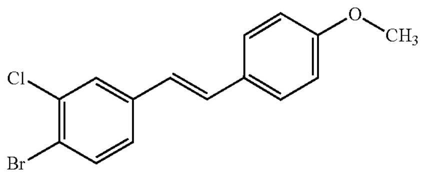

To a stirred solution of diethyl (4-methoxybenzyl)phosphonate (0.619 mL, 2.73 mmol) in N,N-dimethylformamide (3 mL) at 0° C. was added a solution of sodium methoxide (5.4 M in methanol, 0.844 mL, 4.56 mmol). A solution of 4-bromo-3-chlorobenzaldehyde (0.5 g, 2.278 mmol) in N,N-dimethylformamide (1 mL) was added, and the reaction mixture was heated to 65° C. for 4 hours. The reaction mixture was allowed to cool to room temperature and was partitioned between water and ethyl acetate. The organic layer was dried over magnesium sulfate, filtered, and concentrated. Purification by flash column chromatography using 0-10% ethyl acetate/hexanes as eluent provided the title compound as a yellow crystalline solid (0.484 g, 59%): mp 77-88° C.; $^1$H NMR (400 MHz, $CDCl_3$) δ 7.58-7.53 (m, 2H), 7.47-7.39 (m, 2H), 7.22 (dd, J=8.4, 2.1 Hz, 1H), 7.06 (d, J=16.2 Hz, 1H), 6.95-6.87 (m, 2H), 6.84 (d, J=16.3 Hz, 1H), 3.84 (s, 3H); EIMS m/z 324.

The following compounds were prepared in like manner to the procedure outlined in Example 42:

(E)-2-bromo-1-chloro-4-(4-methoxystyryl)benzene (C313)

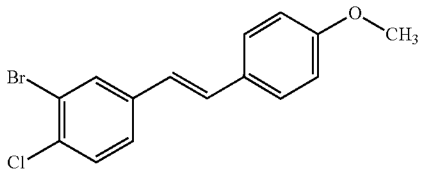

Isolated as a white solid (1.15 g, 70.2%): 87.1-92.3° C.; $^1$H NMR (400 MHz, $CDCl_3$) δ 7.71 (d, J=2.0 Hz, 1H), 7.42 (dd, J=9.5, 7.4 Hz, 2H), 7.37 (s, 1H), 7.32 (dd, J=8.4, 2.1 Hz, 1H), 7.02 (d, J=16.2 Hz, 1H), 6.93-6.86 (m, 2H), 6.82 (d, J=16.3 Hz, 1H), 3.83 (s, 3H); $^{13}$C NMR (101 MHz, $CDCl_3$) δ 159.79, 138.01, 132.53, 131.05, 130.33, 130.17, 129.36, 127.97, 126.03, 123.84, 122.71, 114.26, 55.34; EIMS m/z 324.0.

(E)-1-Bromo-3-chloro-5-(4-methoxystyryl)benzene (C314)

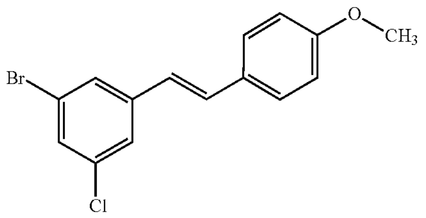

Isolated as a pale yellow oil (2.39 g, 77%): $^1$H NMR (400 MHz, $CDCl_3$) δ 7.48 (d, J=1.7 Hz, 1H), 7.45-7.39 (m, 2H), 7.35 (dt, J=9.6, 1.8 Hz, 2H), 7.04 (d, J=16.2 Hz, 1H), 6.90 (d, J=8.8 Hz, 2H), 6.79 (d, J=16.2 Hz, 1H), 3.83 (s, 3H); $^{13}$C NMR (101 MHz, $CDCl_3$) δ 159.95, 141.10, 135.29, 131.08, 129.49, 129.11, 128.11, 127.37, 124.91, 123.61, 122.95, 114.29, 55.35; EIMS m/z 324.1.

Example 43: Preparation of (E)-2-bromo-1,3-difluoro-5-(4-methoxystyryl)benzene (C315) and (E)-2-bromo-1-fluoro-3-methoxy-5-(4-methoxystyryl) benzene (C316)

C315

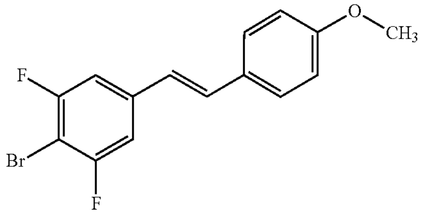

C316

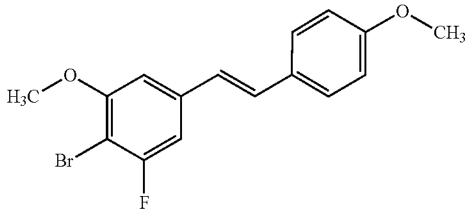

To a stirred solution of diethyl (4-methoxybenzyl)phosphonate (5.54 mL, 24.43 mmol) in N,N-dimethylformamide (27 mL) at 0° C. was added a solution of sodium methoxide (5.4 M in methanol, 4.52 mL, 24.43 mmol). 4-Bromo-3,5-difluorobenzaldehyde (4.5 g, 20.36 mmol) in N,N-dimethylformamide (9 mL) was added, and the reaction mixture was heated to 65° C. for 1 hour. The reaction mixture was allowed to cool to room temperature and was partitioned between water and ethyl acetate. The organic layer was dried over magnesium sulfate, filtered, and concentrated. Purification by flash column chromatography using 0-10% ethyl acetate/hexanes as eluent provided (E)-2-bromo-1,3-difluoro-5-(4-methoxystyryl)benzene (C315) as a white solid (3.28 g, 47%) and (E)-2-bromo-1-fluoro-3-methoxy-5-(4-methoxystyryl)benzene (C316) as a white solid (1.19 g, 16%). C315: mp 104.1-112.7° C.; $^1$H NMR (400 MHz, $CDCl_3$) δ 7.48-7.41 (m, 2H), 7.10-7.02 (m, 3H), 6.94-6.88 (m, 2H), 6.82 (d, J=16.2 Hz, 1H), 3.84 (s, 3H); $^{19}$F NMR (376 MHz, $CDCl_3$) δ −106.11; EIMS m/z 324.0. C316: mp 118.5-123.0° C.; $^1H$ NMR (400 MHz, $CDCl_3$) δ 7.45 (d, J=8.6 Hz, 2H), 7.06 (d, J=16.2 Hz, 1H), 6.91 (dd, J=9.1, 2.2 Hz, 3H), 6.86 (d, J=16.2 Hz, 1H), 6.78 (t, J=1.5 Hz, 1H), 3.96 (s, 3H), 3.84 (s, 3H); $^{19}F$ NMR (376 MHz, $CDCl_3$) δ −106.15; EIMS m/z 336.0.

Example 44: Preparation of (E)-1-bromo-3-fluoro-2-methoxy-5-(4-methoxy-styryl)benzene (C317)

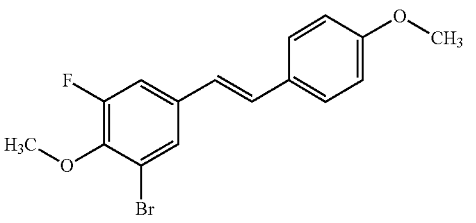

To a stirred solution of diethyl (4-methoxybenzyl)phosphonate (1.85 mL, 8.14 mmol) in N,N-dimethylformamide (9 mL) at 0° C. was added a solution of sodium methoxide (5.4 M in methanol, 1.38 mL, 7.47 mmol). 3-Bromo-4,5-fluorobenzaldehyde (1.5 g, 6.79 mmol) in N,N-dimethylformamide (3 mL) was added, and the reaction mixture was heated to 65° C. for 2 hours. The reaction mixture was allowed to cool to room temperature and was partitioned between water and ethyl acetate. The organic layer was dried over magnesium sulfate, filtered, and concentrated. Purification by flash column chromatography using 0-10% ethyl acetate/hexanes as eluent provided (E)-1-bromo-3-fluoro-2-methoxy-5-(4-methoxystyryl)benzene as a white solid (0.48 g, 20%): mp 78.0-84.8° C.; $^1H$ NMR (400 MHz, $CDCl_3$) δ 7.47 (d, J=8.7 Hz, 2H), 7.39 (d, J=12.5 Hz, 1H), 7.19 (dd, J=16.1, 1.7 Hz, 1H), 7.14 (d, J=8.1 Hz, 1H), 6.94-6.89 (m, 2H), 6.86 (d, J=16.2 Hz, 1H), 3.90 (s, 3H), 3.84 (s, 3H); $^{19}F$ NMR (376 MHz, $CDCl_3$) δ −135.86; EIMS m/z 336.0.

Example 45: Preparation of (E)-2-Chloro-5-(4-methoxystyryl)thiophene (C318)

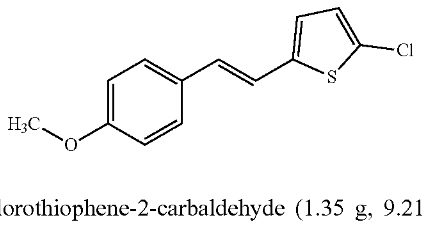

5-Chlorothiophene-2-carbaldehyde (1.35 g, 9.21 mmol) and diethyl 4-methoxybenzylphosphonate (1.59 mL, 9.21 mmol) were dissolved in N,N-dimethylformamide (18 mL). To this mixture was added sodium methoxide (25% in methanol, 2.51 mL, 11.05 mmol) at room temperature. After 16 hours, the reaction mixture was diluted with water with stirring. The precipitate was collected by filtration, was washed with water and was dried. The precipitate was dissolved in ethyl acetate, and the solution was washed with brine. The layers were separated, and the organic layer was dried over sodium sulfate, filtered, and concentrated to give (E)-2-chloro-5-(4-methoxystyryl)thiophene (1.550 g, 67.1%) as a dark yellow powder: $^1H$ NMR (400 MHz, $CDCl_3$) δ 7.41-7.35 (m, 2H), 6.94 (dd, J=16.1, 0.5 Hz, 1H), 6.91-6.83 (m, 2H), 6.81-6.70 (m, 3H), 3.82 (s, 3H); $^{13}C$ NMR (101 MHz, $CDCl_3$) δ 159.47, 142.09, 129.34, 128.13, 127.93, 127.58, 126.63, 124.58, 119.34, 114.21, 55.32; EIMS m/z 250.

Example 46: Preparation of ethyl (E)-3-(4-(trifluoromethoxy)phenyl)but-2-enoate (C319)

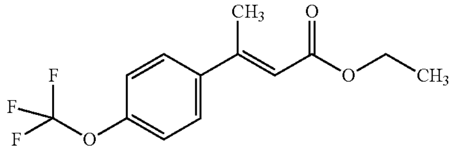 [SMILES: CCOC(=O)/C=C(\C)c1ccc(OC(F)(F)F)cc1]

Based on a procedure by Z—C Duan, X—P Hu, C Zhang and Z Zheng in Org Chem (2010) 75(23), 8319-8321. Neat ethyl 2-(diethoxyphosphoryl)acetate (10.98 g, 49 mmol) was added dropwise under nitrogen to an ice-cold, stirred suspension of 60% sodium hydride in mineral oil (1.96 g, 49 mmol) in dry tetrahydrofuran (80 mL), taking care to maintain the temperature below 3° C. The reactants were stirred for 30 minutes before addition of 1-(4-(trifluoromethoxy)phenyl)ethanone (8.0 g, 39.2 mmol). The reaction mixture was allowed to warm slowly to ambient temperature under nitrogen to give a thick, yellow gum. Saturated aqueous ammonium chloride (80 mL) was added dropwise under rapid stirring. This mixture was extracted with ethyl ether (2×170 mL). The combined organic extracts was washed with water (400 mL) and brine (200 mL), dried over magnesium sulfate, and purified by silica gel chromatography, eluting with a gradient of ethyl acetate in hexane. Two closely eluting fractions were obtained. The desired product was obtained from the faster eluting fraction as a colorless liquid (9.0 g, 84%) after drying in vacuo at 42° C. for 14 hours: $^1H$ NMR (400 MHz, $CDCl_3$) δ 7.50 (dt, J=8.9, 2.1 Hz, 2H), 7.21 (dd, J=8.9, 0.9 Hz, 2H), 6.11 (d, J=1.3 Hz, 1H), 4.22 (q, J=7.1 Hz, 2H), 2.56 (d, J=1.3 Hz, 3H), 1.32 (t, J=7.1 Hz, 3H); $^{13}C$ NMR (101 MHz, $CDCl_3$) δ 166.58, 153.79, 149.63, 149.61, 140.82, 127.82, 124.26, 121.70, 120.81, 119.14, 117.95, 116.58, 60.02, 17.95, 14.33; $^{19}F$ NMR (376 MHz, $CDCl_3$) δ −57.82; IR (thin film) 1712, 1253, 1161 $cm^{-1}$; EIMS m/z 274.

Example 47: Preparation of (E)-3-(4-(trifluoromethoxy)phenyl)but-2-en-1-ol (C320)

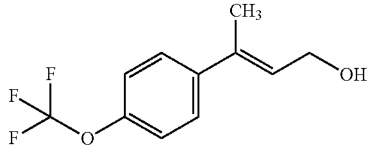 [SMILES: C/C(=C\CO)c1ccc(OC(F)(F)F)cc1]

Based on procedure of G Rai, A A Sayed, W A Lea, H Luecke, H Chakrapani, S Prasr-Nielsen, A Jadhav, W Leister, M Shen, J Inglese, C P Austin, L Keefer, E S Arner, A Simeonov, D J Maloney, D L Williams and CJ Thomas in J Med Chem (2009) 52(20), 6474-6483. A 1.5 M toluene solution of diisobutylaluminum hydride (37.1 mL, 48.1 mmol) was added at a dropwise rate over 90 minutes to another toluene solution of (E)-ethyl 3-(4-(trifluoromethoxy)phenyl)but-2-enoate (6.0 g, 21.88 mmol) at −78°

C. The addition rate was adjusted to maintain temperature between −71 and −78° C. After 4 days at ambient temperature, the reaction mixture was poured into a dilute hydrochloric acid slush (500 mL) and extracted with toluene (3×150 mL). The combined organic extracts were washed with water (300 mL) and brine (200 mL), dried over magnesium sulfate, and concentrated under reduced pressure. Chromatography on a silica column, eluting with 5:1 hexane/ethyl acetate afforded two fractions. The desired product was isolated from Fraction 2 as a pale yellowish liquid (3.0 g, 59%): $^{1}$H NMR (400 MHz, $CDCl_3$) δ 7.42 (dt, J=8.7, 1.2 Hz, 2H), 7.17 (d, J=8.7 Hz, 2H), 5.96 (td, J=6.6, 1.2 Hz, 1H), 4.37 (d, J=6.2 Hz, 2H), 2.07 (s, 3H); $^{13}$C NMR (101 MHz, $CDCl_3$) δ 148.43, 141.55, 136.56, 127.37, 127.11, 124.33, 121.77, 120.73, 119.22, 116.66, 59.91, 16.08; $^{19}$F NMR (376 MHz, $CDCl_3$) δ −57.86; EIMS m/z 232; IR 1253.9 (m), 1209.4 (m), 1158.0 (m) $cm^{-1}$.

Example 48: Preparation of (E)-3-(4-(trifluoromethoxy)phenyl)but-2-en-1-yl)oxy)tetrahydro-2H-pyran (C321)

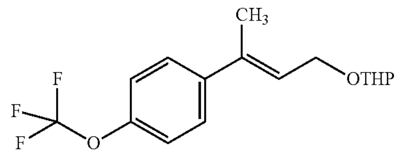

An ice-cold suspension of (E)-3-(4-(trifluoromethoxy)phenyl)but-2-en-1-ol (C320) (2.9 g, 12.49 mmol) in diethyl ether (15 mL) was treated with neat 3,4-dihydro-2H-pyran (1.786 g, 21.23 mmol). After stirring for 10 minutes, solid p-toluenesulfonic acid (0.119 g, 0.624 mmol) was added. The reaction mixture was allowed to warm slowly to ambient temperature under nitrogen over 14 hours. Neat 3,4-dihydro-2H-pyran (0.2 g, 2.38 mmol) was added, and the mixture was stirred at ambient temperature for an additional 62 hours. The reaction mixture was washed with dilute aqueous sodium hydroxide (0.2 N, 150 mL), water (100 mL), and brine (70 mL), dried over magnesium sulfate, concentrated under reduced pressure, applied to a dry flash silica column and eluted with 10:1 hexane/ethyl acetate. The desired fraction was concentrated under reduced pressure and dried in vacuo at 40° C. for 14 hours to leave a pale yellowish liquid (3.4 g, 85%): $^{1}$H NMR (400 MHz, $CDCl_3$) δ 7.43 (dt, J=8.8, 2.1 Hz, 2H), 7.16 (d, J=8.4 Hz, 2H), 5.94 (t, J=6.45 Hz, 1H), 4.69 (t, J=3.4 Hz, 1H), 4.44 (dd, J=12.7, 6.6 Hz, 1H), 4.23 (dd, J=13.1, 7.0 Hz, 1H), 3.98-3.83 (m, 1H), 3.63-3.43 (m, 1H), 2.07 (s, 3H), 1.86 (dd, J=8.8, 3.5 Hz, 1H), 1.80-1.71 (m, 1H), 1.67-1.49 (m, 5H); $^{19}$F NMR (376 MHz, $CDCl_3$) δ −57.85; $^{13}$C NMR (101 MHz, $CDCl_3$) δ 148.31, 141.66, 136.81, 127.09, 125.17, 124.32, 121.77, 120.65, 119.22, 116.66, 98.15, 94.69, 64.15, 62.98, 30.69, 25.47, 19.54, 16.16; EIMS m/z 316); IR (thin film) 1253, 1207, 1051 $cm^{-1}$.

Example 49: Preparation of (E)-2-((3-(4-nitrophenyl)allyl)oxy)tetrahydro-2H-pyran (C322)

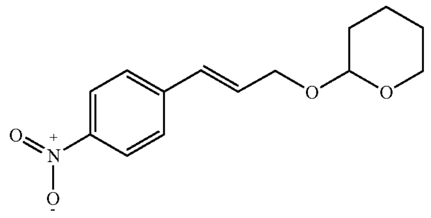

To a solution of (E)-3-(4-nitrophenyl)prop-2-en-1-ol (1.5 g, 8.37 mmol) in diethyl ether (56 mL) was added 3,4-dihydro-2H-pyran (1.298 mL, 14.23 mmol) forming a tan slurry. p-Toluenesulfonic acid (0.080 g, 0.419 mmol) was added, and the reaction mixture was stirred for 10 minutes. Tetrahydrofuran (15 mL) was added to improve the solubility, and after 30 minutes, the reaction mixture had become clear. The reaction mixture was allowed to stir at room temperature overnight. The reaction mixture was quenched with saturated aqueous sodium carbonate, and the layers were separated. The organic layer was dried over sodium sulfate, filtered, and concentrated to afford the title compound as a yellow oil (2.25 g, 97%): $^{1}$H NMR (400 MHz, $CDCl_3$) δ 8.26-8.09 (m, 2H), 7.57-7.44 (m, 2H), 6.79-6.63 (m, 1H), 6.51 (ddd, J=16.0, 5.8, 5.2 Hz, 1H), 4.71 (dd, J=4.2, 3.0 Hz, 1H), 4.46 (ddd, J=13.9, 5.2, 1.7 Hz, 1H), 4.20 (ddd, J=13.9, 5.9, 1.6 Hz, 1H), 3.91 (ddd, J=11.2, 8.2, 3.3 Hz, 1H), 3.65-3.47 (m, 1H), 1.96-1.36 (m, 6H); $^{13}$C NMR (101 MHz, $CDCl_3$) δ 146.95, 143.36, 131.36, 129.36, 126.93, 123.98, 98.33, 67.10, 62.34, 30.58, 25.41, 19.44; IR (thin film) 2939, 2849, 1595, 1513, 1339 $cm^{-1}$.

Example 50: Preparation of trans-(2,2-dichloro-3-methyl-3-(4-(trifluoromethoxy)phenyl)cyclopropyl)methanol (C323)

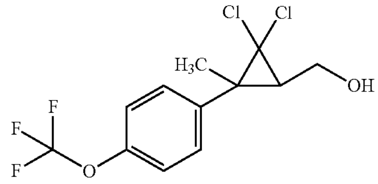 [SMILES: CC1(c2ccc(OC(F)(F)F)cc2)C(CO)C1(Cl)Cl]

p-Toluenesulfonic acid (0.076 g, 0.401 mmol) was added to an ice-cold solution of trans-2-((2,2-dichloro-3-methyl-3-(4-(trifluoromethoxy)phenyl)cyclopropyl)methoxy)tetrahydro-2H-pyran (C230) in methanol (40 mL) and allowed to warm to ambient temperature under nitrogen over 14 hours. The volatiles were removed under reduced pressure. The residue was dissolved in ethyl acetate (70 mL), washed with saturated aqueous sodium bicarbonate (50 mL). The solution was washed with water (50 mL) and brine (50 mL), dried over magnesium sulfate, concentrated under reduced pressure and dried in vacuo at 44° C. for 6 hours to leave a yellow gum (1.86 g, 74%): $^{1}$H NMR (400 MHz, $CDCl_3$) δ 7.35 (dt, J=8.9, 2.0 Hz, 2H), 7.23-7.17 (m, 2H), 4.08-4.00 (m, 1H), 3.97-3.89 (m, 1H), 2.18 (dd, J=7.7, 7.2 Hz, 2H), 1.71 (t, J=5.6 Hz, 1H), 1.54 (s, 3H); $^{19}$F NMR (376 MHz, $CDCl_3$) δ −57.84; $^{13}$C NMR (101 MHz, $CDCl_3$) δ 148.31, 148.29, 140.97, 130.13, 130.05, 124.28, 121.72, 120.98, 120.91, 119.16, 116.61, 59.61, 38.65, 38.27, 19.84; EIMS m/z 283 (M−Cl); IR (thin film) 1254, 1206, 1160 $cm^{-1}$.

Example 51: Preparation of (E)-3-chloro-5-(4-methoxystyryl) benzaldehyde (C324)

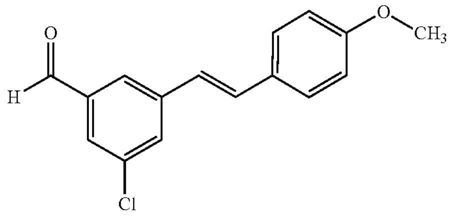

To a stirred solution of 3-bromo-5-chlorobenzaldehyde (20.0 g, 91.32 mmol) in dimethylacetamide, 1-methoxy-4-vinylbenzene (18.3 g, 136.9 mmol) and triethylamine (50 mL, 273.96 mmol) were added, and the reaction mixture was degassed with argon for 5 minutes. Palladium(II) acetate (410 mg, 1.83 mmol) and tri-o-tolylphosphine (1.11 g, 3.65 mmol) were added, and the resulting reaction mixture was heated to 100° C. for 16 hours. The reaction mixture was poured into water and extracted with ethyl acetate. The combined organic layer was dried over sodium sulfate and concentrated under reduced pressure. The resulting crude material was purified by flash column chromatography using 5-10% ethyl acetate in petroleum ether as the eluent to afford the title compound as a yellow solid (13.5 g, 54%): $^1$H NMR (300 MHz, $CDCl_3$) δ 9.99 (s, 1H), 7.85 (s, 1H), 7.69 (s, 2H), 7.47 (d, J=8.4 Hz, 2H), 7.16 (d, J=16.2 Hz, 1H), 6.94 (t, J=8.4 Hz, 3H), 3.84 (s, 3H); ESIMS m/z 273 ([M+H]$^+$).

The following compounds were prepared in like manner to the procedure outlined in Example 51:

(E)-2-Chloro-5-(4-methoxystyryl)benzaldehyde (C325)

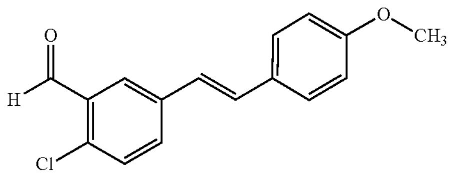

Isolated as a pale yellow solid (11.8 g, 27%): $^1$H NMR (300 MHz, $CDCl_3$) δ 10.45 (s, 1H), 8.02 (s, 1H), 7.62 (d, J=6.4 Hz, 1H), 7.46-7.40 (m, 3H), 7.12 (d, J=16.4 Hz, 1H), 6.95-6.90 (m, 3H), 3.95 (s, 3H); ESIMS m/z 273 ([M+H]$^+$).

(E)-3-Fluoro-5-(4-methoxystyryl)benzaldehyde (C326)

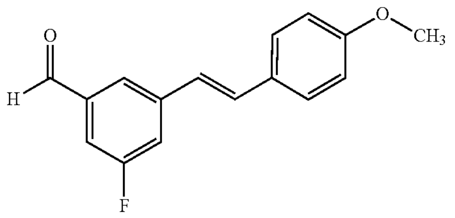

Isolated as a pale yellow solid (25 g, 57%): $^1$H NMR (300 MHz, $CDCl_3$) δ 10 (s, 1H), 7.77 (s, 1H), 7.48-7.40 (m, 4H), 7.16 (d, J=16.2 Hz, 1H), 6.94 (t, J=15.6 Hz, 3H), 3.84 (s, 3H); ESIMS m/z 275 ([M+H]$^+$).

(E)-2-Fluoro-5-(4-methoxystyryl)benzaldehyde (C327)

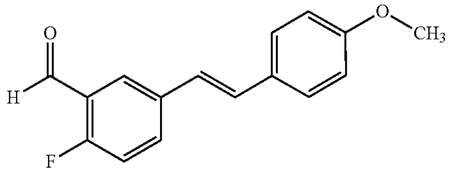

Isolated as an off-white solid (0.25 g, 20%): $^1$H NMR (400 MHz, $CDCl_3$) δ 10.43 (s, 1H), 7.90 (d, J=8.4 Hz, 1H), 7.54-7.46 (m, 4H), 7.20 (d, J=16.0 Hz, 1H), 6.94-6.90 (m, 3H), 3.85 (s, 3H); ESIMS m/z 274 ([M+H]$^+$).

(E)-2-Chloro-4-(4-methoxystyryl)benzaldehyde (C328)

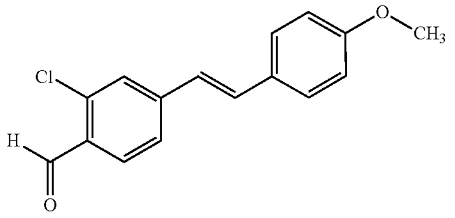

Isolated as an off-white solid (8.0 g, 57%): $^1$H NMR (400 MHz, $CDCl_3$) δ 10.41 (s, 1H), 7.97 (dd, J=2.4, 6.8 Hz, 1H), 7.71-7.67 (m, 1H), 7.44 (d, J=8.0 Hz, 2H), 7.18-7.13 (m, 1H), 7.08-7.04 (m, 1H), 6.95-6.90 (m, 3H), 3.85 (s, 3H); ESIMS m/z 257 ([M+H]$^+$).

(E)-2-Fluoro-4-(4-methoxystyryl)benzaldehyde (C329)

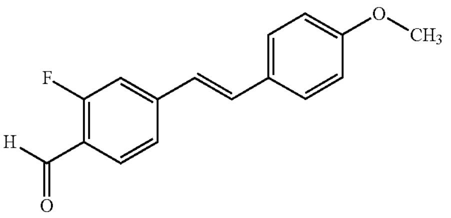 [SMILES: COc1ccc(/C=C/c2ccc(C=O)c(F)c2)cc1]

Isolated as a brown solid (15 g, 78%): $^1$H NMR (400 MHz, $CDCl_3$) δ 10.35 (s, 1H), 7.83 (t, J=7.6 Hz, 1H), 7.48 (d, J=8.8 Hz, 2H), 7.35 (d, J=8.4 Hz, 1H), 7.23-7.18 (m, 2H), 6.96-6.91 (m, 3H), 3.95 (s, 3H); $^{19}$F NMR (376 MHz, $CDCl_3$) δ 122.26; ESIMS m/z 257 ($[M+H]^+$).

(E)-3-(4-methoxystyryl)benzaldehyde (C330)

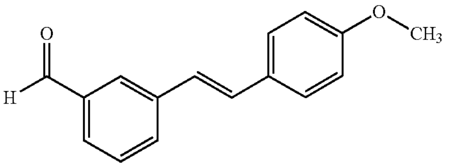 [SMILES: COc1ccc(/C=C/c2cccc(C=O)c2)cc1]

Isolated as a brown solid (18 g, 46%): $^1$H NMR (400 MHz, $CDCl_3$) δ 10.15 (s, 1H), 8.00 (s, 1H), 7.73 (d, J=7.2 Hz, 2H), 7.53-7.46 (m, 3H), 7.17 (d, J=16.8 Hz, 1H), 7.01 (d, J=16.0 Hz, 1H), 6.92 (d, J=8.8 Hz, 2H), 3.84 (s, 3H); ESIMS m/z 239 ($[M+H]^+$).

(E)-4-(4-Methoxystyryl)benzaldehyde (C331)

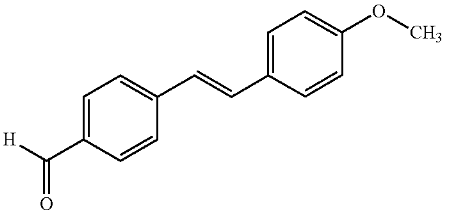 [SMILES: COc1ccc(/C=C/c2ccc(C=O)cc2)cc1]

Isolated as a light brown solid (9.0 g, 47%): $^1$H NMR (400 MHz, $CDCl_3$) δ 10 (s, 1H), 7.84 (d, J=8.0 Hz, 2H), 7.61 (d, J=7.6 Hz, 2H), 7.48 (d, J=8.0 Hz, 2H), 7.23 (t, J=7.6 Hz, 1H), 7.00 (d, J=16.0 Hz, 1H), 6.92 (d, J=8.8 Hz, 2H), 3.84 (s, 3H).

Example 52: Preparation of (E)-1-chloro-3-(difluoromethyl)-5-(4-methoxy-styryl)benzene (C332)

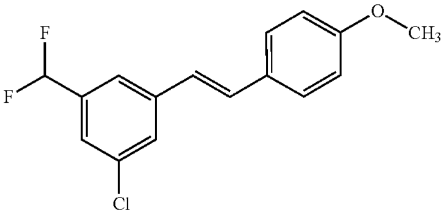

To a stirred solution of (E)-3-chloro-5-(4-methoxystyryl) benzaldehyde (C146) (13 g, 47.79 mmol) in dichloromethane (130 mL) was added diethylaminosulfur trifluoride (31.5 mL, 238.97 mmol) at −78° C. The resulting solution was stirred for 20 hours at room temperature. The reaction mixture was cooled to 0° C., and a solution of saturated aqueous sodium bicarbonate was added dropwise. The layers were separated and the aqueous layer was extracted with dichloromethane (3×75 mL). The combined organic layer was washed with water and brine, dried over sodium sulfate, and concentrated. The crude material was purified by flash column chromatography using 10-20% ethyl acetate in hexanes as the eluent to afford the title compound as a pale yellow oil (13.1 g, 94%): $^1$H NMR (400 MHz, $CDCl_3$) δ 7.55 (s, 1H), 7.45 (d, J=8.8 Hz, 3H), 7.34 (s, 1H), 7.10 (d, J=16 Hz, 1H), 6.90 (t, J=8.4 Hz, 3H), 6.61 (t, J=56.4 Hz, 1H), 3.80 (s, 3H); $^{19}$F NMR (376 MHz, $CDCl_3$) δ −111.72.

The following compounds were prepared in like manner to the procedure outlined in Example 52:

(E)-1-Chloro-2-(difluoromethyl)-4-(4-methoxystyryl)benzene (C333)

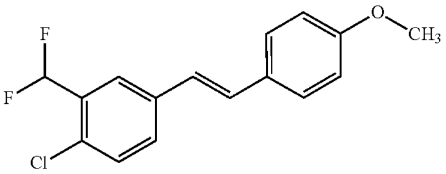

Isolated as an off-white solid (12 g, 94%): $^1$H NMR (300 MHz, $CDCl_3$) δ 7.75 (s, 1H), 7.51-7.44 (m, 3H), 7.37 (d, J=8.4 Hz, 1H), 7.13 (d, J=6.6 Hz, 1H), 7.06 (s, 1H), 6.95-6.89 (m, 3H), 3.95 (s, 3H); $^{19}$F NMR (282 MHz, $CDCl_3$) δ −115.31; ESIMS m/z 295 ($[M+H]^+$).

(E)-1-(Difluoromethyl)-3-fluoro-5-(4-methoxystyryl)benzene (C334)

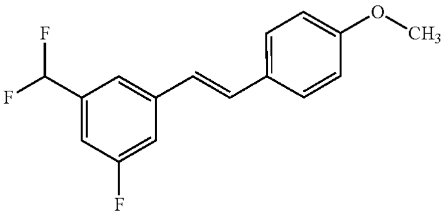

Isolated as an off-white solid (20 g, 75%); $^1$H NMR (300 MHz, $CDCl_3$) δ 7.46 (d, J=8.0 Hz, 2H), 7.38 (s, 1H), 7.28 (s, 1H), 7.08 (t, J=16.2 Hz, 2H), 6.92 (t, J=15.6 Hz, 3H), 6.63 (t, J=56.0 Hz, 1H), 3.84 (s, 3H); ESIMS m/z 279 ([M+H]$^+$).

(E)-2-(Difluoromethyl)-1-fluoro-4-(4-methoxystyryl)benzene (C335)

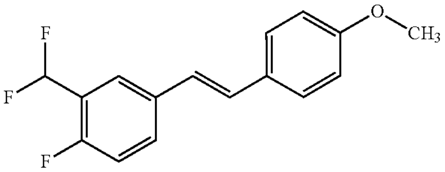 [SMILES: COc1ccc(/C=C/c2ccc(F)c(C(F)F)c2)cc1]

Isolated as an off-white solid (14.0 g, 70%): $^1$H NMR (300 MHz, $CDCl_3$) δ 7.69 (d, J=9.0 Hz, 1H), 7.57-7.53 (m, 1H), 7.45 (d, J=9.9 Hz, 2H), 7.13-7.06 (m, 2H), 7.00-6.89 (m, 4H), 3.85 (s, 3H); ESIMS m/z 279 ([M+H]$^+$).

(E)-2-Chloro-1-(difluoromethyl)-4-(4-methoxystyryl)benzene (C336)

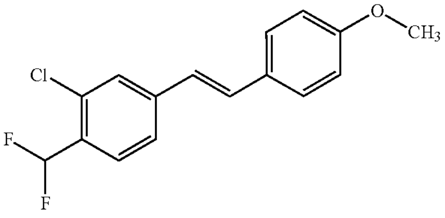 [SMILES: COc1ccc(/C=C/c2ccc(C(F)F)c(Cl)c2)cc1]

Isolated as an off-white solid (18.0 g, 90%): $^1$H NMR (400 MHz, $CDCl_3$) δ 7.61 (d, J=8.0 Hz, 1H), 7.51 (s, 1H), 7.47-7.43 (m, 3H), 7.14-7.07 (m, 1H), 6.94-6.80 (m, 4H), 3.85 (s, 3H); ESIMS m/z 294 ([M+H]$^+$).

(E)-1-(Difluoromethyl)-2-fluoro-4-(4-methoxystyryl)benzene (C337)

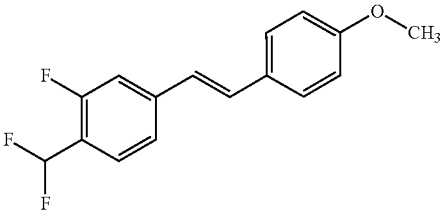 [SMILES: COc1ccc(/C=C/c2ccc(C(F)F)c(F)c2)cc1]

Isolated as a pale yellow solid (9 g, 55%): $^1$H NMR (400 MHz, $CDCl_3$) δ 7.54 (t, J=8.0 Hz, 1H), 7.46 (d, J=8.8 Hz, 2H), 7.32 (d, J=8.0 Hz, 1H), 7.22 (d, J=11.6 Hz, 1H), 7.11 (d, J=16.4 Hz, 1H), 7.01-6.83 (m, 4H), 3.95 (s, 3H); $^{19}$F NMR (376 MHz, $CDCl_3$) δ −113.57, −114.25, −120.33; ESIMS m/z 279 ([M+H]$^+$).

(E)-1-(Difluoromethyl)-3-(4-methoxystyryl)benzene (C338)

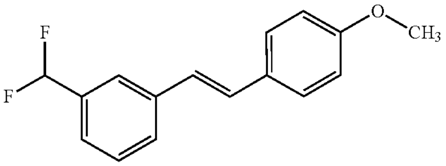 [SMILES: COc1ccc(/C=C/c2cccc(C(F)F)c2)cc1]

Isolated as a pale yellow solid (6 g, 68%): $^1$H NMR (300 MHz, $CDCl_3$) δ 7.62-7.56 (m, 2H), 7.48-7.34 (m, 4H), 7.11 (d, J=16.5 Hz, 1H), 7.00 (s, 1H), 6.95-6.89 (t, 2H), 6.66 (t, 1H), 3.95 (s, 3H); $^{19}$F NMR (282 MHz, $CDCl_3$) δ −110.84; ESIMS m/z 261 ([M+H]$^+$).

(E)-1-(Difluoromethyl)-4-(4-methoxystyryl)benzene (C339)

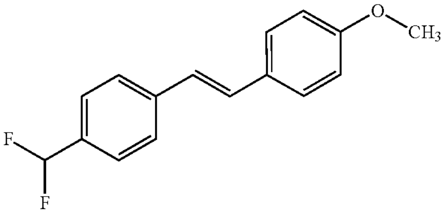

Isolated as an off-white solid (15.4 g, 75%): $^1$H NMR (300 MHz, $CDCl_3$) δ 7.57-7.45 (m, 6H), 7.12 (d, J=15.9 Hz, 1H), 7.00-6.89 (m, 3H), 6.64 (t, J=57 Hz, 1H), 3.92 (s, 3H); ESIMS m/z 260.17 ([M+H]$^+$).

Example 53: Preparation of trans-2-chloro-5-(2,2-dichloro-3-(3,5-dichlorophenyl)cyclopropane-1-carboxamido)benzamide (C340)

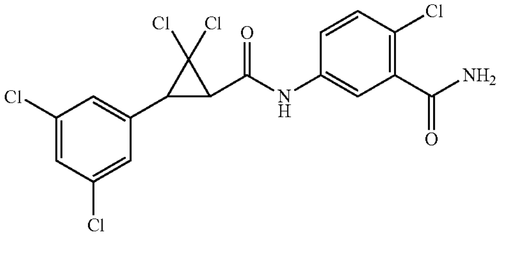 [SMILES: NC(=O)c1cc(NC(=O)C2C(c3cc(Cl)cc(Cl)c3)C2(Cl)Cl)ccc1Cl]

To a solution of 2-chloro-5-(2,2-dichloro-3-(3,5-dichlorophenyl)cyclopropane-1-carboxamido)benzoic acid (C67) (2 g, 4.41 mmol) and N-ethyl-N-isopropylpropan-2-amine (1.152 mL, 6.61 mmol) in tetrahydrofuran (29.4 mL) was added ethyl carbonochloridate (0.464 mL, 4.85 mmol). The reaction mixture was stirred at room temperature for 4 hours. Ammonia (0.5 M in dioxane, 17.64 mL, 8.82 mmol) was added, and the reaction mixture was stirred for 15 minutes. The reaction mixture was concentrated by rotary evaporation to give a pink foam. The foam was suspended in dichloromethane (15 mL) and stirred vigorously at 0° C. for 30 minutes to give a suspension. The solid was collected by vacuum filtration washing multiple times with dichloromethane to remove the pink color, affording the title compound as a white solid (1.79 g, 90%): $^1$H NMR (400 MHz, DMSO-$d_6$) δ 10.84 (s, 1H), 7.91 (s, 1H), 7.76 (d, J=2.6 Hz, 1H), 7.67 (dd, J=8.8, 2.6 Hz, 1H), 7.64-7.60 (m, 2H), 7.55 (d, J=1.8 Hz, 2H), 7.46 (d, J=8.7 Hz, 1H), 3.61 (d, J=8.6 Hz, 1H), 3.50 (d, J=8.5 Hz, 1H); ESIMS m/z 453 ($[M+H]^+$); IR (thin film) 3183, 1665, 1587, 1610, 1566, 1547, 1417 $cm^{-1}$.

Example 54: Preparation of trans-2-chloro-N-(2-cyano-4-nitrophenyl)-5-(2,2-dichloro-3-(3,5-dichlorophenyl)cyclopropane-1-carboxamido)benzamide (F229)

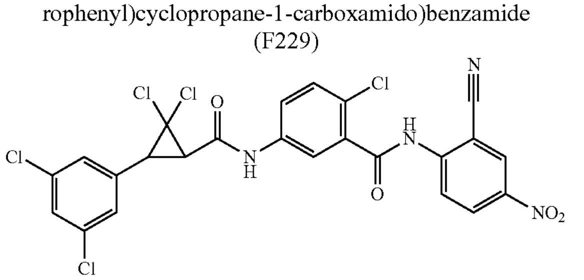

A suspension of 2-chloro-5-(2,2-dichloro-3-(3,5-dichlorophenyl)cyclopropane-1-carboxamido)benzamide (C340) (600 mg, 1.326 mmol), 2-bromo-5-nitrobenzonitrile (361 mg, 1.591 mmol), cesium carbonate (605 mg, 1.856 mmol), tris(dibenzylideneacetone)dipalladium(0) ($Pd_2(dba)_3$, 36.4 mg, 0.040 mmol), and Bis(diphenylphosphino)-9,9-dimethylxanthene (Xantphos, 69.0 mg, 0.119 mmol) in 1,4-dioxane (8.9 mL) was evacuated under vacuum and backfilled with nitrogen three times. The reaction mixture was sealed under a blanket of nitrogen and heated to 60° C. by microwave irradiation for 2 hours. The reaction mixture was diluted with ethyl acetate and filtered through Celite®. The solvent was removed via rotary evaporation to give a deep red solid. The solid was suspended in dichloromethane (10 mL) and then collected by vacuum filtration, washing with more dichloromethane to afford the title compound as a red solid (0.598 g, 75%): $^1$H NMR (400 MHz, Acetone-$d_6$) missing one amide NH in baseline δ 10.26 (s, 1H), 8.73 (d, J=2.6 Hz, 1H), 8.62 (dd, J=9.2, 2.6 Hz, 1H), 8.55 (d, J=9.2 Hz, 1H), 8.13 (d, J=2.6 Hz, 1H), 7.89 (dd, J=8.8, 2.6 Hz, 1H), 7.55 (d, J=8.8 Hz, 1H), 7.51 (s, 3H), 3.67 (d, J=8.3 Hz, 1H), 3.45 (d, J=8.3 Hz, 1H); HRMS-ESI (m/z) $[M+H]^+$ calcd for $C_{24}H_{14}C_{15}N_4O_4$, 596.9452; found, 596.9441; IR (thin film) 3341, 3074, 1673, 1568, 1545, 1509, 1473, 1413 $cm^{-1}$.

The following compounds were prepared in like manner to the procedure outlined in Example 54:

2-Chloro-N-(2-cyano-5-methylphenyl)-5-(trans-2,2-dichloro-3-(3,5-dichlorophenyl)cyclopropane-1-carboxamido)benzamide (F230)

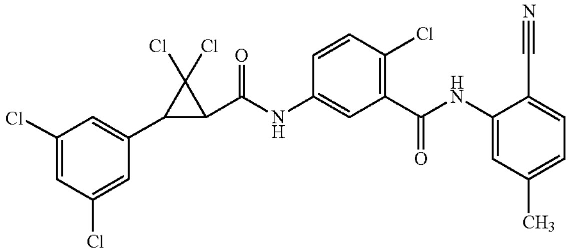 [SMILES: Cc1ccc(C#N)c(NC(=O)c2cc(NC(=O)C3C(c4cc(Cl)cc(Cl)c4)C3(Cl)Cl)ccc2Cl)c1]

Isolated as a white solid (0.1052 g, 84%).

2-Chloro-5-(trans-2,2-dichloro-3-(3,5-dichlorophenyl)cyclopropane-1-carboxamido)-N-(4-methyl-2-nitrophenyl)benzamide (F231)

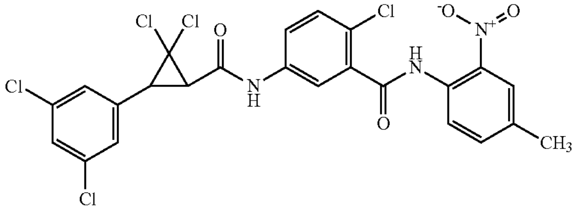

Isolated as a yellow foam (0.0302 g, 31%).

2-Chloro-N-(2-cyano-4-(trifluoromethyl)phenyl)-5-(trans-2,2-dichloro-3-(3,5-dichlorophenyl)cyclopropane-1-carboxamido)benzamide (F232)

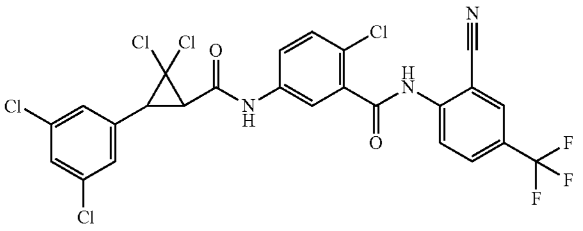 [SMILES: N#Cc1cc(C(F)(F)F)ccc1NC(=O)c1cc(NC(=O)C2C(c3cc(Cl)cc(Cl)c3)C2(Cl)Cl)ccc1Cl]

Isolated as an orange solid (0.0357 g, 35%).

2-Chloro-N-(4-cyano-3-fluorophenyl)-5-(trans-2,2-dichloro-3-(3,5-dichlorophenyl)cyclopropane-1-carboxamido)benzamide (F233)

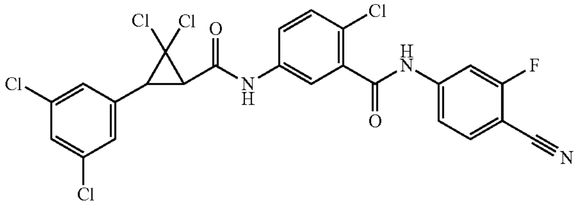 [SMILES: N#Cc1ccc(NC(=O)c2cc(NC(=O)C3C(c4cc(Cl)cc(Cl)c4)C3(Cl)Cl)ccc2Cl)cc1F]

Isolated as a pale yellow solid (0.0461 g, 49%).

2-Chloro-N-(4-cyano-3-methoxyphenyl)-5-(trans-2,2-dichloro-3-(3,5-dichlorophenyl)cyclopropane-1-carboxamido)benzamide (F234)

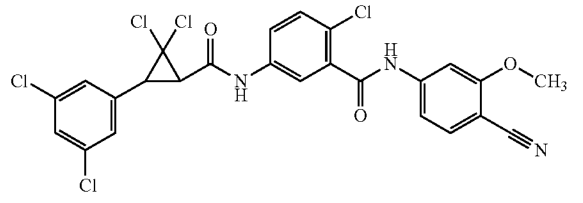 [SMILES: COc1cc(NC(=O)c2cc(NC(=O)C3C(c4cc(Cl)cc(Cl)c4)C3(Cl)Cl)ccc2Cl)ccc1C#N]

Isolated as a pale yellow solid (0.0151 g, 16%).

2-Chloro-N-(4-cyano-3-(trifluoromethyl)phenyl)-5-(trans-2,2-dichloro-3-(3,5-dichlorophenyl)cyclopropane-1-carboxamido)benzamide (F235)

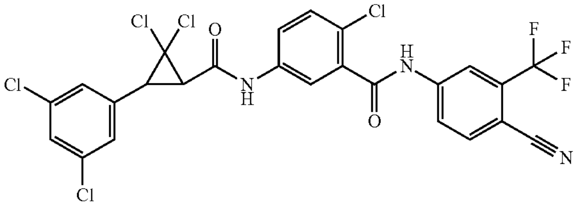 [SMILES: N#Cc1ccc(NC(=O)c2cc(NC(=O)C3C(c4cc(Cl)cc(Cl)c4)C3(Cl)Cl)ccc2Cl)cc1C(F)(F)F]

Isolated as a pale yellow solid (0.0644 g, 63%).

2-Chloro-N-(2-cyano-3-fluorophenyl)-5-(trans-2,2-dichloro-3-(3,5-dichlorophenyl)cyclopropane-1-carboxamido)benzamide (F298)

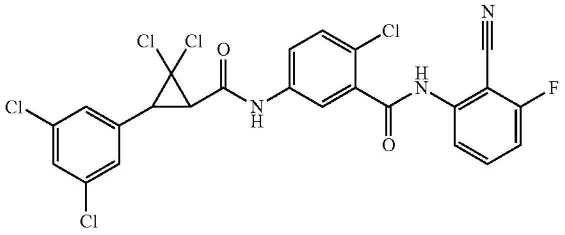 [SMILES: N#Cc1c(F)cccc1NC(=O)c1cc(NC(=O)C2C(c3cc(Cl)cc(Cl)c3)C2(Cl)Cl)ccc1Cl]

Isolated as a white solid (0.0893 g, 71%).

2-Chloro-N-(2-cyano-6-fluorophenyl)-5-(trans-2,2-dichloro-3-(3,5-dichlorophenyl)cyclopropane-1-carboxamido)benzamide (F299)

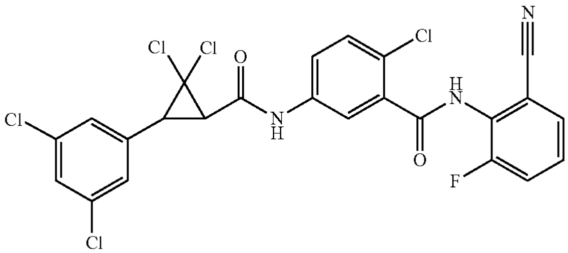 [SMILES: N#Cc1cccc(F)c1NC(=O)c1cc(NC(=O)C2C(c3cc(Cl)cc(Cl)c3)C2(Cl)Cl)ccc1Cl]

Isolated as a white solid (0.0823 g, 65%).

2-Chloro-N-(2-cyano-6-fluoro-4-methylphenyl)-5-(trans-2,2-dichloro-3-(3,5-dichlorophenyl)cyclopropane-1-carboxamido)benzamide (F300)

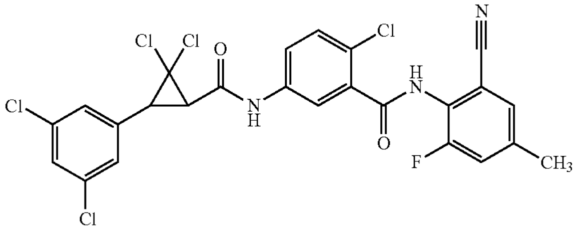 [SMILES: Cc1cc(F)c(NC(=O)c2cc(NC(=O)C3C(c4cc(Cl)cc(Cl)c4)C3(Cl)Cl)ccc2Cl)c(C#N)c1]

Isolated as a white solid (0.086 g, 67%).

2-Chloro-N-(4-chloro-2-cyanophenyl)-5-(trans-2,2-dichloro-3-(3,5-dichlorophenyl)cyclopropane-1-carboxamido)benzamide (F301)

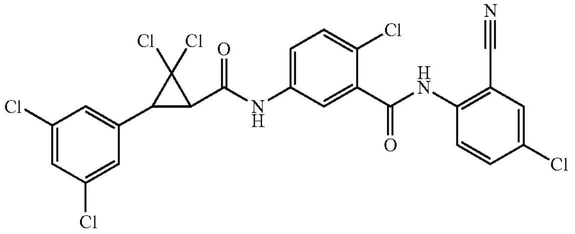 [SMILES: N#Cc1cc(Cl)ccc1NC(=O)c1cc(NC(=O)C2C(c3cc(Cl)cc(Cl)c3)C2(Cl)Cl)ccc1Cl]

Isolated as a white solid (0.098 g, 76%).

2-Chloro-N-(3-chloro-2-cyanophenyl)-5-(trans-2,2-dichloro-3-(3,5-dichlorophenyl)cyclopropane-1-carboxamido)benzamide (F302)

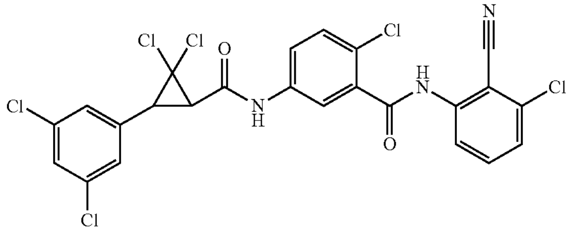 [SMILES: N#Cc1c(Cl)cccc1NC(=O)c1cc(NC(=O)C2C(c3cc(Cl)cc(Cl)c3)C2(Cl)Cl)ccc1Cl]

Isolated as a white solid (0.109 g, 84%).

N-(5-Bromo-2-cyanophenyl)-2-chloro-5-(trans-2,2-dichloro-3-(3,5-dichlorophenyl)cyclopropane-1-carboxamido)benzamide (F303)

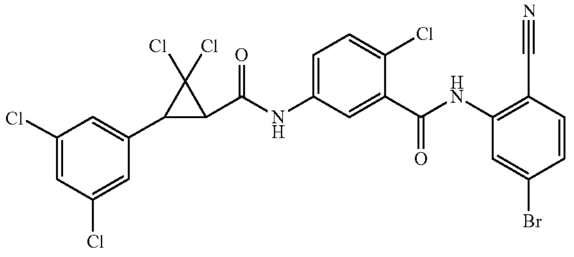 [SMILES: N#Cc1ccc(Br)cc1NC(=O)c1cc(NC(=O)C2C(c3cc(Cl)cc(Cl)c3)C2(Cl)Cl)ccc1Cl]

Isolated as a white solid (0.111 g, 80%).

2-Chloro-N-(2-cyano-3-methylphenyl)-5-(trans-2,2-dichloro-3-(3,5-dichlorophenyl)cyclopropane-1-carboxamido)benzamide (F304)

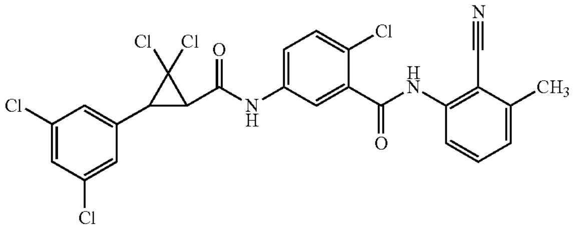 [SMILES: Cc1cccc(NC(=O)c2cc(NC(=O)C3C(c4cc(Cl)cc(Cl)c4)C3(Cl)Cl)ccc2Cl)c1C#N]

Isolated as a white solid (0.1072 g, 86%).

trans-2-Chloro-5-(2,2-dichloro-3-(3,5-dichlorophenyl)cyclopropane-1-carboxamido)-N-(2,4-dicyanophenyl)benzamide (F287)

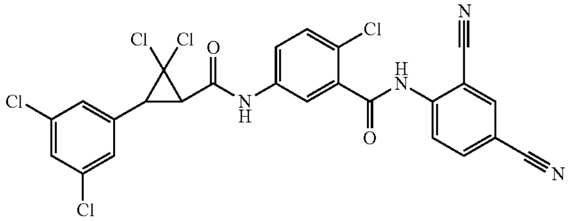 [SMILES: N#Cc1ccc(NC(=O)c2cc(NC(=O)C3C(c4cc(Cl)cc(Cl)c4)C3(Cl)Cl)ccc2Cl)c(C#N)c1]

Isolated as a tan solid (0.043 g, 33%).

Example 55: Preparation of trans-N-(5-bromo-1,3,4-thiadiazol-2-yl)-2-chloro-5-(2,2-dichloro-3-(3,5-dichlorophenyl)cyclopropane-1-carboxamido)benzamide (PF133)

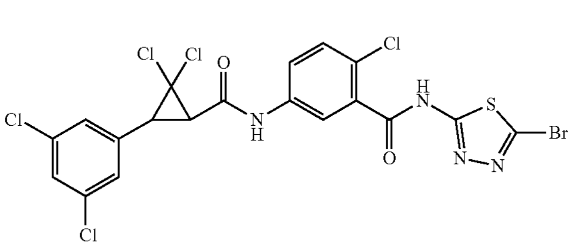 [SMILES: O=C(Nc1nnc(Br)s1)c1cc(NC(=O)C2C(c3cc(Cl)cc(Cl)c3)C2(Cl)Cl)ccc1Cl]

To a solution of trans-2-chloro-5-(2,2-dichloro-3-(3,5-dichlorophenyl)cyclopropane-1-carboxamido)benzoic acid (C67) (0.100 g, 0.220 mmol) and 5-bromo-1,3,4-thiadiazol-2-amine (0.040 g, 0.220 mmol) in ethyl acetate (2.0 mL) was added pyridine (0.036 mL, 0.441 mmol) followed by 2,4,6-tripropyl-1,3,5,2,4,6-trioxatriphosphinane 2,4,6-trioxide (T3P®) as a 50% solution in ethyl acetate (0.210 g, 0.331 mmol). The reaction mixture was stirred for 72 hours at room temperature. The reaction mixture was then diluted with ethyl acetate, and Celite® was added to the mixture. The solvents were removed under reduced pressure to give a dry powder which was subsequently purified by flash column chromatography using 0-35% ethyl acetate/hexanes as eluent to afford the title compound as a white solid (0.075 g, 55%).

The following compounds were prepared in like manner to the procedure outlined in Example 55:

trans-2-Chloro-5-(2,2-dichloro-3-(3,5-dichlorophenyl)cyclopropane-1-carboxamido)-N-(4-(thiophen-2-yl)thiazol-2-yl)benzamide (PF135)

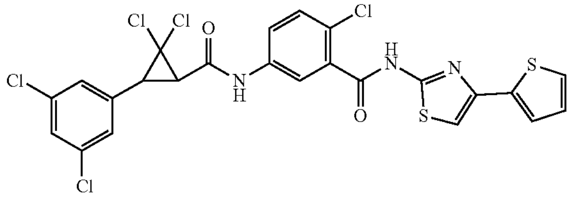 [SMILES: O=C(Nc1nc(-c2cccs2)cs1)c1cc(NC(=O)C2C(c3cc(Cl)cc(Cl)c3)C2(Cl)Cl)ccc1Cl]

Isolated as a white solid (0.046 g, 34%).

trans-2-Chloro-N-(5-cyanopyridin-2-yl)-5-(2,2-dichloro-3-(3,5-dichlorophenyl)cyclopropane-1-carboxamido)benzamide (PF143)

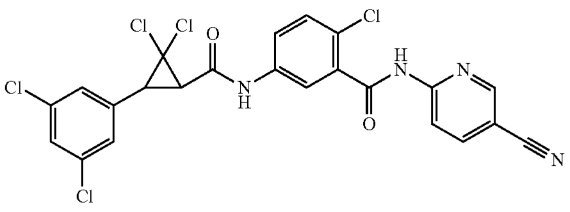 [SMILES: N#Cc1ccc(NC(=O)c2cc(NC(=O)C3C(c4cc(Cl)cc(Cl)c4)C3(Cl)Cl)ccc2Cl)nc1]

Isolated as a white solid (0.065 g, 53%).

trans-2-Chloro-5-(2,2-dichloro-3-(3,5-dichlorophenyl)cyclopropane-1-carboxamido)-N-(5-fluoropyrimidin-2-yl)benzamide (F222)

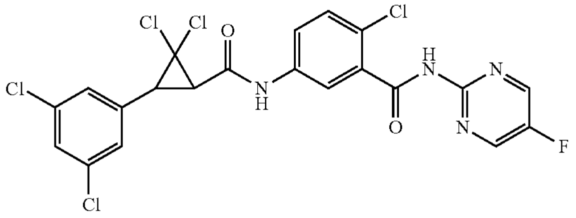 [SMILES: O=C(Nc1ncc(F)cn1)c1cc(NC(=O)C2C(c3cc(Cl)cc(Cl)c3)C2(Cl)Cl)ccc1Cl]

Isolated as a white solid (0.087 g, 72%).

trans-2-Chloro-5-(2,2-dichloro-3-(3,5-dichlorophenyl)cyclopropane-1-carboxamido)-N-(6-fluoropyridin-2-yl)benzamide (F240)

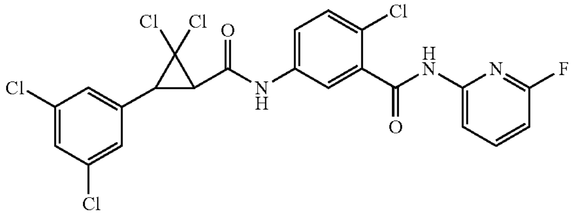 [SMILES: O=C(Nc1cccc(F)n1)c1cc(NC(=O)C2C(c3cc(Cl)cc(Cl)c3)C2(Cl)Cl)ccc1Cl]

Isolated as a white solid (0.104 g, 78%).

trans-2-Chloro-5-(2,2-dichloro-3-(3,5-dichlorophenyl)cyclopropane-1-carboxamido)-N-(3,5-difluoropyridin-2-yl)benzamide (F241)

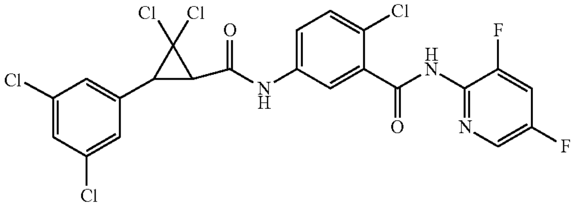 [SMILES: O=C(Nc1ncc(F)cc1F)c1cc(NC(=O)C2C(c3cc(Cl)cc(Cl)c3)C2(Cl)Cl)ccc1Cl]

Isolated as a white solid (0.106 g, 85%).

trans-2-Chloro-5-(2,2-dichloro-3-(3,5-dichlorophenyl)cyclopropane-1-carboxamido)-N-(5-fluoro-3-methylpyridin-2-yl)benzamide (F242)

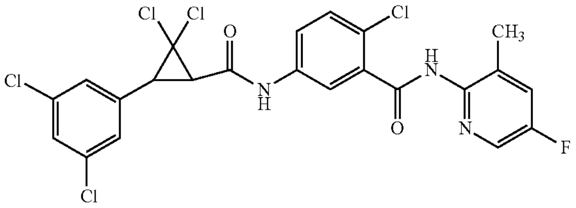 [SMILES: Cc1cc(F)cnc1NC(=O)c1cc(NC(=O)C2C(c3cc(Cl)cc(Cl)c3)C2(Cl)Cl)ccc1Cl]

Isolated as a white solid (0.103 g, 83%).

trans-2-Chloro-5-(2,2-dichloro-3-(3,5-dichlorophenyl)cyclopropane-1-carboxamido)-N-(pyrimidin-2-yl)benzamide (F294)

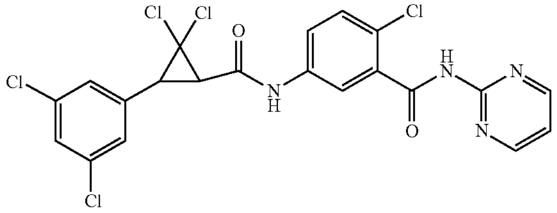 [SMILES: O=C(Nc1ncccn1)c1cc(NC(=O)C2C(c3cc(Cl)cc(Cl)c3)C2(Cl)Cl)ccc1Cl]

Isolated as a white solid (0.021 g, 18%).

trans-2-Chloro-5-(2,2-dichloro-3-(3,5-dichlorophenyl)cyclopropane-1-carboxamido)-N-(pyrimidin-5-yl)benzamide (F295)

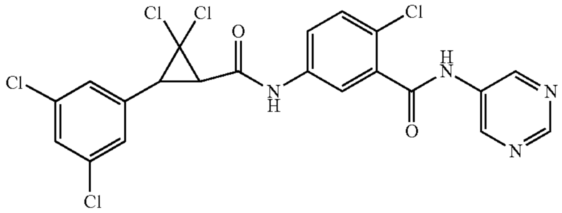 [SMILES: O=C(Nc1cncnc1)c1cc(NC(=O)C2C(c3cc(Cl)cc(Cl)c3)C2(Cl)Cl)ccc1Cl]

Isolated as a white solid (0.094 g, 80%).

trans-2-Chloro-5-(2,2-dichloro-3-(3,5-dichlorophenyl)cyclopropane-1-carboxamido)-N-(pyrimidin-4-yl)benzamide (F296)

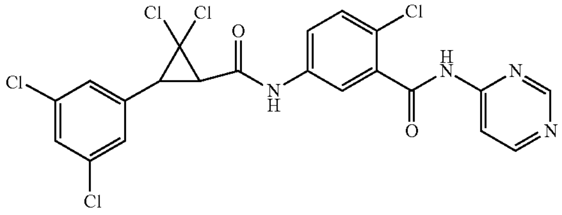 [SMILES: O=C(Nc1ccncn1)c1cc(NC(=O)C2C(c3cc(Cl)cc(Cl)c3)C2(Cl)Cl)ccc1Cl]

Isolated as a white solid (0.059 g, 51%).

trans-2-Chloro-5-(2,2-dichloro-3-(3,5-dichlorophenyl)cyclopropane-1-carboxamido)-N-(5-fluoro-4-methylpyridin-2-yl)benzamide (F297)

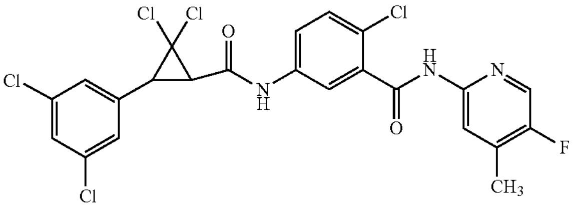 [SMILES: Cc1cc(NC(=O)c2cc(NC(=O)C3C(c4cc(Cl)cc(Cl)c4)C3(Cl)Cl)ccc2Cl)ncc1F]

Isolated as a white solid (0.105 g, 84%).

trans-2-Chloro-5-(2,2-dichloro-3-(3,5-dichlorophenyl)cyclopropane-1-carboxamido)-N-(5-fluoropyrimidin-4-yl)benzamide (F318)

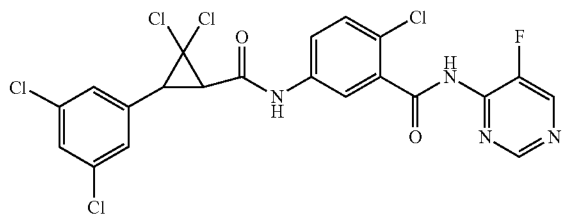 [SMILES: O=C(Nc1ncncc1F)c1cc(NC(=O)C2C(c3cc(Cl)cc(Cl)c3)C2(Cl)Cl)ccc1Cl]

Isolated as a white solid (0.030 g, 25%).

trans-N-(4-Amino-3,5-difluoropyridin-2-yl)-2-chloro-5-(2,2-dichloro-3-(3,5-dichlorophenyl)cyclopropane-1-carboxamido)benzamide (F345)

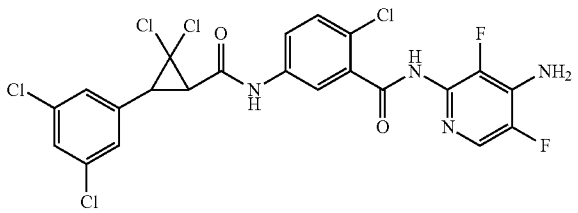 [SMILES: Nc1c(F)cnc(NC(=O)c2cc(NC(=O)C3C(c4cc(Cl)cc(Cl)c4)C3(Cl)Cl)ccc2Cl)c1F]

Isolated as a white solid (0.104 g, 65%).

trans-2-Chloro-5-(2,2-dichloro-3-(3,5-dichlorophenyl)cyclopropane-1-carboxamido)-N-(4-fluoro-2-nitrophenyl)benzamide (F348)

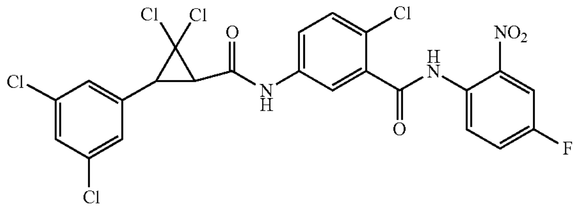

Isolated as a yellow glass (0.146 g, 67%).

N-(4-Amino-3,5-difluoropyridin-2-yl)-2-chloro-5-((1R,3R)-2,2-dichloro-3-(3,5-dichlorophenyl)cyclopropane-1-carboxamido)benzamide (F370)

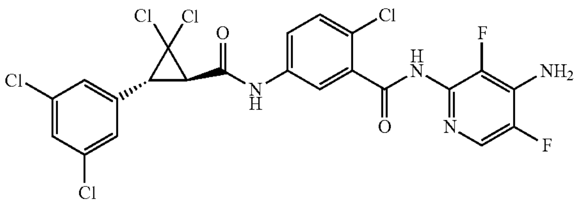 [SMILES: Nc1c(F)cnc(NC(=O)c2cc(NC(=O)[C@H]3[C@H](c4cc(Cl)cc(Cl)c4)C3(Cl)Cl)ccc2Cl)c1F]

Isolated as a white solid (0.064 g, 50%).

N-(4-Amino-3,5-difluoropyridin-2-yl)-2-chloro-5-((1R,3R)-2,2-dichloro-3-(3,4-dichlorophenyl)cyclopropane-1-carboxamido)benzamide (F371)

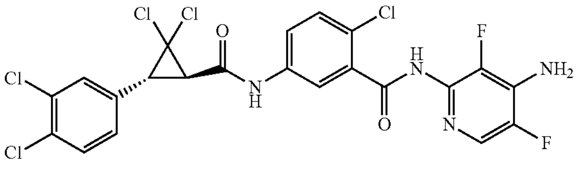 [SMILES: Nc1c(F)cnc(NC(=O)c2cc(NC(=O)[C@H]3[C@H](c4ccc(Cl)c(Cl)c4)C3(Cl)Cl)ccc2Cl)c1F]

Isolated as a white solid (0.062 g, 49%).

N-(4-Amino-3,5-difluoropyridin-2-yl)-2-chloro-5-((1R,3R)-2,2-dichloro-3-(3,4,5-trichlorophenyl)cyclopropane-1-carboxamido)benzamide (F372)

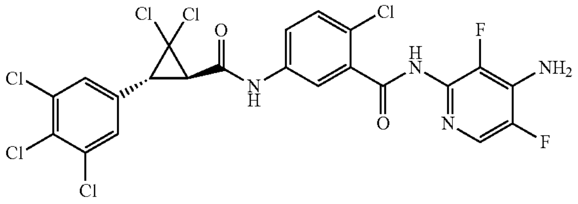 [SMILES: Nc1c(F)cnc(NC(=O)c2cc(NC(=O)[C@H]3[C@H](c4cc(Cl)c(Cl)c(Cl)c4)C3(Cl)Cl)ccc2Cl)c1F]

Isolated as a white solid (0.080 g, 63%).

tert-Butyl-N-((tert-butoxy)carbonyl)-N-(5-(2-chloro-5-((1R,3R)-2,2-dichloro-3-(3,5-dichlorophenyl)cyclopropane-1-carboxamido)benzamido)-2,4-difluorophenyl)carbamate (F519)

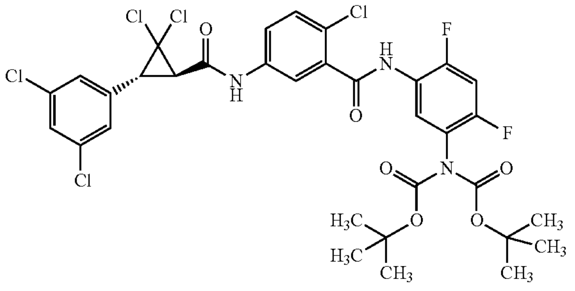 [SMILES: CC(C)(C)OC(=O)N(C(=O)OC(C)(C)C)c1cc(NC(=O)c2cc(NC(=O)[C@H]3[C@H](c4cc(Cl)cc(Cl)c4)C3(Cl)Cl)ccc2Cl)c(F)cc1F]

Isolated as a white solid (0.159 g, 92%).

tert-Butyl-N-((tert-butoxy)carbonyl)-N-(5-(2-chloro-5-((1R,3R)-2,2-dichloro-3-(3,4-dichlorophenyl)cyclopropane-1-carboxamido)benzamido)-2,4-difluorophenyl)carbamate (F520)

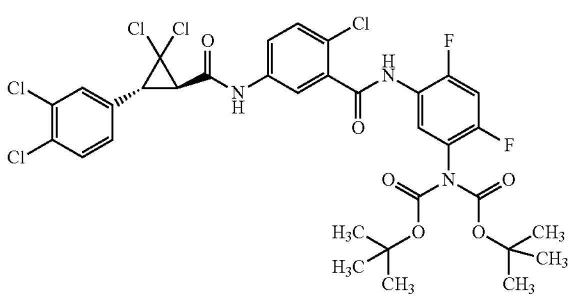 [SMILES: CC(C)(C)OC(=O)N(C(=O)OC(C)(C)C)c1cc(NC(=O)c2cc(NC(=O)[C@H]3[C@H](c4ccc(Cl)c(Cl)c4)C3(Cl)Cl)ccc2Cl)c(F)cc1F]

Isolated as a white solid (0.154 g, 90%).

tert-Butyl-N-((tert-butoxy)carbonyl)-N-(2-(2-chloro-5-((1R,3R)-2,2-dichloro-3-(3,5-dichlorophenyl)cyclopropane-1-carboxamido)benzamido)-4,6-difluorophenyl)carbamate (F521)

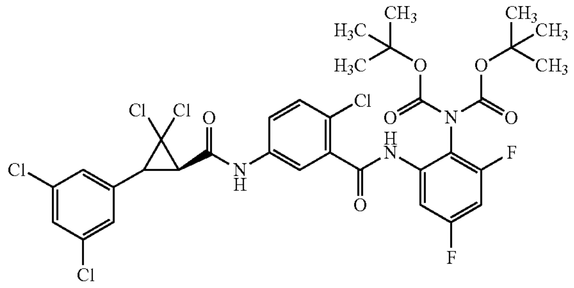 [SMILES: CC(C)(C)OC(=O)N(C(=O)OC(C)(C)C)c1c(F)cc(F)cc1NC(=O)c1cc(NC(=O)[C@H]2C(c3cc(Cl)cc(Cl)c3)C2(Cl)Cl)ccc1Cl]

Isolated as a white solid (0.112 g, 65%).

2-Chloro-5-((1R,3R)-2,2-dichloro-3-(3,5-dichlorophenyl)cyclopropane-1-carboxamido)-N-(4-fluoro-2-nitrophenyl)benzamide (F554)

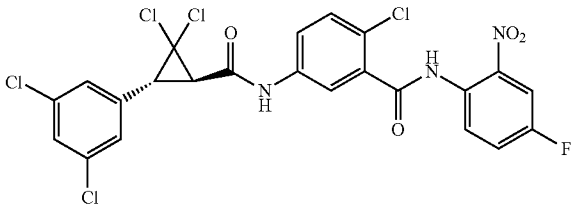

Isolated as a yellow film (0.127 g, 81%).

2-Chloro-5-((1R,3R)-2,2-dichloro-3-(3,4-dichlorophenyl)cyclopropane-1-carboxamido)-N-(4-fluoro-2-nitrophenyl)benzamide (F555)

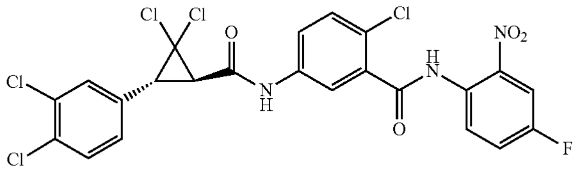 [SMILES: O=C(Nc1ccc(F)cc1[N+](=O)[O-])c1cc(NC(=O)[C@H]2[C@H](c3ccc(Cl)c(Cl)c3)C2(Cl)Cl)ccc1Cl]

Isolated as a yellow film (0.138 g, 88%).

2-Chloro-5-((1R,3R)-2,2-dichloro-3-(3,4,5-trichlorophenyl)cyclopropane-1-carboxamido)-N-(4-fluoro-2-nitrophenyl)benzamide (F556)

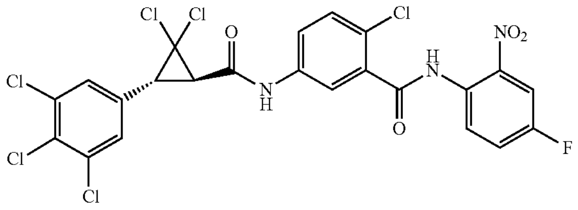

Isolated as a yellow film (0.115 g, 75%).

2-Chloro-5-((1R,3R)-2,2-dichloro-3-(3-chloro-4-fluorophenyl)cyclopropane-1-carboxamido)-N-(4-fluoro-2-nitrophenyl)benzamide (F557)

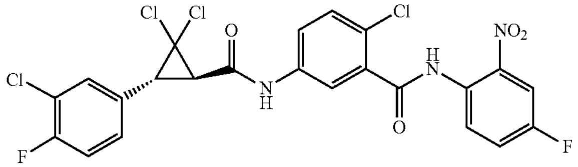

Isolated as a yellow film (0.128 g, 81%).

N-(3-Bromo-4,5-difluorophenyl)-2-chloro-5-((1R,3R)-2,2-dichloro-3-(3,5-dichlorophenyl)cyclopropane-1-carboxamido)benzamide (F583)

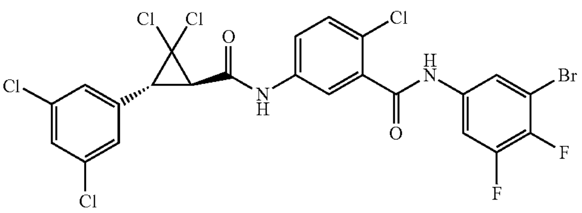 [SMILES: O=C(Nc1cc(F)c(F)c(Br)c1)c1cc(NC(=O)[C@H]2[C@H](c3cc(Cl)cc(Cl)c3)C2(Cl)Cl)ccc1Cl]

Isolated as a white foam (0.188 g, 88%).

tert-Butyl-N-((tert-butoxy)carbonyl)-N-(5-(2-chloro-5-((1R,3R)-2,2-dichloro-3-(3,4,5-trichlorophenyl)cyclopropane-1-carboxamido)benzamido)-2,4-difluorophenyl)carbamate (F610)

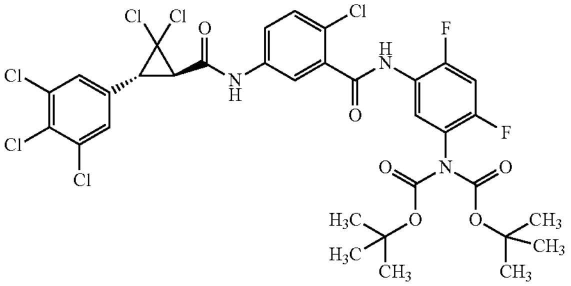 [SMILES: CC(C)(C)OC(=O)N(C(=O)OC(C)(C)C)c1cc(NC(=O)c2cc(NC(=O)[C@H]3[C@H](c4cc(Cl)c(Cl)c(Cl)c4)C3(Cl)Cl)ccc2Cl)c(F)cc1F]

Isolated as a white solid (0.138 g, 83%).

tert-Butyl-N-((tert-butoxy)carbonyl)-N-(5-(2-chloro-5-((1R,3R)-2,2-dichloro-3-(3-chloro-4-fluorophenyl)cyclopropane-1-carboxamido)benzamido)-2,4-difluorophenyl)carbamate (F611)

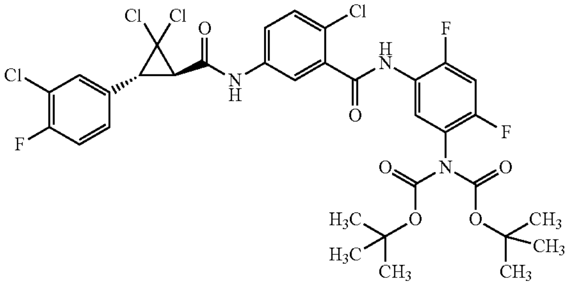 [SMILES: CC(C)(C)OC(=O)N(C(=O)OC(C)(C)C)c1cc(NC(=O)c2cc(NC(=O)[C@H]3[C@H](c4ccc(F)c(Cl)c4)C3(Cl)Cl)ccc2Cl)c(F)cc1F]

Isolated as a white solid (0.164 g, 94%).

tert-Butyl-N-((tert-butoxy)carbonyl)-N-(2-(2-chloro-5-((1R,3R)-2,2-dichloro-3-(3,4,5-trichlorophenyl)cyclopropane-1-carboxamido)benzamido)-4,6-difluorophenyl)carbamate (F612)

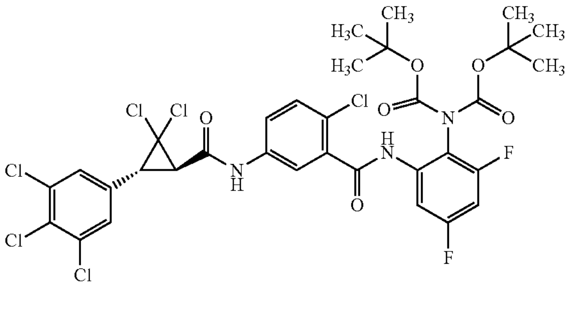 [SMILES: CC(C)(C)OC(=O)N(C(=O)OC(C)(C)C)c1c(F)cc(F)cc1NC(=O)c1cc(NC(=O)[C@H]2[C@H](c3cc(Cl)c(Cl)c(Cl)c3)C2(Cl)Cl)ccc1Cl]

Isolated as a white solid (0.090 g, 38%).

tert-Butyl-N-((tert-butoxy)carbonyl)-N-(2-(2-chloro-5-((1R,3R)-2,2-dichloro-3-(3,4,5-trichlorophenyl)cyclopropane-1-carboxamido)benzamido)-4-fluorophenyl)carbamate (F613)

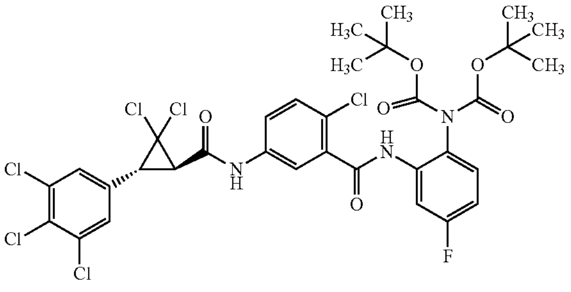 [SMILES: CC(C)(C)OC(=O)N(C(=O)OC(C)(C)C)c1ccc(F)cc1NC(=O)c1cc(NC(=O)[C@H]2[C@H](c3cc(Cl)c(Cl)c(Cl)c3)C2(Cl)Cl)ccc1Cl]

Isolated as a white solid (0.075 g, 46%).

tert-Butyl-N-((tert-butoxy)carbonyl)-N-(2-(2-chloro-5-((1R,3R)-2,2-dichloro-3-(3,5-dichlorophenyl)cyclopropane-1-carboxamido)benzamido)-3,5-difluorophenyl)carbamate (F614)

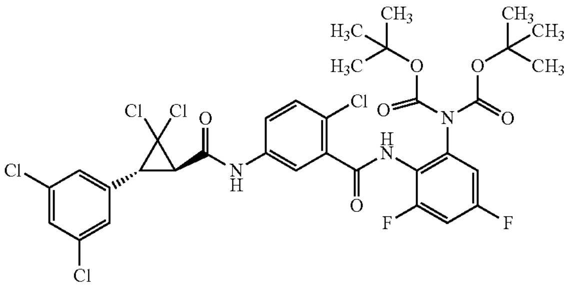 [SMILES: CC(C)(C)OC(=O)N(C(=O)OC(C)(C)C)c1cc(F)cc(F)c1NC(=O)c1cc(NC(=O)[C@H]2[C@H](c3cc(Cl)cc(Cl)c3)C2(Cl)Cl)ccc1Cl]

Isolated as a white solid (0.065 g, 23%).

tert-Butyl-N-((tert-butoxy)carbonyl)-N-(2-(2-chloro-5-((1R,3R)-2,2-dichloro-3-(3,4,5-trichlorophenyl)cyclopropane-1-carboxamido)benzamido)-3,5-difluorophenyl)carbamate (F615)

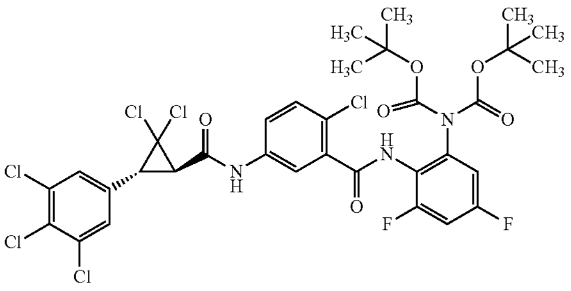 [SMILES: CC(C)(C)OC(=O)N(C(=O)OC(C)(C)C)c1cc(F)cc(F)c1NC(=O)c1cc(NC(=O)[C@H]2[C@H](c3cc(Cl)c(Cl)c(Cl)c3)C2(Cl)Cl)ccc1Cl]

Isolated as a white solid (0.032 g, 19%).

N-(6-Amino-5-cyanopyridin-2-yl)-2-chloro-5-(trans-2,2-dichloro-3-(3,5-dichlorophenyl)cyclopropane-1-carboxamido)benzamide (F292)

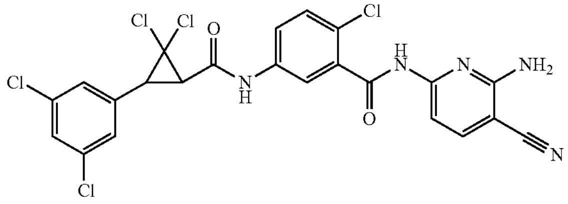 [SMILES: N#Cc1ccc(NC(=O)c2cc(NC(=O)C3C(c4cc(Cl)cc(Cl)c4)C3(Cl)Cl)ccc2Cl)nc1N]

Isolated as a white solid (0.0295 g, 16%).

2-Chloro-5-(trans-2,2-dichloro-3-(3,5-dichlorophenyl)cyclopropane-1-carboxamido)-N-(5-nitropyridin-2-yl)benzamide (F293)

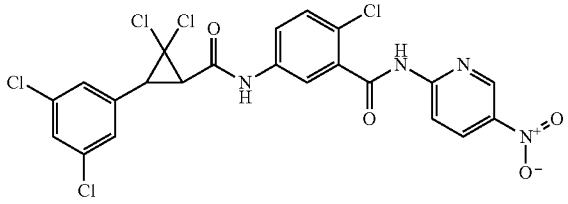 [SMILES: O=C(Nc1ccc([N+](=O)[O-])cn1)c1cc(NC(=O)C2C(c3cc(Cl)cc(Cl)c3)C2(Cl)Cl)ccc1Cl]

Isolated as a white solid (0.0753 mg, 70%).

N-(5-Bromo-6-fluoropyridin-2-yl)-2-chloro-5-(trans-2,2-dichloro-3-(3,5-dichlorophenyl)cyclopropane-1-carboxamido)benzamide (F357)

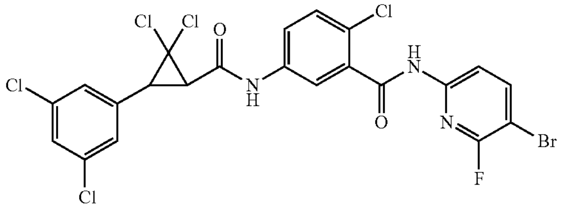

Isolated as a white solid (0.228 g, 83%).

2-Chloro-5-((1R,3R)-2,2-dichloro-3-(3,5-dichlorophenyl)cyclopropane-1-carboxamido)-N-(5-nitropyridin-3-yl)benzamide (F358)

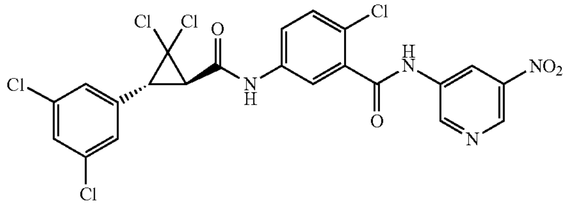 [SMILES: O=C(Nc1cncc([N+](=O)[O-])c1)c1cc(NC(=O)[C@H]2[C@H](c3cc(Cl)cc(Cl)c3)C2(Cl)Cl)ccc1Cl]

Isolated as a white solid (0.158 g, 83%).

2-Chloro-5-((1R,3R)-2,2-dichloro-3-(3,4-dichlorophenyl)cyclopropane-1-carboxamido)-N-(5-nitropyridin-3-yl)benzamide (F359)

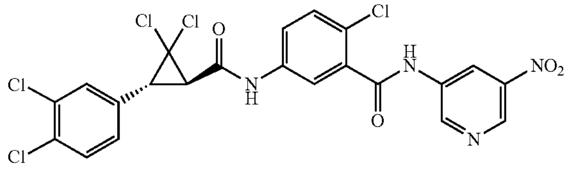 [SMILES: O=C(Nc1cncc([N+](=O)[O-])c1)c1cc(NC(=O)[C@H]2[C@H](c3ccc(Cl)c(Cl)c3)C2(Cl)Cl)ccc1Cl]

Isolated as a white solid (0.166 g, 87%).

2-Chloro-N-(2-chloropyridin-4-yl)-5-((1R,3R)-2,2-dichloro-3-(3,5-dichlorophenyl)cyclopropane-1-carboxamido)benzamide (F368)

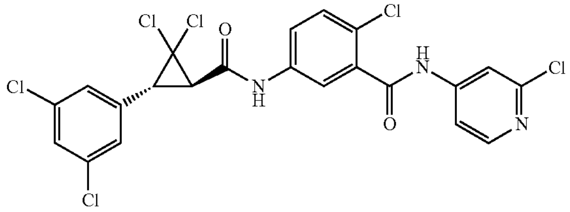 [SMILES: O=C(Nc1ccnc(Cl)c1)c1cc(NC(=O)[C@H]2[C@H](c3cc(Cl)cc(Cl)c3)C2(Cl)Cl)ccc1Cl]

Isolated as a white solid (0.137 g, 73%).

2-Chloro-N-(2-chloropyridin-4-yl)-5-((1R,3R)-2,2-dichloro-3-(3,4-dichlorophenyl)cyclopropane-1-carboxamido)benzamide (F369)

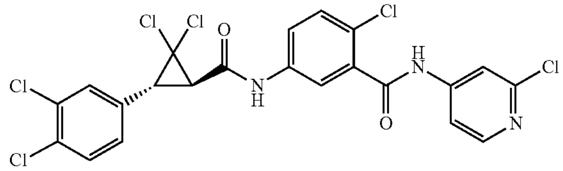 [SMILES: O=C(Nc1ccnc(Cl)c1)c1cc(NC(=O)[C@H]2[C@H](c3ccc(Cl)c(Cl)c3)C2(Cl)Cl)ccc1Cl]

Isolated as a white solid (0.152 g, 81%).

2-Chloro-5-(trans-2,2-dichloro-3-(3,5-dichlorophenyl)cyclopropane-1-carboxamido)-N-(3,5-difluoro-4-iodopyridin-2-yl)benzamide (F388)

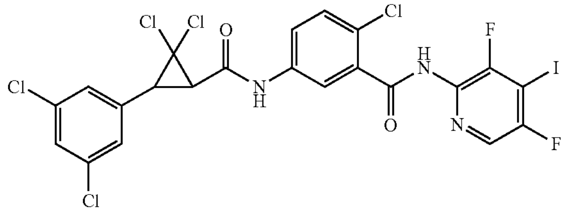 [SMILES: O=C(Nc1ncc(F)c(I)c1F)c1cc(NC(=O)C2C(c3cc(Cl)cc(Cl)c3)C2(Cl)Cl)ccc1Cl]

Isolated as a brown solid (0.253 g, 83%).

N-(5-Bromo-6-fluoropyridin-3-yl)-2-chloro-5-(trans-2,2-dichloro-3-(3,5-dichlorophenyl)cyclopropane-1-carboxamido)benzamide (F395)

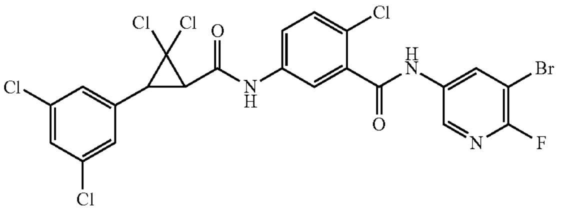 [SMILES: O=C(Nc1cnc(F)c(Br)c1)c1cc(NC(=O)C2C(c3cc(Cl)cc(Cl)c3)C2(Cl)Cl)ccc1Cl]

Isolated as a white solid (0.210 g, 76%).

2-Chloro-5-(trans-2,2-dichloro-3-(3,5-dichlorophenyl)cyclopropane-1-carboxamido)-N-(6-fluoro-5-methylpyridin-3-yl)benzamide (F396)

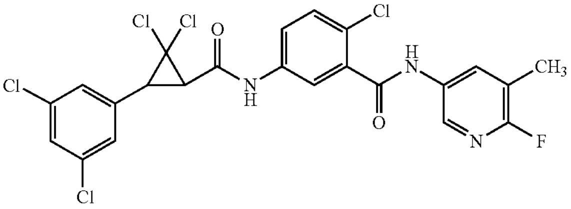 [SMILES: Cc1cc(NC(=O)c2cc(NC(=O)C3C(c4cc(Cl)cc(Cl)c4)C3(Cl)Cl)ccc2Cl)cnc1F]

Isolated as a white foam (0.217 g, 88%).

N-(6-Acetamidopyridin-2-yl)-2-chloro-5-(trans-2,2-dichloro-3-(3,5-dichlorophenyl)cyclopropane-1-carboxamido)benzamide (F494)

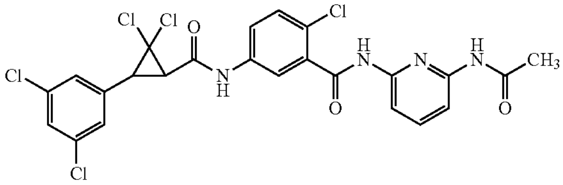 [SMILES: CC(=O)Nc1cccc(NC(=O)c2cc(NC(=O)C3C(c4cc(Cl)cc(Cl)c4)C3(Cl)Cl)ccc2Cl)n1]

Isolated as a white solid (0.137 g, 71%).

tert-Butyl (6-(2-chloro-5-(trans-2,2-dichloro-3-(3,5-dichlorophenyl)cyclopropane-1-carboxamido)benzamido)pyridin-2-yl)carbamate (F505)

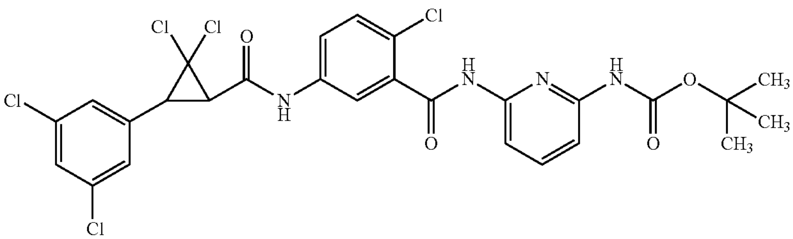 [SMILES: CC(C)(C)OC(=O)Nc1cccc(NC(=O)c2cc(NC(=O)C3C(c4cc(Cl)cc(Cl)c4)C3(Cl)Cl)ccc2Cl)n1]

Isolated as a white solid (0.271 g, 84%).

tert-Butyl (6-(2-chloro-5-(trans-2,2-dichloro-3-(3-chloro-4-fluorophenyl)cyclopropane-1-carboxamido)benzamido)pyridin-2-yl)carbamate (F506)

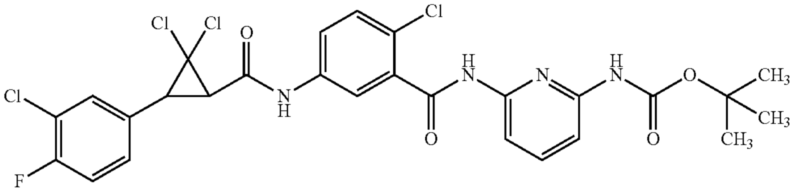 [SMILES: CC(C)(C)OC(=O)Nc1cccc(NC(=O)c2cc(NC(=O)C3C(c4ccc(F)c(Cl)c4)C3(Cl)Cl)ccc2Cl)n1]

Isolated as a white solid (0.229 g, 73%).

tert-Butyl (6-(2-chloro-5-(trans-2,2-dichloro-3-(3,5-dichlorophenyl)cyclopropane-1-carboxamido)benzamido)-4-(trifluoromethyl)pyridin-2-yl)carbamate (F507)

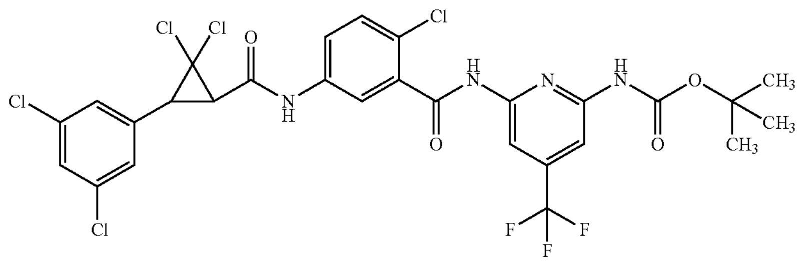 [SMILES: CC(C)(C)OC(=O)Nc1cc(C(F)(F)F)cc(NC(=O)c2cc(NC(=O)C3C(c4cc(Cl)cc(Cl)c4)C3(Cl)Cl)ccc2Cl)n1]

Isolated as a white solid (0.266 g, 75%).

tert-Butyl (6-(2-chloro-5-(trans-2,2-dichloro-3-(3-chloro-4-fluorophenyl)cyclopropane-1-carboxamido)benzamido)-4-(trifluoromethyl)pyridin-2-yl)carbamate (F508)

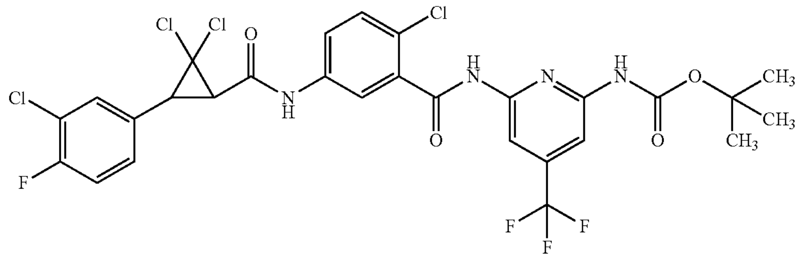 [SMILES: CC(C)(C)OC(=O)Nc1cc(C(F)(F)F)cc(NC(=O)c2cc(NC(=O)C3C(c4ccc(F)c(Cl)c4)C3(Cl)Cl)ccc2Cl)n1]

Isolated as a white solid (0.282 g, 81%).

N-(4-(Benzylamino)-3,5-difluoropyridin-2-yl)-2-chloro-5-((1R,3R)-2,2-dichloro-3-(3,5-dichlorophenyl)cyclopropane-1-carboxamido)benzamide (F524)

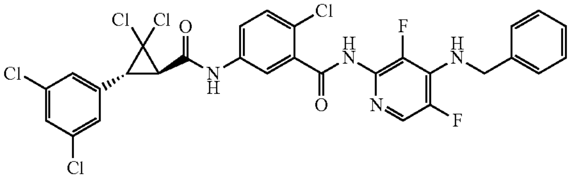 [SMILES: O=C(Nc1ncc(F)c(NCc2ccccc2)c1F)c1cc(NC(=O)[C@H]2[C@H](c3cc(Cl)cc(Cl)c3)C2(Cl)Cl)ccc1Cl]

Isolated as a tan solid (0.0423 g, 17%).

2-Chloro-5-(trans-2,2-dichloro-3-(3,5-dichlorophenyl)cyclopropane-1-carboxamido)-N-(2-methoxypyridin-4-yl)benzamide (F544)

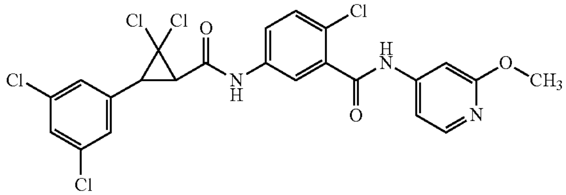 [SMILES: COc1cc(NC(=O)c2cc(NC(=O)C3C(c4cc(Cl)cc(Cl)c4)C3(Cl)Cl)ccc2Cl)ccn1]

Isolated as a white solid (0.022 g, 15%).

2-Chloro-5-(trans-2,2-dichloro-3-(3-chloro-4-fluorophenyl)cyclopropane-1-carboxamido)-N-(2-methoxypyridin-4-yl)benzamide (F545)

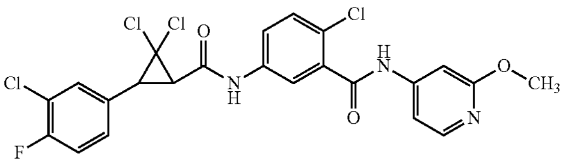 [SMILES: COc1cc(NC(=O)c2cc(NC(=O)C3C(c4ccc(F)c(Cl)c4)C3(Cl)Cl)ccc2Cl)ccn1]

Isolated as a white solid (0.021 g, 15%).

2-Chloro-N-(3-chloro-2-methoxypyridin-4-yl)-5-(trans-2,2-dichloro-3-(3,5-dichlorophenyl)cyclopropane-1-carboxamido)benzamide (F546)

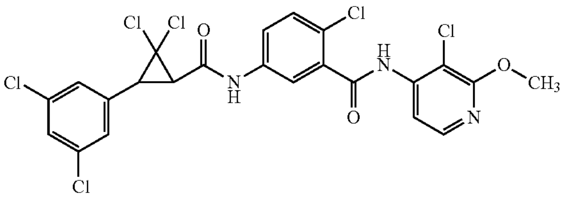 [SMILES: COc1nccc(NC(=O)c2cc(NC(=O)C3C(c4cc(Cl)cc(Cl)c4)C3(Cl)Cl)ccc2Cl)c1Cl]

Isolated as a white solid (0.078 g, 54%).

2-Chloro-N-(3-chloro-2-methoxypyridin-4-yl)-5-(trans-2,2-dichloro-3-(3-chloro-4-fluorophenyl)cyclopropane-1-carboxamido)benzamide (F547)

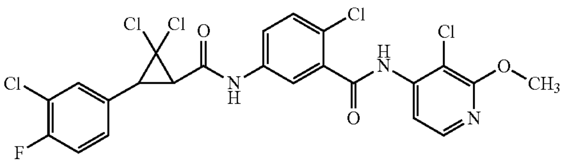 [SMILES: COc1nccc(NC(=O)c2cc(NC(=O)C3C(c4ccc(F)c(Cl)c4)C3(Cl)Cl)ccc2Cl)c1Cl]

Isolated as a white foam (0.081 g, 58%).

N-(5-Bromo-2-methoxypyridin-4-yl)-2-chloro-5-(trans-2,2-dichloro-3-(3,5-dichlorophenyl)cyclopropane-1-carboxamido)benzamide (F548)

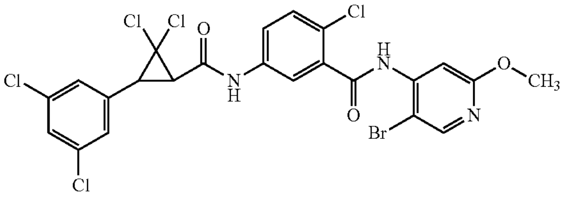 [SMILES: COc1cc(NC(=O)c2cc(NC(=O)C3C(c4cc(Cl)cc(Cl)c4)C3(Cl)Cl)ccc2Cl)c(Br)cn1]

Isolated as a white foam (0.057 g, 37%).

N-(5-Bromo-2-methoxypyridin-4-yl)-2-chloro-5-(trans-2,2-dichloro-3-(3-chloro-4-fluorophenyl)cyclopropane-1-carboxamido)benzamide (F549)

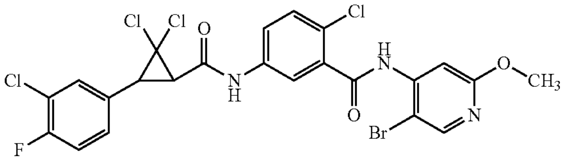 [SMILES: COc1cc(NC(=O)c2cc(NC(=O)C3C(c4ccc(F)c(Cl)c4)C3(Cl)Cl)ccc2Cl)c(Br)cn1]

Isolated as an oil (0.045 g, 30%).

2-Chloro-5-(trans-2,2-dichloro-3-(3,5-dichlorophenyl)cyclopropane-1-carboxamido)-N-(6-methoxypyridin-3-yl)benzamide (F550)

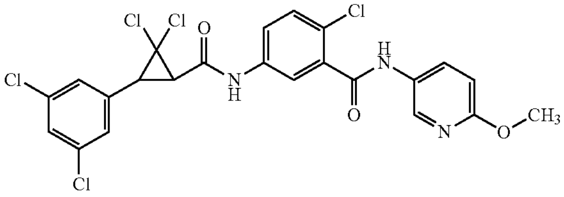 [SMILES: COc1ccc(NC(=O)c2cc(NC(=O)C3C(c4cc(Cl)cc(Cl)c4)C3(Cl)Cl)ccc2Cl)cn1]

Isolated as a beige solid (0.067 g, 50%).

2-Chloro-5-(trans-2,2-dichloro-3-(3-chloro-4-fluorophenyl)cyclopropane-1-carboxamido)-N-(6-methoxypyridin-3-yl)benzamide (F551)

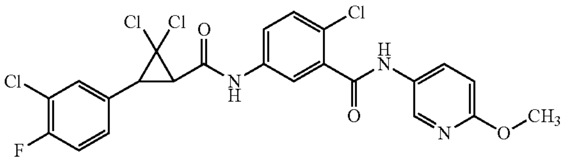 [SMILES: COc1ccc(NC(=O)c2cc(NC(=O)C3C(c4ccc(F)c(Cl)c4)C3(Cl)Cl)ccc2Cl)cn1]

Isolated as a yellow foam (0.040 g, 31%).

2-Chloro-N-(2-chloro-6-methoxypyridin-3-yl)-5-(trans-2,2-dichloro-3-(3,5-dichlorophenyl)cyclopropane-1-carboxamido)benzamide (F552)

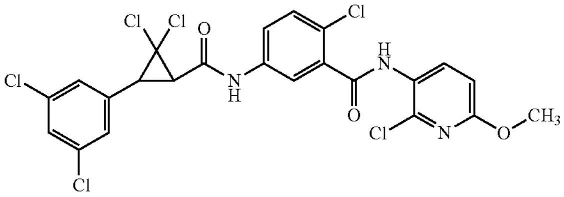 [SMILES: COc1ccc(NC(=O)c2cc(NC(=O)C3C(c4cc(Cl)cc(Cl)c4)C3(Cl)Cl)ccc2Cl)c(Cl)n1]

Isolated as a white solid (0.128 g, 89%).

2-Chloro-N-(2-chloro-6-methoxypyridin-3-yl)-5-(trans-2,2-dichloro-3-(3-chloro-4-fluorophenyl)cyclopropane-1-carboxamido)benzamide (F553)

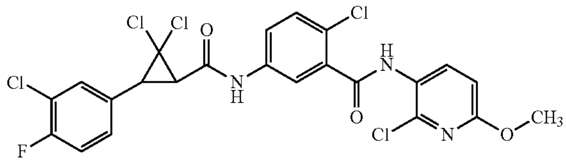 [SMILES: COc1ccc(NC(=O)c2cc(NC(=O)C3C(c4ccc(F)c(Cl)c4)C3(Cl)Cl)ccc2Cl)c(Cl)n1]

Isolated as a beige solid (0.117 g, 84%).

2-Chloro-5-((1R,3R)-2,2-dichloro-3-(3,5-dichlorophenyl)cyclopropane-1-carboxamido)-N-(3-fluoro-5-nitrophenyl)benzamide (F415)

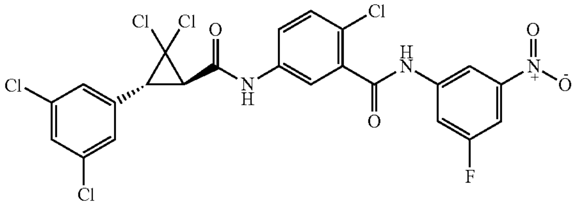

Isolated as a light yellow foam (0.11 g, 83%).

2-Chloro-5-((1R,3R)-2,2-dichloro-3-(3,4-dichlorophenyl)cyclopropane-1-carboxamido)-N-(3-fluoro-5-nitrophenyl)benzamide (F416)

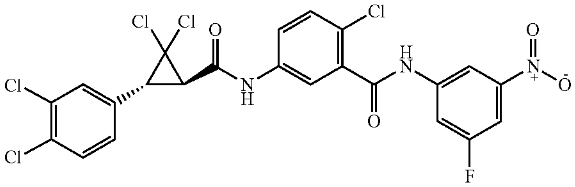

Isolated as a light grey foam (0.114 g, 86%).

2-Chloro-5-((1R,3R)-2,2-dichloro-3-(3,4,5-trichlorophenyl)cyclopropane-1-carboxamido)-N-(3-fluoro-5-nitrophenyl)benzamide (F417)

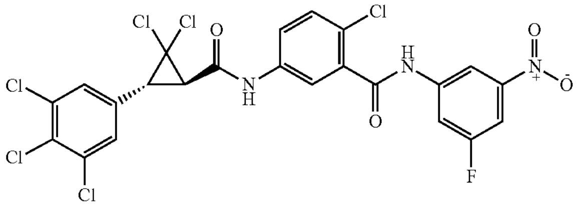

Isolated as a yellow foam (0.114 g, 87%).

2-Chloro-5-((1R,3R)-2,2-dichloro-3-(3-chloro-4-fluorophenyl)cyclopropane-1-carboxamido)-N-(3-fluoro-5-nitrophenyl)benzamide (F418)

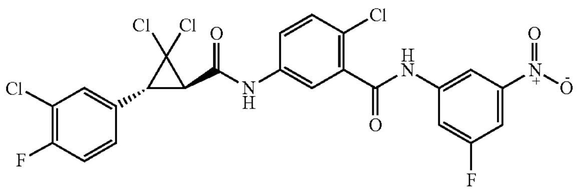

Isolated as an off-white foam (0.101 g, 75%).

trans-2-Chloro-5-(2,2-dichloro-3-(3,5-dichlorophenyl)cyclopropane-1-carboxamido)-N-(1,3-dioxoisoindolin-5-yl)benzamide (F439)

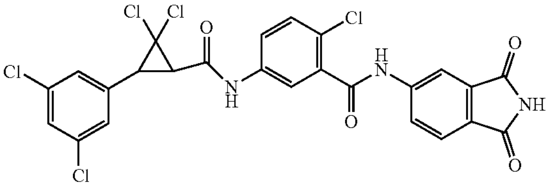 [SMILES: O=C(Nc1ccc2c(c1)C(=O)NC2=O)c1cc(NC(=O)C2C(c3cc(Cl)cc(Cl)c3)C2(Cl)Cl)ccc1Cl]

Isolated as a light orange solid (0.260 g, 78%).

trans-tert-Butyl-N-((tert-butoxy)carbonyl)-N-(3-(2-chloro-5-(2,2-dichloro-3-(3,5-dichlorophenyl)cyclopropane-1-carboxamido)benzamido)-2,6-difluorophenyl)carbamate (F468)

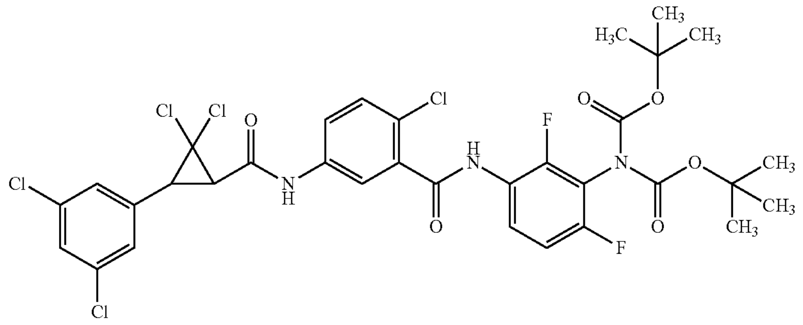 [SMILES: CC(C)(C)OC(=O)N(C(=O)OC(C)(C)C)c1c(F)ccc(NC(=O)c2cc(NC(=O)C3C(c4cc(Cl)cc(Cl)c4)C3(Cl)Cl)ccc2Cl)c1F]

Isolated as an off-white solid (0.166 g, 44%).

trans-tert-Butyl-N-((tert-butoxy)carbonyl)-N-(5-(2-chloro-5-(2,2-dichloro-3-(3,5-dichlorophenyl)cyclopropane-1-carboxamido)benzamido)-2-fluorophenyl) carbamate (F470)

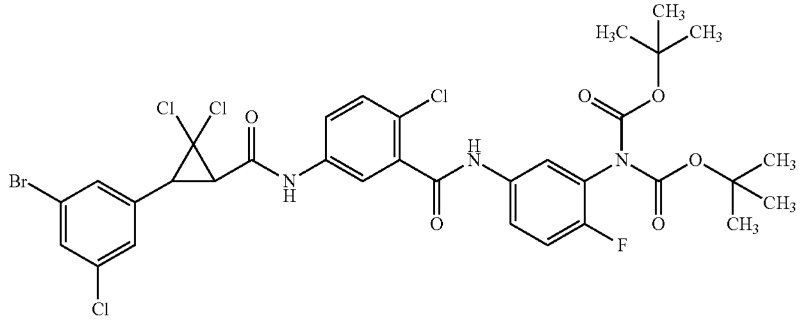

Isolated as an off-white solid (0.300 g, 77%).

trans-tert-Butyl (5-(2-chloro-5-(2,2-dichloro-3-(3,5-dichlorophenyl)cyclopropane-1-carboxamido)benzamido)-2-fluorophenyl)(methyl)carbamate (F471)

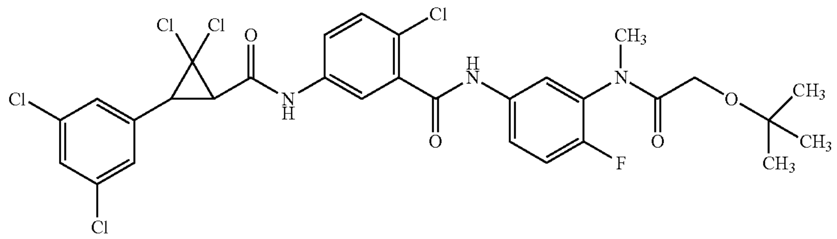 [SMILES: CN(C(=O)COC(C)(C)C)c1cc(NC(=O)c2cc(NC(=O)C3C(c4cc(Cl)cc(Cl)c4)C3(Cl)Cl)ccc2Cl)ccc1F]

Isolated as an off-white solid (0.422 g, 100%).

trans-tert-Butyl(4-(3-(2,2-dichloro-3-(3,5-dichlorophenyl)cyclopropane-1-carboxamido)benzamido)-3-methylphenyl)carbamate (C341 and as known as FC341)

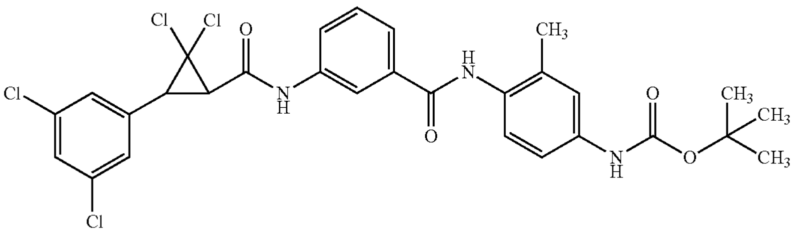 [SMILES: Cc1cc(NC(=O)OC(C)(C)C)ccc1NC(=O)c1cccc(NC(=O)C2C(c3cc(Cl)cc(Cl)c3)C2(Cl)Cl)c1]

Isolated as an off-white solid (0.205 g, 73%): $^1$H NMR (400 MHz, DMSO-$d_6$) δ 10.81 (s, 1H), 9.82 (s, 1H), 9.31 (s, 1H), 8.18 (s, 1H), 7.88 (dd, J=7.7, 1.9 Hz, 1H), 7.72 (d, J=7.8 Hz, 1H), 7.63 (s, 1H), 7.62-7.45 (m, 3H), 7.42-7.36 (m, 1H), 7.27 (dd, J=8.7, 2.4 Hz, 1H), 7.18 (d, J=8.5 Hz, 1H), 3.63 (d, J=8.5 Hz, 1H), 3.52 (d, J=8.6 Hz, 1H), 2.18 (s, 3H), 1.48 (s, 9H); ESIMS m/z 621 ([M−H]$^-$).

tert-Butyl-N-((tert-butoxy)carbonyl)-N-(2-(2-chloro-5-((1R,3R)-2,2-dichloro-3-(3,5-dichlorophenyl)cyclopropane-1-carboxamido)benzamido)-4-fluorophenyl)carbamate (C342 and as known as FC342)

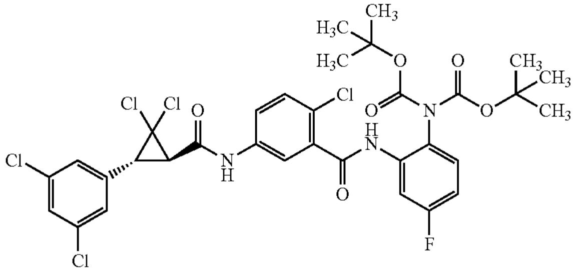 [SMILES: CC(C)(C)OC(=O)N(C(=O)OC(C)(C)C)c1ccc(F)cc1NC(=O)c1cc(NC(=O)[C@H]2[C@H](c3cc(Cl)cc(Cl)c3)C2(Cl)Cl)ccc1Cl]

Isolated as a light brown foam (0.072 g, 37%): $^1$H NMR (400 MHz, DMSO-$d_6$) δ 10.88 (s, 1H), 10.43 (s, 1H), 7.84 (q, J=4.1, 3.2 Hz, 2H), 7.71 (dd, J=8.8, 2.6 Hz, 1H), 7.63 (q, J=1.9 Hz, 1H), 7.57-7.54 (m, 3H), 7.26 (dd, J=8.8, 6.1 Hz, 1H), 7.02 (ddd, J=8.8, 7.8, 3.0 Hz, 1H), 3.61 (dd, J=8.5, 2.7 Hz, 1H), 3.51 (d, J=8.5 Hz, 1H), 1.31 (s, 18H); $^{19}$F NMR (376 MHz, DMSO-$d_6$) δ −113.29; ESIMS m/z 759.8 ([M−H]$^-$).

tert-Butyl-N-((tert-butoxy)carbonyl)-N-(3-(2-chloro-5-((1R,3R)-2,2-dichloro-3-(3,5-dichlorophenyl)cyclopropane-1-carboxamido)benzamido)-2-fluorophenyl)carbamate (C343 and as known as FC343)

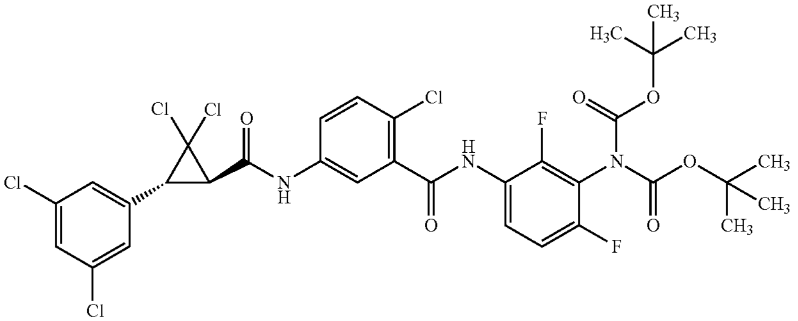 [SMILES: CC(C)(C)OC(=O)N(C(=O)OC(C)(C)C)c1c(F)ccc(NC(=O)c2cc(NC(=O)[C@H]3[C@H](c4cc(Cl)cc(Cl)c4)C3(Cl)Cl)ccc2Cl)c1F]

Isolated as an off-white foam (0.056 g, 32%): $^{1}$H NMR (400 MHz, DMSO-$d_6$) δ 10.91 (s, 1H), 10.49 (s, 1H), 7.91 (d, J=2.6 Hz, 1H), 7.75 (td, J=8.7, 4.1 Hz, 2H), 7.63 (t, J=1.9 Hz, 1H), 7.56 (q, J=4.1, 3.4 Hz, 3H), 7.22 (t, J=5.2 Hz, 2H), 3.63 (d, J=8.5 Hz, 1H), 3.52 (d, J=8.5 Hz, 1H), 1.40 (s, 18H); $^{19}$F NMR (376 MHz, DMSO-$d_6$) δ −131.38; ESIMS m/z 759 ([M−H]$^-$).

tert-Butyl-N-((tert-butoxy)carbonyl)-N-(4-(2-chloro-5-((1R,3R)-2,2-dichloro-3-(3,5-dichlorophenyl)cyclopropane-1-carboxamido)benzamido)-2,5-difluorophenyl)carbamate (C344 and as known as FC344)

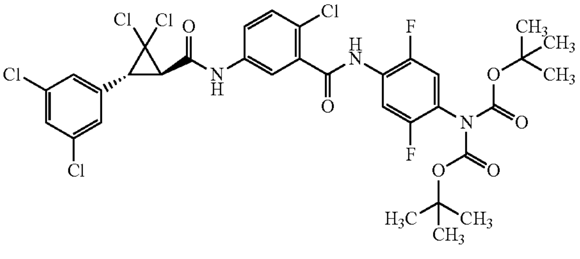 [SMILES: CC(C)(C)OC(=O)N(C(=O)OC(C)(C)C)c1cc(F)c(NC(=O)c2cc(NC(=O)[C@H]3[C@H](c4cc(Cl)cc(Cl)c4)C3(Cl)Cl)ccc2Cl)cc1F]

Isolated as an off-white foam (0.136 g, 86%): $^{1}$H NMR (400 MHz, DMSO-$d_6$) δ 10.96 (s, 1H), 10.69 (s, 1H), 7.96-7.87 (m, 2H), 7.76 (t, J=5.7 Hz, 1H), 7.76 (s, 1H), 7.69 (d, J=8.3 Hz, 1H), 7.61-7.52 (m, 2H), 7.43 (dd, J=8.5, 2.1 Hz, 1H), 3.61 (d, J=8.4 Hz, 1H), 3.47 (d, J=8.5 Hz, 1H), 1.40 (s, 18H); $^{19}$F NMR (376 MHz, DMSO-$d_6$) δ −126.31 (d, J=14.3 Hz), −127.07 (d, J=14.5 Hz); ESIMS m/z 579 ([M+$BOC_2$]$^+$)

tert-Butyl-N-((tert-butoxy)carbonyl)-N-(4-(2-chloro-5-((1R,3R)-2,2-dichloro-3-(3,4-dichlorophenyl)cyclopropane-1-carboxamido)benzamido)-2,5-difluorophenyl)carbamate (C345 and as known as FC345)

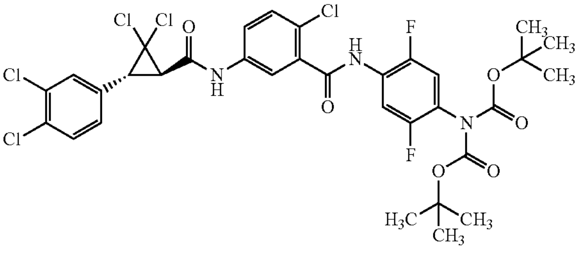 [SMILES: CC(C)(C)OC(=O)N(C(=O)OC(C)(C)C)c1cc(F)c(NC(=O)c2cc(NC(=O)[C@H]3[C@H](c4ccc(Cl)c(Cl)c4)C3(Cl)Cl)ccc2Cl)cc1F]

Isolated as an off-white foam (0.137 g, 86%): Isolated as an off-white foam (0.124 g, 78%): $^{1}$H NMR (400 MHz, DMSO-$d_6$) δ 10.93 (s, 1H), 10.69 (s, 1H), 7.97-7.87 (m, 2H), 7.76 (dd, J=8.7, 2.6 Hz, 1H), 7.62 (d, J=1.9 Hz, 1H), 7.56 (q, J=3.5, 2.4 Hz, 4H), 3.63 (d, J=8.4 Hz, 1H), 3.52 (d, J=8.5 Hz, 1H), 1.41 (s, 18H); $^{19}$F NMR (376 MHz, DMSO-$d_6$) δ −126.31 (d, J=14.6 Hz), −127.08 (d, J=14.6 Hz); ESIMS m/z 579 ([M+$BOC_2$]$^+$)

tert-Butyl-N-((tert-butoxy)carbonyl)-N-(4-(2-chloro-5-((1R,3R)-2,2-dichloro-3-(3,4,5-trichlorophenyl)cyclopropane-1-carboxamido)benzamido)-2,5-difluorophenyl)carbamate (C346 and as known as FC346)

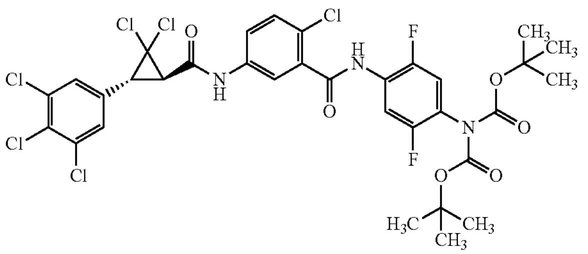 [SMILES: CC(C)(C)OC(=O)N(C(=O)OC(C)(C)C)c1cc(F)c(NC(=O)c2cc(NC(=O)[C@H]3[C@H](c4cc(Cl)c(Cl)c(Cl)c4)C3(Cl)Cl)ccc2Cl)cc1F]

Isolated as an off-white foam (0.137 g, 86%): $^{1}$H NMR (400 MHz, DMSO-$d_6$) δ 10.94 (s, 1H), 10.69 (s, 1H), 7.96-7.87 (m, 2H), 7.80 (s, 2H), 7.76 (dd, J=8.8, 2.6 Hz, 1H), 7.61-7.52 (m, 2H), 3.63 (d, J=8.5 Hz, 1H), 3.55 (d, J=8.5 Hz, 1H), 1.40 (s, 18H); $^{19}$F NMR (376 MHz, DMSO-$d_6$) δ −126.31 (d, J=14.5 Hz), −127.08 (d, J=14.7 Hz). ESIMS m/z 615 ([M+$BOC_2$]$^+$)

tert-Butyl-N-((tert-butoxy)carbonyl)-N-(4-(2-chloro-5-((1R,3R)-2,2-dichloro-3-(3-chloro-4-fluorophenyl)cyclopropane-1-carboxamido)benzamido)-2,5-difluorophenyl)carbamate (C347 and as known as FC347)

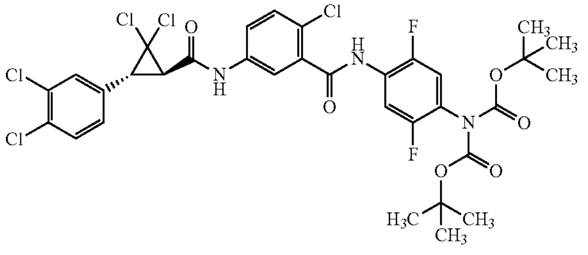 [SMILES: CC(C)(C)OC(=O)N(C(=O)OC(C)(C)C)c1cc(F)c(NC(=O)c2cc(NC(=O)[C@H]3[C@H](c4ccc(Cl)c(Cl)c4)C3(Cl)Cl)ccc2Cl)cc1F]

Isolated as an off-white solid (0.133 g, 82%): $^{1}$H NMR (400 MHz, DMSO-$d_6$) δ 10.95 (s, 1H), 10.69 (s, 1H), 7.96-7.87 (m, 2H), 7.76 (dd, J=8.8, 2.6 Hz, 1H), 7.71 (dd, J=7.1, 1.9 Hz, 1H), 7.61-7.52 (m, 2H), 7.53-7.40 (m, 2H), 3.59 (d, J=8.5 Hz, 1H), 3.44 (d, J=8.5 Hz, 1H), 1.40 (s, 18H); $^{19}$F NMR (376 MHz, DMSO-$d_6$) δ −117.04, −117.28, −117.33, −126.30, −126.34, −127.05, −127.09; ESIMS m/z 563 ([M+$BOC_2$]$^+$).

2-Chloro-5-trans-(2,2-dichloro-3-(3,5-dichlorophenyl)-3-methylcyclopropane-1-carboxamido)-N-(4-fluorophenyl)benzamide (F251)

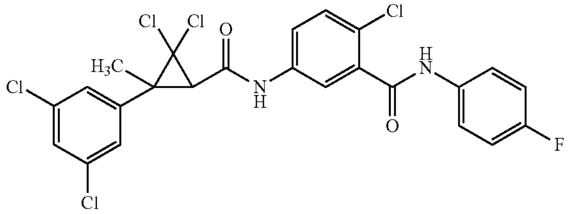

Isolated as a white foam (0.130 g, 71.3%).

2-Chloro-5-trans-(2,2-dichloro-3-(3,5-dichlorophenyl)-3-methylcyclopropane-1-carboxamido)-N-(2,4-difluorophenyl)benzamide (F252)

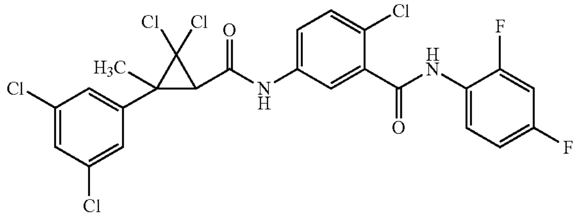 [SMILES: CC1(c2cc(Cl)cc(Cl)c2)C(C(=O)Nc2ccc(Cl)c(C(=O)Nc3ccc(F)cc3F)c2)C1(Cl)Cl]

Isolated as a white solid (0.148 g, 79%).

2-Chloro-5-cis-2,2-dichloro-3-(3,5-dichlorophenyl)-3-methylcyclopropane-1-carboxamido)-N-(4-fluorophenyl)benzamide (F253)

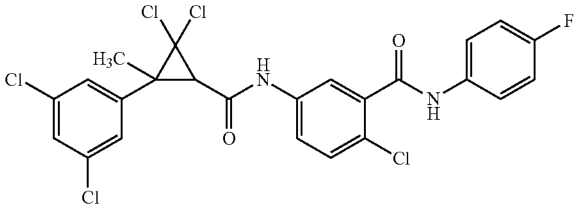 [SMILES: CC1(c2cc(Cl)cc(Cl)c2)C(C(=O)Nc2ccc(Cl)c(C(=O)Nc3ccc(F)cc3)c2)C1(Cl)Cl]

Isolated as a white solid (0.061 g, 76%).

Methyl 2-(4-(2-chloro-5-(trans)-(2,2-dichloro-3-(3,5-dichlorophenyl)cyclopropane-1-carboxamido)benzamido)-3-methylphenyl)-3,3,3-trifluoro-2-hydroxypropanoate (F257)

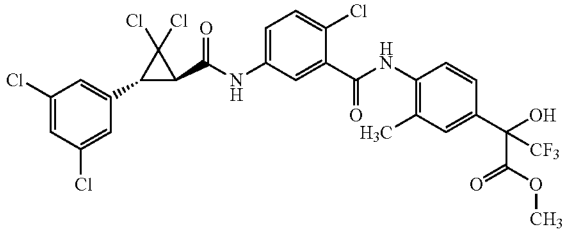 [SMILES: COC(=O)C(O)(c1ccc(NC(=O)c2cc(NC(=O)[C@H]3[C@H](c4cc(Cl)cc(Cl)c4)C3(Cl)Cl)ccc2Cl)c(C)c1)C(F)(F)F]

Isolated as a white foam (0.128 g, 79%).

2-Chloro-5-(trans)-(2,2-dichloro-3-(3,5-dichlorophenyl)cyclopropane-1-carboxamido)-N-(2-methyl-4-(3,3,3-trifluoroprop-1-en-2-yl)phenyl)benzamide (F258)

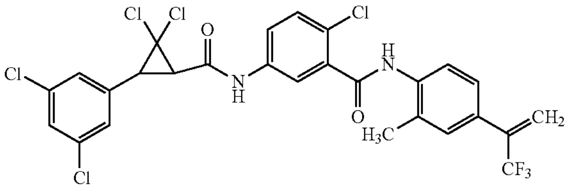 [SMILES: C=C(c1ccc(NC(=O)c2cc(NC(=O)C3C(c4cc(Cl)cc(Cl)c4)C3(Cl)Cl)ccc2Cl)c(C)c1)C(F)(F)F]

Isolated as a tan solid (0.110 g, 74.4%).

2-Chloro-5-(trans)-(2,2-dichloro-3-(3,5-dichlorophenyl)cyclopropane-1-carboxamido)-N-(2-methyl-4-(perfluoropropan-2-yl)phenyl)benzamide (F269)

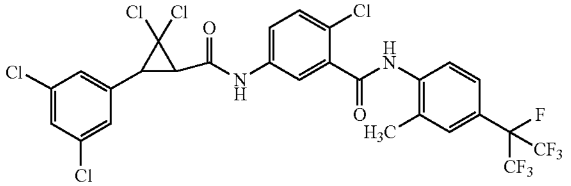 [SMILES: Cc1cc(C(F)(C(F)(F)F)C(F)(F)F)ccc1NC(=O)c1cc(NC(=O)C2C(c3cc(Cl)cc(Cl)c3)C2(Cl)Cl)ccc1Cl]

Isolated as a white solid (0.036 g, 21.8%).

tert-Butyl (4-(2-chloro-5-((1R,3R)-2,2-dichloro-3-(3,5-dichlorophenyl)cyclopropane-1-carboxamido)benzamido)-3-methylphenyl)carbamate (F275)

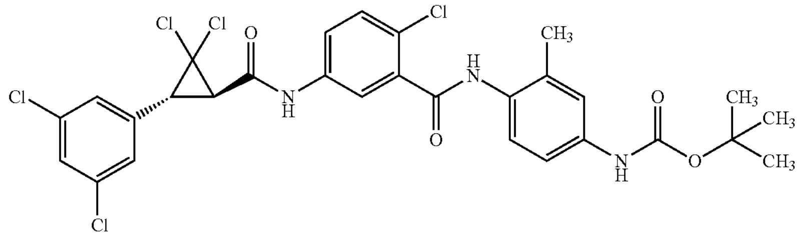 [SMILES: Cc1cc(NC(=O)OC(C)(C)C)ccc1NC(=O)c1cc(NC(=O)[C@H]2[C@H](c3cc(Cl)cc(Cl)c3)C2(Cl)Cl)ccc1Cl]

Isolated as a white solid (0.283 g, 77%).

tert-Butyl (4-(2-chloro-5-((1R,3R)-2,2-dichloro-3-(3,4-dichlorophenyl)cyclopropane-1-carboxamido)benzamido)-3-methylphenyl)carbamate (F277)

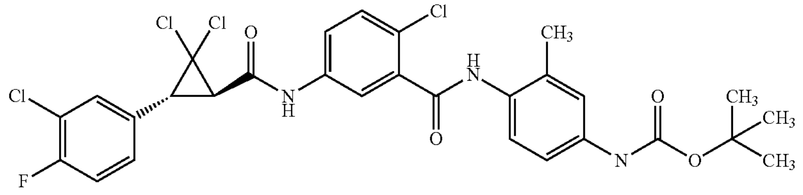

Isolated as a white solid (0.328 g, 89%).

tert-Butyl (4-(2-chloro-5-((1R,3R)-2,2-dichloro-3-(3,4,5-trichlorophenyl)cyclopropane-1-carboxamido)benzamido)-3-methylphenyl)carbamate (F278)

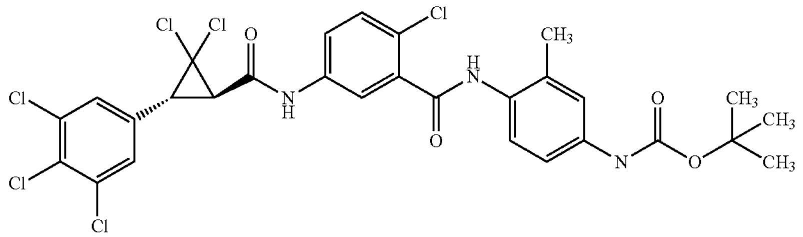 [SMILES: Cc1cc(NC(=O)OC(C)(C)C)ccc1NC(=O)c1cc(NC(=O)[C@H]2[C@H](c3cc(Cl)c(Cl)c(Cl)c3)C2(Cl)Cl)ccc1Cl]

Isolated as a white solid (0.276 g, 79%).

2-Chloro-5-((1R,3R)-2,2-dichloro-3-(3,4,5-trichlorophenyl)cyclopropane-1-carboxamido)-N-(4-fluorophenyl)benzamide (F279)

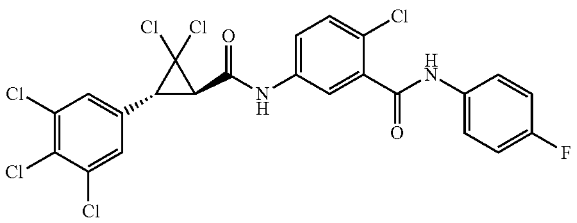 [SMILES: O=C(Nc1ccc(F)cc1)c1cc(NC(=O)[C@H]2[C@H](c3cc(Cl)c(Cl)c(Cl)c3)C2(Cl)Cl)ccc1Cl]

Isolated as a white foam (0.156 g, 85%).

2-Chloro-5-((1S,3S)-2,2-dichloro-3-(3,4,5-trichlorophenyl)cyclopropane-1-carboxamido)-N-(4-fluorophenyl)benzamide (F280)

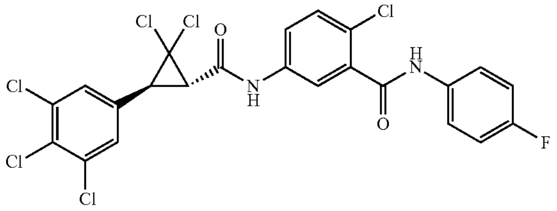 [SMILES: O=C(Nc1ccc(F)cc1)c1cc(NC(=O)[C@@H]2[C@@H](c3cc(Cl)c(Cl)c(Cl)c3)C2(Cl)Cl)ccc1Cl]

Isolated as a white foam (0.153 g, 84%).

2-Chloro-5-((1R,3R)-2,2-dichloro-3-(3,4,5-trichlorophenyl)cyclopropane-1-carboxamido)-N-(2,4-difluorophenyl)benzamide (F281)

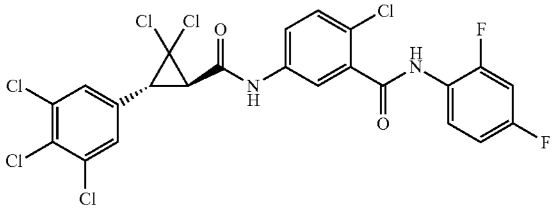

Isolated as a white foam (0.146 g, 77%).

2-Chloro-5-((1S,3S)-2,2-dichloro-3-(3,4,5-trichlorophenyl)cyclopropane-1-carboxamido)-N-(2,4-difluorophenyl)benzamide (F282)

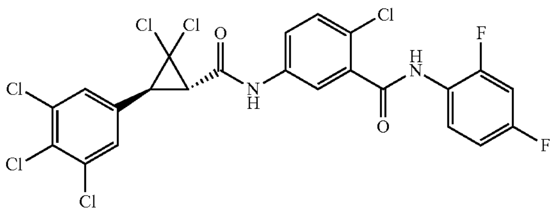 [SMILES: O=C(Nc1ccc(F)cc1F)c1cc(NC(=O)[C@@H]2[C@@H](c3cc(Cl)c(Cl)c(Cl)c3)C2(Cl)Cl)ccc1Cl]

Isolated as a white foam (0.163 g, 86%).

N-(4-Amino-2-methylphenyl)-2-chloro-5-((1R,3R)-2,2-dichloro-3-(3,5-dichlorophenyl)cyclopropane-1-carboxamido)benzamide (F283)

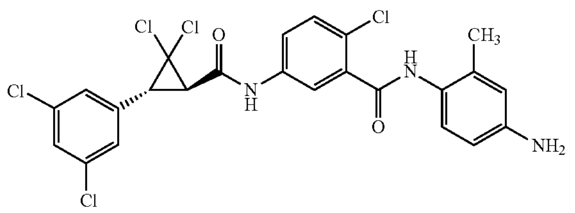 [SMILES: Cc1cc(N)ccc1NC(=O)c1cc(NC(=O)[C@H]2[C@H](c3cc(Cl)cc(Cl)c3)C2(Cl)Cl)ccc1Cl]

Isolated as a tan solid (0.143 g, 60.5%).

N-(4-Amino-2-methylphenyl)-2-chloro-5-((1S,3S)-2,2-dichloro-3-(3,5-dichlorophenyl)cyclopropane-1-carboxamido)benzamide (F284)

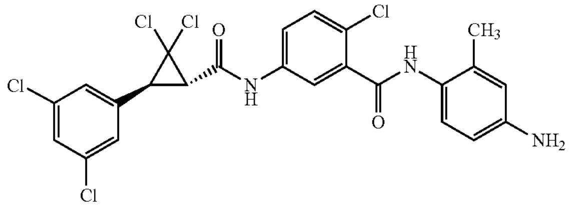 [SMILES: Cc1cc(N)ccc1NC(=O)c1cc(NC(=O)[C@@H]2[C@@H](c3cc(Cl)cc(Cl)c3)C2(Cl)Cl)ccc1Cl]

Isolated as a white solid (0.161 g, 67.1%).

N-(4-Amino-2-methylphenyl)-2-chloro-5-((1R,3R)-2,2-dichloro-3-(3,4-dichlorophenyl)cyclopropane-1-carboxamido)benzamide (F285)

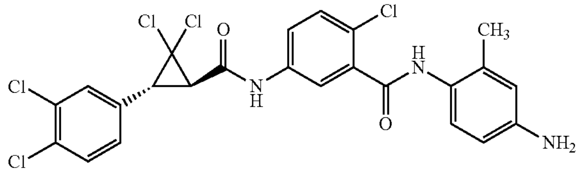 [SMILES: Cc1cc(N)ccc1NC(=O)c1cc(NC(=O)[C@H]2[C@H](c3ccc(Cl)c(Cl)c3)C2(Cl)Cl)ccc1Cl]

Isolated as a white solid (0.153 g, 52.3%).

N-(4-Amino-2-methylphenyl)-2-chloro-5-((1R,3R)-2,2-dichloro-3-(3,4,5-trichlorophenyl)cyclopropane-1-carboxamido)benzamide (F286)

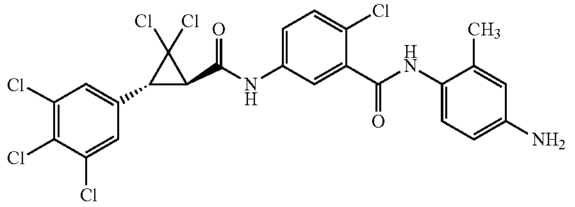 [SMILES: Cc1cc(N)ccc1NC(=O)c1cc(NC(=O)[C@H]2[C@H](c3cc(Cl)c(Cl)c(Cl)c3)C2(Cl)Cl)ccc1Cl]

Isolated as a white solid (0.162 g, 67.6%).

tert-Butyl (4-(2-chloro-5-((1R,3R)-2,2-dichloro-3-(3-chloro-4-fluorophenyl)cyclopropane-1-carboxamido)benzamido)-3-methylphenyl)carbamate (F290)

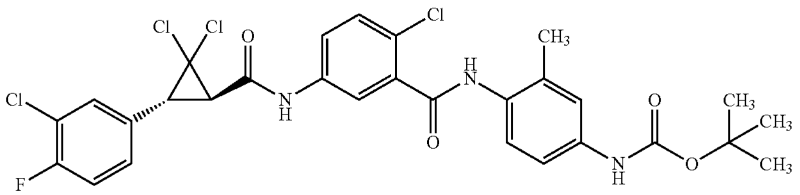

Isolated as a white solid (0.193 g, 81%).

N-(4-Amino-2-methylphenyl)-2-chloro-5-((1R,3R)-2,2-dichloro-3-(3-chloro-4-fluorophenyl)cyclopropane-1-carboxamido)benzamide (F291)

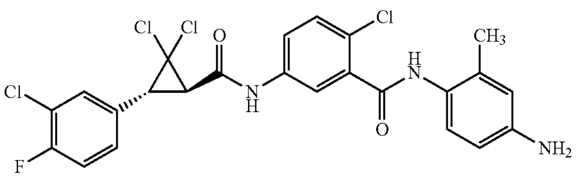 [SMILES: Cc1cc(N)ccc1NC(=O)c1cc(NC(=O)[C@H]2[C@H](c3ccc(F)c(Cl)c3)C2(Cl)Cl)ccc1Cl]

Isolated as a tan solid (0.104 g, 69%).

2-Chloro-5-(trans)-(2,2-dichloro-3-(3,5-dichlorophenyl)cyclopropane-1-carboxamido)-N-(3-fluoro-5-iodopyridin-2-yl)benzamide (F312)

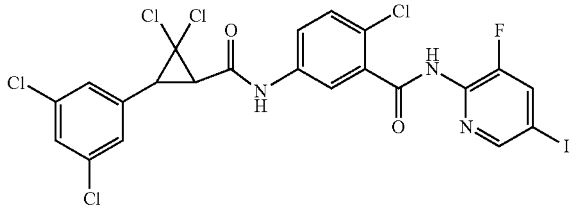 [SMILES: O=C(Nc1ncc(I)cc1F)c1cc(NC(=O)C2C(c3cc(Cl)cc(Cl)c3)C2(Cl)Cl)ccc1Cl]

Isolated as a white foam (0.026 g, 17.2%).

2-Chloro-5-(trans)-(2,2-dichloro-3-(3,4-difluorophenyl)cyclopropane-1-carboxamido)-N-(2,4-difluorophenyl)benzamide (F346)

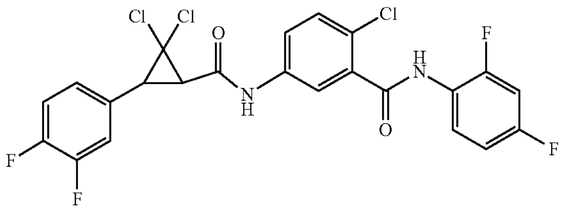 [SMILES: O=C(Nc1ccc(F)cc1F)c1cc(NC(=O)C2C(c3ccc(F)c(F)c3)C2(Cl)Cl)ccc1Cl]

Isolated as a white foam (0.091 g, 57.9%).

2-Chloro-5-(trans)-(2,2-dichloro-3-(3-fluoro-4-(trifluoromethyl)phenyl)cyclopropane-1-carboxamido)-N-(2,4-difluorophenyl)benzamide (F347)

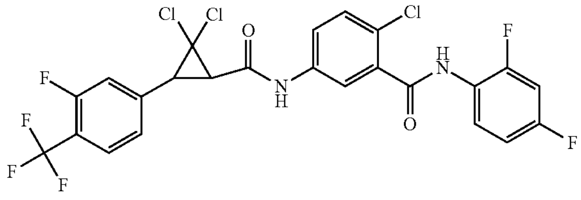 [SMILES: O=C(Nc1ccc(F)cc1F)c1cc(NC(=O)C2C(c3ccc(C(F)(F)F)c(F)c3)C2(Cl)Cl)ccc1Cl]

Isolated as a white foam (0.111 g, 77%).

5-(trans)-(3-(4-Bromo-3-fluorophenyl)-2,2-dichlorocyclopropane-1-carboxamido)-2-chloro-N-(2,4-difluorophenyl)benzamide (F364)

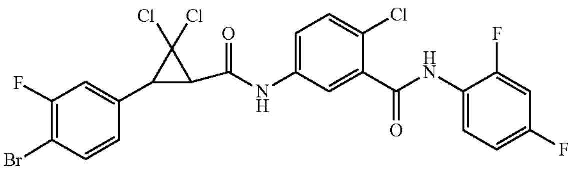 [SMILES: O=C(Nc1ccc(F)cc1F)c1cc(NC(=O)C2C(c3ccc(Br)c(F)c3)C2(Cl)Cl)ccc1Cl]

Isolated as a white foam (0.100 g, 70.1%).

5-(trans)-(3-(3-Bromo-4-(trifluoromethyl)phenyl)-2,2-dichlorocyclopropane-1-carboxamido)-2-chloro-N-(2,4-difluorophenyl)benzamide (F365)

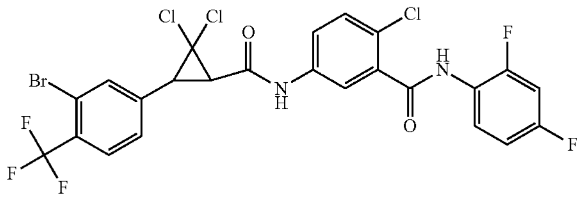 [SMILES: O=C(Nc1ccc(F)cc1F)c1cc(NC(=O)C2C(c3ccc(C(F)(F)F)c(Br)c3)C2(Cl)Cl)ccc1Cl]

Isolated as a white foam (0.094 g, 70%).

5-(trans)-(3-(4-Bromo-3-(trifluoromethyl)phenyl)-2,2-dichlorocyclopropane-1-carboxamido)-2-chloro-N-(2,4-difluorophenyl)benzamide (F366)

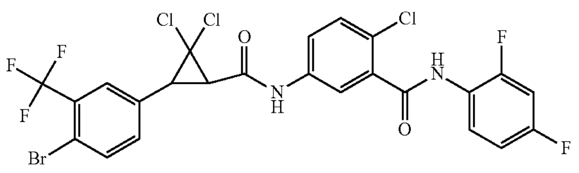 [SMILES: O=C(Nc1ccc(F)cc1F)c1cc(NC(=O)C2C(c3ccc(Br)c(C(F)(F)F)c3)C2(Cl)Cl)ccc1Cl]

Isolated as a white foam (0.101 g, 75%).

2-Chloro-5-(trans)-(2,2-dichloro-3-(3-chloro-4-(trifluoromethyl)phenyl)cyclopropane-1-carboxamido)-N-(2,4-difluorophenyl)benzamide (F367)

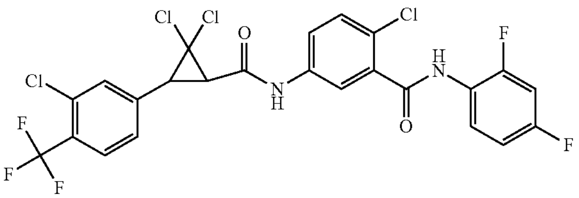 [SMILES: O=C(Nc1ccc(F)cc1F)c1cc(NC(=O)C2C(c3ccc(C(F)(F)F)c(Cl)c3)C2(Cl)Cl)ccc1Cl]

Isolated as a white foam (0.092 g, 65%).

2-Chloro-5-(trans)-(2,2-dichloro-3-(4-chloro-3-(trifluoromethyl)phenyl)cyclopropane-1-carboxamido)-N-(2,4-difluorophenyl)benzamide (F374)

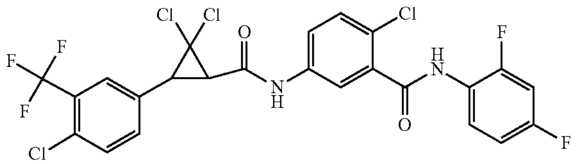 [SMILES: O=C(Nc1ccc(F)cc1F)c1cc(NC(=O)C2C(c3ccc(Cl)c(C(F)(F)F)c3)C2(Cl)Cl)ccc1Cl]

Isolated as a white foam (0.094 g, 66.4%).

5-(trans)-(3-(3-Bromo-4-fluorophenyl)-2,2-dichlorocyclopropane-1-carboxamido)-2-chloro-N-(2,4-difluorophenyl)benzamide (F375)

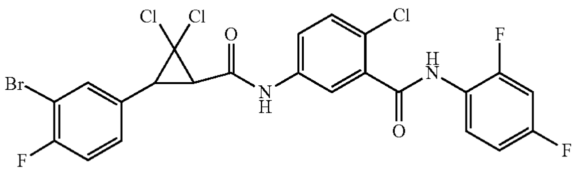 [SMILES: O=C(Nc1ccc(F)cc1F)c1cc(NC(=O)C2C(c3ccc(F)c(Br)c3)C2(Cl)Cl)ccc1Cl]

Isolated as a white foam (0.111 g, 78%).

2-Chloro-5-(trans)-(2,2-dichloro-3-(4-fluoro-3-(trifluoromethyl)phenyl)cyclopropane-1-carboxamido)-N-(2,4-difluorophenyl)benzamide (F376)

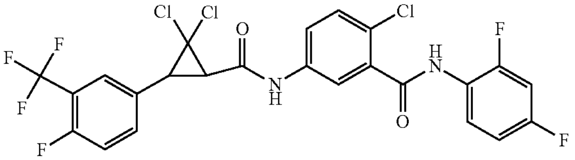 [SMILES: O=C(Nc1ccc(F)cc1F)c1cc(NC(=O)C2C(c3ccc(F)c(C(F)(F)F)c3)C2(Cl)Cl)ccc1Cl]

Isolated as a white foam (0.114 g, 79%).

2-Chloro-5-(trans)-(2,2-dichloro-3-(3,5-difluorophenyl)cyclopropane-1-carboxamido)-N-(2,4-difluorophenyl)benzamide (F411)

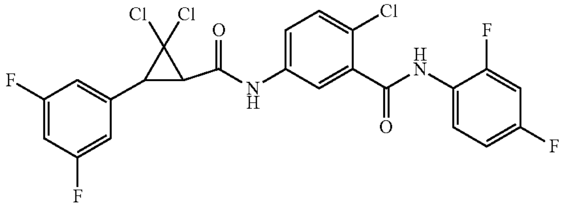 [SMILES: O=C(Nc1ccc(F)cc1F)c1cc(NC(=O)C2C(c3cc(F)cc(F)c3)C2(Cl)Cl)ccc1Cl]

Isolated as a white foam (0.069 g, 43.9%).

2-Chloro-5-(trans)-(2,2-dichloro-3-(3-fluoro-5-(trifluoromethyl)phenyl)cyclopropane-1-carboxamido)-N-(2,4-difluorophenyl)benzamide (F412)

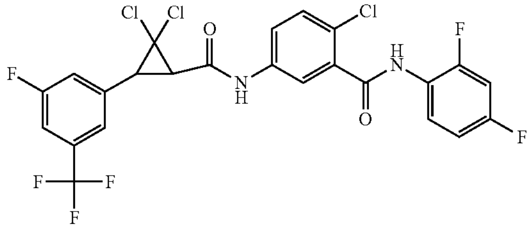 [SMILES: O=C(Nc1ccc(F)cc1F)c1cc(NC(=O)C2C(c3cc(F)cc(C(F)(F)F)c3)C2(Cl)Cl)ccc1Cl]

Isolated as a white foam (0.081 g, 55.9%).

5-(trans)-(3-(3-Bromo-5-fluorophenyl)-2,2-dichlorocyclopropane-1-carboxamido)-2-chloro-N-(2,4-difluorophenyl)benzamide (F423)

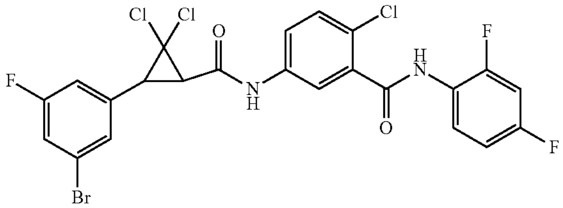 [SMILES: O=C(Nc1ccc(F)cc1F)c1cc(NC(=O)C2C(c3cc(F)cc(Br)c3)C2(Cl)Cl)ccc1Cl]

Isolated as a white foam (0.104 g, 72.9%).

5-(trans)-(3-(3-Bromo-5-(trifluoromethyl)phenyl)-2,2-dichlorocyclopropane-1-carboxamido)-2-chloro-N-(2,4-difluorophenyl)benzamide (F424)

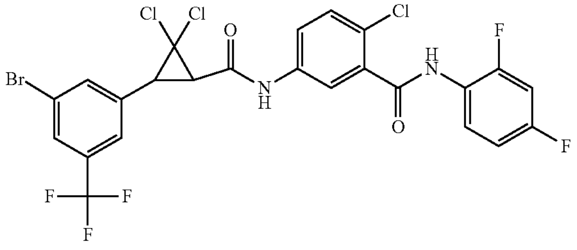 [SMILES: O=C(Nc1ccc(F)cc1F)c1cc(NC(=O)C2C(c3cc(Br)cc(C(F)(F)F)c3)C2(Cl)Cl)ccc1Cl]

Isolated as a white foam (0.108 g, 80%).

N-(1-Benzyl-1H-indol-5-yl)-2-chloro-5-(trans)-(2,2-dichloro-3-(3,5-dichlorophenyl)cyclopropane-1-carboxamido)benzamide (F458)

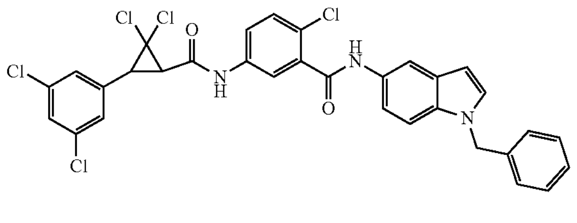 [SMILES: O=C(Nc1ccc2c(ccn2Cc2ccccc2)c1)c1cc(NC(=O)C2C(c3cc(Cl)cc(Cl)c3)C2(Cl)Cl)ccc1Cl]

Isolated as a pink solid (0.112 g, 76%).

2-Chloro-5-(trans)-(2,2-dichloro-3-(3,5-dichlorophenyl)cyclopropane-1-carboxamido)-N-(1-methyl-2-oxoindolin-5-yl)benzamide (F459)

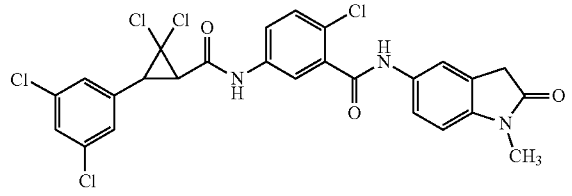 [SMILES: CN1C(=O)Cc2cc(NC(=O)c3cc(NC(=O)C4C(c5cc(Cl)cc(Cl)c5)C4(Cl)Cl)ccc3Cl)ccc21]

Isolated as a white solid (0.075 g, 55.8%).

2-Chloro-5-(trans)-(2,2-dichloro-3-(3,5-dichlorophenyl)cyclopropane-1-carboxamido)-N-(1-methyl-5-(trifluoromethyl)-1H-indazol-3-yl)benzamide (F460)

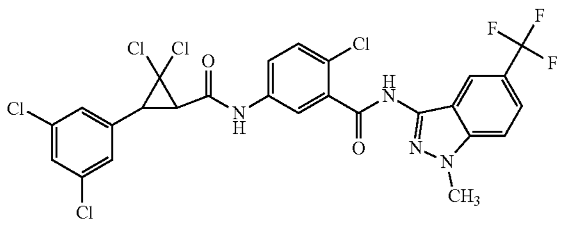 [SMILES: Cn1nc(NC(=O)c2cc(NC(=O)C3C(c4cc(Cl)cc(Cl)c4)C3(Cl)Cl)ccc2Cl)c2cc(C(F)(F)F)ccc21]

Isolated as a white solid (0.095 g, 64.9%).

2-Chloro-5-(trans)-(2,2-dichloro-3-(3,5-dichlorophenyl)cyclopropane-1-carboxamido)-N-(7-fluoro-1H-indol-5-yl)benzamide (F462)

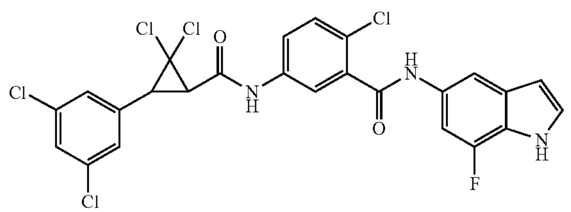 [SMILES: O=C(Nc1cc(F)c2[nH]ccc2c1)c1cc(NC(=O)C2C(c3cc(Cl)cc(Cl)c3)C2(Cl)Cl)ccc1Cl]

Isolated as a white solid (0.086 g, 65.3%).

2-Chloro-N-(4-chloro-1-methyl-1H-indazol-3-yl)-5-(trans)-(2,2-dichloro-3-(3,5-dichlorophenyl)cyclopropane-1-carboxamido)benzamide (F463)

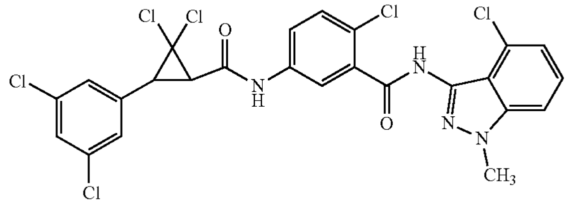 [SMILES: Cn1nc(NC(=O)c2cc(NC(=O)C3C(c4cc(Cl)cc(Cl)c4)C3(Cl)Cl)ccc2Cl)c2c(Cl)cccc21]

Isolated as a white solid (0.020 g, 14.4%).

2-Chloro-5-(trans)-(2,2-dichloro-3-(3,5-dichlorophenyl)cyclopropane-1-carboxamido)-N-(1-methyl-1H-pyrrolo[2,3-b]pyridin-5-yl)benzamide (F464)

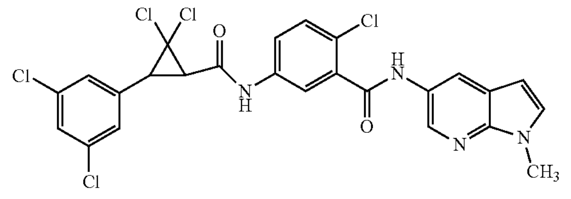

Isolated as a white solid (0.086 g, 65.6%).

2-Chloro-5-(trans)-(2,2-dichloro-3-(3,5-dichlorophenyl)cyclopropane-1-carboxamido)-N-(2-(trifluoromethyl)-1H-indol-5-yl)benzamide (F465)

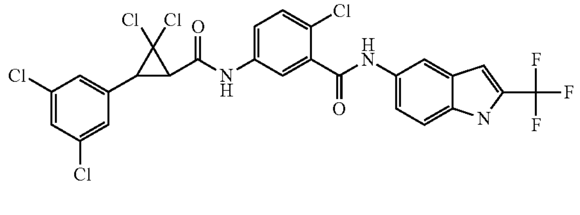 [SMILES: O=C(Nc1ccc2[nH]c(C(F)(F)F)cc2c1)c1cc(NC(=O)C2C(c3cc(Cl)cc(Cl)c3)C2(Cl)Cl)ccc1Cl]

Isolated as a white solid (0.104 g, 72.7%).

2-Chloro-5-(trans)-(2,2-dichloro-3-(3,5-dichlorophenyl)cyclopropane-1-carboxamido)-N-(2-oxoindolin-5-yl)benzamide (F472)

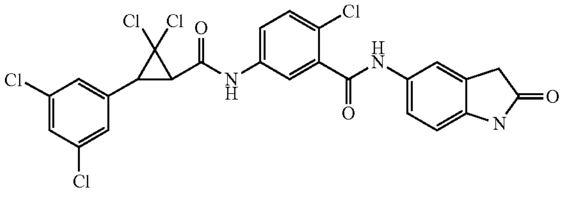 [SMILES: O=C1Cc2cc(NC(=O)c3cc(NC(=O)C4C(c5cc(Cl)cc(Cl)c5)C4(Cl)Cl)ccc3Cl)ccc2N1]

Isolated as a white solid (0.051 g, 38.8%).

2-Chloro-5-(trans)-(2,2-dichloro-3-(3,5-dichlorophenyl)cyclopropane-1-carboxamido)-N-(1-methylindolin-5-yl)benzamide (F473)

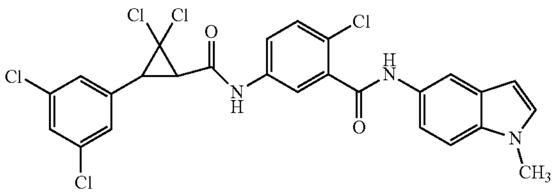 [SMILES: Cn1ccc2cc(NC(=O)c3cc(NC(=O)C4C(c5cc(Cl)cc(Cl)c5)C4(Cl)Cl)ccc3Cl)ccc21]

Isolated as a yellow foam (0.022 mg, 16.2%).

2-Chloro-5-(trans)-(2,2-dichloro-3-(3,5-dichlorophenyl)cyclopropane-1-carboxamido)-N-(1H-pyrrolo[2,3-c]pyridin-5-yl)benzamide (F474)

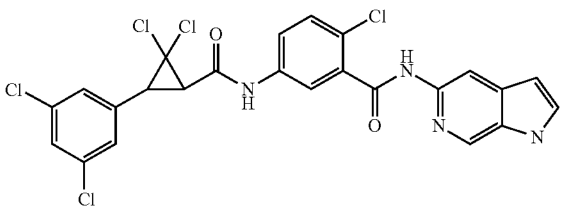 [SMILES: O=C(Nc1cc2cc[nH]c2cn1)c1cc(NC(=O)C2C(c3cc(Cl)cc(Cl)c3)C2(Cl)Cl)ccc1Cl]

Isolated as a tan solid (0.056 g, 42.4%).

2-Chloro-5-(trans)-(2,2-dichloro-3-(3,5-dichlorophenyl)cyclopropane-1-carboxamido)-N-(1-methyl-1H-pyrazolo[3,4-b]pyridin-5-yl)benzamide (F476)

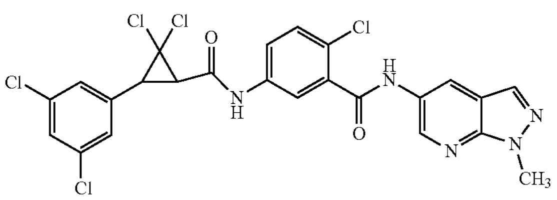 [SMILES: Cn1ncc2cc(NC(=O)c3cc(NC(=O)C4C(c5cc(Cl)cc(Cl)c5)C4(Cl)Cl)ccc3Cl)cnc21]

Isolated as a white solid (0.079 g, 60.2%).

(trans)-N-(3-(3-Amino-6-methyl-1H-indazole-1-carbonyl)-4-chlorophenyl)-2,2-dichloro-3-(3,5-dichlorophenyl)cyclopropane-1-carboxamide (F477)

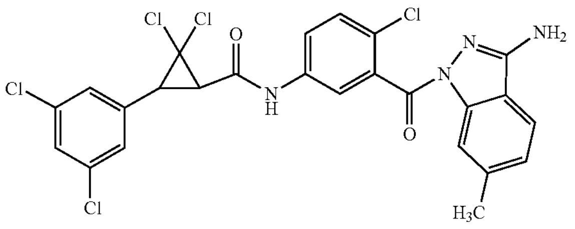 [SMILES: Cc1ccc2c(N)nn(C(=O)c3cc(NC(=O)C4C(c5cc(Cl)cc(Cl)c5)C4(Cl)Cl)ccc3Cl)c2c1]

Isolated as a white solid (0.016 g, 12.2%).

2-Chloro-5-(trans)-(2,2-dichloro-3-(3,5-dichlorophenyl)cyclopropane-1-carboxamido)-N-(6-methyl-1H-indazol-3-yl)benzamide (F478)

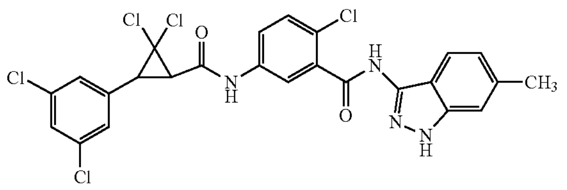 [SMILES: Cc1ccc2c(NC(=O)c3cc(NC(=O)C4C(c5cc(Cl)cc(Cl)c5)C4(Cl)Cl)ccc3Cl)n[nH]c2c1]

Isolated as a white solid (0.043 g, 32.8%).

(trans)-N-(3-(5-Aminoisoindoline-2-carbonyl)-4-chlorophenyl)-2,2-dichloro-3-(3,5-dichlorophenyl)cyclopropane-1-carboxamide (F479)

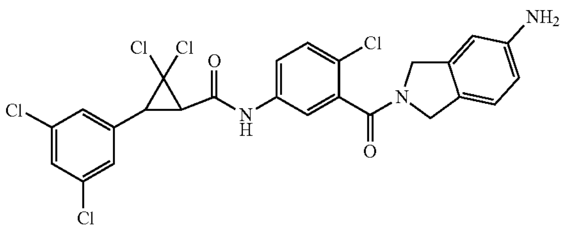 [SMILES: Nc1ccc2c(c1)CN(C(=O)c1cc(NC(=O)C3C(c4cc(Cl)cc(Cl)c4)C3(Cl)Cl)ccc1Cl)C2]

Isolated as a tan solid 0.4 g, 36.3%).

2-Chloro-5-(trans)-(2,2-dichloro-3-(3,5-dichlorophenyl)cyclopropane-1-carboxamido)-N-(1H-pyrrolo[2,3-b]pyridin-5-yl)benzamide (F481)

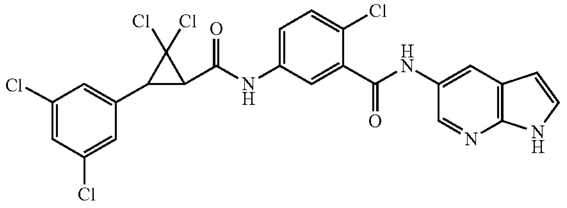 [SMILES: O=C(Nc1cnc2[nH]ccc2c1)c1cc(NC(=O)C2C(c3cc(Cl)cc(Cl)c3)C2(Cl)Cl)ccc1Cl]

Isolated as a white solid (0.061 g, 47.7%).

Ethyl 5-(2-chloro-5-(trans)(2,2-dichloro-3-(3,5-dichlorophenyl)cyclopropane-1-carboxamido)benzamido)-1H-indole-2-carboxylate (F483)

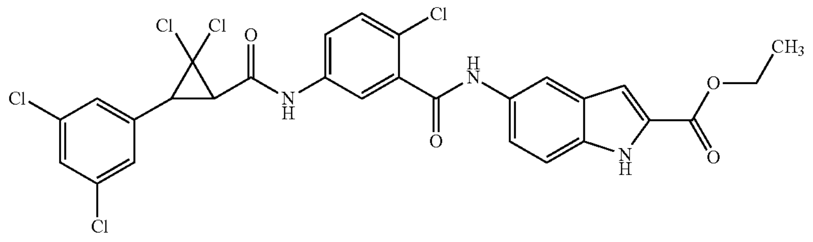 [SMILES: CCOC(=O)c1cc2cc(NC(=O)c3cc(NC(=O)C4C(c5cc(Cl)cc(Cl)c5)C4(Cl)Cl)ccc3Cl)ccc2[nH]1]

Isolated as a white solid (0.068 g, 47%).

tert-Butyl 5-(2-chloro-5-(trans)-(2,2-dichloro-3-(3,5-dichlorophenyl)cyclopropane-1-carboxamido)benzamido)-1H-indole-1-carboxylate (F484)

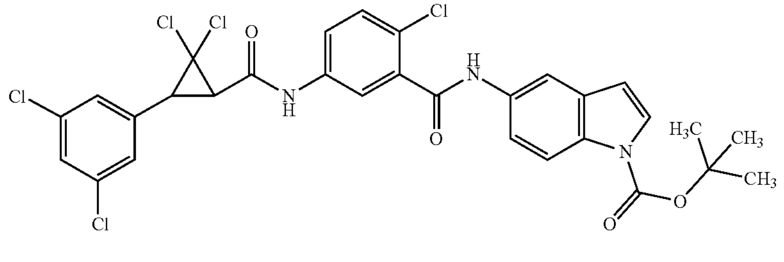

Isolated as a white solid (0.121 g, 81%).

2-Chloro-5-(trans)-(2,2-dichloro-3-(3,5-dichlorophenyl)cyclopropane-1-carboxamido)-N-(4-methyl-1H-indol-5-yl)benzamide (F485)

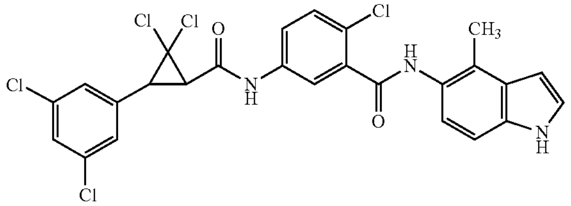 [SMILES: Cc1c(NC(=O)c2cc(NC(=O)C3C(c4cc(Cl)cc(Cl)c4)C3(Cl)Cl)ccc2Cl)ccc2[nH]ccc12]

Isolated as a white foam (0.051 g, 39%).

N-(2-(tert-Butyl)-1H-indol-5-yl)-2-chloro-5-(trans)-(2,2-dichloro-3-(3,5-dichlorophenyl)cyclopropane-1-carboxamido)benzamide (F486)

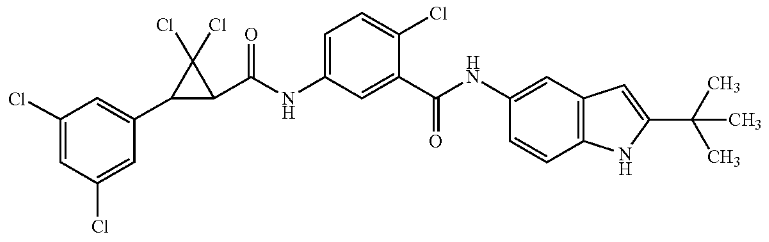 [SMILES: CC(C)(C)c1cc2cc(NC(=O)c3cc(NC(=O)C4C(c5cc(Cl)cc(Cl)c5)C4(Cl)Cl)ccc3Cl)ccc2[nH]1]

Isolated as a yellow foam (0.087 g, 62%).

2-Chloro-5-(trans)-(2,2-dichloro-3-(3,5-dichlorophenyl)cyclopropane-1-carboxamido)-N-(1-ethyl-1H-indol-5-yl)benzamide (F488)

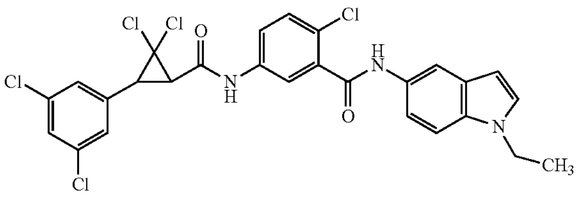 [SMILES: CCn1ccc2cc(NC(=O)c3cc(NC(=O)C4C(c5cc(Cl)cc(Cl)c5)C4(Cl)Cl)ccc3Cl)ccc21]

Isolated as a white foam (0.066 g, 47.7%).

2-chloro-5-(trans)-(2,2-dichloro-3-(3,5-dichlorophenyl)cyclopropane-1-carboxamido)-N-(1-methyl-2-oxo-1,2,3,4-tetrahydroquinolin-6-yl)benzamide (F490)

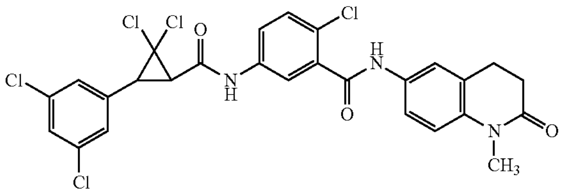 [SMILES: CN1C(=O)CCc2cc(NC(=O)c3cc(NC(=O)C4C(c5cc(Cl)cc(Cl)c5)C4(Cl)Cl)ccc3Cl)ccc21]

Isolated as a white solid (0.098 g, 69%).

2-Chloro-5-(trans)-(2,2-dichloro-3-(3,5-dichlorophenyl)cyclopropane-1-carboxamido)-N-(1-methyl-1,2,3,4-tetrahydroquinolin-6-yl)benzamide (F491)

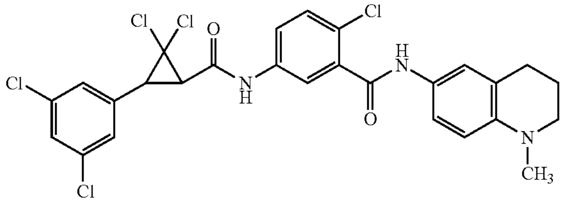 [SMILES: CN1CCCc2cc(NC(=O)c3cc(NC(=O)C4C(c5cc(Cl)cc(Cl)c5)C4(Cl)Cl)ccc3Cl)ccc21]

Isolated as an orange foam (0.051 g, 36.8%).

2-Chloro-5-(trans)-(2,2-dichloro-3-(3,5-dichlorophenyl)cyclopropane-1-carboxamido)-N-(1,2,3,4-tetrahydroquinolin-6-yl)benzamide (F492)

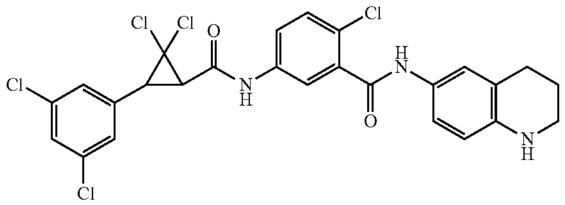 [SMILES: O=C(Nc1ccc2c(c1)CCCN2)c1cc(NC(=O)C2C(c3cc(Cl)cc(Cl)c3)C2(Cl)Cl)ccc1Cl]

Isolated as a yellow foam (0.084 g, 62%).

2-Chloro-5-(trans)-(2,2-dichloro-3-(3,5-dichlorophenyl)cyclopropane-1-carboxamido)-N-(1-(2-fluoroethyl)-1H-indol-5-yl)benzamide (F496)

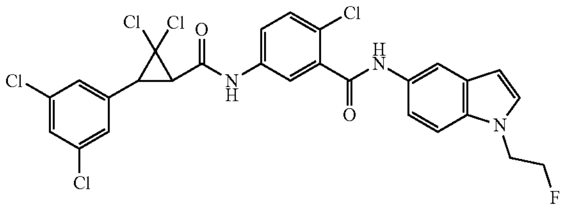 [SMILES: O=C(Nc1ccc2c(ccn2CCF)c1)c1cc(NC(=O)C2C(c3cc(Cl)cc(Cl)c3)C2(Cl)Cl)ccc1Cl]

Isolated as a white solid (0.147 g, 86%).

2-Chloro-5-(trans)-(2,2-dichloro-3-(3,5-dichlorophenyl)cyclopropane-1-carboxamido)-N-(2-phenyl-1H-indol-5-yl)benzamide (F497)

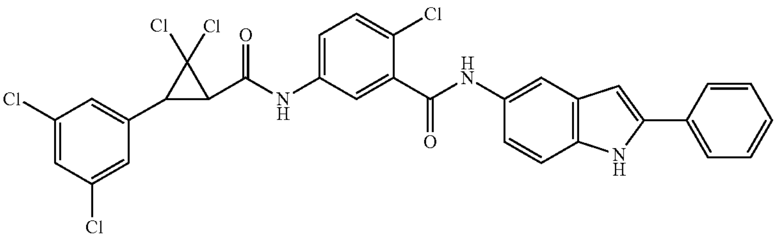 [SMILES: O=C(Nc1ccc2[nH]c(-c3ccccc3)cc2c1)c1cc(NC(=O)C2C(c3cc(Cl)cc(Cl)c3)C2(Cl)Cl)ccc1Cl]

Isolated as a white solid (0.091 g, 60.9%).

2-Chloro-5-(trans)-(2,2-dichloro-3-(3,5-dichlorophenyl)cyclopropane-1-carboxamido)-N-(2-(4-fluorophenyl)-1,3-dioxoisoindolin-5-yl)benzamide (F504)

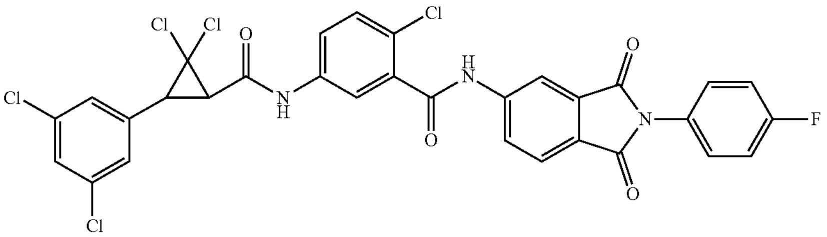 [SMILES: O=C(Nc1ccc2c(c1)C(=O)N(c1ccc(F)cc1)C2=O)c1cc(NC(=O)C2C(c3cc(Cl)cc(Cl)c3)C2(Cl)Cl)ccc1Cl]

Isolated as a white solid (0.056 g, 49.8%).

tert-Butyl 5-(2-chloro-5-(trans)-(2,2-dichloro-3-(3,5-dichlorophenyl)cyclopropane-1-carboxamido)benzamido)indoline-1-carboxylate (F509)

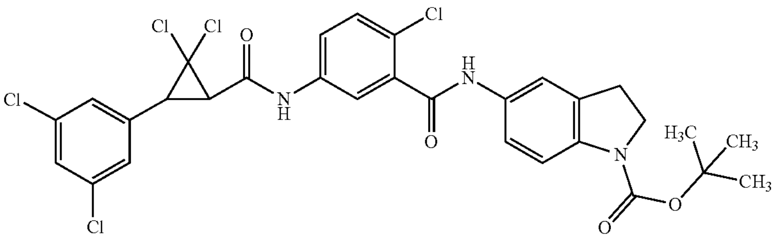 [SMILES: CC(C)(C)OC(=O)N1CCc2cc(NC(=O)c3cc(NC(=O)C4C(c5cc(Cl)cc(Cl)c5)C4(Cl)Cl)ccc3Cl)ccc21]

Isolated as a white solid (0.283 g, 91%).

2-Chloro-5-(trans)-(2,2-dichloro-3-(3,5-dichlorophenyl)cyclopropane-1-carboxamido)-N-(indolin-5-yl)benzamide (F511)

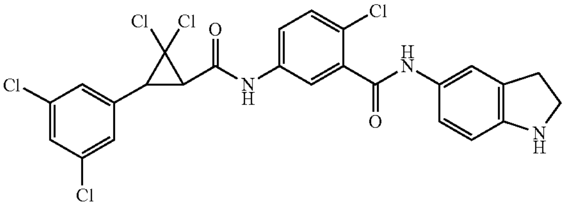 [SMILES: O=C(Nc1ccc2c(c1)CCN2)c1cc(NC(=O)C2C(c3cc(Cl)cc(Cl)c3)C2(Cl)Cl)ccc1Cl]

Isolated as a brown foam (0.100 g, 77%).

2-Chloro-5-(trans)-(2,2-dichloro-3-(3,5-dichlorophenyl)cyclopropane-1-carboxamido)-N-(2-methyl-3-oxoisoindolin-5-yl)benzamide (F517)

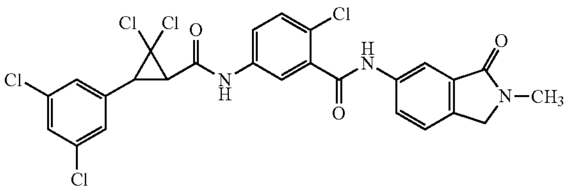 [SMILES: CN1Cc2ccc(NC(=O)c3cc(NC(=O)C4C(c5cc(Cl)cc(Cl)c5)C4(Cl)Cl)ccc3Cl)cc2C1=O]

Isolated as a white solid (0.057 g, 42.4%).

2-Chloro-5-(trans)-(2,2-dichloro-3-(3,5-dichlorophenyl)cyclopropane-1-carboxamido)-N-(2-methyl-1-oxoisoindolin-5-yl)benzamide (F518)

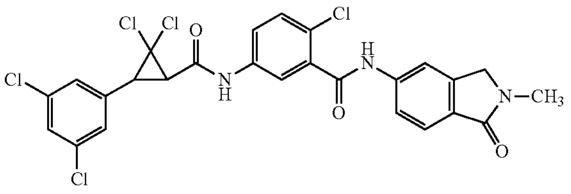 [SMILES: CN1Cc2cc(NC(=O)c3cc(NC(=O)C4C(c5cc(Cl)cc(Cl)c5)C4(Cl)Cl)ccc3Cl)ccc2C1=O]

Isolated as a white solid (0.116 g, 86%).

2-Chloro-5-(trans)-(2,2-dichloro-3-(3,5-dichlorophenyl)cyclopropane-1-carboxamido)-N-(6-fluoro-1H-indol-5-yl)benzamide (F527)

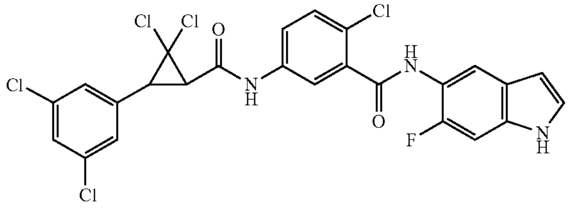 [SMILES: O=C(Nc1cc2cc[nH]c2cc1F)c1cc(NC(=O)C2C(c3cc(Cl)cc(Cl)c3)C2(Cl)Cl)ccc1Cl]

Isolated as a white solid (0.092 g, 67.7%).

2-Chloro-5-(trans)-(2,2-dichloro-3-(3,5-dichlorophenyl)cyclopropane-1-carboxamido)-N-(1H-indol-4-yl)benzamide (F528)

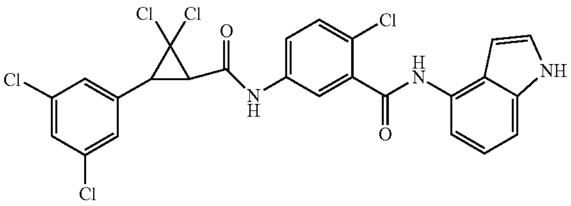 [SMILES: O=C(Nc1cccc2[nH]ccc12)c1cc(NC(=O)C2C(c3cc(Cl)cc(Cl)c3)C2(Cl)Cl)ccc1Cl]

Isolated as a gold foam (0.080 g, 60.7%).

2-Chloro-5-(trans)-(2,2-dichloro-3-(3,5-dichlorophenyl)cyclopropane-1-carboxamido)-N-(1H-indol-7-yl)benzamide (F529)

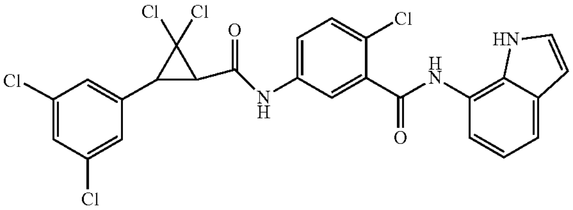 [SMILES: O=C(Nc1cccc2cc[nH]c12)c1cc(NC(=O)C2C(c3cc(Cl)cc(Cl)c3)C2(Cl)Cl)ccc1Cl]

Isolated as a tan foam (0.097 g, 73.6%).

2-Chloro-5-(trans)-(2,2-dichloro-3-(3,5-dichlorophenyl)cyclopropane-1-carboxamido)-N-(1-methyl-1H-indol-4-yl)benzamide (F530)

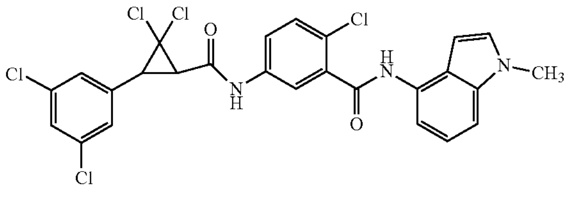 [SMILES: Cn1ccc2c(NC(=O)c3cc(NC(=O)C4C(c5cc(Cl)cc(Cl)c5)C4(Cl)Cl)ccc3Cl)cccc21]

Isolated as a brown foam (0.083 g, 61.5%).

2-Chloro-5-(trans)-(2,2-dichloro-3-(3,5-dichlorophenyl)cyclopropane-1-carboxamido)-N-(1-methyl-1H-indol-7-yl)benzamide (F531)

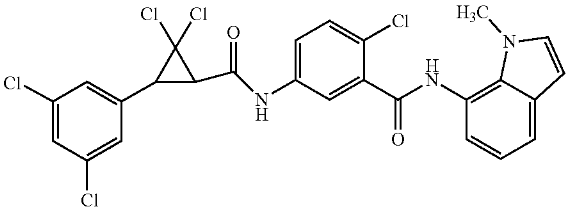 [SMILES: Cn1ccc2cccc(NC(=O)c3cc(NC(=O)C4C(c5cc(Cl)cc(Cl)c5)C4(Cl)Cl)ccc3Cl)c21]

Isolated as a tan foam (0.091 g, 67.4%).

2-Chloro-5-(trans)-(2,2-dichloro-3-(3,4-dibromophenyl)cyclopropane-1-carboxamido)-N-(2,4-difluorophenyl)benzamide (F532)

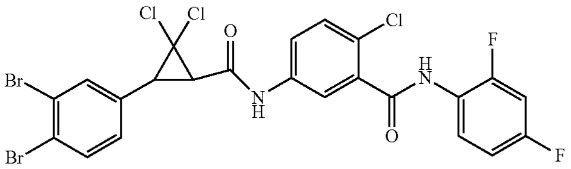 [SMILES: O=C(Nc1ccc(F)cc1F)c1cc(NC(=O)C2C(c3ccc(Br)c(Br)c3)C2(Cl)Cl)ccc1Cl]

Isolated as a white foam (0.105 g, 79%).

2-Chloro-5-((1R,3R)-(2,2-dichloro-3-(3-chloro-4-fluorophenyl)cyclopropane-1-carboxamido)-N-(2,4-difluorophenyl)benzamide (F533)

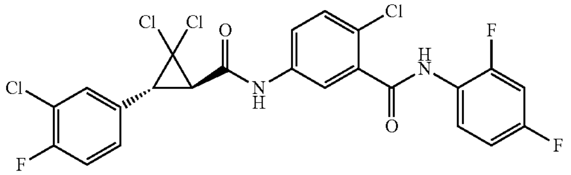

Isolated as a white foam (0.162 g, 82%).

2-Chloro-5-((1S,3S)-2,2-dichloro-3-(3-chloro-4-fluorophenyl)cyclopropane-1-carboxamido)-N-(2,4-difluorophenyl)benzamide (F534)

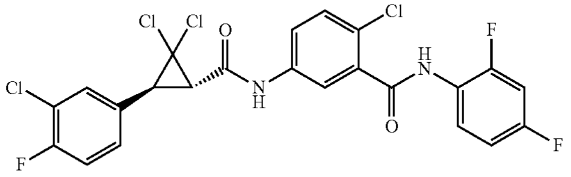 [SMILES: O=C(Nc1ccc(F)cc1F)c1cc(NC(=O)[C@@H]2[C@@H](c3ccc(F)c(Cl)c3)C2(Cl)Cl)ccc1Cl]

Isolated as a white foam (0.164 g, 83%).

2-Chloro-N-(2-cyano-4-fluorophenyl)-5-((1R,3R)-2,2-dichloro-3-(3,5-dichlorophenyl)cyclopropane-1-carboxamido)benzamide (F535)

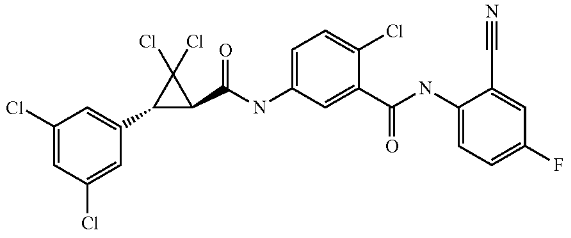 [SMILES: N#Cc1cc(F)ccc1NC(=O)c1cc(NC(=O)[C@H]2[C@H](c3cc(Cl)cc(Cl)c3)C2(Cl)Cl)ccc1Cl]

Isolated as a white foam (0.120 g, 30.9%).

2-Chloro-N-(2-cyano-4-fluorophenyl)-5-((1S,3S)-2,2-dichloro-3-(3,5-dichlorophenyl)cyclopropane-1-carboxamido)benzamide (F536)

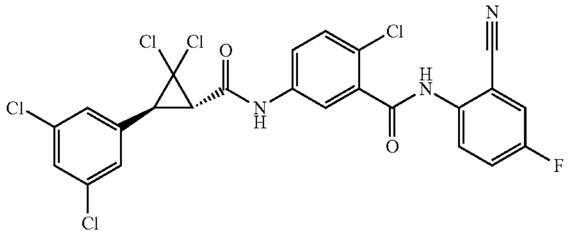 [SMILES: N#Cc1cc(F)ccc1NC(=O)c1cc(NC(=O)[C@@H]2[C@@H](c3cc(Cl)cc(Cl)c3)C2(Cl)Cl)ccc1Cl]

Isolated as a white foam (0.090 g, 23%).

2-Chloro-5-trans-(2,2-dichloro-3-(3,5-difluoro-4-methoxyphenyl)cyclopropane-1-carboxamido)-N-(2,4-difluorophenyl)benzamide (F537)

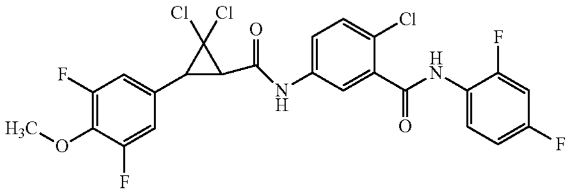 [SMILES: COc1c(F)cc(C2C(C(=O)Nc3ccc(Cl)c(C(=O)Nc4ccc(F)cc4F)c3)C2(Cl)Cl)cc1F]

Isolated as a white foam (0.078 g, 76%).

2-Chloro-5-trans-(2,2-dichloro-3-(3,5-dichlorophenyl)cyclopropane-1-carboxamido)-N-(5,6,7,8-tetrahydroquinolin-6-yl)benzamide (F567)

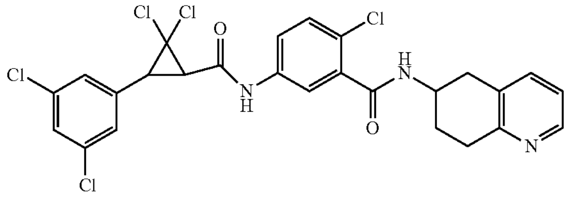 [SMILES: O=C(NC1CCc2ncccc2C1)c1cc(NC(=O)C2C(c3cc(Cl)cc(Cl)c3)C2(Cl)Cl)ccc1Cl]

Isolated as a white foam (0.059 g, 43.5%).

2-Chloro-5-trans-(2,2-dichloro-3-(3,4,5-trifluorophenyl)cyclopropane-1-carboxamido)-N-(2,4-difluorophenyl)benzamide (F581)

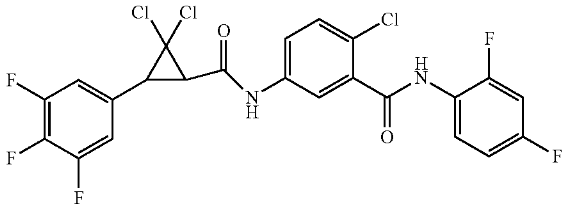 [SMILES: O=C(Nc1ccc(F)cc1F)c1cc(NC(=O)C2C(c3cc(F)c(F)c(F)c3)C2(Cl)Cl)ccc1Cl]

Isolated as a clear colorless oil (0.047 g, 46.3%).

2-Chloro-5-cis-(2,2-dichloro-3-(3,4,5-trifluorophenyl)cyclopropane-1-carboxamido)-N-(2,4-difluorophenyl)benzamide (F582)

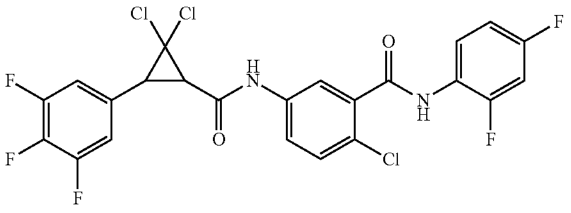 [SMILES: O=C(Nc1ccc(F)cc1F)c1cc(NC(=O)C2C(c3cc(F)c(F)c(F)c3)C2(Cl)Cl)ccc1Cl]

Isolated as a white solid (0.010 g, 9.8%).

trans-N-(2-acetyl-4-fluorophenyl)-2-chloro-5-(2,2-dichloro-3-(3,5-dichlorophenyl)cyclopropane-1-carboxamido)benzamide (PF77)

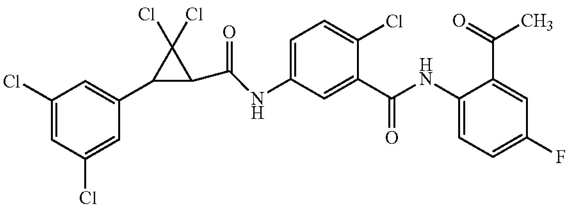 [SMILES: CC(=O)c1cc(F)ccc1NC(=O)c1cc(NC(=O)C2C(c3cc(Cl)cc(Cl)c3)C2(Cl)Cl)ccc1Cl]

Isolated as a pale yellow foam (0.358 g, 92%).

trans-N-(4-acetyl-2-fluorophenyl)-2-chloro-5-(2,2-dichloro-3-(3,5-dichlorophenyl)cyclopropane-1-carboxamido)benzamide (PF78)

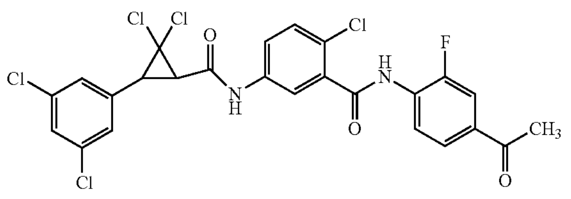 [SMILES: CC(=O)c1ccc(NC(=O)c2cc(NC(=O)C3C(c4cc(Cl)cc(Cl)c4)C3(Cl)Cl)ccc2Cl)c(F)c1]

Isolated as a white solid (0.236 g, 61%).

Example 56: Preparation of trans-2-chloro-5-(2,2-dichloro-3-(3,5-dichloro-4-methoxyphenyl)cyclopropane-1-carboxamido)-N-phenylbenzamide (F179)

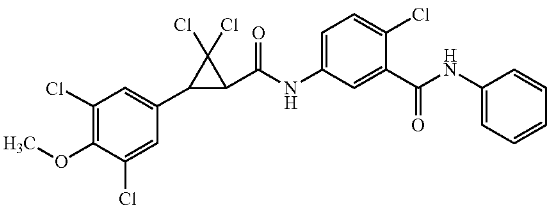 [SMILES: COc1c(Cl)cc(C2C(C(=O)Nc3ccc(Cl)c(C(=O)Nc4ccccc4)c3)C2(Cl)Cl)cc1Cl]

To a solution of trans-2-chloro-5-(2,2-dichloro-3-(3,5-dichloro-4-methoxyphenyl)cyclopropane-1-carboxamido) benzoic acid (C243) (0.125 g, 0.259 mmol) in dichloromethane (2.5 mL) were added 1-[bis(dimethylamino)methylene]-1H-1,2,3-triazolo[4,5-b]pyridinium 3-oxid hexafluorophosphate (0.108 g, 0.284 mmol) followed by diisopropylethylamine (0.0840 g, 0.646 mmol), and the resulting pale-yellow solution was stirred for 15 minutes, treated with aniline (0.0290 g, 0.310 mmol), and stirred at room temperature for approximately 18 hours. The solution was diluted with dichloromethane (5 mL), washed with water (5 mL), and the phases were separated and dried by passing them through a phase separator cartridge. The organic phase was concentrated, purified by flash column chromatography, and dried under vacuum to provide the title compound as tan solid (0.138 g, 96%).

The following compounds were prepared in like manner to the procedure outlined in Example 56:

trans-2-Chloro-5-(2,2-dichloro-3-(3,5-dichloro-4-methoxyphenyl)cyclo-propane-1-carboxamido)-N-(2,4-difluorophenyl)benzamide (F180)

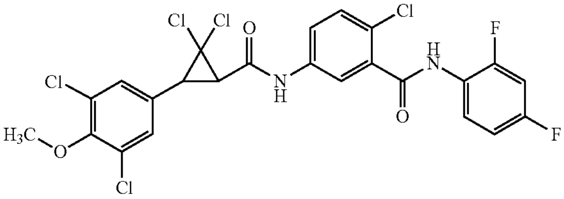 [SMILES: COc1c(Cl)cc(C2C(C(=O)Nc3ccc(Cl)c(C(=O)Nc4ccc(F)cc4F)c3)C2(Cl)Cl)cc1Cl]

Isolated as a tan solid (0.037 g, 24%).

trans-N-(4-Acetamidophenyl)-2-chloro-5-(2,2-dichloro-3-(3,5-dichloro-4-methoxyphenyl)cyclopropane-1-carboxamido)benzamide (F181)

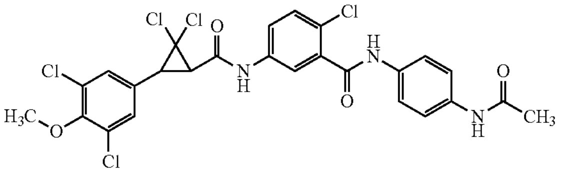 [SMILES: COc1c(Cl)cc(C2C(C(=O)Nc3ccc(Cl)c(C(=O)Nc4ccc(NC(C)=O)cc4)c3)C2(Cl)Cl)cc1Cl]

Isolated as a white solid (0.155 g, 97%).

trans-2-Chloro-5-(2,2-dichloro-3-(3,5-dichloro-4-methoxyphenyl)cyclo-propane-1-carboxamido)-N-(4-(methylamino)phenyl)benzamide (F182)

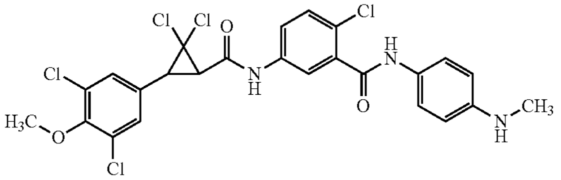

Isolated as a light green solid (0.139 g, 91%).

trans-2,3-Dichloro-5-(2,2-dichloro-3-(3,5-dichlorophenyl)cyclopropane-1-carboxamido)-N-(4-fluorophenyl)benzamide (F216)

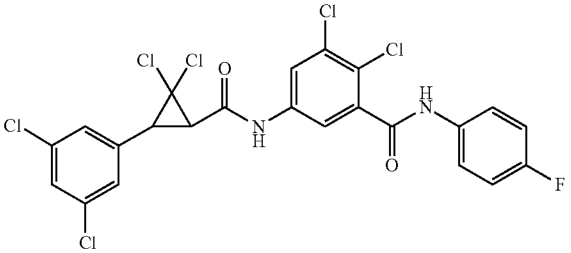 [SMILES: O=C(Nc1ccc(F)cc1)c1cc(NC(=O)C2C(c3cc(Cl)cc(Cl)c3)C2(Cl)Cl)cc(Cl)c1Cl]

Isolated as a white solid (0.059 g, 62%).

trans-2,3-Dichloro-5-(2,2-dichloro-3-(3,5-dichlorophenyl)cyclopropane-1-carboxamido)-N-phenylbenzamide (F246)

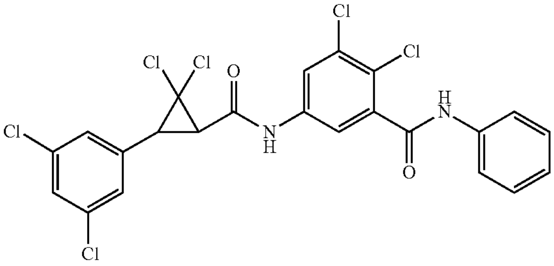 [SMILES: O=C(Nc1ccccc1)c1cc(NC(=O)C2C(c3cc(Cl)cc(Cl)c3)C2(Cl)Cl)cc(Cl)c1Cl]

Isolated as a white solid (0.075 g, 77%).

trans-2,3-Dichloro-5-(2,2-dichloro-3-(3,5-dichlorophenyl)cyclopropane-1-carboxamido)-N-(2,4-difluorophenyl)benzamide (F247)

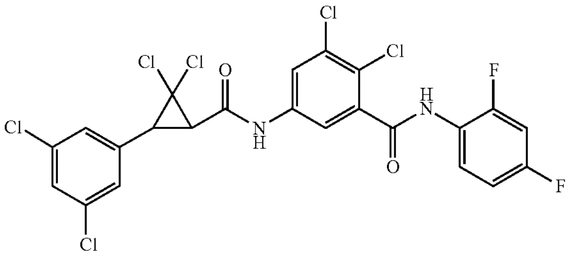 [SMILES: O=C(Nc1ccc(F)cc1F)c1cc(NC(=O)C2C(c3cc(Cl)cc(Cl)c3)C2(Cl)Cl)cc(Cl)c1Cl]

Isolated as an off-white solid (0.014 g, 13%).

trans-N-(4-Acetamidophenyl)-2,3-dichloro-5-(2,2-dichloro-3-(3,5-dichlorophenyl)cyclopropane-1-carboxamido)benzamide (F248)

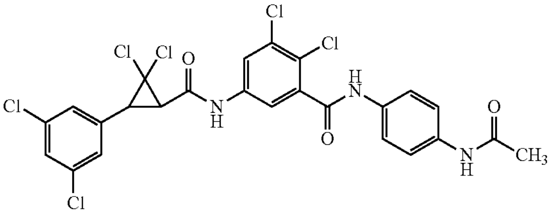 [SMILES: CC(=O)Nc1ccc(NC(=O)c2cc(NC(=O)C3C(c4cc(Cl)cc(Cl)c4)C3(Cl)Cl)cc(Cl)c2Cl)cc1]

Isolated as a white solid (0.032 g, 30%).

trans-2,3-Dichloro-5-(2,2-dichloro-3-(3,5-dichlorophenyl)cyclopropane-1-carboxamido)-N-(4-(methylamino)phenyl)benzamide (F249)

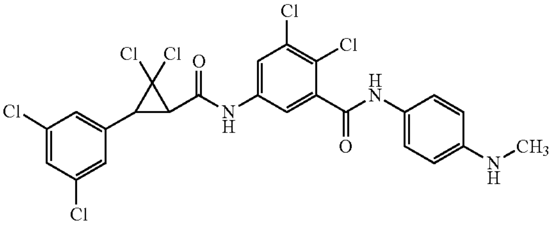 [SMILES: CNc1ccc(NC(=O)c2cc(NC(=O)C3C(c4cc(Cl)cc(Cl)c4)C3(Cl)Cl)cc(Cl)c2Cl)cc1]

Isolated as a yellow-green solid (0.028 g, 27%).

trans-2,4-Dichloro-5-(2,2-dichloro-3-(3,5-dichlorophenyl)cyclopropane-1-carboxamido)-N-(4-fluorophenyl)benzamide (F250)

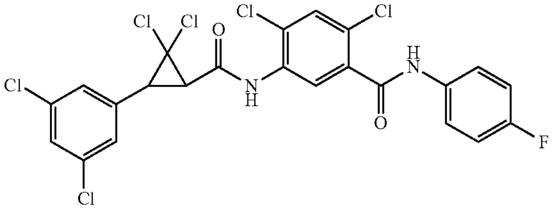 [SMILES: O=C(Nc1ccc(F)cc1)c1cc(NC(=O)C2C(c3cc(Cl)cc(Cl)c3)C2(Cl)Cl)c(Cl)cc1Cl]

Isolated as an orange solid (0.041 g, 41%).

trans-2,4-Dichloro-5-(2,2-dichloro-3-(3,5-dichlorophenyl)cyclopropane-1-carboxamido)-N-phenylbenzamide (F254)

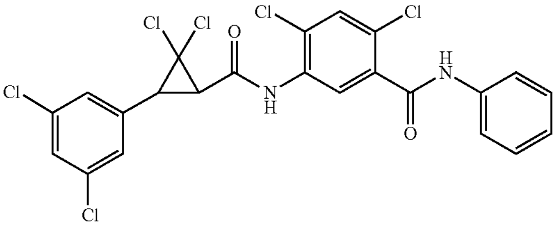 [SMILES: O=C(Nc1ccccc1)c1cc(NC(=O)C2C(c3cc(Cl)cc(Cl)c3)C2(Cl)Cl)c(Cl)cc1Cl]

Isolated as a white solid (0.012 g, 12%).

trans-N-(4-Acetamidophenyl)-2,4-dichloro-5-(2,2-dichloro-3-(3,5-dichlorophenyl)cyclopropane-1-carboxamido)benzamide (F255)

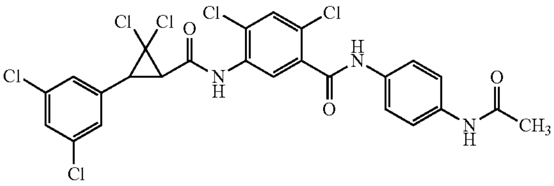 [SMILES: CC(=O)Nc1ccc(NC(=O)c2cc(NC(=O)C3C(c4cc(Cl)cc(Cl)c4)C3(Cl)Cl)c(Cl)cc2Cl)cc1]

Isolated as a white solid (0.029 g, 27%).

trans-2,4-dichloro-5-(2,2-dichloro-3-(3,5-dichlorophenyl)cyclopropane-1-carboxamido)-N-(4-(methylamino)phenyl)benzamide (F256)

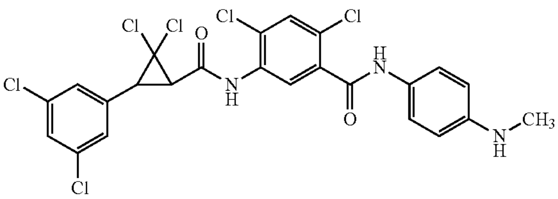 [SMILES: CNc1ccc(NC(=O)c2cc(NC(=O)C3C(c4cc(Cl)cc(Cl)c4)C3(Cl)Cl)c(Cl)cc2Cl)cc1]

Isolated as a gold-colored solid (0.069 g, 68%).

trans-2-Chloro-5-(2,2-dichloro-3-(3-chloro-4-fluorophenyl)cyclopropane-1-carboxamido)-N-phenylbenzamide (F259)

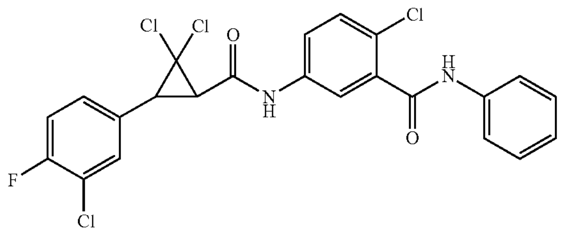 [SMILES: O=C(Nc1ccccc1)c1cc(NC(=O)C2C(c3ccc(F)c(Cl)c3)C2(Cl)Cl)ccc1Cl]

Isolated as a tan solid (0.070 g, 71%).

trans-N-(4-Acetamidophenyl)-2-chloro-5-(2,2-dichloro-3-(3-chloro-4-fluorophenyl)cyclopropane-1-carboxamido)benzamide (F260)

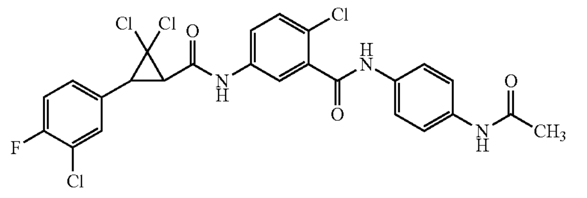 [SMILES: CC(=O)Nc1ccc(NC(=O)c2cc(NC(=O)C3C(c4ccc(F)c(Cl)c4)C3(Cl)Cl)ccc2Cl)cc1]

Isolated as a light-yellow solid (0.038 g, 33%).

trans-2-Chloro-5-(2,2-dichloro-3-(3-chloro-4-fluorophenyl)cyclopropane-1-carboxamido)-N-(4-(methylamino)phenyl)benzamide (F261)

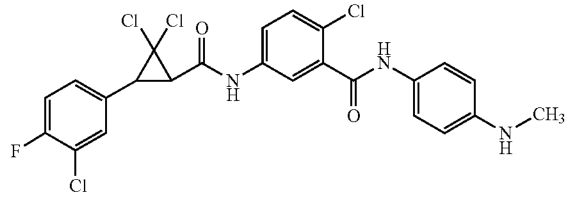 [SMILES: CNc1ccc(NC(=O)c2cc(NC(=O)C3C(c4ccc(F)c(Cl)c4)C3(Cl)Cl)ccc2Cl)cc1]

Isolated as a light-yellow solid (0.054 g, 52%).

trans-2-Chloro-5-(2,2-dichloro-3-(3-chloro-4-fluorophenyl)cyclopropane-1-carboxamido)-N-(2,4-difluorophenyl)benzamide (PF6)

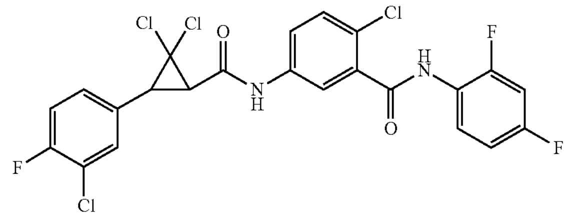

Isolated as a white solid (0.031 g, 29%).

trans-2-Chloro-5-(2,2-dichloro-3-(3,5-dichloro-4-methoxyphenyl)cyclopropane-1-carboxamido)-N-(4-fluorophenyl)benzamide (PF156)

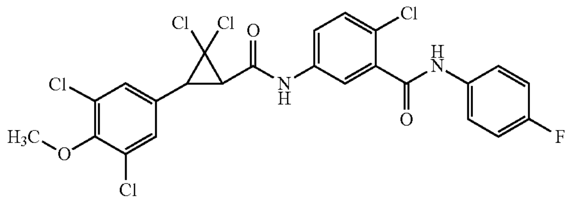 [SMILES: COc1c(Cl)cc(C2C(C(=O)Nc3ccc(Cl)c(C(=O)Nc4ccc(F)cc4)c3)C2(Cl)Cl)cc1Cl]

Isolated as a white solid (0.137 g, 92%).

Example 57: Preparation of trans-N-(2-cyano-4-fluorophenyl)-3-(2,2-dichloro-3-(3,4,5-trichlorophenyl)cyclopropane-1-carboxamido)benzamide (F267)

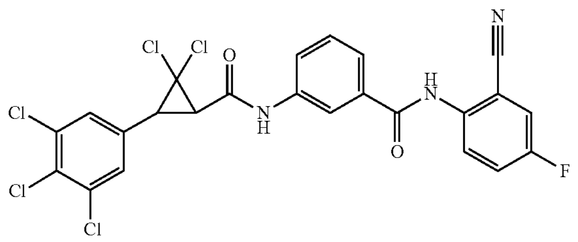 [SMILES: N#Cc1cc(F)ccc1NC(=O)c1cccc(NC(=O)C2C(c3cc(Cl)c(Cl)c(Cl)c3)C2(Cl)Cl)c1]

To a solution of 2,2-dichloro-3-(3,4,5-trichlorophenyl) cyclopropane-1-carboxylic acid (C2) in ethyl acetate (3 mL) were added 3-amino-N-(2-cyano-4-fluorophenyl)benzamide (C258) (89 mg, 0.350 mmol) in ethyl acetate (2916 μL) and added pyridine (56.6 μl, 0.700 mmol), followed by 2,4,6-tripropyl-1,3,5,2,4,6-trioxatriphosphinane 2,4,6-trioxide (312 μL, 0.525 mmol) as a 50% solution in ethyl acetate. The solution was stirred for 72 hours at room temperature. The resulting mixture was then concentrated under vacuum. Purification by flash column chromatography using 0-100% ethyl acetate/hexane as an elutant afforded the product as an off white foam (0.176 g, 79%).

The following compounds were prepared in like manner to the procedure outlined in Example 57:

trans-N-(2-Cyano-4-fluorophenyl)-3-(2,2-dichloro-3-(3,4-dichlorophenyl)cyclopropane-1-carboxamido) benzamide (F268)

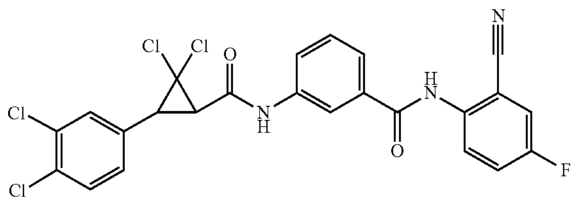 [SMILES: N#Cc1cc(F)ccc1NC(=O)c1cccc(NC(=O)C2C(c3ccc(Cl)c(Cl)c3)C2(Cl)Cl)c1]

Isolated as an off-white foam (0.175 g, 79%).

trans-tert-Butyl (5-(2-chloro-5-((1S,3S)-2,2-dichloro-3-(3,5-dichlorophenyl)cyclopropane-1-carboxamido)benzamido)-2-fluorophenyl)(methyl)carbamate (F471)

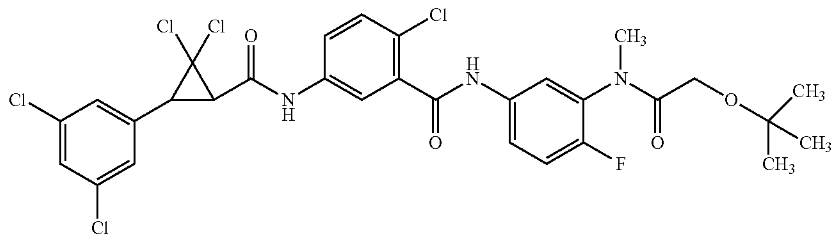 [SMILES: CN(C(=O)COC(C)(C)C)c1cc(NC(=O)c2cc(NC(=O)C3C(c4cc(Cl)cc(Cl)c4)C3(Cl)Cl)ccc2Cl)ccc1F]

Isolated as an off-white solid (0.422 g, quant).

2-Chloro-5-(trans-2,2-dichloro-3-(3-chloro-5-(difluoromethyl)phenyl)cyclopropane-1-carboxamido)-N-(2,4-difluorophenyl)benzamide (F558)

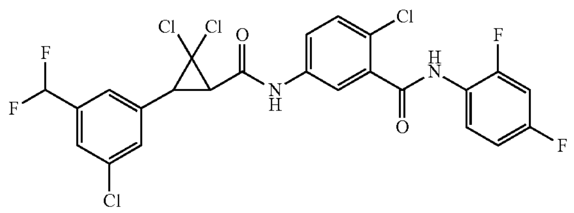 [SMILES: O=C(Nc1ccc(F)cc1F)c1cc(NC(=O)C2C(c3cc(Cl)cc(C(F)F)c3)C2(Cl)Cl)ccc1Cl]

Isolated as a colorless oil (0.107 g, 88%).

2-Chloro-5-(trans-2,2-dichloro-3-(4-chloro-3-(difluoromethyl)phenyl)cyclopropane-1-carboxamido)-N-(2,4-difluorophenyl)benzamide (F559)

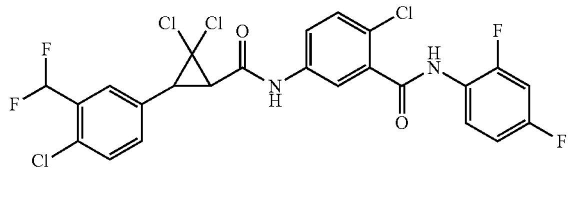 [SMILES: O=C(Nc1ccc(F)cc1F)c1cc(NC(=O)C2C(c3ccc(Cl)c(C(F)F)c3)C2(Cl)Cl)ccc1Cl]

Isolated as a colorless oil (0.098 g, 80%).

2-Chloro-5-(trans-2,2-dichloro-3-(3-(difluoromethyl)-5-fluorophenyl)cyclopropane-1-carboxamido)-N-(2,4-difluorophenyl)benzamide (F560)

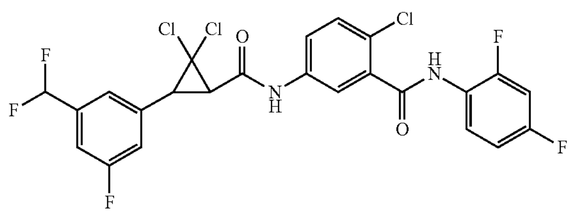

Isolated as a colorless oil (0.115 g, 97%).

2-Chloro-5-(trans-2,2-dichloro-3-(3-(difluoromethyl)-4-fluorophenyl)cyclopropane-1-carboxamido)-N-(2,4-difluorophenyl)benzamide (F561)

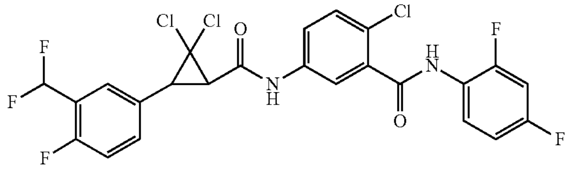

Isolated as a colorless oil (0.115 g, 97%).

2-Chloro-5-(trans-2,2-dichloro-3-(3-chloro-4-(difluoromethyl)phenyl)cyclopropane-1-carboxamido)-N-(2,4-difluorophenyl)benzamide (F562)

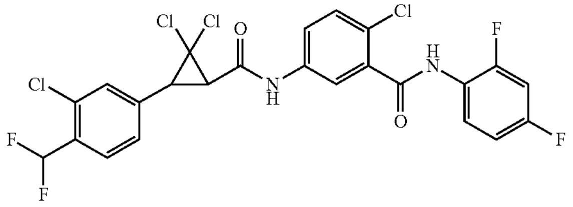 [SMILES: O=C(Nc1ccc(F)cc1F)c1cc(NC(=O)C2C(c3ccc(C(F)F)c(Cl)c3)C2(Cl)Cl)ccc1Cl]

Isolated as a colorless oil (0.094 g, 77%).

2-Chloro-5-(trans-2,2-dichloro-3-(4-(difluoromethyl)-3-fluorophenyl)cyclopropane-1-carboxamido)-N-(2,4-difluorophenyl)benzamide (F563)

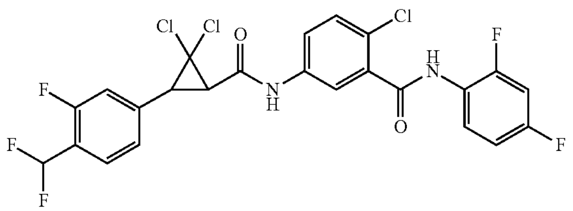

Isolated as a colorless oil (0.087 g, 73%).

2-Chloro-5-(trans-2,2-dichloro-3-(3-(difluoromethyl)phenyl)cyclopropane-1-carboxamido)-N-(2,4-difluorophenyl)benzamide (F564)

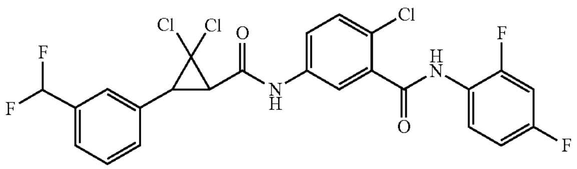 [SMILES: O=C(Nc1ccc(F)cc1F)c1cc(NC(=O)C2C(c3cccc(C(F)F)c3)C2(Cl)Cl)ccc1Cl]

Isolated as a colorless oil (0.090 g, 78%).

2-Chloro-5-(trans-2,2-dichloro-3-(4-(difluoromethyl)phenyl)cyclopropane-1-carboxamido)-N-(2,4-difluorophenyl)benzamide (F565)

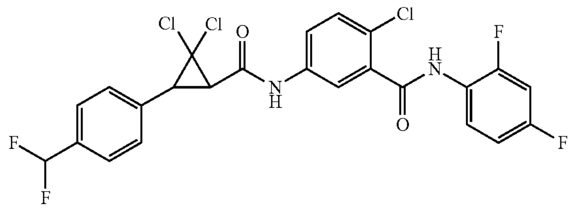

Isolated as a colorless oil (0.090 g, 78%).

2-Chloro-5-(trans-2,2-dichloro-3-(3-chloro-5-(difluoromethyl)phenyl)cyclopropane-1-carboxamido)-N-(3,5-difluoropyridin-2-yl)benzamide (F584)

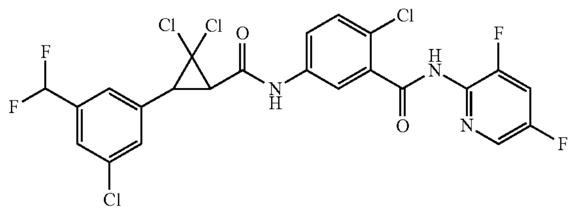

Isolated as a pale yellow oil (0.055 g, 60%).

2-Chloro-5-(trans-2,2-dichloro-3-(4-chloro-3-(difluoromethyl)phenyl)cyclopropane-1-carboxamido)-N-(3,5-difluoropyridin-2-yl)benzamide (F585)

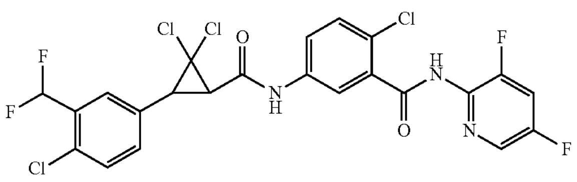 [SMILES: O=C(Nc1ncc(F)cc1F)c1cc(NC(=O)C2C(c3ccc(Cl)c(C(F)F)c3)C2(Cl)Cl)ccc1Cl]

Isolated as a pale yellow oil (0.046 g, 50%).

2-Chloro-5-(trans-2,2-dichloro-3-(3-(difluoromethyl)-5-fluorophenyl)cyclopropane-1-carboxamido)-N-(3,5-difluoropyridin-2-yl)benzamide (F586)

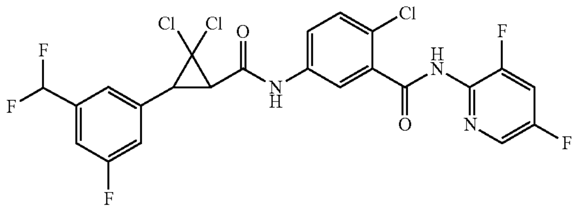

Isolated as a white foam (0.045 g, 50%).

2-Chloro-5-(trans-2,2-dichloro-3-(3-(difluoromethyl)-4-fluorophenyl)cyclopropane-1-carboxamido)-N-(3,5-difluoropyridin-2-yl)benzamide (F587)

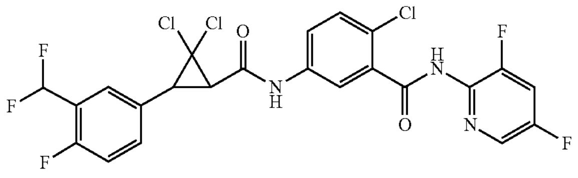 [SMILES: O=C(Nc1ncc(F)cc1F)c1cc(NC(=O)C2C(c3ccc(F)c(C(F)F)c3)C2(Cl)Cl)ccc1Cl]

Isolated as a pale yellow oil (0.045 g, 50%).

2-Chloro-5-(trans-2,2-dichloro-3-(3-chloro-4-(difluoromethyl)phenyl)cyclopropane-1-carboxamido)-N-(3,5-difluoropyridin-2-yl)benzamide (F588)

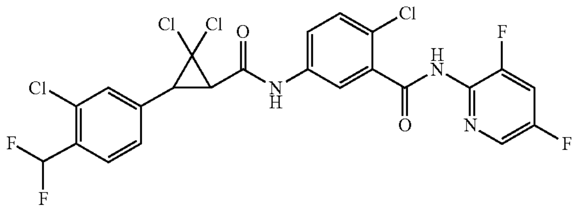

Isolated as a white foam (0.055 g, 60%).

2-chloro-5-(trans-2,2-dichloro-3-(4-(difluoromethyl)-3-fluorophenyl)cyclopropane-1-carboxamido)-N-(3,5-difluoropyridin-2-yl)benzamide (F589)

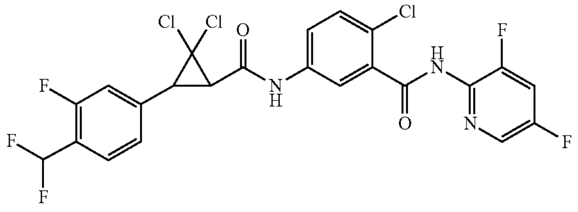

Isolated as a white foam (0.036 g, 40%).

2-Chloro-5-(trans-2,2-dichloro-3-(3-(difluoromethyl)phenyl)cyclopropane-1-carboxamido)-N-(3,5-difluoropyridin-2-yl)benzamide (F590)

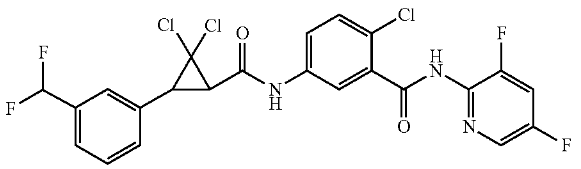 [SMILES: O=C(Nc1ncc(F)cc1F)c1cc(NC(=O)C2C(c3cccc(C(F)F)c3)C2(Cl)Cl)ccc1Cl]

Isolated as a pale yellow oil (0.052 g, 60%).

2-Chloro-5-(trans-2,2-dichloro-3-(4-(difluoromethyl)phenyl)cyclopropane-1-carboxamido)-N-(3,5-difluoropyridin-2-yl)benzamide (F591)

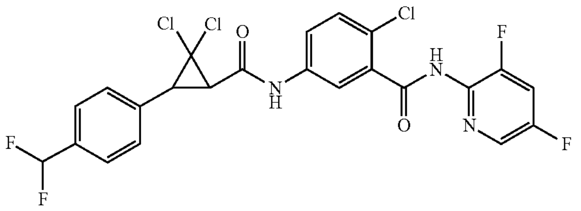

Isolated as a white foam (0.043 g, 50%).

2-Chloro-5-(trans-2,2-dichloro-3-(3-chloro-5-(difluoromethyl)phenyl)cyclopropane-1-carboxamido)-N-(4-fluorophenyl)-N-methylbenzamide (F592)

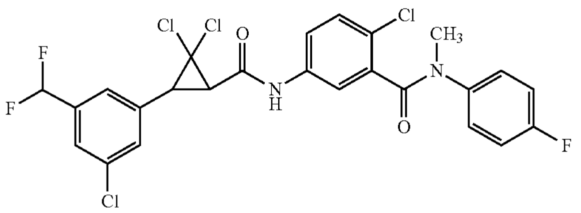

Isolated as a pale yellow oil (0.064 g, 70%).

2-Chloro-5-(trans-2,2-dichloro-3-(4-chloro-3-(difluoromethyl)phenyl)cyclopropane-1-carboxamido)-N-(4-fluorophenyl)-N-methylbenzamide (F593)

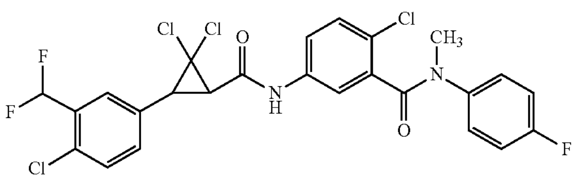 [SMILES: CN(C(=O)c1cc(NC(=O)C2C(c3ccc(Cl)c(C(F)F)c3)C2(Cl)Cl)ccc1Cl)c1ccc(F)cc1]

Isolated as a pale yellow oil (0.064 g, 70%).

2-Chloro-5-(trans-2,2-dichloro-3-(3-(difluoromethyl)-5-fluorophenyl)cyclopropane-1-carboxamido)-N-(4-fluorophenyl)-N-methylbenzamide (F594)

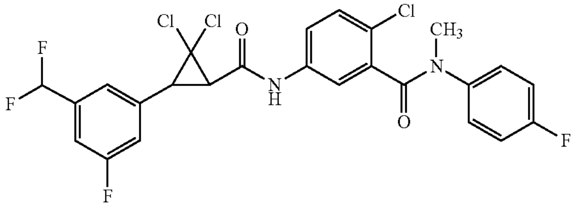

Isolated as a colorless oil (0.053 g, 60%).

2-Chloro-5-(trans-2,2-dichloro-3-(3-(difluoromethyl)-4-fluorophenyl)cyclopropane-1-carboxamido)-N-(4-fluorophenyl)-N-methylbenzamide (F595)

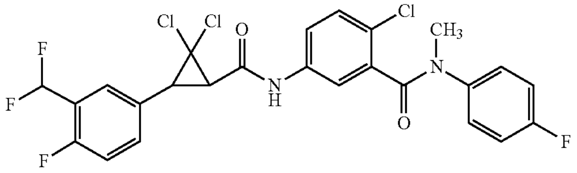 [SMILES: CN(C(=O)c1cc(NC(=O)C2C(c3ccc(F)c(C(F)F)c3)C2(Cl)Cl)ccc1Cl)c1ccc(F)cc1]

Isolated as a colorless oil (0.053 g, 60%).

2-Chloro-5-(trans-2,2-dichloro-3-(3-chloro-4-(difluoromethyl)phenyl)cyclopropane-1-carboxamido)-N-(4-fluorophenyl)-N-methylbenzamide (F596)

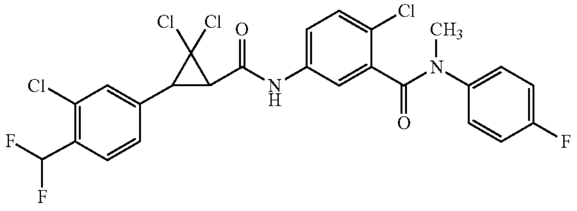 [SMILES: CN(C(=O)c1cc(NC(=O)C2C(c3ccc(C(F)F)c(Cl)c3)C2(Cl)Cl)ccc1Cl)c1ccc(F)cc1]

Isolated as a pale yellow oil (0.064 g, 70%).

2-Chloro-5-(trans-2,2-dichloro-3-(4-(difluoromethyl)-3-fluorophenyl)cyclopropane-1-carboxamido)-N-(4-fluorophenyl)-N-methylbenzamide (F597)

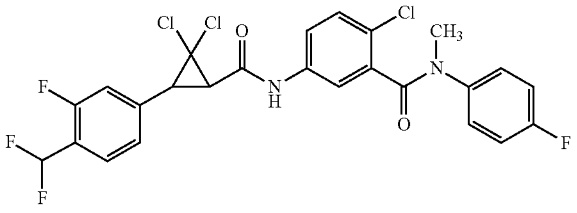

Isolated as a pale yellow oil (0.062 g, 70%).

2-Chloro-5-(trans-2,2-dichloro-3-(3-(difluoromethyl)phenyl)cyclopropane-1-carboxamido)-N-(4-fluorophenyl)-N-methylbenzamide (F598)

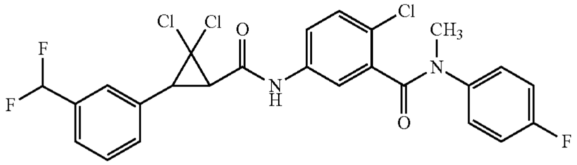 [SMILES: CN(C(=O)c1cc(NC(=O)C2C(c3cccc(C(F)F)c3)C2(Cl)Cl)ccc1Cl)c1ccc(F)cc1]

Isolated as a colorless oil (0.043 g, 50%).

2-Chloro-5-(trans-2,2-dichloro-3-(4-(difluoromethyl)phenyl)cyclopropane-1-carboxamido)-N-(4-fluorophenyl)-N-methylbenzamide (F599)

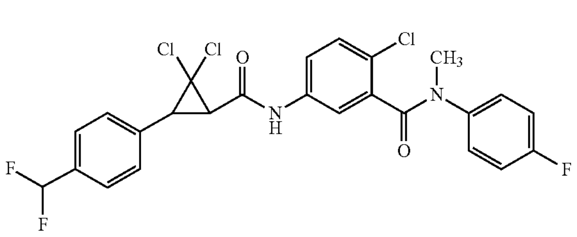 [SMILES: CN(C(=O)c1cc(NC(=O)C2C(c3ccc(C(F)F)cc3)C2(Cl)Cl)ccc1Cl)c1ccc(F)cc1]

Isolated as a white foam (0.051 g, 60%).

2-Chloro-5-(trans)-2,2-dichloro-3-(4-chloro-3-fluorophenyl)cyclopropane-1-carboxamido)-N-(2,4-difluorophenyl)benzamide (PF36)

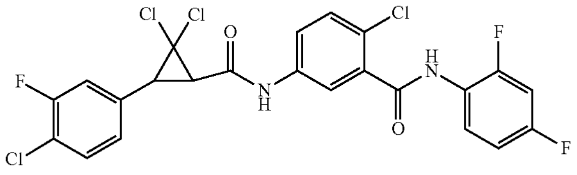 [SMILES: O=C(Nc1ccc(F)cc1F)c1cc(NC(=O)C2C(c3ccc(Cl)c(F)c3)C2(Cl)Cl)ccc1Cl]

Isolated as a white foam. (0.116 g, 76%).

Example 58: Preparation of trans-2-chloro-5-(2,2-dichloro-3-(3,5-dichlorophenyl)cyclopropane-1-carboxamido)-N-(4-fluoro-2-(trifluoromethyl)phenyl)benzamide (PF69)

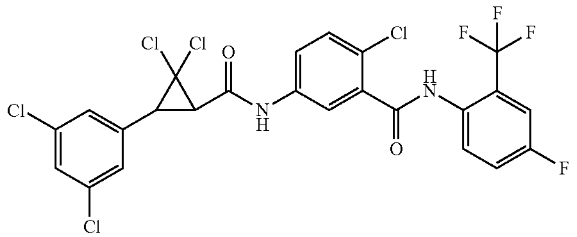 [SMILES: O=C(Nc1ccc(F)cc1C(F)(F)F)c1cc(NC(=O)C2C(c3cc(Cl)cc(Cl)c3)C2(Cl)Cl)ccc1Cl]

To a solution of 2-chloro-N-(4-fluoro-2-(trifluoromethyl)phenyl)-5-nitrobenzamide 2,2-dichloro-3-(3,4,5-trichlorophenyl)cyclopropane-1-carboxylic acid (C268) (0.15 g, 0.414 mmol) in methanol (1.3 mL) and water (0.66 mL) were added iron (0.115 g, 2.068 mmol) and ammonium chloride (0.066 g, 1.241 mmol). The reaction was heated at 60° C. for 2 hours. The reaction was filtered through Celite®. The filtrate was concentrated to a slurry, diluted with dichloromethane and washed with water. The organic phase was dried (magnesium sulfate) and concentrated to give a yellow solid. The solid was then purged with a nitrogen atmosphere, dissolved in dichloromethane, charged with triethylamine (0.122 mL, 0.889 mmol), and cooled to 0° C.

To a solution of 2,2-dichloro-3-(3,5-dichlorophenyl)cyclopropane-1-carboxylic acid (C67) (612 mg, 2.041 mmol) in dichloromethane (10 mL) cooled to 0° C. were added oxalyl chloride (0.3 mL, 3.43 mmol) followed by N,N-dimethylformamide (0.014 mL, 0.184 mmol). The solution was capped with a drying tube and stirred overnight slowly warming to room temperature. The resulting acid chloride solution was then concentrated under vacuum to form a dark brown gum residue. The resulting trans-2,2-dichloro-3-(3,5-dichlorophenyl)cyclopropanecarbonyl chloride residue was dissolved in dichloromethane resulting in a solution of 1 N concentration. A portion of this trans-2,2-dichloro-3-(3,5-dichlorophenyl)cyclopropanecarbonyl chloride solution (0.453 mL, 0.462 mmol) was added to the 5-amino-2-chloro-N-(4-fluoro-2-(trifluoromethyl)phenyl)benzamide/triethylamine mixture, and the combined mixture was stirred overnight slowly while warming to room temperature. The mixture was then dried to a residue and purified by flash column chromatography using 0-100% ethyl acetate/hexanes as the elutant providing the title compound as an off-white foam (0.028 g, 9%).

Example 59: Preparation of trans-N-(4-amino-2-cyanophenyl)-2-chloro-5-(2,2-dichloro-3-(3,5-dichlorophenyl)cyclopropane-1-carboxamido)benzamide (F236)

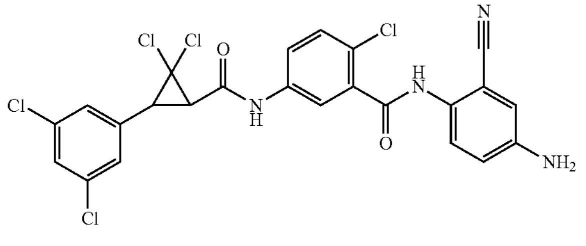 [SMILES: N#Cc1cc(N)ccc1NC(=O)c1cc(NC(=O)C2C(c3cc(Cl)cc(Cl)c3)C2(Cl)Cl)ccc1Cl]

A suspension of 2-chloro-N-(2-cyano-4-nitrophenyl)-5-(2,2-dichloro-3-(3,5-dichlorophenyl)cyclopropane-1-carboxamido)benzamide (F229) (618 mg, 1.032 mmol) and 10% palladium on carbon (54.9 mg, 0.052 mmol) in ethyl acetate (6.9 mL) was fitted with a balloon filled with hydrogen gas, evacuated under vacuum, and backfilled with hydrogen three times. Then, the reaction mixture was stirred under a hydrogen atmosphere overnight. The reaction mixture was filtered through Celite®, rinsing with ethyl acetate, and then the solvent was evaporated to give a yellow foam. The foam was suspended in dichloromethane and then the solids were collected by vacuum filtration and dried under vacuum. The crude material was purified by flash column chromatography using 0-100% ethyl acetate in hexanes as the eluent to afford the title compound as a pale yellow powder (0.446 g, 76%).

The following compounds were prepared in like manner to the procedure outlined in Example 59:

N-(5-Aminopyridin-2-yl)-2-chloro-5-(trans-2,2-dichloro-3-(3,5-dichlorophenyl)cyclopropane-1-carboxamido)benzamide (F305)

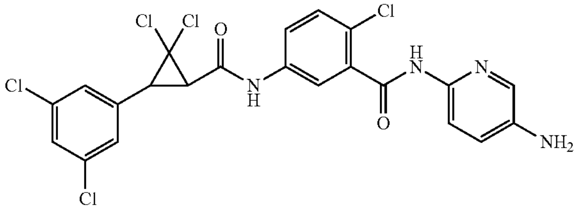 [SMILES: Nc1ccc(NC(=O)c2cc(NC(=O)C3C(c4cc(Cl)cc(Cl)c4)C3(Cl)Cl)ccc2Cl)nc1]

Isolated as a yellow solid (0.0148 mg, 32%).

N-(5-aminopyridin-3-yl)-2-chloro-5-((1R,3R)-2,2-dichloro-3-(3,5-dichlorophenyl)cyclopropane-1-carboxamido)benzamide (F362)

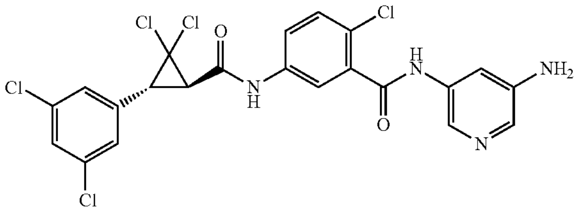 [SMILES: Nc1cncc(NC(=O)c2cc(NC(=O)[C@H]3[C@H](c4cc(Cl)cc(Cl)c4)C3(Cl)Cl)ccc2Cl)c1]

Isolated as a white solid (0.0377 g, 37%).

N-(5-Aminopyridin-3-yl)-2-chloro-5-((1R,3R)-2,2-dichloro-3-(3,4-dichlorophenyl)cyclopropane-1-carboxamido)benzamide (F363)

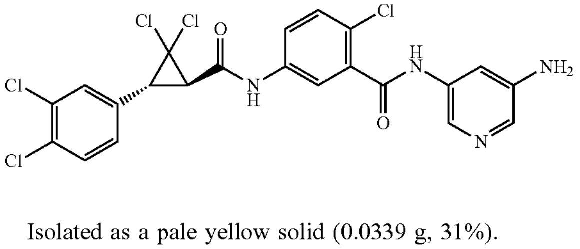

Isolated as a pale yellow solid (0.0339 g, 31%).

2-Chloro-5-((1R,3R)-2,2-dichloro-3-(3,5-dichlorophenyl)cyclopropane-1-carboxamido)-N-(5-(hydroxyamino)pyridin-3-yl)benzamide (F525)

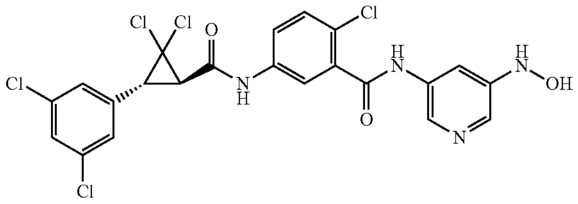 [SMILES: O=C(Nc1cncc(NO)c1)c1cc(NC(=O)[C@H]2[C@H](c3cc(Cl)cc(Cl)c3)C2(Cl)Cl)ccc1Cl]

Isolated as a white solid (0.0438 g, 42%).

2-Chloro-5-((1R,3R)-2,2-dichloro-3-(3,4-dichlorophenyl)cyclopropane-1-carboxamido)-N-(5-(hydroxyamino)pyridin-3-yl)benzamide (F526)

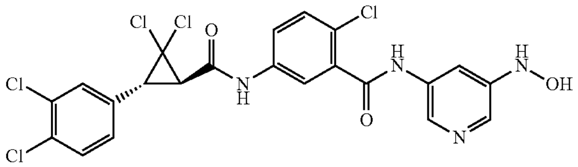 [SMILES: O=C(Nc1cncc(NO)c1)c1cc(NC(=O)[C@H]2[C@H](c3ccc(Cl)c(Cl)c3)C2(Cl)Cl)ccc1Cl]

Isolated as a yellow solid (0.0523 mg, 46%).

Example 60: Preparation of trans-N-(2-amino-4-fluorophenyl)-2-chloro-5-(2,2-dichloro-3-(3,5-dichlorophenyl)cyclopropane-1-carboxamido)benzamide (F361)

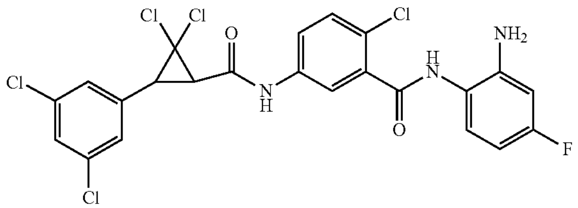 [SMILES: Nc1cc(F)ccc1NC(=O)c1cc(NC(=O)C2C(c3cc(Cl)cc(Cl)c3)C2(Cl)Cl)ccc1Cl]

To a slurry of trans-2-chloro-5-(2,2-dichloro-3-(3,5-dichlorophenyl)cyclopropane-1-carboxamido)-N-(4-fluoro-2-nitrophenyl)benzamide (F348) (0.055 g, 0.093 mmol) in methanol (0.9 mL) and water (0.3 mL) were added iron powder (0.026 g, 0.465 mmol) and ammonium chloride (0.015 g, 0.279 mmol). The slurry was warmed to 55° C. for three hours then cooled to room temperature and allowed to stir overnight. The reaction mixture was filtered thru a plug of Celite®, washing with ethyl acetate. The filtrates were concentrated under reduced pressure, and the residue partitioned between ethyl acetate and water. The phases were separated, and the organic layer was washed with brine, poured through a phase separator, and then concentrated. The residue was purified by flash column chromatography using 0-40% ethyl acetate/hexanes as eluent to yield the title compound as a yellow solid (0.033 g, 54%).

The following compounds were prepared in like manner to the procedure outlined in Example 60:

N-(2-Amino-4-fluorophenyl)-2-chloro-5-((1R,3R)-2,2-dichloro-3-(3,5-dichlorophenyl)cyclopropane-1-carboxamido)benzamide (F575)

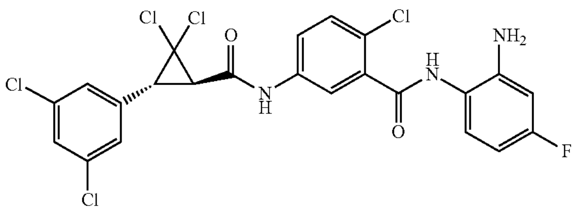 [SMILES: Nc1cc(F)ccc1NC(=O)c1cc(NC(=O)[C@H]2[C@H](c3cc(Cl)cc(Cl)c3)C2(Cl)Cl)ccc1Cl]

Isolated as a yellow solid (0.071 g, 67%).

N-(2-Amino-4-fluorophenyl)-2-chloro-5-((1R,3R)-2,2-dichloro-3-(3,4-dichlorophenyl)cyclopropane-1-carboxamido)benzamide (F576)

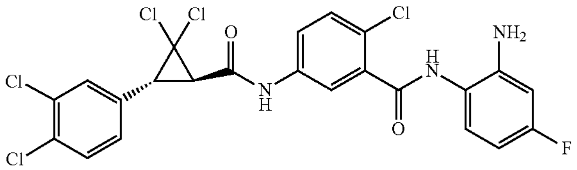

Isolated as a yellow solid (0.071 g, 64%).

N-(2-Amino-4-fluorophenyl)-2-chloro-5-((1R,3R)-2,2-dichloro-3-(3,4,5-trichlorophenyl)cyclopropane-1-carboxamido)benzamide (F577)

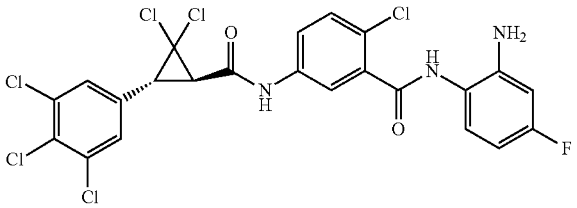 [SMILES: Nc1cc(F)ccc1NC(=O)c1cc(NC(=O)[C@H]2[C@H](c3cc(Cl)c(Cl)c(Cl)c3)C2(Cl)Cl)ccc1Cl]

Isolated as a yellow solid (0.046 g, 62%).

N-(2-Amino-4-fluorophenyl)-2-chloro-5-((1R,3R)-2,2-dichloro-3-(3-chloro-4-fluorophenyl)cyclopropane-1-carboxamido)benzamide (F578)

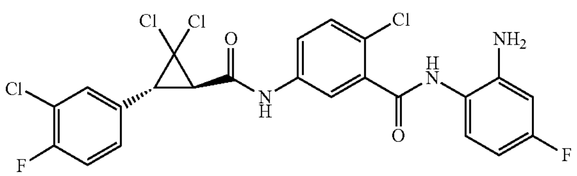 [SMILES: Nc1cc(F)ccc1NC(=O)c1cc(NC(=O)[C@H]2[C@H](c3ccc(F)c(Cl)c3)C2(Cl)Cl)ccc1Cl]

Isolated as a yellow solid (0.068 g, 64%).

N-(3-Amino-5-fluorophenyl)-2-chloro-5-((1R,3R)-2,2-dichloro-3-(3,4-dichlorophenyl)cyclopropane-1-carboxamido)benzamide (F431)

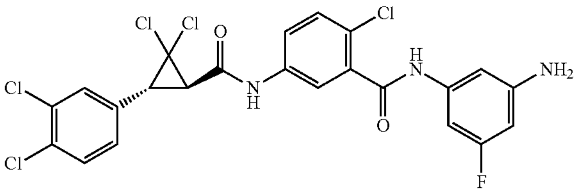 [SMILES: Nc1cc(F)cc(NC(=O)c2cc(NC(=O)[C@H]3[C@H](c4ccc(Cl)c(Cl)c4)C3(Cl)Cl)ccc2Cl)c1]

Isolated as a light brown foam (0.057 g, 60%).

N-(3-Amino-5-fluorophenyl)-2-chloro-5-((1R,3R)-2,2-dichloro-3-(3,4,5-trichlorophenyl)cyclopropane-1-carboxamido)benzamide (F432)

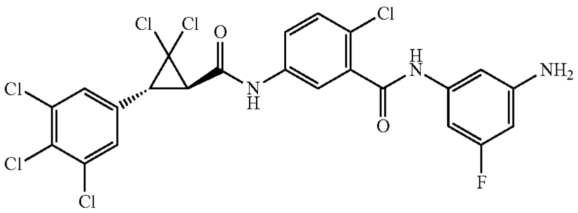 [SMILES: Nc1cc(F)cc(NC(=O)c2cc(NC(=O)[C@H]3[C@H](c4cc(Cl)c(Cl)c(Cl)c4)C3(Cl)Cl)ccc2Cl)c1]

Isolated as a light brown foam (0.083 g, 87%).

N-(3-Amino-5-fluorophenyl)-2-chloro-5-((1R,3R)-2,2-dichloro-3-(3-chloro-4-fluorophenyl)cyclopropane-1-carboxamido)benzamide (F433)

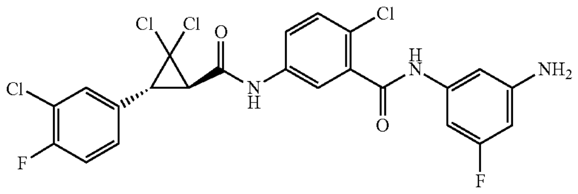 [SMILES: Nc1cc(F)cc(NC(=O)c2cc(NC(=O)[C@H]3[C@H](c4ccc(F)c(Cl)c4)C3(Cl)Cl)ccc2Cl)c1]

Isolated as a light brown foam (0.069 g, 72%).

N-(3-Amino-5-fluorophenyl)-2-chloro-5-((1R,3R)-2,2-dichloro-3-(3,5-dichlorophenyl)cyclopropane-1-carboxamido)benzamide (F419)

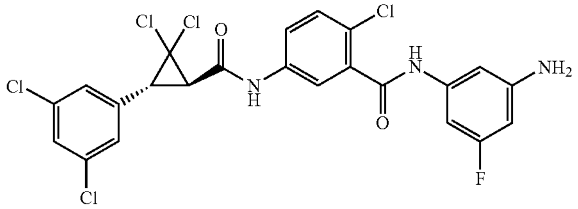 [SMILES: Nc1cc(F)cc(NC(=O)c2cc(NC(=O)[C@H]3[C@H](c4cc(Cl)cc(Cl)c4)C3(Cl)Cl)ccc2Cl)c1]

Isolated as a brown foam (0.048 g, 47.8%).

Example 61: Preparation of 5-(trans-3-(4-aminophenyl)-2,2-dichlorocyclopropane-1-carboxamido)-2-chloro-N-(4-fluorophenyl)benzamide (F425)

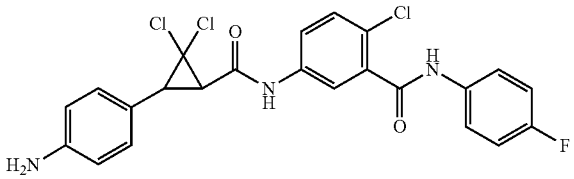 [SMILES: Nc1ccc(C2C(C(=O)Nc3ccc(Cl)c(C(=O)Nc4ccc(F)cc4)c3)C2(Cl)Cl)cc1]

To a slurry of 2-chloro-5-(trans-2,2-dichloro-3-(4-nitrophenyl)cyclopropane-1-carboxamido)-N-(4-fluorophenyl) benzamide (F422) (90 mg, 0.172 mmol) in methanol (3 mL) and water (1 mL) were added iron powder (48 mg, 0.861 mmol) and ammonium chloride (28 mg, 0.517 mmol). The slurry was stirred at 55° C. for 3 hours. The reaction mixture was filtered through a pad of Celite®, washing with ethyl acetate, and the filtrate was concentrated. Purification by flash column chromatography provided the title compound as a yellow foam (0.0707 g, 79%).

Example 62: Preparation of trans-N-(6-aminopyridin-2-yl)-2-chloro-5-(2,2-dichloro-3-(3,5-dichlorophenyl)cyclopropane-1-carboxamido)benzamide (F326)

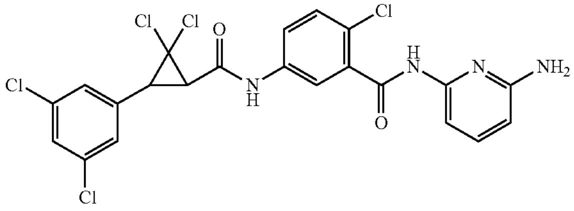 [SMILES: Nc1cccc(NC(=O)c2cc(NC(=O)C3C(c4cc(Cl)cc(Cl)c4)C3(Cl)Cl)ccc2Cl)n1]

To a solution of tert-butyl (6-(2-chloro-5-(2,2-dichloro-3-(3,5-dichlorophenyl)cyclopropane-1-carboxamido)benzamido)pyridin-2-yl)carbamate (F505) (216 mg, 0.335 mmol) in dichloromethane (3 mL) was added a 4 M solution of hydrogen chloride in 1,4-dioxane (0.67 mL, 2.68 mmol). The reaction mixture was stirred at room temperature overnight, the solvent was evaporated, and the crude residue was partitioned between saturated aqueous sodium bicarbonate (10 mL) and ethyl acetate (20 mL). The layers were separated, and the organic layer was dried by passing through a phase separator cartridge. The solvent was then evaporated to afford the title compound as a white solid (0.155 g, 85%).

The following compounds were prepared in like manner to the procedure outlined in Example 62:

N-(6-Aminopyridin-2-yl)-2-chloro-5-(trans-2,2-dichloro-3-(3-chloro-4-fluorophenyl)cyclopropane-1-carboxamido)benzamide (F327)

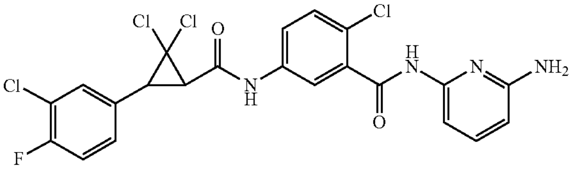 [SMILES: Nc1cccc(NC(=O)c2cc(NC(=O)C3C(c4ccc(F)c(Cl)c4)C3(Cl)Cl)ccc2Cl)n1]

Isolated as a white solid (0.140 g, 95%).

N-(6-Amino-4-(trifluoromethyl)pyridin-2-yl)-2-chloro-5-(trans-2,2-dichloro-3-(3,5-dichlorophenyl) cyclopropane-1-carboxamido)benzamide (F328)

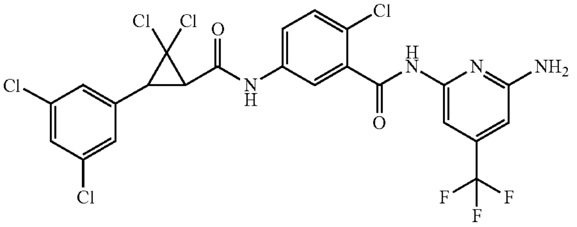 [SMILES: Nc1cc(C(F)(F)F)cc(NC(=O)c2cc(NC(=O)C3C(c4cc(Cl)cc(Cl)c4)C3(Cl)Cl)ccc2Cl)n1]

Isolated as a white solid (0.161 g, 88%).

trans-2-Chloro-5-(2,2-dichloro-3-(3,5-dichlorophenyl)cyclopropane-1-carboxamido)-N-(4-(methylamino)phenyl)benzamide hydrochloride (PF22)

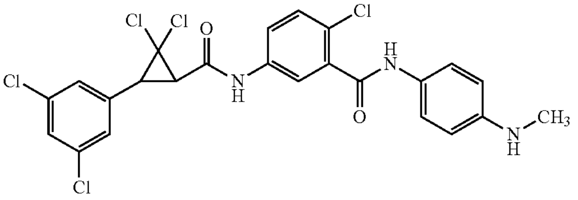 [SMILES: CNc1ccc(NC(=O)c2cc(NC(=O)C3C(c4cc(Cl)cc(Cl)c4)C3(Cl)Cl)ccc2Cl)cc1]

Isolated as a white solid (0.205 g, 97%).

trans-N-(4-Amino-3-fluorophenyl)-2-chloro-5-(2,2-dichloro-3-(3,5-dichlorophenyl)cyclopropane-1-carboxamido)benzamide (F174)

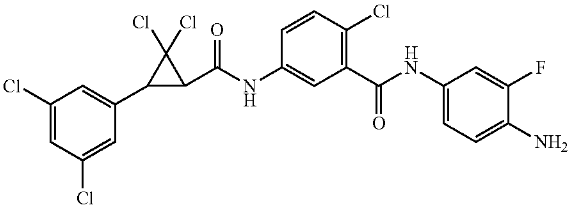 [SMILES: Nc1ccc(NC(=O)c2cc(NC(=O)C3C(c4cc(Cl)cc(Cl)c4)C3(Cl)Cl)ccc2Cl)cc1F]

Isolated as a light brown foam (0.061 g, 91%).

trans-N-(4-amino-2-fluorophenyl)-2-chloro-5-(2,2-dichloro-3-(3,5-dichlorophenyl)cyclopropane-1-carboxamido)benzamide (F175)

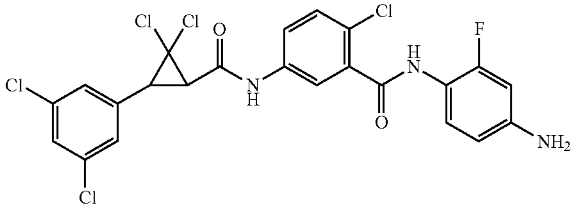 [SMILES: Nc1ccc(NC(=O)c2cc(NC(=O)C3C(c4cc(Cl)cc(Cl)c4)C3(Cl)Cl)ccc2Cl)c(F)c1]

Isolated as a light yellow foam (0.017 g, 85%).

trans-2-Chloro-5-(2,2-dichloro-3-(3,5-dichlorophenyl)cyclopropane-1-carboxamido)-N-(3-fluoro-4-(methylamino)phenyl)benzamide (F176)

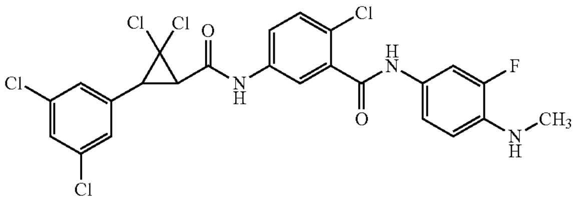 [SMILES: CNc1ccc(NC(=O)c2cc(NC(=O)C3C(c4cc(Cl)cc(Cl)c4)C3(Cl)Cl)ccc2Cl)cc1F]

Isolated as a brown solid (0.068 g, 89%).

trans-2-Chloro-5-(2,2-dichloro-3-(3,5-dichlorophenyl)cyclopropane-1-carboxamido)-N-(2-fluoro-4-(methylamino)phenyl)benzamide (F177)

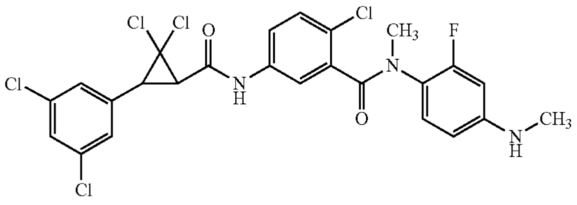 [SMILES: CNc1ccc(N(C)C(=O)c2cc(NC(=O)C3C(c4cc(Cl)cc(Cl)c4)C3(Cl)Cl)ccc2Cl)c(F)c1]

Isolated as a yellow foam (0.027 g, 76%).

trans-N-(4-Amino-2-methylphenyl)-2-chloro-5-(2,2-dichloro-3-(3,5-dichlorophenyl)cyclopropane-1-carboxamido)benzamide (F195)

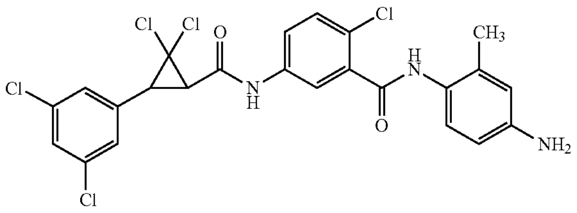

Isolated as a white solid (0.053 g, 83%).

trans-2-Chloro-5-(2,2-dichloro-3-(3,5-dichlorophenyl)cyclopropane-1-carboxamido)-N-(2-methyl-4-(methylamino)phenyl)benzamide (F196)

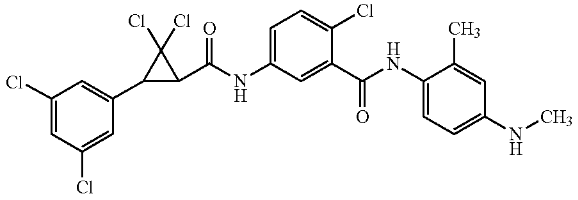 [SMILES: CNc1ccc(NC(=O)c2cc(NC(=O)C3C(c4cc(Cl)cc(Cl)c4)C3(Cl)Cl)ccc2Cl)c(C)c1]

Isolated as a white solid (0.093 g, 81%).

trans-N-(3-Amino-4-methoxyphenyl)-2-chloro-5-(2,2-dichloro-3-(3,5-dichlorophenyl)cyclopropane-1-carboxamido)benzamide (F199)

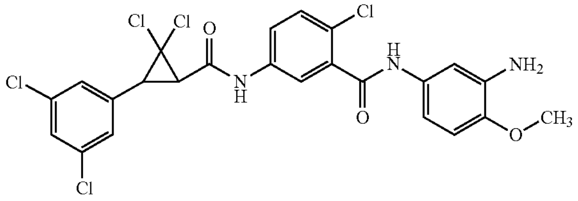 [SMILES: COc1ccc(NC(=O)c2cc(NC(=O)C3C(c4cc(Cl)cc(Cl)c4)C3(Cl)Cl)ccc2Cl)cc1N]

Isolated as a grey solid (0.083 g, 85%).

trans-2-Chloro-5-(2,2-dichloro-3-(3,5-dichlorophenyl)cyclopropane-1-carboxamido)-N-(4-methoxy-3-(methylamino)phenyl)benzamide (F200)

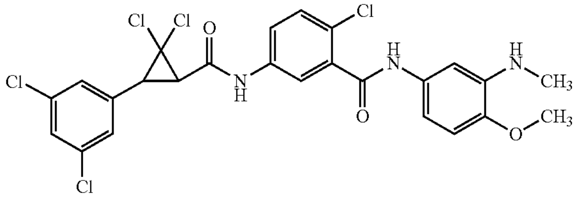 [SMILES: CNc1cc(NC(=O)c2cc(NC(=O)C3C(c4cc(Cl)cc(Cl)c4)C3(Cl)Cl)ccc2Cl)ccc1OC]

Isolated as a grey solid (0.091 g, 92%).

trans-N-(3-Aminophenyl)-2-chloro-5-(2,2-dichloro-3-(3,5-dichlorophenyl)cyclopropane-1-carboxamido)benzamide (F201)

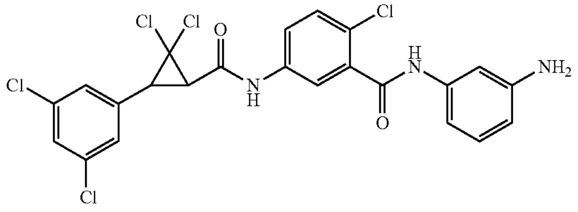 [SMILES: Nc1cccc(NC(=O)c2cc(NC(=O)C3C(c4cc(Cl)cc(Cl)c4)C3(Cl)Cl)ccc2Cl)c1]

Isolated as a white solid (0.063 g, 85%).

trans-2-Chloro-5-(2,2-dichloro-3-(3,5-dichlorophenyl)cyclopropane-1-carboxamido)-N-(3-(methylamino)phenyl)benzamide (F202)

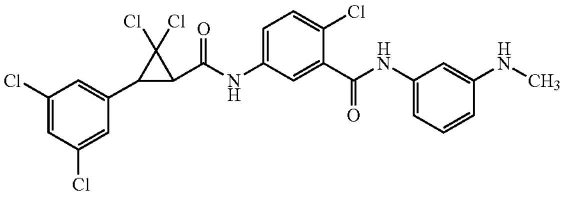 [SMILES: CNc1cccc(NC(=O)c2cc(NC(=O)C3C(c4cc(Cl)cc(Cl)c4)C3(Cl)Cl)ccc2Cl)c1]

Isolated as a white solid (0.055 g, 74%).

trans-2-Chloro-5-(2,2-dichloro-3-(3,4,5-trichlorophenyl)cyclopropane-1-carboxamido)-N-(2-methyl-4-(methylamino)phenyl)benzamide (F223)

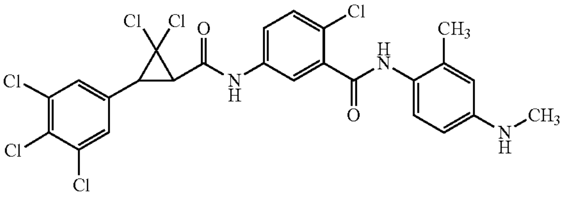 [SMILES: CNc1ccc(NC(=O)c2cc(NC(=O)C3C(c4cc(Cl)c(Cl)c(Cl)c4)C3(Cl)Cl)ccc2Cl)c(C)c1]

Isolated as a white solid (0.059 g, 88%).

trans-2-Chloro-5-(2,2-dichloro-3-(3-chloro-4-fluorophenyl)cyclopropane-1-carboxamido)-N-(2-methyl-4-(methylamino)phenyl)benzamide (F224)

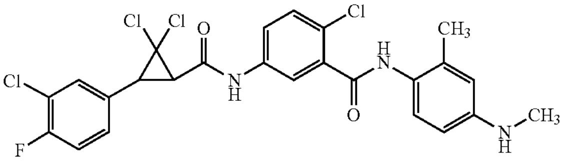 [SMILES: CNc1ccc(NC(=O)c2cc(NC(=O)C3C(c4ccc(F)c(Cl)c4)C3(Cl)Cl)ccc2Cl)c(C)c1]

Isolated as a white solid (0.064 g, 92%).

trans-2-Chloro-5-(2,2-dichloro-3-(3,5-dichlorophenyl)cyclopropane-1-carboxamido)-N-methyl-N-(2-methyl-4-(methylamino)phenyl)benzamide (F225)

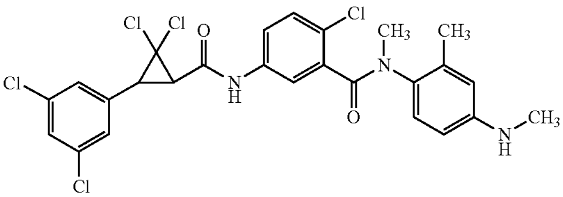 [SMILES: CNc1ccc(N(C)C(=O)c2cc(NC(=O)C3C(c4cc(Cl)cc(Cl)c4)C3(Cl)Cl)ccc2Cl)c(C)c1]

Isolated as a white solid (0.078 g, 92%).

trans-2-Chloro-5-(2,2-dichloro-3-(3,4,5-trichlorophenyl)cyclopropane-1-carboxamido)-N-methyl-N-(2-methyl-4-(methylamino)phenyl)benzamide (F226)

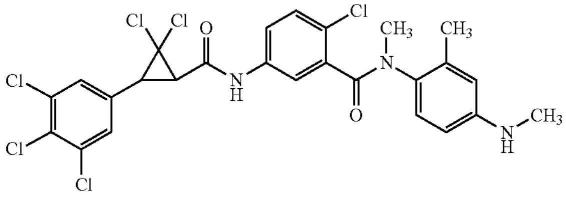 [SMILES: CNc1ccc(N(C)C(=O)c2cc(NC(=O)C3C(c4cc(Cl)c(Cl)c(Cl)c4)C3(Cl)Cl)ccc2Cl)c(C)c1]

Isolated as a white solid (0.057 g, 90%).

trans-N-(4-Amino-2-methylphenyl)-2-chloro-5-(2,2-dichloro-3-(3,4,5-trichlorophenyl)cyclopropane-1-carboxamido)benzamide (F227)

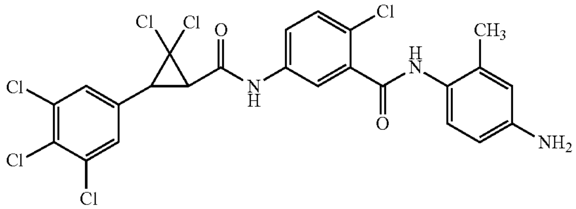 [SMILES: Cc1cc(N)ccc1NC(=O)c1cc(NC(=O)C2C(c3cc(Cl)c(Cl)c(Cl)c3)C2(Cl)Cl)ccc1Cl]

Isolated as a white solid (0.048 g, 92%).

trans-N-(4-Amino-2-methylphenyl)-2-chloro-5-(2,2-dichloro-3-(3-chloro-4-fluorophenyl)cyclopropane-1-carboxamido)benzamide (F228)

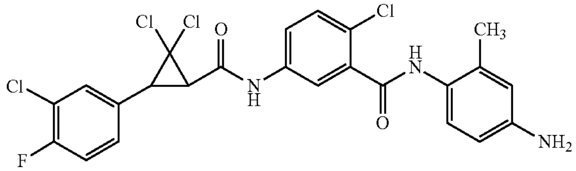 [SMILES: Cc1cc(N)ccc1NC(=O)c1cc(NC(=O)C2C(c3ccc(F)c(Cl)c3)C2(Cl)Cl)ccc1Cl]

Isolated as a white solid (0.043 g, 86%).

N-(3-Amino-2,4-difluorophenyl)-2-chloro-5-((1R,3R)-2,2-dichloro-3-(3,5-dichlorophenyl)cyclopropane-1-carboxamido)benzamide (F313)

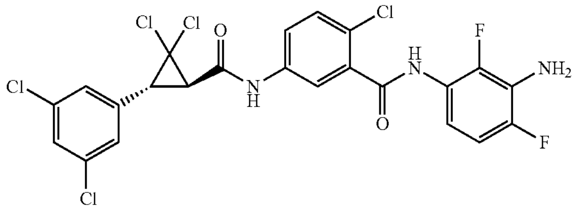 [SMILES: Nc1c(F)ccc(NC(=O)c2cc(NC(=O)[C@H]3[C@H](c4cc(Cl)cc(Cl)c4)C3(Cl)Cl)ccc2Cl)c1F]

Isolated as a white solid (0.115 g, 86%).

N-(3-Amino-2,4-difluorophenyl)-2-chloro-5-((1R, 3R)-2,2-dichloro-3-(3,4-dichlorophenyl)cyclopropane-1-carboxamido)benzamide (F314)

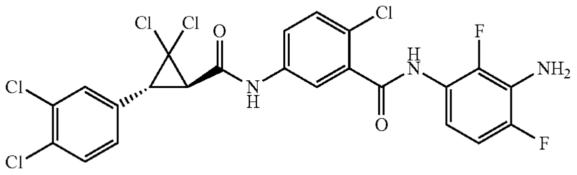 [SMILES: Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white solid (0.115 g, 89%).

N-(3-Amino-2,4-difluorophenyl)-2-chloro-5-((1R, 3R)-2,2-dichloro-3-(3,4,5-trichlorophenyl)cyclopropane-1-carboxamido)benzamide (F315)

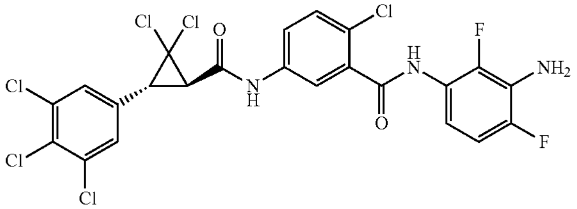 [SMILES: Nc1c(F)ccc(NC(=O)c2cc(NC(=O)[C@H]3[C@H](c4cc(Cl)c(Cl)c(Cl)c4)C3(Cl)Cl)ccc2Cl)c1F]

Isolated as a white solid (0.108 g, 84%).

N-(3-Amino-2,4-difluorophenyl)-2-chloro-5-((1R, 3R)-2,2-dichloro-3-(3-chloro-4-fluorophenyl)cyclopropane-1-carboxamido)benzamide (F317)

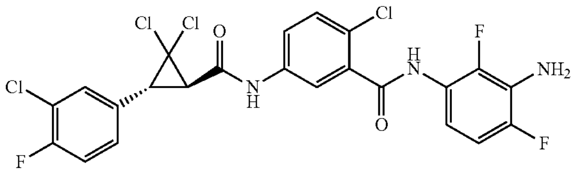 [SMILES: Nc1c(F)ccc(NC(=O)c2cc(NC(=O)[C@H]3[C@H](c4ccc(F)c(Cl)c4)C3(Cl)Cl)ccc2Cl)c1F]

Isolated as a white solid (0.087 g, 84%).

trans-N-(3-Amino-2,4-difluorophenyl)-2-chloro-5-(2,2-dichloro-3-(3-(trifluoromethyl)phenyl)cyclopropane-1-carboxamido)benzamide (F341)

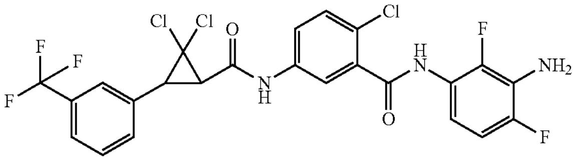 [SMILES: Nc1c(F)ccc(NC(=O)c2cc(NC(=O)C3C(c4cccc(C(F)(F)F)c4)C3(Cl)Cl)ccc2Cl)c1F]

Isolated as a white solid (0.104 g, 89%).

trans-N-(3-Amino-2,4-difluorophenyl)-2-chloro-5-(2,2-dichloro-3-(3-chloro-5-cyanophenyl)cyclopropane-1-carboxamido)benzamide (F344)

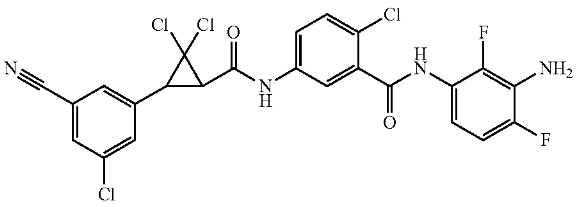 [SMILES: N#Cc1cc(Cl)cc(C2C(C(=O)Nc3ccc(Cl)c(C(=O)Nc4ccc(F)c(N)c4F)c3)C2(Cl)Cl)c1]

Isolated as a white solid (0.073 g, 86%).

N-(5-Amino-2,4-difluorophenyl)-2-chloro-5-((1R, 3R)-2,2-dichloro-3-(3,5-dichlorophenyl)cyclopropane-1-carboxamido)benzamide (F353)

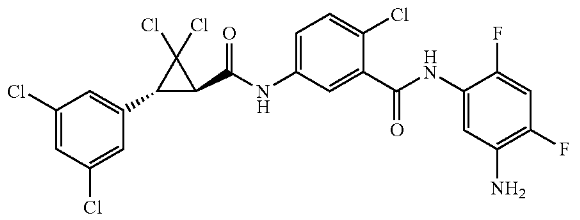 [SMILES: Nc1cc(NC(=O)c2cc(NC(=O)[C@H]3[C@H](c4cc(Cl)cc(Cl)c4)C3(Cl)Cl)ccc2Cl)c(F)cc1F]

Isolated as a light brown solid (0.112 g, 97%).

N-(5-Amino-2,4-difluorophenyl)-2-chloro-5-((1R, 3R)-2,2-dichloro-3-(3,4-dichlorophenyl)cyclopropane-1-carboxamido)benzamide (F354)

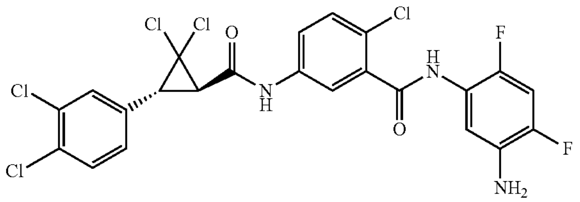 [SMILES: Nc1cc(NC(=O)c2cc(NC(=O)[C@H]3[C@H](c4ccc(Cl)c(Cl)c4)C3(Cl)Cl)ccc2Cl)c(F)cc1F]

Isolated as a white solid (0.107 g, 96%).

N-(2-Amino-3,5-difluorophenyl)-2-chloro-5-((1R, 3R)-2,2-dichloro-3-(3,5-dichlorophenyl)cyclopropane-1-carboxamido)benzamide (F360)

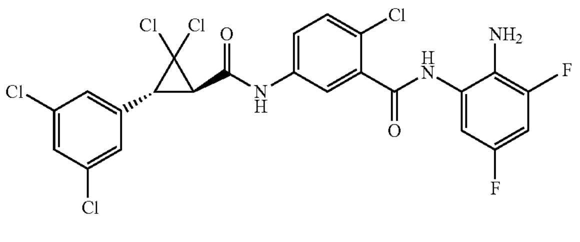 [SMILES: Nc1c(F)cc(F)cc1NC(=O)c1cc(NC(=O)[C@H]2[C@H](c3cc(Cl)cc(Cl)c3)C2(Cl)Cl)ccc1Cl]

Isolated as a white solid (0.031 g, 49%).

N-(5-Amino-2,4-difluorophenyl)-2-chloro-5-((1R,3R)-2,2-dichloro-3-(3,4,5-trichlorophenyl)cyclopropane-1-carboxamido)benzamide (F402)

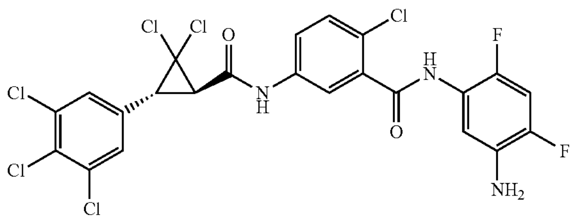 [SMILES: Nc1cc(NC(=O)c2cc(NC(=O)[C@H]3[C@H](c4cc(Cl)c(Cl)c(Cl)c4)C3(Cl)Cl)ccc2Cl)c(F)cc1F]

Isolated as a grey solid (0.088 g, 87%).

N-(5-Amino-2,4-difluorophenyl)-2-chloro-5-((1R,3R)-2,2-dichloro-3-(3-chloro-4-fluorophenyl)cyclopropane-1-carboxamido)benzamide (F403)

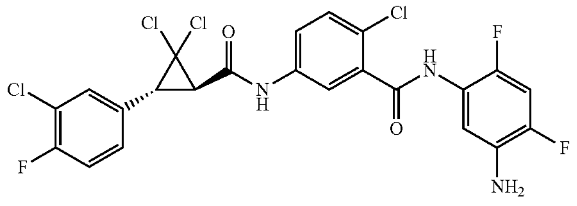 [SMILES: Nc1cc(NC(=O)c2cc(NC(=O)[C@H]3[C@H](c4ccc(F)c(Cl)c4)C3(Cl)Cl)ccc2Cl)c(F)cc1F]

Isolated as a white solid (0.096 g, 84%).

N-(2-Amino-3,5-difluorophenyl)-2-chloro-5-((1R,3R)-2,2-dichloro-3-(3,4,5-trichlorophenyl)cyclopropane-1-carboxamido)benzamide (F404)

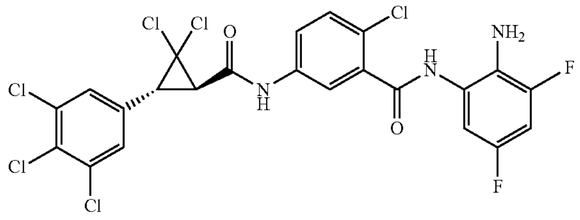 [SMILES: Nc1c(F)cc(F)cc1NC(=O)c1cc(NC(=O)[C@H]2[C@H](c3cc(Cl)c(Cl)c(Cl)c3)C2(Cl)Cl)ccc1Cl]

Isolated as a grey solid (0.021 g, 33%).

N-(2-Amino-5-fluorophenyl)-2-chloro-5-((1R,3R)-2,2-dichloro-3-(3,4,5-trichlorophenyl)cyclopropane-1-carboxamido)benzamide (F405)

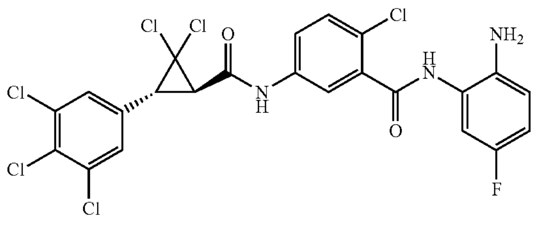 [SMILES: Nc1ccc(F)cc1NC(=O)c1cc(NC(=O)[C@H]2[C@H](c3cc(Cl)c(Cl)c(Cl)c3)C2(Cl)Cl)ccc1Cl]

Isolated as a white solid (0.033 g, 61%).

N-(2-Amino-4,6-difluorophenyl)-2-chloro-5-((1R,3R)-2,2-dichloro-3-(3,5-dichlorophenyl)cyclopropane-1-carboxamido)benzamide (F406)

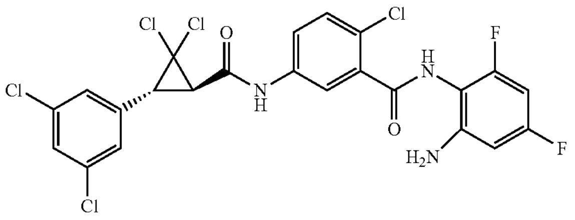 [SMILES: Nc1cc(F)cc(F)c1NC(=O)c1cc(NC(=O)[C@H]2[C@H](c3cc(Cl)cc(Cl)c3)C2(Cl)Cl)ccc1Cl]

Isolated as a white solid (0.021 g, 44%).

N-(2-Amino-4,6-difluorophenyl)-2-chloro-5-((1R,3R)-2,2-dichloro-3-(3,4,5-trichlorophenyl)cyclopropane-1-carboxamido)benzamide (F408)

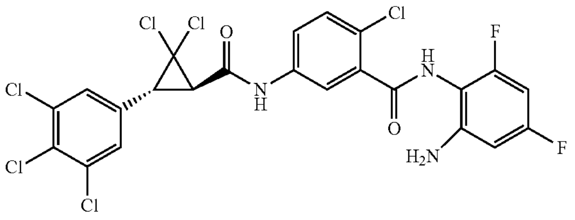 [SMILES: Nc1cc(F)cc(F)c1NC(=O)c1cc(NC(=O)[C@H]2[C@H](c3cc(Cl)c(Cl)c(Cl)c3)C2(Cl)Cl)ccc1Cl]

Isolated as a white solid (0.013 g, 57%).

trans-N-(3-Amino-4-methylphenyl)-2-chloro-5-(2,2-dichloro-3-(3,5-dichlorophenyl)cyclopropane-1-carboxamido)benzamide (F205)

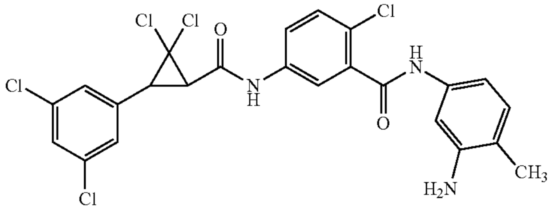 [SMILES: Cc1ccc(NC(=O)c2cc(NC(=O)C3C(c4cc(Cl)cc(Cl)c4)C3(Cl)Cl)ccc2Cl)cc1N]

Isolated as an off-white solid (0.078 g, 85%)

trans-2-Chloro-5-(2,2-dichloro-3-(3,5-dichlorophenyl)cyclopropane-1-carboxamido)-N-(3-methyl-4-(methylamino)phenyl)benzamide (F206)

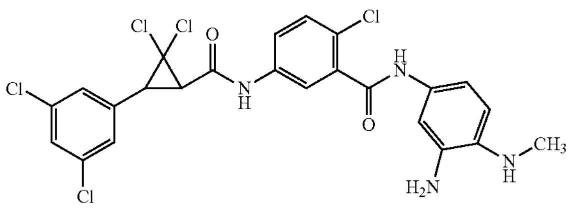 [SMILES: CNc1ccc(NC(=O)c2cc(NC(=O)C3C(c4cc(Cl)cc(Cl)c4)C3(Cl)Cl)ccc2Cl)cc1N]

Isolated as an off-white solid (0.076 g, 88%).

trans-2-Chloro-5-(2,2-dichloro-3-(3,5-dichlorophenyl)cyclopropane-1-carboxamido)-N-(4-methyl-3-(methylamino)phenyl)benzamide (F207)

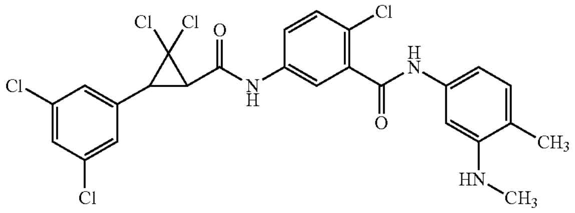 [SMILES: CNc1cc(NC(=O)c2cc(NC(=O)C3C(c4cc(Cl)cc(Cl)c4)C3(Cl)Cl)ccc2Cl)ccc1C]

Isolated as an off-white solid (0.025 gr, 44%).

trans-N-(3-Amino-4-fluorophenyl)-2-chloro-5-(2,2-dichloro-3-(3,5-dichlorophenyl)cyclopropane-1-carboxamido)benzamide (F238)

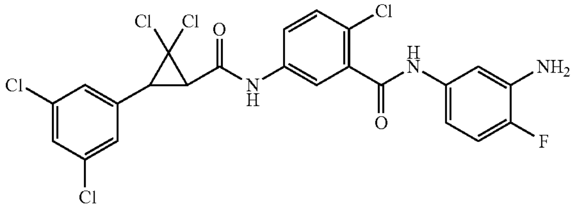 [SMILES: Nc1cc(NC(=O)c2cc(NC(=O)C3C(c4cc(Cl)cc(Cl)c4)C3(Cl)Cl)ccc2Cl)ccc1F]

Isolated as an off-white solid (0.153 g, 78%).

trans-2-Chloro-5-(2,2-dichloro-3-(3,5-dichlorophenyl)cyclopropane-1-carboxamido)-N-(4-fluoro-3-(methylamino)phenyl)benzamide (F239)

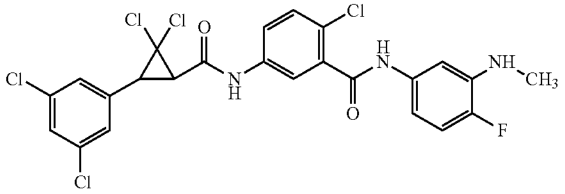 [SMILES: CNc1cc(NC(=O)c2cc(NC(=O)C3C(c4cc(Cl)cc(Cl)c4)C3(Cl)Cl)ccc2Cl)ccc1F]

Isolated as an off-white foam (0.254 g, 70%).

trans-N-(3-Amino-2,4-difluorophenyl)-2-chloro-5-(2,2-dichloro-3-(3,5-dichlorophenyl)cyclopropane-1-carboxamido)benzamide (F245)

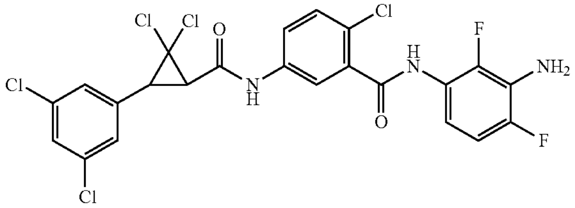 [SMILES: Nc1c(F)ccc(NC(=O)c2cc(NC(=O)C3C(c4cc(Cl)cc(Cl)c4)C3(Cl)Cl)ccc2Cl)c1F]

Isolated as an off-white foam (0.045 g, 58%).

trans-N-(4-Amino-2-methylphenyl)-3-(2,2-dichloro-3-(3,4,5-trichlorophenyl)cyclopropane-1-carboxamido)benzamide (F264)

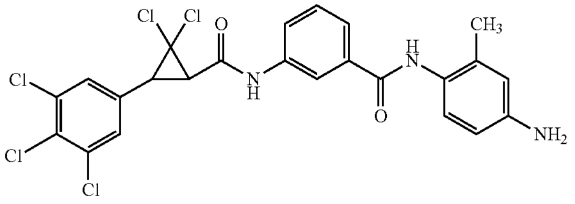 [SMILES: Cc1cc(N)ccc1NC(=O)c1cccc(NC(=O)C2C(c3cc(Cl)c(Cl)c(Cl)c3)C2(Cl)Cl)c1]

Isolated as a yellow foam (0.146 g, 71.4%).

trans-N-(4-Amino-2-methylphenyl)-3-(2,2-dichloro-3-(3,4-dichlorophenyl)cyclopropane-1-carboxamido)benzamide (F265)

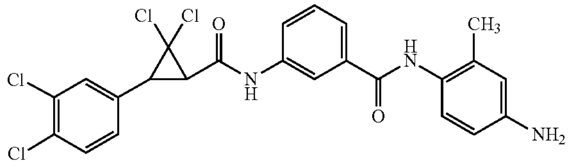 [SMILES: Cc1cc(N)ccc1NC(=O)c1cccc(NC(=O)C2C(c3ccc(Cl)c(Cl)c3)C2(Cl)Cl)c1]

Isolated as a yellow foam (0.146 g, 76%).

trans-N-(4-Amino-2-methylphenyl)-3-(2,2-dichloro-3-(3,5-dichlorophenyl)cyclopropane-1-carboxamido)benzamide (F266)

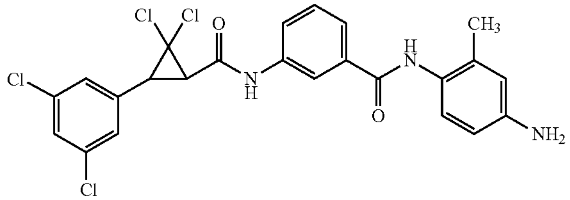 [SMILES: Cc1cc(N)ccc1NC(=O)c1cccc(NC(=O)C2C(c3cc(Cl)cc(Cl)c3)C2(Cl)Cl)c1]

Isolated as a light yellow foam (0.149 g, 78%).

N-(2-Amino-5-fluorophenyl)-2-chloro-5-((1R,3R)-2,2-dichloro-3-(3,5-dichlorophenyl)cyclopropane-1-carboxamido)benzamide (F373)

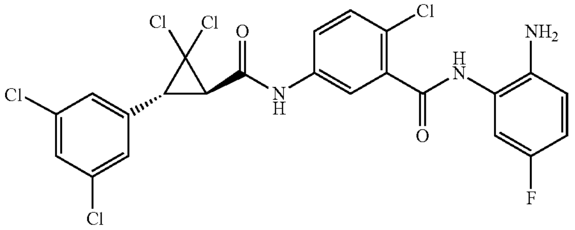 [SMILES: Nc1ccc(F)cc1NC(=O)c1cc(NC(=O)[C@H]2[C@H](c3cc(Cl)cc(Cl)c3)C2(Cl)Cl)ccc1Cl]

Isolated as a yellow solid (0.030 g, 73.3%).

N-(2-Amino-3,5-difluorophenyl)-2-chloro-5-((1R,3R)-2,2-dichloro-3-(3,4-dichlorophenyl)cyclopropane-1-carboxamido)benzamide (F377)

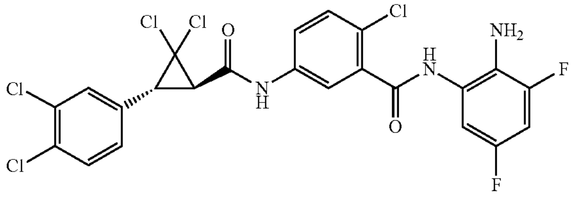 [SMILES: Nc1c(F)cc(F)cc1NC(=O)c1cc(NC(=O)[C@H]2[C@H](c3ccc(Cl)c(Cl)c3)C2(Cl)Cl)ccc1Cl]

Isolated as a light brown foam (0.040 g, 86%).

N-(4-Amino-3,5-difluorophenyl)-2-chloro-5-((1R,3R)-2,2-dichloro-3-(3,5-dichlorophenyl)cyclopropane-1-carboxamido)benzamide (F378)

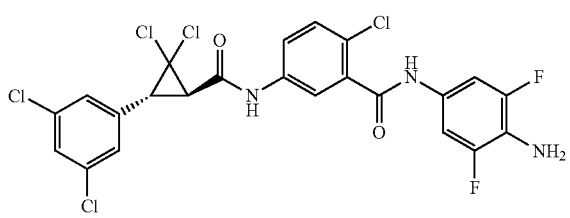 [SMILES: Nc1c(F)cc(NC(=O)c2cc(NC(=O)[C@H]3[C@H](c4cc(Cl)cc(Cl)c4)C3(Cl)Cl)ccc2Cl)cc1F]

Isolated as a light rose foam (0.087 g, 88%).

N-(4-Amino-3,5-difluorophenyl)-2-chloro-5-((1R,3R)-2,2-dichloro-3-(3,4-dichlorophenyl)cyclopropane-1-carboxamido)benzamide (F379)

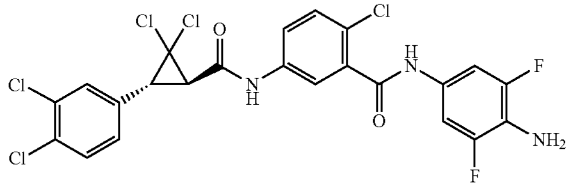

Isolated as a light rose foam (0.057 g, 62.7%).

N-(4-Amino-3,5-difluorophenyl)-2-chloro-5-((1R,3R)-2,2-dichloro-3-(3,4,5-trichlorophenyl)cyclopropane-1-carboxamido)benzamide (F380)

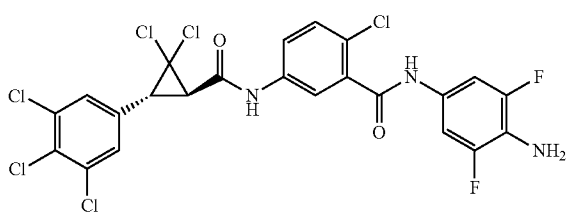 [SMILES: Nc1c(F)cc(NC(=O)c2cc(NC(=O)[C@H]3[C@H](c4cc(Cl)c(Cl)c(Cl)c4)C3(Cl)Cl)ccc2Cl)cc1F]

Isolated as a light rose foam (0.076 g, 79%).

N-(4-Amino-3,5-difluorophenyl)-2-chloro-5-((1R,3R)-2,2-dichloro-3-(3-chloro-4-fluorophenyl)cyclopropane-1-carboxamido)benzamide (F381)

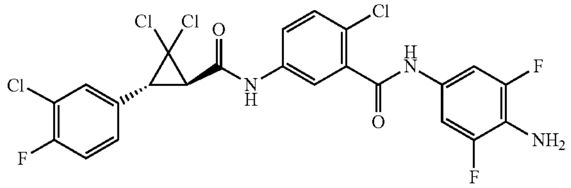 [SMILES: Nc1c(F)cc(NC(=O)c2cc(NC(=O)[C@H]3[C@H](c4ccc(F)c(Cl)c4)C3(Cl)Cl)ccc2Cl)cc1F]

Isolated as a light rose foam (0.1 g, 85%).

N-(3-Amino-2-fluorophenyl)-2-chloro-5-((1R,3R)-2,2-dichloro-3-(3,5-dichlorophenyl)cyclopropane-1-carboxamido)benzamide (F426)

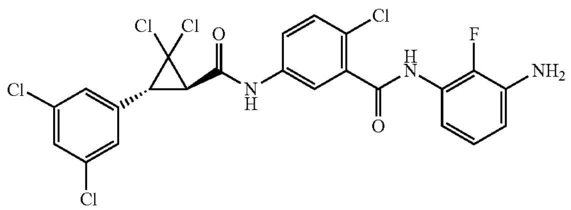 [SMILES: Nc1cccc(NC(=O)c2cc(NC(=O)[C@H]3[C@H](c4cc(Cl)cc(Cl)c4)C3(Cl)Cl)ccc2Cl)c1F]

Isolated as a light brown foam (0.038 g, 93%).

N-(5-Amino-2-fluorophenyl)-2-chloro-5-((1R,3R)-2,2-dichloro-3-(3,5-dichlorophenyl)cyclopropane-1-carboxamido)benzamide (F427)

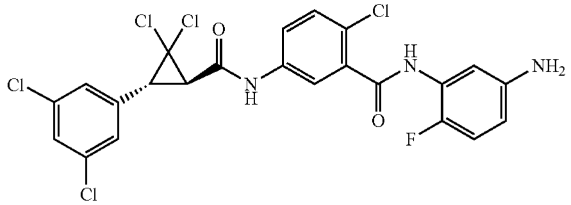 [SMILES: Nc1ccc(F)c(NC(=O)c2cc(NC(=O)[C@H]3[C@H](c4cc(Cl)cc(Cl)c4)C3(Cl)Cl)ccc2Cl)c1]

Isolated as a light brown foam (0.081 g, 86%).

N-(5-Amino-2-fluorophenyl)-2-chloro-5-((1R,3R)-2,2-dichloro-3-(3,4-dichlorophenyl)cyclopropane-1-carboxamido)benzamide (F428)

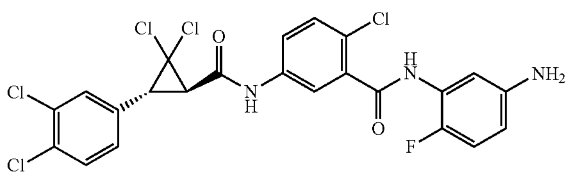 [SMILES: Nc1ccc(F)c(NC(=O)c2cc(NC(=O)[C@H]3[C@H](c4ccc(Cl)c(Cl)c4)C3(Cl)Cl)ccc2Cl)c1]

Isolated as a light brown foam (0.1 g, 96%).

N-(5-Amino-2-fluorophenyl)-2-chloro-5-((1R,3R)-2,2-dichloro-3-(3,4,5-trichlorophenyl)cyclopropane-1-carboxamido)benzamide (F429)

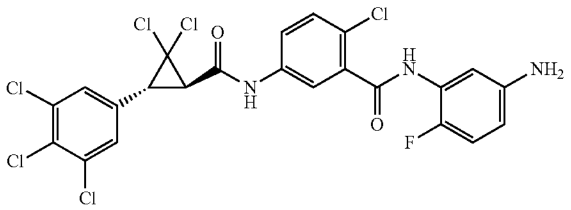 [SMILES: Nc1ccc(F)c(NC(=O)c2cc(NC(=O)[C@H]3[C@H](c4cc(Cl)c(Cl)c(Cl)c4)C3(Cl)Cl)ccc2Cl)c1]

Isolated as a light brown foam (0.089 g, 93%).

N-(5-Amino-2-fluorophenyl)-2-chloro-5-((1R,3R)-2,2-dichloro-3-(3-chloro-4-fluorophenyl)cyclopropane-1-carboxamido)benzamide (F430)

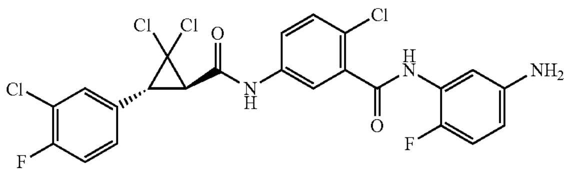 [SMILES: Nc1ccc(F)c(NC(=O)c2cc(NC(=O)[C@H]3[C@H](c4ccc(F)c(Cl)c4)C3(Cl)Cl)ccc2Cl)c1]

Isolated as a light brown foam (0.072 g, 77%).

trans-N-(4-Amino-2,5-difluorophenyl)-2-chloro-5-((1R,3R)-2,2-dichloro-3-(3,5-dichlorophenyl)cyclopropane-1-carboxamido)benzamide (F568)

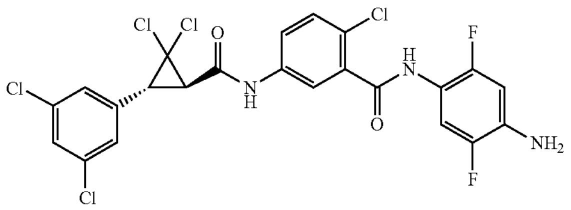 [SMILES: Nc1cc(F)c(NC(=O)c2cc(NC(=O)[C@H]3[C@H](c4cc(Cl)cc(Cl)c4)C3(Cl)Cl)ccc2Cl)cc1F]

Isolated as a light brown foam (0.083 g, 87%).

trans-N-(4-Amino-2,5-difluorophenyl)-2-chloro-5-((1R,3R)-2,2-dichloro-3-(3,4-dichlorophenyl)cyclopropane-1-carboxamido)benzamide (F569)

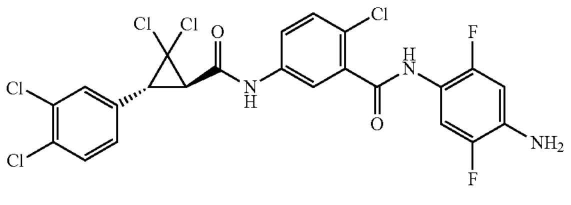

Isolated as a light brown foam (0.094 g, 95%).

trans-N-(4-Amino-2,5-difluorophenyl)-2-chloro-5-((1R,3R)-2,2-dichloro-3-(3,4,5-trichlorophenyl)cyclopropane-1-carboxamido)benzamide (F570)

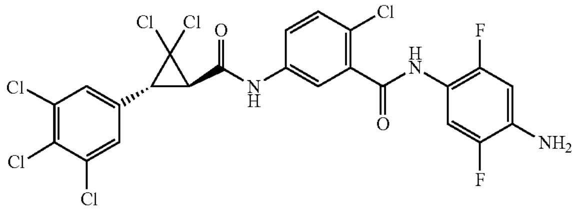 [SMILES: Nc1cc(F)c(NC(=O)c2cc(NC(=O)[C@H]3[C@H](c4cc(Cl)c(Cl)c(Cl)c4)C3(Cl)Cl)ccc2Cl)cc1F]

Isolated as a light brown foam (0.106 g, 100%).

trans-N-(4-Amino-2,5-difluorophenyl)-2-chloro-5-((1R,3R)-2,2-dichloro-3-(3-chloro-4-fluorophenyl)cyclopropane-1-carboxamido)benzamide (F571)

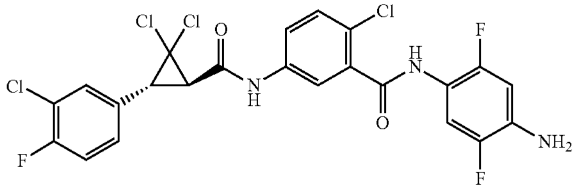 [SMILES: Nc1cc(F)c(NC(=O)c2cc(NC(=O)[C@H]3[C@H](c4ccc(F)c(Cl)c4)C3(Cl)Cl)ccc2Cl)cc1F]

Isolated as a light brown foam (0.092 g, 94%).

5-(trans-3-(4-bromo-3-chlorophenyl)-2,2-dichlorocyclopropane-1-carboxamido)-2-chloro-N-(2-methyl-4-(methylamino)phenyl)benzamide (F323)

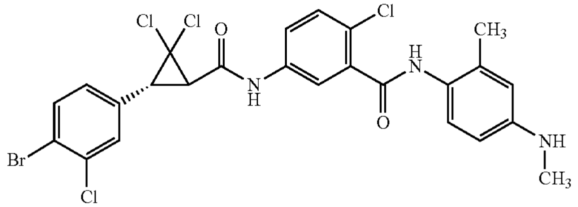 [SMILES: CNc1ccc(NC(=O)c2cc(NC(=O)C3[C@H](c4ccc(Br)c(Cl)c4)C3(Cl)Cl)ccc2Cl)c(C)c1]

Isolated as a yellow foam (0.0646 g, 97%).

N-(4-Amino-2-methylphenyl)-5-(trans-3-(4-bromo-3-chlorophenyl)-2,2-dichlorocyclopropane-1-carboxamido)-2-chlorobenzamide (F324)

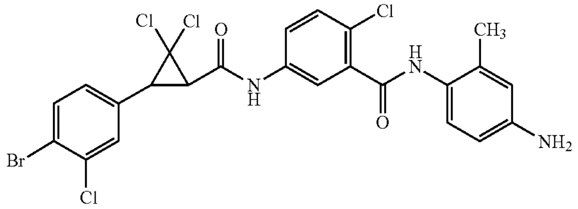 [SMILES: Cc1cc(N)ccc1NC(=O)c1cc(NC(=O)C2C(c3ccc(Br)c(Cl)c3)C2(Cl)Cl)ccc1Cl]

Isolated as a yellow solid (0.0449 g, 70%).

N-(3-Amino-2,4-difluorophenyl)-5-(trans-3-(4-bromo-3-chlorophenyl)-2,2-dichlorocyclopropane-1-carboxamido)-2-chlorobenzamide (F325)

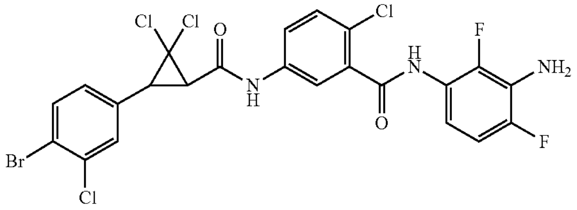 [SMILES: Nc1c(F)ccc(NC(=O)c2cc(NC(=O)C3C(c4ccc(Br)c(Cl)c4)C3(Cl)Cl)ccc2Cl)c1F]

Isolated as a pale yellow foam (0.0603 g, 63%).

N-(4-Amino-2-methylphenyl)-5-(trans-3-(3-bromo-4-chlorophenyl)-2,2-dichlorocyclopropane-1-carboxamido)-2-chlorobenzamide (F336)

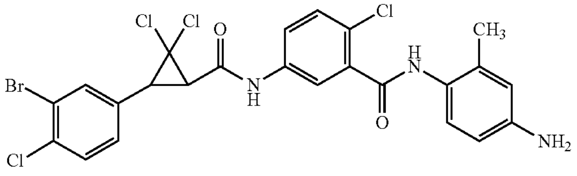 [SMILES: Cc1cc(N)ccc1NC(=O)c1cc(NC(=O)C2C(c3ccc(Cl)c(Br)c3)C2(Cl)Cl)ccc1Cl]

Isolated as an orange solid (0.0354 g, 78%).

N-(4-Amino-2-methylphenyl)-5-(trans-3-(3-bromo-5-chlorophenyl)-2,2-dichlorocyclopropane-1-carboxamido)-2-chlorobenzamide (F337)

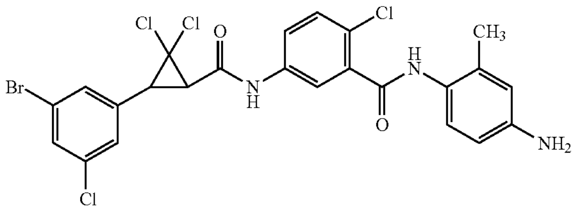 [SMILES: Cc1cc(N)ccc1NC(=O)c1cc(NC(=O)C2C(c3cc(Cl)cc(Br)c3)C2(Cl)Cl)ccc1Cl]

Isolated as a tan foam (0.0434 g, 96%).

N-(3-Amino-2,4-difluorophenyl)-5-(trans-3-(3-bromo-4-chlorophenyl)-2,2-dichlorocyclopropane-1-carboxamido)-2-chlorobenzamide (F338)

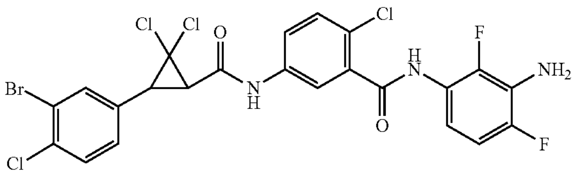 [SMILES: Nc1c(F)ccc(NC(=O)c2cc(NC(=O)C3C(c4ccc(Cl)c(Br)c4)C3(Cl)Cl)ccc2Cl)c1F]

Isolated as an orange foam (0.0435 g, 91%).

N-(3-Amino-2,4-difluorophenyl)-5-(trans-3-(3-bromo-5-chlorophenyl)-2,2-dichlorocyclopropane-1-carboxamido)-2-chlorobenzamide (F339)

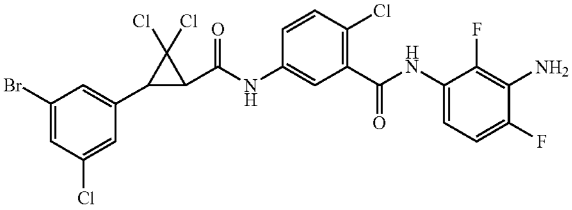 [SMILES: Nc1c(F)ccc(NC(=O)c2cc(NC(=O)C3C(c4cc(Cl)cc(Br)c4)C3(Cl)Cl)ccc2Cl)c1F]

Isolated as a tan foam (0.0499 g, 99%).

N-(3-Amino-2,4-difluorophenyl)-2-chloro-5-(trans-2,2-dichloro-3-(3-chloro-4-vinylphenyl)cyclopropane-1-carboxamido)benzamide (F355)

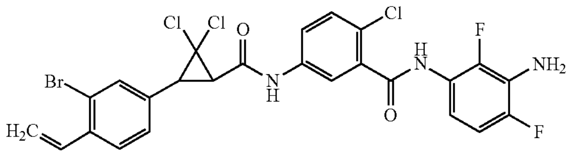 [SMILES: C=Cc1ccc(C2C(C(=O)Nc3ccc(Cl)c(C(=O)Nc4ccc(F)c(N)c4F)c3)C2(Cl)Cl)cc1Br]

Isolated as a yellow foam (0.0152 g, 86%).

N-(3-Amino-2,4-difluorophenyl)-2-chloro-5-(trans-2,2-dichloro-3-(3-chloro-5-vinylphenyl)cyclopropane-1-carboxamido)benzamide (F356)

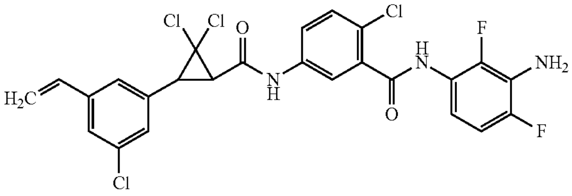 [SMILES: C=Cc1cc(Cl)cc(C2C(C(=O)Nc3ccc(Cl)c(C(=O)Nc4ccc(F)c(N)c4F)c3)C2(Cl)Cl)c1]

Isolated as a yellow foam (0.0345 g, 89%).

N-(3-Amino-2,4-difluorophenyl)-5-((1R,3R)-3-(3-bromo-4-chlorophenyl)-2,2-dichlorocyclopropane-1-carboxamido)-2-chlorobenzamide (F579)

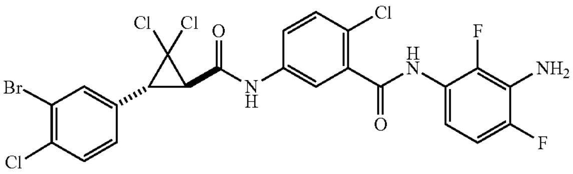

Isolated as a yellow foam (0.0751 g, 89%).

N-(5-Amino-2,4-difluorophenyl)-5-((1R,3R)-3-(3-bromo-4-chlorophenyl)-2,2-dichlorocyclopropane-1-carboxamido)-2-chlorobenzamide (F580)

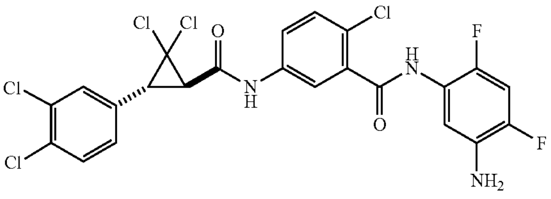

Isolated as a yellow foam (0.0385 g, 95%).

N-(3-Amino-2,4-difluorophenyl)-5-(3-trans-(3-bromo-4,5-dichlorophenyl)-2,2-dichlorocyclopropane-1-carboxamido)-2-chlorobenzamide (F621)

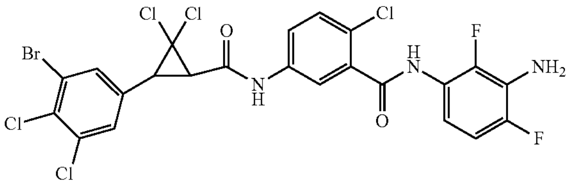 [SMILES: Nc1c(F)ccc(NC(=O)c2cc(NC(=O)C3C(c4cc(Cl)c(Cl)c(Br)c4)C3(Cl)Cl)ccc2Cl)c1F]

Isolated as a white foam (0.045 g, 61%).

N-(3-Amino-2,4-difluorophenyl)-5-(3-trans-(3-bromo-5-fluorophenyl)-2,2-dichlorocyclopropane-1-carboxamido)-2-chlorobenzamide (F622)

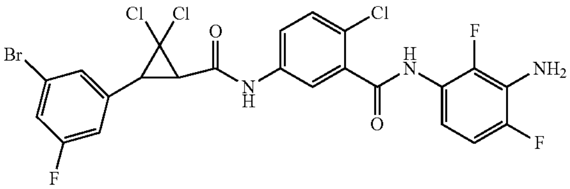 [SMILES: Nc1c(F)ccc(NC(=O)c2cc(NC(=O)C3C(c4cc(F)cc(Br)c4)C3(Cl)Cl)ccc2Cl)c1F]

Isolated as a white foam (0.043 g, 58%).

N-(3-Amino-2,4-difluorophenyl)-2-chloro-5-(2,2-dichloro-3-trans-(3-fluoro-5-(trifluoromethyl)phenyl)cyclopropane-1-carboxamido)benzamide (F623)

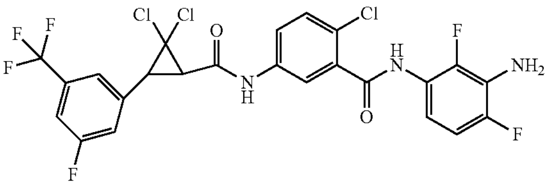 [SMILES: Nc1c(F)ccc(NC(=O)c2cc(NC(=O)C3C(c4cc(F)cc(C(F)(F)F)c4)C3(Cl)Cl)ccc2Cl)c1F]

Isolated as a white foam (0.019 g, 24%).

N-(3-Amino-2,4-difluorophenyl)-2-chloro-5-(2,2-dichloro-3-trans-(4-fluoro-3-(trifluoromethyl)phenyl)cyclopropane-1-carboxamido)benzamide (F624)

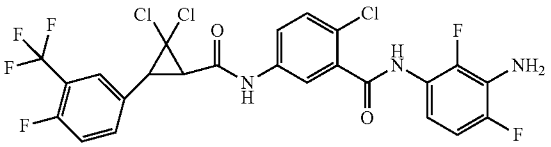 [SMILES: Nc1c(F)ccc(NC(=O)c2cc(NC(=O)C3C(c4ccc(F)c(C(F)(F)F)c4)C3(Cl)Cl)ccc2Cl)c1F]

Isolated as a white foam (0.043 g, 53%).

N-(3-Amino-2,4-difluorophenyl)-5-(3-trans-(3-bromo-4-fluorophenyl)-2,2-dichlorocyclopropane-1-carboxamido)-2-chlorobenzamide (F625)

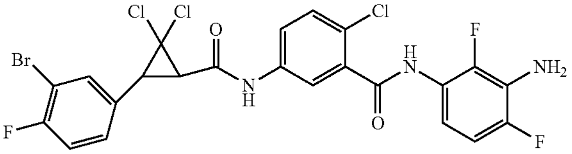 [SMILES: Nc1c(F)ccc(NC(=O)c2cc(NC(=O)C3C(c4ccc(F)c(Br)c4)C3(Cl)Cl)ccc2Cl)c1F]

Isolated as a white foam (0.040 g, 43%).

N-(3-Amino-2,4-difluorophenyl)-2-chloro-5-(2,2-dichloro-3-trans-(perfluorophenyl)cyclopropane-1-carboxamido)benzamide (F626)

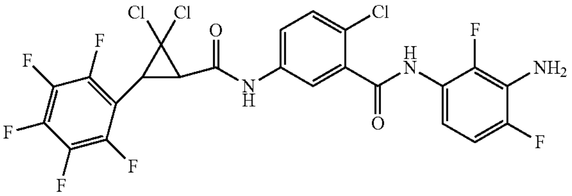 [SMILES: Nc1c(F)ccc(NC(=O)c2cc(NC(=O)C3C(c4c(F)c(F)c(F)c(F)c4F)C3(Cl)Cl)ccc2Cl)c1F]

Isolated as a white foam (0.032 g, 36%).

N-(3-Amino-2,4-difluorophenyl)-2-chloro-5-(2,2-dichloro-3-trans-(3,4,5-trifluorophenyl)cyclopropane-1-carboxamido)benzamide (F627)

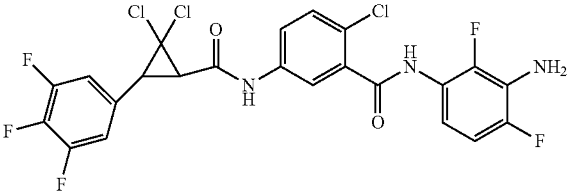 [SMILES: Nc1c(F)ccc(NC(=O)c2cc(NC(=O)C3C(c4cc(F)c(F)c(F)c4)C3(Cl)Cl)ccc2Cl)c1F]

Isolated as a white foam (0.016 g, 33%).

N-(3-Amino-2,4-difluorophenyl)-2-chloro-5-(2,2-dichloro-3-cis-(3,4,5-trifluorophenyl)cyclopropane-1-carboxamido)benzamide (F628)

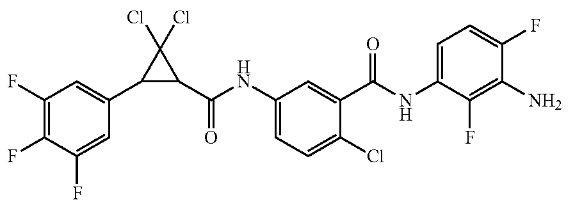 [SMILES: Nc1c(F)ccc(NC(=O)c2cc(NC(=O)C3C(c4cc(F)c(F)c(F)c4)C3(Cl)Cl)ccc2Cl)c1F]

Isolated as a white foam (0.010 g, 39%).

Example 63: Preparation of N-(2-amino-4,6-difluorophenyl)-2-chloro-5-((1R,3R)-2,2-dichloro-3-(3,4-dichlorophenyl)cyclopropane-1-carboxamido)benzamide (F407)

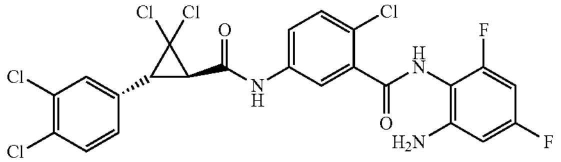

To a solution of 2-chloro-5-((1R,3R)-2,2-dichloro-3-(3,4-dichlorophenyl)cyclopropane-1-carboxamido)benzoic acid (C240) (0.100 g, 0.220 mmol) and tert-butyl-N-((tert-butoxy)carbonyl)-N-(2-amino-3,5-difluorophenyl)carbamate (C401) (0.076 g, 0.220 mmol) in ethyl acetate (2 mL) was added pyridine (0.036 mL, 0.441 mmol) and 2,4,6-tripropyl-1,3,5,2,4,6-trioxatriphosphinane 2,4,6-trioxide (T3P®) as a 50% solution in ethyl acetate (0.210 g, 0.331 mmol). The mixture was warmed to 45° C. for 24 hours. The reaction mixture was cooled to room temperature and concentrated under a stream of nitrogen. The residue was purified by flash column chromatography using 0-30% ethyl acetate/hexanes as eluent. Product fractions were combined and concentrated under reduced pressure. The resulting residue was dissolved in dichloromethane (2 mL), and a 4 M solution of hydrogen chloride in dioxane (0.096 mL, 0.385 mmol) was added. The reaction mixture was stirred at room temperature for 18 hours. The solvent was evaporated under a stream of nitrogen. The residue was partitioned between ethyl acetate and saturated aqueous sodium bicarbonate. The phases were separated, and the organic layer was washed with saturated aqueous sodium bicarbonate and brine and then passed through a phase separator to dry. The solvent was evaporated under reduced pressure to afford the title compound as a white solid (0.021 g, 17%).

The following compounds were prepared in like manner to the procedure outlined in Example 63:

N-(2-Amino-4,6-difluorophenyl)-2-chloro-5-((1R,3R)-2,2-dichloro-3-(3-chloro-4-fluorophenyl)cyclopropane-1-carboxamido)benzamide (F409)

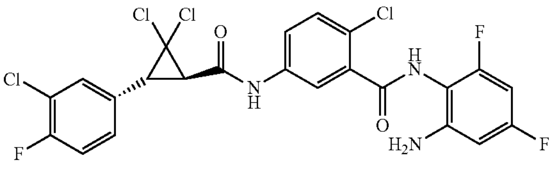

Isolated as a white solid (0.025 g, 20%).

N-(2-Amino-3,5-difluorophenyl)-2-chloro-5-((1R,3R)-2,2-dichloro-3-(3-chloro-4-fluorophenyl)cyclopropane-1-carboxamido)benzamide (F420)

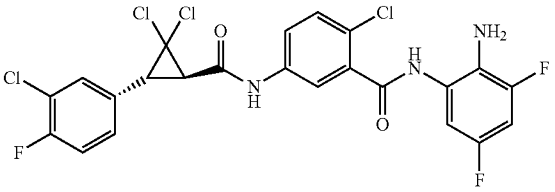

Isolated as a white solid (0.075 g, 58%).

N-(2-Amino-5-fluorophenyl)-2-chloro-5-((1R,3R)-2,2-dichloro-3-(3-chloro-4-fluorophenyl)cyclopropane-1-carboxamido)benzamide (F421)

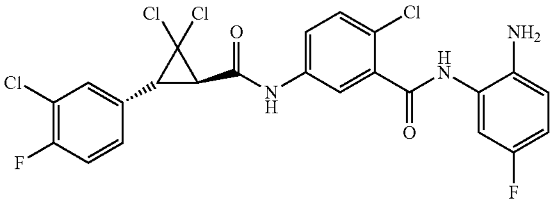

Isolated as a light pink solid (0.031 g, 37%).

trans-N-(4-Amino-2-methylphenyl)-2-chloro-5-(2,2-dichloro-3-(3,4-dichlorophenyl)cyclopropane-1-carboxamido)benzamide (F574)

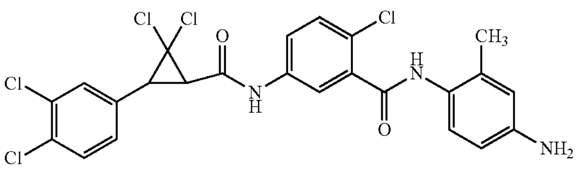 [SMILES: Cc1cc(N)ccc1NC(=O)c1cc(NC(=O)C2C(c3ccc(Cl)c(Cl)c3)C2(Cl)Cl)ccc1Cl]

Isolated as a white foam (0.838 g, 99%).

Example 64: Preparation of trans-N-(4-aminophenyl)-2-chloro-5-(2,2-dichloro-3-(3,5-dichlorophenyl) cyclopropane-1-carboxamido)benzamide hydrochloride (PF21)

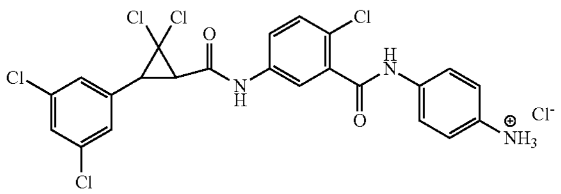 [SMILES: [NH3+]c1ccc(NC(=O)c2cc(NC(=O)C3C(c4cc(Cl)cc(Cl)c4)C3(Cl)Cl)ccc2Cl)cc1 ; [Cl-]]

To a solution of trans-tert-butyl-(4-(2-chloro-5-(2,2-dichloro-3-(3,5-dichlorophenyl) cyclopropane-1-carboxamido)benzamido)phenyl)carbamate (PF13) (0.410 g, 0.637 mmol) in dichloromethane (5 mL) was added a 4 M solution of hydrogen chloride in dioxane (0.478 mL, 1.911 mmol), and the reaction mixture was stirred at room temperature for three hours. The solvent was evaporated from the reaction under a stream of nitrogen, and the resulting residue was dried under vacuum at room temperature for 72 hours to yield the title compound as a white solid (0.371 g, 100%).

Example 65: Preparation of trans-2-chloro-N-(2-cyano-4-(methylamino)phenyl)-5-(2,2-dichloro-3-(3,5-dichlorophenyl)cyclopropane-1-carboxamido)benzamide (F237)

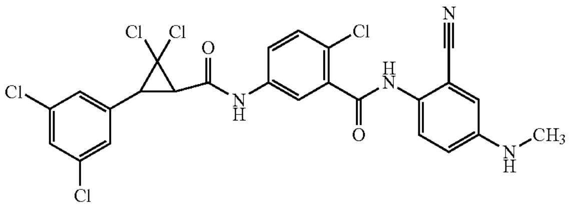 [SMILES: CNc1ccc(NC(=O)c2cc(NC(=O)C3C(c4cc(Cl)cc(Cl)c4)C3(Cl)Cl)ccc2Cl)c(C#N)c1]

A suspension of N-(4-amino-2-cyanophenyl)-2-chloro-5-(2,2-dichloro-3-(3,5-dichlorophenyl)cyclopropane-1-carboxamido)benzamide (F236) (60 mg, 0.106 mmol), pyridine (29.7 μL, 0.369 mmol), and diacetoxycopper (47.9 mg, 0.264 mmol) in dioxane (1.4 mL) was stirred at room temperature for 15 minutes. Methylboronic acid (15.79 mg, 0.264 mmol) was added, and the reaction mixture was heated to 110° C. via microwave irradiation for 2 hours. The reaction mixture was filtered through Celite®, rinsing with ethyl acetate. The filtrate was concentrated, and the crude material was purified by flash column chromatography using 0-100% ethyl acetate in hexanes as the eluent to afford the title compound as a yellow powder (0.0111 g, 18%).

Example 66: Preparation of trans-N-(4-(N-acetylacetamido)-2-cyanophenyl)-2-chloro-5-(2,2-dichloro-3-(3,5-dichlorophenyl)cyclopropane-1-carboxamido) benzamide (F469)

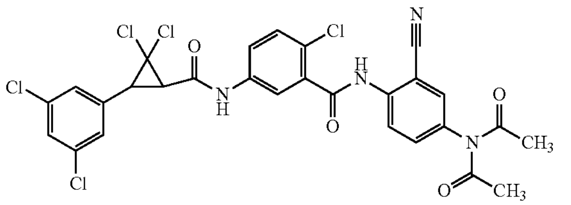 [SMILES: CC(=O)N(C(C)=O)c1ccc(NC(=O)c2cc(NC(=O)C3C(c4cc(Cl)cc(Cl)c4)C3(Cl)Cl)ccc2Cl)c(C#N)c1]

To a suspension of N-(4-amino-2-cyanophenyl)-2-chloro-5-(2,2-dichloro-3-(3,5-dichlorophenyl)cyclopropane-1-carboxamido)benzamide (F236) (60 mg, 0.106 mmol) in dichloromethane (1.1 mL) were added triethylamine (29.4 μL, 0.211 mmol) followed by acetyl chloride (11.29 μL, 0.158 mmol). The reaction mixture was sealed under an atmosphere of nitrogen and stirred overnight at room temperature. Additional acetyl chloride (11 μL) and triethylamine (30 μL) were added, and the reaction was continued for 3 hours. Additional acetyl chloride (11 μL) and triethylamine (30 μL) were added, and the reaction was continued for 15 minutes. The reaction mixture was diluted with dichloromethane and quenched with saturated aqueous ammonium chloride. The organic phase was dried by passing through a phase separator cartridge, and the solvent was evaporated. The resulting crude residue was purified by flash column chromatography using 0-100% ethyl acetate in hexanes as the eluent to afford the title compound as a yellow solid (0.0468 g, 68%).

Example 67: Preparation of trans-2-chloro-5-(2,2-dichloro-3-(3,5-dichlorophenyl)cyclopropane-1-carboxamido)-N-(4-(3,3,3-trifluoropropanamido) phenyl)benzamide (PF25)

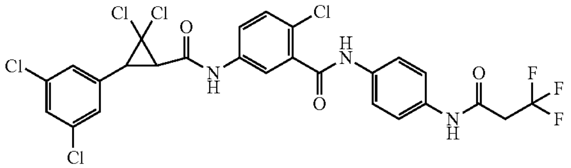 [SMILES: O=C(CC(F)(F)F)Nc1ccc(NC(=O)c2cc(NC(=O)C3C(c4cc(Cl)cc(Cl)c4)C3(Cl)Cl)ccc2Cl)cc1]

To a solution of trans-N-(4-aminophenyl)-2-chloro-5-(2,2-dichloro-3-(3,5-dichlorophenyl)cyclopropane-1-carboxamido)benzamide hydrochloride (PF21) (0.060 g, 0.103 mmol) and triethylamine (0.022 mL, 0.155 mmol) in dichloromethane (1 mL) was added 3,3,3-trifluoropropanoyl chloride (0.015 g, 0.103 mmol). The reaction mixture was stirred at room temperature overnight. The reaction mixture was diluted with ethyl acetate and washed with hydrochloric acid (2 N) (2×) and saturated aqueous sodium bicarbonate (2×). The organic layer was poured through a phase separator and concentrated under reduced pressure to yield the title compound as a white solid (0.066 g, 97%).

The following compounds were prepared in like manner to the procedure outlined in Example 67:

trans-N-(4-Acrylamidophenyl)-2-chloro-5-(2,2-dichloro-3-(3,5-dichlorophenyl)cyclopropane-1-carboxamido)benzamide (PF26)

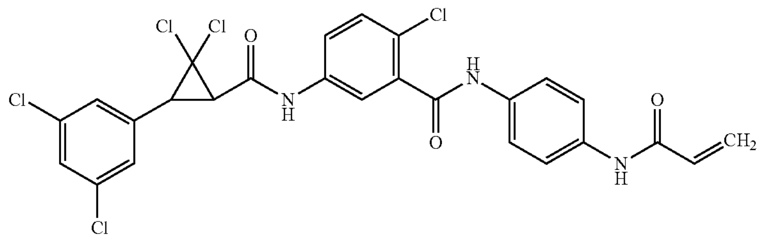 [SMILES: C=CC(=O)Nc1ccc(NC(=O)c2cc(NC(=O)C3C(c4cc(Cl)cc(Cl)c4)C3(Cl)Cl)ccc2Cl)cc1]

Isolated as a white solid (0.034 g, 56%).

trans-2-Chloro-5-(2,2-dichloro-3-(3,5-dichlorophenyl)cyclopropane-1-carboxamido)-N-(4-(2-methoxyacetamido)phenyl)benzamide (PF27)

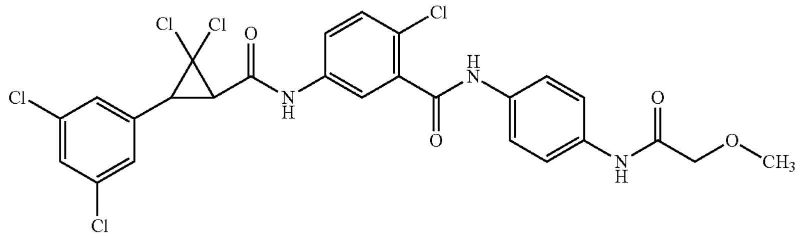 [SMILES: COCC(=O)Nc1ccc(NC(=O)c2cc(NC(=O)C3C(c4cc(Cl)cc(Cl)c4)C3(Cl)Cl)ccc2Cl)cc1]

Isolated as a white solid (0.054 g, 84%).

trans-2-Chloro-5-(2,2-dichloro-3-(3,5-dichlorophenyl)cyclopropane-1-carboxamido)-N-(4-(2-phenylacetamido)phenyl)benzamide (PF28)

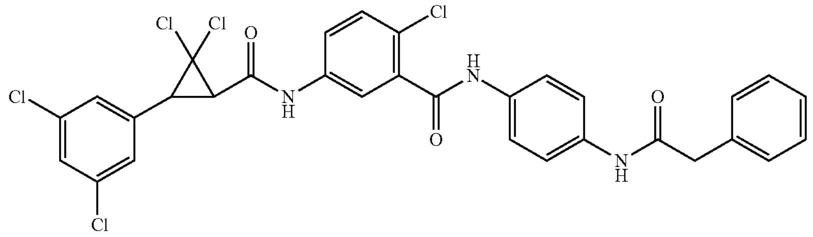 [SMILES: O=C(Cc1ccccc1)Nc1ccc(NC(=O)c2cc(NC(=O)C3C(c4cc(Cl)cc(Cl)c4)C3(Cl)Cl)ccc2Cl)cc1]

Isolated as a yellow solid (0.055 g, 81%).

trans-2-Chloro-5-(2,2-dichloro-3-(3,5-dichlorophenyl)cyclopropane-1-carboxamido)-N-(4-(3,3,3-trifluoro-N-methylpropanamido)phenyl)benzamide (PF30)

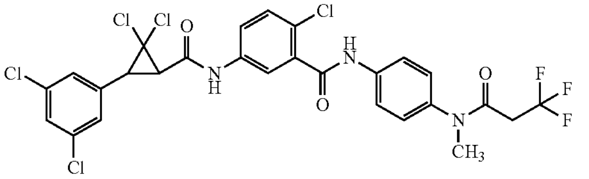 [SMILES: CN(C(=O)CC(F)(F)F)c1ccc(NC(=O)c2cc(NC(=O)C3C(c4cc(Cl)cc(Cl)c4)C3(Cl)Cl)ccc2Cl)cc1]

Isolated as a white solid (0.056 g, 83%).

trans-2-Chloro-5-(2,2-dichloro-3-(3,5-dichlorophenyl)cyclopropane-1-carboxamido)-N-(4-(2-methoxy-N-methylacetamido)phenyl)benzamide (PF31)

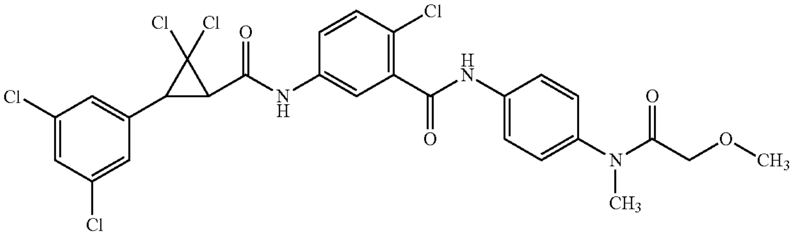 [SMILES: COCC(=O)N(C)c1ccc(NC(=O)c2cc(NC(=O)C3C(c4cc(Cl)cc(Cl)c4)C3(Cl)Cl)ccc2Cl)cc1]

Isolated as a white solid (0.048 g, 83%).

trans-N-(4-Benzamidophenyl)-2-chloro-5-(2,2-dichloro-3-(3,5-dichlorophenyl)cyclopropane-1-carboxamido)benzamide (PF104)

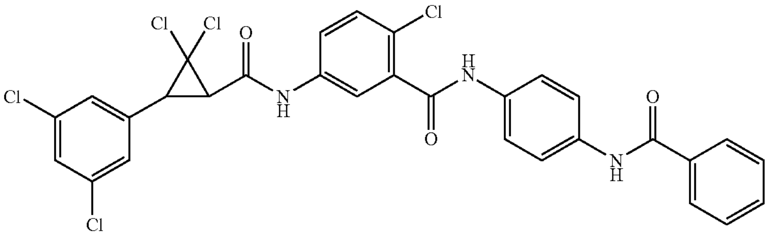 [SMILES: O=C(Nc1ccc(NC(=O)c2cc(NC(=O)C3C(c4cc(Cl)cc(Cl)c4)C3(Cl)Cl)ccc2Cl)cc1)c1ccccc1]

Isolated as a yellow solid (0.030 g, 36%).

trans-2-Chloro-N-(4-(cyclopropane-1-carboxamido)phenyl)-5-(2,2-dichloro-3-(3,5-dichlorophenyl)cyclopropane-1-carboxamido)benzamide (PF107)

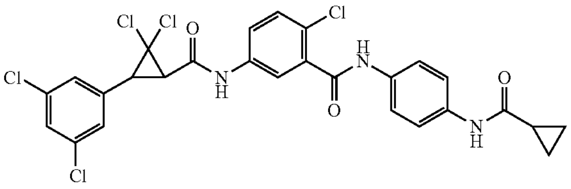 [SMILES: O=C(Nc1ccc(NC(=O)C2CC2)cc1)c1cc(NC(=O)C2C(c3cc(Cl)cc(Cl)c3)C2(Cl)Cl)ccc1Cl]

Isolated as a white solid (0.037 g, 46%).

trans-2-Chloro-N-(4-(2-cyclopropylacetamido)phenyl)-5-(2,2-dichloro-3-(3,5-dichlorophenyl)cyclopropane-1-carboxamido)benzamide (PF163)

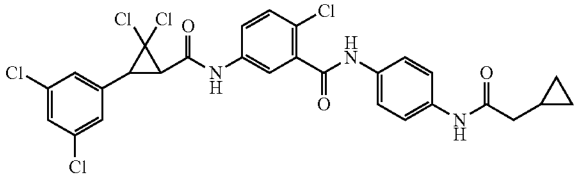 [SMILES: O=C(CC1CC1)Nc1ccc(NC(=O)c2cc(NC(=O)C3C(c4cc(Cl)cc(Cl)c4)C3(Cl)Cl)ccc2Cl)cc1]

Isolated as a white foam (0.050 g, 61%).

Example 68: Preparation of trans-2-chloro-5-(2,2-dichloro-3-(3,5-dichlorophenyl)cyclopropane-1-carboxamido)-N-(4-(2,2-difluorocyclopropane-1-carboxamido)phenyl)benzamide (PF108)

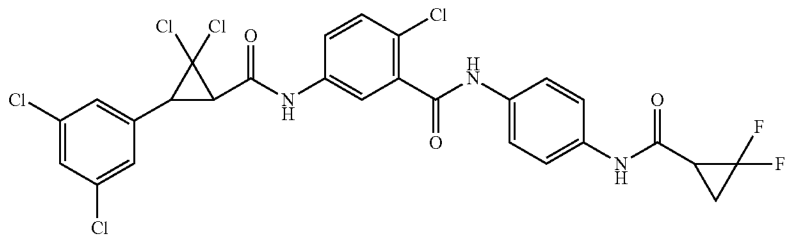 [SMILES: O=C(Nc1ccc(NC(=O)C2CC2(F)F)cc1)c1cc(NC(=O)C2C(c3cc(Cl)cc(Cl)c3)C2(Cl)Cl)ccc1Cl]

To a solution of trans-N-(4-aminophenyl)-2-chloro-5-(2,2-dichloro-3-(3,5-dichlorophenyl)cyclopropanecarboxamido)benzamide hydrochloride (PF21) (0.075 g, 0.129 mmol) in dichloromethane (1.0 mL) was added triethylamine (0.027 mL, 0.194 mmol), 1-ethyl-3-(3-dimethylaminopropyl)carbodiimide hydrochloride (0.037 g, 0.194 mmol), 4-dimethylaminopyridine (0.017 g, 0.142 mmol) and 2,2-difluorocyclopropanecarboxylic acid (0.016 g, 0.129 mmol). The reaction mixture was stirred at room temperature overnight and then directly loaded onto Celite® and purified by flash column chromatography using 0-80% ethyl acetate/hexanes as eluent to afford the title compound as a white solid (0.054 g, 64%).

The following compounds were prepared in like manner to the procedure outlined in Example 68:

trans-2-Chloro-N-(4-(1-cyanocyclopropane-1-carboxamido)phenyl)-5-(2,2-dichloro-3-(3,5-dichlorophenyl)cyclopropane-1-carboxamido)benzamide (PF109)

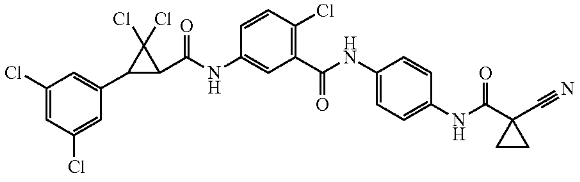 [SMILES: N#CC1(C(=O)Nc2ccc(NC(=O)c3cc(NC(=O)C4C(c5cc(Cl)cc(Cl)c5)C4(Cl)Cl)ccc3Cl)cc2)CC1]

Isolated as a white foam (0.027 g, 32%).

trans-2-Chloro-5-(2,2-dichloro-3-(3,5-dichlorophenyl)cyclopropane-1-carboxamido)-N-(4-(1-(methoxymethyl)cyclopropane-1-carboxamido)phenyl)benzamide (PF161)

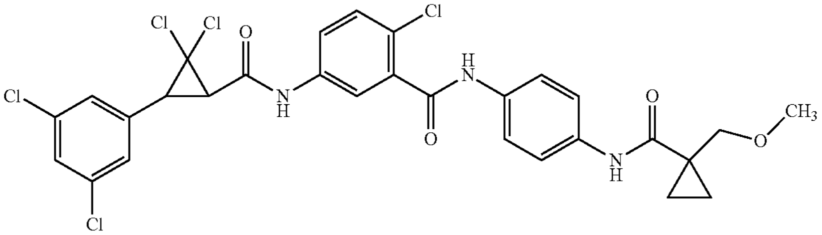 [SMILES: COCC1(C(=O)Nc2ccc(NC(=O)c3cc(NC(=O)C4C(c5cc(Cl)cc(Cl)c5)C4(Cl)Cl)ccc3Cl)cc2)CC1]

Isolated as a white foam (0.040 g, 47%).

trans-2-Chloro-5-(2,2-dichloro-3-(3,5-dichlorophenyl)cyclopropane-1-carboxamido)-N-(4-(1-(trifluoromethyl)cyclopropane-1-carboxamido)phenyl)benzamide (PF162)

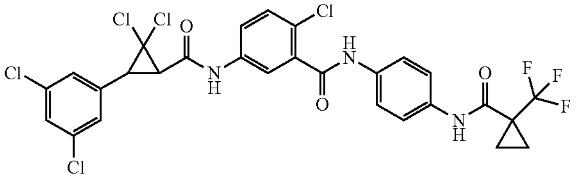 [SMILES: O=C(Nc1ccc(NC(=O)C2(C(F)(F)F)CC2)cc1)c1cc(NC(=O)C2C(c3cc(Cl)cc(Cl)c3)C2(Cl)Cl)ccc1Cl]

Isolated as a white solid (0.027 g, 31%).

trans-2-Chloro-5-(2,2-dichloro-3-(3,5-dichlorophenyl)cyclopropane-1-carboxamido)-N-(4-(3,3-dimethylbutanamido)phenyl)benzamide (PF164)

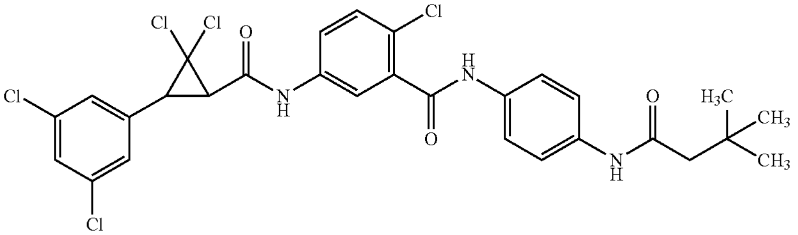 [SMILES: CC(C)(C)CC(=O)Nc1ccc(NC(=O)c2cc(NC(=O)C3C(c4cc(Cl)cc(Cl)c4)C3(Cl)Cl)ccc2Cl)cc1]

Isolated as a white solid (0.064 g, 77%).

Example 69: Preparation of trans-2-chloro-5-(2,2-dichloro-3-(3,5-dichlorophenyl)cyclopropane-1-carboxamido)-N-(4-(2,2,2-trifluoroacetamido)phenyl)benzamide (PF24)

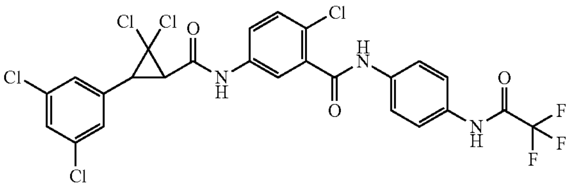 [SMILES: O=C(Nc1ccc(NC(=O)C(F)(F)F)cc1)c1cc(NC(=O)C2C(c3cc(Cl)cc(Cl)c3)C2(Cl)Cl)ccc1Cl]

To a solution of trans-N-(4-aminophenyl)-2-chloro-5-(2,2-dichloro-3-(3,5-dichlorophenyl)cyclopropane-1-carboxamido)benzamide hydrochloride (PF21) (0.060 g, 0.103 mmol) and triethylamine (0.022 mL, 0.155 mmol) in dichloromethane (1.0 mL) was added trifluoroacetic anhydride (0.016 mL, 0.114 mmol). The reaction mixture was stirred at room temperature overnight. The reaction mixture was diluted with ethyl acetate and washed with hydrochloric acid (2 N, 2×) and saturated aqueous sodium bicarbonate (2×). The organic layer was poured through a phase separator and concentrated under reduced pressure to yield the title compound (0.051 g, 76%).

The following compounds were prepared in like manner to the procedure outlined in Example 69:

trans-2-Chloro-5-(2,2-dichloro-3-(3,5-dichlorophenyl)cyclopropane-1-carboxamido)-N-(4-(2,2,2-trifluoro-N-methylacetamido)phenyl)benzamide (PF29)

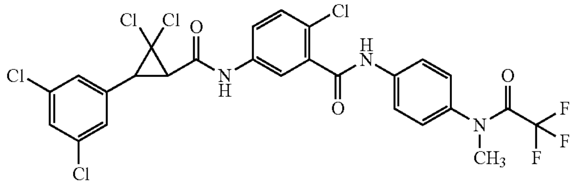 [SMILES: CN(C(=O)C(F)(F)F)c1ccc(NC(=O)c2cc(NC(=O)C3C(c4cc(Cl)cc(Cl)c4)C3(Cl)Cl)ccc2Cl)cc1]

Isolated as a white foam (0.055 g, 84%).

Example 70: Preparation of trans-methyl (4-(2-chloro-5-(2,2-dichloro-3-(3,5-dichlorophenyl)cyclopropane-1-carboxamido)benzamido)-3-methylphenyl)glycinate (F288)

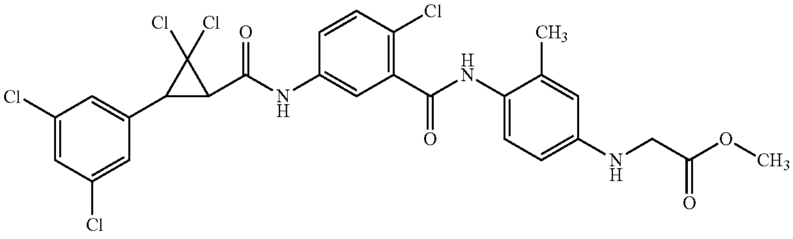 [SMILES: COC(=O)CNc1ccc(NC(=O)c2cc(NC(=O)C3C(c4cc(Cl)cc(Cl)c4)C3(Cl)Cl)ccc2Cl)c(C)c1]

To a solution of trans-N-(4-amino-2-methylphenyl)-2-chloro-5-(2,2-dichloro-3-(3,5-dichlorophenyl)cyclopropane-1-carboxamido)benzamide (F195) (0.070 g, 0.126 mmol) in acetone (1.5 mL) was added potassium carbonate (0.035 g, 0.251 mmol) and methyl 2-bromoacetate (0.021 g, 0.138 mmol). The reaction mixture was warmed to 50° C. for 16 hours. The reaction mixture was then concentrated under a stream of nitrogen. Purification by flash column chromatography using 0-50% ethyl acetate/hexanes as eluent afforded the title compound as a yellow glass (0.016 g, 20%).

Example 71: Preparation of 2-chloro-N-(4-((E)-4-chlorobenzylidene)amino)-2-methylphenyl)-5-(trans)-2,2-dichloro-3-(3,5-dichlorophenyl)cyclopropane-1-carboxamido)benzamide (F510)

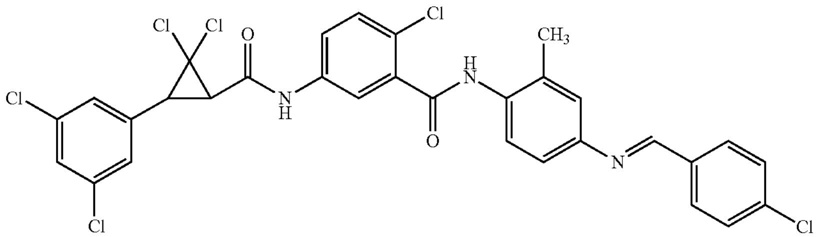 [SMILES: Cc1cc(/N=C/c2ccc(Cl)cc2)ccc1NC(=O)c1cc(NC(=O)C2C(c3cc(Cl)cc(Cl)c3)C2(Cl)Cl)ccc1Cl]

4-Chlorobenzaldehyde (12.6 mg, 0.090 mmol) was added in one portion to a stirred solution of N-(4-amino-2-methylphenyl)-2-chloro-5-(trans)-2,2-dichloro-3-(3,5-dichlorophenyl)cyclopropane-1-carboxamido)benzamide (F284) (50 mg, 0.090 mmol) and anhydrous magnesium sulfate (108 mg, 0.900 mmol) in tetrahydrofuran (3 mL) at room temperature. After 12 hours, the reaction mixture was concentrated under vacuum on a rotary evaporator. Purification by silica gel flash chromatography with a mobile phase of ethyl acetate and hexanes provided 2-chlor—the title compound as a white solid (0.027 g, 42.1%).

Example 72: Preparation of trans-2-chloro-N-(4-(N-cyano-S-methylsulfinimidoyl)phenyl)-5-(2,2-dichloro-3-(3,5-dichlorophenyl)cyclopropane-1-carboxamido)benzamide (F495)

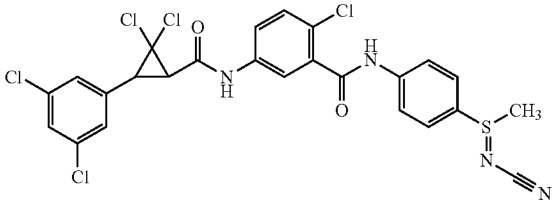 [SMILES: C/S(=N\C#N)c1ccc(NC(=O)c2cc(NC(=O)C3C(c4cc(Cl)cc(Cl)c4)C3(Cl)Cl)ccc2Cl)cc1]

To a solution of trans-2-chloro-5-(2,2-dichloro-3-(3,5-dichlorophenyl)cyclopropane-1-carboxamido)-N-(4-(methylthio)phenyl)benzamide (F149) (0.180 g, 0.31 mmol) in methanol (3.1 mL) were sequentially added cyanamide (0.017 g, 0.41 mmol), solid potassium tert-butoxide (0.042 g, 0.38 mmol), and N-bromosuccinimide (0.084 g, 0.47 mmol). The reaction mixture was stirred at room temperature for 1 hour. Water was added, and the mixture was extracted with dichloromethane. The combined organic phases were dried over magnesium sulfate, filtered, and concentrated. The residue was slurried in hexane and vacuum filtered to provide the title compound as an off-white foam (0.175 g, 91%).

Example 73: Preparation of 2-chloro-5-(trans-2,2-dichloro-3-(3,5-dichlorophenyl)cyclopropane-1-carboxamido)-N-(4-(2,5-dioxo-2,5-dihydro-1H-pyrrol-1-yl)-2-methylphenyl)benzamide (F480)

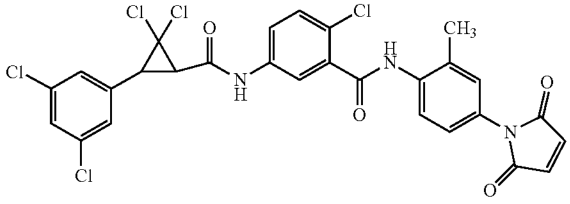 [SMILES: Cc1cc(N2C(=O)C=CC2=O)ccc1NC(=O)c1cc(NC(=O)C2C(c3cc(Cl)cc(Cl)c3)C2(Cl)Cl)ccc1Cl]

Maleic anhydride (16.1 mg, 0.164 mmol) was added in one portion to a stirred solution of N-(4-amino-2-methylphenyl)-2-chloro-5-(trans)-2,2-dichloro-3-(3,5-dichlorophenyl)cyclopropane-1-carboxamido)benzamide (F284) (83 mg, 0.149 mmol) in anhydrous chloroform (3 mL) at room temperature. The mixture was stirred at room temperature for 12 hours. The resulting suspension of white solid was concentrated to dryness under a stream of nitrogen. The residue was dissolved in acetic anhydride (0.6 mL, 5.95 mmol) and treated with sodium acetate (12.2 mg, 0.149 mmol). The reaction mixture was heated at 85° C. for 2 hours, then cooled and stirred at room temperature for 13 hours. The reaction mixture was concentrated under vacuum on a rotary evaporator. Purification by flash chromatography with a mobile phase of ethyl acetate and hexanes gave 2-chloro-5-(trans)-2,2-dichloro-3-(3,5-dichlorophenyl)cyclopropane-1-carboxamido)-N-(4-(2,5-dioxo-2,5-dihydro-1H-pyrrol-1-yl)-2-methylphenyl)benzamide (0.046 g, 46%) as a yellow solid.

Example 74: Preparation of 2-chloro-5-(trans)-2,2-dichloro-3-(3,5-dichlorophenyl)cyclopropane-1-carboxamido)-N-(2-methyl-4-(methylsulfonamido)phenyl)benzamide (F487)

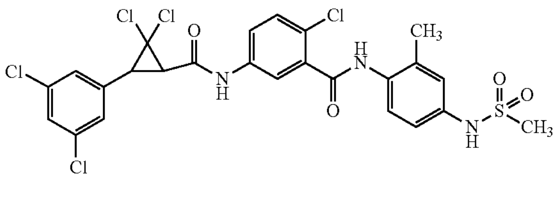 [SMILES: Cc1cc(NS(C)(=O)=O)ccc1NC(=O)c1cc(NC(=O)C2C(c3cc(Cl)cc(Cl)c3)C2(Cl)Cl)ccc1Cl]

Methane sulfonyl chloride (32.9 mg, 0.287 mmol) was added in one portion to a stirred solution of N-(4-amino-2-methylphenyl)-2-chloro-5-(trans)-2,2-dichloro-3-(3,5-dichlorophenyl)cyclopropane-1-carboxamido)benzamide (F284) (160 mg, 0.287 mmol) and triethyl amine (58.1 mg, 0.574 mmol) in dichloromethane (5 mL) at room temperature. After 12 hours, the reaction mixture was concentrated under vacuum on a rotary evaporator. Purification by silica gel flash chromatography with a mobile phase of ethyl acetate and hexanes gave 2-chloro-5-(trans)-2,2-dichloro-3-(3,5-dichlorophenyl)cyclopropane-1-carboxamido)-N-(2-methyl-4-(methylsulfonamido)phenyl)benzamide (0.014 g, 7.5%) as a white solid.

Example 75: Preparation of trans-2-chloro-N-(4-(N-cyano-S-methylsulfonimidoyl)phenyl)-5-(2,2-dichloro-3-(3,5-dichlorophenyl)cyclopropane-1-carboxamido)benzamide (F502)

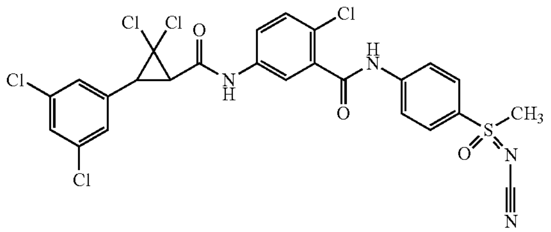 [SMILES: CS(=O)(=NC#N)c1ccc(NC(=O)c2cc(NC(=O)C3C(c4cc(Cl)cc(Cl)c4)C3(Cl)Cl)ccc2Cl)cc1]

To a solution of trans-2-chloro-N-(4-(N-cyano-S-methylsulfinimidoyl)phenyl)-5-(2,2-dichloro-3-(3,5-dichlorophenyl)cyclopropane-1-carboxamido)benzamide (F495) (0.090 g, 0.15 mmol) in 2:1:1 ethanol:dichloromethane:water (2.0 mL) was added potassium carbonate (0.045 g, 0.32 mmol) and meta-chloroperoxybenzoic acid (0.036 g, 0.16 mmol). The reaction mixture was stirred at room temperature for 24 hours. Water was added, and the mixture was extracted with dichloromethane. The combined organic phases were dried over magnesium sulfate, filtered, and concentrated. Purification by reverse phase column chromatography using a 5% acetonitrile to 100% acetonitrile gradient provided the title compound as a pale yellow powder (0.027 g, 29%).

Example 76: Preparation of trans-2-chloro-5-(2,2-dichloro-3-(3,5-dichlorophenyl)cyclopropane-1-carboxamido)-N-(3,5-difluoro-4-vinylpyridin-2-yl)benzamide (F393)

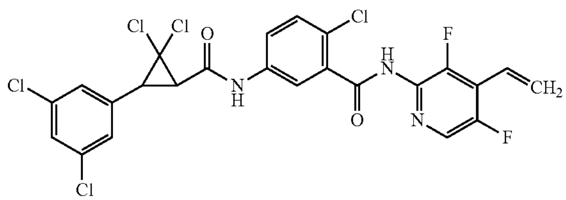 [SMILES: C=Cc1c(F)cnc(NC(=O)c2cc(NC(=O)C3C(c4cc(Cl)cc(Cl)c4)C3(Cl)Cl)ccc2Cl)c1F]

A solution of 2-chloro-5-(2,2-dichloro-3-(3,5-dichlorophenyl)cyclopropane-1-carboxamido)-N-(3,5-difluoro-4-iodopyridin-2-yl)benzamide (F388) (100 mg, 0.145 mmol), bis(triphenylphosphine)palladium(II) dichloride (20.30 mg, 0.029 mmol), and tributyl(vinyl)stannane (0.127 mL, 0.434 mmol), in 1,4-dioxane (1 mL) was sealed under an atmosphere of nitrogen and heated to 90° C. via microwave irradiation for 1 hour. The reaction mixture was diluted with ethyl acetate, then filtered through 10:1 silica gel:potassium carbonate (15 g), rinsing with ethyl acetate. The solution was concentrated, and the resulting crude material was loaded onto a preload cartridge containing 5:1 silica gel:potassium fluoride (5 g). Purification by flash column chromatography using 0-50% ethyl acetate in hexanes as the eluent afforded the title compound as a tan solid (0.0596 g, 70%).

The following compounds were prepared in like manner to the procedure outlined in Example 76:

2-Chloro-5-(trans-2,2-dichloro-3-(3,5-dichlorophenyl)cyclopropane-1-carboxamido)-N-(3,5-difluoro-4-(1-fluorovinyl)pyridin-2-yl)benzamide (F394)

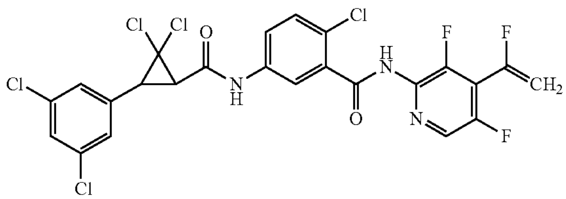 [SMILES: C=C(F)c1c(F)cnc(NC(=O)c2cc(NC(=O)C3C(c4cc(Cl)cc(Cl)c4)C3(Cl)Cl)ccc2Cl)c1F]

Isolated as a tan solid (0.0615 g, 70%).

2-Chloro-5-(trans-2,2-dichloro-3-(3,5-dichlorophenyl)cyclopropane-1-carboxamido)-N-(6-fluoro-5-vinylpyridin-2-yl)benzamide (F397)

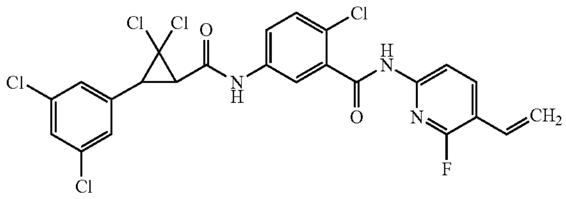 [SMILES: C=Cc1ccc(NC(=O)c2cc(NC(=O)C3C(c4cc(Cl)cc(Cl)c4)C3(Cl)Cl)ccc2Cl)nc1F]

Isolated as a tan solid (0.0508 g, 66%).

2-chloro-5-(trans-2,2-dichloro-3-(3,5-dichlorophenyl)cyclopropane-1-carboxamido)-N-(6-fluoro-5-(1-fluorovinyl)pyridin-2-yl)benzamide (F398)

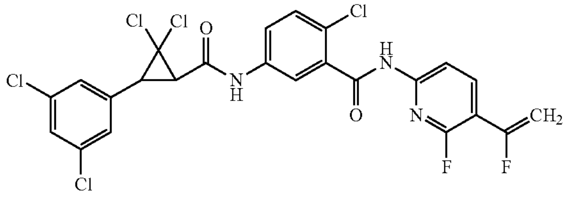 [SMILES: C=C(F)c1ccc(NC(=O)c2cc(NC(=O)C3C(c4cc(Cl)cc(Cl)c4)C3(Cl)Cl)ccc2Cl)nc1F]

Isolated as a tan solid (0.0701 g, 88%).

2-Chloro-5-(trans-2,2-dichloro-3-(3,5-dichlorophenyl)cyclopropane-1-carboxamido)-N-(6-fluoro-5-vinylpyridin-3-yl)benzamide (F399)

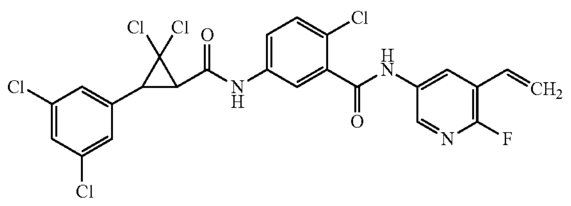 [SMILES: C=Cc1cc(NC(=O)c2cc(NC(=O)C3C(c4cc(Cl)cc(Cl)c4)C3(Cl)Cl)ccc2Cl)cnc1F]

Isolated as a yellow solid (0.0515 g, 71%).

2-Chloro-5-(trans-2,2-dichloro-3-(3,5-dichlorophenyl)cyclopropane-1-carboxamido)-N-(6-fluoro-5-(1-fluorovinyl)pyridin-3-yl)benzamide (F400)

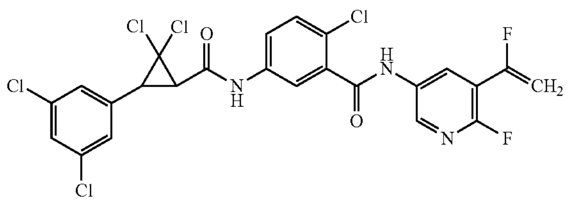 [SMILES: C=C(F)c1cc(NC(=O)c2cc(NC(=O)C3C(c4cc(Cl)cc(Cl)c4)C3(Cl)Cl)ccc2Cl)cnc1F]

Isolated as a yellow solid (0.0551 g, 74%).

Example 77: Preparation of 2-chloro-5-(trans-2,2-dichloro-3-(3-chloro-4-vinylphenyl)cyclopropane-1-carboxamido)-N-(4-fluorophenyl)benzamide (F289)

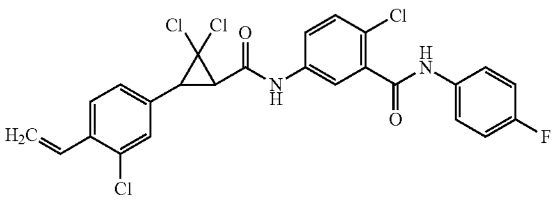 [SMILES: C=Cc1ccc(C2C(C(=O)Nc3ccc(Cl)c(C(=O)Nc4ccc(F)cc4)c3)C2(Cl)Cl)cc1Cl]

A solution of 5-(trans-3-(4-bromo-3-chlorophenyl)-2,2-dichlorocyclopropane-1-carboxamido)-2-chloro-N-(4-fluorophenyl)benzamide (F270) (0.065 g, 0.110 mmol), bis(triphenylphosphine)palladium(II) dichloride (0.008 g, 0.011 mmol), and tributyl(vinyl)stannane (0.096 mL, 0.105 mmol), in 1,4-dioxane (1 mL) was sealed under an atmosphere of nitrogen and heated to 90° C. via microwave irradiation for 1 hour. The reaction mixture was diluted with ethyl acetate, then filtered through 10:1 silica gel:potassium carbonate (15 g), rinsing with ethyl acetate. The solution was concentrated, and the resulting crude material was loaded onto a preload cartridge containing 5:1 silica gel:potassium fluoride (5 g). Purification by flash column chromatography using 0-25% ethyl acetate in hexanes as the eluent afforded the title compound as a pale yellow solid (0.0265 g, 43%).

The following compounds were prepared in like manner to the procedure outlined in Example 77:

2-Chloro-5-(trans-2,2-dichloro-3-(3-chloro-4-vinylphenyl)cyclopropane-1-carboxamido)-N-(2,4-difluorophenyl)benzamide (F319)

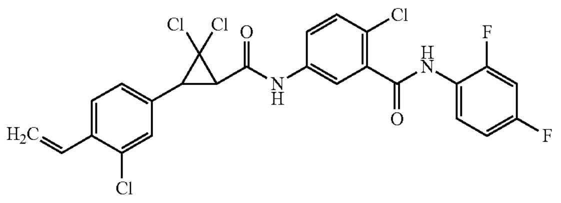 [SMILES: C=Cc1ccc(C2C(C(=O)Nc3ccc(Cl)c(C(=O)Nc4ccc(F)cc4F)c3)C2(Cl)Cl)cc1Cl]

Isolated as a colorless film (0.007 g, 14%).

2-Chloro-5-(trans-2,2-dichloro-3-(3-chloro-4-vinylphenyl)cyclopropane-1-carboxamido)-N-(4-fluorophenyl)-N-methylbenzamide (F329)

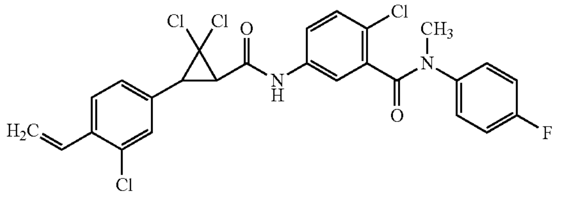 [SMILES: C=Cc1ccc(C2C(C(=O)Nc3ccc(Cl)c(C(=O)N(C)c4ccc(F)cc4)c3)C2(Cl)Cl)cc1Cl]

Isolated as a pale yellow powder (0.0764 g, 71%).

2-Chloro-5-(trans-2,2-dichloro-3-(4-chloro-3-vinylphenyl)cyclopropane-1-carboxamido)-N-(4-fluorophenyl)benzamide (F349)

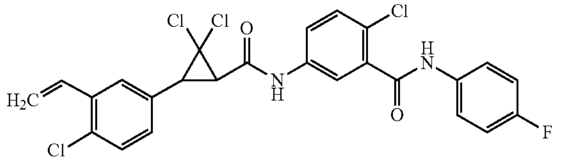 [SMILES: C=Cc1cc(C2C(C(=O)Nc3ccc(Cl)c(C(=O)Nc4ccc(F)cc4)c3)C2(Cl)Cl)ccc1Cl]

Isolated as a yellow foam (0.0366 g, 59%).

2-Chloro-5-(trans-2,2-dichloro-3-(3-chloro-5-vinylphenyl)cyclopropane-1-carboxamido)-N-(4-fluorophenyl)benzamide (F350)

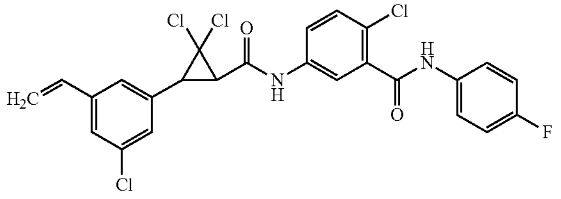 [SMILES: C=Cc1cc(Cl)cc(C2C(C(=O)Nc3ccc(Cl)c(C(=O)Nc4ccc(F)cc4)c3)C2(Cl)Cl)c1]

Isolated as a yellow foam (0.0909 g, 64%).

2-Chloro-5-(trans-2,2-dichloro-3-(4-chloro-3-vinylphenyl)cyclopropane-1-carboxamido)-N-(2,4-difluorophenyl)benzamide (F351)

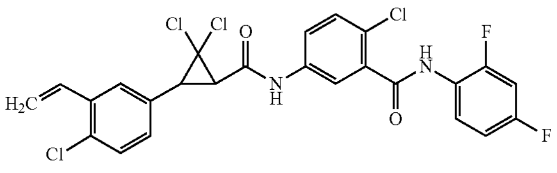 [SMILES: C=Cc1cc(C2C(C(=O)Nc3ccc(Cl)c(C(=O)Nc4ccc(F)cc4F)c3)C2(Cl)Cl)ccc1Cl]

Isolated as a yellow foam (0.0351 g, 73%).

2-Chloro-5-(trans-2,2-dichloro-3-(3-chloro-5-vinylphenyl)cyclopropane-1-carboxamido)-N-(2,4-difluorophenyl)benzamide (F352)

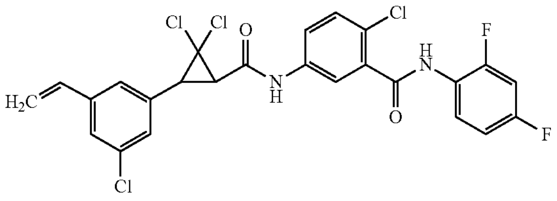 [SMILES: C=Cc1cc(Cl)cc(C2C(C(=O)Nc3ccc(Cl)c(C(=O)Nc4ccc(F)cc4F)c3)C2(Cl)Cl)c1]

Isolated as a yellow foam (0.0488 g, 78%).

2-Chloro-5-(trans-2,2-dichloro-3-(3-chloro-4-(1-fluorovinyl)phenyl)cyclopropane-1-carboxamido)-N-(4-fluorophenyl)benzamide (F382)

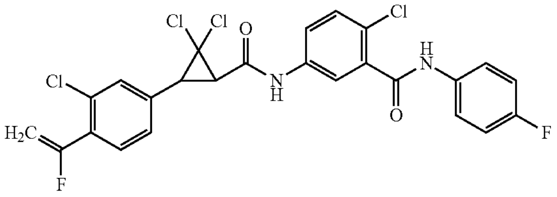 [SMILES: C=C(F)c1ccc(C2C(C(=O)Nc3ccc(Cl)c(C(=O)Nc4ccc(F)cc4)c3)C2(Cl)Cl)cc1Cl]

Isolated as a yellow foam (0.0684 g, 69%).

2-Chloro-5-(trans-2,2-dichloro-3-(3-chloro-4-(1-fluorovinyl)phenyl)cyclopropane-1-carboxamido)-N-(2,4-difluorophenyl)benzamide (F383)

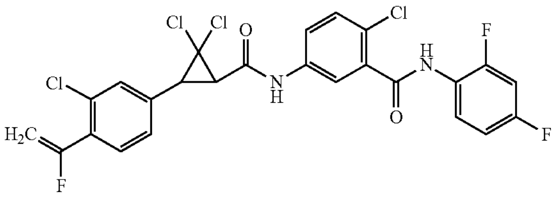 [SMILES: C=C(F)c1ccc(C2C(C(=O)Nc3ccc(Cl)c(C(=O)Nc4ccc(F)cc4F)c3)C2(Cl)Cl)cc1Cl]

Isolated as a brown foam (0.0788 g, 96%).

2-Chloro-5-(trans-2,2-dichloro-3-(4-chloro-3-(1-fluorovinyl)phenyl)cyclopropane-1-carboxamido)-N-(4-fluorophenyl)benzamide (F384)

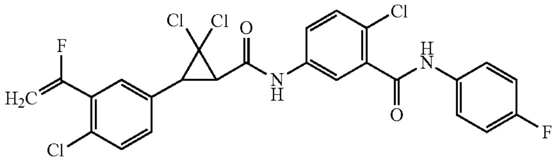 [SMILES: C=C(F)c1cc(C2C(C(=O)Nc3ccc(Cl)c(C(=O)Nc4ccc(F)cc4)c3)C2(Cl)Cl)ccc1Cl]

Isolated as a yellow foam (0.0657 g, 83%).

2-Chloro-5-(trans-2,2-dichloro-3-(4-chloro-3-(1-fluorovinyl)phenyl)cyclopropane-1-carboxamido)-N-(2,4-difluorophenyl)benzamide (F385)

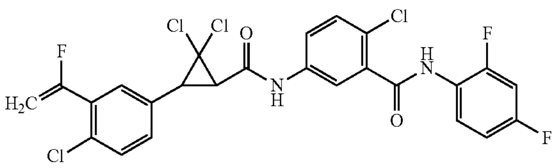 [SMILES: C=C(F)c1cc(C2C(C(=O)Nc3ccc(Cl)c(C(=O)Nc4ccc(F)cc4F)c3)C2(Cl)Cl)ccc1Cl]

Isolated as a yellow foam (0.0614 g, 77%).

2-Chloro-5-(trans-2,2-dichloro-3-(3-chloro-5-(1-fluorovinyl)phenyl)cyclopropane-1-carboxamido)-N-(2,4-difluorophenyl)benzamide (F386)

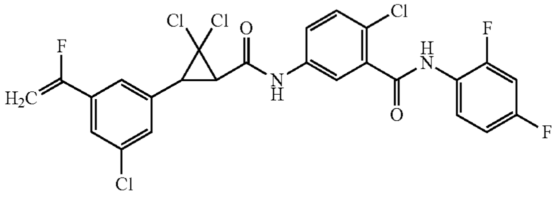 [SMILES: C=C(F)c1cc(Cl)cc(C2C(C(=O)Nc3ccc(Cl)c(C(=O)Nc4ccc(F)cc4F)c3)C2(Cl)Cl)c1]

Isolated as a yellow foam (0.0651 g, 82%).

2-Chloro-N-(2-cyano-4-fluorophenyl)-5-(trans-2,2-dichloro-3-(3-chloro-5-(1-fluorovinyl)phenyl)cyclopropane-1-carboxamido)benzamide (F387)

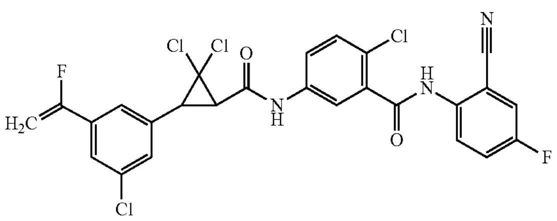 [SMILES: C=C(F)c1cc(Cl)cc(C2C(C(=O)Nc3ccc(Cl)c(C(=O)Nc4ccc(F)cc4C#N)c3)C2(Cl)Cl)c1]

Isolated as a yellow foam (0.0603 g, 76%).

2-Chloro-5-(trans-2,2-dichloro-3-(3-fluoro-4-vinylphenyl)cyclopropane-1-carboxamido)-N-(2,4-difluorophenyl)benzamide (F389)

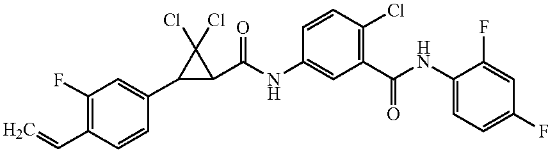 [SMILES: C=Cc1ccc(C2C(C(=O)Nc3ccc(Cl)c(C(=O)Nc4ccc(F)cc4F)c3)C2(Cl)Cl)cc1F]

Isolated as a yellow foam (0.0357 g, 63%).

2-Chloro-5-(trans-2,2-dichloro-3-(4-fluoro-3-vinylphenyl)cyclopropane-1-carboxamido)-N-(2,4-difluorophenyl)benzamide (F390)

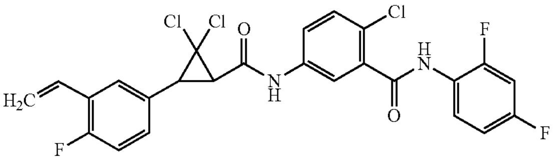 [SMILES: C=Cc1cc(C2C(C(=O)Nc3ccc(Cl)c(C(=O)Nc4ccc(F)cc4F)c3)C2(Cl)Cl)ccc1F]

Isolated as a yellow foam (0.0498 g, 69%).

2-Chloro-5-(trans-2,2-dichloro-3-(3-(trifluoromethyl)-4-vinylphenyl)cyclopropane-1-carboxamido)-N-(2,4-difluorophenyl)benzamide (F391)

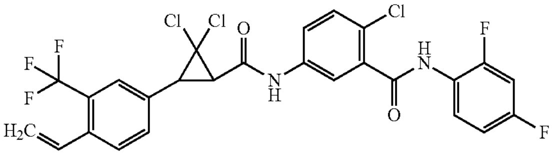 [SMILES: C=Cc1ccc(C2C(C(=O)Nc3ccc(Cl)c(C(=O)Nc4ccc(F)cc4F)c3)C2(Cl)Cl)cc1C(F)(F)F]

Isolated as a yellow foam (0.0475 g, 66%).

2-Chloro-5-(trans-2,2-dichloro-3-(4-(trifluoromethyl)-3-vinylphenyl)cyclopropane-1-carboxamido)-N-(2,4-difluorophenyl)benzamide (F392)

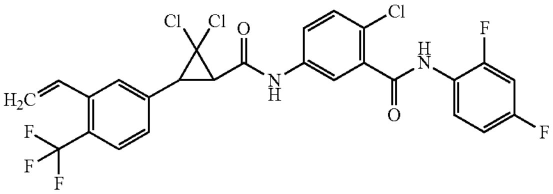 [SMILES: C=Cc1cc(C2C(C(=O)Nc3ccc(Cl)c(C(=O)Nc4ccc(F)cc4F)c3)C2(Cl)Cl)ccc1C(F)(F)F]

Isolated as a yellow foam (0.0307 g, 52%).

tert-Butyl-N-((tert-butoxyl)carbonyl)-N-(3-(2-chloro-5-(2,2-dichloro-3-(4-chloro-3-vinylphenyl)cyclopropane-1-carboxamido)benzamido)-2,6-difluorophenyl)carbamate (F522)

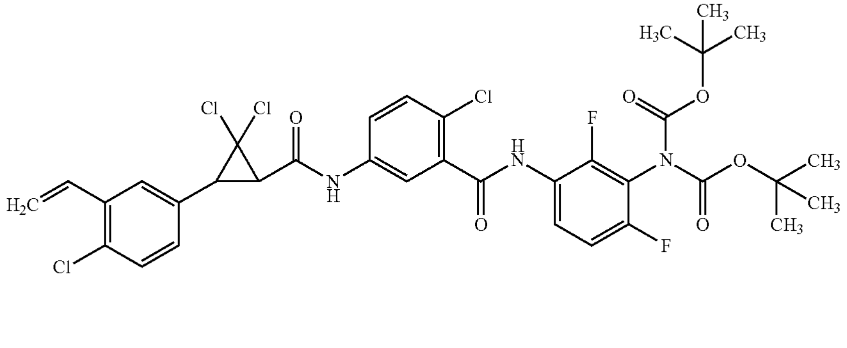 [SMILES: C=Cc1cc(C2C(C(=O)Nc3ccc(Cl)c(C(=O)Nc4ccc(F)c(N(C(=O)OC(C)(C)C)C(=O)OC(C)(C)C)c4F)c3)C2(Cl)Cl)ccc1Cl]

Isolated as a yellow foam (0.0276 g, 27%).

tert-Butyl-N-((tert-butoxyl)carbonyl)-N-(3-(2-chloro-5-(2,2-dichloro-3-(3-chloro-5-vinylphenyl)cyclopropane-1-carboxamido)benzamido)-2,6-difluorophenyl)carbamate (F523)

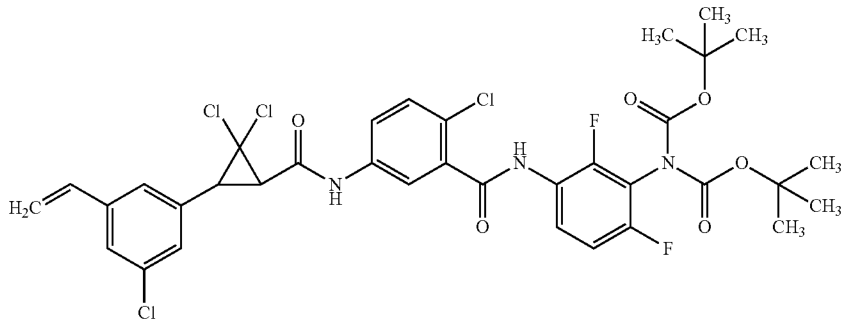 [SMILES: C=Cc1cc(Cl)cc(C2C(C(=O)Nc3ccc(Cl)c(C(=O)Nc4ccc(F)c(N(C(=O)OC(C)(C)C)C(=O)OC(C)(C)C)c4F)c3)C2(Cl)Cl)c1]

Isolated as a yellow foam (0.0748 g, 76%).

2-Chloro-5-(trans-2,2-dichloro-3-(3,5-difluoro-4-vinylphenyl)cyclopropane-1-carboxamido)-N-(2,4-difluorophenyl)benzamide (F566)

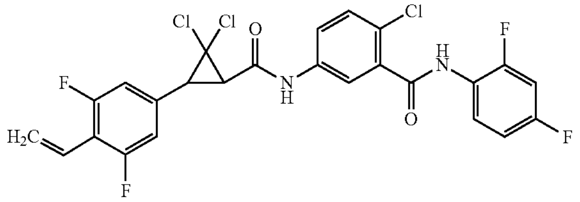 [SMILES: C=Cc1c(F)cc(C2C(C(=O)Nc3ccc(Cl)c(C(=O)Nc4ccc(F)cc4F)c3)C2(Cl)Cl)cc1F]

Isolated as a yellow oil (0.0088 g, 10%).

Example 78: Preparation of 2-chloro-N-(2-cyano-4-fluorophenyl)-5-(trans-2,2-dichloro-3-(3-chloro-4-((trimethylsilyl)ethynyl)phenyl)cyclopropane-1-carboxamido)benzamide (C348)

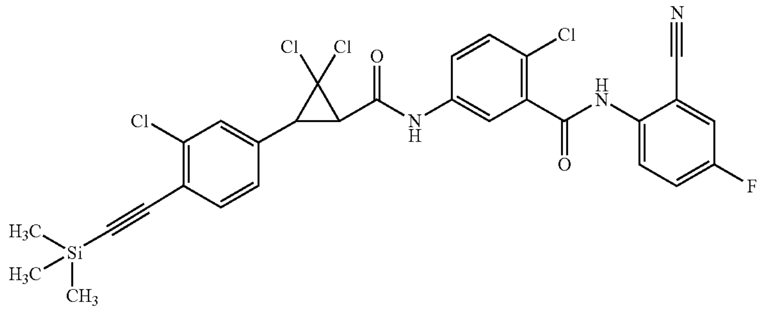 [SMILES: C[Si](C)(C)C#Cc1ccc(C2C(C(=O)Nc3ccc(Cl)c(C(=O)Nc4ccc(F)cc4C#N)c3)C2(Cl)Cl)cc1Cl]

A solution of 5-(trans-3-(4-bromo-3-chlorophenyl)-2,2-dichlorocyclopropane-1-carboxamido)-2-chloro-N-(2-cyano-4-fluorophenyl)benzamide (F320) (0.070 g, 0.114 mmol), bis(triphenylphosphine)palladium(II) dichloride (0.016 g, 0.023 mmol), and trimethyl((tributylstannyl)ethynyl)silane (0.132 g, 0.341 mmol), in 1,4-dioxane (1 mL) was sealed under an atmosphere of nitrogen and heated to 90° C. via microwave irradiation for 1 hour. The reaction mixture was diluted with ethyl acetate, then filtered through 10:1 silica gel:potassium carbonate (15 g), rinsing with ethyl acetate. The solution was concentrated, and the resulting crude material was loaded onto a preload cartridge containing 5:1 silica gel:potassium fluoride (5 g). Purification by flash column chromatography using 0-25% ethyl acetate in hexanes as the eluent afforded the title compound as a yellow foam (0.0402 g, 53%): $^1$H NMR (400 MHz, Acetone-$d_6$) δ 10.23 (s, 1H), 9.77 (s, 1H), 8.02 (t, J=3.8 Hz, 2H), 7.90 (dd, J=8.8, 2.6 Hz, 1H), 7.71 (dd, J=8.2, 2.9 Hz, 1H), 7.64-7.56 (m, 3H), 7.52 (d, J=8.7 Hz, 1H), 7.42 (ddd, J=8.1, 1.8, 0.7 Hz, 1H), 3.65 (d, J=8.3 Hz, 1H), 3.41 (d, J=8.4 Hz, 1H), 0.26 (s, 9H); $^{19}$F NMR (376 MHz, Acetone-$d_6$) δ −116.21; IR (thin film) 1667, 1588, 1526, 1494, 1474, 1414 $cm^{-1}$; HRMS-ESI (m/z) $[M+H]^+$ calcd for $C_{29}H_{23}Cl_4FN_3O_2Si$, 632.0292; found, 632.0283.

The following compounds were prepared in like manner to the procedure outlined in Example 78:

trans-2-chloro-5-(2,2-dichloro-3-(4-chloro-3-((trimethylsilyl)ethynyl)phenyl)cyclopropane-1-carboxamido)-N-(4-fluorophenyl)benzamide (C349)

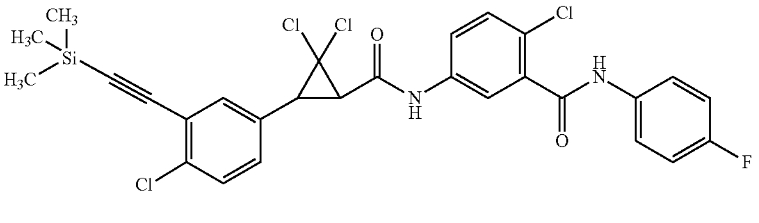 [SMILES: C[Si](C)(C)C#Cc1cc(C2C(C(=O)Nc3ccc(Cl)c(C(=O)Nc4ccc(F)cc4)c3)C2(Cl)Cl)ccc1Cl]

Isolated as a brown foam (0.1243 g, 76%); $^1$H NMR (400 MHz, Acetone-$d_6$) S 10.15 (s, 1H), 9.64 (s, 1H), 7.99 (d, J=2.6 Hz, 1H), 7.85 (ddd, J=9.1, 4.9, 1.5 Hz, 2H), 7.80 (dd, J=8.8, 2.6 Hz, 1H), 7.60-7.57 (m, 1H), 7.55 (d, J=8.3 Hz, 1H), 7.51-7.45 (m, 2H), 7.20-7.12 (m, 2H), 3.64-3.58 (m, 1H), 3.36 (d, J=8.3 Hz, 1H), 0.26 (s, 9H); $^{19}$F NMR (376 MHz, Acetone-$d_6$) δ −120.05; IR (thin film) 1655, 1588, 1543, 1509, 1473 $cm^{-1}$; HRMS-ESI (m/z) $[M+H]^+$ calcd for $C_{28}H_{24}Cl_4FN_2O_2Si$, 607.034; found, 607.0337.

Example 79: Preparation of 2-chloro-N-(2-cyano-4-fluorophenyl)-5-(trans-2,2-dichloro-3-(3-chloro-4-ethynylphenyl)cyclopropane-1-carboxamido)benzamide (F401)

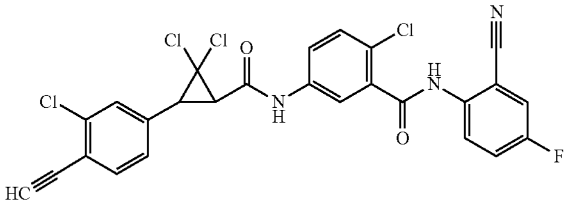 [SMILES: C#Cc1ccc(C2C(C(=O)Nc3ccc(Cl)c(C(=O)Nc4ccc(F)cc4C#N)c3)C2(Cl)Cl)cc1Cl]

To a stirred solution of 2-chloro-N-(2-cyano-4-fluorophenyl)-5-(trans-2,2-dichloro-3-(3-chloro-4-((trimethylsilyl)ethynyl)phenyl)cyclopropane-1-carboxamido)benzamide (C348) (40 mg, 0.063 mmol) in dichloromethane (0.63 mL) and methanol (0.2 mL) was added potassium fluoride (33 mg, 0.567 mmol). The reaction mixture was stirred at room temperature for 3 days. The reaction mixture was directly loaded onto a prepacked Celite® cartridge. Purification by flash column chromatography provided the title compound as a white foam (0.021 g, 56%).

The following compounds were prepared in like manner to the procedure outlined in Example 79:

2-Chloro-5-(trans-2,2-dichloro-3-(4-chloro-3-ethynylphenyl)cyclopropane-1-carboxamido)-N-(4-fluorophenyl)benzamide (F410)

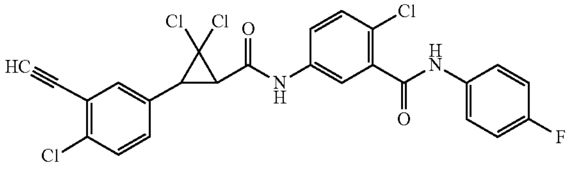 [SMILES: C#Cc1cc(C2C(C(=O)Nc3ccc(Cl)c(C(=O)Nc4ccc(F)cc4)c3)C2(Cl)Cl)ccc1Cl]

Isolated as an orange foam (0.063 g, 85%).

Example 80: Preparation of trans-2-chloro-5-(2,2-dichloro-3-(3,5-dichlorophenyl)cyclopropane-1-carboxamido)-N-(4-((2,2,2-trifluoroethyl)sulfonyl)phenyl)benzamide (PF17) and trans-2-Chloro-5-(2,2-dichloro-3-(3,5-dichlorophenyl)cyclopropane-1-carboxamido)-N-(4-((2,2,2-trifluoroethyl)sulfinyl)phenyl)benzamide (PF18)

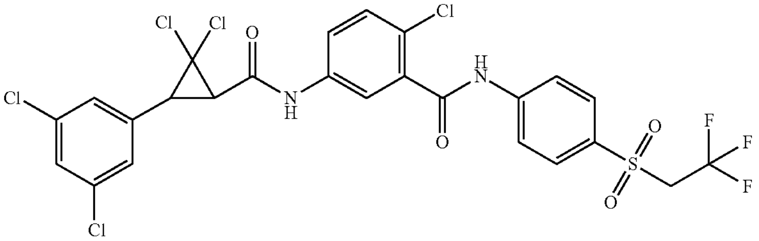

PF17

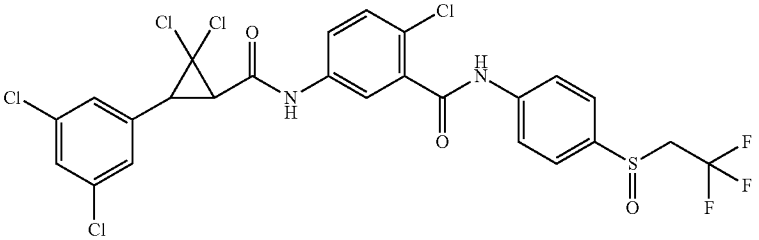

PF18

To a solution of trans-2-chloro-5-((2,2-dichloro-3-(3,5-dichlorophenyl)cyclopropane-1-carboxamido)-N-(4-((2,2,2-trifluoroethyl)thio)phenyl)benzamide (PF10) (0.224 g, 0.349 mmol) in dichloromethane (10 mL) was added meta-chloroperoxybenzoic acid (0.117 g, 0.523 mmol). The reaction mixture was stirred at room temperature for two hours and then diluted with ethyl acetate. The mixture was washed twice with saturated aqueous sodium bicarbonate solution. The organic layer was poured through a phase separator and Celite® was added. The mixture was concentrated under reduced pressure to give a dry powder. Purification of the powder by flash column chromatography using 0-60% ethyl acetate/hexanes as eluent afforded the title compounds: PF17 isolated as a white solid (0.137 g, 58%); PF18 isolated as a white solid (0.068 g, 30%).

The following compounds were prepared in like manner to the procedure outlined in Example 80:

trans-2-Chloro-5-(2,2-dichloro-3-(3,5-dichlorophenyl)cyclopropane-1-carboxamido)-N-(4-((trifluoromethyl)sulfonyl)phenyl)benzamide (PF19)

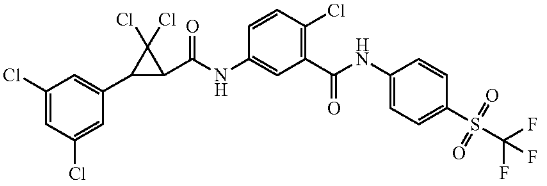 [SMILES: O=C(Nc1ccc(S(=O)(=O)C(F)(F)F)cc1)c1cc(NC(=O)C2C(c3cc(Cl)cc(Cl)c3)C2(Cl)Cl)ccc1Cl]

Isolated as a white solid (0.084 g, 39%).

trans-2-Chloro-5-(2,2-dichloro-3-(3,5-dichlorophenyl)cyclopropane-1-carboxamido)-N-(4-((trifluoromethyl)sulfinyl)phenyl)benzamide (PF20)

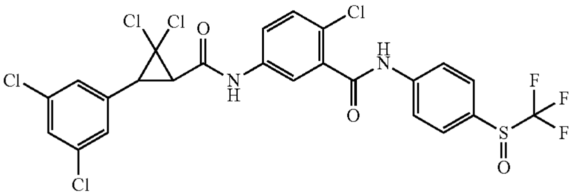 [SMILES: O=C(Nc1ccc(S(=O)C(F)(F)F)cc1)c1cc(NC(=O)C2C(c3cc(Cl)cc(Cl)c3)C2(Cl)Cl)ccc1Cl]

Isolated as a white solid (0.077 g, 37%).

Example 81: Preparation of 2-chloro-N-(3,5-difluoropyridin-2-yl)-5-nitrobenzamide (C350)

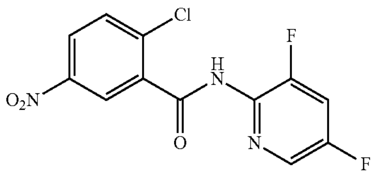

To a solution of 2-chloro-5-nitrobenzoic acid (2.00 g, 9.92 mmol) and 3,5-difluoropyridin-2-amine (1.29 g, 9.92 mmol) in ethyl acetate (50 mL) were added sequentially pyridine (1.6 mL, 19.9 mmol) and 2,4,6-tripropyl-1,3,5,2,4,6-trioxatriphosphinane 2,4,6-trioxide (T3P®) as a 50% solution in ethyl acetate (9.47 g, 14.88 mmol). The reaction mixture was stirred at room temperature for 16 hours. The reaction mixture was the washed with aqueous hydrochloric acid (1 N), saturated aqueous sodium bicarbonate, and brine. The organic layer was dried over magnesium sulfate, filtered and concentrated. The residue was dissolved in ethyl acetate, and Celite® was added to the solution. The solvent was removed under vacuum. Purification by flash column chromatography using 0-30% ethyl acetate/hexanes as eluent afforded the title compound as a white solid (1.97 g, 63%): $^1$H NMR (400 MHz, DMSO-$d_6$) δ 11.20 (s, 1H), 8.51-8.28 (m, 3H), 8.12 (ddd, J=10.7, 8.6, 2.6 Hz, 1H), 7.90 (d, J=8.7 Hz, 1H); $^{19}$F NMR (376 MHz, DMSO-$d_6$) δ −117.71, −126.11; ESIMS m/z 314 ([M+H]$^+$).

Example 82: Preparation of N-(4-fluorophenyl)-5-nitro-2-vinylbenzamide (C351)

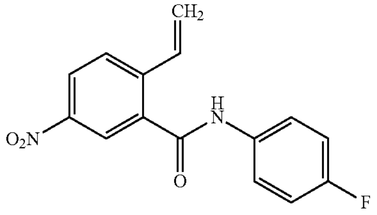

To a suspension of 4,4,5,5-tetramethyl-2-vinyl-1,3,2-dioxaborolane (0.300 mL, 1.769 mmol) in toluene (3.93 mL) were added 2-bromo-N-(4-fluorophenyl)-5-nitrobenzamide (C152) (0.200 g, 0.590 mmol) followed by ethanol (2 mL) and 2 M potassium carbonate (0.590 mL, 1.180 mmol). The solution was degassed by applying vacuum and then purging with nitrogen (3 times). To the reaction mixture was added tetrakis(triphenylphosphine)palladium(0) (0.034 g, 0.029 mmol), and the reaction mixture was heated at 110° C. under nitrogen for 18 hours. Water (5 mL) was added, and the mixture was extracted with ethyl acetate. The organic phase was dried over magnesium sulfate, and concentrated. Purification by chromatography (0-100% ethyl acetate/hexanes) gave N-(4-fluorophenyl)-5-nitro-2-vinylbenzamide (0.060 g, 33.8% yield) as a yellow solid: mp 158-160° C., $^1$H NMR (400 MHz, $CDCl_3$) δ 8.40 (d, J=2.3 Hz, 1H), 8.26 (dd, J=8.6, 2.3 Hz, 1H), 7.77 (d, J=8.7 Hz, 1H), 7.69 (s, 1H), 7.64-7.53 (m, 2H), 7.19-7.02 (m, 3H), 5.94 (d, J=17.4 Hz, 1H), 5.62 (d, J=11.1 Hz, 1H); ESIMS m/z 287 [(M+H)+].

Example 83: Preparation of tert-butyl (4-(5-amino-2-chloro-N-methylbenzamido)-3-methylphenyl)(methyl)carbamate (C352)

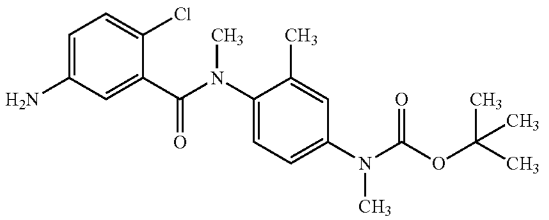

To a solution of tert-butyl (4-(2-chloro-N-methyl-5-nitrobenzamido)-3-methylphenyl)(methyl)carbamate (C297) (0.207 g, 0.477 mmol) in ethyl acetate (10 mL) was added 5% palladium on carbon (0.051 g, 0.024 mmol). The suspension was placed under an atmosphere of hydrogen (balloon) and stirred vigorously for 16 hours at room temperature. The suspension was filtered through a pad of Celite® and washed with ethyl acetate. The filtrate was concentrated, and the residue dried under a stream of nitrogen to afford the title compound as a yellow oil (0.200 g, 93%): $^1$H NMR (300 MHz, DMSO-$d_6$) δ rotamers 7.28-7.09 (m, 3H), 6.96 (dd, J=8.4, 2.7 Hz, 0.5H), 6.85 (d, J=8.5 Hz, 0.5H), 6.67-6.60 (m, 1H), 6.42-6.28 (m, 1H), 5.50 (s, 1H), 5.21 (s, 1H), 3.20 (d, J=2.8 Hz, 3H), 3.09 (s, 1.5H), 3.03 (s, 1.5H), 2.25 (d, J=6.3 Hz, 3H), 1.42 (s, 4H), 1.32 (s, 5H); IR (thin film) 3351, 2927, 1689, 1641, 1602 cm$^{-1}$; HRMS-ESI (m/z) [M+H]$^+$ calcd for $C_{21}H_{26}ClN_3O_3$, 404.1735; found, 404.1737.

The following compounds were prepared in like manner to the procedure outlined in Example 83:

N-(4-Acetamido-2-fluorophenyl)-5-amino-2-chlorobenzamide (C353)

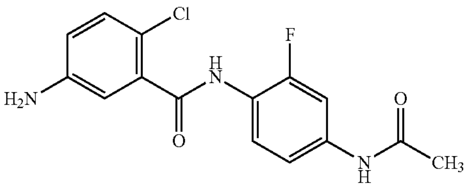

Isolated as a white solid (0.654 g, 93%): $^1$H NMR (400 MHz, DMSO-$d_6$) δ 10.14 (s, 1H), 10.01 (s, 1H), 7.67 (dd, J=13.0, 2.3 Hz, 1H), 7.55 (t, J=8.7 Hz, 1H), 7.28-7.21 (m, 1H), 7.11 (d, J=8.6 Hz, 1H), 6.71 (d, J=2.7 Hz, 1H), 6.63 (dd, J=8.6, 2.8 Hz, 1H), 5.46 (s, 2H), 2.05 (s, 3H); $^{19}$F NMR (376 MHz, DMSO) δ −120.31; ESIMS m/z 322 ([M+H]$^+$).

5-Amino-2-chloro-N-(4-fluoro-2-methylphenyl)-N-methylbenzamide (C354)

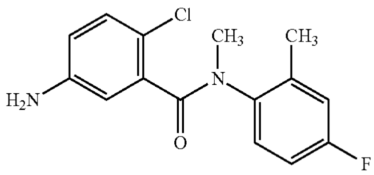

Isolated as a white solid (0.230 g, 46%): $^1$H NMR (400 MHz, DMSO-$d_6$) rotamers δ 7.27-6.82 (m, 4H), 6.67-6.57 (m, 1H), 6.35 (dt, J=7.2, 2.7 Hz, 1H), 5.49 (s, 1H), 5.22 (s, 1H), 3.19 (s, 2H), 3.03 (s, 1H), 2.28 (s, 2H), 2.26 (s, 1H); $^{19}$F NMR (376 MHz, DMSO-$d_6$) rotamers δ −114.39, −115.17; ESIMS m/z 293 ([M+H]$^+$).

N-(4-Acetamido-2-methylphenyl)-5-amino-2-chlorobenzamide (C355)

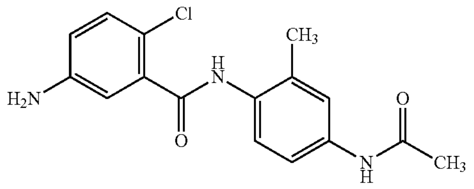

Isolated as a white solid (0.125 g, 40%): $^1$H NMR (400 MHz, DMSO-$d_6$) δ 9.88 (s, 1H), 9.71 (s, 1H), 7.46 (d, J=2.3 Hz, 1H), 7.38 (dd, J=8.5, 2.5 Hz, 1H), 7.23 (d, J=8.5 Hz, 1H), 7.11 (d, J=8.6 Hz, 1H), 6.73 (d, J=2.7 Hz, 1H), 6.62 (dd, J=8.6, 2.7 Hz, 1H), 5.45 (s, 2H), 2.23 (s, 3H), 2.03 (s, 3H); IR (thin film) 3245, 2358, 1652, 1506 cm$^{-1}$; ESIMS m/z 318 ([M+H]$^+$).

tert-Butyl (4-(5-amino-2-chlorobenzamido)-3-methylphenyl)(methyl)carbamate (C356)

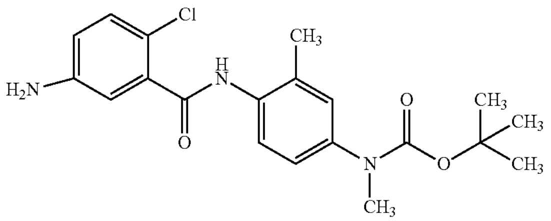 [SMILES: Cc1cc(N(C)C(=O)OC(C)(C)C)ccc1NC(=O)c1cc(N)ccc1Cl]

Isolated as a brown foam (1.60 g, 86%): $^1$H NMR (400 MHz, DMSO-$d_6$) δ 9.80 (s, 1H), 7.31 (d, J=8.5 Hz, 1H), 7.18-7.07 (m, 3H), 6.75 (d, J=2.7 Hz, 1H), 6.64 (dd, J=8.6, 2.7 Hz, 1H), 5.52 (s, 2H), 3.17 (s, 3H), 2.26 (s, 3H), 1.40 (s, 9H); $^{13}$C NMR (101 MHz, DMSO-$d_6$) δ 165.71, 153.74, 147.60, 140.98, 137.16, 133.26, 133.03, 129.80, 127.01, 125.90, 122.96, 115.86, 115.30, 113.65, 79.47, 37.08, 27.97, 17.95; ESIMS m/z 388 ([M−H]$^-$).

tert-Butyl (4-(5-amino-2-chlorobenzamido)-3-methylphenyl)carbamate (C357)

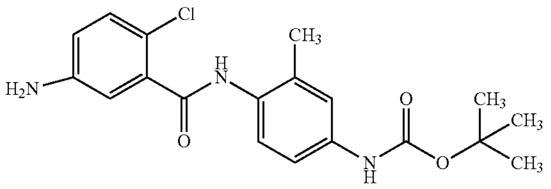 [SMILES: Cc1cc(NC(=O)OC(C)(C)C)ccc1NC(=O)c1cc(N)ccc1Cl]

Isolated as a brown foam (2.09 g, 92%): $^1$H NMR (400 MHz, DMSO-$d_6$) δ 9.68 (s, 1H), 9.28 (s, 1H), 7.35 (d, J=2.2 Hz, 1H), 7.26 (dd, J=8.6, 2.4 Hz, 1H), 7.18 (d, J=8.6 Hz, 1H), 7.12 (d, J=8.6 Hz, 1H), 6.75 (d, J=2.7 Hz, 1H), 6.64 (dd, J=8.6, 2.7 Hz, 1H), 5.64 (s, 2H), 2.21 (s, 3H), 1.48 (s, 9H); $^{13}$C NMR (101 MHz, DMSO-$d_6$) δ 165.69, 152.77, 147.30, 137.32, 137.27, 133.57, 130.14, 129.79, 126.41, 119.77, 115.93, 115.55, 113.84, 78.91, 54.86, 28.13, 18.21; ESIMS m/z 374 ([M−H]$^-$).

5-Amino-2-chloro-N-(3,5-difluoropyridin-2-yl)benzamide (C358)

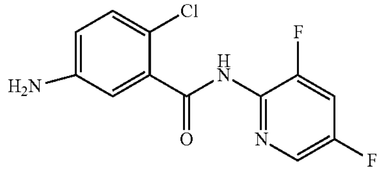 [SMILES: Nc1ccc(Cl)c(C(=O)Nc2ncc(F)cc2F)c1]

Isolated as a white solid (1.78 g, 85%): $^1$H NMR (400 MHz, DMSO-$d_6$) δ 10.71 (s, 1H), 8.38 (d, J=2.5 Hz, 1H), 8.06 (ddd, J=9.6, 8.5, 2.6 Hz, 1H), 7.12 (d, J=8.6 Hz, 1H), 6.74 (d, J=2.7 Hz, 1H), 6.65 (dd, J=8.6, 2.7 Hz, 1H), 5.49 (s, 2H); $^{19}$F NMR (376 MHz, DMSO-$d_6$) δ −118.04, −126.68 (d, J=6.2 Hz); ESIMS m/z 284 ([M+H]').

tert-Butyl-N-((tert-butoxy)carbonyl)-N-(3-(5-amino-2-chlorobenzamido)-2,6-difluorophenyl)carbamate (C359)

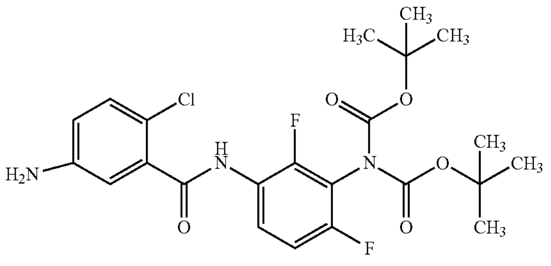

Isolated as a white solid (2.89 g, 59%): $^1$H NMR (400 MHz, DMSO-$d_6$) δ 10.28 (s, 1H), 7.67 (td, J=8.8, 5.8 Hz, 1H), 7.24 (td, J=9.3, 1.7 Hz, 1H), 7.13 (d, J=8.6 Hz, 1H), 6.73 (d, J=2.7 Hz, 1H), 6.65 (dd, J=8.6, 2.8 Hz, 1H), 5.48 (s, 2H), 1.40 (s, 18H); $^{19}$F NMR (376 MHz, DMSO-$d_6$) δ −123.86, −126.24; ESIMS m/z 496 ([M−H]$^-$).

Example 84: Preparation of 4-chloro-3-((4-fluorophenyl)carbamoyl)-N-methylbenzenaminium chloride (C360)

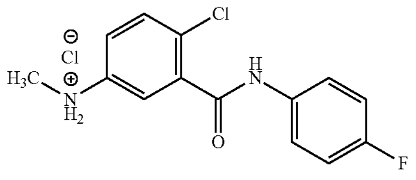 [SMILES: C[NH2+]c1ccc(Cl)c(C(=O)Nc2ccc(F)cc2)c1 ; Cl]

To a solution of tert-butyl (4-chloro-3-((4-fluorophenyl) carbamoyl)phenyl) (methyl)carbamate (C276) (0.360 g, 0.950 mmol) in dichloromethane (5 mL) was added a 4 M solution of hydrogen chloride in dioxane (1.18 mL, 4.75 mmol), and the reaction mixture was stirred at room temperature overnight. The reaction mixture was concentrated under reduced pressure to afford the title compound as a white solid (0.314 g, 100%): $^{1}H$ NMR (400 MHz, DMSO-$d_6$) δ 10.50 (s, 1H), 7.79-7.70 (m, 2H), 7.31 (d, J=8.6 Hz, 1H), 7.23-7.13 (m, 2H), 6.91-6.82 (m, 2H), 3.17 (s, 1H), 2.74 (s, 3H); $^{19}F$ NMR (376 MHz, DMSO-$d_6$) δ −118.78; ESIMS m/z 279 ($[M+H]^+$).

Example 85: Preparation of tert-butyl-N-((tert-butoxyl)carbonyl)-N-(5-(5-amino-2-chlorobenzamido)-2,4-difluorophenyl)carbamate (C361)

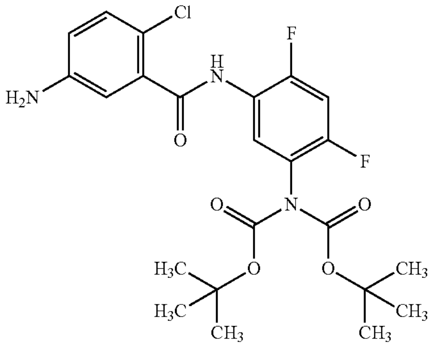 [SMILES: CC(C)(C)OC(=O)N(C(=O)OC(C)(C)C)c1cc(NC(=O)c2cc(N)ccc2Cl)c(F)cc1F]

To a vial containing tert-butyl-N-((tert-butoxy)carbonyl)-N-(5-amino-2,4-difluorophenyl)carbamate (C398) (0.4 g, 1.16 mmol) were added 2-chloro-5-nitrobenzoic acid (0.23 g, 1.16 mmol), 4-dimethylaminopyridine (0.15 g, 1.28 mmol), 1-ethyl-3-(3-dimethylaminopropyl)carbodiimide (0.33 g, 1.74 mmol), and dichloromethane (6 mL). The reaction mixture was stirred at room temperature for 18 h then was directly loaded onto a prepacked Celite® cartridge and flushed through a silica gel column with ethyl acetate/hexanes. The resulting yellow foam was dissolved in ethyl acetate (2 mL) and 10% palladium on carbon (10 mg, 0.009 mmol) was added. The slurry was stirred under an atmosphere of hydrogen gas (balloon) for 7 hours. The slurry was filtered through a pad of Celite® with ethyl acetate and concentrated. Purification by flash column chromatography gave the title compound as a white foam (0.1479 g, 25%): 1H NMR (400 MHz, DMSO-$d_6$) δ 10.27 (s, 1H), 7.67 (t, J=8.1 Hz, 1H), 7.50 (t, J=10.1 Hz, 1H), 7.12 (d, J=8.6 Hz, 1H), 6.73 (d, J=2.7 Hz, 1H), 6.65 (dd, J=8.6, 2.7 Hz, 1H), 5.48 (s, 2H), 1.40 (s, 18H); $^{19}F$ NMR (376 MHz, DMSO-$d_6$) δ −117.30 (d, J=6.4 Hz), −122.18 (d, J=6.4 Hz); ESIMS m/z 495.6 $[(M-H)^-]$.

Example 86: Preparation of methyl 5-((tert-butoxycarbonyl)amino)-2-chlorobenzoate (C362)

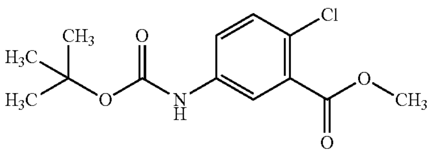 [SMILES: COC(=O)c1cc(NC(=O)OC(C)(C)C)ccc1Cl]

To a solution of methyl 5-amino-2-chlorobenzoate (1.00 g, 5.39 mmol) in dichloromethane (20 mL) was added di-tert-butyl dicarbonate (1.293 g, 5.93 mmol). The reaction mixture was stirred for 72 hours at room temperature. Additional di-tert-butyl dicarbonate (0.600 g, 2.75 mmol) was added, and the reaction mixture was allowed to stir for 16 hours. The reaction mixture was washed with aqueous hydrochloric acid (1 N), and the organic layer was concentrated. Purification of the residue by flash column chromatography using 0-30% ethyl acetate/hexane as eluent afforded the title compound as a colorless oil (0.749 g, 49%): $^{1}H$ NMR (400 MHz, $CDCl_3$) δ 7.85 (d, J=2.8 Hz, 1H), 7.49 (dd, J=8.7, 2.8 Hz, 1H), 7.35 (d, J=8.7 Hz, 1H), 6.64 (s, 1H), 3.92 (s, 3H), 1.52 (s, 9H); $^{13}C$ NMR (101 MHz, $CDCl_3$) δ 165.82, 152.38, 137.15, 131.45, 130.25, 127.18, 122.35, 120.91, 81.21, 52.46, 28.26; HRMS-ESI (m/z) $[M+H]^+$ calcd for $C_{13}H_{16}ClNO_4$, 285.0768; found, 285.0772.

Example 87: Preparation of methyl 5-((tert-butoxycarbonyl)(methyl)amino)-2-chlorobenzoate (C363)

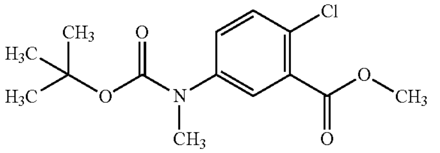 [SMILES: COC(=O)c1cc(N(C)C(=O)OC(C)(C)C)ccc1Cl]

To a solution of methyl 5-((tert-butoxycarbonyl)amino)-2-chlorobenzoate (C362) (0.350 g, 1.225 mmol) in dry N,N-dimethylformamide (6 mL) cooled in an ice bath was added sodium hydride (60% oil immersion, 0.068 g, 1.715 mmol). The slurry was stirred for 30 minutes before iodomethane (0.435 g, 3.06 mmol) was added. The reaction mixture was stirred overnight at room temperature. The reaction mixture was quenched with water and diluted with ethyl acetate. The phases were separated, and the organic layer was washed four times with 1:1 brine/water. The organic layer was poured through a phase separator to dry and concentrated under reduced pressure to afford the title compound as a yellow oil (0.340 g, 93%): $^{1}H$ NMR (300 MHz, $CDCl_3$) δ 7.76-7.71 (m, 1H), 7.39 (dd, J=8.7, 0.5 Hz, 1H), 7.33 (dd, J=8.6, 2.6 Hz, 1H), 3.93 (s, 3H), 3.26 (s, 3H), 1.46 (s, 9H); IR (thin film) 2975, 1737. 1702, 1479 $cm^{-1}$; HRMS-ESI (m/z) $[M+H]^+$ calcd for $C_{14}H_{18}ClNO_4$, 300.0997; found, 300.0994.

Example 88: Preparation of 5-((tert-butoxycarbonyl)(methyl)amino)-2-chlorobenzoic acid (C364)

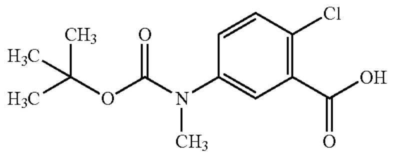 [SMILES: CN(C(=O)OC(C)(C)C)c1ccc(Cl)c(C(=O)O)c1]

To a solution of methyl 5-((tert-butoxycarbonyl)(methyl)amino)-2-chlorobenzoate (C363) (0.340 g, 1.134 mmol) in tetrahydrofuran (3.8 mL) and water (1.9 mL) was added lithium hydroxide (0.109 g, 4.54 mmol). The reaction mixture was stirred vigorously for six hours at room temperature. The reaction mixture was then diluted with ethyl acetate and washed twice with hydrochloric acid (1 N). The organic layer was then washed with brine, poured through a phase separator, and concentrated under reduced pressure to afford the title compound as a white solid (0.328 g, 100%): $^{1}H$ NMR (400 MHz, DMSO-$d_6$) δ 13.54 (s, 1H), 7.67 (d, J=2.6 Hz, 1H), 7.48 (d, J=8.6 Hz, 1H), 7.43 (dd, J=8.7, 2.7 Hz, 1H), 3.19 (s, 3H), 1.40 (s, 9H); $^{13}C$ NMR (101 MHz, DMSO-$d_6$) δ 153.30, 142.16, 130.47, 128.65, 127.37, 126.93, 80.16, 36.54, 27.83; ESIMS m/z 284 ($[M-H]^-$).

Example 89: Preparation of tert-butyl (3-fluoro-4-nitrophenyl)carbamate (C365) and tert-butyl-N-((tert-butoxy)carbonyl)-N-(3-fluoro-4-nitrophenyl) carbamate (C366)

C365

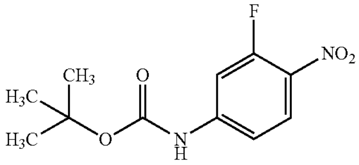

C366

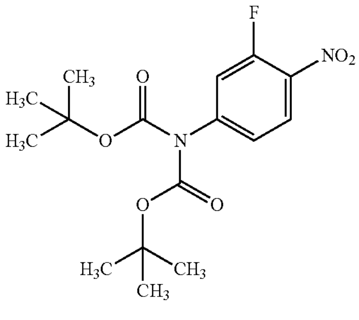

To a solution of 3-fluoro-4-nitroaniline (0.500 g, 3.20 mmol) in dichloromethane (16.0 mL) was added di-tert-butyl dicarbonate (0.769 g, 3.52 mmol) followed by 4-dimethylaminopyridine (0.039 g, 0.320 mmol). The reaction mixture was stirred for 72 hours at room temperature. The reaction mixture was quenched with water and poured through a phase separator. The organic layer was concentrated, and the residue was purified by flash column chromatography using 0-20% ethyl acetate/hexanes as eluent to afford the title compounds. (C366) was isolated as a yellow solid (0.282 g, 25%): 1H NMR (400 MHz, $CDCl_3$) δ 8.09 (dd, J=8.8, 8.1 Hz, 1H), 7.15 (dd, J=11.3, 2.2 Hz, 1H), 7.10 (ddd, J=8.8, 2.2, 1.2 Hz, 1H), 1.46 (s, 18H); $^{19}F$ NMR (376 MHz, $CDCl_3$) δ −115.44; ESIMS m/z 379 ($[M+Na]^+$). (C365) was isolated as a white solid (0.317 g, 39%): $^{1}H$ NMR (400 MHz, $CDCl_3$) δ 8.05 (dd, J=9.1, 8.3 Hz, 1H), 7.61 (dd, J=13.4, 2.4 Hz, 1H), 7.06 (ddd, J=9.2, 2.4, 1.1 Hz, 1H), 6.84 (s, 1H), 1.54 (s, 9H); $^{19}F$ NMR (376 MHz, $CDCl_3$) δ −113.29; ESIMS m/z 255 ($[M-H]^-$).

The following compounds were prepared in like manner to the procedure outlined in Example 89:

tert-Butyl-N-((tert-butoxy)carbonyl)-N-(2-fluoro-4-nitrophenyl)carbamate (C367)

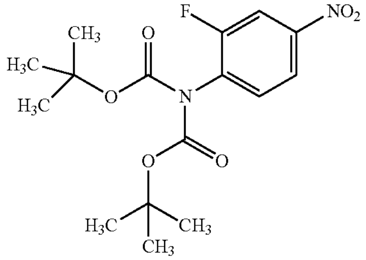 [SMILES: CC(C)(C)OC(=O)N(C(=O)OC(C)(C)C)c1ccc([N+](=O)[O-])cc1F]

Isolated as a yellow solid (0.426 g, 100%): $^{1}H$ NMR (400 MHz, $CDCl_3$) δ 8.06 (ddd, J=8.6, 2.5, 1.2 Hz, 1H), 8.02 (dd, J=9.2, 2.4 Hz, 1H), 7.39 (dd, J=8.7, 7.4 Hz, 1H), 1.43 (s, 18H); $^{19}F$ NMR (376 MHz, $CDCl_3$) δ −115.99; ESIMS m/z 379 ($[M+Na]^+$).

tert-Butyl (2-fluoro-4-nitrophenyl)carbamate (C368)

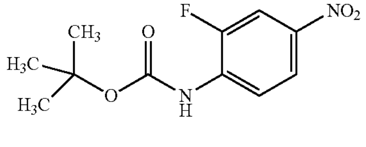 [SMILES: CC(C)(C)OC(=O)Nc1ccc([N+](=O)[O-])cc1F]

Isolated as a yellow solid (0.356 g, 43%): $^{1}H$ NMR (400 MHz, $CDCl_3$) δ 8.37 (dd, J=9.2, 7.9 Hz, 1H), 8.10-8.02 (m, 1H), 7.98 (dd, J=10.9, 2.5 Hz, 1H), 7.00 (s, 1H), 1.55 (s, 9H); $^{19}F$ NMR (376 MHz, $CDCl_3$) δ −129.82; ESIMS m/z 255 ($[M-H]^-$).

tert-Butyl-N-((tert-butoxy)carbonyl)-N-(2,6-difluoro-3-nitrophenyl)carbamate (C369)

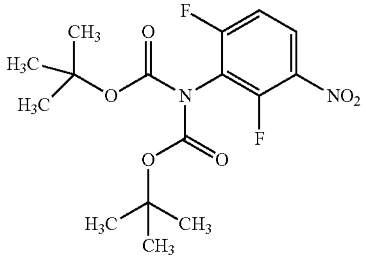 [SMILES: CC(C)(C)OC(=O)N(C(=O)OC(C)(C)C)c1c(F)ccc([N+](=O)[O-])c1F]

Isolated as a white foam (5.2 g, 69%): $^{1}H$ NMR (300 MHz, $CDCl_3$) δ 8.14 (ddd, J=9.2, 8.1, 5.5 Hz, 1H), 7.10

(ddd, J=9.7, 8.0, 2.0 Hz, 1H), 1.45 (s, 18H); $^{19}$F NMR (376 MHz, $CDCl_3$) δ −105.95 (dd, J=10.9, 2.7 Hz), −119.53 (d, J=10.6 Hz); ESIMS m/z 397 ($[M+Na]^+$).

tert-butyl-N-((tert-butoxy)carbonyl)-N-(2,4-difluoro-5-nitrophenyl)carbamate (C370)

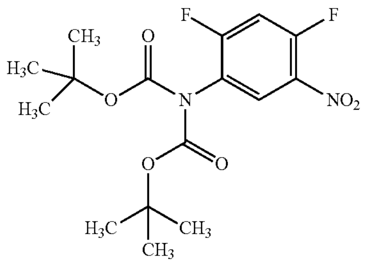 [SMILES: CC(C)(C)OC(=O)N(C(=O)OC(C)(C)C)c1cc([N+](=O)[O-])c(F)cc1F]

Isolated as a white solid (1.2 g, 56%): $^1$H NMR (400 MHz, $CDCl_3$) δ 8.05 (t, J=7.7 Hz, 1H), 7.11 (dd, J=10.2, 8.9 Hz, 1H), 1.46 (s, 18H); $^{19}$F NMR (376 MHz, $CDCl_3$) δ −105.08 (dd, J=14.8, 2.2 Hz), −111.35 (dd, J=14.6, 2.3 Hz); ESIMS m/z 397 ($[M+Na]^+$).

tert-Butyl-N-((tert-butoxy)carbonyl)-N-(2,4-difluoro-6-nitrophenyl)carbamate (C371)

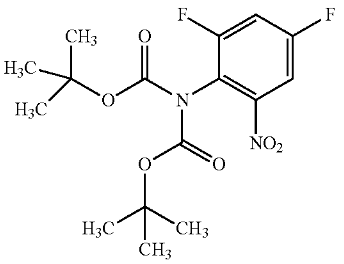

Isolated as a brown solid (2.1 g, 88%): $^1$H NMR (400 MHz, DMSO-$d_6$) δ 8.14-7.99 (m, 2H), 1.36 (s, 18H); $^{19}$F NMR (376 MHz, DMSO-$d_6$) δ −105.41 (d, J=8.4 Hz), −115.11 (d, J=8.4 Hz); ESIMS m/z 374 ($[M+H]^+$).

tert-Butyl-N-((tert-butoxy)carbonyl)-N-(4-fluoro-2-nitrophenyl)carbamate (C372)

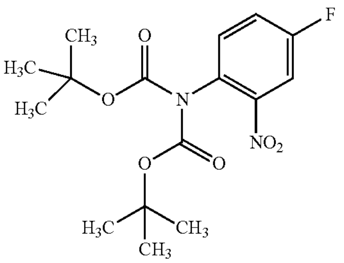 [SMILES: CC(C)(C)OC(=O)N(C(=O)OC(C)(C)C)c1ccc(F)cc1[N+](=O)[O-]]

Isolated as a brown solid (2.2 g, 87%): $^1$H NMR (400 MHz, DMSO-$d_6$) δ 8.10 (dt, J=8.4, 1.6 Hz, 1H), 7.78-7.68 (m, 2H), 1.33 (s, 18H); $^{19}$F NMR (376 MHz, DMSO-$d_6$) δ −109.89; ESIMS m/z 357 ($[M+H]^+$).

tert-Butyl-N-((tert-butoxy)carbonyl)-N-(3,5-difluoro-2-nitrophenyl)carbamate (C373)

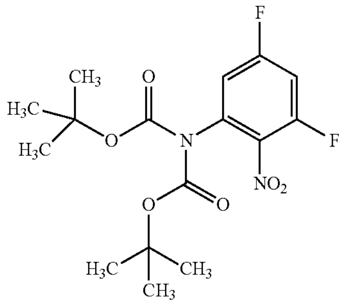 [SMILES: CC(C)(C)OC(=O)N(C(=O)OC(C)(C)C)c1cc(F)cc(F)c1[N+](=O)[O-]]

Isolated as a light yellow oil (1.1 g, 51%): $^1$H NMR (400 MHz, $CDCl_3$) δ 7.04 (ddd, J=9.7, 8.0, 2.7 Hz, 1H), 6.90 (ddd, J=8.2, 2.7, 2.0 Hz, 1H), 1.43 (s, 18H); $^{19}$F NMR (376 MHz, $CDCl_3$) δ −101.60 (d, J=9.1 Hz), −115.67 (d, J=9.4 Hz); ESIMS m/z 273 ($[M-C_5H_9O_2+H]^+$).

tert-Butyl (2-methyl-5-nitrophenyl)carbamate (C374)

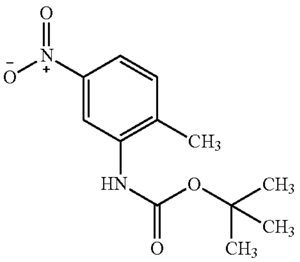 [SMILES: Cc1ccc([N+](=O)[O-])cc1NC(=O)OC(C)(C)C]

Isolated as a pale yellow solid product (0.085 g, 85%); mp 137-145° C.; $^1$H NMR (400 MHz, DMSO-$d_6$) δ 8.93 (s, 1H), 8.39 (d, J=2.5 Hz, 1H), 7.87 (dd, J=8.4, 2.5 Hz, 1H), 7.45 (d, J=8.5 Hz, 1H), 2.33 (s, 3H), 1.50 (s, 9H); ESIMS m/z 251 ($[M-H]^-$).

tert-Butyl (2-fluoro-5-nitrophenyl)carbamate (C375)

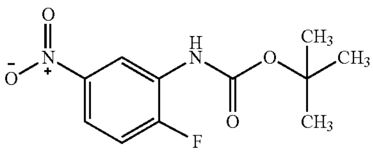 [SMILES: CC(C)(C)OC(=O)Nc1cc([N+](=O)[O-])ccc1F]

Isolated as a white foam (0.32 g, 20%): $^1$H NMR (400 MHz, $CDCl_3$) δ 8.39-8.23 (m, 2H), 7.33 (t, J=8.8 Hz, 1H), 1.47 (s, 9H); $^{19}$F NMR (376 MHz, $CDCl_3$) δ −110.17; ESIMS m/z 256 ($[M-H]^-$).

tert-Butyl-N-((tert-butoxy)carbonyl)-(4-fluoro-3-nitrophenyl)carbamate (C376)

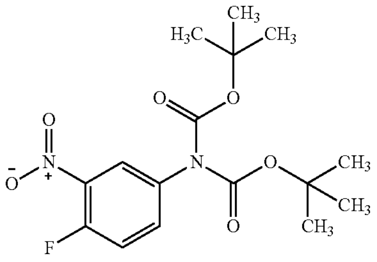 [SMILES: CC(C)(C)OC(=O)N(C(=O)OC(C)(C)C)c1ccc(F)c([N+](=O)[O-])c1]

Isolated as a yellow oil (1.250 g, 43%): $^{1}H$ NMR (400 MHz, DMSO-$d_6$) δ 8.14 (dd, J=6.7, 2.7 Hz, 1H), 7.77 (ddd, J=8.9, 4.0, 2.7 Hz, 1H), 7.63 (dd, J=11.0, 8.9 Hz, 1H), 1.39 (s, 18H); $^{19}F$ NMR (376 MHz, DMSO-$d_6$) δ −120.67; ESIMS m/z 379 ([M+Na]$^+$).

tert-Butyl-N-((tert-butoxy)carbonyl)-(2-fluoro-3-nitrophenyl)carbamate (C377)

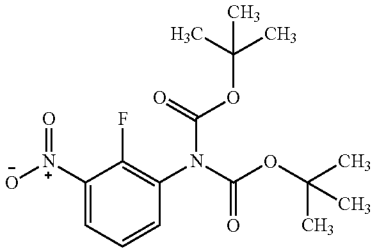 [SMILES: CC(C)(C)OC(=O)N(C(=O)OC(C)(C)C)c1cccc([N+](=O)[O-])c1F]

Isolated as a yellow oil (0.071 g, 3.1%): $^{1}H$ NMR (400 MHz, DMSO-$d_6$) δ 8.17 (ddd, J=8.5, 7.0, 1.7 Hz, 1H), 7.90 (ddd, J=8.3, 6.8, 1.7 Hz, 1H), 7.49 (td, J=8.2, 1.4 Hz, 1H), 1.39 (s, 18H); $^{19}F$ NMR (376 MHz, DMSO-$d_6$) δ −129.40; ESIMS m/z 379 ([M+Na]$^+$).

tert-Butyl-N-((tert-butoxy)carbonyl)-N-(2-fluoro-5-nitrophenyl)carbamate (C378)

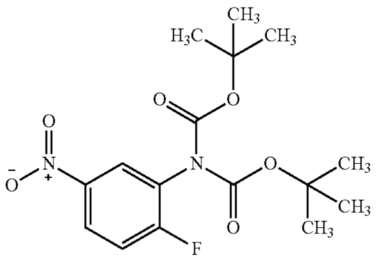 [SMILES: CC(C)(C)OC(=O)N(C(=O)OC(C)(C)C)c1cc([N+](=O)[O-])ccc1F]

Isolated as a white foam (1.50 g, 65%): $^{1}H$ NMR (400 MHz, $CDCl_3$) δ 8.24 (ddd, J=9.0, 4.2, 2.8 Hz, 1H), 8.15 (dd, J=6.5, 2.8 Hz, 1H), 7.33-7.26 (m, 1H), 1.45 (s, 18H); $^{19}F$ NMR (376 MHz, $CDCl_3$) δ −110.17; ESIMS m/z 256 ([M−BOC]$^-$).

tert-Butyl-N-((tert-butoxy)carbonyl)-N-(2,5-difluoro-4-nitrophenyl)carbamate (C379)

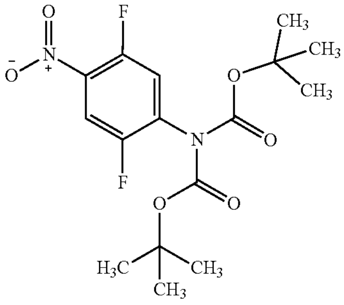 [SMILES: CC(C)(C)OC(=O)N(C(=O)OC(C)(C)C)c1cc(F)c([N+](=O)[O-])cc1F]

Isolated as a white solid (2.1 g, 84%): $^{1}H$ NMR (400 MHz, DMSO-$d_6$) δ8.31 (dd, J=9.4, 6.7 Hz, 1H), 8.02 (dd, J=11.5, 6.4 Hz, 1H), 1.40 (s, 18H); $^{19}F$ NMR (376 MHz, DMSO-$d_6$) δ −122.00 (d, J=16.1 Hz), −123.68 (d, J=15.8 Hz); ESIMS m/z 397 ([M+Na]$^+$).

tert-Butyl-N-((tert-butoxy)carbonyl)-(2,6-difluoro-4-nitrophenyl)carbamate (C380)

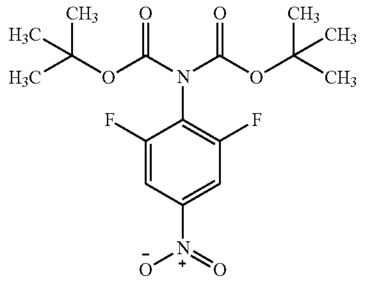 [SMILES: CC(C)(C)OC(=O)N(C(=O)OC(C)(C)C)c1c(F)cc([N+](=O)[O-])cc1F]

Isolated as a light yellow solid (2.0 g, 84%): $^{1}H$ NMR (400 MHz, DMSO-$d_6$) δ 8.33-8.24 (m, 2H), 1.40 (s, 18H); $^{19}F$ NMR (376 MHz, DMSO-$d_6$) δ −115.68; ESIMS m/z 374 ([M−H]$^-$).

tert-Butyl (2-fluoro-5-nitrophenyl)(methyl)carbamate (C381)

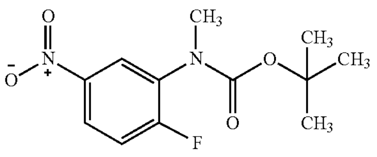 [SMILES: CN(C(=O)OC(C)(C)C)c1cc([N+](=O)[O-])ccc1F]

Isolated as a light yellow foam (0.228 g, 60%): $^{1}H$ NMR (400 MHz, DMSO-$d_6$) δ 8.35 (dd, J=6.7, 2.9 Hz, 1H), 8.22 (ddd, J=9.1, 4.1, 2.9 Hz, 1H), 7.59 (t, J=9.4 Hz, 1H), 3.19 (s, 3H), 1.36 (s, 9H); $^{19}F$ NMR (376 MHz, DMSO-$d_6$) δ −109.93; ESIMS m/z 270 ([M−H]$^-$).

tert-Butyl-methyl(2-methyl-4-nitrophenyl)carbamate (C382)

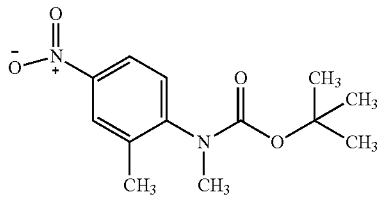 [SMILES: Cc1cc([N+](=O)[O-])ccc1N(C)C(=O)OC(C)(C)C]

Isolated as an off-white solid (0.094 g, 65%): mp 98-101° C.; $^1H$ NMR (500 MHz, $CDCl_3$) δ 8.12 (d, J=2.5 Hz, 1H), 8.05 (dd, J=8.6, 2.6 Hz, 1H), 7.29-7.23 (m, 1H), 3.18 (s, 3H), 2.32 (s, 3H), 1.44 (d, J=86.1 Hz, 9H); $^{13}C$ NMR (126 MHz, $CDCl_3$) δ 154.01, 148.41, 146.25, 137.41, 128.15, 125.81, 122.08, 80.82, 36.55, 28.22, 17.91.

tert-Butyl-methyl(2-methyl-5-nitrophenyl)carbamate (C383)

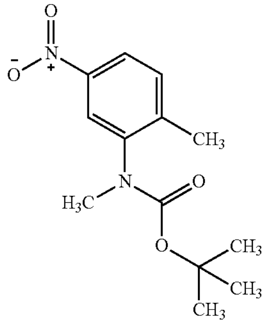 [SMILES: Cc1ccc([N+](=O)[O-])cc1N(C)C(=O)OC(C)(C)C]

Isolated as a yellow solid (0.74 g, 65%): mp 57-60° C.; $^1H$ NMR (500 MHz, $CDCl^3$) δ 8.05 (dd, J=8.5, 2.1 Hz, 1H), 7.99 (s, 1H), 7.39 (d, J=8.4 Hz, 1H), 3.19 (s, 3H), 2.35-2.31 (m, 7H), 1.44 (d, J=94.3 Hz, 9H); 13C NMR (126 MHz, $CDCl^3$) δ 154.24, 146.74, 143.89, 143.29, 131.25, 122.74, 121.99, 99.98, 80.71, 37.48, 36.65, 28.19, 17.96.

Example 90: Preparation of tert-Butyl (3-fluoro-4-nitrophenyl)(methyl)carbamate (C384)

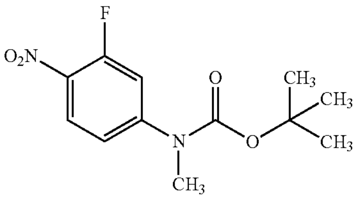 [SMILES: CN(C(=O)OC(C)(C)C)c1ccc([N+](=O)[O-])c(F)c1]

To a solution of tert-butyl (3-fluoro-4-nitrophenyl)carbamate (C365) (0.310 g, 1.210 mmol) in dry N,N-dimethylformamide (6 mL) cooled in an ice bath was added sodium hydride (60% oil dispersion, 0.068 g, 1.694 mmol). The slurry was stirred for 30 minutes before iodomethane (0.189 mL, 3.02 mmol) was added. The reaction mixture was warmed to room temperature and stirred overnight. The reaction mixture was quenched with water and diluted with ethyl acetate. The phases were separated, and the organic layer was washed with 1:1 brine/water four times. The organic layer was poured through a phase separator to dry and then concentrated under reduced pressure to afford the title compound as a yellow oil (0.325 g, 99%): $^1H$ NMR (400 MHz, $CDCl_3$) δ 8.06 (dd, J=9.1, 8.5 Hz, 1H), 7.35 (dd, J=13.3, 2.4 Hz, 1H), 7.24 (ddd, J=9.2, 2.4, 1.2 Hz, 1H), 3.34 (s, 3H), 1.52 (s, 9H); $^{19}F$ NMR (376 MHz, $CDCl_3$) δ −115.17; ESIMS m/z 215 ($[M-C_4H_9+H]^+$).

The following compounds were prepared in like manner to the procedure outlined in Example 90:

tert-Butyl (2-fluoro-4-nitrophenyl)(methyl)carbamate (C385)

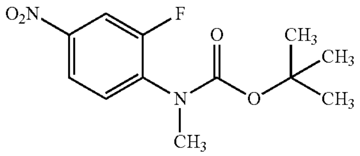 [SMILES: CN(C(=O)OC(C)(C)C)c1ccc([N+](=O)[O-])cc1F]

Isolated as a yellow oil (0.359 g, 100%): $^1H$ NMR (400 MHz, $CDCl_3$) δ 8.15-7.86 (m, 2H), 7.43 (dd, J=8.7, 7.5 Hz, 1H), 3.26 (d, J=1.0 Hz, 3H), 1.44 (s, 9H); $^{19}F$ NMR (376 MHz, $CDCl_3$) δ −114.41; EIMS m/z 270.

tert-Butyl methyl(3-methyl-4-nitrophenyl)carbamate (C386)

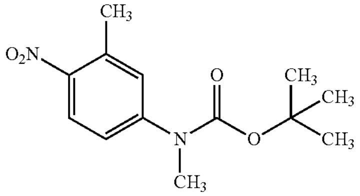 [SMILES: Cc1cc(N(C)C(=O)OC(C)(C)C)ccc1[N+](=O)[O-]]

Isolated as a yellow oil (0.265 g, 100%): $^1H$ NMR (400 MHz, $CDCl_3$) δ 8.01 (dt, J=8.7, 0.9 Hz, 1H), 7.27 (d, J=1.1 Hz, 2H), 7.26-7.24 (m, 1H), 3.31 (s, 3H), 2.62 (s, 3H), 1.50 (s, 9H); $^{13}C$ NMR (101 MHz, $CDCl_3$) δ 153.81, 147.91, 145.00, 134.74, 127.79, 125.46, 122.33, 81.62, 36.75, 28.26, 21.08; ESIMS m/z 211 ($[M-C_4H_9+H]^+$).

tert-Butyl (2-methoxy-5-nitrophenyl)(methyl)carbamate (C387)

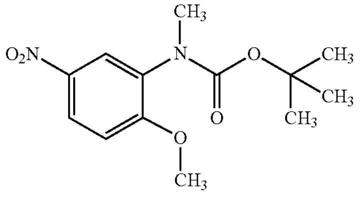 [SMILES: COc1ccc([N+](=O)[O-])cc1N(C)C(=O)OC(C)(C)C]

Isolated as a yellow oil (0.171 g, 100%): $^{1}H$ NMR (300 MHz, $CDCl_3$) δ 8.18 (dd, J=9.1, 2.8 Hz, 1H), 8.09 (s, 1H), 6.98 (d, J=9.1 Hz, 1H), 3.96 (s, 3H), 3.15 (s, 3H), 1.39 (s, 9H); IR (thin film) 2975, 1699, 1519 $cm^{-1}$; ESIMS m/z 183 ($[M-C_5H_9O_2+H]^+$).

tert-Butyl-methyl(2-methyl-4-nitrophenyl)carbamate (C388)

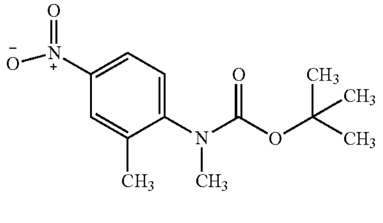 [SMILES: Cc1cc([N+](=O)[O-])ccc1N(C)C(=O)OC(C)(C)C]

Isolated as an off-white solid product (0.094 g, 65%): mp 98-101° C.; $^{1}H$ NMR (500 MHz, $CDCl_3$) δ 8.12 (d, J=2.5 Hz, 1H), 8.05 (dd, J=8.6, 2.6 Hz, 1H), 7.29-7.23 (m, 1H), 3.18 (s, 3H), 2.32 (s, 3H), 1.44 (d, J=86.1 Hz, 9H); $^{13}C$ NMR (126 MHz, $CDCl_3$) δ 154.01, 148.41, 146.25, 137.41, 128.15, 125.81, 122.08, 80.82, 36.55, 28.22, 17.91.

tert-Butyl-methyl(2-methyl-5-nitrophenyl)carbamate (C389)

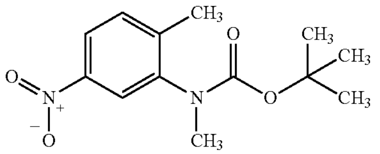

Isolated as a yellow solid (0.74 g, 65%): mp 57-60° C.; $^{1}H$ NMR (500 MHz, $CDCl_3$) δ 8.05 (dd, J=8.5, 2.1 Hz, 1H), 7.99 (s, 1H), 7.39 (d, J=8.4 Hz, 1H), 3.19 (s, 3H), 2.35-2.31 (m, 7H), 1.44 (d, J=94.3 Hz, 9H); $^{13}C$ NMR (126 MHz, $CDCl^3$) δ 154.24, 146.74, 143.89, 143.29, 131.25, 122.74, 121.99, 99.98, 80.71, 37.48, 36.65, 28.19, 17.96.

Example 91: Preparation of tert-butyl (4-amino-3-fluorophenyl)(methyl) carbamate (C390)

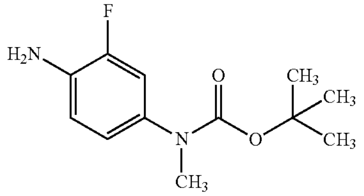

To a solution of tert-butyl (3-fluoro-4-nitrophenyl)(methyl)carbamate (C384) (0.325 g, 1.203 mmol) in ethyl acetate (10 mL) was added 5% palladium on carbon (0.128 g, 0.060 mmol). The reaction mixture was stirred vigorously overnight at room temperature under a balloon of hydrogen. The reaction was filtered through a pad of Celite® and washed with ethyl acetate. The filtrates were concentrated under reduced pressure to afford the title compound as a red oil (0.225 g, 78%): $^{1}H$ NMR (400 MHz, $CDCl_3$) δ 6.89 (d, J=12.2 Hz, 1H), 6.80 (d, J=8.6 Hz, 1H), 6.71 (dd, J=9.7, 8.5 Hz, 1H), 3.67 (s, 2H), 1.43 (s, 9H); $^{19}F$ NMR (376 MHz, $CDCl_3$) δ −133.96; ESIMS m/z 185 ($[M-C_4H_9+H]^+$).

The following compounds were prepared in like manner to the procedure outlined in Example 91:

N-(4-Amino-3-fluorophenyl)acetamide (C391)

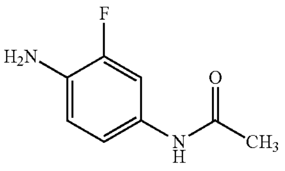

Isolated as a light brown foam (0.460 g, 100%): $^{1}H$ NMR (400 MHz, DMSO-$d_6$) δ 9.68 (s, 1H), 7.38 (dd, J=13.7, 2.3 Hz, 1H), 6.94 (ddd, J=8.5, 2.3, 0.9 Hz, 1H), 6.67 (dd, J=10.1, 8.5 Hz, 1H), 4.85 (s, 2H), 1.97 (s, 3H); $^{19}F$ NMR (376 MHz, DMSO-$d_6$) δ −133.53; ESIMS m/z 169 ($[M+H]^+$).

tert-Butyl-N-((tert-butoxy)carbonyl)-N-(4-amino-2-fluorophenyl)carbamate (C392)

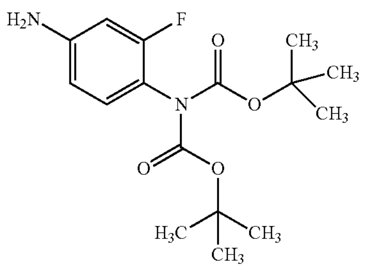

Isolated as a white foam (0.426 g, 100%): $^{1}H$ NMR (400 MHz, $CDCl_3$) δ 6.94-6.85 (m, 1H), 6.44-6.40 (m, 1H), 6.39 (d, J=1.8 Hz, 1H), 3.78 (s, 2H), 1.42 (s, 18H); $^{19}F$ NMR (376 MHz, $CDCl_3$) δ −121.91; ESIMS m/z 327 ($[M+H]^+$).

tert-Butyl-N-((tert-butoxy)carbonyl)-N-(4-amino-3-fluorophenyl)carbamate (C393)

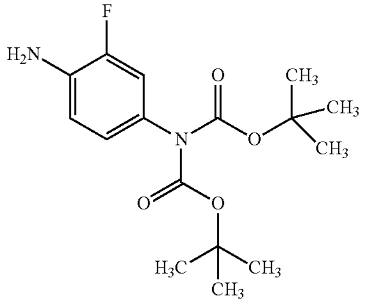 [SMILES: CC(C)(C)OC(=O)N(C(=O)OC(C)(C)C)c1ccc(N)c(F)c1]

Isolated as a white solid (0.290 g, 100%): $^{1}H$ NMR (400 MHz, $CDCl_3$) δ 6.83-6.78 (m, 1H), 6.74-6.71 (m, 2H), 3.75

(s, 2H), 1.43 (s, 18H); $^{19}$F NMR (376 MHz, $CDCl_3$) δ −134.34; ESIMS m/z 327 ($[M+H]^+$).

tert-Butyl (4-amino-2-fluorophenyl)(methyl)carbamate (C394)

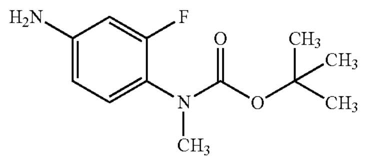

Isolated as a colorless oil (0.339 g, 100%): $^1$H NMR (400 MHz, $CDCl_3$) δ 6.93 (s, 1H), 6.45-6.34 (m, 2H), 3.73 (s, 2H), 3.14 (s, 3H), 1.36 (s, 9H); $^{19}$F NMR (376 MHz, $CDCl_3$) δ −121.26; ESIMS m/z 241 ($[M+H]^+$).

tert-Butyl (4-amino-3-methylphenyl)(methyl)carbamate (C395)

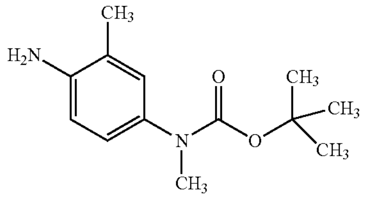 [SMILES: Cc1cc(N(C)C(=O)OC(C)(C)C)ccc1N]

Isolated as a white solid (0.238 g, 100%): $^1$H NMR (400 MHz, DMSO-$d_6$) δ 6.78 (d, J=2.5 Hz, 1H), 6.73 (dd, J=8.3, 2.6 Hz, 1H), 6.53 (d, J=8.3 Hz, 1H), 4.77 (s, 2H), 3.05 (s, 3H), 2.02 (s, 3H), 1.35 (s, 9H); IR (thin film) 3374, 2925, 1680, 1630, 1511 $cm^{-1}$; ESIMS m/z 237 ($[M+H]^+$).

tert-Butyl (5-amino-2-methoxyphenyl)(methyl)carbamate (C396)

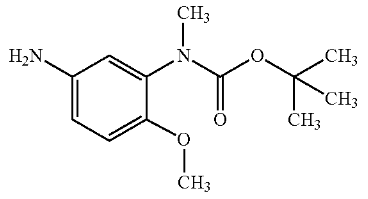

Isolated as a light brown oil (0.150 g, 99%): $^1$H NMR (300 MHz, DMSO-$d_6$) δ 6.74 (d, J=8.5 Hz, 1H), 6.43 (dd, J=8.6, 2.8 Hz, 1H), 6.39 (d, J=2.7 Hz, 1H), 4.67 (s, 2H), 3.65 (s, 3H), 2.96 (s, 3H), 1.29 (s, 9H); IR (thin film) 3351, 2975, 1683, 1630, 1509 $cm^{-1}$; ESIMS m/z 153 ($[M-C_5H_9O_2+H]^+$).

tert-Butyl-N-((tert-butoxy)carbonyl)-N-(3-amino-2,6-difluorophenyl)carbamate (C397)

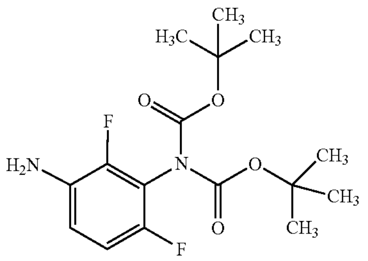 [SMILES: CC(C)(C)OC(=O)N(C(=O)OC(C)(C)C)c1c(F)ccc(N)c1F]

Isolated as a white solid (5.06 g, 100%): $^1$H NMR (400 MHz, DMSO-$d_6$) δ 6.87 (td, J=9.3, 1.7 Hz, 1H), 6.74 (td, J=9.4, 5.7 Hz, 1H), 5.12 (s, 2H), 1.39 (s, 18H); $^{19}$F NMR (376 MHz, DMSO-$d_6$) δ −137.96 (d, J=3.7 Hz), −141.10 (d, J=3.7 Hz); ESIMS m/z 244 ($[M-BOC]^-$).

tert-Butyl-N-((tert-butoxy)carbonyl)-N-(5-amino-2,4-difluorophenyl)carbamate (C398)

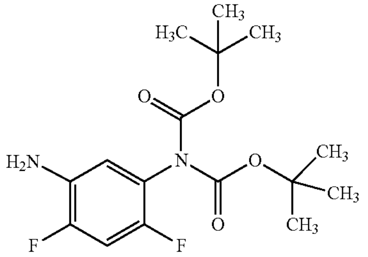 [SMILES: CC(C)(C)OC(=O)N(C(=O)OC(C)(C)C)c1cc(N)c(F)cc1F]

Isolated as a cream colored solid (1.05 g, 88%): $^1$H NMR (400 MHz, $CDCl_3$) δ 6.82 (dd, J=10.5, 9.3 Hz, 1H), 6.60 (dd, J=9.1, 7.5 Hz, 1H), 3.59 (s, 2H), 1.43 (s, 18H); $^{19}$F NMR (376 MHz, $CDCl_3$) δ −131.04 (t, J=2.2 Hz), −131.38 (d, J=2.0 Hz); ESIMS m/z 245 ($[M-C_5H_9O_2+H]^+$).

tert-Butyl-N-((tert-butoxy)carbonyl)-N-(2-amino-4,6-difluorophenyl)carbamate (C399)

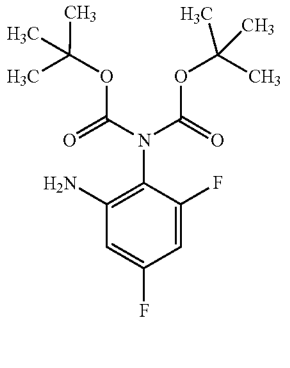

Isolated as a light orange solid (1.3 g, 61%): mp 102-107° C.; $^1$H NMR (300 MHz, DMSO-$d_6$) δ 6.36-6.21 (m, 2H), 5.72 (s, 2H), 1.36 (s, 18H); ESIMS m/z 345 ($[M+H]^+$).

tert-Butyl-N-((tert-butoxy)carbonyl)-N-(2-amino-4-fluorophenyl)carbamate (C400)

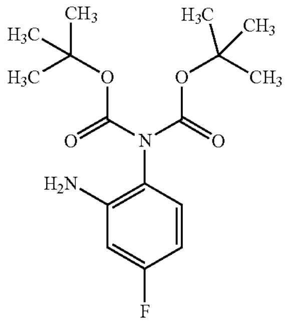 [SMILES: CC(C)(C)OC(=O)N(C(=O)OC(C)(C)C)c1ccc(F)cc1N]

Isolated as an off-white solid (1.8 g, 80%): mp 104-115° C.; $^{1}$H NMR (300 MHz, DMSO-$d_6$) δ 6.94-6.79 (m, 1H), 6.44 (dd, J=11.3, 2.9 Hz, 1H), 6.26 (td, J=8.5, 2.9 Hz, 1H), 5.23 (s, 2H), 1.36 (s, 18H); ESIMS m/z 327 ([M+H]$^+$).

tert-Butyl-N-((tert-butoxy)carbonyl)-N-(2-amino-3,5-difluorophenyl)carbamate (C401)

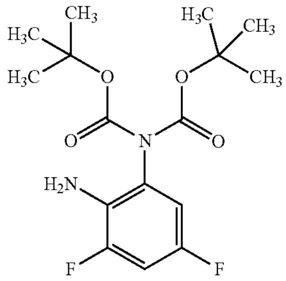 [SMILES: CC(C)(C)OC(=O)N(C(=O)OC(C)(C)C)c1cc(F)cc(F)c1N]

Isolated as a white solid (0.90 g, 98%): $^{1}$H NMR (400 MHz, DMSO-$d_6$) δ 7.07 (ddd, J=11.6, 8.9, 2.9 Hz, 1H), 6.79 (ddd, J=9.3, 2.9, 1.9 Hz, 1H), 4.87 (s, 2H), 1.36 (s, 18H); $^{19}$F NMR (376 MHz, DMSO-$d_6$) δ −128.55, −129.76; ESIMS m/z 245 ([M-$C_5H_9O_2$+H]$^+$).

tert-Butyl (5-amino-2-methylphenyl)carbamate (C402)

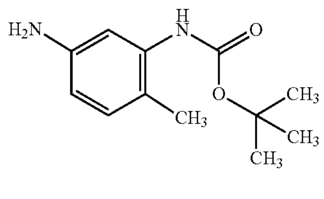 [SMILES: Cc1ccc(N)cc1NC(=O)OC(C)(C)C]

Isolated as a light pink solid (0.06 g, 90%): $^{1}$H NMR (500 MHz, DMSO-$d_6$) δ 8.17 (s, 1H), 6.76 (d, J=8.1 Hz, 1H), 6.61 (d, J=2.4 Hz, 1H), 6.25 (dd, J=8.0, 2.3 Hz, 1H), 4.81 (s, 2H), 2.00 (s, 3H), 1.44 (s, 9H); $^{13}$C NMR (126 MHz, DMSO-$d_6$) δ 153.92, 147.16, 137.23, 130.67, 118.69, 111.13, 78.73, 28.66, 17.35; IR (thin film) 3425, 3314, 2981, 2928, 1695, 1621, 1582, 1531 cm$^{-1}$.

tert-Butyl (4-amino-2-methylphenyl)(methyl)carbamate (C403)

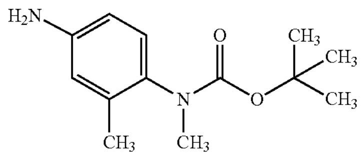 [SMILES: Cc1cc(N)ccc1N(C)C(=O)OC(C)(C)C]

Isolated as a brown gel (0.035 g, 58%): $^{1}$H NMR (500 MHz, DMSO-$d_6$) δ 6.74 (d, J=8.4 Hz, 1H), 6.38 (d, J=2.6 Hz, 1H), 6.34 (dd, J=8.3, 2.7 Hz, 1H), 4.96 (d, J=7.6 Hz, 2H), 2.98 (d, J=19.9 Hz, 3H), 1.98 (d, J=11.3 Hz, 3H), 1.35 (d, J=84.4 Hz, 9H); $^{13}$C NMR (126 MHz, DMSO-$d_6$) δ 155.12, 147.74, 135.12, 131.46, 127.85, 115.69, 112.47, 78.63, 37.53, 28.48, 17.72; IR (thin film) 3357, 2975, 2928, 1677, 1506 cm$^{-1}$.

tert-Butyl (5-amino-2-methylphenyl)(methyl)carbamate (C404)

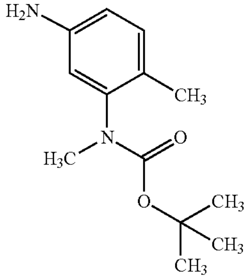 [SMILES: Cc1ccc(N)cc1N(C)C(=O)OC(C)(C)C]

Isolated as a pale brown solid (0.037 g, 77%): $^{1}$H NMR (500 MHz, DMSO-$d_6$) δ 6.86 (d, J=8.1 Hz, 1H), 6.39 (d, J=7.4 Hz, 1H), 6.33 (s, 1H), 4.90 (s, 2H), 2.99 (d, J=17.0 Hz, 3H), 1.95 (d, J=8.1 Hz, 3H), 1.36 (d, J=81.4 Hz, 9H); $^{13}$C NMR (126 MHz, DMSO-$d_6$) δ 154.52, 147.78, 142.83, 130.99, 121.55, 113.50, 112.90, 78.94, 37.15, 28.46, 16.66; IR (thin film) 3461, 3366, 2924, 1664, 1616, 1513 cm$^{-1}$.

tert-Butyl (5-amino-2-fluorophenyl)(methyl)carbamate (C405)

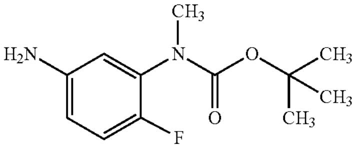 [SMILES: CN(C(=O)OC(C)(C)C)c1cc(N)ccc1F]

Isolated as an off-white solid (0.170 g, 80%): $^{1}$H NMR (300 MHz, DMSO-$d_6$) δ 6.87 (dd, J=10.4, 8.6 Hz, 1H), 6.50-6.36 (m, 2H), 5.00 (s, 2H), 3.04 (s, 3H), 1.34 (s, 9H); $^{19}$F NMR (376 MHz, DMSO-$d_6$) δ −138.52; ESIMS m/z 241 ([M+H]$^+$).

tert-Butyl (4-amino-3-methylphenyl)carbamate (C406)

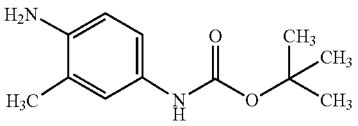 [SMILES: Cc1cc(NC(=O)OC(C)(C)C)ccc1N]

Isolated as a light pink solid (12.4 g, 87%): $^{1}$H NMR (400 MHz, DMSO-$d_6$) δ 8.72 (s, 1H), 7.01 (s, 1H), 6.93 (d, J=8.5 Hz, 1H), 6.49 (d, J=8.4 Hz, 1H), 4.49 (s, 2H), 2.00 (s, 3H), 1.44 (s, 9H); ESIMS m/z 223 ([M+H]$^+$).

tert-Butyl-N-((tert-butoxy)carbonyl (4-amino-2,6-difluorophenyl)carbamate (C407)

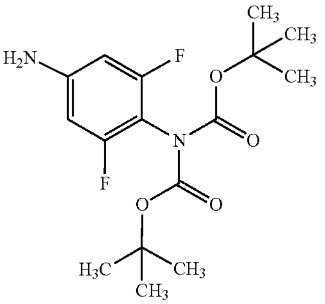 [SMILES: CC(C)(C)OC(=O)N(C(=O)OC(C)(C)C)c1c(F)cc(N)cc1F]

Isolated as an off-white solid (1.5 g, 73%): $^{1}$H NMR (400 MHz, DMSO-$d_6$) δ 6.28-6.18 (m, 2H), 5.83 (s, 2H), 1.37 (s, 18H); $^{19}$F NMR (376 MHz, DMSO-$d_6$) δ −122.91; ESIMS m/z 345 ([M+H]$^+$).

tert-Butyl-N-((tert-butoxy)carbonyl)-(3-amino-2-fluorophenyl)carbamate (C408)

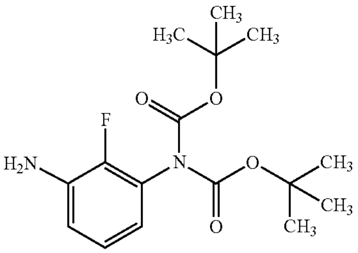 [SMILES: CC(C)(C)OC(=O)N(C(=O)OC(C)(C)C)c1cccc(N)c1F]

Isolated as an light pink solid (0.047 g, 71%): $^{1}$H NMR (400 MHz, DMSO-$d_6$) δ 6.83 (td, J=8.0, 1.3 Hz, 1H), 6.71 (td, J=8.2, 1.7 Hz, 1H), 6.37 (ddd, J=8.2, 6.8, 1.6 Hz, 1H), 5.22 (s, 2H), 1.39 (s, 18H); $^{19}$F NMR (376 MHz, DMSO-$d_6$) δ −144.87; ESIMS m/z 327 ([M+H]$^+$).

tert-Butyl-N-((tert-butoxy)carbonyl)-(3-amino-4-fluorophenyl)carbamate (C409)

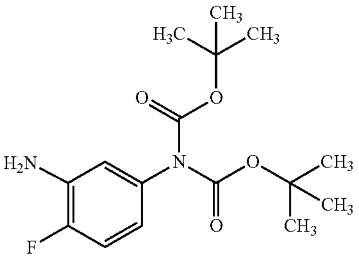 [SMILES: CC(C)(C)OC(=O)N(C(=O)OC(C)(C)C)c1ccc(F)c(N)c1]

Isolated as a light pink solid (1.0 g, 89%): $^{1}$H NMR (400 MHz, DMSO-$d_6$) δ 7.03-6.90 (m, 1H), 6.54 (dd, J=8.1, 2.6 Hz, 1H), 6.29 (ddd, J=8.5, 4.0, 2.7 Hz, 1H), 5.22 (s, 2H), 1.39 (s, 18H); $^{19}$F NMR (376 MHz, DMSO-$d_6$) δ −136.69; ESIMS m/z 327 ([M+H]$^+$).

tert-Butyl-N-((tert-butoxy)carbonyl)-(5-amino-2-fluorophenyl)carbamate (C410)

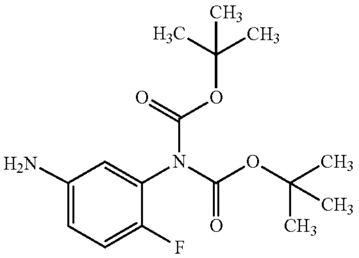 [SMILES: CC(C)(C)OC(=O)N(C(=O)OC(C)(C)C)c1cc(N)ccc1F]

Isolated as a grey solid (1.048 g, 68%): $^{1}$H NMR (400 MHz, DMSO-$d_6$) δ 6.91 (dd, J=10.1, 8.8 Hz, 1H), 6.49 (ddd, J=8.8, 4.1, 2.8 Hz, 1H), 6.39 (dd, J=6.7, 2.8 Hz, 1H), 5.03 (s, 2H), 1.39 (s, 18H): $^{19}$F NMR (376 MHz, DMSO-$d_6$) δ −139.75; ESIMS m/z 226 ([M−BOC]$^-$).

tert-Butyl-N-((tert-butoxy)carbonyl)-N-(4-amino-2,5-difluorophenyl)carbamate (C411)

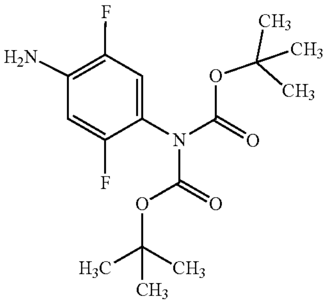 [SMILES: CC(C)(C)OC(=O)N(C(=O)OC(C)(C)C)c1cc(F)c(N)cc1F]

Isolated as a grey solid (1.5 g, 83%): $^{1}$H NMR (400 MHz, DMSO-$d_6$) δ 7.09-6.99 (m, 1H), 6.56 (dd, J=11.8, 8.0 Hz, 1H), 5.55 (s, 2H), 1.37 (d, J=1.4 Hz, 18H); $^{19}$F NMR (376 MHz, DMSO-$d_6$) δ −128.64 (d, J=13.9 Hz), −139.89 (d, J=13.8 Hz); ESIMS m/z 345 ([M−H]$^-$).

Example 92: Preparation of $N^4$-benzyl-3,5-difluoropyridine-2,4-diamine (C412)

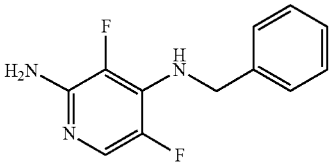 [SMILES: Nc1ncc(F)c(NCc2ccccc2)c1F]

A suspension of 3,5-difluoro-4-iodopyridin-2-amine (200 mg, 0.781 mmol), tris(dibenzylideneacetone)dipalladium(0) (71.5 mg, 0.078 mmol), 2,2'-bis(diphenylphosphanyl)-1,1'-binaphthalene (97 mg, 0.156 mmol), sodium 2-methylpropan-2-olate (90 mg, 0.938 mmol), and benzylamine (112 μL, 0.938 mmol) in toluene (3.9 mL) was evacuated under vacuum and backfilled with nitrogen three times. The reaction mixture was then sealed under a blanket of nitrogen and heated via microwave irradiation to 130° C. for 2 hours. The reaction mixture was diluted with ethyl acetate and quenched with aqueous sodium hydroxide (2 N). The layers were separated, and the aqueous phase was extracted with ethyl acetate three times. The combined organic phase was washed with brine, dried over sodium sulfate and filtered. The solvent was evaporated. Purification by flash column chromatography using 0-100% ethyl acetate in hexanes as the eluent afforded the title compound as a yellow solid (0.093 g, 51%): $^1H$ NMR (300 MHz, $CDCl_3$) δ 7.56 (dd, J=2.9, 1.0 Hz, 1H), 7.42-7.23 (m, 5H), 4.62 (dt, J=6.3, 1.4 Hz, 2H), 4.36 (t, J=9.9 Hz, 3H); ESIMS m/z 236 ($[M+H]^+$); IR (thin film) 3307, 3181, 3030, 2924, 1631, 1577, 1530, 1475, 1453 $cm^{-1}$.

Example 93: Preparation of tert-butyl (6-amino-4-(trifluoromethyl)pyridin-2-yl)carbamate (C413)

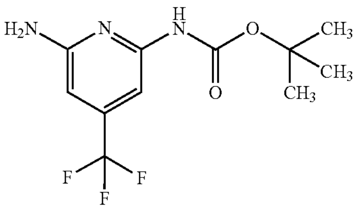 [SMILES: CC(C)(C)OC(=O)Nc1cc(C(F)(F)F)cc(N)n1]

A solution of di-tert-butyl dicarbonate (3.93 g, 18.00 mmol) in tetrahydrofuran (10 mL) was added dropwise to a solution of 4-(trifluoromethyl)pyridine-2,6-diamine (3.19 g, 18 mmol) in tetrahydrofuran (20 mL) at room temperature. Upon completion of the addition, the reaction mixture was fitted with a reflux condenser and heated to 60° C. overnight. The solvent was evaporated. Purification by flash column chromatography using 5-10% ethyl acetate in dichloromethane as the eluent afforded the title compound as a thick, pale yellow oil (2.80 g, 56%): $^1H$ NMR (400 MHz, $CDCl_3$) δ 7.86 (s, 1H), 7.47 (s, 1H), 6.35 (s, 1H), 4.71 (s, 2H), 1.52 (s, 9H); $^{19}F$ NMR (376 MHz, $CDCl_3$) δ −65.27; ESIMS m/z 278 ($[M+H]^+$).

Example 94: Preparation of 3,5-difluoropyridine-2,4-diamine (C414)

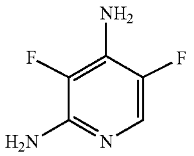

2,3,5-Trifluoropyridin-4-amine (0.200 g, 1.351 mmol) was suspended in ammonium hydroxide (5 mL, 128 mmol) in a high pressure reactor equipped with a magnetic stir bar. The reactor was sealed and, with stirring, heated to 120° C. for 24 hours and then to 160° C. for an additional 24 hours. The reaction mixture was cooled to room temperature and extracted with ethyl acetate four times. The combined organic layers were dried over magnesium sulfate, filtered, and concentrated under reduced pressure to afford the title compound as a light brown solid (0.163 g, 83%): $^1H$ NMR (400 MHz, DMSO-$d_6$) δ 7.46 (d, J=2.0 Hz, 1H), 5.90 (s, 2H), 5.47 (s, 2H); $^{19}F$ NMR (376 MHz, DMSO-$d_6$) δ −160.20 (d, J=5.4 Hz), −160.96 (d, J=5.4 Hz); EIMS m/z 145.

Example 95: Preparation of 1-ethyl-1H-indol-5-amine (C415)

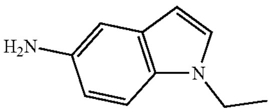

Ethyl iodide (289 mg, 1.85 mmol) was added in one portion to a stirred solution of 5-nitro-1H-indole (250 mg, 1.542 mmol) and potassium carbonate (426 mg, 3.08 mmol) in DMF (5 mL) at room temperature. The resulting brown suspension was poured into water (50 mL), and the resulting precipitate was collected by vacuum filtration and dried in vacuo at 40° C. to a constant weight. 1-Ethyl-5-nitro-1H-indole was isolated as a pale yellow solid (0.220 g, 71.3%): $^1H$ NMR (400 MHz, DMSO-$d_6$) δ 8.57 (d, J=2.3 Hz, 1H), 8.03 (dd, J=9.1, 2.3 Hz, 1H), 7.74-7.65 (m, 2H), 6.76 (d, J=3.2 Hz, 1H), 4.30 (q, J=7.2 Hz, 2H), 1.38 (t, J=7.2 Hz, 3H); $^{13}C$ NMR (101 MHz, DMSO-$d_6$) δ 140.61, 138.27, 131.90, 127.33, 117.53, 116.23, 110.18, 103.59, 40.85, 40.17, 39.96, 39.75, 39.54, 39.33, 39.13, 38.92, 15.34; ESIMS m/z 191 ($[M+H]^+$).

Palladium hydroxide (10% on carbon, 78 mg, 0.055 mmol) was added in one portion to a stirred solution of 1-ethyl-5-nitro-1H-indole (210 mg, 1.104 mmol) in ethyl acetate (50 mL). A balloon filled with hydrogen was attached to the flask, and the vessel was filled with hydrogen, evacuated, and refilled with hydrogen. The heterogenous mixture was stirred at room temperature for 16 hours, after which the reaction mixture was filtered through a pad of Celite®, and the filtrate was concentrated under vacuum on a rotary evaporator. Purification by silica gel column chromatography gave 1-ethyl-1H-indol-5-amine as an amber oil (0.144 g, 80%): $^1H$ NMR (400 MHz, $CDCl_3$) δ 7.14 (d, J=8.5 Hz, 1H), 7.02 (d, J=3.1 Hz, 1H), 6.92 (d, J=2.2 Hz, 1H), 6.67 (dd, J=8.6, 2.2 Hz, 1H), 6.29 (dd, J=3.1, 0.8 Hz, 1H), 4.08 (q, J=7.3 Hz, 2H), 3.46 (s, 2H), 1.42 (t, J=7.3 Hz, 3H); $^{13}C$ NMR (101 MHz, $CDCl_3$) δ 139.18, 130.88, 129.52, 127.33, 112.39, 109.81, 105.85, 99.67, 77.38, 77.26, 77.06, 76.75, 41.00, 15.46. ESIMS m/z 161 ($[M+H]^+$).

The following compounds were prepared in like manner to the procedure outlined in Example 95:

1-(2-Fluoroethyl)-1H-indol-5-amine (C416)

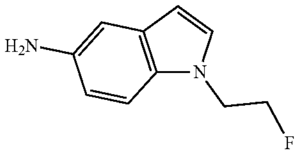 [SMILES: Nc1ccc2c(ccn2CCF)c1]

Isolated as an amber oil (0.120 g, 92%): ESIMS m/z 179 ($[M+H]^+$).

Example 96: Preparation of trans-2,2-dichloro-3-(3,5-dichlorophenyl)cyclo-propane carboxylic acid (C1)

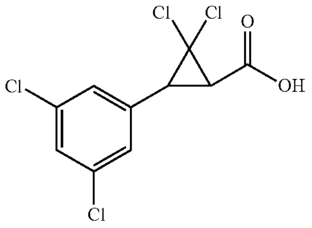 [SMILES: O=C(O)C1C(c2cc(Cl)cc(Cl)c2)C1(Cl)Cl]

Sodium permanganate (40% aqueous) (84 g, 236 mmol) was added dropwise to a stirred mixture of trans-2,2-dichloro-3-(3,5-dichlorophenyl)cyclopropane-1-carbaldehyde (C437) (58.7 g, 196 mmol) in acetone (982 mL) at 15° C. The resulting mixture was stirred at 20° C. for 2 hours. The reaction mixture was diluted with isopropyl alcohol (20 mL) and concentrated to remove the acetone. Celite® and aqueous hydrochloric acid (1 N, 295 mL, 295 mmol) were added to the brown residue. The resulting mixture was diluted with ethyl acetate (500 mL) and filtered through Celite®. The filtrate was washed with brine (200 mL). The organic layer was dried over sodium sulfate, filtered and concentrated. The resulting slurry was diluted with heptane (~200 mL) and allowed to solidify at 20° C. The solid was collected, washed with heptane and dried to afford the title product as a white solid (54.68 g, 91%): $^1H$ NMR (300 MHz, $CDCl_3$) δ 7.36 (t, J=1.9 Hz, 1H), 7.17 (dd, J=1.9, 0.7 Hz, 2H), 3.48-3.37 (m, 1H), 2.87 (d, J=8.3 Hz, 1H); $^{13}C$ NMR (400 MHz, $CDCl_3$) δ 135.44, 135.28, 128.66, 127.30, 39.68, 36.88; ESIMS m/z=298.9 ($[M-H]^-$).

The following compounds were prepared in like manner to the procedure outlined in Example 96:

trans-2,2-Dichloro-3-(3,4,5-trichlorophenyl)cyclopropane-1-carboxylic acid (C2)

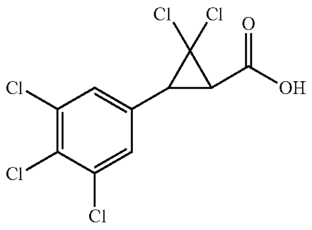 [SMILES: O=C(O)C1C(c2cc(Cl)c(Cl)c(Cl)c2)C1(Cl)Cl]

Isolated as a white solid (2.78 g, 95%): $^1H$ NMR (400 MHz, DMSO-$d_6$) δ 13.41 (s, 1H), 7.81 (d, J=0.6 Hz, 2H), 3.62 (d, J=8.6 Hz, 1H), 3.52 (d, J=8.6 Hz, 1H); ESIMS m/z 332 ($[M-H]^-$).

trans-2,2-Dichloro-3-(3,4-dichlorophenyl)cyclopropane-1-carboxylic acid (C3)

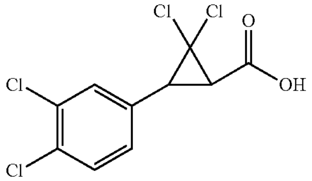 [SMILES: O=C(O)C1C(c2ccc(Cl)c(Cl)c2)C1(Cl)Cl]

Isolated as a white solid (124 g, 82%): mp 133-135° C.: $^1H$ NMR (500 MHz, DMSO-$d_6$) δ 13.39 (s, 1H), 7.76 (d, J=2.0 Hz, 1H), 7.64 (d, J=8.3 Hz, 1H), 7.44 (dd, J=8.4, 2.1 Hz, 1H), 3.49 (s, 2H). $^{13}C$ NMR (126 MHz, DMSO-$d_6$) δ 166.34, 133.35, 130.47, 130.33, 130.09, 129.77, 128.81, 61.43, 37.00, 36.06.

trans-2,2-Dichloro-3-(3-chloro-4-fluorophenyl)cyclopropane-1-carboxylic acid (C16)

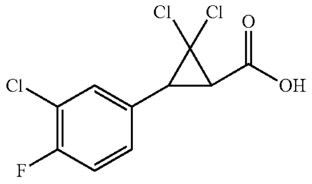

Isolated as a white solid (165 g, 71%): $^1H$ NMR (400 MHz, $CDCl_3$) δ 11.57 (s, 1H), 7.42 (dd, J=8.2, 7.6 Hz, 1H), 7.11-6.98 (m, 2H), 3.46 (d, J=8.2 Hz, 1H), 2.85 (d, J=8.3 Hz, 1H); $^{19}F$ NMR (376 MHz, $CDCl_3$) δ −114.07; ESIMS m/z 282 ($[M-H]^-$).

In another preparation, isolated as a white powder (10.385 g, 77%): 119-121° C.; $^1H$ NMR (400 MHz, $CDCl_3$) δ 11.83 (s, 1H), 7.32 (d, J=6.9 Hz, 1H), 7.16 (d, J=6.7 Hz, 2H), 3.45 (d, J=8.3 Hz, 1H), 2.85 (d, J=8.3 Hz, 1H); $^{13}C$ NMR (101 MHz, $CDCl_3$) δ 172.18, 159.26, 156.77, 130.95, 129.26, 129.22, 128.57, 128.50, 121.52, 121.34, 116.94, 116.73, 61.59, 39.64, 37.30; $^{19}F$ NMR (376 MHz, $CDCl_3$) δ −115.16; ESIMS m/z 281 [$(M-H)^-$].

trans-2,2-Dichloro-3-(3,5-dichloro-4-methoxyphenyl)cyclopropane-1-carboxylic acid (C417)

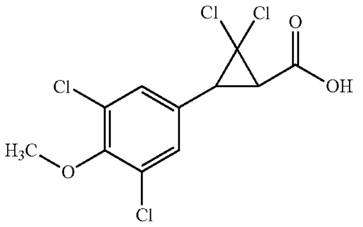

Isolated as an off-white solid (1.33 g, 96%): mp 161-164° C.; $^{1}$H NMR (400 MHz, DMSO-$d_6$) δ 13.35 (s, 1H), 7.63 (s, 2H), 3.83 (s, 3H), 3.52 (d, J=8.6 Hz, 1H), 3.45 (d, J=8.6 Hz, 1H); $^{13}$C NMR (126 MHz, DMSO-$d_6$) δ 166.81, 151.02, 131.07, 129.63, 128.03, 61.93, 60.52, 37.22, 36.54; ESIMS m/z 329 [(M−H)$^-$].

trans-2,2-Dichloro-3-(3-chloro-5-cyanophenyl)cyclopropane-1-carboxylic acid (C418)

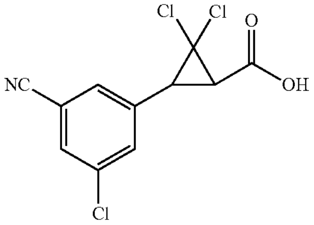 [SMILES: N#Cc1cc(Cl)cc(C2C(C(=O)O)C2(Cl)Cl)c1]

Isolated as a white solid (2.92 g, 60%): mp: 173-175° C.; $^{1}$H NMR (500 MHz, DMSO-$d_6$) δ 13.42 (s, 1H), 8.03 (t, J=1.7 Hz, 1H), 7.98 (t, J=1.9 Hz, 2H), 3.65 (d, J=8.6 Hz, 1H), 3.57 (d, J=8.6 Hz, 1H); ESIMS m/z 290 ([M]).

trans-2,2-Dichloro-3-(4-nitrophenyl)cyclopropane-1-carboxylic acid (C419)

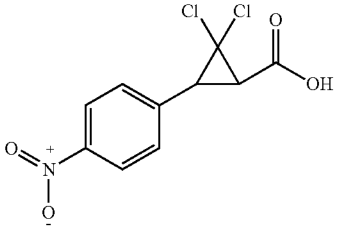

Isolated as a pink solid (0.158 g, 48%): $^{1}$H NMR (400 MHz, $CDCl_3$) δ 8.26 (d, J=8.3 Hz, 2H), 7.47 (d, J=8.4 Hz, 2H), 3.57 (d, J=8.3 Hz, 1H), 2.98 (d, J=8.3 Hz, 1H); $^{13}$C NMR (101 MHz, $CDCl_3$) δ 171.34, 147.88, 139.21, 129.75, 123.85, 61.33, 40.14, 37.43; IR (thin film) 2923, 2603, 1709, 1601, 1520, 1446 cm$^{-1}$; ESIMS m/z 273.9 [(M−H)$^-$].

trans-2,2-Dichloro-3-(3-chloro-4-fluorophenyl)cyclopropane-1-carboxylic acid (C420)

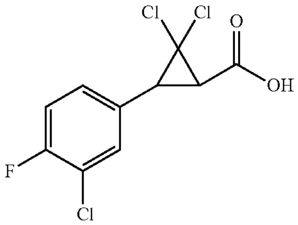 [SMILES: O=C(O)C1C(c2ccc(F)c(Cl)c2)C1(Cl)Cl]

Isolated as a white powder (10.385 g, 77%): mp 119-121° C.; $^{1}$H NMR (400 MHz, $CDCl_3$) δ 11.83 (s, 1H), 7.32 (d, J=6.9 Hz, 1H), 7.16 (d, J=6.7 Hz, 2H), 3.45 (d, J=8.3 Hz, 1H), 2.85 (d, J=8.3 Hz, 1H); $^{13}$C NMR (101 MHz, $CDCl_3$) δ 172.18, 159.26, 156.77, 130.95, 129.26, 129.22, 128.57, 128.50, 121.52, 121.34, 116.94, 116.73, 61.59, 39.64, 37.30; $^{19}$F NMR (376 MHz, $CDCl_3$) δ −115.16; ESIMS m/z 281 [(M−H)$^-$].

trans-2,2-Dichloro-3-(3,4-difluorophenyl)cyclopropane-1-carboxylic acid (C421)

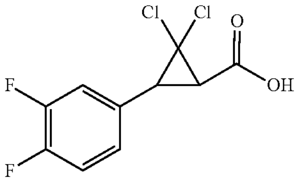

Isolated as a white solid (1.44 g, 67%): $^{1}$H NMR (400 MHz, $CDCl_3$) δ 8.69 (s, 1H), 7.18 (dt, J=9.9, 8.3 Hz, 1H), 7.10 (ddd, J=10.8, 7.3, 2.3 Hz, 1H), 7.01 (ddt, J=8.1, 3.8, 1.7 Hz, 1H), 3.44 (dd, J=8.4, 1.0 Hz, 1H), 2.83 (d, J=8.3 Hz, 1H); $^{19}$F NMR (376 MHz, $CDCl_3$) δ −136.40, −136.46, −137.42, −137.48; ESIMS m/z 266 ([M−H]$^-$).

trans-3-(3-Bromo-4-chlorophenyl)-2,2-dichlorocyclopropane-1-carboxylic acid

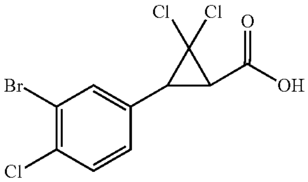

Isolated as a white solid (1.05 g, 63%): $^{1}$H NMR (400 MHz, $CDCl_3$) δ 8.07-7.63 (m, 1H), 7.58-7.42 (m, 2H), 7.17 (dd, J=8.3, 2.1 Hz, 1H), 3.43 (d, J=8.3 Hz, 1H), 2.86 (d, J=8.3 Hz, 1H); $^{13}$C NMR (101 MHz, $CDCl_3$) δ 171.46, 134.71, 133.88, 132.43, 130.42, 128.70, 122.73, 77.33, 77.22, 77.01, 76.69, 61.51, 39.50, 37.21; ESIMS m/z 343 ([M−H]$^-$).

trans-2,2-Dichloro-3-(3,4-dibromophenyl)cyclopropane-1-carboxylic acid

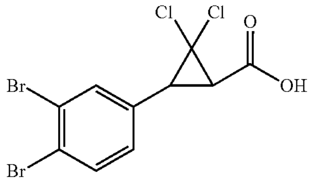

Isolated as a white solid (0.488 g, 57%): $^{1}H$ NMR (400 MHz, $CDCl_3$) δ 8.85 (s, 1H), 7.77-7.47 (m, 2H), 7.08 (ddd, J=8.3, 2.1, 0.7 Hz, 1H), 3.57-3.25 (m, 1H), 2.86 (d, J=8.3 Hz, 1H); $^{13}C$ NMR (101 MHz, $CDCl_3$) δ 171.54, 133.82, 133.78, 133.08, 128.78, 125.13, 124.98, 77.33, 77.22, 77.01, 76.70, 61.41, 39.59, 37.14, 0.01; ESIMS m/z 387 ($[M-H]^-$).

trans-2,2-Dichloro-3-(3-fluoro-4-(trifluoromethyl)phenyl)cyclopropane-1-carboxylic acid (C424)

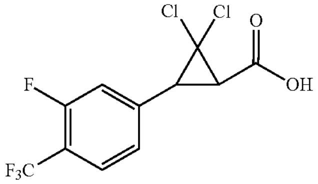 [SMILES: O=C(O)C1C(c2ccc(C(F)(F)F)c(F)c2)C1(Cl)Cl]

Isolated as a waxy tan solid (4.09 g, 68.7%): $^{1}H$ NMR (400 MHz, $CDCl_3$) δ 7.83 (s, 1H), 7.63 (t, J=7.7 Hz, 1H), 7.23-7.04 (m, 2H), 3.51 (d, J=8.3 Hz, 1H), 2.92 (d, J=8.3 Hz, 1H); $^{19}F$ NMR (376 MHz, $CDCl_3$) δ −61.40, −61.43, −113.24, −113.27; ESIMS m/z 316 ($[M-H]^-$).

trans-3-(4-Bromo-3-fluorophenyl)-2,2-dichlorocyclopropane-1-carboxylic acid (C425)

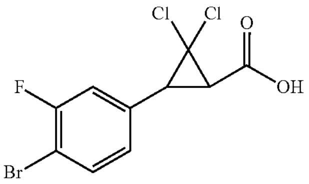

Isolated as a white solid (0.41 g, 42.1%): $^{1}H$ NMR (400 MHz, $CDCl_3$) δ 8.04 (s, 1H), 7.57 (dd, J=8.2, 7.1 Hz, 1H), 7.00 (ddd, J=33.6, 8.7, 2.1 Hz, 2H), 3.43 (d, J=8.3 Hz, 1H), 2.85 (d, J=8.3 Hz, 1H); $^{19}F$ NMR (376 MHz, $CDCl_3$) δ −106.06; ESIMS m/z 327 ($[M-H]^-$).

trans-3-(3-Bromo-4-(trifluoromethyl)-2,2-dichlorophenyl)cyclopropane-1-carboxylic acid (C426)

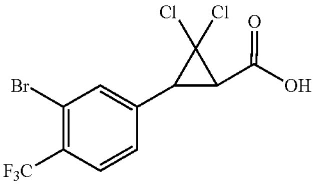 [SMILES: O=C(O)C1C(c2ccc(C(F)(F)F)c(Br)c2)C1(Cl)Cl]

Isolated as a white solid (0.55 g, 53.8%): $^{1}H$ NMR (400 MHz, $CDCl_3$) δ 7.78-7.57 (m, 2H), 7.42-7.29 (m, 1H), 3.50 (d, J=8.3 Hz, 1H), 2.93 (d, J=8.3 Hz, 1H); $^{19}F$ NMR (376 MHz, $CDCl_3$) δ −62.66, −62.67, −62.81; ESIMS m/z 377 ($[M-H]^-$).

trans-3-(4-Bromo-3-(trifluoromethyl)phenyl)-2,2-dichlorocyclopropane-1-carboxylic acid (C427)

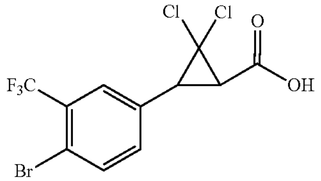

Isolated as a white solid (1.21 g, 51%): $^{1}H$ NMR (400 MHz, $CDCl_3$) δ 10.87 (s, 1H), 7.74 (d, J=8.3 Hz, 1H), 7.58 (d, J=2.2 Hz, 1H), 7.30 (dd, J=8.3, 2.2 Hz, 1H), 3.49 (d, J=8.3 Hz, 1H), 2.91 (d, J=8.3 Hz, 1H); $^{19}F$ NMR (376 MHz, $CDCl_3$) δ −62.77, −62.78; ESIMS m/z 377 ($[M-H]^-$).

trans-2,2-Dichloro-3-(3-chloro-4-(trifluoromethyl)phenyl)cyclopropane-1-carboxylic acid (C428)

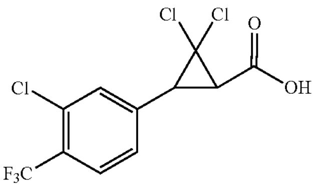 [SMILES: O=C(O)C1C(c2ccc(C(F)(F)F)c(Cl)c2)C1(Cl)Cl]

Isolated as a white solid (0.778 g, 43.4%): $^{1}H$ NMR (400 MHz, $CDCl_3$) δ 9.72 (s, 1H), 7.71 (d, J=8.2 Hz, 1H), 7.53-7.39 (m, 1H), 7.35-7.19 (m, 1H), 3.50 (d, J=8.3 Hz, 1H), 2.93 (d, J=8.3 Hz, 1H); $^{19}F$ NMR (376 MHz, $CDCl_3$) δ −62.63; ESIMS m/z 332 ($[M-H]^-$).

trans-2,2-Dichloro-3-(4-chloro-3-(trifluoromethyl)phenyl)cyclopropane-1-carboxylic acid (C429)

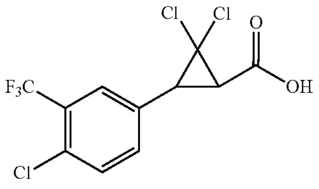 [SMILES: O=C(O)C1C(c2ccc(Cl)c(C(F)(F)F)c2)C1(Cl)Cl]

Isolated as a white solid (2.02 g, 43%): $^{1}$H NMR (400 MHz, $CDCl_3$) δ 7.96-7.51 (in, 3H), 7.39 (dd, J=8.3, 2.2 Hz, 1H), 3.50 (d, J=8.3 Hz, 1H), 2.90 (d, J=8.3 Hz, 1H); $^{19}$F NMR (376 MHz, $CDCl_3$) δ −62.75, −62.75; ESIMS m/z 332 ([M−H]$^-$).

trans-3-(3-Bromo-4-fluorophenyl)-2,2-dichlorocyclopropane-1-carboxylic acid (C430)

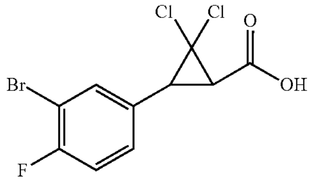

Isolated as a white solid (0.850 g, 43.9%): $^{1}$H NMR (400 MHz, $CDCl_3$) δ 8.47 (s, 1H), 7.47 (ddd, J=6.3, 2.3, 0.7 Hz, 1H), 7.32-7.08 (m, 2H), 3.44 (dd, J=8.3, 1.0 Hz, 1H), 2.84 (d, J=8.3 Hz, 1H); $^{19}$F NMR (376 MHz, $CDCl_3$) δ −107.16; ESIMS m/z 327 ([M−H]$^-$).

trans-2,2-Dichloro-3-(4-fluoro-3-(trifluoromethyl)phenyl)cyclopropane-1-carboxylic acid (C431)

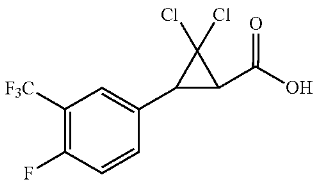 [SMILES: O=C(O)C1C(c2ccc(F)c(C(F)(F)F)c2)C1(Cl)Cl]

Isolated as a white solid (3.08 g, 66.9%): $^{1}$H NMR (400 MHz, $CDCl_3$) δ 8.18 (s, 1H), 7.64-7.39 (m, 2H), 7.24 (t, J=9.3 Hz, 1H), 3.50 (dd, J=8.4, 1.0 Hz, 1H), 2.89 (d, J=8.3 Hz, 1H); $^{19}$F NMR (376 MHz, $CDCl_3$) δ −61.48, −61.51, −114.23, −114.26, −114.29; ESIMS m/z 316 ([M−H]$^-$).

trans-2,2-Dichloro-3-(4-chloro-3-fluorophenyl)cyclopropane-1-carboxylic acid (C432)

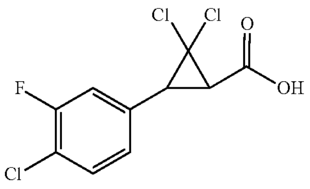

Isolated as a white solid (0.96 g, 36.2%): $^{1}$H NMR (400 MHz, $CDCl_3$) δ 11.57 (s, 1H), 7.42 (dd, J=8.2, 7.6 Hz, 1H), 7.11-6.98 (m, 2H), 3.46 (d, J=8.2 Hz, 1H), 2.85 (d, J=8.3 Hz, 1H); $^{19}$F NMR (376 MHz, $CDCl_3$) δ −114.07; ESIMS m/z 282 ([M−H]$^-$).

trans-2,2-Dichloro-3-(3,5-difluorophenyl)cyclopropane-1-carboxylic acid (C433)

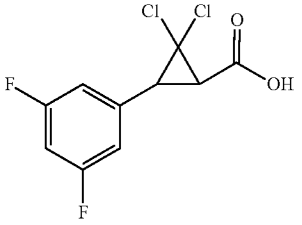

Isolated as a clear colorless oil (1.55 g, 28.9%): $^{1}$H NMR (400 MHz, $CDCl_3$) δ 10.44 (s, 1H), 6.82 (qd, J=6.4, 2.3 Hz, 3H), 3.44 (d, J=8.3 Hz, 1H), 2.86 (d, J=8.3 Hz, 1H); $^{19}$F NMR (376 MHz, $CDCl_3$) δ −108.49, −108.69, −108.82, −109.85; ESIMS m/z 266 ([M−H]$^-$).

trans-2,2-Dichloro-3-(3-fluoro-5-(trifluoromethyl)phenyl)cyclopropane-1-carboxylic acid (C434)

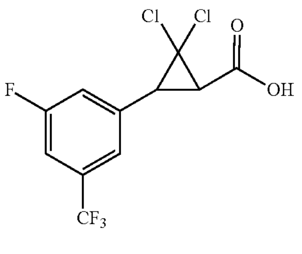

Isolated as a white solid (3.7 g, 54.7%): $^{1}$H NMR (400 MHz, $CDCl_3$) δ 11.40 (s, 1H), 7.42-7.27 (m, 2H), 7.20 (dt, J=8.9, 2.0 Hz, 1H), 3.53 (d, J=8.3 Hz, 1H), 2.93 (d, J=8.3 Hz, 1H); $^{19}$F NMR (376 MHz, $CDCl_3$) δ −62.86, −109.49; ESIMS m/z 316 ([M−H]$^-$).

trans-3-(3-Bromo-5-fluorophenyl)-2,2-dichlorocyclopropane-1-carboxylic acid (C435)

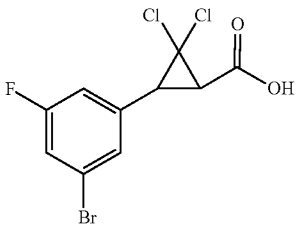 [SMILES: O=C(O)C1C(c2cc(F)cc(Br)c2)C1(Cl)Cl]

Isolated as a white solid (0.76 g, 47%): $^1$H NMR (400 MHz, $CDCl_3$) δ 11.06 (s, 1H), 7.36-7.14 (m, 2H), 7.03-6.87 (m, 1H), 3.45 (d, J=8.3 Hz, 1H), 2.87 (d, J=8.3 Hz, 1H); $^{19}$F NMR (376 MHz, $CDCl_3$) δ −109.73, −109.73; ESIMS m/z 327 ([M−H]$^-$).

trans-3-(3-Bromo-5-(trifluoromethyl)phenyl)-2,2-dichlorocyclopropane-1-carboxylic acid (C436)

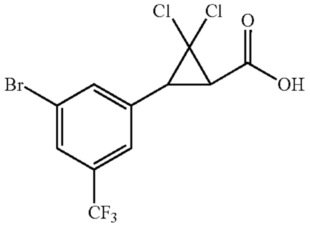

Isolated as a tan solid (0.375 g, 31%): $^1$H NMR (400 MHz, $CDCl_3$) δ 10.52 (s, 1H), 7.77 (s, 1H), 7.62 (d, J=1.8 Hz, 1H), 7.46 (s, 1H), 3.52 (d, J=8.2 Hz, 1H), 2.93 (d, J=8.3 Hz, 1H); $^{19}$F NMR (376 MHz, $CDCl_3$) δ −62.84; ESIMS m/z 377 ([M−H]$^-$).

Example 97: Preparation of trans-2,2-dichloro-3-(3,5-dichlorophenyl)cyclo-propane-1-carbaldehyde (C437)

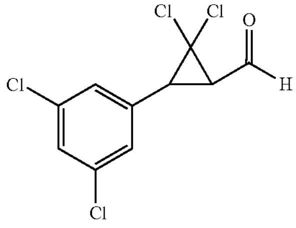 [SMILES: O=CC1C(c2cc(Cl)cc(Cl)c2)C1(Cl)Cl]

Aqueous hydrochloric acid (2 N, 237 mL) was added to a stirred solution of 1,3-dichloro-5-((trans-2,2-dichloro-3-(diethoxymethyl)cyclopropyl)benzene (C443) (85.7 g, 227 mmol) in acetonitrile (1184 mL). The mixture was stirred at 20° C. for 16 hours. The resulting mixture was diluted with water (200 mL) and concentrated to remove the acetonitrile. The resulting aqueous mixture was extracted with hexanes (600 mL). The organic layer was washed water (300 mL), dried over anhydrous sodium sulfate, filtered and concentrated. The crude product was purified by flash column chromatography using 0-20% ethyl acetate/hexanes as eluent to afford the title product as a yellow oil (58.7 g, 86%, purity 95%): $^1$H NMR (400 MHz, $CDCl_3$) δ 9.54 (d, J=4.0 Hz, 1H), 7.46-7.09 (m, 3H), 3.51 (d, J=8.0 Hz, 1H), 2.92 (dd, J=8.0, 4.0 Hz, 1H); $^{13}$C NMR (126 MHz, $CDCl_3$) δ 193.41, 135.33, 135.09, 128.78, 127.34, 42.89, 39.31; IR (thin film) 3078, 2847, 1714, 1590, 1566, 1417, 1387.

The following compounds were prepared in like manner to the procedure outlined in Example 97:

trans-2,2-Dichloro-3-(3,4-dichlorophenyl)cyclopropane-1-carbaldehyde (C438)

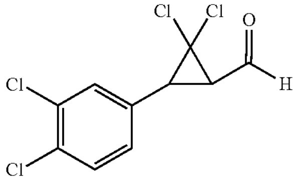 [SMILES: O=CC1C(c2ccc(Cl)c(Cl)c2)C1(Cl)Cl]

Isolated as orange oil (143 g, 98%): $^1$H NMR (400 MHz, $CDCl_3$) δ 9.53 (d, J=4.1 Hz, 1H), 7.47 (d, J=8.3 Hz, 1H), 7.37 (dd, J=2.2, 0.7 Hz, 1H), 7.12 (ddd, J=8.3, 2.2, 0.7 Hz, 1H), 3.51 (dd, J=7.9, 0.8 Hz, 1H), 2.90 (dd, J=8.0, 4.1 Hz, 1H).

trans-2,2-Dichloro-3-(3,4,5-trichlorophenyl)cyclopropane-1-carbaldehyde (C439)

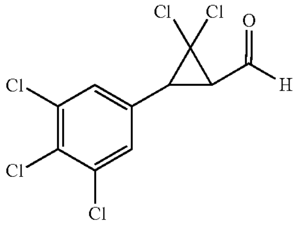 [SMILES: O=CC1C(c2cc(Cl)c(Cl)c(Cl)c2)C1(Cl)Cl]

Isolated as a yellow solid (2.8 g, 69%): $^1$H NMR (400 MHz, $CDCl_3$) δ 9.55 (d, J=3.9 Hz, 1H), 7.30 (d, J=0.7 Hz, 2H), 3.48 (dt, J=8.0, 0.8 Hz, 1H), 2.92 (dd, J=7.9, 3.9 Hz, 1H).

trans-2,2-Dichloro-3-(3,5-dichloro-4-methoxyphenyl)cyclopropane-1-carbaldehyde (C440)

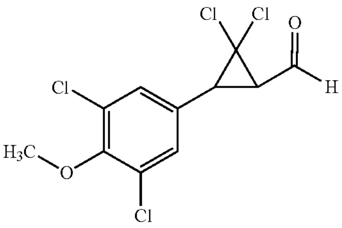 [SMILES: COc1c(Cl)cc(C2C(C=O)C2(Cl)Cl)cc1Cl]

Isolated as a light-yellow oil (1.346 g, 74%): $^1$H NMR (400 MHz, $CDCl_3$) δ 9.52 (d, J=4.0 Hz, 1H), 7.22 (s, 2H), 3.90 (s, 3H), 3.48 (d, J=8.0 Hz, 1H), 2.91 (dd, J=8.0, 4.0 Hz, 1H); $^{13}C$ NMR (101 MHz, $CDCl_3$) δ 191.67, 150.58, 127.74, 127.54, 127.35, 59.76, 58.94, 41.14, 37.13; EIMS m/z 314.

trans-2,2-Dichloro-3-(3-chloro-4-fluorophenyl)cyclopropane-1-carbaldehyde (C441)

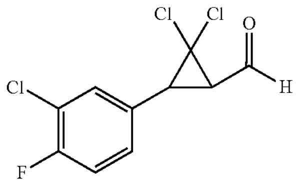 [SMILES: O=CC1C(c2ccc(F)c(Cl)c2)C1(Cl)Cl]

Isolated as orange oil (230 g, 97%): $^1H$ NMR (300 MHz, $CDCl_3$) δ 9.52 (d, J=4.2 Hz, 1H), 7.36-7.30 (m, 1H), 7.19-7.16 (m, 1H), 7.15 (d, J=1.2 Hz, 1H), 3.51 (dt, J=7.9, 0.7 Hz, 1H), 2.88 (dd, J=7.9, 4.2 Hz, 1H).

In another preparation, isolated as a yellow oil (12.496 g, 71%): $^1H$ NMR (400 MHz, $CDCl_3$) δ 9.52 (d, J=4.1 Hz, 1H), 7.33 (d, J=7.2 Hz, 1H), 7.16 (dd, J=6.8, 1.0 Hz, 2H), 3.53 (d, J=7.9 Hz, 1H), 2.90 (dd, J=7.9, 4.1 Hz, 1H); $^{13}C$ NMR (101 MHz, $CDCl_3$) δ 193.77, 159.27, 156.78, 131.03, 129.04, 129.00, 128.66, 128.59, 121.49, 121.31, 116.95, 116.74, 61.68, 43.10, 39.25; $^{19}F$ NMR (376 MHz, $CDCl_3$) δ −115.01; EIMS m/z 266.

3-Chloro-5-(trans-2,2-dichloro-3-formylcyclopropyl)benzonitrile (C442)

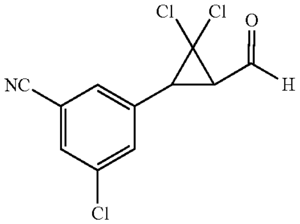 [SMILES: N#Cc1cc(Cl)cc(C2C(C=O)C2(Cl)Cl)c1]

Isolated as yellow solid (2.9 g, 77%): $^1H$ NMR (300 MHz, $CDCl_3$) δ 9.59 (d, J=3.6 Hz, 1H), 7.65 (ddd, J=1.9, 1.4, 0.5 Hz, 1H), 7.52 (td, J=1.8, 0.7 Hz, 1H), 7.48 (td, J=1.5, 0.7 Hz, 1H), 3.56 (dq, J=8.0, 0.6 Hz, 1H), 2.98 (dd, J=8.0, 3.7 Hz, 1H).

Example 98: Preparation of 1,3-dichloro-5-(trans-2,2-dichloro-3-(diethoxy-methyl)cyclopropyl)benzene (C443)

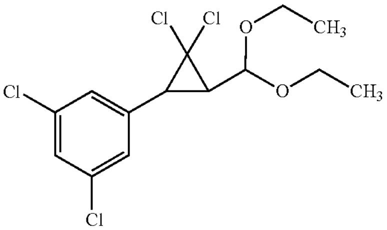 [SMILES: CCOC(OCC)C1C(c2cc(Cl)cc(Cl)c2)C1(Cl)Cl]

A 1 L 4-neck flask equipped with a mechanical stirrer, condenser, temperature probe and nitrogen inlet was charged with (E)-1,3-dichloro-5-(3,3-diethoxyprop-1-en-1-yl)benzene (C449) (40 g, 138 mmol) and $CHCl_3$ (447 mL). Tetrabutylammonium hexafluorophosphate (V) (1.081 g, 2.76 mmol) was added. The light yellow solution was heated to 45° C. With vigorous stirring (~400 rpm), aqueous sodium hydroxide (50%, 182 mL) was added dropwise via addition funnel (over 1 hour). After 20 hours, the mixture was allowed to cool. The mixture was diluted with hexane (200 mL). The organic top layer was decanted (off the aqueous lower suspension) through Celite®, washing the filtercake with hexane (200 mL). The filtrate was washed with brine (~200 mL), dried over sodium sulfate, filtered and concentrated to provide the title compound as a brown oil (50.2 g, 97%, purity 95%): $^1H$ NMR (300 MHz, $CDCl_3$) δ 7.31 (t, J=1.9 Hz, 1H), 7.15 (dd, J=1.9, 0.7 Hz, 2H), 4.59 (d, J=6.2 Hz, 1H), 3.80-3.57 (m, 4H), 2.77 (d, J=8.5 Hz, 1H), 2.25 (dd, J=8.5, 6.2 Hz, 1H), 1.30 (t, J=7.0 Hz, 3H), 1.20 (t, J=7.1 Hz, 3H).

The following compounds were prepared in like manner to the procedure outlined in Example 98:

1,2-Dichloro-4-(trans-2,2-dichloro-3-(diethoxymethyl)cyclopropyl)benzene (C444)

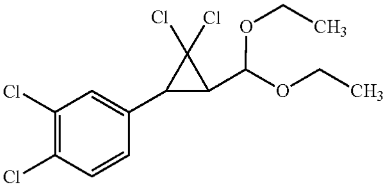 [SMILES: CCOC(OCC)C1C(c2ccc(Cl)c(Cl)c2)C1(Cl)Cl]

Isolated as a brown oil (184 g, 99%): $^1H$ NMR (400 MHz, $CDCl_3$) δ 7.43 (d, J=8.2 Hz, 1H), 7.36 (dd, J=2.2, 0.7 Hz, 1H), 7.10 (ddd, J=8.3, 2.1, 0.7 Hz, 1H), 4.59 (d, J=6.2 Hz, 1H), 3.82-3.55 (m, 4H), 2.77 (d, J=8.5 Hz, 1H), 2.24 (dd, J=8.5, 6.3 Hz, 1H), 1.30 (t, J=7.0 Hz, 3H), 1.20 (t, J=7.1 Hz, 3H).

1,2,3-Trichloro-5-(trans-2,2-dichloro-3-(diethoxymethyl)cyclopropyl)benzene (C445)

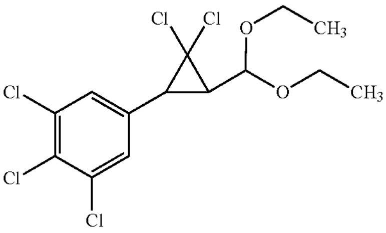 [SMILES: CCOC(OCC)C1C(c2cc(Cl)c(Cl)c(Cl)c2)C1(Cl)Cl]

Isolated as a brown oil (146 g, 93%): $^1H$ NMR (400 MHz, $CDCl_3$) δ 7.29 (d, J=0.7 Hz, 2H), 4.59 (d, J=6.1 Hz, 1H), 3.82-3.54 (m, 4H), 2.75 (d, J=8.5 Hz, 1H), 2.23 (dd, J=8.5, 6.1 Hz, 1H), 1.30 (t, J=7.0 Hz, 3H), 1.20 (t, J=7.0 Hz, 3H).

trans-1,3-Dichloro-5-(2,2-dichloro-3-(diethoxymethyl)cyclopropyl)-2-methoxybenzene (C446)

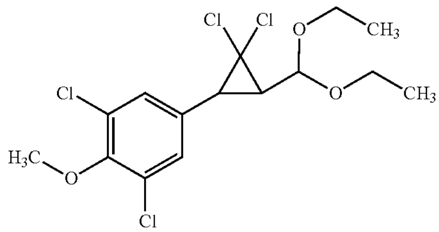 [SMILES: CCOC(OCC)C1C(c2cc(Cl)c(OC)c(Cl)c2)C1(Cl)Cl]

Isolated as an orange oil (2.254 g, 80%): $^1$H NMR (400 MHz, $CDCl_3$) δ 7.20 (d, J=0.5 Hz, 2H), 4.58 (d, J=6.2 Hz, 1H), 3.90 (s, 3H), 3.67 (m, 4H), 2.74 (d, J=8.5 Hz, 1H), 2.22 (dd, J=8.5, 6.2 Hz, 1H), 1.31 (m, 3H), 1.21 (m, 3H); $^{13}$C NMR (101 MHz, $CDCl_3$) δ 151.87, 131.55, 129.27, 129.20, 127.21, 101.21, 62.39, 61.88, 61.68, 60.70, 37.67, 36.96, 15.34, 15.25; EIMS m/z 387.

2-Chloro-4-(trans-2,2-dichloro-3-(diethoxymethyl)cyclopropyl)-1-fluoro-benzene (C447)

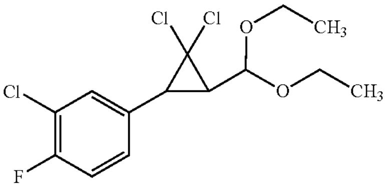 [SMILES: CCOC(OCC)C1C(c2ccc(F)c(Cl)c2)C1(Cl)Cl]

Isolated as a brown oil (63 g, 96%): $^1$H NMR (400 MHz, $CDCl_3$) δ 7.44 (dd, J=7.0, 2.2 Hz, 1H), 7.29-7.22 (m, 1H), 7.09 (t, J=8.7 Hz, 1H), 6.62 (dd, J=16.1, 1.2 Hz, 1H), 6.14 (dd, J=16.1, 5.0 Hz, 1H), 5.05 (dd, J=4.9, 1.2 Hz, 1H), 3.70 (dq, J=9.3, 7.0 Hz, 2H), 3.56 (dq, J=9.4, 7.1 Hz, 2H), 1.25 (t, J=7.1 Hz, 6H); $^{13}$C NMR (101 MHz, $CDCl_3$) δ 158.91, 156.42, 133.65, 133.62, 130.47, 128.65, 128.07, 128.05, 126.39, 126.32, 121.26, 121.08, 116.72, 116.51, 100.93, 61.17, 15.24; $^{19}$F NMR (376 MHz, $CDCl_3$) δ −116.36.

In another preparation, isolated as an amber oil (22.38 g, 88%): $^1$H NMR (400 MHz, $CDCl_3$) δ 7.31 (m, 1H), 7.13 (m, 2H), 4.59 (d, J=6.3 Hz, 1H), 3.69 (m, 4H), 2.78 (d, J=8.5 Hz, 1H), 2.23 (dd, J=8.5, 6.3 Hz, 1H), 1.30 (t, J=7.1 Hz, 3H), 1.20 (t, J=7.1 Hz, 3H); $^{19}$F NMR (376 MHz, $CDCl_3$) δ −116.48; EIMS m/z 295 [M-OEt].

3-Chloro-5-(trans-2,2-dichloro-3-(diethoxymethyl)cyclopropyl)benzonitrile (C448)

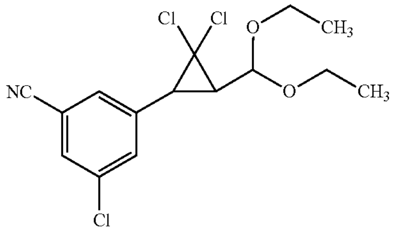 [SMILES: CCOC(OCC)C1C(c2cc(Cl)cc(C#N)c2)C1(Cl)Cl]

Isolated as yellow oil (4.8 g, 74%): $^1$H NMR (400 MHz, $CDCl_3$) δ 7.59 (t, J=1.7 Hz, 1H), 7.50 (t, J=1.9 Hz, 1H), 7.45 (t, J=1.5 Hz, 1H), 4.61 (d, J=6.0 Hz, 1H), 3.89-3.50 (m, 4H), 2.83 (d, J=8.5 Hz, 1H), 2.28 (dd, J=8.4, 6.0 Hz, 1H), 1.31 (t, J=7.1 Hz, 3H), 1.21 (t, J=7.0 Hz, 3H).

Example 99: Preparation of (E)-1,3-dichloro-5-(3,3-diethoxyprop-1-en-1-yl)benzene (C449)

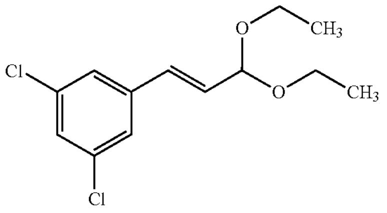 [SMILES: CCOC(/C=C/c1cc(Cl)cc(Cl)c1)OCC]

Step 1a: Acetaldehyde (120 g, 2688 mmol) was added to a stirred mixture of 3,5-dichlorobenzaldehyde (96 g, 538 mmol) in toluene (400 mL) at 0° C. A solution of potassium hydroxide (3.35 g, 53.8 mmol) in methyl alcohol (10 mL) was added dropwise via addition funnel. The resulting mixture was stirred at 0° C. for 4 hours until all of the 3,5-dichlorobenzaldehyde was consumed by thin layer chromatography. Step 1b: Ethyl acetate (500 mL) and concentrated hydrochloric acid (37% aqueous, 44.1 mL, 538 mmol) were added to the reaction mixture. The resulting mixture was heated at 80° C., and a colorless liquid was allowed to distill (200 mL). The reaction mixture was diluted with water (500 mL) and extracted with ethyl acetate. The organic layer was washed with brine, dried over sodium sulfate, filtered, and concentrated to afford (E)-3-(3,5-dichlorophenyl) acrylaldehyde as a light yellow solid (115 g) which was used directly without further purification: $^1$H NMR (300 MHz, $CDCl_3$) δ 9.72 (dd, J=7.4, 0.5 Hz, 1H), 7.43 (q, J=1.8 Hz, 3H), 7.35 (d, J=16.0 Hz, 1H), 6.69 (dd, J=16.0, 7.4 Hz, 1H).

Step 2: Triethoxymethane (31.4 g, 208 mmol) and pyridin-1-ium 4-methylbenzenesulfonate (0.528 g, 2.079 mmol) were added to a stirred solution of (E)-3-(3,5-dichlorophenyl) acrylaldehyde (44 g, 208 mmol) in ethanol (416 mL). The resulting mixture was stirred at 20° C. for 20 hours. A solution of saturated aqueous sodium carbonate (50 mL) was added to the reaction mixture. The resulting mixture was concentrated at 45° C. to remove the ethanol. The concentrate was diluted with water and extracted with hexane. The organic layer was washed with brine, dried over sodium sulfate, filtered and concentrated to afford the title product as a light yellow oil (56.13 g, 93%): $^1$H NMR (400 MHz, $CDCl_3$) δ 7.25 (dt, J=10.6, 1.9 Hz, 3H), 6.61 (dd, J=16.1, 1.1 Hz, 1H), 6.22 (dd, J=16.1, 4.7 Hz, 1H), 5.17 (s, 1H), 5.14-5.00 (m, 1H), 3.78-3.49 (m, 4H), 1.24 (q, J=7.2 Hz, 6H); $^{13}$C NMR (101 MHz, $CDCl_3$) δ 139.34, 135.14, 130.27, 129.88, 127.71, 125.08, 100.60, 61.20, 15.25.

The following compounds were prepared in like manner to the procedure outlined in Example 99:

(E)-1,2-Dichloro-4-(3,3-diethoxyprop-1-en-1-yl) benzene (C450)

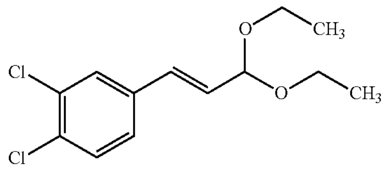 [SMILES: CCOC(/C=C/c1ccc(Cl)c(Cl)c1)OCC]

Isolated as an orange oil (142 g, 91%): $^1$H NMR (300 MHz, $CDCl_3$) δ 7.48 (d, J=2.0 Hz, 1H), 7.39 (dd, J=8.3, 0.8 Hz, 1H), 6.62 (d, J=16.1 Hz, 1H), 6.20 (ddd, J=16.1, 4.9, 0.8 Hz, 1H), 5.06 (dt, J=4.9, 1.0 Hz, 1H), 3.78-3.48 (m, 4H), 1.25 (td, J=7.1, 0.8 Hz, 6H).

(E)-1,2,3-Trichloro-5-(3,3-diethoxyprop-1-en-1-yl) benzene (C451)

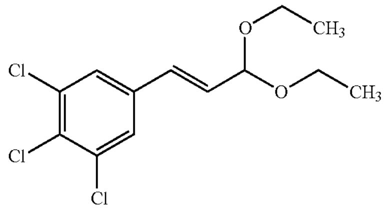 [SMILES: CCOC(/C=C/c1cc(Cl)c(Cl)c(Cl)c1)OCC]

Isolated as an orange oil (40 g, 91%): $^1$H NMR (400 MHz, $CDCl_3$) δ 7.41 (s, 2H), 6.58 (dd, J=16.1, 1.2 Hz, 1H), 6.21 (dd, J=16.1, 4.6 Hz, 1H), 5.06 (dd, J=4.7, 1.2 Hz, 1H), 3.69 (dq, J=9.3, 7.1 Hz, 2H), 3.55 (dq, J=9.5, 7.0 Hz, 2H), 1.25 (t, J=7.1 Hz, 6H).

(E)-1,3-Dichloro-5-(3,3-diethoxyprop-1-en-1-yl)-2-methoxybenzene (C452)

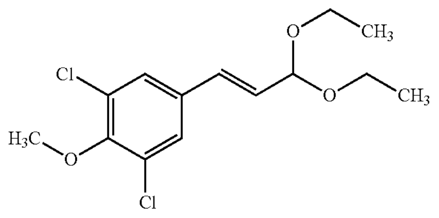 [SMILES: CCOC(/C=C/c1cc(Cl)c(OC)c(Cl)c1)OCC]

Isolated as a yellow oil (2.305 g, 56%): $^1$H NMR (400 MHz, $CDCl_3$) δ 7.32 (s, 2H), 6.56 (d, J=16.0 Hz, 1H), 6.14 (dd, J=16.1, 4.8 Hz, 1H), 5.05 (dd, J=4.8, 1.0 Hz, 1H), 3.89 (s, 3H), 3.69 (m, 2H), 3.55 (m, 2H), 1.25 (t, J=7.1 Hz, 6H); $^{13}$C NMR (101 MHz, $CDCl_3$) δ 151.75, 133.87, 129.87, 129.45, 128.85, 126.91, 100.68, 61.14, 60.73, 15.24; EIMS m/z 304.

(E)-2-Chloro-4-(3,3-diethoxyprop-1-en-1-yl)-1-fluorobenzene (C453)

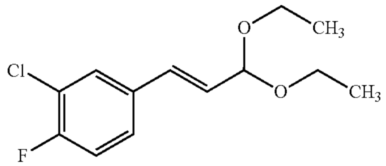 [SMILES: CCOC(/C=C/c1ccc(F)c(Cl)c1)OCC]

Isolated as an orange oil (283 g, 84%): $^1$H NMR (400 MHz, $CDCl_3$) δ 7.44 (dd, J=7.0, 2.2 Hz, 1H), 7.29-7.22 (m, 1H), 7.09 (t, J=8.7 Hz, 1H), 6.62 (dd, J=16.1, 1.2 Hz, 1H), 6.14 (dd, J=16.1, 5.0 Hz, 1H), 5.05 (dd, J=4.9, 1.2 Hz, 1H), 3.70 (dq, J=9.3, 7.0 Hz, 2H), 3.56 (dq, J=9.4, 7.1 Hz, 2H), 1.25 (t, J=7.1 Hz, 6H); $^{13}$C NMR (101 MHz, $CDCl_3$) δ 158.91, 156.42, 133.65, 133.62, 130.47, 128.65, 128.07, 128.05, 126.39, 126.32, 121.26, 121.08, 116.72, 116.51, 100.93, 61.17, 15.24; $^{19}$F NMR (376 MHz, $CDCl_3$) δ −116.36.

In another preparation, isolated as a colorless oil (16.75 g, 64%): $^1$H NMR (400 MHz, $CDCl_3$) δ 7.43 (dd, J=7.0, 2.2 Hz, 1H), 7.25 (m, 1H), 7.07 (t, J=8.7 Hz, 1H), 6.62 (d, J=16.1 Hz, 1H), 6.13 (dd, J=16.1, 4.9 Hz, 1H), 5.05 (dd, J=4.9, 1.0 Hz, 1H), 3.70 (dq, J=9.4, 7.1 Hz, 2H), 3.56 (dq, J=9.4, 7.0 Hz, 2H), 1.25 (t, J=7.1 Hz, 6H); $^{13}$C NMR (101 MHz, $CDCl_3$) δ 158.91, 156.42, 133.65, 133.62, 130.47, 128.65, 128.07, 128.05, 126.39, 126.32, 121.26, 121.08, 116.72, 116.51, 100.93, 61.17, 15.24; $^{19}$F NMR (376 MHz, $CDCl_3$) δ −116.36; EIMS m/z 258.

(E)-3-Chloro-5-(3,3-diethoxyprop-1-en-1-yl)benzonitrile (C454)

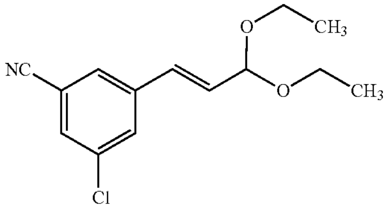 [SMILES: CCOC(/C=C/c1cc(Cl)cc(C#N)c1)OCC]

Isolated as colorless oil (7.62 g, 62%): $^1$H NMR (400 MHz, $CDCl_3$) δ 7.61 (t, J=1.8 Hz, 1H), 7.58-7.53 (m, 1H), 7.51 (t, J=1.7 Hz, 1H), 6.72-6.61 (m, 1H), 6.28 (dd, J=16.1, 4.5 Hz, 1H), 5.09 (dd, J=4.5, 1.3 Hz, 1H), 3.70 (dq, J=9.4, 7.1 Hz, 2H), 3.56 (dq, J=9.4, 7.0 Hz, 2H), 1.26 (t, J=7.0 Hz, 6H).

Example 100: Preparation of (1R,3R)-2,2-dichloro-3-(3,5-dichlorophenyl)-cyclopropane-1-carboxylic acid (C455)

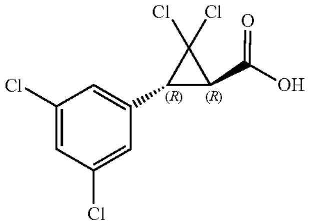

$1^{st}$ resolution: (R)-1-Phenylethanamine (6.49 g, 53.0 mmol) was slowly added to a stirred solution of rac-2,2-dichloro-3-(3,5-dichlorophenyl)cyclopropane-carboxylic acid) (32.45 g, 106 mmol) in acetone (106 mL). The resulting solution was stirred at 45° C. After a solid began to deposit, the mixture was placed at 5° C. for 4 hours. The solid was collected, washed with minimal cold acetone and dried. The white solid salt was diluted with ethyl acetate (100 mL) and washed with aqueous hydrochloric acid (1 N, 10 mL) and brine (30 mL). The organic layer was dried over sodium sulfate, filtered and concentrated to afford the title product as a white solid (10.33 g, 88% enantiomeric excess "ee").

$2^{nd}$ resolution: (R)-1-Phenylethanamine (3.4 g, 28 mmol) was slowly added to a stirred solution of rac-2,2-dichloro-3-(3,5-dichlorophenyl)cyclopropane-carboxylic acid) (10.33 g, 88% ee) in acetone (100 mL). After 2 hours, a solid was collected, washed with minimal cold acetone and dried. The solid was treated with aqueous hydrochloric acid to afford the title compound as a white solid (7.84 g, 97% ee, 24.2%): Specific Rotation: +47.4 (10 mg/mL in acetonitrile, 589 nm, 25.2° C.); $^{1}H$ NMR (300 MHz, $CDCl_3$) δ 7.36 (t, J=1.9 Hz, 1H), 7.17 (dd, J=1.9, 0.7 Hz, 2H), 3.48-3.37 (m, 1H), 2.87 (d, J=8.3 Hz, 1H); $^{13}C$ NMR (400 MHz, DMSO-$d_6$) δ 166.28, 136.40, 133.39, 127.27, 127.04, 61.36, 37.10, 35.98; ESIMS m/z 298.9 ($[M-H]^-$).

ee was determined by Chiral HPLC method as follows: Column: CHIRALPAK© ZWIX(+), particle size 3 μm, dimension 3 mm×150 mm, DAIC 511584; Mobile phase: 49% acetonitrile/49% methanol/water with 50 mM formic acid and diethylamine; Flow rate: 0.5 mL/min; Time: 9 min; Temperature: 25° C.

The following compounds were prepared in like manner to the procedure outlined in Example 100:

(1R,3R)-2,2-Dichloro-3-(3,4-dichlorophenyl)cyclopropane-1-carboxylic acid (C456)

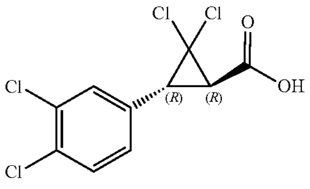

Isolated as a white solid (6.7 g, 30%, 96% ee). Analytical data are consistent with racemic acid $C_3$.

(1R,3R)-2,2-Dichloro-3-(3-chloro-4-fluorophenyl) cyclopropane-1-carboxylic acid (C457)

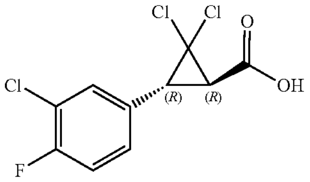

Isolated as a white solid (0.5 g, 13%, 99% ee). Analytical data are consistent with racemic acid $C_{16}$.

(1R,3R)-2,2-Dichloro-3-(3,4,5-trichlorophenyl)cyclopropane-1-carboxylic acid (C458)

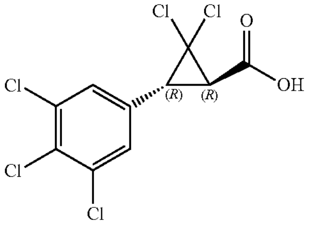

Isolated as a white solid (2 g, 29%, 99% ee). Analytical data are consistent with racemic acid C2.

Example 101: Preparation of (1S,3S)-2,2-Dichloro-3-(3,5-dichlorophenyl)-cyclopropane-1-carboxylic acid (C459)

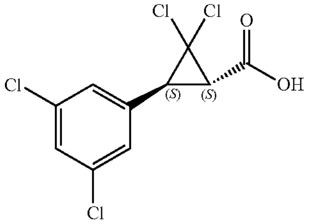

The mother liquor from the $1^{st}$ R,R-acid resolution (from Example 100) was concentrated and dissolved in acetone (~100 mL) and warmed to 45° C. With swirling, (S)-1-phenylethanamine (5.0 g, 41.2 mmol, 0.8 eq.) was added. The resulting solution was stirred at 45° C. After a solid began to deposit, the mixture was placed at 5° C. for 2 hours. A solid was collected, washed with minimal cold acetone and vacuum-dried at 35° C. The solid was treated with aqueous hydrochloric acid to provide the free S,S-acid as a white solid (9.87 g, 85% ee, 59% yield). A second resolution of the 85% ee combined S,S-acid (13.45 g, 41.7 mmol, 85% ee) using the same procedure with (S)-1-phenylethanamine (3.8 g, 31.3 mmol, 0.75 eq.) provided the S,S-acid as a white solid (8.53 g, 26%, 99% ee). Specific Rotation: −51.9 (10 mg/mL in acetonitrile, 589 nm, 25.2° C.). Analytical data are consistent with racemic acid $C_1$.

ee was determined by Chiral HPLC method as follows: Column: CHIRALPAK© ZWIX(+), particle size 3 μm, dimension 3 mm×150 mm L, DAIC 511584; Mobile phase: 49% acetonitrile/49% methanol/water with 50 mM formic acid and diethylamine; Flow rate: 0.5 mL/min; Time: 9 min; Temperature: 25° C.

The following compounds were prepared in like manner to the procedure outlined in Example 101:

(1S,3S)-2,2-Dichloro-3-(3,4-dichlorophenyl)cyclopropane-1-carboxylic acid (C460)

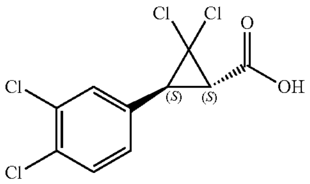

Isolated as a white solid (7 g, 35%, 98% ee). Analytical data are consistent with racemic acid C3.

(1S,3S)-2,2-Dichloro-3-(3-chloro-4-fluorophenyl)cyclopropane-1-carboxylic acid (C461)

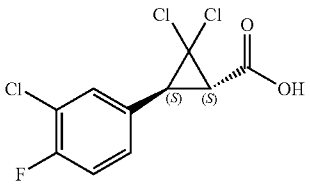

Isolated as a white solid (0.64 g, 27%, 98% ee). Analytical data are consistent with racemic acid C16.

(1S,3S)-2,2-Dichloro-3-(3,4,5-trichlorophenyl)cyclopropane-1-carboxylic acid (C462)

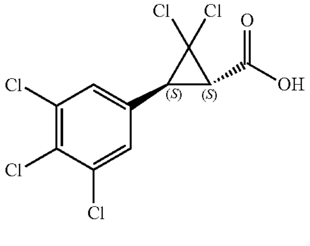

Isolated as a white solid (0.75 g, 41%, 99% ee). Analytical data are consistent with racemic acid $C_2$.

The following compounds were prepared in like manner to the procedure outlined in Example 1:

trans-2,2-dichloro-3-(perfluorophenyl)cyclopropane-1-carboxylic acid (C463)

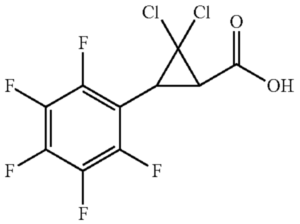

Isolated as a white solid (1.44 g, 67%): $^1$H NMR (400 MHz, $CDCl_3$) δ 10.19 (s, 1H), 3.30 (d, J=8.2 Hz, 1H), 3.09 (d, J=8.3 Hz, 1H); $^{19}$F NMR (376 MHz, $CDCl_3$) δ −140.52, −140.54, −140.58, −140.60, −152.14, −152.20, −152.25, −160.82, −160.84, −160.87, −160.89, −160.93, −160.95; ESIMS m/z 320 ([M−H]$^-$).

The following compounds were prepared in like manner to the procedure outlined in Example 4:

trans-1-(2,2-dichloro-3-(4-methoxyphenyl)cyclopropyl)-2,3,4,5,6-pentafluorobenzene (C464)

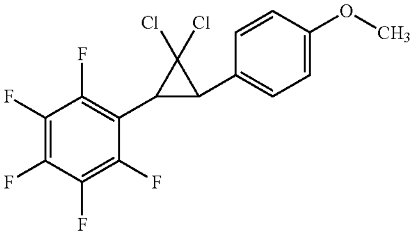 [SMILES: COc1ccc(C2C(c3c(F)c(F)c(F)c(F)c3F)C2(Cl)Cl)cc1]

Isolated as a gold oil (1.38 g, 77%): $^1$H NMR (400 MHz, Chloroform-d) δ 7.32-7.22 (m, 2H), 6.99-6.89 (m, 2H), 3.83 (s, 3H), 3.30 (d, J=8.8 Hz, 1H), 2.89 (d, J=8.8 Hz, 1H). $^{19}$F NMR (376 MHz, $CDCl_3$) δ −140.30, −140.34, −153.63, −153.74, -61.68, −161.70, −161.73.

EIMS m/z 383.

Example 102: Preparation of (E/Z)-1,2,3,4,5-pentafluoro-6-(4-methoxystyryl)benzene (C465)

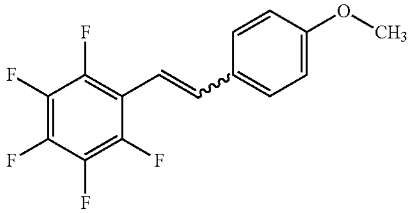 [SMILES: COc1ccc(C=Cc2c(F)c(F)c(F)c(F)c2F)cc1]

n-Butyl lithium solution (2.5 M in hexane, 4.1 mL, 10.2 mmol) was added dropwise to a stirred solution of (4-methoxybenzyl)triphenylphosphonium chloride (4.27 g, 10.2 mmol), in dry tetrahydrofuran (50 mL) at −30° C. The resulting reddish slurry was stirred at −25 to −30° C. for 30 minutes. 2,3,4,5,6-Pentafluorobenzaldehyde (2.0 g, 10.2 mmol) in dry tetrahydrofuran (5 mL) was added dropwise, and the resulting white slurry was stirred at −30° C. for 2 hours and at room temperature overnight. The reaction mixture was carefully quenched with water (~100 mL), and the aqueous mixture was extracted with ethyl ether (3×50 mL). The combined organic extracts were washed with water and brine, dried over anhydrous magnesium sulfate, filtered, and concentrated under reduced pressure on a rotary evaporator. Purification of the crude mixture by silica gel flash chromatography with a mobile phase of 100% hexanes to 25% ethyl acetate in hexanes gave E/Z-1,2,3,4,5-pentafluoro-6-(4-methoxystyryl)benzene (about an 8:2 mixture of E- and Z-isomers) as a white solid (1.7 g, 52.7%): $^{1}H$ NMR (400 MHz, $CDCl_3$) δ 7.53-7.43 (m, 2H), 7.38 (d, J=16.7 Hz, 1H), 7.00-6.74 (m, 3H), 3.82 (d, J=21.1 Hz, 3H). $^{13}C$ NMR (101 MHz, $CDCl_3$) δ 160.38, 136.73, 129.32, 129.27, 128.28, 114.30, 113.92, 112.78, 110.43, 110.40, 77.32, 77.20, 77.00, 76.68, 55.36, 55.20; EIMS m/z 300.

Example 103: Preparation of cis-2,2-dichloro-3-(3,5-dichlorophenyl)cyclopropanecarboxylic acid (C466)

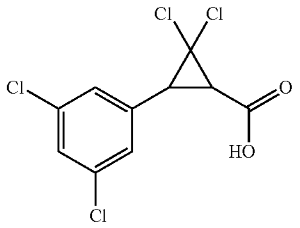 [SMILES: O=C(O)C1C(c2cc(Cl)cc(Cl)c2)C1(Cl)Cl]

Sodium chloride (1.0 g, 11.06 mmol) was added portionwise to a stirred solution of cis-2,2-dichloro-3-(3,5-dichlorophenyl)cyclopropane-1-carbaldehyde (C467) (0.897 g, 3.16 mmol), sodium dihydrogenphosphate (0.758 g, 6.32 mmol), 2-methylbut-2-ene (2.0 M solution in tetrahydrofuran, 7.1 mL, 14.21 mmol) in acetone (12 mL) and water (4 mL). The resulting pale yellow solution was stirred at room temperature for 4 hours, then poured into water (100 mL) and acidified to pH=2 with aqueous hydrochloric acid (1 N). The aqueous mixture was extracted with ethyl acetate (3×50 mL). The combined organic extracts were washed with water and brine, dried over anhydrous magnesium sulfate, filtered, and concentrated under reduced pressure on a rotary evaporator. Purification by C-18 flash chromatography (to remove the trans isomer byproduct) gave cis-2,2-dichloro-3-(3,5-dichlorophenyl)cyclopropane-1-carboxylic acid as a white solid (0.225 g, 22.6%): $^{1}H$ NMR (400 MHz, $CDCl_3$) δ 8.04 (s, 1H), 7.32 (td, J=1.9, 0.8 Hz, 1H), 7.21 (dd, J=1.9, 1.0 Hz, 2H), 3.28 (dt, J=11.2, 1.0 Hz, 1H), 2.93 (d, J=11.1 Hz, 1H).

Example 104: Preparation of cis-2,2-dichloro-3-(3,5-dichlorophenyl)cyclopropane-1-carbaldehyde (C467)

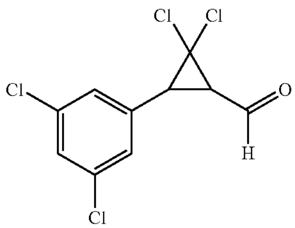 [SMILES: O=CC1C(c2cc(Cl)cc(Cl)c2)C1(Cl)Cl]

p-Toluenesulfonic acid monohydrate (2.19 g, 11.52 mmol) was added to a stirred solution of 2-(trans-2,2-dichloro-3-(3,5-dichlorophenyl)cyclopropyl)-1,3-dioxolane (C468) (0.945 g, 2.88 mmol), in 1:1 tetrahydrofuran/water (20 mL). The solution was heated at 70° C. for a total of 36 hours, cooled, and poured into water (200 mL). The aqueous mixture was extracted with ethyl acetate (3×50 mL). The combined organic extracts were washed with water and brine, dried over anhydrous magnesium sulfate, filtered, and concentrated under reduced pressure on a rotary evaporator. Purification by silica gel flash chromatography yielded cis-2,2-dichloro-3-(3,5-dichlorophenyl)cyclopropane-1-carbaldehyde as a yellow oil (0.897 g, 93%): EIMS m/z 284.

Example 105: Preparation of 2-(cis-2,2-dichloro-3-(3,5-dichlorophenyl)cyclopropyl)-1,3-dioxolane (C468)

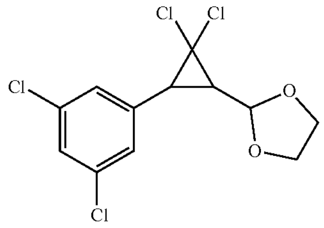 [SMILES: Clc1cc(Cl)cc(C2C(C3OCCO3)C2(Cl)Cl)c1]

Powdered sodium hydroxide (8.16 g, 204 mmol) was added portionwise to a stirred solution of (Z)-2-(3,5-dichlorostyryl)-1,3-dioxolane (C469) (5 g, 20.4 mmol), and tetrabutylammonium hexafluorophosphate(V) (0.395 g, 1.02 mmol) in chloroform (32.7 mL) and water (0.294 mL). The heterogeneous mixture was stirred at 35° C. for 12 hours and then was poured into water (100 mL). The aqueous mixture was extracted with ethyl acetate (3×100 mL). The combined organic extracts were washed with water and brine, dried over anhydrous magnesium sulfate, filtered, and concentrated under reduced pressure on a rotary evaporator. Purification by silica gel flash chromatography with a mobile phase of ethyl acetate and hexanes afforded 2-(cis-2,2-dichloro-3-(3,5-dichlorophenyl)cyclopropyl)-1,3-dioxolane as a clear colorless oil (4.4 g, 62%): $^{1}H$ NMR (400 MHz, $CDCl_3$) δ 7.41 (dd, J=2.0, 1.1 Hz, 2H), 7.36-7.25 (m, 2H), 4.57 (d, J=8.0 Hz, 1H), 4.22-4.03 (m, 2H), 4.04-3.85 (m, 2H), 3.00 (dt, J=11.2, 1.1 Hz, 1H), 2.19 (dd, J=11.1, 8.0 Hz, 1H); $^{13}C$ NMR (101 MHz, $CDCl_3$) δ 135.17, 134.94, 128.95, 128.08, 127.28, 102.06, 77.32, 77.20, 77.00, 76.68, 65.39, 65.28, 59.78, 36.38, 35.96; EIMS m/z 328.

Example 106: Preparation of (Z)-2-(3,5-dichlorostyryl)-1,3-dioxolane (C469)

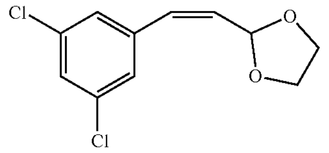 [SMILES: Clc1cc(Cl)cc(/C=C\C2OCCO2)c1]

Tris(dioxa-3,6-heptyl)amine (27.7 g, 86.0 mmol) was added dropwise to a stirred solution of 3,5-dichlorobenzaldehyde (15 g, 86 mmol), and ((1,3-dioxolan-2-yl)methyl) triphenylphosphonium bromide (36.8 g, 86 mmol) in 1:1 dichloromethane/water (400 mL). To the biphasic mixture was then added potassium carbonate (11.85 g, 86 mmol). The reaction mixture was heated at reflux for a total of 20 hours, cooled, and poured into water (200 mL). The aqueous mixture was extracted with dichloromethane (3×100 mL). The combined organic extracts were washed with water and brine, dried over anhydrous magnesium sulfate, filtered, and concentrated under reduced pressure on a rotary evaporator. Purification by silica gel flash chromatography with a mobile phase of ethyl acetate and hexanes gave (Z)-2-(3,5-dichlorostyryl)-1,3-dioxolane as a waxy white solid (11.2 g, 53%): $^1H$ NMR (400 MHz, $CDCl_3$) δ 7.37-7.18 (m, 3H), 6.65 (d, J=11.7 Hz, 1H), 5.80 (dd, J=11.8, 7.4 Hz, 1H), 5.43 (dd, J=7.4, 0.9 Hz, 1H), 4.18-4.02 (m, 2H), 4.03-3.87 (m, 2H); EIMS m/z 245.

Example 107: Preparation of trans-2-bromo-2-chloro-3-(3,5-dichlorophenyl)cyclopropane-1-carboxylic acid (C470)

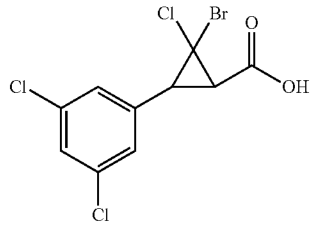 [SMILES: O=C(O)C1C(c2cc(Cl)cc(Cl)c2)C1(Cl)Br]

Powdered sodium hydroxide (0.727 g, 18.17 mmol) was added portionwise to a stirring solution of (E)-1,3-dichloro-5-(3,3-diethoxyprop-1-en-1-yl)benzene (C449) (0.5 g, 1.82 mmol) and tetrabutylammonium hexafluorophosphate (0.07 g, 0.182 mmol) dibromochloromethane (5 mL). The resulting yellow suspension of solids was heated to 45° C. for a total of 7 hours, cooled, and quenched with water (100 mL). The mixture was extracted with ether (3×50 mL). The combined organic extracts were washed with water and brine, dried over anhydrous magnesium sulfate, filtered, and concentrated under reduced pressure on a rotary evaporator. Purification by silica gel flash chromatography with a mobile phase of ethyl acetate and hexanes gave trans-1-(2-bromo-2-chloro-3-(diethoxymethyl)cyclopropyl)-3,5-dichlorobenzene (0.38 g, 34.2%) as a yellow oil.

Aqueous hydrochloric acid (2 N, 5 mL, 10 mmol) was added dropwise to a stirring solution of trans-1-(2-bromo-2-chloro-3-(diethoxymethyl)cyclopropyl)-3,5-dichlorobenzene (0.38 g, 0.956 mmol) in acetone (10 mL). The resulting colorless solution was heated at 35° C. for a total of 8 hours, cooled, and poured into water (100 mL). The aqueous mixture was extracted with ethyl acetate (3×50 mL). The combined organic extracts were washed with water and brine, dried over anhydrous magnesium sulfate, filtered, and concentrated under reduced pressure on a rotary evaporator. Purification by silica gel flash chromatography with a mobile phase of ethyl acetate and hexanes afforded trans-2-bromo-2-chloro-3-(3,5-dichlorophenyl)cyclopropane-1-carbaldehyde (120 mg, 36.3%) as a yellow oil.

2-Methylbutene (2.0 M in tetrahydrofuran, 0.82 mL, 1.644 mmol) was added dropwise to a stirring solution of trans-2-bromo-2-chloro-3-(3,5-dichlorophenyl)cyclopropane-1-carbaldehyde (120 mg, 0.365 mmol) and sodium dihydrogenphosphate (88 mg, 0.731 mmol) in acetone (3 mL) and water (1 mL). The resulting colorless cloudy suspension was treated with 80% sodium chlorite (147 mg, 1.297 mmol). The reaction mixture was stirred at room temperature for 12 hours, quenched with aqueous hydrochloric acid (1 N, 10 mL), and extracted with ethyl acetate (3×50 mL). The combined organic extracts were washed with water and brine, dried over anhydrous magnesium sulfate, filtered, and concentrated under reduced pressure on a rotary evaporator. Purification by C-18 flash chromatography (acetonitrile/water) provided trans-2-bromo-2-chloro-3-(3,5-dichlorophenyl)cyclopropane-1-carboxylic acid as a white solid (0.083 g, 62.7%): $^1H$ NMR (400 MHz, $CDCl_3$) δ 7.37 (q, J=1.8 Hz, 2H), 7.17 (ddd, J=7.0, 1.9, 0.7 Hz, 1H), 3.39 (dd, J=56.9, 8.2 Hz, 1H), 2.88 (dd, J=45.2, 8.3 Hz, 1H); ESIMS m/z 343 ([M−H]$^-$).

The following compounds were prepared in like manner to the procedure outlined in Example 107:

trans-2-Bromo-3-(3,5-dichlorophenyl)-2-fluorocyclopropane-1-carboxylic acid (C471)

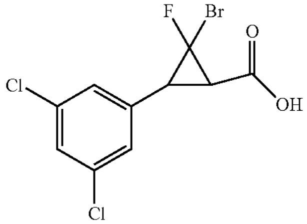 [SMILES: O=C(O)C1C(c2cc(Cl)cc(Cl)c2)C1(F)Br]

Isolated as a white solid (0.098 g, 51.2%): $^1H$ NMR (400 MHz, $CDCl_3$) δ 8.31 (s, 1H), 7.35 (dt, J=6.0, 1.9 Hz, 1H), 7.15 (dd, J=15.6, 1.8 Hz, 2H), 3.61-3.18 (m, 1H), 2.95-2.68 (m, 1H); $^{19}F$ NMR (376 MHz, $CDCl_3$) δ −134.90, −135.76, −135.78; ESIMS m/z 327 ([M−H]$^-$).

trans-2-Chloro-3-(3,5-dichlorophenyl)-2-fluorocyclopropane-1-carboxylic acid (C472)

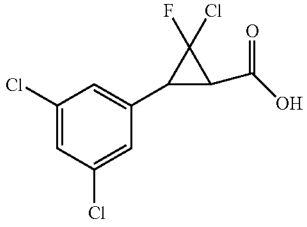 [SMILES: O=C(O)C1C(c2cc(Cl)cc(Cl)c2)C1(F)Cl]

Isolated as a pale yellow solid (0.107 g, 46.1%): $^1$H NMR (400 MHz, $CDCl_3$) δ 8.69 (s, 1H), 7.35 (dt, J=4.0, 1.9 Hz, 1H), 7.26-7.10 (m, 2H), 3.77-3.12 (m, 1H), 3.07-2.63 (m, 1H); ESIMS m/z 282 ($[M-H]^-$).

It is recognized that some reagents and reaction conditions may not be compatible with certain functionalities that may be present in certain molecules of Formula One or certain molecules used in the preparation of certain molecules of Formula One. In such cases, it may be necessary to employ standard protection and deprotection protocols comprehensively reported in the literature and well known to a person skilled in the art. In addition, in some cases it may be necessary to perform further routine synthetic steps not described herein to complete the synthesis of desired molecules. A person skilled in the art will also recognize that it may be possible to achieve the synthesis of desired molecules by performing some of the steps of the synthetic routes in a different order to that described. A person skilled in the art will also recognize that it may be possible to perform standard functional group interconversions or substitution reactions on desired molecules to introduce or modify substituents.

Biological Assays

The following bioassays against Beet Armyworm (*Spodoptera exigua*), Cabbage Looper (*Trichoplusia ni*), Green Peach Aphid (*Myzus persicae*), and Yellow Fever Mosquito (*Aedes aegypti*), are included herein due to the damage they inflict. Furthermore, the Beet Armyworm and Cabbage Looper are two good indicator species for a broad range of chewing pests. Additionally, the Green Peach Aphid is a good indicator species for a broad range of sap-feeding pests. The results with these three indicator species along with the Yellow Fever Mosquito show the broad usefulness of the molecules of Formula One in controlling pests in Phyla Arthropoda, Mollusca, and Nematoda (Drewes et al.)

Example A: Bioassays on Beet Armyworm (*Spodoptera exigua*, LAPHEG) ("BAW"), and Cabbage Looper (*Trichoplusia ni*, TRIPNI) ("CL")

Beet armyworm is a serious pest of economic concern for alfalfa, asparagus, beets, citrus, corn, cotton, onions, peas, peppers, potatoes, soybeans, sugar beets, sunflowers, tobacco, and tomatoes, among other crops. It is native to Southeast Asia but is now found in Africa, Australia, Japan, North America, and Southern Europe. The larvae may feed in large swarms causing devastating crop losses. It is known to be resistant to several pesticides.

Cabbage looper is a serious pest found throughout the world. It attacks alfalfa, beans, beets, broccoli, Brussel sprouts, cabbage, cantaloupe, cauliflower, celery, collards, cotton, cucumbers, eggplant, kale, lettuce, melons, mustard, parsley, peas, peppers, potatoes, soybeans, spinach, squash, tomatoes, turnips, and watermelons, among other crops. This species is very destructive to plants due to its voracious appetite. The larvae consume three times their weight in food daily. The feeding sites are marked by large accumulations of sticky, wet, fecal material, which may contribute to higher disease pressure thereby causing secondary problems on the plants in the site. It is known to be resistant to several pesticides.

Consequently, because of the above factors control of these pests is important. Furthermore, molecules that control these pests (BAW and CL), which are known as chewing pests, will be useful in controlling other pests that chew on plants.

Certain molecules disclosed in this document were tested against BAW and CL using procedures described in the following examples. In the reporting of the results, the "BAW & CL Rating Table" was used (See Table Section).

Bioassays on BAW

Bioassays on BAW were conducted using a 128-well diet tray assay. One to five second instar BAW larvae were placed in each well (3 mL) of the diet tray that had been previously filled with approximately 1.5 mL of artificial diet to which 50 μg/cm$^2$ of the test molecule (dissolved in 50 μL of 90:10 acetone-water mixture) had been applied (to each of eight wells) and then allowed to dry. Trays were covered with a clear self-adhesive cover, vented to allow gas exchange, and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Bioassays on CL

Bioassays on CL were conducted using a 128-well diet tray assay. one to five second instar CL larvae were placed in each well (3 mL) of the diet tray that had been previously filled with 1 mL of artificial diet to which 50 μg/cm$^2$ of the test molecule (dissolved in 50 μL of 90:10 acetone-water mixture) had been applied (to each of eight wells) and then allowed to dry. Trays were covered with a clear self-adhesive cover, vented to allow gas exchange, and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Example B: Bioassays on Green Peach Aphid (*Myzus persicae*, MYZUPE) ("GPA")

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other crops. GPA also attacks many ornamental crops such as carnation, chrysanthemum, flowering white cabbage, poinsettia, and roses. GPA has developed resistance to many pesticides. Currently, it is a pest that has the third largest number of reported cases of insect resistance (Sparks et al.). Consequently, because of the above factors control of this pest is important. Furthermore, molecules that control this pest (GPA), which is known as a sap-feeding pest, are useful in controlling other pests that feed on the sap from plants.

Certain molecules disclosed in this document were tested against GPA using procedures described in the following example. In the reporting of the results, the "GPA & YFM Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test molecules (2 mg) were dissolved in 2 mL of acetone/methanol (1:1) solvent, forming stock solutions of 1000 ppm test molecule. The stock solutions were diluted 5× with 0.025% Tween 20 in water to obtain the solution at 200 ppm test molecule. A hand-held aspirator-type sprayer was used for spraying a solution to both sides of cabbage leaves until runoff. Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent control was measured using Abbott's correction formula (W. S. Abbott, "A Method of Computing the Effectiveness of an Insecticide" J. Econ. Entomol. 18 (1925), pp. 265-267) as follows. Corrected % Control=100*(X−Y)/X where X=No. of live aphids on solvent check plants and Y=No. of live aphids on treated plants. The results are indicated in the table entitled "Table ABC: Biological Results" (See Table Section).

Example C: Bioassays on Yellow Fever Mosquito (*Aedes aegypti*, AEDSAE) ("YFM")

YFM prefers to feed on humans during the daytime and is most frequently found in or near human habitations. YFM is a vector for transmitting several diseases. It is a mosquito that can spread the dengue fever and yellow fever viruses. Yellow fever is the second most dangerous mosquito-borne disease after malaria. Yellow fever is an acute viral hemorrhagic disease and up to 50% of severely affected persons without treatment will die from yellow fever. There are an estimated 200,000 cases of yellow fever, causing 30,000 deaths worldwide each year. Dengue fever is a nasty, viral disease; it is sometimes called "breakbone fever" or "breakheart fever" because of the intense pain it can produce. Dengue fever kills about 20,000 people annually. Consequently, because of the above factors control of this pest is important. Furthermore, molecules that control this pest (YFM), which is known as a sucking pest, are useful in controlling other pests that cause human and animal suffering.

Certain molecules disclosed in this document were tested against YFM using procedures described in the following paragraph. In the reporting of the results, the "GPA & YFM Rating Table" was used (See Table Section).

Master plates containing 400 μg of a molecule dissolved in 100 μL of dimethyl sulfoxide (DMSO) (equivalent to a 4000 ppm solution) are used. A master plate of assembled molecules contains 15 μL per well. To this plate, 135 μL of a 90:10 water/acetone mixture is added to each well. A robot is programmed to dispense 15 μL aspirations from the master plate into an empty 96-well shallow plate ("daughter" plate). There are 6 reps ("daughter" plates) created per master. The created "daughter" plates are then immediately infested with YFM larvae.

The day before plates are to be treated, mosquito eggs are placed in Millipore water containing liver powder to begin hatching (4 g. into 400 mL). After the "daughter" plates are created using the robot, they are infested with 220 μL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality. The results are indicated in the table entitled "Table ABC: Biological Results" (See Table Section).

Agriculturally Acceptable Acid Addition Salts, Salt Derivatives, Solvates, Ester Derivatives, Polymorphs, Isotopes, and Radionuclides Molecules of Formula One may be formulated into agriculturally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxyl-methanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative may be prepared by contacting a free base with a sufficient amount of the desired acid to produce a salt. A free base may be regenerated by treating the salt with a suitable dilute aqueous base solution such as dilute aqueous sodium hydroxide, potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One containing an acid functionality may be made into ester derivatives. These ester derivatives can then be applied in the same manner as the molecules disclosed in this document are applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2H$ (also known as deuterium) or $^3H$ (also known as tritium) in place of $^1H$. Molecules of Formula One may be made with different radionuclides. Of particular importance are molecules having $^{14}C$ (also known as radiocarbon). Molecules of Formula One having deuterium, tritium, or $^{14}C$ may be used in biological studies allowing tracing in chemical and physiological processes and half-life studies, as well as, MoA studies.

Combinations

In another embodiment of this invention, molecules of Formula One may be used in combination (such as, in a compositional mixture, or a simultaneous or sequential application) with one or more active ingredients.

In another embodiment of this invention, molecules of Formula One may be used in combination (such as, in a compositional mixture, or a simultaneous or sequential application) with one or more active ingredients each having a MoA that is the same as, similar to, but more likely—different from, the MoA of the molecules of Formula One.

In another embodiment, molecules of Formula One may be used in combination (such as, in a compositional mixture, or a simultaneous or sequential application) with one or more molecules having acaricidal, algicidal, avicidal, bactericidal, fungicidal, herbicidal, insecticidal, molluscicidal, nematicidal, rodenticidal, and/or virucidal properties.

In another embodiment, the molecules of Formula One may be used in combination (such as, in a compositional mixture, or a simultaneous or sequential application) with one or more molecules that are antifeedants, bird repellents, chemosterilants, herbicide safeners, insect attractants, insect repellents, mammal repellents, mating disrupters, plant activators, plant growth regulators, and/or synergists.

In another embodiment, molecules of Formula One may also be used in combination (such as in a compositional mixture, or a simultaneous or sequential application) with one or more biopesticides.

In another embodiment, in a pesticidal composition combinations of a molecule of Formula One and an active ingredient may be used in a wide variety of weight ratios. For example, in a two-component mixture, the weight ratio of a molecule of Formula One to an active ingredient, the weight ratios in Table B may be used. However, in general, weight ratios less than about 10:1 to about 1:10 are preferred. It is also preferred sometimes to use a three, four, five, six, seven, or more, component mixture comprising a molecule of Formula One and an additional two or more active ingredients.

Weight ratios of a molecule of Formula One to an active ingredient may also be depicted as X:Y; wherein X is the parts by weight of a molecule of Formula One and Y is the parts by weight of active ingredient. The numerical range of the parts by weight for X is $0<X\leq 100$ and the parts by weight for Y is $0<Y\leq 100$ and is shown graphically in TABLE C. By way of non-limiting example, the weight ratio of a molecule of Formula One to an active ingredient may be 20:1.

Ranges of weight ratios of a molecule of Formula One to an active ingredient may be depicted as $X_1:Y_1$ to $X_2:Y_2$, wherein X and Y are defined as above.

In one embodiment, the range of weight ratios may be $X_1:Y_1$ to $X_2:Y_2$, wherein $X_1>Y_1$ and $X_2<Y_2$. By way of non-limiting example, the range of a weight ratio of a molecule of Formula One to an active ingredient may be between 3:1 and 1:3, inclusive of the endpoints.

In another embodiment, the range of weight ratios may be $X_1:Y_1$ to $X_2:Y_2$, wherein $X_1>Y_1$ and $X_2>Y_2$. By way of non-limiting example, the range of weight ratio of a molecule of Formula One to an active ingredient may be between 15:1 and 3:1, inclusive of the endpoints.

In another embodiment, the range of weight ratios may be $X_1:Y_1$ to $X_2:Y_2$, wherein $X_1<Y_1$ and $X_2<Y_2$. By way of non-limiting example, the range of weight ratios of a molecule of Formula One to an active ingredient may be between about 1:3 and about 1:20, inclusive of the endpoints.

Formulations

A pesticide is many times not suitable for application in its pure form. It is usually necessary to add other substances so that the pesticide may be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions.

Pesticides are applied most often as aqueous suspensions or emulsions prepared from concentrated formulations of such pesticides. Such water-soluble, water-suspendable, or emulsifiable formulations are either solids, usually known as wettable powders, water dispersible granules, liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may, also be added to increase the density and viscosity of the aqueous carrier. It is often most effective to grind and mix the pesticide at the same time by preparing the aqueous mixture and homogenizing it in an implement such as a sand mill, ball mill, or piston-type homogenizer. The pesticide in suspension might be microencapsulated in plastic polymer.

Oil dispersions (OD) comprise suspensions of organic solvent-insoluble pesticides finely dispersed in a mixture of organic solvent and emulsifiers at a concentration in the range from about 2% to about 50% by weight. One or more pesticide might be dissolved in the organic solvent. Useful organic solvents include aromatics, especially xylenes and petroleum fractions, especially the high-boiling naphthalenic and olefinic portions of petroleum such as heavy aromatic naphtha. Other solvents may include vegetable oils, seed oils, and esters of vegetable and seed oils. Suitable emulsifiers for oil dispersions are selected from conventional anionic and non-ionic surfactants. Thickeners or gelling agents are added in the formulation of oil dispersions to modify the rheology or flow properties of the liquid and to prevent separation and settling of the dispersed particles or droplets.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier, which has been pre-formed to the appropriate particle size, in the range of from about 0.5 mm to about 3 mm. Such compositions may also be formulated by making a dough or paste of the carrier and molecule, and then crushing and drying to obtain the desired granular particle size. Another form of granules is a water emulsifiable granule (EG). It is a formulation consisting of granules to be applied as a conventional oil-in-water emulsion of the active ingredient(s), either solubilized or diluted in an organic solvent, after disintegration and dissolution in water. Water emulsifiable granules comprise one or several active ingredient(s), either solubilized or diluted in a suitable organic solvent that is (are) absorbed in a water soluble polymeric shell or some other type of soluble or insoluble matrix.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. Dusts may be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions, the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait, they also consume the pesticide. Baits may take the form of granules, gels, flowable powders, liquids, or solids. Baits may be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings, or in special chambers.

Pesticides may be microencapsulated by suspending the pesticide particles or droplets in plastic polymers of various types. By altering, the chemistry of the polymer or by changing factors in the processing, microcapsules may be formed of various sizes, solubility, wall thicknesses, and degrees of penetrability. These factors govern the speed with which the active ingredient within is released, which in turn, affects the residual performance, speed of action, and odor of the product. The microcapsules might be formulated as suspension concentrates or water dispersible granules.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one molecule which is agriculturally active, and is individually coated with a monolamellar or oligolamellar layer comprising: (1) at least one non-ionic lipophilic surface-active agent, (2) at least one non-ionic hydrophilic surface-active agent, and (3) at least one ionic surface-active agent, wherein the globules having a mean particle diameter of less than 800 nanometers.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance that adsorbs onto the surface of particles, helps to preserve the state of dispersion of the particles, and prevents them from reaggregating. Dispersing agents are added to agrochemical formulations to facilitate dispersion and suspension during manufacture, and to ensure the particles redisperse into water in a spray tank. They are widely used in wettable powders, suspension concentrates, and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium-naphthalene-sulfonate-formaldehyde-condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol-ethoxylate-phosphate-esters; aliphatic alcohol ethoxylates; alkyl ethoxylates; EO-PO block copolymers; and graft copolymers.

An emulsifying agent is a substance that stabilizes a suspension of droplets of one liquid phase in another liquid phase. Without the emulsifying agent, the two liquids would separate into two immiscible liquid phases. The most commonly used emulsifier blends contain an alkylphenol or an aliphatic alcohol with twelve or more ethylene oxide units and the oil-soluble calcium salt of dodecylbenzenesulfonic acid. A range of hydrophile-lipophile balance ("HLB") values from about 8 to about 18 will normally provide good stable emulsions. Emulsion stability can sometimes be improved by the addition of a small amount of an EO-PO block copolymer surfactant.

A solubilizing agent is a surfactant that will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; and aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules, and water-dispersible granules.

Organic solvents are used mainly in the formulation of emulsifiable concentrates, oil-in-water emulsions, suspoemulsions, oil dispersions, and ultra-low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, oil dispersions, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate and oil dispersion formulations using clays and silicas. Examples of these types of materials, include, but are not limited to, montmorillonite, bentonite, magnesium aluminum silicate, and attapulgite. Water-soluble polysaccharides in water based suspension concentrates have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); and hydroxyethyl cellulose (HEC). Other types of anti-settling agents are based on modified starches, polyacrylates, polyvinyl alcohol, and polyethylene oxide. Another good anti-settling agent is xanthan gum.

Microorganisms can cause spoilage of formulated products. Therefore, preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

Applications

Molecules of Formula One may be applied to any locus. Particular loci to apply such molecules include loci where alfalfa, almonds, apples, barley, beans, canola, corn, cotton, crucifers, flowers, fodder species (Rye Grass, Sudan Grass, Tall Fescue, Kentucky Blue Grass, and Clover), fruits, lettuce, oats, oil seed crops, oranges, peanuts, pears, peppers, potatoes, rice, sorghum, soybeans, strawberries, sugarcane, sugarbeets, sunflowers, tobacco, tomatoes, wheat (for example, Hard Red Winter Wheat, Soft Red Winter Wheat, White Winter Wheat, Hard Red Spring Wheat, and Durum Spring Wheat), and other valuable crops are growing or the seeds thereof are going to be planted.

Molecules of Formula One may also be applied where plants, such as crops, are growing and where there are low levels (even no actual presence) of pests that can commercially damage such plants. Applying such molecules in such locus is to benefit the plants being grown in such locus. Such benefits, may include, but are not limited to: helping the plant grow a better root system; helping the plant better withstand stressful growing conditions; improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

Molecules of Formula One may be applied with ammonium sulfate when growing various plants as this may provide additional benefits.

Molecules of Formula One may be applied on, in, or around plants genetically modified to express specialized traits, such as *Bacillus thuringiensis* (for example, Cry1Ab, Cry1Ac, Cry1Fa, Cry1A.105, Cry2Ab, Vip3A, mCry3A, Cry3Ab, Cry3Bb, Cry34Ab1/Cry35Ab1), other insecticidal toxins, or those expressing herbicide tolerance, or those with "stacked" foreign genes expressing insecticidal toxins, herbicide tolerance, nutrition-enhancement, or any other beneficial traits.

Molecules of Formula One may be applied to the foliar and/or fruiting portions of plants to control pests. Either such molecules will come in direct contact with the pest, or the pest will consume such molecules when eating the plant or while extracting sap or other nutrients from the plant.

Molecules of Formula One may also be applied to the soil, and when applied in this manner, root and stem feeding pests may be controlled. The roots may absorb such molecules thereby taking it up into the foliar portions of the plant to control above ground chewing and sap feeding pests.

Systemic movement of pesticides in plants may be utilized to control pests on one portion of the plant by applying (for example by spraying a locus) a molecule of Formula One to a different portion of the plant. For example, control of foliar-feeding insects may be achieved by drip irrigation or furrow application, by treating the soil with for example pre- or post-planting soil drench, or by treating the seeds of a plant before planting.

Molecules of Formula One may be used with baits. Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait.

Molecules of Formula One may be encapsulated inside, or placed on the surface of a capsule. The size of the capsules can range from nanometer size (about 100-900 nanometers in diameter) to micrometer size (about 10-900 microns in diameter).

Molecules of Formula One may be applied to eggs of pests. Because of the unique ability of the eggs of some pests to resist certain pesticides, repeated applications of such molecules may be desirable to control newly emerged larvae.

Molecules of Formula One may be applied as seed treatments. Seed treatment may be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide tolerance, such as "Roundup Ready" seed, or those with "stacked" foreign genes expressing insecticidal toxins, herbicide tolerance, nutrition-enhancement, drought tolerance, or any other beneficial traits. Furthermore, such seed treatments with molecules of Formula One may further enhance the ability of a plant to withstand stressful growing conditions better. This results in a healthier, more vigorous plant, which can lead to higher yields at harvest time. Generally, about 1 gram of such molecules to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits. Molecules of Formula One may be applied with one or more active ingredients in a soil amendment.

Molecules of Formula One may be used for controlling endoparasites and ectoparasites in the veterinary medicine sector or in the field of non-human-animal keeping. Such molecules may be applied by oral administration in the form of, for example, tablets, capsules, drinks, granules, by dermal application in the form of, for example, dipping, spraying, pouring on, spotting on, and dusting, and by parenteral administration in the form of, for example, an injection.

Molecules of Formula One may also be employed advantageously in livestock keeping, for example, cattle, chickens, geese, goats, pigs, sheep, and turkeys. They may also be employed advantageously in pets such as, horses, dogs, and cats. Particular pests to control would be flies, fleas, and ticks that are bothersome to such animals. Suitable formulations are administered orally to the animals with the drinking water or feed. The dosages and formulations that are suitable depend on the species.

Molecules of Formula One may also be used for controlling parasitic worms, especially of the intestine, in the animals listed above.

Molecules of Formula One may also be employed in therapeutic methods for human health care. Such methods include, but are limited to, oral administration in the form of, for example, tablets, capsules, drinks, granules, and by dermal application.

Molecules of Formula One may also be applied to invasive pests. Pests around the world have been migrating to new environments (for such pest) and thereafter becoming a new invasive species in such new environment. Such molecules may also be used on such new invasive species to control them in such new environments.

Before a pesticide may be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

Molecules according to Formula One may be tested to determine its efficacy against pests. Furthermore, mode of action studies may be conducted to determine if said molecule has a different mode of action than other pesticides. Thereafter, such acquired data may be disseminated, such as by the internet, to third parties.

The headings in this document are for convenience only and must not be used to interpret any portion hereof.

TABLES

TABLE B

| Weight Ratios<br>Molecule of the Formula One:active ingredient |
|---|
| 100:1 to 1:100 |
| 50:1 to 1:50 |
| 20:1 to 1:20 |
| 10:1 to 1:10 |
| 5:1 to 1:5 |
| 3:1 to 1:3 |
| 2:1 to 1:2 |
| 1:1 |

TABLE C
| | | | | | | | | | | |
|---|---|---|---|---|---|---|---|---|---|---|
| active ingredient | 100 | X, Y | | X, Y | | | X, Y | | | |
| (Y) | 50 | X, Y | X, Y | X, Y | | | X, Y | X, Y | | |
| Parts by weight | 20 | X, Y | | X, Y | X, Y | | X, Y | | X, Y | |
| | 15 | X, Y | X, Y | | | | | X, Y | X, Y | X, Y |
| | 10 | X, Y | | X, Y | | | | | | |
| | 5 | X, Y | X, Y | X, Y | | | | X, Y | | |
| | 3 | X, Y | X, Y | | X, Y | X, Y | | X, Y | X, Y | X, Y |
| | 2 | X, Y | | X, Y | X, Y | | X, Y | | X, Y | |
| | 1 | X, Y | X, Y | X, Y | X, Y | X, Y | X, Y | X, Y | X, Y | X, Y |
| | | 1 | 2 | 3 | 5 | 10 | 15 | 20 | 50 | 100 |
| | | molecule of Formula One (X) Parts by weight | | | | | | | | |
TABLE 2
Structure and preparation method for F Series molecules
| No. | Structure | Prep.* |
|---|---|---|
| F1 | 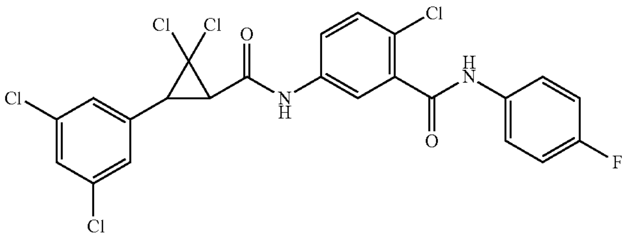 | 13 |
| F2 | 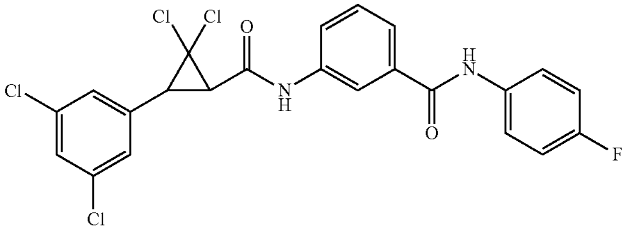 [SMILES: O=C(Nc1ccc(F)cc1)c1cccc(NC(=O)C2C(c3cc(Cl)cc(Cl)c3)C2(Cl)Cl)c1] | 13 |
| F3 | 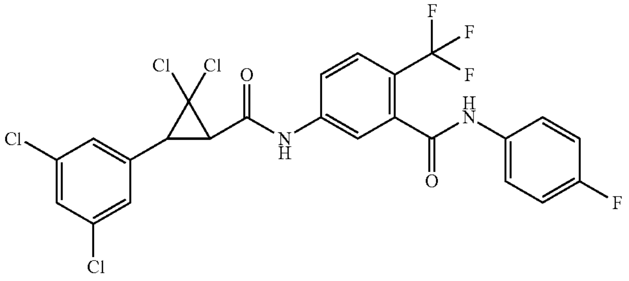 [SMILES: O=C(Nc1ccc(F)cc1)c1cc(NC(=O)C2C(c3cc(Cl)cc(Cl)c3)C2(Cl)Cl)ccc1C(F)(F)F] | 13 |
| F4 | 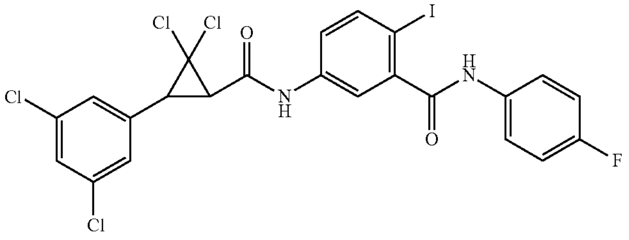 [SMILES: O=C(Nc1ccc(F)cc1)c1cc(NC(=O)C2C(c3cc(Cl)cc(Cl)c3)C2(Cl)Cl)ccc1I] | 13 |

TABLE 2-continued
| Structure and preparation method for F Series molecules | | |
|---|---|---|
| No. | Structure | Prep.* |
| F5 | 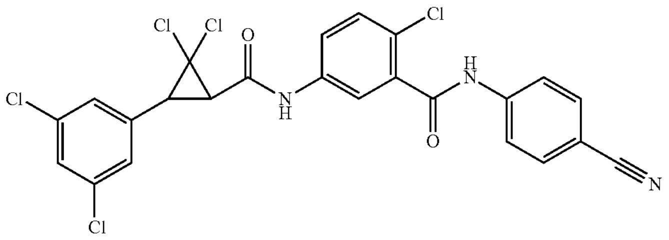 [SMILES: N#Cc1ccc(NC(=O)c2cc(NC(=O)C3C(c4cc(Cl)cc(Cl)c4)C3(Cl)Cl)ccc2Cl)cc1] | 13 |
| F6 | 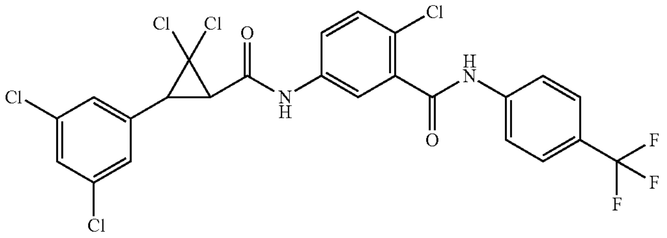 [SMILES: O=C(Nc1ccc(C(F)(F)F)cc1)c1cc(NC(=O)C2C(c3cc(Cl)cc(Cl)c3)C2(Cl)Cl)ccc1Cl] | 13 |
| F7 | 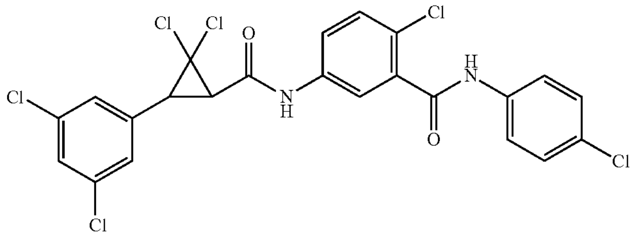 [SMILES: O=C(Nc1ccc(Cl)cc1)c1cc(NC(=O)C2C(c3cc(Cl)cc(Cl)c3)C2(Cl)Cl)ccc1Cl] | 13 |
| F8 | 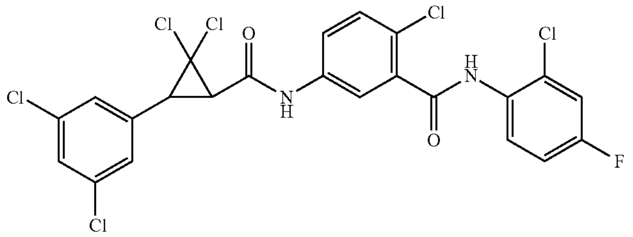 | 13 |
| F9 | 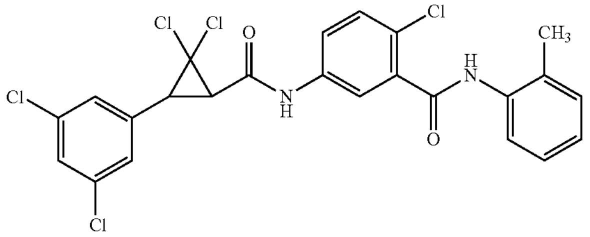 [SMILES: Cc1ccccc1NC(=O)c1cc(NC(=O)C2C(c3cc(Cl)cc(Cl)c3)C2(Cl)Cl)ccc1Cl] | 13 |
| F10 | 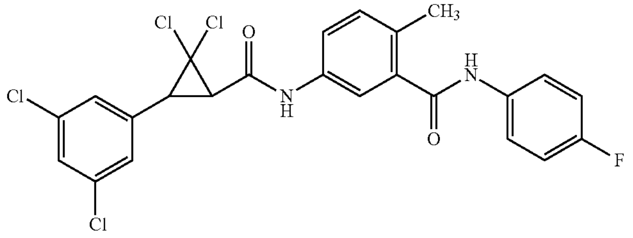 [SMILES: Cc1ccc(NC(=O)C2C(c3cc(Cl)cc(Cl)c3)C2(Cl)Cl)cc1C(=O)Nc1ccc(F)cc1] | 13 |

TABLE 2-continued
| Structure and preparation method for F Series molecules | | |
|---|---|---|
| No. | Structure | Prep.* |
| F11 | 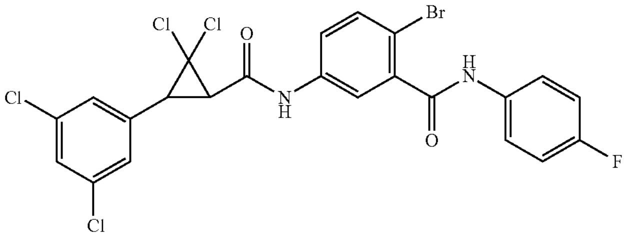 | 13 |
| F12 | 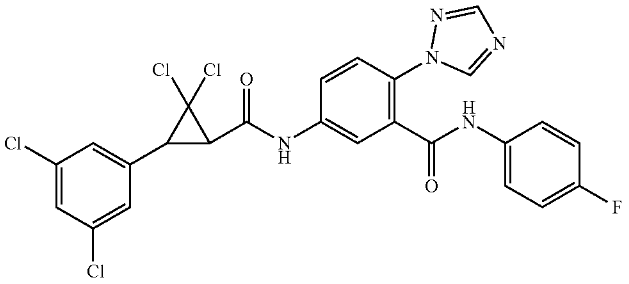 [SMILES: O=C(Nc1ccc(F)cc1)c1cc(NC(=O)C2C(c3cc(Cl)cc(Cl)c3)C2(Cl)Cl)ccc1-n1cncn1] | 13 |
| F13 | 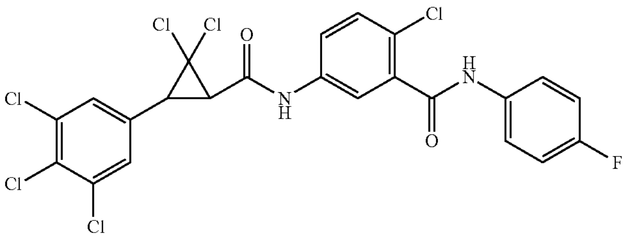 | 13 |
| F14 | 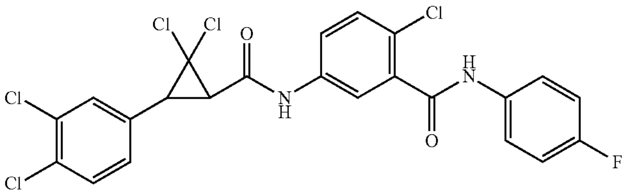 | 13 |
| F15 | 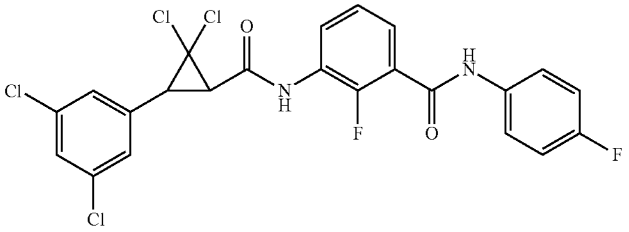 [SMILES: O=C(Nc1ccc(F)cc1)c1cccc(NC(=O)C2C(c3cc(Cl)cc(Cl)c3)C2(Cl)Cl)c1F] | 13 |
| F16 | 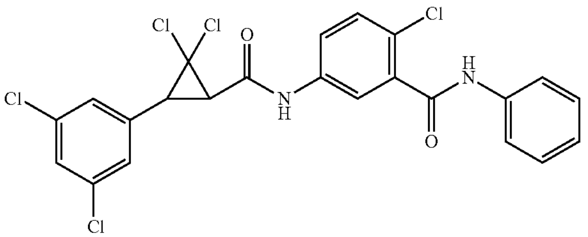 [SMILES: O=C(Nc1ccccc1)c1cc(NC(=O)C2C(c3cc(Cl)cc(Cl)c3)C2(Cl)Cl)ccc1Cl] | 13 |

TABLE 2-continued
| Structure and preparation method for F Series molecules | | |
|---|---|---|
| No. | Structure | Prep.* |
| F17 | 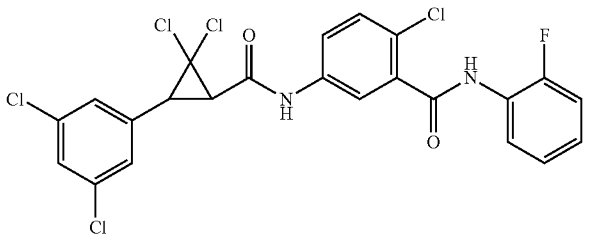 | 13 |
| F18 | 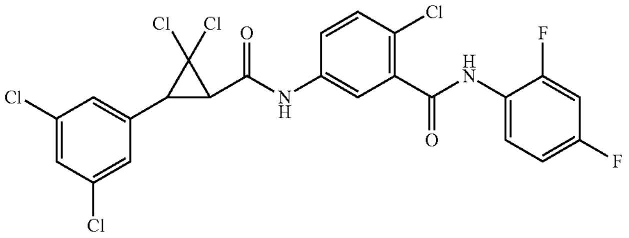 [SMILES: O=C(Nc1ccc(F)cc1F)c1cc(NC(=O)C2C(c3cc(Cl)cc(Cl)c3)C2(Cl)Cl)ccc1Cl] | 13 |
| F19 | 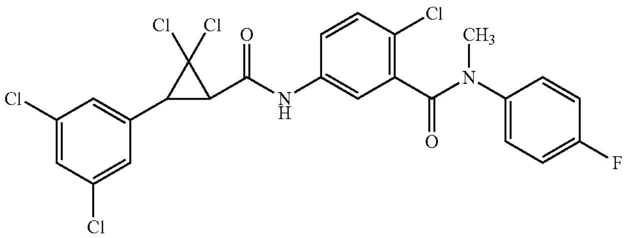 [SMILES: CN(C(=O)c1cc(NC(=O)C2C(c3cc(Cl)cc(Cl)c3)C2(Cl)Cl)ccc1Cl)c1ccc(F)cc1] | 13 |
| F20 | 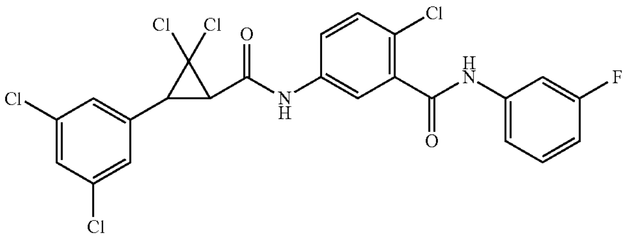 [SMILES: O=C(Nc1cccc(F)c1)c1cc(NC(=O)C2C(c3cc(Cl)cc(Cl)c3)C2(Cl)Cl)ccc1Cl] | 13 |
| F21 | 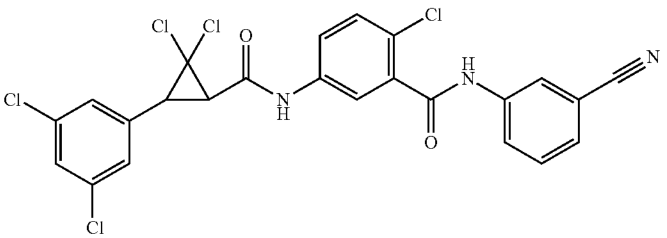 [SMILES: N#Cc1cccc(NC(=O)c2cc(NC(=O)C3C(c4cc(Cl)cc(Cl)c4)C3(Cl)Cl)ccc2Cl)c1] | 13 |
| F22 | 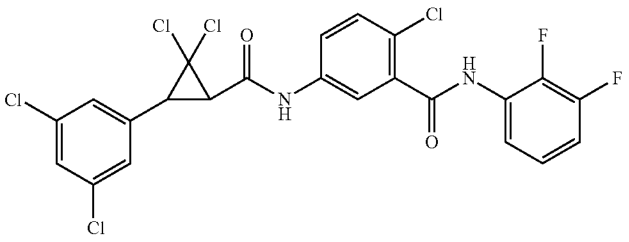 [SMILES: O=C(Nc1cccc(F)c1F)c1cc(NC(=O)C2C(c3cc(Cl)cc(Cl)c3)C2(Cl)Cl)ccc1Cl] | 13 |

TABLE 2-continued
| Structure and preparation method for F Series molecules | | |
|---|---|---|
| No. | Structure | Prep.* |
| F23 | 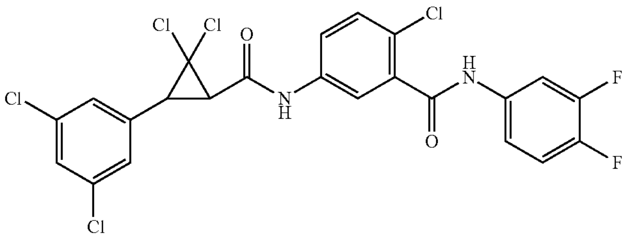 [SMILES: O=C(Nc1ccc(F)c(F)c1)c1cc(NC(=O)C2C(c3cc(Cl)cc(Cl)c3)C2(Cl)Cl)ccc1Cl] | 13 |
| F24 | 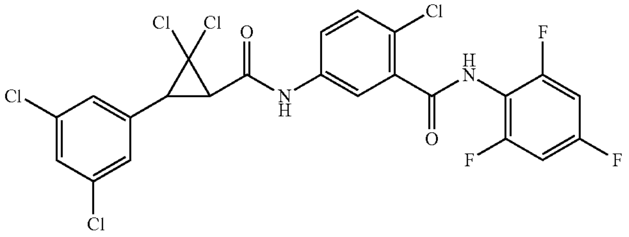 | 13 |
| F25 | 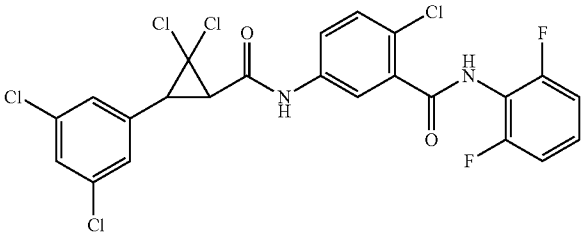 | 13 |
| F26 | 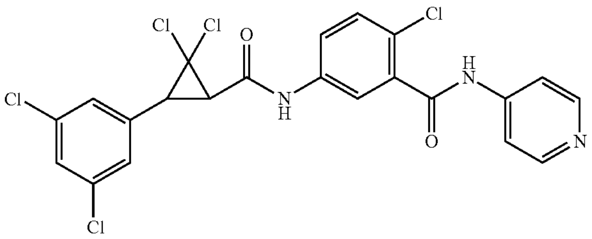 [SMILES: O=C(Nc1ccncc1)c1cc(NC(=O)C2C(c3cc(Cl)cc(Cl)c3)C2(Cl)Cl)ccc1Cl] | 13 |
| F27 | 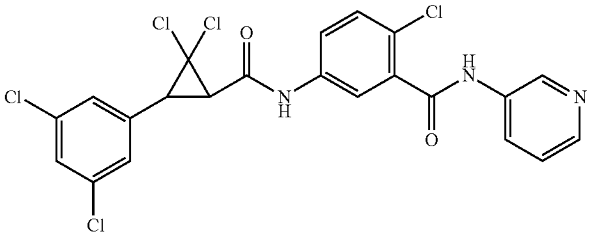 [SMILES: O=C(Nc1cccnc1)c1cc(NC(=O)C2C(c3cc(Cl)cc(Cl)c3)C2(Cl)Cl)ccc1Cl] | 13 |
| F28 | 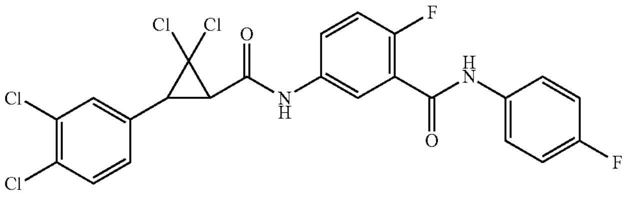 | 13 |

TABLE 2-continued
| Structure and preparation method for F Series molecules | | |
|---|---|---|
| No. | Structure | Prep.* |
| F29 | 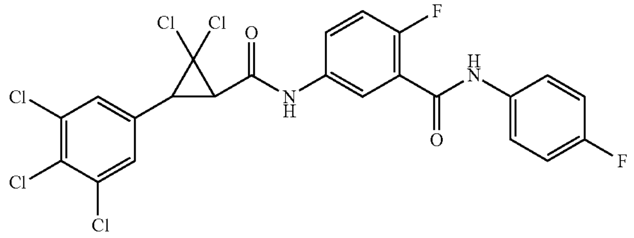 [SMILES: O=C(Nc1ccc(F)cc1)c1cc(NC(=O)C2C(c3cc(Cl)c(Cl)c(Cl)c3)C2(Cl)Cl)ccc1F] | 13 |
| F30 | 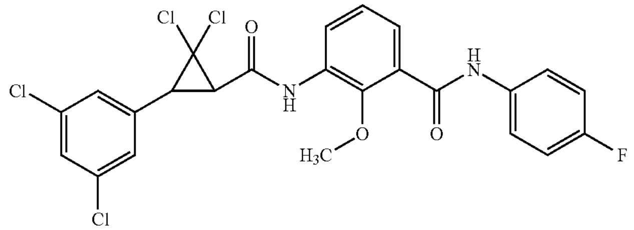 [SMILES: COc1c(NC(=O)C2C(c3cc(Cl)cc(Cl)c3)C2(Cl)Cl)cccc1C(=O)Nc1ccc(F)cc1] | 13 |
| F31 | 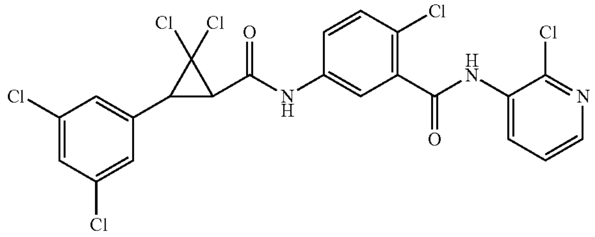 [SMILES: O=C(Nc1cccnc1Cl)c1cc(NC(=O)C2C(c3cc(Cl)cc(Cl)c3)C2(Cl)Cl)ccc1Cl] | 13 |
| F32 | 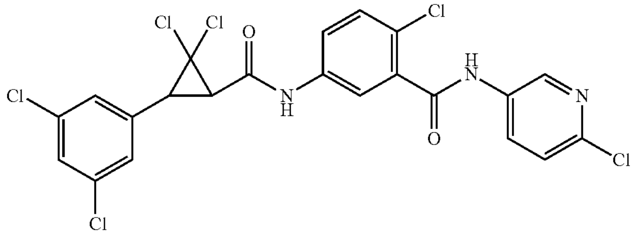 [SMILES: O=C(Nc1ccc(Cl)nc1)c1cc(NC(=O)C2C(c3cc(Cl)cc(Cl)c3)C2(Cl)Cl)ccc1Cl] | 13 |
| F33 | 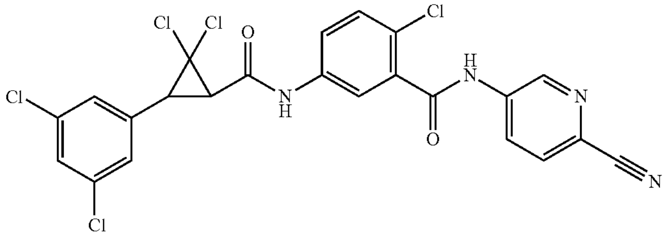 [SMILES: N#Cc1ccc(NC(=O)c2cc(NC(=O)C3C(c4cc(Cl)cc(Cl)c4)C3(Cl)Cl)ccc2Cl)cn1] | 13 |
| F34 | 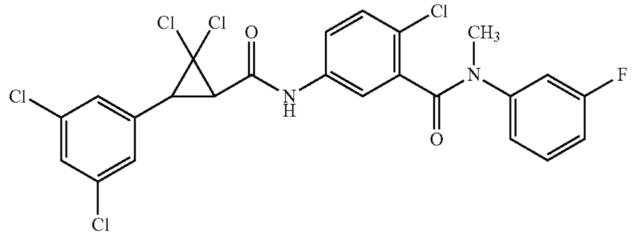 | 13 |

TABLE 2-continued
| No. | Structure | Prep.* |
|---|---|---|
| | Structure and preparation method for F Series molecules | |
| F35 | 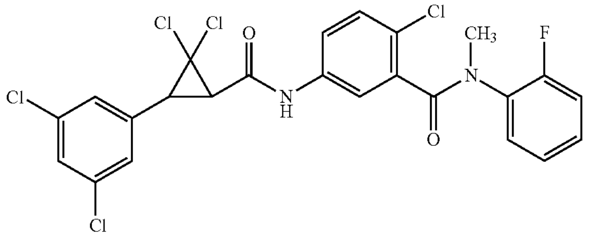 [SMILES: CN(C(=O)c1cc(NC(=O)C2C(c3cc(Cl)cc(Cl)c3)C2(Cl)Cl)ccc1Cl)c1ccccc1F] | 13 |
| F36 | 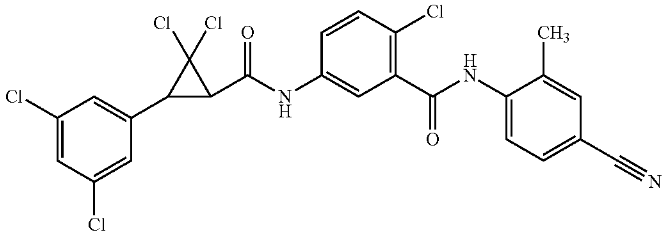 [SMILES: Cc1cc(C#N)ccc1NC(=O)c1cc(NC(=O)C2C(c3cc(Cl)cc(Cl)c3)C2(Cl)Cl)ccc1Cl] | 13 |
| F37 | 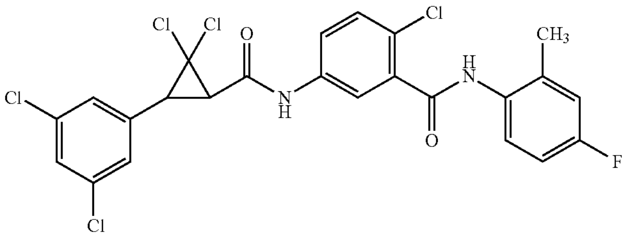 | 13 |
| F38 | 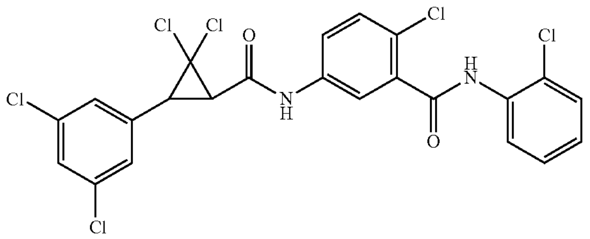 | 13 |
| F39 | 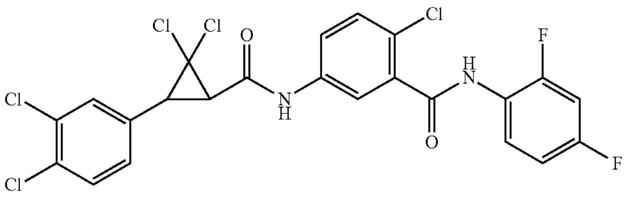 | 13 |
| F40 | 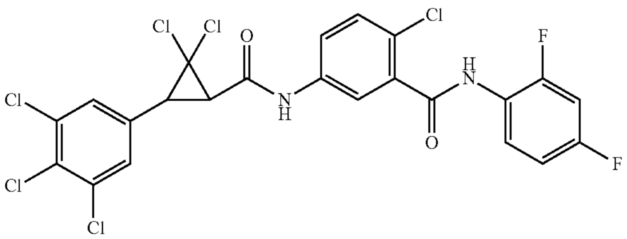 [SMILES: O=C(Nc1ccc(F)cc1F)c1cc(NC(=O)C2C(c3cc(Cl)c(Cl)c(Cl)c3)C2(Cl)Cl)ccc1Cl] | 13 |

TABLE 2-continued
| No. | Structure | Prep.* |
| --- | --- | --- |
| F41 | 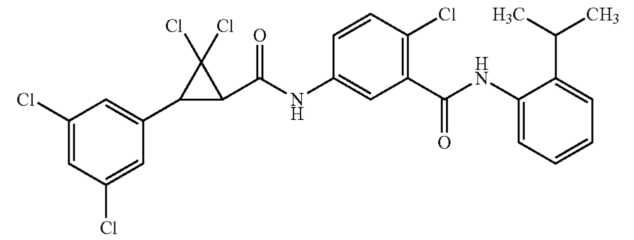 [SMILES: CC(C)c1ccccc1NC(=O)c1cc(NC(=O)C2C(c3cc(Cl)cc(Cl)c3)C2(Cl)Cl)ccc1Cl] | 13 |
| F42 | 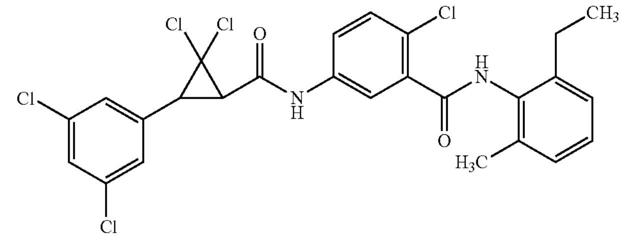 [SMILES: CCc1cccc(C)c1NC(=O)c1cc(NC(=O)C2C(c3cc(Cl)cc(Cl)c3)C2(Cl)Cl)ccc1Cl] | 13 |
| F43 | 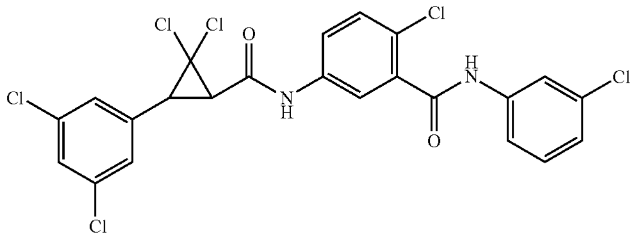 | 13 |
| F44 | 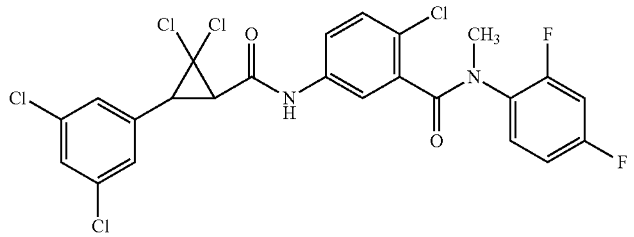 | 13 |
| F45 | 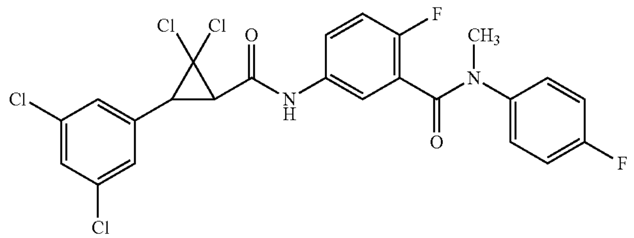 | 13 |
| F46 | 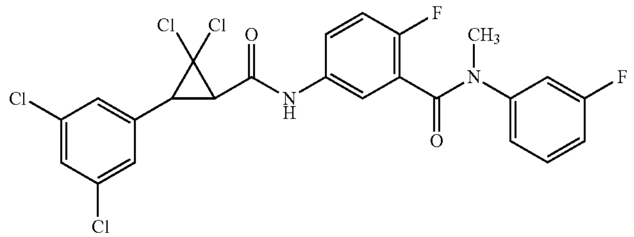 [SMILES: CN(C(=O)c1cc(NC(=O)C2C(c3cc(Cl)cc(Cl)c3)C2(Cl)Cl)ccc1F)c1cccc(F)c1] | 13 |
Structure and preparation method for F Series molecules TABLE 2-continued
| Structure and preparation method for F Series molecules | | |
|---|---|---|
| No. | Structure | Prep.* |
| F47 | 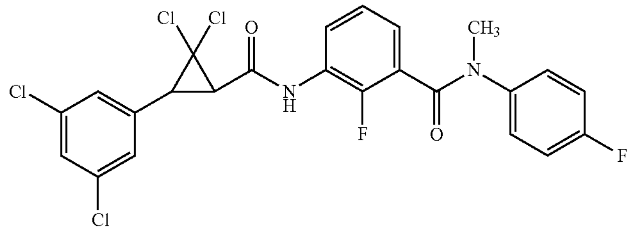 [SMILES: CN(C(=O)c1cccc(NC(=O)C2C(c3cc(Cl)cc(Cl)c3)C2(Cl)Cl)c1F)c1ccc(F)cc1] | 13 |
| F48 | 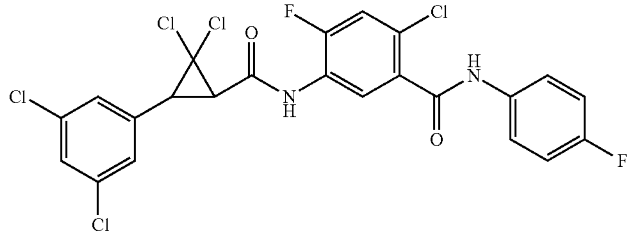 [SMILES: O=C(Nc1ccc(F)cc1)c1cc(NC(=O)C2C(c3cc(Cl)cc(Cl)c3)C2(Cl)Cl)c(F)cc1Cl] | 13 |
| F49 | 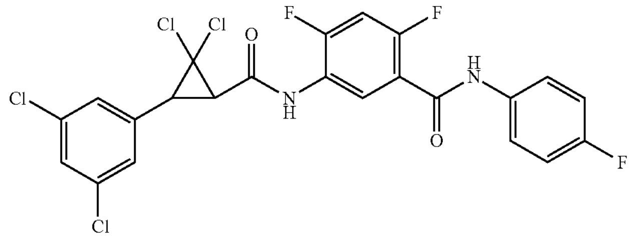 | 13 |
| F50 | 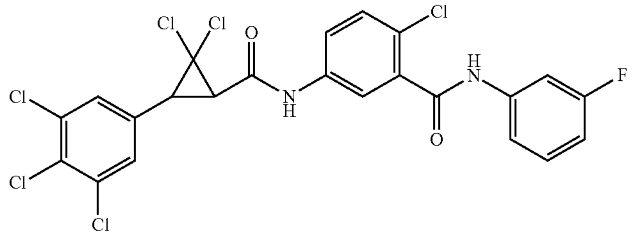 [SMILES: O=C(Nc1cccc(F)c1)c1cc(NC(=O)C2C(c3cc(Cl)c(Cl)c(Cl)c3)C2(Cl)Cl)ccc1Cl] | 13 |
| F51 | 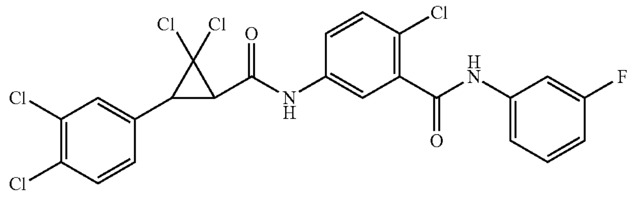 [SMILES: O=C(Nc1cccc(F)c1)c1cc(NC(=O)C2C(c3ccc(Cl)c(Cl)c3)C2(Cl)Cl)ccc1Cl] | 13 |
| F52 | 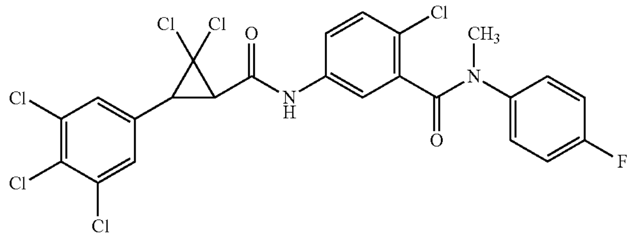 [SMILES: CN(C(=O)c1cc(NC(=O)C2C(c3cc(Cl)c(Cl)c(Cl)c3)C2(Cl)Cl)ccc1Cl)c1ccc(F)cc1] | 13 |

TABLE 2-continued
| Structure and preparation method for F Series molecules | | |
|---|---|---|
| No. | Structure | Prep.* |
| F53 | 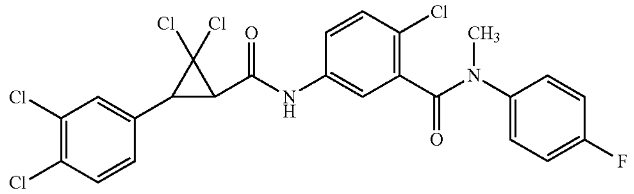 | 13 |
| F54 | 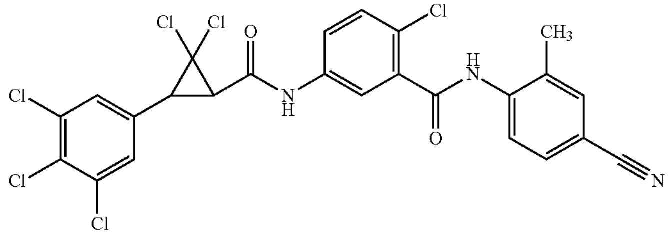 [SMILES: Cc1cc(C#N)ccc1NC(=O)c1cc(NC(=O)C2C(c3cc(Cl)c(Cl)c(Cl)c3)C2(Cl)Cl)ccc1Cl] | 13 |
| F55 | 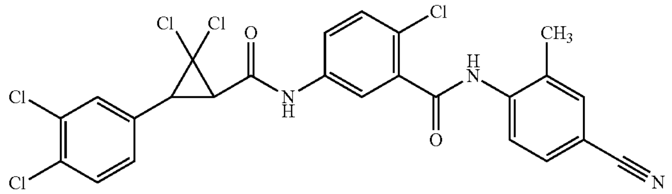 [SMILES: Cc1cc(C#N)ccc1NC(=O)c1cc(NC(=O)C2C(c3ccc(Cl)c(Cl)c3)C2(Cl)Cl)ccc1Cl] | 13 |
| F56 | 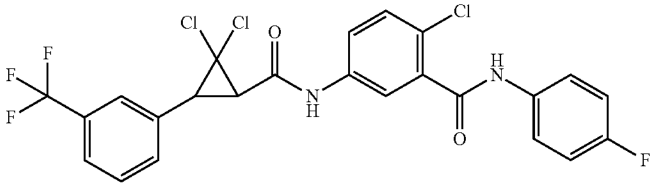 [SMILES: O=C(Nc1ccc(F)cc1)c1cc(NC(=O)C2C(c3cccc(C(F)(F)F)c3)C2(Cl)Cl)ccc1Cl] | 13 |
| F57 | 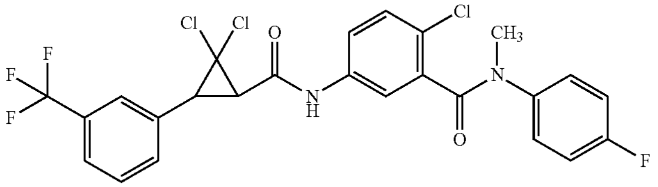 [SMILES: CN(C(=O)c1cc(NC(=O)C2C(c3cccc(C(F)(F)F)c3)C2(Cl)Cl)ccc1Cl)c1ccc(F)cc1] | 13 |
| F58 | 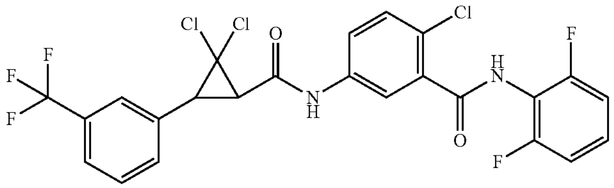 [SMILES: O=C(Nc1c(F)cccc1F)c1cc(NC(=O)C2C(c3cccc(C(F)(F)F)c3)C2(Cl)Cl)ccc1Cl] | 13 |
| F59 | 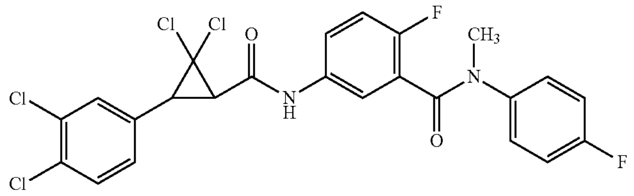 [SMILES: CN(C(=O)c1cc(NC(=O)C2C(c3ccc(Cl)c(Cl)c3)C2(Cl)Cl)ccc1F)c1ccc(F)cc1] | 13 |

TABLE 2-continued
Structure and preparation method for F Series molecules
| No. | Structure | Prep.* |
|---|---|---|
| F60 | 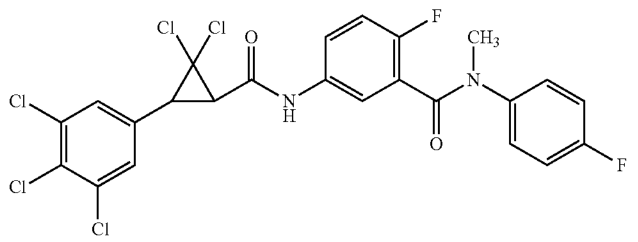 | 13 |
| F61 | 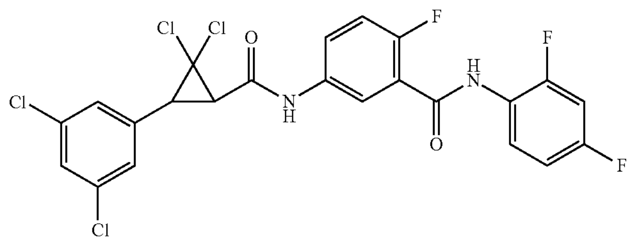 [SMILES: O=C(Nc1ccc(F)cc1F)c1cc(NC(=O)C2C(c3cc(Cl)cc(Cl)c3)C2(Cl)Cl)ccc1F] | 13 |
| F62 | 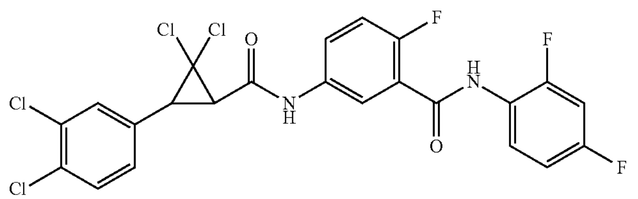 | 13 |
| F63 | 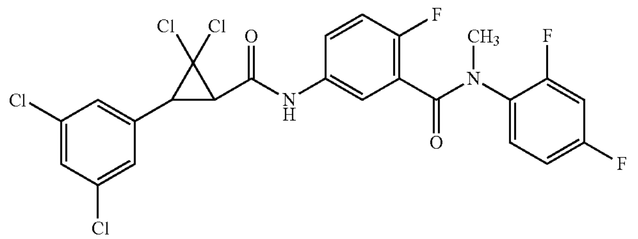 [SMILES: CN(C(=O)c1cc(NC(=O)C2C(c3cc(Cl)cc(Cl)c3)C2(Cl)Cl)ccc1F)c1ccc(F)cc1F] | 13 |
| F64 | 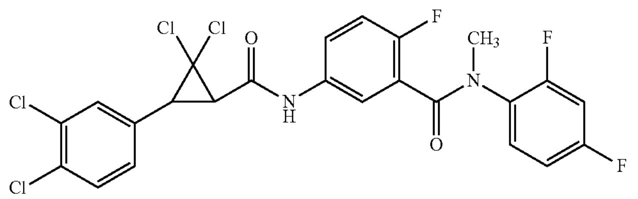 | 13 |
| F65 | 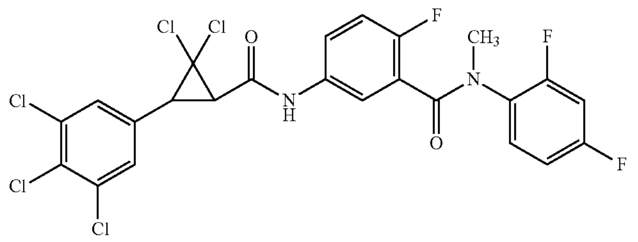 [SMILES: CN(C(=O)c1cc(NC(=O)C2C(c3cc(Cl)c(Cl)c(Cl)c3)C2(Cl)Cl)ccc1F)c1ccc(F)cc1F] | 13 |

TABLE 2-continued
| Structure and preparation method for F Series molecules | | |
|---|---|---|
| No. | Structure | Prep.* |
| F66 | 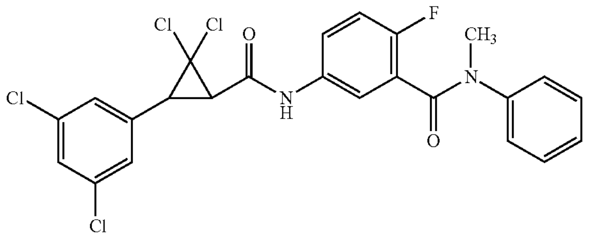 [SMILES: CN(C(=O)c1cc(NC(=O)C2C(c3cc(Cl)cc(Cl)c3)C2(Cl)Cl)ccc1F)c1ccccc1] | 13 |
| F67 | 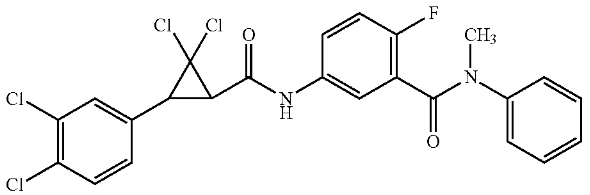 [SMILES: CN(C(=O)c1cc(NC(=O)C2C(c3ccc(Cl)c(Cl)c3)C2(Cl)Cl)ccc1F)c1ccccc1] | 13 |
| F68 | 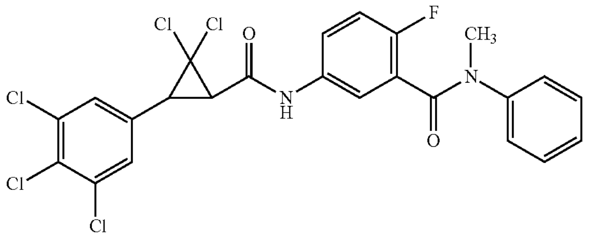 [SMILES: CN(C(=O)c1cc(NC(=O)C2C(c3cc(Cl)c(Cl)c(Cl)c3)C2(Cl)Cl)ccc1F)c1ccccc1] | 13 |
| F69 | 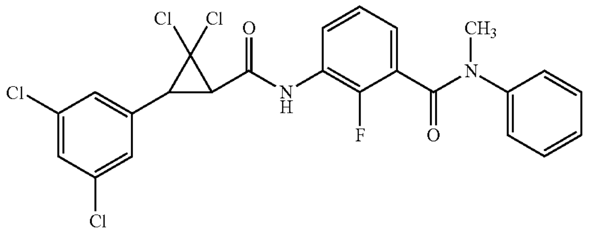 [SMILES: CN(C(=O)c1cccc(NC(=O)C2C(c3cc(Cl)cc(Cl)c3)C2(Cl)Cl)c1F)c1ccccc1] | 13 |
| F70 | 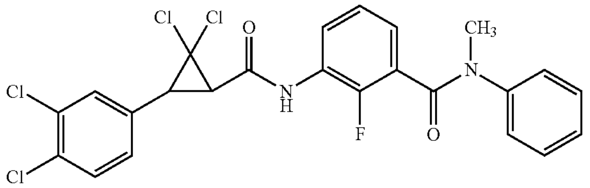 [SMILES: CN(C(=O)c1cccc(NC(=O)C2C(c3ccc(Cl)c(Cl)c3)C2(Cl)Cl)c1F)c1ccccc1] | 13 |
| F71 | 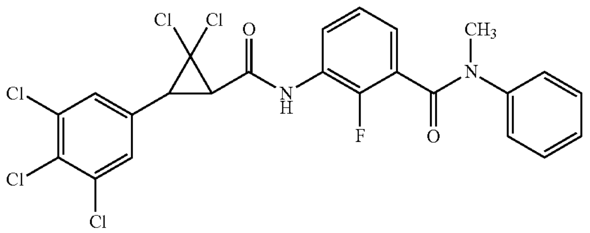 [SMILES: CN(C(=O)c1cccc(NC(=O)C2C(c3cc(Cl)c(Cl)c(Cl)c3)C2(Cl)Cl)c1F)c1ccccc1] | 13 |

TABLE 2-continued
| Structure and preparation method for F Series molecules | | |
|---|---|---|
| No. | Structure | Prep.* |
| F72 | 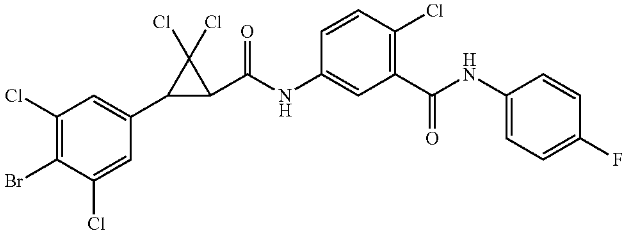 | 13 |
| F73 | 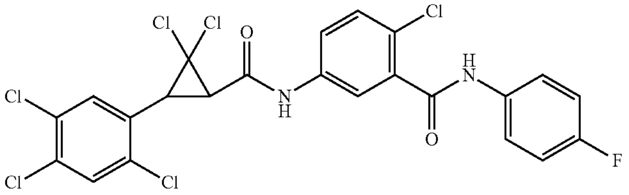 [SMILES: O=C(Nc1ccc(F)cc1)c1cc(NC(=O)C2C(c3cc(Cl)c(Cl)cc3Cl)C2(Cl)Cl)ccc1Cl] | 13 |
| F74 | 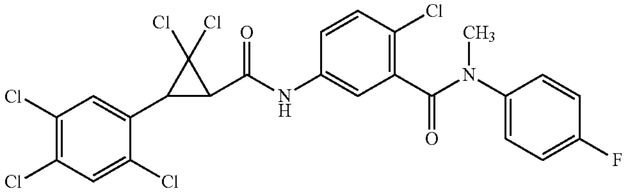 [SMILES: CN(C(=O)c1cc(NC(=O)C2C(c3cc(Cl)c(Cl)cc3Cl)C2(Cl)Cl)ccc1Cl)c1ccc(F)cc1] | 13 |
| F75 | 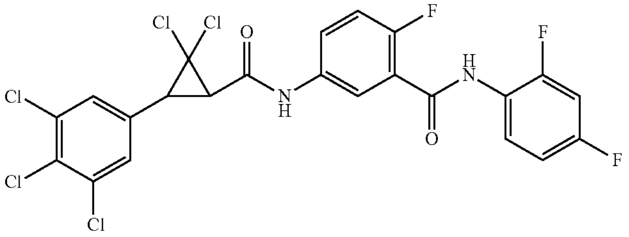 | 13 |
| F76 | 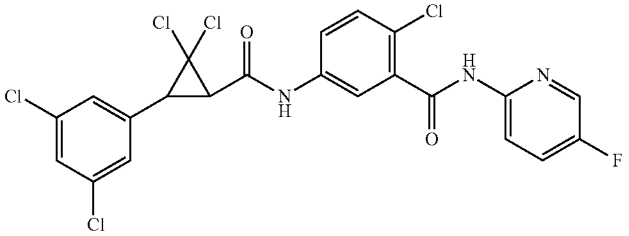 | 13 |
| F77 | 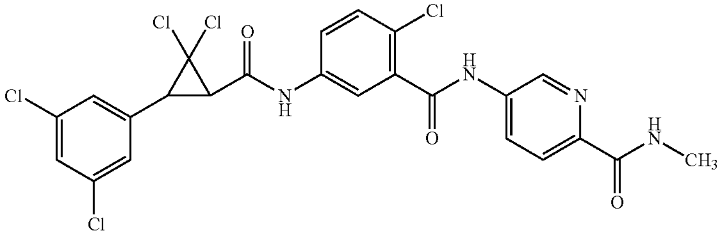 | 13 |

TABLE 2-continued
| Structure and preparation method for F Series molecules | | |
|---|---|---|
| No. | Structure | Prep.* |
| F78 | 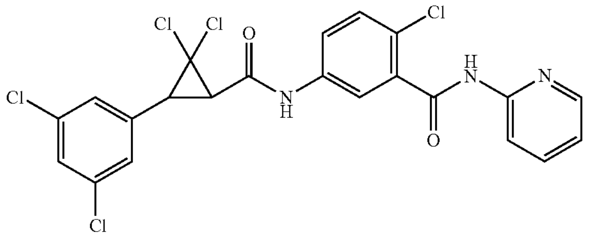 [SMILES: O=C(Nc1ccccn1)c1cc(NC(=O)C2C(c3cc(Cl)cc(Cl)c3)C2(Cl)Cl)ccc1Cl] | 13 |
| F79 | 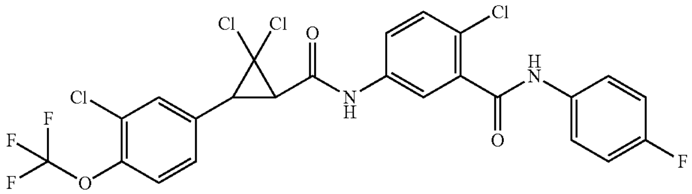 [SMILES: O=C(Nc1ccc(F)cc1)c1cc(NC(=O)C2C(c3ccc(OC(F)(F)F)c(Cl)c3)C2(Cl)Cl)ccc1Cl] | 13 |
| F80 | 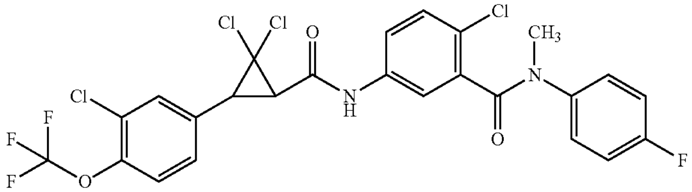 [SMILES: CN(C(=O)c1cc(NC(=O)C2C(c3ccc(OC(F)(F)F)c(Cl)c3)C2(Cl)Cl)ccc1Cl)c1ccc(F)cc1] | 13 |
| F81 | 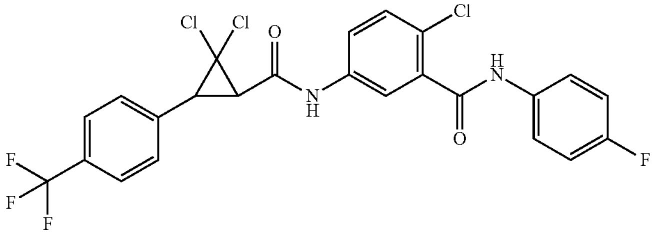 [SMILES: O=C(Nc1ccc(F)cc1)c1cc(NC(=O)C2C(c3ccc(C(F)(F)F)cc3)C2(Cl)Cl)ccc1Cl] | 13 |
| F82 | 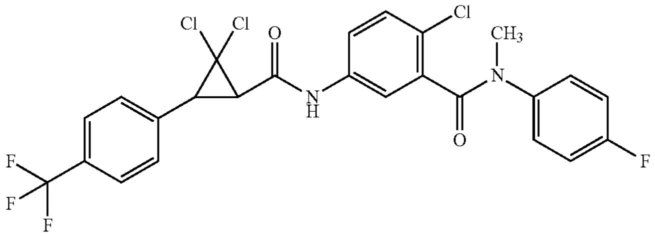 [SMILES: CN(C(=O)c1cc(NC(=O)C2C(c3ccc(C(F)(F)F)cc3)C2(Cl)Cl)ccc1Cl)c1ccc(F)cc1] | 13 |
| F83 | 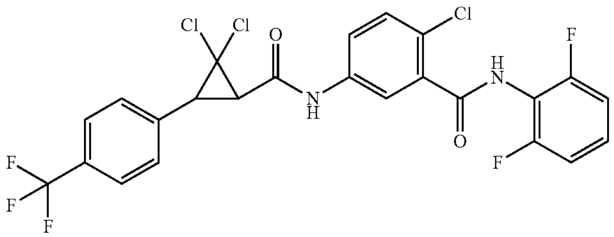 [SMILES: O=C(Nc1c(F)cccc1F)c1cc(NC(=O)C2C(c3ccc(C(F)(F)F)cc3)C2(Cl)Cl)ccc1Cl] | 13 |

TABLE 2-continued
Structure and preparation method for F Series molecules
| No. | Structure | Prep.* |
|---|---|---|
| F84 | 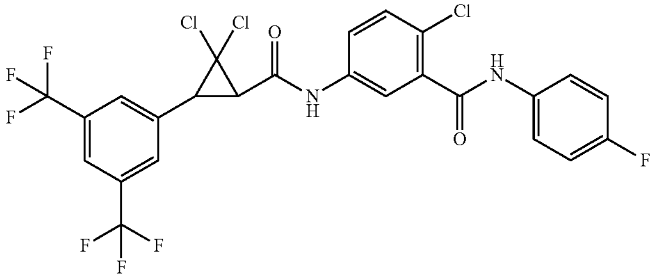 [SMILES: O=C(Nc1ccc(F)cc1)c1cc(NC(=O)C2C(c3cc(C(F)(F)F)cc(C(F)(F)F)c3)C2(Cl)Cl)ccc1Cl] | 13 |
| F85 | 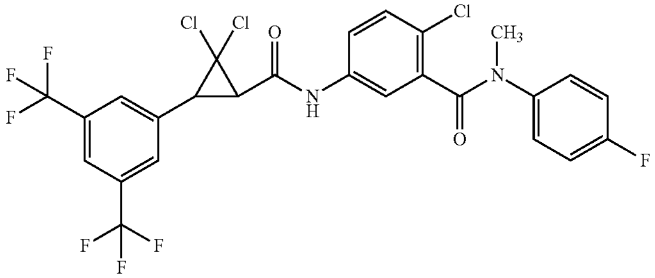 [SMILES: CN(C(=O)c1cc(NC(=O)C2C(c3cc(C(F)(F)F)cc(C(F)(F)F)c3)C2(Cl)Cl)ccc1Cl)c1ccc(F)cc1] | 13 |
| F86 | 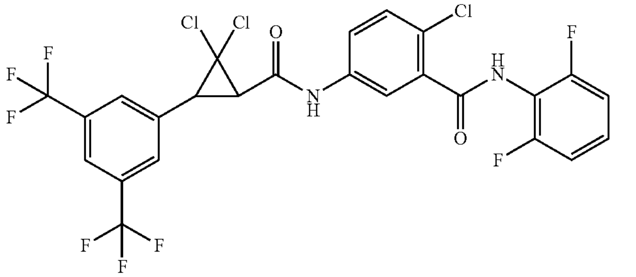 [SMILES: O=C(Nc1c(F)cccc1F)c1cc(NC(=O)C2C(c3cc(C(F)(F)F)cc(C(F)(F)F)c3)C2(Cl)Cl)ccc1Cl] | 13 |
| F87 | 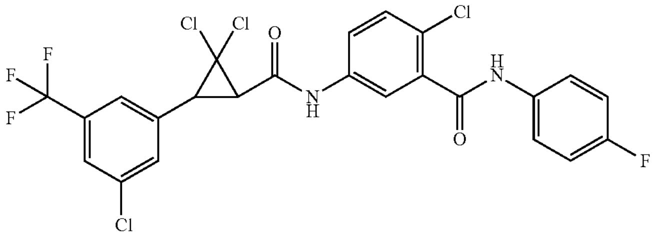 [SMILES: O=C(Nc1ccc(F)cc1)c1cc(NC(=O)C2C(c3cc(Cl)cc(C(F)(F)F)c3)C2(Cl)Cl)ccc1Cl] | 13 |
| F88 | 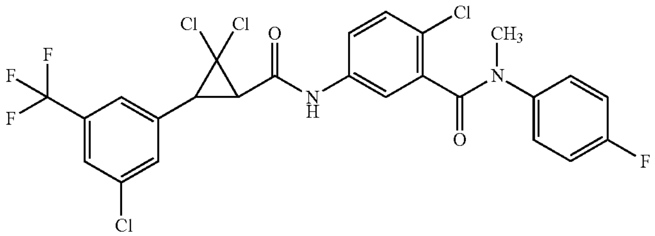 [SMILES: CN(C(=O)c1cc(NC(=O)C2C(c3cc(Cl)cc(C(F)(F)F)c3)C2(Cl)Cl)ccc1Cl)c1ccc(F)cc1] | 13 |

TABLE 2-continued
| Structure and preparation method for F Series molecules | | |
|---|---|---|
| No. | Structure | Prep.* |
| F89 | 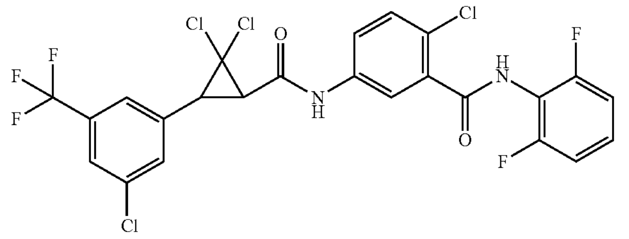 [SMILES: O=C(Nc1c(F)cccc1F)c1cc(NC(=O)C2C(c3cc(Cl)cc(C(F)(F)F)c3)C2(Cl)Cl)ccc1Cl] | 13 |
| F90 | 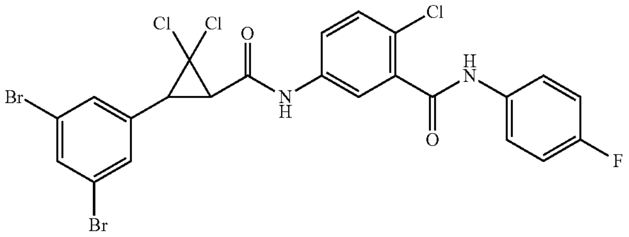 | 13 |
| F91 | 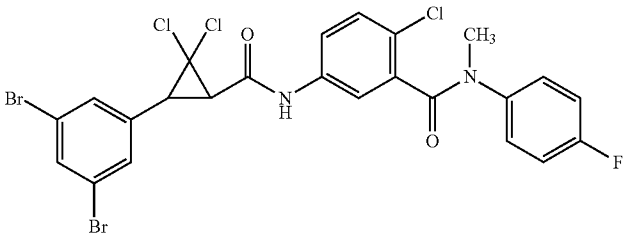 | 13 |
| F92 | 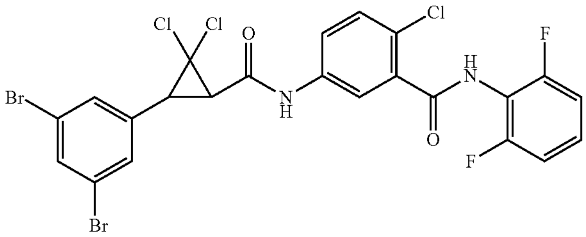 | 13 |
| F93 | 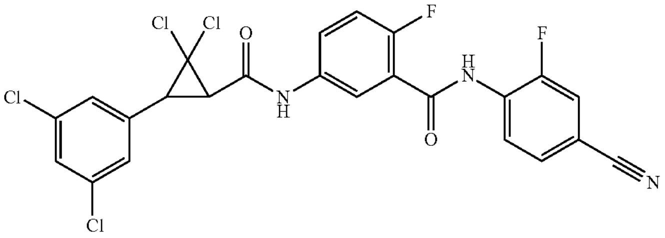 [SMILES: N#Cc1ccc(NC(=O)c2cc(NC(=O)C3C(c4cc(Cl)cc(Cl)c4)C3(Cl)Cl)ccc2F)c(F)c1] | 13 |
| F94 | 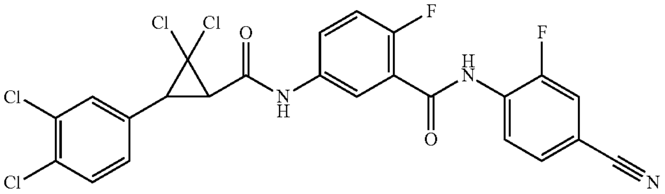 [SMILES: N#Cc1ccc(NC(=O)c2cc(NC(=O)C3C(c4ccc(Cl)c(Cl)c4)C3(Cl)Cl)ccc2F)c(F)c1] | 13 |

TABLE 2-continued
| Structure and preparation method for F Series molecules | | |
|---|---|---|
| No. | Structure | Prep.* |
| F95 | 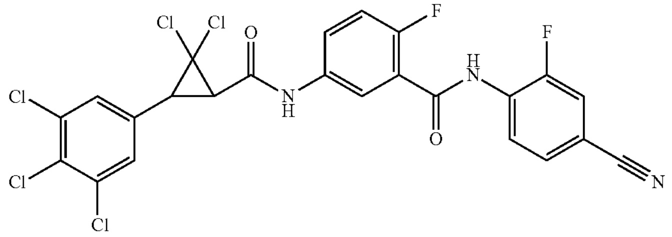 | 13 |
| F96 | 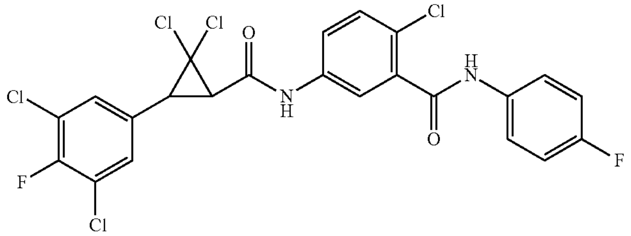 [SMILES: O=C(Nc1ccc(F)cc1)c1cc(NC(=O)C2C(c3cc(Cl)c(F)c(Cl)c3)C2(Cl)Cl)ccc1Cl] | 13 |
| F97 | 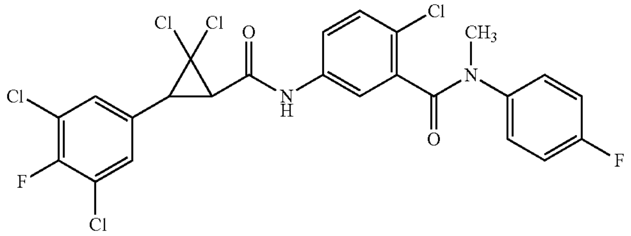 | 13 |
| F98 | 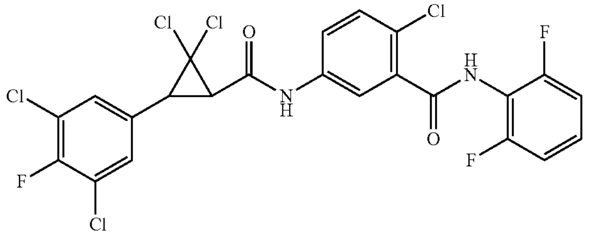 [SMILES: O=C(Nc1c(F)cccc1F)c1cc(NC(=O)C2C(c3cc(Cl)c(F)c(Cl)c3)C2(Cl)Cl)ccc1Cl] | 13 |
| F99 | 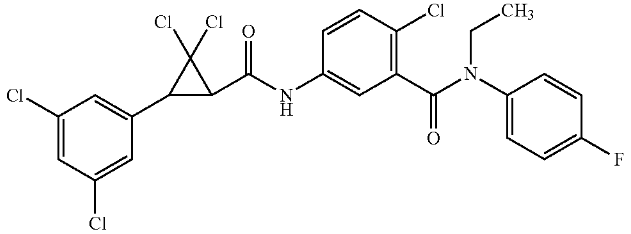 [SMILES: CCN(C(=O)c1cc(NC(=O)C2C(c3cc(Cl)cc(Cl)c3)C2(Cl)Cl)ccc1Cl)c1ccc(F)cc1] | 13 |
| F100 | 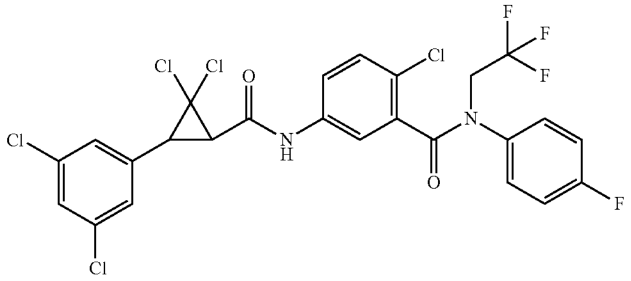 [SMILES: O=C(Nc1ccc(Cl)c(C(=O)N(CC(F)(F)F)c2ccc(F)cc2)c1)C1C(c2cc(Cl)cc(Cl)c2)C1(Cl)Cl] | 13 |

TABLE 2-continued
| Structure and preparation method for F Series molecules | | |
|---|---|---|
| No. | Structure | Prep.* |
| F101 | 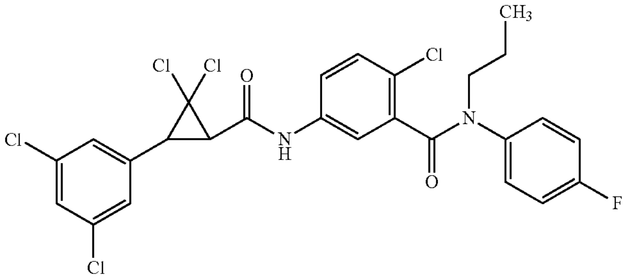 [SMILES: CCCN(C(=O)c1cc(NC(=O)C2C(c3cc(Cl)cc(Cl)c3)C2(Cl)Cl)ccc1Cl)c1ccc(F)cc1] | 13 |
| F102 | 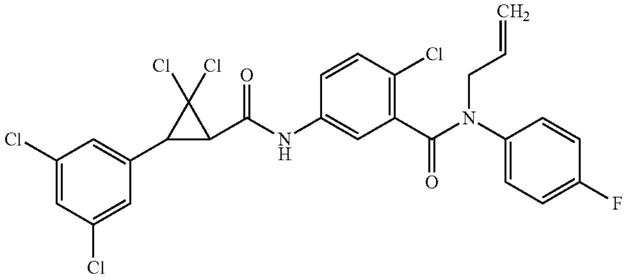 [SMILES: C=CCN(C(=O)c1cc(NC(=O)C2C(c3cc(Cl)cc(Cl)c3)C2(Cl)Cl)ccc1Cl)c1ccc(F)cc1] | 13 |
| F103 | 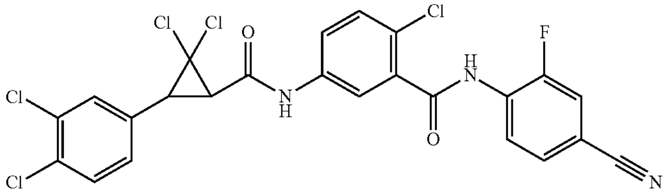 | 13 |
| F104 | 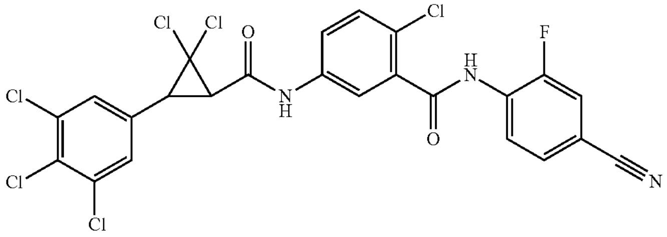 [SMILES: N#Cc1ccc(NC(=O)c2cc(NC(=O)C3C(c4cc(Cl)c(Cl)c(Cl)c4)C3(Cl)Cl)ccc2Cl)c(F)c1] | 13 |
| F105 | 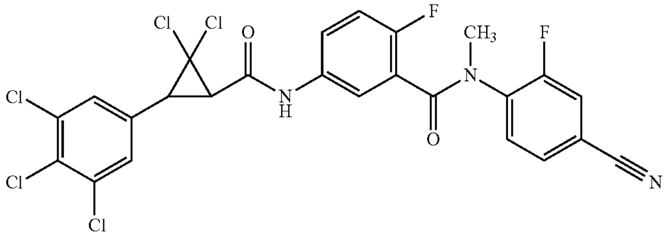 [SMILES: CN(C(=O)c1cc(NC(=O)C2C(c3cc(Cl)c(Cl)c(Cl)c3)C2(Cl)Cl)ccc1F)c1ccc(C#N)cc1F] | 13 |
| F106 | 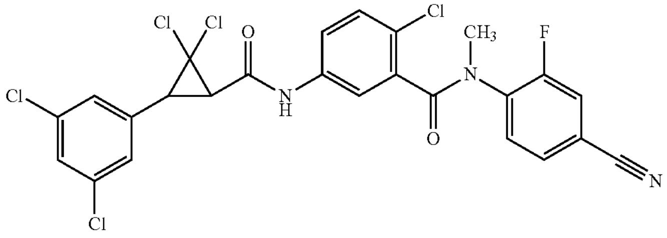 | 13 |

TABLE 2-continued
| No. | Structure | Prep.* |
|---|---|---|
| F107 | 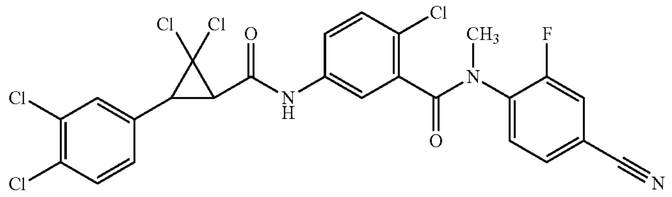 [SMILES: CN(C(=O)c1cc(NC(=O)C2C(c3ccc(Cl)c(Cl)c3)C2(Cl)Cl)ccc1Cl)c1ccc(C#N)cc1F] | 13 |
| F108 | 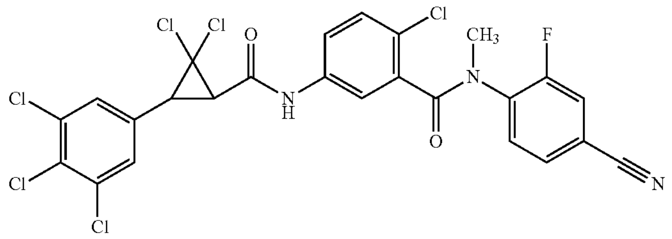 [SMILES: CN(C(=O)c1cc(NC(=O)C2C(c3cc(Cl)c(Cl)c(Cl)c3)C2(Cl)Cl)ccc1Cl)c1ccc(C#N)cc1F] | 13 |
| F109 | 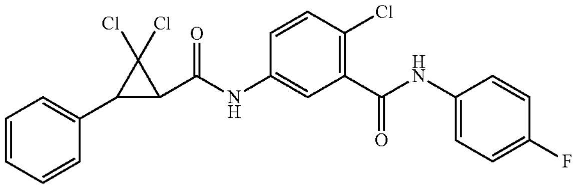 [SMILES: O=C(Nc1ccc(F)cc1)c1cc(NC(=O)C2C(c3ccccc3)C2(Cl)Cl)ccc1Cl] | 13 |
| F110 | 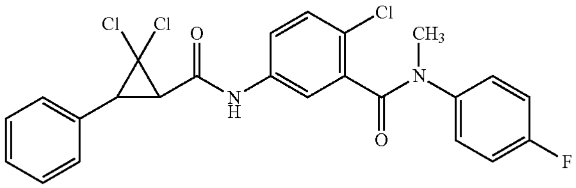 [SMILES: CN(C(=O)c1cc(NC(=O)C2C(c3ccccc3)C2(Cl)Cl)ccc1Cl)c1ccc(F)cc1] | 13 |
| F111 | 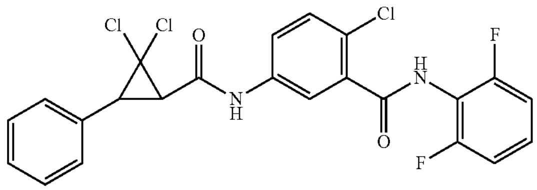 [SMILES: O=C(Nc1c(F)cccc1F)c1cc(NC(=O)C2C(c3ccccc3)C2(Cl)Cl)ccc1Cl] | 13 |
| F112 | 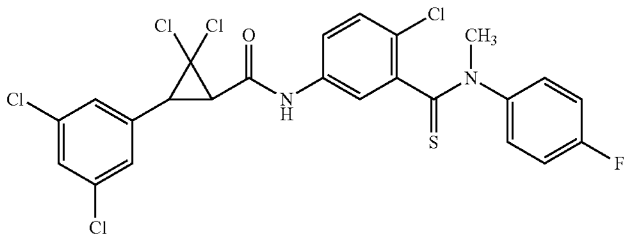 | 13 |
| F113 | 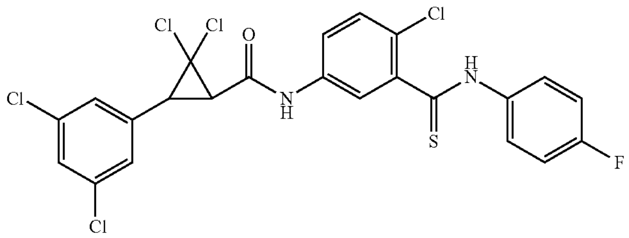 | 13 |
Structure and preparation method for F Series molecules TABLE 2-continued
Structure and preparation method for F Series molecules
| No. | Structure | Prep.* |
| --- | --- | --- |
| F114 | 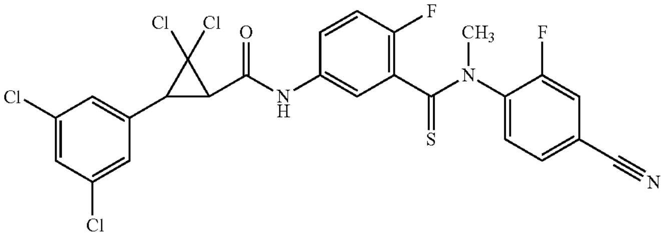 [SMILES: CN(C(=S)c1cc(NC(=O)C2C(c3cc(Cl)cc(Cl)c3)C2(Cl)Cl)ccc1F)c1ccc(C#N)cc1F] | 13 |
| F115 | 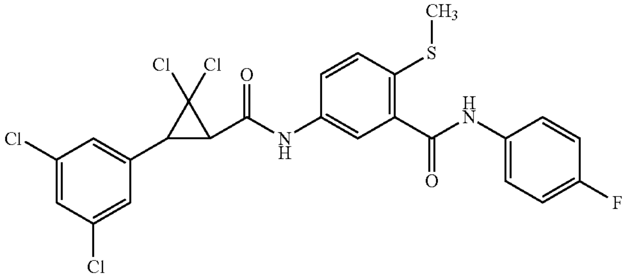 | 13 |
| F116 | 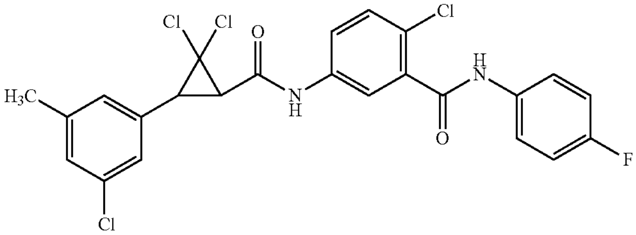 [SMILES: Cc1cc(Cl)cc(C2C(C(=O)Nc3ccc(Cl)c(C(=O)Nc4ccc(F)cc4)c3)C2(Cl)Cl)c1] | 13 |
| F117 | 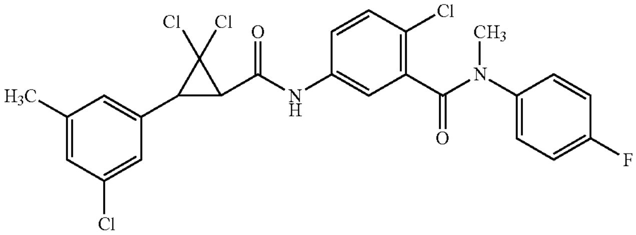 [SMILES: Cc1cc(Cl)cc(C2C(C(=O)Nc3ccc(Cl)c(C(=O)N(C)c4ccc(F)cc4)c3)C2(Cl)Cl)c1] | 13 |
| F118 | 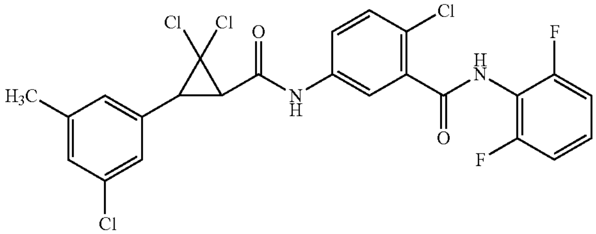 [SMILES: Cc1cc(Cl)cc(C2C(C(=O)Nc3ccc(Cl)c(C(=O)Nc4c(F)cccc4F)c3)C2(Cl)Cl)c1] | 13 |
| F119 | 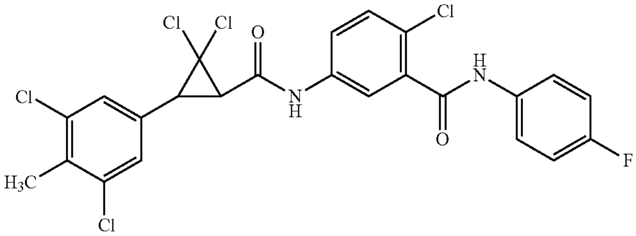 [SMILES: Cc1c(Cl)cc(C2C(C(=O)Nc3ccc(Cl)c(C(=O)Nc4ccc(F)cc4)c3)C2(Cl)Cl)cc1Cl] | 13 |

TABLE 2-continued
| Structure and preparation method for F Series molecules | | |
|---|---|---|
| No. | Structure | Prep.* |
| F120 | 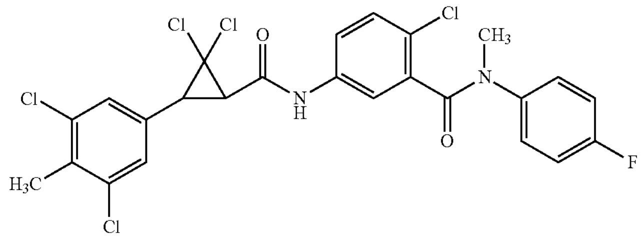 [SMILES: Cc1c(Cl)cc(C2C(C(=O)Nc3ccc(Cl)c(C(=O)N(C)c4ccc(F)cc4)c3)C2(Cl)Cl)cc1Cl] | 13 |
| F121 | 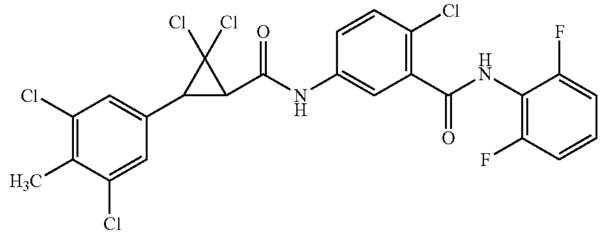 [SMILES: Cc1c(Cl)cc(C2C(C(=O)Nc3ccc(Cl)c(C(=O)Nc4c(F)cccc4F)c3)C2(Cl)Cl)cc1Cl] | 13 |
| F122 | 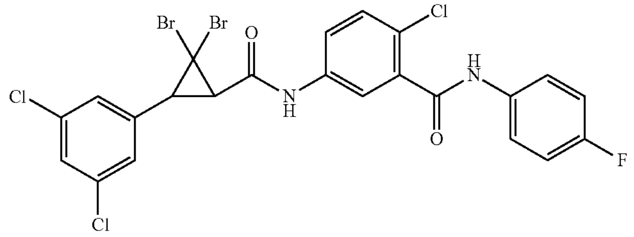 | 13 |
| F123 | 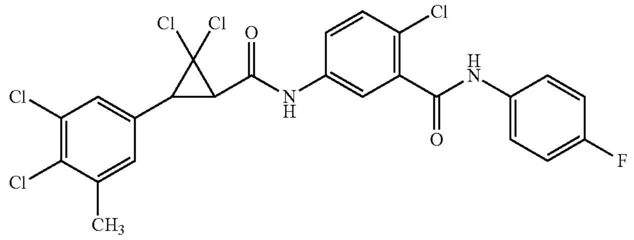 [SMILES: Cc1cc(C2C(C(=O)Nc3ccc(Cl)c(C(=O)Nc4ccc(F)cc4)c3)C2(Cl)Cl)cc(Cl)c1Cl] | 13 |
| F124 | 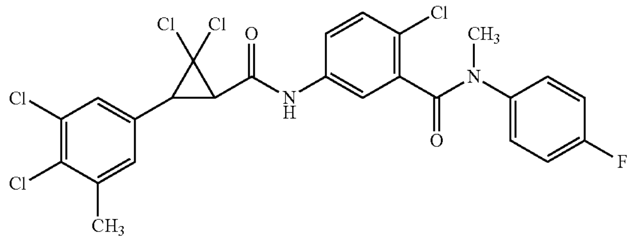 [SMILES: Cc1cc(C2C(C(=O)Nc3ccc(Cl)c(C(=O)N(C)c4ccc(F)cc4)c3)C2(Cl)Cl)cc(Cl)c1Cl] | 13 |
| F125 | 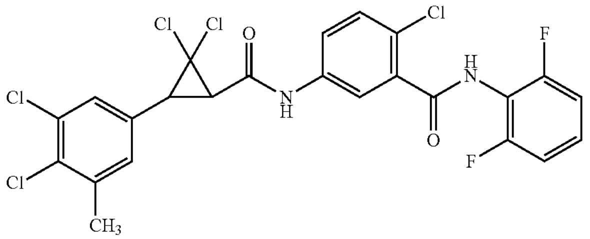 [SMILES: Cc1cc(C2C(C(=O)Nc3ccc(Cl)c(C(=O)Nc4c(F)cccc4F)c3)C2(Cl)Cl)cc(Cl)c1Cl] | 13 |

TABLE 2-continued
| Structure and preparation method for F Series molecules | | |
|---|---|---|
| No. | Structure | Prep.* |
| F126 | 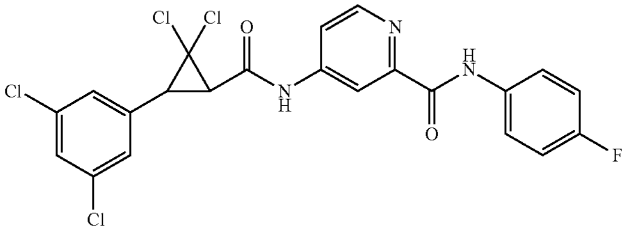 | 14 |
| F127 | 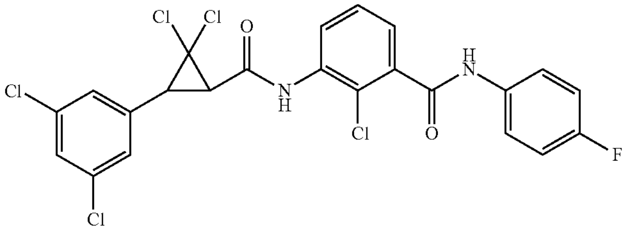 [SMILES: O=C(Nc1ccc(F)cc1)c1cccc(NC(=O)C2C(c3cc(Cl)cc(Cl)c3)C2(Cl)Cl)c1Cl] | 14 |
| F128 | 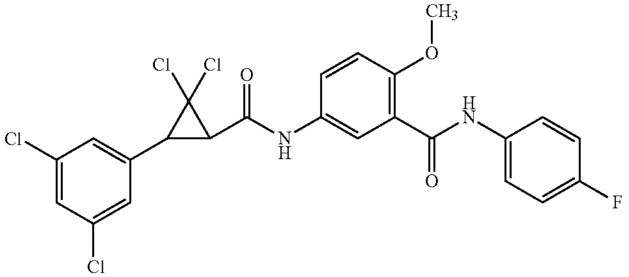 | 14 |
| F129 | 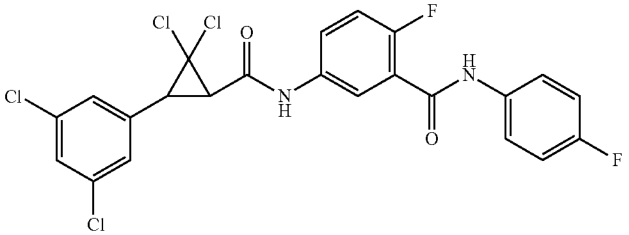 | 14 |
| F130 | 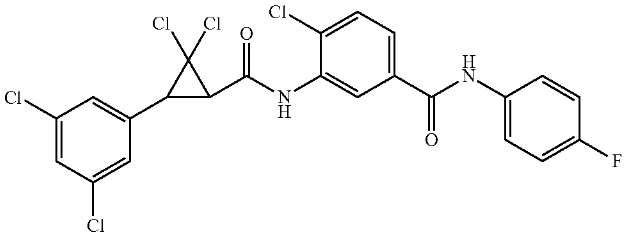 [SMILES: O=C(Nc1ccc(F)cc1)c1ccc(Cl)c(NC(=O)C2C(c3cc(Cl)cc(Cl)c3)C2(Cl)Cl)c1] | 14 |
| F131 | 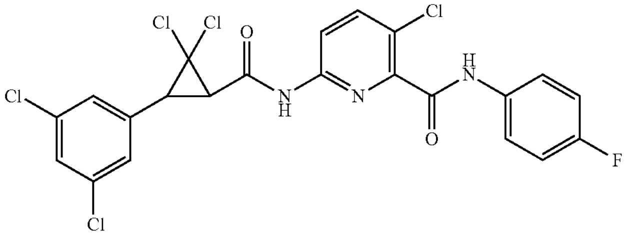 | 14 |

TABLE 2-continued
| Structure and preparation method for F Series molecules | | |
|---|---|---|
| No. | Structure | Prep.* |
| F132 | 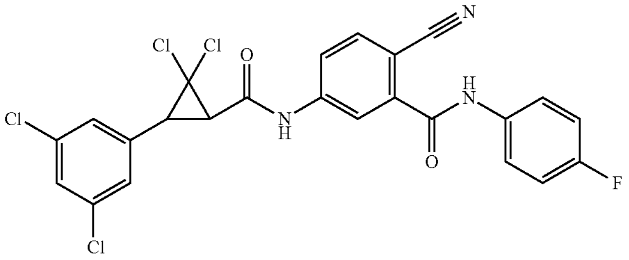 [SMILES: N#Cc1ccc(NC(=O)C2C(c3cc(Cl)cc(Cl)c3)C2(Cl)Cl)cc1C(=O)Nc1ccc(F)cc1] | 14 |
| F133 | 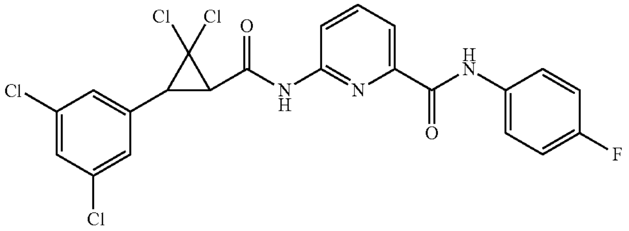 | 14 |
| F134 | 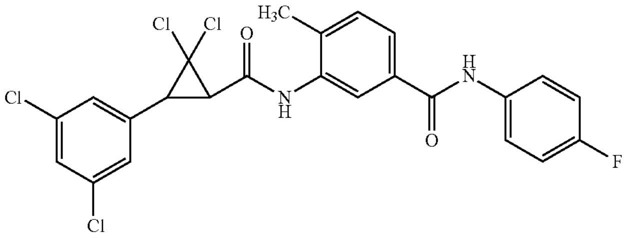 [SMILES: Cc1ccc(C(=O)Nc2ccc(F)cc2)cc1NC(=O)C1C(c2cc(Cl)cc(Cl)c2)C1(Cl)Cl] | 14 |
| F135 | 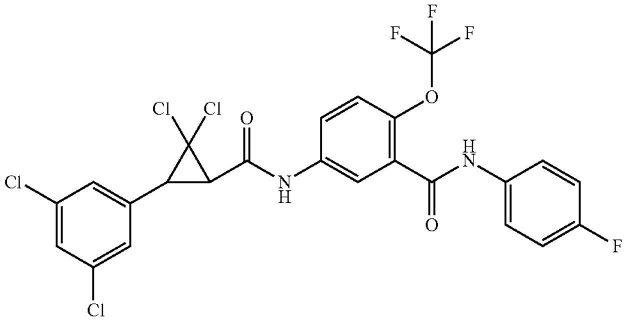 [SMILES: O=C(Nc1ccc(F)cc1)c1cc(NC(=O)C2C(c3cc(Cl)cc(Cl)c3)C2(Cl)Cl)ccc1OC(F)(F)F] | 14 |
| F136 | 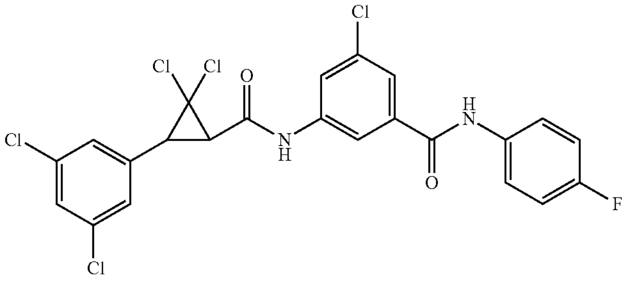 [SMILES: O=C(Nc1ccc(F)cc1)c1cc(Cl)cc(NC(=O)C2C(c3cc(Cl)cc(Cl)c3)C2(Cl)Cl)c1] | 14 |

TABLE 2-continued
| Structure and preparation method for F Series molecules | | |
|---|---|---|
| No. | Structure | Prep.* |
| F137 | 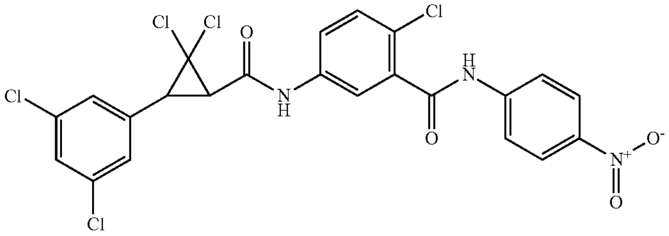 [SMILES: O=C(Nc1ccc([N+](=O)[O-])cc1)c1cc(NC(=O)C2C(c3cc(Cl)cc(Cl)c3)C2(Cl)Cl)ccc1Cl] | 15 |
| F138 | 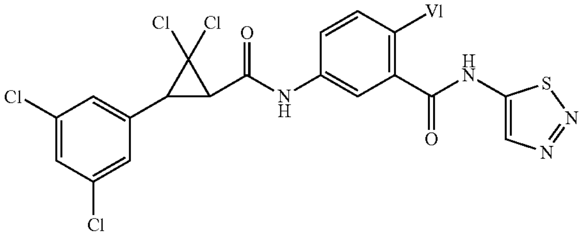 | 15 |
| F139 | 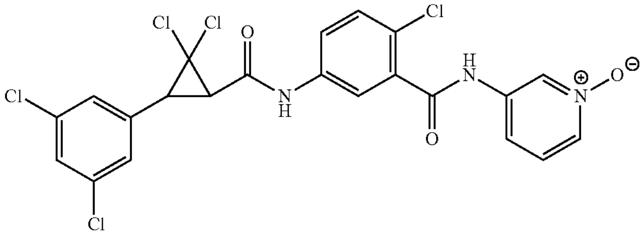 [SMILES: O=C(Nc1ccc[n+]([O-])c1)c1cc(NC(=O)C2C(c3cc(Cl)cc(Cl)c3)C2(Cl)Cl)ccc1Cl] | 16 |
| F140 | 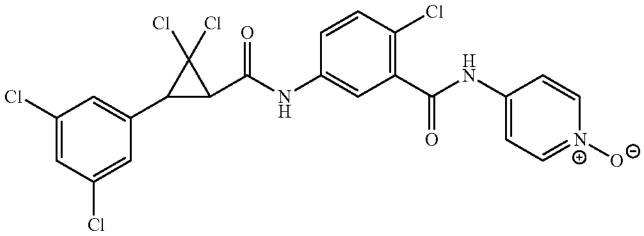 [SMILES: O=C(Nc1cc[n+]([O-])cc1)c1cc(NC(=O)C2C(c3cc(Cl)cc(Cl)c3)C2(Cl)Cl)ccc1Cl] | 16 |
| F141 | 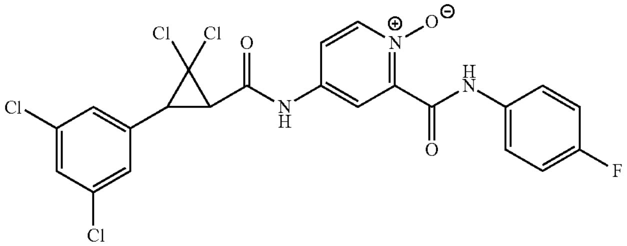 [SMILES: O=C(Nc1ccc(F)cc1)c1cc(NC(=O)C2C(c3cc(Cl)cc(Cl)c3)C2(Cl)Cl)cc[n+]1[O-]] | 16 |
| F142 | 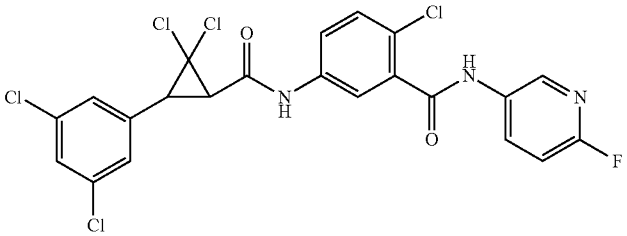 | 17 |

TABLE 2-continued
| Structure and preparation method for F Series molecules | | |
|---|---|---|
| No. | Structure | Prep.* |
| F143 | 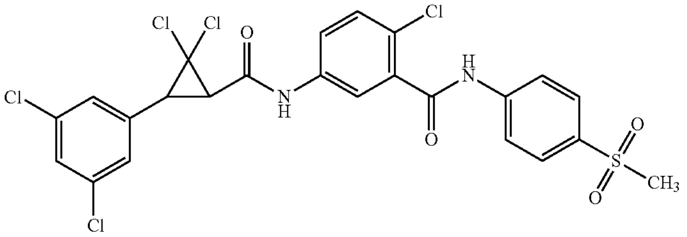 [SMILES: CS(=O)(=O)c1ccc(NC(=O)c2cc(NC(=O)C3C(c4cc(Cl)cc(Cl)c4)C3(Cl)Cl)ccc2Cl)cc1] | 17 |
| F144 | 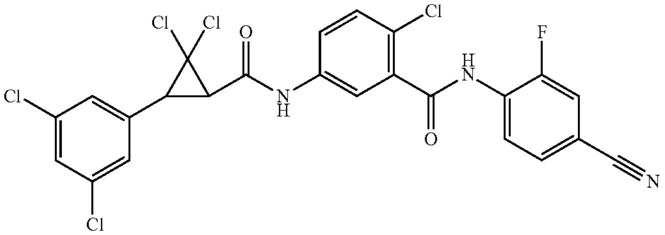 | 17 |
| F145 | 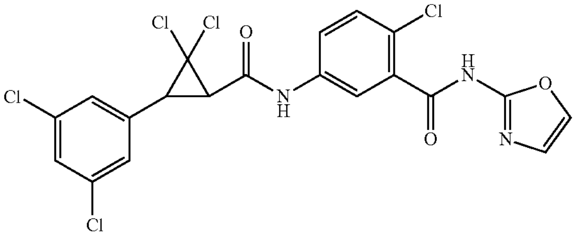 [SMILES: O=C(Nc1ncco1)c1cc(NC(=O)C2C(c3cc(Cl)cc(Cl)c3)C2(Cl)Cl)ccc1Cl] | 17 |
| F146 | 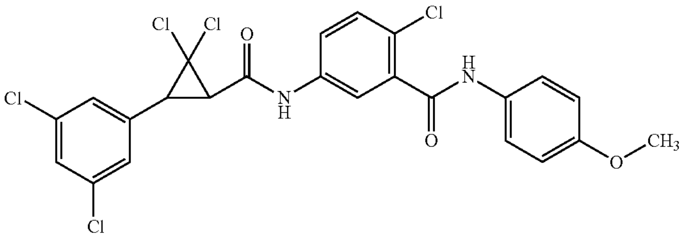 [SMILES: COc1ccc(NC(=O)c2cc(NC(=O)C3C(c4cc(Cl)cc(Cl)c4)C3(Cl)Cl)ccc2Cl)cc1] | 18 |
| F147 | 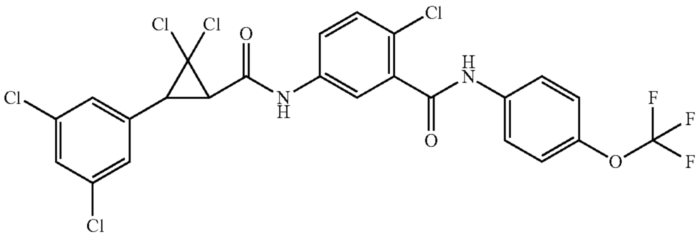 [SMILES: O=C(Nc1ccc(OC(F)(F)F)cc1)c1cc(NC(=O)C2C(c3cc(Cl)cc(Cl)c3)C2(Cl)Cl)ccc1Cl] | 18 |
| F148 | 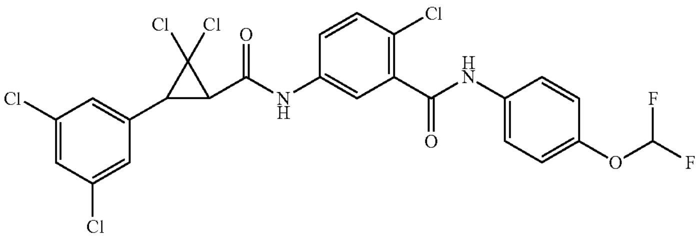 [SMILES: O=C(Nc1ccc(OC(F)F)cc1)c1cc(NC(=O)C2C(c3cc(Cl)cc(Cl)c3)C2(Cl)Cl)ccc1Cl] | 18 |

TABLE 2-continued
| Structure and preparation method for F Series molecules | | |
|---|---|---|
| No. | Structure | Prep.* |
| F149 | 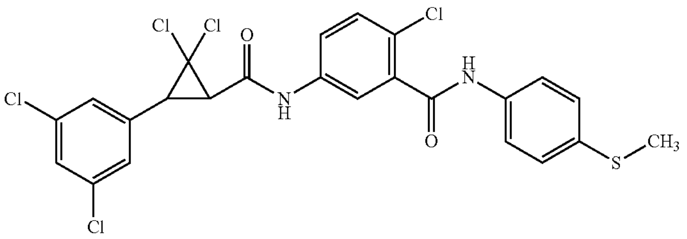 | 18 |
| F150 | 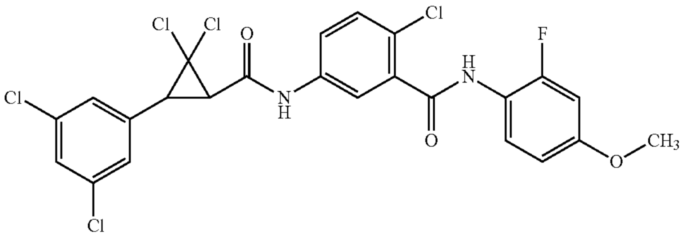 [SMILES: COc1ccc(NC(=O)c2cc(NC(=O)C3C(c4cc(Cl)cc(Cl)c4)C3(Cl)Cl)ccc2Cl)c(F)c1] | 18 |
| F151 | 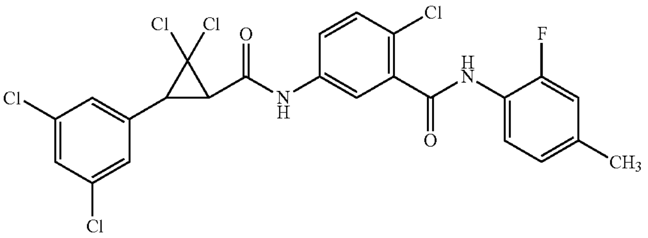 [SMILES: Cc1ccc(NC(=O)c2cc(NC(=O)C3C(c4cc(Cl)cc(Cl)c4)C3(Cl)Cl)ccc2Cl)c(F)c1] | 18 |
| F152 | 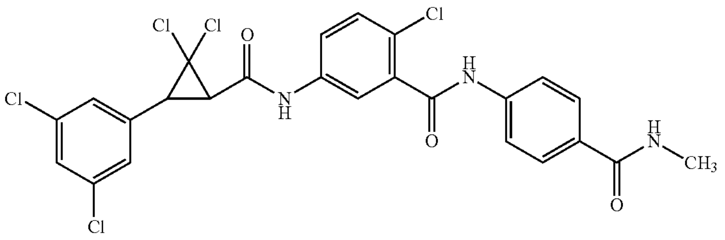 [SMILES: CNC(=O)c1ccc(NC(=O)c2cc(NC(=O)C3C(c4cc(Cl)cc(Cl)c4)C3(Cl)Cl)ccc2Cl)cc1] | 18 |
| F153 | 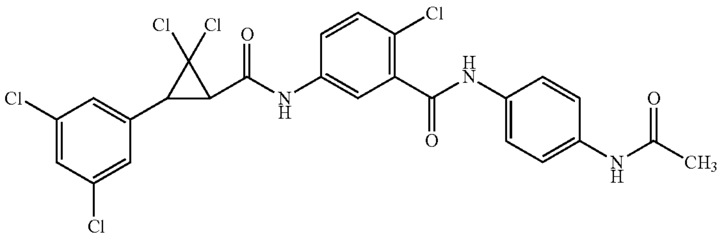 [SMILES: CC(=O)Nc1ccc(NC(=O)c2cc(NC(=O)C3C(c4cc(Cl)cc(Cl)c4)C3(Cl)Cl)ccc2Cl)cc1] | 18 |
| F154 | 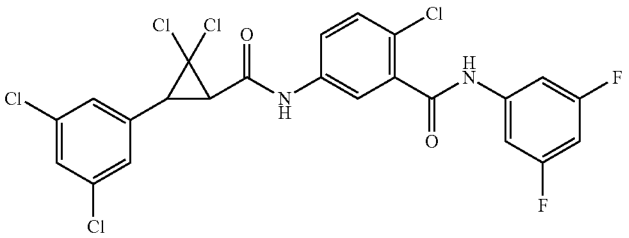 [SMILES: O=C(Nc1cc(F)cc(F)c1)c1cc(NC(=O)C2C(c3cc(Cl)cc(Cl)c3)C2(Cl)Cl)ccc1Cl] | 18 |

TABLE 2-continued
| No. | Structure | Prep.* |
| --- | --- | --- |
| F155 | 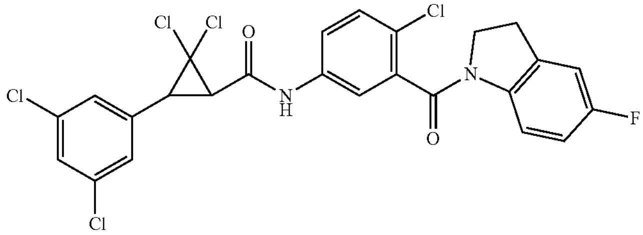 [SMILES: O=C(Nc1ccc(Cl)c(C(=O)N2CCc3cc(F)ccc32)c1)C1C(c2cc(Cl)cc(Cl)c2)C1(Cl)Cl] | 18 |
| F156 | 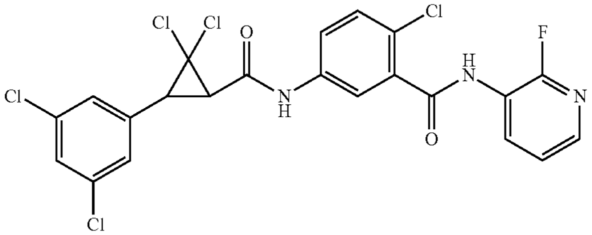 [SMILES: O=C(Nc1cccnc1F)c1cc(NC(=O)C2C(c3cc(Cl)cc(Cl)c3)C2(Cl)Cl)ccc1Cl] | 18 |
| F157 | 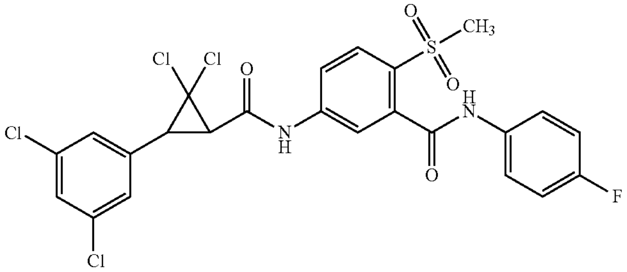 [SMILES: CS(=O)(=O)c1ccc(NC(=O)C2C(c3cc(Cl)cc(Cl)c3)C2(Cl)Cl)cc1C(=O)Nc1ccc(F)cc1] | 19 |
| F158 | 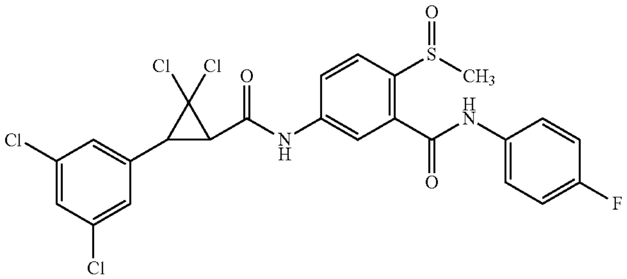 [SMILES: CS(=O)c1ccc(NC(=O)C2C(c3cc(Cl)cc(Cl)c3)C2(Cl)Cl)cc1C(=O)Nc1ccc(F)cc1] | 20 |
| F159 | 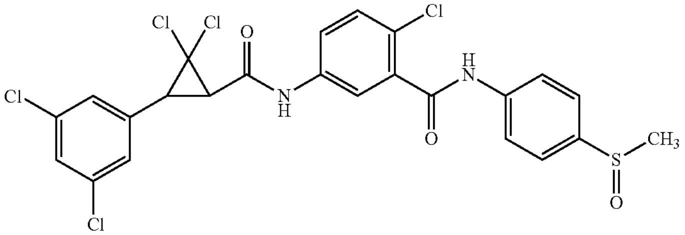 [SMILES: CS(=O)c1ccc(NC(=O)c2cc(NC(=O)C3C(c4cc(Cl)cc(Cl)c4)C3(Cl)Cl)ccc2Cl)cc1] | 20 |
| F160 | 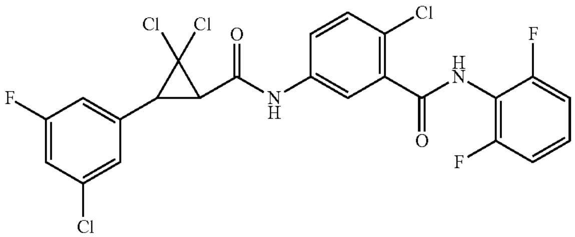 [SMILES: O=C(Nc1c(F)cccc1F)c1cc(NC(=O)C2C(c3cc(F)cc(Cl)c3)C2(Cl)Cl)ccc1Cl] | 13 |
Structure and preparation method for F Series molecules TABLE 2-continued
| Structure and preparation method for F Series molecules | | |
|---|---|---|
| No. | Structure | Prep.* |
| F161 | 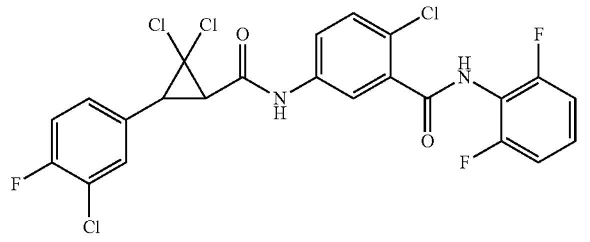 [SMILES: O=C(Nc1c(F)cccc1F)c1cc(NC(=O)C2C(c3ccc(F)c(Cl)c3)C2(Cl)Cl)ccc1Cl] | 13 |
| F162 | 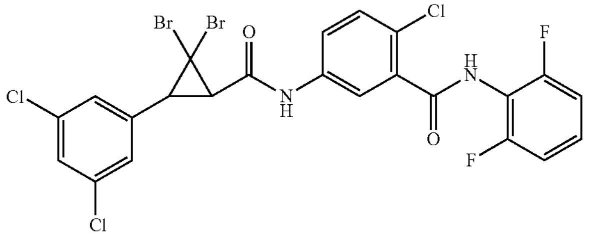 | 13 |
| F163 | 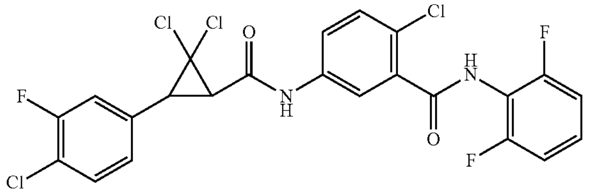 [SMILES: O=C(Nc1c(F)cccc1F)c1cc(NC(=O)C2C(c3ccc(Cl)c(F)c3)C2(Cl)Cl)ccc1Cl] | 13 |
| F164 | 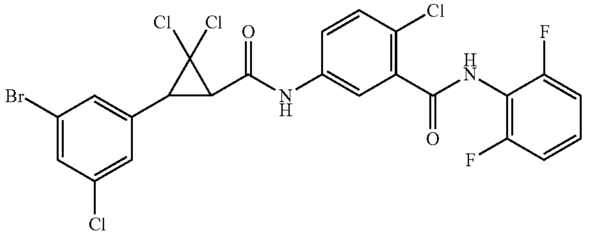 [SMILES: O=C(Nc1c(F)cccc1F)c1cc(NC(=O)C2C(c3cc(Cl)cc(Br)c3)C2(Cl)Cl)ccc1Cl] | 13 |
| F165 | 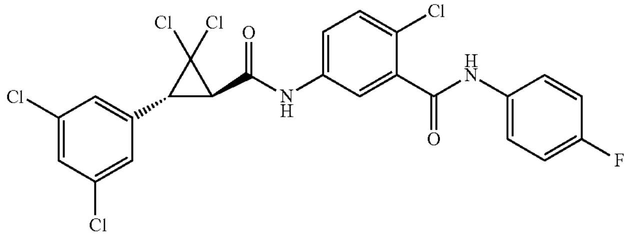 [SMILES: O=C(Nc1ccc(F)cc1)c1cc(NC(=O)[C@H]2[C@H](c3cc(Cl)cc(Cl)c3)C2(Cl)Cl)ccc1Cl] | 14 |
| F166 | 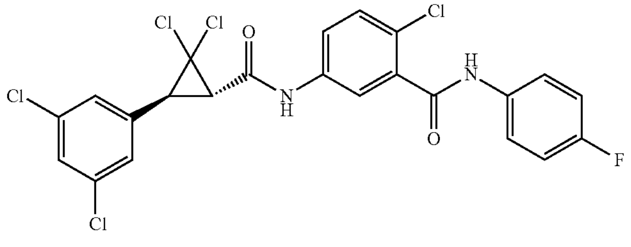 [SMILES: O=C(Nc1ccc(F)cc1)c1cc(NC(=O)[C@@H]2[C@@H](c3cc(Cl)cc(Cl)c3)C2(Cl)Cl)ccc1Cl] | 14 |

TABLE 2-continued
| No. | Structure | Prep.* |
|---|---|---|
| | Structure and preparation method for F Series molecules | |
| F167 | 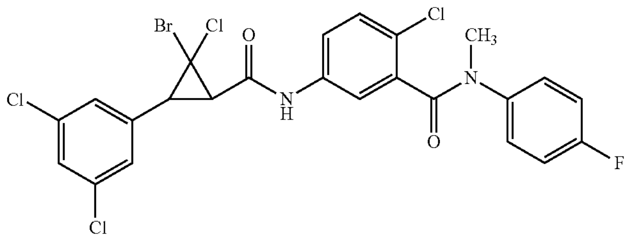 [SMILES: CN(C(=O)c1cc(NC(=O)C2C(c3cc(Cl)cc(Cl)c3)C2(Cl)Br)ccc1Cl)c1ccc(F)cc1] | 15 |
| F168 | 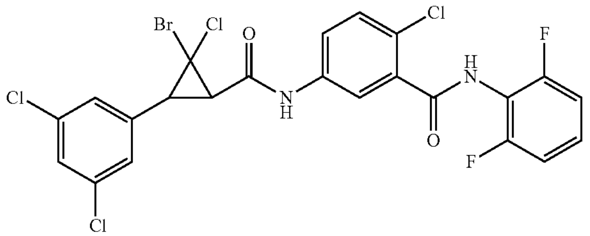 [SMILES: O=C(Nc1c(F)cccc1F)c1cc(NC(=O)C2C(c3cc(Cl)cc(Cl)c3)C2(Cl)Br)ccc1Cl] | 15 |
| F169 | 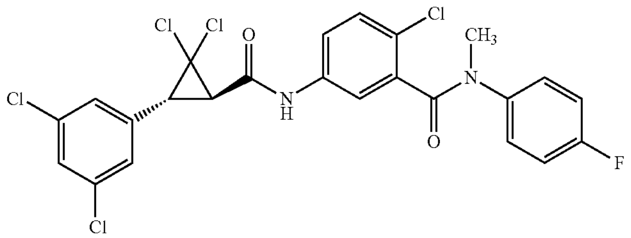 [SMILES: CN(C(=O)c1cc(NC(=O)[C@H]2[C@H](c3cc(Cl)cc(Cl)c3)C2(Cl)Cl)ccc1Cl)c1ccc(F)cc1] | 14 |
| F170 | 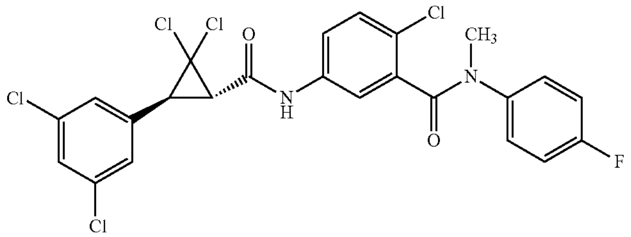 [SMILES: CN(C(=O)c1cc(NC(=O)[C@@H]2[C@@H](c3cc(Cl)cc(Cl)c3)C2(Cl)Cl)ccc1Cl)c1ccc(F)cc1] | 14 |
| F171 | 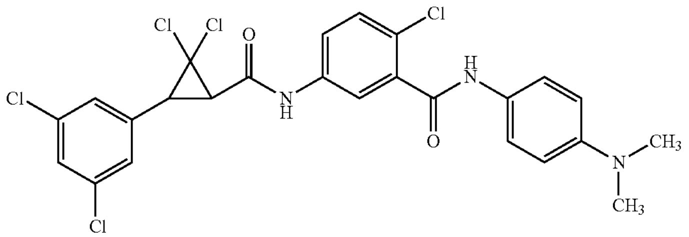 [SMILES: CN(C)c1ccc(NC(=O)c2cc(NC(=O)C3C(c4cc(Cl)cc(Cl)c4)C3(Cl)Cl)ccc2Cl)cc1] | 18 |
| F172 | 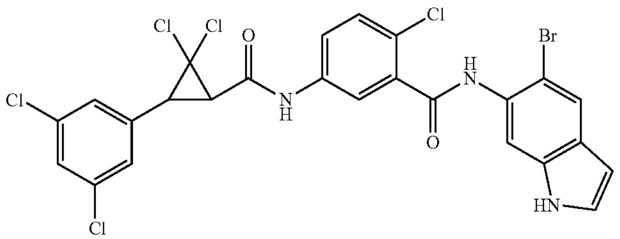 [SMILES: O=C(Nc1cc2[nH]ccc2cc1Br)c1cc(NC(=O)C2C(c3cc(Cl)cc(Cl)c3)C2(Cl)Cl)ccc1Cl] | 15 |

TABLE 2-continued
| Structure and preparation method for F Series molecules | | |
|---|---|---|
| No. | Structure | Prep.* |
| F173 | 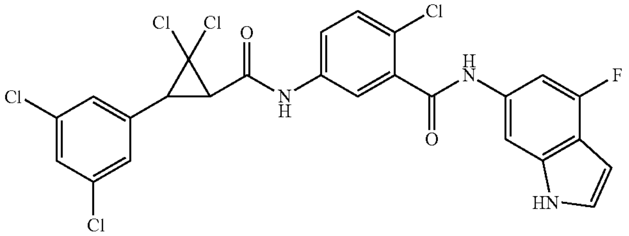 [SMILES: O=C(Nc1cc(F)c2cc[nH]c2c1)c1cc(NC(=O)C2C(c3cc(Cl)cc(Cl)c3)C2(Cl)Cl)ccc1Cl] | 15 |
| F174 | 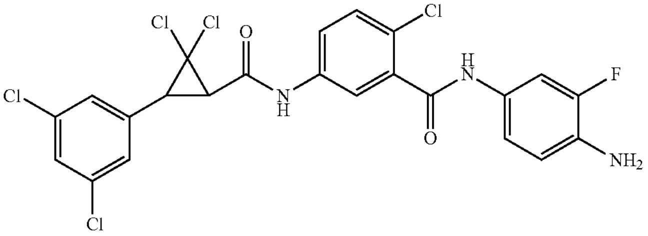 [SMILES: Nc1ccc(NC(=O)c2cc(NC(=O)C3C(c4cc(Cl)cc(Cl)c4)C3(Cl)Cl)ccc2Cl)cc1F] | 62 |
| F175 | 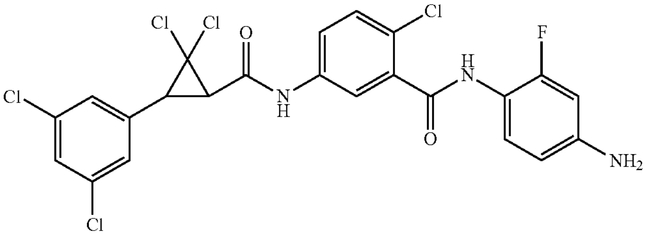 [SMILES: Nc1ccc(NC(=O)c2cc(NC(=O)C3C(c4cc(Cl)cc(Cl)c4)C3(Cl)Cl)ccc2Cl)c(F)c1] | 62 |
| F176 | 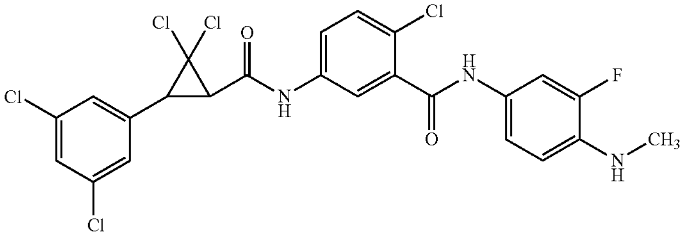 [SMILES: CNc1ccc(NC(=O)c2cc(NC(=O)C3C(c4cc(Cl)cc(Cl)c4)C3(Cl)Cl)ccc2Cl)cc1F] | 62 |
| F177 | 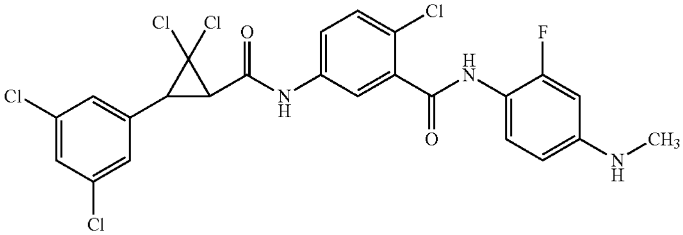 [SMILES: CNc1ccc(NC(=O)c2cc(NC(=O)C3C(c4cc(Cl)cc(Cl)c4)C3(Cl)Cl)ccc2Cl)c(F)c1] | 62 |
| F178 | 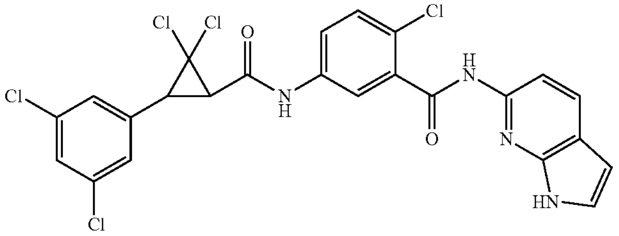 [SMILES: O=C(Nc1ccc2cc[nH]c2n1)c1cc(NC(=O)C2C(c3cc(Cl)cc(Cl)c3)C2(Cl)Cl)ccc1Cl] | 15 |

TABLE 2-continued
| Structure and preparation method for F Series molecules | | |
|---|---|---|
| No. | Structure | Prep.* |
| F179 | 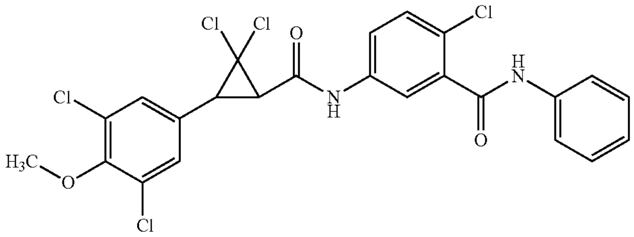 [SMILES: COc1c(Cl)cc(C2C(C(=O)Nc3ccc(Cl)c(C(=O)Nc4ccccc4)c3)C2(Cl)Cl)cc1Cl] | 56 |
| F180 | 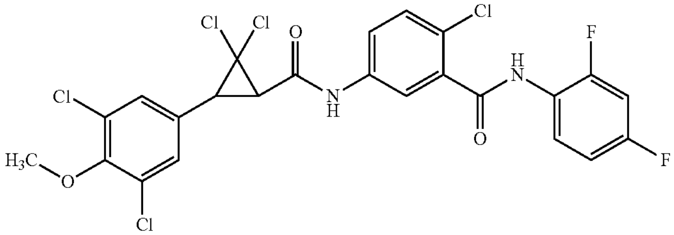 [SMILES: COc1c(Cl)cc(C2C(C(=O)Nc3ccc(Cl)c(C(=O)Nc4ccc(F)cc4F)c3)C2(Cl)Cl)cc1Cl] | 56 |
| F181 | 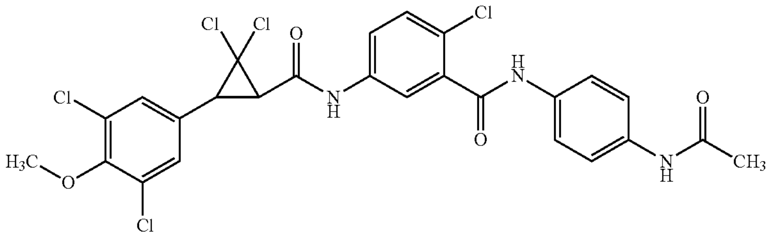 [SMILES: COc1c(Cl)cc(C2C(C(=O)Nc3ccc(Cl)c(C(=O)Nc4ccc(NC(C)=O)cc4)c3)C2(Cl)Cl)cc1Cl] | 56 |
| F182 | 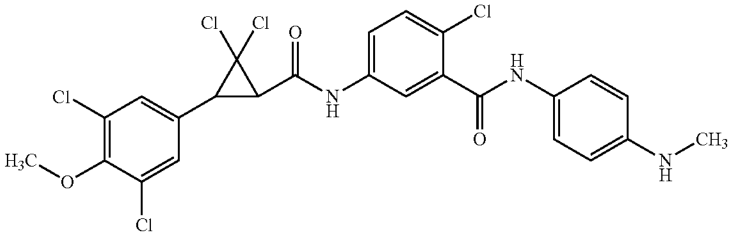 | 56 |
| F183 | 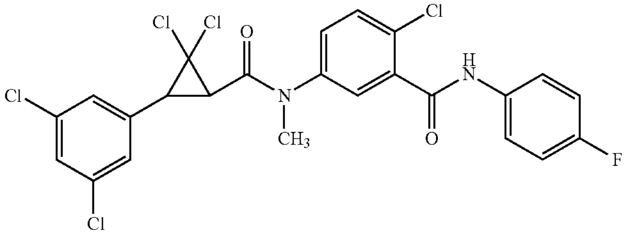 [SMILES: CN(C(=O)C1C(c2cc(Cl)cc(Cl)c2)C1(Cl)Cl)c1ccc(Cl)c(C(=O)Nc2ccc(F)cc2)c1] | 13 |
| F184 | 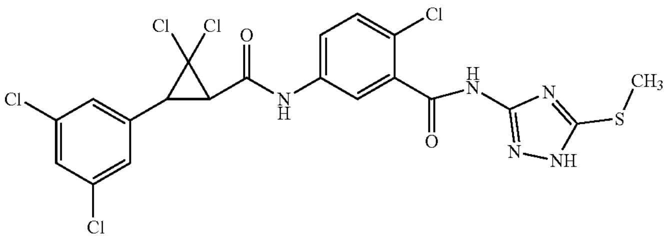 [SMILES: CSc1nc(NC(=O)c2cc(NC(=O)C3C(c4cc(Cl)cc(Cl)c4)C3(Cl)Cl)ccc2Cl)n[nH]1] | 15 |

TABLE 2-continued
| Structure and preparation method for F Series molecules | | |
|---|---|---|
| No. | Structure | Prep.* |
| F185 | 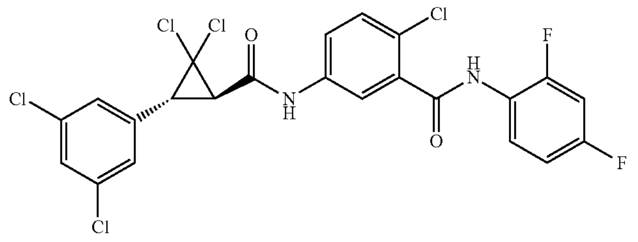 [SMILES: O=C(Nc1ccc(F)cc1F)c1cc(NC(=O)[C@H]2[C@H](c3cc(Cl)cc(Cl)c3)C2(Cl)Cl)ccc1Cl] | 14 |
| F186 | 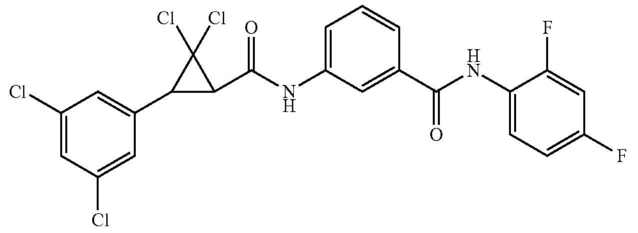 [SMILES: O=C(Nc1ccc(F)cc1F)c1cccc(NC(=O)C2C(c3cc(Cl)cc(Cl)c3)C2(Cl)Cl)c1] | 14 |
| F187 | 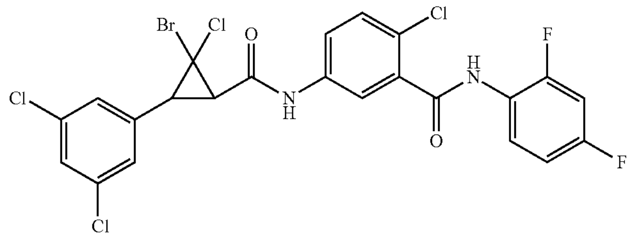 [SMILES: O=C(Nc1ccc(F)cc1F)c1cc(NC(=O)C2C(c3cc(Cl)cc(Cl)c3)C2(Cl)Br)ccc1Cl] | 15 |
| F188 | 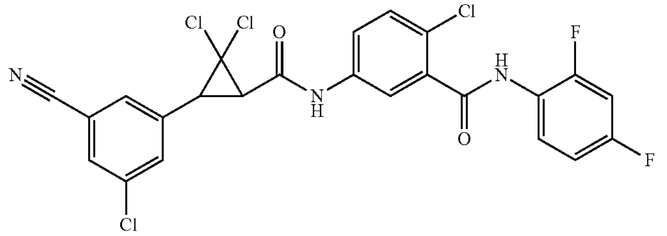 [SMILES: N#Cc1cc(Cl)cc(C2C(C(=O)Nc3ccc(Cl)c(C(=O)Nc4ccc(F)cc4F)c3)C2(Cl)Cl)c1] | 15 |
| F189 | 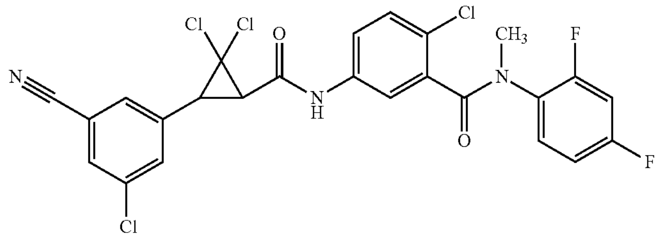 [SMILES: CN(C(=O)c1cc(NC(=O)C2C(c3cc(Cl)cc(C#N)c3)C2(Cl)Cl)ccc1Cl)c1ccc(F)cc1F] | 15 |
| F190 | 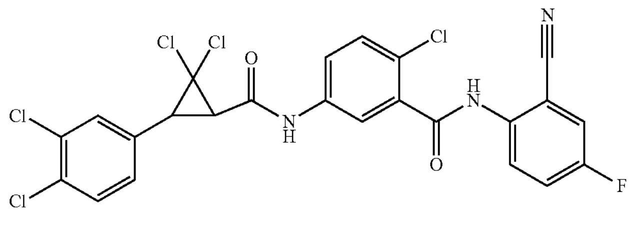 [SMILES: N#Cc1cc(F)ccc1NC(=O)c1cc(NC(=O)C2C(c3ccc(Cl)c(Cl)c3)C2(Cl)Cl)ccc1Cl] | 13 |

TABLE 2-continued
| Structure and preparation method for F Series molecules | | |
|---|---|---|
| No. | Structure | Prep.* |
| F191 | 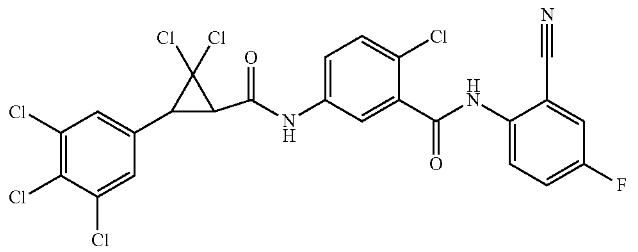 [SMILES: N#Cc1cc(F)ccc1NC(=O)c1cc(NC(=O)C2C(c3cc(Cl)c(Cl)c(Cl)c3)C2(Cl)Cl)ccc1Cl] | 13 |
| F192 | 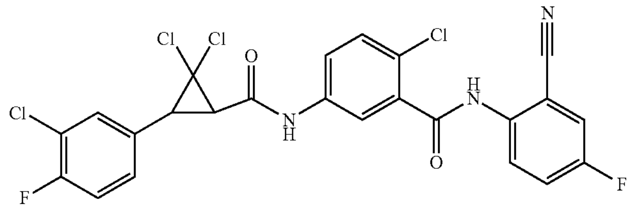 [SMILES: N#Cc1cc(F)ccc1NC(=O)c1cc(NC(=O)C2C(c3ccc(F)c(Cl)c3)C2(Cl)Cl)ccc1Cl] | 13 |
| F193 | 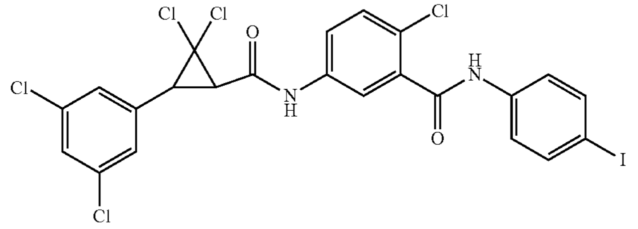 [SMILES: O=C(Nc1ccc(I)cc1)c1cc(NC(=O)C2C(c3cc(Cl)cc(Cl)c3)C2(Cl)Cl)ccc1Cl] | 13 |
| F194 | 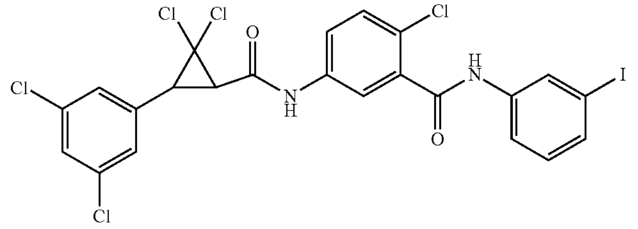 [SMILES: O=C(Nc1cccc(I)c1)c1cc(NC(=O)C2C(c3cc(Cl)cc(Cl)c3)C2(Cl)Cl)ccc1Cl] | 13 |
| F195 | 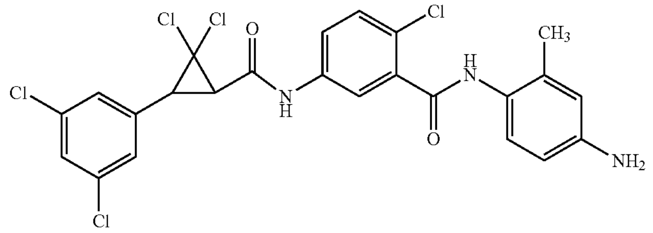 [SMILES: Cc1cc(N)ccc1NC(=O)c1cc(NC(=O)C2C(c3cc(Cl)cc(Cl)c3)C2(Cl)Cl)ccc1Cl] | 62 |
| F196 | 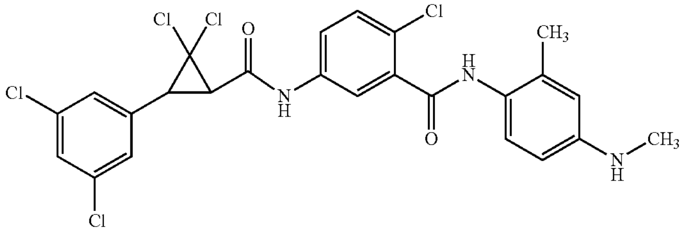 [SMILES: CNc1ccc(NC(=O)c2cc(NC(=O)C3C(c4cc(Cl)cc(Cl)c4)C3(Cl)Cl)ccc2Cl)c(C)c1] | 62 |

TABLE 2-continued
Structure and preparation method for F Series molecules
| No. | Structure | Prep.* |
| --- | --- | --- |
| F197 | 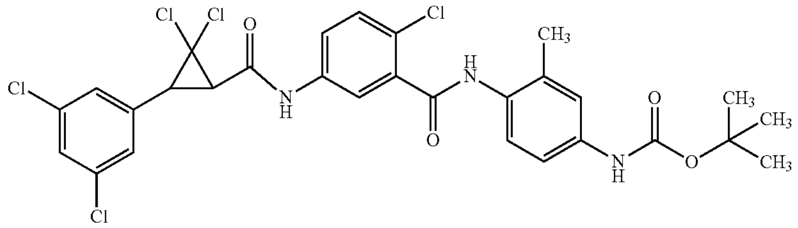 [SMILES: Cc1cc(NC(=O)OC(C)(C)C)ccc1NC(=O)c1cc(NC(=O)C2C(c3cc(Cl)cc(Cl)c3)C2(Cl)Cl)ccc1Cl] | 15 |
| F198 | 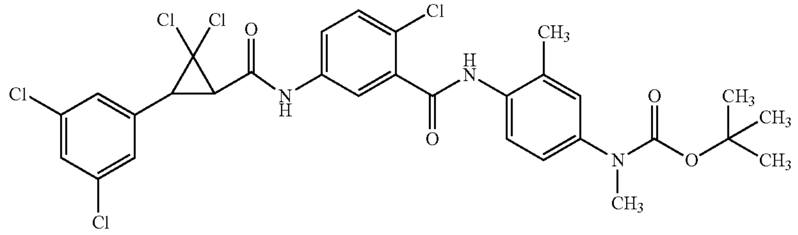 [SMILES: Cc1cc(N(C)C(=O)OC(C)(C)C)ccc1NC(=O)c1cc(NC(=O)C2C(c3cc(Cl)cc(Cl)c3)C2(Cl)Cl)ccc1Cl] | 15 |
| F199 | 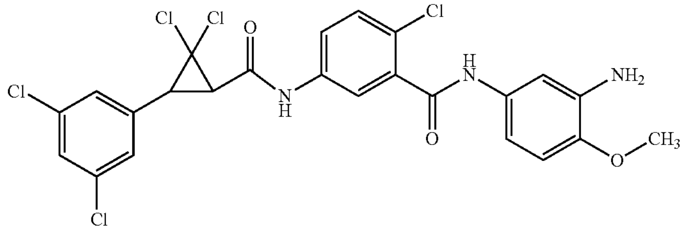 [SMILES: COc1ccc(NC(=O)c2cc(NC(=O)C3C(c4cc(Cl)cc(Cl)c4)C3(Cl)Cl)ccc2Cl)cc1N] | 62 |
| F200 | 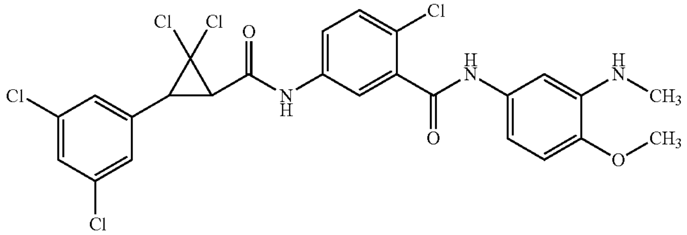 [SMILES: CNc1cc(NC(=O)c2cc(NC(=O)C3C(c4cc(Cl)cc(Cl)c4)C3(Cl)Cl)ccc2Cl)ccc1OC] | 62 |
| F201 | 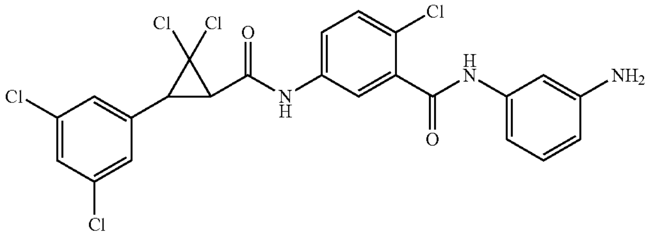 [SMILES: Nc1cccc(NC(=O)c2cc(NC(=O)C3C(c4cc(Cl)cc(Cl)c4)C3(Cl)Cl)ccc2Cl)c1] | 62 |
| F202 | 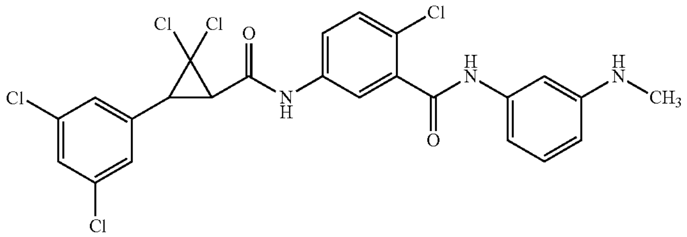 [SMILES: CNc1cccc(NC(=O)c2cc(NC(=O)C3C(c4cc(Cl)cc(Cl)c4)C3(Cl)Cl)ccc2Cl)c1] | 62 |

TABLE 2-continued
| Structure and preparation method for F Series molecules | | |
|---|---|---|
| No. | Structure | Prep.* |
| F203 | 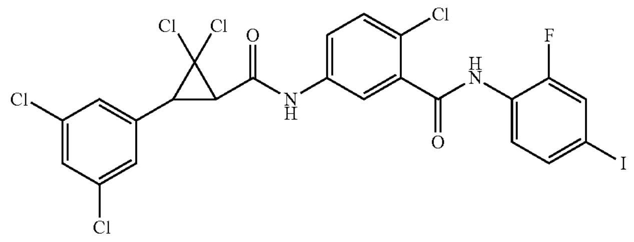 [SMILES: O=C(Nc1ccc(I)cc1F)c1cc(NC(=O)C2C(c3cc(Cl)cc(Cl)c3)C2(Cl)Cl)ccc1Cl] | 13 |
| F204 | 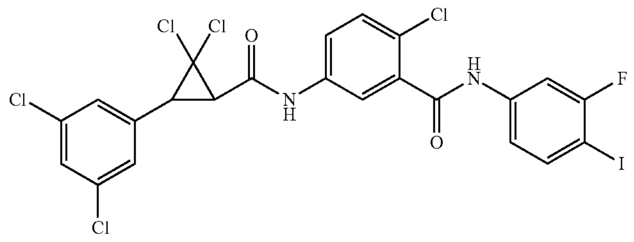 [SMILES: O=C(Nc1ccc(I)c(F)c1)c1cc(NC(=O)C2C(c3cc(Cl)cc(Cl)c3)C2(Cl)Cl)ccc1Cl] | 13 |
| F205 | 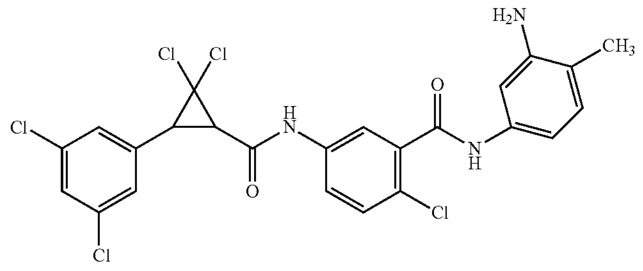 [SMILES: Cc1ccc(NC(=O)c2cc(NC(=O)C3C(c4cc(Cl)cc(Cl)c4)C3(Cl)Cl)ccc2Cl)cc1N] | 62 |
| F206 | 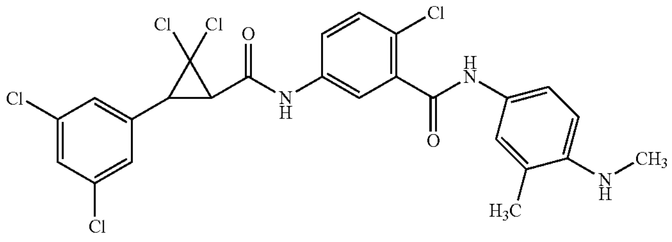 [SMILES: CNc1ccc(NC(=O)c2cc(NC(=O)C3C(c4cc(Cl)cc(Cl)c4)C3(Cl)Cl)ccc2Cl)cc1C] | 62 |
| F207 | 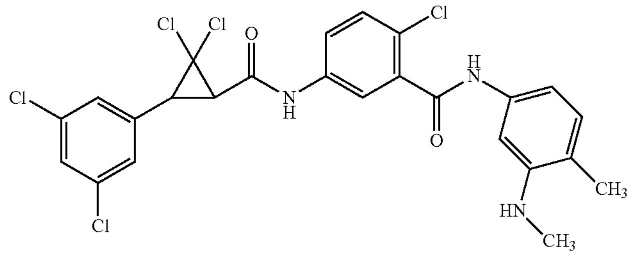 [SMILES: CNc1cc(NC(=O)c2cc(NC(=O)C3C(c4cc(Cl)cc(Cl)c4)C3(Cl)Cl)ccc2Cl)ccc1C] | 62 |
| F208 | 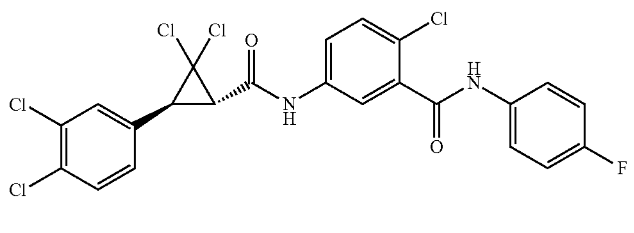 [SMILES: O=C(Nc1ccc(F)cc1)c1cc(NC(=O)[C@@H]2[C@@H](c3ccc(Cl)c(Cl)c3)C2(Cl)Cl)ccc1Cl] | 14 |

TABLE 2-continued
| Structure and preparation method for F Series molecules | | |
|---|---|---|
| No. | Structure | Prep.* |
| F209 | 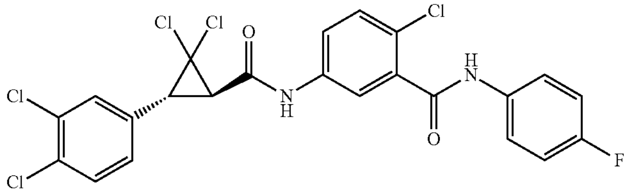 [SMILES: O=C(Nc1ccc(F)cc1)c1cc(NC(=O)[C@H]2[C@H](c3ccc(Cl)c(Cl)c3)C2(Cl)Cl)ccc1Cl] | 14 |
| F210 | 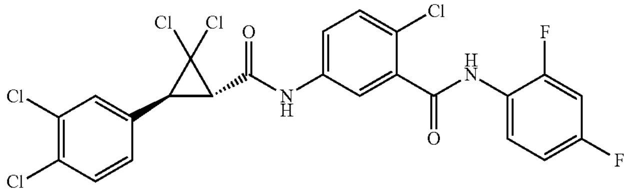 [SMILES: O=C(Nc1ccc(F)cc1F)c1cc(NC(=O)[C@@H]2[C@@H](c3ccc(Cl)c(Cl)c3)C2(Cl)Cl)ccc1Cl] | 14 |
| F211 | 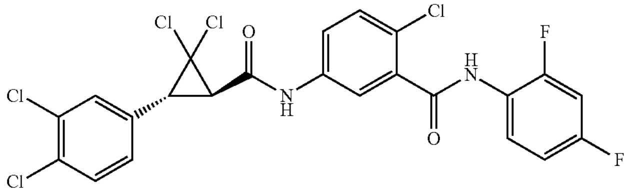 [SMILES: O=C(Nc1ccc(F)cc1F)c1cc(NC(=O)[C@H]2[C@H](c3ccc(Cl)c(Cl)c3)C2(Cl)Cl)ccc1Cl] | 14 |
| F212 | 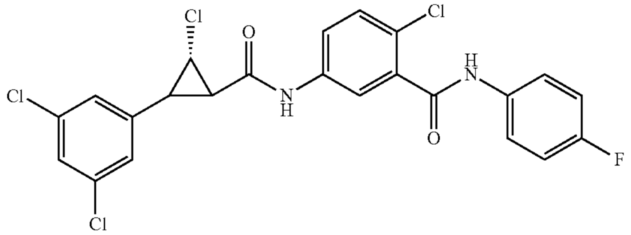 [SMILES: O=C(Nc1ccc(F)cc1)c1cc(NC(=O)C2C(c3cc(Cl)cc(Cl)c3)[C@@H]2Cl)ccc1Cl] | 15 |
| F213 | 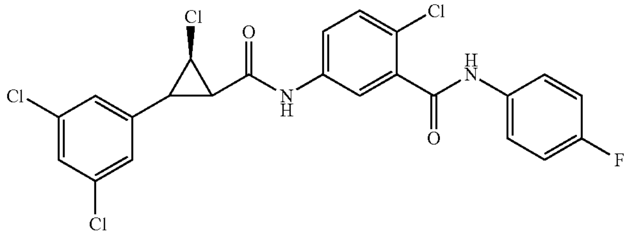 [SMILES: O=C(Nc1ccc(F)cc1)c1cc(NC(=O)C2C(c3cc(Cl)cc(Cl)c3)[C@H]2Cl)ccc1Cl] | 15 |
| F214 | 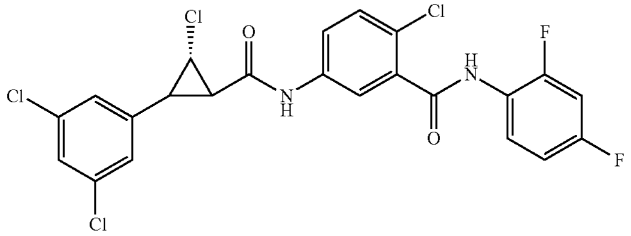 | 15 |

TABLE 2-continued
| Structure and preparation method for F Series molecules | | |
|---|---|---|
| No. | Structure | Prep.* |
| F215 | 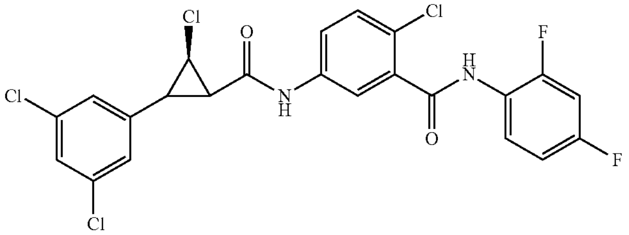 [SMILES: O=C(Nc1ccc(F)cc1F)c1cc(NC(=O)C2C(c3cc(Cl)cc(Cl)c3)[C@H]2Cl)ccc1Cl] | 15 |
| F216 | 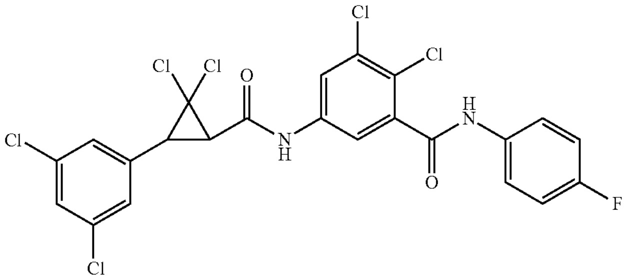 [SMILES: O=C(Nc1ccc(F)cc1)c1cc(NC(=O)C2C(c3cc(Cl)cc(Cl)c3)C2(Cl)Cl)cc(Cl)c1Cl] | 56 |
| F217 | 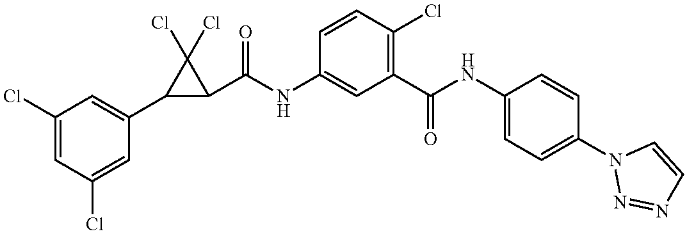 | 13 |
| F218 | 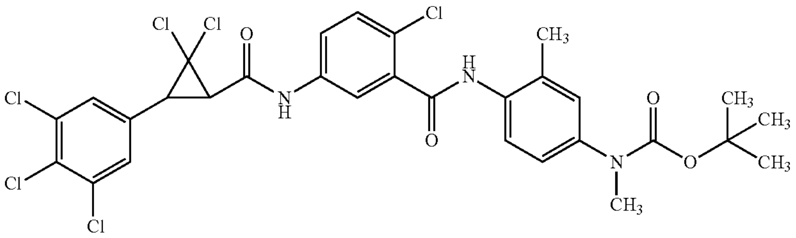 [SMILES: Cc1cc(N(C)C(=O)OC(C)(C)C)ccc1NC(=O)c1cc(NC(=O)C2C(c3cc(Cl)c(Cl)c(Cl)c3)C2(Cl)Cl)ccc1Cl] | 13 |
| F219 | 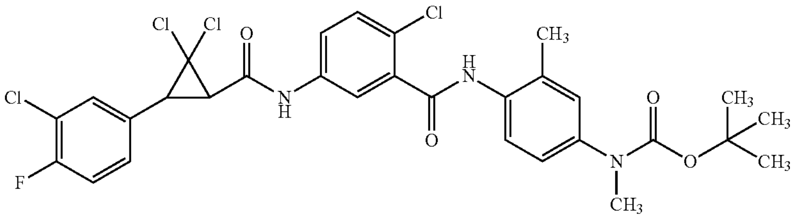 [SMILES: Cc1cc(N(C)C(=O)OC(C)(C)C)ccc1NC(=O)c1cc(NC(=O)C2C(c3ccc(F)c(Cl)c3)C2(Cl)Cl)ccc1Cl] | 13 |
| F220 | 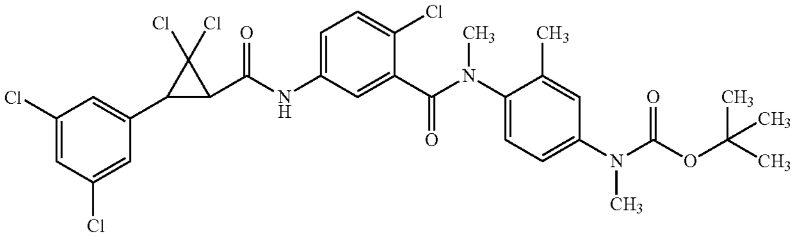 [SMILES: Cc1cc(N(C)C(=O)OC(C)(C)C)ccc1N(C)C(=O)c1cc(NC(=O)C2C(c3cc(Cl)cc(Cl)c3)C2(Cl)Cl)ccc1Cl] | 13 |

TABLE 2-continued
| Structure and preparation method for F Series molecules | | |
|---|---|---|
| No. | Structure | Prep.* |
| F221 | 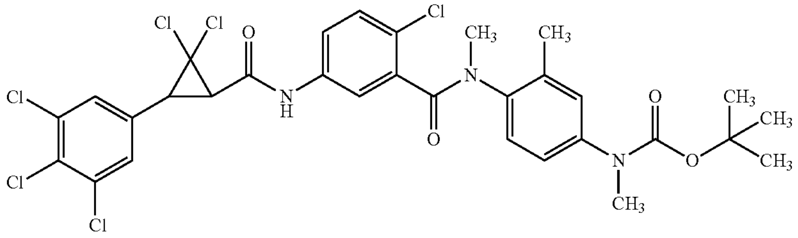 [SMILES: Cc1cc(N(C)C(=O)OC(C)(C)C)ccc1N(C)C(=O)c1cc(NC(=O)C2C(c3cc(Cl)c(Cl)c(Cl)c3)C2(Cl)Cl)ccc1Cl] | 13 |
| F222 | 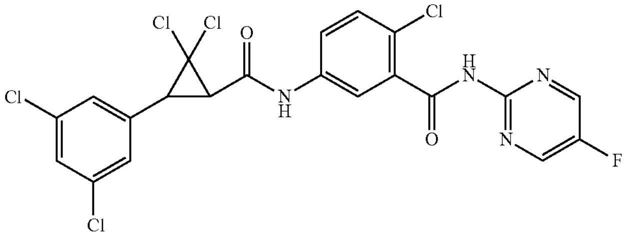 [SMILES: O=C(Nc1ncc(F)cn1)c1cc(NC(=O)C2C(c3cc(Cl)cc(Cl)c3)C2(Cl)Cl)ccc1Cl] | 55 |
| F223 | 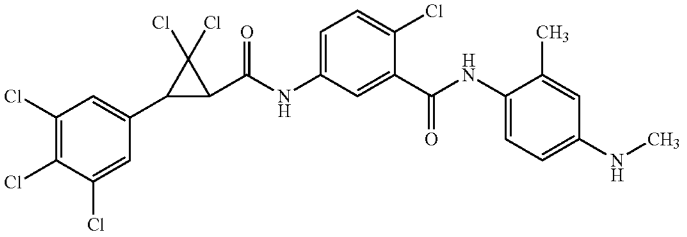 [SMILES: CNc1ccc(NC(=O)c2cc(NC(=O)C3C(c4cc(Cl)c(Cl)c(Cl)c4)C3(Cl)Cl)ccc2Cl)c(C)c1] | 62 |
| F224 | 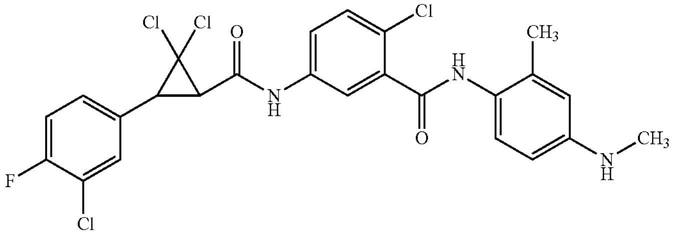 [SMILES: CNc1ccc(NC(=O)c2cc(NC(=O)C3C(c4ccc(F)c(Cl)c4)C3(Cl)Cl)ccc2Cl)c(C)c1] | 62 |
| F225 | 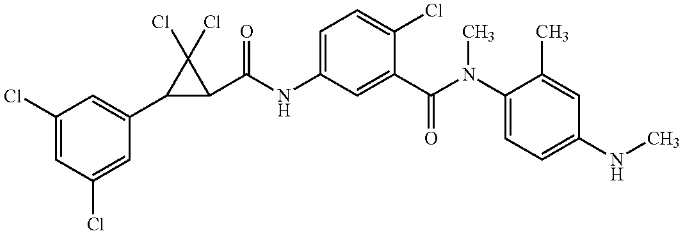 [SMILES: CNc1ccc(N(C)C(=O)c2cc(NC(=O)C3C(c4cc(Cl)cc(Cl)c4)C3(Cl)Cl)ccc2Cl)c(C)c1] | 62 |
| F226 | 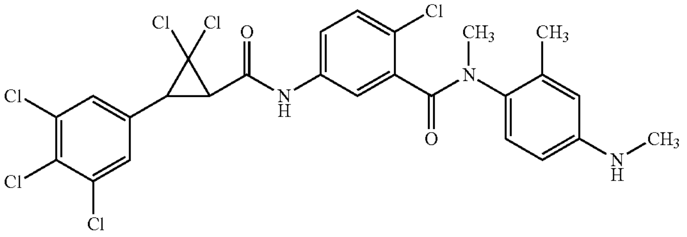 [SMILES: CNc1ccc(N(C)C(=O)c2cc(NC(=O)C3C(c4cc(Cl)c(Cl)c(Cl)c4)C3(Cl)Cl)ccc2Cl)c(C)c1] | 62 |

TABLE 2-continued
| No. | Structure | Prep.* |
|---|---|---|
| | Structure and preparation method for F Series molecules | |
| F227 | 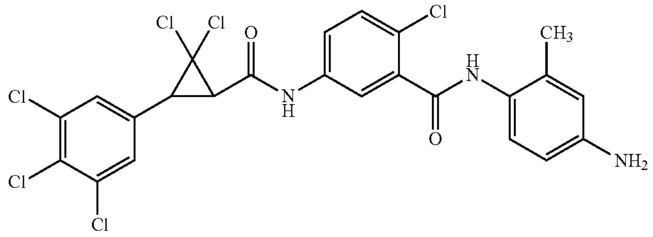 [SMILES: Cc1cc(N)ccc1NC(=O)c1cc(NC(=O)C2C(c3cc(Cl)c(Cl)c(Cl)c3)C2(Cl)Cl)ccc1Cl] | 62 |
| F228 | 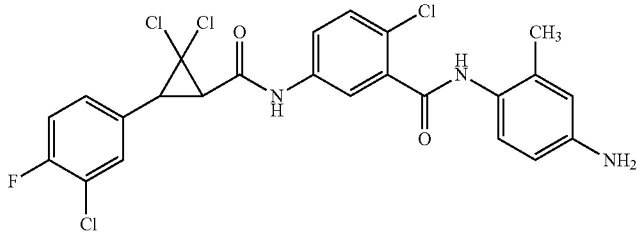 [SMILES: Cc1cc(N)ccc1NC(=O)c1cc(NC(=O)C2C(c3ccc(F)c(Cl)c3)C2(Cl)Cl)ccc1Cl] | 62 |
| F229 | 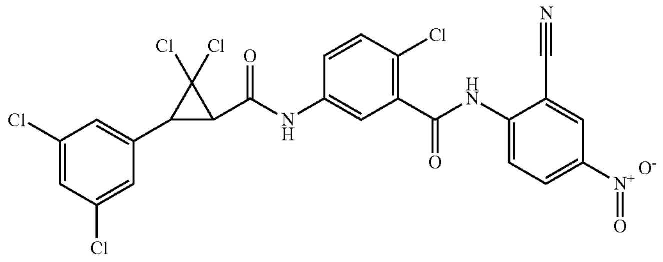 | 54 |
| F230 | 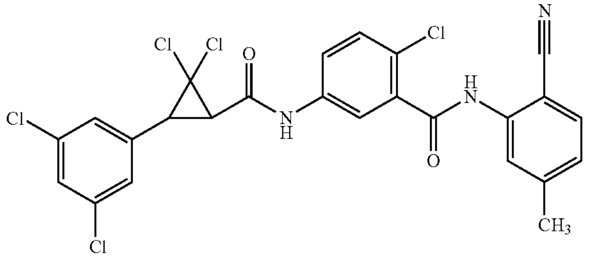 [SMILES: Cc1ccc(C#N)c(NC(=O)c2cc(NC(=O)C3C(c4cc(Cl)cc(Cl)c4)C3(Cl)Cl)ccc2Cl)c1] | 54 |
| F231 | 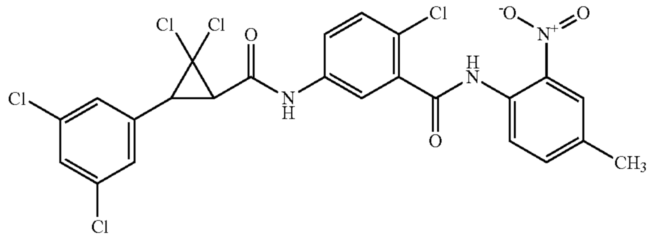 | 54 |
| F232 | 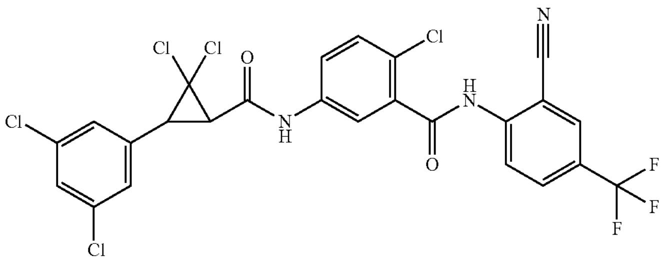 [SMILES: N#Cc1cc(C(F)(F)F)ccc1NC(=O)c1cc(NC(=O)C2C(c3cc(Cl)cc(Cl)c3)C2(Cl)Cl)ccc1Cl] | 54 |

TABLE 2-continued
| No. | Structure | Prep.* |
| --- | --- | --- |
| F233 | 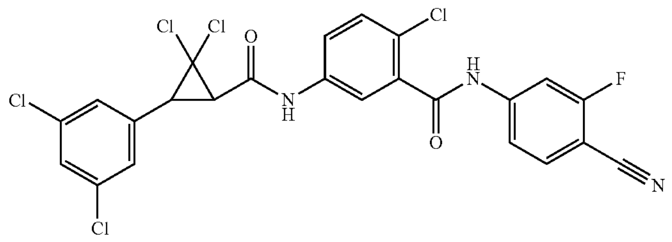 [SMILES: N#Cc1ccc(NC(=O)c2cc(NC(=O)C3C(c4cc(Cl)cc(Cl)c4)C3(Cl)Cl)ccc2Cl)cc1F] | 54 |
| F234 | 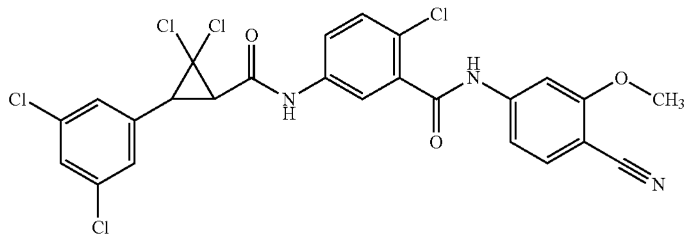 [SMILES: COc1cc(NC(=O)c2cc(NC(=O)C3C(c4cc(Cl)cc(Cl)c4)C3(Cl)Cl)ccc2Cl)ccc1C#N] | 54 |
| F235 | 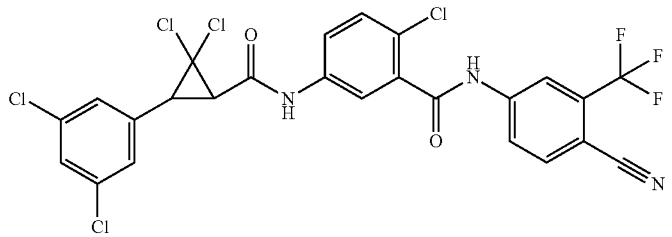 [SMILES: N#Cc1ccc(NC(=O)c2cc(NC(=O)C3C(c4cc(Cl)cc(Cl)c4)C3(Cl)Cl)ccc2Cl)cc1C(F)(F)F] | 54 |
| F236 | 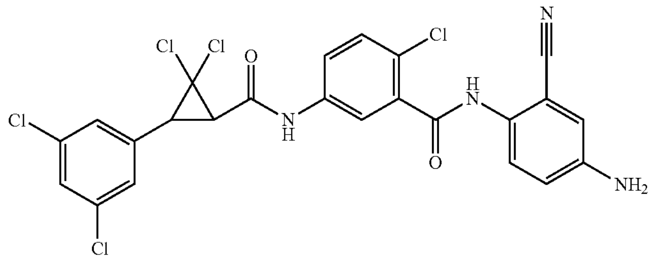 [SMILES: N#Cc1cc(N)ccc1NC(=O)c1cc(NC(=O)C2C(c3cc(Cl)cc(Cl)c3)C2(Cl)Cl)ccc1Cl] | 59 |
| F237 | 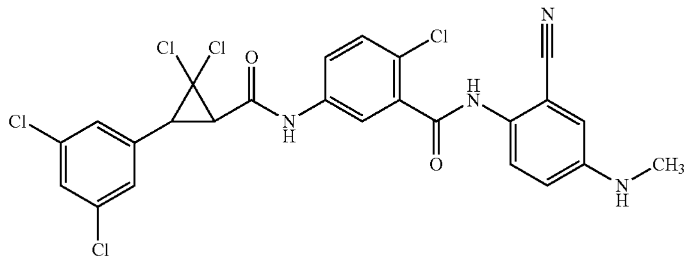 [SMILES: CNc1ccc(NC(=O)c2cc(NC(=O)C3C(c4cc(Cl)cc(Cl)c4)C3(Cl)Cl)ccc2Cl)c(C#N)c1] | 65 |
| F238 | 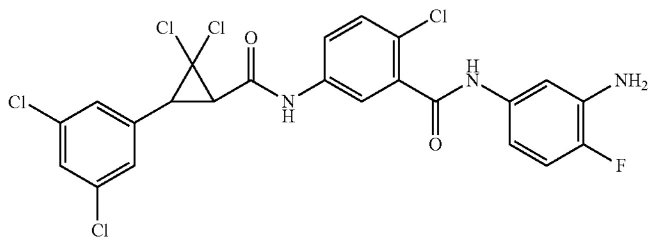 [SMILES: Nc1cc(NC(=O)c2cc(NC(=O)C3C(c4cc(Cl)cc(Cl)c4)C3(Cl)Cl)ccc2Cl)ccc1F] | 62 |
Structure and preparation method for F Series molecules TABLE 2-continued
Structure and preparation method for F Series molecules
| No. | Structure | Prep.* |
|---|---|---|
| F239 | 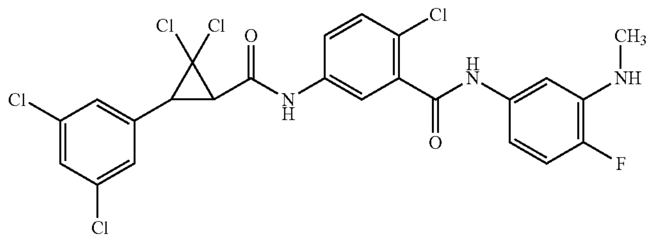 [SMILES: CNc1cc(NC(=O)c2cc(NC(=O)C3C(c4cc(Cl)cc(Cl)c4)C3(Cl)Cl)ccc2Cl)ccc1F] | 62 |
| F240 | 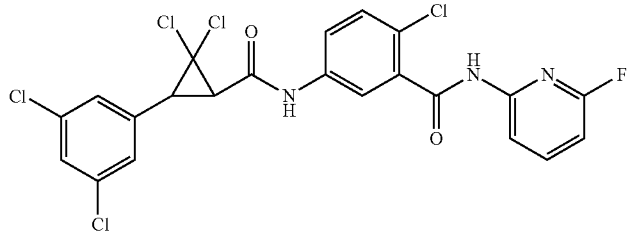 | 55 |
| F241 | 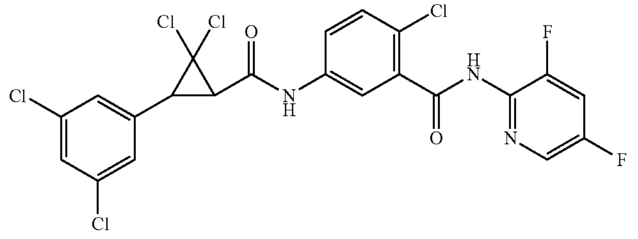 | 55 |
| F242 | 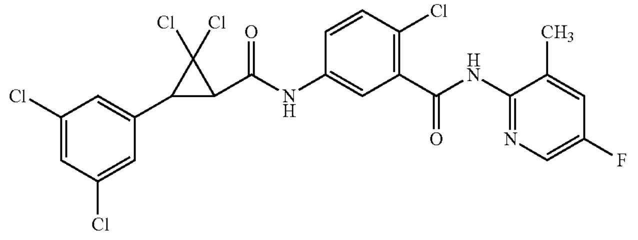 [SMILES: Cc1cc(F)cnc1NC(=O)c1cc(NC(=O)C2C(c3cc(Cl)cc(Cl)c3)C2(Cl)Cl)ccc1Cl] | 55 |
| F243 | 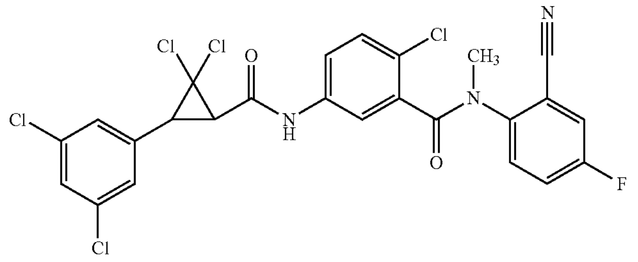 [SMILES: CN(C(=O)c1cc(NC(=O)C2C(c3cc(Cl)cc(Cl)c3)C2(Cl)Cl)ccc1Cl)c1ccc(F)cc1C#N] | 13 |
| F244 | 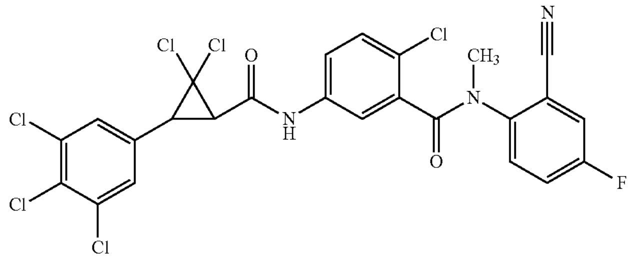 [SMILES: CN(C(=O)c1cc(NC(=O)C2C(c3cc(Cl)c(Cl)c(Cl)c3)C2(Cl)Cl)ccc1Cl)c1ccc(F)cc1C#N] | 13 |

TABLE 2-continued
| Structure and preparation method for F Series molecules | | |
|---|---|---|
| No. | Structure | Prep.* |
| F245 | 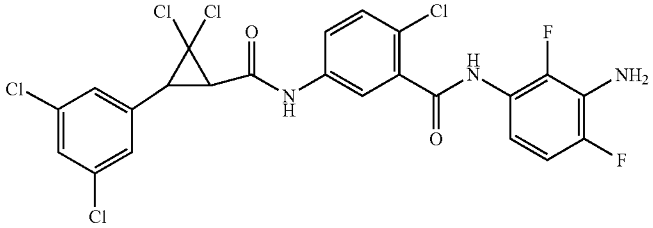 [SMILES: Nc1c(F)ccc(NC(=O)c2cc(NC(=O)C3C(c4cc(Cl)cc(Cl)c4)C3(Cl)Cl)ccc2Cl)c1F] | 62 |
| F246 | 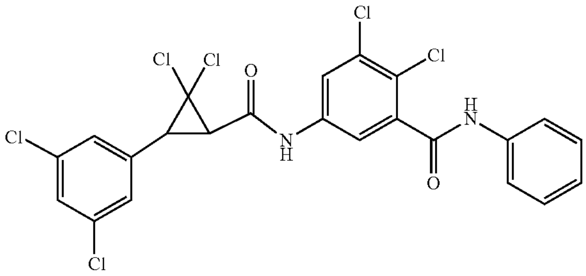 [SMILES: O=C(Nc1ccccc1)c1cc(NC(=O)C2C(c3cc(Cl)cc(Cl)c3)C2(Cl)Cl)cc(Cl)c1Cl] | 56 |
| F247 | 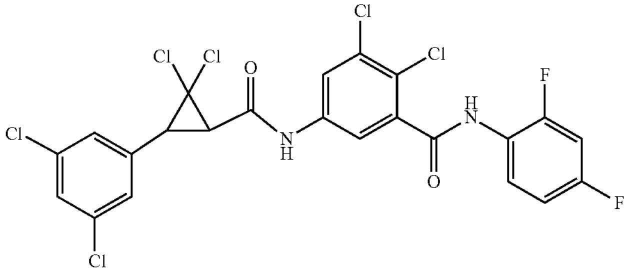 [SMILES: O=C(Nc1ccc(F)cc1F)c1cc(NC(=O)C2C(c3cc(Cl)cc(Cl)c3)C2(Cl)Cl)cc(Cl)c1Cl] | 56 |
| F248 | 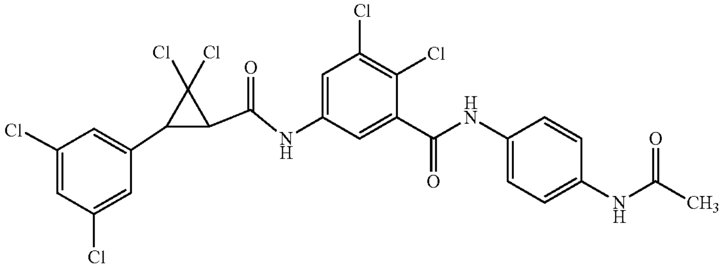 [SMILES: CC(=O)Nc1ccc(NC(=O)c2cc(NC(=O)C3C(c4cc(Cl)cc(Cl)c4)C3(Cl)Cl)cc(Cl)c2Cl)cc1] | 56 |
| F249 | 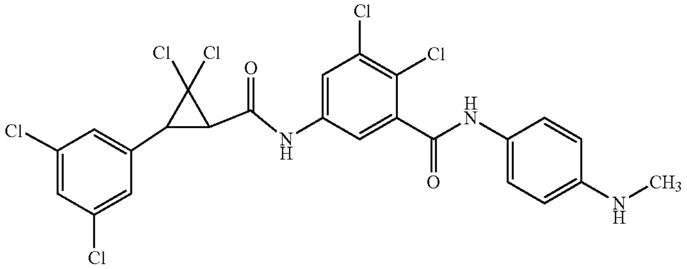 [SMILES: CNc1ccc(NC(=O)c2cc(NC(=O)C3C(c4cc(Cl)cc(Cl)c4)C3(Cl)Cl)cc(Cl)c2Cl)cc1] | 56 |

TABLE 2-continued
| Structure and preparation method for F Series molecules | | |
|---|---|---|
| No. | Structure | Prep.* |
| F250 | 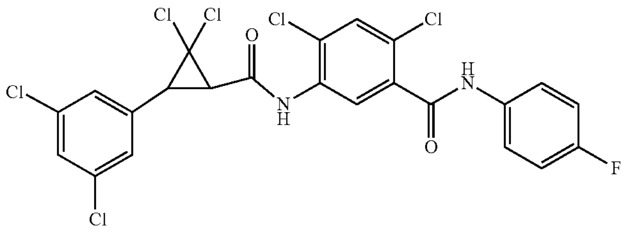 [SMILES: O=C(Nc1ccc(F)cc1)c1cc(NC(=O)C2C(c3cc(Cl)cc(Cl)c3)C2(Cl)Cl)c(Cl)cc1Cl] | 56 |
| F251 | 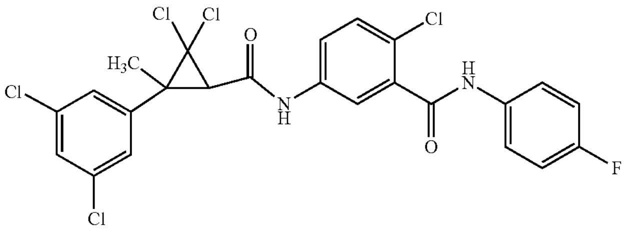 [SMILES: CC1(c2cc(Cl)cc(Cl)c2)C(C(=O)Nc2ccc(Cl)c(C(=O)Nc3ccc(F)cc3)c2)C1(Cl)Cl] | 55 |
| F252 | 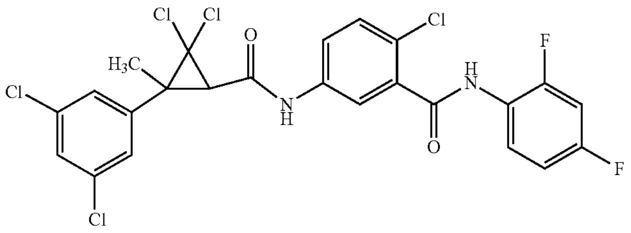 [SMILES: CC1(c2cc(Cl)cc(Cl)c2)C(C(=O)Nc2ccc(Cl)c(C(=O)Nc3ccc(F)cc3F)c2)C1(Cl)Cl] | 55 |
| F253 | 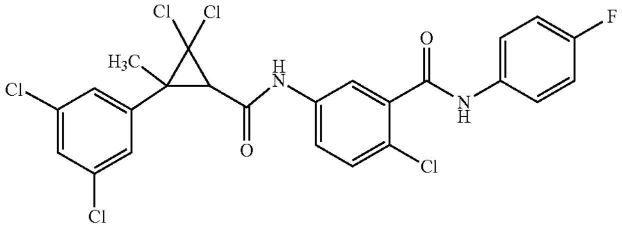 [SMILES: CC1(c2cc(Cl)cc(Cl)c2)C(C(=O)Nc2ccc(Cl)c(C(=O)Nc3ccc(F)cc3)c2)C1(Cl)Cl] | 55 |
| F254 | 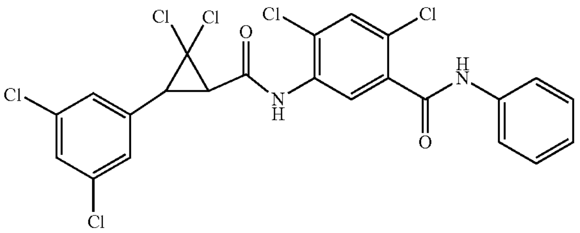 [SMILES: O=C(Nc1ccccc1)c1cc(NC(=O)C2C(c3cc(Cl)cc(Cl)c3)C2(Cl)Cl)c(Cl)cc1Cl] | 56 |
| F255 | 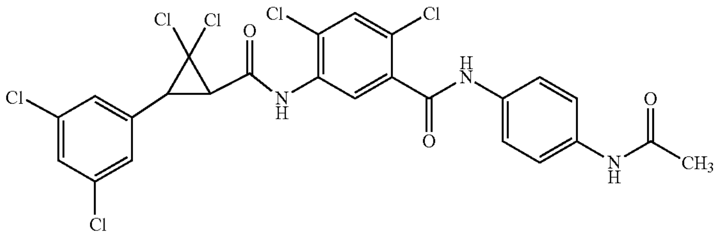 [SMILES: CC(=O)Nc1ccc(NC(=O)c2cc(NC(=O)C3C(c4cc(Cl)cc(Cl)c4)C3(Cl)Cl)c(Cl)cc2Cl)cc1] | 56 |

TABLE 2-continued
| Structure and preparation method for F Series molecules | | |
|---|---|---|
| No. | Structure | Prep.* |
| F256 | 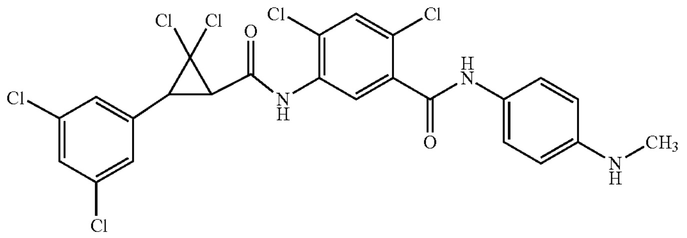 [SMILES: CNc1ccc(NC(=O)c2cc(NC(=O)C3C(c4cc(Cl)cc(Cl)c4)C3(Cl)Cl)c(Cl)cc2Cl)cc1] | 56 |
| F257 | 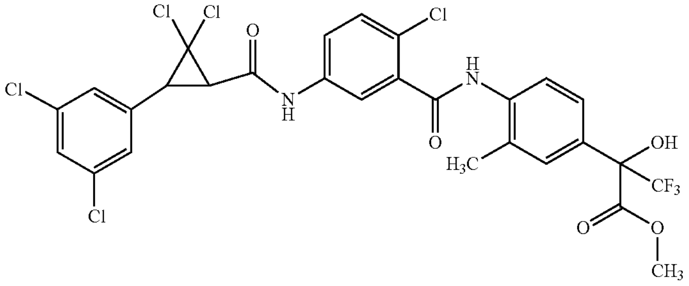 [SMILES: COC(=O)C(O)(c1ccc(NC(=O)c2cc(NC(=O)C3C(c4cc(Cl)cc(Cl)c4)C3(Cl)Cl)ccc2Cl)c(C)c1)C(F)(F)F] | 55 |
| F258 | 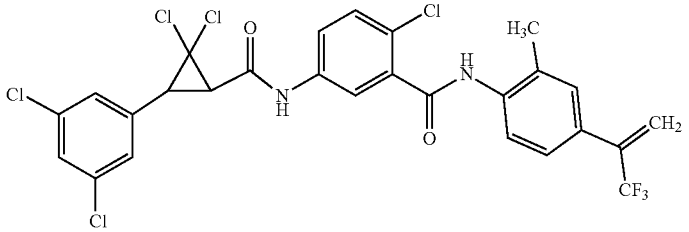 [SMILES: C=C(c1ccc(NC(=O)c2cc(NC(=O)C3C(c4cc(Cl)cc(Cl)c4)C3(Cl)Cl)ccc2Cl)c(C)c1)C(F)(F)F] | 55 |
| F259 | 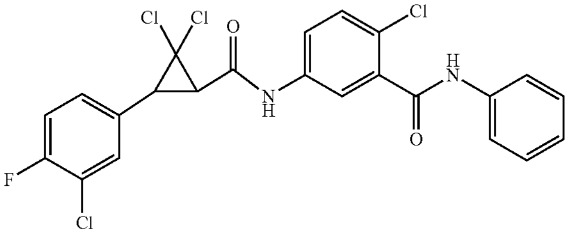 [SMILES: O=C(Nc1ccccc1)c1cc(NC(=O)C2C(c3ccc(F)c(Cl)c3)C2(Cl)Cl)ccc1Cl] | 56 |
| F260 | 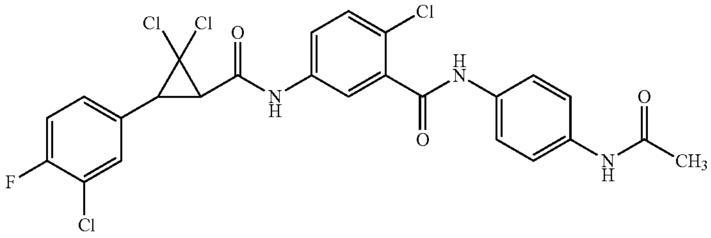 [SMILES: CC(=O)Nc1ccc(NC(=O)c2cc(NC(=O)C3C(c4ccc(F)c(Cl)c4)C3(Cl)Cl)ccc2Cl)cc1] | 56 |
| F261 | 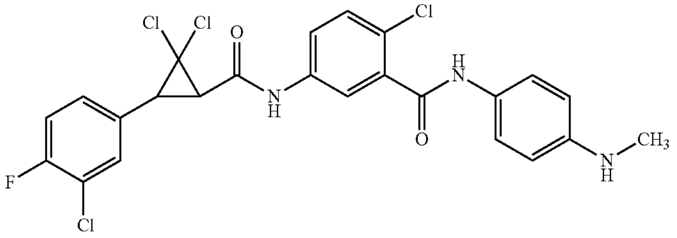 [SMILES: CNc1ccc(NC(=O)c2cc(NC(=O)C3C(c4ccc(F)c(Cl)c4)C3(Cl)Cl)ccc2Cl)cc1] | 56 |

TABLE 2-continued
| Structure and preparation method for F Series molecules | | |
|---|---|---|
| No. | Structure | Prep.* |
| F262 | 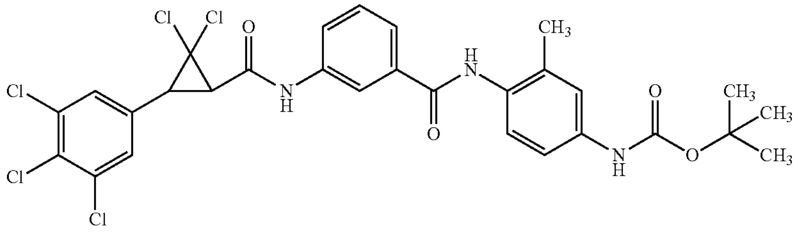 [SMILES: Cc1cc(NC(=O)OC(C)(C)C)ccc1NC(=O)c1cccc(NC(=O)C2C(c3cc(Cl)c(Cl)c(Cl)c3)C2(Cl)Cl)c1] | 13 |
| F263 | 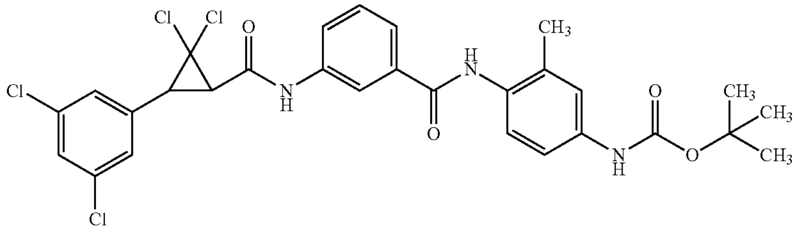 [SMILES: Cc1cc(NC(=O)OC(C)(C)C)ccc1NC(=O)c1cccc(NC(=O)C2C(c3cc(Cl)cc(Cl)c3)C2(Cl)Cl)c1] | 13 |
| F264 | 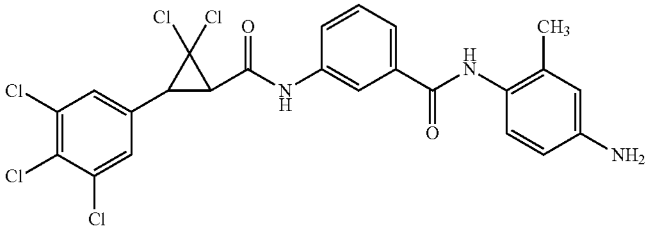 [SMILES: Cc1cc(N)ccc1NC(=O)c1cccc(NC(=O)C2C(c3cc(Cl)c(Cl)c(Cl)c3)C2(Cl)Cl)c1] | 62 |
| F265 | 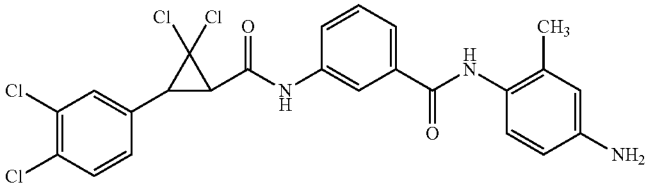 [SMILES: Cc1cc(N)ccc1NC(=O)c1cccc(NC(=O)C2C(c3ccc(Cl)c(Cl)c3)C2(Cl)Cl)c1] | 62 |
| F266 | 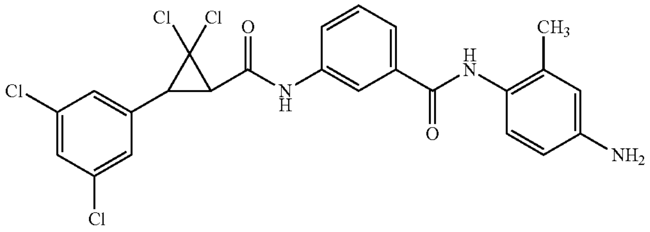 [SMILES: Cc1cc(N)ccc1NC(=O)c1cccc(NC(=O)C2C(c3cc(Cl)cc(Cl)c3)C2(Cl)Cl)c1] | 62 |
| F267 | 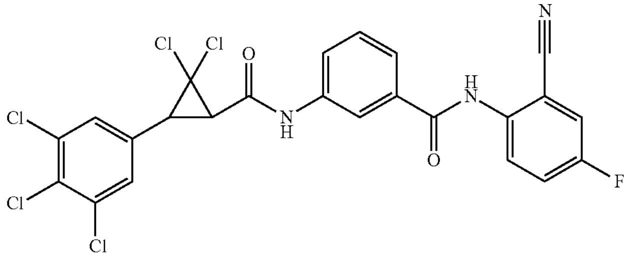 [SMILES: N#Cc1cc(F)ccc1NC(=O)c1cccc(NC(=O)C2C(c3cc(Cl)c(Cl)c(Cl)c3)C2(Cl)Cl)c1] | 57 |

TABLE 2-continued
| Structure and preparation method for F Series molecules | | |
|---|---|---|
| No. | Structure | Prep.* |
| F268 | 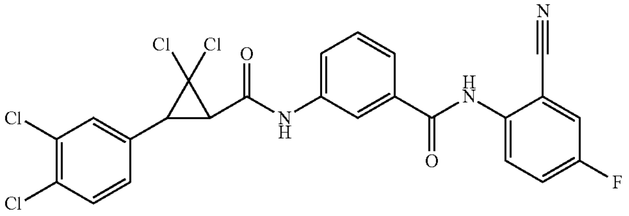 [SMILES: N#Cc1cc(F)ccc1NC(=O)c1cccc(NC(=O)C2C(c3ccc(Cl)c(Cl)c3)C2(Cl)Cl)c1] | 57 |
| F269 | 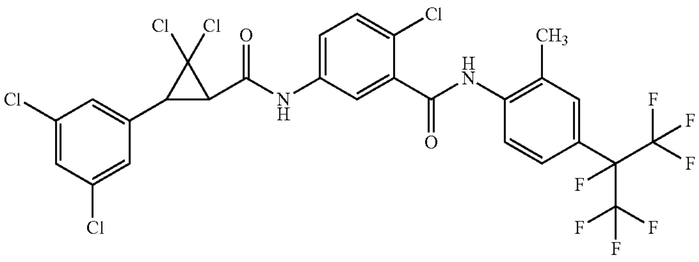 [SMILES: Cc1cc(C(F)(C(F)(F)F)C(F)(F)F)ccc1NC(=O)c1cc(NC(=O)C2C(c3cc(Cl)cc(Cl)c3)C2(Cl)Cl)ccc1Cl] | 55 |
| F270 | 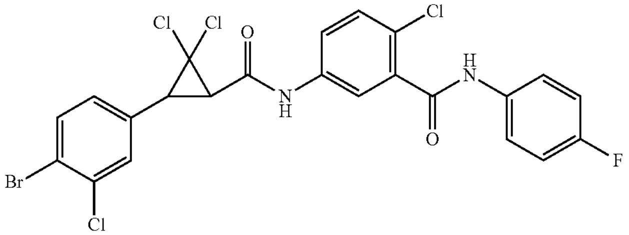 [SMILES: O=C(Nc1ccc(F)cc1)c1cc(NC(=O)C2C(c3ccc(Br)c(Cl)c3)C2(Cl)Cl)ccc1Cl] | 13 |
| F271 | 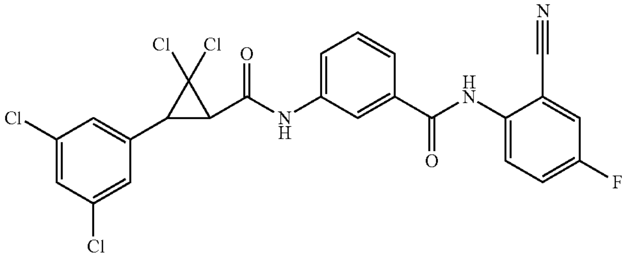 [SMILES: N#Cc1cc(F)ccc1NC(=O)c1cccc(NC(=O)C2C(c3cc(Cl)cc(Cl)c3)C2(Cl)Cl)c1] | 13 |
| F272 | 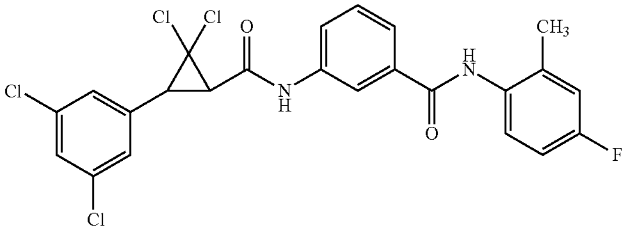 [SMILES: Cc1cc(F)ccc1NC(=O)c1cccc(NC(=O)C2C(c3cc(Cl)cc(Cl)c3)C2(Cl)Cl)c1] | 13 |
| F273 | 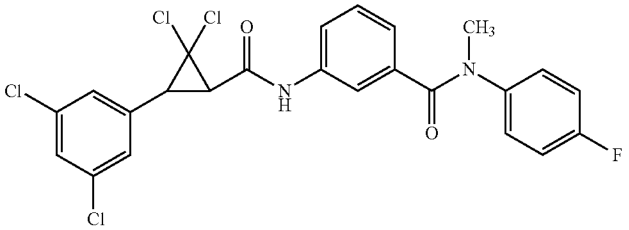 [SMILES: CN(C(=O)c1cccc(NC(=O)C2C(c3cc(Cl)cc(Cl)c3)C2(Cl)Cl)c1)c1ccc(F)cc1] | 13 |

TABLE 2-continued
| Structure and preparation method for F Series molecules | | |
|---|---|---|
| No. | Structure | Prep.* |
| F274 | 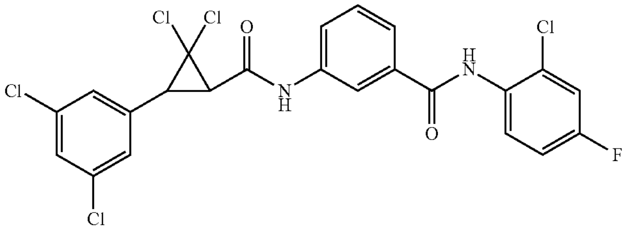 [SMILES: O=C(Nc1ccc(F)cc1Cl)c1cccc(NC(=O)C2C(c3cc(Cl)cc(Cl)c3)C2(Cl)Cl)c1] | 13 |
| F275 | 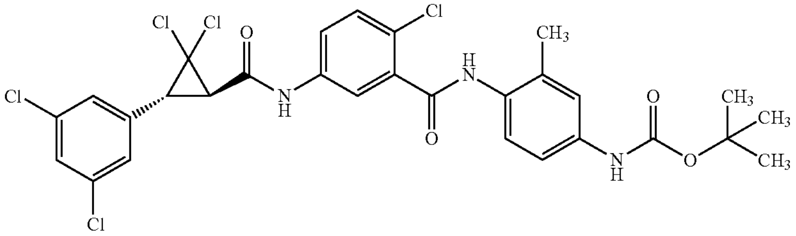 [SMILES: Cc1cc(NC(=O)OC(C)(C)C)ccc1NC(=O)c1cc(NC(=O)[C@H]2[C@H](c3cc(Cl)cc(Cl)c3)C2(Cl)Cl)ccc1Cl] | 55 |
| F277 | 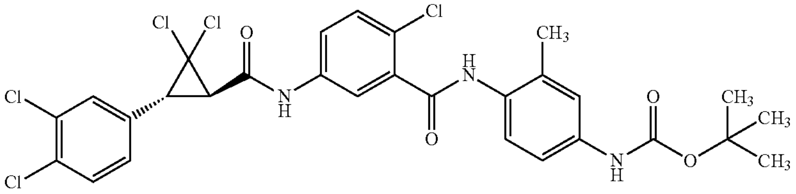 [SMILES: Cc1cc(NC(=O)OC(C)(C)C)ccc1NC(=O)c1cc(NC(=O)[C@H]2[C@H](c3ccc(Cl)c(Cl)c3)C2(Cl)Cl)ccc1Cl] | 55 |
| F278 | 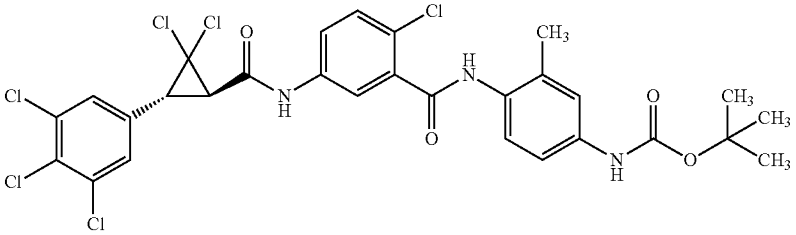 [SMILES: Cc1cc(NC(=O)OC(C)(C)C)ccc1NC(=O)c1cc(NC(=O)[C@H]2[C@H](c3cc(Cl)c(Cl)c(Cl)c3)C2(Cl)Cl)ccc1Cl] | 55 |
| F279 | 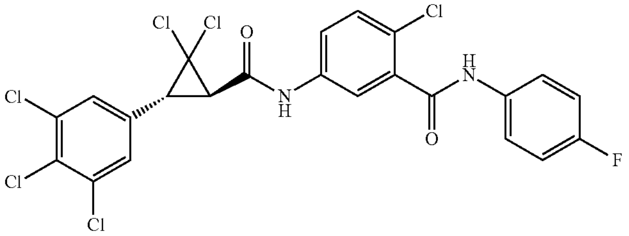 [SMILES: O=C(Nc1ccc(F)cc1)c1cc(NC(=O)[C@H]2[C@H](c3cc(Cl)c(Cl)c(Cl)c3)C2(Cl)Cl)ccc1Cl] | 55 |
| F280 | 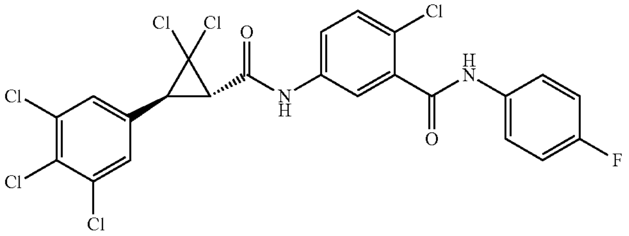 [SMILES: O=C(Nc1ccc(F)cc1)c1cc(NC(=O)[C@@H]2[C@@H](c3cc(Cl)c(Cl)c(Cl)c3)C2(Cl)Cl)ccc1Cl] | 55 |

TABLE 2-continued
| No. | Structure | Prep.* |
| --- | --- | --- |
| F281 | 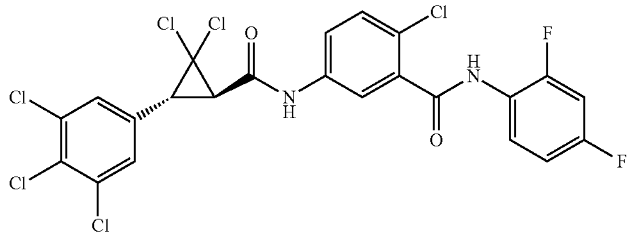 [SMILES: O=C(Nc1ccc(F)cc1F)c1cc(NC(=O)[C@H]2[C@H](c3cc(Cl)c(Cl)c(Cl)c3)C2(Cl)Cl)ccc1Cl] | 55 |
| F282 | 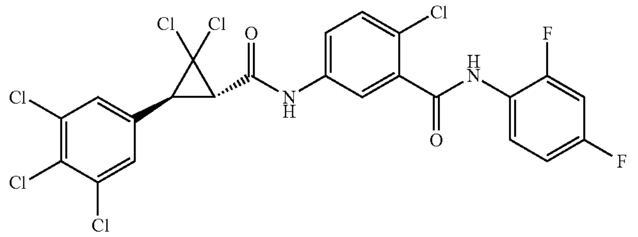 [SMILES: O=C(Nc1ccc(F)cc1F)c1cc(NC(=O)[C@@H]2[C@@H](c3cc(Cl)c(Cl)c(Cl)c3)C2(Cl)Cl)ccc1Cl] | 55 |
| F283 | 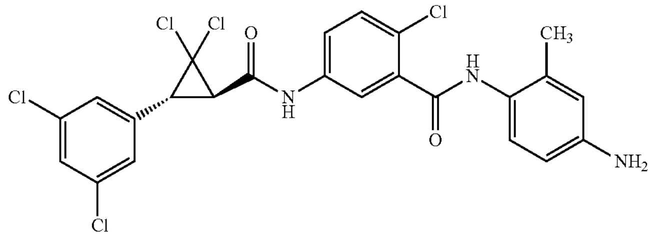 [SMILES: Cc1cc(N)ccc1NC(=O)c1cc(NC(=O)[C@H]2[C@H](c3cc(Cl)cc(Cl)c3)C2(Cl)Cl)ccc1Cl] | 55 |
| F284 | 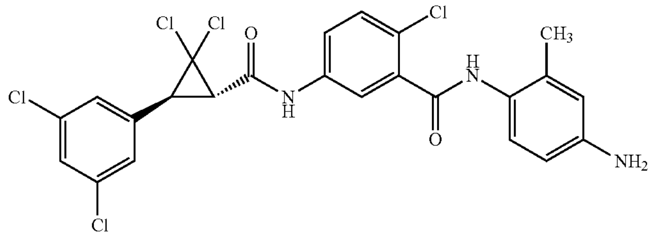 [SMILES: Cc1cc(N)ccc1NC(=O)c1cc(NC(=O)[C@@H]2[C@@H](c3cc(Cl)cc(Cl)c3)C2(Cl)Cl)ccc1Cl] | 55 |
| F285 | 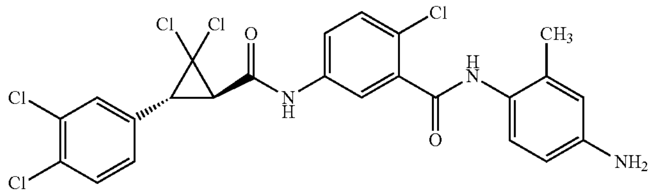 [SMILES: Cc1cc(N)ccc1NC(=O)c1cc(NC(=O)[C@H]2[C@H](c3ccc(Cl)c(Cl)c3)C2(Cl)Cl)ccc1Cl] | 55 |
| F286 | 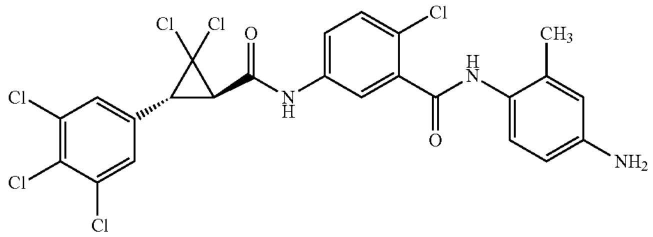 [SMILES: Cc1cc(N)ccc1NC(=O)c1cc(NC(=O)[C@H]2[C@H](c3cc(Cl)c(Cl)c(Cl)c3)C2(Cl)Cl)ccc1Cl] | 55 |
Structure and preparation method for F Series molecules TABLE 2-continued
| Structure and preparation method for F Series molecules | | |
|---|---|---|
| No. | Structure | Prep.* |
| F287 | 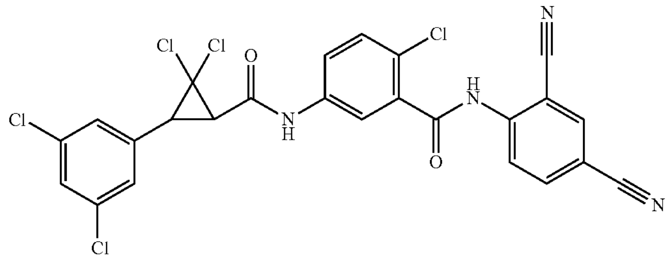 [SMILES: N#Cc1ccc(NC(=O)c2cc(NC(=O)C3C(c4cc(Cl)cc(Cl)c4)C3(Cl)Cl)ccc2Cl)c(C#N)c1] | 54 |
| F288 | 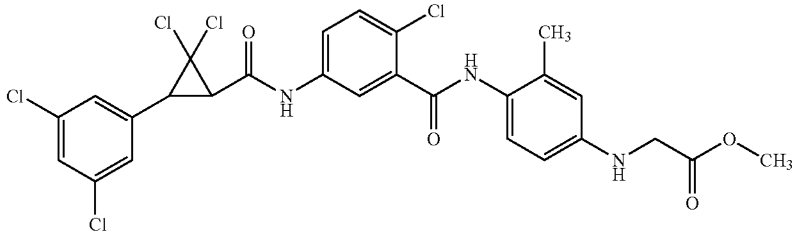 [SMILES: COC(=O)CNc1ccc(NC(=O)c2cc(NC(=O)C3C(c4cc(Cl)cc(Cl)c4)C3(Cl)Cl)ccc2Cl)c(C)c1] | 70 |
| F289 | 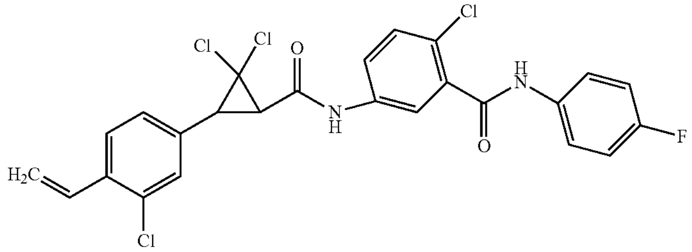 [SMILES: C=Cc1ccc(C2C(C(=O)Nc3ccc(Cl)c(C(=O)Nc4ccc(F)cc4)c3)C2(Cl)Cl)cc1Cl] | 77 |
| F290 | 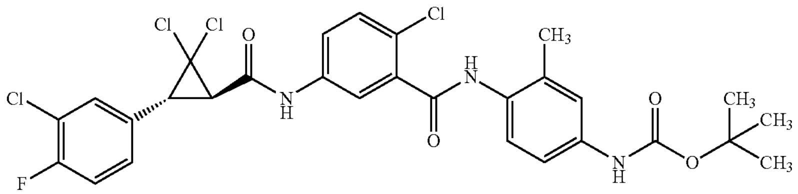 [SMILES: Cc1cc(NC(=O)OC(C)(C)C)ccc1NC(=O)c1cc(NC(=O)[C@H]2[C@H](c3ccc(F)c(Cl)c3)C2(Cl)Cl)ccc1Cl] | 55 |
| F291 | 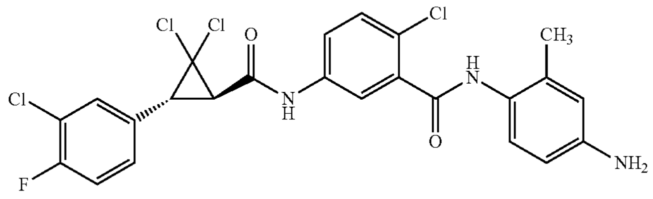 [SMILES: Cc1cc(N)ccc1NC(=O)c1cc(NC(=O)[C@H]2[C@H](c3ccc(F)c(Cl)c3)C2(Cl)Cl)ccc1Cl] | 55 |
| F292 | 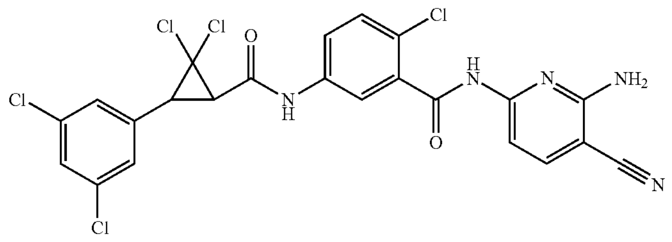 [SMILES: N#Cc1ccc(NC(=O)c2cc(NC(=O)C3C(c4cc(Cl)cc(Cl)c4)C3(Cl)Cl)ccc2Cl)nc1N] | 55 |

TABLE 2-continued
Structure and preparation method for F Series molecules
| No. | Structure | Prep.* |
|---|---|---|
| F293 | 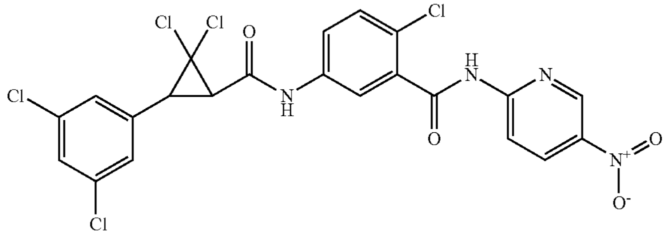 [SMILES: O=C(Nc1ccc([N+](=O)[O-])cn1)c1cc(NC(=O)C2C(c3cc(Cl)cc(Cl)c3)C2(Cl)Cl)ccc1Cl] | 55 |
| F294 | 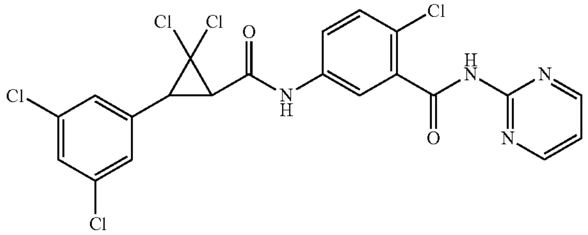 | 55 |
| F295 | 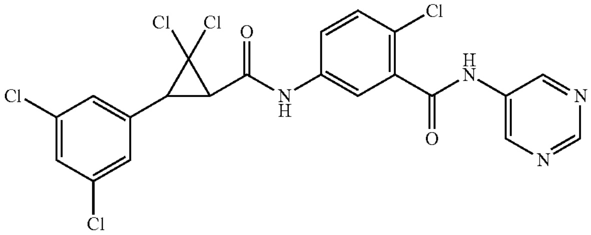 [SMILES: O=C(Nc1cncnc1)c1cc(NC(=O)C2C(c3cc(Cl)cc(Cl)c3)C2(Cl)Cl)ccc1Cl] | 55 |
| F296 | 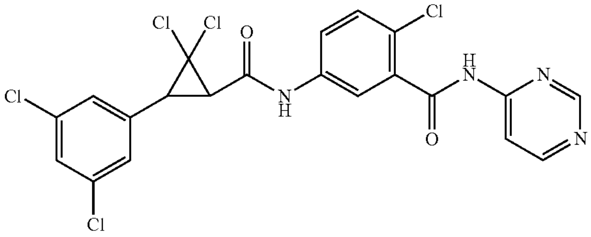 | 55 |
| F297 | 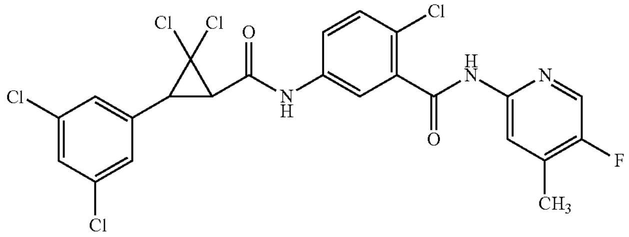 [SMILES: Cc1cc(NC(=O)c2cc(NC(=O)C3C(c4cc(Cl)cc(Cl)c4)C3(Cl)Cl)ccc2Cl)ncc1F] | 55 |
| F298 | 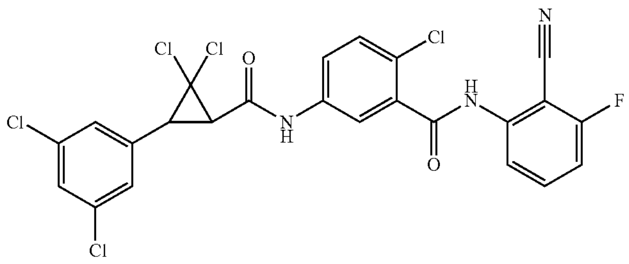 [SMILES: N#Cc1c(F)cccc1NC(=O)c1cc(NC(=O)C2C(c3cc(Cl)cc(Cl)c3)C2(Cl)Cl)ccc1Cl] | 54 |

TABLE 2-continued
Structure and preparation method for F Series molecules
| No. | Structure | Prep.* |
| --- | --- | --- |
| F299 | 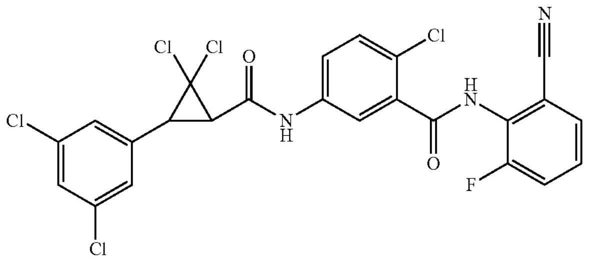 [SMILES: N#Cc1cccc(F)c1NC(=O)c1cc(NC(=O)C2C(c3cc(Cl)cc(Cl)c3)C2(Cl)Cl)ccc1Cl] | 54 |
| F300 | 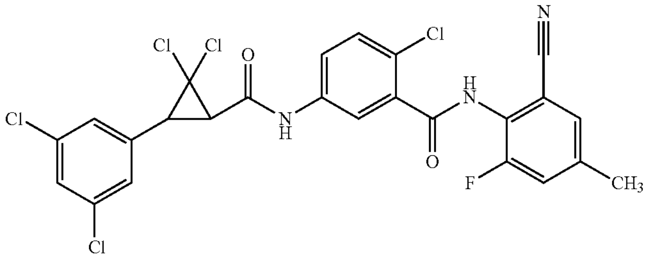 [SMILES: Cc1cc(F)c(NC(=O)c2cc(NC(=O)C3C(c4cc(Cl)cc(Cl)c4)C3(Cl)Cl)ccc2Cl)c(C#N)c1] | 54 |
| F301 | 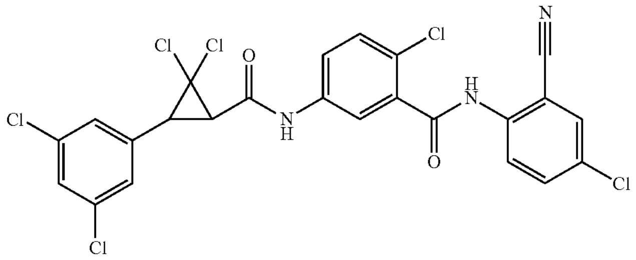 [SMILES: N#Cc1cc(Cl)ccc1NC(=O)c1cc(NC(=O)C2C(c3cc(Cl)cc(Cl)c3)C2(Cl)Cl)ccc1Cl] | 54 |
| F302 | 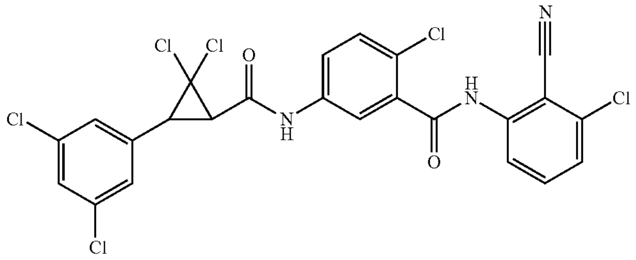 [SMILES: N#Cc1c(Cl)cccc1NC(=O)c1cc(NC(=O)C2C(c3cc(Cl)cc(Cl)c3)C2(Cl)Cl)ccc1Cl] | 54 |
| F303 | 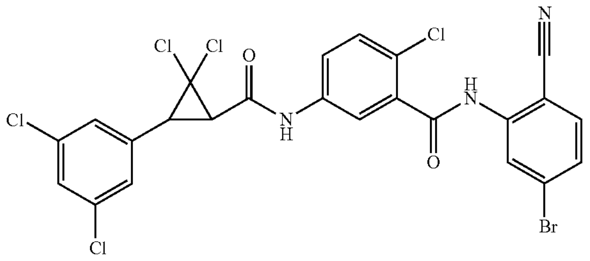 [SMILES: N#Cc1ccc(Br)cc1NC(=O)c1cc(NC(=O)C2C(c3cc(Cl)cc(Cl)c3)C2(Cl)Cl)ccc1Cl] | 54 |

TABLE 2-continued
Structure and preparation method for F Series molecules
| No. | Structure | Prep.* |
| --- | --- | --- |
| F304 | 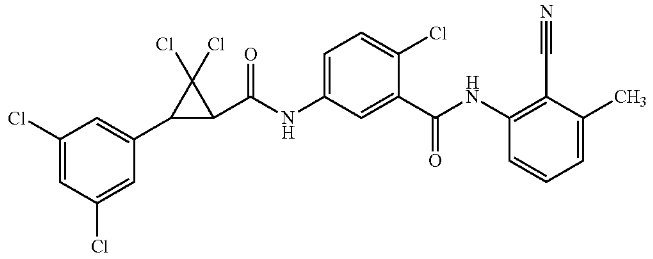 [SMILES: Cc1cccc(NC(=O)c2cc(NC(=O)C3C(c4cc(Cl)cc(Cl)c4)C3(Cl)Cl)ccc2Cl)c1C#N] | 54 |
| F305 | 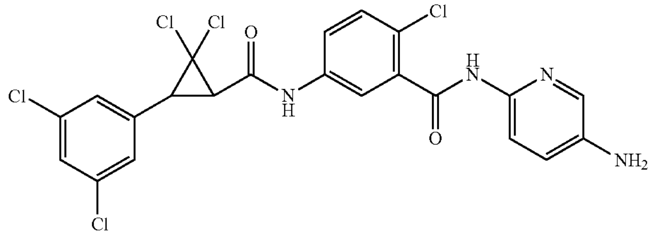 [SMILES: Nc1ccc(NC(=O)c2cc(NC(=O)C3C(c4cc(Cl)cc(Cl)c4)C3(Cl)Cl)ccc2Cl)nc1] | 59 |
| F306 | 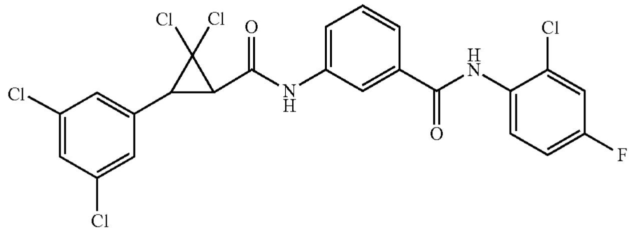 [SMILES: O=C(Nc1ccc(F)cc1Cl)c1cccc(NC(=O)C2C(c3cc(Cl)cc(Cl)c3)C2(Cl)Cl)c1] | 13 |
| F307 | 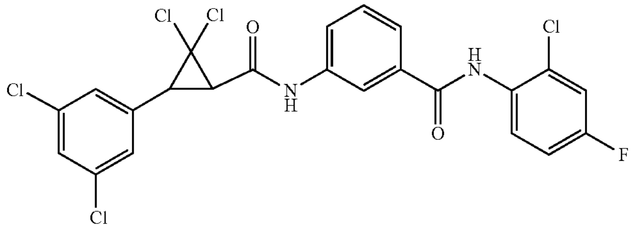 [SMILES: O=C(Nc1ccc(F)cc1Cl)c1cccc(NC(=O)C2C(c3cc(Cl)cc(Cl)c3)C2(Cl)Cl)c1] | 13 |
| F308 | 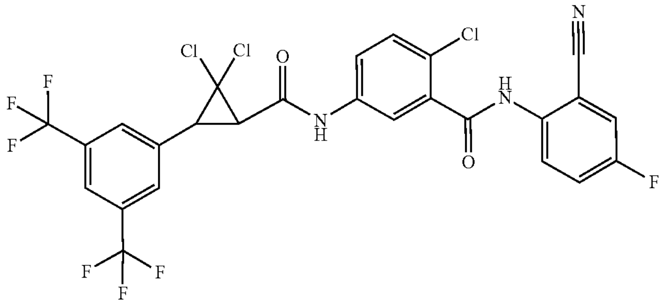 [SMILES: N#Cc1cc(F)ccc1NC(=O)c1cc(NC(=O)C2C(c3cc(C(F)(F)F)cc(C(F)(F)F)c3)C2(Cl)Cl)ccc1Cl] | 13 |
| F309 | 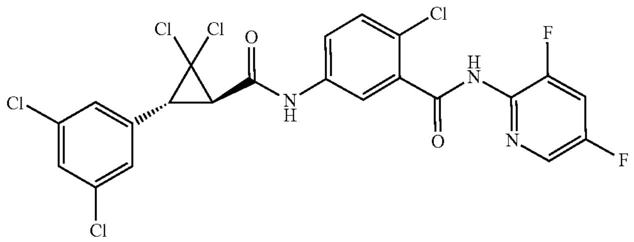 [SMILES: O=C(Nc1ncc(F)cc1F)c1cc(NC(=O)[C@H]2[C@H](c3cc(Cl)cc(Cl)c3)C2(Cl)Cl)ccc1Cl] | 13 |

TABLE 2-continued
Structure and preparation method for F Series molecules
| No. | Structure | Prep.* |
| --- | --- | --- |
| F310 | 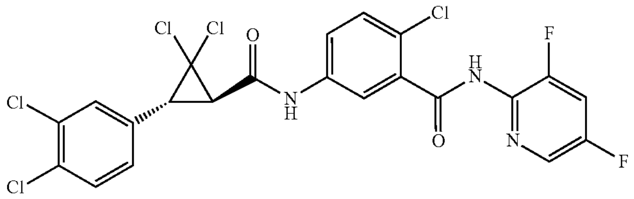 [SMILES: O=C(Nc1ncc(F)cc1F)c1cc(NC(=O)[C@H]2[C@H](c3ccc(Cl)c(Cl)c3)C2(Cl)Cl)ccc1Cl] | 13 |
| F311 | 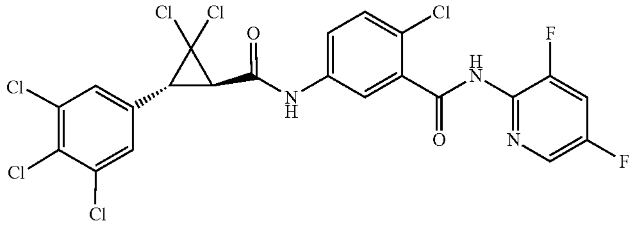 [SMILES: O=C(Nc1ncc(F)cc1F)c1cc(NC(=O)[C@H]2[C@H](c3cc(Cl)c(Cl)c(Cl)c3)C2(Cl)Cl)ccc1Cl] | 13 |
| F312 | 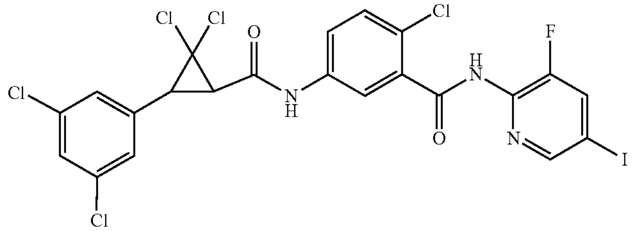 [SMILES: O=C(Nc1ncc(I)cc1F)c1cc(NC(=O)C2C(c3cc(Cl)cc(Cl)c3)C2(Cl)Cl)ccc1Cl] | 55 |
| F313 | 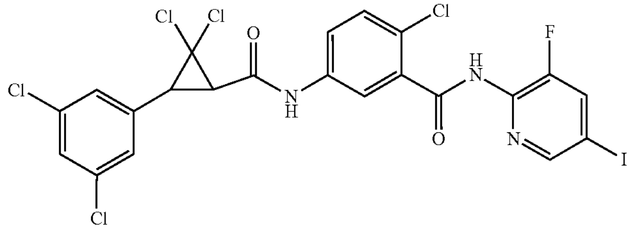 [SMILES: O=C(Nc1ncc(I)cc1F)c1cc(NC(=O)C2C(c3cc(Cl)cc(Cl)c3)C2(Cl)Cl)ccc1Cl] | 62 |
| F314 | 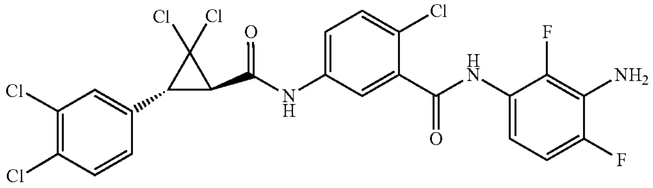 [SMILES: Nc1c(F)ccc(NC(=O)c2cc(NC(=O)[C@H]3[C@H](c4ccc(Cl)c(Cl)c4)C3(Cl)Cl)ccc2Cl)c1F] | 62 |
| F315 | 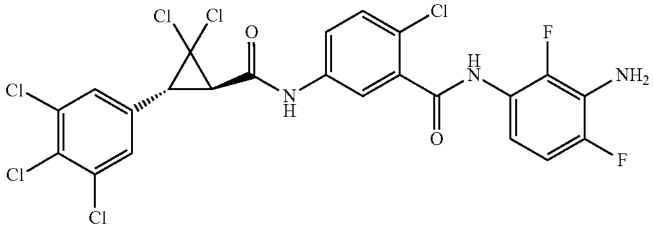 [SMILES: Nc1c(F)ccc(NC(=O)c2cc(NC(=O)[C@H]3[C@H](c4cc(Cl)c(Cl)c(Cl)c4)C3(Cl)Cl)ccc2Cl)c1F] | 62 |
| F316 | 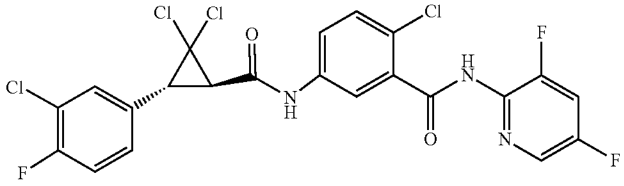 [SMILES: O=C(Nc1ncc(F)cc1F)c1cc(NC(=O)[C@H]2[C@H](c3ccc(F)c(Cl)c3)C2(Cl)Cl)ccc1Cl] | 13 |

TABLE 2-continued
| Structure and preparation method for F Series molecules | | |
|---|---|---|
| No. | Structure | Prep.* |
| F317 | 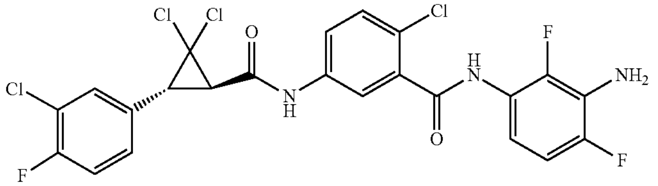 [SMILES: Nc1c(F)ccc(NC(=O)c2cc(NC(=O)[C@H]3[C@H](c4ccc(F)c(Cl)c4)C3(Cl)Cl)ccc2Cl)c1F] | 62 |
| F318 | 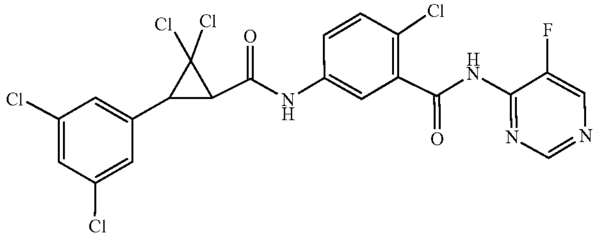 [SMILES: O=C(Nc1ncncc1F)c1cc(NC(=O)C2C(c3cc(Cl)cc(Cl)c3)C2(Cl)Cl)ccc1Cl] | 55 |
| F319 | 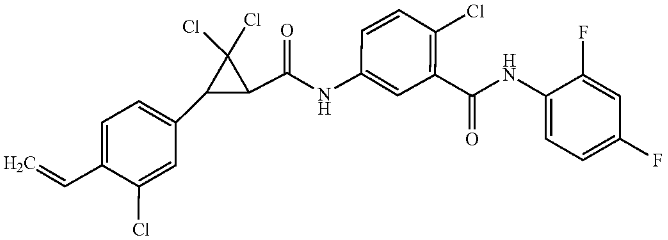 [SMILES: C=Cc1ccc(C2C(C(=O)Nc3ccc(Cl)c(C(=O)Nc4ccc(F)cc4F)c3)C2(Cl)Cl)cc1Cl] | 77 |
| F320 | 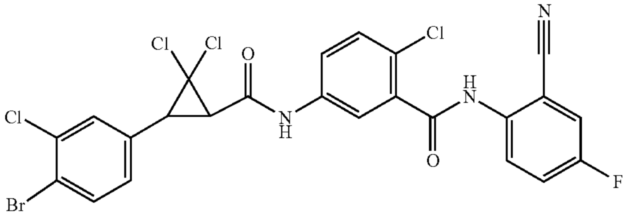 [SMILES: N#Cc1cc(F)ccc1NC(=O)c1cc(NC(=O)C2C(c3ccc(Br)c(Cl)c3)C2(Cl)Cl)ccc1Cl] | 13 |
| F321 | 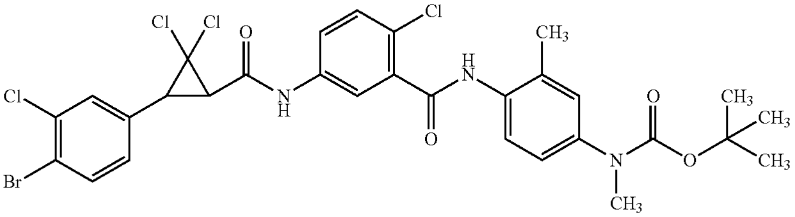 [SMILES: Cc1cc(N(C)C(=O)OC(C)(C)C)ccc1NC(=O)c1cc(NC(=O)C2C(c3ccc(Br)c(Cl)c3)C2(Cl)Cl)ccc1Cl] | 13 |
| F322 | 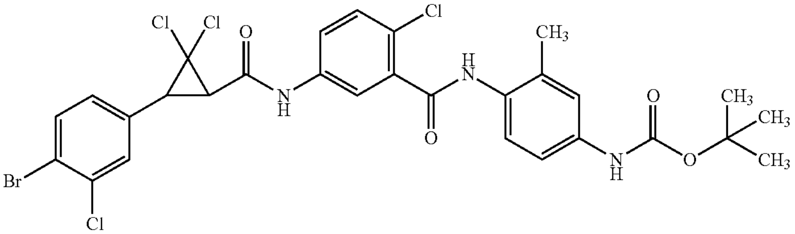 [SMILES: Cc1cc(NC(=O)OC(C)(C)C)ccc1NC(=O)c1cc(NC(=O)C2C(c3ccc(Br)c(Cl)c3)C2(Cl)Cl)ccc1Cl] | 13 |

TABLE 2-continued
| Structure and preparation method for F Series molecules | | |
|---|---|---|
| No. | Structure | Prep.* |
| F323 | 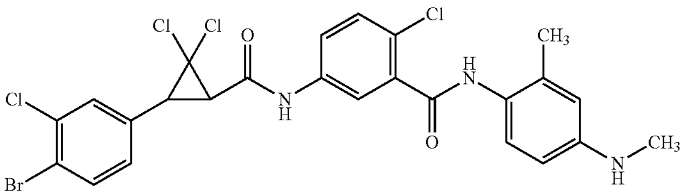 [SMILES: CNc1ccc(NC(=O)c2cc(NC(=O)C3C(c4ccc(Br)c(Cl)c4)C3(Cl)Cl)ccc2Cl)c(C)c1] | 62 |
| F324 | 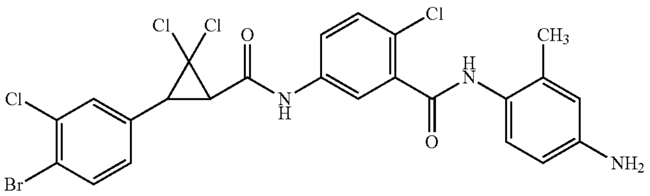 [SMILES: Cc1cc(N)ccc1NC(=O)c1cc(NC(=O)C2C(c3ccc(Br)c(Cl)c3)C2(Cl)Cl)ccc1Cl] | 62 |
| F325 | 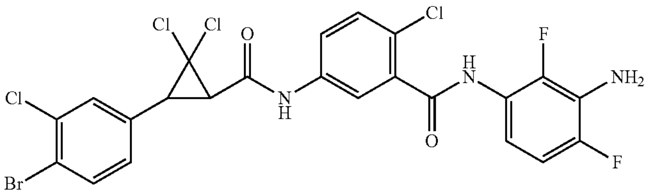 [SMILES: Nc1c(F)ccc(NC(=O)c2cc(NC(=O)C3C(c4ccc(Br)c(Cl)c4)C3(Cl)Cl)ccc2Cl)c1F] | 62 |
| F326 | 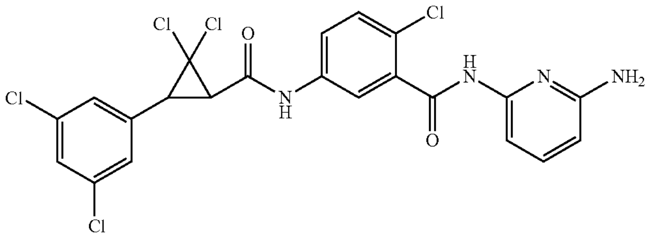 [SMILES: Nc1cccc(NC(=O)c2cc(NC(=O)C3C(c4cc(Cl)cc(Cl)c4)C3(Cl)Cl)ccc2Cl)n1] | 62 |
| F327 | 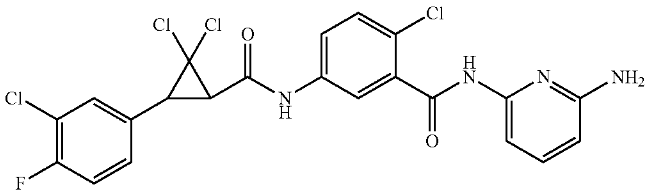 [SMILES: Nc1cccc(NC(=O)c2cc(NC(=O)C3C(c4ccc(F)c(Cl)c4)C3(Cl)Cl)ccc2Cl)n1] | 62 |
| F328 | 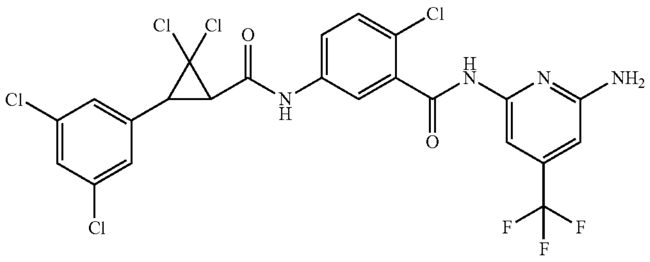 [SMILES: Nc1cc(C(F)(F)F)cc(NC(=O)c2cc(NC(=O)C3C(c4cc(Cl)cc(Cl)c4)C3(Cl)Cl)ccc2Cl)n1] | 62 |

TABLE 2-continued
Structure and preparation method for F Series molecules
| No. | Structure | Prep.* |
|---|---|---|
| F329 | 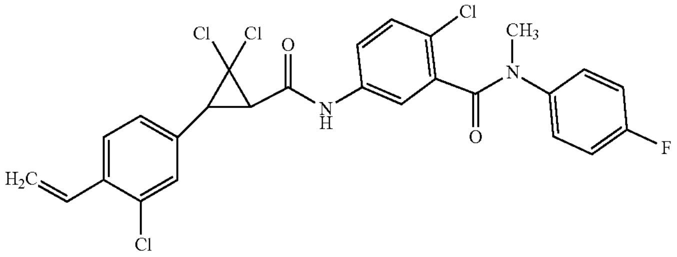 [SMILES: C=Cc1ccc(C2C(C(=O)Nc3ccc(Cl)c(C(=O)N(C)c4ccc(F)cc4)c3)C2(Cl)Cl)cc1Cl] | 77 |
| F330 | 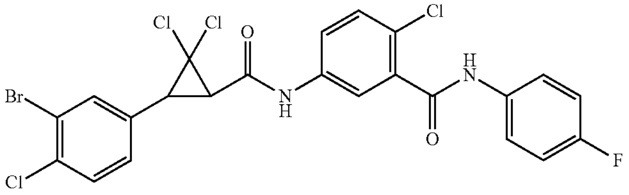 | 13 |
| F331 | 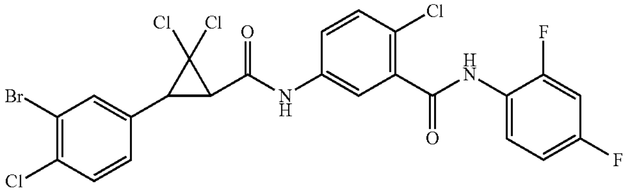 | 13 |
| F332 | 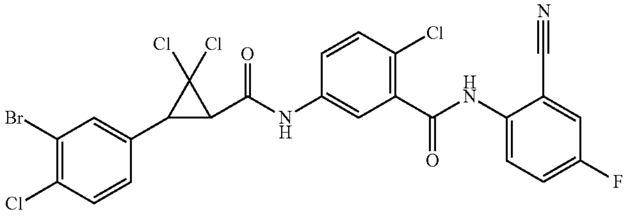 [SMILES: N#Cc1cc(F)ccc1NC(=O)c1cc(NC(=O)C2C(c3ccc(Cl)c(Br)c3)C2(Cl)Cl)ccc1Cl] | 13 |
| F333 | 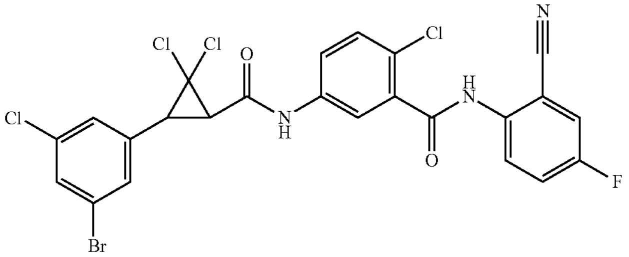 [SMILES: N#Cc1cc(F)ccc1NC(=O)c1cc(NC(=O)C2C(c3cc(Cl)cc(Br)c3)C2(Cl)Cl)ccc1Cl] | 13 |
| F334 | 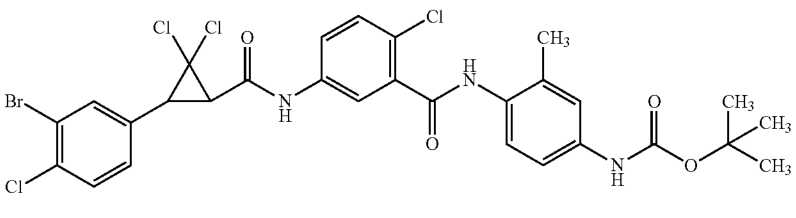 [SMILES: Cc1cc(NC(=O)OC(C)(C)C)ccc1NC(=O)c1cc(NC(=O)C2C(c3ccc(Cl)c(Br)c3)C2(Cl)Cl)ccc1Cl] | 13 |

TABLE 2-continued
Structure and preparation method for F Series molecules
| No. | Structure | Prep.* |
| --- | --- | --- |
| F335 | 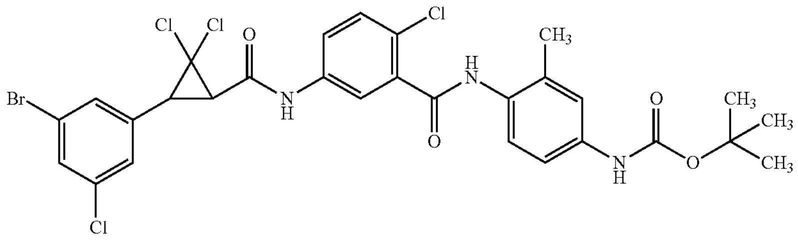 [SMILES: Cc1cc(NC(=O)OC(C)(C)C)ccc1NC(=O)c1cc(NC(=O)C2C(c3cc(Cl)cc(Br)c3)C2(Cl)Cl)ccc1Cl] | 13 |
| F336 | 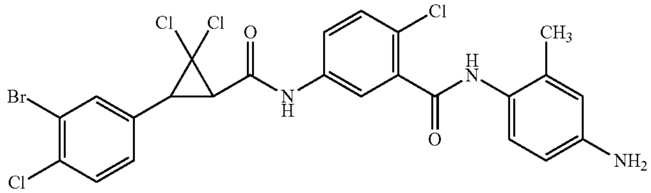 [SMILES: Cc1cc(N)ccc1NC(=O)c1cc(NC(=O)C2C(c3ccc(Cl)c(Br)c3)C2(Cl)Cl)ccc1Cl] | 62 |
| F337 | 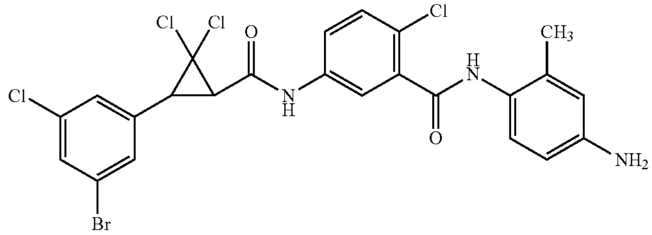 [SMILES: Cc1cc(N)ccc1NC(=O)c1cc(NC(=O)C2C(c3cc(Cl)cc(Br)c3)C2(Cl)Cl)ccc1Cl] | 62 |
| F338 | 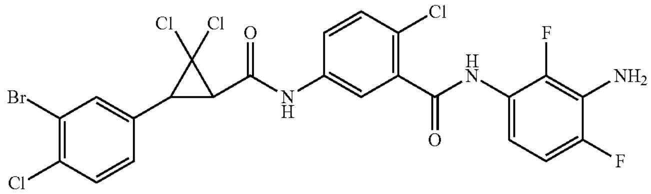 [SMILES: Nc1c(F)ccc(NC(=O)c2cc(NC(=O)C3C(c4ccc(Cl)c(Br)c4)C3(Cl)Cl)ccc2Cl)c1F] | 62 |
| F339 | 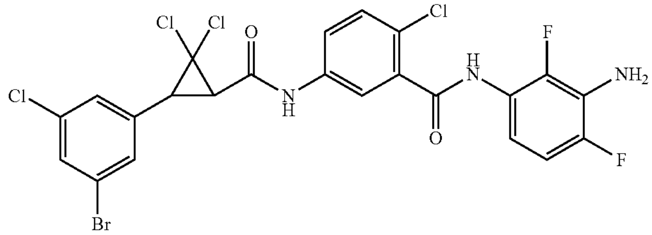 | 62 |
| F340 | 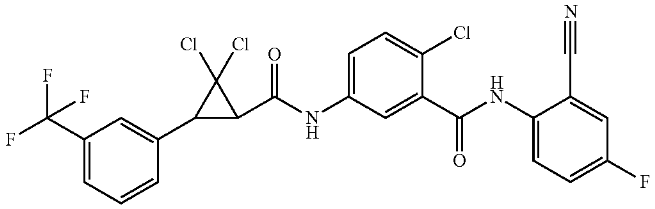 [SMILES: N#Cc1cc(F)ccc1NC(=O)c1cc(NC(=O)C2C(c3cccc(C(F)(F)F)c3)C2(Cl)Cl)ccc1Cl] | 13 |
| F341 | 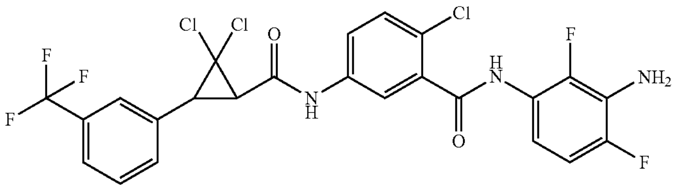 [SMILES: Nc1c(F)ccc(NC(=O)c2cc(NC(=O)C3C(c4cccc(C(F)(F)F)c4)C3(Cl)Cl)ccc2Cl)c1F] | 62 |

TABLE 2-continued
| Structure and preparation method for F Series molecules | | |
|---|---|---|
| No. | Structure | Prep.* |
| F342 | 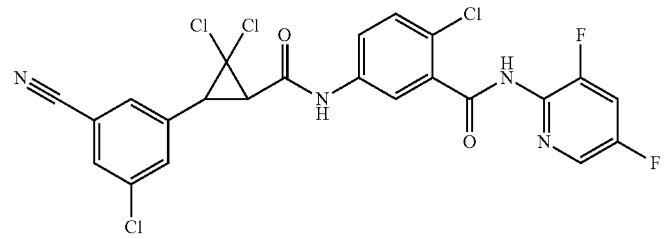 | 13 |
| F343 | 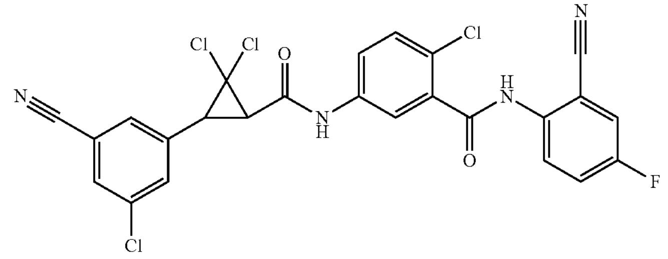 [SMILES: N#Cc1cc(Cl)cc(C2C(C(=O)Nc3ccc(Cl)c(C(=O)Nc4ccc(F)cc4C#N)c3)C2(Cl)Cl)c1] | 13 |
| F344 | 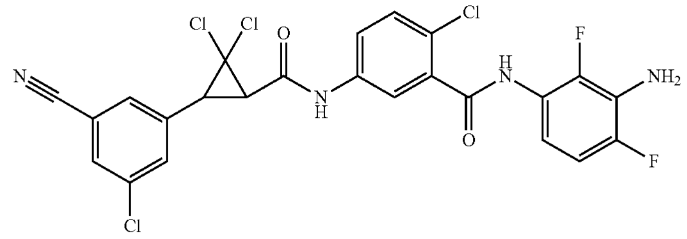 [SMILES: N#Cc1cc(Cl)cc(C2C(C(=O)Nc3ccc(Cl)c(C(=O)Nc4ccc(F)c(N)c4F)c3)C2(Cl)Cl)c1] | 62 |
| F345 | 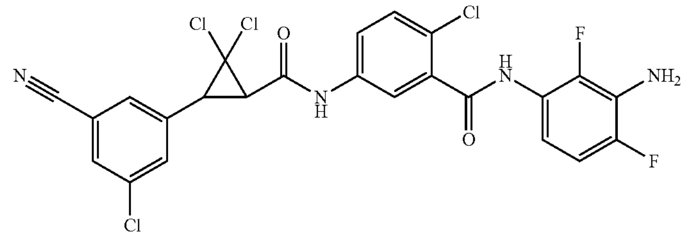 [SMILES: N#Cc1cc(Cl)cc(C2C(C(=O)Nc3ccc(Cl)c(C(=O)Nc4ccc(F)c(N)c4F)c3)C2(Cl)Cl)c1] | 55 |
| F346 | 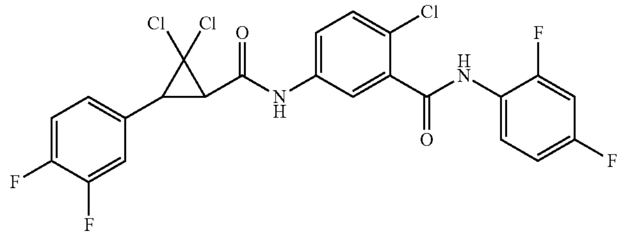 [SMILES: O=C(Nc1ccc(F)cc1F)c1cc(NC(=O)C2C(c3ccc(F)c(F)c3)C2(Cl)Cl)ccc1Cl] | 55 |
| F347 | 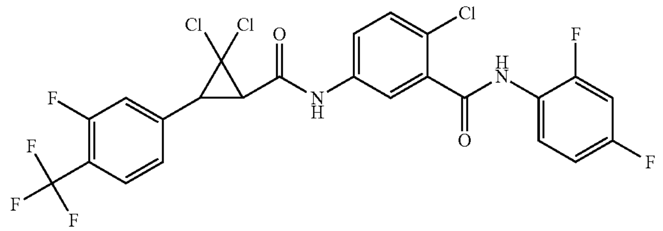 | 55 |

TABLE 2-continued
| Structure and preparation method for F Series molecules | | |
|---|---|---|
| No. | Structure | Prep.* |
| F348 | 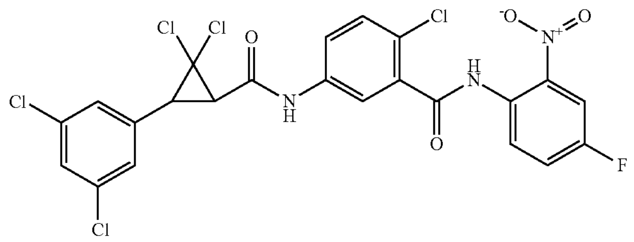 | 55 |
| F349 | 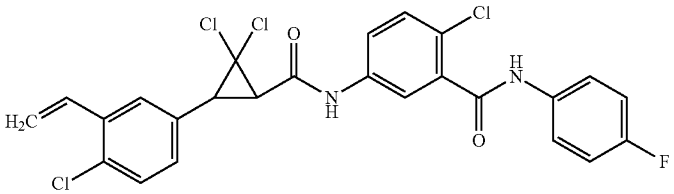 [SMILES: C=Cc1cc(C2C(C(=O)Nc3ccc(Cl)c(C(=O)Nc4ccc(F)cc4)c3)C2(Cl)Cl)ccc1Cl] | 77 |
| F350 | 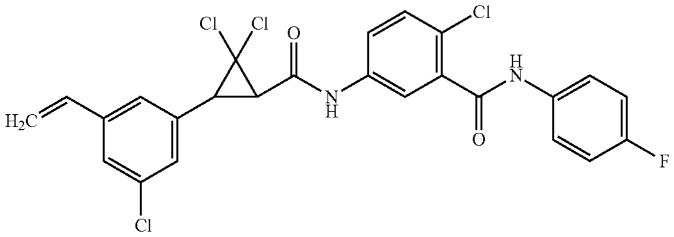 [SMILES: C=Cc1cc(Cl)cc(C2C(C(=O)Nc3ccc(Cl)c(C(=O)Nc4ccc(F)cc4)c3)C2(Cl)Cl)c1] | 77 |
| F351 | 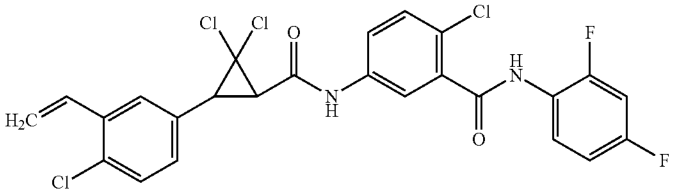 [SMILES: C=Cc1cc(C2C(C(=O)Nc3ccc(Cl)c(C(=O)Nc4ccc(F)cc4F)c3)C2(Cl)Cl)ccc1Cl] | 77 |
| F352 | 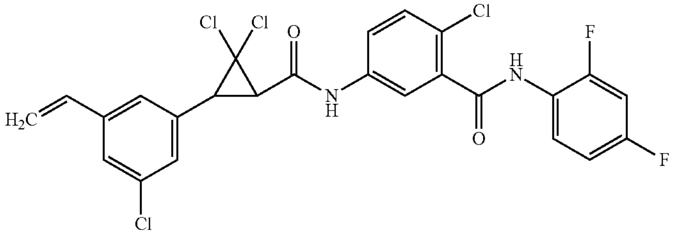 [SMILES: C=Cc1cc(Cl)cc(C2C(C(=O)Nc3ccc(Cl)c(C(=O)Nc4ccc(F)cc4F)c3)C2(Cl)Cl)c1] | 77 |
| F353 | 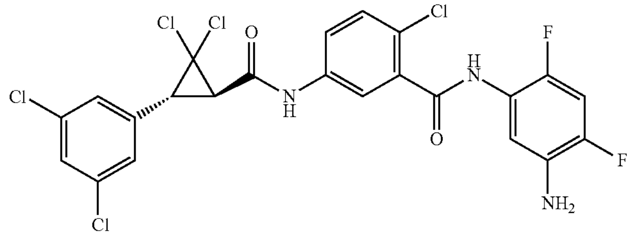 [SMILES: Nc1cc(NC(=O)c2cc(NC(=O)[C@H]3[C@H](c4cc(Cl)cc(Cl)c4)C3(Cl)Cl)ccc2Cl)c(F)cc1F] | 62 |

TABLE 2-continued
| Structure and preparation method for F Series molecules | | |
|---|---|---|
| No. | Structure | Prep.* |
| F354 | 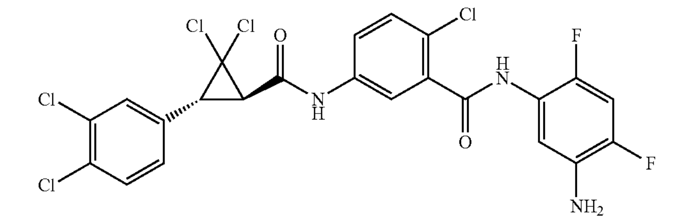 | 62 |
| F355 | 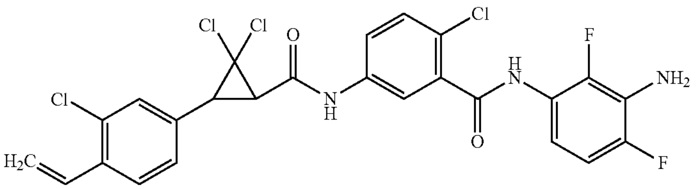 [SMILES: C=Cc1ccc(C2C(C(=O)Nc3ccc(Cl)c(C(=O)Nc4ccc(F)c(N)c4F)c3)C2(Cl)Cl)cc1Cl] | 62 |
| F356 | 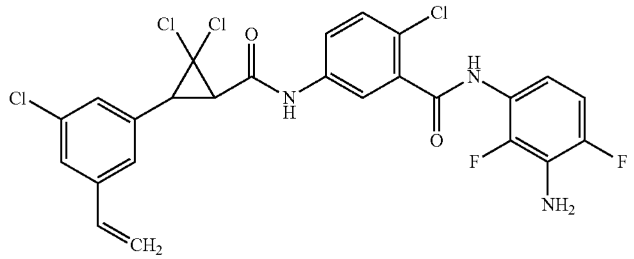 [SMILES: C=Cc1cc(Cl)cc(C2C(C(=O)Nc3ccc(Cl)c(C(=O)Nc4ccc(F)c(N)c4F)c3)C2(Cl)Cl)c1] | 62 |
| F357 | 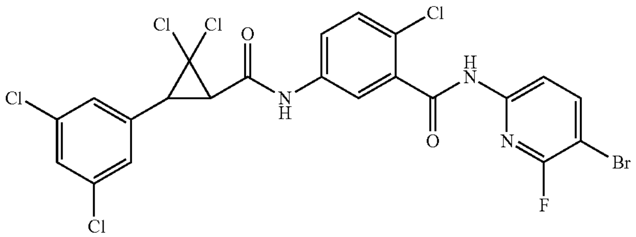 [SMILES: O=C(Nc1ccc(Br)c(F)n1)c1cc(NC(=O)C2C(c3cc(Cl)cc(Cl)c3)C2(Cl)Cl)ccc1Cl] | 55 |
| F358 | 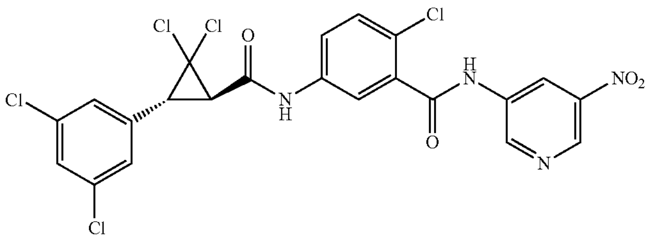 [SMILES: O=C(Nc1cncc([N+](=O)[O-])c1)c1cc(NC(=O)[C@H]2[C@H](c3cc(Cl)cc(Cl)c3)C2(Cl)Cl)ccc1Cl] | 55 |
| F359 | 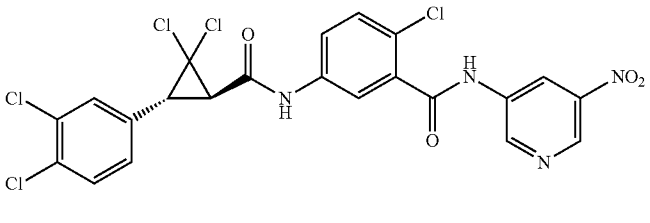 [SMILES: O=C(Nc1cncc([N+](=O)[O-])c1)c1cc(NC(=O)[C@H]2[C@H](c3ccc(Cl)c(Cl)c3)C2(Cl)Cl)ccc1Cl] | 55 |

TABLE 2-continued
| No. | Structure | Prep.* |
| --- | --- | --- |
| | Structure and preparation method for F Series molecules | |
| F360 | 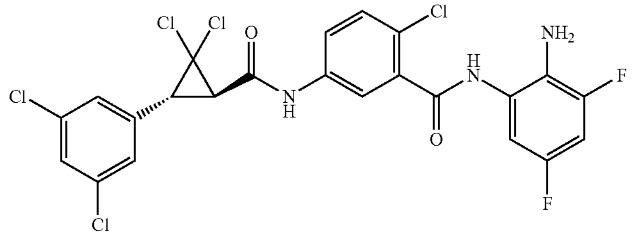 [SMILES: Nc1c(F)cc(F)cc1NC(=O)c1cc(NC(=O)[C@H]2[C@H](c3cc(Cl)cc(Cl)c3)C2(Cl)Cl)ccc1Cl] | 62 |
| F361 | 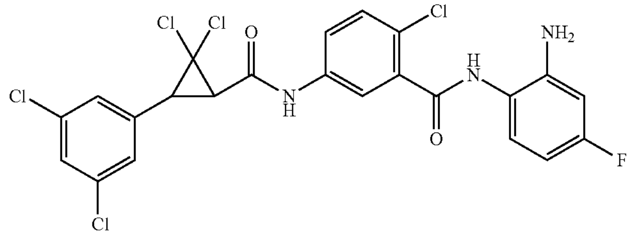 [SMILES: Nc1cc(F)ccc1NC(=O)c1cc(NC(=O)C2C(c3cc(Cl)cc(Cl)c3)C2(Cl)Cl)ccc1Cl] | 60 |
| F362 | 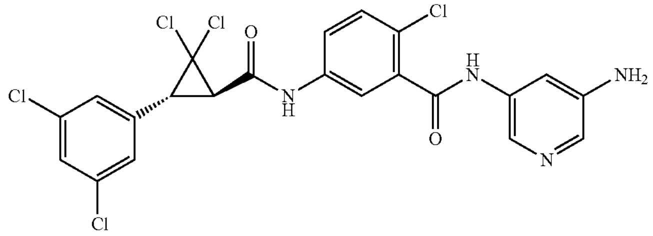 [SMILES: Nc1cncc(NC(=O)c2cc(NC(=O)[C@H]3[C@H](c4cc(Cl)cc(Cl)c4)C3(Cl)Cl)ccc2Cl)c1] | 59 |
| F363 | 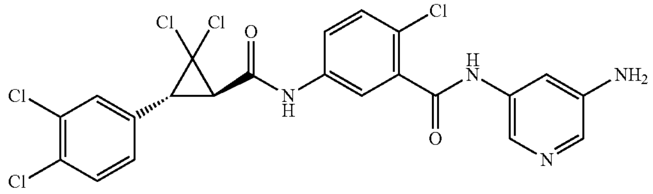 [SMILES: Nc1cncc(NC(=O)c2cc(NC(=O)[C@H]3[C@H](c4ccc(Cl)c(Cl)c4)C3(Cl)Cl)ccc2Cl)c1] | 59 |
| F364 | 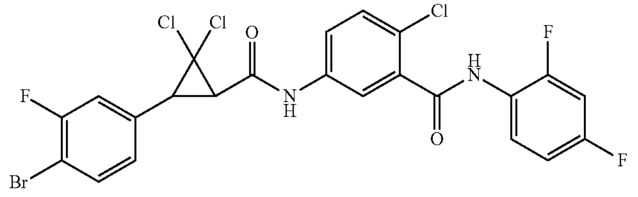 [SMILES: O=C(Nc1ccc(F)cc1F)c1cc(NC(=O)C2C(c3ccc(Br)c(F)c3)C2(Cl)Cl)ccc1Cl] | 55 |
| F365 | 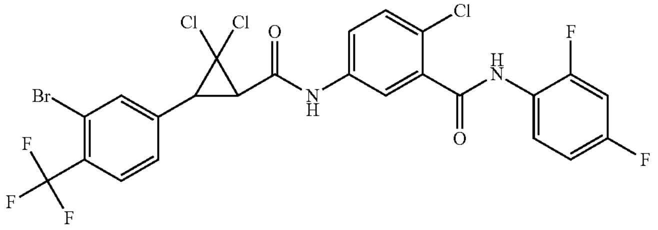 [SMILES: O=C(Nc1ccc(F)cc1F)c1cc(NC(=O)C2C(c3ccc(C(F)(F)F)c(Br)c3)C2(Cl)Cl)ccc1Cl] | 55 |
| F366 | 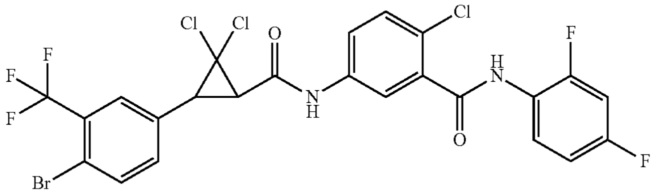 [SMILES: O=C(Nc1ccc(F)cc1F)c1cc(NC(=O)C2C(c3ccc(Br)c(C(F)(F)F)c3)C2(Cl)Cl)ccc1Cl] | 55 |

TABLE 2-continued
| Structure and preparation method for F Series molecules | | |
|---|---|---|
| No. | Structure | Prep.* |
| F367 | 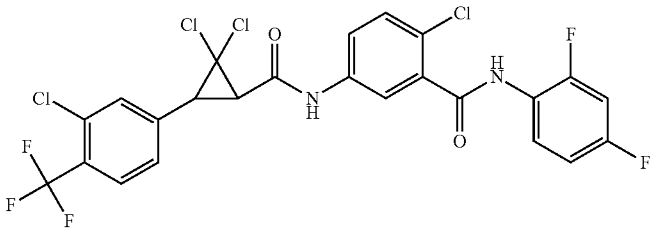 | 55 |
| F368 | 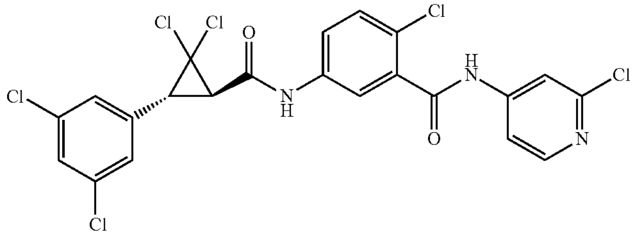 [SMILES: O=C(Nc1ccnc(Cl)c1)c1cc(NC(=O)[C@H]2[C@H](c3cc(Cl)cc(Cl)c3)C2(Cl)Cl)ccc1Cl] | 55 |
| F369 | 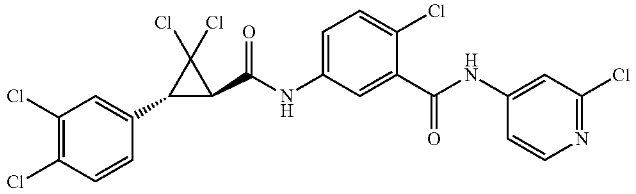 [SMILES: O=C(Nc1ccnc(Cl)c1)c1cc(NC(=O)[C@H]2[C@H](c3ccc(Cl)c(Cl)c3)C2(Cl)Cl)ccc1Cl] | 55 |
| F370 | 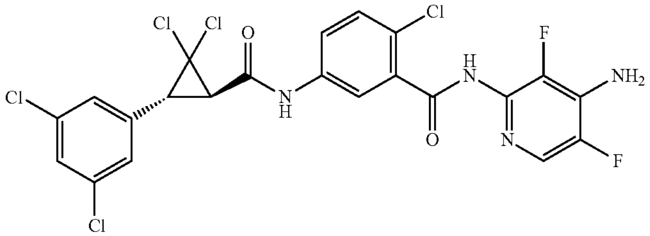 [SMILES: Nc1c(F)cnc(NC(=O)c2cc(NC(=O)[C@H]3[C@H](c4cc(Cl)cc(Cl)c4)C3(Cl)Cl)ccc2Cl)c1F] | 55 |
| F371 | 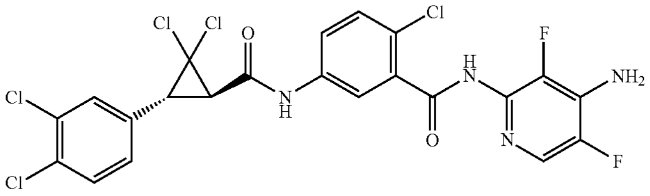 [SMILES: Nc1c(F)cnc(NC(=O)c2cc(NC(=O)[C@H]3[C@H](c4ccc(Cl)c(Cl)c4)C3(Cl)Cl)ccc2Cl)c1F] | 55 |
| F372 | 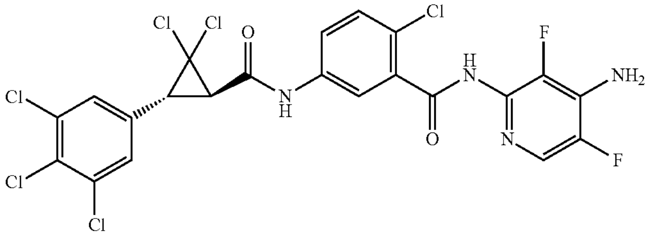 [SMILES: Nc1c(F)cnc(NC(=O)c2cc(NC(=O)[C@H]3[C@H](c4cc(Cl)c(Cl)c(Cl)c4)C3(Cl)Cl)ccc2Cl)c1F] | 55 |

TABLE 2-continued
| Structure and preparation method for F Series molecules | | |
|---|---|---|
| No. | Structure | Prep.* |
| F373 | 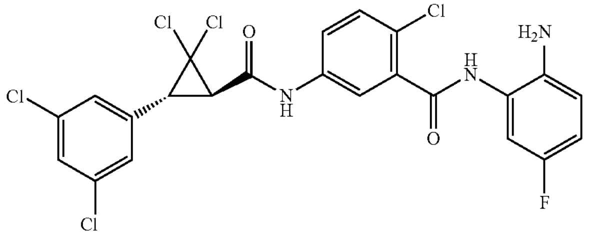 [SMILES: Nc1ccc(F)cc1NC(=O)c1cc(NC(=O)[C@H]2[C@H](c3cc(Cl)cc(Cl)c3)C2(Cl)Cl)ccc1Cl] | 62 |
| F374 | 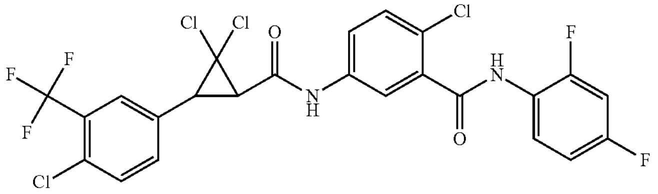 [SMILES: O=C(Nc1ccc(F)cc1F)c1cc(NC(=O)C2C(c3ccc(Cl)c(C(F)(F)F)c3)C2(Cl)Cl)ccc1Cl] | 55 |
| F375 | 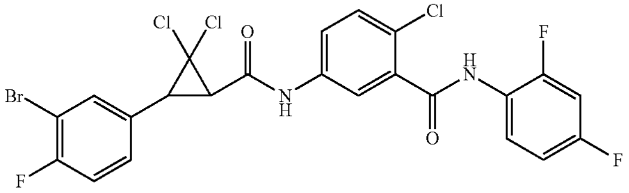 [SMILES: O=C(Nc1ccc(F)cc1F)c1cc(NC(=O)C2C(c3ccc(F)c(Br)c3)C2(Cl)Cl)ccc1Cl] | 55 |
| F376 | 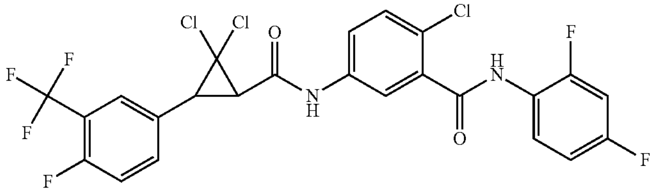 [SMILES: O=C(Nc1ccc(F)cc1F)c1cc(NC(=O)C2C(c3ccc(F)c(C(F)(F)F)c3)C2(Cl)Cl)ccc1Cl] | 55 |
| F377 | 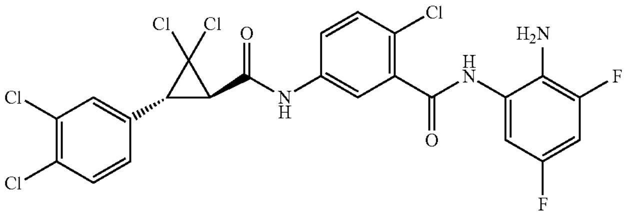 [SMILES: Nc1c(F)cc(F)cc1NC(=O)c1cc(NC(=O)[C@H]2[C@H](c3ccc(Cl)c(Cl)c3)C2(Cl)Cl)ccc1Cl] | 62 |
| F378 | 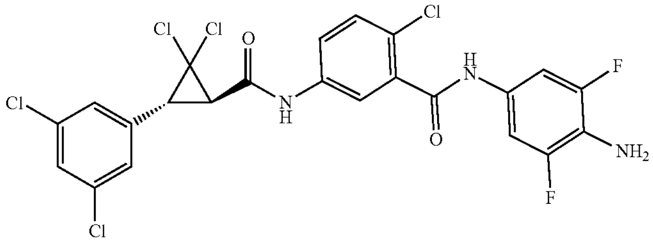 [SMILES: Nc1c(F)cc(NC(=O)c2cc(NC(=O)[C@H]3[C@H](c4cc(Cl)cc(Cl)c4)C3(Cl)Cl)ccc2Cl)cc1F] | 62 |
| F379 | 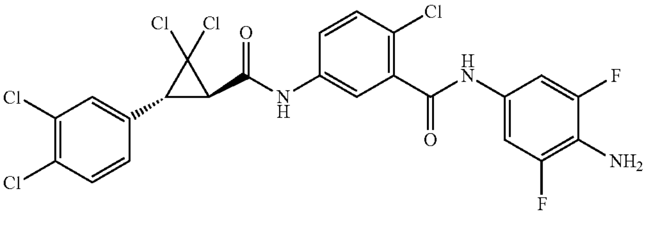 [SMILES: Nc1c(F)cc(NC(=O)c2cc(NC(=O)[C@H]3[C@H](c4ccc(Cl)c(Cl)c4)C3(Cl)Cl)ccc2Cl)cc1F] | 62 |

TABLE 2-continued
| Structure and preparation method for F Series molecules | | |
|---|---|---|
| No. | Structure | Prep.* |
| F380 | 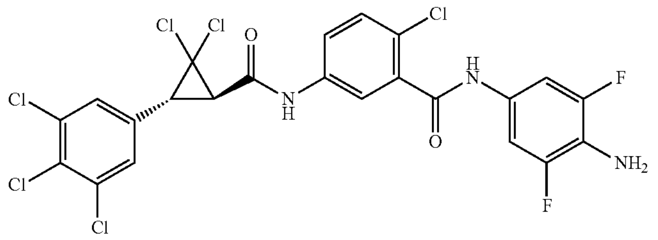 [SMILES: Nc1c(F)cc(NC(=O)c2cc(NC(=O)[C@H]3[C@H](c4cc(Cl)c(Cl)c(Cl)c4)C3(Cl)Cl)ccc2Cl)cc1F] | 62 |
| F381 | 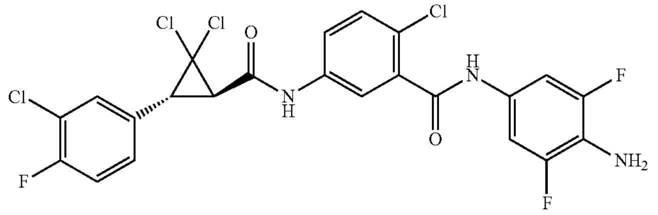 [SMILES: Nc1c(F)cc(NC(=O)c2cc(NC(=O)[C@H]3[C@H](c4ccc(F)c(Cl)c4)C3(Cl)Cl)ccc2Cl)cc1F] | 62 |
| F382 | 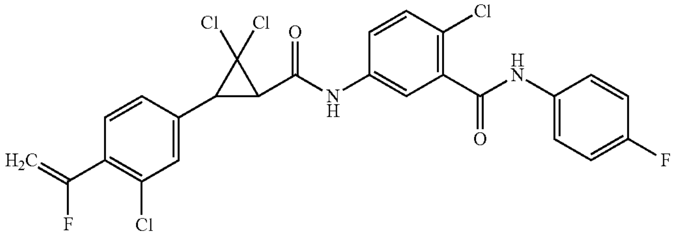 [SMILES: C=C(F)c1ccc(C2C(C(=O)Nc3ccc(Cl)c(C(=O)Nc4ccc(F)cc4)c3)C2(Cl)Cl)cc1Cl] | 77 |
| F383 | 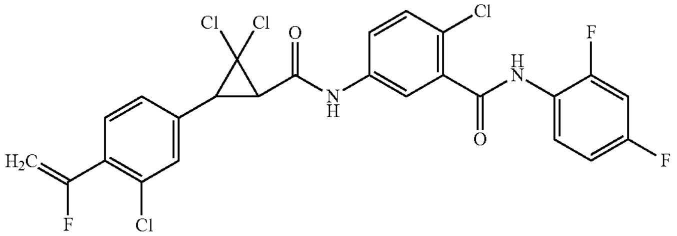 [SMILES: C=C(F)c1ccc(C2C(C(=O)Nc3ccc(Cl)c(C(=O)Nc4ccc(F)cc4F)c3)C2(Cl)Cl)cc1Cl] | 77 |
| F384 | 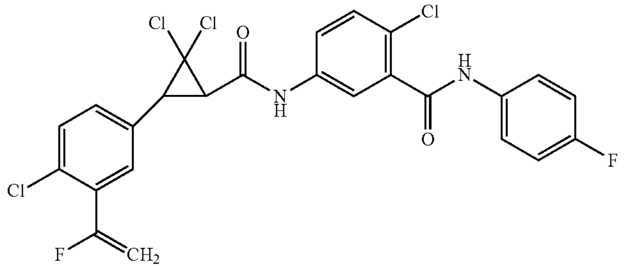 [SMILES: C=C(F)c1cc(C2C(C(=O)Nc3ccc(Cl)c(C(=O)Nc4ccc(F)cc4)c3)C2(Cl)Cl)ccc1Cl] | 77 |
| F385 | 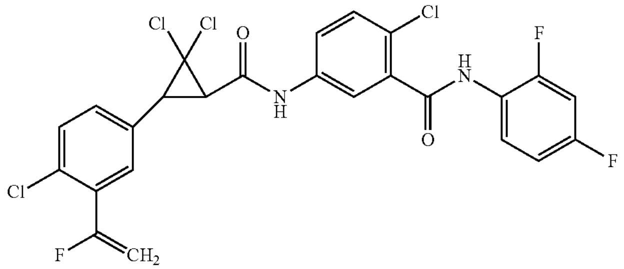 [SMILES: C=C(F)c1cc(C2C(C(=O)Nc3ccc(Cl)c(C(=O)Nc4ccc(F)cc4F)c3)C2(Cl)Cl)ccc1Cl] | 77 |

TABLE 2-continued
| Structure and preparation method for F Series molecules | | |
|---|---|---|
| No. | Structure | Prep.* |
| F386 | 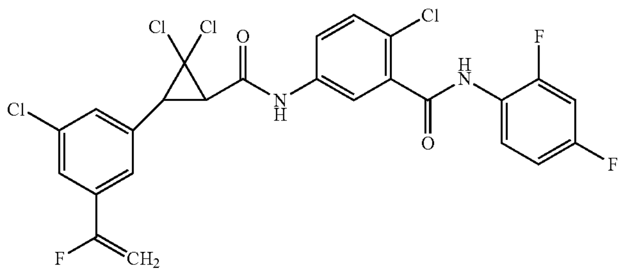 [SMILES: C=C(F)c1cc(Cl)cc(C2C(C(=O)Nc3ccc(Cl)c(C(=O)Nc4ccc(F)cc4F)c3)C2(Cl)Cl)c1] | 77 |
| F387 | 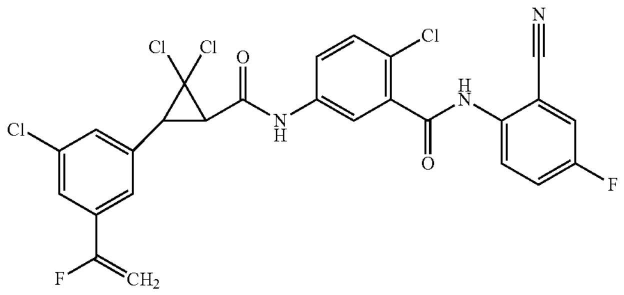 [SMILES: C=C(F)c1cc(Cl)cc(C2C(C(=O)Nc3ccc(Cl)c(C(=O)Nc4ccc(F)cc4C#N)c3)C2(Cl)Cl)c1] | 77 |
| F388 | 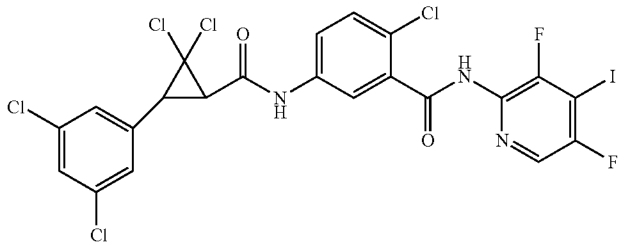 [SMILES: O=C(Nc1ncc(F)c(I)c1F)c1cc(NC(=O)C2C(c3cc(Cl)cc(Cl)c3)C2(Cl)Cl)ccc1Cl] | 55 |
| F389 | 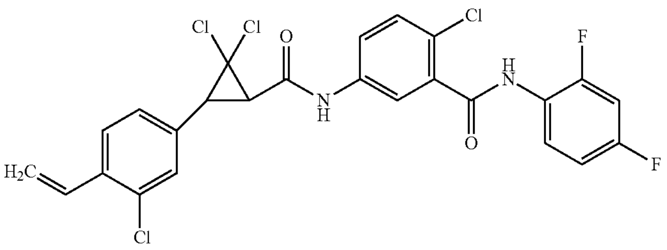 [SMILES: C=Cc1ccc(C2C(C(=O)Nc3ccc(Cl)c(C(=O)Nc4ccc(F)cc4F)c3)C2(Cl)Cl)cc1Cl] | 77 |
| F390 | 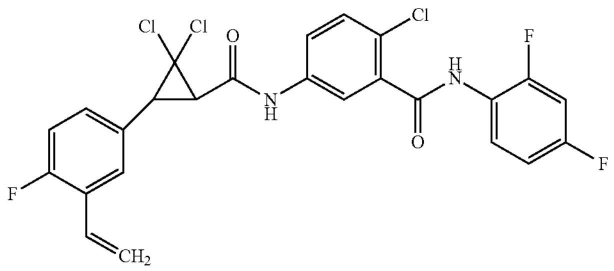 [SMILES: C=Cc1cc(C2C(C(=O)Nc3ccc(Cl)c(C(=O)Nc4ccc(F)cc4F)c3)C2(Cl)Cl)ccc1F] | 77 |

TABLE 2-continued
| Structure and preparation method for F Series molecules | | |
|---|---|---|
| No. | Structure | Prep.* |
| F391 | 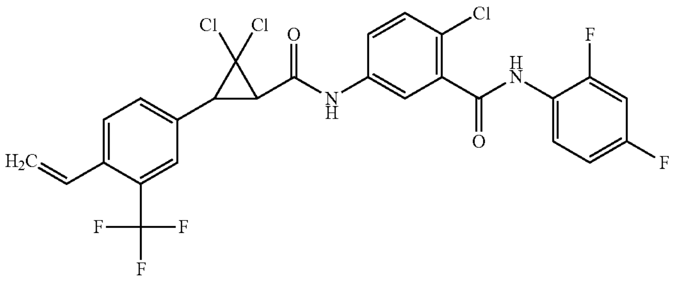 [SMILES: C=Cc1ccc(C2C(C(=O)Nc3ccc(Cl)c(C(=O)Nc4ccc(F)cc4F)c3)C2(Cl)Cl)cc1C(F)(F)F] | 77 |
| F392 | 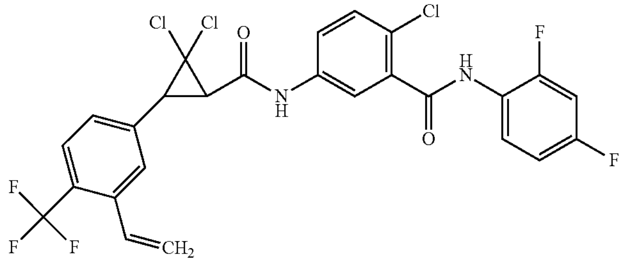 [SMILES: C=Cc1cc(C2C(C(=O)Nc3ccc(Cl)c(C(=O)Nc4ccc(F)cc4F)c3)C2(Cl)Cl)ccc1C(F)(F)F] | 77 |
| F393 | 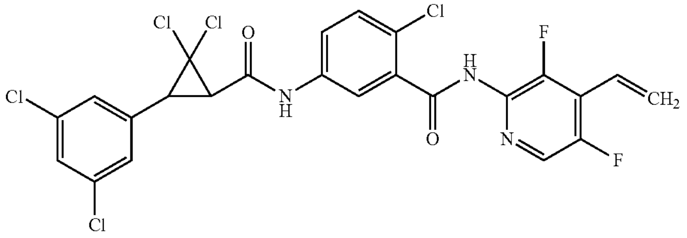 [SMILES: C=Cc1c(F)cnc(NC(=O)c2cc(NC(=O)C3C(c4cc(Cl)cc(Cl)c4)C3(Cl)Cl)ccc2Cl)c1F] | 76 |
| F394 | 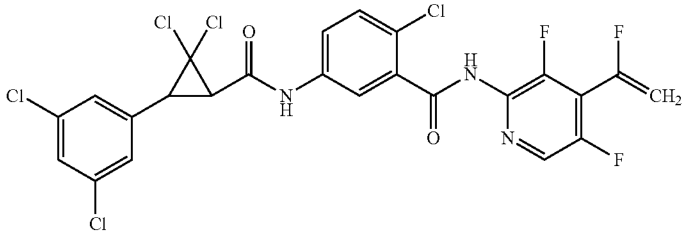 [SMILES: C=C(F)c1c(F)cnc(NC(=O)c2cc(NC(=O)C3C(c4cc(Cl)cc(Cl)c4)C3(Cl)Cl)ccc2Cl)c1F] | 76 |
| F395 | 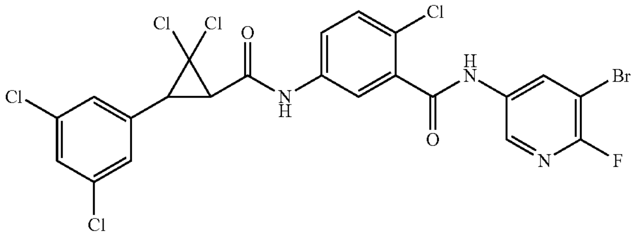 [SMILES: O=C(Nc1cnc(F)c(Br)c1)c1cc(NC(=O)C2C(c3cc(Cl)cc(Cl)c3)C2(Cl)Cl)ccc1Cl] | 55 |
| F396 | 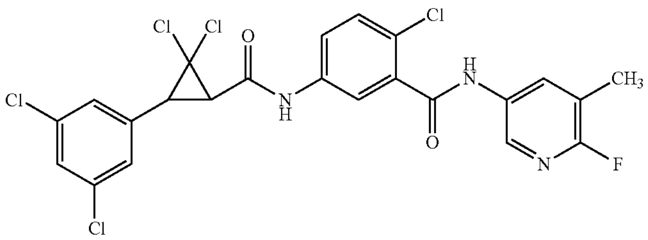 [SMILES: Cc1cc(NC(=O)c2cc(NC(=O)C3C(c4cc(Cl)cc(Cl)c4)C3(Cl)Cl)ccc2Cl)cnc1F] | 55 |

TABLE 2-continued
| Structure and preparation method for F Series molecules | | |
|---|---|---|
| No. | Structure | Prep.* |
| F397 | 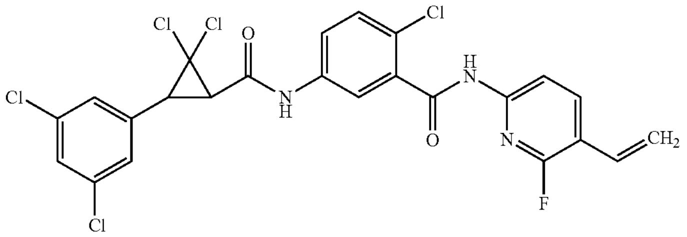 [SMILES: C=Cc1ccc(NC(=O)c2cc(NC(=O)C3C(c4cc(Cl)cc(Cl)c4)C3(Cl)Cl)ccc2Cl)nc1F] | 76 |
| F398 | 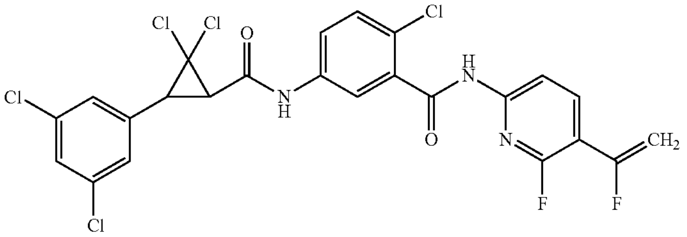 [SMILES: C=C(F)c1ccc(NC(=O)c2cc(NC(=O)C3C(c4cc(Cl)cc(Cl)c4)C3(Cl)Cl)ccc2Cl)nc1F] | 76 |
| F399 | 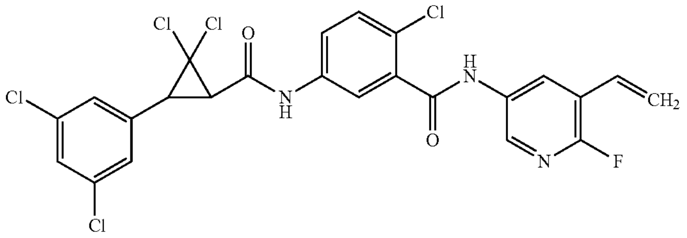 [SMILES: C=Cc1cc(NC(=O)c2cc(NC(=O)C3C(c4cc(Cl)cc(Cl)c4)C3(Cl)Cl)ccc2Cl)cnc1F] | 76 |
| F400 | 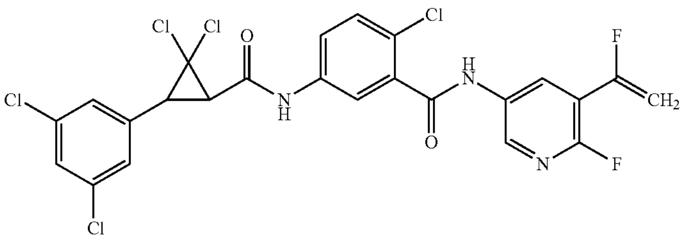 [SMILES: C=C(F)c1cc(NC(=O)c2cc(NC(=O)C3C(c4cc(Cl)cc(Cl)c4)C3(Cl)Cl)ccc2Cl)cnc1F] | 76 |
| F401 | 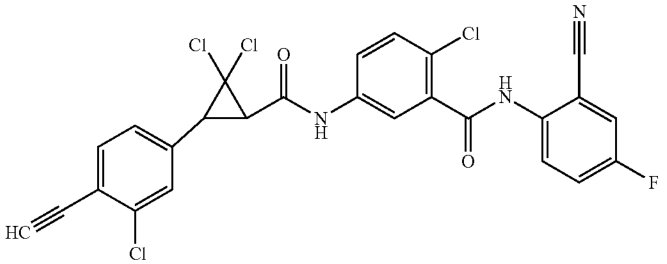 [SMILES: C#Cc1ccc(C2C(C(=O)Nc3ccc(Cl)c(C(=O)Nc4ccc(F)cc4C#N)c3)C2(Cl)Cl)cc1Cl] | 79 |
| F402 | 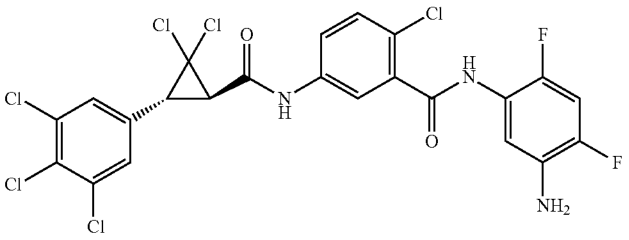 [SMILES: Nc1cc(NC(=O)c2cc(NC(=O)[C@H]3[C@H](c4cc(Cl)c(Cl)c(Cl)c4)C3(Cl)Cl)ccc2Cl)c(F)cc1F] | 62 |

TABLE 2-continued
Structure and preparation method for F Series molecules
| No. | Structure | Prep.* |
| --- | --- | --- |
| F403 | 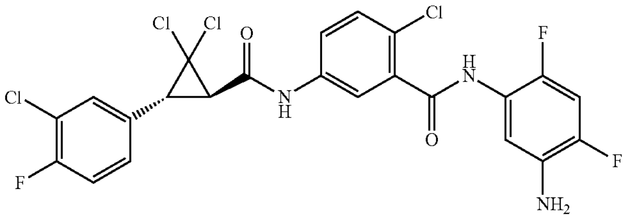 | 62 |
| F404 | 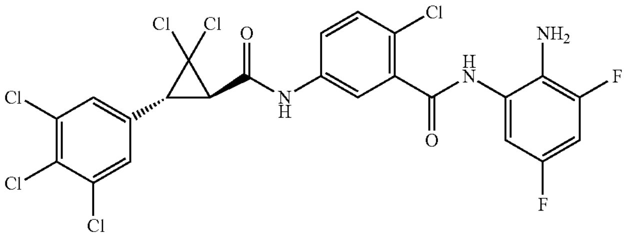 [SMILES: Nc1c(F)cc(F)cc1NC(=O)c1cc(NC(=O)[C@H]2[C@H](c3cc(Cl)c(Cl)c(Cl)c3)C2(Cl)Cl)ccc1Cl] | 62 |
| F405 | 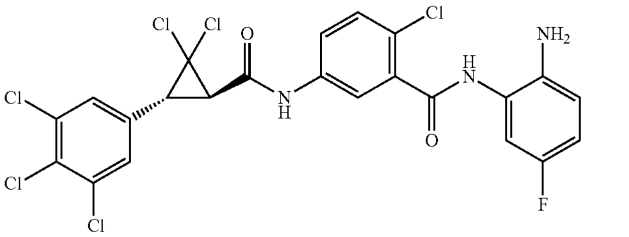 [SMILES: Nc1ccc(F)cc1NC(=O)c1cc(NC(=O)[C@H]2[C@H](c3cc(Cl)c(Cl)c(Cl)c3)C2(Cl)Cl)ccc1Cl] | 62 |
| F406 | 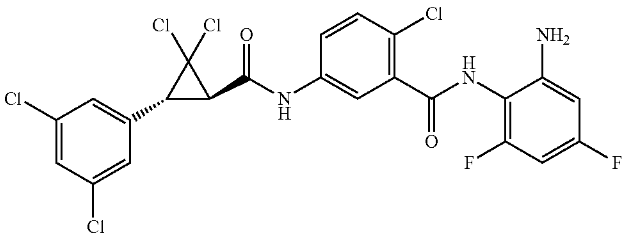 [SMILES: Nc1cc(F)cc(F)c1NC(=O)c1cc(NC(=O)[C@H]2[C@H](c3cc(Cl)cc(Cl)c3)C2(Cl)Cl)ccc1Cl] | 62 |
| F407 | 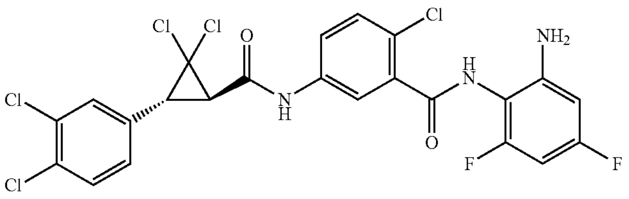 [SMILES: Nc1cc(F)cc(F)c1NC(=O)c1cc(NC(=O)[C@H]2[C@H](c3ccc(Cl)c(Cl)c3)C2(Cl)Cl)ccc1Cl] | 63 |
| F408 | 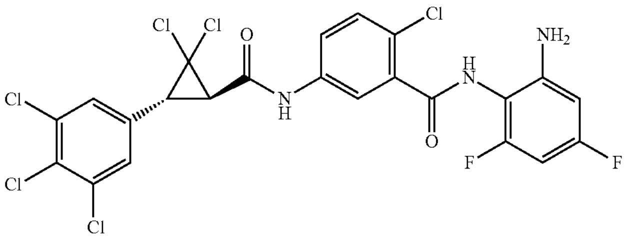 [SMILES: Nc1cc(F)cc(F)c1NC(=O)c1cc(NC(=O)[C@H]2[C@H](c3cc(Cl)c(Cl)c(Cl)c3)C2(Cl)Cl)ccc1Cl] | 62 |

TABLE 2-continued
| Structure and preparation method for F Series molecules | | |
|---|---|---|
| No. | Structure | Prep.* |
| F409 | 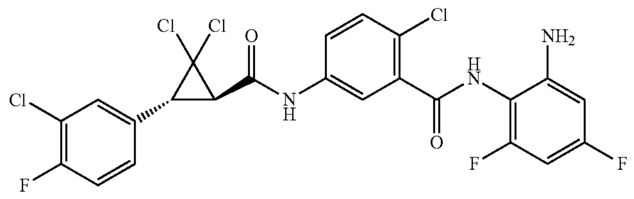 [SMILES: Nc1cc(F)cc(F)c1NC(=O)c1cc(NC(=O)[C@H]2[C@H](c3ccc(F)c(Cl)c3)C2(Cl)Cl)ccc1Cl] | 63 |
| F410 | 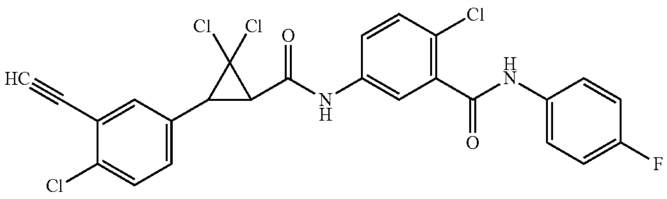 [SMILES: C#Cc1cc(C2C(C(=O)Nc3ccc(Cl)c(C(=O)Nc4ccc(F)cc4)c3)C2(Cl)Cl)ccc1Cl] | 79 |
| F411 | 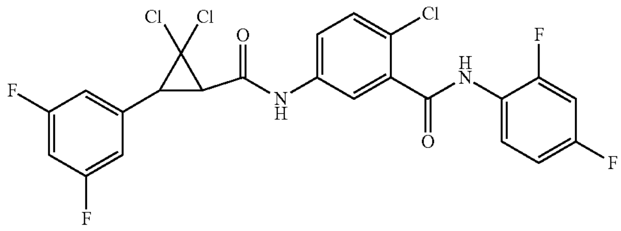 [SMILES: O=C(Nc1ccc(F)cc1F)c1cc(NC(=O)C2C(c3cc(F)cc(F)c3)C2(Cl)Cl)ccc1Cl] | 55 |
| F412 | 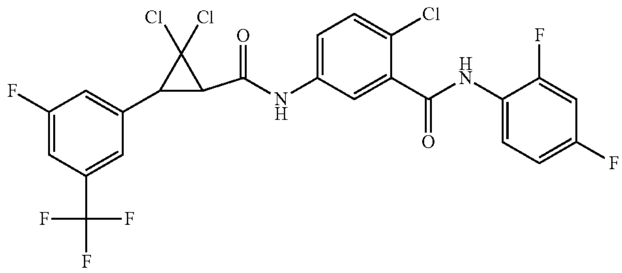 [SMILES: O=C(Nc1ccc(F)cc1F)c1cc(NC(=O)C2C(c3cc(F)cc(C(F)(F)F)c3)C2(Cl)Cl)ccc1Cl] | 55 |
| F413 | 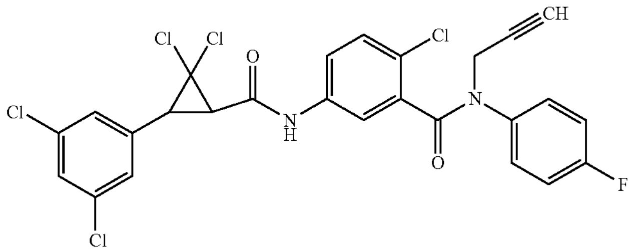 [SMILES: C#CCN(C(=O)c1cc(NC(=O)C2C(c3cc(Cl)cc(Cl)c3)C2(Cl)Cl)ccc1Cl)c1ccc(F)cc1] | 13 |
| F414 | 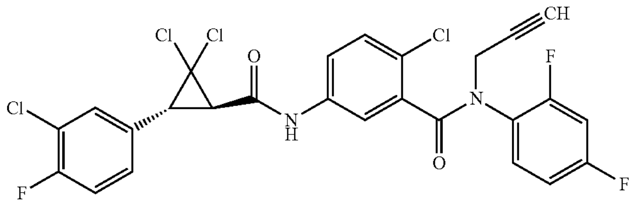 [SMILES: C#CCN(C(=O)c1cc(NC(=O)[C@H]2[C@H](c3ccc(F)c(Cl)c3)C2(Cl)Cl)ccc1Cl)c1ccc(F)cc1F] | 13 |

TABLE 2-continued
| Structure and preparation method for F Series molecules | | |
|---|---|---|
| No. | Structure | Prep.* |
| F415 | 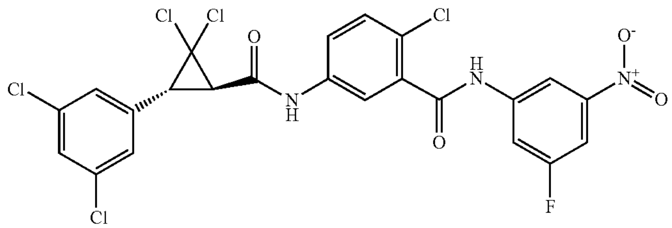 [SMILES: O=C(Nc1cc(F)cc([N+](=O)[O-])c1)c1cc(NC(=O)[C@H]2[C@H](c3cc(Cl)cc(Cl)c3)C2(Cl)Cl)ccc1Cl] | 55 |
| F416 | 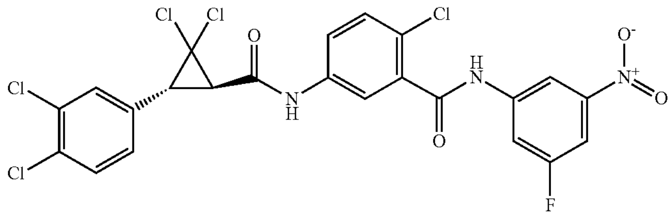 [SMILES: O=C(Nc1cc(F)cc([N+](=O)[O-])c1)c1cc(NC(=O)[C@H]2[C@H](c3ccc(Cl)c(Cl)c3)C2(Cl)Cl)ccc1Cl] | 55 |
| F417 | 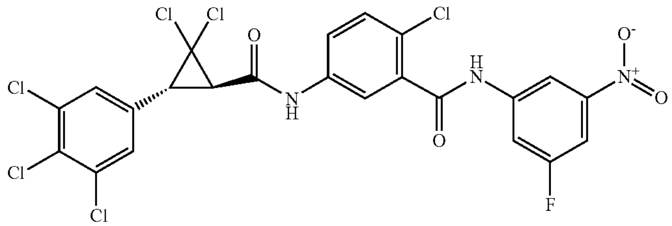 [SMILES: O=C(Nc1cc(F)cc([N+](=O)[O-])c1)c1cc(NC(=O)[C@H]2[C@H](c3cc(Cl)c(Cl)c(Cl)c3)C2(Cl)Cl)ccc1Cl] | 55 |
| F418 | 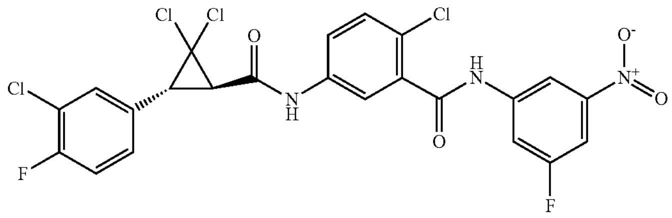 [SMILES: O=C(Nc1cc(F)cc([N+](=O)[O-])c1)c1cc(NC(=O)[C@H]2[C@H](c3ccc(F)c(Cl)c3)C2(Cl)Cl)ccc1Cl] | 55 |
| F419 | 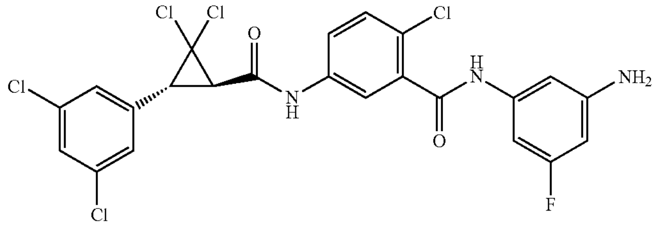 [SMILES: Nc1cc(F)cc(NC(=O)c2cc(NC(=O)[C@H]3[C@H](c4cc(Cl)cc(Cl)c4)C3(Cl)Cl)ccc2Cl)c1] | 60 |
| F420 | 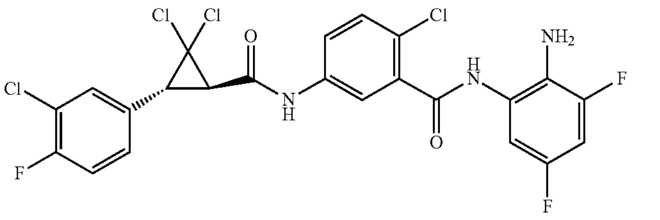 [SMILES: Nc1c(F)cc(F)cc1NC(=O)c1cc(NC(=O)[C@H]2[C@H](c3ccc(F)c(Cl)c3)C2(Cl)Cl)ccc1Cl] | 63 |

TABLE 2-continued
| Structure and preparation method for F Series molecules | | |
|---|---|---|
| No. | Structure | Prep.* |
| F421 | 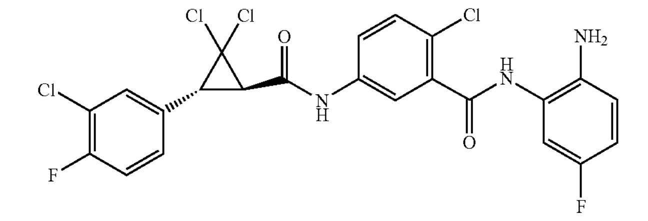 [SMILES: Nc1ccc(F)cc1NC(=O)c1cc(NC(=O)[C@H]2[C@H](c3ccc(F)c(Cl)c3)C2(Cl)Cl)ccc1Cl] | 63 |
| F422 | 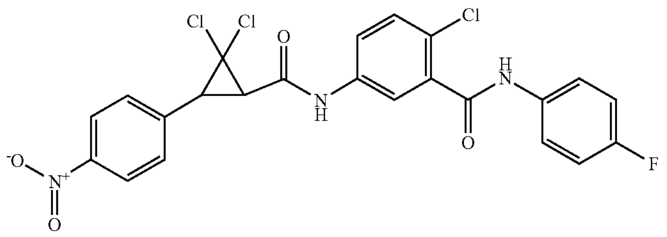 | 13 |
| F423 | 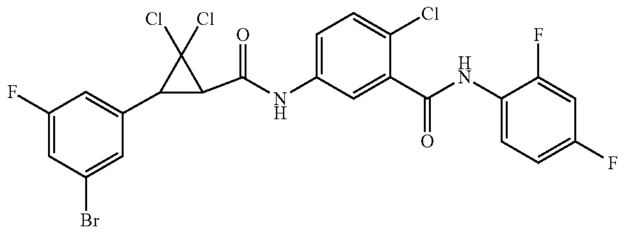 [SMILES: O=C(Nc1ccc(F)cc1F)c1cc(NC(=O)C2C(c3cc(F)cc(Br)c3)C2(Cl)Cl)ccc1Cl] | 55 |
| F424 | 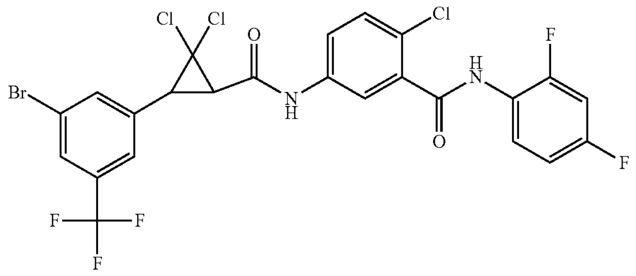 [SMILES: O=C(Nc1ccc(F)cc1F)c1cc(NC(=O)C2C(c3cc(Br)cc(C(F)(F)F)c3)C2(Cl)Cl)ccc1Cl] | 55 |
| F425 | 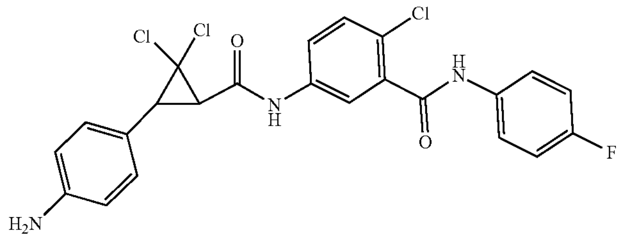 [SMILES: Nc1ccc(C2C(C(=O)Nc3ccc(Cl)c(C(=O)Nc4ccc(F)cc4)c3)C2(Cl)Cl)cc1] | 61 |
| F426 | 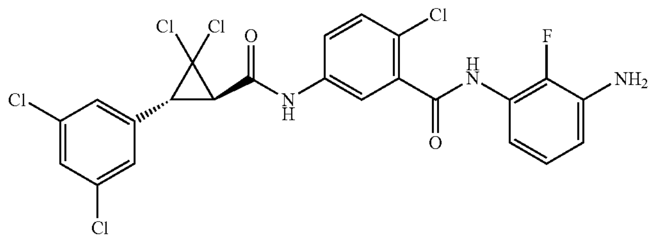 [SMILES: Nc1cccc(NC(=O)c2cc(NC(=O)[C@H]3[C@H](c4cc(Cl)cc(Cl)c4)C3(Cl)Cl)ccc2Cl)c1F] | 62 |

TABLE 2-continued
| Structure and preparation method for F Series molecules | | |
|---|---|---|
| No. | Structure | Prep.* |
| F427 | 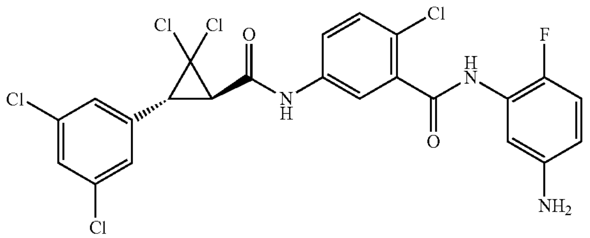 [SMILES: Nc1ccc(F)c(NC(=O)c2cc(NC(=O)[C@H]3[C@H](c4cc(Cl)cc(Cl)c4)C3(Cl)Cl)ccc2Cl)c1] | 62 |
| F428 | 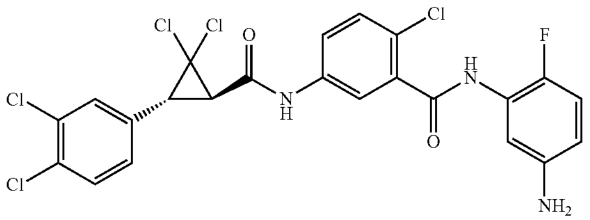 [SMILES: Nc1ccc(F)c(NC(=O)c2cc(NC(=O)[C@H]3[C@H](c4ccc(Cl)c(Cl)c4)C3(Cl)Cl)ccc2Cl)c1] | 62 |
| F429 | 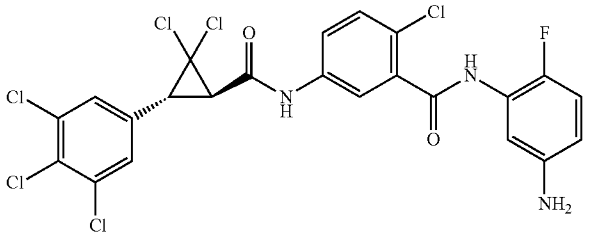 [SMILES: Nc1ccc(F)c(NC(=O)c2cc(NC(=O)[C@H]3[C@H](c4cc(Cl)c(Cl)c(Cl)c4)C3(Cl)Cl)ccc2Cl)c1] | 62 |
| F430 | 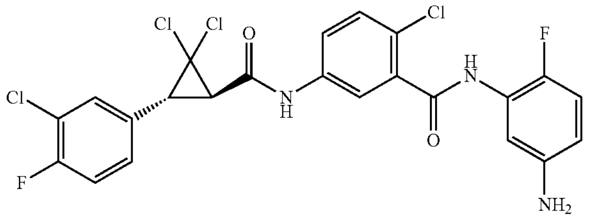 [SMILES: Nc1ccc(F)c(NC(=O)c2cc(NC(=O)[C@H]3[C@H](c4ccc(F)c(Cl)c4)C3(Cl)Cl)ccc2Cl)c1] | 62 |
| F431 | 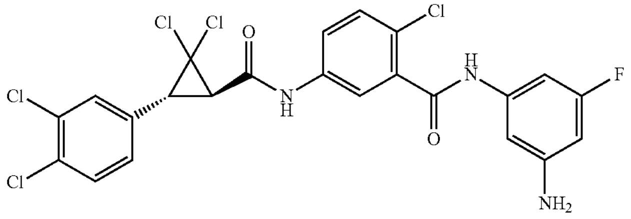 [SMILES: Nc1cc(F)cc(NC(=O)c2cc(NC(=O)[C@H]3[C@H](c4ccc(Cl)c(Cl)c4)C3(Cl)Cl)ccc2Cl)c1] | 60 |
| F432 | 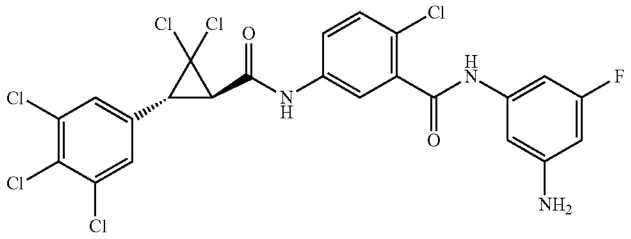 [SMILES: Nc1cc(F)cc(NC(=O)c2cc(NC(=O)[C@H]3[C@H](c4cc(Cl)c(Cl)c(Cl)c4)C3(Cl)Cl)ccc2Cl)c1] | 60 |

TABLE 2-continued
Structure and preparation method for F Series molecules
| No. | Structure | Prep.* |
| --- | --- | --- |
| F433 | 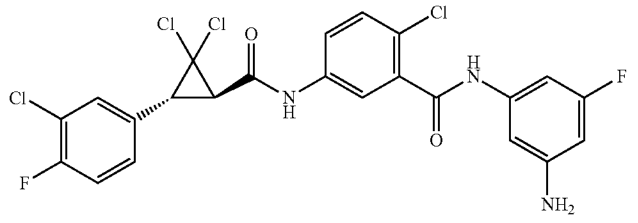 [SMILES: Nc1cc(F)cc(NC(=O)c2cc(NC(=O)[C@H]3[C@H](c4ccc(F)c(Cl)c4)C3(Cl)Cl)ccc2Cl)c1] | 60 |
| F434 | 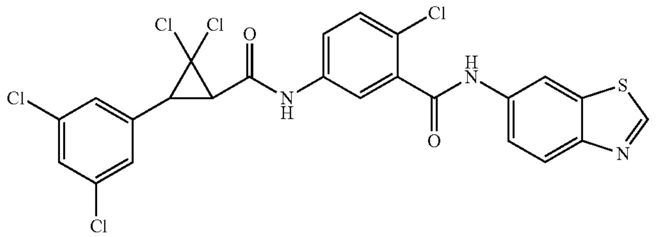 [SMILES: O=C(Nc1ccc2ncsc2c1)c1cc(NC(=O)C2C(c3cc(Cl)cc(Cl)c3)C2(Cl)Cl)ccc1Cl] | 15 |
| F435 | 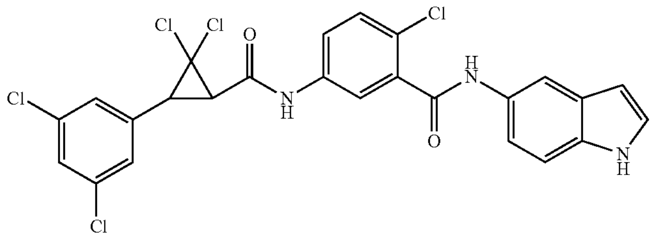 [SMILES: O=C(Nc1ccc2[nH]ccc2c1)c1cc(NC(=O)C2C(c3cc(Cl)cc(Cl)c3)C2(Cl)Cl)ccc1Cl] | 15 |
| F436 | 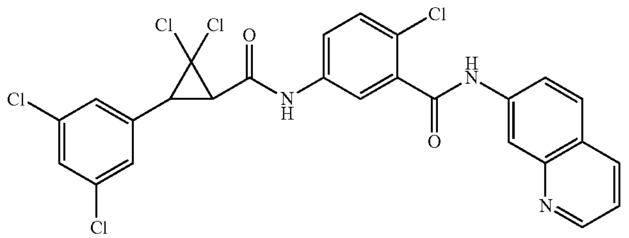 [SMILES: O=C(Nc1ccc2cccnc2c1)c1cc(NC(=O)C2C(c3cc(Cl)cc(Cl)c3)C2(Cl)Cl)ccc1Cl] | 15 |
| F437 | 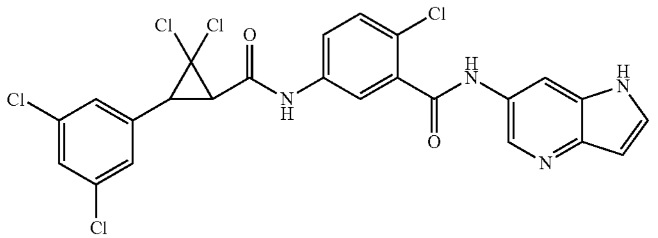 [SMILES: O=C(Nc1cnc2cc[nH]c2c1)c1cc(NC(=O)C2C(c3cc(Cl)cc(Cl)c3)C2(Cl)Cl)ccc1Cl] | 15 |
| F438 | 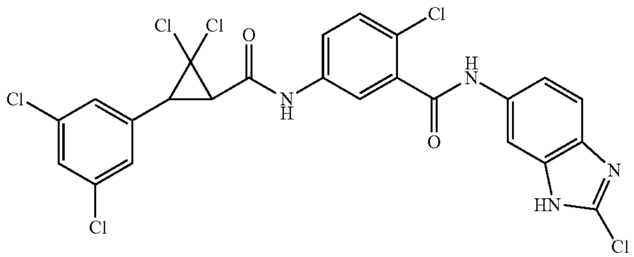 [SMILES: O=C(Nc1ccc2nc(Cl)[nH]c2c1)c1cc(NC(=O)C2C(c3cc(Cl)cc(Cl)c3)C2(Cl)Cl)ccc1Cl] | 15 |

TABLE 2-continued
| Structure and preparation method for F Series molecules | | |
|---|---|---|
| No. | Structure | Prep.* |
| F439 | 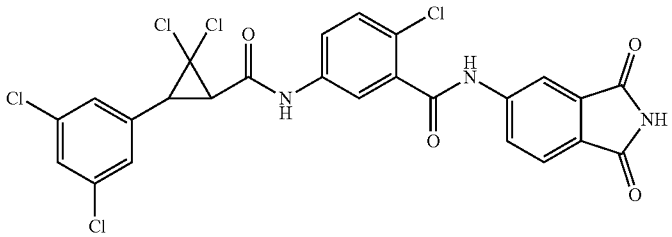 [SMILES: O=C(Nc1ccc2c(c1)C(=O)NC2=O)c1cc(NC(=O)C2C(c3cc(Cl)cc(Cl)c3)C2(Cl)Cl)ccc1Cl] | 55 |
| F440 | 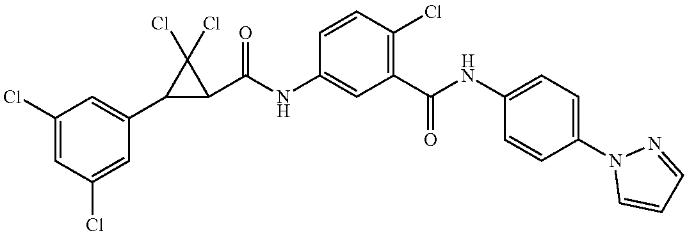 [SMILES: O=C(Nc1ccc(-n2cccn2)cc1)c1cc(NC(=O)C2C(c3cc(Cl)cc(Cl)c3)C2(Cl)Cl)ccc1Cl] | 13 |
| F441 | 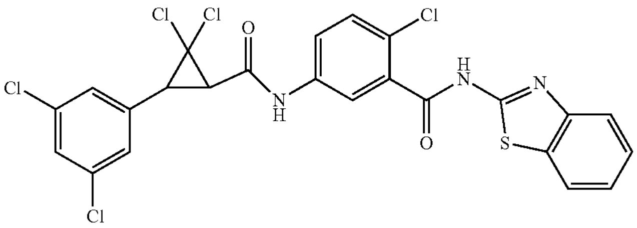 [SMILES: O=C(Nc1nc2ccccc2s1)c1cc(NC(=O)C2C(c3cc(Cl)cc(Cl)c3)C2(Cl)Cl)ccc1Cl] | 15 |
| F442 | 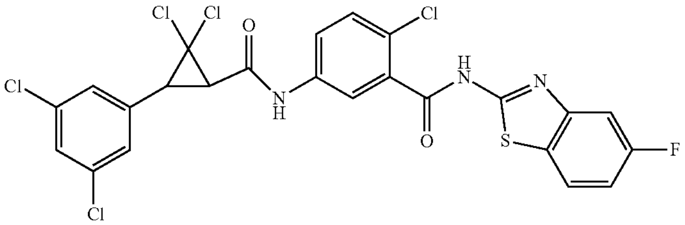 [SMILES: O=C(Nc1nc2cc(F)ccc2s1)c1cc(NC(=O)C2C(c3cc(Cl)cc(Cl)c3)C2(Cl)Cl)ccc1Cl] | 15 |
| F443 | 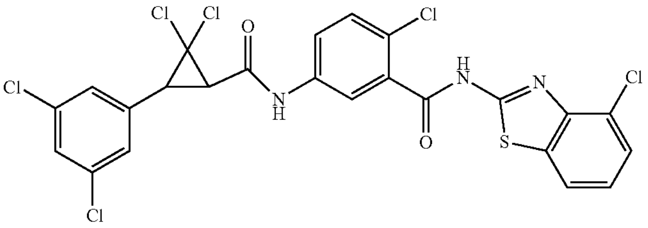 [SMILES: O=C(Nc1nc2c(Cl)cccc2s1)c1cc(NC(=O)C2C(c3cc(Cl)cc(Cl)c3)C2(Cl)Cl)ccc1Cl] | 15 |
| F444 | 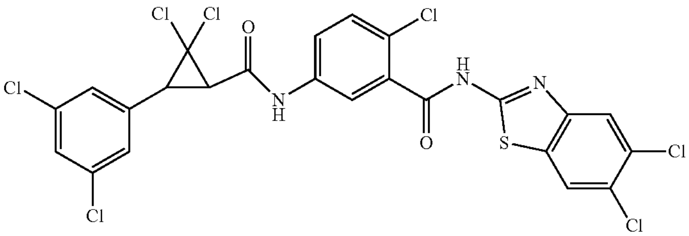 [SMILES: O=C(Nc1nc2cc(Cl)c(Cl)cc2s1)c1cc(NC(=O)C2C(c3cc(Cl)cc(Cl)c3)C2(Cl)Cl)ccc1Cl] | 15 |

TABLE 2-continued
Structure and preparation method for F Series molecules
| No. | Structure | Prep.* |
| --- | --- | --- |
| F445 | 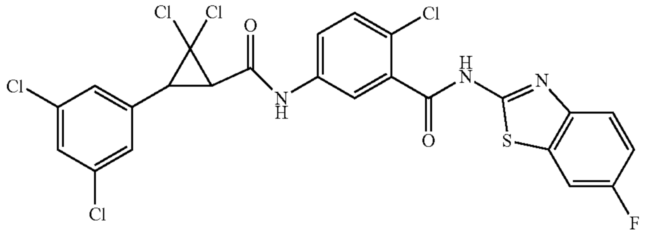 [SMILES: O=C(Nc1nc2ccc(F)cc2s1)c1cc(NC(=O)C2C(c3cc(Cl)cc(Cl)c3)C2(Cl)Cl)ccc1Cl] | 15 |
| F446 | 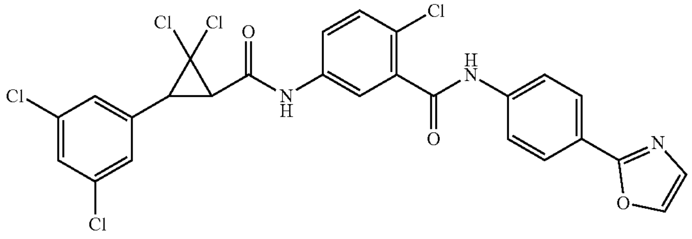 [SMILES: O=C(Nc1ccc(-c2ncco2)cc1)c1cc(NC(=O)C2C(c3cc(Cl)cc(Cl)c3)C2(Cl)Cl)ccc1Cl] | 13 |
| F447 | 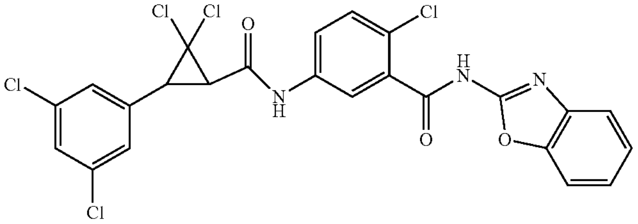 [SMILES: O=C(Nc1nc2ccccc2o1)c1cc(NC(=O)C2C(c3cc(Cl)cc(Cl)c3)C2(Cl)Cl)ccc1Cl] | 15 |
| F448 | 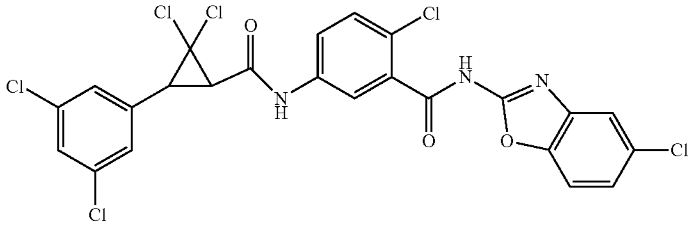 [SMILES: O=C(Nc1nc2cc(Cl)ccc2o1)c1cc(NC(=O)C2C(c3cc(Cl)cc(Cl)c3)C2(Cl)Cl)ccc1Cl] | 15 |
| F449 | 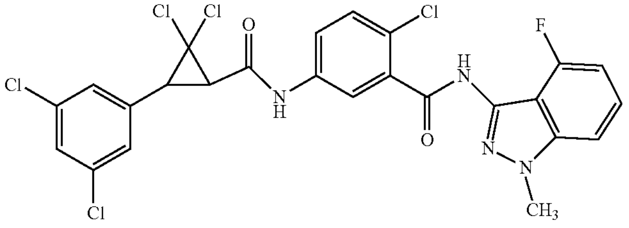 [SMILES: Cn1nc(NC(=O)c2cc(NC(=O)C3C(c4cc(Cl)cc(Cl)c4)C3(Cl)Cl)ccc2Cl)c2c(F)cccc21] | 15 |
| F450 | 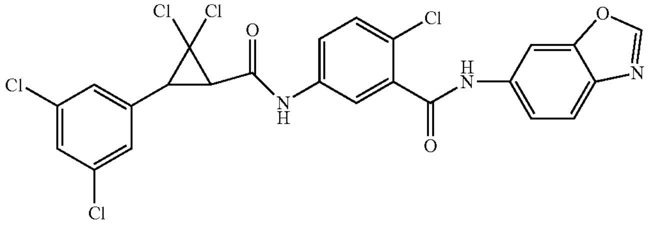 [SMILES: O=C(Nc1ccc2ncoc2c1)c1cc(NC(=O)C2C(c3cc(Cl)cc(Cl)c3)C2(Cl)Cl)ccc1Cl] | 15 |

TABLE 2-continued
| Structure and preparation method for F Series molecules | | |
|---|---|---|
| No. | Structure | Prep.* |
| F451 | 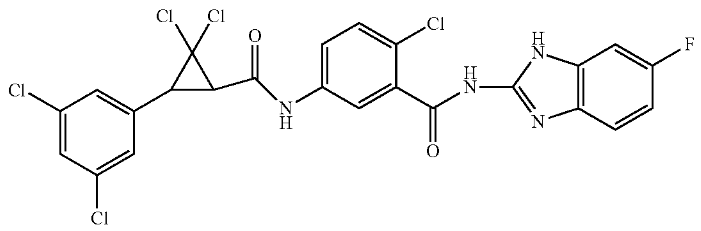 [SMILES: O=C(Nc1nc2ccc(F)cc2[nH]1)c1cc(NC(=O)C2C(c3cc(Cl)cc(Cl)c3)C2(Cl)Cl)ccc1Cl] | 15 |
| F452 | 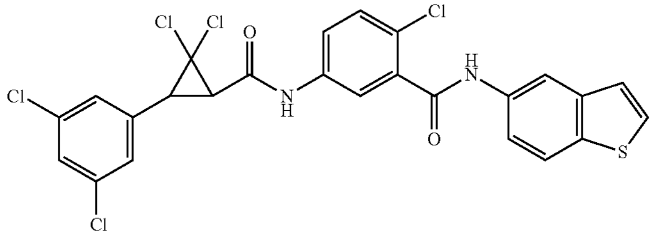 [SMILES: O=C(Nc1ccc2sccc2c1)c1cc(NC(=O)C2C(c3cc(Cl)cc(Cl)c3)C2(Cl)Cl)ccc1Cl] | 15 |
| F453 | 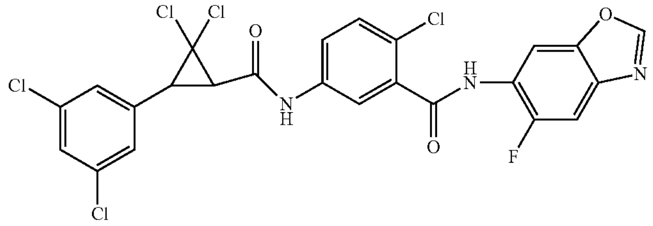 [SMILES: O=C(Nc1cc2ocnc2cc1F)c1cc(NC(=O)C2C(c3cc(Cl)cc(Cl)c3)C2(Cl)Cl)ccc1Cl] | 15 |
| F454 | 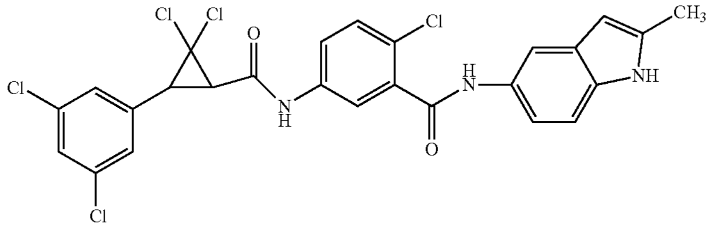 [SMILES: Cc1cc2cc(NC(=O)c3cc(NC(=O)C4C(c5cc(Cl)cc(Cl)c5)C4(Cl)Cl)ccc3Cl)ccc2[nH]1] | 15 |
| F455 | 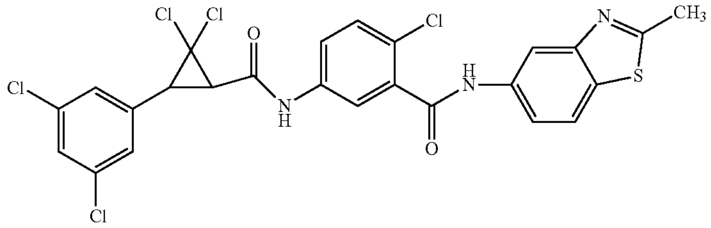 [SMILES: Cc1nc2cc(NC(=O)c3cc(NC(=O)C4C(c5cc(Cl)cc(Cl)c5)C4(Cl)Cl)ccc3Cl)ccc2s1] | 15 |
| F456 | 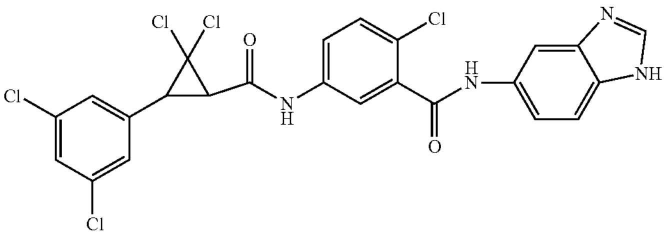 [SMILES: O=C(Nc1ccc2[nH]cnc2c1)c1cc(NC(=O)C2C(c3cc(Cl)cc(Cl)c3)C2(Cl)Cl)ccc1Cl] | 15 |

TABLE 2-continued
| Structure and preparation method for F Series molecules | | |
|---|---|---|
| No. | Structure | Prep.* |
| F457 | 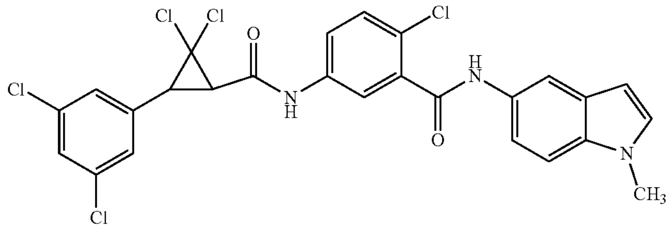 [SMILES: Cn1ccc2cc(NC(=O)c3cc(NC(=O)C4C(c5cc(Cl)cc(Cl)c5)C4(Cl)Cl)ccc3Cl)ccc21] | 15 |
| F458 | 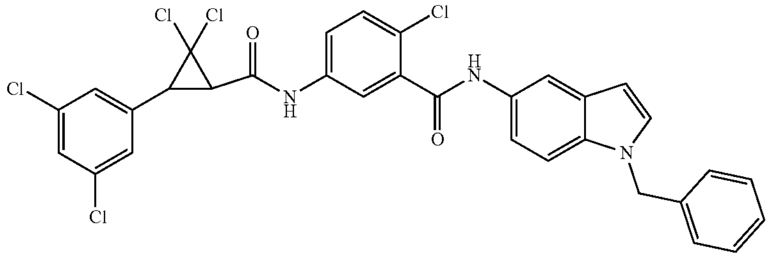 [SMILES: O=C(Nc1ccc2c(ccn2Cc2ccccc2)c1)c1cc(NC(=O)C2C(c3cc(Cl)cc(Cl)c3)C2(Cl)Cl)ccc1Cl] | 55 |
| F459 | 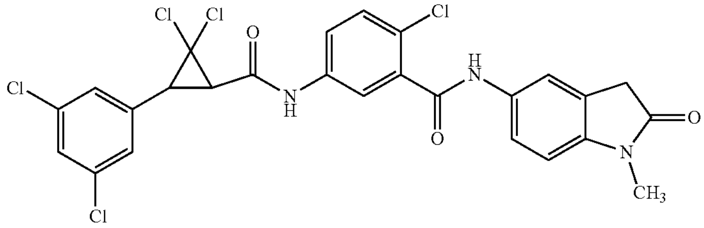 [SMILES: CN1C(=O)Cc2cc(NC(=O)c3cc(NC(=O)C4C(c5cc(Cl)cc(Cl)c5)C4(Cl)Cl)ccc3Cl)ccc21] | 55 |
| F460 | 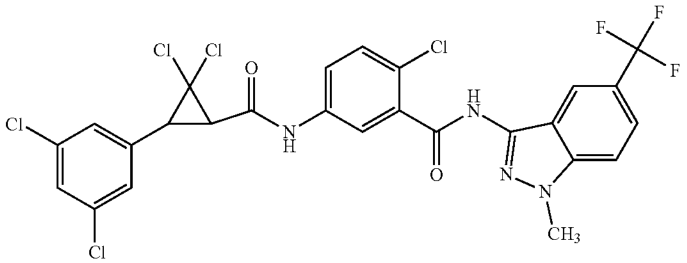 [SMILES: Cn1nc(NC(=O)c2cc(NC(=O)C3C(c4cc(Cl)cc(Cl)c4)C3(Cl)Cl)ccc2Cl)c2cc(C(F)(F)F)ccc21] | 55 |
| F461 | 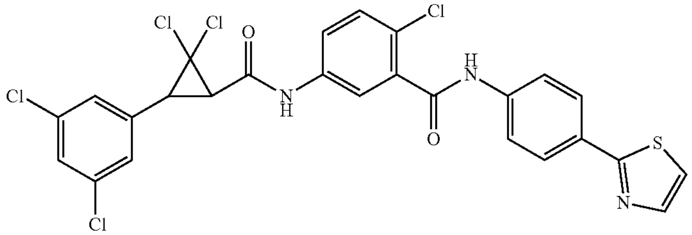 [SMILES: O=C(Nc1ccc(-c2nccs2)cc1)c1cc(NC(=O)C2C(c3cc(Cl)cc(Cl)c3)C2(Cl)Cl)ccc1Cl] | 15 |
| F462 | 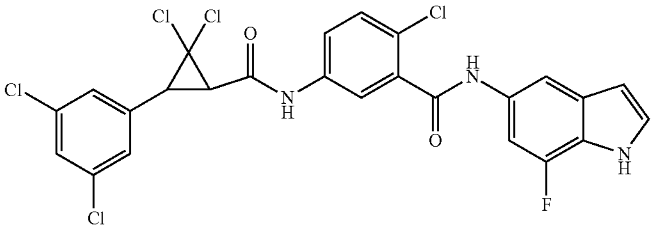 [SMILES: O=C(Nc1cc(F)c2[nH]ccc2c1)c1cc(NC(=O)C2C(c3cc(Cl)cc(Cl)c3)C2(Cl)Cl)ccc1Cl] | 55 |

TABLE 2-continued
| No. | Structure | Prep.* |
| --- | --- | --- |
| F463 | 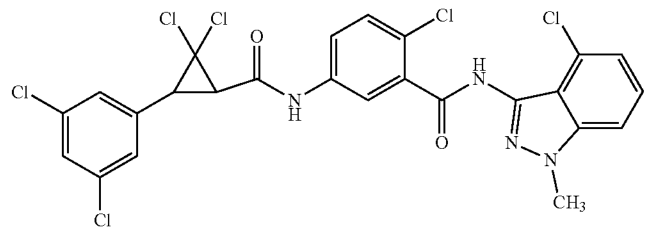 [SMILES: Cn1nc(NC(=O)c2cc(NC(=O)C3C(c4cc(Cl)cc(Cl)c4)C3(Cl)Cl)ccc2Cl)c2c(Cl)cccc21] | 55 |
| F464 | 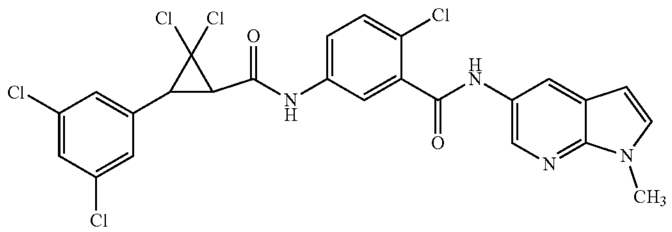 [SMILES: Cn1ccc2cc(NC(=O)c3cc(NC(=O)C4C(c5cc(Cl)cc(Cl)c5)C4(Cl)Cl)ccc3Cl)cnc21] | 55 |
| F465 | 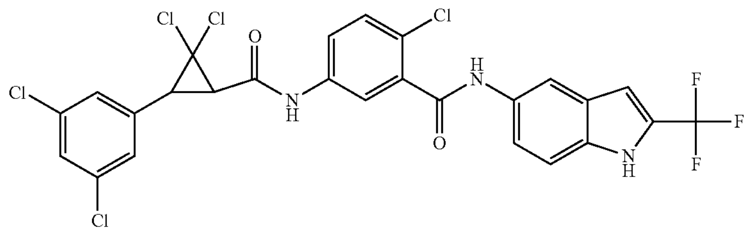 [SMILES: O=C(Nc1ccc2[nH]c(C(F)(F)F)cc2c1)c1cc(NC(=O)C2C(c3cc(Cl)cc(Cl)c3)C2(Cl)Cl)ccc1Cl] | 55 |
| F468 | 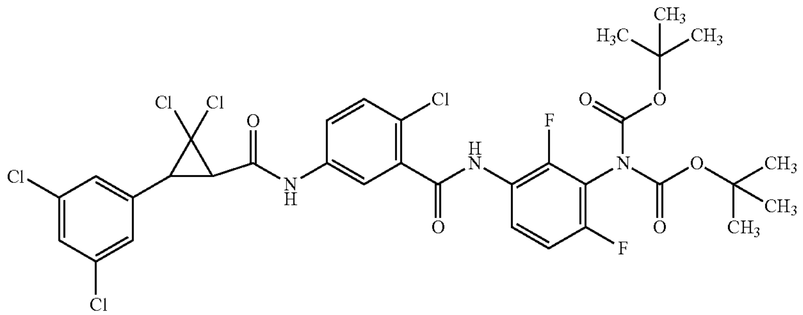 [SMILES: CC(C)(C)OC(=O)N(C(=O)OC(C)(C)C)c1c(F)ccc(NC(=O)c2cc(NC(=O)C3C(c4cc(Cl)cc(Cl)c4)C3(Cl)Cl)ccc2Cl)c1F] | 55 |
| F469 | 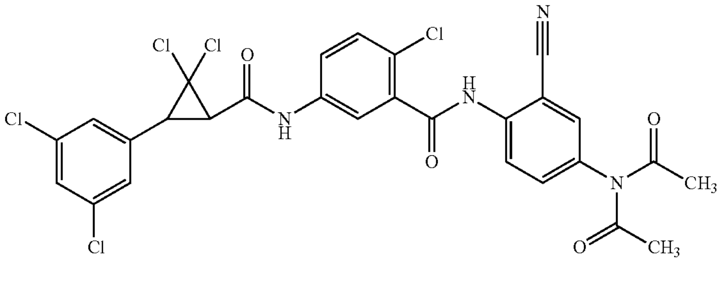 [SMILES: CC(=O)N(C(C)=O)c1ccc(NC(=O)c2cc(NC(=O)C3C(c4cc(Cl)cc(Cl)c4)C3(Cl)Cl)ccc2Cl)c(C#N)c1] | 66 |
Structure and preparation method for F Series molecules TABLE 2-continued
| Structure and preparation method for F Series molecules | | |
|---|---|---|
| No. | Structure | Prep.* |
| F470 | 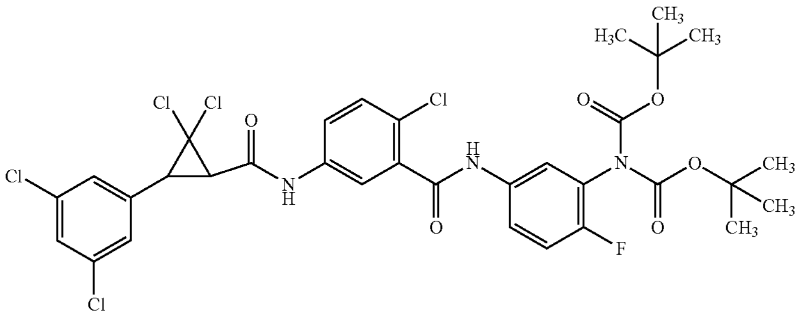 [SMILES: CC(C)(C)OC(=O)N(C(=O)OC(C)(C)C)c1cc(NC(=O)c2cc(NC(=O)C3C(c4cc(Cl)cc(Cl)c4)C3(Cl)Cl)ccc2Cl)ccc1F] | 55 |
| F471 | 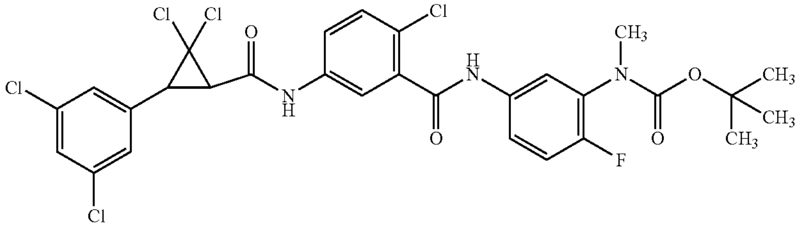 [SMILES: CN(C(=O)OC(C)(C)C)c1cc(NC(=O)c2cc(NC(=O)C3C(c4cc(Cl)cc(Cl)c4)C3(Cl)Cl)ccc2Cl)ccc1F] | 55 or 57 |
| F472 | 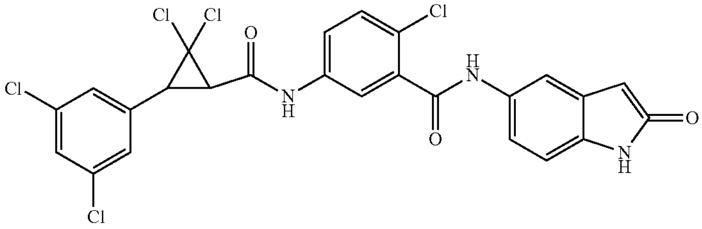 | 55 |
| F473 | 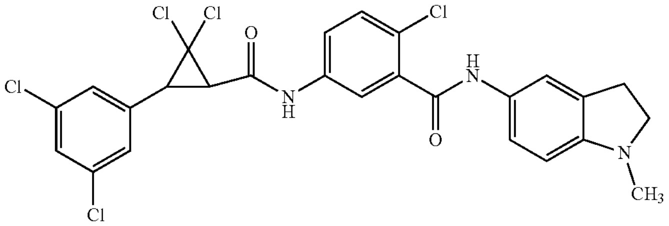 [SMILES: CN1CCc2cc(NC(=O)c3cc(NC(=O)C4C(c5cc(Cl)cc(Cl)c5)C4(Cl)Cl)ccc3Cl)ccc21] | 55 |
| F474 | 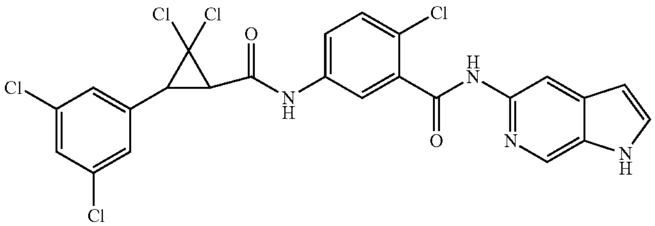 [SMILES: O=C(Nc1cc2cc[nH]c2cn1)c1cc(NC(=O)C2C(c3cc(Cl)cc(Cl)c3)C2(Cl)Cl)ccc1Cl] | 55 |
| F475 | 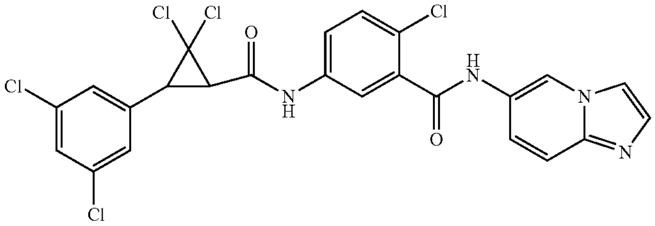 [SMILES: O=C(Nc1ccc2nccn2c1)c1cc(NC(=O)C2C(c3cc(Cl)cc(Cl)c3)C2(Cl)Cl)ccc1Cl] | 15 |

TABLE 2-continued
| Structure and preparation method for F Series molecules | | |
|---|---|---|
| No. | Structure | Prep.* |
| F476 | 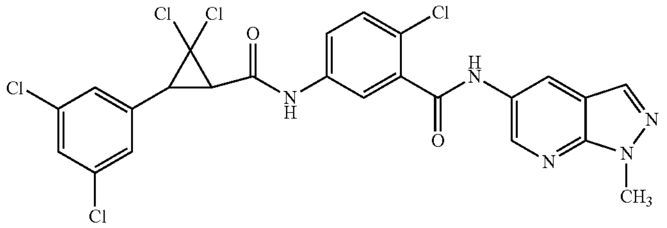 [SMILES: Cn1ncc2cc(NC(=O)c3cc(NC(=O)C4C(c5cc(Cl)cc(Cl)c5)C4(Cl)Cl)ccc3Cl)cnc21] | 55 |
| F477 | 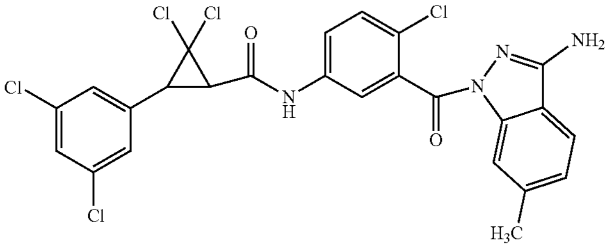 [SMILES: Cc1ccc2c(N)nn(C(=O)c3cc(NC(=O)C4C(c5cc(Cl)cc(Cl)c5)C4(Cl)Cl)ccc3Cl)c2c1] | 55 |
| F478 | 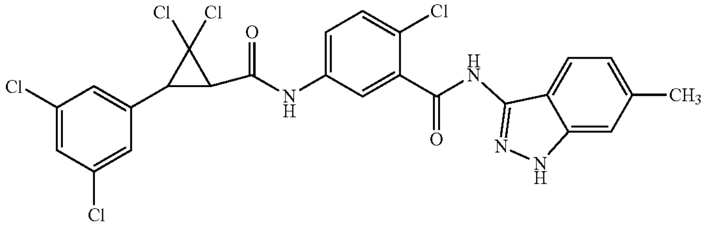 [SMILES: Cc1ccc2c(NC(=O)c3cc(NC(=O)C4C(c5cc(Cl)cc(Cl)c5)C4(Cl)Cl)ccc3Cl)n[nH]c2c1] | 55 |
| F479 | 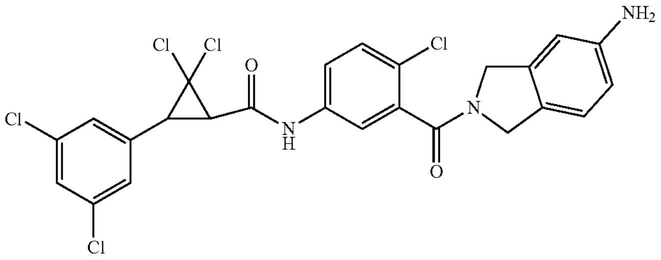 [SMILES: Nc1ccc2c(c1)CN(C(=O)c1cc(NC(=O)C3C(c4cc(Cl)cc(Cl)c4)C3(Cl)Cl)ccc1Cl)C2] | 55 |
| F480 | 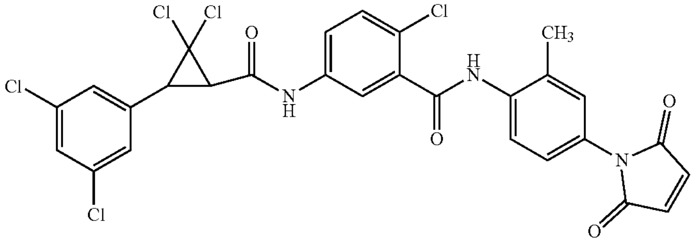 [SMILES: Cc1cc(N2C(=O)C=CC2=O)ccc1NC(=O)c1cc(NC(=O)C2C(c3cc(Cl)cc(Cl)c3)C2(Cl)Cl)ccc1Cl] | 73 |
| F481 | 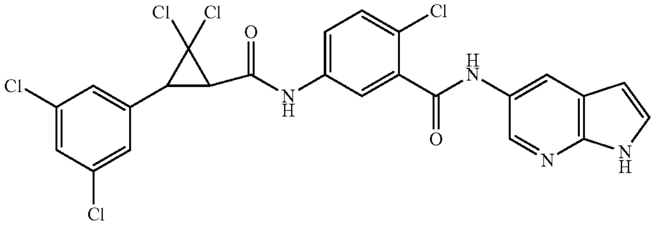 [SMILES: O=C(Nc1cnc2[nH]ccc2c1)c1cc(NC(=O)C2C(c3cc(Cl)cc(Cl)c3)C2(Cl)Cl)ccc1Cl] | 55 |

TABLE 2-continued
| Structure and preparation method for F Series molecules | | |
|---|---|---|
| No. | Structure | Prep.* |
| F482 | 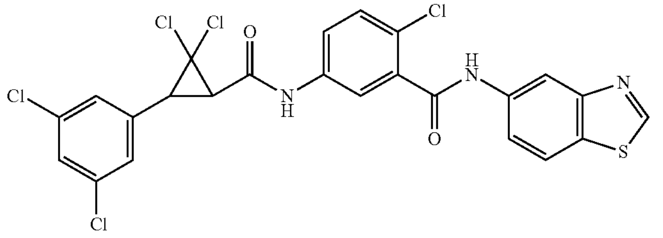 [SMILES: O=C(Nc1ccc2scnc2c1)c1cc(NC(=O)C2C(c3cc(Cl)cc(Cl)c3)C2(Cl)Cl)ccc1Cl] | 15 |
| F483 | 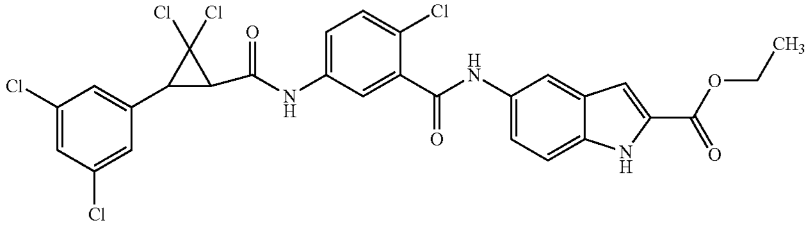 [SMILES: CCOC(=O)c1cc2cc(NC(=O)c3cc(NC(=O)C4C(c5cc(Cl)cc(Cl)c5)C4(Cl)Cl)ccc3Cl)ccc2[nH]1] | 55 |
| F484 | 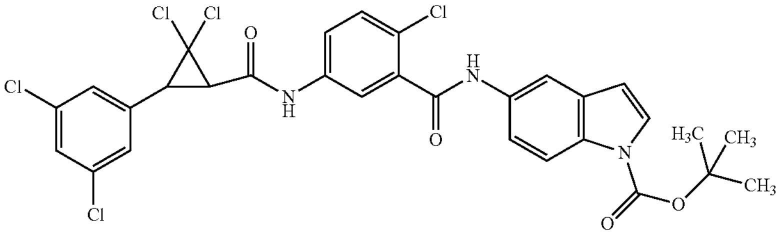 [SMILES: CC(C)(C)OC(=O)n1ccc2cc(NC(=O)c3cc(NC(=O)C4C(c5cc(Cl)cc(Cl)c5)C4(Cl)Cl)ccc3Cl)ccc21] | 55 |
| F485 | 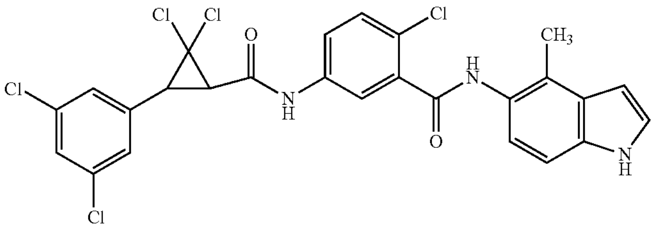 [SMILES: Cc1c(NC(=O)c2cc(NC(=O)C3C(c4cc(Cl)cc(Cl)c4)C3(Cl)Cl)ccc2Cl)ccc2[nH]ccc12] | 55 |
| F486 | 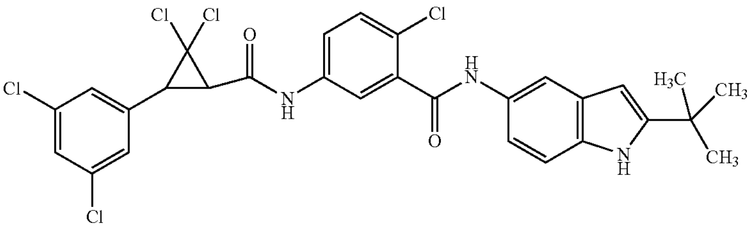 [SMILES: CC(C)(C)c1cc2cc(NC(=O)c3cc(NC(=O)C4C(c5cc(Cl)cc(Cl)c5)C4(Cl)Cl)ccc3Cl)ccc2[nH]1] | 55 |
| F487 | 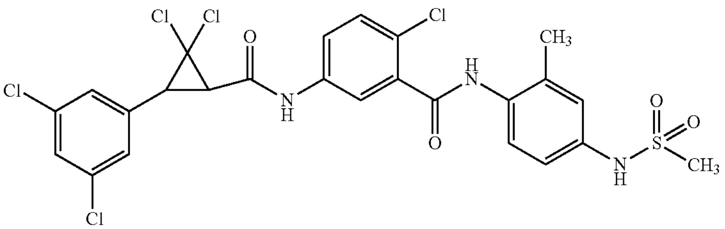 [SMILES: Cc1cc(NS(C)(=O)=O)ccc1NC(=O)c1cc(NC(=O)C2C(c3cc(Cl)cc(Cl)c3)C2(Cl)Cl)ccc1Cl] | 74 |

TABLE 2-continued
| No. | Structure | Prep.* |
| --- | --- | --- |
| F488 | 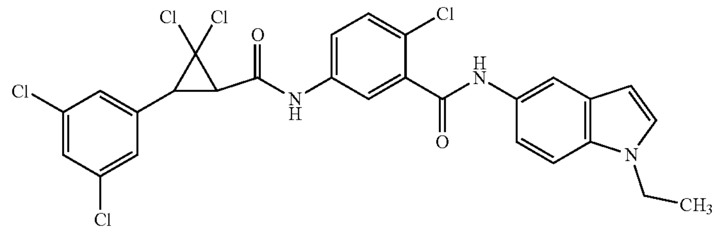 [SMILES: CCn1ccc2cc(NC(=O)c3cc(NC(=O)C4C(c5cc(Cl)cc(Cl)c5)C4(Cl)Cl)ccc3Cl)ccc21] | 55 |
| F490 | 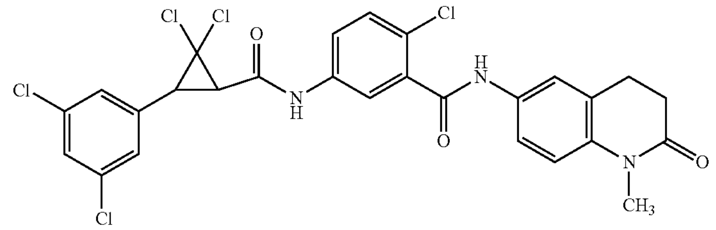 [SMILES: CN1C(=O)CCc2cc(NC(=O)c3cc(NC(=O)C4C(c5cc(Cl)cc(Cl)c5)C4(Cl)Cl)ccc3Cl)ccc21] | 55 |
| F491 | 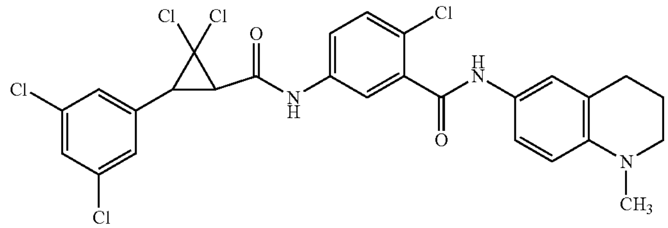 [SMILES: CN1CCCc2cc(NC(=O)c3cc(NC(=O)C4C(c5cc(Cl)cc(Cl)c5)C4(Cl)Cl)ccc3Cl)ccc21] | 55 |
| F492 | 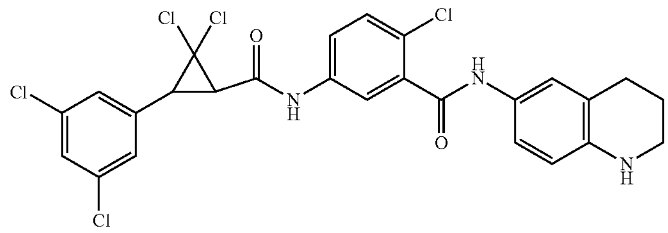 [SMILES: O=C(Nc1ccc2c(c1)CCCN2)c1cc(NC(=O)C2C(c3cc(Cl)cc(Cl)c3)C2(Cl)Cl)ccc1Cl] | 55 |
| F493 | 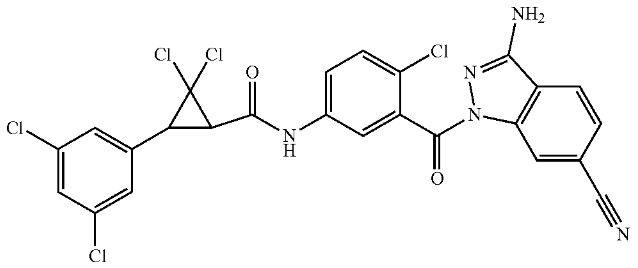 [SMILES: N#Cc1ccc2c(N)nn(C(=O)c3cc(NC(=O)C4C(c5cc(Cl)cc(Cl)c5)C4(Cl)Cl)ccc3Cl)c2c1] | 15 |
| F494 | 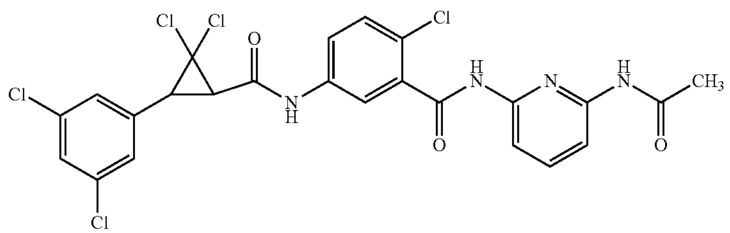 [SMILES: CC(=O)Nc1cccc(NC(=O)c2cc(NC(=O)C3C(c4cc(Cl)cc(Cl)c4)C3(Cl)Cl)ccc2Cl)n1] | 55 |
Structure and preparation method for F Series molecules TABLE 2-continued
| Structure and preparation method for F Series molecules | | |
|---|---|---|
| No. | Structure | Prep.* |
| F495 | 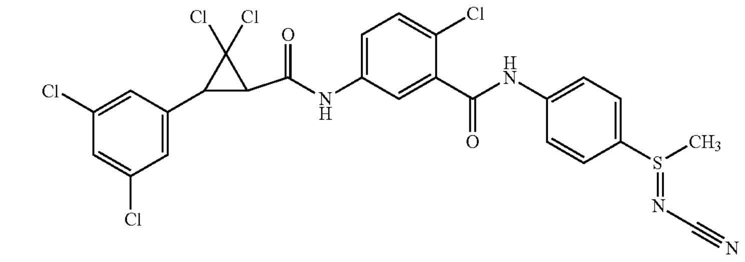 [SMILES: C/S(=N\C#N)c1ccc(NC(=O)c2cc(NC(=O)C3C(c4cc(Cl)cc(Cl)c4)C3(Cl)Cl)ccc2Cl)cc1] | 72 |
| F496 | 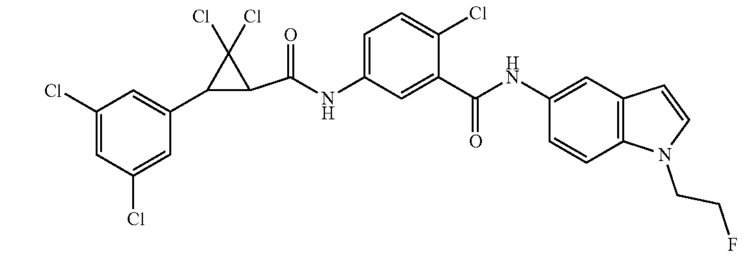 [SMILES: O=C(Nc1ccc2c(ccn2CCF)c1)c1cc(NC(=O)C2C(c3cc(Cl)cc(Cl)c3)C2(Cl)Cl)ccc1Cl] | 55 |
| F497 | 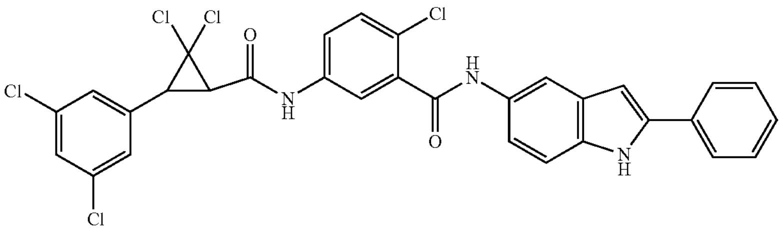 [SMILES: O=C(Nc1ccc2[nH]c(-c3ccccc3)cc2c1)c1cc(NC(=O)C2C(c3cc(Cl)cc(Cl)c3)C2(Cl)Cl)ccc1Cl] | 55 |
| F498 | 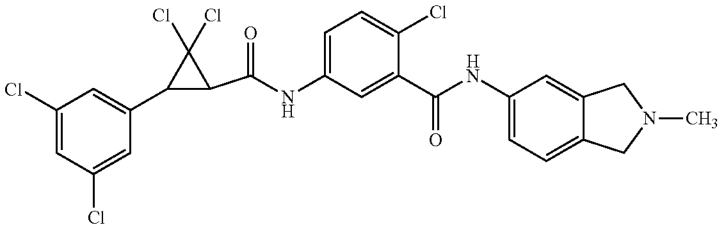 [SMILES: CN1Cc2ccc(NC(=O)c3cc(NC(=O)C4C(c5cc(Cl)cc(Cl)c5)C4(Cl)Cl)ccc3Cl)cc2C1] | 14 |
| F499 | 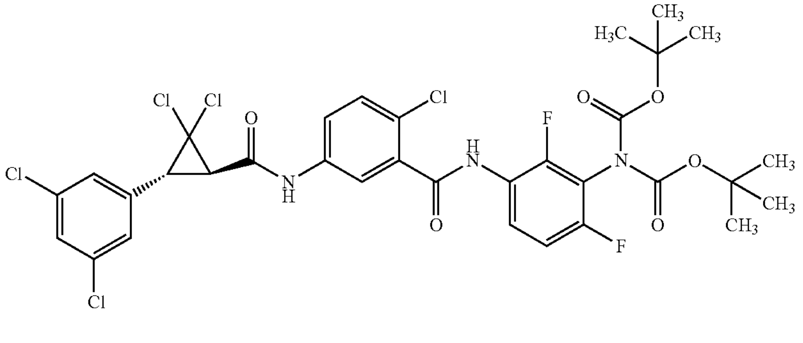 [SMILES: CC(C)(C)OC(=O)N(C(=O)OC(C)(C)C)c1c(F)ccc(NC(=O)c2cc(NC(=O)[C@H]3[C@H](c4cc(Cl)cc(Cl)c4)C3(Cl)Cl)ccc2Cl)c1F] | 13 |

TABLE 2-continued
| Structure and preparation method for F Series molecules | | |
|---|---|---|
| No. | Structure | Prep.* |
| F500 | 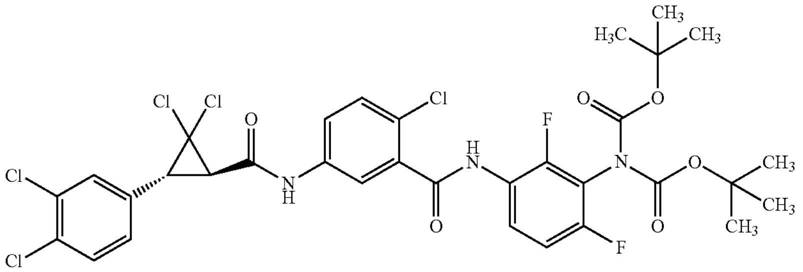 [SMILES: CC(C)(C)OC(=O)N(C(=O)OC(C)(C)C)c1c(F)ccc(NC(=O)c2cc(NC(=O)[C@H]3[C@H](c4ccc(Cl)c(Cl)c4)C3(Cl)Cl)ccc2Cl)c1F] | 13 |
| F501 | 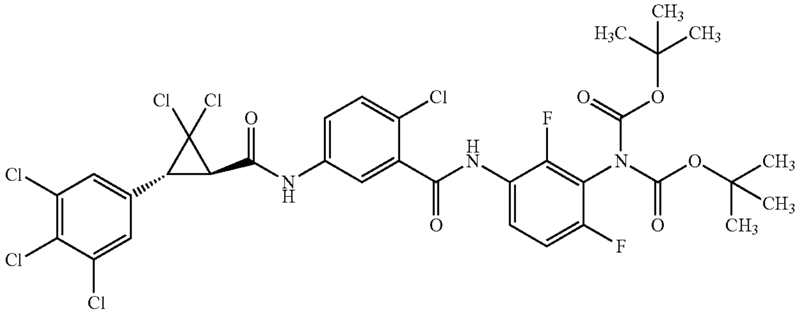 [SMILES: CC(C)(C)OC(=O)N(C(=O)OC(C)(C)C)c1c(F)ccc(NC(=O)c2cc(NC(=O)[C@H]3[C@H](c4cc(Cl)c(Cl)c(Cl)c4)C3(Cl)Cl)ccc2Cl)c1F] | 13 |
| F502 | 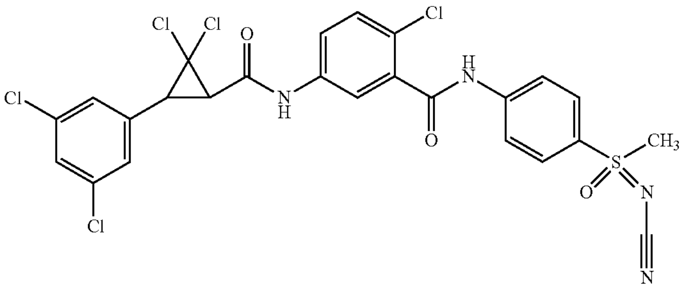 [SMILES: CS(=O)(=NC#N)c1ccc(NC(=O)c2cc(NC(=O)C3C(c4cc(Cl)cc(Cl)c4)C3(Cl)Cl)ccc2Cl)cc1] | 75 |
| F503 | 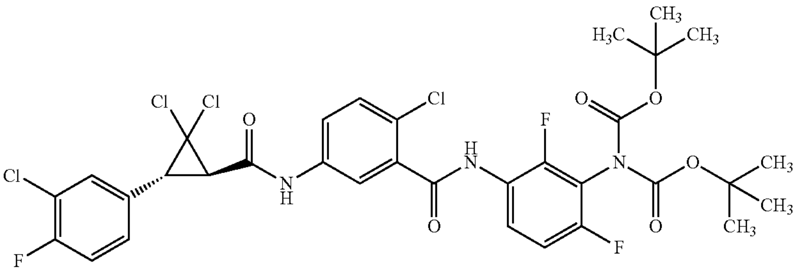 [SMILES: CC(C)(C)OC(=O)N(C(=O)OC(C)(C)C)c1c(F)ccc(NC(=O)c2cc(NC(=O)[C@H]3[C@H](c4ccc(F)c(Cl)c4)C3(Cl)Cl)ccc2Cl)c1F] | 13 |
| F504 | 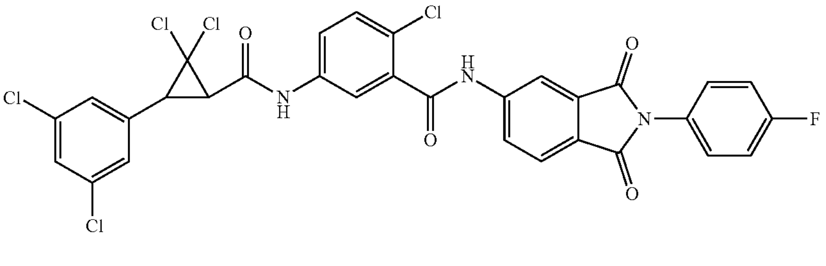 [SMILES: O=C(Nc1ccc2c(c1)C(=O)N(c1ccc(F)cc1)C2=O)c1cc(NC(=O)C2C(c3cc(Cl)cc(Cl)c3)C2(Cl)Cl)ccc1Cl] | 55 |

TABLE 2-continued
Structure and preparation method for F Series molecules
| No. | Structure | Prep.* |
|---|---|---|
| F505 | 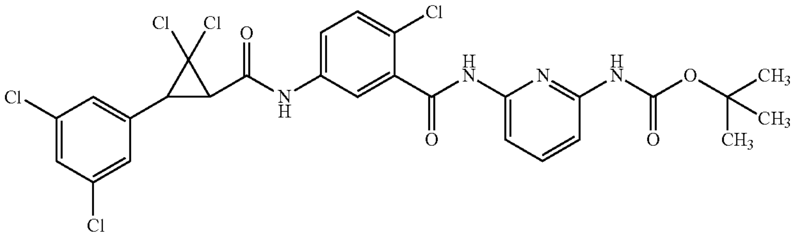 [SMILES: CC(C)(C)OC(=O)Nc1cccc(NC(=O)c2cc(NC(=O)C3C(c4cc(Cl)cc(Cl)c4)C3(Cl)Cl)ccc2Cl)n1] | 55 |
| F506 | 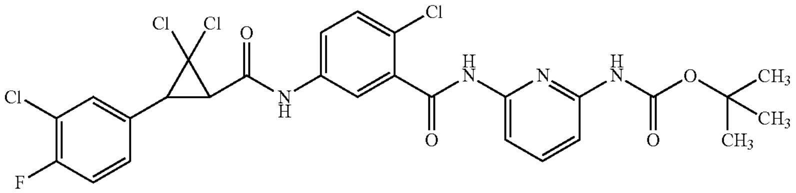 [SMILES: CC(C)(C)OC(=O)Nc1cccc(NC(=O)c2cc(NC(=O)C3C(c4ccc(F)c(Cl)c4)C3(Cl)Cl)ccc2Cl)n1] | 55 |
| F507 | 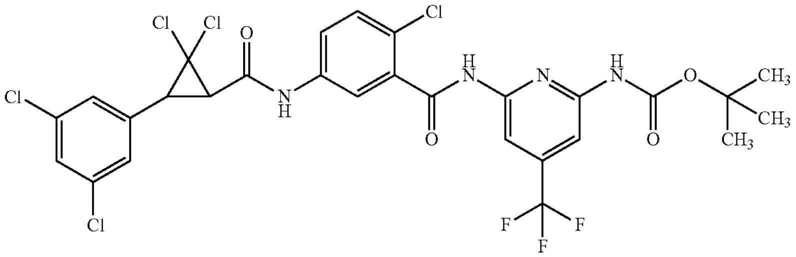 [SMILES: CC(C)(C)OC(=O)Nc1cc(C(F)(F)F)cc(NC(=O)c2cc(NC(=O)C3C(c4cc(Cl)cc(Cl)c4)C3(Cl)Cl)ccc2Cl)n1] | 55 |
| F508 | 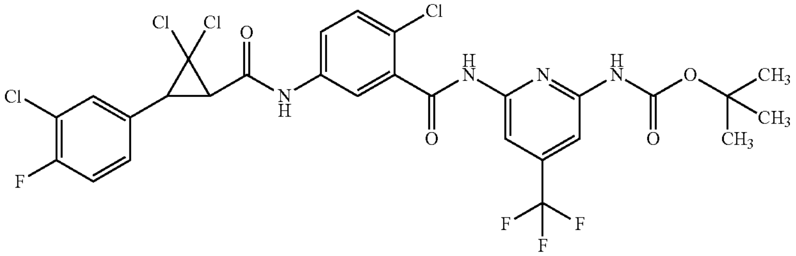 [SMILES: CC(C)(C)OC(=O)Nc1cc(C(F)(F)F)cc(NC(=O)c2cc(NC(=O)C3C(c4ccc(F)c(Cl)c4)C3(Cl)Cl)ccc2Cl)n1] | 55 |
| F509 | 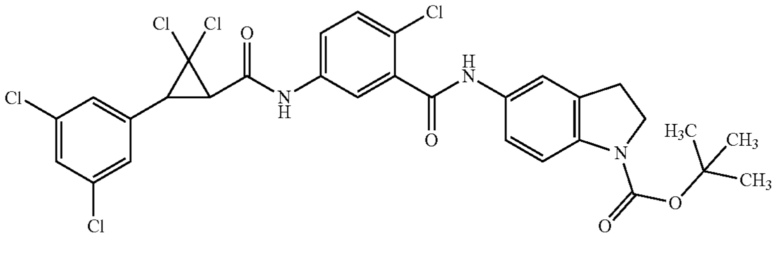 [SMILES: CC(C)(C)OC(=O)N1CCc2cc(NC(=O)c3cc(NC(=O)C4C(c5cc(Cl)cc(Cl)c5)C4(Cl)Cl)ccc3Cl)ccc21] | 55 |
| F510 | 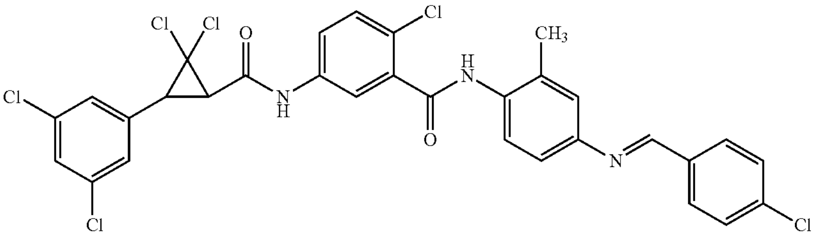 [SMILES: Cc1cc(/N=C/c2ccc(Cl)cc2)ccc1NC(=O)c1cc(NC(=O)C2C(c3cc(Cl)cc(Cl)c3)C2(Cl)Cl)ccc1Cl] | 71 |

TABLE 2-continued
| Structure and preparation method for F Series molecules | | |
| --- | --- | --- |
| No. | Structure | Prep.* |
| F511 | 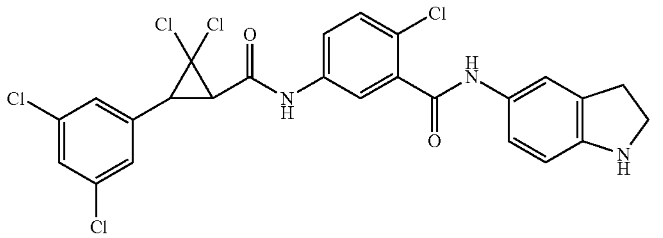 [SMILES: O=C(Nc1ccc2c(c1)CCN2)c1cc(NC(=O)C2C(c3cc(Cl)cc(Cl)c3)C2(Cl)Cl)ccc1Cl] | 55 |
| F512 | 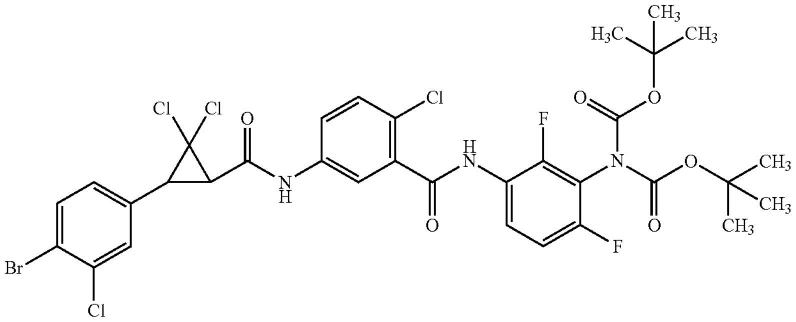 [SMILES: CC(C)(C)OC(=O)N(C(=O)OC(C)(C)C)c1c(F)ccc(NC(=O)c2cc(NC(=O)C3C(c4ccc(Br)c(Cl)c4)C3(Cl)Cl)ccc2Cl)c1F] | 13 |
| F513 | 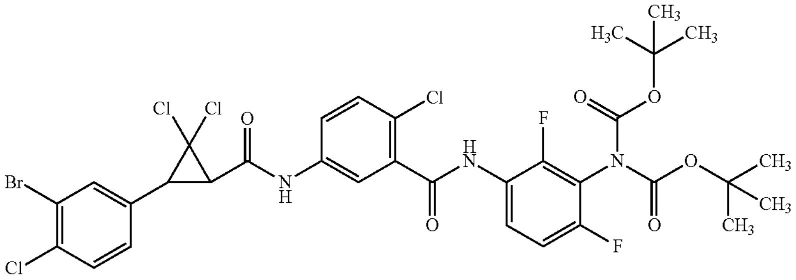 [SMILES: CC(C)(C)OC(=O)N(C(=O)OC(C)(C)C)c1c(F)ccc(NC(=O)c2cc(NC(=O)C3C(c4ccc(Cl)c(Br)c4)C3(Cl)Cl)ccc2Cl)c1F] | 13 |
| F514 | 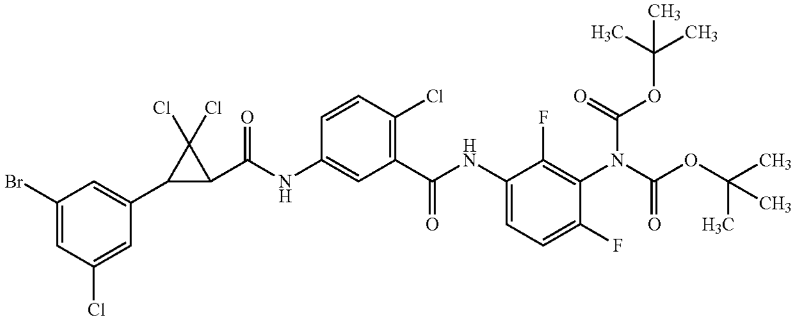 [SMILES: CC(C)(C)OC(=O)N(C(=O)OC(C)(C)C)c1c(F)ccc(NC(=O)c2cc(NC(=O)C3C(c4cc(Cl)cc(Br)c4)C3(Cl)Cl)ccc2Cl)c1F] | 13 |
| F515 | 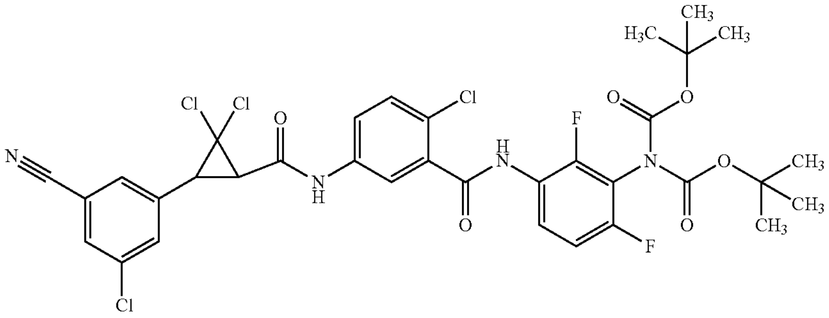 [SMILES: CC(C)(C)OC(=O)N(C(=O)OC(C)(C)C)c1c(F)ccc(NC(=O)c2cc(NC(=O)C3C(c4cc(Cl)cc(C#N)c4)C3(Cl)Cl)ccc2Cl)c1F] | 13 |

TABLE 2-continued
Structure and preparation method for F Series molecules
| No. | Structure | Prep.* |
|---|---|---|
| F516 | 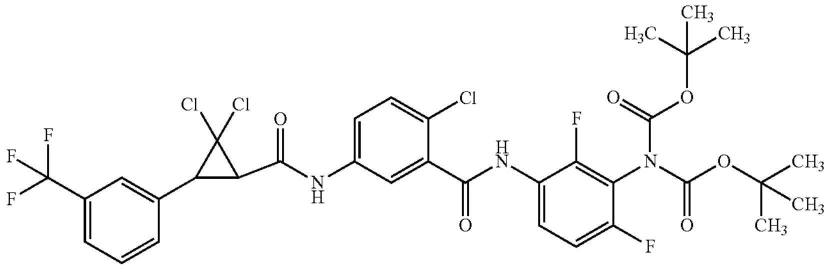 [SMILES: CC(C)(C)OC(=O)N(C(=O)OC(C)(C)C)c1c(F)ccc(NC(=O)c2cc(NC(=O)C3C(c4cccc(C(F)(F)F)c4)C3(Cl)Cl)ccc2Cl)c1F] | 13 |
| F517 | 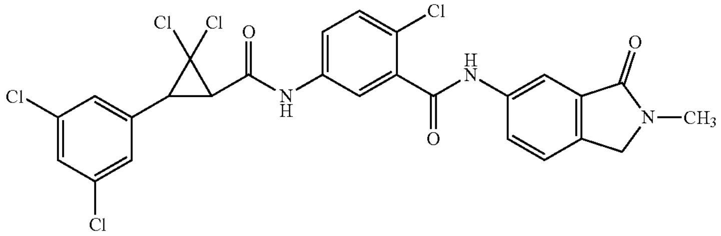 [SMILES: CN1Cc2ccc(NC(=O)c3cc(NC(=O)C4C(c5cc(Cl)cc(Cl)c5)C4(Cl)Cl)ccc3Cl)cc2C1=O] | 55 |
| F518 | 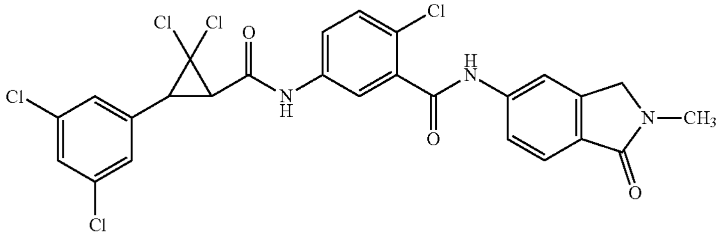 [SMILES: CN1Cc2cc(NC(=O)c3cc(NC(=O)C4C(c5cc(Cl)cc(Cl)c5)C4(Cl)Cl)ccc3Cl)ccc2C1=O] | 55 |
| F519 | 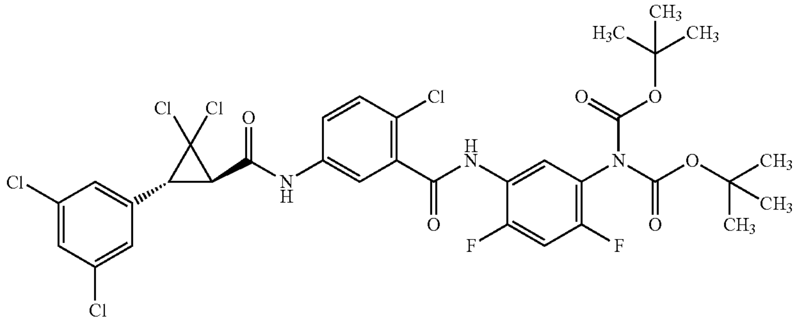 [SMILES: CC(C)(C)OC(=O)N(C(=O)OC(C)(C)C)c1cc(NC(=O)c2cc(NC(=O)[C@H]3[C@H](c4cc(Cl)cc(Cl)c4)C3(Cl)Cl)ccc2Cl)c(F)cc1F] | 55 |
| F520 | 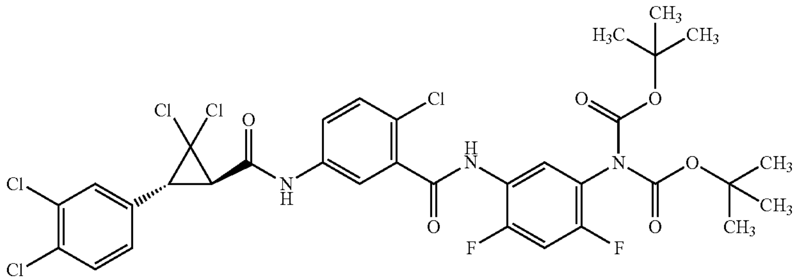 [SMILES: CC(C)(C)OC(=O)N(C(=O)OC(C)(C)C)c1cc(NC(=O)c2cc(NC(=O)[C@H]3[C@H](c4ccc(Cl)c(Cl)c4)C3(Cl)Cl)ccc2Cl)c(F)cc1F] | 55 |

TABLE 2-continued
| Structure and preparation method for F Series molecules | | |
|---|---|---|
| No. | Structure | Prep.* |
| F521 | 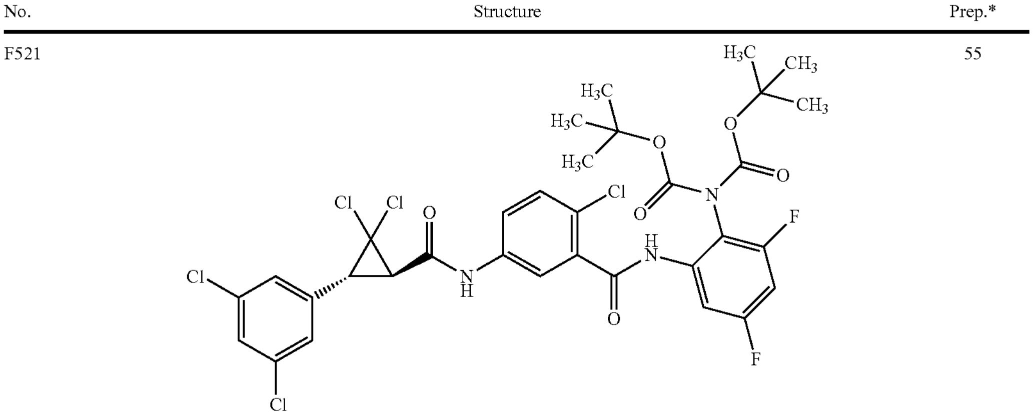 | 55 |
| F522 | 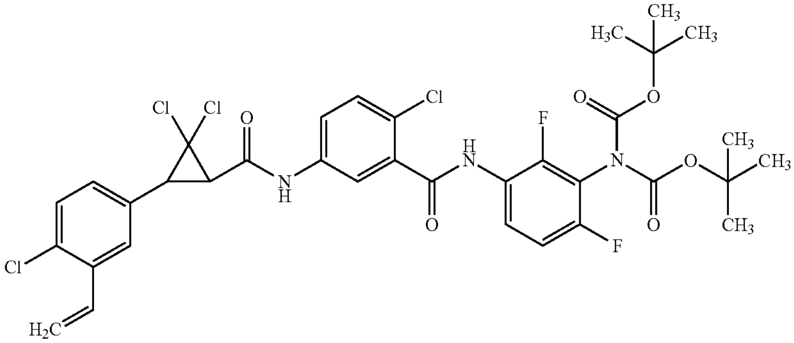 [SMILES: C=Cc1cc(C2C(C(=O)Nc3ccc(Cl)c(C(=O)Nc4ccc(F)c(N(C(=O)OC(C)(C)C)C(=O)OC(C)(C)C)c4F)c3)C2(Cl)Cl)ccc1Cl] | 77 |
| F523 | 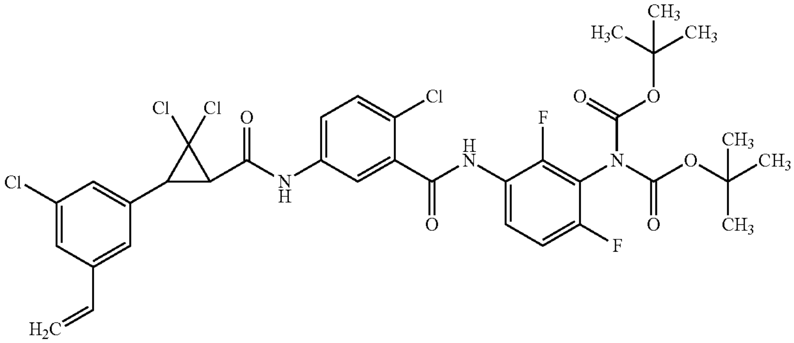 [SMILES: C=Cc1cc(Cl)cc(C2C(C(=O)Nc3ccc(Cl)c(C(=O)Nc4ccc(F)c(N(C(=O)OC(C)(C)C)C(=O)OC(C)(C)C)c4F)c3)C2(Cl)Cl)c1] | 77 |
| F524 | 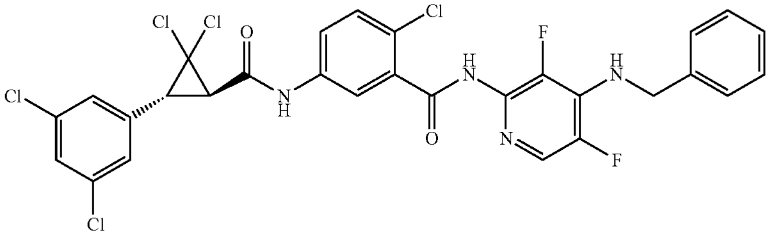 [SMILES: O=C(Nc1ncc(F)c(NCc2ccccc2)c1F)c1cc(NC(=O)[C@H]2[C@H](c3cc(Cl)cc(Cl)c3)C2(Cl)Cl)ccc1Cl] | 55 |
| F525 | 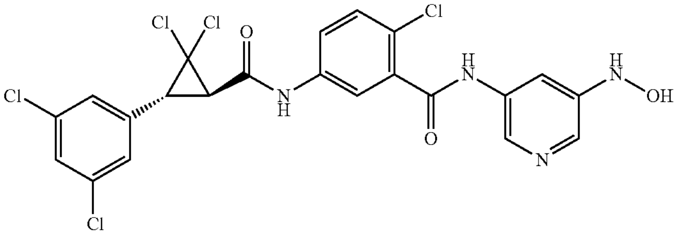 [SMILES: O=C(Nc1cncc(NO)c1)c1cc(NC(=O)[C@H]2[C@H](c3cc(Cl)cc(Cl)c3)C2(Cl)Cl)ccc1Cl] | 59 |

TABLE 2-continued
| Structure and preparation method for F Series molecules | | |
|---|---|---|
| No. | Structure | Prep.* |
| F526 | 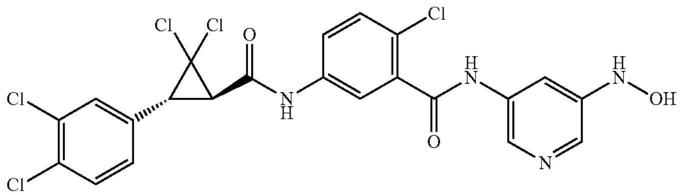 [SMILES: O=C(Nc1cncc(NO)c1)c1cc(NC(=O)[C@H]2[C@H](c3ccc(Cl)c(Cl)c3)C2(Cl)Cl)ccc1Cl] | 59 |
| F527 | 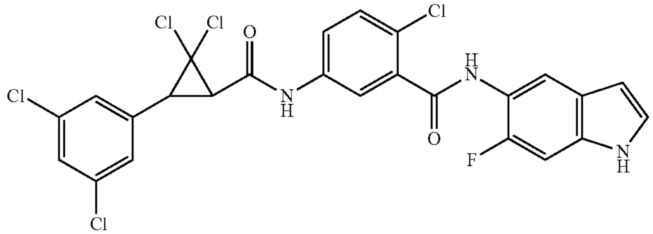 [SMILES: O=C(Nc1cc2cc[nH]c2cc1F)c1cc(NC(=O)C2C(c3cc(Cl)cc(Cl)c3)C2(Cl)Cl)ccc1Cl] | 55 |
| F528 | 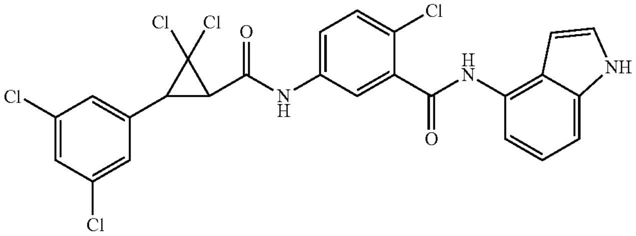 [SMILES: O=C(Nc1cccc2[nH]ccc12)c1cc(NC(=O)C2C(c3cc(Cl)cc(Cl)c3)C2(Cl)Cl)ccc1Cl] | 55 |
| F529 | 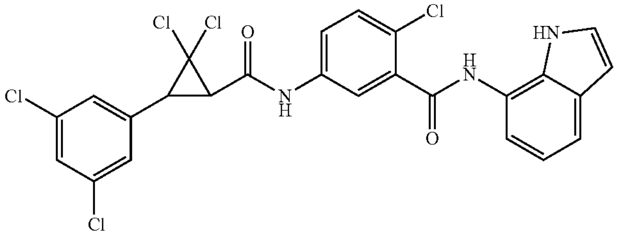 [SMILES: O=C(Nc1cccc2cc[nH]c12)c1cc(NC(=O)C2C(c3cc(Cl)cc(Cl)c3)C2(Cl)Cl)ccc1Cl] | 55 |
| F530 | 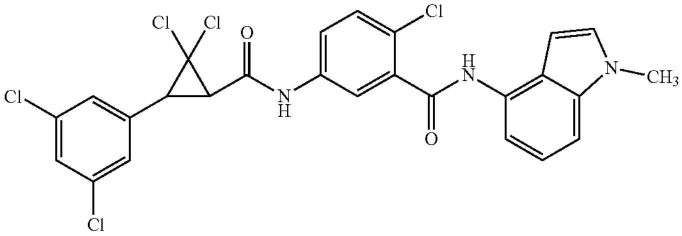 [SMILES: Cn1ccc2c(NC(=O)c3cc(NC(=O)C4C(c5cc(Cl)cc(Cl)c5)C4(Cl)Cl)ccc3Cl)cccc21] | 55 |
| F531 | 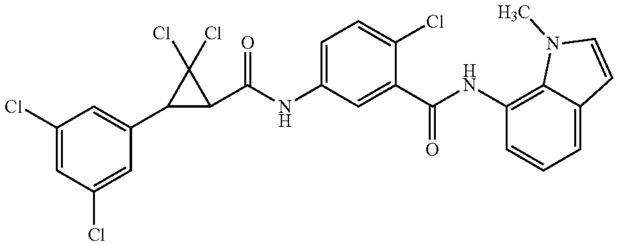 [SMILES: Cn1ccc2cccc(NC(=O)c3cc(NC(=O)C4C(c5cc(Cl)cc(Cl)c5)C4(Cl)Cl)ccc3Cl)c21] | 55 |

TABLE 2-continued
| Structure and preparation method for F Series molecules | | |
|---|---|---|
| No. | Structure | Prep.* |
| F532 | 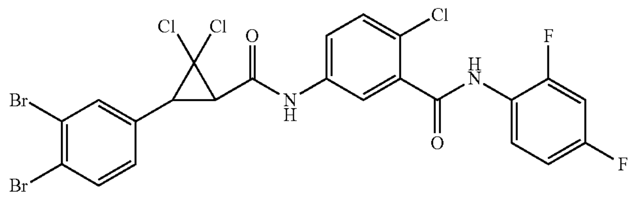 [SMILES: O=C(Nc1ccc(F)cc1F)c1cc(NC(=O)C2C(c3ccc(Br)c(Br)c3)C2(Cl)Cl)ccc1Cl] | 55 |
| F533 | 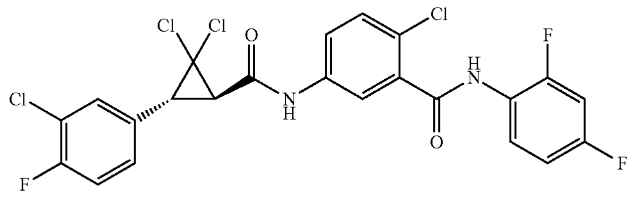 | 55 |
| F534 | 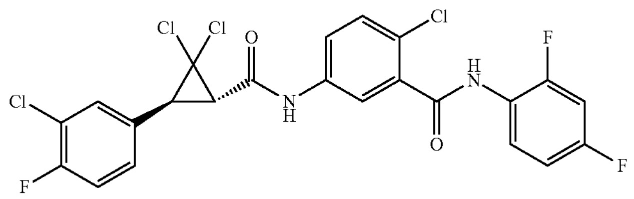 | 55 |
| F535 | 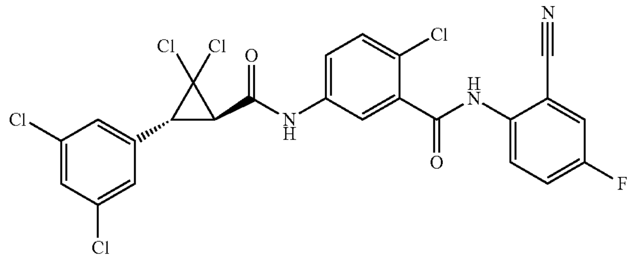 [SMILES: N#Cc1cc(F)ccc1NC(=O)c1cc(NC(=O)[C@H]2[C@H](c3cc(Cl)cc(Cl)c3)C2(Cl)Cl)ccc1Cl] | 55 |
| F536 | 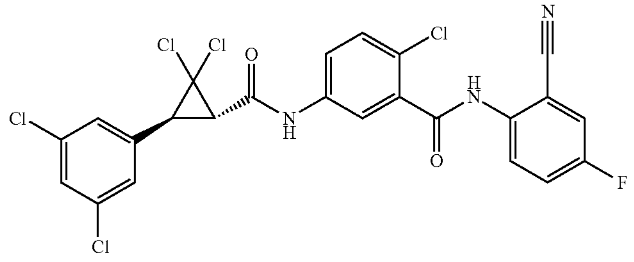 [SMILES: N#Cc1cc(F)ccc1NC(=O)c1cc(NC(=O)[C@@H]2[C@@H](c3cc(Cl)cc(Cl)c3)C2(Cl)Cl)ccc1Cl] | 55 |
| F537 | 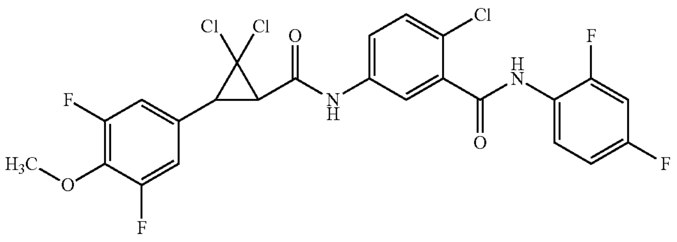 [SMILES: COc1c(F)cc(C2C(C(=O)Nc3ccc(Cl)c(C(=O)Nc4ccc(F)cc4F)c3)C2(Cl)Cl)cc1F] | 55 |

TABLE 2-continued
| Structure and preparation method for F Series molecules | | |
|---|---|---|
| No. | Structure | Prep.* |
| F538 | 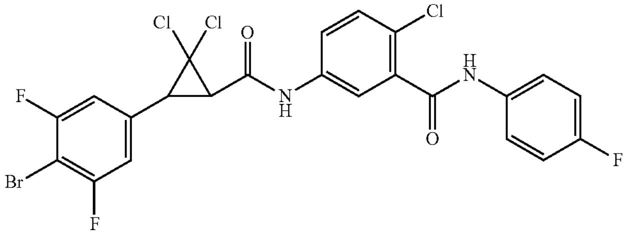 [SMILES: O=C(Nc1ccc(F)cc1)c1cc(NC(=O)C2C(c3cc(F)c(Br)c(F)c3)C2(Cl)Cl)ccc1Cl] | 13 |
| F539 | 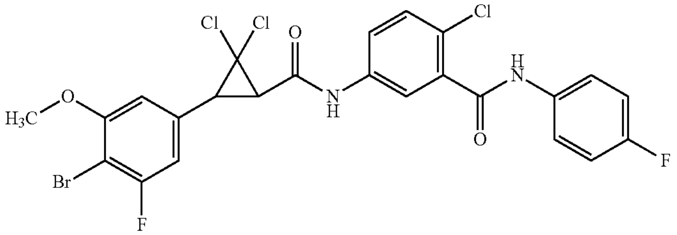 [SMILES: COc1cc(C2C(C(=O)Nc3ccc(Cl)c(C(=O)Nc4ccc(F)cc4)c3)C2(Cl)Cl)cc(F)c1Br] | 13 |
| F540 | 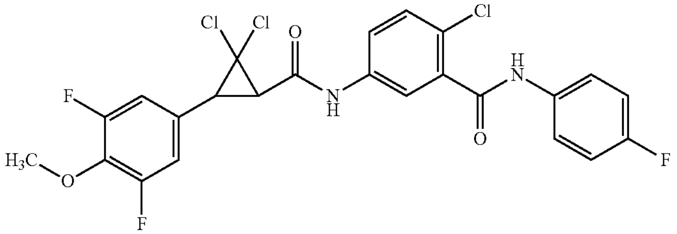 [SMILES: COc1c(F)cc(C2C(C(=O)Nc3ccc(Cl)c(C(=O)Nc4ccc(F)cc4)c3)C2(Cl)Cl)cc1F] | 13 |
| F541 | 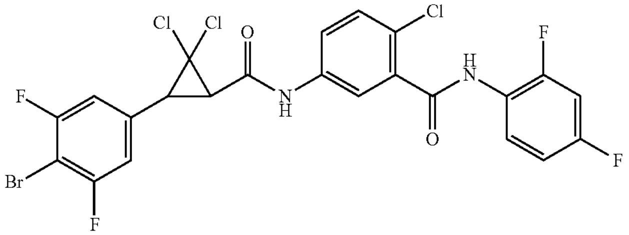 [SMILES: O=C(Nc1ccc(F)cc1F)c1cc(NC(=O)C2C(c3cc(F)c(Br)c(F)c3)C2(Cl)Cl)ccc1Cl] | 13 |
| F542 | 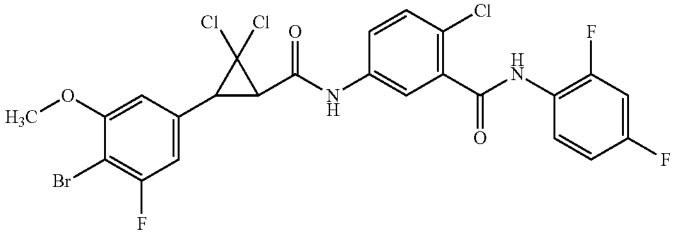 [SMILES: COc1cc(C2C(C(=O)Nc3ccc(Cl)c(C(=O)Nc4ccc(F)cc4F)c3)C2(Cl)Cl)cc(F)c1Br] | 13 |
| F543 | 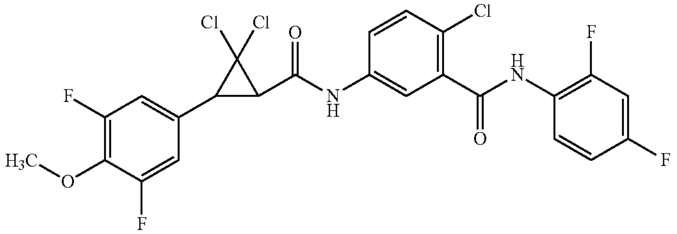 [SMILES: COc1c(F)cc(C2C(C(=O)Nc3ccc(Cl)c(C(=O)Nc4ccc(F)cc4F)c3)C2(Cl)Cl)cc1F] | 13 |

TABLE 2-continued
| Structure and preparation method for F Series molecules | | |
|---|---|---|
| No. | Structure | Prep.* |
| F544 | 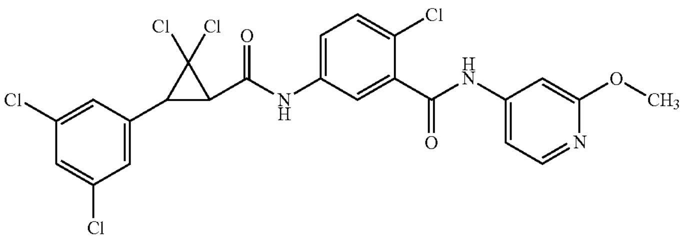 [SMILES: COc1cc(NC(=O)c2cc(NC(=O)C3C(c4cc(Cl)cc(Cl)c4)C3(Cl)Cl)ccc2Cl)ccn1] | 55 |
| F545 | 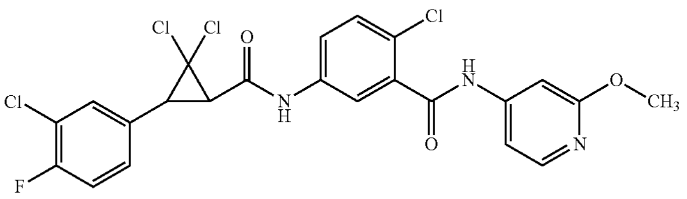 [SMILES: COc1cc(NC(=O)c2cc(NC(=O)C3C(c4ccc(F)c(Cl)c4)C3(Cl)Cl)ccc2Cl)ccn1] | 55 |
| F546 | 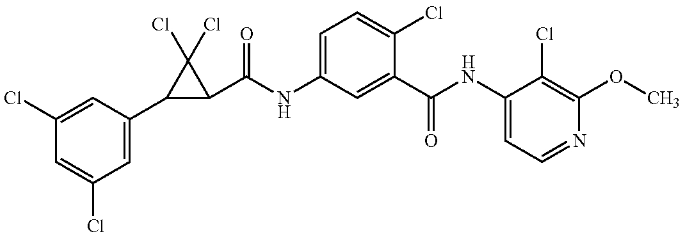 [SMILES: COc1nccc(NC(=O)c2cc(NC(=O)C3C(c4cc(Cl)cc(Cl)c4)C3(Cl)Cl)ccc2Cl)c1Cl] | 55 |
| F547 | 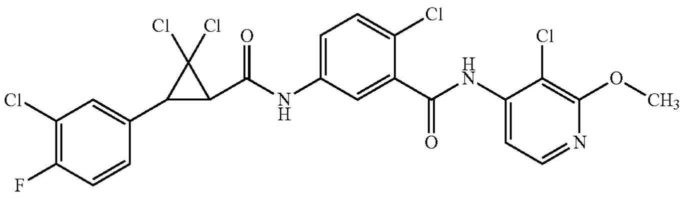 [SMILES: COc1nccc(NC(=O)c2cc(NC(=O)C3C(c4ccc(F)c(Cl)c4)C3(Cl)Cl)ccc2Cl)c1Cl] | 55 |
| F548 | 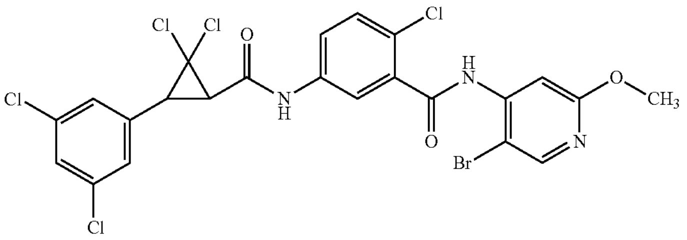 [SMILES: COc1cc(NC(=O)c2cc(NC(=O)C3C(c4cc(Cl)cc(Cl)c4)C3(Cl)Cl)ccc2Cl)c(Br)cn1] | 55 |
| F549 | 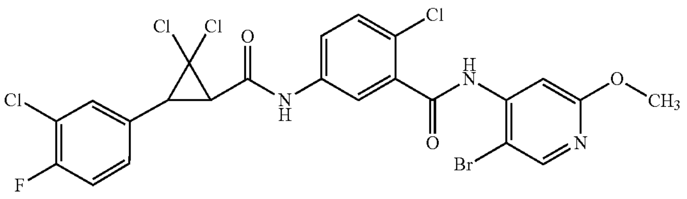 [SMILES: COc1cc(NC(=O)c2cc(NC(=O)C3C(c4ccc(F)c(Cl)c4)C3(Cl)Cl)ccc2Cl)c(Br)cn1] | 55 |

TABLE 2-continued
| Structure and preparation method for F Series molecules | | |
|---|---|---|
| No. | Structure | Prep.* |
| F550 | 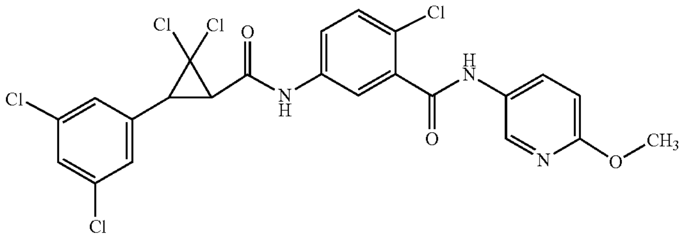 [SMILES: COc1ccc(NC(=O)c2cc(NC(=O)C3C(c4cc(Cl)cc(Cl)c4)C3(Cl)Cl)ccc2Cl)cn1] | 55 |
| F551 | 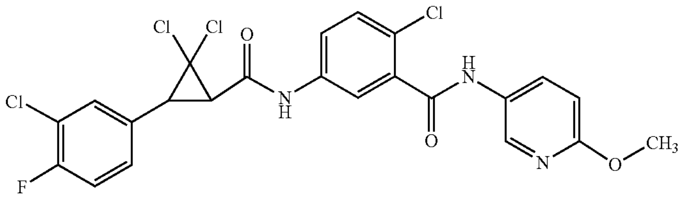 [SMILES: COc1ccc(NC(=O)c2cc(NC(=O)C3C(c4ccc(F)c(Cl)c4)C3(Cl)Cl)ccc2Cl)cn1] | 55 |
| F552 | 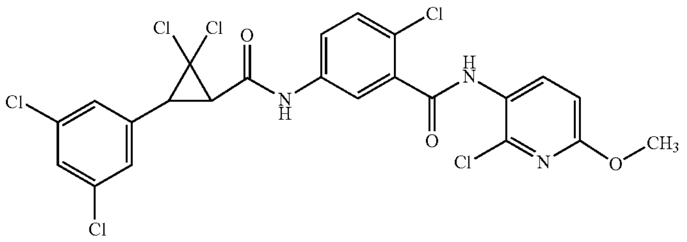 [SMILES: COc1ccc(NC(=O)c2cc(NC(=O)C3C(c4cc(Cl)cc(Cl)c4)C3(Cl)Cl)ccc2Cl)c(Cl)n1] | 55 |
| F553 | 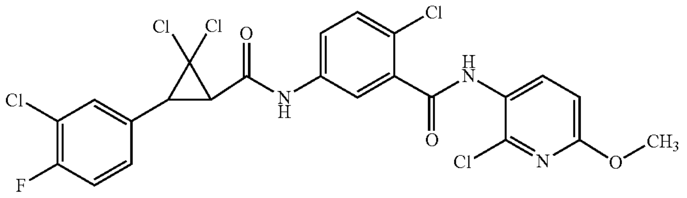 [SMILES: COc1ccc(NC(=O)c2cc(NC(=O)C3C(c4ccc(F)c(Cl)c4)C3(Cl)Cl)ccc2Cl)c(Cl)n1] | 55 |
| F554 | 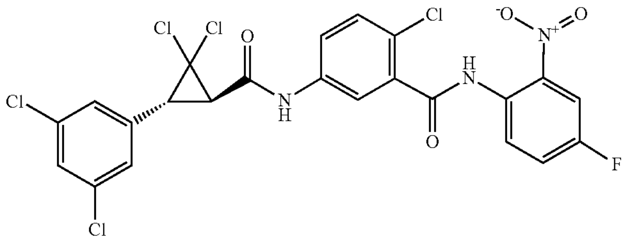 | 55 |
| F555 | 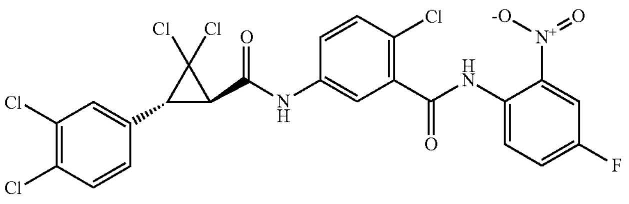 | 55 |

TABLE 2-continued
| Structure and preparation method for F Series molecules | | |
|---|---|---|
| No. | Structure | Prep.* |
| F556 | 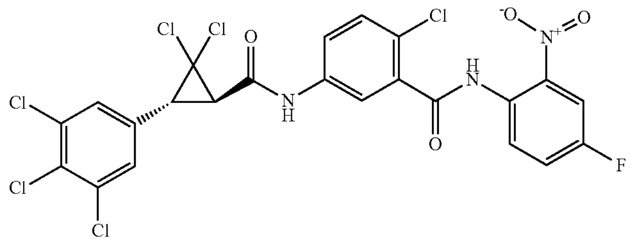 | 55 |
| F557 | 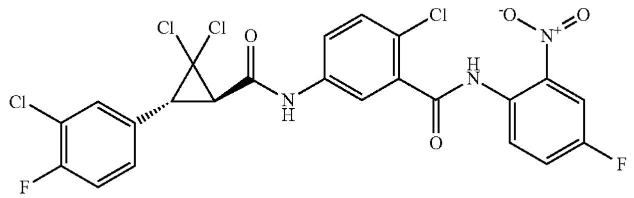 | 55 |
| F558 | 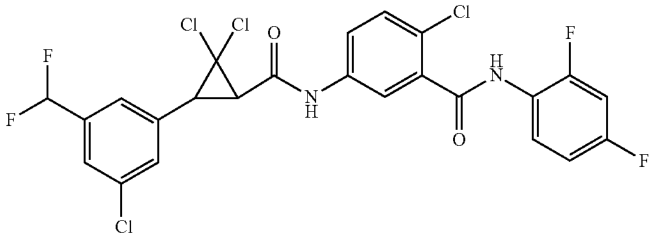 [SMILES: O=C(Nc1ccc(F)cc1F)c1cc(NC(=O)C2C(c3cc(Cl)cc(C(F)F)c3)C2(Cl)Cl)ccc1Cl] | 57 |
| F559 | 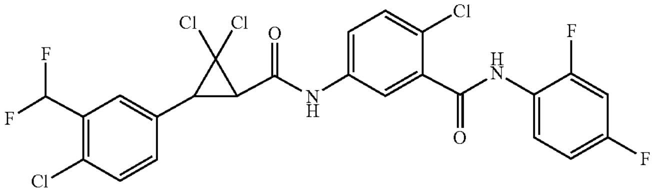 [SMILES: O=C(Nc1ccc(F)cc1F)c1cc(NC(=O)C2C(c3ccc(Cl)c(C(F)F)c3)C2(Cl)Cl)ccc1Cl] | 57 |
| F560 | 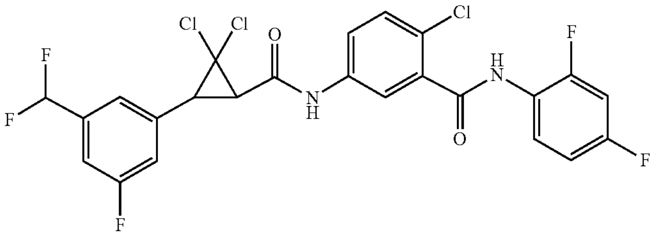 [SMILES: O=C(Nc1ccc(F)cc1F)c1cc(NC(=O)C2C(c3cc(F)cc(C(F)F)c3)C2(Cl)Cl)ccc1Cl] | 57 |
| F561 | 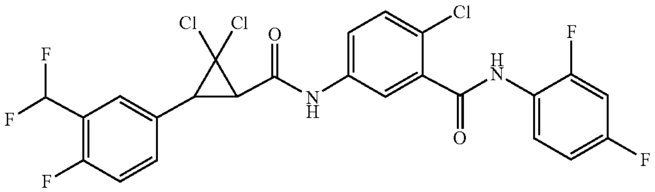 | 57 |

TABLE 2-continued
| Structure and preparation method for F Series molecules | | |
|---|---|---|
| No. | Structure | Prep.* |
| F562 | 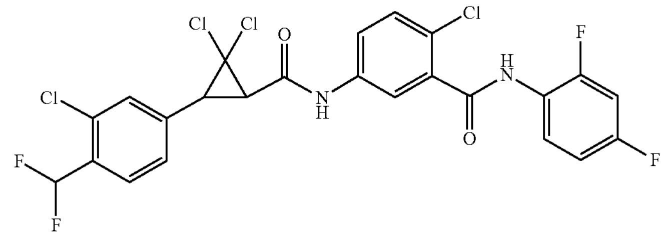 | 57 |
| F563 | 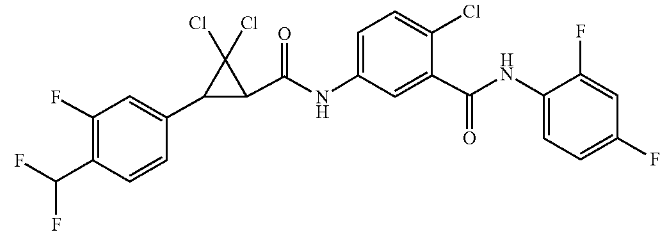 [SMILES: O=C(Nc1ccc(F)cc1F)c1cc(NC(=O)C2C(c3ccc(C(F)F)c(Cl)c3)C2(Cl)Cl)ccc1Cl] | 57 |
| F564 | 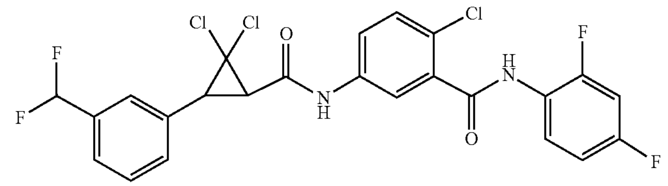 [SMILES: O=C(Nc1ccc(F)cc1F)c1cc(NC(=O)C2C(c3cccc(C(F)F)c3)C2(Cl)Cl)ccc1Cl] | 57 |
| F565 | 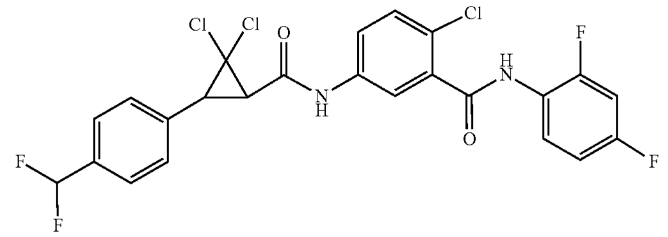 [SMILES: O=C(Nc1ccc(F)cc1F)c1cc(NC(=O)C2C(c3ccc(C(F)F)cc3)C2(Cl)Cl)ccc1Cl] | 57 |
| F566 | 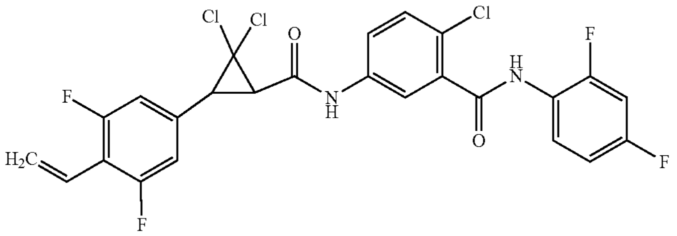 [SMILES: C=Cc1c(F)cc(C2C(C(=O)Nc3ccc(Cl)c(C(=O)Nc4ccc(F)cc4F)c3)C2(Cl)Cl)cc1F] | 77 |
| F567 | 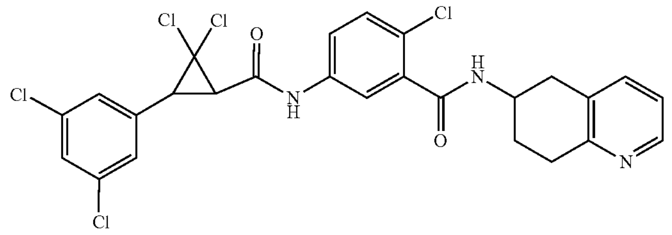 [SMILES: O=C(NC1CCc2ncccc2C1)c1cc(NC(=O)C2C(c3cc(Cl)cc(Cl)c3)C2(Cl)Cl)ccc1Cl] | 55 |

TABLE 2-continued
| Structure and preparation method for F Series molecules | | |
|---|---|---|
| No. | Structure | Prep.* |
| F568 | 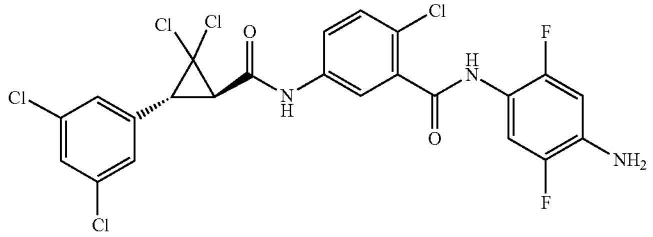 [SMILES: Nc1cc(F)c(NC(=O)c2cc(NC(=O)[C@H]3[C@H](c4cc(Cl)cc(Cl)c4)C3(Cl)Cl)ccc2Cl)cc1F] | 62 |
| F569 | 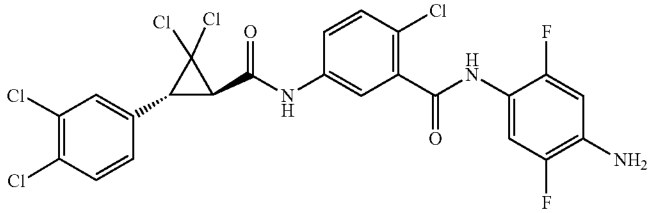 [SMILES: Nc1cc(F)c(NC(=O)c2cc(NC(=O)[C@H]3[C@H](c4ccc(Cl)c(Cl)c4)C3(Cl)Cl)ccc2Cl)cc1F] | 62 |
| F570 | 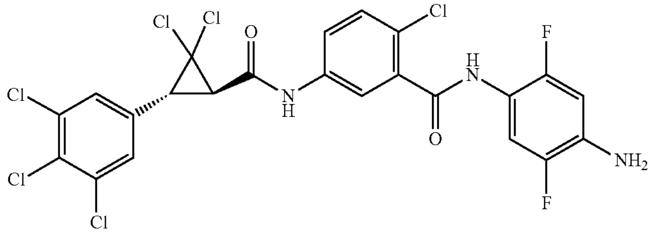 [SMILES: Nc1cc(F)c(NC(=O)c2cc(NC(=O)[C@H]3[C@H](c4cc(Cl)c(Cl)c(Cl)c4)C3(Cl)Cl)ccc2Cl)cc1F] | 62 |
| F571 | 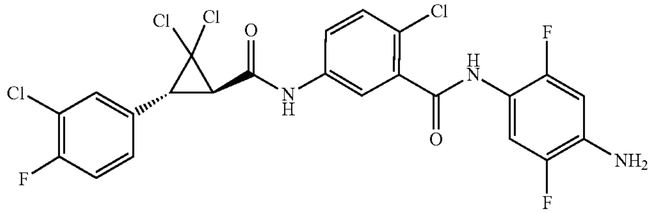 [SMILES: Nc1cc(F)c(NC(=O)c2cc(NC(=O)[C@H]3[C@H](c4ccc(F)c(Cl)c4)C3(Cl)Cl)ccc2Cl)cc1F] | 62 |
| F572 | 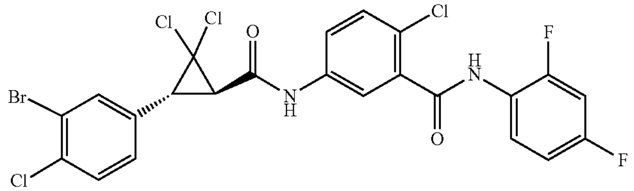 [SMILES: O=C(Nc1ccc(F)cc1F)c1cc(NC(=O)[C@H]2[C@H](c3ccc(Cl)c(Br)c3)C2(Cl)Cl)ccc1Cl] | 13 |
| F573 | 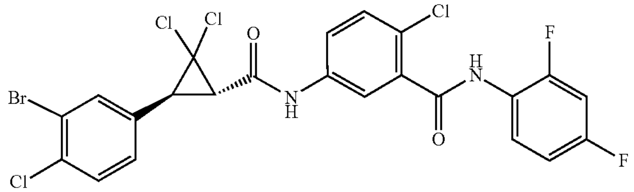 [SMILES: O=C(Nc1ccc(F)cc1F)c1cc(NC(=O)[C@@H]2[C@@H](c3ccc(Cl)c(Br)c3)C2(Cl)Cl)ccc1Cl] | 13 |
| F574 | 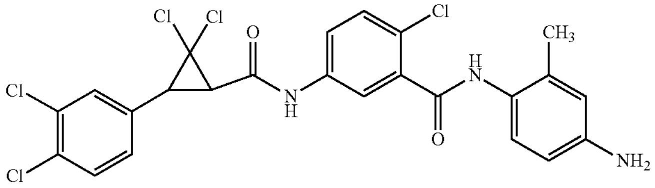 [SMILES: Cc1cc(N)ccc1NC(=O)c1cc(NC(=O)C2C(c3ccc(Cl)c(Cl)c3)C2(Cl)Cl)ccc1Cl] | 63 |

TABLE 2-continued
Structure and preparation method for F Series molecules
| No. | Structure | Prep.* |
| --- | --- | --- |
| F575 | 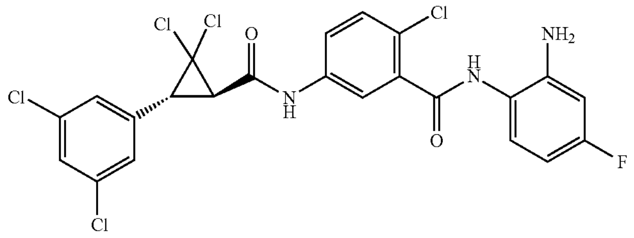 [SMILES: Nc1cc(F)ccc1NC(=O)c1cc(NC(=O)[C@H]2[C@H](c3cc(Cl)cc(Cl)c3)C2(Cl)Cl)ccc1Cl] | 60 |
| F576 | 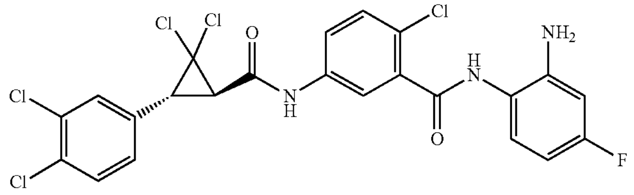 [SMILES: Nc1cc(F)ccc1NC(=O)c1cc(NC(=O)[C@H]2[C@H](c3ccc(Cl)c(Cl)c3)C2(Cl)Cl)ccc1Cl] | 60 |
| F577 | 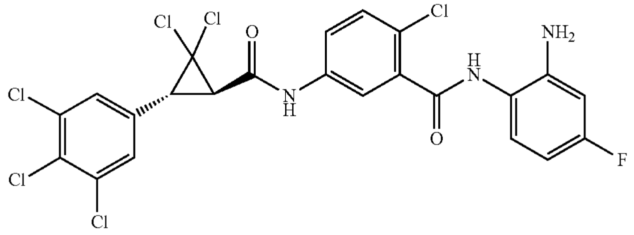 [SMILES: Nc1cc(F)ccc1NC(=O)c1cc(NC(=O)[C@H]2[C@H](c3cc(Cl)c(Cl)c(Cl)c3)C2(Cl)Cl)ccc1Cl] | 60 |
| F578 | 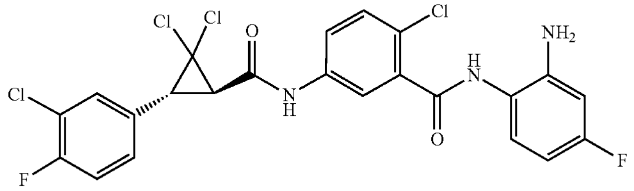 [SMILES: Nc1cc(F)ccc1NC(=O)c1cc(NC(=O)[C@H]2[C@H](c3ccc(F)c(Cl)c3)C2(Cl)Cl)ccc1Cl] | 60 |
| F579 | 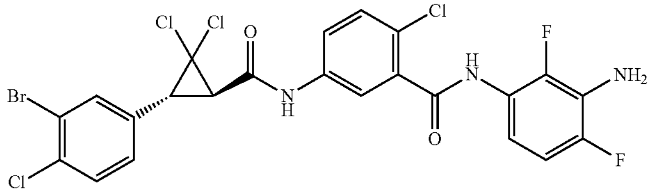 | 62 |
| F580 | 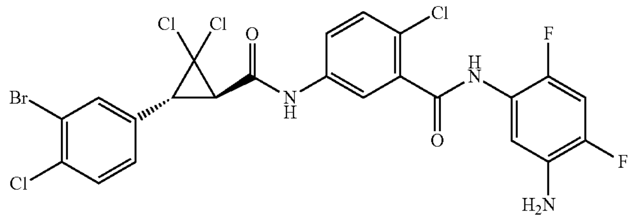 [SMILES: Nc1cc(NC(=O)c2cc(NC(=O)[C@H]3[C@H](c4ccc(Cl)c(Br)c4)C3(Cl)Cl)ccc2Cl)c(F)cc1F] | 62 |
| F581 | 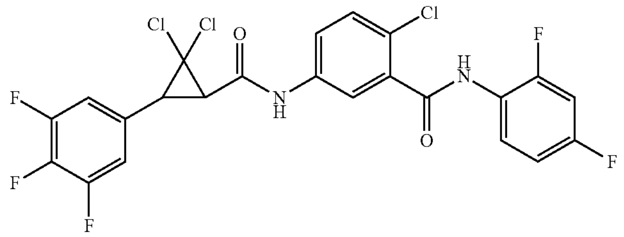 [SMILES: O=C(Nc1ccc(F)cc1F)c1cc(NC(=O)C2C(c3cc(F)c(F)c(F)c3)C2(Cl)Cl)ccc1Cl] | 55 |

TABLE 2-continued
| Structure and preparation method for F Series molecules | | |
|---|---|---|
| No. | Structure | Prep.* |
| F582 | 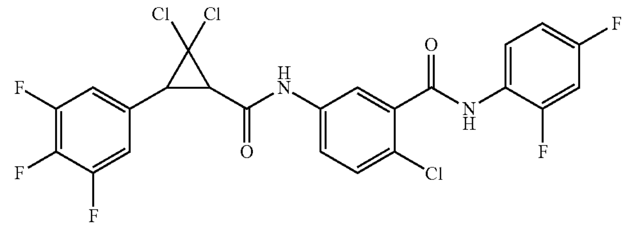 [SMILES: O=C(Nc1ccc(F)cc1F)c1cc(NC(=O)C2C(c3cc(F)c(F)c(F)c3)C2(Cl)Cl)ccc1Cl] | 55 |
| F583 | 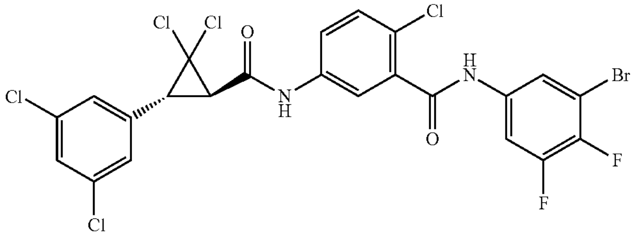 [SMILES: O=C(Nc1cc(F)c(F)c(Br)c1)c1cc(NC(=O)[C@H]2[C@H](c3cc(Cl)cc(Cl)c3)C2(Cl)Cl)ccc1Cl] | 55 |
| F584 | 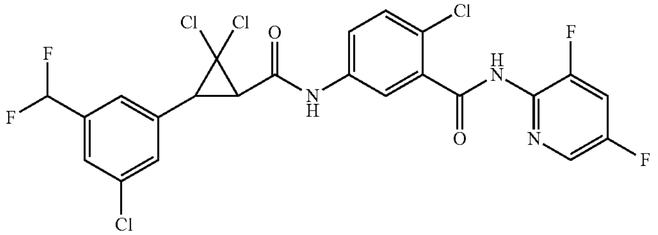 [SMILES: O=C(Nc1ncc(F)cc1F)c1cc(NC(=O)C2C(c3cc(Cl)cc(C(F)F)c3)C2(Cl)Cl)ccc1Cl] | 57 |
| F585 | 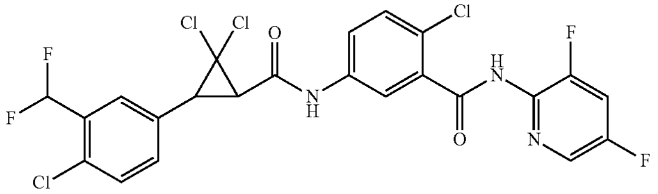 [SMILES: O=C(Nc1ncc(F)cc1F)c1cc(NC(=O)C2C(c3ccc(Cl)c(C(F)F)c3)C2(Cl)Cl)ccc1Cl] | 57 |
| F586 | 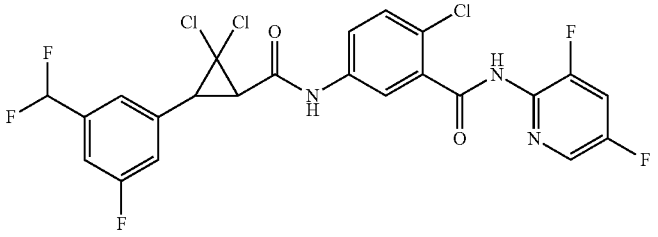 [SMILES: O=C(Nc1ncc(F)cc1F)c1cc(NC(=O)C2C(c3cc(F)cc(C(F)F)c3)C2(Cl)Cl)ccc1Cl] | 57 |
| F587 | 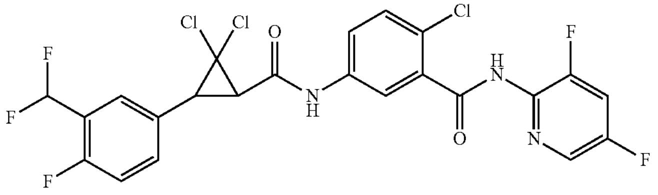 [SMILES: O=C(Nc1ncc(F)cc1F)c1cc(NC(=O)C2C(c3ccc(F)c(C(F)F)c3)C2(Cl)Cl)ccc1Cl] | 57 |

TABLE 2-continued
| Structure and preparation method for F Series molecules | | |
| --- | --- | --- |
| No. | Structure | Prep.* |
| F588 | 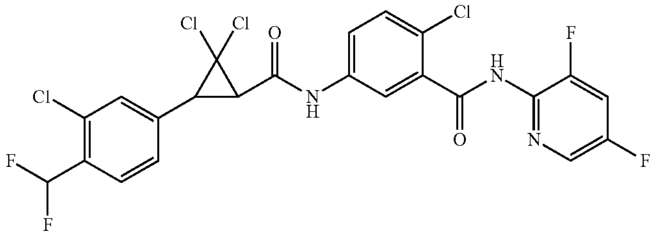 [SMILES: O=C(Nc1ncc(F)cc1F)c1cc(NC(=O)C2C(c3ccc(C(F)F)c(Cl)c3)C2(Cl)Cl)ccc1Cl] | 57 |
| F589 | 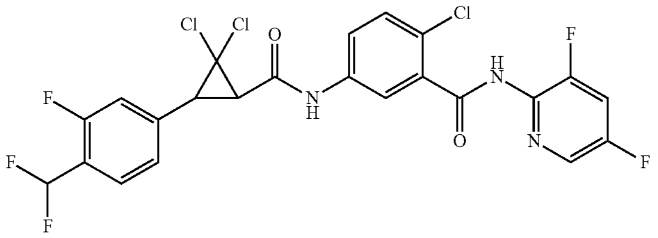 [SMILES: O=C(Nc1ncc(F)cc1F)c1cc(NC(=O)C2C(c3ccc(C(F)F)c(F)c3)C2(Cl)Cl)ccc1Cl] | 57 |
| F590 | 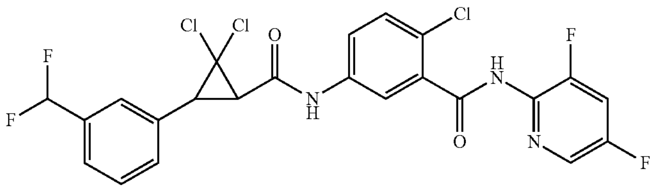 [SMILES: O=C(Nc1ncc(F)cc1F)c1cc(NC(=O)C2C(c3cccc(C(F)F)c3)C2(Cl)Cl)ccc1Cl] | 57 |
| F591 | 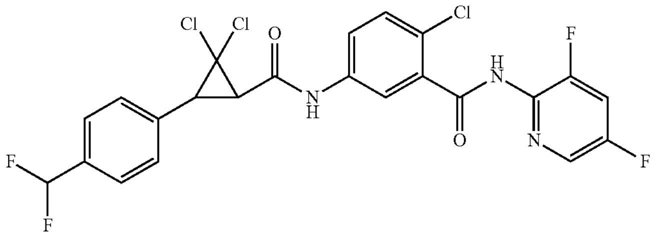 [SMILES: O=C(Nc1ncc(F)cc1F)c1cc(NC(=O)C2C(c3ccc(C(F)F)cc3)C2(Cl)Cl)ccc1Cl] | 57 |
| F592 | 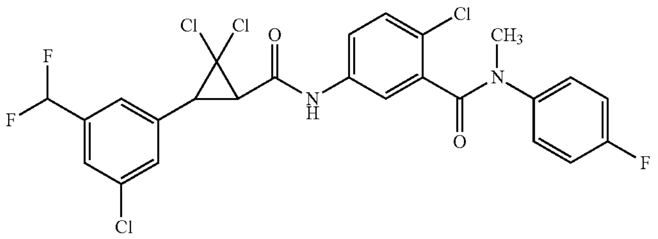 [SMILES: CN(C(=O)c1cc(NC(=O)C2C(c3cc(Cl)cc(C(F)F)c3)C2(Cl)Cl)ccc1Cl)c1ccc(F)cc1] | 57 |
| F593 | 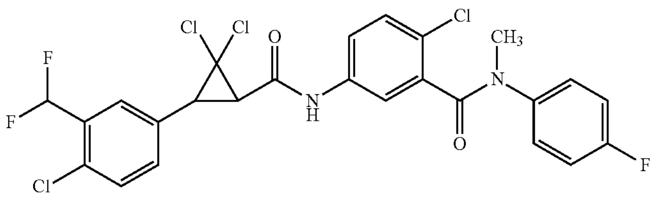 [SMILES: CN(C(=O)c1cc(NC(=O)C2C(c3ccc(Cl)c(C(F)F)c3)C2(Cl)Cl)ccc1Cl)c1ccc(F)cc1] | 57 |

TABLE 2-continued
| Structure and preparation method for F Series molecules | | |
|---|---|---|
| No. | Structure | Prep.* |
| F594 | 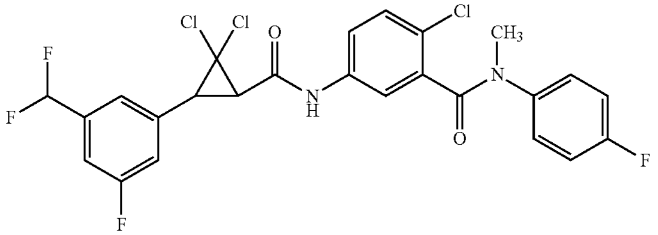 | 57 |
| F595 | 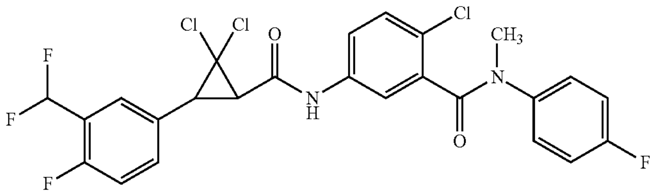 | 57 |
| F596 | 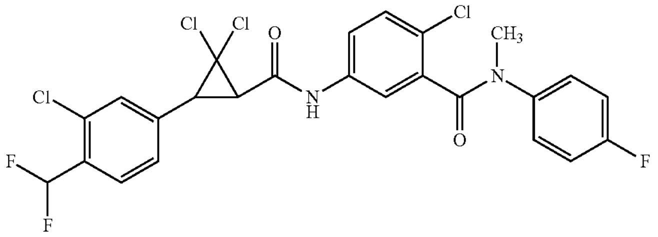 | 57 |
| F597 | 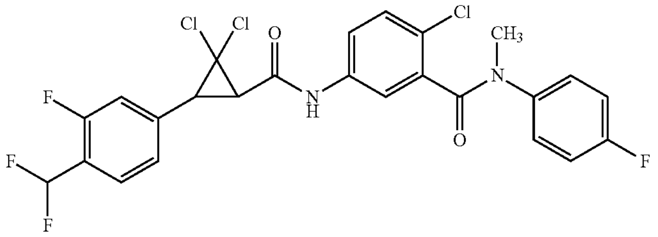 [SMILES: CN(C(=O)c1cc(NC(=O)C2C(c3ccc(C(F)F)c(F)c3)C2(Cl)Cl)ccc1Cl)c1ccc(F)cc1] | 57 |
| F598 | 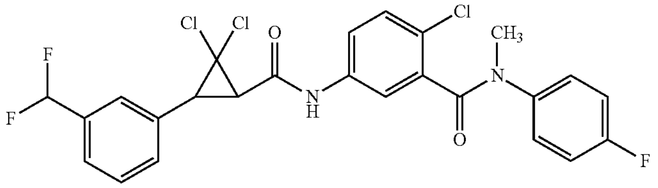 [SMILES: CN(C(=O)c1cc(NC(=O)C2C(c3cccc(C(F)F)c3)C2(Cl)Cl)ccc1Cl)c1ccc(F)cc1] | 57 |
| F599 | 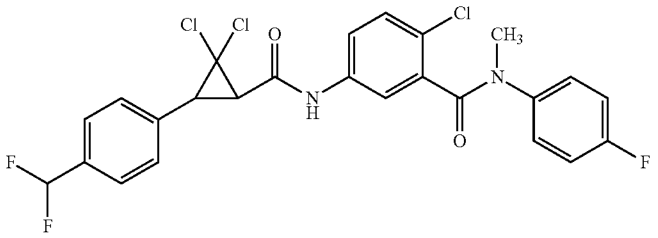 [SMILES: CN(C(=O)c1cc(NC(=O)C2C(c3ccc(C(F)F)cc3)C2(Cl)Cl)ccc1Cl)c1ccc(F)cc1] | 57 |

TABLE 2-continued
| Structure and preparation method for F Series molecules | | |
|---|---|---|
| No. | Structure | Prep.* |
| F600 | 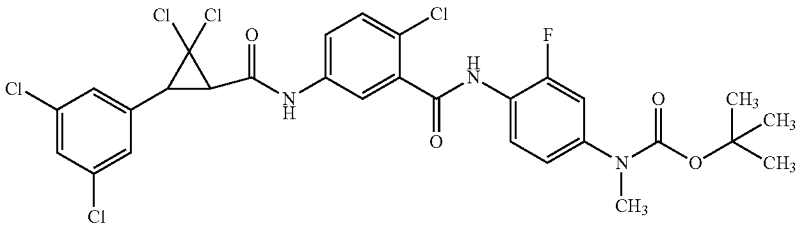 [SMILES: CN(C(=O)OC(C)(C)C)c1ccc(NC(=O)c2cc(NC(=O)C3C(c4cc(Cl)cc(Cl)c4)C3(Cl)Cl)ccc2Cl)c(F)c1] | 15 |
| F601 | 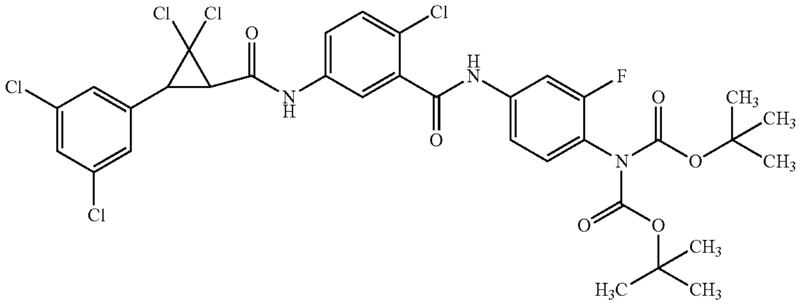 [SMILES: CC(C)(C)OC(=O)N(C(=O)OC(C)(C)C)c1ccc(NC(=O)c2cc(NC(=O)C3C(c4cc(Cl)cc(Cl)c4)C3(Cl)Cl)ccc2Cl)cc1F] | 15 |
| F602 | 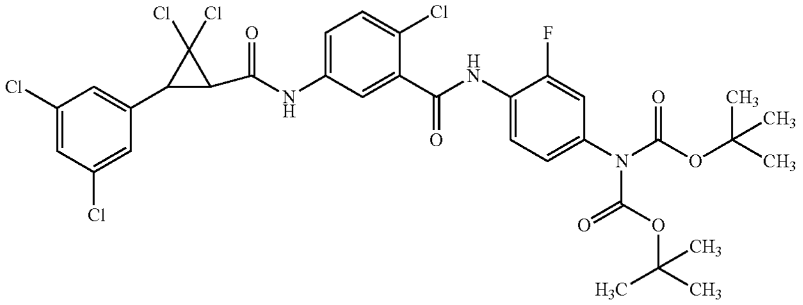 [SMILES: CC(C)(C)OC(=O)N(C(=O)OC(C)(C)C)c1ccc(NC(=O)c2cc(NC(=O)C3C(c4cc(Cl)cc(Cl)c4)C3(Cl)Cl)ccc2Cl)c(F)c1] | 15 |
| F603 | 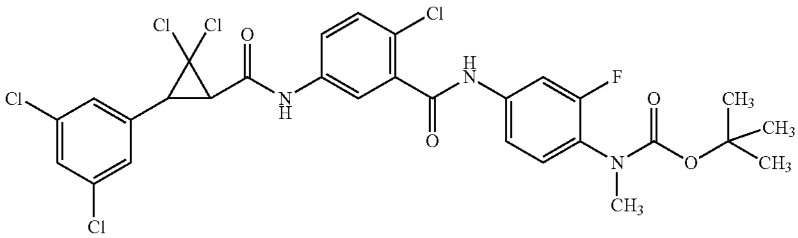 [SMILES: CN(C(=O)OC(C)(C)C)c1ccc(NC(=O)c2cc(NC(=O)C3C(c4cc(Cl)cc(Cl)c4)C3(Cl)Cl)ccc2Cl)cc1F] | 15 |
| F604 | 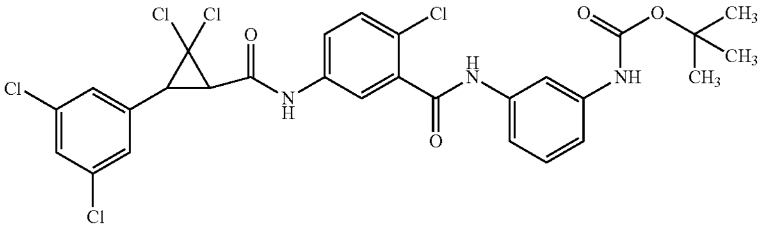 [SMILES: CC(C)(C)OC(=O)Nc1cccc(NC(=O)c2cc(NC(=O)C3C(c4cc(Cl)cc(Cl)c4)C3(Cl)Cl)ccc2Cl)c1] | 15 |
| F605 | 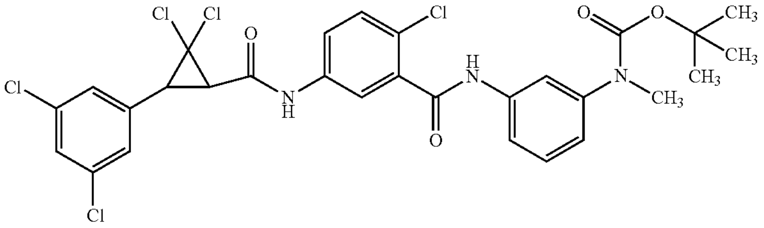 [SMILES: CN(C(=O)OC(C)(C)C)c1cccc(NC(=O)c2cc(NC(=O)C3C(c4cc(Cl)cc(Cl)c4)C3(Cl)Cl)ccc2Cl)c1] | 15 |

TABLE 2-continued
| Structure and preparation method for F Series molecules | | |
|---|---|---|
| No. | Structure | Prep.* |
| F606 | 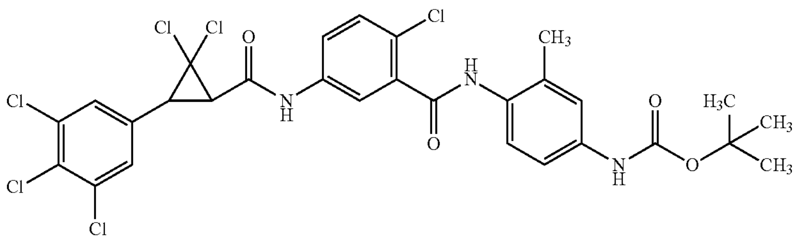 [SMILES: Cc1cc(NC(=O)OC(C)(C)C)ccc1NC(=O)c1cc(NC(=O)C2C(c3cc(Cl)c(Cl)c(Cl)c3)C2(Cl)Cl)ccc1Cl] | 13 |
| F607 | 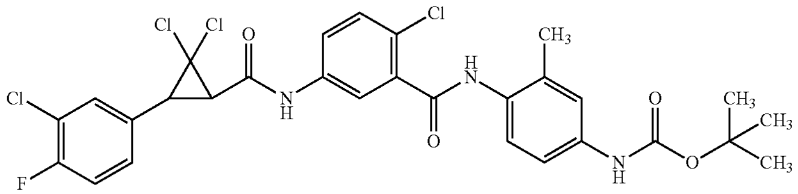 [SMILES: Cc1cc(NC(=O)OC(C)(C)C)ccc1NC(=O)c1cc(NC(=O)C2C(c3ccc(F)c(Cl)c3)C2(Cl)Cl)ccc1Cl] | 13 |
| F608 | 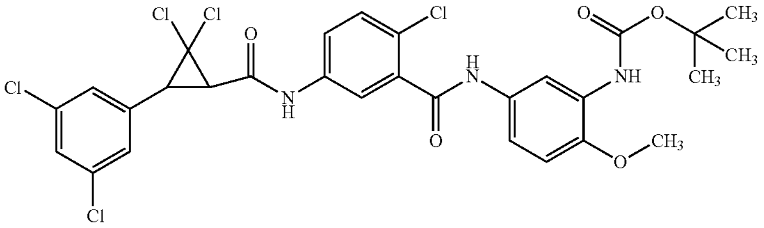 [SMILES: COc1ccc(NC(=O)c2cc(NC(=O)C3C(c4cc(Cl)cc(Cl)c4)C3(Cl)Cl)ccc2Cl)cc1NC(=O)OC(C)(C)C] | 15 |
| F609 | 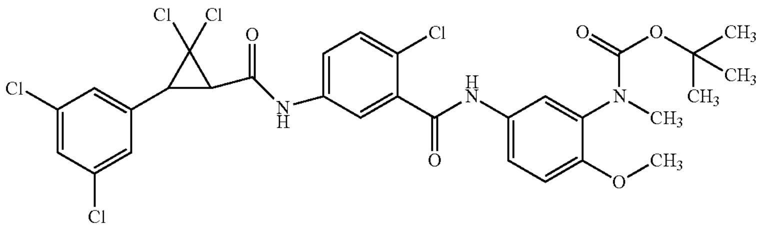 [SMILES: COc1ccc(NC(=O)c2cc(NC(=O)C3C(c4cc(Cl)cc(Cl)c4)C3(Cl)Cl)ccc2Cl)cc1N(C)C(=O)OC(C)(C)C] | 15 |
| F610 | 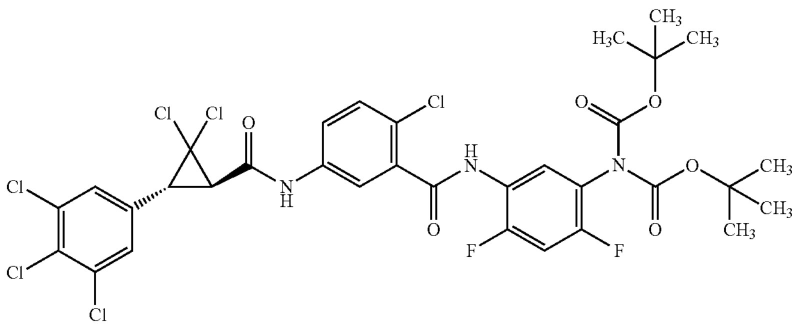 [SMILES: CC(C)(C)OC(=O)N(C(=O)OC(C)(C)C)c1cc(NC(=O)c2cc(NC(=O)[C@H]3[C@H](c4cc(Cl)c(Cl)c(Cl)c4)C3(Cl)Cl)ccc2Cl)c(F)cc1F] | 55 |

TABLE 2-continued
| Structure and preparation method for F Series molecules | | |
|---|---|---|
| No. | Structure | Prep.* |
| F611 | 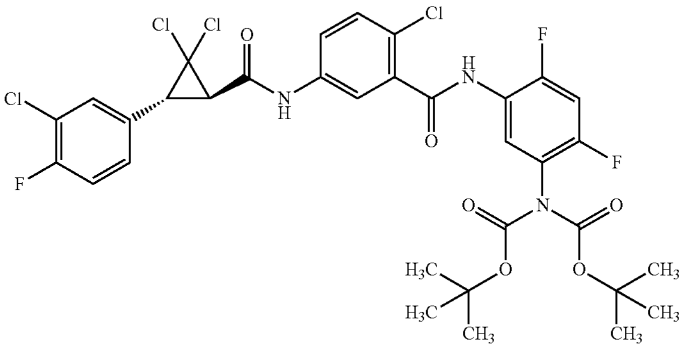 [SMILES: CC(C)(C)OC(=O)N(C(=O)OC(C)(C)C)c1cc(NC(=O)c2cc(NC(=O)[C@H]3[C@H](c4ccc(F)c(Cl)c4)C3(Cl)Cl)ccc2Cl)c(F)cc1F] | 55 |
| F612 | 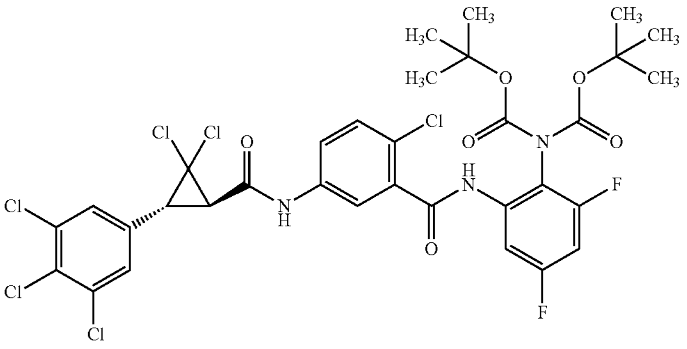 [SMILES: CC(C)(C)OC(=O)N(C(=O)OC(C)(C)C)c1c(F)cc(F)cc1NC(=O)c1cc(NC(=O)[C@H]2[C@H](c3cc(Cl)c(Cl)c(Cl)c3)C2(Cl)Cl)ccc1Cl] | 55 |
| F613 | 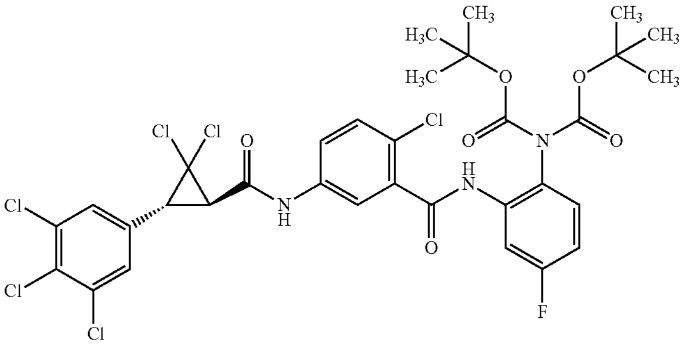 [SMILES: CC(C)(C)OC(=O)N(C(=O)OC(C)(C)C)c1ccc(F)cc1NC(=O)c1cc(NC(=O)[C@H]2[C@H](c3cc(Cl)c(Cl)c(Cl)c3)C2(Cl)Cl)ccc1Cl] | 55 |
| F614 | 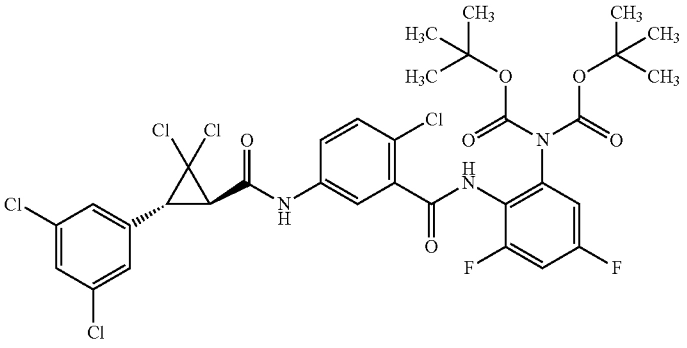 [SMILES: CC(C)(C)OC(=O)N(C(=O)OC(C)(C)C)c1cc(F)cc(F)c1NC(=O)c1cc(NC(=O)[C@H]2[C@H](c3cc(Cl)cc(Cl)c3)C2(Cl)Cl)ccc1Cl] | 55 |

TABLE 2-continued
| Structure and preparation method for F Series molecules | | |
|---|---|---|
| No. | Structure | Prep.* |
| F615 | 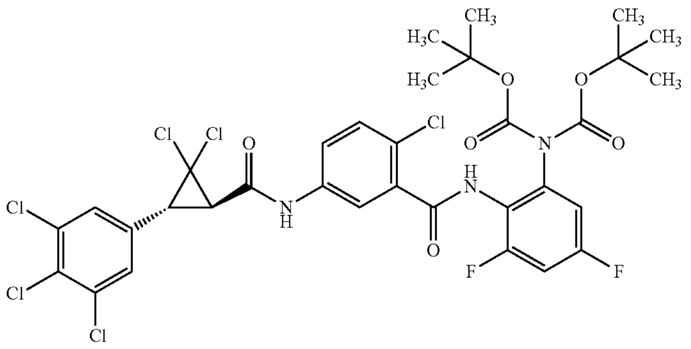 [SMILES: CC(C)(C)OC(=O)N(C(=O)OC(C)(C)C)c1cc(F)cc(F)c1NC(=O)c1cc(NC(=O)[C@H]2[C@H](c3cc(Cl)c(Cl)c(Cl)c3)C2(Cl)Cl)ccc1Cl] | 55 |
| F616 | 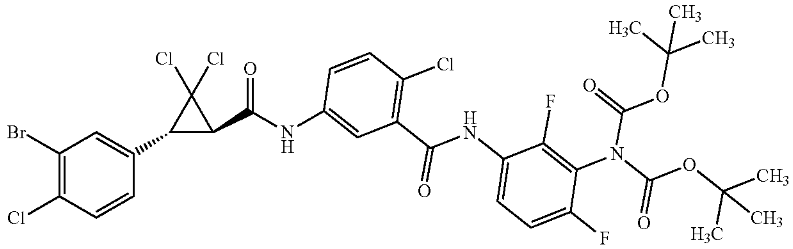 [SMILES: CC(C)(C)OC(=O)N(C(=O)OC(C)(C)C)c1c(F)ccc(NC(=O)c2cc(NC(=O)[C@H]3[C@H](c4ccc(Cl)c(Br)c4)C3(Cl)Cl)ccc2Cl)c1F] | 13 |
| F617 | 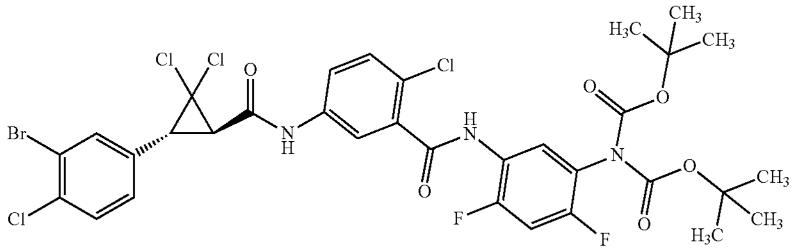 [SMILES: CC(C)(C)OC(=O)N(C(=O)OC(C)(C)C)c1cc(NC(=O)c2cc(NC(=O)[C@H]3[C@H](c4ccc(Cl)c(Br)c4)C3(Cl)Cl)ccc2Cl)c(F)cc1F] | 13 |
| F618 | 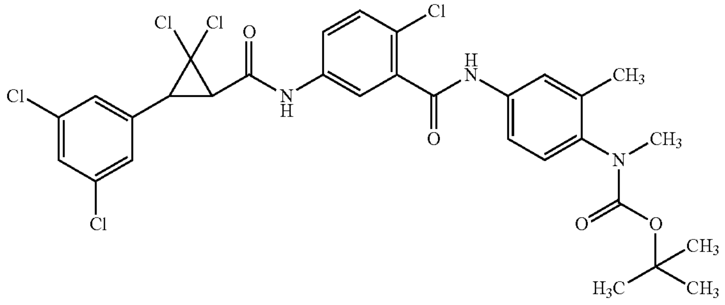 [SMILES: Cc1cc(NC(=O)c2cc(NC(=O)C3C(c4cc(Cl)cc(Cl)c4)C3(Cl)Cl)ccc2Cl)ccc1N(C)C(=O)OC(C)(C)C] | 15 |
| F619 | 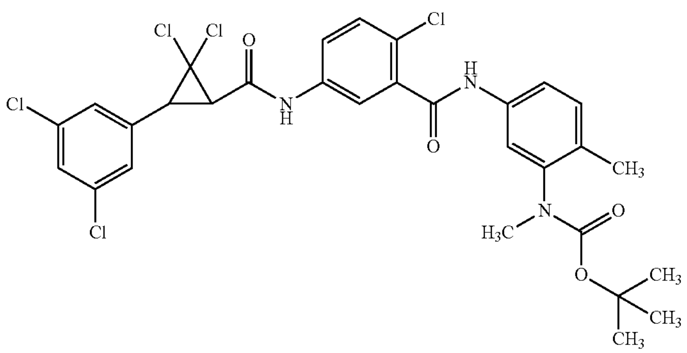 [SMILES: Cc1ccc(NC(=O)c2cc(NC(=O)C3C(c4cc(Cl)cc(Cl)c4)C3(Cl)Cl)ccc2Cl)cc1N(C)C(=O)OC(C)(C)C] | 15 |

TABLE 2-continued
| Structure and preparation method for F Series molecules | | |
|---|---|---|
| No. | Structure | Prep.* |
| F620 | 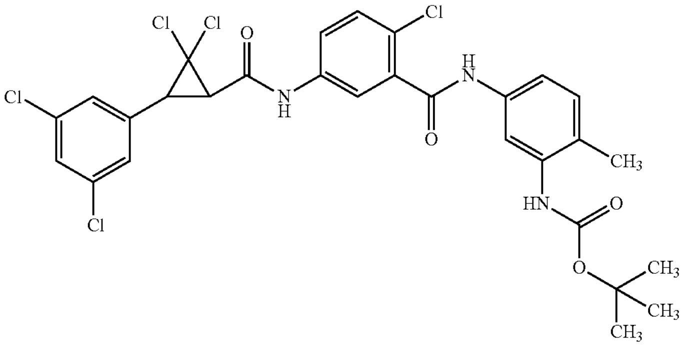 [SMILES: Cc1ccc(NC(=O)c2cc(NC(=O)C3C(c4cc(Cl)cc(Cl)c4)C3(Cl)Cl)ccc2Cl)cc1NC(=O)OC(C)(C)C] | 15 |
| F621 | 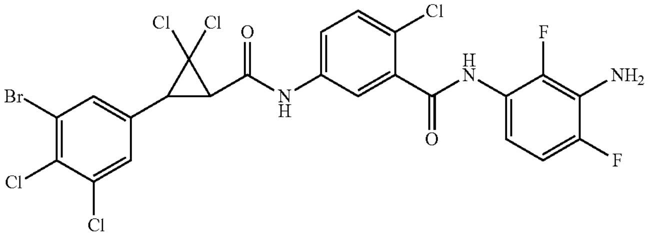 [SMILES: Nc1c(F)ccc(NC(=O)c2cc(NC(=O)C3C(c4cc(Cl)c(Cl)c(Br)c4)C3(Cl)Cl)ccc2Cl)c1F] | 62 |
| F622 | 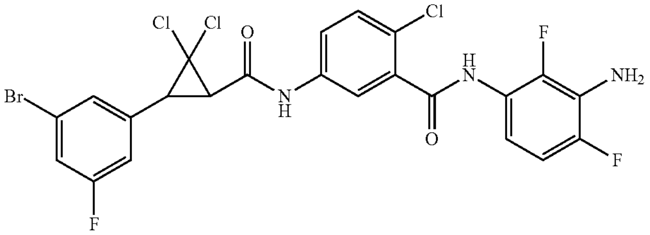 [SMILES: Nc1c(F)ccc(NC(=O)c2cc(NC(=O)C3C(c4cc(F)cc(Br)c4)C3(Cl)Cl)ccc2Cl)c1F] | 62 |
| F623 | 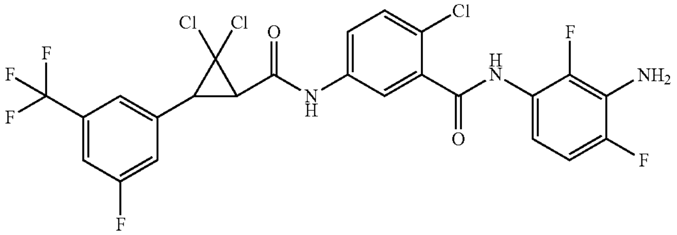 [SMILES: Nc1c(F)ccc(NC(=O)c2cc(NC(=O)C3C(c4cc(F)cc(C(F)(F)F)c4)C3(Cl)Cl)ccc2Cl)c1F] | 62 |
| F624 | 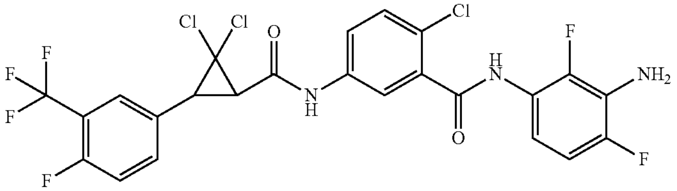 [SMILES: Nc1c(F)ccc(NC(=O)c2cc(NC(=O)C3C(c4ccc(F)c(C(F)(F)F)c4)C3(Cl)Cl)ccc2Cl)c1F] | 62 |
| F625 | 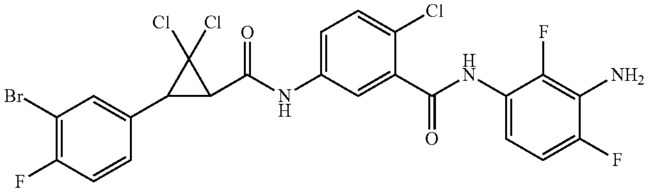 [SMILES: Nc1c(F)ccc(NC(=O)c2cc(NC(=O)C3C(c4ccc(F)c(Br)c4)C3(Cl)Cl)ccc2Cl)c1F] | 62 |

TABLE 2-continued
| Structure and preparation method for F Series molecules | | |
|---|---|---|
| No. | Structure | Prep.* |
| F626 | 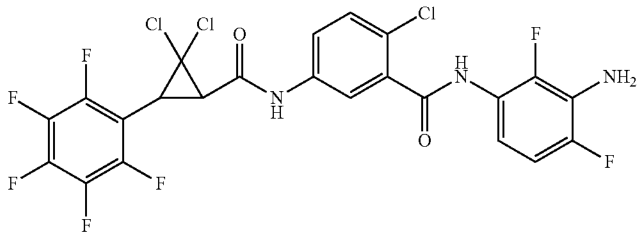 [SMILES: Nc1c(F)ccc(NC(=O)c2cc(NC(=O)C3C(c4c(F)c(F)c(F)c(F)c4F)C3(Cl)Cl)ccc2Cl)c1F] | 62 |
| F627 | 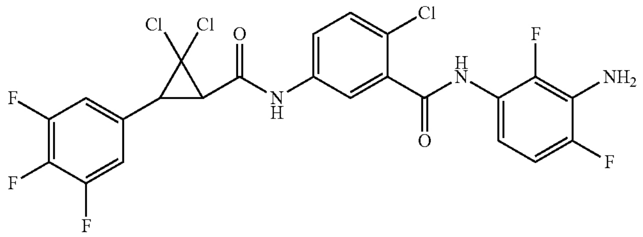 [SMILES: Nc1c(F)ccc(NC(=O)c2cc(NC(=O)C3C(c4cc(F)c(F)c(F)c4)C3(Cl)Cl)ccc2Cl)c1F] | 62 |
| F628 | 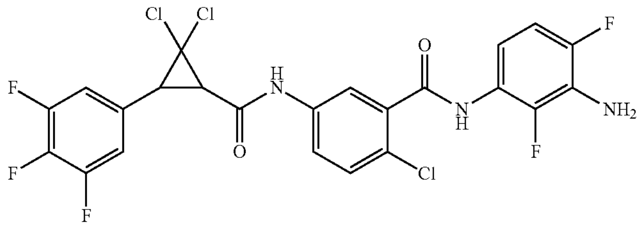 [SMILES: Nc1c(F)ccc(NC(=O)c2cc(NC(=O)C3C(c4cc(F)c(F)c(F)c4)C3(Cl)Cl)ccc2Cl)c1F] | 62 |
| F629 | 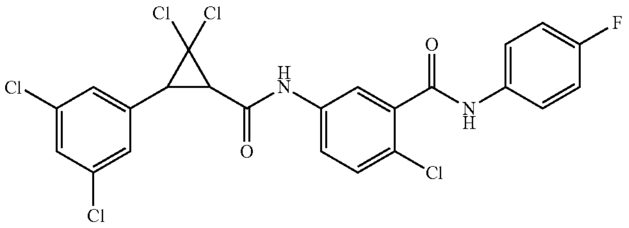 [SMILES: O=C(Nc1ccc(F)cc1)c1cc(NC(=O)C2C(c3cc(Cl)cc(Cl)c3)C2(Cl)Cl)ccc1Cl] | 14 |
| PF1 | 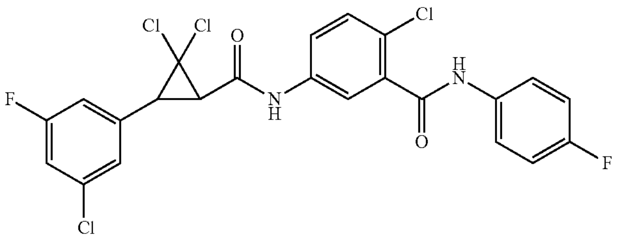 [SMILES: O=C(Nc1ccc(F)cc1)c1cc(NC(=O)C2C(c3cc(F)cc(Cl)c3)C2(Cl)Cl)ccc1Cl] | 13 |
| PF2 | 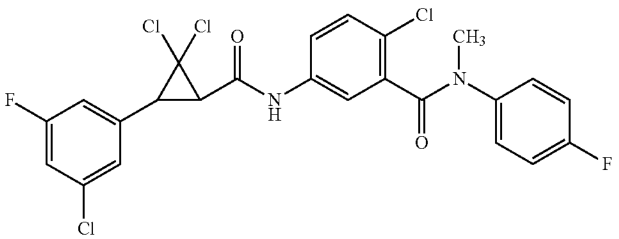 [SMILES: CN(C(=O)c1cc(NC(=O)C2C(c3cc(F)cc(Cl)c3)C2(Cl)Cl)ccc1Cl)c1ccc(F)cc1] | 13 |

TABLE 2-continued
| No. | Structure | Prep.* |
| --- | --- | --- |
| PF4 | 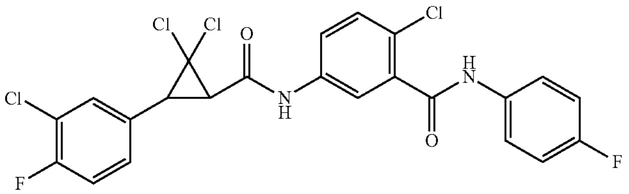 | 13 |
| PF5 | 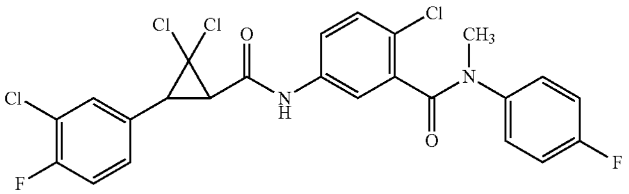 | 13 |
| PF6 | 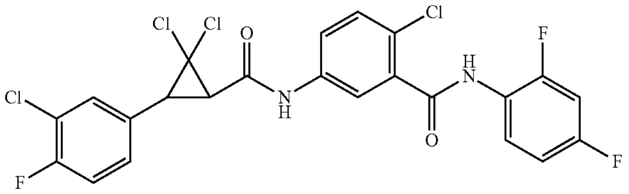 | 56 |
| PF7 | 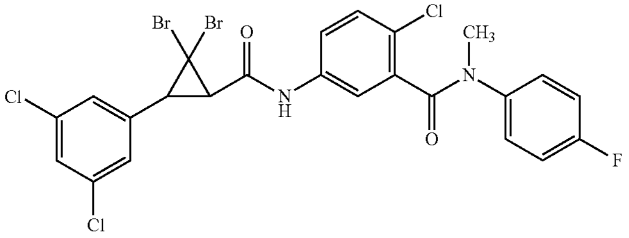 | 13 |
| PF8 | 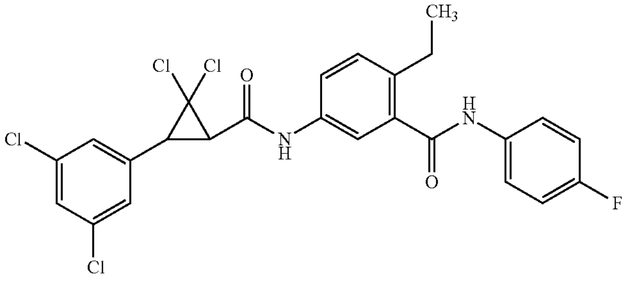 [SMILES: CCc1ccc(NC(=O)C2C(c3cc(Cl)cc(Cl)c3)C2(Cl)Cl)cc1C(=O)Nc1ccc(F)cc1] | 13 |
| PF9 | 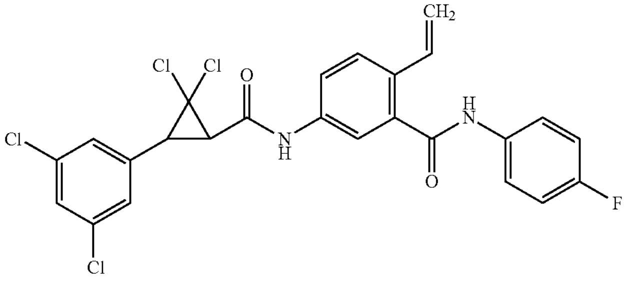 | 13 |
Structure and preparation method for F Series molecules TABLE 2-continued
| Structure and preparation method for F Series molecules | | |
|---|---|---|
| No. | Structure | Prep.* |
| PF10 | 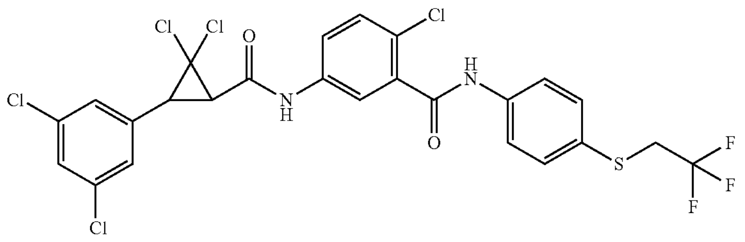 | 18 |
| PF11 | 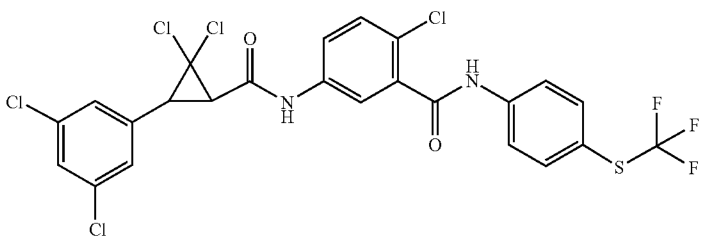 [SMILES: O=C(Nc1ccc(SC(F)(F)F)cc1)c1cc(NC(=O)C2C(c3cc(Cl)cc(Cl)c3)C2(Cl)Cl)ccc1Cl] | 18 |
| PF12 | 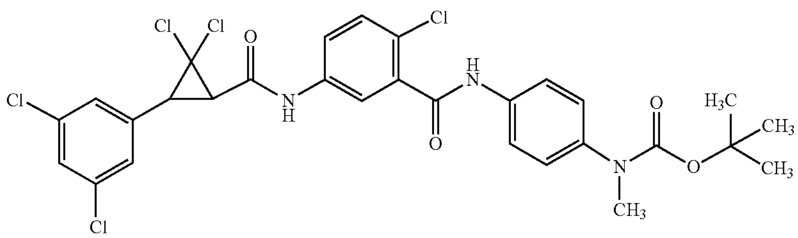 [SMILES: CN(C(=O)OC(C)(C)C)c1ccc(NC(=O)c2cc(NC(=O)C3C(c4cc(Cl)cc(Cl)c4)C3(Cl)Cl)ccc2Cl)cc1] | 18 |
| PF13 | 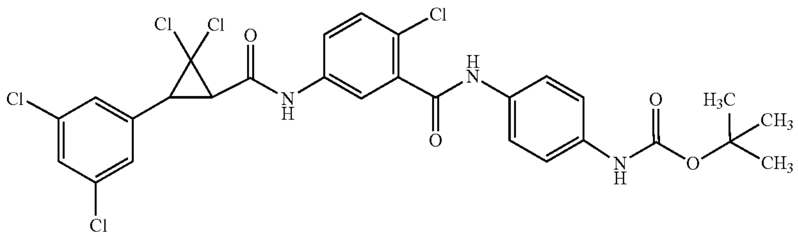 [SMILES: CC(C)(C)OC(=O)Nc1ccc(NC(=O)c2cc(NC(=O)C3C(c4cc(Cl)cc(Cl)c4)C3(Cl)Cl)ccc2Cl)cc1] | 18 |
| PF14 | 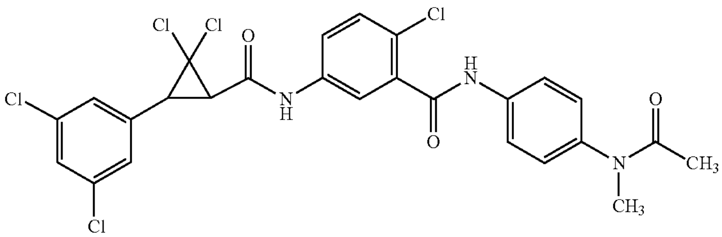 [SMILES: CC(=O)N(C)c1ccc(NC(=O)c2cc(NC(=O)C3C(c4cc(Cl)cc(Cl)c4)C3(Cl)Cl)ccc2Cl)cc1] | 18 |
| PF15 | 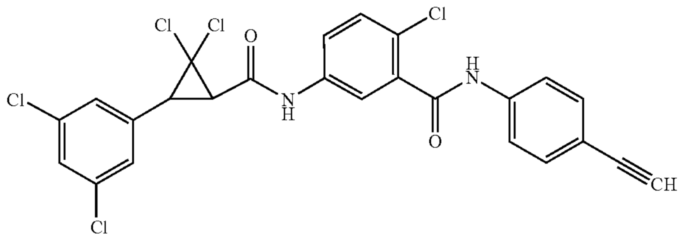 [SMILES: C#Cc1ccc(NC(=O)c2cc(NC(=O)C3C(c4cc(Cl)cc(Cl)c4)C3(Cl)Cl)ccc2Cl)cc1] | 18 |

TABLE 2-continued
| Structure and preparation method for F Series molecules | | |
|---|---|---|
| No. | Structure | Prep.* |
| PF16 | 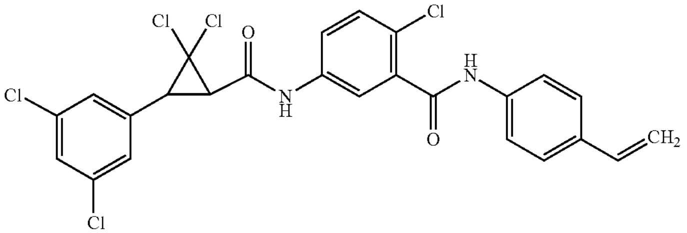 [SMILES: C=Cc1ccc(NC(=O)c2cc(NC(=O)C3C(c4cc(Cl)cc(Cl)c4)C3(Cl)Cl)ccc2Cl)cc1] | 18 |
| PF17 | 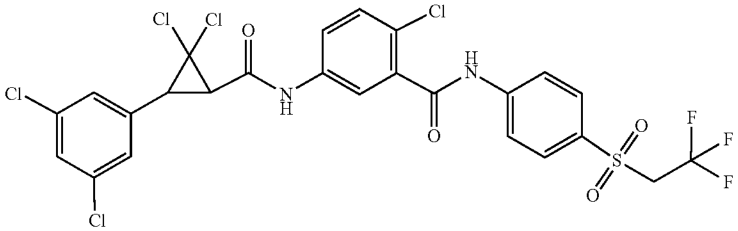 [SMILES: O=C(Nc1ccc(S(=O)(=O)CC(F)(F)F)cc1)c1cc(NC(=O)C2C(c3cc(Cl)cc(Cl)c3)C2(Cl)Cl)ccc1Cl] | 80 |
| PF18 | 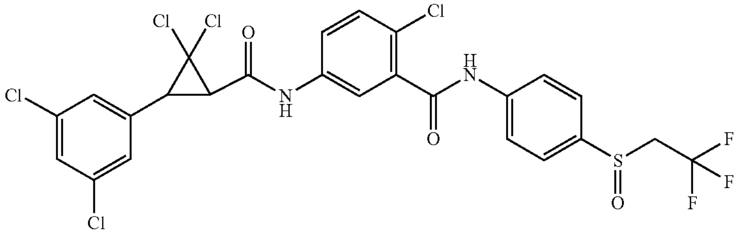 [SMILES: O=C(Nc1ccc(S(=O)CC(F)(F)F)cc1)c1cc(NC(=O)C2C(c3cc(Cl)cc(Cl)c3)C2(Cl)Cl)ccc1Cl] | 80 |
| PF19 | 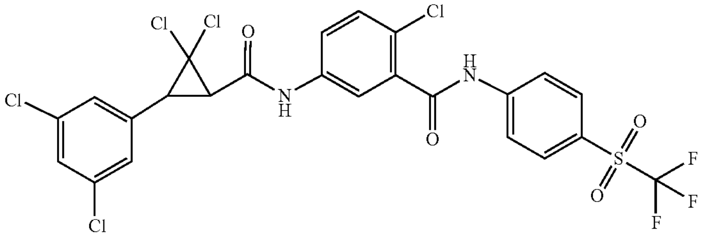 [SMILES: O=C(Nc1ccc(S(=O)(=O)C(F)(F)F)cc1)c1cc(NC(=O)C2C(c3cc(Cl)cc(Cl)c3)C2(Cl)Cl)ccc1Cl] | 80 |
| PF20 | 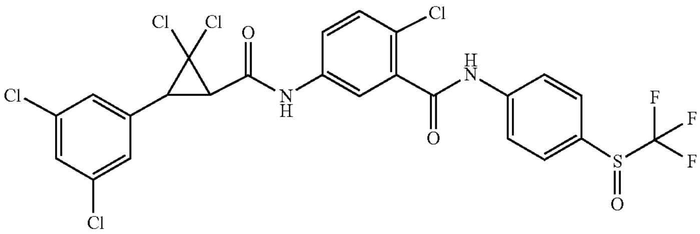 [SMILES: O=C(Nc1ccc(S(=O)C(F)(F)F)cc1)c1cc(NC(=O)C2C(c3cc(Cl)cc(Cl)c3)C2(Cl)Cl)ccc1Cl] | 80 |
| PF21 | 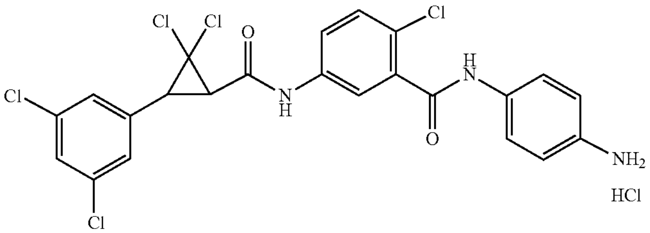 [SMILES: Nc1ccc(NC(=O)c2cc(NC(=O)C3C(c4cc(Cl)cc(Cl)c4)C3(Cl)Cl)ccc2Cl)cc1 ; Cl] | 64 |

TABLE 2-continued
Structure and preparation method for F Series molecules
| No. | Structure | Prep.* |
| --- | --- | --- |
| PF22 | 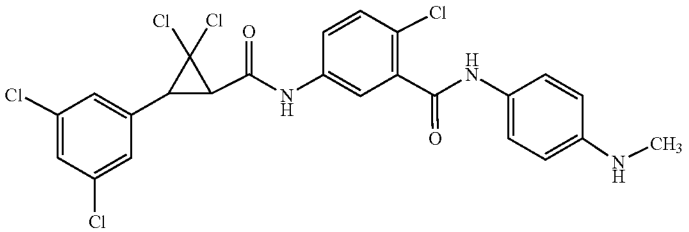 [SMILES: CNc1ccc(NC(=O)c2cc(NC(=O)C3C(c4cc(Cl)cc(Cl)c4)C3(Cl)Cl)ccc2Cl)cc1] | 62 |
| PF24 | 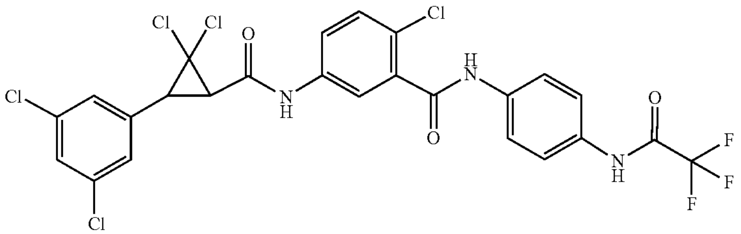 [SMILES: O=C(Nc1ccc(NC(=O)C(F)(F)F)cc1)c1cc(NC(=O)C2C(c3cc(Cl)cc(Cl)c3)C2(Cl)Cl)ccc1Cl] | 69 |
| PF25 | 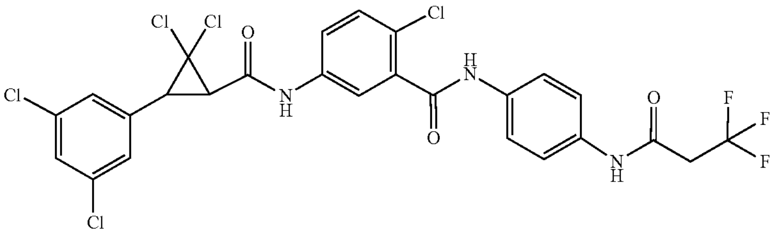 [SMILES: O=C(CC(F)(F)F)Nc1ccc(NC(=O)c2cc(NC(=O)C3C(c4cc(Cl)cc(Cl)c4)C3(Cl)Cl)ccc2Cl)cc1] | 67 |
| PF26 | 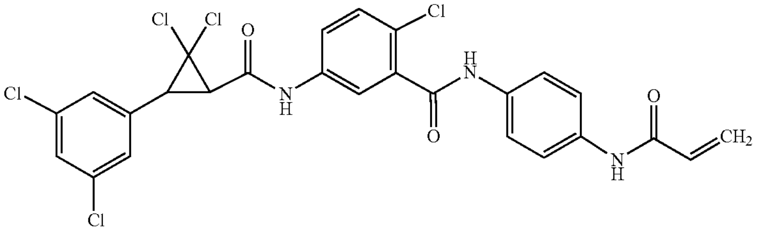 [SMILES: C=CC(=O)Nc1ccc(NC(=O)c2cc(NC(=O)C3C(c4cc(Cl)cc(Cl)c4)C3(Cl)Cl)ccc2Cl)cc1] | 67 |
| PF27 | 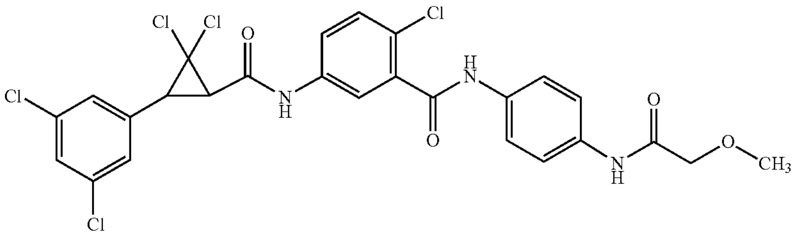 [SMILES: COCC(=O)Nc1ccc(NC(=O)c2cc(NC(=O)C3C(c4cc(Cl)cc(Cl)c4)C3(Cl)Cl)ccc2Cl)cc1] | 67 |
| PF28 | 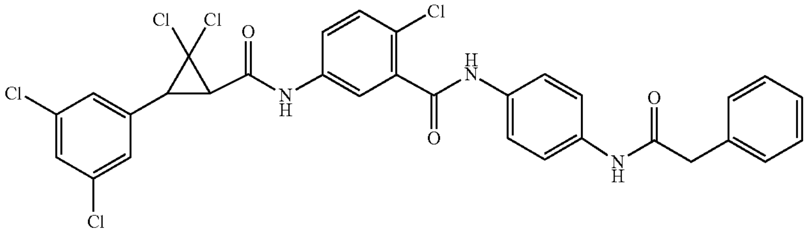 [SMILES: O=C(Cc1ccccc1)Nc1ccc(NC(=O)c2cc(NC(=O)C3C(c4cc(Cl)cc(Cl)c4)C3(Cl)Cl)ccc2Cl)cc1] | 67 |

TABLE 2-continued
| Structure and preparation method for F Series molecules | | |
|---|---|---|
| No. | Structure | Prep.* |
| PF29 | 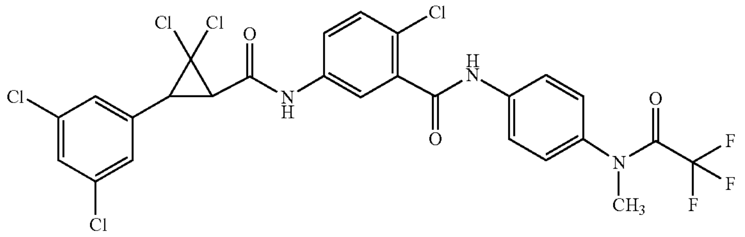 [SMILES: CN(C(=O)C(F)(F)F)c1ccc(NC(=O)c2cc(NC(=O)C3C(c4cc(Cl)cc(Cl)c4)C3(Cl)Cl)ccc2Cl)cc1] | 69 |
| PF30 | 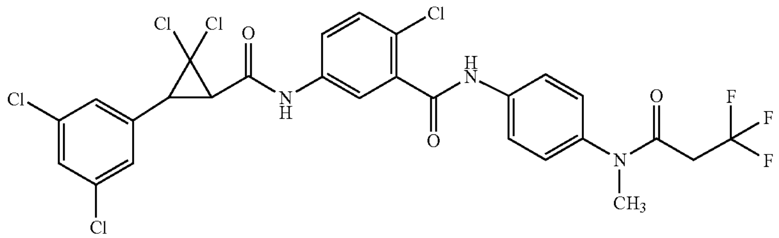 [SMILES: CN(C(=O)CC(F)(F)F)c1ccc(NC(=O)c2cc(NC(=O)C3C(c4cc(Cl)cc(Cl)c4)C3(Cl)Cl)ccc2Cl)cc1] | 67 |
| PF31 | 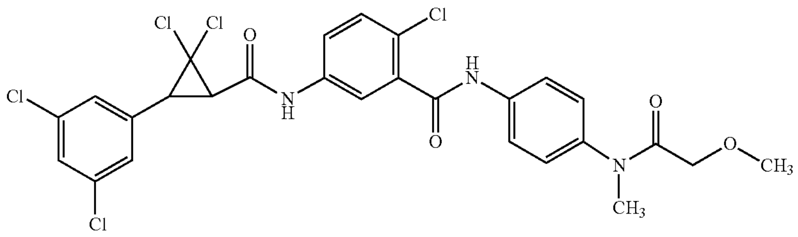 [SMILES: COCC(=O)N(C)c1ccc(NC(=O)c2cc(NC(=O)C3C(c4cc(Cl)cc(Cl)c4)C3(Cl)Cl)ccc2Cl)cc1] | 67 |
| PF32 | 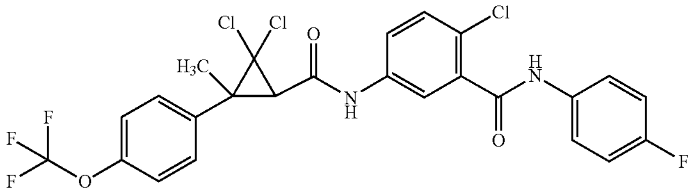 [SMILES: CC1(c2ccc(OC(F)(F)F)cc2)C(C(=O)Nc2ccc(Cl)c(C(=O)Nc3ccc(F)cc3)c2)C1(Cl)Cl] | 13 |
| PF33 | 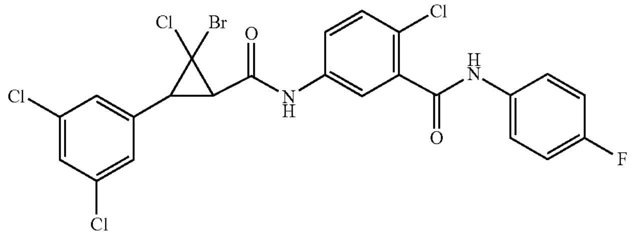 [SMILES: O=C(Nc1ccc(F)cc1)c1cc(NC(=O)C2C(c3cc(Cl)cc(Cl)c3)C2(Cl)Br)ccc1Cl] | 13 |
| PF34 | 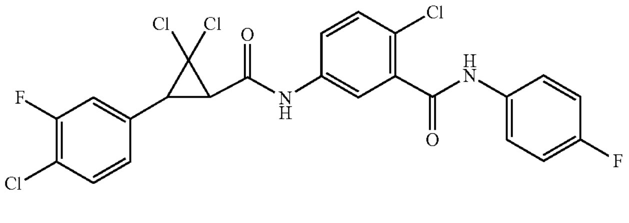 [SMILES: O=C(Nc1ccc(F)cc1)c1cc(NC(=O)C2C(c3ccc(Cl)c(F)c3)C2(Cl)Cl)ccc1Cl] | 13 |

TABLE 2-continued
| Structure and preparation method for F Series molecules | | |
|---|---|---|
| No. | Structure | Prep.* |
| PF35 | 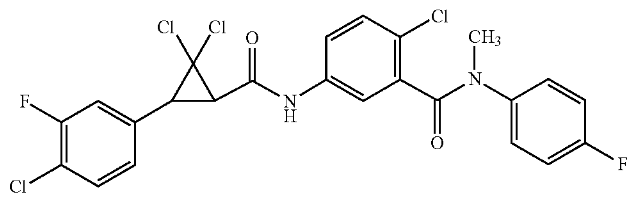 [SMILES: CN(C(=O)c1cc(NC(=O)C2C(c3ccc(Cl)c(F)c3)C2(Cl)Cl)ccc1Cl)c1ccc(F)cc1] | 13 |
| PF36 | 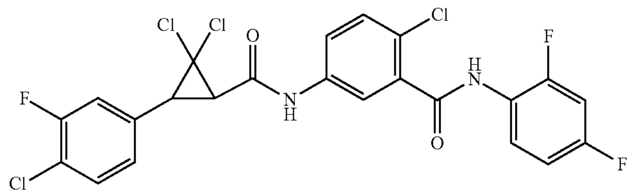 [SMILES: O=C(Nc1ccc(F)cc1F)c1cc(NC(=O)C2C(c3ccc(Cl)c(F)c3)C2(Cl)Cl)ccc1Cl] | 57 |
| PF37 | 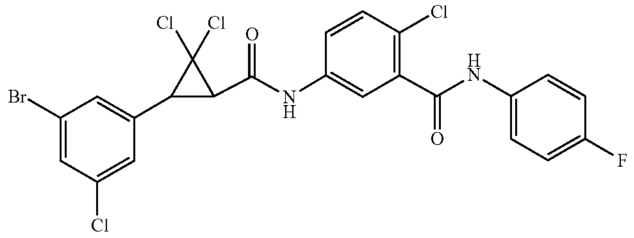 [SMILES: O=C(Nc1ccc(F)cc1)c1cc(NC(=O)C2C(c3cc(Cl)cc(Br)c3)C2(Cl)Cl)ccc1Cl] | 13 |
| PF38 | 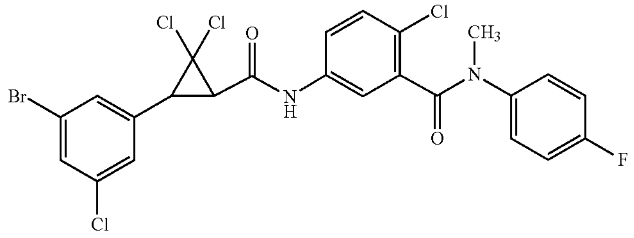 [SMILES: CN(C(=O)c1cc(NC(=O)C2C(c3cc(Cl)cc(Br)c3)C2(Cl)Cl)ccc1Cl)c1ccc(F)cc1] | 13 |
| PF39 | 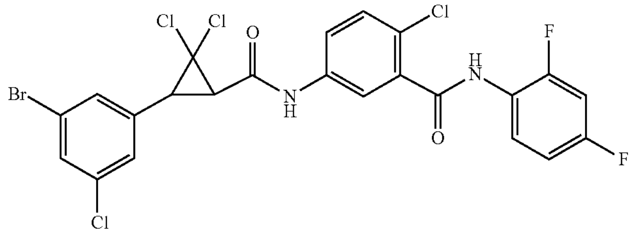 [SMILES: O=C(Nc1ccc(F)cc1F)c1cc(NC(=O)C2C(c3cc(Cl)cc(Br)c3)C2(Cl)Cl)ccc1Cl] | 13 |
| PF40 | 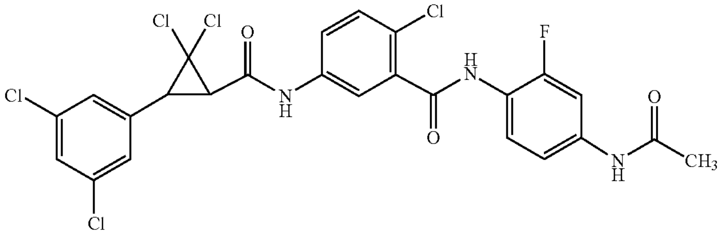 [SMILES: CC(=O)Nc1ccc(NC(=O)c2cc(NC(=O)C3C(c4cc(Cl)cc(Cl)c4)C3(Cl)Cl)ccc2Cl)c(F)c1] | 13 |

TABLE 2-continued
| Structure and preparation method for F Series molecules | | |
|---|---|---|
| No. | Structure | Prep.* |
| PF41 | 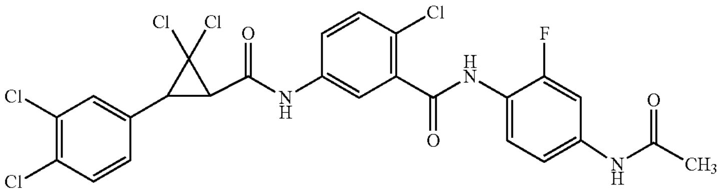 [SMILES: CC(=O)Nc1ccc(NC(=O)c2cc(NC(=O)C3C(c4ccc(Cl)c(Cl)c4)C3(Cl)Cl)ccc2Cl)c(F)c1] | 13 |
| PF42 | 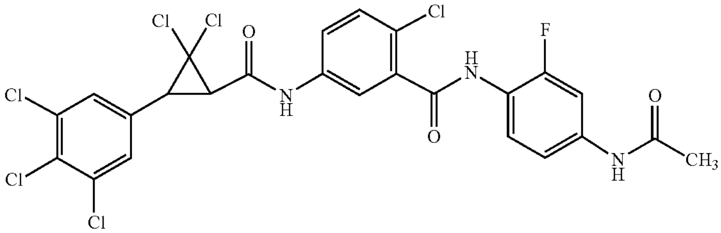 [SMILES: CC(=O)Nc1ccc(NC(=O)c2cc(NC(=O)C3C(c4cc(Cl)c(Cl)c(Cl)c4)C3(Cl)Cl)ccc2Cl)c(F)c1] | 13 |
| PF43 | 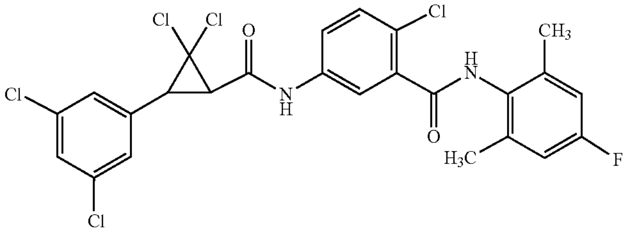 [SMILES: Cc1cc(F)cc(C)c1NC(=O)c1cc(NC(=O)C2C(c3cc(Cl)cc(Cl)c3)C2(Cl)Cl)ccc1Cl] | 18 |
| PF44 | 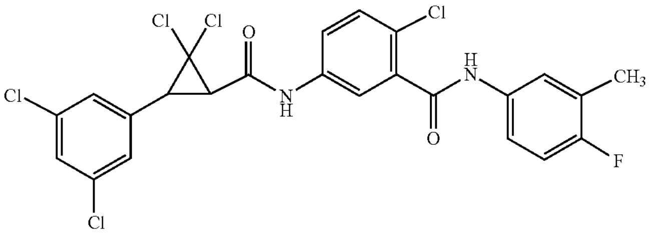 | 18 |
| PF45 | 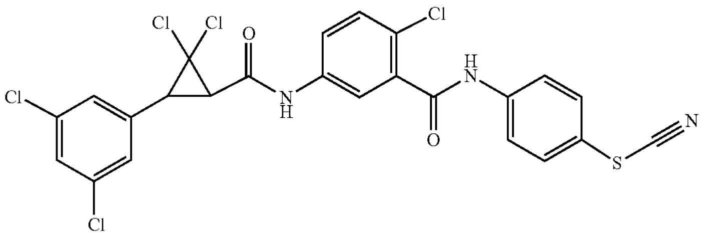 [SMILES: N#CSc1ccc(NC(=O)c2cc(NC(=O)C3C(c4cc(Cl)cc(Cl)c4)C3(Cl)Cl)ccc2Cl)cc1] | 18 |
| PF46 | 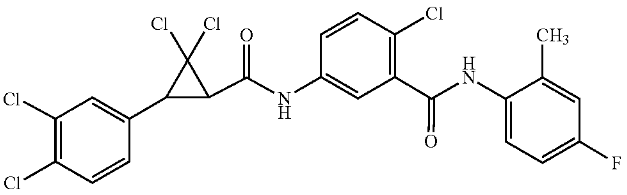 [SMILES: Cc1cc(F)ccc1NC(=O)c1cc(NC(=O)C2C(c3ccc(Cl)c(Cl)c3)C2(Cl)Cl)ccc1Cl] | 13 |

TABLE 2-continued
| Structure and preparation method for F Series molecules | | |
|---|---|---|
| No. | Structure | Prep.* |
| PF47 | 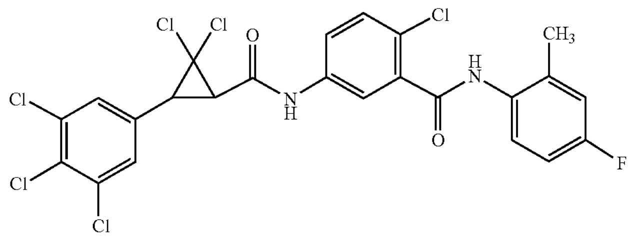 [SMILES: Cc1cc(F)ccc1NC(=O)c1cc(NC(=O)C2C(c3cc(Cl)c(Cl)c(Cl)c3)C2(Cl)Cl)ccc1Cl] | 13 |
| PF48 | 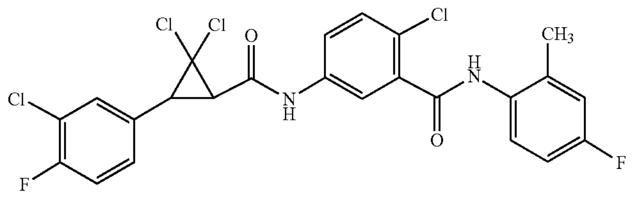 [SMILES: Cc1cc(F)ccc1NC(=O)c1cc(NC(=O)C2C(c3ccc(F)c(Cl)c3)C2(Cl)Cl)ccc1Cl] | 13 |
| PF49 | 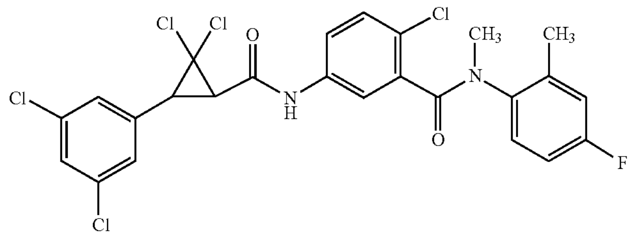 [SMILES: Cc1cc(F)ccc1N(C)C(=O)c1cc(NC(=O)C2C(c3cc(Cl)cc(Cl)c3)C2(Cl)Cl)ccc1Cl] | 13 |
| PF50 | 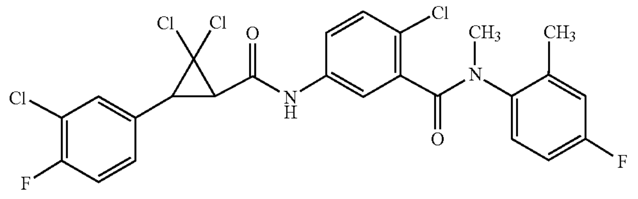 [SMILES: Cc1cc(F)ccc1N(C)C(=O)c1cc(NC(=O)C2C(c3ccc(F)c(Cl)c3)C2(Cl)Cl)ccc1Cl] | 13 |
| PF51 | 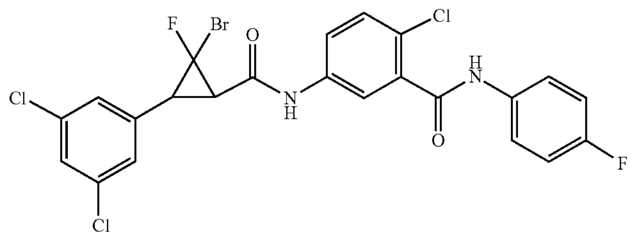 [SMILES: O=C(Nc1ccc(F)cc1)c1cc(NC(=O)C2C(c3cc(Cl)cc(Cl)c3)C2(F)Br)ccc1Cl] | 13 |
| PF52 | 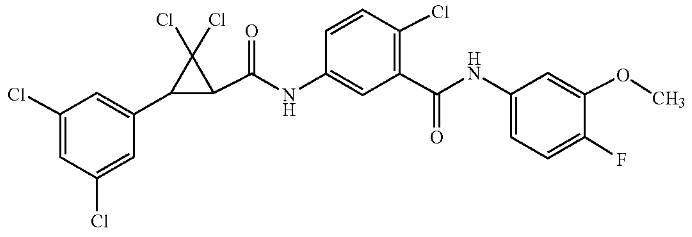 [SMILES: COc1cc(NC(=O)c2cc(NC(=O)C3C(c4cc(Cl)cc(Cl)c4)C3(Cl)Cl)ccc2Cl)ccc1F] | 15 |

TABLE 2-continued
| Structure and preparation method for F Series molecules | | |
|---|---|---|
| No. | Structure | Prep.* |
| PF53 | 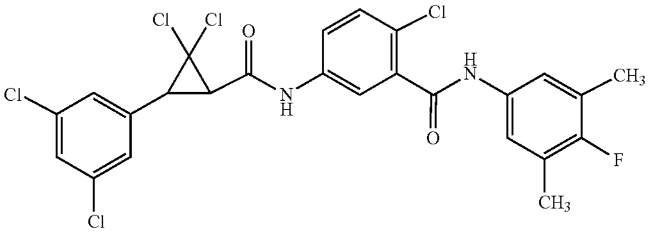 [SMILES: Cc1cc(NC(=O)c2cc(NC(=O)C3C(c4cc(Cl)cc(Cl)c4)C3(Cl)Cl)ccc2Cl)cc(C)c1F] | 15 |
| PF54 | 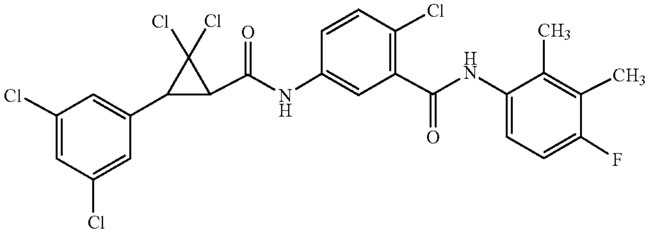 [SMILES: Cc1c(F)ccc(NC(=O)c2cc(NC(=O)C3C(c4cc(Cl)cc(Cl)c4)C3(Cl)Cl)ccc2Cl)c1C] | 15 |
| PF55 | 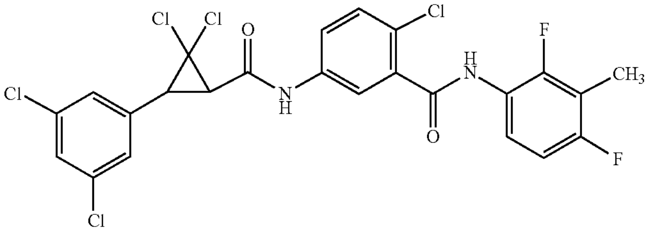 [SMILES: Cc1c(F)ccc(NC(=O)c2cc(NC(=O)C3C(c4cc(Cl)cc(Cl)c4)C3(Cl)Cl)ccc2Cl)c1F] | 15 |
| PF56 | 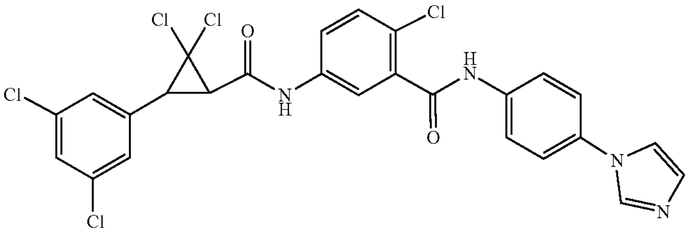 [SMILES: O=C(Nc1ccc(-n2ccnc2)cc1)c1cc(NC(=O)C2C(c3cc(Cl)cc(Cl)c3)C2(Cl)Cl)ccc1Cl] | 17 |
| PF57 | 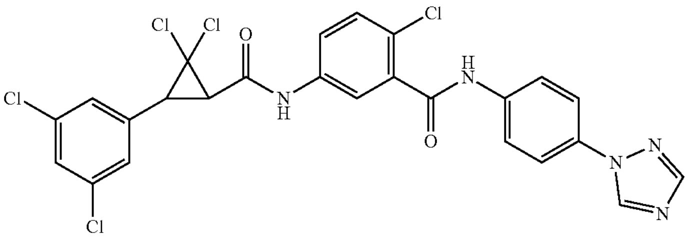 [SMILES: O=C(Nc1ccc(-n2cncn2)cc1)c1cc(NC(=O)C2C(c3cc(Cl)cc(Cl)c3)C2(Cl)Cl)ccc1Cl] | 17 |
| PF58 | 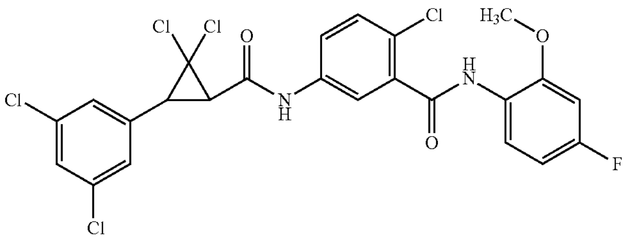 [SMILES: COc1cc(F)ccc1NC(=O)c1cc(NC(=O)C2C(c3cc(Cl)cc(Cl)c3)C2(Cl)Cl)ccc1Cl] | 15 |

TABLE 2-continued
| Structure and preparation method for F Series molecules | | |
|---|---|---|
| No. | Structure | Prep.* |
| PF59 | 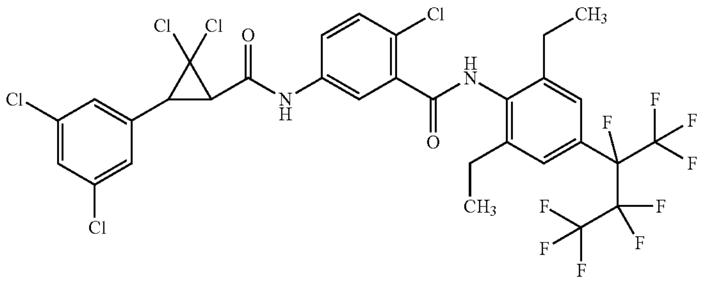 [SMILES: CCc1cc(C(F)(C(F)(F)F)C(F)(F)C(F)(F)F)cc(CC)c1NC(=O)c1cc(NC(=O)C2C(c3cc(Cl)cc(Cl)c3)C2(Cl)Cl)ccc1Cl] | 17 |
| PF60 | 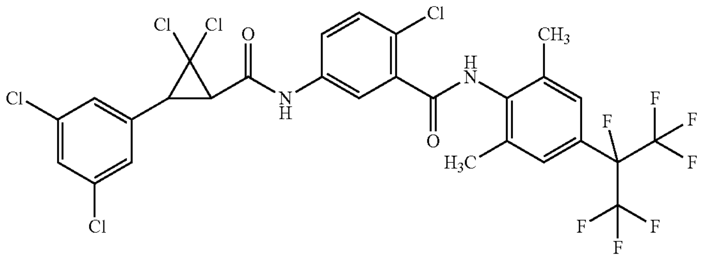 [SMILES: Cc1cc(C(F)(C(F)(F)F)C(F)(F)F)cc(C)c1NC(=O)c1cc(NC(=O)C2C(c3cc(Cl)cc(Cl)c3)C2(Cl)Cl)ccc1Cl] | 17 |
| PF61 | 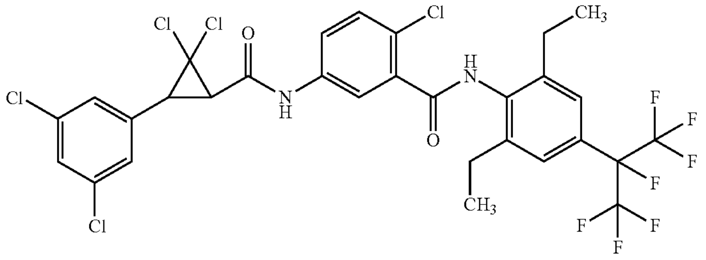 [SMILES: CCc1cc(C(F)(C(F)(F)F)C(F)(F)F)cc(CC)c1NC(=O)c1cc(NC(=O)C2C(c3cc(Cl)cc(Cl)c3)C2(Cl)Cl)ccc1Cl] | 17 |
| PF62 | 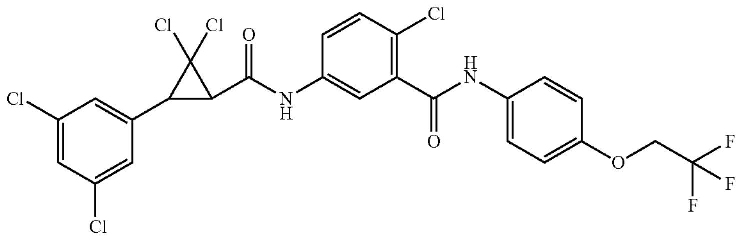 | 17 |
| PF65 | 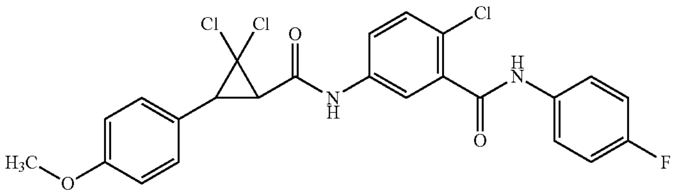 [SMILES: COc1ccc(C2C(C(=O)Nc3ccc(Cl)c(C(=O)Nc4ccc(F)cc4)c3)C2(Cl)Cl)cc1] | 13 |
| PF66 | 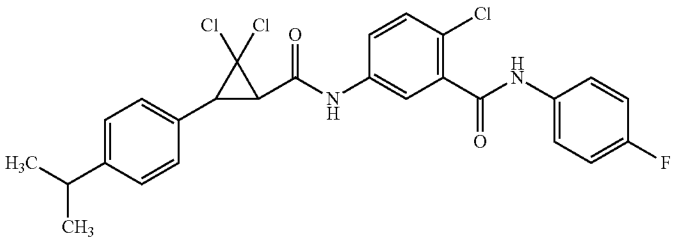 [SMILES: CC(C)c1ccc(C2C(C(=O)Nc3ccc(Cl)c(C(=O)Nc4ccc(F)cc4)c3)C2(Cl)Cl)cc1] | 13 |

TABLE 2-continued
Structure and preparation method for F Series molecules
| No. | Structure | Prep.* |
| --- | --- | --- |
| PF67 | 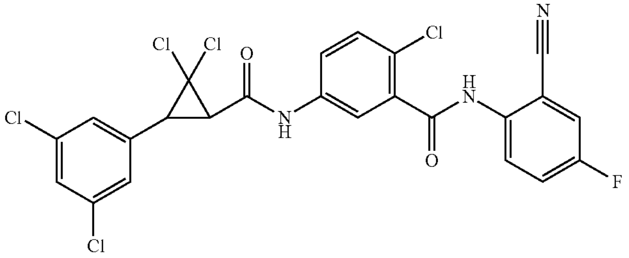 [SMILES: N#Cc1cc(F)ccc1NC(=O)c1cc(NC(=O)C2C(c3cc(Cl)cc(Cl)c3)C2(Cl)Cl)ccc1Cl] | 13 |
| PF68 | 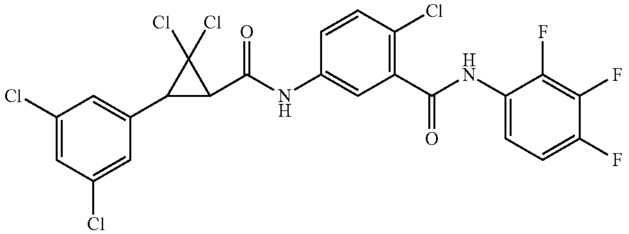 [SMILES: O=C(Nc1ccc(F)c(F)c1F)c1cc(NC(=O)C2C(c3cc(Cl)cc(Cl)c3)C2(Cl)Cl)ccc1Cl] | 13 |
| PF69 | 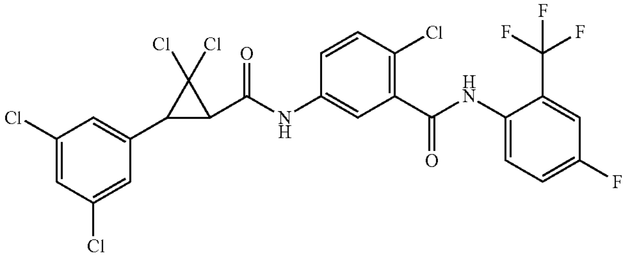 [SMILES: O=C(Nc1ccc(F)cc1C(F)(F)F)c1cc(NC(=O)C2C(c3cc(Cl)cc(Cl)c3)C2(Cl)Cl)ccc1Cl] | 58 |
| PF70 | 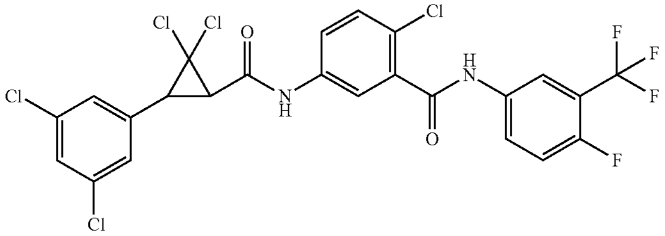 [SMILES: O=C(Nc1ccc(F)c(C(F)(F)F)c1)c1cc(NC(=O)C2C(c3cc(Cl)cc(Cl)c3)C2(Cl)Cl)ccc1Cl] | 14 |
| PF71 | 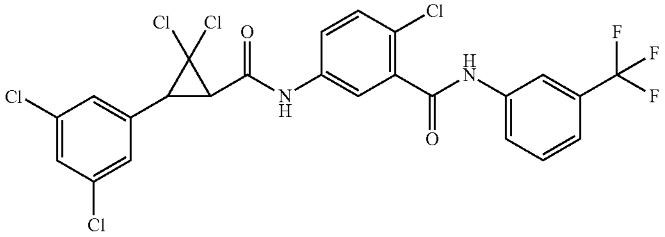 [SMILES: O=C(Nc1cccc(C(F)(F)F)c1)c1cc(NC(=O)C2C(c3cc(Cl)cc(Cl)c3)C2(Cl)Cl)ccc1Cl] | 14 |
| PF72 | 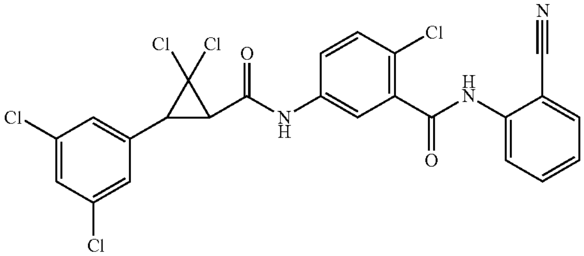 [SMILES: N#Cc1ccccc1NC(=O)c1cc(NC(=O)C2C(c3cc(Cl)cc(Cl)c3)C2(Cl)Cl)ccc1Cl] | 13 |

TABLE 2-continued
| Structure and preparation method for F Series molecules | | |
|---|---|---|
| No. | Structure | Prep.* |
| PF73 | 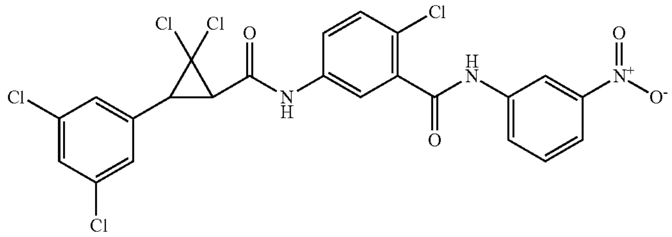 [SMILES: O=C(Nc1cccc([N+](=O)[O-])c1)c1cc(NC(=O)C2C(c3cc(Cl)cc(Cl)c3)C2(Cl)Cl)ccc1Cl] | 17 |
| PF74 | 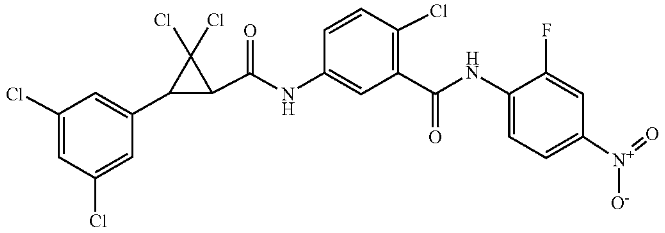 [SMILES: O=C(Nc1ccc([N+](=O)[O-])cc1F)c1cc(NC(=O)C2C(c3cc(Cl)cc(Cl)c3)C2(Cl)Cl)ccc1Cl] | 17 |
| PF75 | 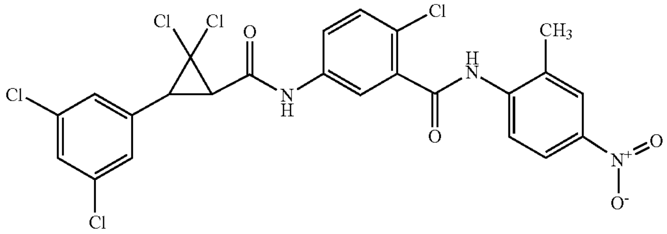 [SMILES: Cc1cc([N+](=O)[O-])ccc1NC(=O)c1cc(NC(=O)C2C(c3cc(Cl)cc(Cl)c3)C2(Cl)Cl)ccc1Cl] | 17 |
| PF76 | 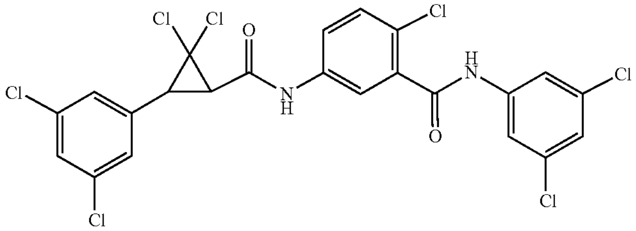 [SMILES: O=C(Nc1cc(Cl)cc(Cl)c1)c1cc(NC(=O)C2C(c3cc(Cl)cc(Cl)c3)C2(Cl)Cl)ccc1Cl] | 18 |
| PF77 | 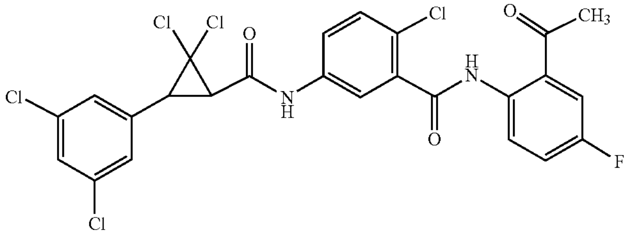 [SMILES: CC(=O)c1cc(F)ccc1NC(=O)c1cc(NC(=O)C2C(c3cc(Cl)cc(Cl)c3)C2(Cl)Cl)ccc1Cl] | 55 |
| PF78 | 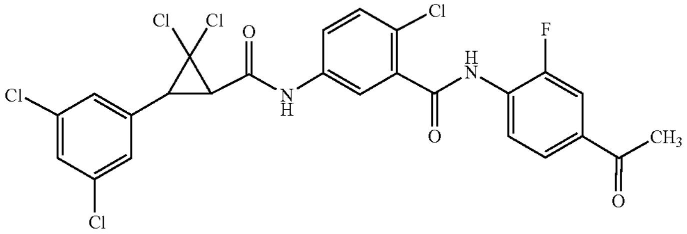 [SMILES: CC(=O)c1ccc(NC(=O)c2cc(NC(=O)C3C(c4cc(Cl)cc(Cl)c4)C3(Cl)Cl)ccc2Cl)c(F)c1] | 55 |

TABLE 2-continued
Structure and preparation method for F Series molecules
| No. | Structure | Prep.* |
| --- | --- | --- |
| PF102 | 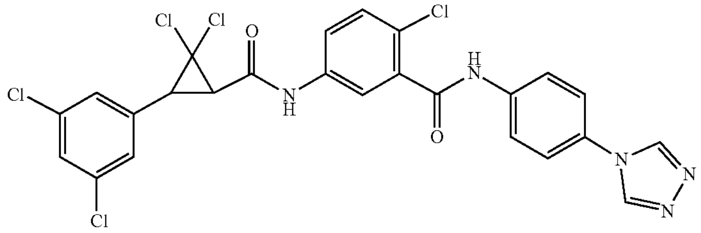 [SMILES: O=C(Nc1ccc(-n2cnnc2)cc1)c1cc(NC(=O)C2C(c3cc(Cl)cc(Cl)c3)C2(Cl)Cl)ccc1Cl] | 17 |
| PF104 | 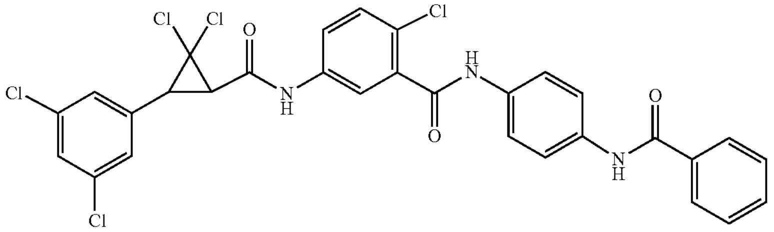 [SMILES: O=C(Nc1ccc(NC(=O)c2cc(NC(=O)C3C(c4cc(Cl)cc(Cl)c4)C3(Cl)Cl)ccc2Cl)cc1)c1ccccc1] | 67 |
| PF107 | 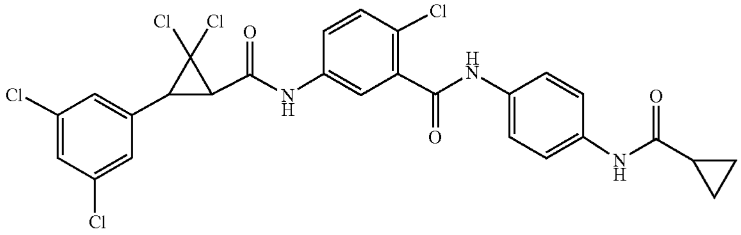 [SMILES: O=C(Nc1ccc(NC(=O)C2CC2)cc1)c1cc(NC(=O)C2C(c3cc(Cl)cc(Cl)c3)C2(Cl)Cl)ccc1Cl] | 67 |
| PF108 | 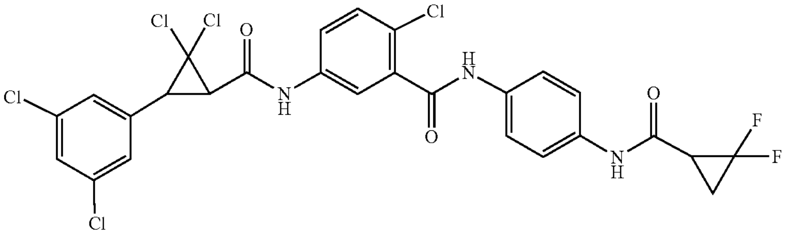 [SMILES: O=C(Nc1ccc(NC(=O)C2CC2(F)F)cc1)c1cc(NC(=O)C2C(c3cc(Cl)cc(Cl)c3)C2(Cl)Cl)ccc1Cl] | 68 |
| PF109 | 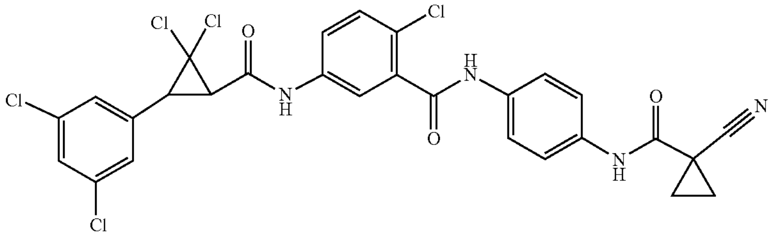 [SMILES: N#CC1(C(=O)Nc2ccc(NC(=O)c3cc(NC(=O)C4C(c5cc(Cl)cc(Cl)c5)C4(Cl)Cl)ccc3Cl)cc2)CC1] | 68 |
| PF110 | 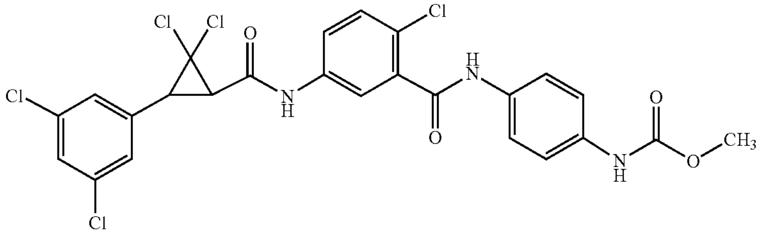 [SMILES: COC(=O)Nc1ccc(NC(=O)c2cc(NC(=O)C3C(c4cc(Cl)cc(Cl)c4)C3(Cl)Cl)ccc2Cl)cc1] | 15 |

TABLE 2-continued
| Structure and preparation method for F Series molecules | | |
|---|---|---|
| No. | Structure | Prep.* |
| PF113 | 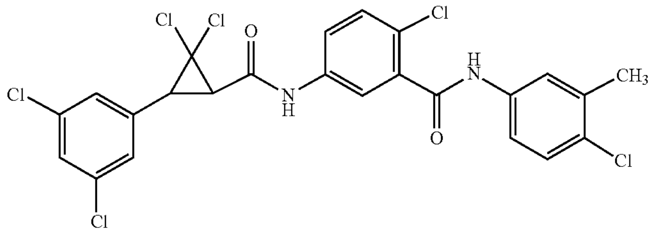 [SMILES: Cc1cc(NC(=O)c2cc(NC(=O)C3C(c4cc(Cl)cc(Cl)c4)C3(Cl)Cl)ccc2Cl)ccc1Cl] | 14 |
| PF114 | 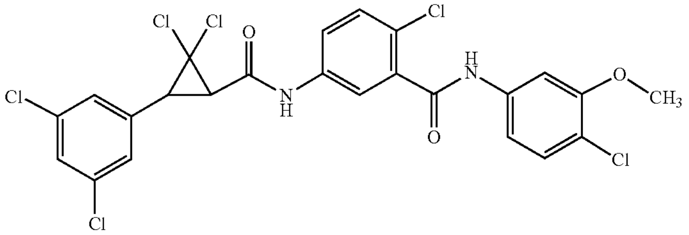 [SMILES: COc1cc(NC(=O)c2cc(NC(=O)C3C(c4cc(Cl)cc(Cl)c4)C3(Cl)Cl)ccc2Cl)ccc1Cl] | 14 |
| PF115 | 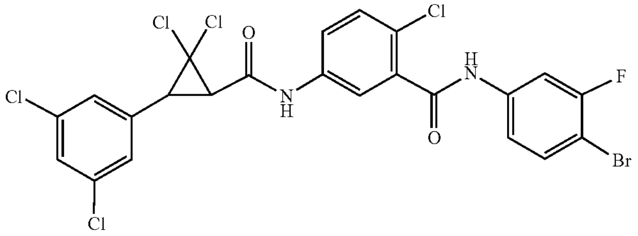 [SMILES: O=C(Nc1ccc(Br)c(F)c1)c1cc(NC(=O)C2C(c3cc(Cl)cc(Cl)c3)C2(Cl)Cl)ccc1Cl] | 14 |
| PF116 | 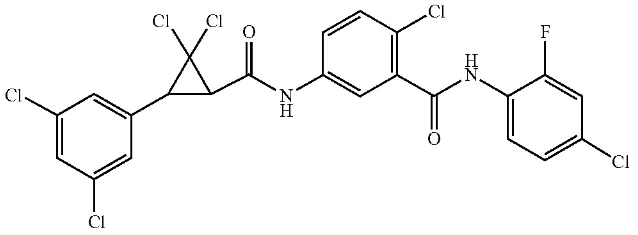 [SMILES: O=C(Nc1ccc(Cl)cc1F)c1cc(NC(=O)C2C(c3cc(Cl)cc(Cl)c3)C2(Cl)Cl)ccc1Cl] | 14 |
| PF117 | 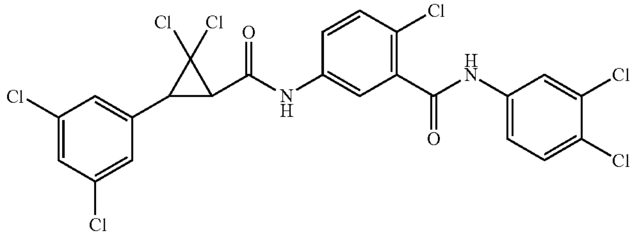 | 14 |
| PF118 | 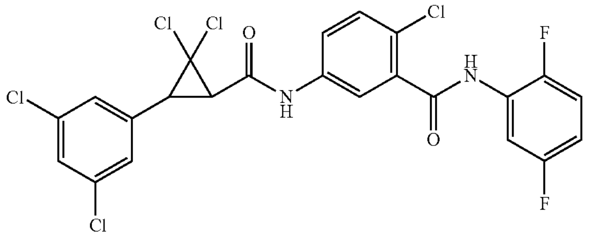 [SMILES: O=C(Nc1cc(F)ccc1F)c1cc(NC(=O)C2C(c3cc(Cl)cc(Cl)c3)C2(Cl)Cl)ccc1Cl] | 14 |

TABLE 2-continued
Structure and preparation method for F Series molecules
| No. | Structure | Prep.* |
|---|---|---|
| PF119 | 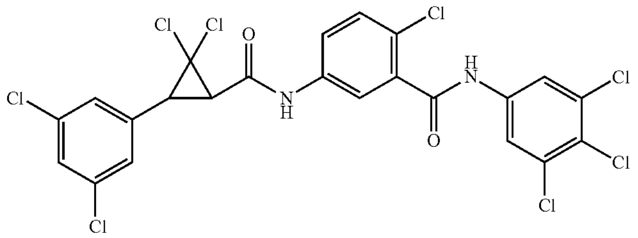 [SMILES: O=C(Nc1cc(Cl)c(Cl)c(Cl)c1)c1cc(NC(=O)C2C(c3cc(Cl)cc(Cl)c3)C2(Cl)Cl)ccc1Cl] | 13 |
| PF120 | 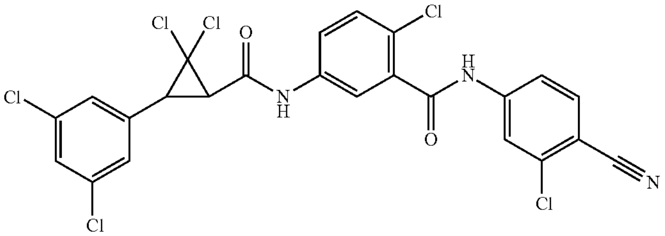 [SMILES: N#Cc1ccc(NC(=O)c2cc(NC(=O)C3C(c4cc(Cl)cc(Cl)c4)C3(Cl)Cl)ccc2Cl)cc1Cl] | 14 |
| PF122 | 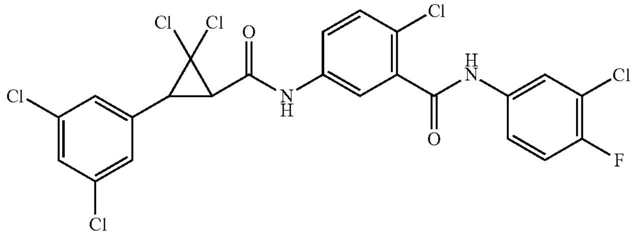 [SMILES: O=C(Nc1ccc(F)c(Cl)c1)c1cc(NC(=O)C2C(c3cc(Cl)cc(Cl)c3)C2(Cl)Cl)ccc1Cl] | 14 |
| PF123 | 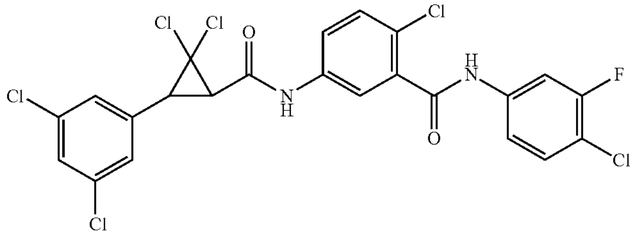 [SMILES: O=C(Nc1ccc(Cl)c(F)c1)c1cc(NC(=O)C2C(c3cc(Cl)cc(Cl)c3)C2(Cl)Cl)ccc1Cl] | 14 |
| PF124 | 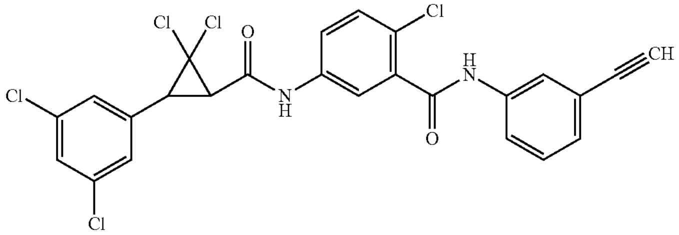 [SMILES: C#Cc1cccc(NC(=O)c2cc(NC(=O)C3C(c4cc(Cl)cc(Cl)c4)C3(Cl)Cl)ccc2Cl)c1] | 14 |
| PF125 | 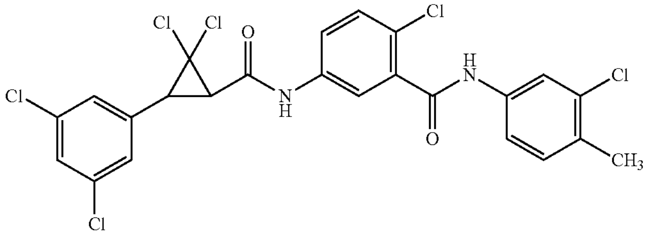 [SMILES: Cc1ccc(NC(=O)c2cc(NC(=O)C3C(c4cc(Cl)cc(Cl)c4)C3(Cl)Cl)ccc2Cl)cc1Cl] | 14 |

TABLE 2-continued
| Structure and preparation method for F Series molecules | | |
|---|---|---|
| No. | Structure | Prep.* |
| PF126 | 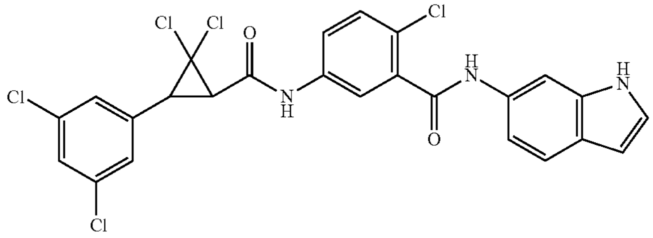 [SMILES: O=C(Nc1ccc2cc[nH]c2c1)c1cc(NC(=O)C2C(c3cc(Cl)cc(Cl)c3)C2(Cl)Cl)ccc1Cl] | 14 |
| PF127 | 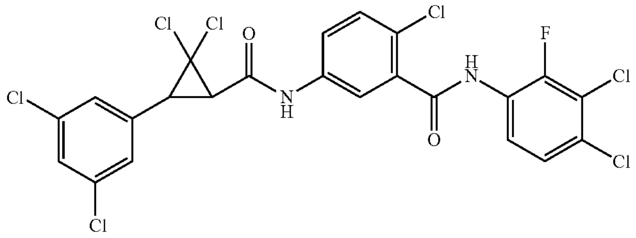 [SMILES: O=C(Nc1ccc(Cl)c(Cl)c1F)c1cc(NC(=O)C2C(c3cc(Cl)cc(Cl)c3)C2(Cl)Cl)ccc1Cl] | 14 |
| PF130 | 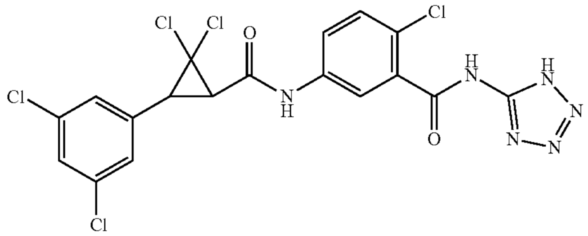 [SMILES: O=C(Nc1nnn[nH]1)c1cc(NC(=O)C2C(c3cc(Cl)cc(Cl)c3)C2(Cl)Cl)ccc1Cl] | 17 |
| PF133 | 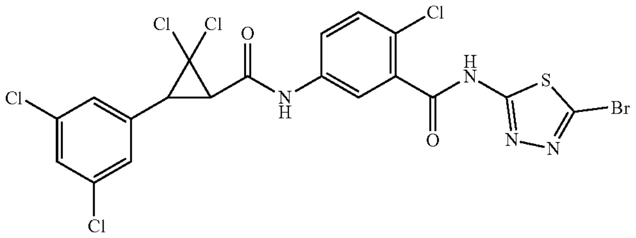 [SMILES: O=C(Nc1nnc(Br)s1)c1cc(NC(=O)C2C(c3cc(Cl)cc(Cl)c3)C2(Cl)Cl)ccc1Cl] | 55 |
| PF134 | 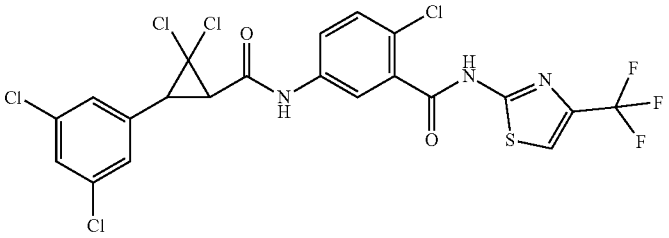 [SMILES: O=C(Nc1nc(C(F)(F)F)cs1)c1cc(NC(=O)C2C(c3cc(Cl)cc(Cl)c3)C2(Cl)Cl)ccc1Cl] | 13 |
| PF135 | 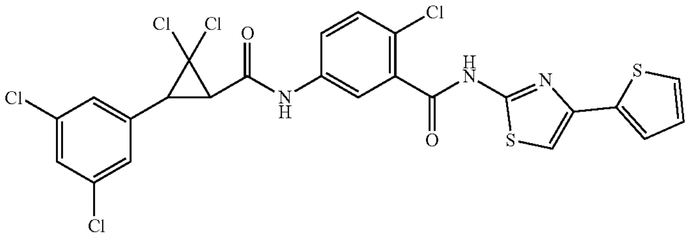 [SMILES: O=C(Nc1nc(-c2cccs2)cs1)c1cc(NC(=O)C2C(c3cc(Cl)cc(Cl)c3)C2(Cl)Cl)ccc1Cl] | 55 |

TABLE 2-continued
| Structure and preparation method for F Series molecules | | |
|---|---|---|
| No. | Structure | Prep.* |
| PF136 | 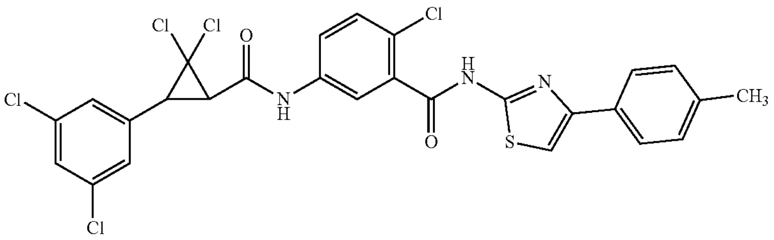 [SMILES: Cc1ccc(-c2csc(NC(=O)c3cc(NC(=O)C4C(c5cc(Cl)cc(Cl)c5)C4(Cl)Cl)ccc3Cl)n2)cc1] | 15 |
| PF138 | 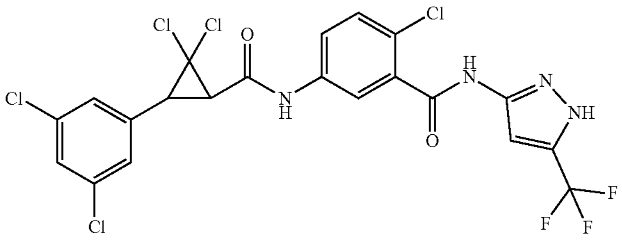 [SMILES: O=C(Nc1cc(C(F)(F)F)[nH]n1)c1cc(NC(=O)C2C(c3cc(Cl)cc(Cl)c3)C2(Cl)Cl)ccc1Cl] | 13 |
| PF139 | 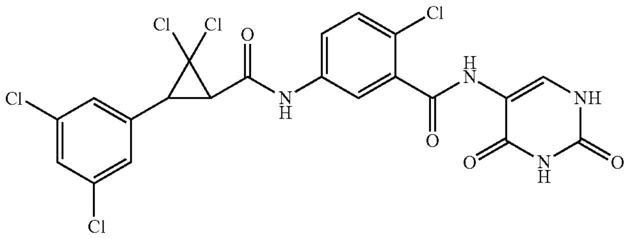 [SMILES: O=C(Nc1c[nH]c(=O)[nH]c1=O)c1cc(NC(=O)C2C(c3cc(Cl)cc(Cl)c3)C2(Cl)Cl)ccc1Cl] | 13 |
| PF140 | 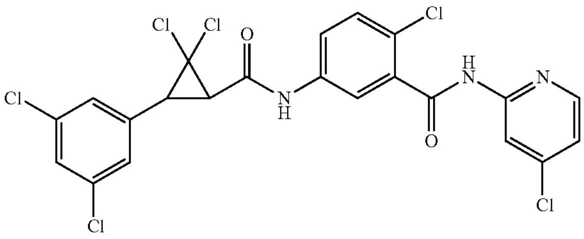 [SMILES: O=C(Nc1cc(Cl)ccn1)c1cc(NC(=O)C2C(c3cc(Cl)cc(Cl)c3)C2(Cl)Cl)ccc1Cl] | 13 |
| PF141 | 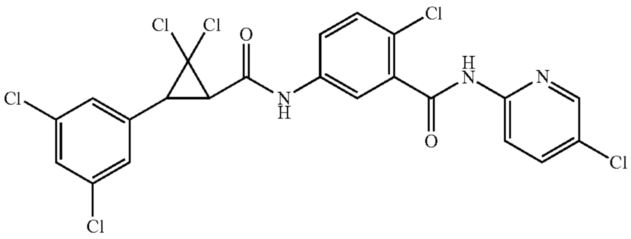 [SMILES: O=C(Nc1ccc(Cl)cn1)c1cc(NC(=O)C2C(c3cc(Cl)cc(Cl)c3)C2(Cl)Cl)ccc1Cl] | 13 |
| PF143 | 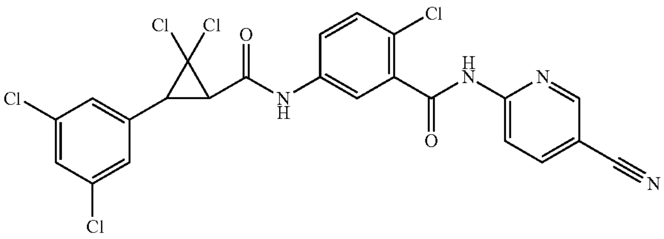 [SMILES: N#Cc1ccc(NC(=O)c2cc(NC(=O)C3C(c4cc(Cl)cc(Cl)c4)C3(Cl)Cl)ccc2Cl)nc1] | 55 |

TABLE 2-continued
| Structure and preparation method for F Series molecules | | |
|---|---|---|
| No. | Structure | Prep.* |
| PF148 | 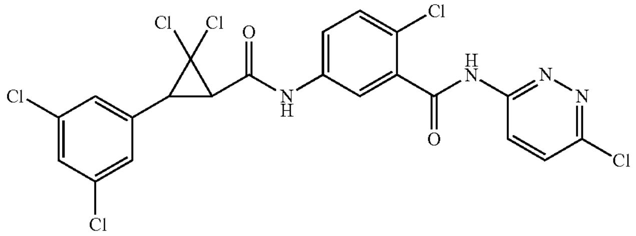 [SMILES: O=C(Nc1ccc(Cl)nn1)c1cc(NC(=O)C2C(c3cc(Cl)cc(Cl)c3)C2(Cl)Cl)ccc1Cl] | 13 |
| PF152 | 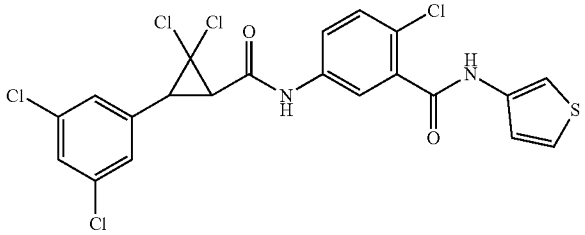 [SMILES: O=C(Nc1ccsc1)c1cc(NC(=O)C2C(c3cc(Cl)cc(Cl)c3)C2(Cl)Cl)ccc1Cl] | 15 |
| PF153 | 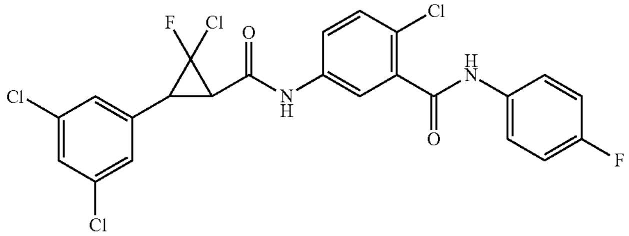 [SMILES: O=C(Nc1ccc(F)cc1)c1cc(NC(=O)C2C(c3cc(Cl)cc(Cl)c3)C2(F)Cl)ccc1Cl] | 13 |
| PF155 | 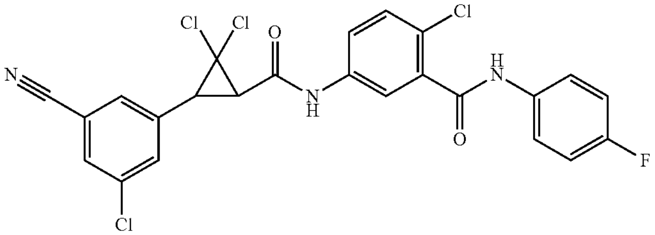 [SMILES: N#Cc1cc(Cl)cc(C2C(C(=O)Nc3ccc(Cl)c(C(=O)Nc4ccc(F)cc4)c3)C2(Cl)Cl)c1] | 13 |
| PF156 | 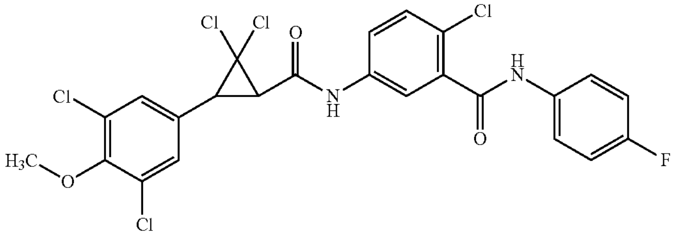 [SMILES: COc1c(Cl)cc(C2C(C(=O)Nc3ccc(Cl)c(C(=O)Nc4ccc(F)cc4)c3)C2(Cl)Cl)cc1Cl] | 56 |
| PF158 | 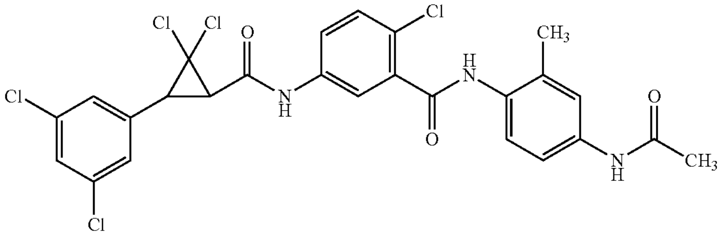 [SMILES: CC(=O)Nc1ccc(NC(=O)c2cc(NC(=O)C3C(c4cc(Cl)cc(Cl)c4)C3(Cl)Cl)ccc2Cl)c(C)c1] | 13 |

TABLE 2-continued
| Structure and preparation method for F Series molecules | | |
|---|---|---|
| No. | Structure | Prep.* |
| PF161 | 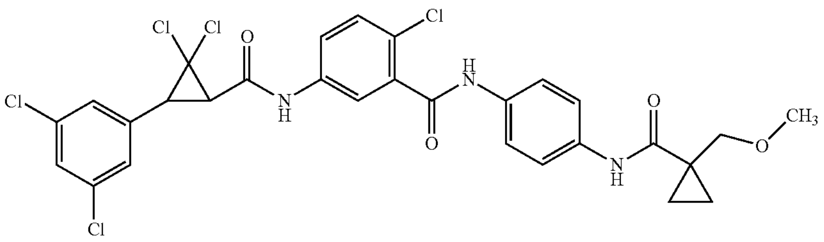 [SMILES: COCC1(C(=O)Nc2ccc(NC(=O)c3cc(NC(=O)C4C(c5cc(Cl)cc(Cl)c5)C4(Cl)Cl)ccc3Cl)cc2)CC1] | 68 |
| PF162 | 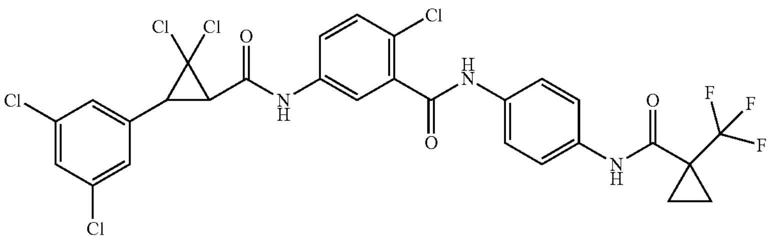 [SMILES: O=C(Nc1ccc(NC(=O)C2(C(F)(F)F)CC2)cc1)c1cc(NC(=O)C2C(c3cc(Cl)cc(Cl)c3)C2(Cl)Cl)ccc1Cl] | 68 |
| PF163 | 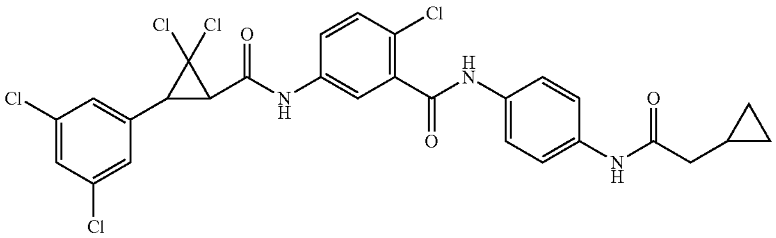 [SMILES: O=C(CC1CC1)Nc1ccc(NC(=O)c2cc(NC(=O)C3C(c4cc(Cl)cc(Cl)c4)C3(Cl)Cl)ccc2Cl)cc1] | 67 |
| PF164 | 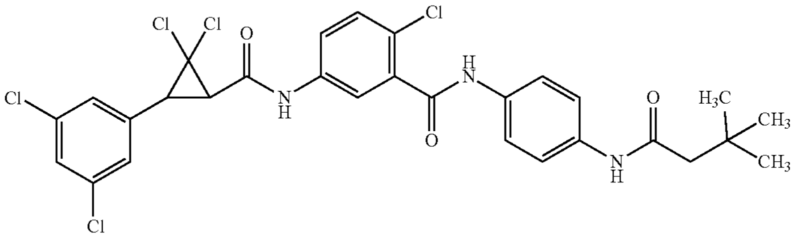 [SMILES: CC(C)(C)CC(=O)Nc1ccc(NC(=O)c2cc(NC(=O)C3C(c4cc(Cl)cc(Cl)c4)C3(Cl)Cl)ccc2Cl)cc1] | 68 |
*prepared according to example number
TABLE 3
| Structure and preparation method for C series molecules | | |
|---|---|---|
| No. | Structure | Prep* |
| C1 | 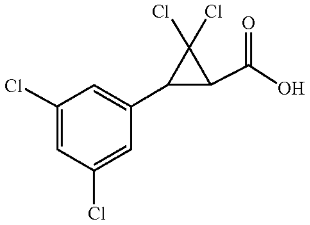 [SMILES: O=C(O)C1C(c2cc(Cl)cc(Cl)c2)C1(Cl)Cl] | 1 |

TABLE 3-continued
| Structure and preparation method for C series molecules | | |
|---|---|---|
| No. | Structure | Prep* |
| C2 | 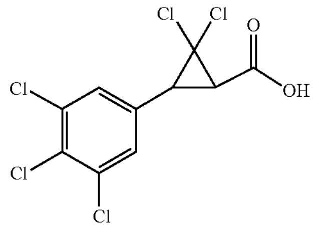 [SMILES: O=C(O)C1C(c2cc(Cl)c(Cl)c(Cl)c2)C1(Cl)Cl] | 1 |
| C3 | 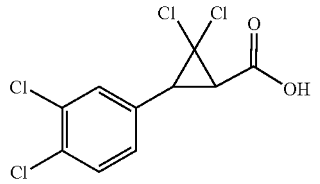 [SMILES: O=C(O)C1C(c2ccc(Cl)c(Cl)c2)C1(Cl)Cl] | 1 |
| C4 | 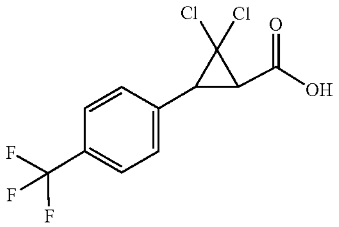 [SMILES: O=C(O)C1C(c2ccc(C(F)(F)F)cc2)C1(Cl)Cl] | 2 |
| C5 | 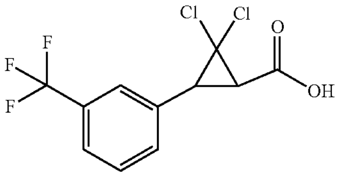 [SMILES: O=C(O)C1C(c2cccc(C(F)(F)F)c2)C1(Cl)Cl] | 2 |
| C6 | 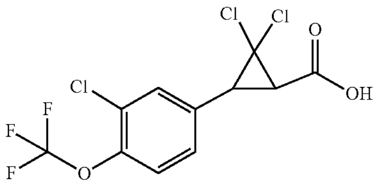 [SMILES: O=C(O)C1C(c2ccc(OC(F)(F)F)c(Cl)c2)C1(Cl)Cl] | 2 |
| C7 | 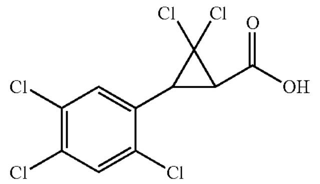 [SMILES: O=C(O)C1C(c2cc(Cl)c(Cl)cc2Cl)C1(Cl)Cl] | 2 |
| C8 | 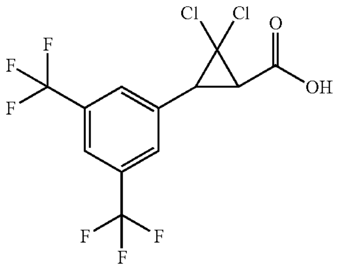 [SMILES: O=C(O)C1C(c2cc(C(F)(F)F)cc(C(F)(F)F)c2)C1(Cl)Cl] | 2 |

TABLE 3-continued
| Structure and preparation method for C series molecules | | |
|---|---|---|
| No. | Structure | Prep* |
| C9 | 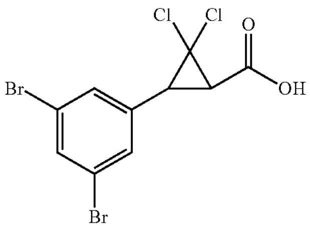 | 2 |
| C10 | 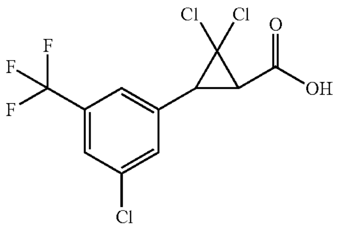 [SMILES: O=C(O)C1C(c2cc(Cl)cc(C(F)(F)F)c2)C1(Cl)Cl] | 2 |
| C11 | 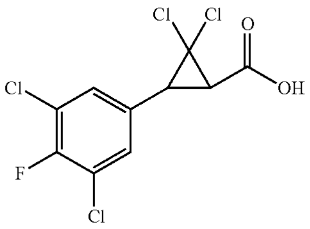 | 2 |
| C12 | 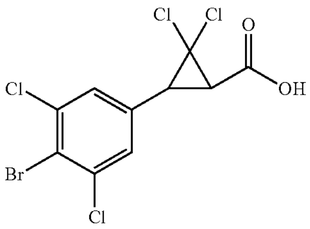 | 2 |
| C13 | 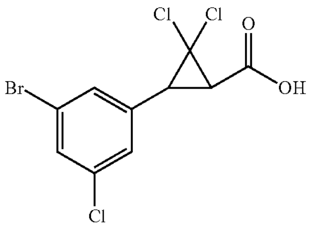 | 2 |
| C14 | 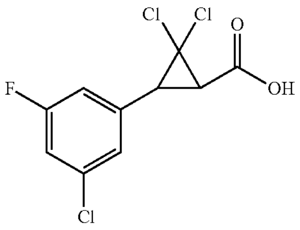 [SMILES: O=C(O)C1C(c2cc(F)cc(Cl)c2)C1(Cl)Cl] | 2 |

TABLE 3-continued
| Structure and preparation method for C series molecules | | |
|---|---|---|
| No. | Structure | Prep* |
| C15 | 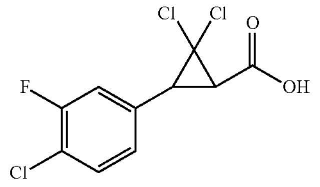 | 2 |
| C16 | 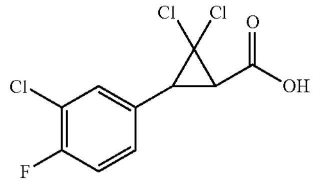 | 2 |
| C17 | 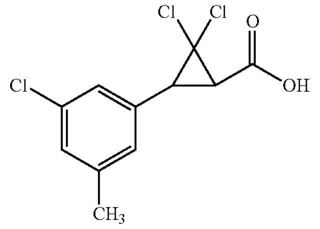 [SMILES: Cc1cc(Cl)cc(C2C(C(=O)O)C2(Cl)Cl)c1] | 2 |
| C18 | 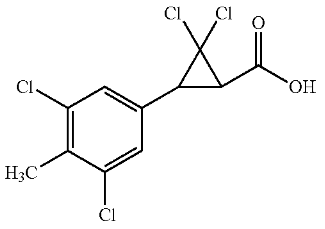 [SMILES: Cc1c(Cl)cc(C2C(C(=O)O)C2(Cl)Cl)cc1Cl] | 2 |
| C19 | 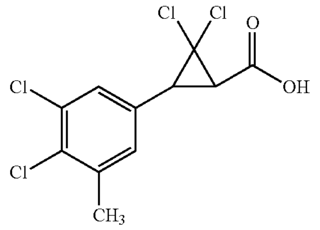 [SMILES: Cc1cc(C2C(C(=O)O)C2(Cl)Cl)cc(Cl)c1Cl] | 2 |
| C20 | 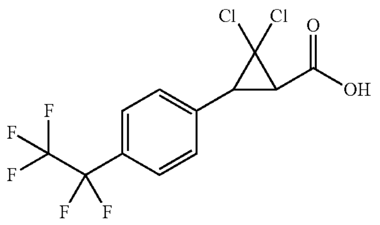 [SMILES: O=C(O)C1C(c2ccc(C(F)(F)C(F)(F)F)cc2)C1(Cl)Cl] | 2 |
| C21 | 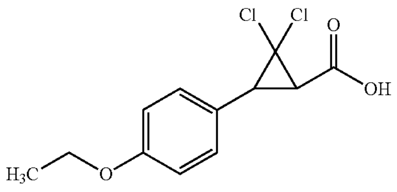 [SMILES: CCOc1ccc(C2C(C(=O)O)C2(Cl)Cl)cc1] | 2 |

TABLE 3-continued
| Structure and preparation method for C series molecules | | |
|---|---|---|
| No. | Structure | Prep* |
| C22 | 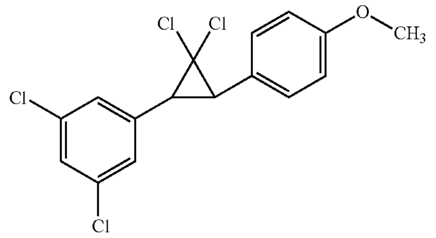 [SMILES: COc1ccc(C2C(c3cc(Cl)cc(Cl)c3)C2(Cl)Cl)cc1] | 3 |
| C23 | 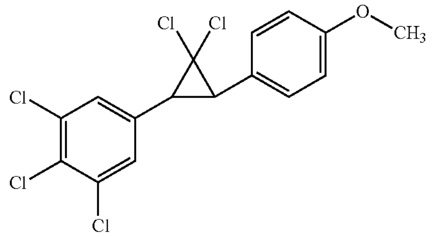 [SMILES: COc1ccc(C2C(c3cc(Cl)c(Cl)c(Cl)c3)C2(Cl)Cl)cc1] | 3 |
| C24 | 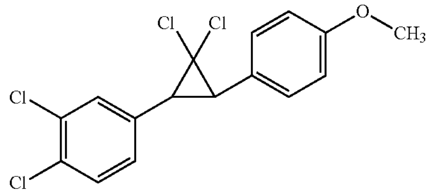 [SMILES: COc1ccc(C2C(c3ccc(Cl)c(Cl)c3)C2(Cl)Cl)cc1] | 3 |
| C25 | 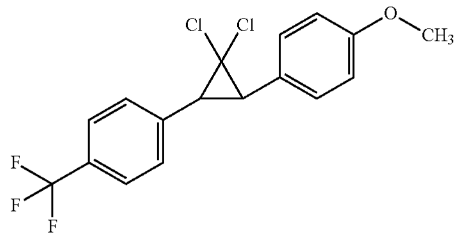 [SMILES: COc1ccc(C2C(c3ccc(C(F)(F)F)cc3)C2(Cl)Cl)cc1] | 4 |
| C26 | 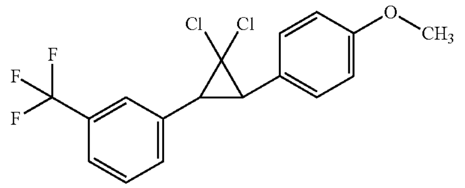 [SMILES: COc1ccc(C2C(c3cccc(C(F)(F)F)c3)C2(Cl)Cl)cc1] | 4 |
| C27 | 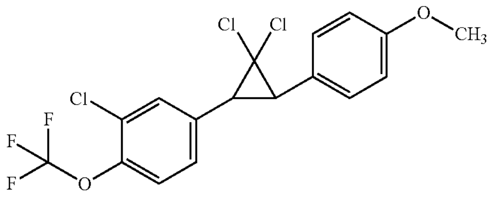 [SMILES: COc1ccc(C2C(c3ccc(OC(F)(F)F)c(Cl)c3)C2(Cl)Cl)cc1] | 4 |
| C28 | 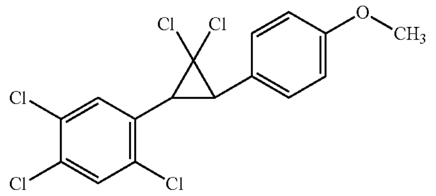 [SMILES: COc1ccc(C2C(c3cc(Cl)c(Cl)cc3Cl)C2(Cl)Cl)cc1] | 4 |

TABLE 3-continued
| Structure and preparation method for C series molecules | | |
|---|---|---|
| No. | Structure | Prep* |
| C29 | 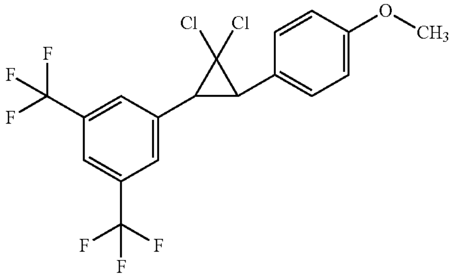 [SMILES: COc1ccc(C2C(c3cc(C(F)(F)F)cc(C(F)(F)F)c3)C2(Cl)Cl)cc1] | 4 |
| C30 | 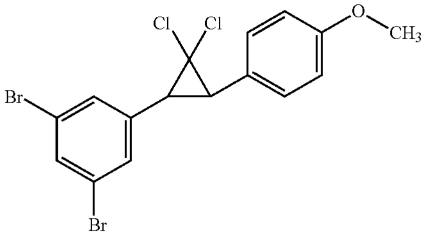 [SMILES: COc1ccc(C2C(c3cc(Br)cc(Br)c3)C2(Cl)Cl)cc1] | 4 |
| C31 | 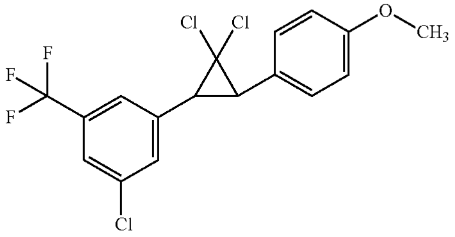 [SMILES: COc1ccc(C2C(c3cc(Cl)cc(C(F)(F)F)c3)C2(Cl)Cl)cc1] | 4 |
| C32 | 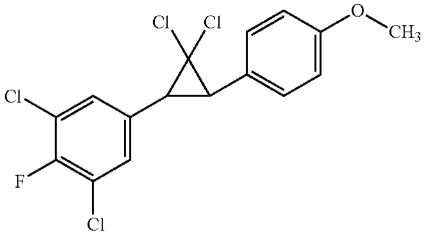 | 4 |
| C33 | 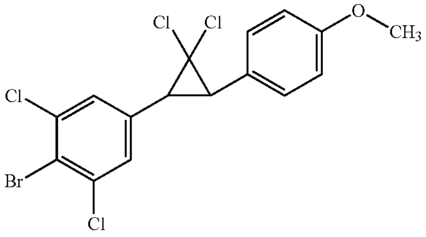 [SMILES: COc1ccc(C2C(c3cc(Cl)c(F)c(Cl)c3)C2(Cl)Cl)cc1] | 4 |
| C34 | 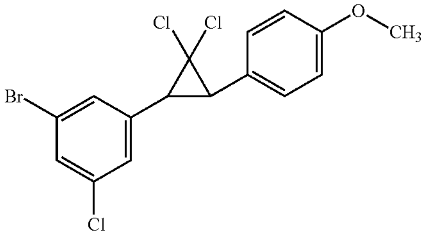 [SMILES: COc1ccc(C2C(c3cc(Cl)cc(Br)c3)C2(Cl)Cl)cc1] | 4 |

TABLE 3-continued
| Structure and preparation method for C series molecules | | |
|---|---|---|
| No. | Structure | Prep* |
| C35 | 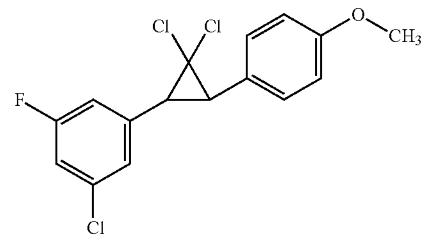 [SMILES: COc1ccc(C2C(c3cc(F)cc(Cl)c3)C2(Cl)Cl)cc1] | 4 |
| C36 | 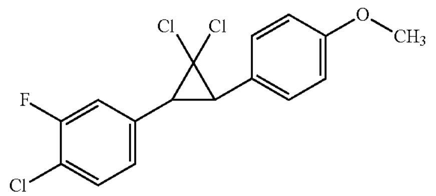 [SMILES: COc1ccc(C2C(c3ccc(Cl)c(F)c3)C2(Cl)Cl)cc1] | 4 |
| C37 | 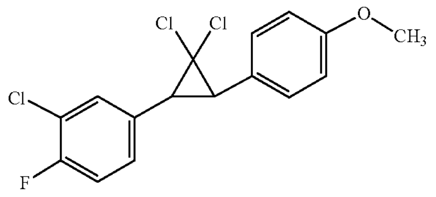 [SMILES: COc1ccc(C2C(c3ccc(F)c(Cl)c3)C2(Cl)Cl)cc1] | 4 |
| C38 | 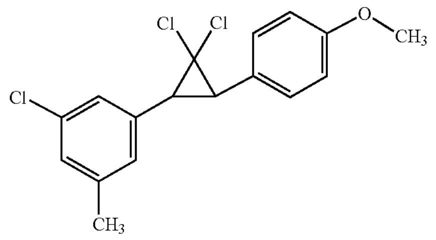 [SMILES: COc1ccc(C2C(c3cc(C)cc(Cl)c3)C2(Cl)Cl)cc1] | 4 |
| C39 | 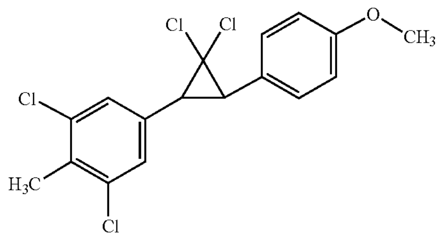 [SMILES: COc1ccc(C2C(c3cc(Cl)c(C)c(Cl)c3)C2(Cl)Cl)cc1] | 4 |
| C40 | 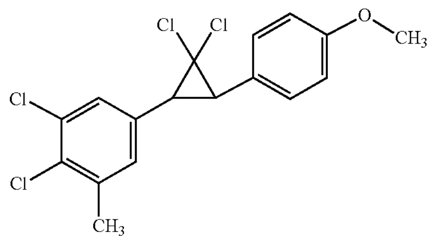 [SMILES: COc1ccc(C2C(c3cc(C)c(Cl)c(Cl)c3)C2(Cl)Cl)cc1] | 4 |

TABLE 3-continued
Structure and preparation method for C series molecules
| No. | Structure | Prep* |
|---|---|---|
| C41 | 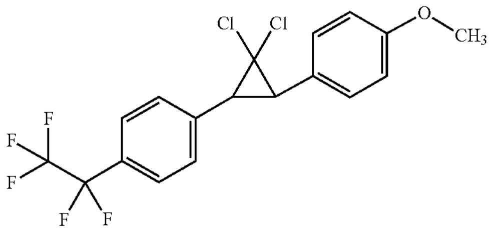 [SMILES: COc1ccc(C2C(c3ccc(C(F)(F)C(F)(F)F)cc3)C2(Cl)Cl)cc1] | 4 |
| C42 | 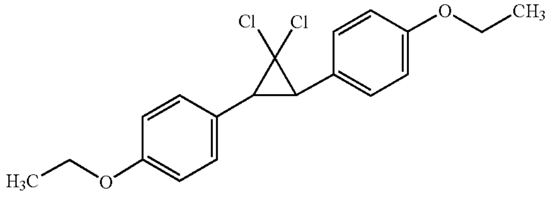 [SMILES: CCOc1ccc(C2C(c3ccc(OCC)cc3)C2(Cl)Cl)cc1] | 4 |
| C43 | 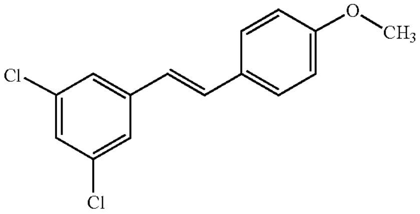 [SMILES: COc1ccc(/C=C/c2cc(Cl)cc(Cl)c2)cc1] | 5 |
| C44 | 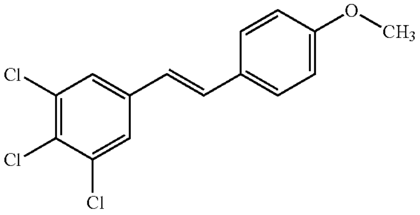 [SMILES: COc1ccc(/C=C/c2cc(Cl)c(Cl)c(Cl)c2)cc1] | 5 |
| C45 | 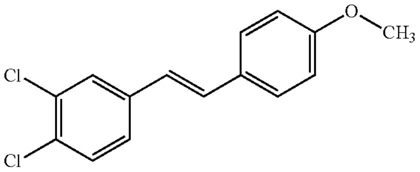 [SMILES: COc1ccc(/C=C/c2ccc(Cl)c(Cl)c2)cc1] | 5 |
| C46 | 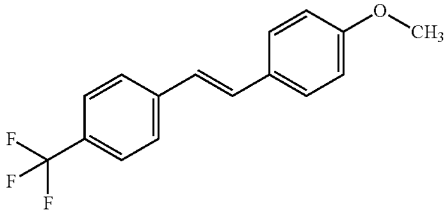 [SMILES: COc1ccc(/C=C/c2ccc(C(F)(F)F)cc2)cc1] | 6 |
| C47 | 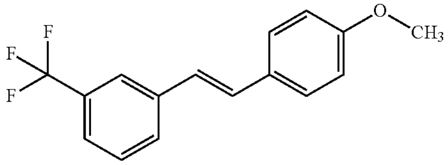 [SMILES: COc1ccc(/C=C/c2cccc(C(F)(F)F)c2)cc1] | 6 |

TABLE 3-continued
| Structure and preparation method for C series molecules | | |
|---|---|---|
| No. | Structure | Prep* |
| C48 | 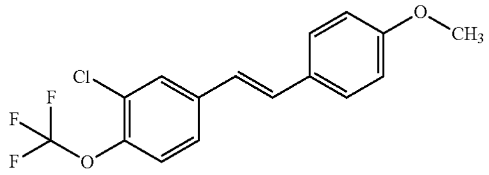 [SMILES: COc1ccc(/C=C/c2ccc(OC(F)(F)F)c(Cl)c2)cc1] | 6 |
| C49 | 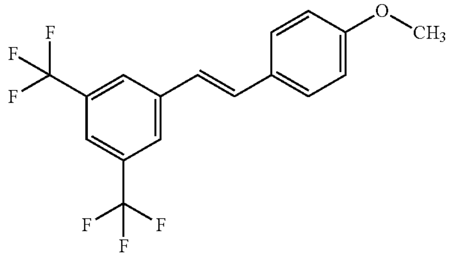 [SMILES: COc1ccc(/C=C/c2cc(C(F)(F)F)cc(C(F)(F)F)c2)cc1] | 6 |
| C50 | 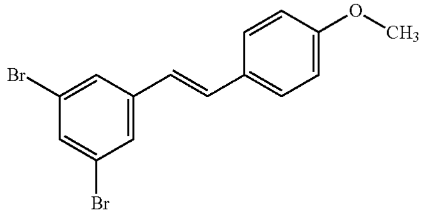 [SMILES: COc1ccc(/C=C/c2cc(Br)cc(Br)c2)cc1] | 6 |
| C51 | 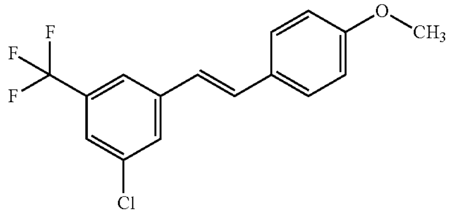 [SMILES: COc1ccc(/C=C/c2cc(Cl)cc(C(F)(F)F)c2)cc1] | 6 |
| C52 | 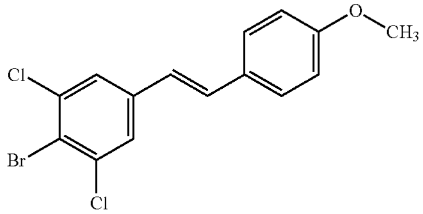 [SMILES: COc1ccc(/C=C/c2cc(Cl)c(Br)c(Cl)c2)cc1] | 6 |
| C53 | 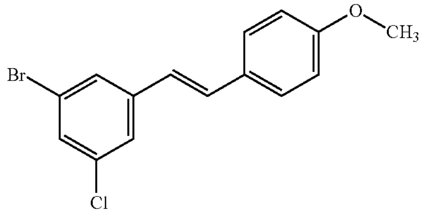 [SMILES: COc1ccc(/C=C/c2cc(Cl)cc(Br)c2)cc1] | 6 |
| C54 | 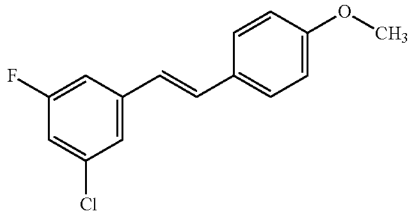 [SMILES: COc1ccc(/C=C/c2cc(F)cc(Cl)c2)cc1] | 6 |

TABLE 3-continued
Structure and preparation method for C series molecules
| No. | Structure | Prep* |
|---|---|---|
| C55 | 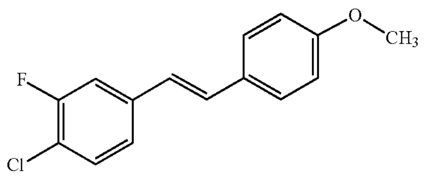 [SMILES: COc1ccc(/C=C/c2ccc(Cl)c(F)c2)cc1] | 6 |
| C56 | 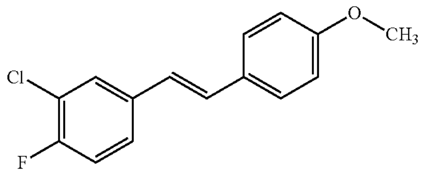 | 6 |
| C57 | 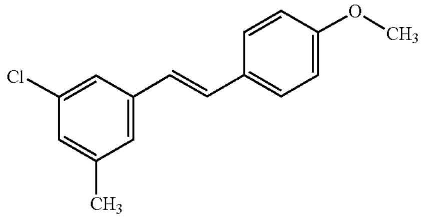 [SMILES: COc1ccc(/C=C/c2cc(C)cc(Cl)c2)cc1] | 6 |
| C58 | 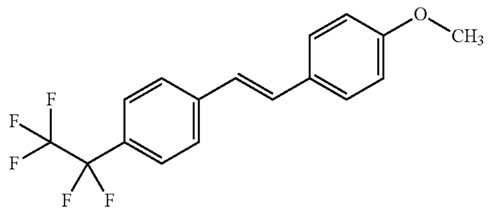 [SMILES: COc1ccc(/C=C/c2ccc(C(F)(F)C(F)(F)F)cc2)cc1] | 6 |
| C59 | 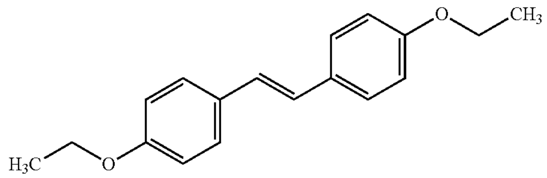 [SMILES: CCOc1ccc(/C=C/c2ccc(OCC)cc2)cc1] | 6 |
| C60 | 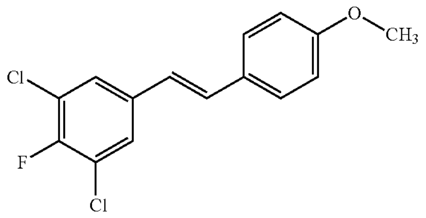 [SMILES: COc1ccc(/C=C/c2cc(Cl)c(F)c(Cl)c2)cc1] | 7 |
| C61 | 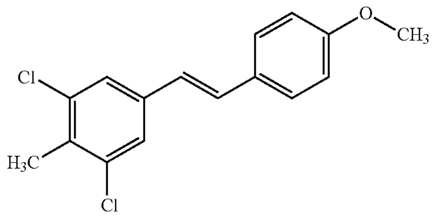 | 7 |

TABLE 3-continued
| No. | Structure | Prep* |
|---|---|---|
| C62 | 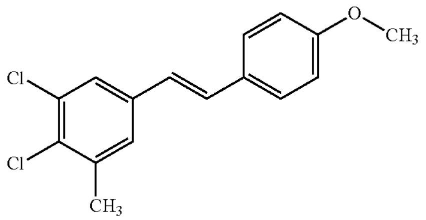 [SMILES: COc1ccc(/C=C/c2cc(C)c(Cl)c(Cl)c2)cc1] | 7 |
| C63 | 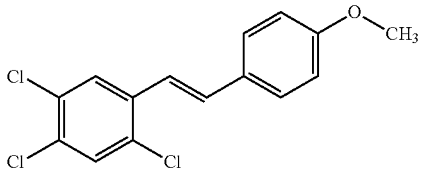 [SMILES: COc1ccc(/C=C/c2cc(Cl)c(Cl)cc2Cl)cc1] | 8 |
| C64 | 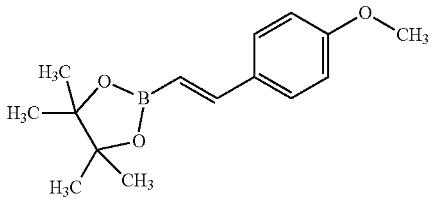 | 9 |
| C65 | 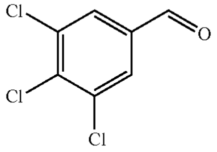 [SMILES: O=Cc1cc(Cl)c(Cl)c(Cl)c1] | 10 |
| C66 | 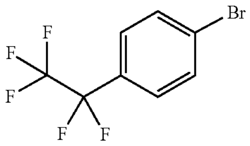 [SMILES: FC(F)(F)C(F)(F)c1ccc(Br)cc1] | 11 |
| C67 | 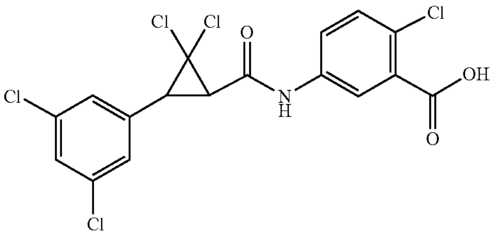 [SMILES: O=C(O)c1cc(NC(=O)C2C(c3cc(Cl)cc(Cl)c3)C2(Cl)Cl)ccc1Cl] | 12 |
| C68 | 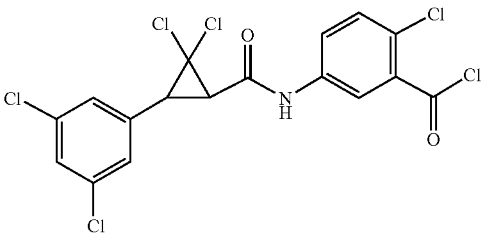 [SMILES: O=C(Cl)c1cc(NC(=O)C2C(c3cc(Cl)cc(Cl)c3)C2(Cl)Cl)ccc1Cl] | 21 |
Structure and preparation method for C series molecules TABLE 3-continued
| Structure and preparation method for C series molecules | | |
|---|---|---|
| No. | Structure | Prep* |
| C69 | 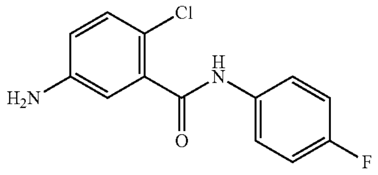 | 22 |
| C70 | 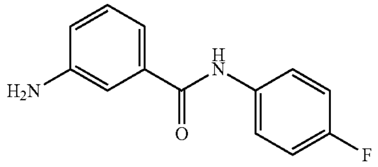 [SMILES: Nc1cccc(C(=O)Nc2ccc(F)cc2)c1] | 22 |
| C71 | 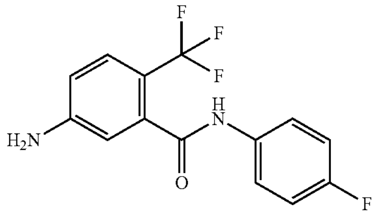 [SMILES: Nc1ccc(C(F)(F)F)c(C(=O)Nc2ccc(F)cc2)c1] | 23 |
| C72 | 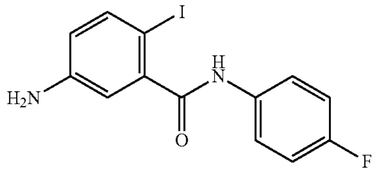 | 23 |
| C73 | 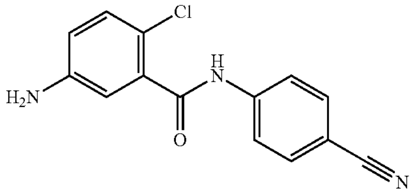 [SMILES: N#Cc1ccc(NC(=O)c2cc(N)ccc2Cl)cc1] | 23 |
| C74 | 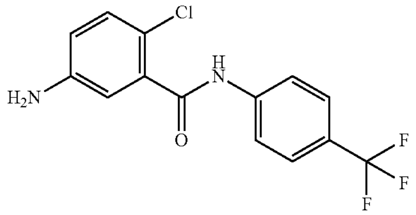 [SMILES: Nc1ccc(Cl)c(C(=O)Nc2ccc(C(F)(F)F)cc2)c1] | 23 |
| C75 | 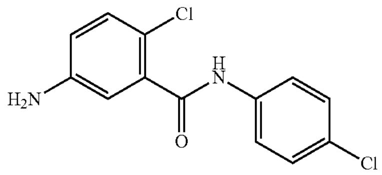 [SMILES: Nc1ccc(Cl)c(C(=O)Nc2ccc(Cl)cc2)c1] | 23 |
| C76 | 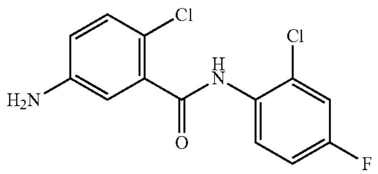 | 23 |

TABLE 3-continued
| Structure and preparation method for C series molecules | | |
|---|---|---|
| No. | Structure | Prep* |
| C77 | 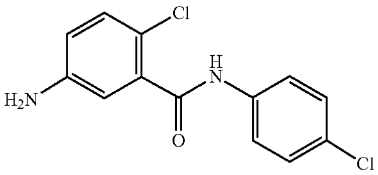 [SMILES: Nc1ccc(Cl)c(C(=O)Nc2ccc(Cl)cc2)c1] | 23 |
| C78 | 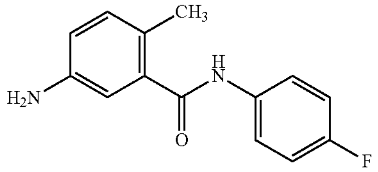 | 23 |
| C79 | 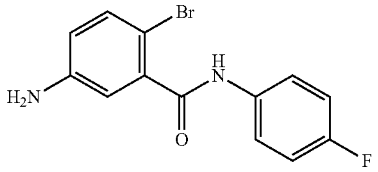 | 23 |
| C80 | 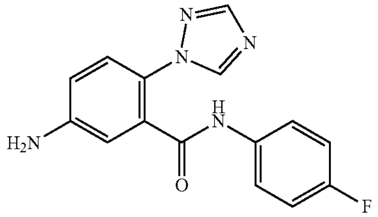 [SMILES: Nc1ccc(-n2cncn2)c(C(=O)Nc2ccc(F)cc2)c1] | 23 |
| C81 | 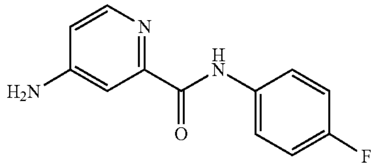 [SMILES: Nc1ccnc(C(=O)Nc2ccc(F)cc2)c1] | 23 |
| C82 | 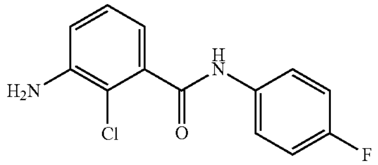 | 23 |
| C83 | 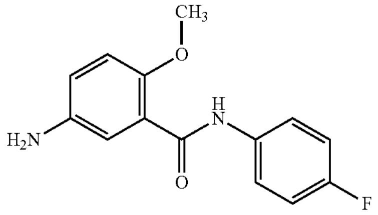 [SMILES: COc1ccc(N)cc1C(=O)Nc1ccc(F)cc1] | 23 |
| C84 | 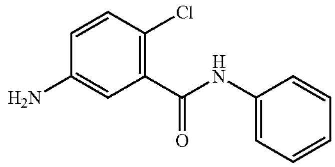 | 23 |

TABLE 3-continued
| No. | Structure | Prep* |
|---|---|---|
| C85 | 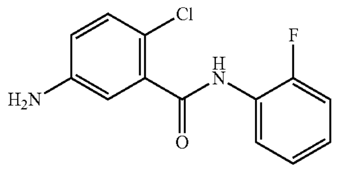 [SMILES: Nc1ccc(Cl)c(C(=O)Nc2ccccc2F)c1] | 23 |
| C86 | 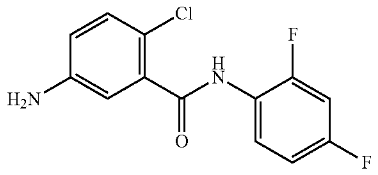 | 23 |
| C87 | 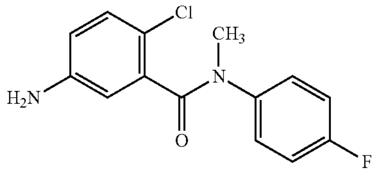 | 23 |
| C88 | 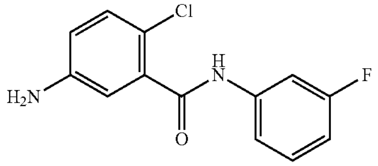 [SMILES: Nc1ccc(Cl)c(C(=O)Nc2cccc(F)c2)c1] | 23 |
| C89 | 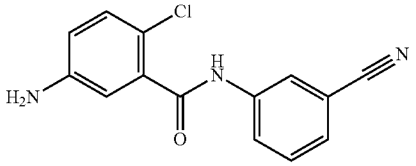 [SMILES: N#Cc1cccc(NC(=O)c2cc(N)ccc2Cl)c1] | 23 |
| C90 | 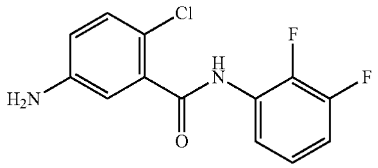 [SMILES: Nc1ccc(Cl)c(C(=O)Nc2cccc(F)c2F)c1] | 23 |
| C91 | 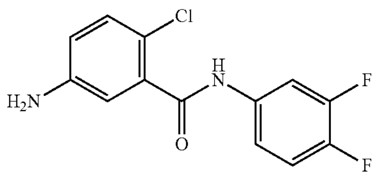 [SMILES: Nc1ccc(Cl)c(C(=O)Nc2ccc(F)c(F)c2)c1] | 23 |
| C92 | 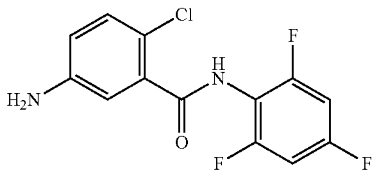 [SMILES: Nc1ccc(Cl)c(C(=O)Nc2c(F)cc(F)cc2F)c1] | 23 |
Structure and preparation method for C series molecules TABLE 3-continued
| No. | Structure | Prep* |
| --- | --- | --- |
| C93 | 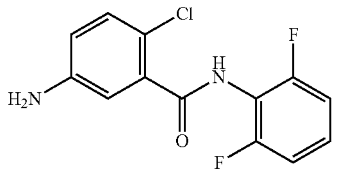 | 23 |
| C94 | 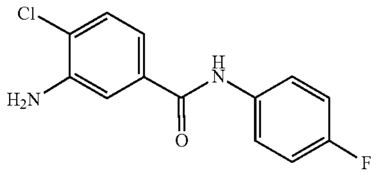 [SMILES: Nc1cc(C(=O)Nc2ccc(F)cc2)ccc1Cl] | 23 |
| C95 | 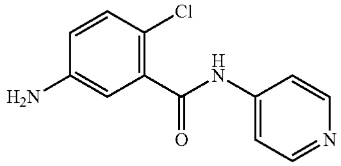 [SMILES: Nc1ccc(Cl)c(C(=O)Nc2ccncc2)c1] | 23 |
| C96 | 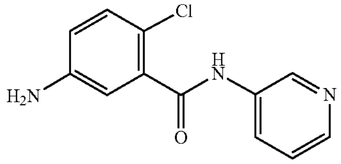 [SMILES: Nc1ccc(Cl)c(C(=O)Nc2cccnc2)c1] | 23 |
| C97 | 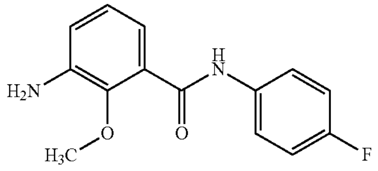 [SMILES: COc1c(N)cccc1C(=O)Nc1ccc(F)cc1] | 23 |
| C98 | 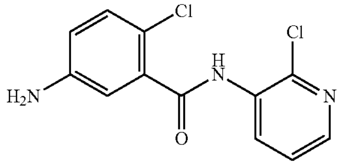 [SMILES: Nc1ccc(Cl)c(C(=O)Nc2cccnc2Cl)c1] | 23 |
| C99 | 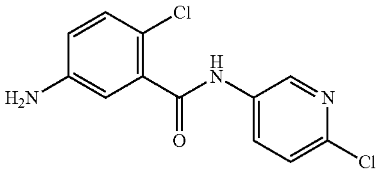 [SMILES: Nc1ccc(Cl)c(C(=O)Nc2ccc(Cl)nc2)c1] | 23 |
| C100 | 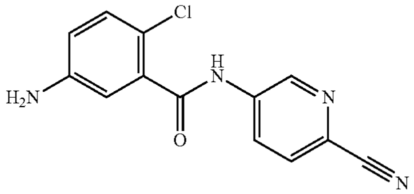 [SMILES: N#Cc1ccc(NC(=O)c2cc(N)ccc2Cl)cn1] | 23 |
Structure and preparation method for C series molecules TABLE 3-continued
| Structure and preparation method for C series molecules | | |
|---|---|---|
| No. | Structure | Prep* |
| C101 | 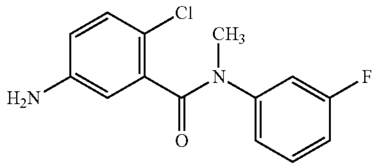 [SMILES: CN(C(=O)c1cc(N)ccc1Cl)c1cccc(F)c1] | 23 |
| C102 | 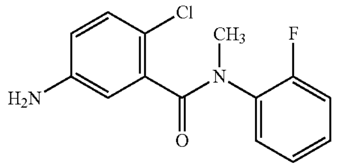 [SMILES: CN(C(=O)c1cc(N)ccc1Cl)c1ccccc1F] | 23 |
| C103 | 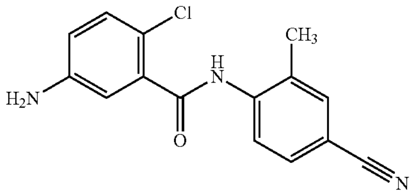 | 23 |
| C104 | 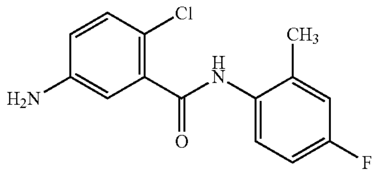 [SMILES: Cc1cc(F)ccc1NC(=O)c1cc(N)ccc1Cl] | 23 |
| C105 | 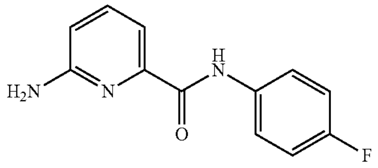 [SMILES: Nc1cccc(C(=O)Nc2ccc(F)cc2)n1] | 23 |
| C106 | 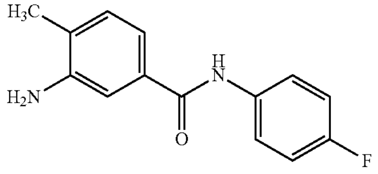 [SMILES: Cc1ccc(C(=O)Nc2ccc(F)cc2)cc1N] | 23 |
| C107 | 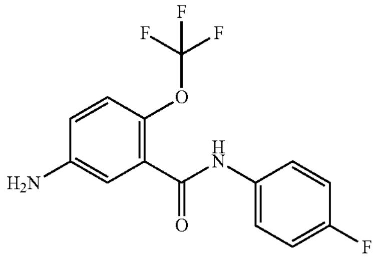 [SMILES: Nc1ccc(OC(F)(F)F)c(C(=O)Nc2ccc(F)cc2)c1] | 23 |

TABLE 3-continued
| Structure and preparation method for C series molecules | | |
|---|---|---|
| No. | Structure | Prep* |
| C108 | 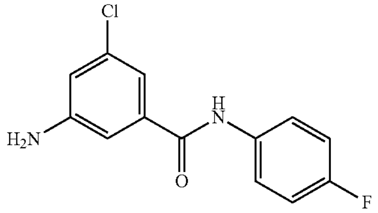 [SMILES: Nc1cc(Cl)cc(C(=O)Nc2ccc(F)cc2)c1] | 23 |
| C109 | 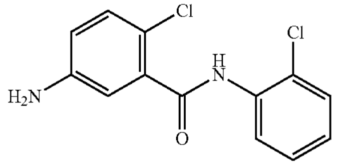 | 23 |
| C110 | 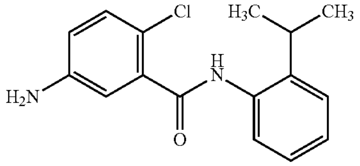 [SMILES: CC(C)c1ccccc1NC(=O)c1cc(N)ccc1Cl] | 23 |
| C111 | 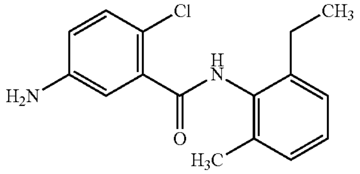 [SMILES: CCc1cccc(C)c1NC(=O)c1cc(N)ccc1Cl] | 23 |
| C112 | 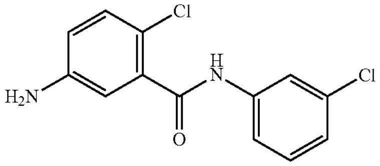 [SMILES: Nc1ccc(Cl)c(C(=O)Nc2cccc(Cl)c2)c1] | 23 |
| C113 | 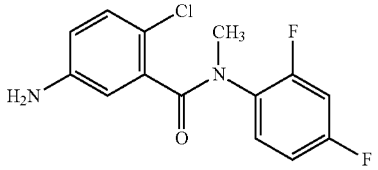 | 23 |
| C114 | 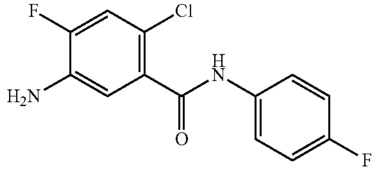 | 23 |
| C115 | 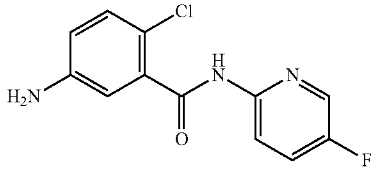 | 23 |

TABLE 3-continued
| Structure and preparation method for C series molecules | | |
|---|---|---|
| No. | Structure | Prep* |
| C116 | 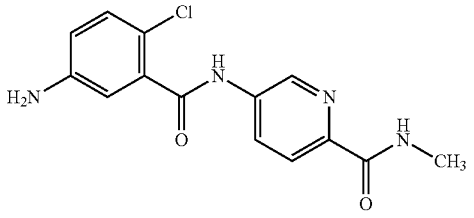 [SMILES: CNC(=O)c1ccc(NC(=O)c2cc(N)ccc2Cl)cn1] | 23 |
| C117 | 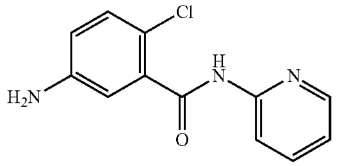 [SMILES: Nc1ccc(Cl)c(C(=O)Nc2ccccn2)c1] | 23 |
| C118 | 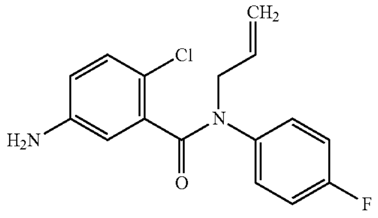 | 23 |
| C119 | 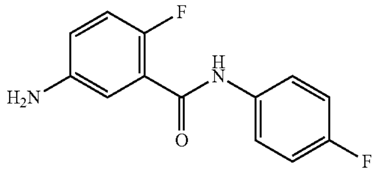 | 24 |
| C120 | 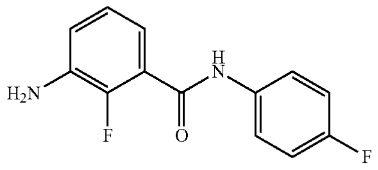 [SMILES: Nc1cccc(C(=O)Nc2ccc(F)cc2)c1F] | 24 |
| C121 | 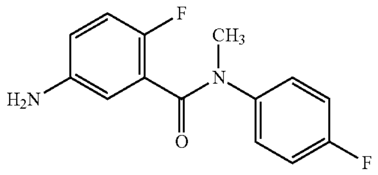 | 24 |
| C122 | 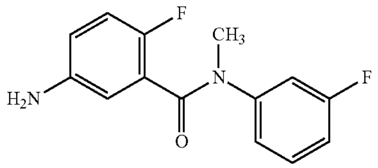 [SMILES: CN(C(=O)c1cc(N)ccc1F)c1cccc(F)c1] | 24 |
| C123 | 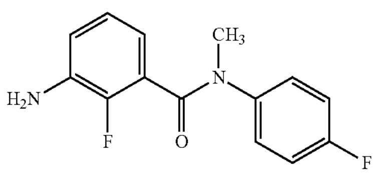 [SMILES: CN(C(=O)c1cccc(N)c1F)c1ccc(F)cc1] | 24 |

TABLE 3-continued
| Structure and preparation method for C series molecules | | |
|---|---|---|
| No. | Structure | Prep* |
| C124 | 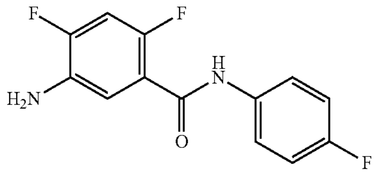 [SMILES: Nc1cc(C(=O)Nc2ccc(F)cc2)c(F)cc1F] | 24 |
| C125 | 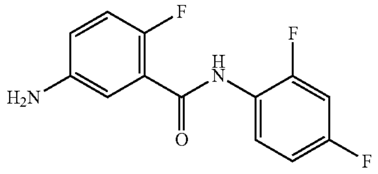 | 24 |
| C126 | 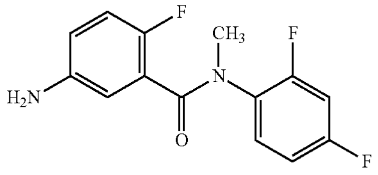 | 24 |
| C127 | 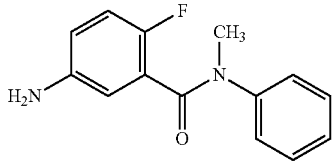 [SMILES: CN(C(=O)c1cc(N)ccc1F)c1ccccc1] | 24 |
| C128 | 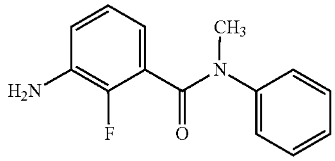 [SMILES: CN(C(=O)c1cccc(N)c1F)c1ccccc1] | 24 |
| C129 | 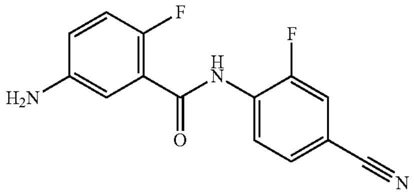 [SMILES: N#Cc1ccc(NC(=O)c2cc(N)ccc2F)c(F)c1] | 24 |
| C130 | 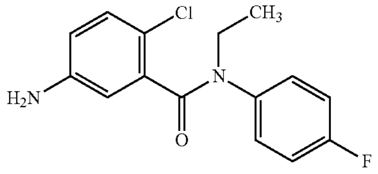 [SMILES: CCN(C(=O)c1cc(N)ccc1Cl)c1ccc(F)cc1] | 24 |
| C131 | 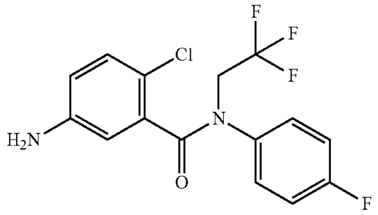 [SMILES: Nc1ccc(Cl)c(C(=O)N(CC(F)(F)F)c2ccc(F)cc2)c1] | 24 |

TABLE 3-continued
| Structure and preparation method for C series molecules | | |
|---|---|---|
| No. | Structure | Prep* |
| C132 | 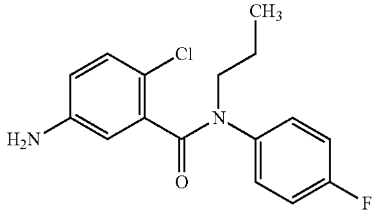 [SMILES: CCCN(C(=O)c1cc(N)ccc1Cl)c1ccc(F)cc1] | 24 |
| C133 | 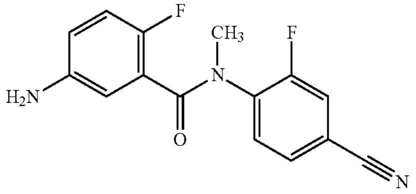 | 24 |
| C134 | 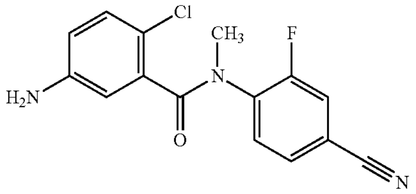 [SMILES: CN(C(=O)c1cc(N)ccc1F)c1ccc(C#N)cc1F] | 24 |
| C135 | 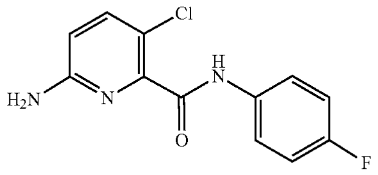 [SMILES: Nc1ccc(Cl)c(C(=O)Nc2ccc(F)cc2)n1] | 25 |
| C136 | 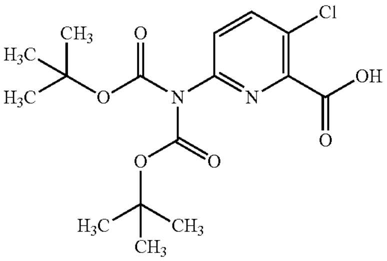 [SMILES: CC(C)(C)OC(=O)N(C(=O)OC(C)(C)C)c1ccc(Cl)c(C(=O)O)n1] | 25 |
| C137 | 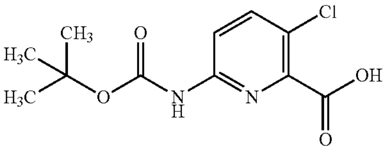 [SMILES: CC(C)(C)OC(=O)Nc1ccc(Cl)c(C(=O)O)n1] | 25 |
| C138 | 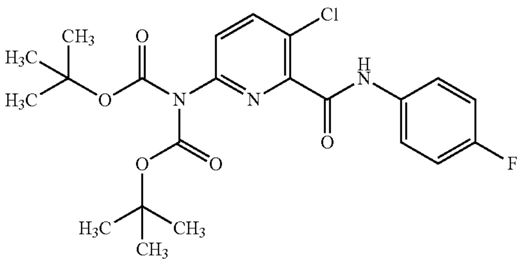 [SMILES: CC(C)(C)OC(=O)N(C(=O)OC(C)(C)C)c1ccc(Cl)c(C(=O)Nc2ccc(F)cc2)n1] | 25 |

TABLE 3-continued
| Structure and preparation method for C series molecules | | |
|---|---|---|
| No. | Structure | Prep* |
| C139 | 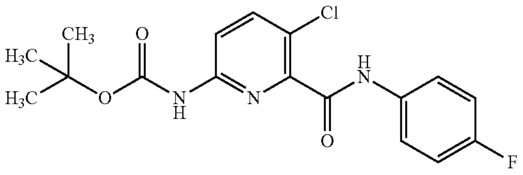 [SMILES: CC(C)(C)OC(=O)Nc1ccc(Cl)c(C(=O)Nc2ccc(F)cc2)n1] | 25 |
| C140 | 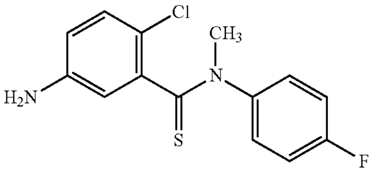 | 26 |
| C141 | 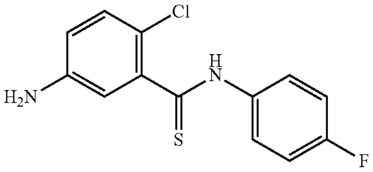 | 26 |
| C142 | 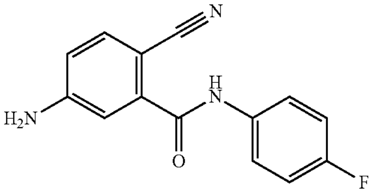 [SMILES: N#Cc1ccc(N)cc1C(=O)Nc1ccc(F)cc1] | 27 |
| C143 | 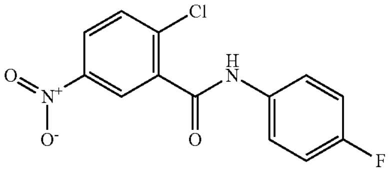 [SMILES: O=C(Nc1ccc(F)cc1)c1cc([N+](=O)[O-])ccc1Cl] | 28 |
| C144 | 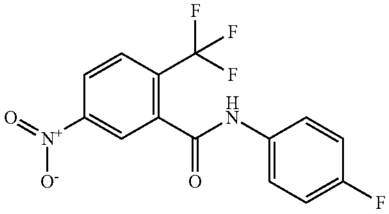 [SMILES: O=C(Nc1ccc(F)cc1)c1cc([N+](=O)[O-])ccc1C(F)(F)F] | 28 |
| C145 | 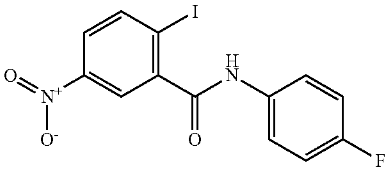 [SMILES: O=C(Nc1ccc(F)cc1)c1cc([N+](=O)[O-])ccc1I] | 28 |
| C146 | 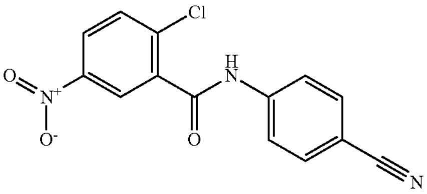 | 28 |

TABLE 3-continued
| Structure and preparation method for C series molecules | | |
|---|---|---|
| No. | Structure | Prep* |
| C147 | 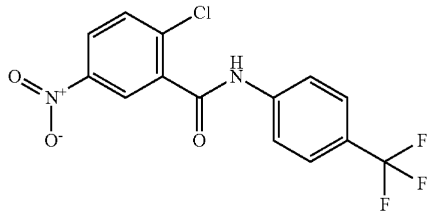 [SMILES: O=C(Nc1ccc(C(F)(F)F)cc1)c1cc([N+](=O)[O-])ccc1Cl] | 28 |
| C148 | 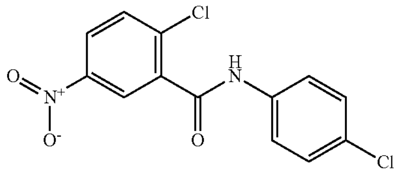 [SMILES: O=C(Nc1ccc(Cl)cc1)c1cc([N+](=O)[O-])ccc1Cl] | 28 |
| C149 | 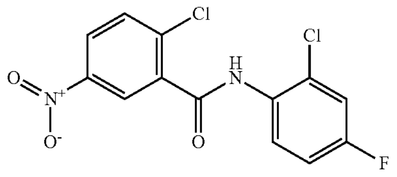 [SMILES: O=C(Nc1ccc(F)cc1Cl)c1cc([N+](=O)[O-])ccc1Cl] | 28 |
| C150 | 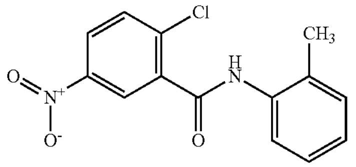 [SMILES: Cc1ccccc1NC(=O)c1cc([N+](=O)[O-])ccc1Cl] | 28 |
| C151 | 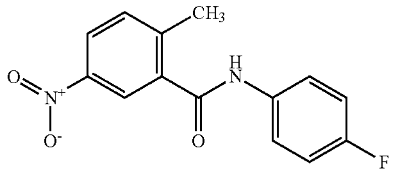 [SMILES: Cc1ccc([N+](=O)[O-])cc1C(=O)Nc1ccc(F)cc1] | 28 |
| C152 | 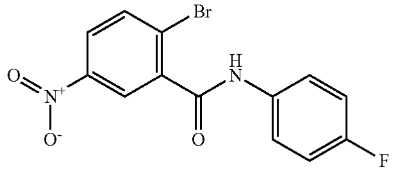 [SMILES: O=C(Nc1ccc(F)cc1)c1cc([N+](=O)[O-])ccc1Br] | 28 |
| C153 | 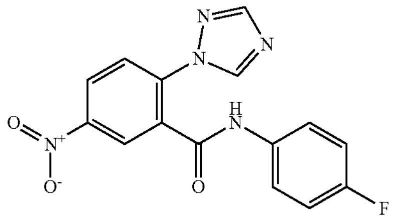 [SMILES: O=C(Nc1ccc(F)cc1)c1cc([N+](=O)[O-])ccc1-n1cncn1] | 28 |
| C154 | 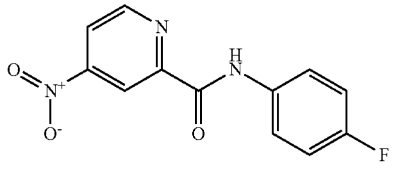 [SMILES: O=C(Nc1ccc(F)cc1)c1cc([N+](=O)[O-])ccn1] | 28 |

TABLE 3-continued
| Structure and preparation method for C series molecules | | |
|---|---|---|
| No. | Structure | Prep* |
| C155 | 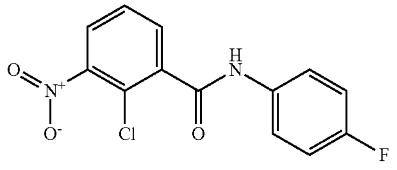 [SMILES: O=C(Nc1ccc(F)cc1)c1cccc([N+](=O)[O-])c1Cl] | 28 |
| C156 | 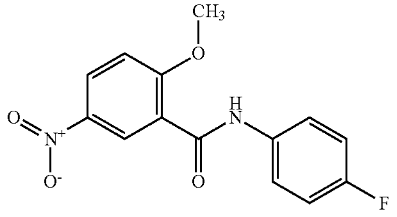 [SMILES: COc1ccc([N+](=O)[O-])cc1C(=O)Nc1ccc(F)cc1] | 28 |
| C157 | 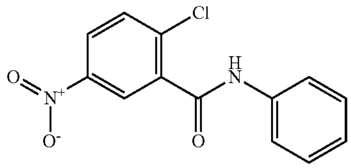 [SMILES: O=C(Nc1ccccc1)c1cc([N+](=O)[O-])ccc1Cl] | 28 |
| C158 | 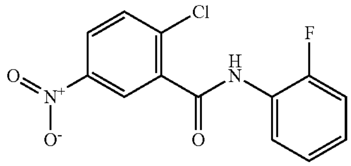 [SMILES: O=C(Nc1ccccc1F)c1cc([N+](=O)[O-])ccc1Cl] | 28 |
| C159 | 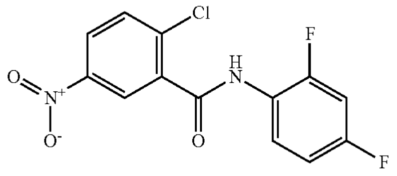 [SMILES: O=C(Nc1ccc(F)cc1F)c1cc([N+](=O)[O-])ccc1Cl] | 28 |
| C160 | 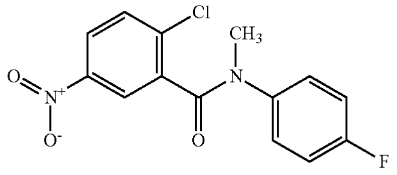 [SMILES: CN(C(=O)c1cc([N+](=O)[O-])ccc1Cl)c1ccc(F)cc1] | 28 |
| C161 | 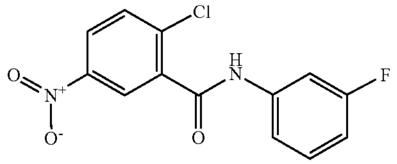 [SMILES: O=C(Nc1cccc(F)c1)c1cc([N+](=O)[O-])ccc1Cl] | 28 |
| C162 | 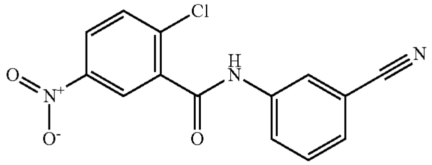 [SMILES: N#Cc1cccc(NC(=O)c2cc([N+](=O)[O-])ccc2Cl)c1] | 28 |

TABLE 3-continued
| Structure and preparation method for C series molecules | | |
|---|---|---|
| No. | Structure | Prep* |
| C163 | 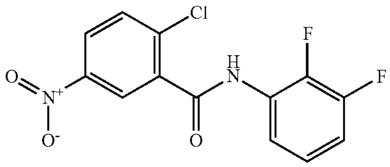 | 28 |
| C164 | 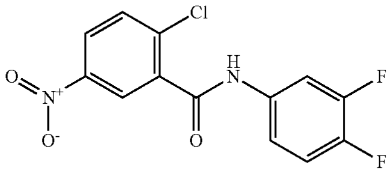 [SMILES: O=C(Nc1ccc(F)c(F)c1)c1cc([N+](=O)[O-])ccc1Cl] | 28 |
| C165 | 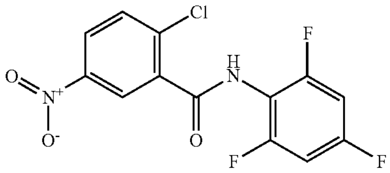 | 28 |
| C166 | 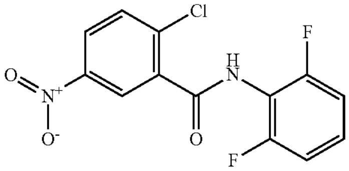 [SMILES: O=C(Nc1c(F)cccc1F)c1cc([N+](=O)[O-])ccc1Cl] | 28 |
| C167 | 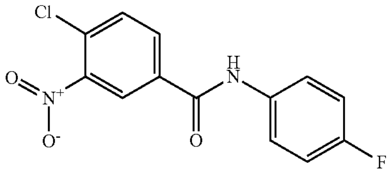 [SMILES: O=C(Nc1ccc(F)cc1)c1ccc(Cl)c([N+](=O)[O-])c1] | 28 |
| C168 | 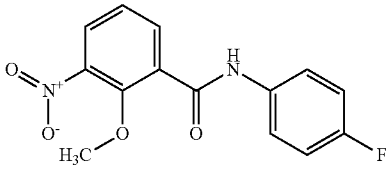 [SMILES: COc1c(C(=O)Nc2ccc(F)cc2)cccc1[N+](=O)[O-]] | 28 |
| C169 | 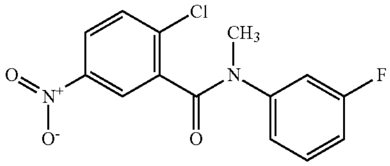 | 28 |
| C170 | 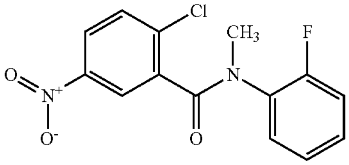 [SMILES: CN(C(=O)c1cc([N+](=O)[O-])ccc1Cl)c1ccccc1F] | 28 |

TABLE 3-continued
| Structure and preparation method for C series molecules | | |
|---|---|---|
| No. | Structure | Prep* |
| C171 | 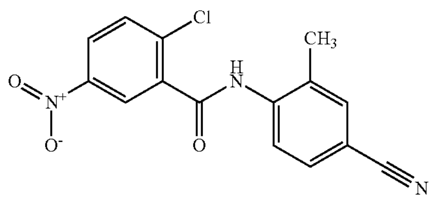 [SMILES: Cc1cc(C#N)ccc1NC(=O)c1cc([N+](=O)[O-])ccc1Cl] | 28 |
| C172 | 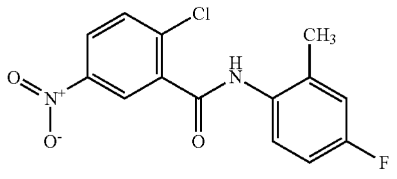 [SMILES: Cc1cc(F)ccc1NC(=O)c1cc([N+](=O)[O-])ccc1Cl] | 28 |
| C173 | 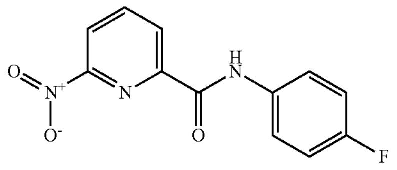 [SMILES: O=C(Nc1ccc(F)cc1)c1cccc([N+](=O)[O-])n1] | 28 |
| C174 | 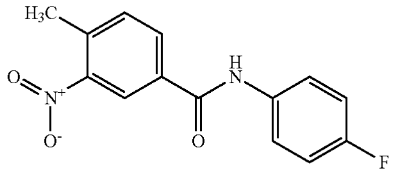 [SMILES: Cc1ccc(C(=O)Nc2ccc(F)cc2)cc1[N+](=O)[O-]] | 28 |
| C175 | 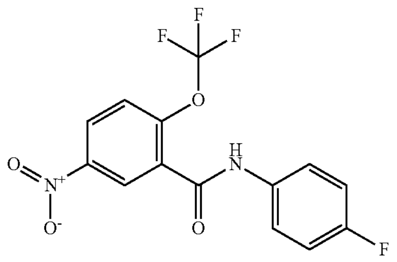 [SMILES: O=C(Nc1ccc(F)cc1)c1cc([N+](=O)[O-])ccc1OC(F)(F)F] | 28 |
| C176 | 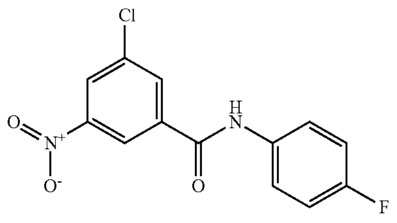 [SMILES: O=C(Nc1ccc(F)cc1)c1cc(Cl)cc([N+](=O)[O-])c1] | 28 |
| C177 | 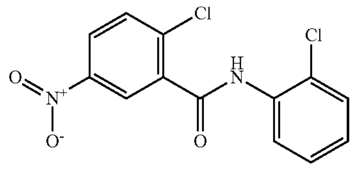 [SMILES: O=C(Nc1ccccc1Cl)c1cc([N+](=O)[O-])ccc1Cl] | 28 |

TABLE 3-continued
| Structure and preparation method for C series molecules | | |
|---|---|---|
| No. | Structure | Prep* |
| C178 | 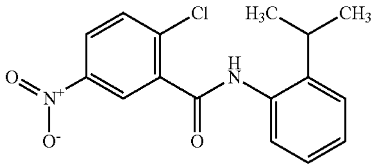 [SMILES: CC(C)c1ccccc1NC(=O)c1cc([N+](=O)[O-])ccc1Cl] | 28 |
| C179 | 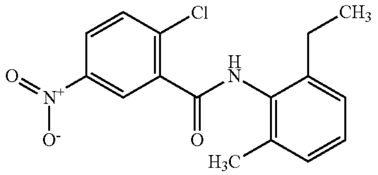 [SMILES: CCc1cccc(C)c1NC(=O)c1cc([N+](=O)[O-])ccc1Cl] | 28 |
| C180 | 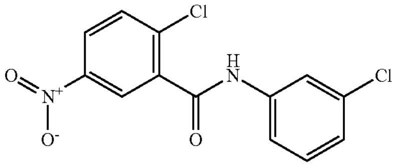 [SMILES: O=C(Nc1cccc(Cl)c1)c1cc([N+](=O)[O-])ccc1Cl] | 28 |
| C181 | 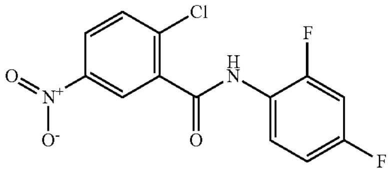 [SMILES: O=C(Nc1ccc(F)cc1F)c1cc([N+](=O)[O-])ccc1Cl] | 28 |
| C182 | 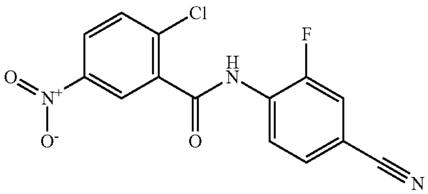 [SMILES: N#Cc1ccc(NC(=O)c2cc([N+](=O)[O-])ccc2Cl)c(F)c1] | 28 |
| C183 | 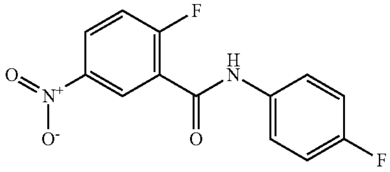 [SMILES: O=C(Nc1ccc(F)cc1)c1cc([N+](=O)[O-])ccc1F] | 29 |
| C184 | 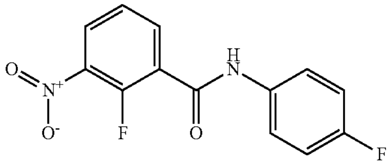 [SMILES: O=C(Nc1ccc(F)cc1)c1cccc([N+](=O)[O-])c1F] | 29 |
| C185 | 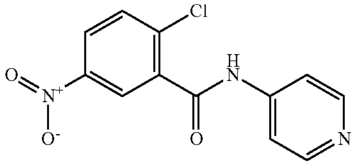 [SMILES: O=C(Nc1ccncc1)c1cc([N+](=O)[O-])ccc1Cl] | 30 |

TABLE 3-continued
| Structure and preparation method for C series molecules | | |
|---|---|---|
| No. | Structure | Prep* |
| C186 | 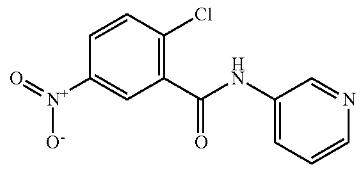 [SMILES: O=C(Nc1cccnc1)c1cc([N+](=O)[O-])ccc1Cl] | 30 |
| C187 | 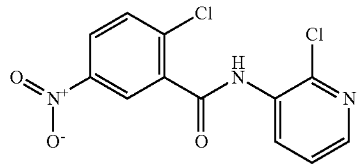 [SMILES: O=C(Nc1cccnc1Cl)c1cc([N+](=O)[O-])ccc1Cl] | 30 |
| C188 | 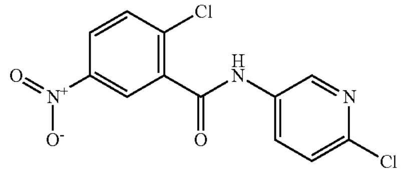 [SMILES: O=C(Nc1ccc(Cl)nc1)c1cc([N+](=O)[O-])ccc1Cl] | 30 |
| C189 | 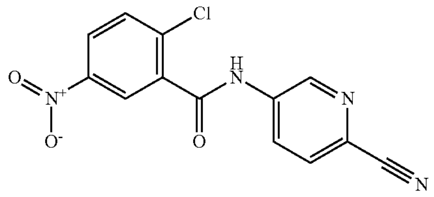 | 30 |
| C190 | 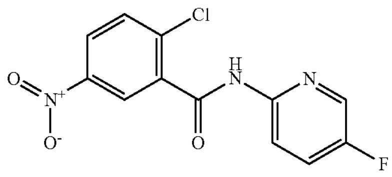 | 30 |
| C191 | 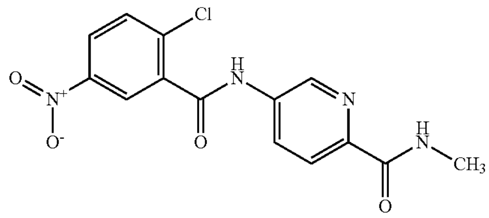 [SMILES: CNC(=O)c1ccc(NC(=O)c2cc([N+](=O)[O-])ccc2Cl)cn1] | 30 |
| C192 | 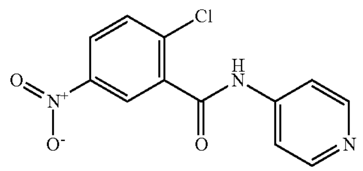 [SMILES: O=C(Nc1ccncc1)c1cc([N+](=O)[O-])ccc1Cl] | 30 |
| C193 | 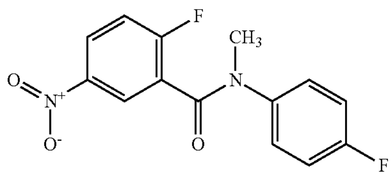 [SMILES: CN(C(=O)c1cc([N+](=O)[O-])ccc1F)c1ccc(F)cc1] | 31 |

TABLE 3-continued
Structure and preparation method for C series molecules
| No. | Structure | Prep* |
| --- | --- | --- |
| C194 | 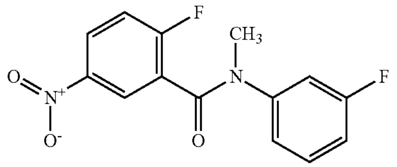 [SMILES: CN(C(=O)c1cc([N+](=O)[O-])ccc1F)c1cccc(F)c1] | 31 |
| C195 | 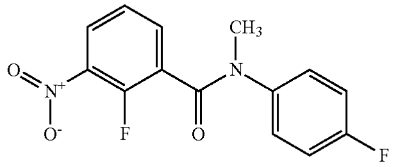 [SMILES: CN(C(=O)c1cccc([N+](=O)[O-])c1F)c1ccc(F)cc1] | 31 |
| C196 | 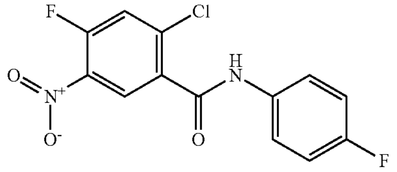 | 31 |
| C197 | 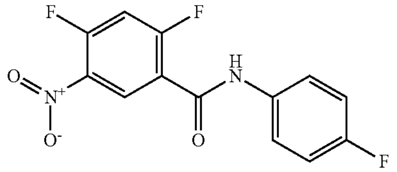 [SMILES: O=C(Nc1ccc(F)cc1)c1cc([N+](=O)[O-])c(F)cc1F] | 31 |
| C198 | 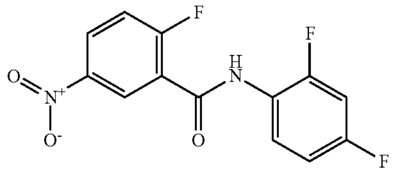 [SMILES: O=C(Nc1ccc(F)cc1F)c1cc([N+](=O)[O-])ccc1F] | 31 |
| C199 | 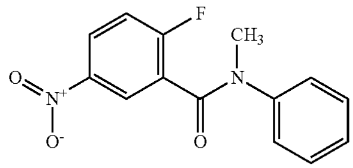 [SMILES: CN(C(=O)c1cc([N+](=O)[O-])ccc1F)c1ccccc1] | 31 |
| C200 | 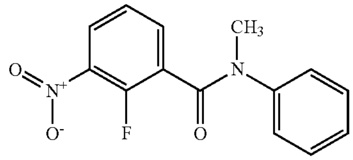 [SMILES: CN(C(=O)c1cccc([N+](=O)[O-])c1F)c1ccccc1] | 31 |
| C201 | 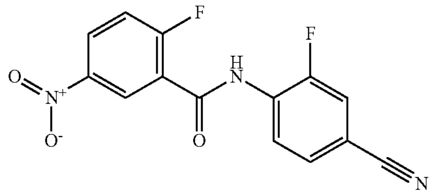 | 31 |

TABLE 3-continued
Structure and preparation method for C series molecules
| No. | Structure | Prep* |
| --- | --- | --- |
| C202 | 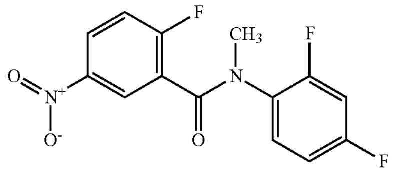 [SMILES: CN(C(=O)c1cc([N+](=O)[O-])ccc1F)c1ccc(F)cc1F] | 32 |
| C203 | 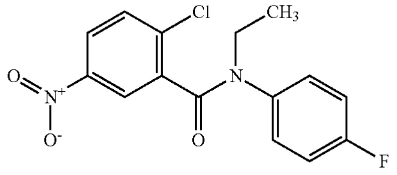 [SMILES: CCN(C(=O)c1cc([N+](=O)[O-])ccc1Cl)c1ccc(F)cc1] | 32 |
| C204 | 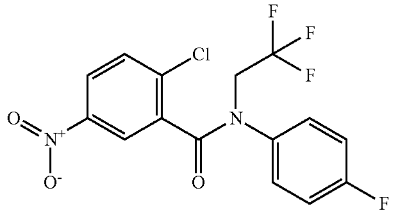 [SMILES: O=C(c1cc([N+](=O)[O-])ccc1Cl)N(CC(F)(F)F)c1ccc(F)cc1] | 32 |
| C205 | 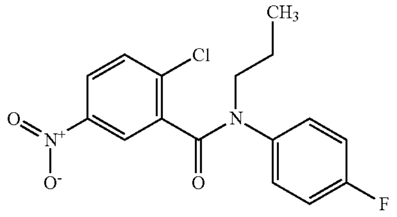 | 32 |
| C206 | 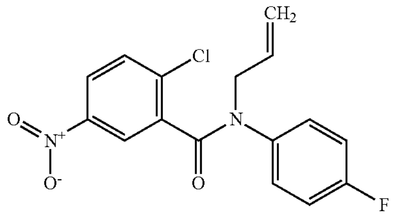 | 32 |
| C207 | 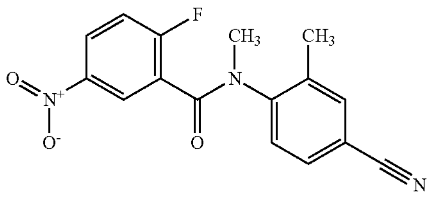 [SMILES: Cc1cc(C#N)ccc1N(C)C(=O)c1cc([N+](=O)[O-])ccc1F] | 32 |
| C208 | 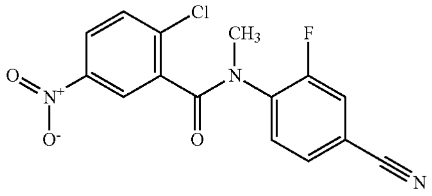 | 32 |

TABLE 3-continued
| Structure and preparation method for C series molecules | | |
|---|---|---|
| No. | Structure | Prep* |
| C209 | 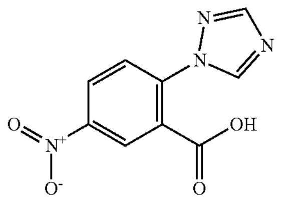 [SMILES: O=C(O)c1cc([N+](=O)[O-])ccc1-n1cncn1] | 33 |
| C210 | 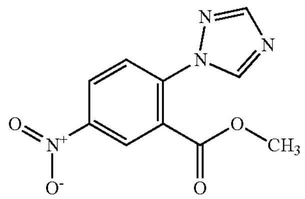 [SMILES: COC(=O)c1cc([N+](=O)[O-])ccc1-n1cncn1] | 34 |
| C211 | 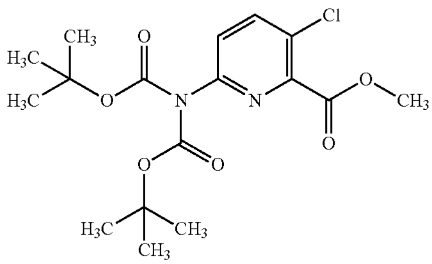 [SMILES: COC(=O)c1nc(N(C(=O)OC(C)(C)C)C(=O)OC(C)(C)C)ccc1Cl] | 35 |
| C212 | 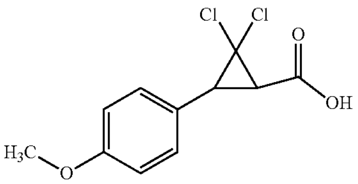 [SMILES: COc1ccc(C2C(C(=O)O)C2(Cl)Cl)cc1] | 2 |
| C213 | 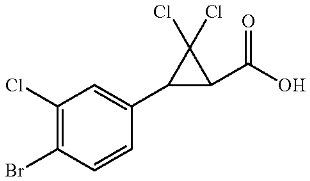 | 2 |
| C214 | 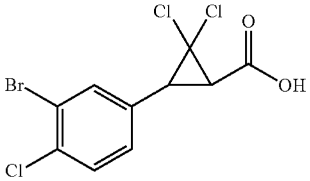 | 2 |
| C215 | 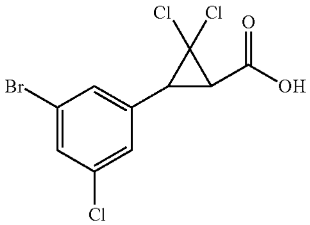 | 2 |

TABLE 3-continued
| Structure and preparation method for C series molecules | | |
|---|---|---|
| No. | Structure | Prep* |
| C216 | 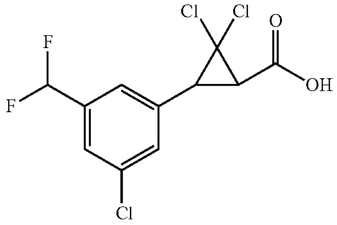 [SMILES: O=C(O)C1C(c2cc(Cl)cc(C(F)F)c2)C1(Cl)Cl] | 2 |
| C217 | 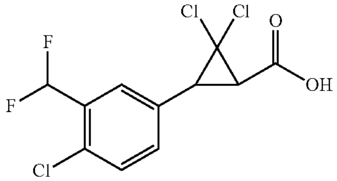 [SMILES: O=C(O)C1C(c2ccc(Cl)c(C(F)F)c2)C1(Cl)Cl] | 2 |
| C218 | 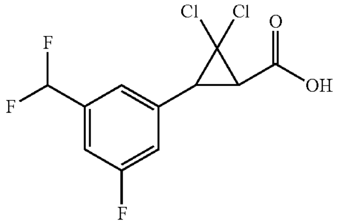 | 2 |
| C219 | 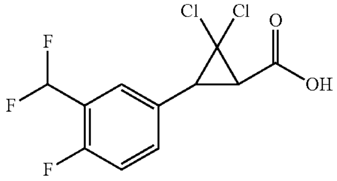 [SMILES: O=C(O)C1C(c2ccc(F)c(C(F)F)c2)C1(Cl)Cl] | 2 |
| C220 | 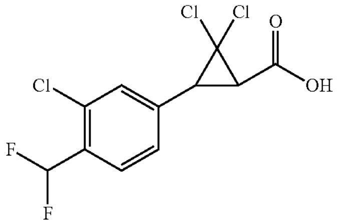 [SMILES: O=C(O)C1C(c2ccc(C(F)F)c(Cl)c2)C1(Cl)Cl] | 2 |
| C221 | 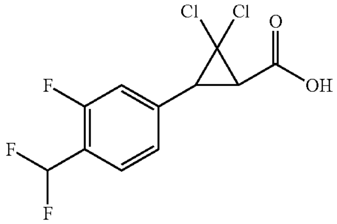 [SMILES: O=C(O)C1C(c2ccc(C(F)F)c(F)c2)C1(Cl)Cl] | 2 |
| C222 | 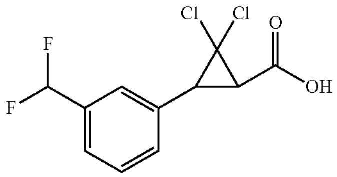 [SMILES: O=C(O)C1C(c2cccc(C(F)F)c2)C1(Cl)Cl] | 2 |

TABLE 3-continued
| Structure and preparation method for C series molecules | | |
|---|---|---|
| No. | Structure | Prep* |
| C223 | 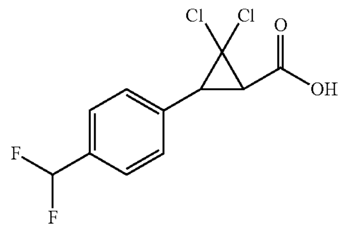 [SMILES: O=C(O)C1C(c2ccc(C(F)F)cc2)C1(Cl)Cl] | 2 |
| C224 | 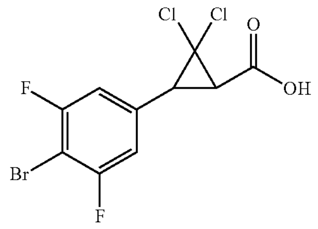 [SMILES: O=C(O)C1C(c2cc(F)c(Br)c(F)c2)C1(Cl)Cl] | 2 |
| C225 | 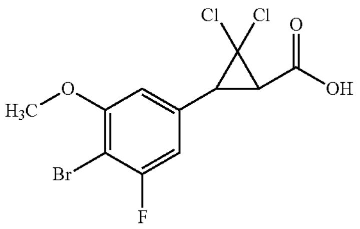 [SMILES: COc1cc(C2C(C(=O)O)C2(Cl)Cl)cc(F)c1Br] | 2 |
| C226 | 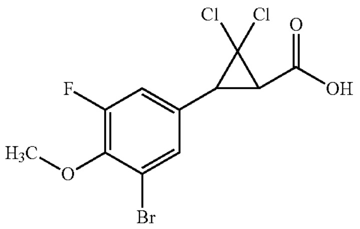 [SMILES: COc1c(F)cc(C2C(C(=O)O)C2(Cl)Cl)cc1Br] | 2 |
| C227 | 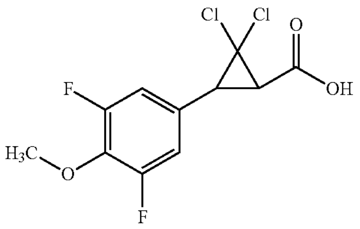 [SMILES: COc1c(F)cc(C2C(C(=O)O)C2(Cl)Cl)cc1F] | 2 |
| C228 | 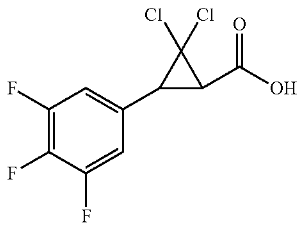 [SMILES: O=C(O)C1C(c2cc(F)c(F)c(F)c2)C1(Cl)Cl] | 2 |

TABLE 3-continued
| Structure and preparation method for C series molecules | | |
|---|---|---|
| No. | Structure | Prep* |
| C229 | 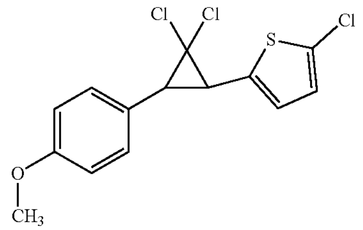 [SMILES: COc1ccc(C2C(c3ccc(Cl)s3)C2(Cl)Cl)cc1] | 3 |
| C230 | 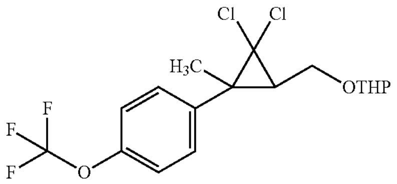 | 3 |
| C231 | 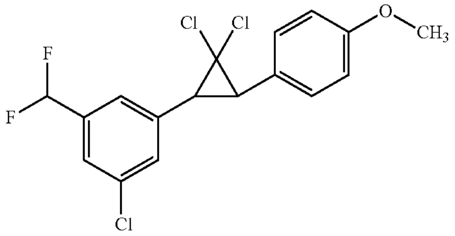 [SMILES: COc1ccc(C2C(c3cc(Cl)cc(C(F)F)c3)C2(Cl)Cl)cc1] | 3 |
| C232 | 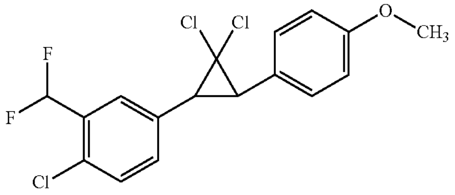 [SMILES: COc1ccc(C2C(c3ccc(Cl)c(C(F)F)c3)C2(Cl)Cl)cc1] | 3 |
| C233 | 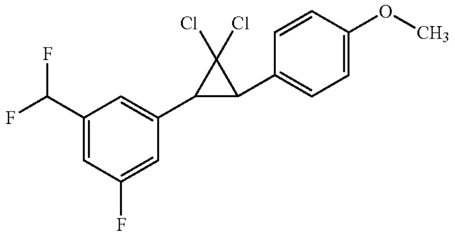 | 3 |
| C234 | 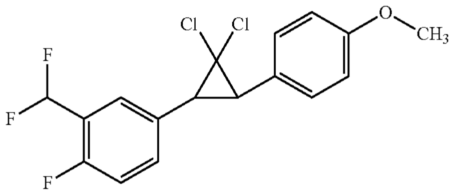 | 3 |
| C235 | 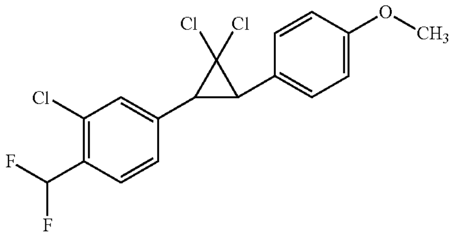 | 3 |

TABLE 3-continued
| Structure and preparation method for C series molecules | | |
|---|---|---|
| No. | Structure | Prep* |
| C236 | 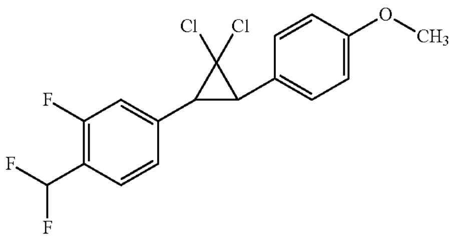 | 3 |
| C237 | 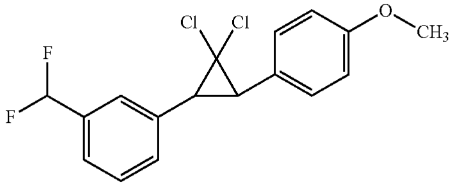 [SMILES: COc1ccc(C2C(c3cccc(C(F)F)c3)C2(Cl)Cl)cc1] | 3 |
| C238 | 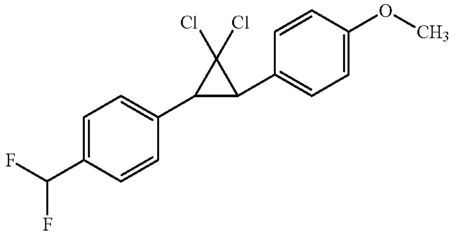 [SMILES: COc1ccc(C2C(c3ccc(C(F)F)cc3)C2(Cl)Cl)cc1] | 3 |
| C239 | 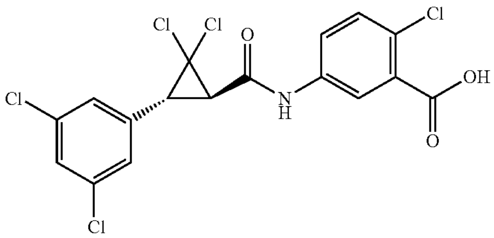 [SMILES: O=C(O)c1cc(NC(=O)[C@H]2[C@H](c3cc(Cl)cc(Cl)c3)C2(Cl)Cl)ccc1Cl] | 12 |
| C240 | 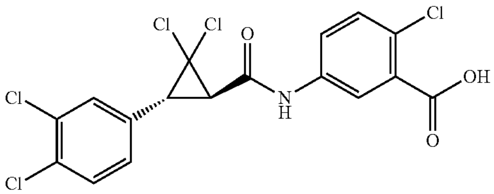 [SMILES: O=C(O)c1cc(NC(=O)[C@H]2[C@H](c3ccc(Cl)c(Cl)c3)C2(Cl)Cl)ccc1Cl] | 12 |
| C241 | 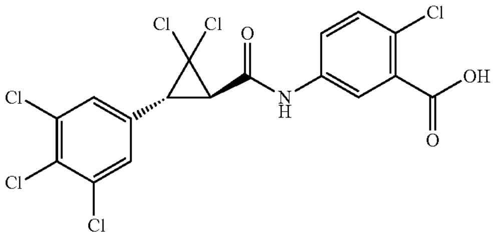 [SMILES: O=C(O)c1cc(NC(=O)[C@H]2[C@H](c3cc(Cl)c(Cl)c(Cl)c3)C2(Cl)Cl)ccc1Cl] | 12 |

TABLE 3-continued
| Structure and preparation method for C series molecules | | |
|---|---|---|
| No. | Structure | Prep* |
| C242 | 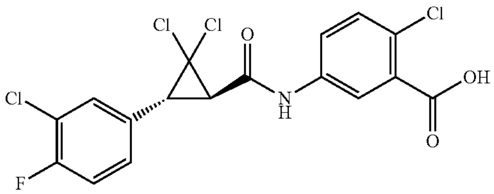 [SMILES: O=C(O)c1cc(NC(=O)[C@H]2[C@H](c3ccc(F)c(Cl)c3)C2(Cl)Cl)ccc1Cl] | 12 |
| C243 | 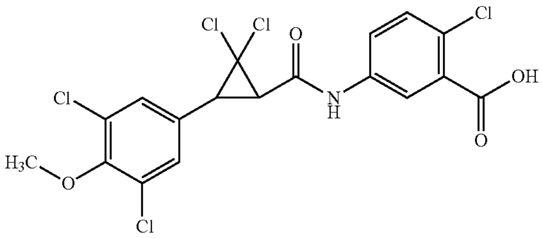 [SMILES: COc1c(Cl)cc(C2C(C(=O)Nc3ccc(Cl)c(C(=O)O)c3)C2(Cl)Cl)cc1Cl] | 12 |
| C244 | 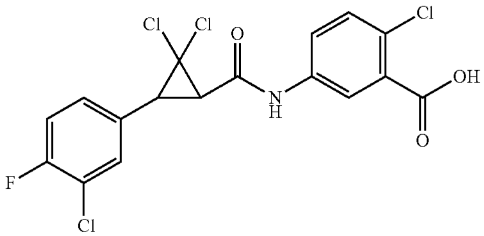 [SMILES: O=C(O)c1cc(NC(=O)C2C(c3ccc(F)c(Cl)c3)C2(Cl)Cl)ccc1Cl] | 12 |
| C245 | 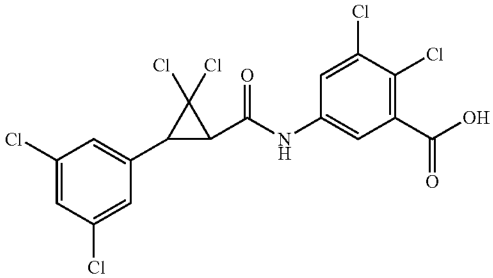 [SMILES: O=C(O)c1cc(NC(=O)C2C(c3cc(Cl)cc(Cl)c3)C2(Cl)Cl)cc(Cl)c1Cl] | 12 |
| C246 | 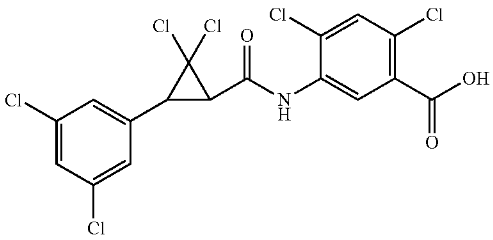 [SMILES: O=C(O)c1cc(NC(=O)C2C(c3cc(Cl)cc(Cl)c3)C2(Cl)Cl)c(Cl)cc1Cl] | 12 |
| C247 | 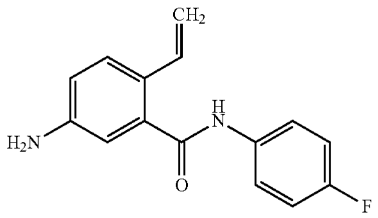 | 23 |

TABLE 3-continued
Structure and preparation method for C series molecules
| No. | Structure | Prep* |
| --- | --- | --- |
| C248 | 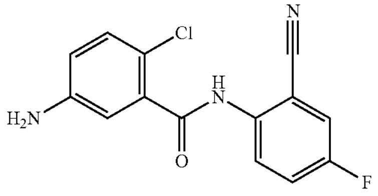 | 23 |
| C249 | 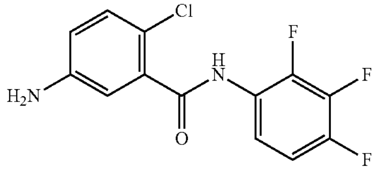 | 23 |
| C250 | 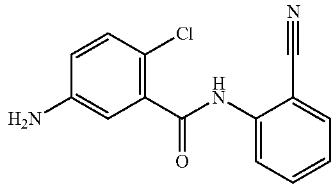 | 23 |
| C251 | 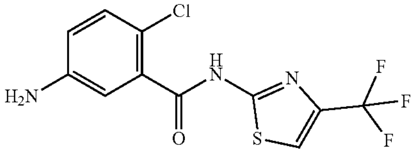 | 23 |
| C252 | 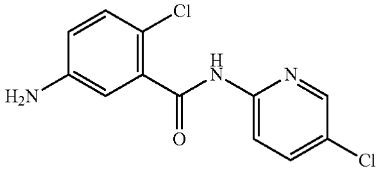 | 23 |
| C253 | 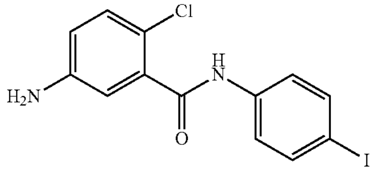 | 23 |
| C254 | 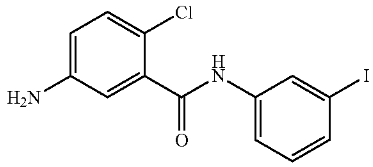 | 23 |
| C255 | 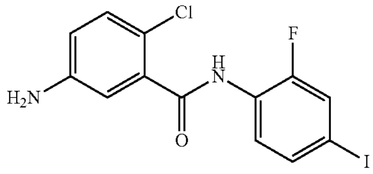 | 23 |

TABLE 3-continued
Structure and preparation method for C series molecules
| No. | Structure | Prep* |
| --- | --- | --- |
| C256 | 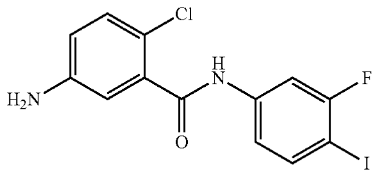 | 23 |
| C257 | 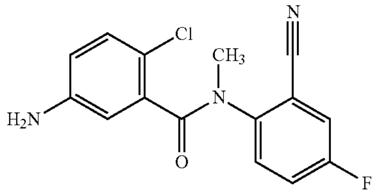 [SMILES: CN(C(=O)c1cc(N)ccc1Cl)c1ccc(F)cc1C#N] | 23 |
| C258 | 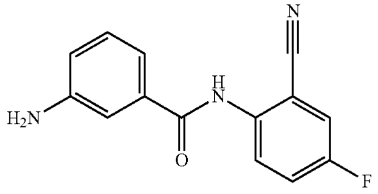 [SMILES: N#Cc1cc(F)ccc1NC(=O)c1cccc(N)c1] | 23 |
| C259 | 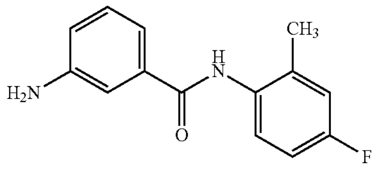 | 23 |
| C260 | 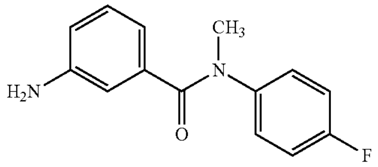 [SMILES: CN(C(=O)c1cccc(N)c1)c1ccc(F)cc1] | 23 |
| C261 | 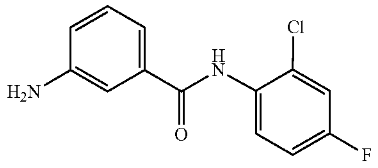 [SMILES: Nc1cccc(C(=O)Nc2ccc(F)cc2Cl)c1] | 23 |
| C262 | 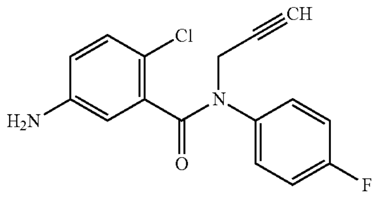 [SMILES: C#CCN(C(=O)c1cc(N)ccc1Cl)c1ccc(F)cc1] | 23 |
| C263 | 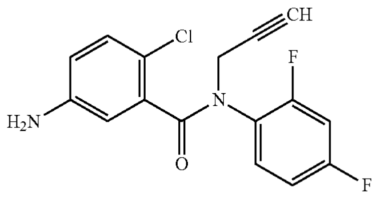 | 23 |

TABLE 3-continued
| No. | Structure | Prep* |
|---|---|---|
| | Structure and preparation method for C series molecules | |
| C264 | 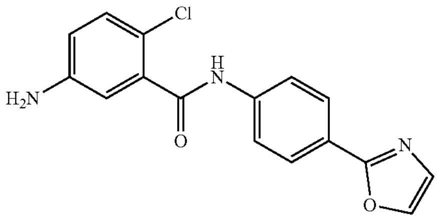 | 23 |
| C265 | 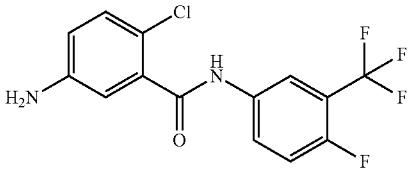 | 23 |
| C266 | 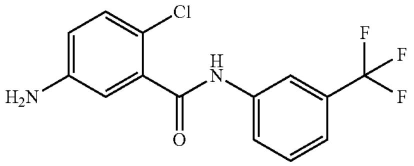 | 23 |
| C267 | 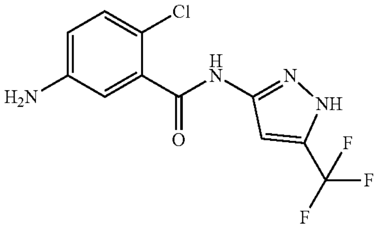 | 23 |
| C268 | 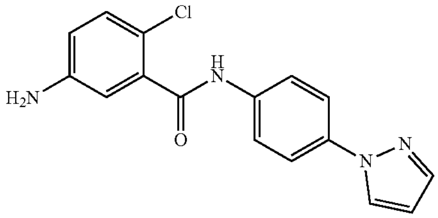 | 23 |
| C269 | 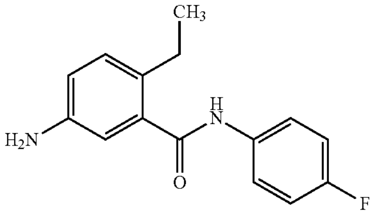 [SMILES: CCc1ccc(N)cc1C(=O)Nc1ccc(F)cc1] | 24 |

TABLE 3-continued
| Structure and preparation method for C series molecules | | |
|---|---|---|
| No. | Structure | Prep* |
| C270 | 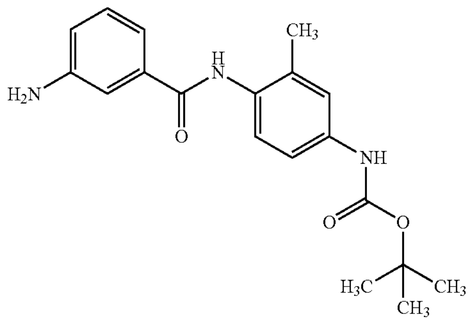 [SMILES: Cc1cc(NC(=O)OC(C)(C)C)ccc1NC(=O)c1cccc(N)c1] | 24 |
| C271 | 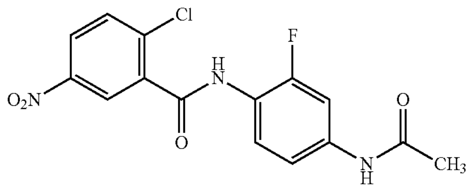 [SMILES: CC(=O)Nc1ccc(NC(=O)c2cc([N+](=O)[O-])ccc2Cl)c(F)c1] | 28 |
| C272 | 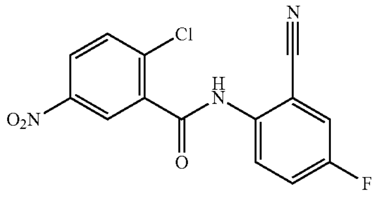 [SMILES: N#Cc1cc(F)ccc1NC(=O)c1cc([N+](=O)[O-])ccc1Cl] | 28 |
| C273 | 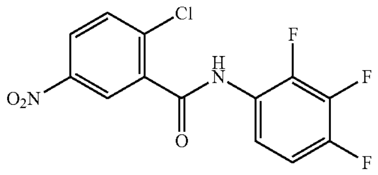 [SMILES: O=C(Nc1ccc(F)c(F)c1F)c1cc([N+](=O)[O-])ccc1Cl] | 28 |
| C274 | 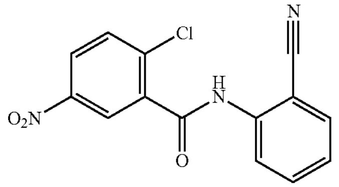 [SMILES: N#Cc1ccccc1NC(=O)c1cc([N+](=O)[O-])ccc1Cl] | 28 |
| C275 | 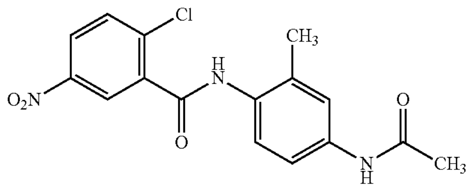 [SMILES: CC(=O)Nc1ccc(NC(=O)c2cc([N+](=O)[O-])ccc2Cl)c(C)c1] | 28 |
| C276 | 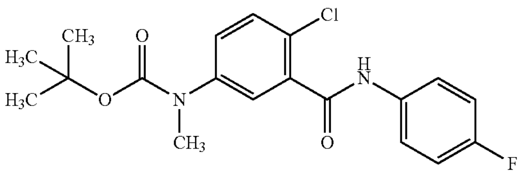 [SMILES: CN(C(=O)OC(C)(C)C)c1ccc(Cl)c(C(=O)Nc2ccc(F)cc2)c1] | 28 |

TABLE 3-continued
| Structure and preparation method for C series molecules | | |
|---|---|---|
| No. | Structure | Prep* |
| C277 | 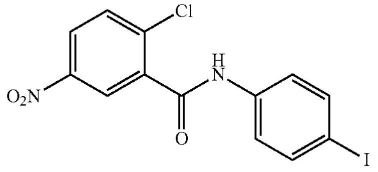 [SMILES: O=C(Nc1ccc(I)cc1)c1cc([N+](=O)[O-])ccc1Cl] | 28 |
| C278 | 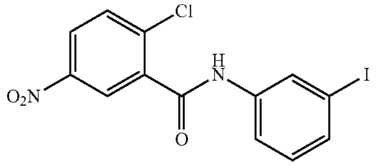 [SMILES: O=C(Nc1cccc(I)c1)c1cc([N+](=O)[O-])ccc1Cl] | 28 |
| C279 | 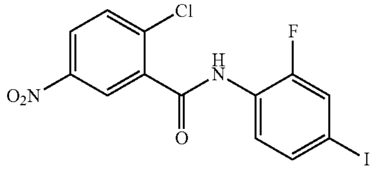 [SMILES: O=C(Nc1ccc(I)cc1F)c1cc([N+](=O)[O-])ccc1Cl] | 28 |
| C280 | 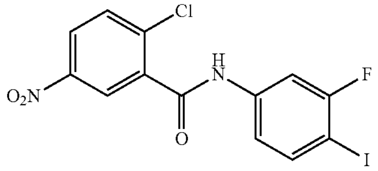 | 28 |
| C281 | 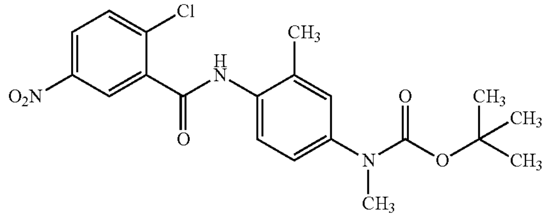 [SMILES: Cc1cc(N(C)C(=O)OC(C)(C)C)ccc1NC(=O)c1cc([N+](=O)[O-])ccc1Cl] | 28 |
| C282 | 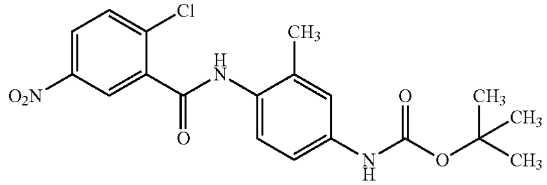 [SMILES: Cc1cc(NC(=O)OC(C)(C)C)ccc1NC(=O)c1cc([N+](=O)[O-])ccc1Cl] | 28 |
| C283 | 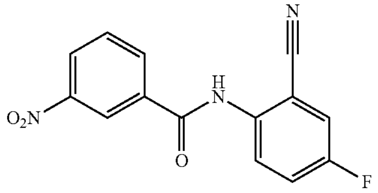 [SMILES: N#Cc1cc(F)ccc1NC(=O)c1cccc([N+](=O)[O-])c1] | 28 |
| C284 | 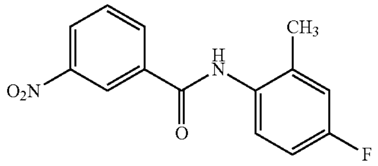 [SMILES: Cc1cc(F)ccc1NC(=O)c1cccc([N+](=O)[O-])c1] | 28 |

TABLE 3-continued
| No. | Structure | Prep* |
|---|---|---|
| C285 | 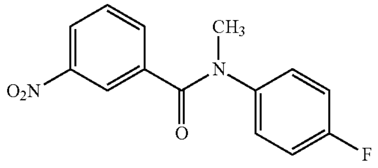 [SMILES: CN(C(=O)c1cccc([N+](=O)[O-])c1)c1ccc(F)cc1] | 28 |
| C286 | 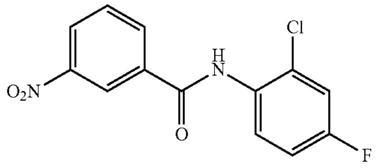 [SMILES: O=C(Nc1ccc(F)cc1Cl)c1cccc([N+](=O)[O-])c1] | 28 |
| C287 | 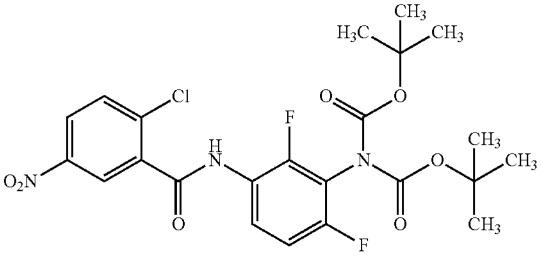 [SMILES: CC(C)(C)OC(=O)N(C(=O)OC(C)(C)C)c1c(F)ccc(NC(=O)c2cc([N+](=O)[O-])ccc2Cl)c1F] | 28 |
| C288 | 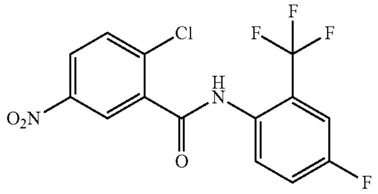 [SMILES: O=C(Nc1ccc(F)cc1C(F)(F)F)c1cc([N+](=O)[O-])ccc1Cl] | 28 |
| C289 | 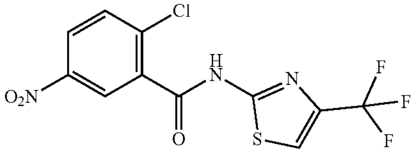 [SMILES: O=C(Nc1nc(C(F)(F)F)cs1)c1cc([N+](=O)[O-])ccc1Cl] | 30 |
| C290 | 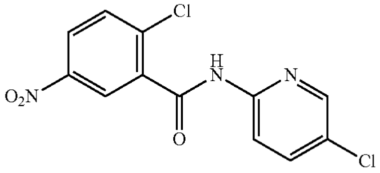 [SMILES: O=C(Nc1ccc(Cl)cn1)c1cc([N+](=O)[O-])ccc1Cl] | 30 |
| C291 | 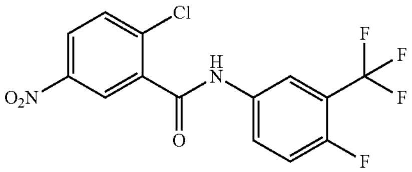 | 31 |
| C292 | 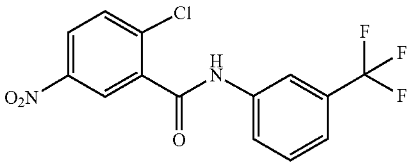 [SMILES: O=C(Nc1cccc(C(F)(F)F)c1)c1cc([N+](=O)[O-])ccc1Cl] | 31 |
Structure and preparation method for C series molecules TABLE 3-continued
| Structure and preparation method for C series molecules | | |
|---|---|---|
| No. | Structure | Prep* |
| C293 | 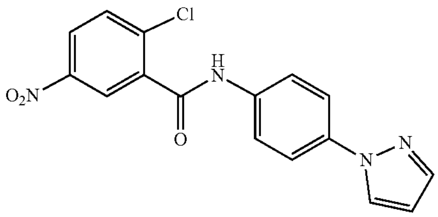 [SMILES: O=C(Nc1ccc(-n2cccn2)cc1)c1cc([N+](=O)[O-])ccc1Cl] | 31 |
| C294 | 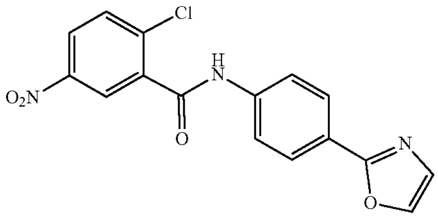 [SMILES: O=C(Nc1ccc(-c2ncco2)cc1)c1cc([N+](=O)[O-])ccc1Cl] | 31 |
| C295 | 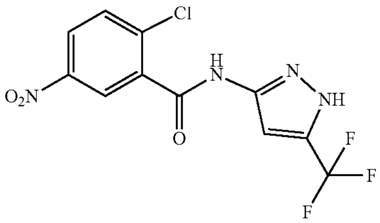 [SMILES: O=C(Nc1cc(C(F)(F)F)[nH]n1)c1cc([N+](=O)[O-])ccc1Cl] | 31 |
| C296 | 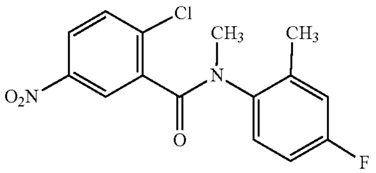 [SMILES: Cc1cc(F)ccc1N(C)C(=O)c1cc([N+](=O)[O-])ccc1Cl] | 32 |
| C297 | 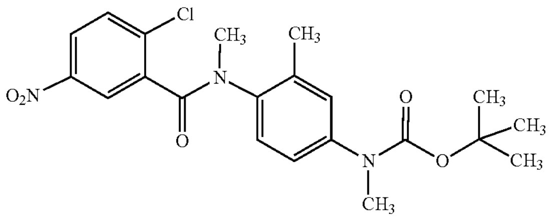 [SMILES: Cc1cc(N(C)C(=O)OC(C)(C)C)ccc1N(C)C(=O)c1cc([N+](=O)[O-])ccc1Cl] | 32 |
| C298 | 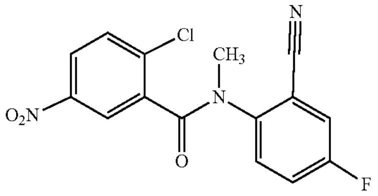 [SMILES: CN(C(=O)c1cc([N+](=O)[O-])ccc1Cl)c1ccc(F)cc1C#N] | 32 |
| C299 | 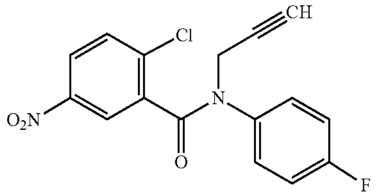 [SMILES: C#CCN(C(=O)c1cc([N+](=O)[O-])ccc1Cl)c1ccc(F)cc1] | 32 |

TABLE 3-continued
| Structure and preparation method for C series molecules | | |
|---|---|---|
| No. | Structure | Prep* |
| C300 | 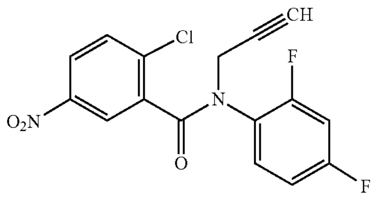 [SMILES: C#CCN(C(=O)c1cc([N+](=O)[O-])ccc1Cl)c1ccc(F)cc1F] | 32 |
| C301 | 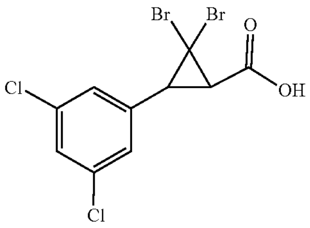 [SMILES: O=C(O)C1C(c2cc(Cl)cc(Cl)c2)C1(Br)Br] | 36 |
| C302 | 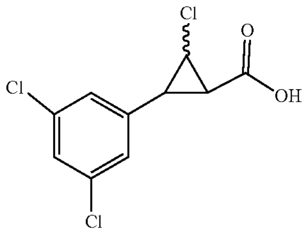 [SMILES: O=C(O)C1C(Cl)C1c1cc(Cl)cc(Cl)c1] | 37 |
| C303 | 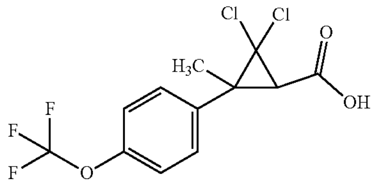 [SMILES: CC1(c2ccc(OC(F)(F)F)cc2)C(C(=O)O)C1(Cl)Cl] | 38 |
| C304 | 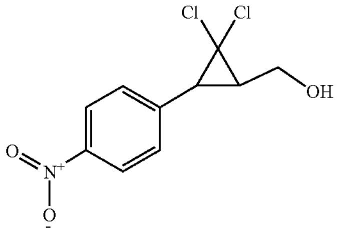 | 39 |
| C305 | 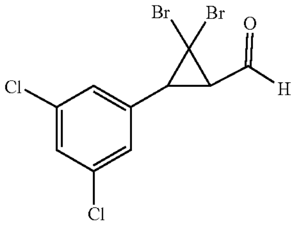 [SMILES: O=CC1C(c2cc(Cl)cc(Cl)c2)C1(Br)Br] | 40 |
| C306 | 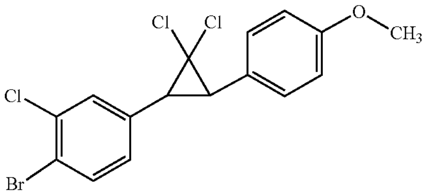 [SMILES: COc1ccc(C2C(c3ccc(Br)c(Cl)c3)C2(Cl)Cl)cc1] | 41 |

TABLE 3-continued
| No. | Structure | Prep* |
|---|---|---|
| Structure and preparation method for C series molecules | | |
| C307 | 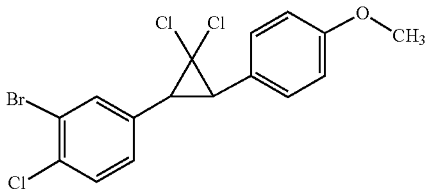 [SMILES: COc1ccc(C2C(c3ccc(Cl)c(Br)c3)C2(Cl)Cl)cc1] | 41 |
| C308 | 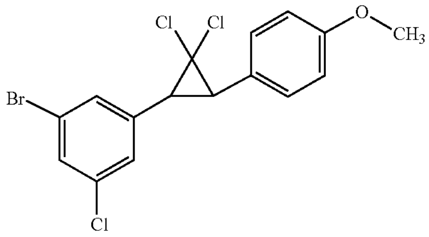 [SMILES: COc1ccc(C2C(c3cc(Cl)cc(Br)c3)C2(Cl)Cl)cc1] | 41 |
| C309 | 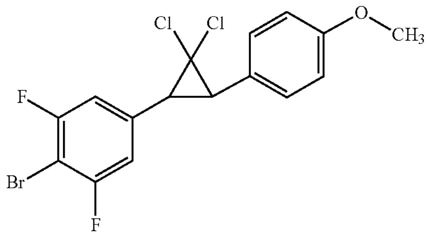 [SMILES: COc1ccc(C2C(c3cc(F)c(Br)c(F)c3)C2(Cl)Cl)cc1] | 41 |
| C310 | 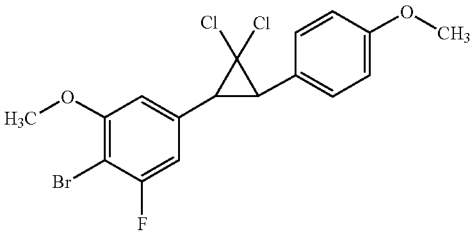 | 41 |
| C311 | 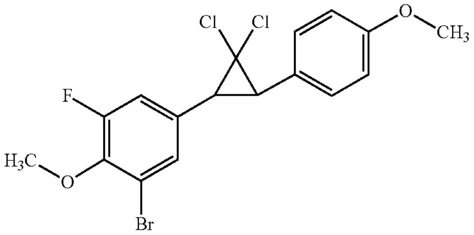 | 41 |
| C312 | 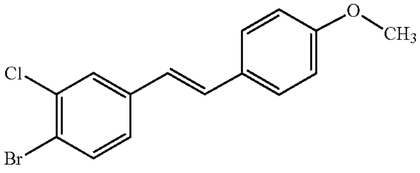 [SMILES: COc1ccc(/C=C/c2ccc(Br)c(Cl)c2)cc1] | 42 |
| C313 | 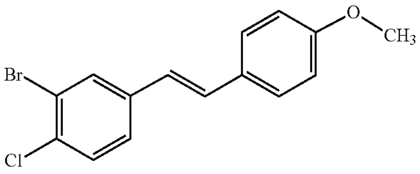 [SMILES: COc1ccc(/C=C/c2ccc(Cl)c(Br)c2)cc1] | 42 |

TABLE 3-continued
| Structure and preparation method for C series molecules | | |
|---|---|---|
| No. | Structure | Prep* |
| C314 | 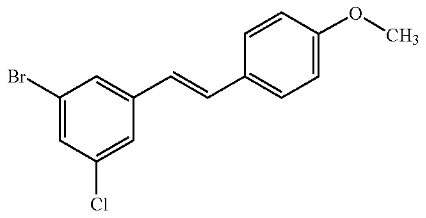 | 42 |
| C315 | 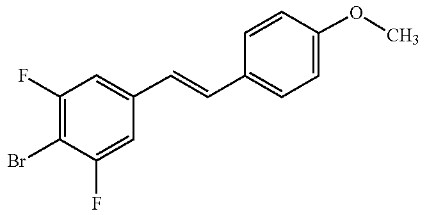 [SMILES: COc1ccc(/C=C/c2cc(F)c(Br)c(F)c2)cc1] | 43 |
| C316 | 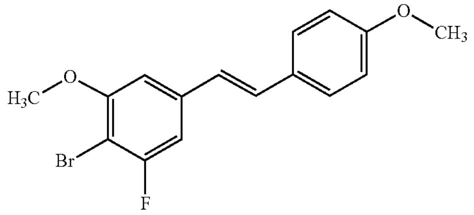 | 43 |
| C317 | 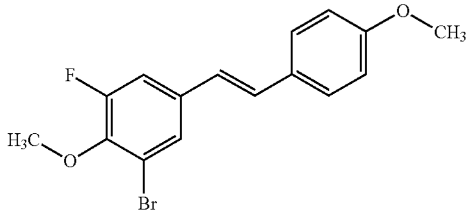 | 44 |
| C318 | 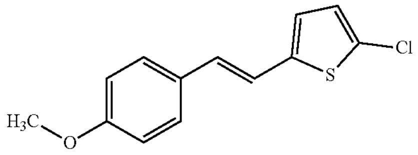 [SMILES: COc1ccc(/C=C/c2ccc(Cl)s2)cc1] | 45 |
| C319 | 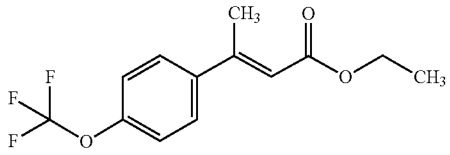 [SMILES: CCOC(=O)/C=C(\C)c1ccc(OC(F)(F)F)cc1] | 46 |
| C320 | 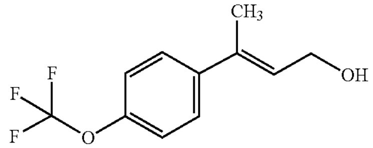 [SMILES: C/C(=C\CO)c1ccc(OC(F)(F)F)cc1] | 47 |
| C321 | 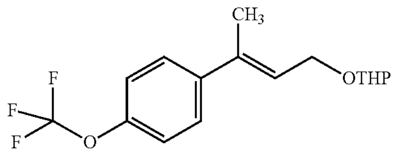 | 48 |

TABLE 3-continued
Structure and preparation method for C series molecules
| No. | Structure | Prep* |
|---|---|---|
| C322 | 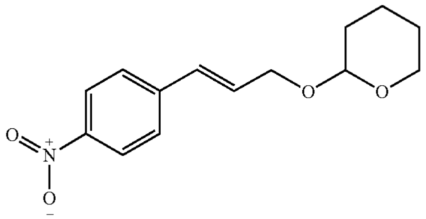 | 49 |
| C323 | 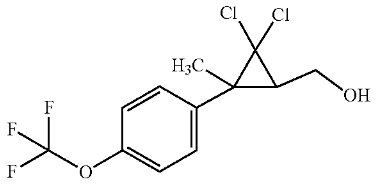 [SMILES: CC1(c2ccc(OC(F)(F)F)cc2)C(CO)C1(Cl)Cl] | 50 |
| C324 | 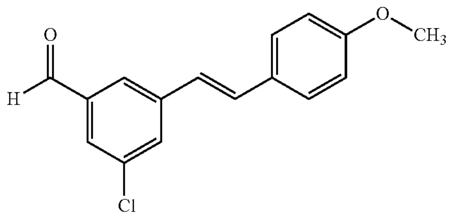 | 51 |
| C325 | 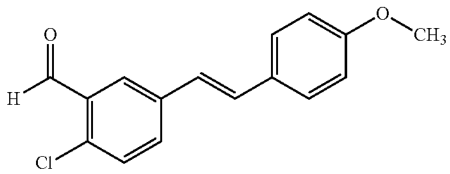 | 51 |
| C326 | 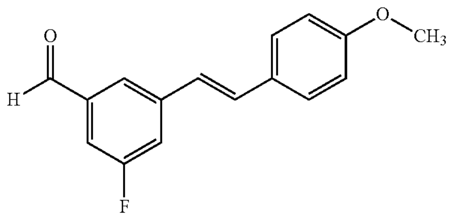 | 51 |
| C327 | 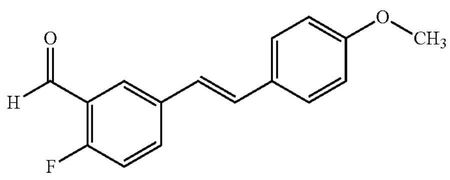 | 51 |
| C328 | 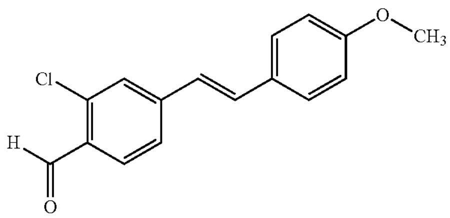 | 51 |

TABLE 3-continued
| Structure and preparation method for C series molecules | | |
|---|---|---|
| No. | Structure | Prep* |
| C329 | 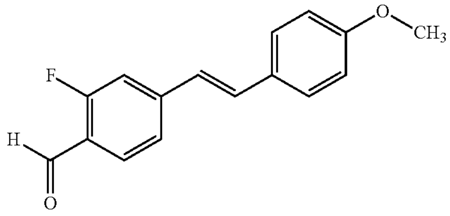 [SMILES: COc1ccc(/C=C/c2ccc(C=O)c(F)c2)cc1] | 51 |
| C330 | 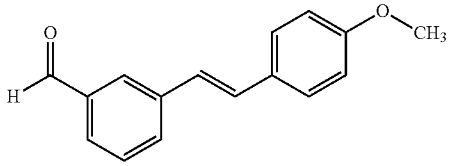 | 51 |
| C331 | 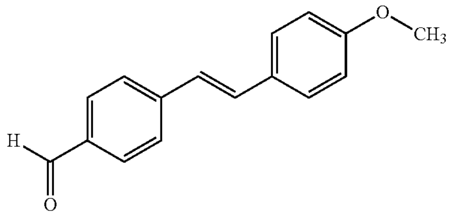 | 51 |
| C332 | 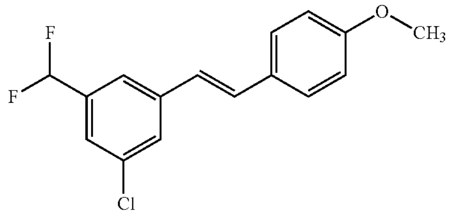 [SMILES: COc1ccc(/C=C/c2cc(Cl)cc(C(F)F)c2)cc1] | 52 |
| C333 | 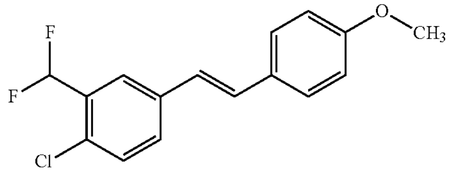 | 52 |
| C334 | 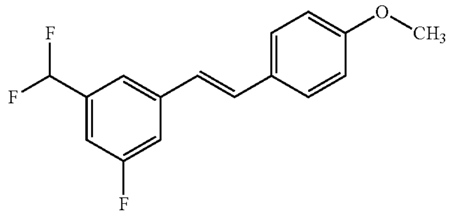 [SMILES: COc1ccc(/C=C/c2cc(F)cc(C(F)F)c2)cc1] | 52 |
| C335 | 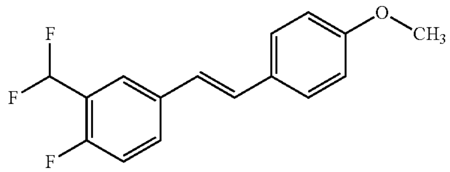 [SMILES: COc1ccc(/C=C/c2ccc(F)c(C(F)F)c2)cc1] | 52 |

TABLE 3-continued
Structure and preparation method for C series molecules
| No. | Structure | Prep* |
| --- | --- | --- |
| C336 | 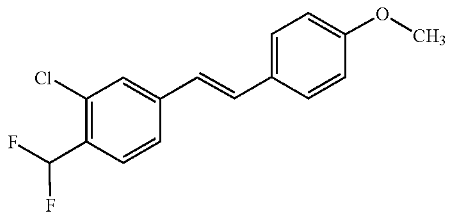 [SMILES: COc1ccc(/C=C/c2ccc(C(F)F)c(Cl)c2)cc1] | 52 |
| C337 | 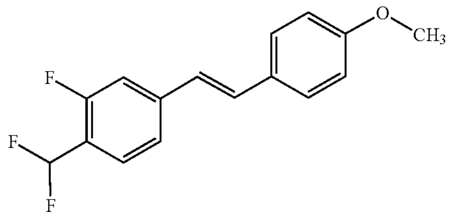 [SMILES: COc1ccc(/C=C/c2ccc(C(F)F)c(F)c2)cc1] | 52 |
| C338 | 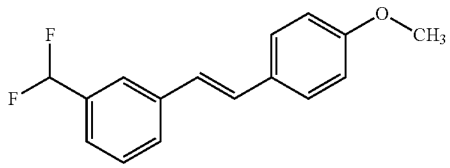 [SMILES: COc1ccc(/C=C/c2cccc(C(F)F)c2)cc1] | 52 |
| C339 | 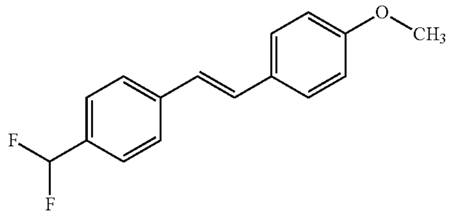 [SMILES: COc1ccc(/C=C/c2ccc(C(F)F)cc2)cc1] | 52 |
| C340 | 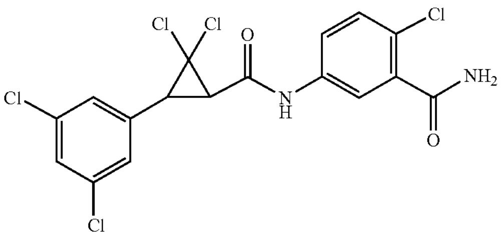 [SMILES: NC(=O)c1cc(NC(=O)C2C(c3cc(Cl)cc(Cl)c3)C2(Cl)Cl)ccc1Cl] | 53 |
| C341 | 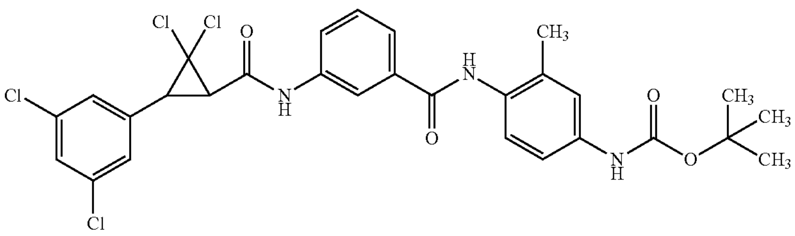 [SMILES: Cc1cc(NC(=O)OC(C)(C)C)ccc1NC(=O)c1cccc(NC(=O)C2C(c3cc(Cl)cc(Cl)c3)C2(Cl)Cl)c1] | 55 |

TABLE 3-continued
| Structure and preparation method for C series molecules | | |
|---|---|---|
| No. | Structure | Prep* |
| C342 | 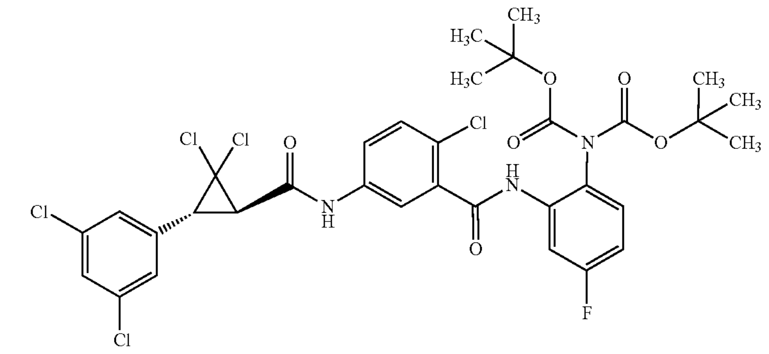 [SMILES: CC(C)(C)OC(=O)N(C(=O)OC(C)(C)C)c1ccc(F)cc1NC(=O)c1cc(NC(=O)[C@H]2[C@H](c3cc(Cl)cc(Cl)c3)C2(Cl)Cl)ccc1Cl] | 55 |
| C343 | 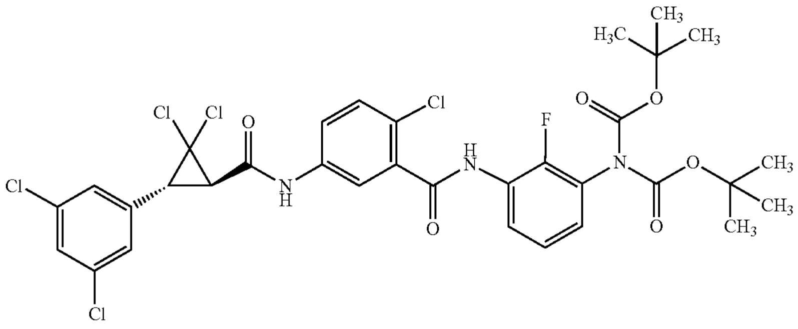 [SMILES: CC(C)(C)OC(=O)N(C(=O)OC(C)(C)C)c1cccc(NC(=O)c2cc(NC(=O)[C@H]3[C@H](c4cc(Cl)cc(Cl)c4)C3(Cl)Cl)ccc2Cl)c1F] | 55 |
| C344 | 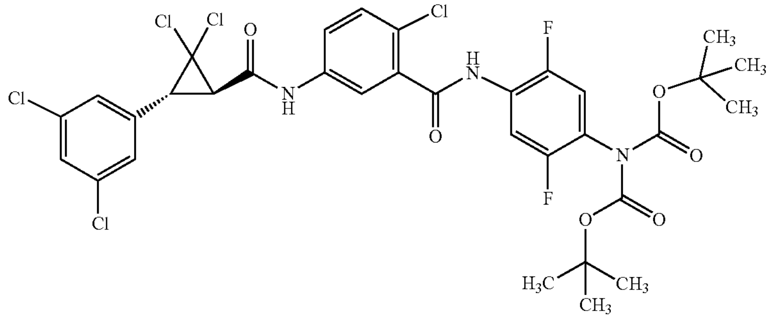 [SMILES: CC(C)(C)OC(=O)N(C(=O)OC(C)(C)C)c1cc(F)c(NC(=O)c2cc(NC(=O)[C@H]3[C@H](c4cc(Cl)cc(Cl)c4)C3(Cl)Cl)ccc2Cl)cc1F] | 55 |
| C345 | 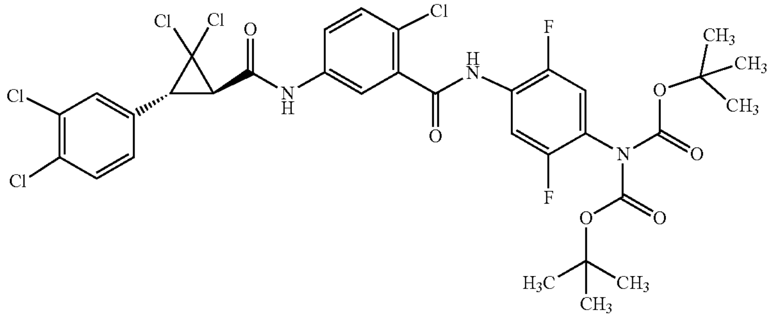 [SMILES: CC(C)(C)OC(=O)N(C(=O)OC(C)(C)C)c1cc(F)c(NC(=O)c2cc(NC(=O)[C@H]3[C@H](c4ccc(Cl)c(Cl)c4)C3(Cl)Cl)ccc2Cl)cc1F] | 55 |

TABLE 3-continued
Structure and preparation method for C series molecules
| No. | Structure | Prep* |
| --- | --- | --- |
| C346 | 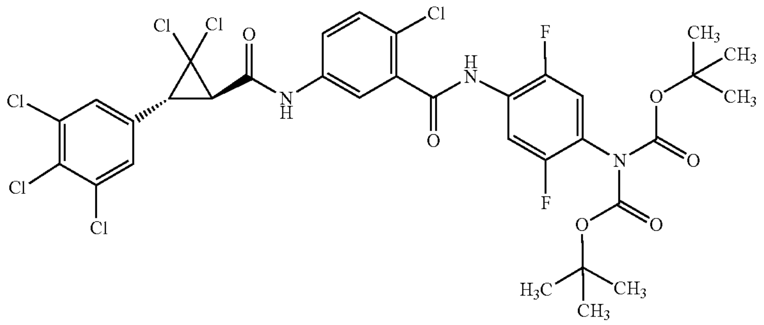 [SMILES: CC(C)(C)OC(=O)N(C(=O)OC(C)(C)C)c1cc(F)c(NC(=O)c2cc(NC(=O)[C@H]3[C@H](c4cc(Cl)c(Cl)c(Cl)c4)C3(Cl)Cl)ccc2Cl)cc1F] | 55 |
| C347 | 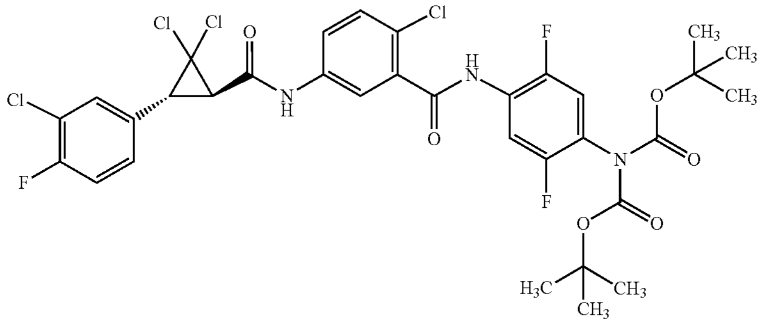 [SMILES: CC(C)(C)OC(=O)N(C(=O)OC(C)(C)C)c1cc(F)c(NC(=O)c2cc(NC(=O)[C@H]3[C@H](c4ccc(F)c(Cl)c4)C3(Cl)Cl)ccc2Cl)cc1F] | 55 |
| C348 | 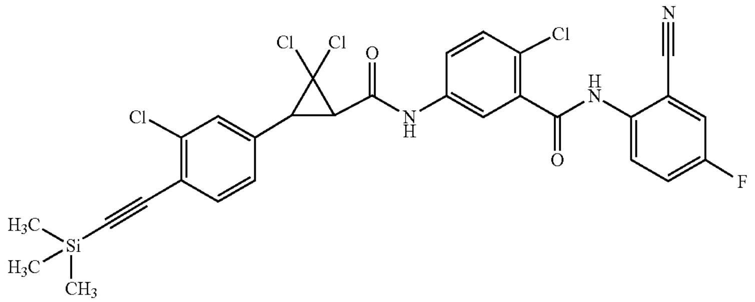 [SMILES: C[Si](C)(C)C#Cc1ccc(C2C(C(=O)Nc3ccc(Cl)c(C(=O)Nc4ccc(F)cc4C#N)c3)C2(Cl)Cl)cc1Cl] | 78 |
| C349 | 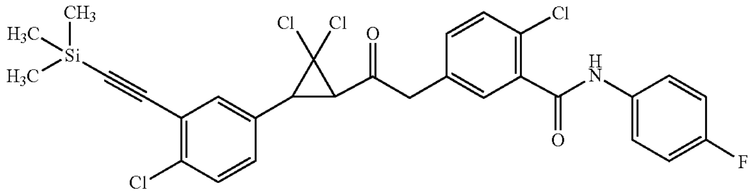 [SMILES: C[Si](C)(C)C#Cc1cc(C2C(C(=O)Cc3ccc(Cl)c(C(=O)Nc4ccc(F)cc4)c3)C2(Cl)Cl)ccc1Cl] | 78 |
| C350 | 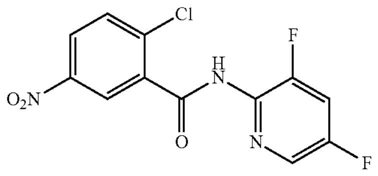 | 81 |
| C351 | 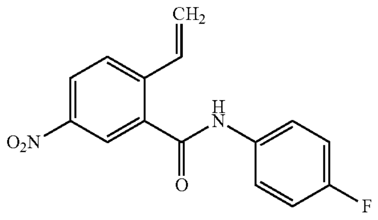 [SMILES: C=Cc1ccc([N+](=O)[O-])cc1C(=O)Nc1ccc(F)cc1] | 82 |

TABLE 3-continued
| Structure and preparation method for C series molecules | | |
|---|---|---|
| No. | Structure | Prep* |
| C352 | 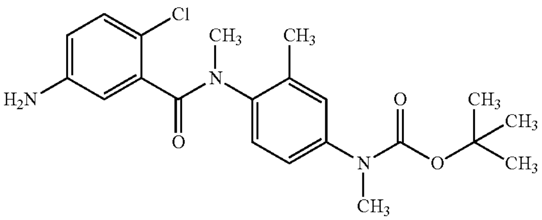 | 83 |
| C353 | 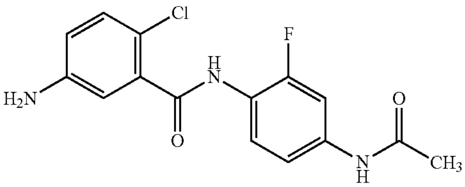 | 83 |
| C354 | 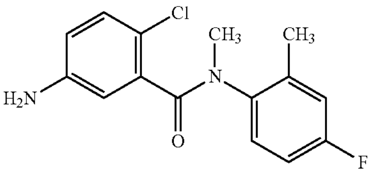 | 83 |
| C355 | 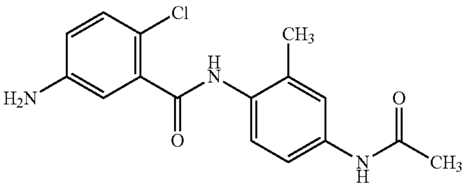 | 83 |
| C356 | 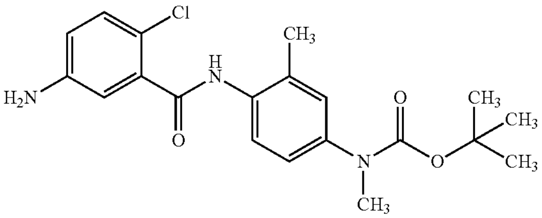 | 83 |
| C357 | 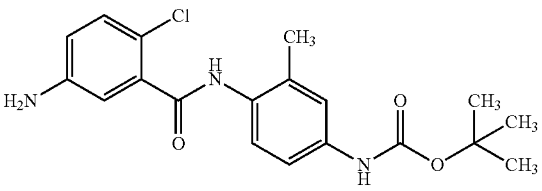 | 83 |
| C358 | 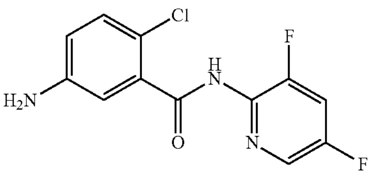 [SMILES: Nc1ccc(Cl)c(C(=O)Nc2ncc(F)cc2F)c1] | 83 |

TABLE 3-continued
Structure and preparation method for C series molecules
| No. | Structure | Prep* |
| --- | --- | --- |
| C359 | 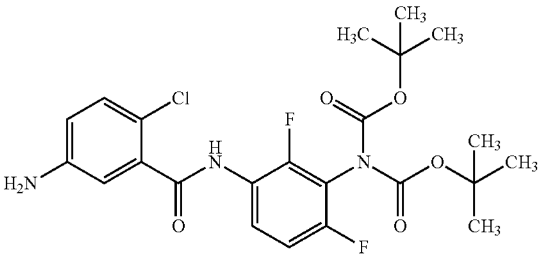 | 83 |
| C360 | 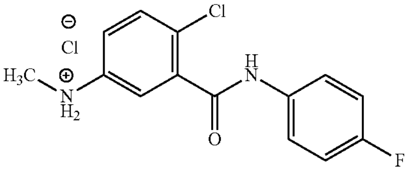 [SMILES: C[NH2+]c1ccc(Cl)c(C(=O)Nc2ccc(F)cc2)c1 ; [Cl-]] | 84 |
| C361 | 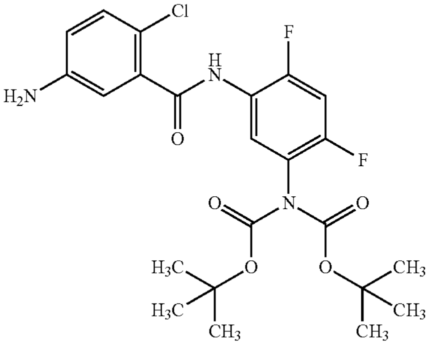 [SMILES: CC(C)(C)OC(=O)N(C(=O)OC(C)(C)C)c1cc(NC(=O)c2cc(N)ccc2Cl)c(F)cc1F] | 85 |
| C362 | 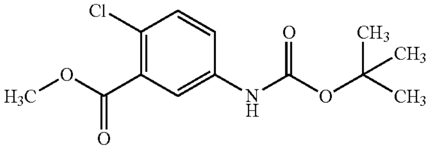 [SMILES: COC(=O)c1cc(NC(=O)OC(C)(C)C)ccc1Cl] | 86 |
| C363 | 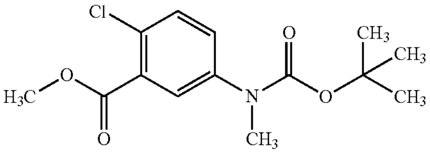 [SMILES: COC(=O)c1cc(N(C)C(=O)OC(C)(C)C)ccc1Cl] | 87 |
| C364 | 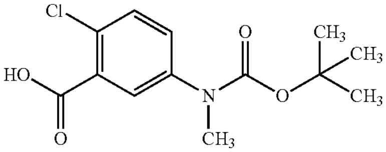 [SMILES: CN(C(=O)OC(C)(C)C)c1ccc(Cl)c(C(=O)O)c1] | 88 |
| C365 | 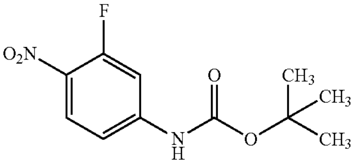 [SMILES: CC(C)(C)OC(=O)Nc1ccc([N+](=O)[O-])c(F)c1] | 89 |

TABLE 3-continued
| No. | Structure | Prep* |
|---|---|---|
| Structure and preparation method for C series molecules | | |
| C366 | 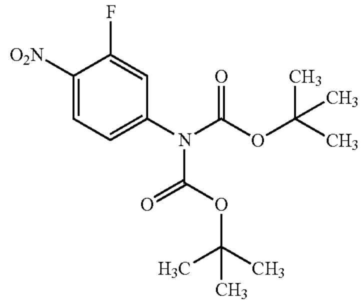 | 89 |
| C367 | 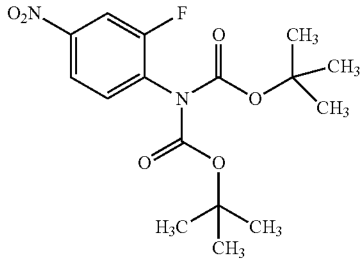 [SMILES: CC(C)(C)OC(=O)N(C(=O)OC(C)(C)C)c1ccc([N+](=O)[O-])cc1F] | 89 |
| C368 | 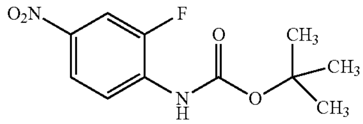 [SMILES: CC(C)(C)OC(=O)Nc1ccc([N+](=O)[O-])cc1F] | 89 |
| C369 | 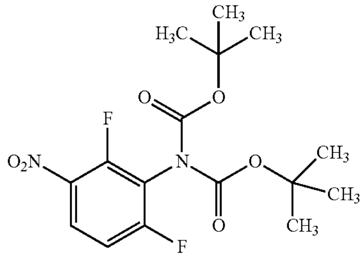 [SMILES: CC(C)(C)OC(=O)N(C(=O)OC(C)(C)C)c1c(F)ccc([N+](=O)[O-])c1F] | 89 |
| C370 | 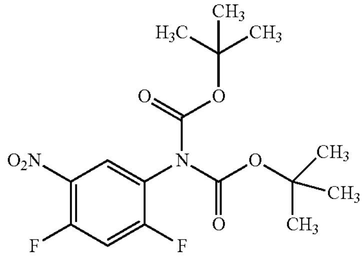 [SMILES: CC(C)(C)OC(=O)N(C(=O)OC(C)(C)C)c1cc([N+](=O)[O-])c(F)cc1F] | 89 |
| C371 | 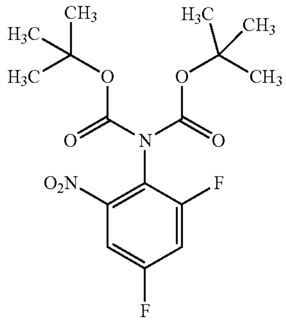 [SMILES: CC(C)(C)OC(=O)N(C(=O)OC(C)(C)C)c1c(F)cc(F)cc1[N+](=O)[O-]] | 89 |

TABLE 3-continued
| Structure and preparation method for C series molecules | | |
|---|---|---|
| No. | Structure | Prep* |
| C372 | 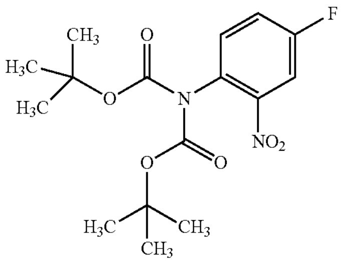 [SMILES: CC(C)(C)OC(=O)N(C(=O)OC(C)(C)C)c1ccc(F)cc1[N+](=O)[O-]] | 89 |
| C373 | 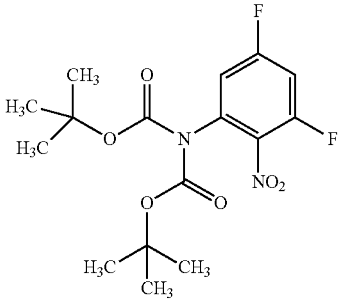 [SMILES: CC(C)(C)OC(=O)N(C(=O)OC(C)(C)C)c1cc(F)cc(F)c1[N+](=O)[O-]] | 89 |
| C374 | 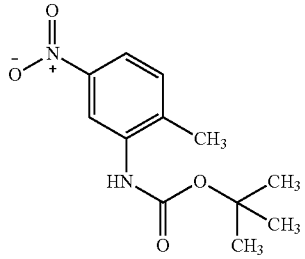 [SMILES: Cc1ccc([N+](=O)[O-])cc1NC(=O)OC(C)(C)C] | 89 |
| C375 | 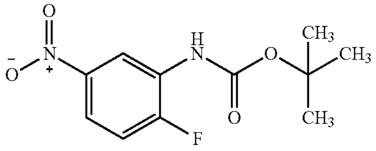 [SMILES: CC(C)(C)OC(=O)Nc1cc([N+](=O)[O-])ccc1F] | 89 |
| C376 | 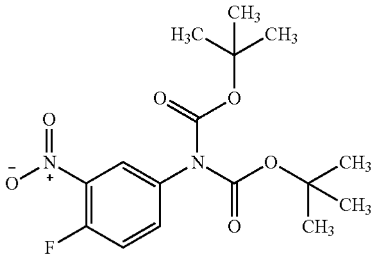 [SMILES: CC(C)(C)OC(=O)N(C(=O)OC(C)(C)C)c1ccc(F)c([N+](=O)[O-])c1] | 89 |
| C377 | 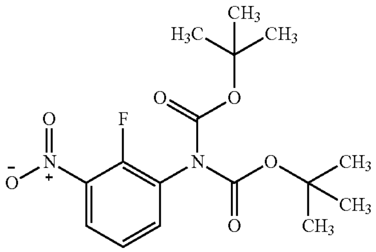 [SMILES: CC(C)(C)OC(=O)N(C(=O)OC(C)(C)C)c1cccc([N+](=O)[O-])c1F] | 89 |

TABLE 3-continued
| Structure and preparation method for C series molecules | | |
|---|---|---|
| No. | Structure | Prep* |
| C378 | 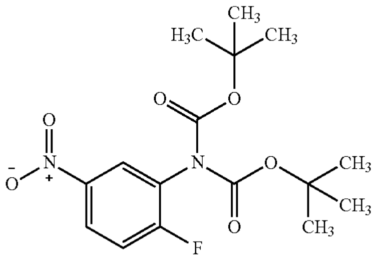 [SMILES: CC(C)(C)OC(=O)N(C(=O)OC(C)(C)C)c1cc([N+](=O)[O-])ccc1F] | 89 |
| C379 | 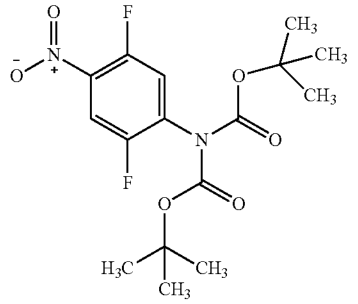 [SMILES: CC(C)(C)OC(=O)N(C(=O)OC(C)(C)C)c1cc(F)c([N+](=O)[O-])cc1F] | 89 |
| C380 | 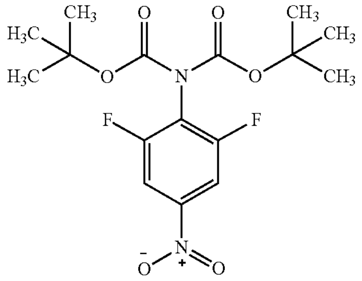 [SMILES: CC(C)(C)OC(=O)N(C(=O)OC(C)(C)C)c1c(F)cc([N+](=O)[O-])cc1F] | 89 |
| C381 | 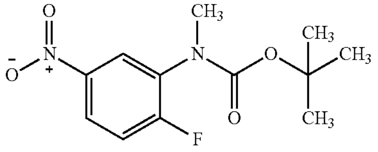 [SMILES: CN(C(=O)OC(C)(C)C)c1cc([N+](=O)[O-])ccc1F] | 89 |
| C382 | 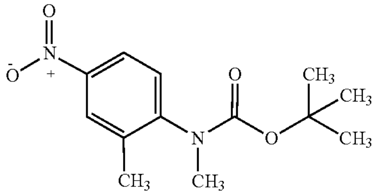 | 89 |
| C383 | 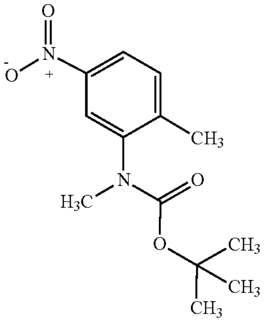 | 89 |

TABLE 3-continued
| Structure and preparation method for C series molecules | | |
|---|---|---|
| No. | Structure | Prep* |
| C384 | 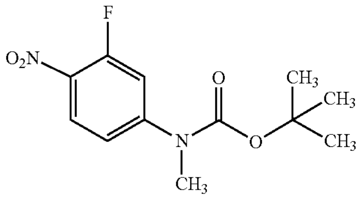 [SMILES: CN(C(=O)OC(C)(C)C)c1ccc([N+](=O)[O-])c(F)c1] | 90 |
| C385 | 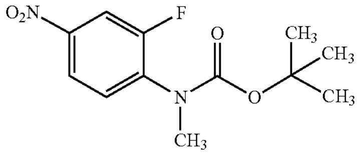 | 90 |
| C386 | 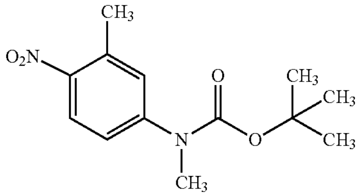 [SMILES: Cc1cc(N(C)C(=O)OC(C)(C)C)ccc1[N+](=O)[O-]] | 90 |
| C387 | 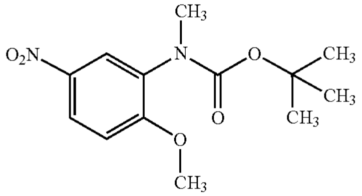 | 90 |
| C388 | 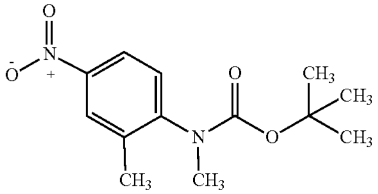 | 90 |
| C389 | 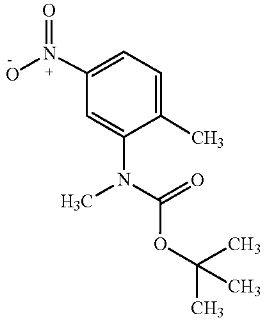 | 90 |
| C390 | 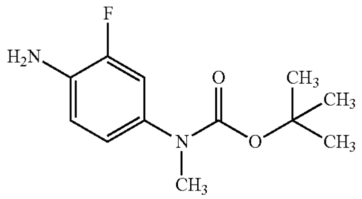 | 91 |

TABLE 3-continued
| Structure and preparation method for C series molecules | | |
|---|---|---|
| No. | Structure | Prep* |
| C392 | 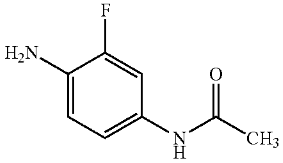 | 91 |
| C393 | 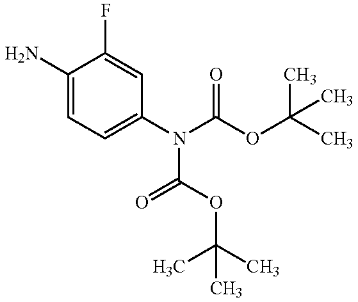 | 91 |
| C394 | 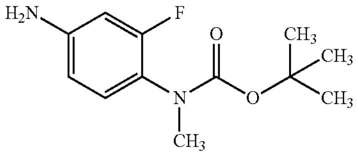 | 91 |
| C395 | 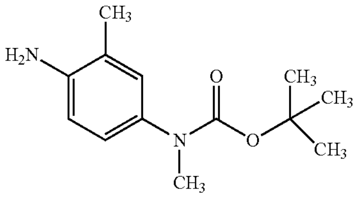 [SMILES: Cc1cc(N(C)C(=O)OC(C)(C)C)ccc1N] | 91 |
| C396 | 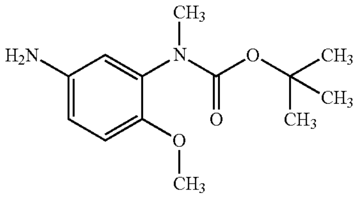 | 91 |
| C397 | 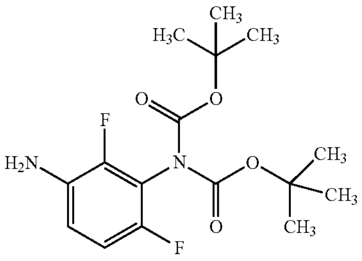 | 91 |

TABLE 3-continued
| Structure and preparation method for C series molecules | | |
|---|---|---|
| No. | Structure | Prep* |
| C398 | 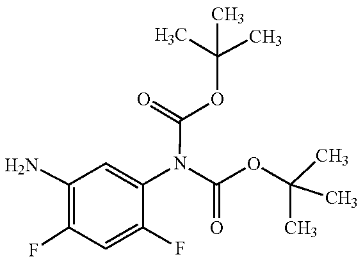 [SMILES: CC(C)(C)OC(=O)N(C(=O)OC(C)(C)C)c1cc(N)c(F)cc1F] | 91 |
| C399 | 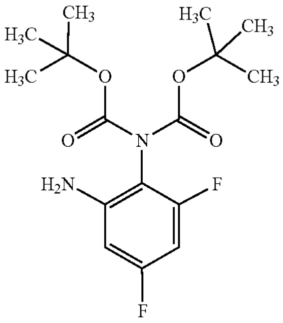 [SMILES: CC(C)(C)OC(=O)N(C(=O)OC(C)(C)C)c1c(N)cc(F)cc1F] | 91 |
| C400 | 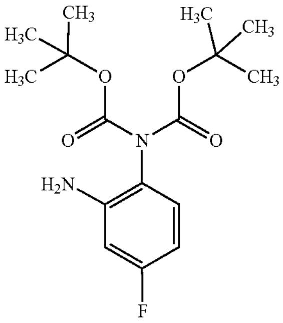 [SMILES: CC(C)(C)OC(=O)N(C(=O)OC(C)(C)C)c1ccc(F)cc1N] | 91 |
| C401 | 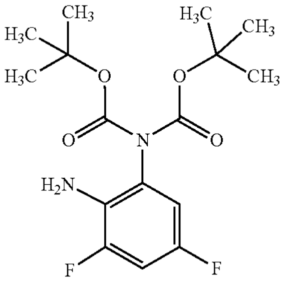 [SMILES: CC(C)(C)OC(=O)N(C(=O)OC(C)(C)C)c1cc(F)cc(F)c1N] | 91 |
| C402 | 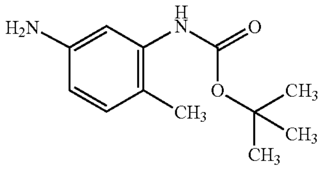 [SMILES: Cc1ccc(N)cc1NC(=O)OC(C)(C)C] | 91 |
| C403 | 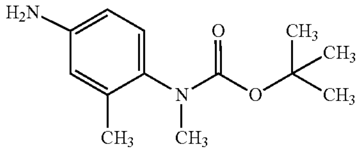 [SMILES: Cc1cc(N)ccc1N(C)C(=O)OC(C)(C)C] | 91 |

TABLE 3-continued
| Structure and preparation method for C series molecules | | |
|---|---|---|
| No. | Structure | Prep* |
| C404 | 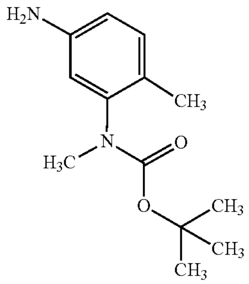 [SMILES: Cc1ccc(N)cc1N(C)C(=O)OC(C)(C)C] | 91 |
| C405 | 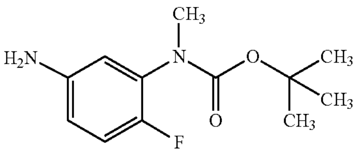 [SMILES: CN(C(=O)OC(C)(C)C)c1cc(N)ccc1F] | 91 |
| C406 | 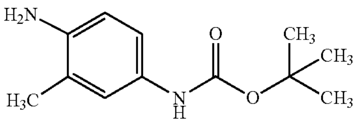 [SMILES: Cc1cc(NC(=O)OC(C)(C)C)ccc1N] | 91 |
| C407 | 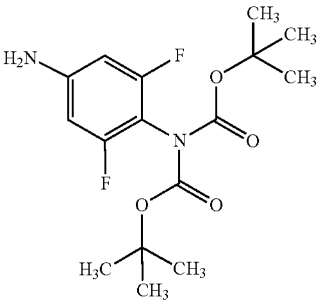 [SMILES: CC(C)(C)OC(=O)N(C(=O)OC(C)(C)C)c1c(F)cc(N)cc1F] | 91 |
| C408 | 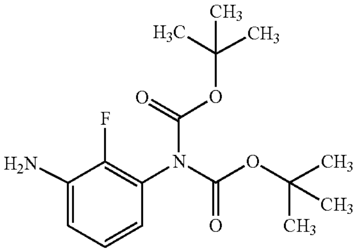 [SMILES: CC(C)(C)OC(=O)N(C(=O)OC(C)(C)C)c1cccc(N)c1F] | 91 |
| C409 | 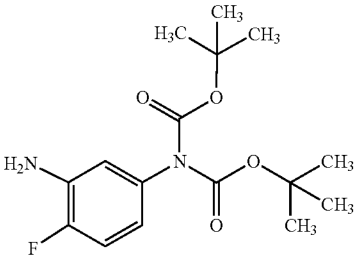 [SMILES: CC(C)(C)OC(=O)N(C(=O)OC(C)(C)C)c1ccc(F)c(N)c1] | |

TABLE 3-continued
| No. | Structure | Prep* |
|---|---|---|
| C410 | 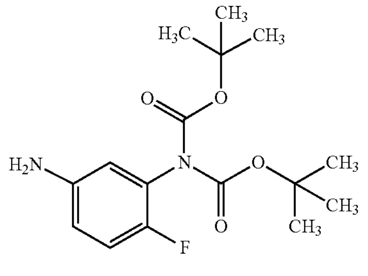 [SMILES: CC(C)(C)OC(=O)N(C(=O)OC(C)(C)C)c1cc(N)ccc1F] | 91 |
| C411 | 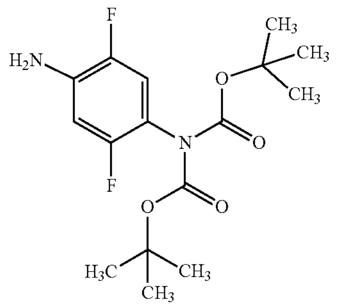 [SMILES: CC(C)(C)OC(=O)N(C(=O)OC(C)(C)C)c1cc(F)c(N)cc1F] | 91 |
| C412 | 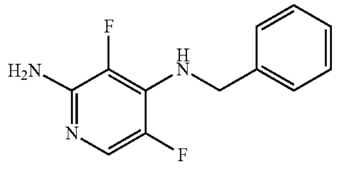 [SMILES: Nc1ncc(F)c(NCc2ccccc2)c1F] | 92 |
| C413 | 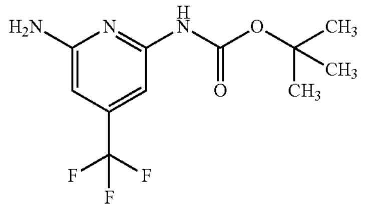 [SMILES: CC(C)(C)OC(=O)Nc1cc(C(F)(F)F)cc(N)n1] | 93 |
| C414 | 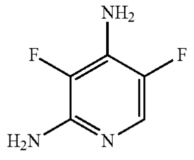 | 94 |
| C415 | 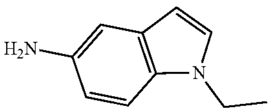 | 95 |
| C416 | 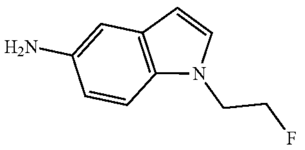 [SMILES: Nc1ccc2c(ccn2CCF)c1] | 95 |
Structure and preparation method for C series molecules TABLE 3-continued
| Structure and preparation method for C series molecules | | |
|---|---|---|
| No. | Structure | Prep* |
| C417 | 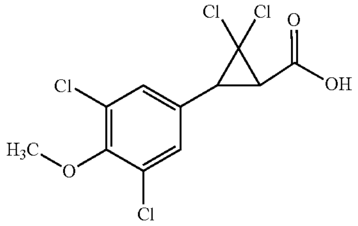 [SMILES: COc1c(Cl)cc(C2C(C(=O)O)C2(Cl)Cl)cc1Cl] | 96 |
| C418 | 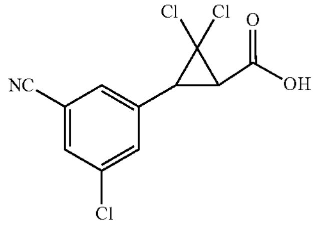 [SMILES: N#Cc1cc(Cl)cc(C2C(C(=O)O)C2(Cl)Cl)c1] | 96 |
| C419 | 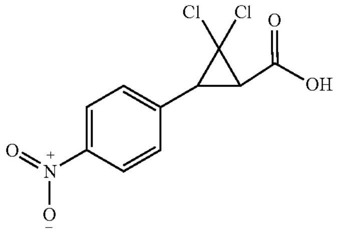 | 96 |
| C420 | 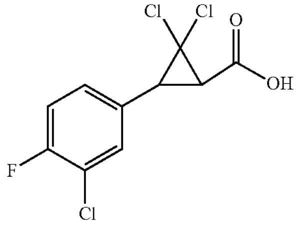 [SMILES: O=C(O)C1C(c2ccc(F)c(Cl)c2)C1(Cl)Cl] | 96 |
| C421 | 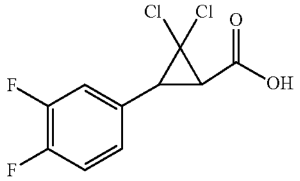 [SMILES: O=C(O)C1C(c2ccc(F)c(F)c2)C1(Cl)Cl] | 96 |
| C422 | 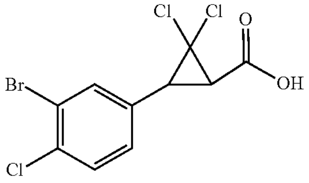 [SMILES: O=C(O)C1C(c2ccc(Cl)c(Br)c2)C1(Cl)Cl] | 96 |
| C423 | 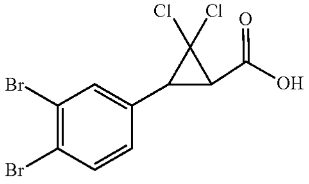 | 96 |

TABLE 3-continued
| Structure and preparation method for C series molecules | | |
|---|---|---|
| No. | Structure | Prep* |
| C424 | 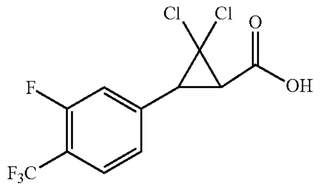 | 96 |
| C425 | 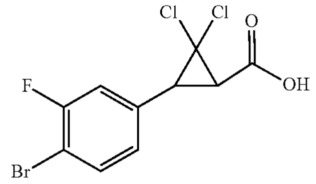 | 96 |
| C426 | 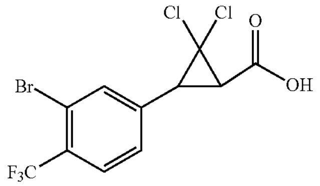 | 96 |
| C427 | 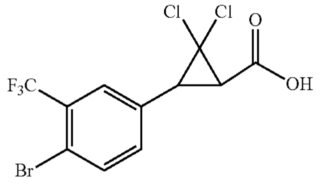 | 96 |
| C428 | 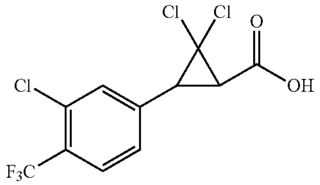 [SMILES: O=C(O)C1C(c2ccc(C(F)(F)F)c(Cl)c2)C1(Cl)Cl] | 96 |
| C429 | 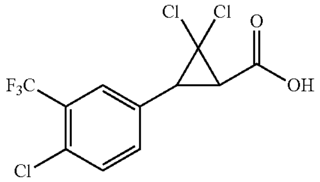 [SMILES: O=C(O)C1C(c2ccc(Cl)c(C(F)(F)F)c2)C1(Cl)Cl] | 96 |
| C430 | 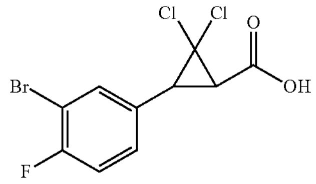 | 96 |
| C431 | 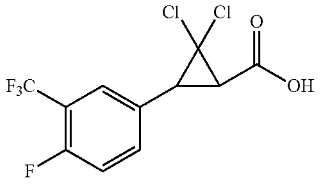 | 96 |

TABLE 3-continued
| Structure and preparation method for C series molecules | | |
|---|---|---|
| No. | Structure | Prep* |
| C432 | 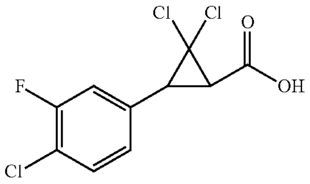 [SMILES: O=C(O)C1C(c2ccc(Cl)c(F)c2)C1(Cl)Cl] | 96 |
| C433 | 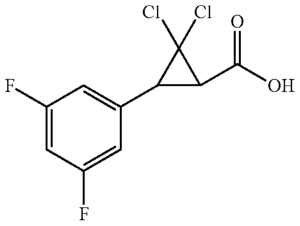 [SMILES: O=C(O)C1C(c2cc(F)cc(F)c2)C1(Cl)Cl] | 96 |
| C434 | 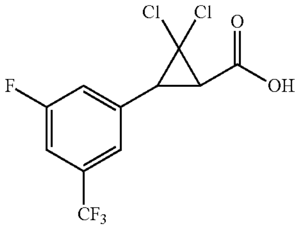 [SMILES: O=C(O)C1C(c2cc(F)cc(C(F)(F)F)c2)C1(Cl)Cl] | 96 |
| C435 | 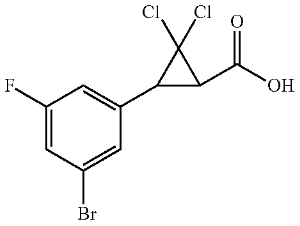 [SMILES: O=C(O)C1C(c2cc(F)cc(Br)c2)C1(Cl)Cl] | 96 |
| C436 | 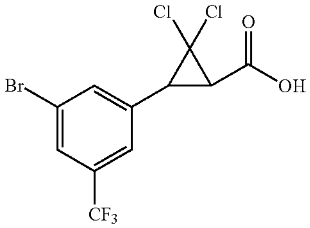 | 96 |
| C437 | 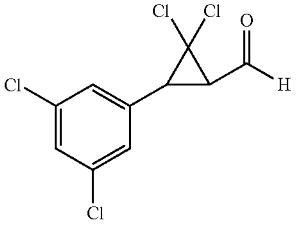 | 97 |
| C438 | 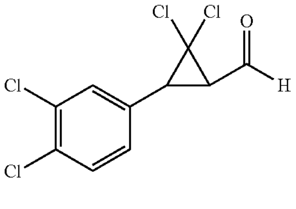 | 97 |

TABLE 3-continued
| Structure and preparation method for C series molecules | | |
|---|---|---|
| No. | Structure | Prep* |
| C439 | 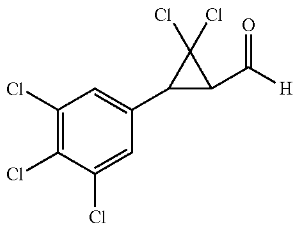 [SMILES: O=CC1C(c2cc(Cl)c(Cl)c(Cl)c2)C1(Cl)Cl] | 97 |
| C440 | 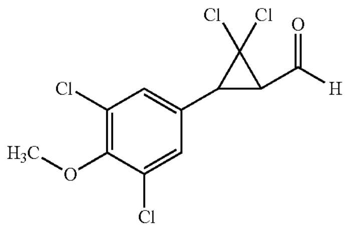 [SMILES: COc1c(Cl)cc(C2C(C=O)C2(Cl)Cl)cc1Cl] | 97 |
| C441 | 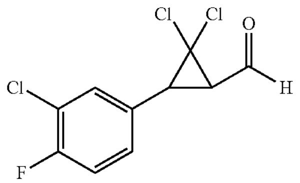 | 97 |
| C442 | 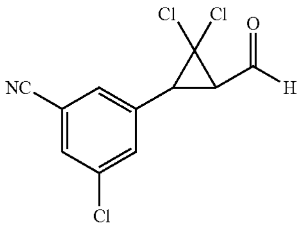 [SMILES: N#Cc1cc(Cl)cc(C2C(C=O)C2(Cl)Cl)c1] | 97 |
| C443 | 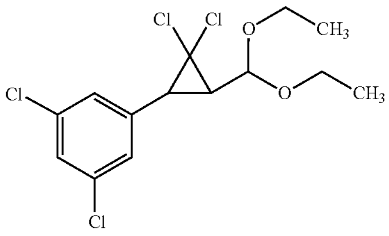 [SMILES: CCOC(OCC)C1C(c2cc(Cl)cc(Cl)c2)C1(Cl)Cl] | 98 |
| C444 | 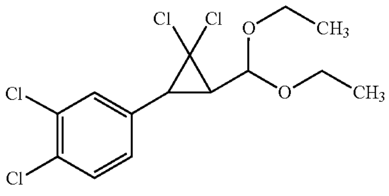 [SMILES: CCOC(OCC)C1C(c2ccc(Cl)c(Cl)c2)C1(Cl)Cl] | 98 |

TABLE 3-continued
| Structure and preparation method for C series molecules | | |
|---|---|---|
| No. | Structure | Prep* |
| C445 | 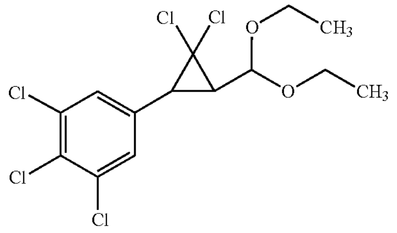 [SMILES: CCOC(OCC)C1C(c2cc(Cl)c(Cl)c(Cl)c2)C1(Cl)Cl] | 98 |
| C446 | 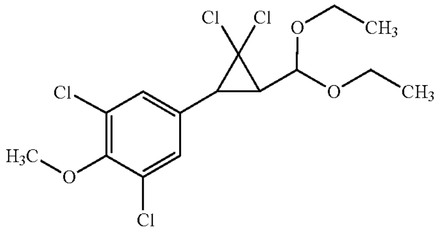 [SMILES: CCOC(OCC)C1C(c2cc(Cl)c(OC)c(Cl)c2)C1(Cl)Cl] | 98 |
| C447 | 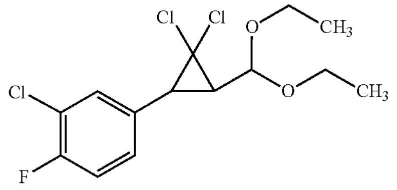 [SMILES: CCOC(OCC)C1C(c2ccc(F)c(Cl)c2)C1(Cl)Cl] | 98 |
| C448 | 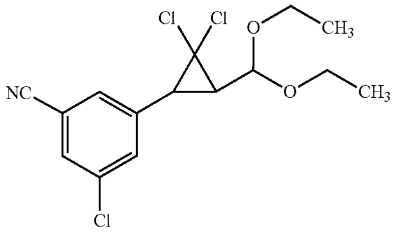 [SMILES: CCOC(OCC)C1C(c2cc(Cl)cc(C#N)c2)C1(Cl)Cl] | 98 |
| C449 | 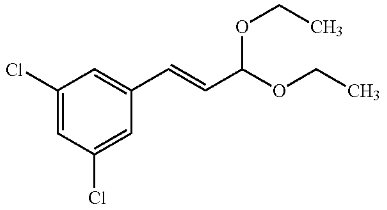 [SMILES: CCOC(/C=C/c1cc(Cl)cc(Cl)c1)OCC] | 99 |
| C450 | 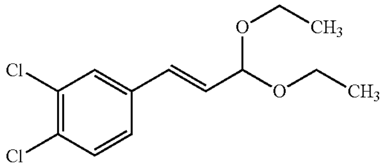 [SMILES: CCOC(/C=C/c1ccc(Cl)c(Cl)c1)OCC] | 99 |
| C451 | 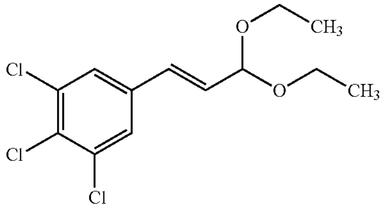 [SMILES: CCOC(/C=C/c1cc(Cl)c(Cl)c(Cl)c1)OCC] | 99 |

TABLE 3-continued
| Structure and preparation method for C series molecules | | |
|---|---|---|
| No. | Structure | Prep* |
| C452 | 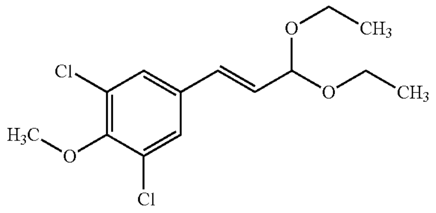 [SMILES: CCOC(/C=C/c1cc(Cl)c(OC)c(Cl)c1)OCC] | 99 |
| C453 | 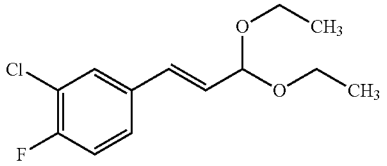 [SMILES: CCOC(/C=C/c1ccc(F)c(Cl)c1)OCC] | 99 |
| C454 | 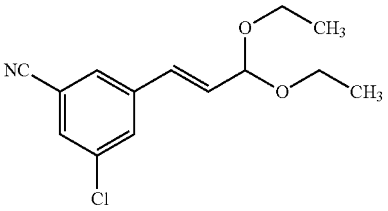 [SMILES: CCOC(/C=C/c1cc(Cl)cc(C#N)c1)OCC] | 99 |
| C455 | 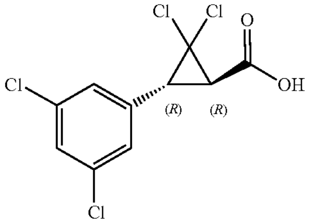 | 100 |
| C456 | 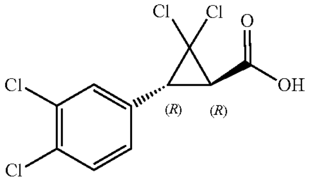 | 100 |
| C457 | 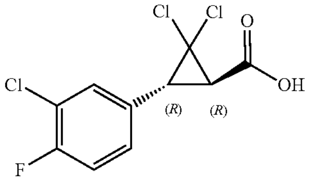 | 100 |
| C458 | 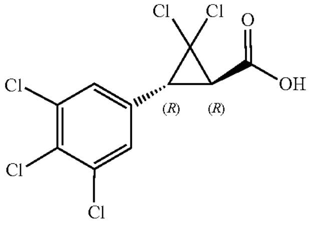 | 100 |

TABLE 3-continued
| Structure and preparation method for C series molecules | | |
|---|---|---|
| No. | Structure | Prep* |
| C459 | 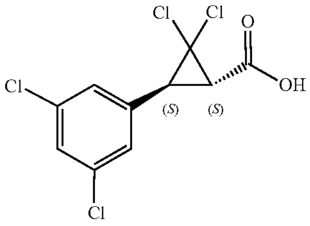 | 101 |
| C460 | 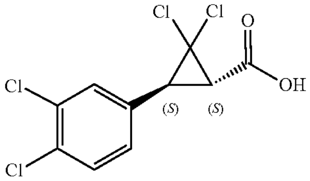 | 101 |
| C461 | 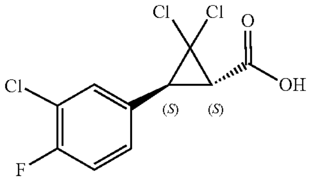 | 101 |
| C462 | 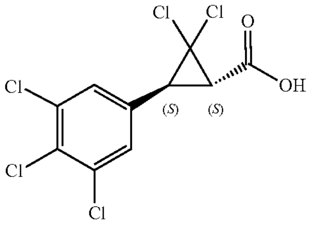 | 101 |
| C463 | 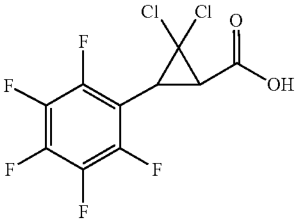 [SMILES: O=C(O)C1C(c2c(F)c(F)c(F)c(F)c2F)C1(Cl)Cl] | 1 |
| C464 | 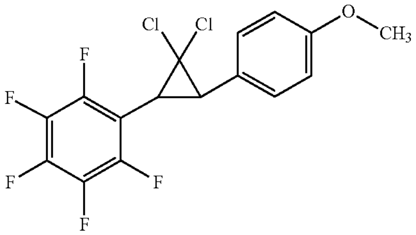 [SMILES: COc1ccc(C2C(c3c(F)c(F)c(F)c(F)c3F)C2(Cl)Cl)cc1] | 4 |
| C465 | 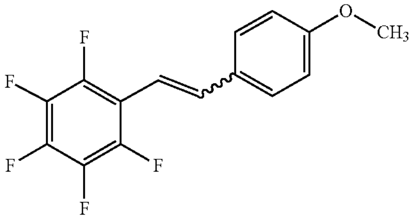 [SMILES: COc1ccc(C=Cc2c(F)c(F)c(F)c(F)c2F)cc1] | 102 |

TABLE 3-continued
| Structure and preparation method for C series molecules | | |
|---|---|---|
| No. | Structure | Prep* |
| C466 | 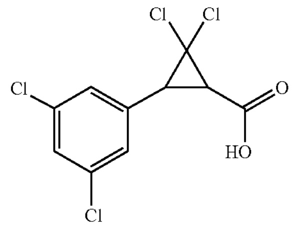 [SMILES: O=C(O)C1C(c2cc(Cl)cc(Cl)c2)C1(Cl)Cl] | 103 |
| C467 | 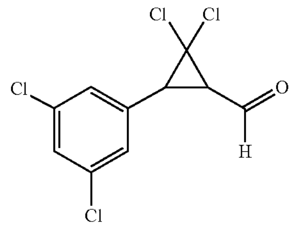 [SMILES: O=CC1C(c2cc(Cl)cc(Cl)c2)C1(Cl)Cl] | 104 |
| C468 | 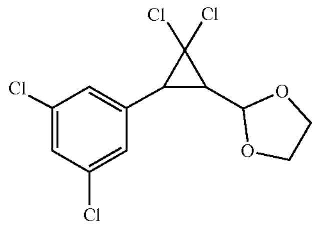 [SMILES: Clc1cc(Cl)cc(C2C(C3OCCO3)C2(Cl)Cl)c1] | 105 |
| C469 | 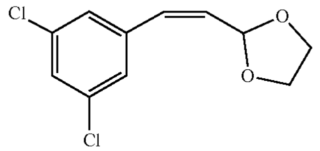 [SMILES: Clc1cc(Cl)cc(/C=C\C2OCCO2)c1] | 106 |
| C470 | 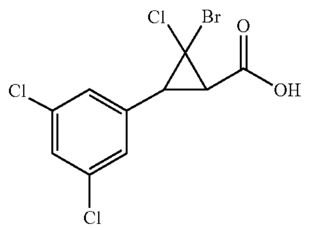 [SMILES: O=C(O)C1C(c2cc(Cl)cc(Cl)c2)C1(Cl)Br] | 107 |

TABLE 3-continued

| Structure and preparation method for C series molecules | | |
|---|---|---|
| No. | Structure | Prep* |
| C471 | 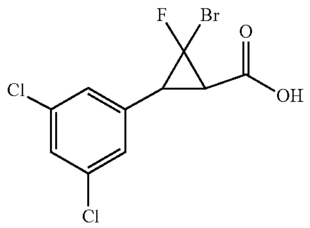 [SMILES: O=C(O)C1C(c2cc(Cl)cc(Cl)c2)C1(F)Br] | 107 |
| C472 | 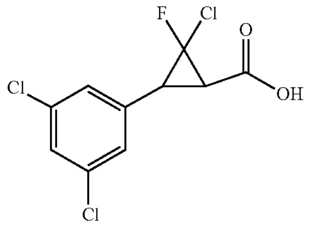 | 107 |

*prepared according to example number

| Lengthy table referenced here |
|---|
| US12490741-20251209-T00001 |
| Please refer to the end of the specification for access instructions. |

| Lengthy table referenced here |
|---|
| US12490741-20251209-T00002 |
| Please refer to the end of the specification for access instructions. |

| Lengthy table referenced here |
|---|
| US12490741-20251209-T00003 |
| Please refer to the end of the specification for access instructions. |

| Lengthy table referenced here |
|---|
| US12490741-20251209-T00004 |
| Please refer to the end of the specification for access instructions. |

LENGTHY TABLES

The patent contains a lengthy table section. A copy of the table is available in electronic form from the USPTO web site (https://seqdata.uspto.gov/docdetail?docId=US12490741B2). An electronic copy of the table will also be available from the USPTO upon request and payment of the fee set forth in 37 CFR 1.19(b)(3).

The invention claimed is:
1. A molecule selected from one of the molecules listed in the following Table.
| No. | Structure |
|---|---|
| F63 | 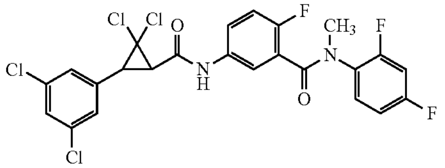 [SMILES: CN(C(=O)c1cc(NC(=O)C2C(c3cc(Cl)cc(Cl)c3)C2(Cl)Cl)ccc1F)c1ccc(F)cc1F] |
| F64 | 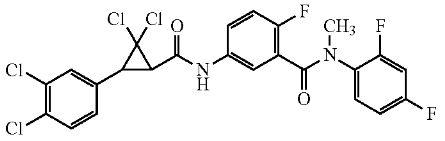 [SMILES: CN(C(=O)c1cc(NC(=O)C2C(c3ccc(Cl)c(Cl)c3)C2(Cl)Cl)ccc1F)c1ccc(F)cc1F] |
| F65 | 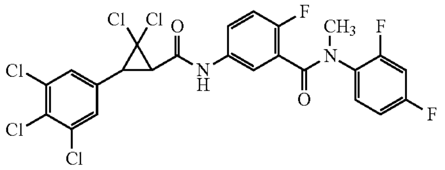 [SMILES: CN(C(=O)c1cc(NC(=O)C2C(c3cc(Cl)c(Cl)c(Cl)c3)C2(Cl)Cl)ccc1F)c1ccc(F)cc1F] |
| F75 | 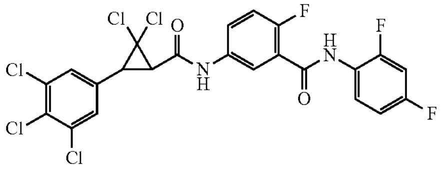 [SMILES: O=C(Nc1ccc(F)cc1F)c1cc(NC(=O)C2C(c3cc(Cl)c(Cl)c(Cl)c3)C2(Cl)Cl)ccc1F] |
| F180 | 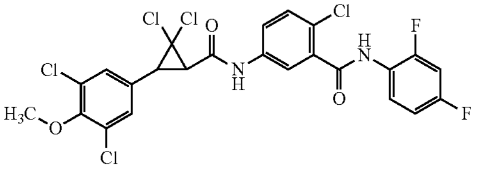 [SMILES: COc1c(Cl)cc(C2C(C(=O)Nc3ccc(Cl)c(C(=O)Nc4ccc(F)cc4F)c3)C2(Cl)Cl)cc1Cl] |
| F187 | 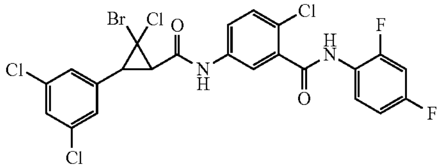 [SMILES: O=C(Nc1ccc(F)cc1F)c1cc(NC(=O)C2C(c3cc(Cl)cc(Cl)c3)C2(Cl)Br)ccc1Cl] |
| F203 | 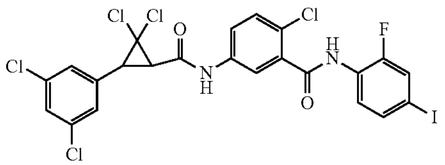 [SMILES: O=C(Nc1ccc(I)cc1F)c1cc(NC(=O)C2C(c3cc(Cl)cc(Cl)c3)C2(Cl)Cl)ccc1Cl] |
| F211 | 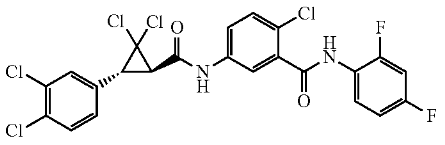 [SMILES: O=C(Nc1ccc(F)cc1F)c1cc(NC(=O)[C@H]2[C@H](c3ccc(Cl)c(Cl)c3)C2(Cl)Cl)ccc1Cl] |
-continued
| No. | Structure |
|---|---|
| F241 | 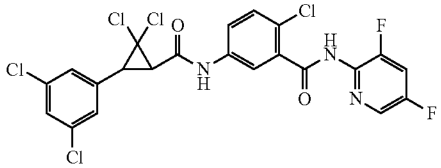 [SMILES: O=C(Nc1ncc(F)cc1F)c1cc(NC(=O)C2C(c3cc(Cl)cc(Cl)c3)C2(Cl)Cl)ccc1Cl] |
| F242 | 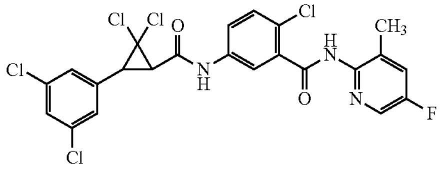 [SMILES: Cc1cc(F)cnc1NC(=O)c1cc(NC(=O)C2C(c3cc(Cl)cc(Cl)c3)C2(Cl)Cl)ccc1Cl] |
| F247 | 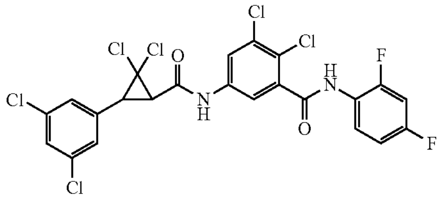 [SMILES: O=C(Nc1ccc(F)cc1F)c1cc(NC(=O)C2C(c3cc(Cl)cc(Cl)c3)C2(Cl)Cl)cc(Cl)c1Cl] |
| F252 | 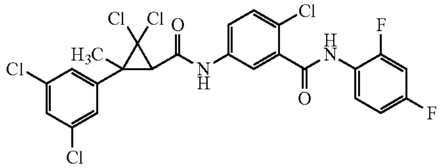 [SMILES: CC1(c2cc(Cl)cc(Cl)c2)C(C(=O)Nc2ccc(Cl)c(C(=O)Nc3ccc(F)cc3F)c2)C1(Cl)Cl] |
| F281 | 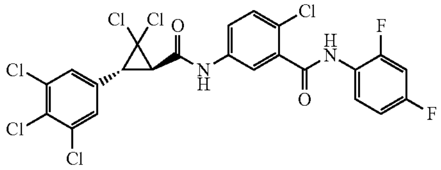 [SMILES: O=C(Nc1ccc(F)cc1F)c1cc(NC(=O)[C@H]2[C@H](c3cc(Cl)c(Cl)c(Cl)c3)C2(Cl)Cl)ccc1Cl] |
| F297 | 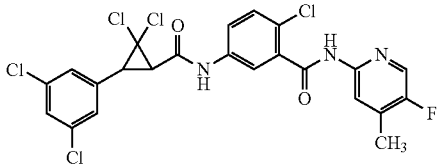 [SMILES: Cc1cc(NC(=O)c2cc(NC(=O)C3C(c4cc(Cl)cc(Cl)c4)C3(Cl)Cl)ccc2Cl)ncc1F] |
| F306 | 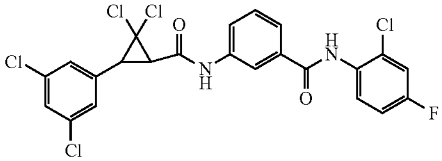 [SMILES: O=C(Nc1ccc(F)cc1Cl)c1cccc(NC(=O)C2C(c3cc(Cl)cc(Cl)c3)C2(Cl)Cl)c1] |
| F309 | 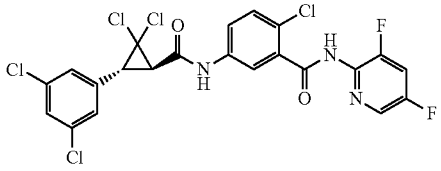 [SMILES: O=C(Nc1ncc(F)cc1F)c1cc(NC(=O)[C@H]2[C@H](c3cc(Cl)cc(Cl)c3)C2(Cl)Cl)ccc1Cl] |

-continued
| No. | Structure |
| --- | --- |
| F310 | 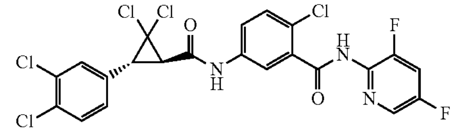 |
| F311 | 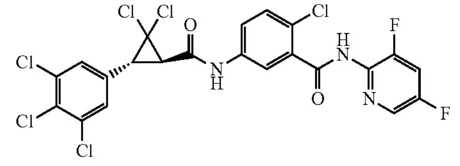 [SMILES: O=C(Nc1ncc(F)cc1F)c1cc(NC(=O)[C@H]2[C@H](c3cc(Cl)c(Cl)c(Cl)c3)C2(Cl)Cl)ccc1Cl] |
| F312 | 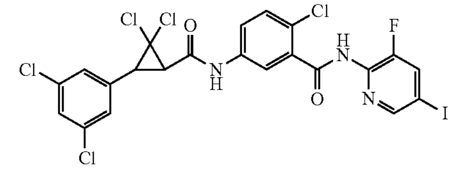 [SMILES: O=C(Nc1ncc(I)cc1F)c1cc(NC(=O)C2C(c3cc(Cl)cc(Cl)c3)C2(Cl)Cl)ccc1Cl] |
| F316 | 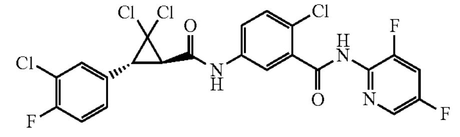 [SMILES: O=C(Nc1ncc(F)cc1F)c1cc(NC(=O)[C@H]2[C@H](c3ccc(F)c(Cl)c3)C2(Cl)Cl)ccc1Cl] |
| F319 | 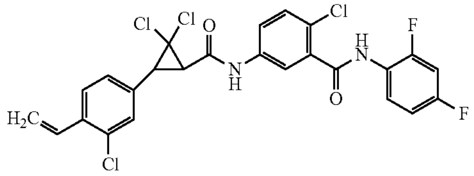 [SMILES: C=Cc1ccc(C2C(C(=O)Nc3ccc(Cl)c(C(=O)Nc4ccc(F)cc4F)c3)C2(Cl)Cl)cc1Cl] |
| F330 | 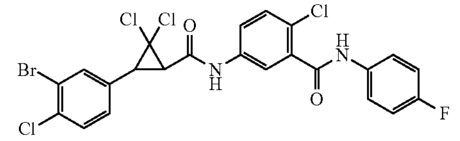 [SMILES: O=C(Nc1ccc(F)cc1)c1cc(NC(=O)C2C(c3ccc(Cl)c(Br)c3)C2(Cl)Cl)ccc1Cl] |
| F331 | 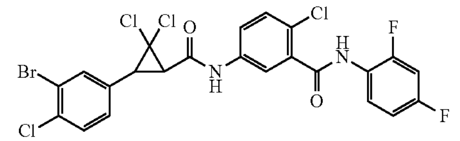 [SMILES: O=C(Nc1ccc(F)cc1F)c1cc(NC(=O)C2C(c3ccc(Cl)c(Br)c3)C2(Cl)Cl)ccc1Cl] |
| F342 | 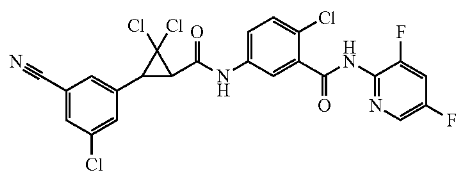 [SMILES: N#Cc1cc(Cl)cc(C2C(C(=O)Nc3ccc(Cl)c(C(=O)Nc4ncc(F)cc4F)c3)C2(Cl)Cl)c1] |
| F351 | 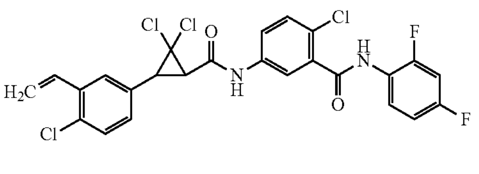 [SMILES: C=Cc1cc(C2C(C(=O)Nc3ccc(Cl)c(C(=O)Nc4ccc(F)cc4F)c3)C2(Cl)Cl)ccc1Cl] |
-continued
| No. | Structure |
| --- | --- |
| F352 | 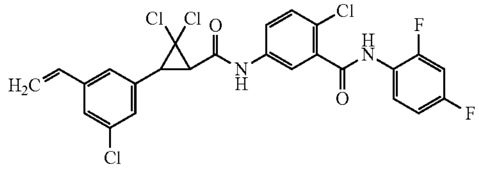 [SMILES: C=Cc1cc(Cl)cc(C2C(C(=O)Nc3ccc(Cl)c(C(=O)Nc4ccc(F)cc4F)c3)C2(Cl)Cl)c1] |
| F353 | 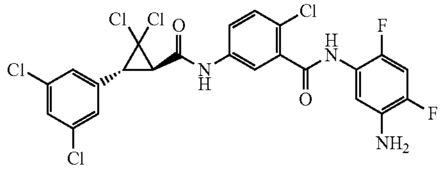 [SMILES: Nc1cc(NC(=O)c2cc(NC(=O)[C@H]3[C@H](c4cc(Cl)cc(Cl)c4)C3(Cl)Cl)ccc2Cl)c(F)cc1F] |
| F354 | 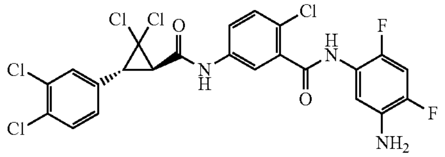 [SMILES: Nc1cc(NC(=O)c2cc(NC(=O)[C@H]3[C@H](c4ccc(Cl)c(Cl)c4)C3(Cl)Cl)ccc2Cl)c(F)cc1F] |
| F357 | 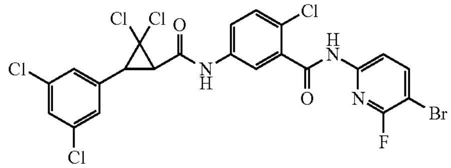 [SMILES: O=C(Nc1ccc(Br)c(F)n1)c1cc(NC(=O)C2C(c3cc(Cl)cc(Cl)c3)C2(Cl)Cl)ccc1Cl] |
| F383 | 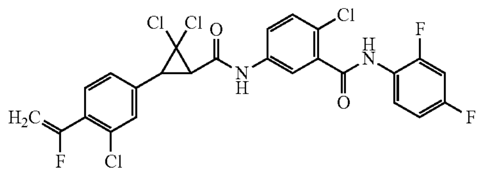 [SMILES: C=C(F)c1ccc(C2C(C(=O)Nc3ccc(Cl)c(C(=O)Nc4ccc(F)cc4F)c3)C2(Cl)Cl)cc1Cl] |
| F385 | 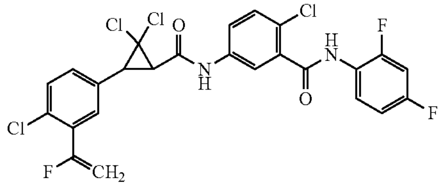 [SMILES: C=C(F)c1cc(C2C(C(=O)Nc3ccc(Cl)c(C(=O)Nc4ccc(F)cc4F)c3)C2(Cl)Cl)ccc1Cl] |
| F386 | 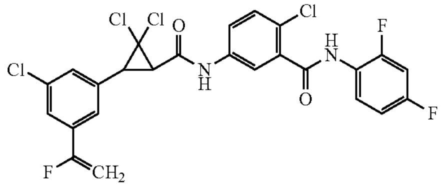 [SMILES: C=C(F)c1cc(Cl)cc(C2C(C(=O)Nc3ccc(Cl)c(C(=O)Nc4ccc(F)cc4F)c3)C2(Cl)Cl)c1] |
| F389 | 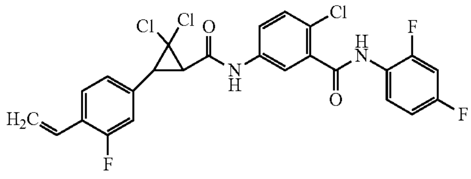 |

-continued
| No. | Structure |
| --- | --- |
| F390 | 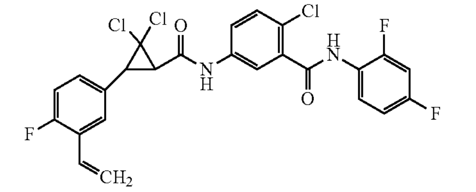 [SMILES: C=Cc1cc(C2C(C(=O)Nc3ccc(Cl)c(C(=O)Nc4ccc(F)cc4F)c3)C2(Cl)Cl)ccc1F] |
| F391 | 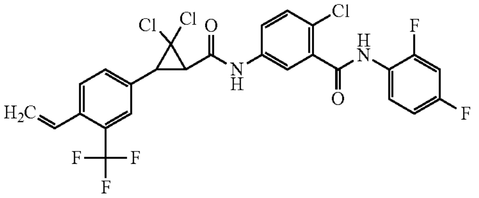 [SMILES: C=Cc1ccc(C2C(C(=O)Nc3ccc(Cl)c(C(=O)Nc4ccc(F)cc4F)c3)C2(Cl)Cl)cc1C(F)(F)F] |
| F392 | 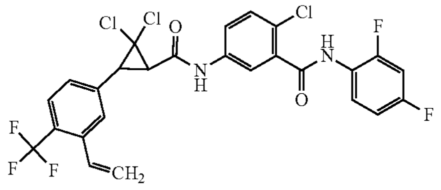 [SMILES: C=Cc1cc(C2C(C(=O)Nc3ccc(Cl)c(C(=O)Nc4ccc(F)cc4F)c3)C2(Cl)Cl)ccc1C(F)(F)F] |
| F395 | 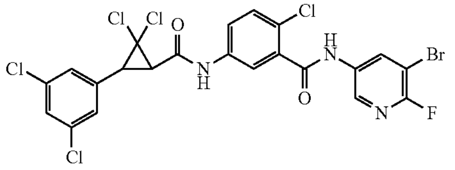 [SMILES: O=C(Nc1cnc(F)c(Br)c1)c1cc(NC(=O)C2C(c3cc(Cl)cc(Cl)c3)C2(Cl)Cl)ccc1Cl] |
| F396 | 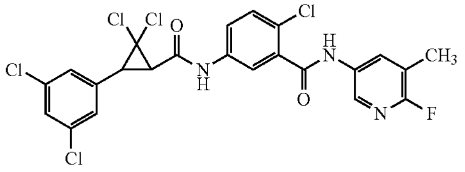 [SMILES: Cc1cc(NC(=O)c2cc(NC(=O)C3C(c4cc(Cl)cc(Cl)c4)C3(Cl)Cl)ccc2Cl)cnc1F] |
| F397 | 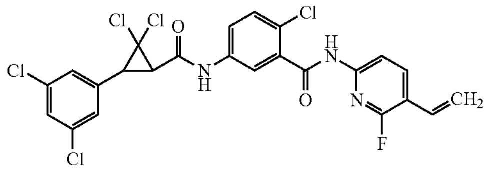 [SMILES: C=Cc1ccc(NC(=O)c2cc(NC(=O)C3C(c4cc(Cl)cc(Cl)c4)C3(Cl)Cl)ccc2Cl)nc1F] |
| F398 | 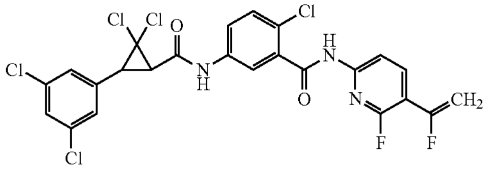 [SMILES: C=C(F)c1ccc(NC(=O)c2cc(NC(=O)C3C(c4cc(Cl)cc(Cl)c4)C3(Cl)Cl)ccc2Cl)nc1F] |
| F399 | 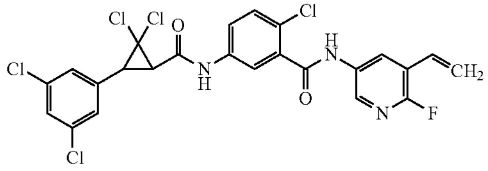 [SMILES: C=Cc1cc(NC(=O)c2cc(NC(=O)C3C(c4cc(Cl)cc(Cl)c4)C3(Cl)Cl)ccc2Cl)cnc1F] |
| F400 | 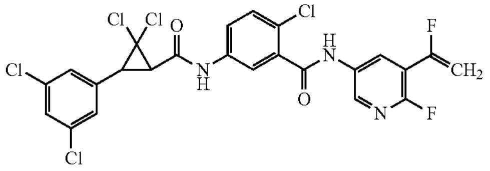 [SMILES: C=C(F)c1cc(NC(=O)c2cc(NC(=O)C3C(c4cc(Cl)cc(Cl)c4)C3(Cl)Cl)ccc2Cl)cnc1F] |
| F533 | 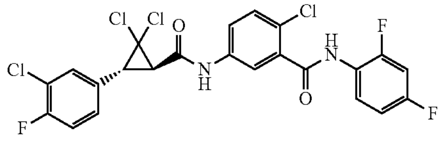 [SMILES: O=C(Nc1ccc(F)cc1F)c1cc(NC(=O)[C@H]2[C@H](c3ccc(F)c(Cl)c3)C2(Cl)Cl)ccc1Cl] |
| F541 | 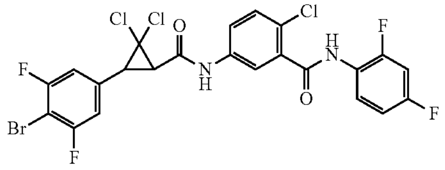 [SMILES: O=C(Nc1ccc(F)cc1F)c1cc(NC(=O)C2C(c3cc(F)c(Br)c(F)c3)C2(Cl)Cl)ccc1Cl] |
| F542 | 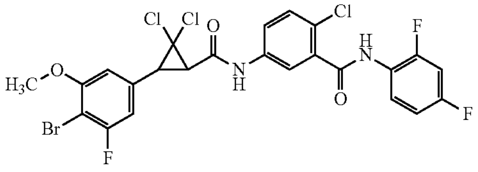 [SMILES: COc1cc(C2C(C(=O)Nc3ccc(Cl)c(C(=O)Nc4ccc(F)cc4F)c3)C2(Cl)Cl)cc(F)c1Br] |
| F543 | 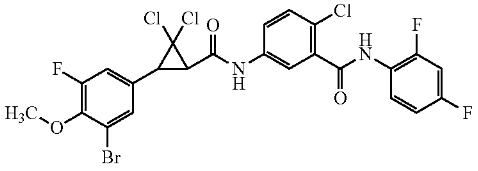 [SMILES: COc1c(F)cc(C2C(C(=O)Nc3ccc(Cl)c(C(=O)Nc4ccc(F)cc4F)c3)C2(Cl)Cl)cc1Br] |
| F546 | 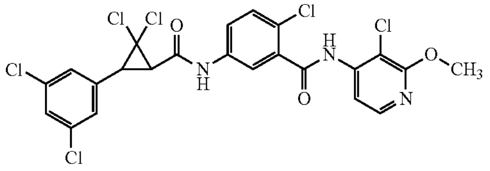 [SMILES: COc1nccc(NC(=O)c2cc(NC(=O)C3C(c4cc(Cl)cc(Cl)c4)C3(Cl)Cl)ccc2Cl)c1Cl] |
| F547 | 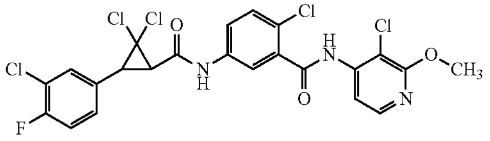 [SMILES: COc1nccc(NC(=O)c2cc(NC(=O)C3C(c4ccc(F)c(Cl)c4)C3(Cl)Cl)ccc2Cl)c1Cl] |
| F548 | 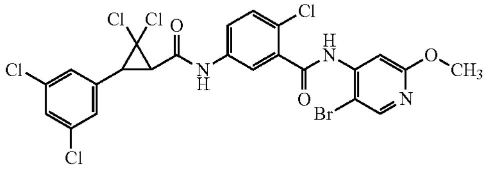 [SMILES: COc1cc(NC(=O)c2cc(NC(=O)C3C(c4cc(Cl)cc(Cl)c4)C3(Cl)Cl)ccc2Cl)c(Br)cn1] |
| F549 | 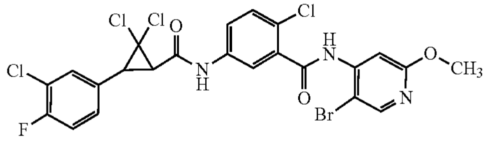 [SMILES: COc1cc(NC(=O)c2cc(NC(=O)C3C(c4ccc(F)c(Cl)c4)C3(Cl)Cl)ccc2Cl)c(Br)cn1] |

-continued
| No. | Structure |
|---|---|
| F552 | 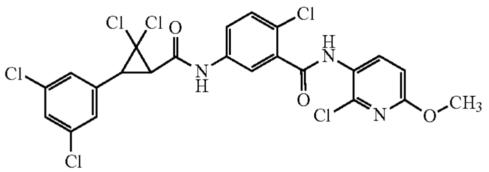 [SMILES: COc1ccc(NC(=O)c2cc(NC(=O)C3C(c4cc(Cl)cc(Cl)c4)C3(Cl)Cl)ccc2Cl)c(Cl)n1] |
| F553 | 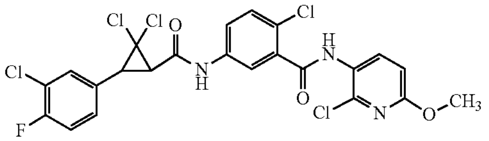 [SMILES: COc1ccc(NC(=O)c2cc(NC(=O)C3C(c4ccc(F)c(Cl)c4)C3(Cl)Cl)ccc2Cl)c(Cl)n1] |
| F558 | 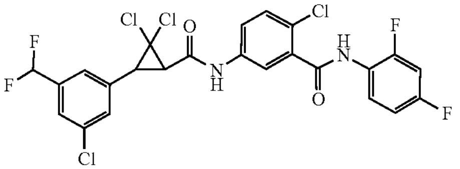 [SMILES: O=C(Nc1ccc(F)cc1F)c1cc(NC(=O)C2C(c3cc(Cl)cc(C(F)F)c3)C2(Cl)Cl)ccc1Cl] |
| F559 | 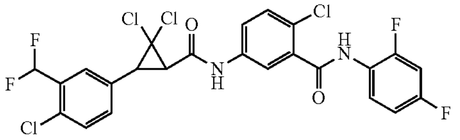 [SMILES: O=C(Nc1ccc(F)cc1F)c1cc(NC(=O)C2C(c3ccc(Cl)c(C(F)F)c3)C2(Cl)Cl)ccc1Cl] |
| F560 | 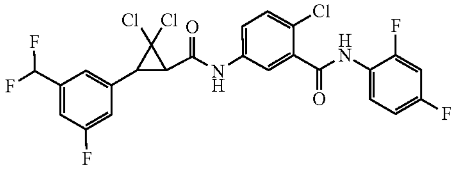 [SMILES: O=C(Nc1ccc(F)cc1F)c1cc(NC(=O)C2C(c3cc(F)cc(C(F)F)c3)C2(Cl)Cl)ccc1Cl] |
| F561 | 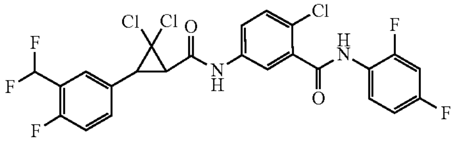 [SMILES: O=C(Nc1ccc(F)cc1F)c1cc(NC(=O)C2C(c3ccc(F)c(C(F)F)c3)C2(Cl)Cl)ccc1Cl] |
| F562 | 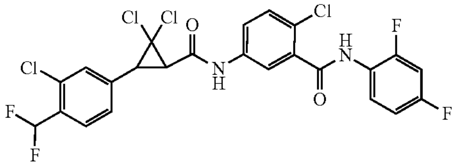 [SMILES: O=C(Nc1ccc(F)cc1F)c1cc(NC(=O)C2C(c3ccc(C(F)F)c(Cl)c3)C2(Cl)Cl)ccc1Cl] |
| F563 | 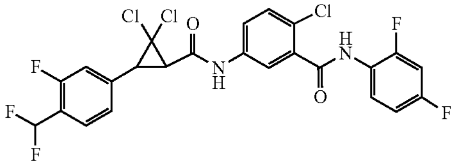 [SMILES: O=C(Nc1ccc(F)cc1F)c1cc(NC(=O)C2C(c3ccc(C(F)F)c(F)c3)C2(Cl)Cl)ccc1Cl] |
| F564 | 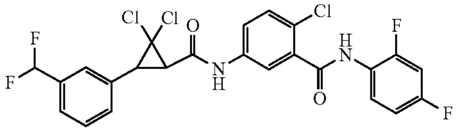 [SMILES: O=C(Nc1ccc(F)cc1F)c1cc(NC(=O)C2C(c3cccc(C(F)F)c3)C2(Cl)Cl)ccc1Cl] |
-continued
| No. | Structure |
|---|---|
| F565 | 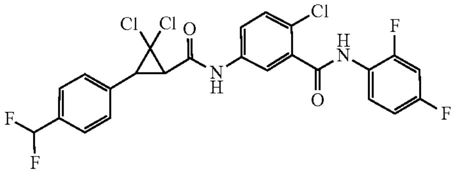 [SMILES: O=C(Nc1ccc(F)cc1F)c1cc(NC(=O)C2C(c3ccc(C(F)F)cc3)C2(Cl)Cl)ccc1Cl] |
| F566 | 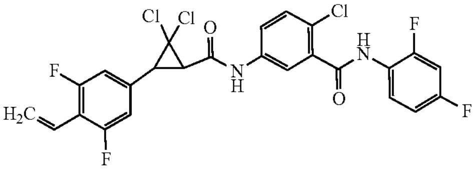 [SMILES: C=Cc1c(F)cc(C2C(C(=O)Nc3ccc(Cl)c(C(=O)Nc4ccc(F)cc4F)c3)C2(Cl)Cl)cc1F] |
| F572 | 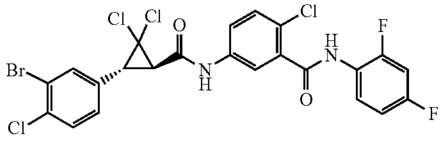 [SMILES: O=C(Nc1ccc(F)cc1F)c1cc(NC(=O)[C@H]2[C@H](c3ccc(Cl)c(Br)c3)C2(Cl)Cl)ccc1Cl] |
| F580 | 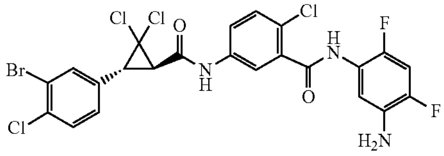 [SMILES: Nc1cc(NC(=O)c2cc(NC(=O)[C@H]3[C@H](c4ccc(Cl)c(Br)c4)C3(Cl)Cl)ccc2Cl)c(F)cc1F] |
| F584 | 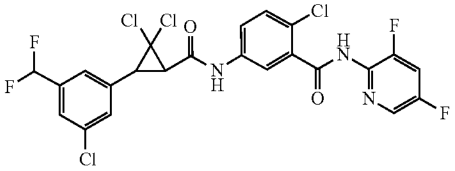 [SMILES: O=C(Nc1ncc(F)cc1F)c1cc(NC(=O)C2C(c3cc(Cl)cc(C(F)F)c3)C2(Cl)Cl)ccc1Cl] |
| F585 | 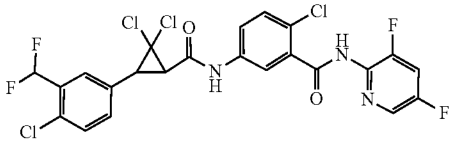 [SMILES: O=C(Nc1ncc(F)cc1F)c1cc(NC(=O)C2C(c3ccc(Cl)c(C(F)F)c3)C2(Cl)Cl)ccc1Cl] |
| F586 | 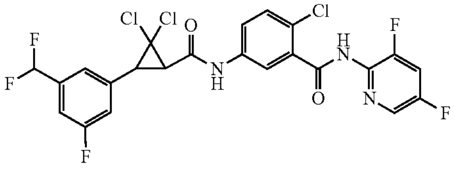 [SMILES: O=C(Nc1ncc(F)cc1F)c1cc(NC(=O)C2C(c3cc(F)cc(C(F)F)c3)C2(Cl)Cl)ccc1Cl] |
| F587 | 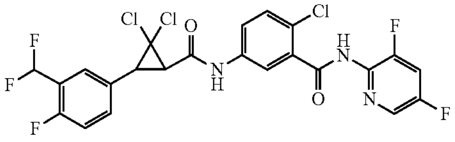 [SMILES: O=C(Nc1ncc(F)cc1F)c1cc(NC(=O)C2C(c3ccc(F)c(C(F)F)c3)C2(Cl)Cl)ccc1Cl] |
| F588 | 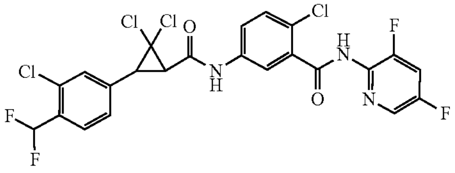 [SMILES: O=C(Nc1ncc(F)cc1F)c1cc(NC(=O)C2C(c3ccc(C(F)F)c(Cl)c3)C2(Cl)Cl)ccc1Cl] |

-continued

| No. | Structure |
|---|---|
| F589 | 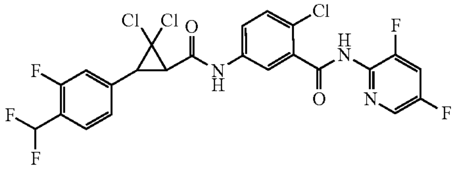 [SMILES: O=C(Nc1ncc(F)cc1F)c1cc(NC(=O)C2C(c3ccc(C(F)F)c(F)c3)C2(Cl)Cl)ccc1Cl] |
| F590 | 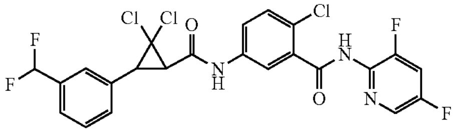 [SMILES: O=C(Nc1ncc(F)cc1F)c1cc(NC(=O)C2C(c3cccc(C(F)F)c3)C2(Cl)Cl)ccc1Cl] |
| F591 | 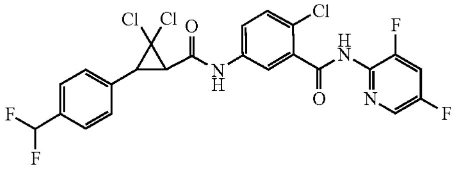 [SMILES: O=C(Nc1ncc(F)cc1F)c1cc(NC(=O)C2C(c3ccc(C(F)F)cc3)C2(Cl)Cl)ccc1Cl] |
| PF6 | 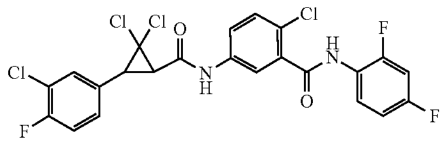 [SMILES: O=C(Nc1ccc(F)cc1F)c1cc(NC(=O)C2C(c3ccc(F)c(Cl)c3)C2(Cl)Cl)ccc1Cl] |

-continued

| No. | Structure |
|---|---|
| PF39 | 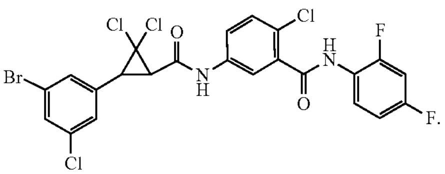 [SMILES: O=C(Nc1ccc(F)cc1F)c1cc(NC(=O)C2C(c3cc(Cl)cc(Br)c3)C2(Cl)Cl)ccc1Cl] |

2. A molecule according to claim 1, wherein the carboxamido, and the phenyl, which are bonded to the cyclopropane, are in the R,R configuration.

3. A composition comprising a molecule according to claim 1, further comprises a carrier and/or an active ingredient.

4. A composition according to claim 3, the composition further comprises an active ingredient selected from acaricides, algicides, antifeedants, avicides, bactericides, bird repellents, chemosterilants, fungicides, herbicide safeners, herbicides, insect attractants, insect repellents, insecticides, mammal repellents, mating disrupters, molluscicides, nematicides, plant activators, plant growth regulators, rodenticides, synergists, and virucides, an active ingredient selected from AIGA, AI-1, AI-2, or AIGA-2, or further comprising Lotilaner, a structure selected from Table A, or a biopesticide.

TABLE A

| Structure of M#—active ingredients | |
|---|---|
| M# | Structure |
| M1 | 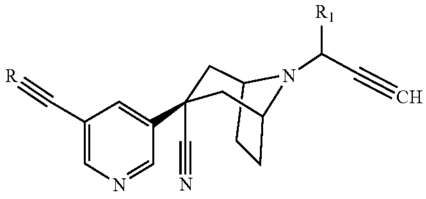 R = CH, N<br>$R_1$ = H, Me |
| M2 | 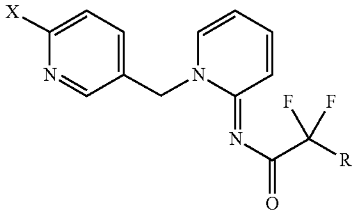 X = F, Cl,<br>R = H, F |

TABLE A-continued

| Structure of M#—active ingredients | |
|---|---|
| M# | Structure |
| M3 | 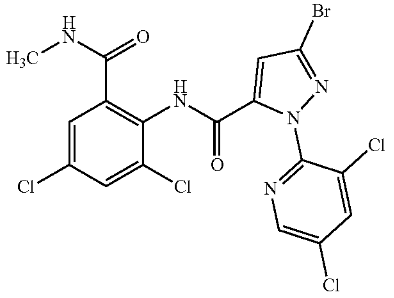 [SMILES: CNC(=O)c1cc(Cl)cc(Cl)c1NC(=O)c1cc(Br)nn1-c1ncc(Cl)cc1Cl] |
| M4 | 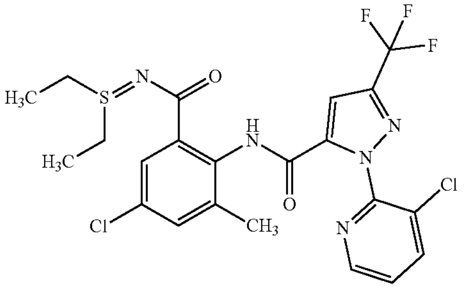 [SMILES: CCS(CC)=NC(=O)c1cc(Cl)cc(C)c1NC(=O)c1cc(C(F)(F)F)nn1-c1ncccc1Cl] |
| M5 | 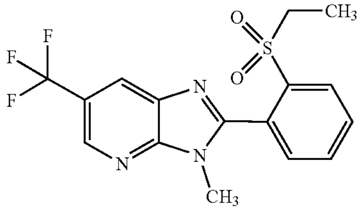 [SMILES: CCS(=O)(=O)c1ccccc1-c1nc2cc(C(F)(F)F)cnc2n1C] |
| M6 | 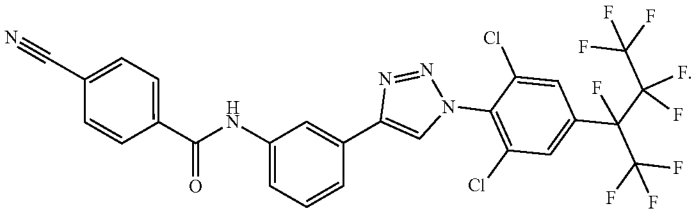 [SMILES: N#Cc1ccc(C(=O)Nc2cccc(-c3cn(-c4c(Cl)cc(C(F)(C(F)(F)F)C(F)(F)C(F)(F)F)cc4Cl)nn3)c2)cc1] |

5. A composition according to claim 3, the composition further comprises an active ingredient from Acetylcholinesterase (AChE) inhibitors; GABA-gated chloride channel antagonists; Sodium channel modulators; Nicotinic acetylcholine receptor (nAChR) agonists; Nicotinic acetylcholine receptor (nAChR) allosteric activators; Chloride channel activators; Juvenile hormone mimics; Miscellaneous non-specific (multi-site) inhibitors; Modulators of Chordotonal Organs; Mite growth inhibitors; Microbial disruptors of insect midgut membranes; Inhibitors of mitochondrial ATP synthase; Uncouplers of oxidative phosphorylation via disruption of the proton gradient; Nicotinic acetylcholine receptor (nAChR) channel blockers; Inhibitors of chitin biosynthesis, type 0; Inhibitors of chitin biosynthesis, type 1; Moulting disruptor, Dipteran; Ecdysone receptor agonists; Octopamine receptor agonists; Mitochondrial complex III electron transport inhibitors; Mitochondrial complex I electron transport inhibitors; Voltage-dependent sodium channel blockers; Inhibitors of acetyl CoA carboxylase; Mitochondrial complex IV electron transport inhibitors; Mitochondrial complex II electron transport inhibitors; Ryanodine receptor modulators; or Group UN.

6. A composition according to claim 3, further comprises an active ingredient selected from group consisting of emamectin, eprinomectin, moxidectin and milbemycin oxime.

7. A composition according to claim 5, wherein the weight ratio of the molecule to the active ingredient is 100:1 to 1:100, 50:1 to 1:50, 20:1 to 1:20, 10:1 to 1:10, 5:1 to 1:5, 3:1 to 1:3, 2:1 to 1:2, or 1:1; and/or wherein the weight ratio of the molecule to the active ingredient is X:Y; wherein X is the parts by weight of the molecule and Y is the parts by weight of the active ingredient; further wherein the numerical range of the parts by weight for X is $0<X\leq 100$ and the parts by weight for Y is $0<Y\leq 100$; and further wherein X and Y are selected from Table C, optionally wherein a range of weight ratios of the molecule to the active ingredient is $X_1:Y_1$ to $X_2:Y_2$; further wherein $X_1>Y_1$ and $X_2<Y_2$; or wherein $X_1>Y_1$ and $X_2>Y_2$; or wherein $X_1<Y_1$ and $X_2<Y_2$.

TABLE C

| | | | | | | |
|---|---|---|---|---|---|---|
| active | 100 | X, Y | | X, Y | | |
| ingredient (Y) | 50 | X, Y | X, Y | X, Y | | |
| Parts by weight | 20 | X, Y | | X, Y | X, Y | |
| | 15 | X, Y | X, Y | | | |
| | 10 | X, Y | | X, Y | | |
| | 5 | X, Y | X, Y | X, Y | | |
| | 3 | X, Y | X, Y | | X, Y | X, Y |
| | 2 | X, Y | | X, Y | X, Y | |
| | 1 | X, Y | X, Y | X, Y | X, Y | X, Y |
| | | 1 | 2 | 3 | 5 | 10 |
| | | molecule (X) Parts by weight | | | | |

| | | | | | |
|---|---|---|---|---|---|
| active | 100 | X, Y | | | |
| ingredient (Y) | 50 | X, Y | X, Y | | |
| Parts by weight | 20 | X, Y | | X, Y | |
| | 15 | | X, Y | X, Y | X, Y |
| | 10 | | | | |
| | 5 | | X, Y | | |
| | 3 | | X, Y | X, Y | X, Y |
| | 2 | X, Y | | X, Y | |
| | 1 | X, Y | X, Y | X, Y | X, Y |
| | | 15 | 20 | 50 | 100 |
| | | molecule (X) Parts by weight. | | | |

8. A process to control a pest, wherein the process comprises applying to a locus, a pesticidally effective amount of a molecule or a composition according to claim 3.

9. A process according to claim 7, wherein the pest is selected from the group consisting of ants, aphids, bed bugs, beetles, bristletails, caterpillars, cockroaches, crickets, earwigs, fleas, flies, grasshoppers, grubs, leafhoppers, lice, locusts, maggots, mites, nematodes, planthoppers, psyllids, sawflies, scales, silverfish, slugs, snails, spiders, springtails, stink bugs, symphylans, termites, thrips, ticks, wasps, whiteflies, and wireworms.

10. A process according claim 7, wherein the pest is a sap-feeding pest or a chewing pest; or wherein the pest is selected from the group consisting of aphids, leafhoppers, moths, scales, thrips, psyllids, mealybugs, stinkbugs, and whiteflies; or from the group consisting of caterpillars, beetles, grasshoppers, and locusts; or wherein the pest is selected from the group consisting of Orders Anoplura and Hemiptera; or from the group consisting of Coleoptera and Lepidoptera; or wherein the pest is selected from the group consisting of *Aulacaspis* spp., *Aphrophora* spp., *Aphis* spp., *Bemisia* spp., *Coccus* spp., *Euschistus* spp., *Lygus* spp., *Macrosiphum* spp., *Nezara* spp., and *Rhopalosiphum* spp; or from the group consisting of *Anthonomus* spp., *Cerotoma* spp., *Chaetocnema* spp., *Colaspis* spp., *Cyclocephala* spp., *Diabrotica* spp., *Hypera* spp., *Phyllophaga* spp., *Phyllotreta* spp., *Sphenophorus* spp., and *Sitophilus* spp.

* * * * *